US012201809B2

(12) United States Patent
Gibson et al.

(10) Patent No.: US 12,201,809 B2
(45) Date of Patent: Jan. 21, 2025

(54) DRUG DELIVERY DEVICE, METHOD OF MANUFACTURE, AND METHOD OF USE

(71) Applicant: AMGEN INC., Thousand Oaks, CA (US)

(72) Inventors: Scott R. Gibson, Simi Valley, CA (US); Sheldon B. Moberg, Thousand Oaks, CA (US); Basel Hasan Taha, Thousand Oaks, CA (US); Margaux Frances Boyaval, Newbury Park, CA (US); Mark A. Destefano, Collegeville, PA (US); Lawton Laurence, Phoenixville, PA (US); John C. Love, San Diego, CA (US); Ian B. Hanson, Wayne, PA (US); Paul F. Bente, IV, Wayne, PA (US); Matthew J. Clemente, Carmel, IN (US); Antonio Ubach, Tucson, AZ (US); Rajan Ramaswamy, San Diego, CA (US); Daniel S. Codd, Escondido, CA (US); Scott Beaver, San Marcos, CA (US); Kevin L. Bokelman, San Diego, CA (US); Ian P. Dardani, Radnor, PA (US); Sean M. O'connor, West Chester, PA (US); Danielle Feldman, Philadelphia, PA (US)

(73) Assignee: AMGEN INC., Thousand Oaks, CA (US)

( * ) Notice: Subject to any disclaimer, the term of this patent is extended or adjusted under 35 U.S.C. 154(b) by 220 days.

(21) Appl. No.: 17/386,659

(22) Filed: Jul. 28, 2021

(65) Prior Publication Data

US 2021/0402083 A1 Dec. 30, 2021

Related U.S. Application Data

(63) Continuation of application No. 16/089,685, filed as application No. PCT/US2017/026524 on Apr. 7, 2017, now Pat. No. 11,129,936.

(Continued)

(30) Foreign Application Priority Data

Feb. 13, 2017 (WO) ............... PCT/US2017/017627

(51) Int. Cl.
*A61M 5/142* (2006.01)
*A61M 5/145* (2006.01)
(Continued)

(52) U.S. Cl.
CPC .... *A61M 5/14566* (2013.01); *A61M 5/14248* (2013.01); *A61M 5/158* (2013.01);
(Continued)

(58) Field of Classification Search
CPC .... A61M 5/142; A61M 5/145; A61M 5/1452; A61M 5/14248; A61M 5/158; A61M 2005/14506; A61M 2005/14252
See application file for complete search history.

(56) References Cited

U.S. PATENT DOCUMENTS

| 4,894,054 A | 1/1990 | Miskinyar |
| 5,380,315 A | 1/1995 | Isono et al. |

(Continued)

FOREIGN PATENT DOCUMENTS

| EP | 1965449 A2 | 9/2008 |
| EP | 3260146 A1 | 12/2017 |

(Continued)

OTHER PUBLICATIONS

European Patent Applicaiton No. 21154819, Extended European Search Report, dated Apr. 29, 2021.

(Continued)

*Primary Examiner* — Laura A Bouchelle
(74) *Attorney, Agent, or Firm* — MARSHALL, GERSTEIN & BORUN LLP

(57) ABSTRACT

Disclosed herein is a wearable drug delivery device including a container filled at least partially with a drug including (Continued)

at least one of a PCSK9 (Proprotein Convertase Subtilisin/ Kexin Type 9) specific antibody, a granulocyte colony-stimulating factor (G-CSF), a sclerostin antibody, or a calcitonin gene-related peptide (CGRP) antibody. The wearable drug delivery device may include a needle and an insertion mechanism configured to insert the needle into a patient. A fluid pathway connector may define a sterile fluid flowpath between the container and the insertion mechanism. Optionally, a cannula initially disposed about the needle may be included. The cannula may be retained in the patient at an injection site created by the needle after the needle is withdrawn from the patient. Methods of assembly and operation are also provided.

21 Claims, 208 Drawing Sheets

Related U.S. Application Data

(60) Provisional application No. 62/320,438, filed on Apr. 8, 2016.

(51) Int. Cl.
  *A61M 5/158* (2006.01)
  *A61M 5/168* (2006.01)

(52) U.S. Cl.
  CPC .......... *A61M 2005/14252* (2013.01); *A61M 2005/1585* (2013.01); *A61M 2202/0441* (2013.01); *A61M 2202/0447* (2013.01); *A61M 2205/103* (2013.01); *A61M 2205/12* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/36* (2013.01); *A61M 2205/8206* (2013.01)

(56) References Cited

U.S. PATENT DOCUMENTS

| | | | |
|---|---|---|---|
| 7,455,663 B2 * | 11/2008 | Bikovsky | A61M 25/0606 604/181 |
| 7,708,717 B2 * | 5/2010 | Estes | A61M 5/14244 604/890.1 |
| 7,981,085 B2 | 7/2011 | Ethelfeld | |
| 8,226,610 B2 | 7/2012 | Edwards et al. | |
| 8,282,601 B2 | 10/2012 | Mernoe et al. | |
| 8,668,675 B2 | 3/2014 | Chase et al. | |
| 8,939,935 B2 | 1/2015 | O'Connor et al. | |
| 9,061,097 B2 * | 6/2015 | Holt | A61M 5/14248 |
| 9,987,419 B2 | 6/2018 | Hanson et al. | |
| 10,342,918 B2 | 7/2019 | Politis et al. | |
| 2005/0197625 A1 * | 9/2005 | Haueter | A61M 5/1454 604/131 |
| 2011/0066012 A1 | 3/2011 | Hanson et al. | |
| 2012/0004640 A1 | 1/2012 | Rosen et al. | |
| 2012/0323183 A1 | 12/2012 | Peterson et al. | |
| 2013/0060196 A1 | 3/2013 | O'Connor et al. | |
| 2013/0060233 A1 | 3/2013 | O'Connor et al. | |
| 2013/0066274 A1 | 3/2013 | O'Connor et al. | |
| 2013/0237916 A1 | 9/2013 | Hanson et al. | |
| 2013/0331791 A1 | 12/2013 | Gross et al. | |
| 2014/0200510 A1 | 7/2014 | Agard et al. | |
| 2014/0213975 A1 | 7/2014 | Clemente et al. | |
| 2014/0288511 A1 | 9/2014 | Tan-Malecki et al. | |
| 2014/0296787 A1 | 10/2014 | Agard et al. | |
| 2014/0316337 A1 | 10/2014 | Kadamus et al. | |
| 2015/0057613 A1 | 2/2015 | Clemente et al. | |
| 2015/0190588 A1 | 7/2015 | Hanson et al. | |
| 2015/0209505 A1 | 7/2015 | Hanson et al. | |
| 2015/0217045 A1 | 8/2015 | Bente, IV et al. | |
| 2015/0290390 A1 | 10/2015 | Ring et al. | |
| 2015/0297827 A1 | 10/2015 | Hanson et al. | |
| 2015/0359965 A1 | 12/2015 | O'Connor et al. | |
| 2015/0374919 A1 | 12/2015 | Gibson | |
| 2016/0082189 A1 | 3/2016 | Anderson et al. | |
| 2016/0175515 A1 | 6/2016 | McCullough | |
| 2016/0175527 A1 | 6/2016 | McCullough | |
| 2017/0361015 A1 | 12/2017 | McCullough | |
| 2018/0021508 A1 | 1/2018 | Destefano et al. | |
| 2018/0028747 A1 | 2/2018 | Hanson et al. | |
| 2018/0036476 A1 | 2/2018 | McCullough et al. | |
| 2018/0085517 A1 | 3/2018 | Laurence et al. | |
| 2018/0353682 A1 | 12/2018 | Laurence et al. | |

FOREIGN PATENT DOCUMENTS

| | | | | |
|---|---|---|---|---|
| JP | S4828863 A | 4/1973 | | |
| JP | S53146489 A | 12/1978 | | |
| JP | 2008245505 A | 10/2008 | | |
| JP | 2010533525 A | 10/2010 | | |
| JP | 2014510571 A | 5/2014 | | |
| WO | WO-2009010399 A1 | 1/2009 | | |
| WO | WO-2011/133823 A1 | 10/2011 | | |
| WO | WO-2013/040032 A1 | 3/2013 | | |
| WO | WO-2013/033467 A3 | 4/2013 | | |
| WO | WO-2013/033421 A3 | 6/2013 | | |
| WO | WO-2014036308 A2 * | 3/2014 | .......... | A61M 5/1452 |
| WO | WO-2014/116274 A1 | 7/2014 | | |
| WO | WO-2015/027174 A4 | 4/2015 | | |
| WO | WO-2015/061386 A1 | 4/2015 | | |
| WO | WO-2015/061389 A1 | 4/2015 | | |
| WO | WO-2015/171777 A1 | 11/2015 | | |
| WO | WO-2015187793 A1 | 12/2015 | | |
| WO | WO-2015187797 A1 | 12/2015 | | |
| WO | WO-2015187799 A1 | 12/2015 | | |
| WO | WO-2015187802 A1 | 12/2015 | | |
| WO | WO-2016/003813 A1 | 1/2016 | | |
| WO | WO-2016/033496 A1 | 3/2016 | | |
| WO | WO-2016/049501 A1 | 3/2016 | | |
| WO | WO-2016/049532 A1 | 3/2016 | | |
| WO | WO-2015/187805 A3 | 4/2016 | | |
| WO | WO-2016/033507 A3 | 4/2016 | | |
| WO | WO-2016/053954 A8 | 6/2016 | | |
| WO | WO-2016/100781 A1 | 6/2016 | | |
| WO | WO-2016/130679 A2 | 8/2016 | | |
| WO | WO-2016/133947 A1 | 8/2016 | | |
| WO | WO-2016141082 A1 | 9/2016 | | |
| WO | WO-2016/145094 A3 | 11/2016 | | |
| WO | WO-2016/186706 A1 | 11/2016 | | |
| WO | WO-2017/093803 A1 | 6/2017 | | |
| WO | WO-2017/106247 A1 | 6/2017 | | |
| WO | WO-2017/139003 A1 | 8/2017 | | |
| WO | WO-2017/139573 A1 | 8/2017 | | |

OTHER PUBLICATIONS

International Search Report and Written Opinion for International Application No. PCT/US2017/017627, mailed Jul. 27, 2017.
International Search Report and Written Opinion for International Application No. PCT/US2017/026524, mailed Sep. 22, 2017.
U.S. Appl. No. 16/089,685, Nonfinal Office Action, dated Dec. 18, 2020.
U.S. Appl. No. 16/071,873, Nonfinal Office Action, dated Jul. 6, 2021.
European Patent Application No. 21154819, Communication Pursuant to Article 94(3) EPC, dated Oct. 17, 2023.
Japanese Patent Application No. 2022-078231, Decision of Rejection, mailed Dec. 19, 2023.
Japanese Patent Application No. 2022-010712, Office Action, dated Jan. 10, 2023.
Taiwan Patent Application No. 110109360, Office Action and Search Report, dated Dec. 7, 2021.

(56) References Cited

OTHER PUBLICATIONS

U.S. Appl. No. 17/688,578, Nonfinal Office Action, dated Aug. 2, 2024.

* cited by examiner

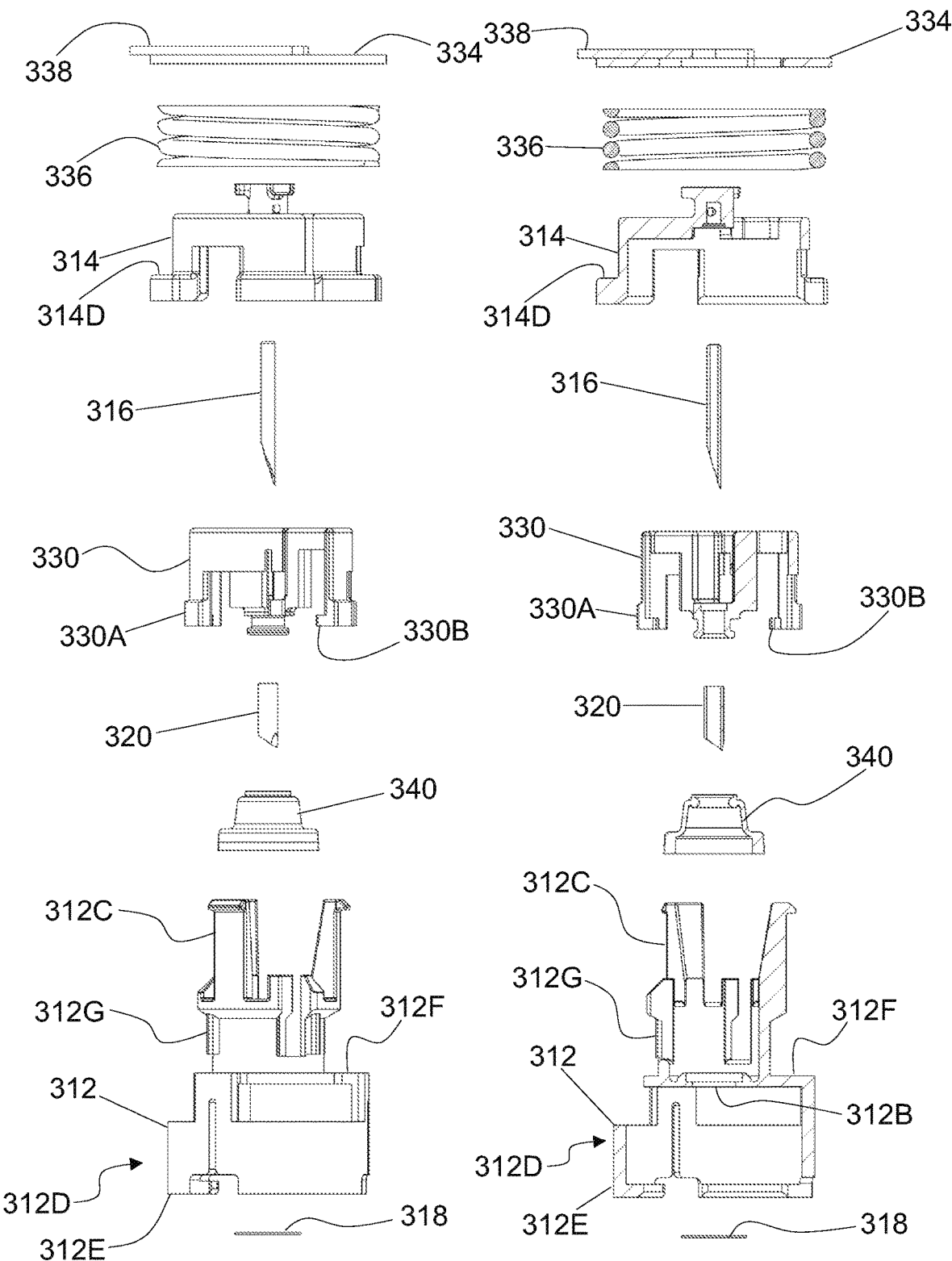

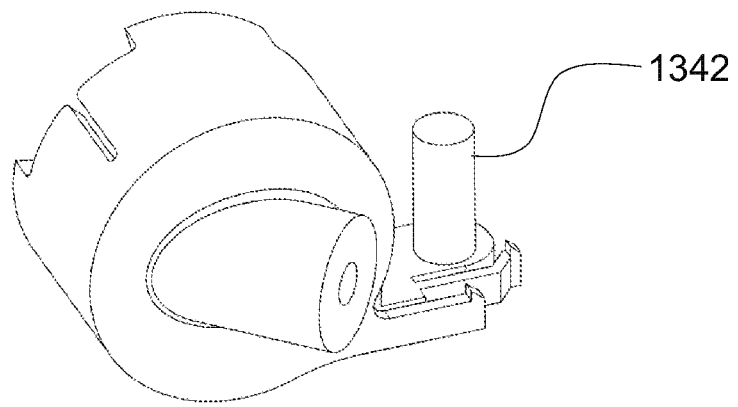
FIG. 20
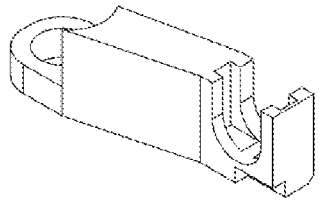
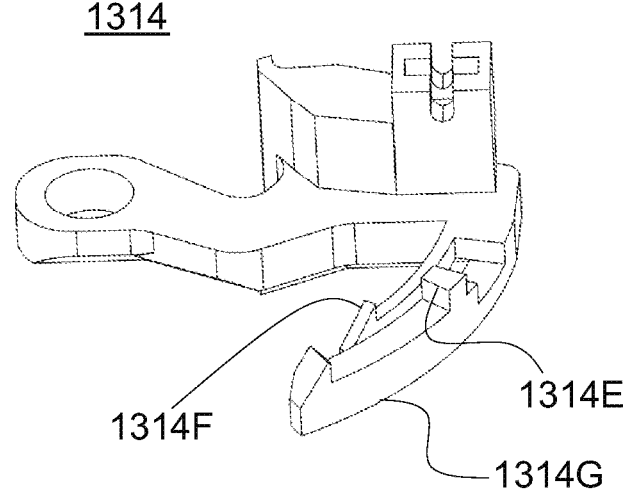
FIG. 21
FIG. 22

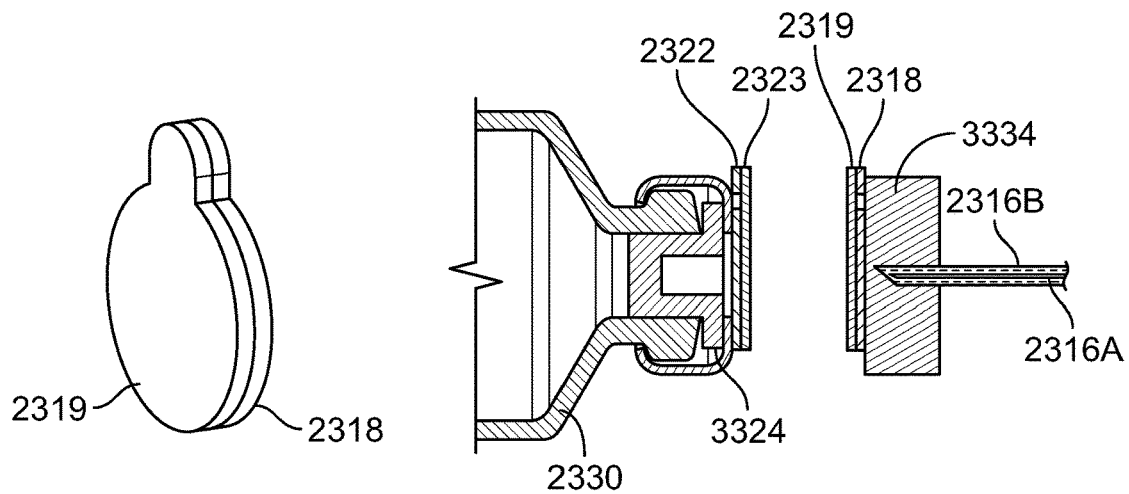
FIG. 38A
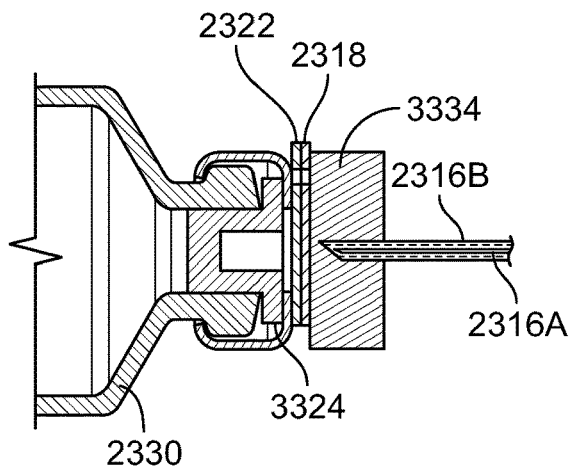
FIG. 38B
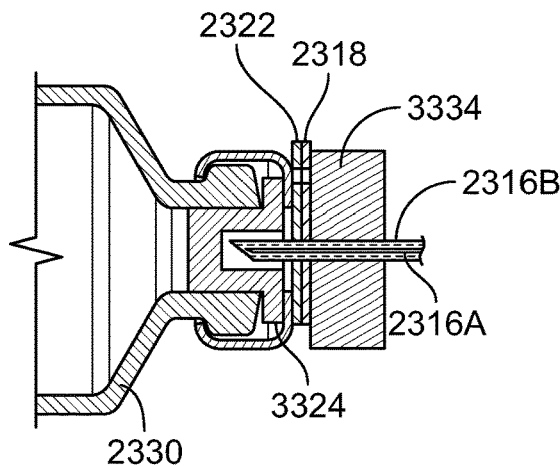 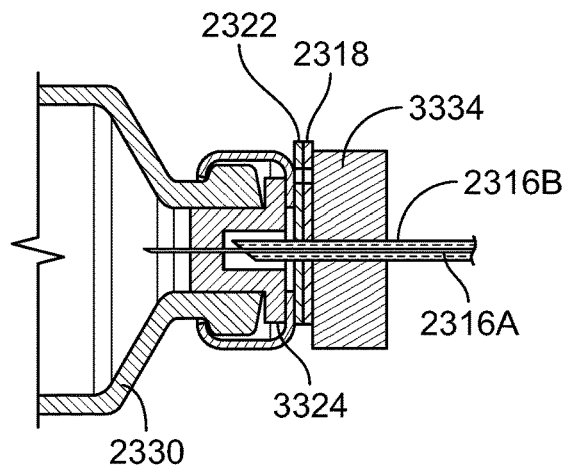
FIG. 38C  FIG. 38D

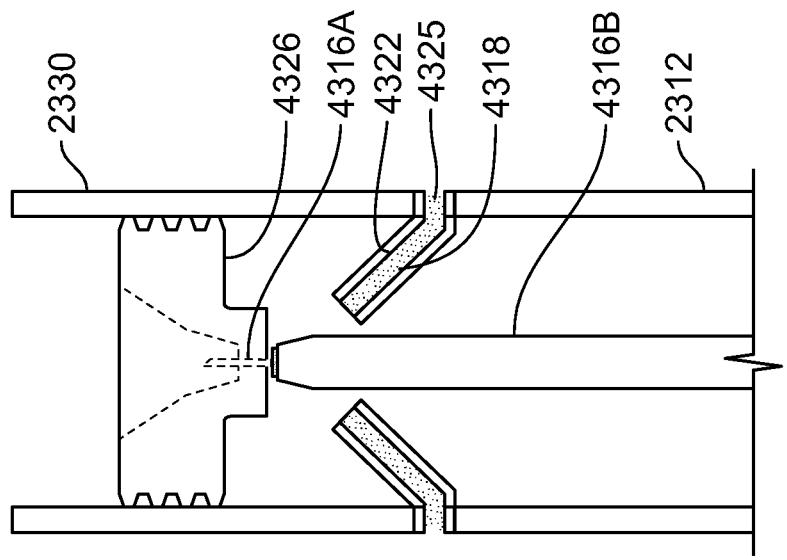
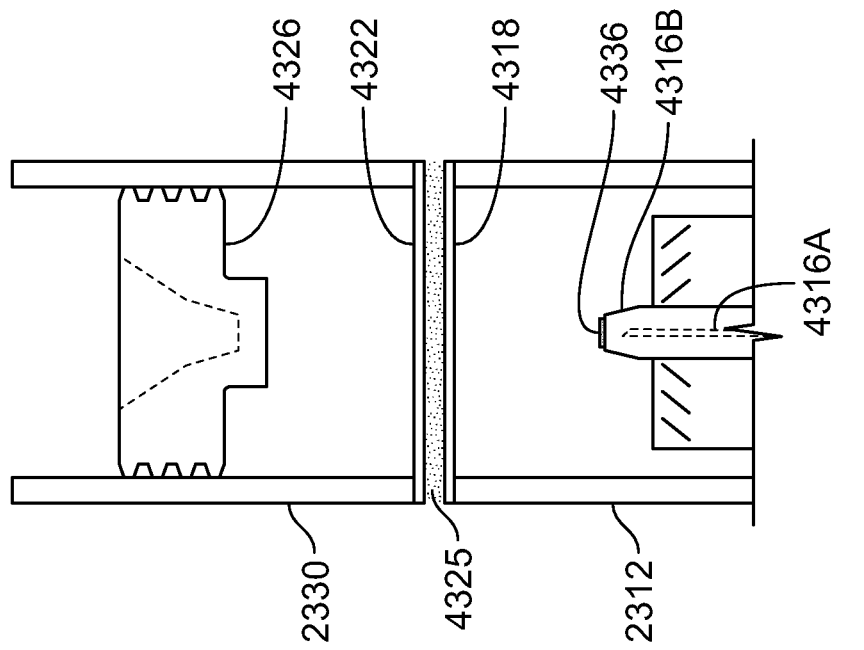
FIG. 39B
FIG. 39A

Section A-A
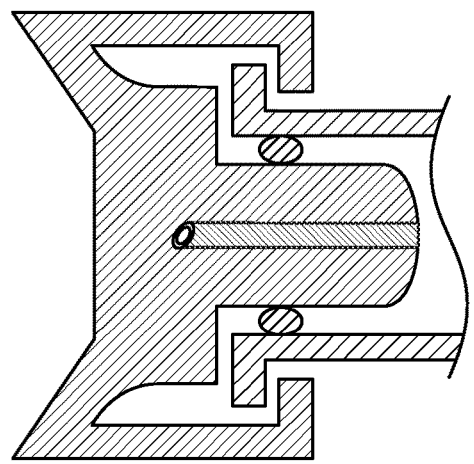
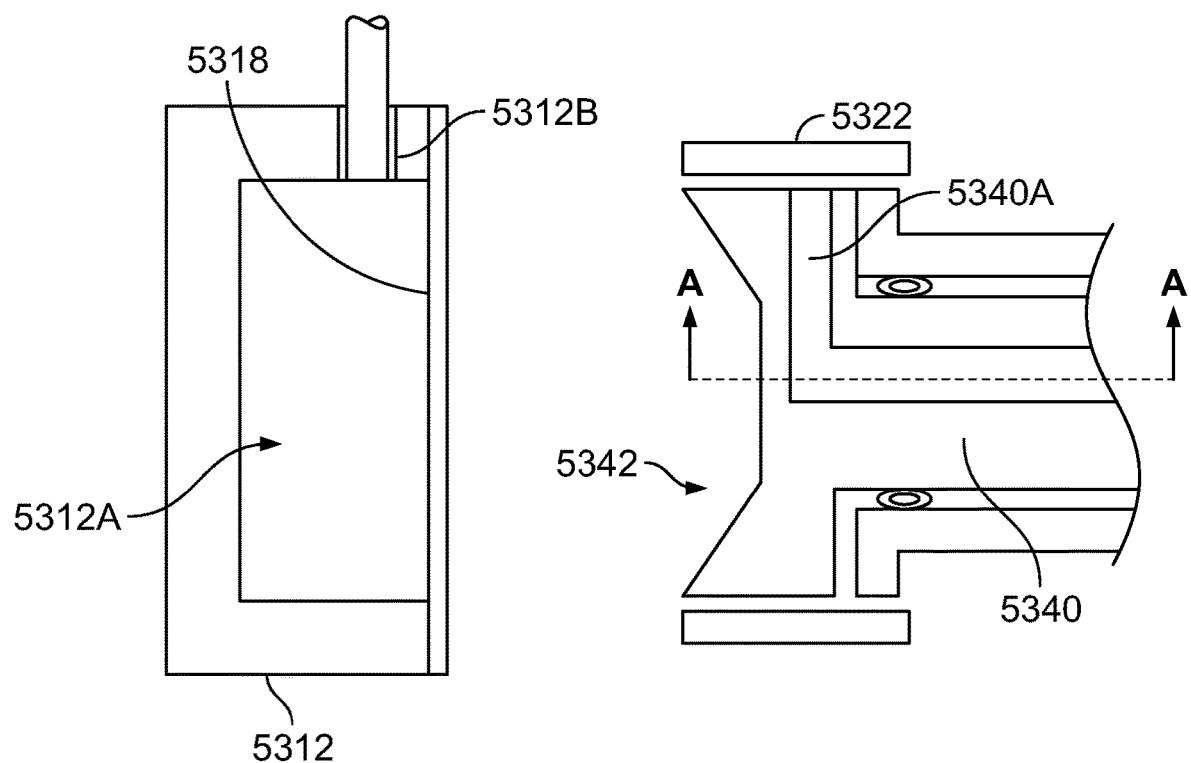
FIG. 42

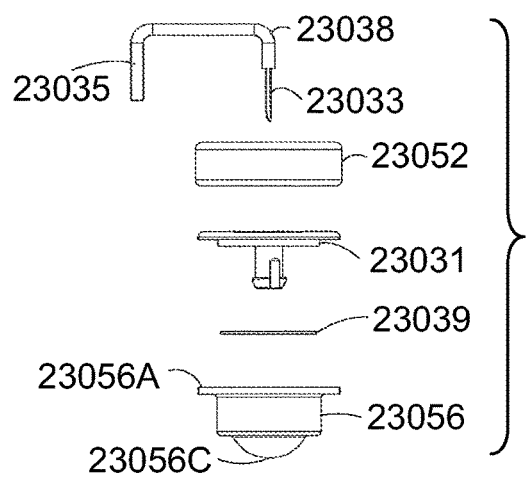
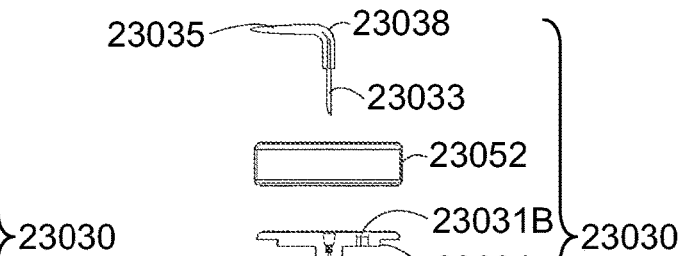
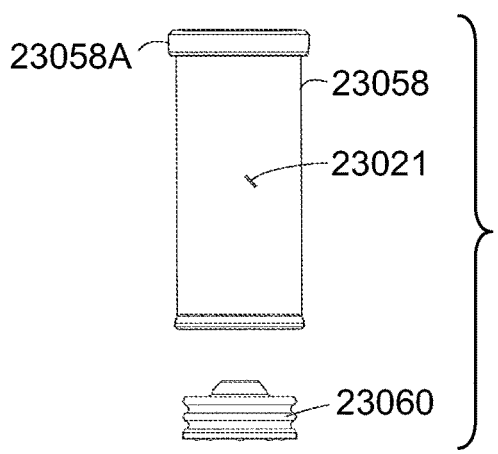
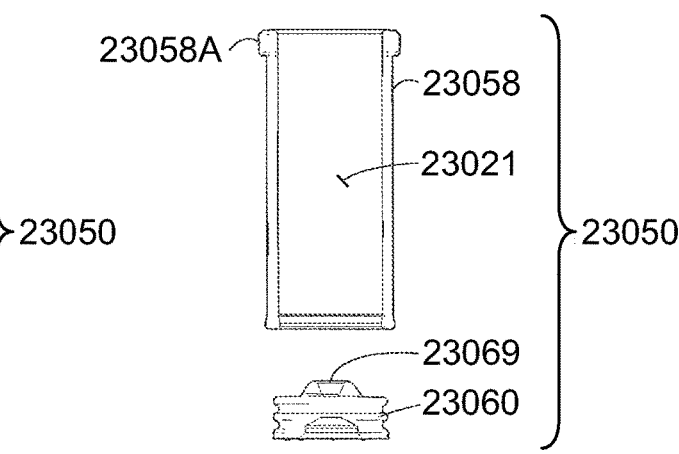
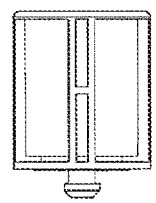
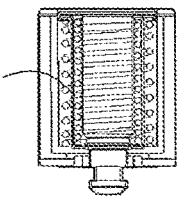
FIG. 54A    FIG. 54B

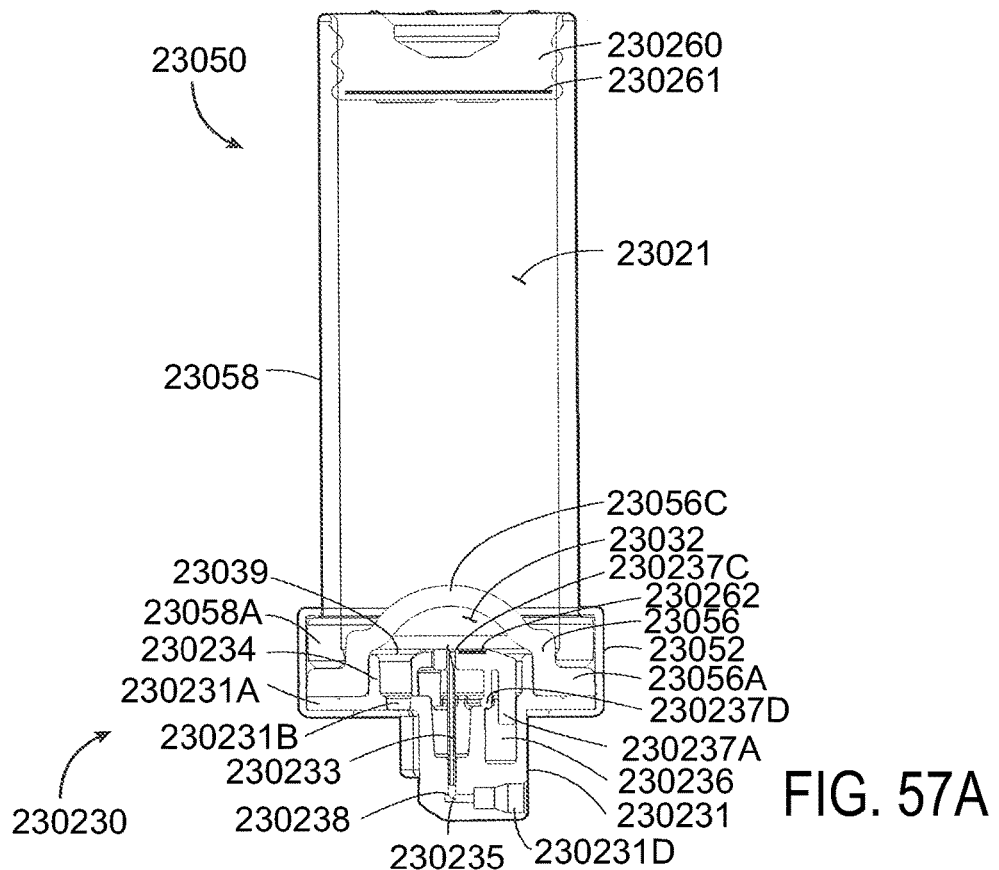
FIG. 57A
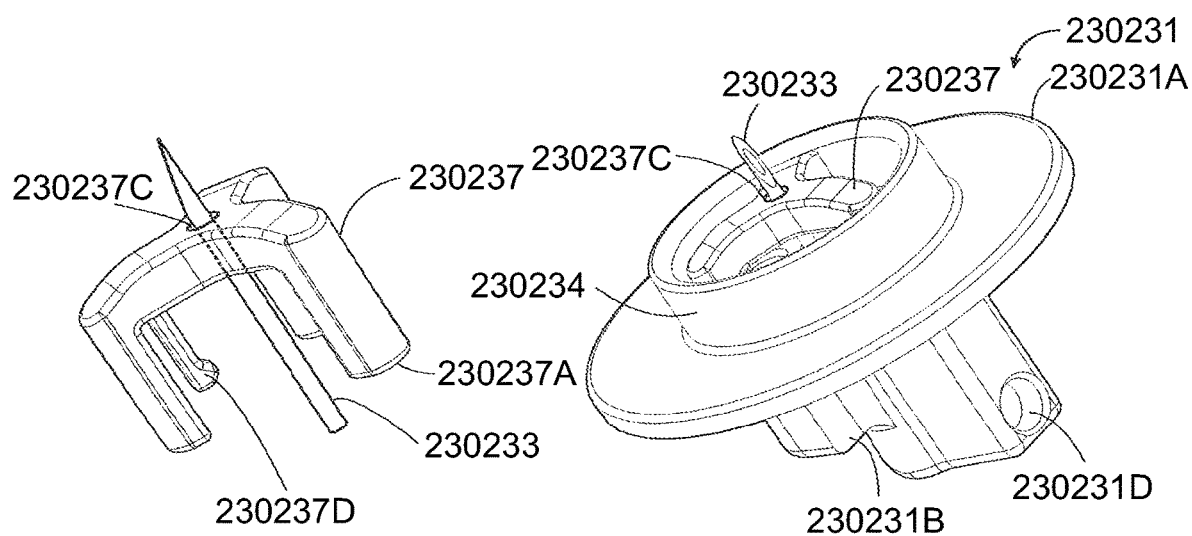
FIG. 57B
FIG. 57C

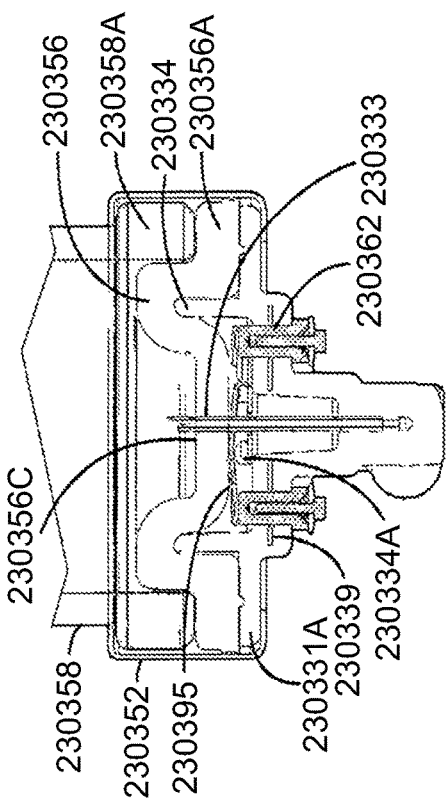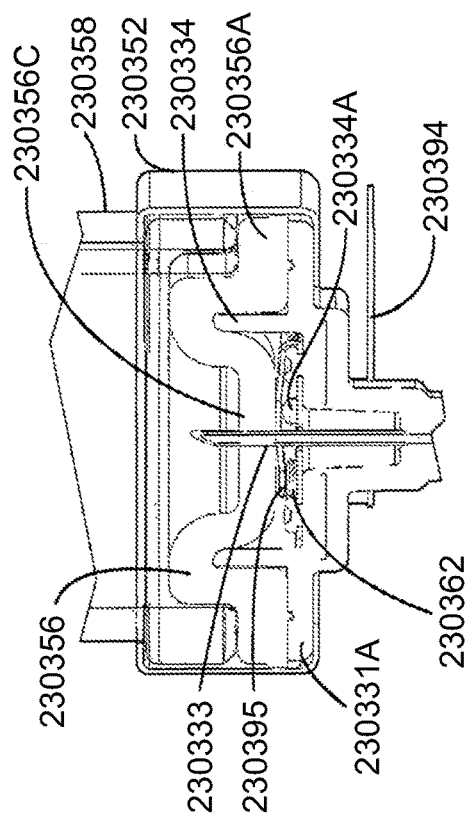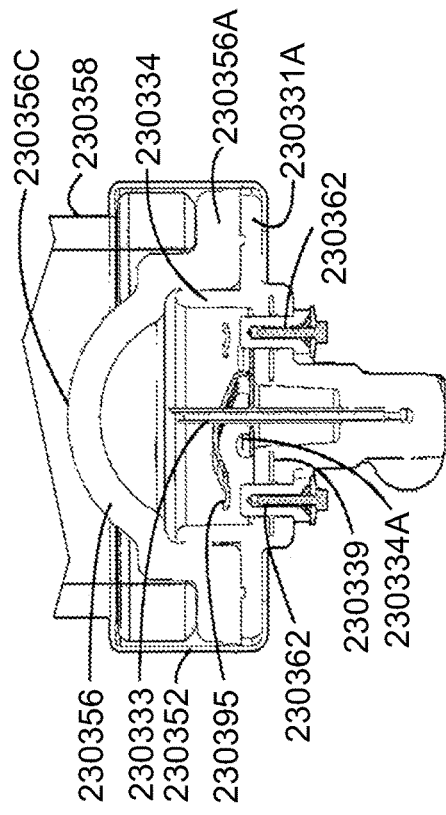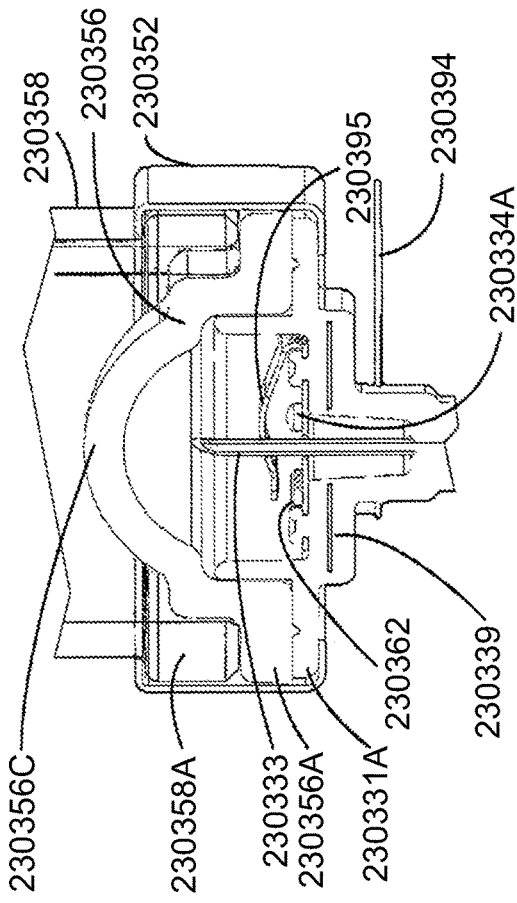

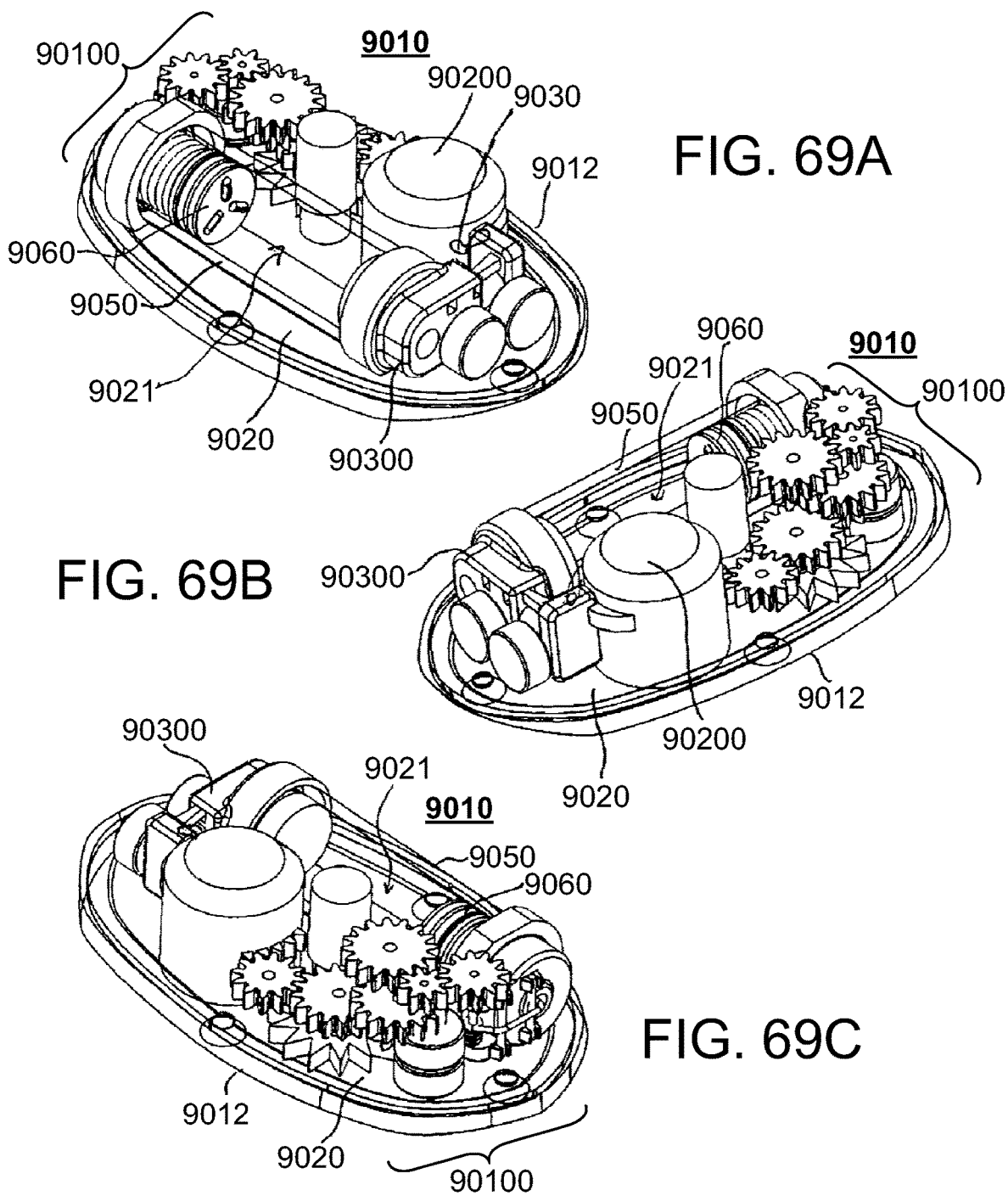

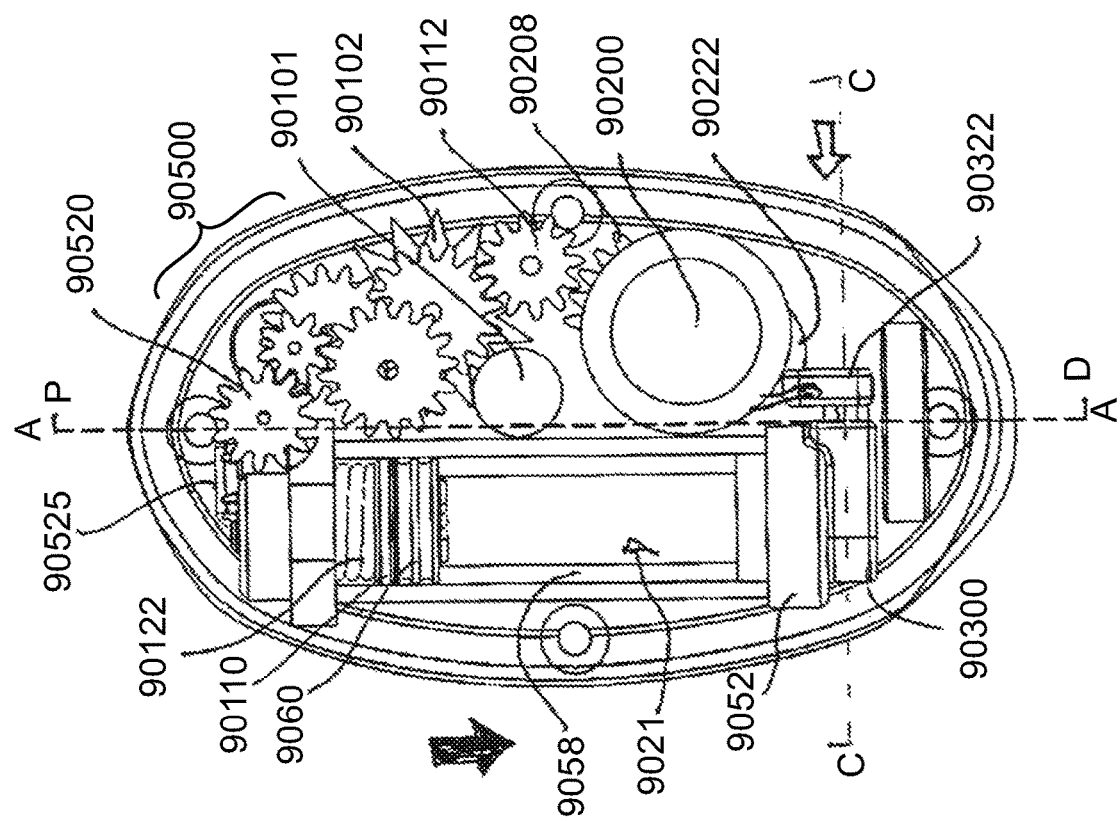
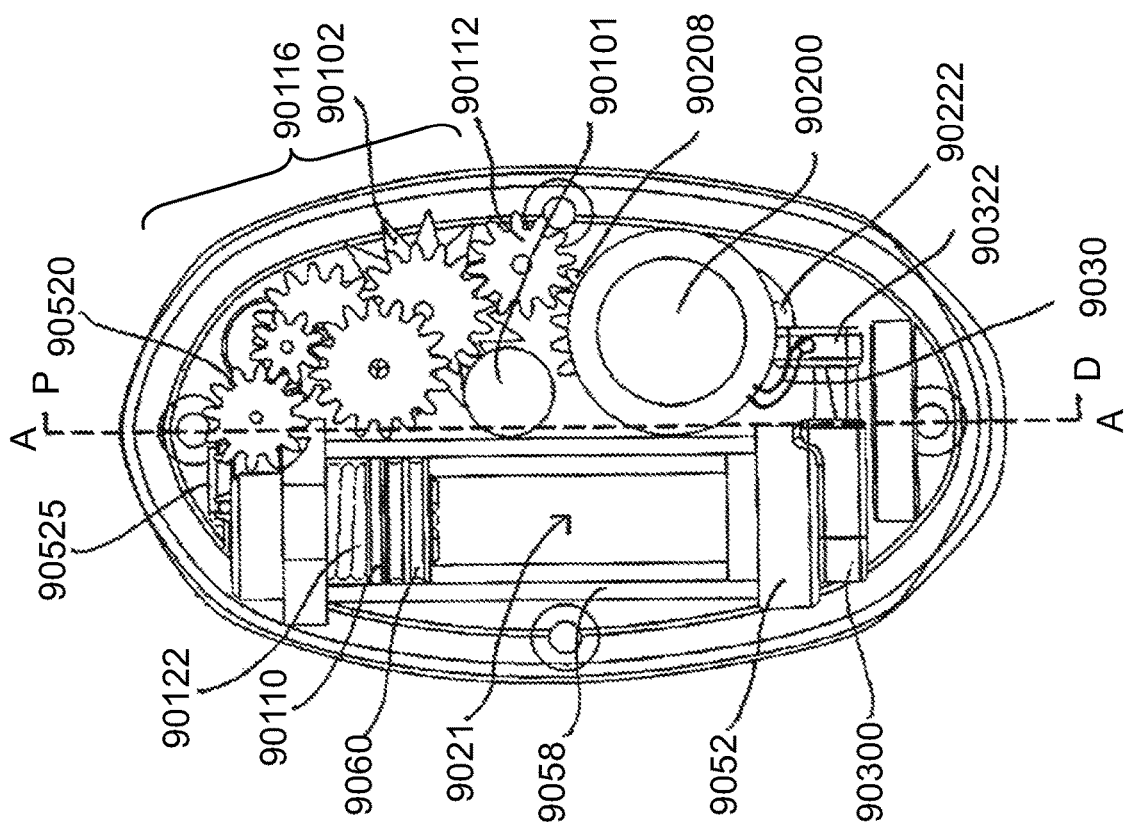

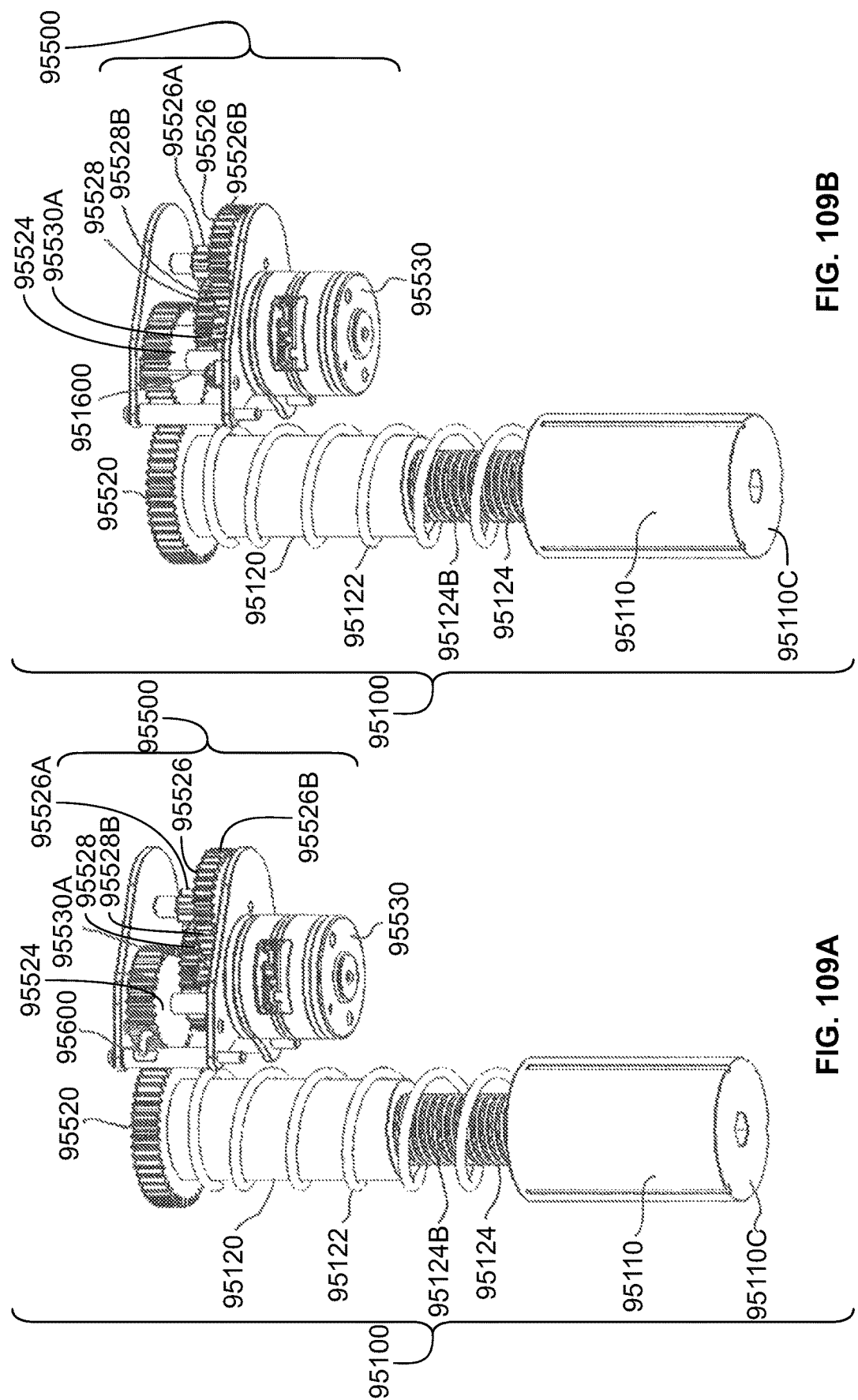

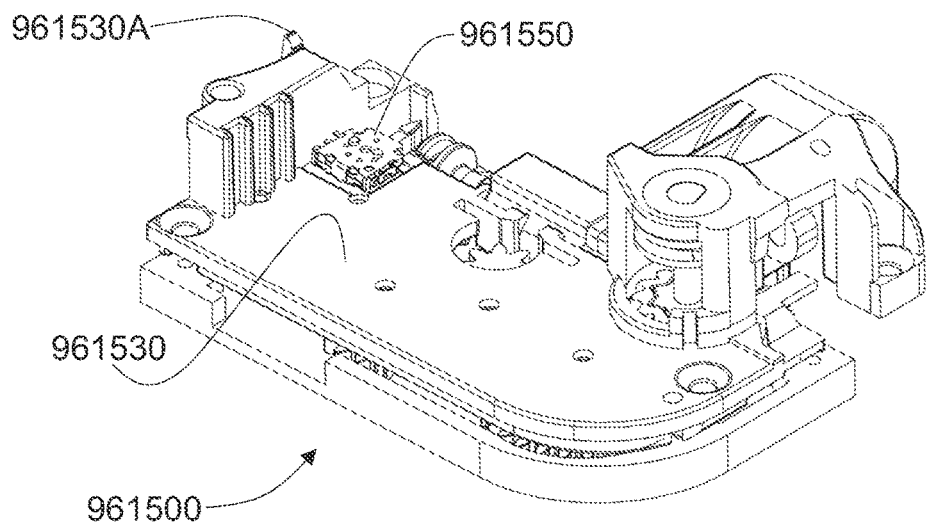
FIG. 123
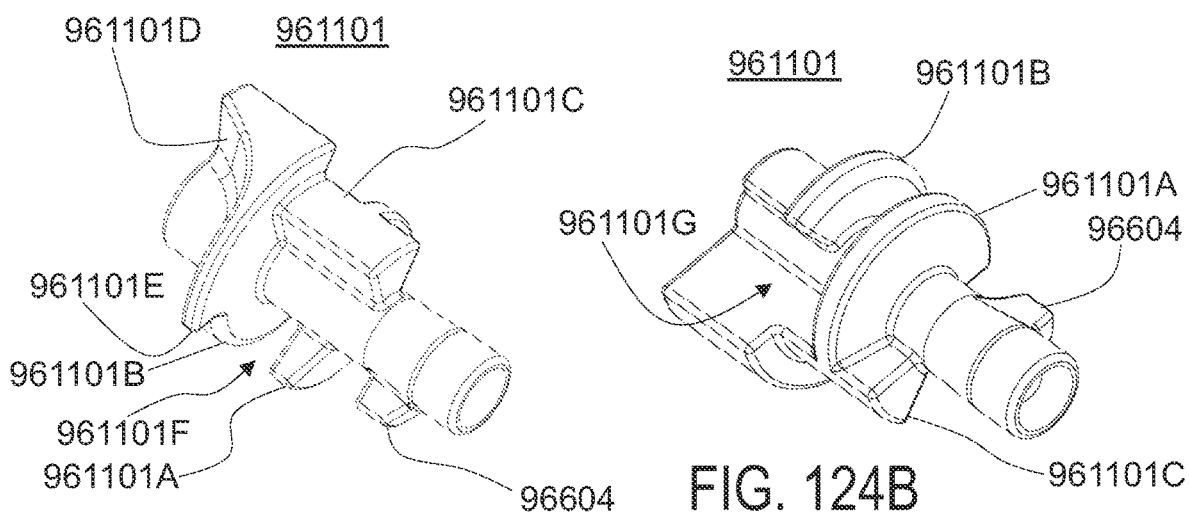
FIG. 124A
FIG. 124B
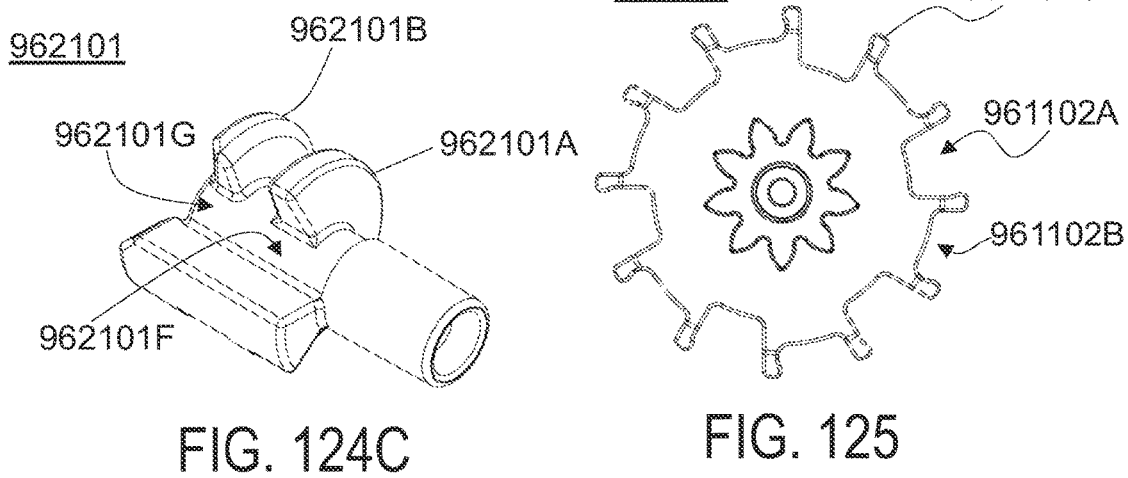
FIG. 124C
FIG. 125

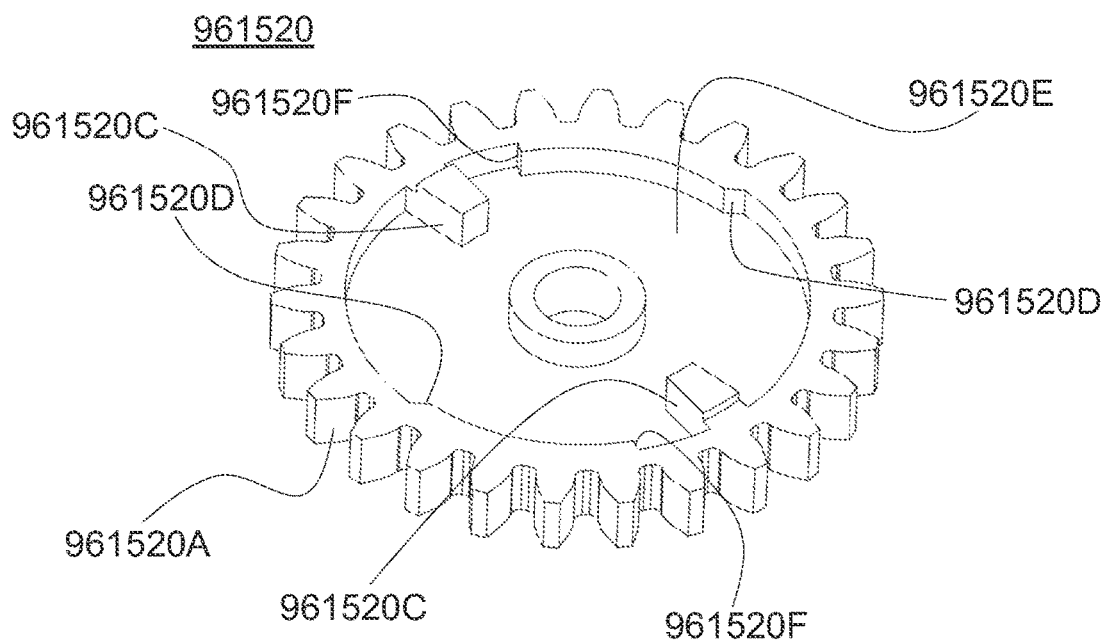
FIG. 131
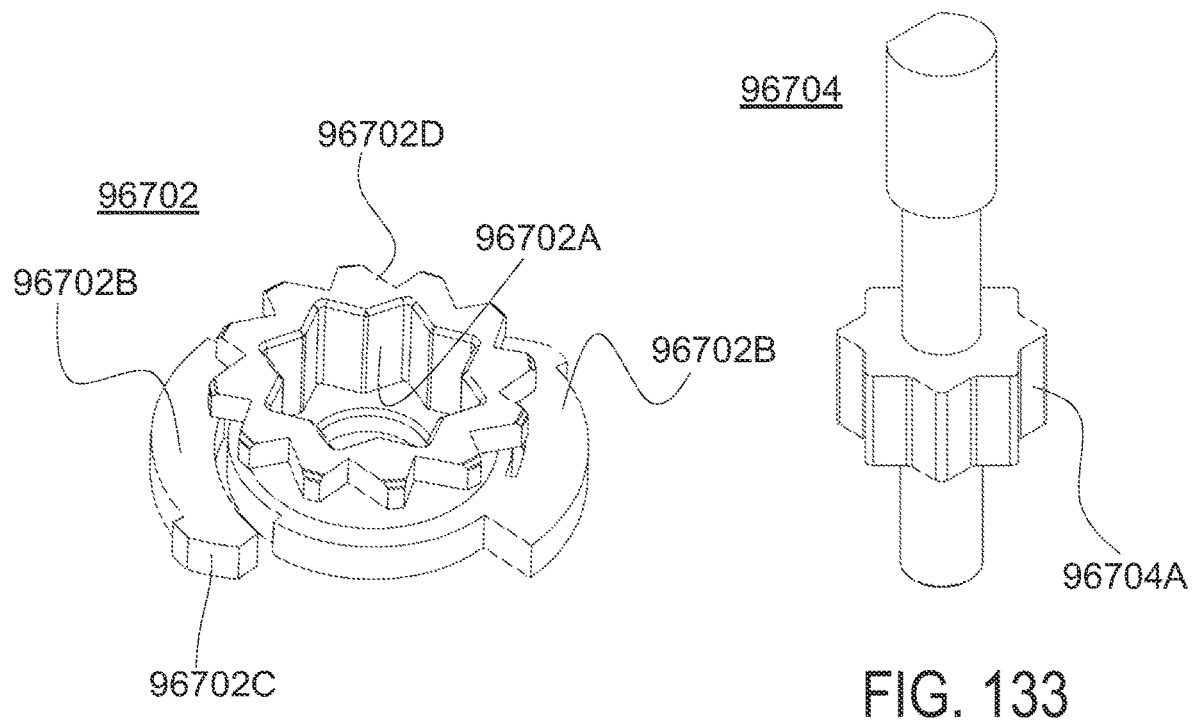
FIG. 132
FIG. 133

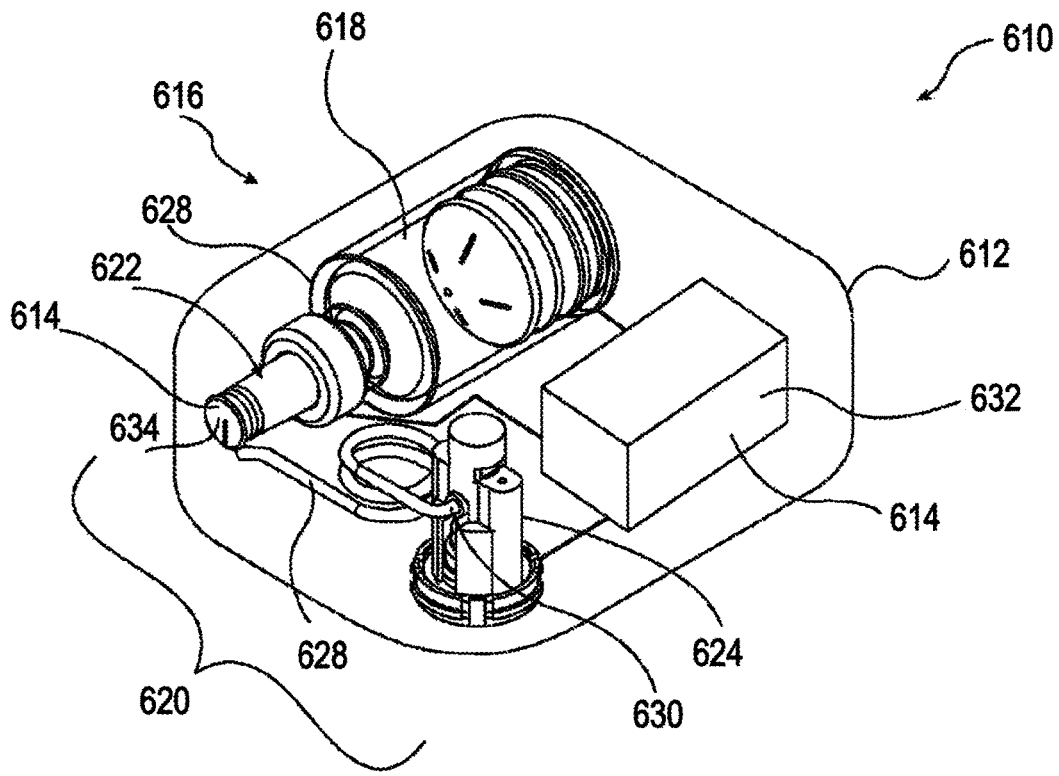

FIG. 165

| Fluid Pathway Connection with Drug Container | Fluid Pathway Connection Attachment to Needle Insertion Mechanism | Fill-Finish Cartridge Alignment | Carrier |
|---|---|---|---|
| Mounted | Snap | Axial fill and use | None |
| Integrated | Threaded | Axial fill and non-axial use | Integrated |
| Other | Interference | Non-axial fill and axial use | Fully Disposable |
|  | Tongue and groove | Non-axial fill and use | Partially Disposable |
|  | External support |  |  |
|  | Other |  |  |

FIG. 166B

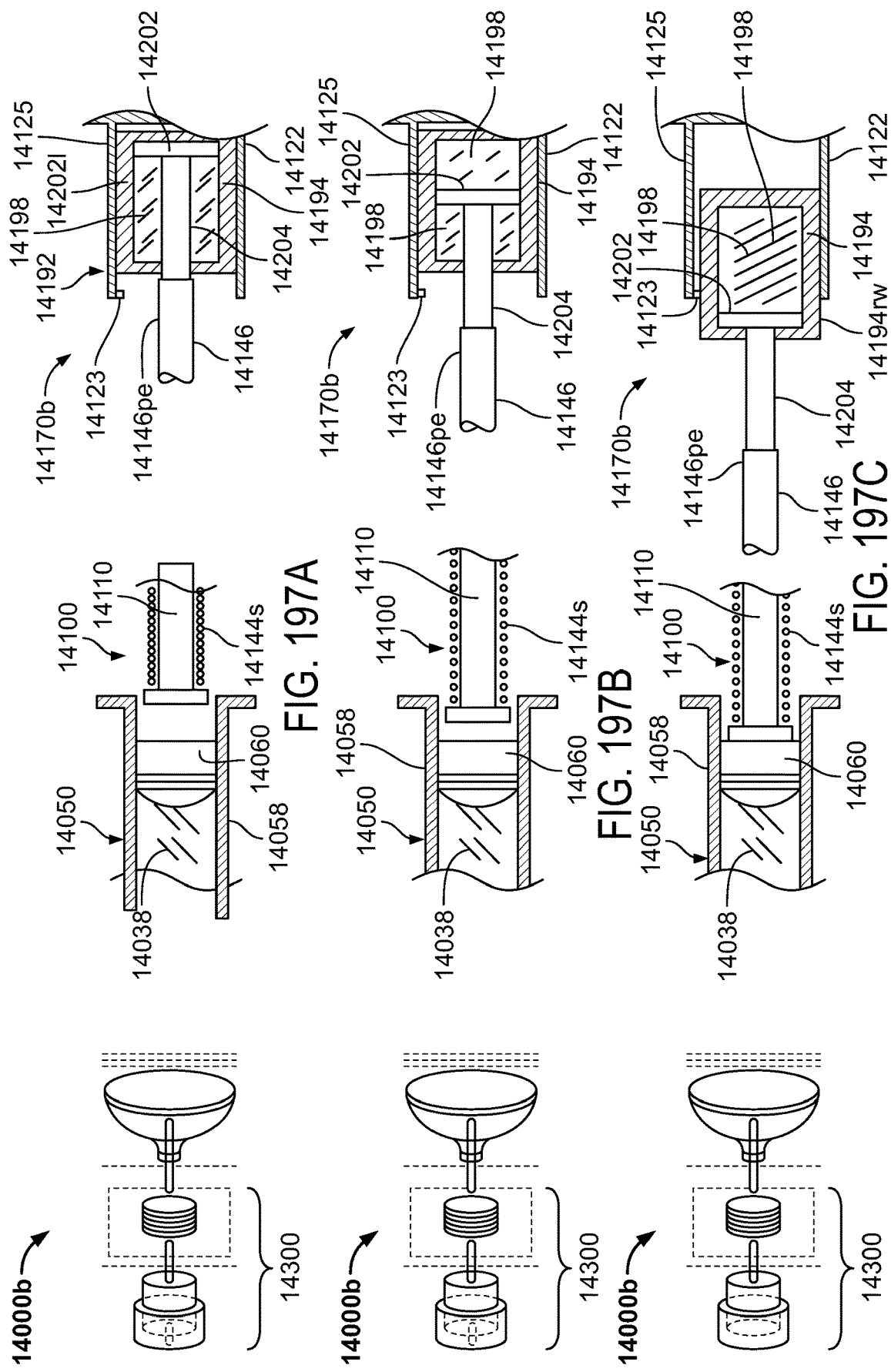

DRUG DELIVERY DEVICE, METHOD OF MANUFACTURE, AND METHOD OF USE

CROSS-REFERENCE TO RELATED APPLICATIONS

This application is a continuation of U.S. application Ser. No. 16/089,685, filed Sep. 28, 2018, which is the United States national phase of International Patent Application No. PCT/US2017/026524, having an international filing date of Apr. 7, 2017, which claims the priority benefit of each of U.S. Provisional Patent Application No. 62/320,438, filed Apr. 8, 2016, and International Patent Application No. PCT/US2017/017627, filed Feb. 13, 2017. The entire contents of each of the foregoing are expressly incorporated by reference herein for all purposes.

FIELD OF THE DISCLOSURE

The present disclosure generally relates to drug delivery devices and, more particularly, a drug delivery device capable of being worn by a patient while the drug delivery device delivers a drug to the patient.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

There is a strong market demand for drug delivery devices which are easy-to-use, cost-efficient, and which include integrated safety features. However, manufacturing of such devices can be cost intensive, which results in higher costs to patients. Much of the manufacturing costs can be attributed to the need to maintain a sterile fluid pathway from the drug container to the needle, prior to introduction of the drug to the patient. Some commercial products seek to maintain the sterility of the device by manufacturing the components in a non-sterile environment and then sterilizing the entire device. A recognized downside of such processes is the need to separately fill the drug container after device sterilization but prior to drug injection, as most pharmaceutical compounds are not capable of withstanding the device sterilization process. Alternatively, the drug delivery device may be manufactured as a pre-filled device, wherein the device is filled with the drug aseptically during assembly. Such manufacturing processes may be costly since the entire process must be kept sterile and because the fill and assembly lines need to be specially-tailored for the device. Accordingly, this adds substantial operating costs to pharmaceutical companies and contract drug-fillers.

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, conventional drug delivery devices are packaged and sterilized. Such delivery devices have been classified into several general types. The first type is assembled and placed in sterile packaging which can be shipped with a vial or ampoule of a drug or other injectable solution. The delivery device is filled with the drug or other solution at the point of use and injected into the patient. These devices have the disadvantage of increasing the time and difficulty of filling the device at the point of use, increasing the risk of contamination of the delivery device and/or drug solution, and increasing the likelihood of accidental spills of the drug. There is a further risk of glass particles from the ampoules contaminating the drug solution when the ampoules are opened. Furthermore, the healthcare provider and/or patient may be require training to ensure that they fill the device properly Several of these disadvantages are overcome by providing prefilled delivery devices which can be filled with a suitable drug solution prior to use. Prefilled delivery devices, as the term is known in the art, are devices that are filled by the drug manufacturer and shipped to the health care provider or self-administering patient in a condition that is ready for use. The vial or ampoule is generally made of glass or other clear material that does not interfere with the stability of the drug during prolonged storage. Prefilled delivery devices have the advantage of convenience and ease of application with reduced risk of contamination of the drug solution. Prefilled drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases. Various operations are able to form clean and sterile drug delivery devices. However, subsequent handling, filling and printing of the drug delivery device can contaminate the device. It is then necessary to clean and sterilize such conventional drug delivery devices before use. Accordingly, there is a continuing need in the industry for an improved system for manufacturing and assembling clean and sterile medical devices and filling such devices.

SUMMARY

One aspect of the present disclosure provides a wearable drug delivery device including a main housing, a container, a drug, a window, a trocar or introducer needle, a cannula, a drive mechanism, an insertion mechanism, a fluid pathway connector, a button, and a trigger assembly. The container may be disposed in the main housing. The container may include a barrel, a plunger seal moveable through the barrel, and a first pierceable seal controlling access to an interior of the barrel. The drug may be disposed in the barrel. The drug may include at least one of a: Proprotein Convertase Subtilisin/Kexin Type 9 (PCSK9) specific antibody, a granulocyte colony-stimulating factor (G-CSF), a sclerostin antibody, or a calcitonin gene-related peptide (CGRP) antibody. The trocar or introducer needle may have a proximal end and a distal end. The cannula may initially be disposed around the distal end of the trocar or introducer needle. The drive mechanism may be disposed in the main housing. The drive mechanism may include a drive housing, a piston moveable relative to the drive housing and configured to impart movement to the plunger seal, a gear assembly, an electrical actuator, a gear interface, a piston biasing member, and a tether. The gear interface may be rotatable by the electrical actuator. Rotation of the gear interface may cause the gear interface to selectively engage the gear assembly to prevent or allow rotation of the gear assembly. The piston biasing member may be disposed between the drive housing and the piston. The piston biasing member maybe initially retained in a piston biasing member energized state. The piston biasing member may be configured to move the piston as the piston biasing member de-energizes. The tether may be connected at opposite ends to the gear assembly and the piston. The tether may initially retain the piston biasing member in the piston biasing member energized state. Rotation of the gear assembly may create slack in the tether which allows the piston biasing member to de-energize. The fluid pathway connector may define a sterile fluid flowpath between the container and the insertion mechanism. The fluid pathway connector may include a tubular conduit, a container access needle, and a connection hub. The tubular conduit may have a first end and a second end. The second end of the tubular conduit may be in fluid communication with a hollow interior of the cannula during drug delivery. The container access needle may be configured to pierce the first pierceable seal to establish fluid communication between the between the barrel and the tubular conduit during drug delivery. The connection hub may be connected to the container access needle and the first end of the tubular conduit. The connection hub may provide fluid communication between the container access needle and the tubular conduit during drug delivery. The insertion mechanism may be disposed in the main housing. The insertion mechanism may include a base, an insertion mechanism housing rotatable relative to the base, a rotational biasing member connected to the insertion mechanism housing, a first retainer, a hub, a retraction biasing member, and a second retainer. The rotational biasing member may be initially retained in a rotational biasing member energized state. The rotational biasing member may be configured to rotate the insertion mechanism housing as the rotational biasing member de-energizes. The first retainer may be moveable between: (i) a first retainer retaining position, where the first retainer retains the rotational biasing member in the rotational biasing member energized state, and (ii) a first retainer releasing position, where the first retainer allows the rotational biasing member to de-energize. The hub may be connected to the proximal end of the trocar or introducer needle, and the hub may be configured to translate relative to the insertion mechanism housing. The retraction biasing member may be disposed between the hub and the base. The retraction biasing member may have a retraction biasing member energized state. The retraction biasing member may be configured to translate the hub in a proximal direction as the retraction biasing member de-energizes. The second retainer may be moveable between: (i) a second retainer retaining position, where the second retainer retains the retraction biasing member in the retraction biasing member energized state, and (ii) a second retainer releasing position, where the second retainer allows the retraction biasing member to de-energize. The button may protrude from the main housing and manually displaceable by a user. The trigger assembly may be configured to move the first retainer from the first retainer retaining position to the first retainer releasing position in response to displacement of the button by the user.

Another aspect of the present disclosure provides a wearable drug delivery device including a container, a drug disposed in the container, a trocar or introducer needle, an activation member manually operable by a patient, an insertion mechanism, a fluid pathway connector, a locking assembly, and a selector. The drug may include at least one of a: Proprotein Convertase Subtilisin/Kexin Type 9 (PCSK9) specific antibody, a granulocyte colony-stimulating factor (G-CSF), a sclerostin antibody, or a calcitonin gene-related peptide (CGRP) antibody. The insertion mechanism may be configured to move the trocar or introducer needle between a retracted position and an inserted position, the insertion mechanism including a rotatable housing and a rotational biasing member initially held in an energized state. The fluid pathway connector may define a sterile fluid flowpath between the container and the insertion mechanism. The locking assembly may have: (i) a lock configuration, where the locking assembly engages the rotatable housing to inhibit rotation of the rotatable housing, and (ii) an unlock configuration, where the locking assembly disengages the rotatable housing to permit rotation of the rotatable housing. The selector may have: (i) a first configuration, where the selector operatively decouples the activation member and the locking assembly, and (ii) a second configuration, where the selector operatively couples the activation member and the locking assembly to allow the activation member to change the locking assembly from the lock configuration to the unlock configuration.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. Also, none of the drawings is necessarily to scale.

FIG. 4A shows an exploded view of a fluid pathway connection assembly according to at least one embodiment of the present invention;

FIG. 4B shows a cross-sectional view of the exploded fluid pathway connection assembly of FIG. 4A;

FIG. 20 shows an isometric view of a connection hub according to at least one embodiment of the present invention;

FIG. 21 shows an isometric view of an embodiment of an introducer member retainer according to at least one embodiment of the present invention;

FIG. 22 shows an isometric view of an embodiment of a piercing member retainer according to at least one embodiment of the present invention;

FIG. 38A is a cross-sectional side view of an embodiment of a fluid path connection mechanism and a drug container in an unmounted configuration;

FIG. 38B is a cross-sectional side view of the embodiment shown in FIG. 38A in a mounted configuration;

FIG. 38C is a cross-sectional side view of the embodiment shown in FIG. 38A after piercing of the first and second films by the outer piercing member;

FIG. 38D is a cross-sectional side view of the embodiment shown in FIG. 38A after connection of the fluid path;

FIG. 39A is a cross-sectional side view of an embodiment of a fluid path connection mechanism and a drug container in a mounted configuration;

FIG. 39B is a cross-sectional side view of the embodiment of FIG. 39A after connection of the fluid path;

FIG. 42 shows a fluid path connection according to at least one embodiment of the present disclosure;

FIG. 54A is an exploded, side view of the components of an embodiment of an integrated sterile fluid pathway connection and drug container, exploded along a longitudinal axis;

FIG. 54B is a sectional exploded view of the embodiment of FIG. 54A;

FIG. 57A is a sectional view of an embodiment of an integrated sterile fluid pathway connection, having a piercing member guide and drug container, prior to user activation;

FIG. 57B shows an isometric perspective view of the piercing member guide and piercing member of the embodiment shown in FIG. 57A; and FIG. 57C is an isometric view of the piercing member guide, piercing member, and connector hub of the embodiment of FIG. 57A;

FIG. 62A to FIG. 62D are sectional and isomeric sectional views of another embodiment of a sterile fluid connector capable of transmitting a signal indicating the status of fluid transfer from the sterile fluid container to the connector, showing more specific configurations of a sensor in the open and closed positions;

FIG. 63A to FIG. 63D are perspective and sectional views of an embodiment of a sterile fluid connector capable of transmitting a signal indicating the status of fluid transfer from the sterile fluid container to the connector, illustrating the unpressurized (FIG. 63B), pressurized (FIG. 63C), and end-of-delivery (FIG. 63D) positions of components of a sterile fluid connector;

FIG. 64A to FIG. 64C are perspective and sectional views of another embodiment of a sterile fluid connector capable of transmitting a signal indicating the status of fluid transfer from the sterile fluid container to the connector;

FIG. 65A is a sectional view and FIG. 65B is an isometric sectional view of another embodiment of a sterile fluid connector capable of transmitting a signal indicating the status of fluid transfer from the sterile fluid container to the connector;

FIG. 66A and FIG. 66B are sectional isometric views of another embodiment of a sterile fluid connector capable of transmitting a signal indicating the status of fluid transfer from the sterile fluid container to the connector, in which the pierceable seal comprises a conductive material or coating;

FIG. 67 is a sectional isometric view of another an embodiment of a sterile fluid connector capable of transmitting a signal indicating the status of fluid transfer from the sterile fluid container to the connector, in which signal is mediated using an conductive elastomeric film;

FIG. 68 is a sectional isometric view of another embodiment of a sterile fluid connector capable of transmitting a signal indicating the status of fluid transfer from the sterile fluid container to the connector, in which signal is mediated using a dome switch;

FIG. 69A shows an isometric view of the interior components of a drug delivery pump having a multi-function drive mechanism, according to one embodiment of the present invention (shown without the adhesive patch);

FIG. 69B shows an isometric view of the interior components of the drug delivery pump shown in FIG. 69A (shown without the adhesive patch) from another viewpoint;

FIG. 69C shows an isometric view of the interior components of the drug delivery pump shown in FIG. 69A (shown without the adhesive patch) from yet another viewpoint;

FIG. 69D shows a top view, along an axis "A," of the interior components of the drug delivery pump shown in FIG. 69A;

FIG. 70A shows an isometric view of a multi-function drive mechanism, according to at least one embodiment of the present invention prior to activation;

FIG. 70B shows an isometric view of a multi-function drive mechanism, according to at least one embodiment of the present invention during activation;

Figure 70A:
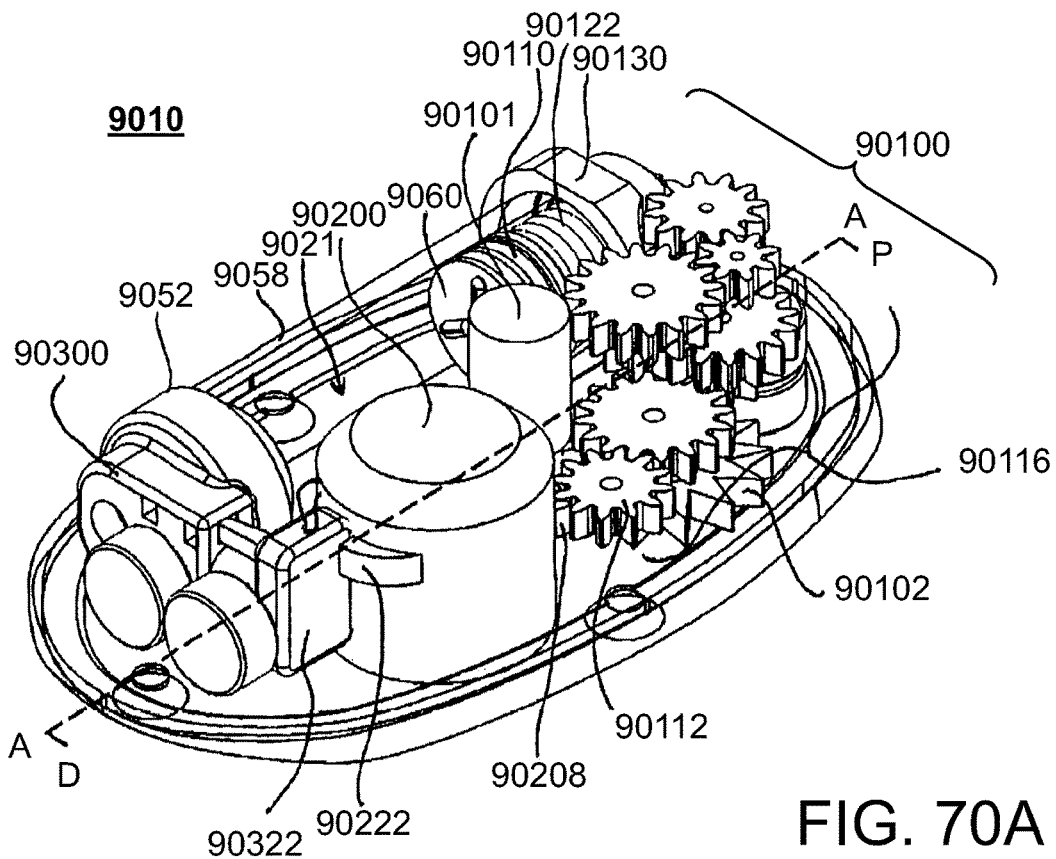
Figure 70B:
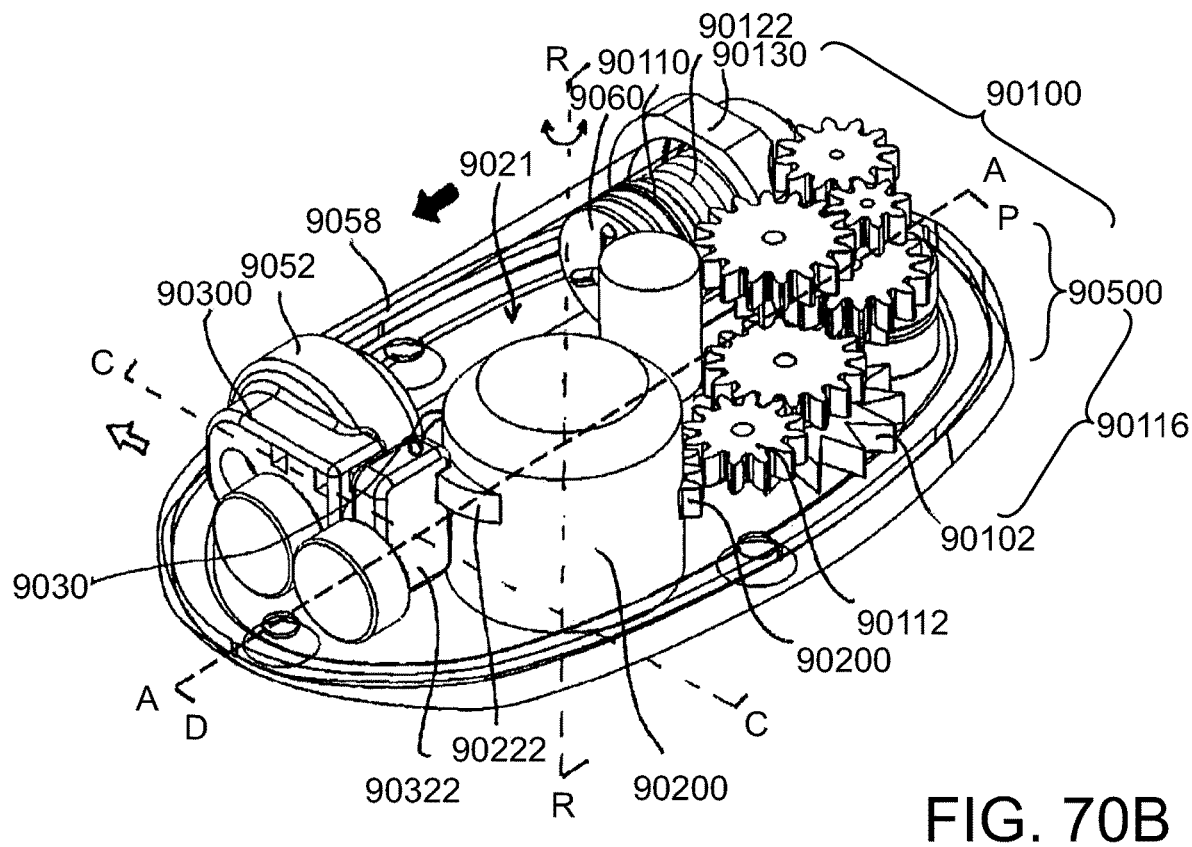
Figure 70C:
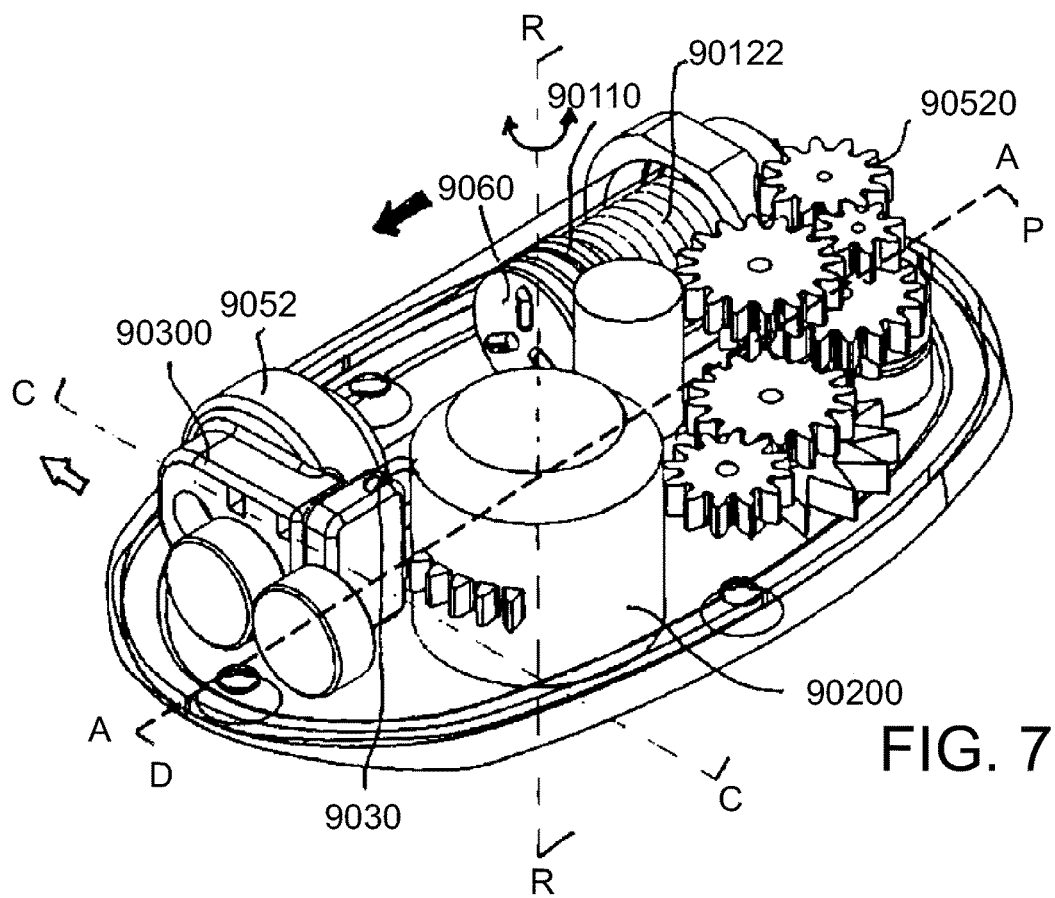
Figure 70D:
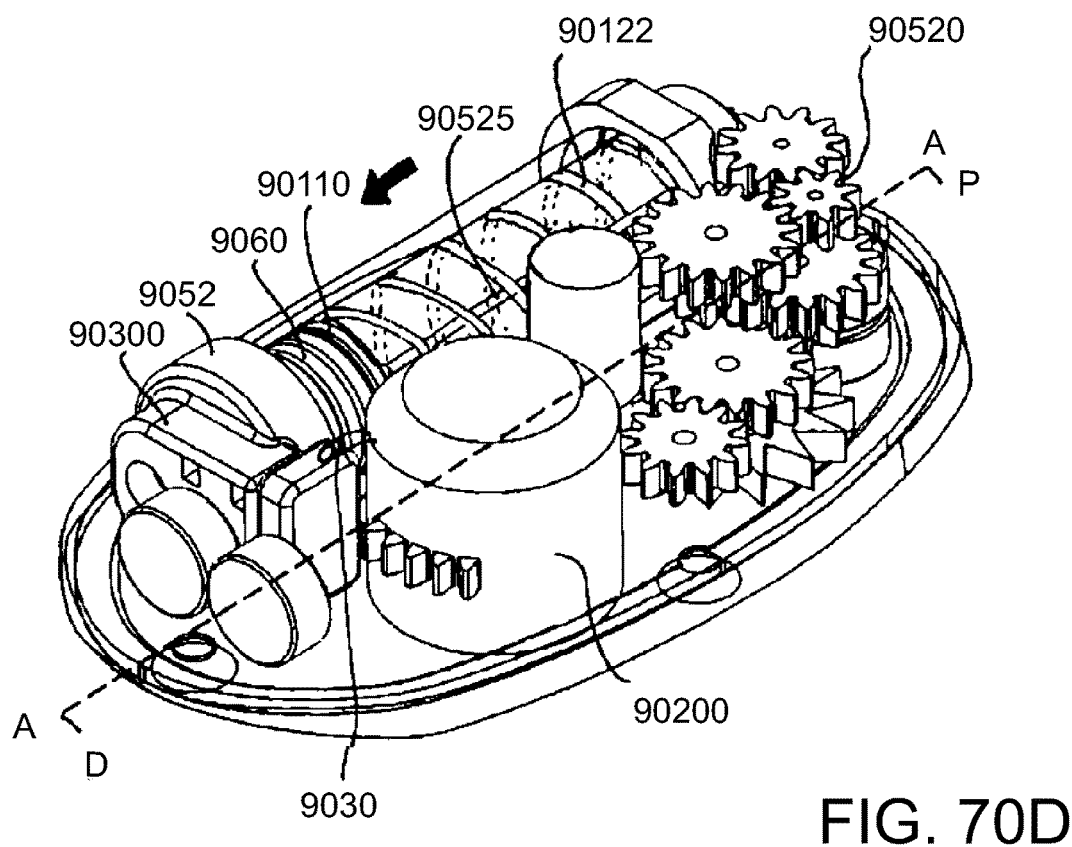
Figure 72:
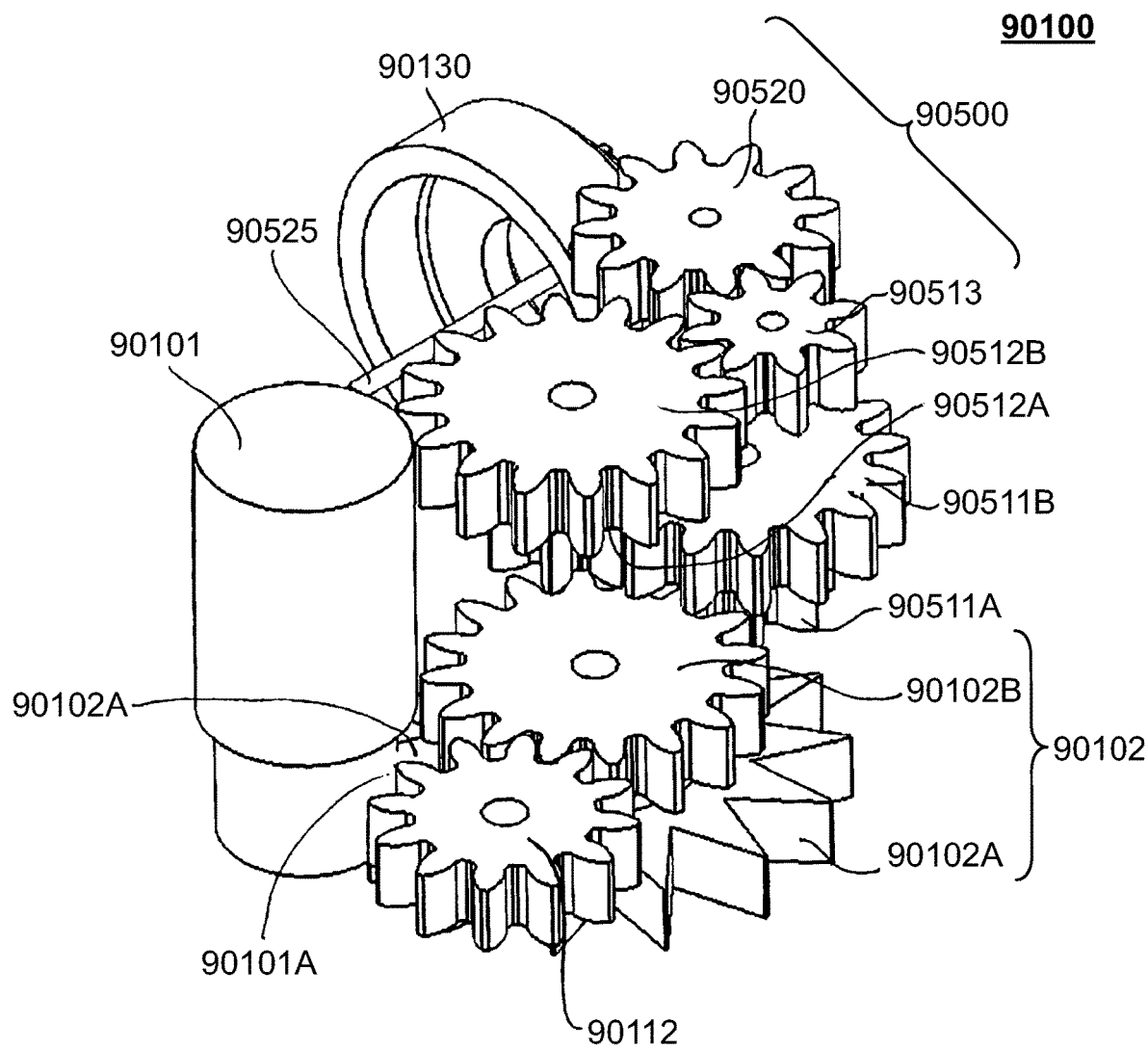
Figure 73A:
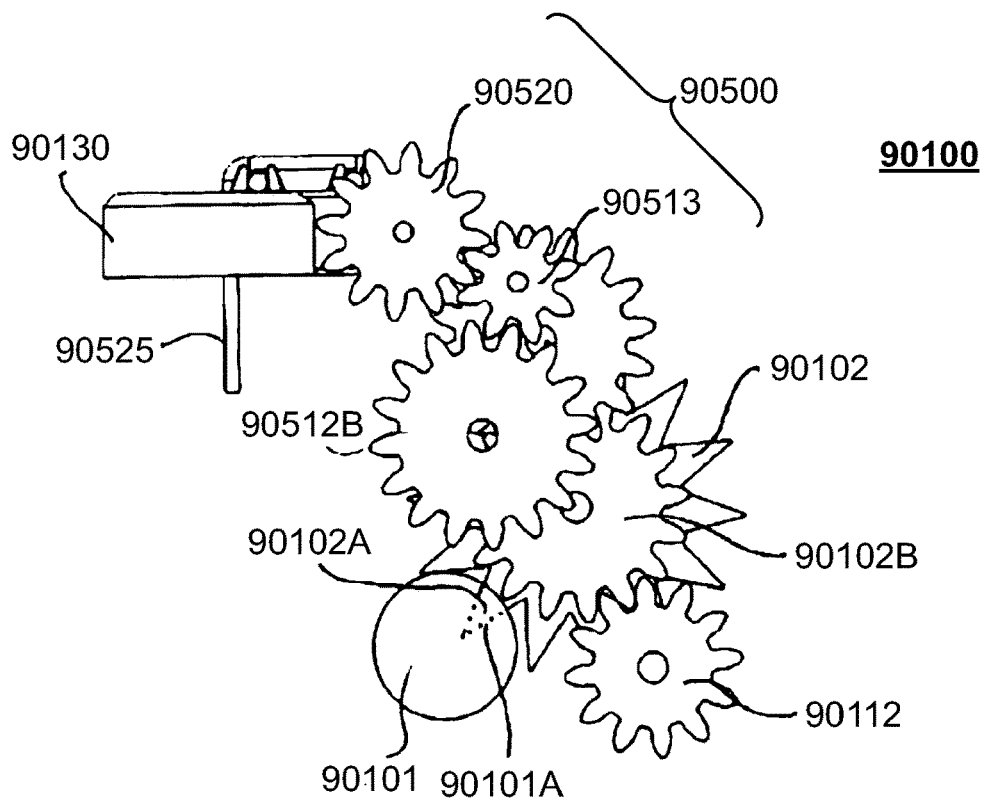
Figure 73B:
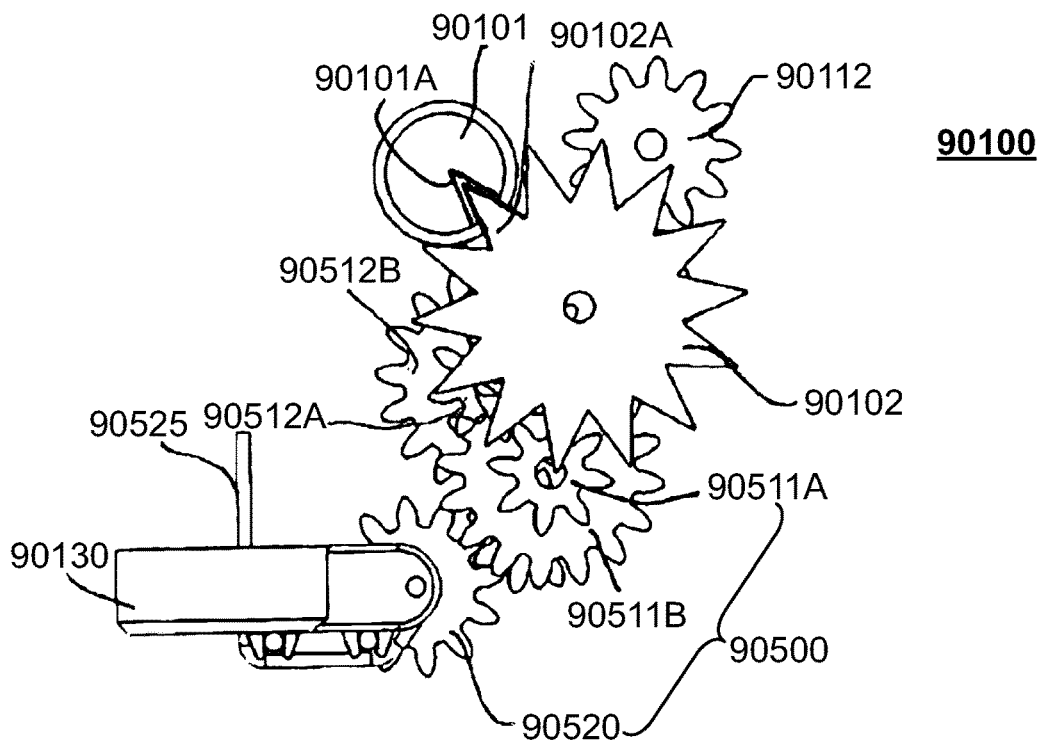
Figure 73C:
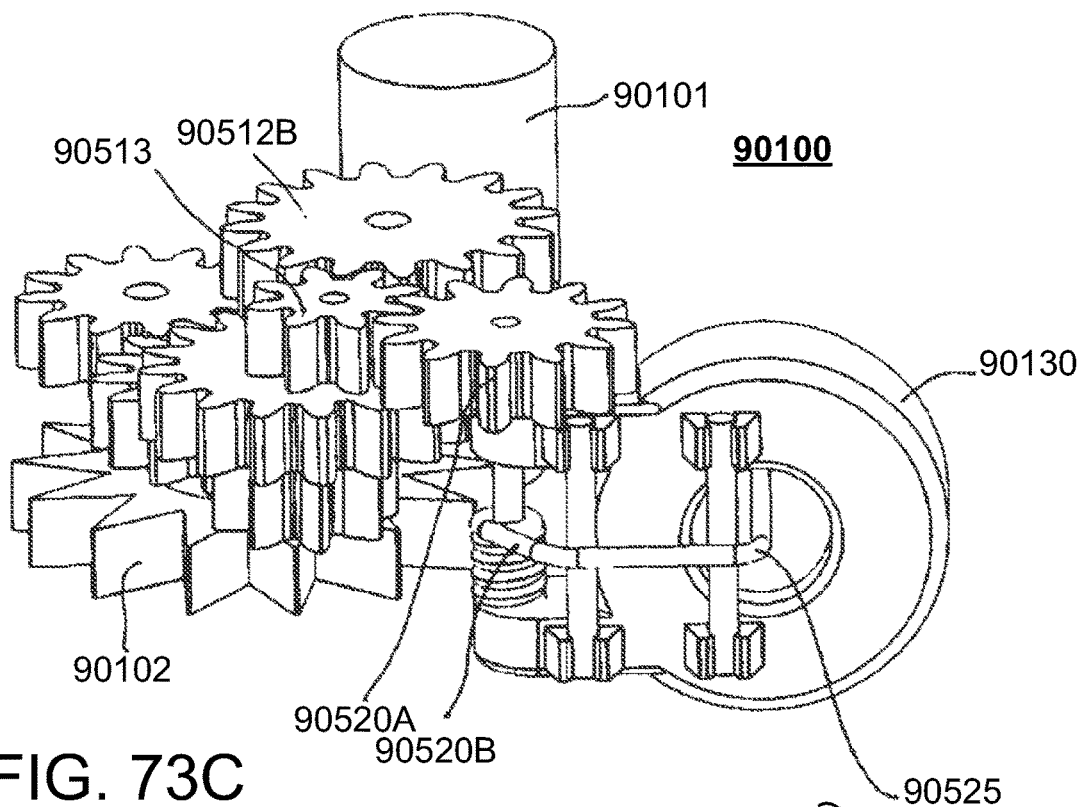
Figure 73D:
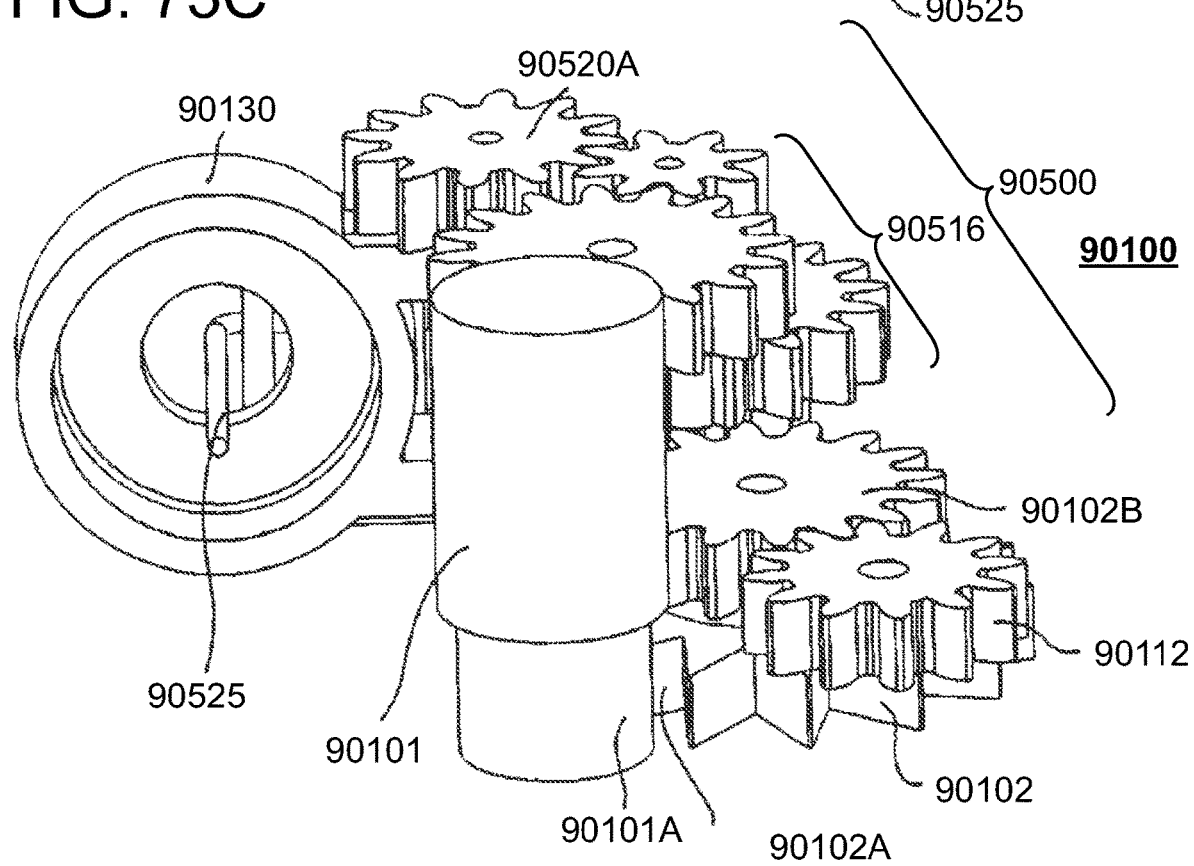
Figure 74A:
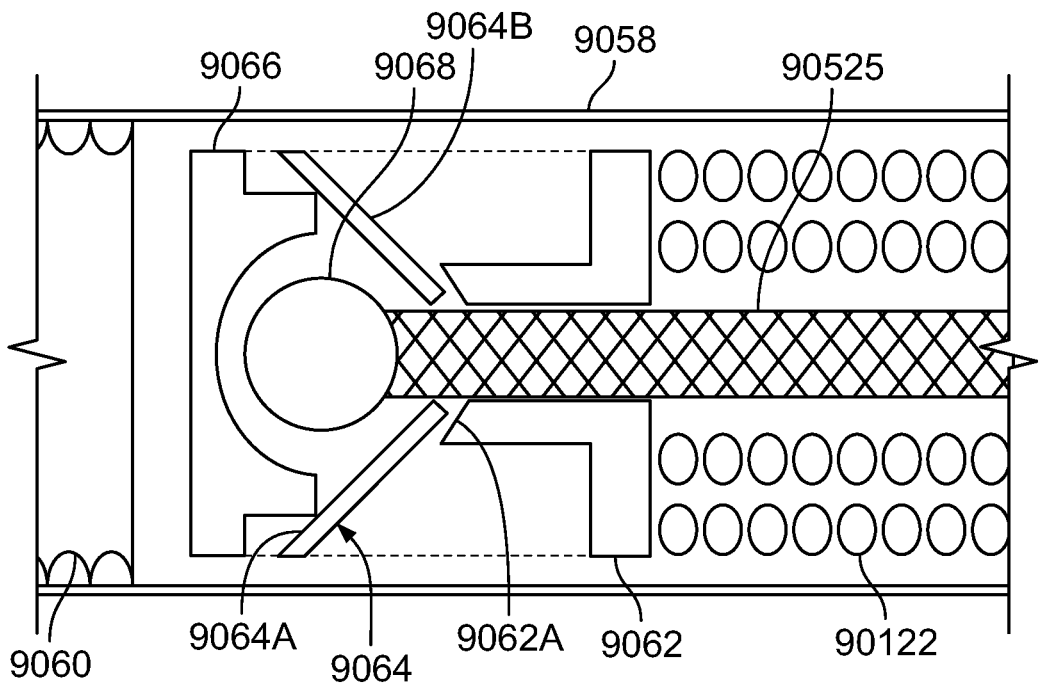
Figure 74B:
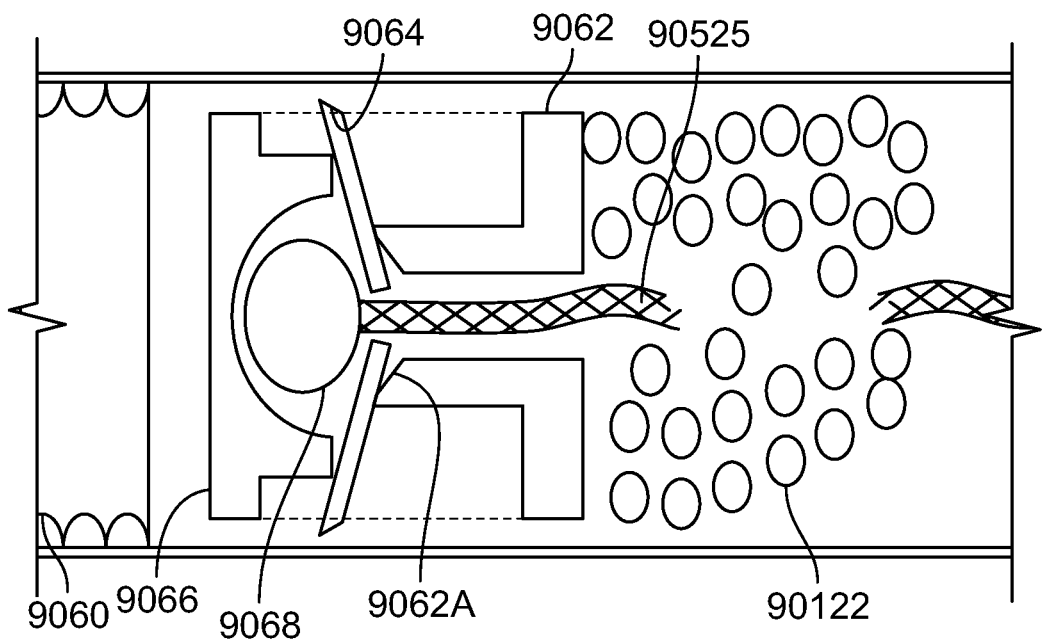
Figure 75A:
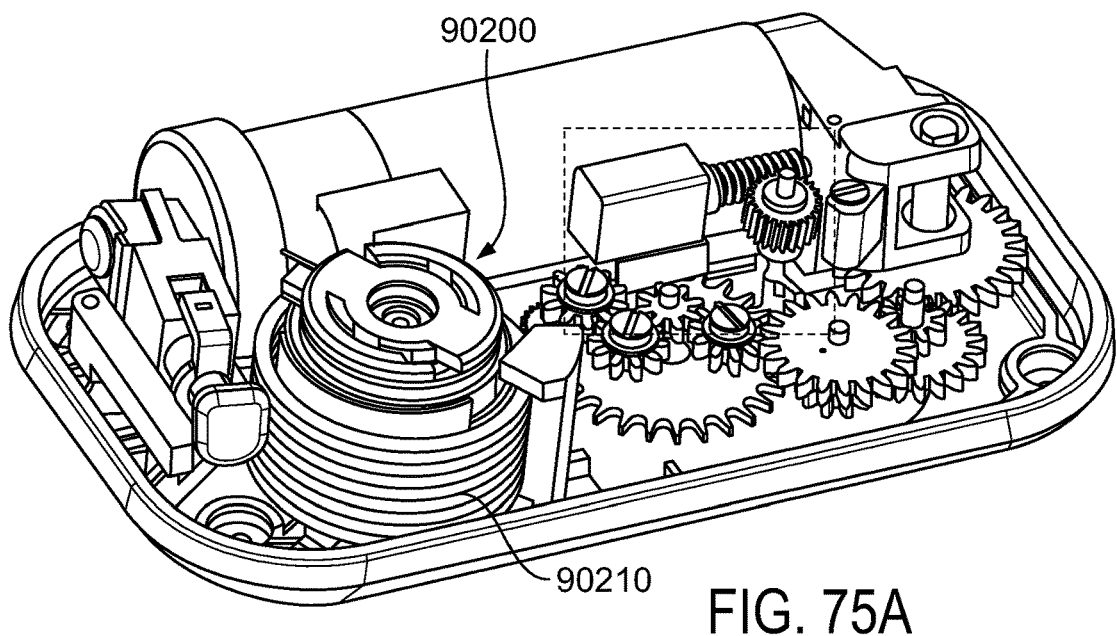
Figure 75B:
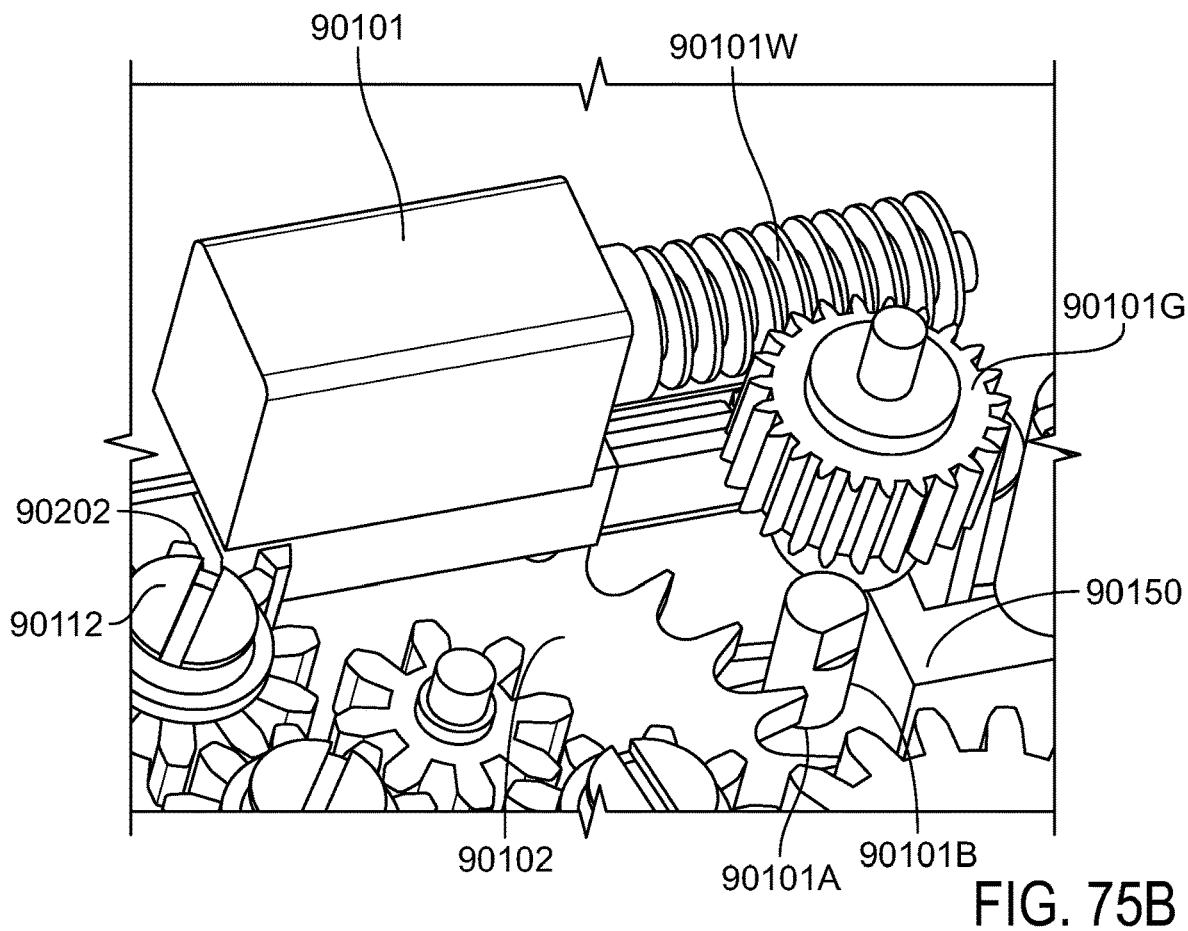

FIG. 70C shows an isometric view of a multi-function drive mechanism, according to at least one embodiment of the present invention at a later stage during activation;

FIG. 70D shows an isometric view of a multi-function drive mechanism, according to at least one embodiment of the present invention near or at completion of drug delivery;

FIGS. 71A-71D show top views which correspond with the stages of operation shown in FIGS. 70A-70D, respectively;

FIG. 72 shows the multi-function drive mechanism, according to at least one embodiment of the present invention, in isolation from the drug delivery device;

FIGS. 73A-73B show top and bottom views, respectively, of the multi-function drive mechanism shown in FIG. 72;

FIGS. 73C-73D show front and back perspective views, respectively, of the multi-function drive mechanism shown in FIG. 72;

FIG. 74A shows a cross-sectional view of a drug container and safety mechanism in an initial, unrestrained configuration;

FIG. 74B shows a cross-sectional view of the drug container and safety mechanism of FIG. 74A in an activated configuration;

FIG. 75A shows an isometric view of a drug delivery pump in which the insertion mechanism includes a rotational biasing member;

FIG. 75B shows an enlarged view of the drive mechanism shown in FIG. 75A.

Figure 76A:
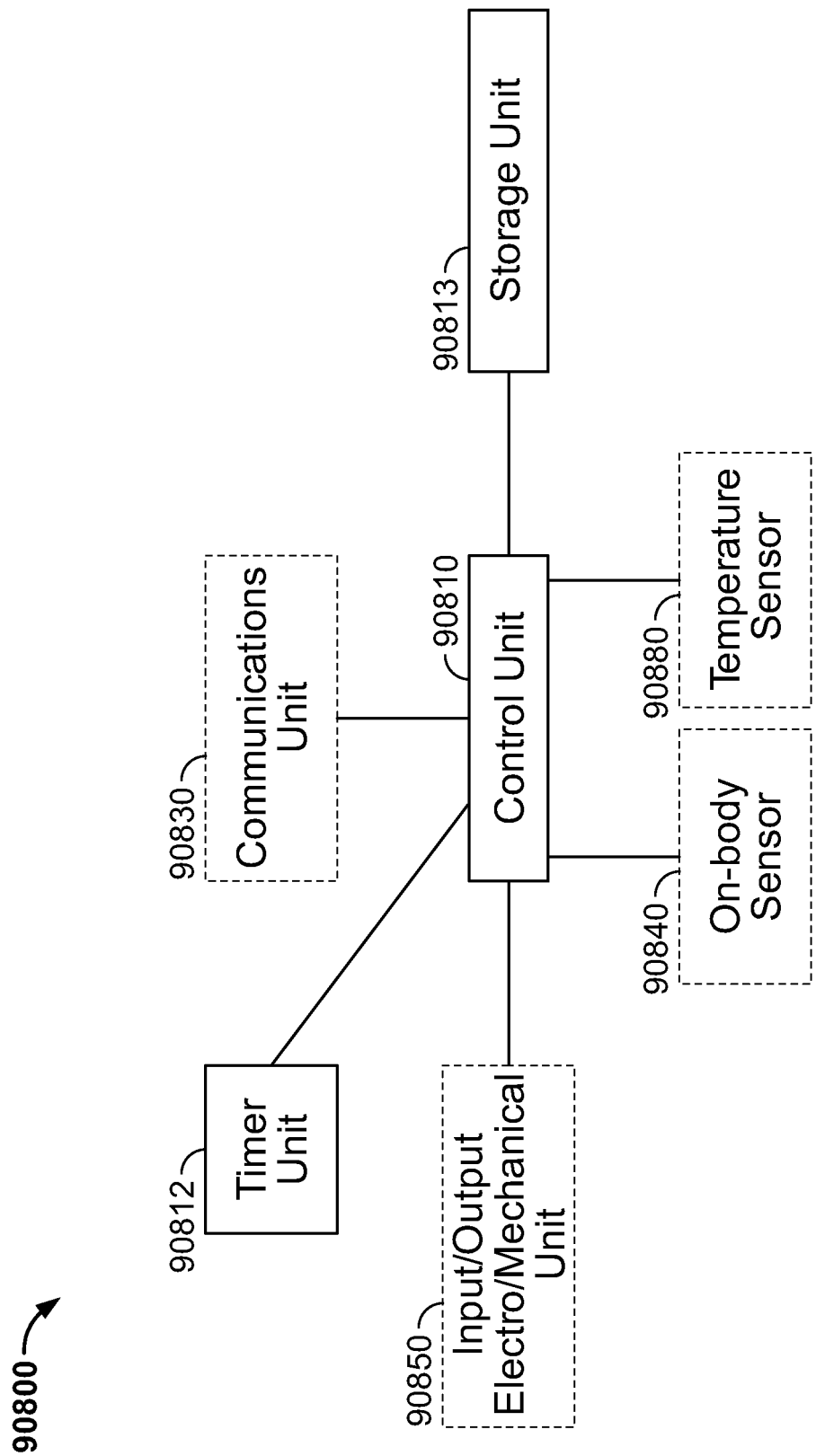
Figure 76B:
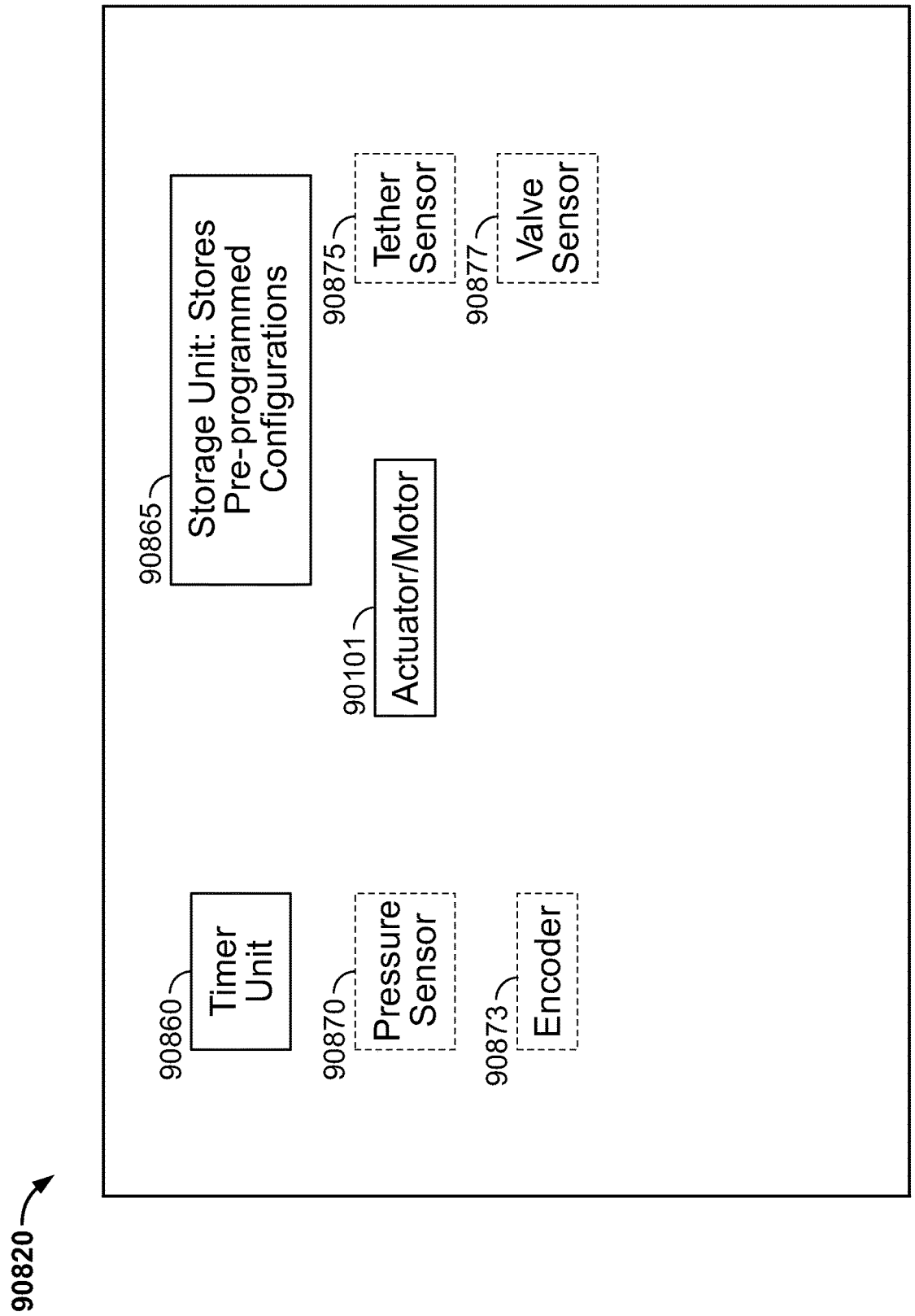
Figure 76C:
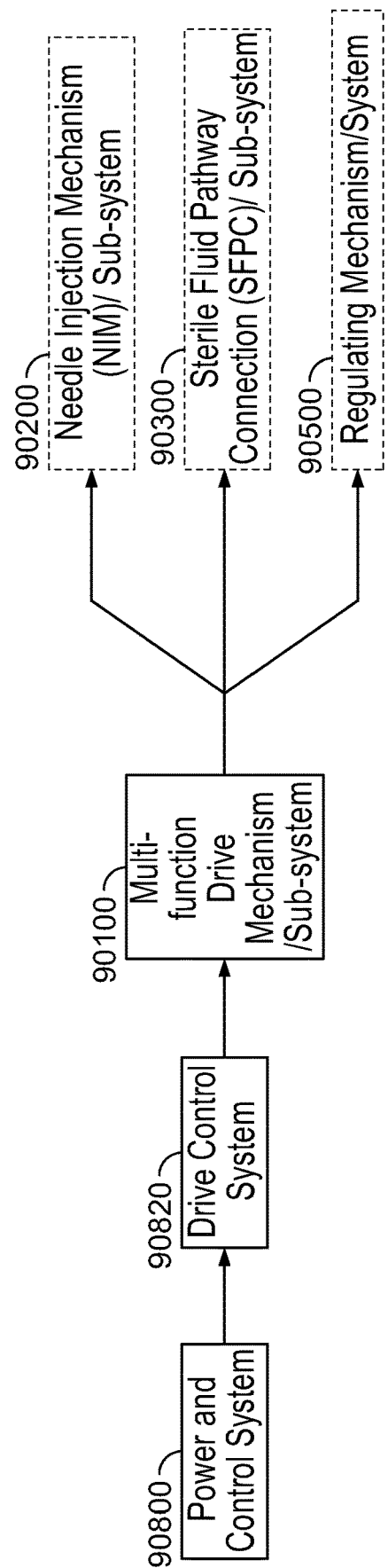
Figure 76D:
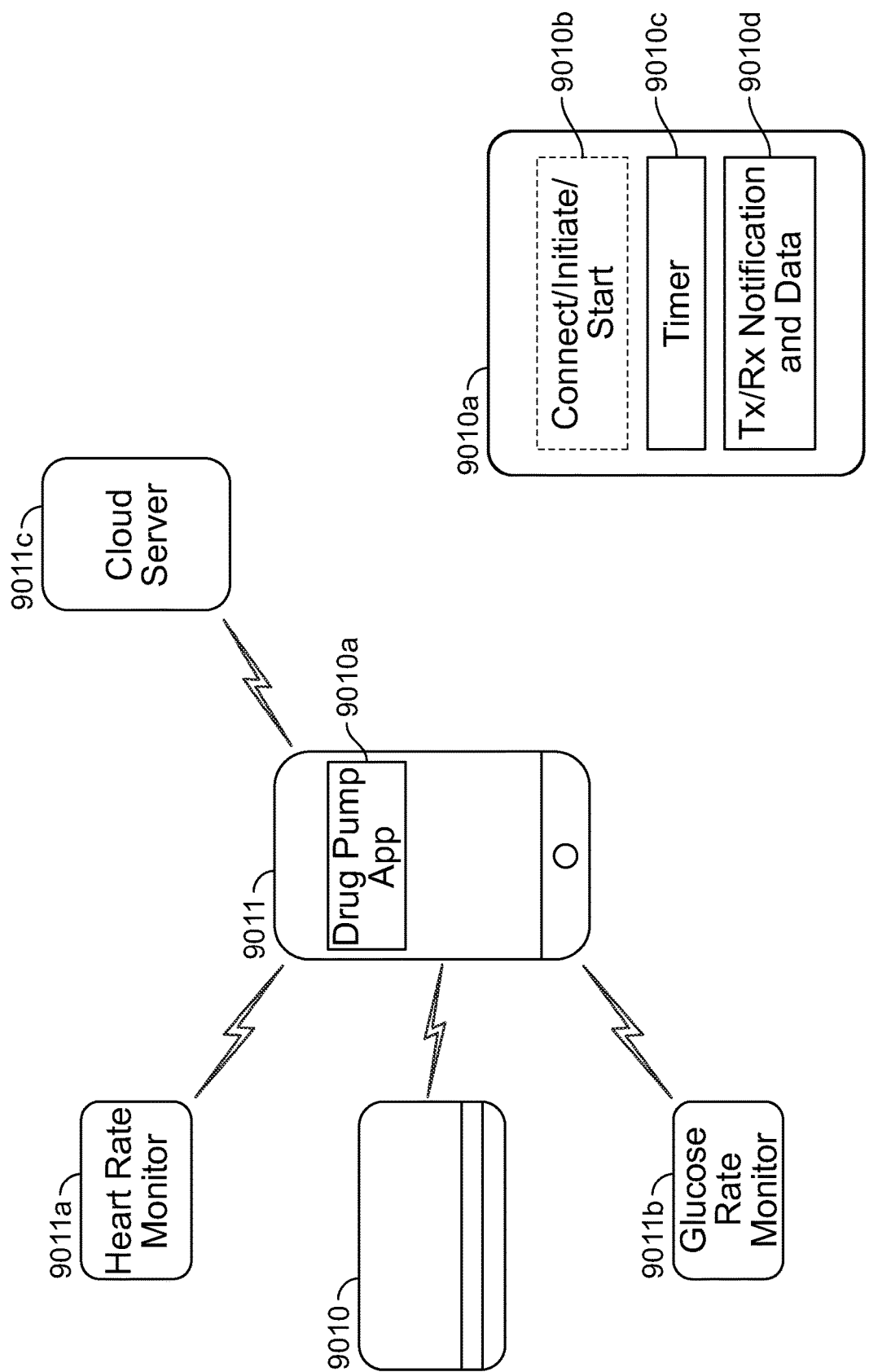
Figure 77A:
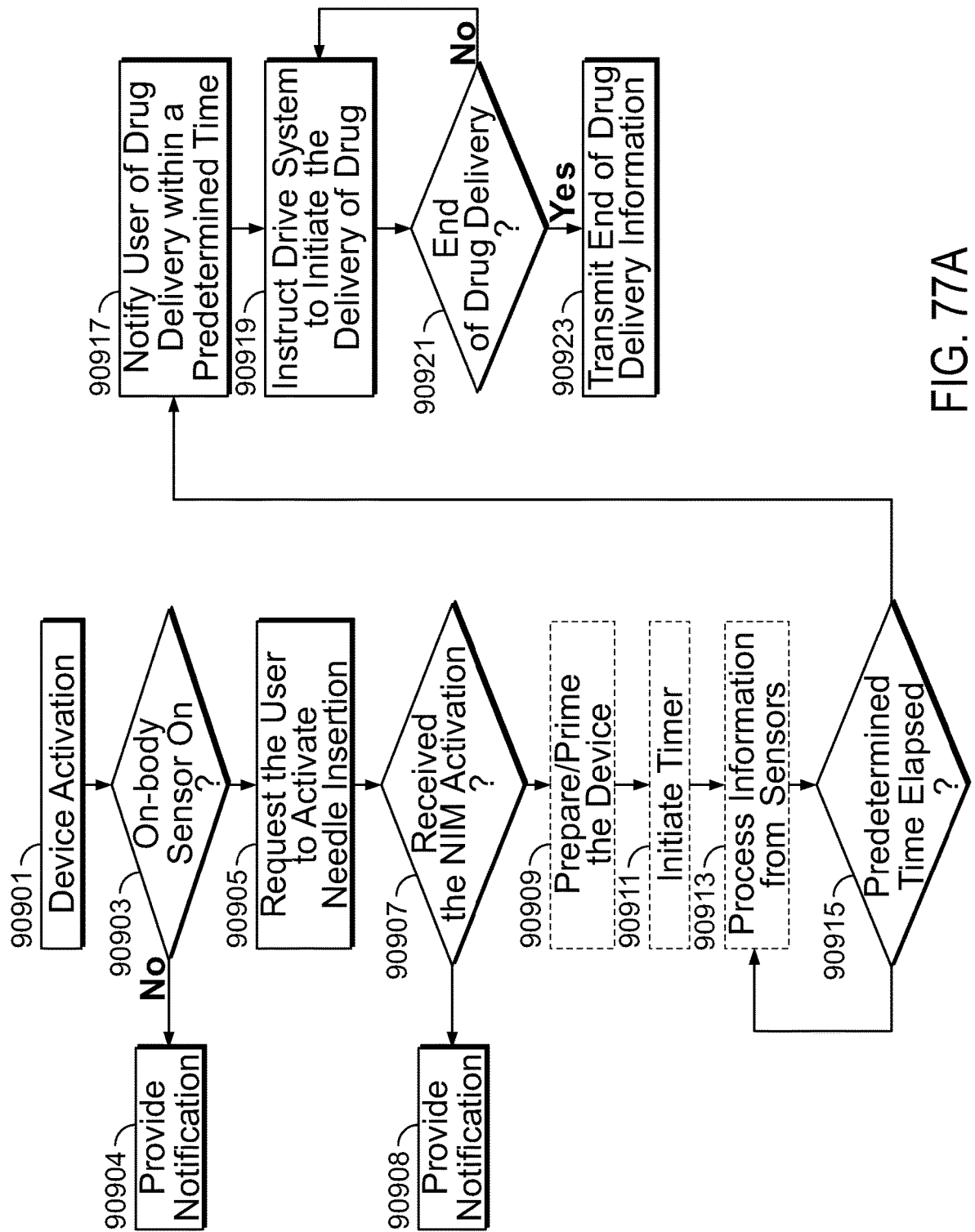
Figure 77B:
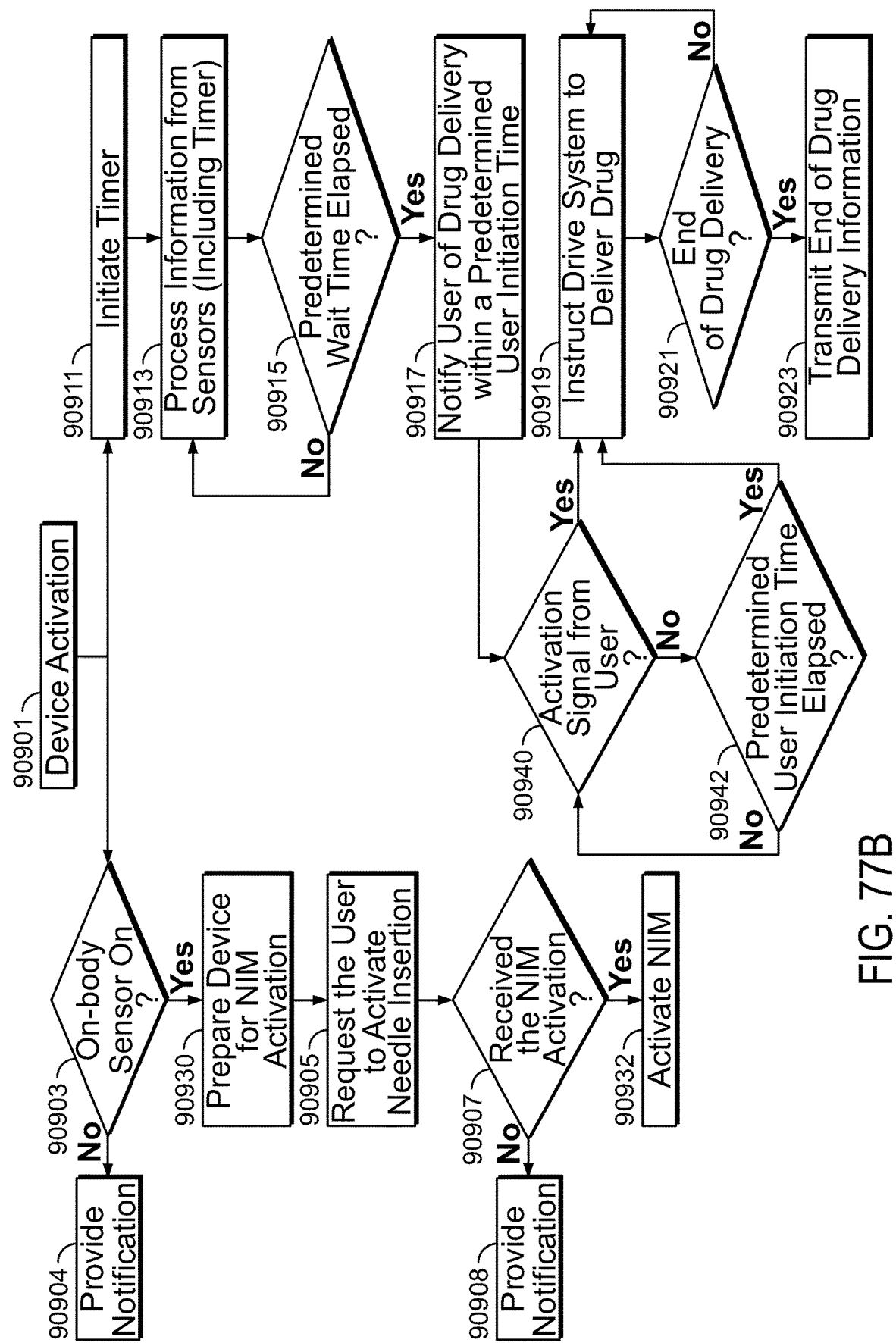
Figure 77C:
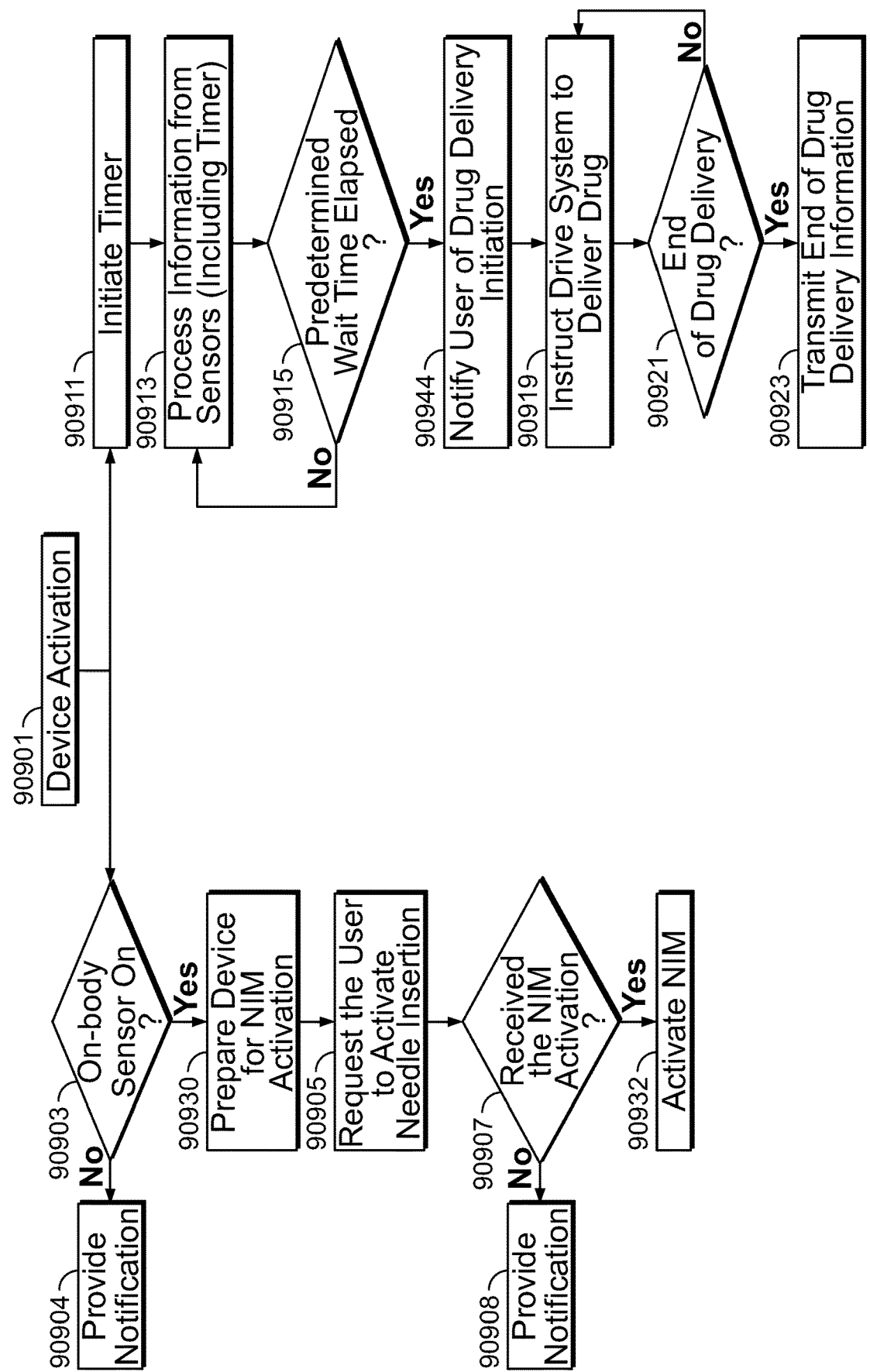
Figure 78A:
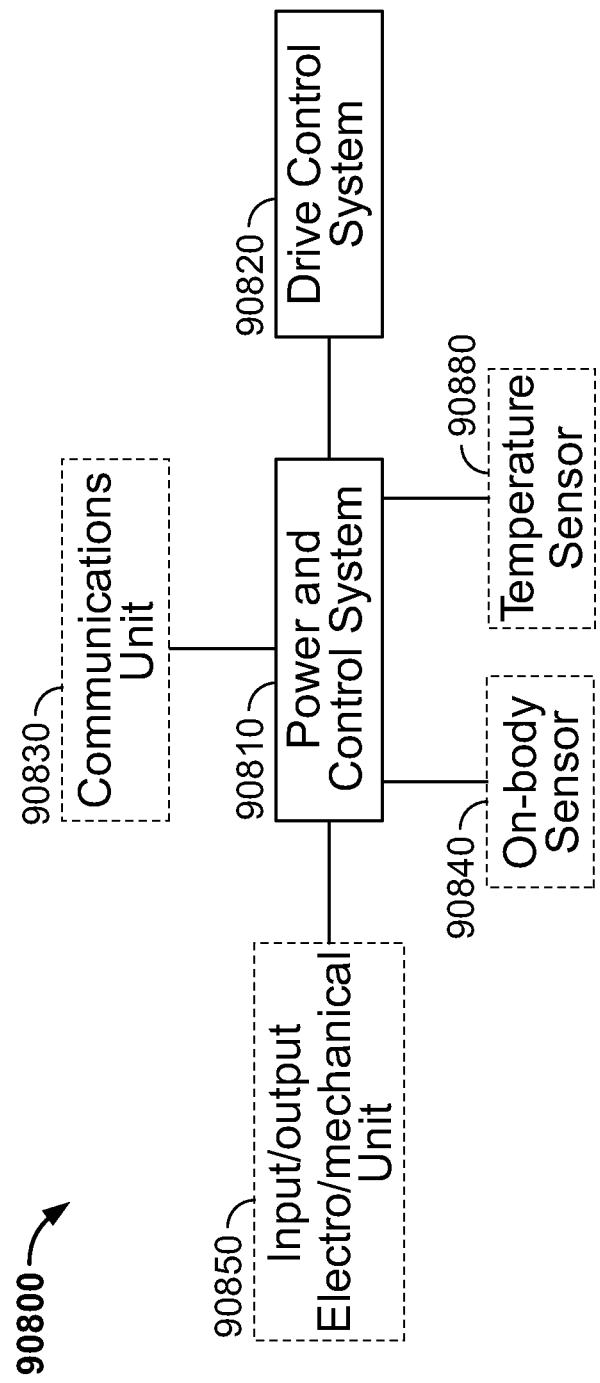
Figure 78B:
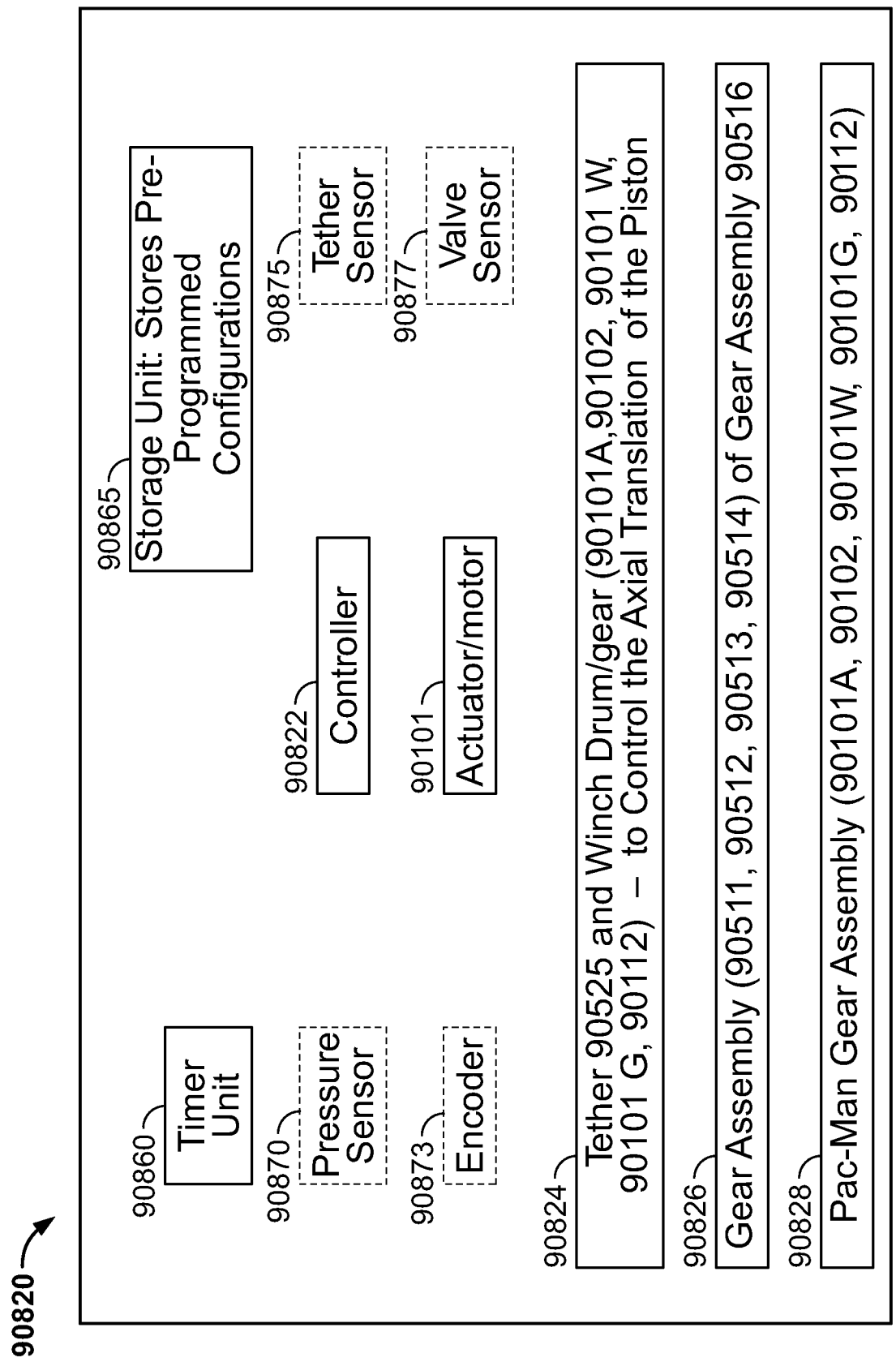
Figure 78C:
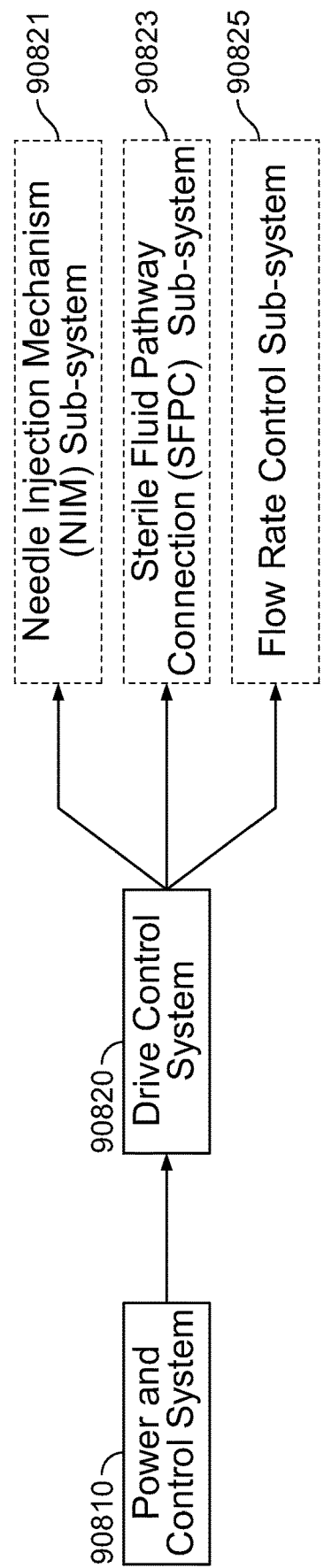
Figure 79A:
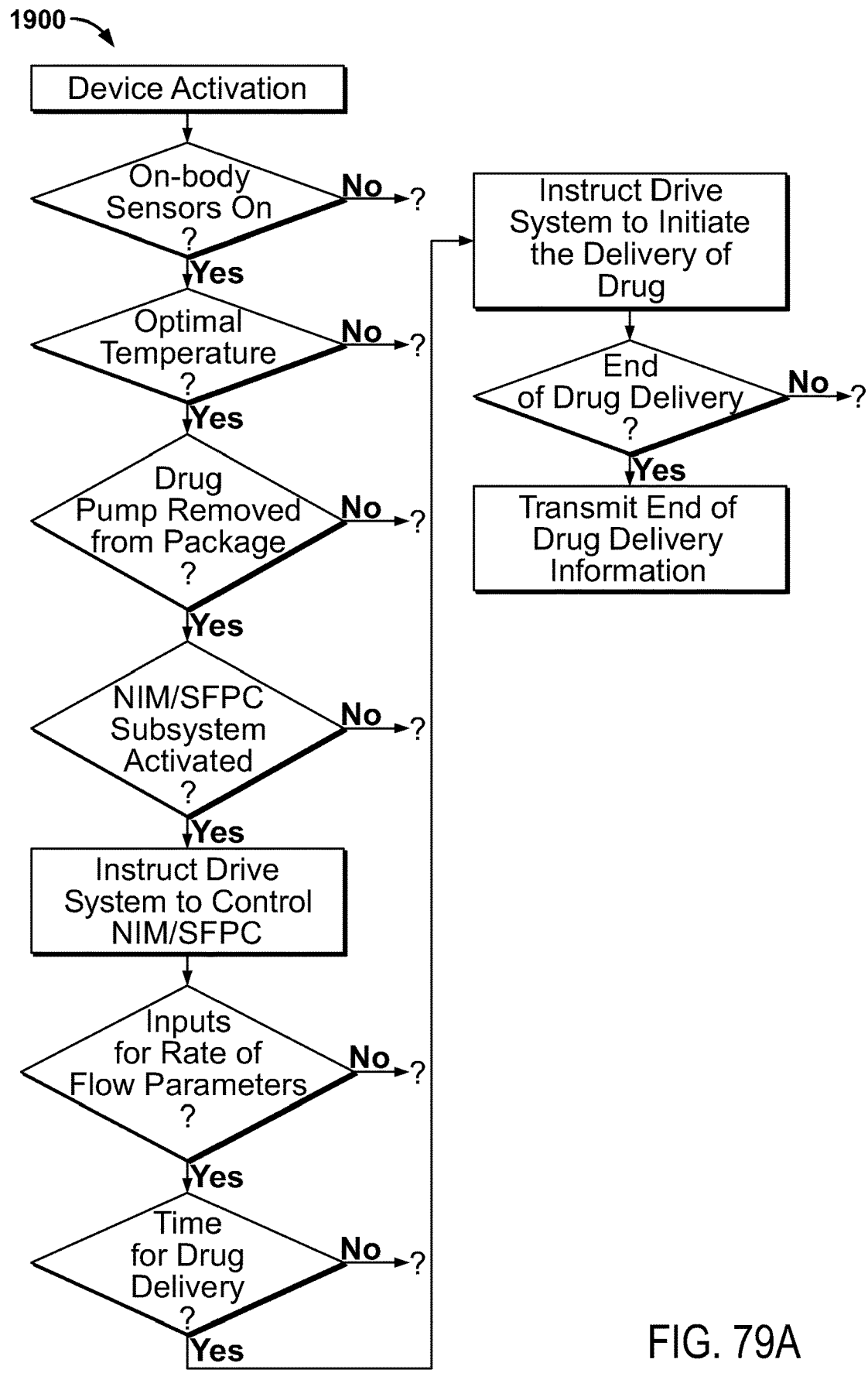
Figure 79B:
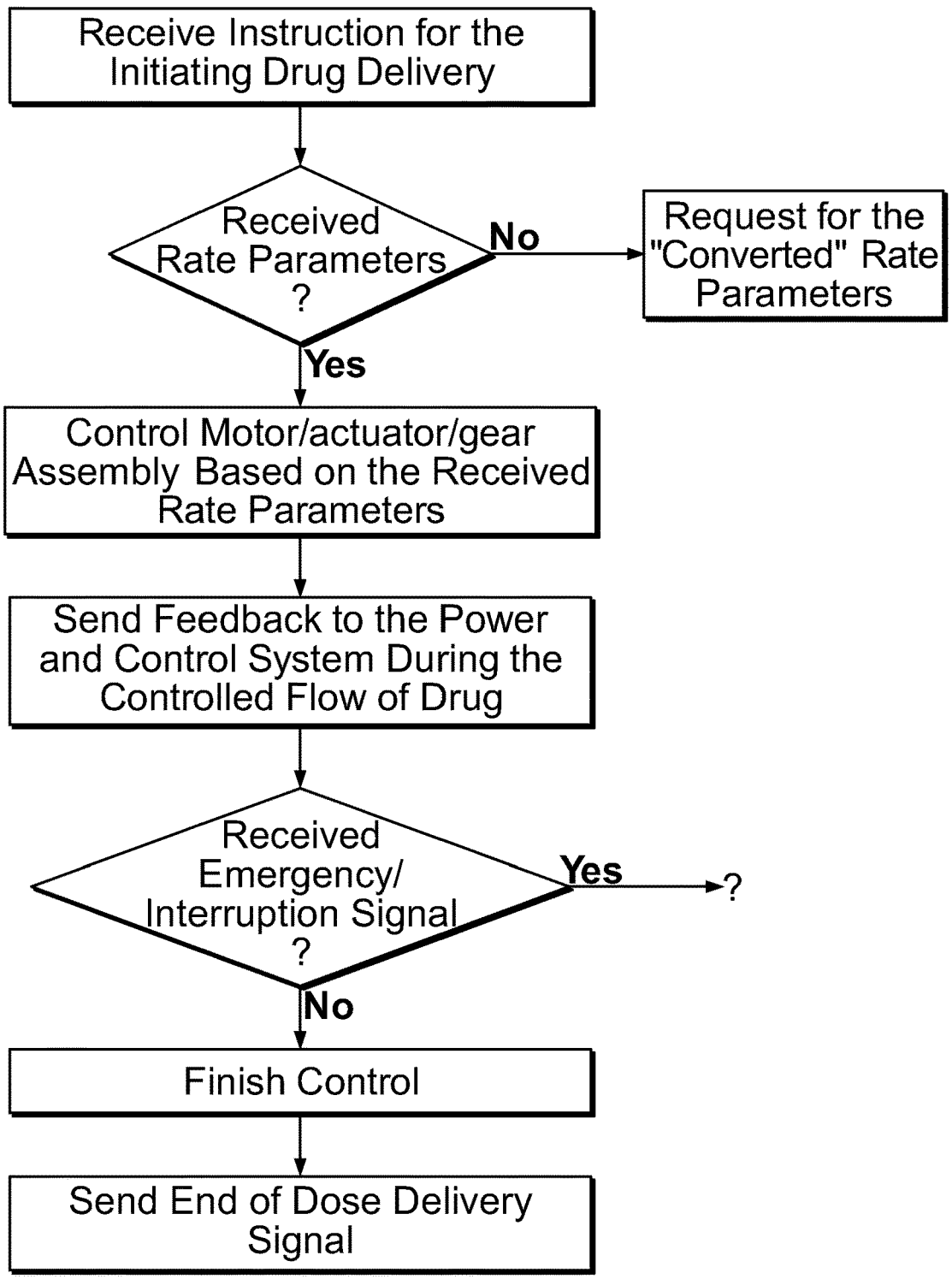
Figure 80A:
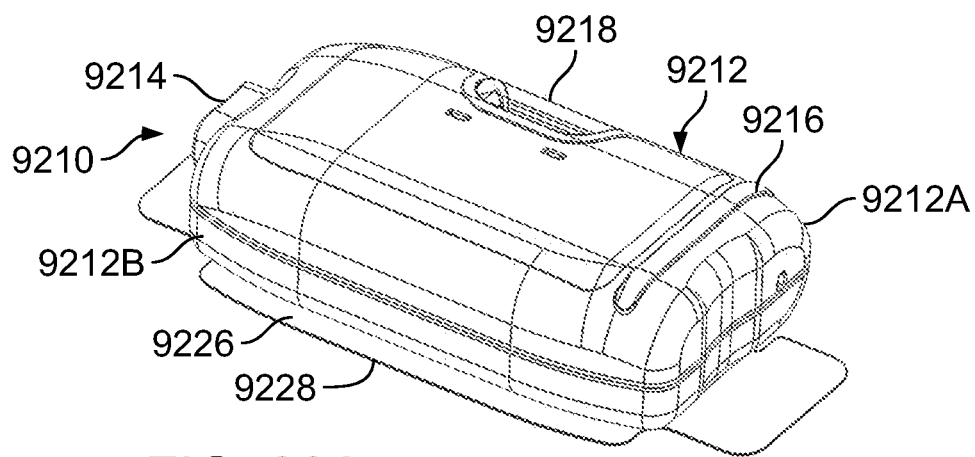
Figure 80B:
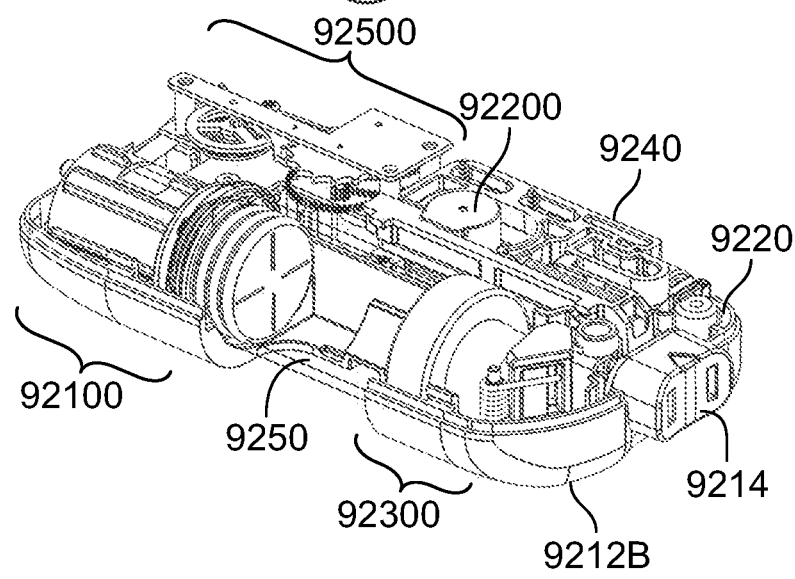
Figure 80C:
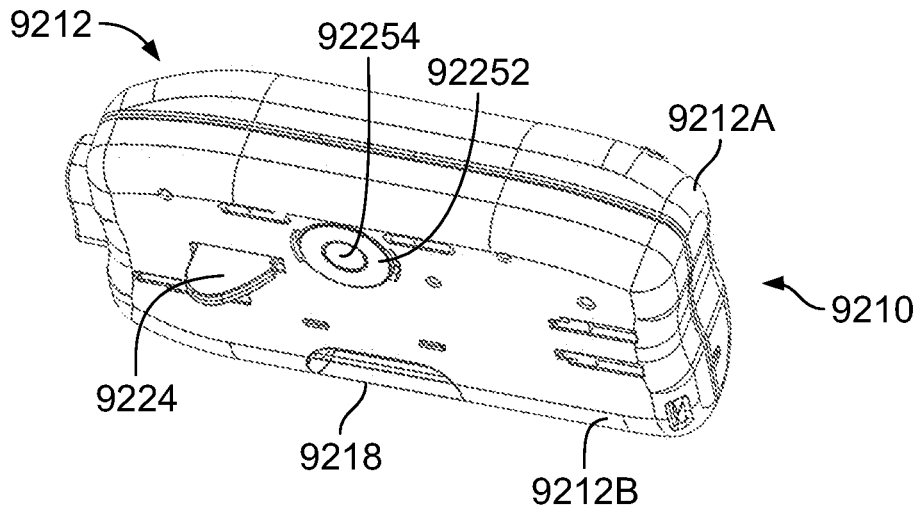
Figure 81A:
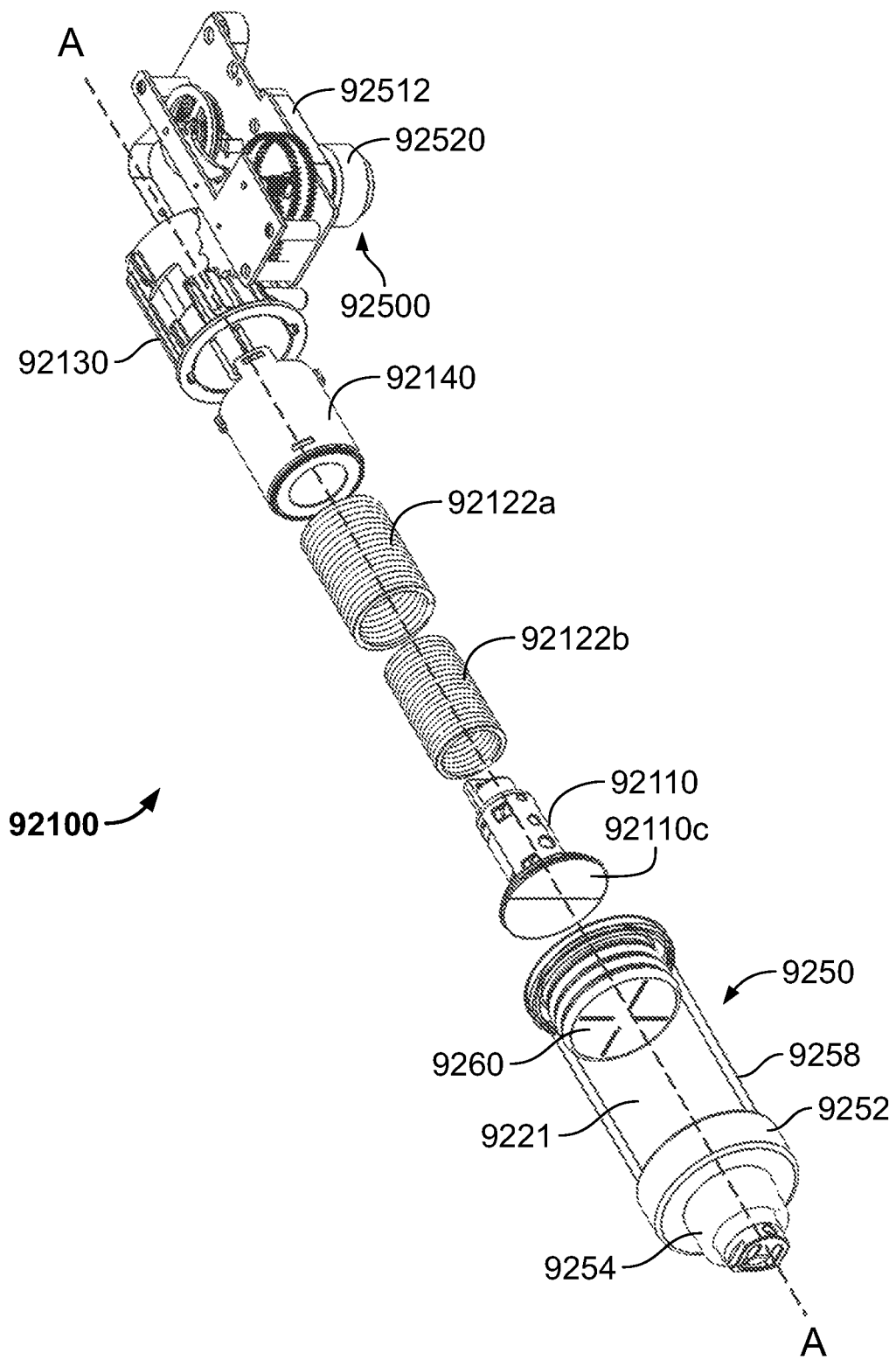
Figure 81B:
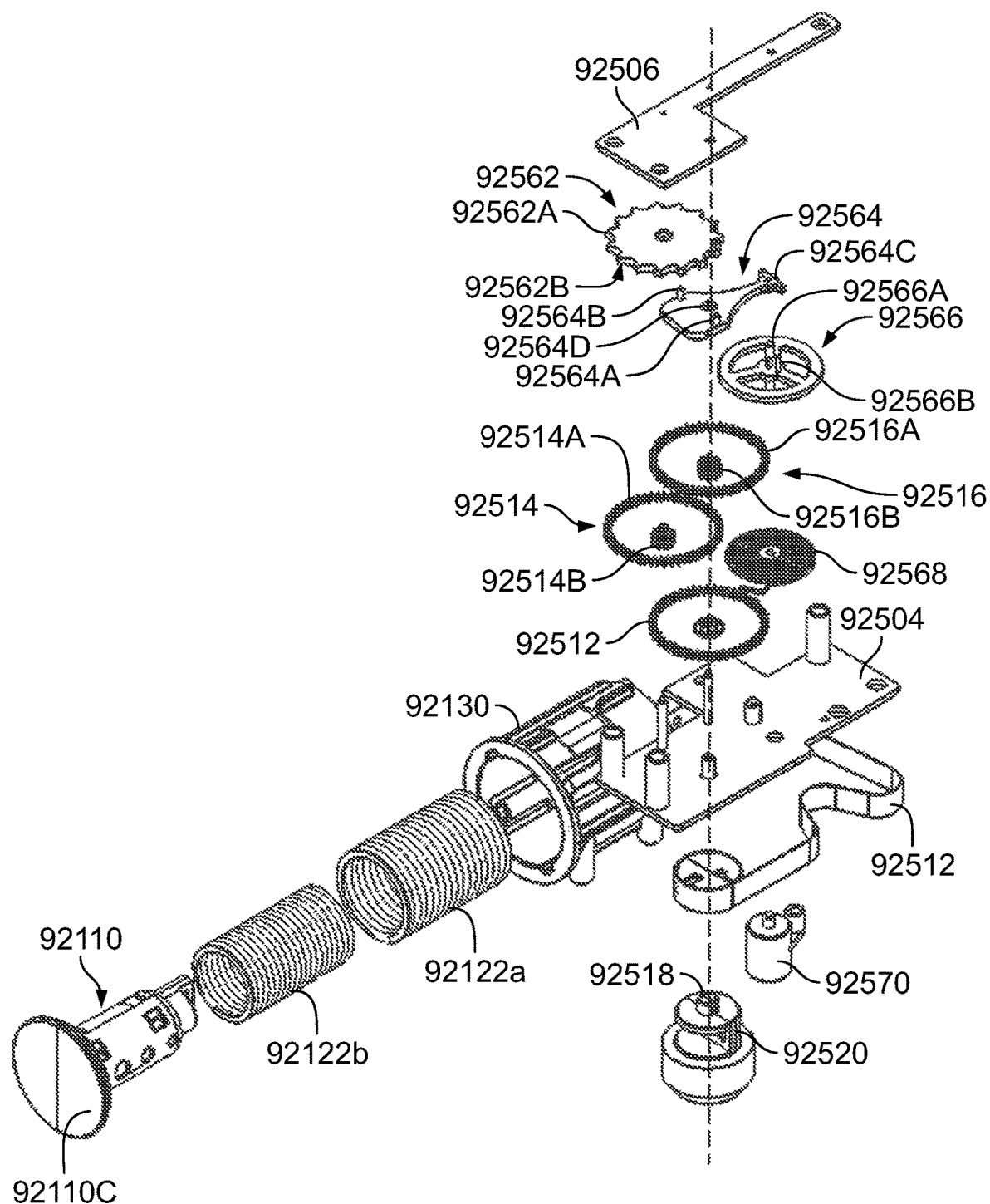
Figure 82A:
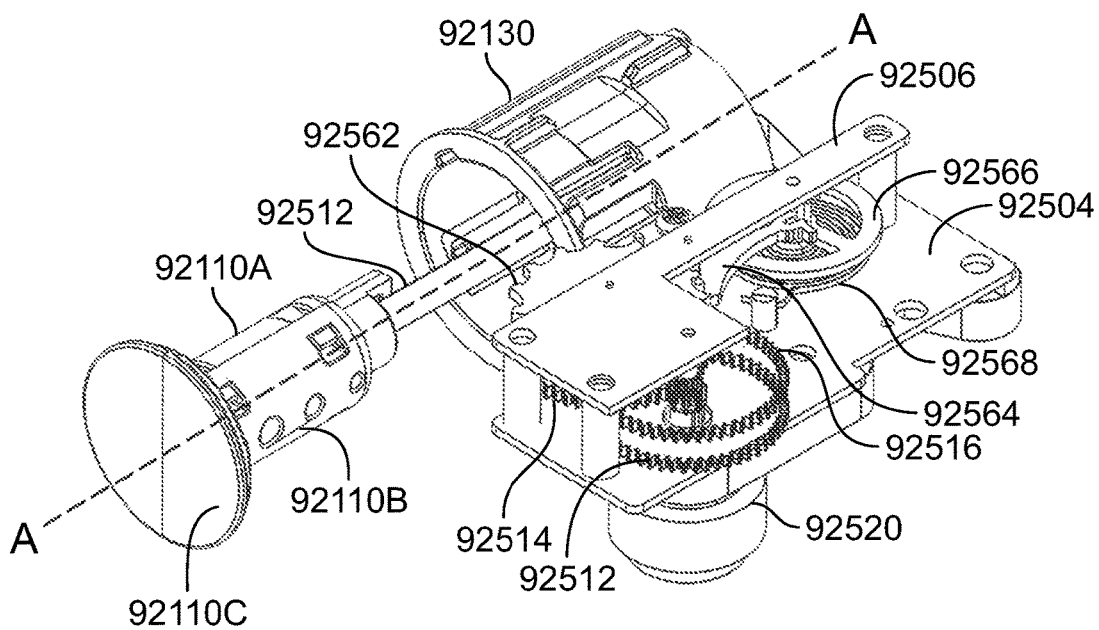
Figure 82B:
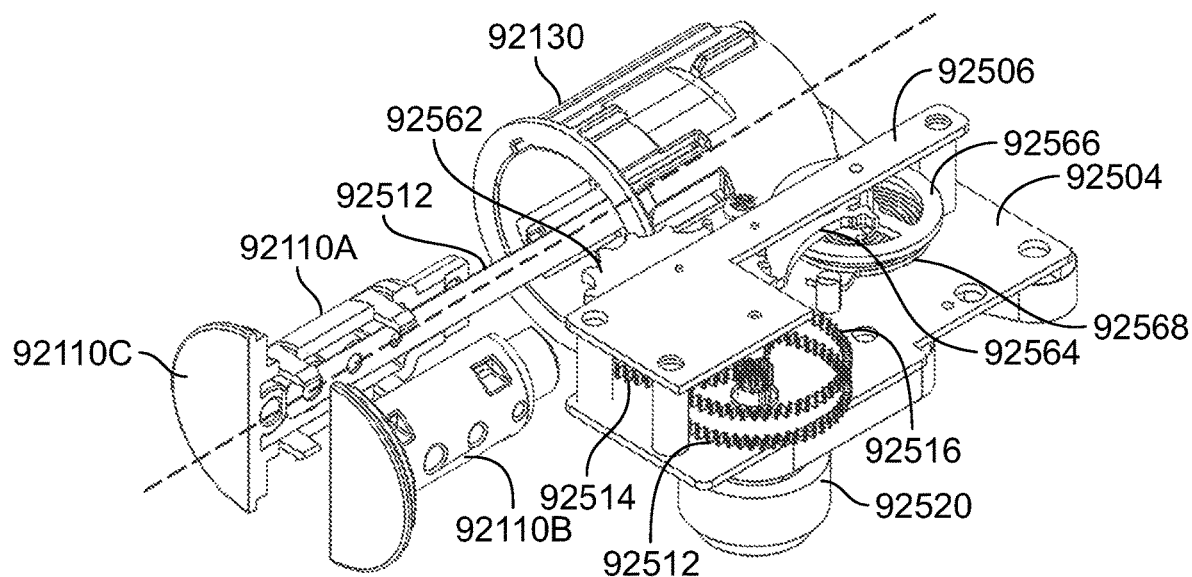
Figure 83A:
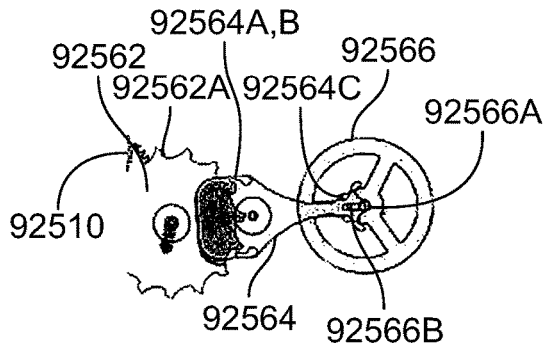
Figure 83B:
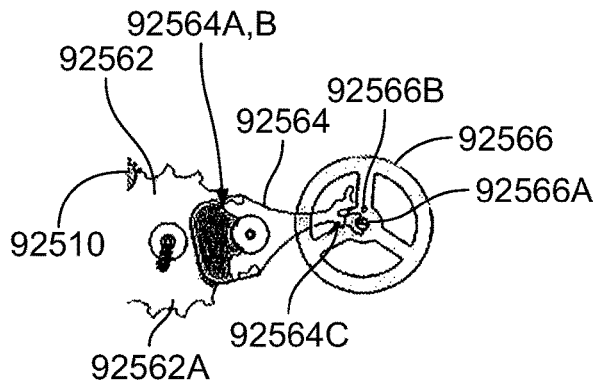
Figure 83C:
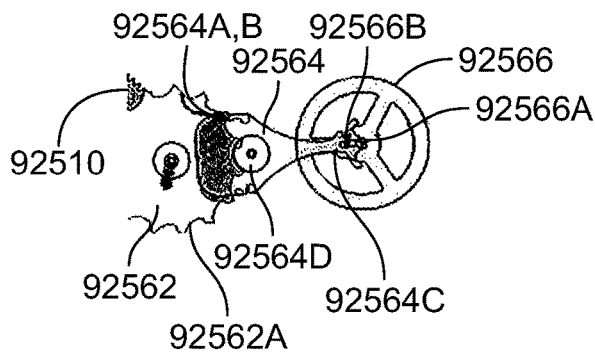
Figure 83D:
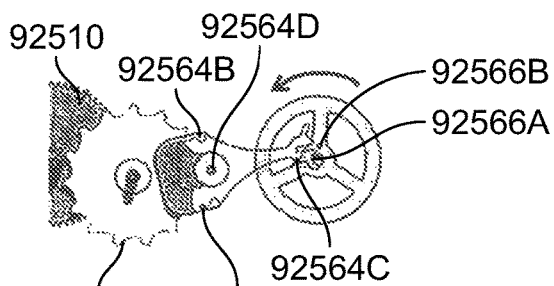
Figure 83E:
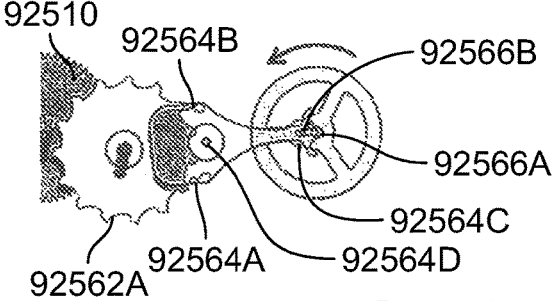
Figure 83F:
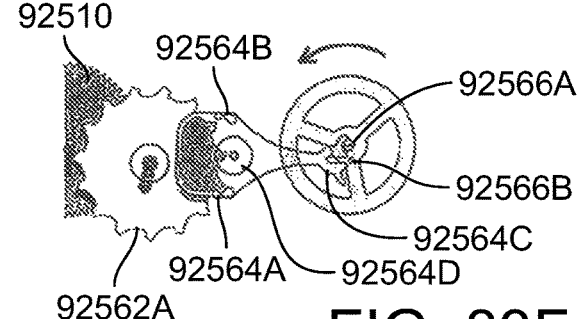
Figure 83G:
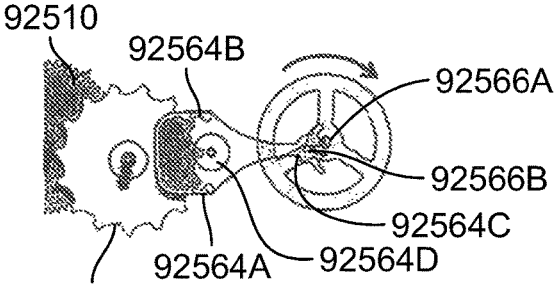
Figure 83H:
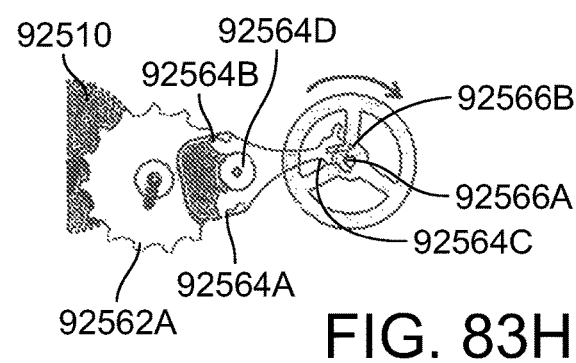
Figure 84A:
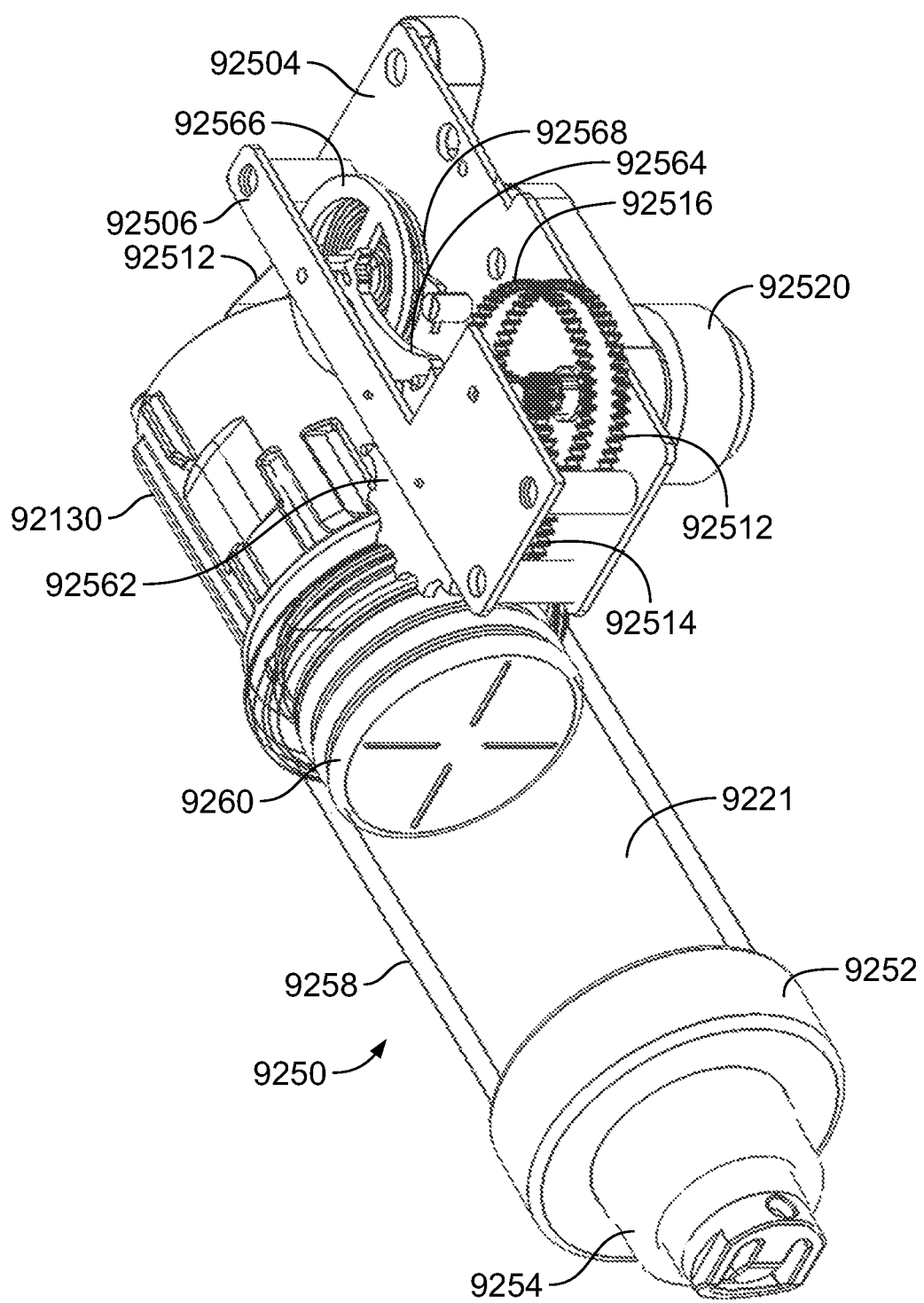
Figure 84B:
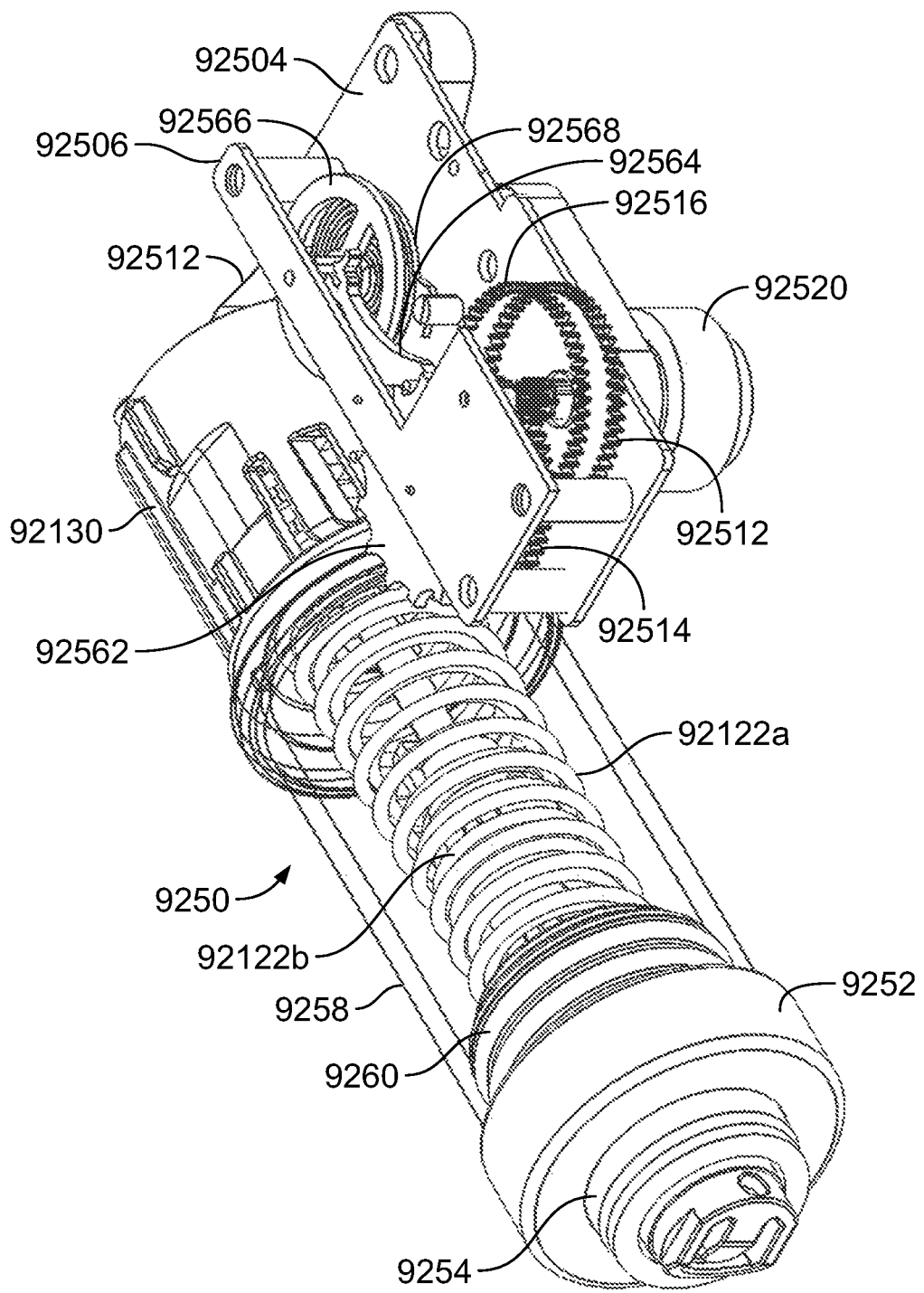
Figure 85A:
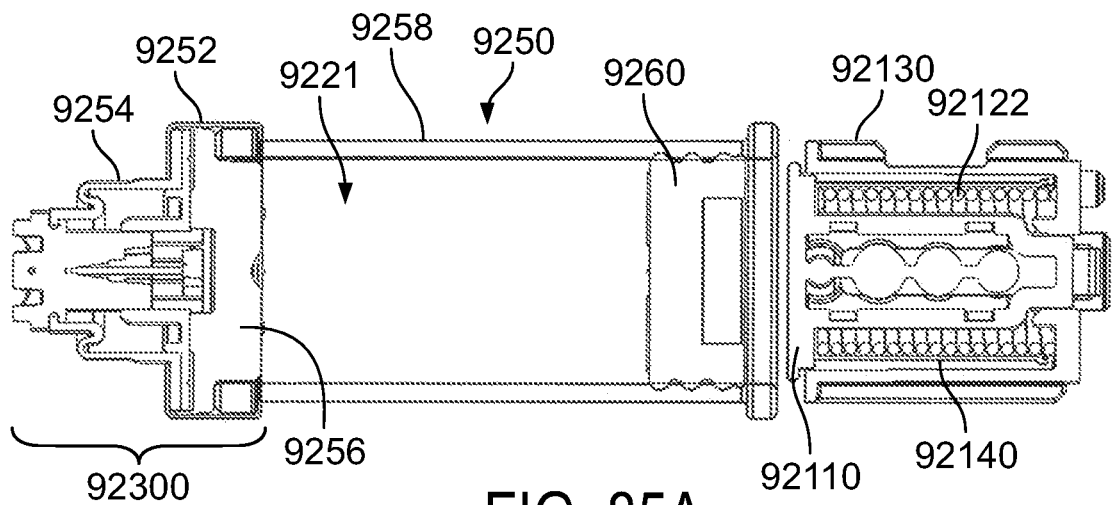
Figure 85B:
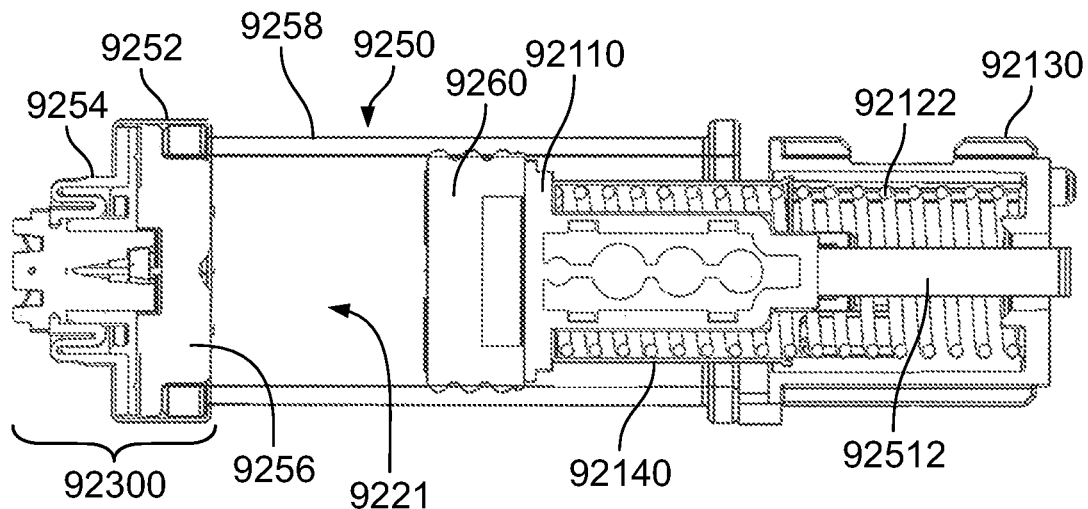
Figure 85C:
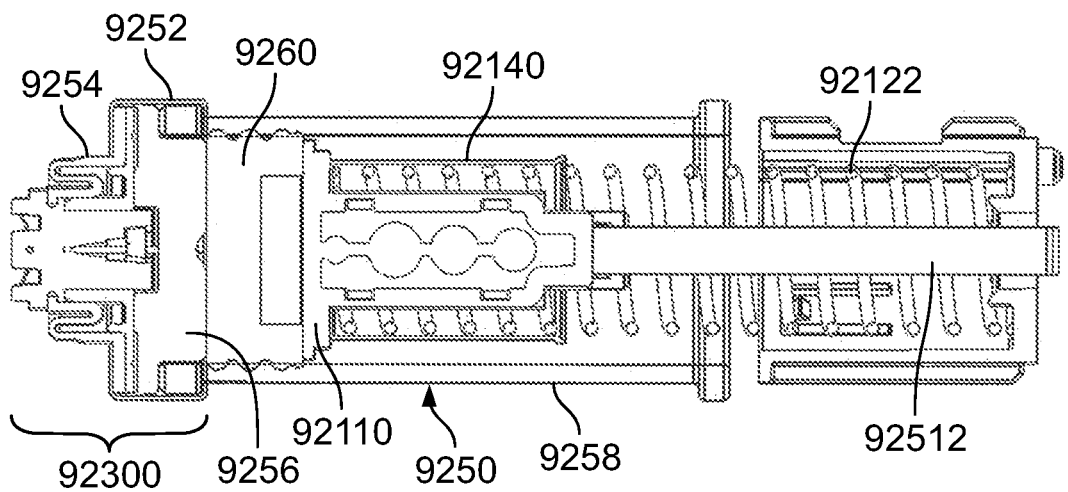
Figure 86A:
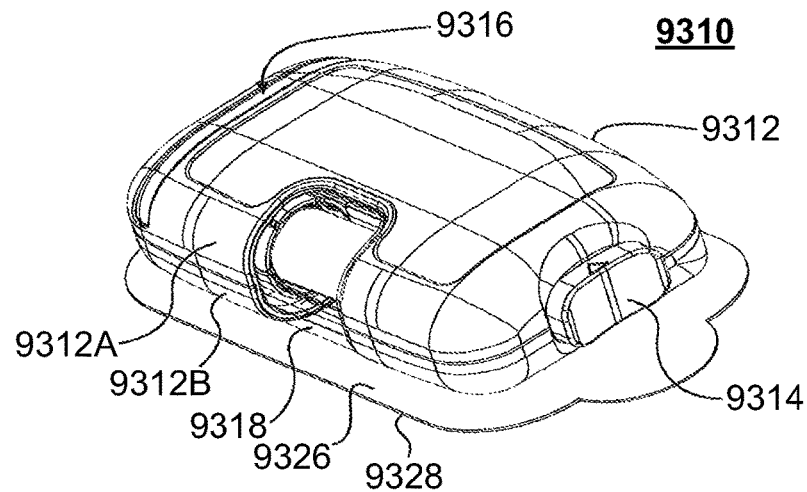
Figure 86B:
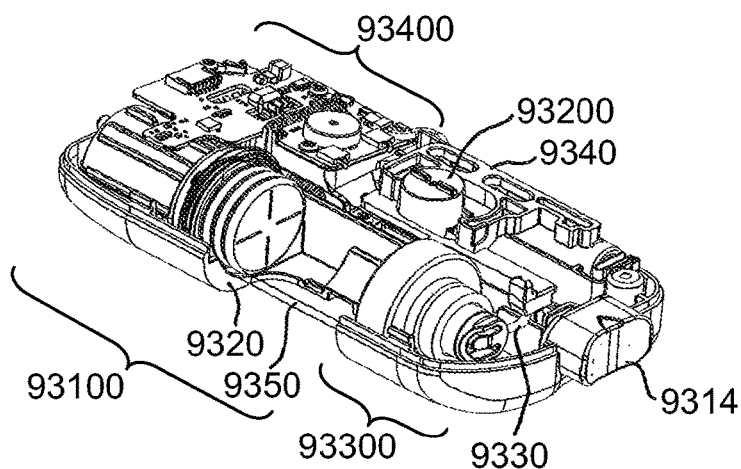
Figure 86C:
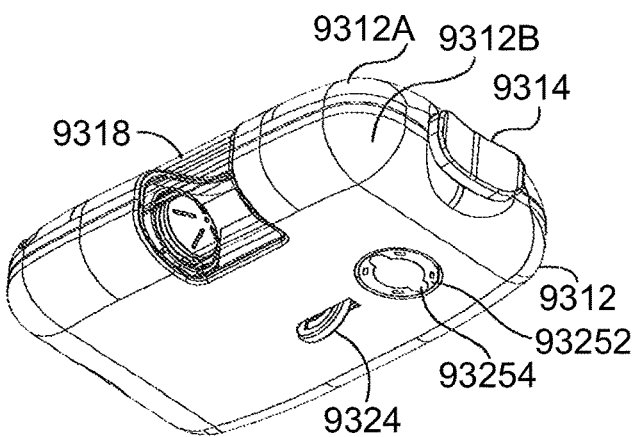
Figure 87:
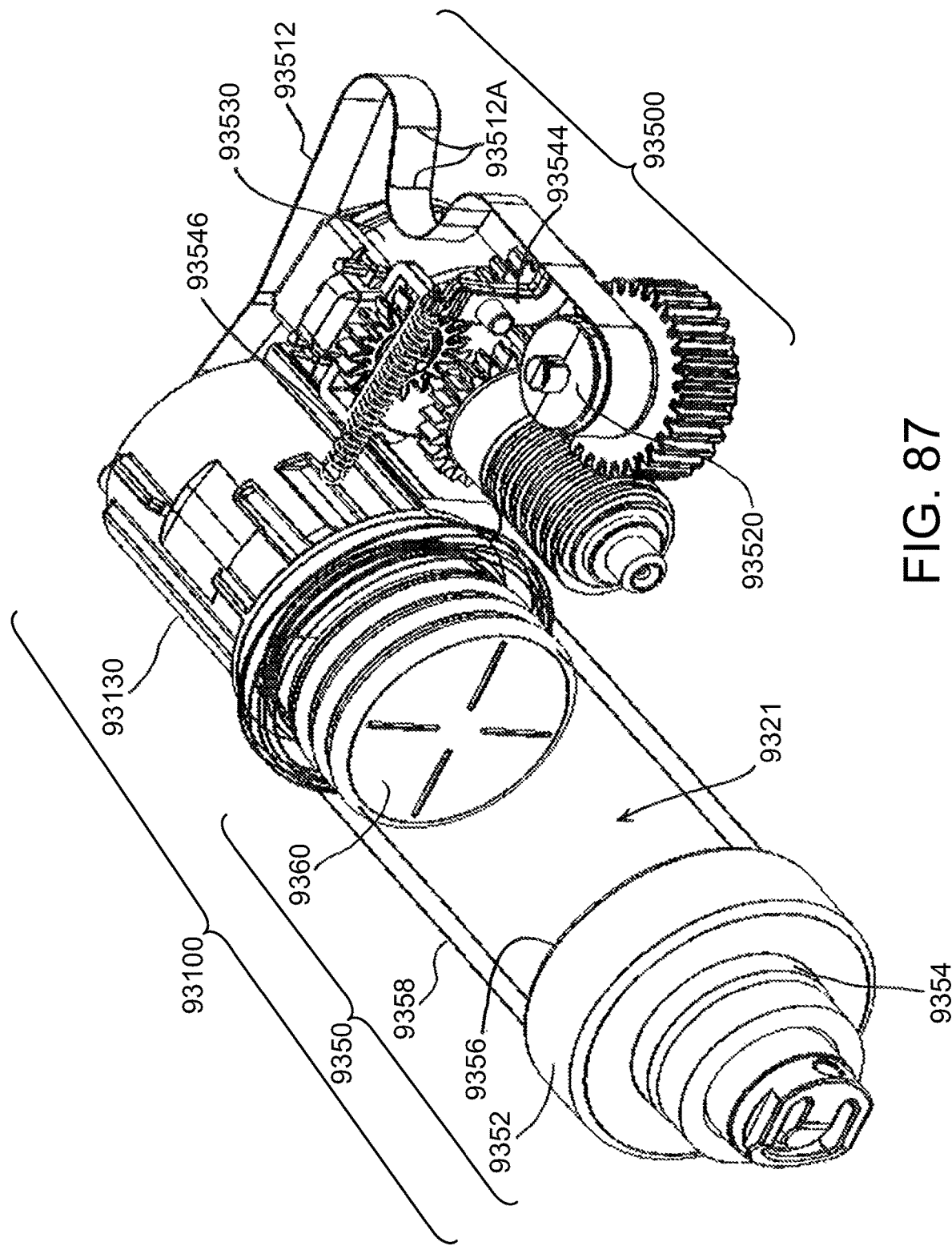
Figure 88:
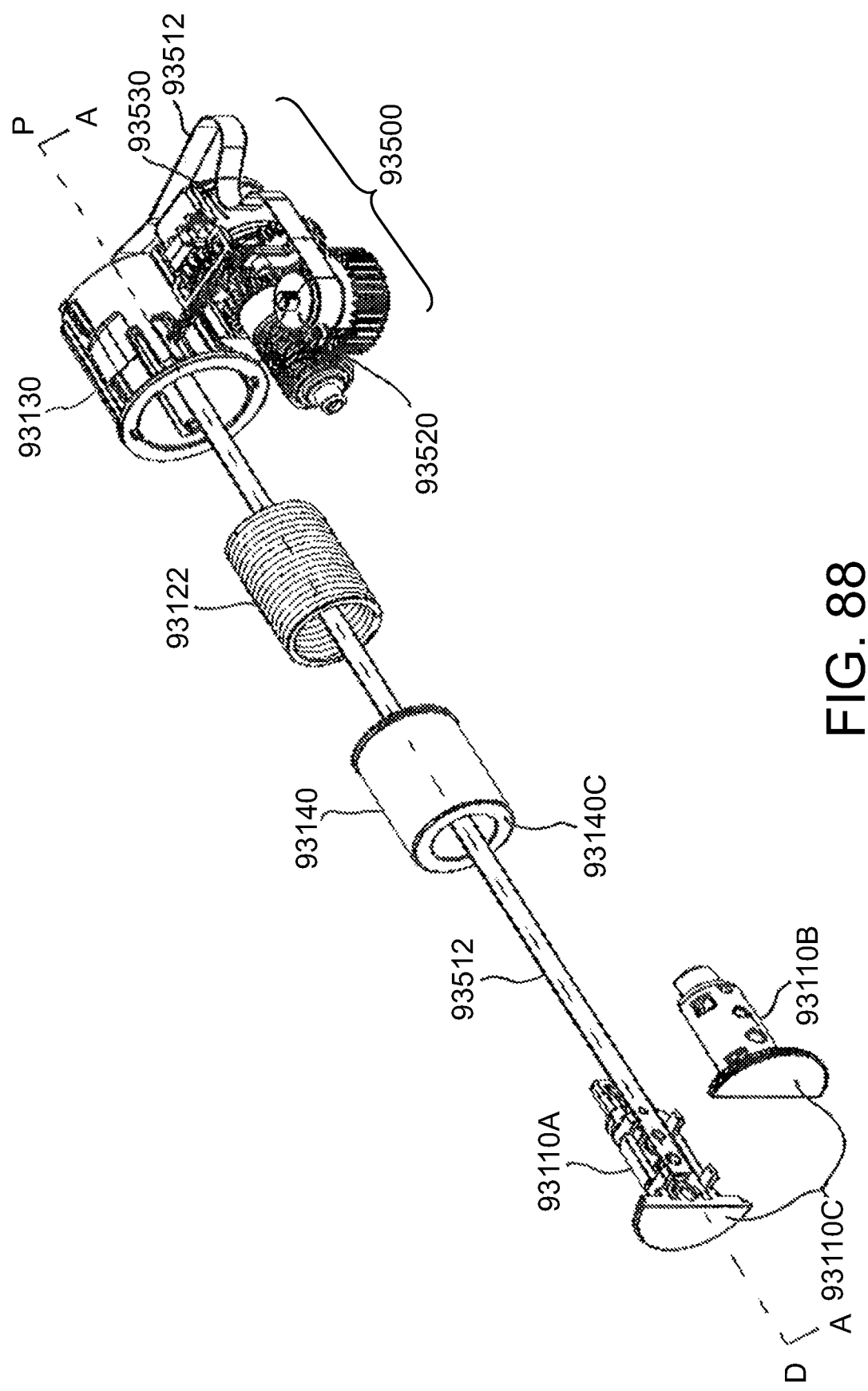
Figure 89A:
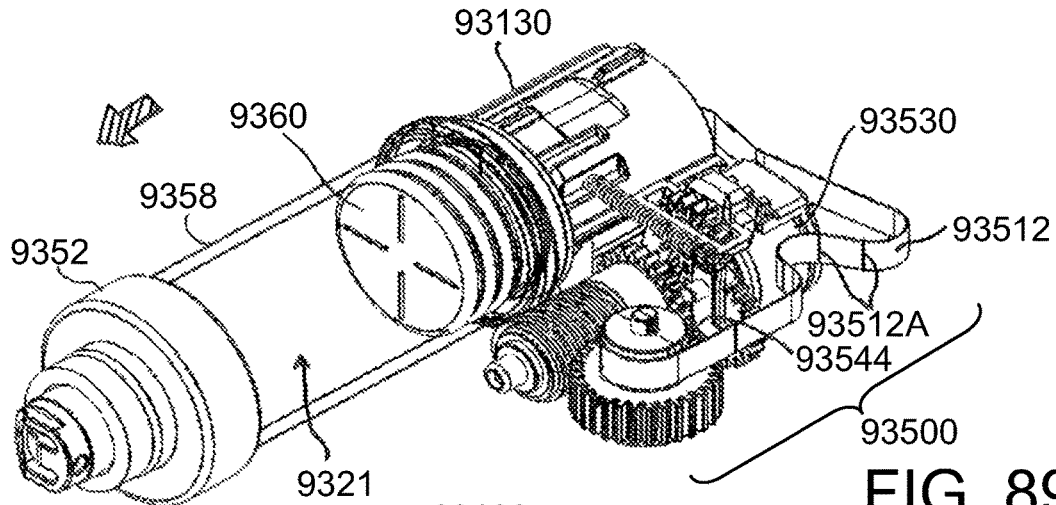
Figure 89B:
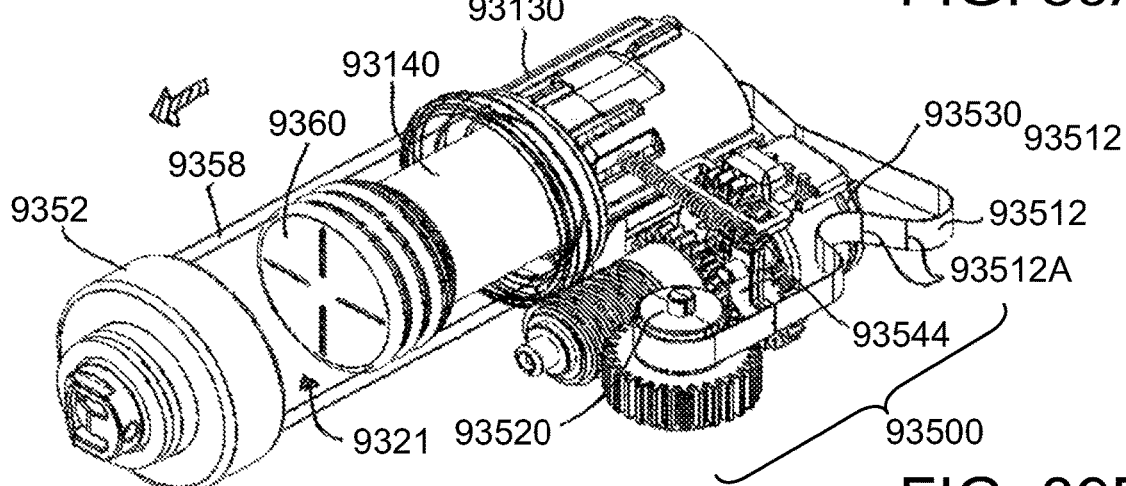
Figure 89C:
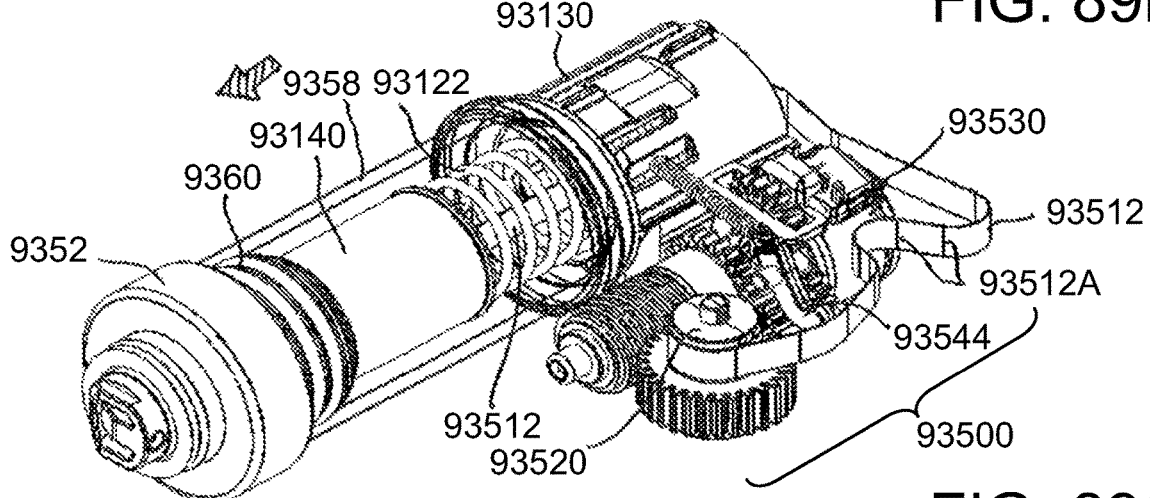
Figure 90A:
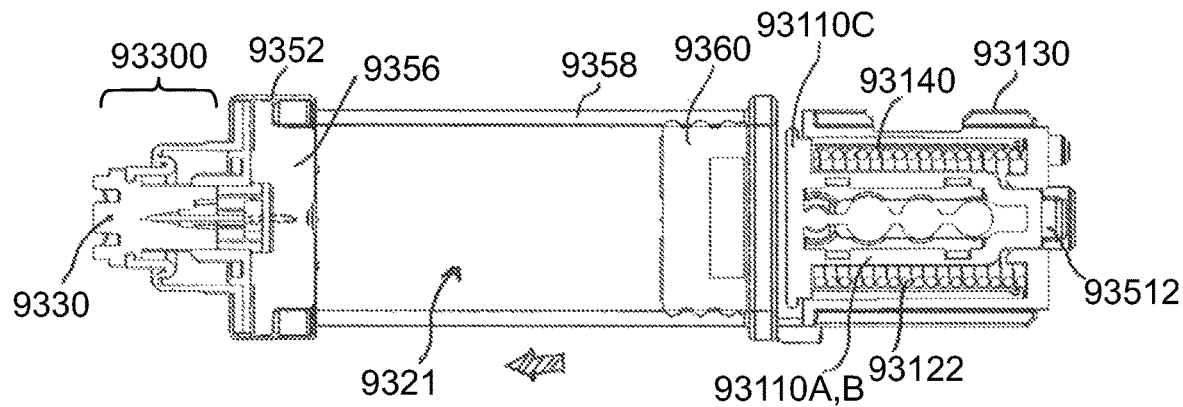
Figure 90B:
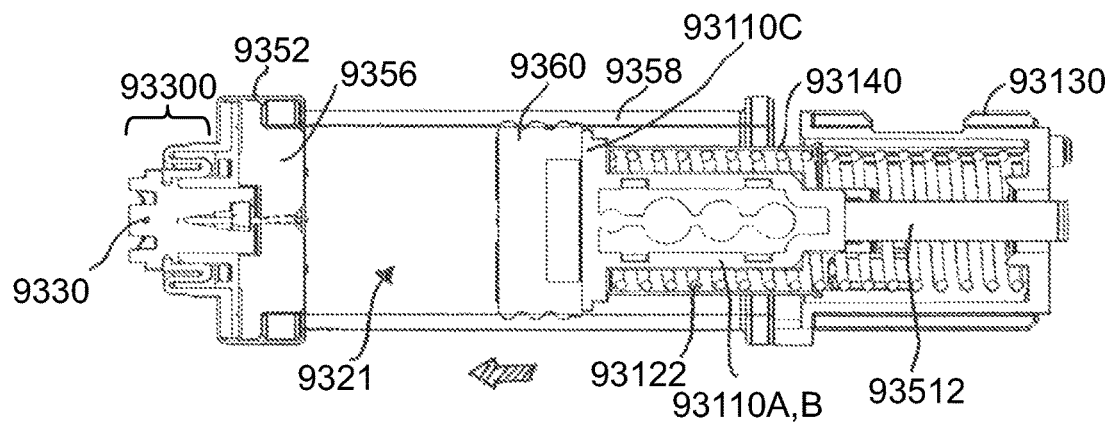
Figure 90C:
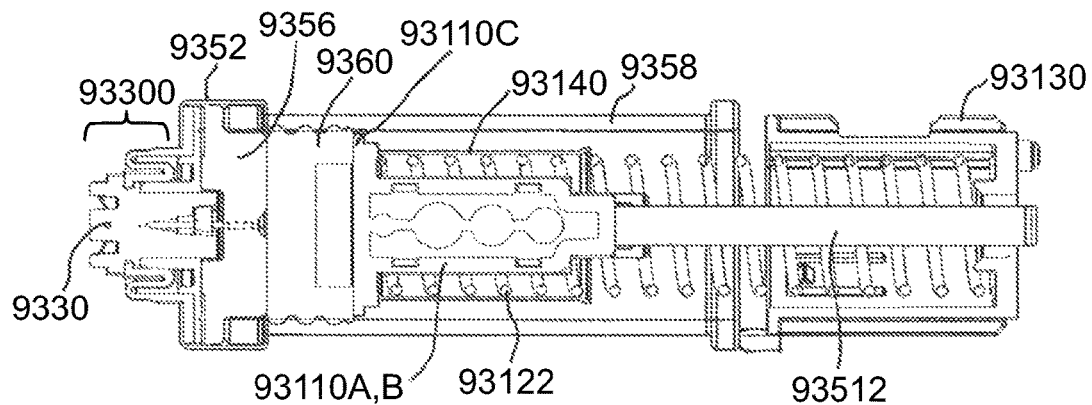
Figure 91:
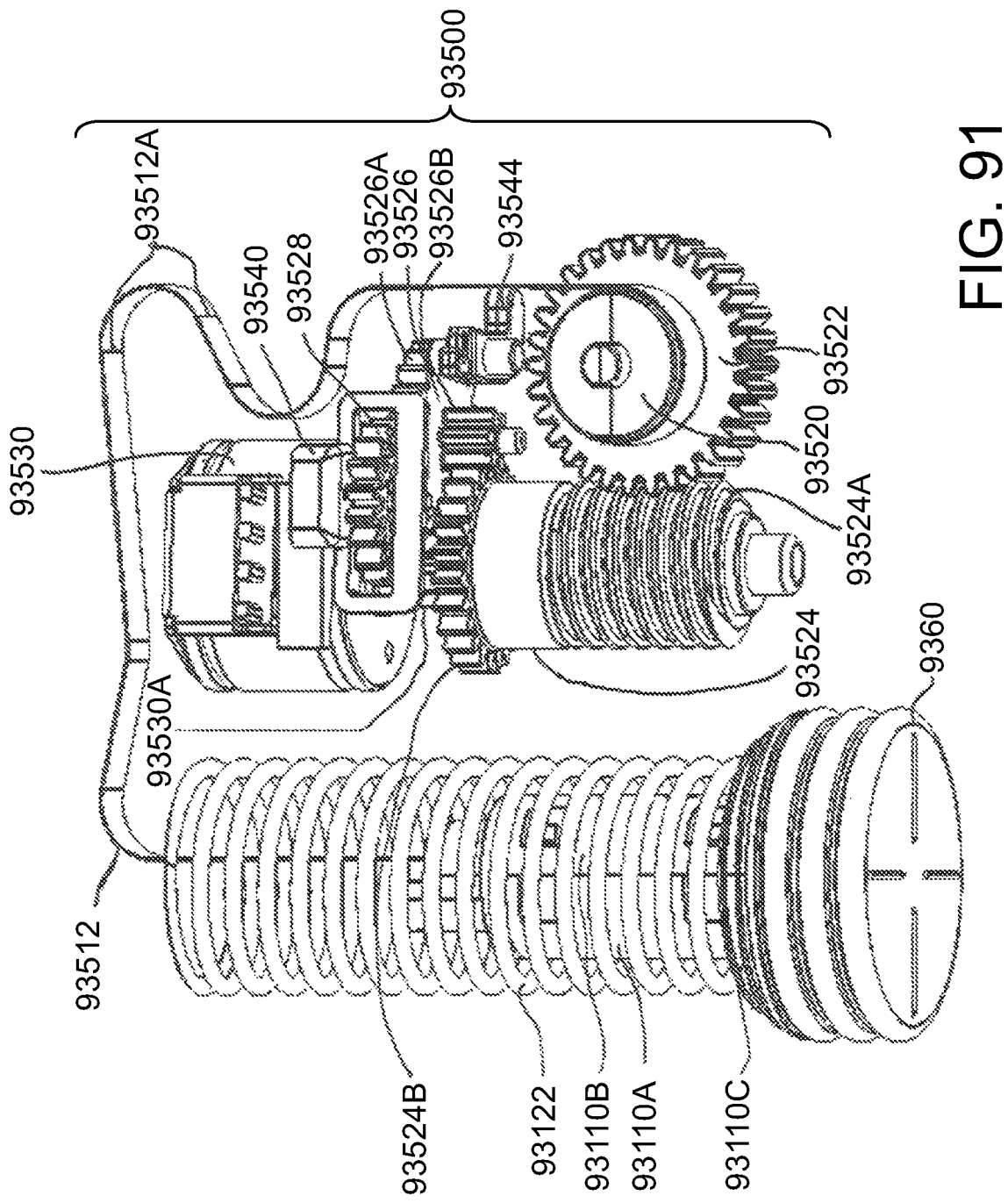
Figure 92A:
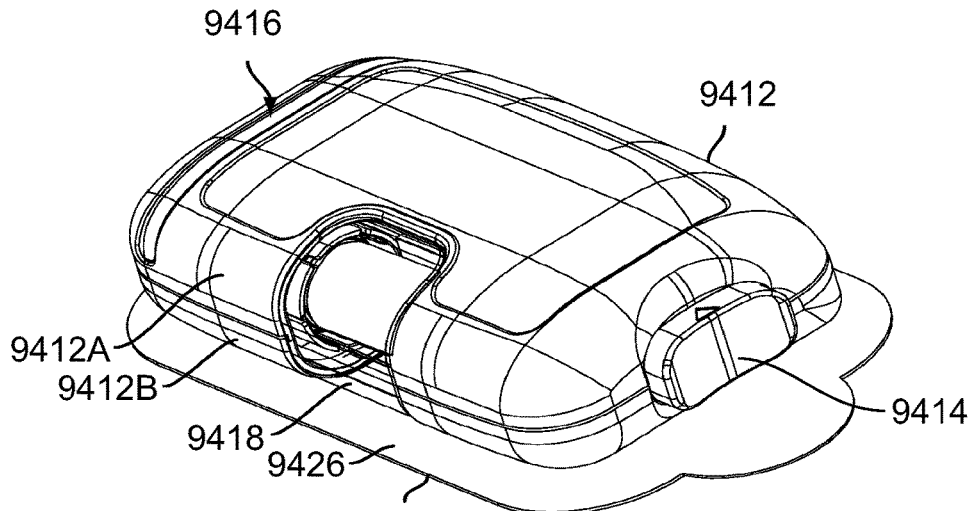
Figure 92B:
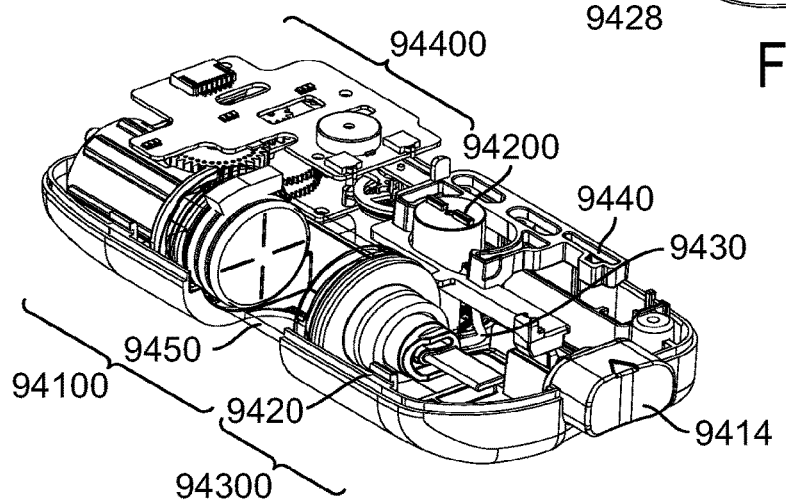
Figure 92C:
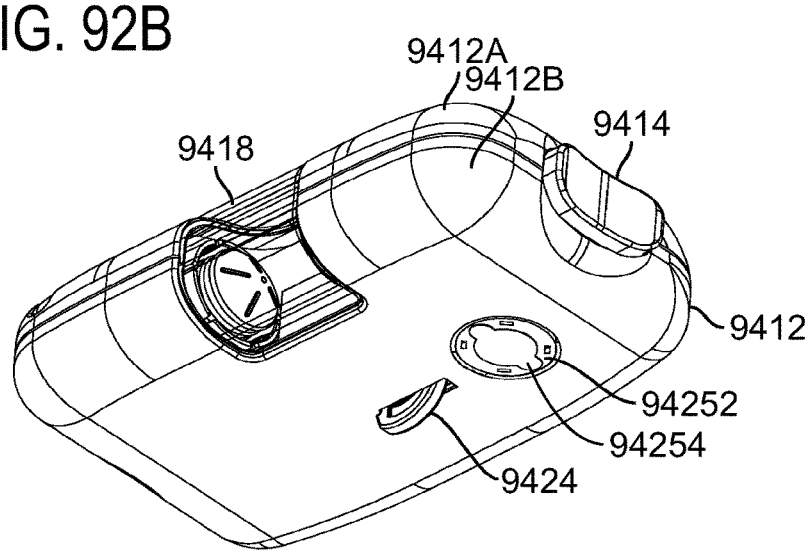
Figure 93:
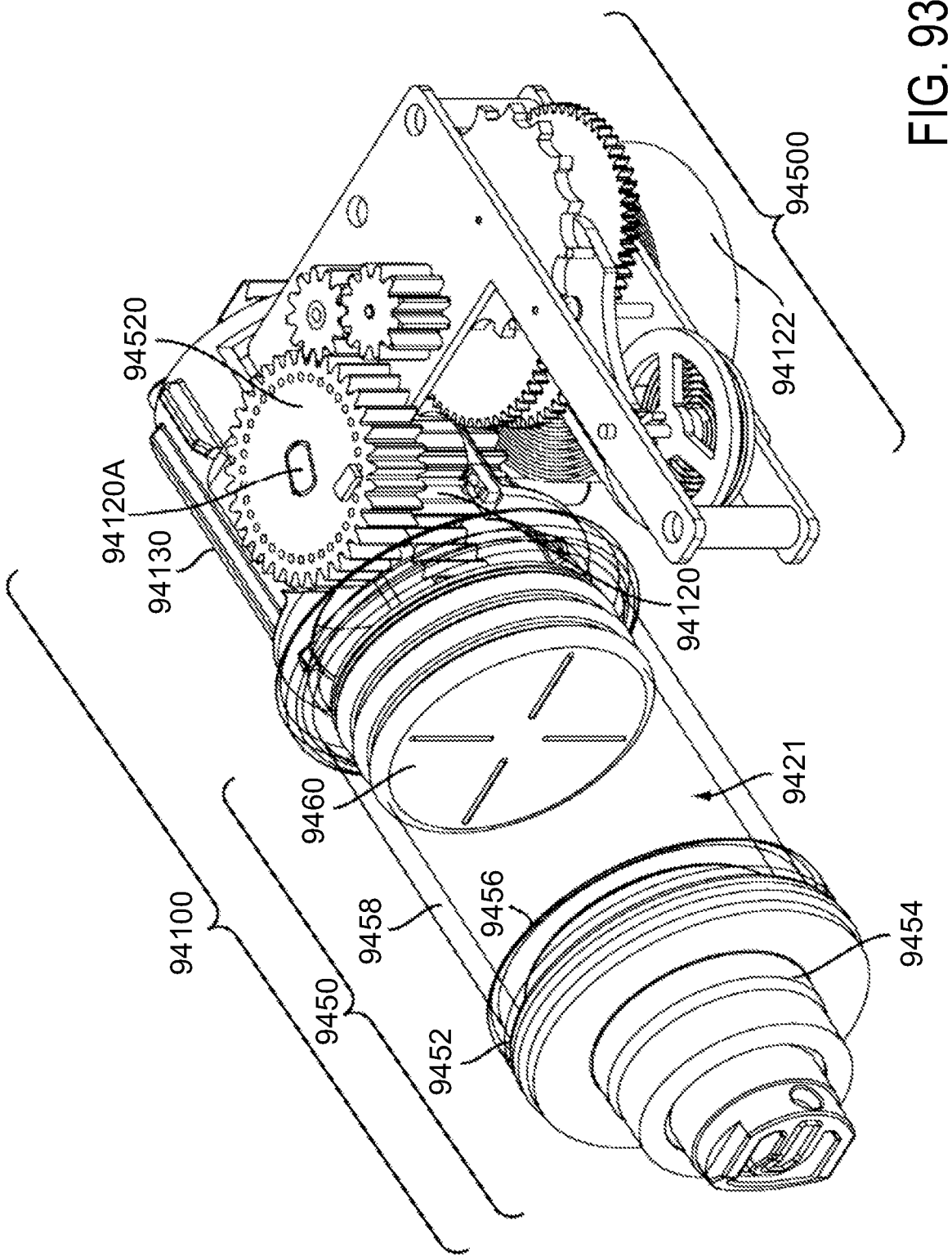
Figure 94A:
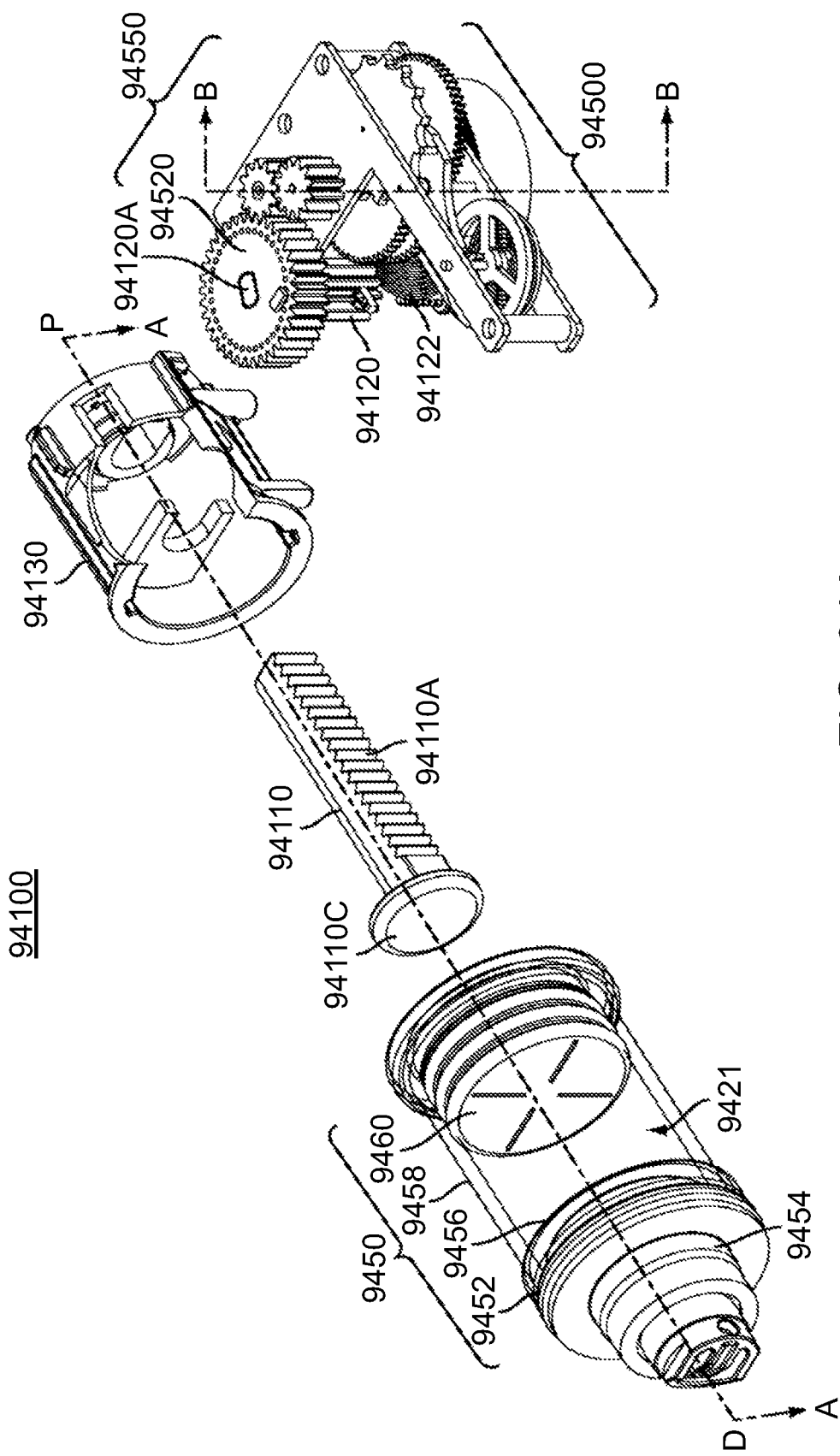
Figure 94B:
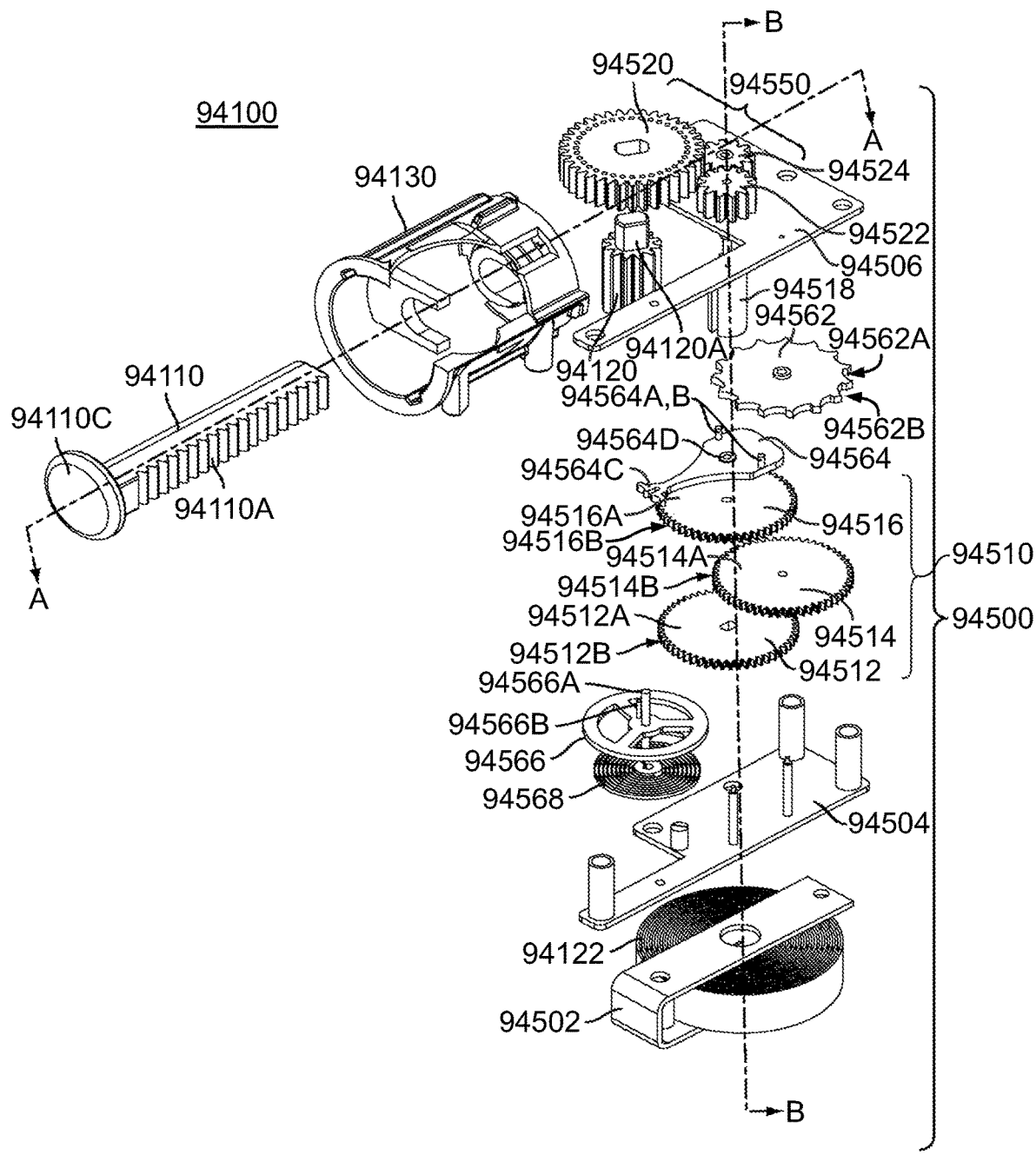
Figure 95A:
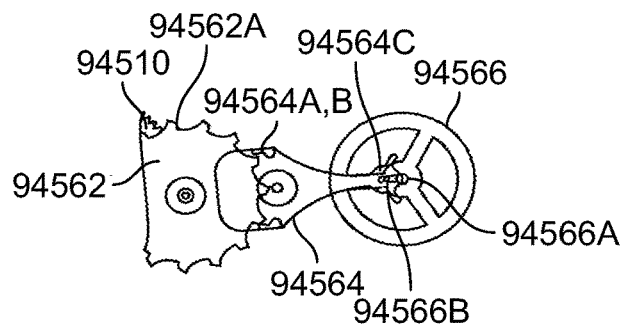
Figure 95B:
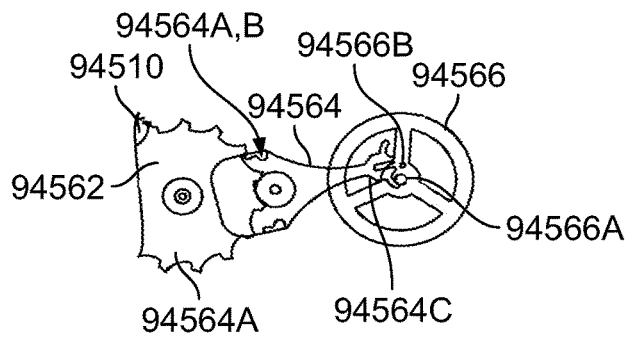
Figure 95C:
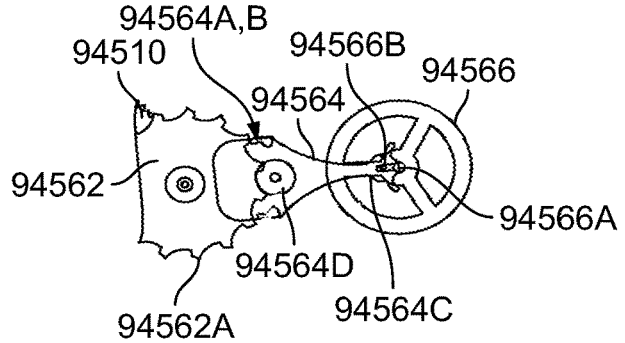
Figure 95D:
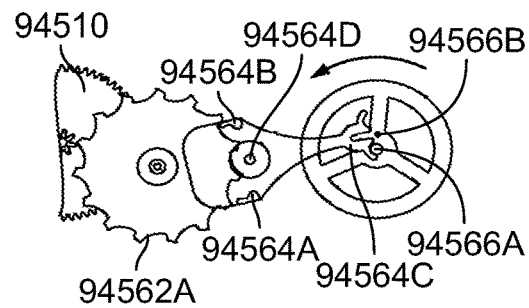
Figure 95E:
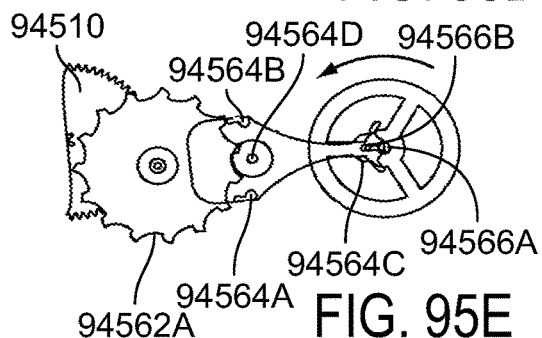
Figure 95F:
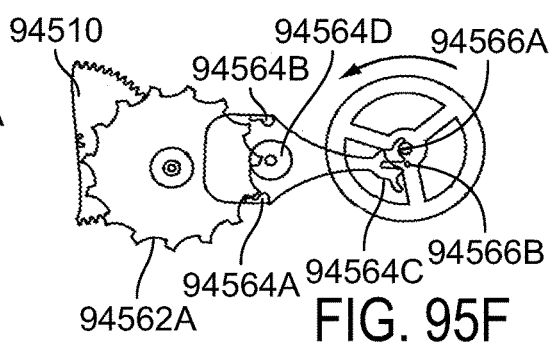
Figure 95G:
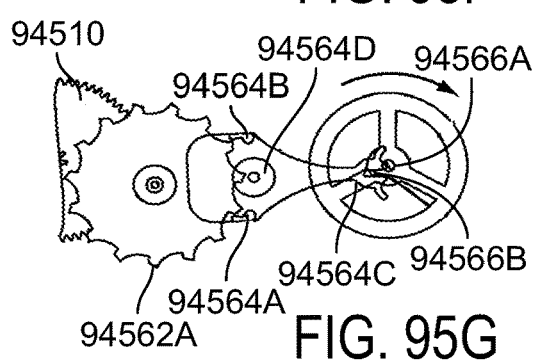
Figure 95H:
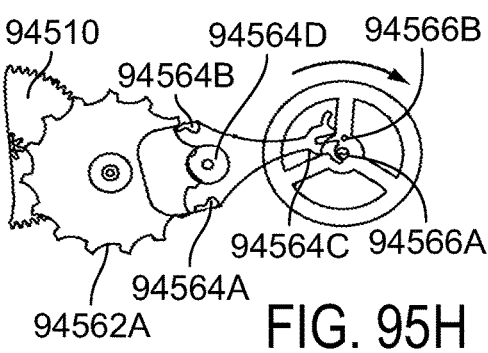
Figure 96A:
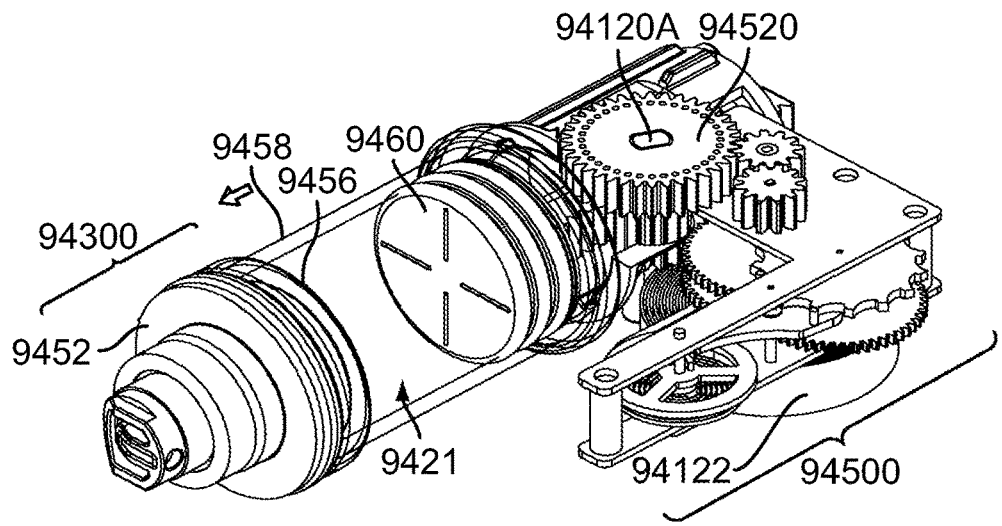
Figure 96B:
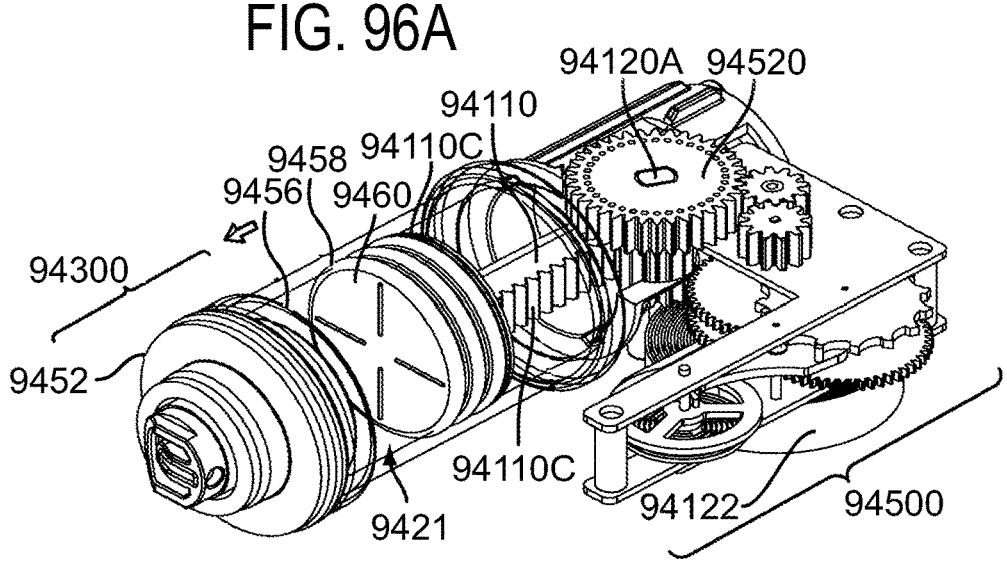
Figure 96C:
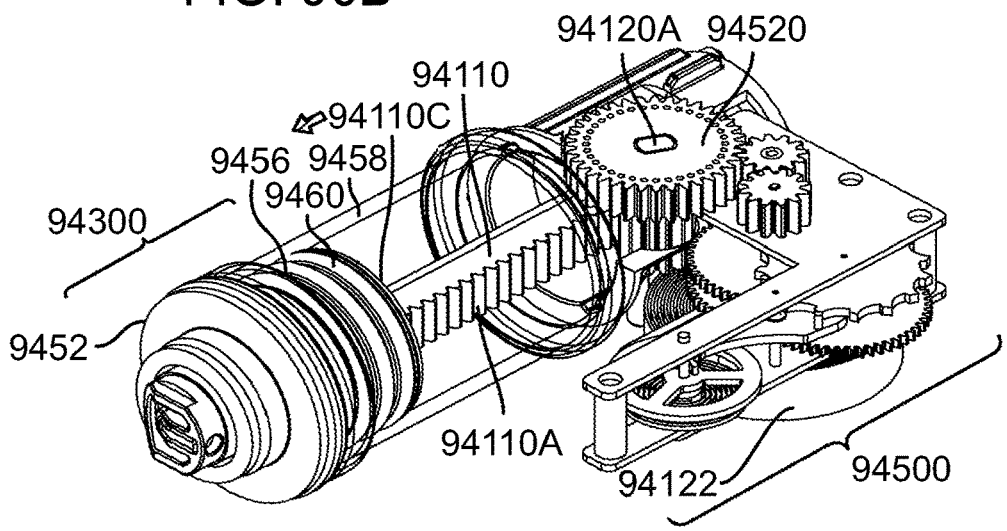
Figure 97A:
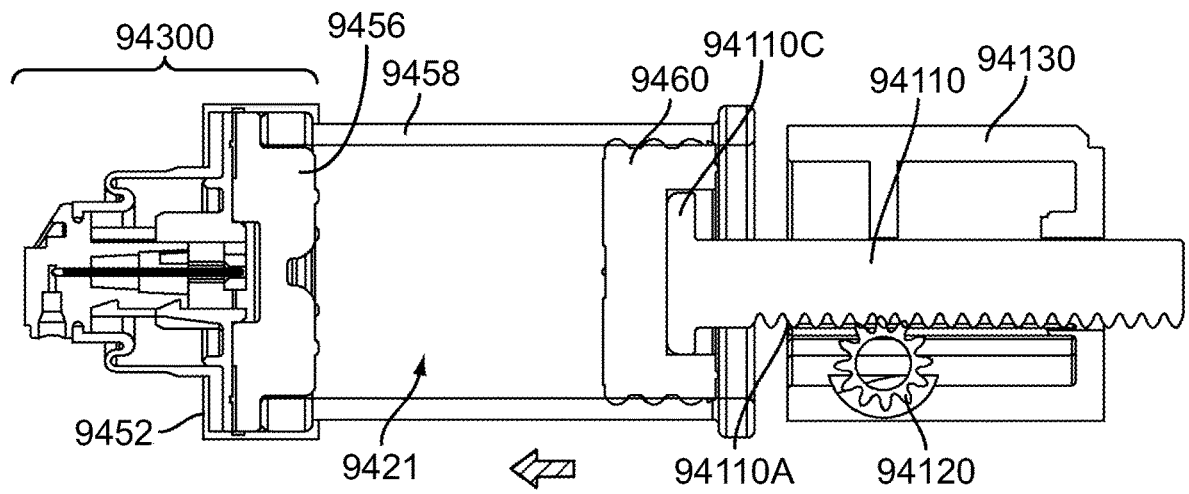
Figure 97B:
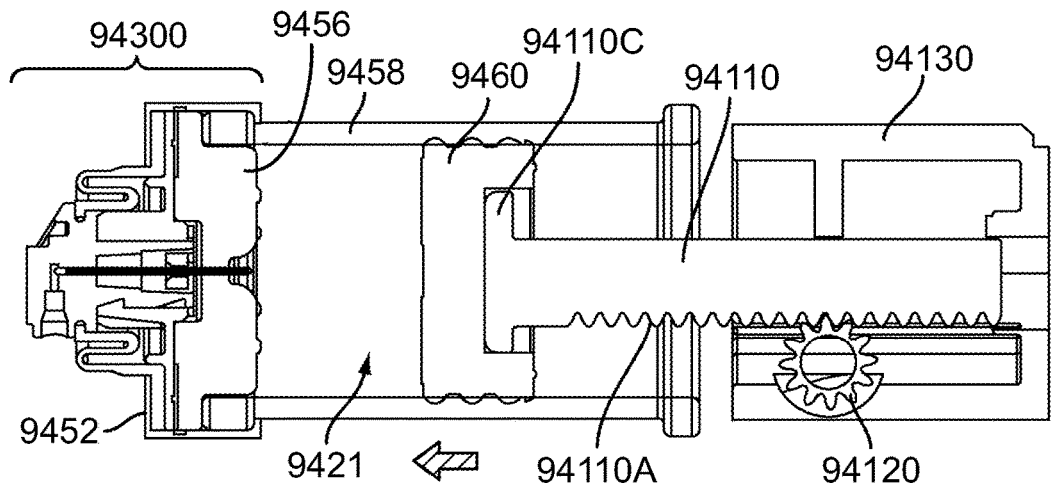
Figure 97C:
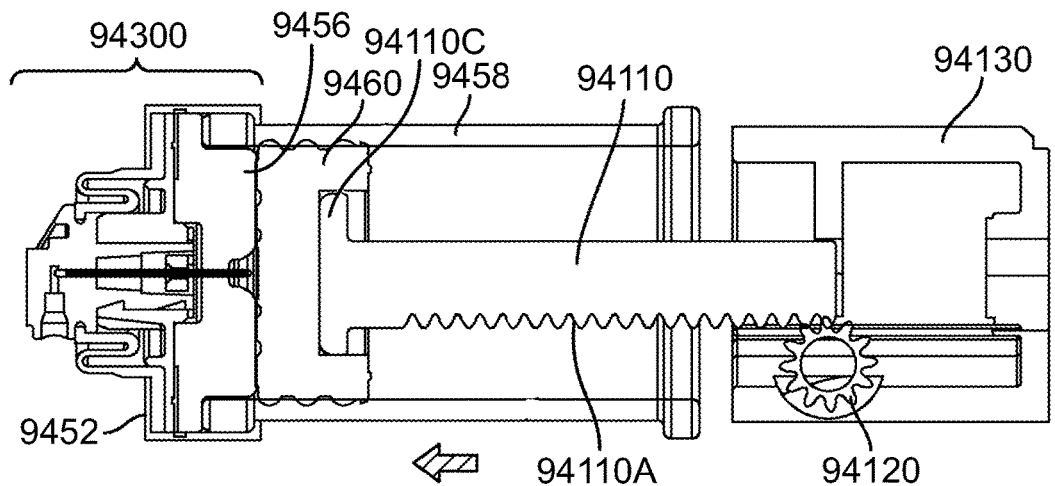
Figure 98:
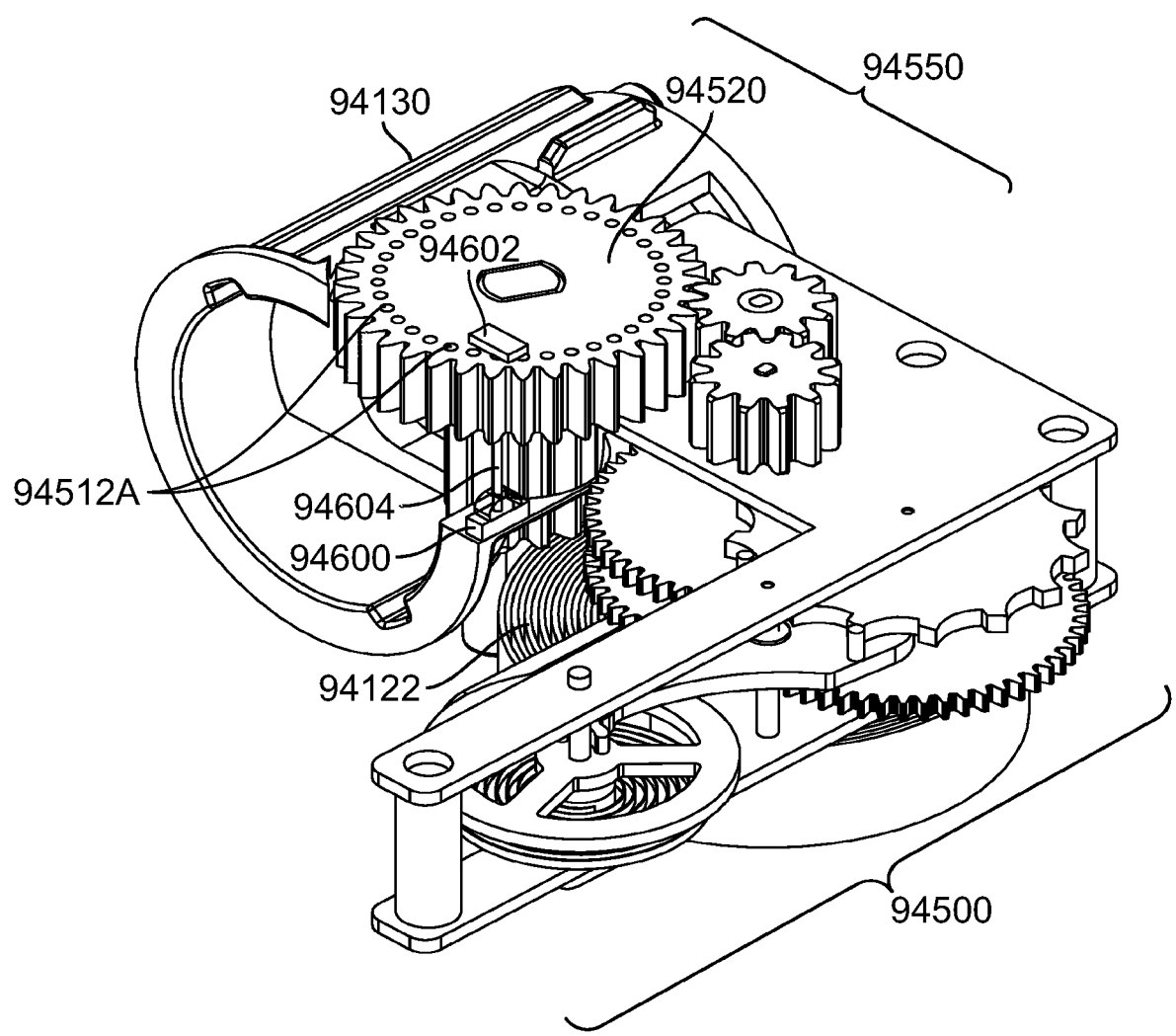
Figure 99:
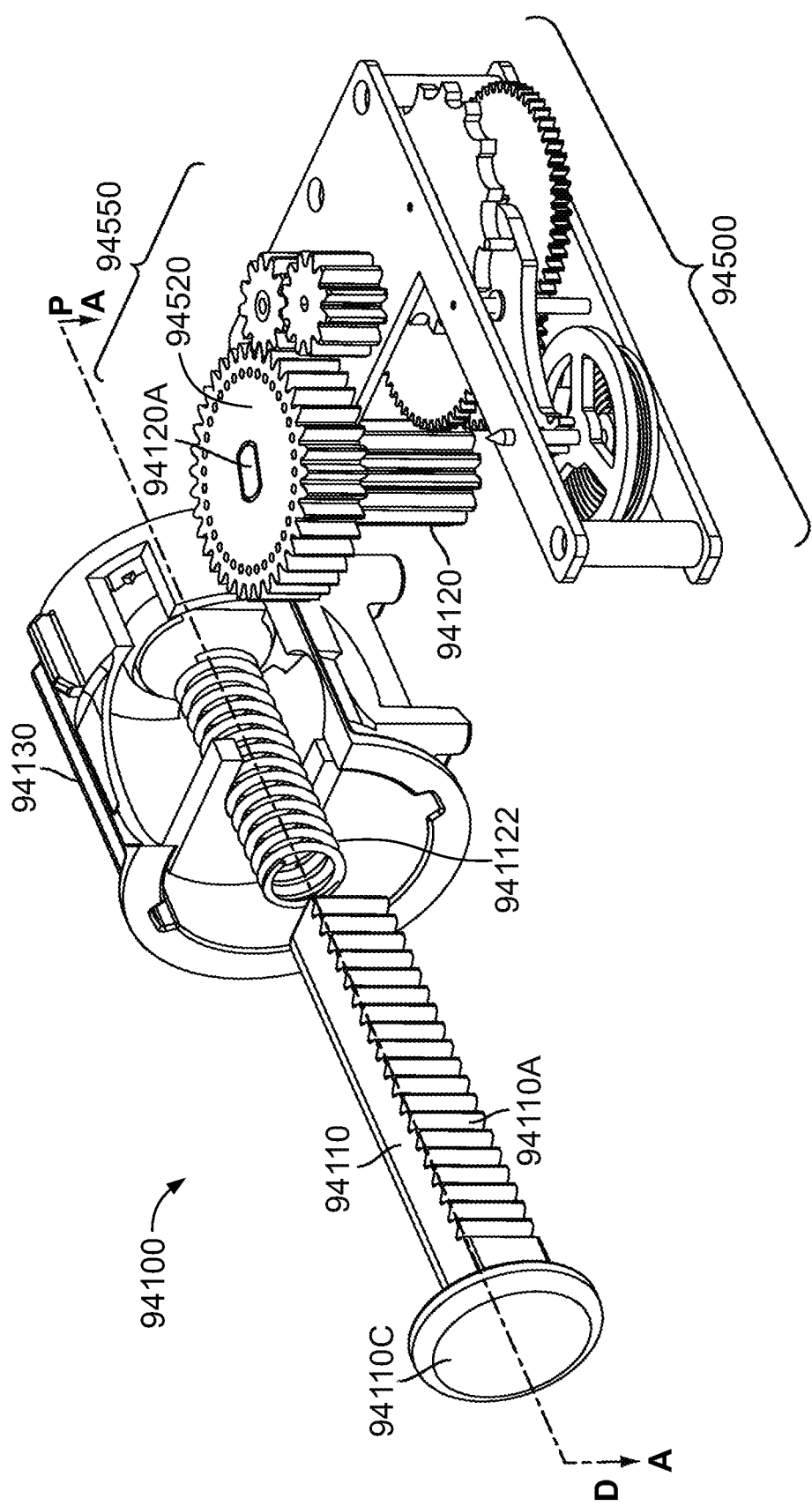
Figure 100A:
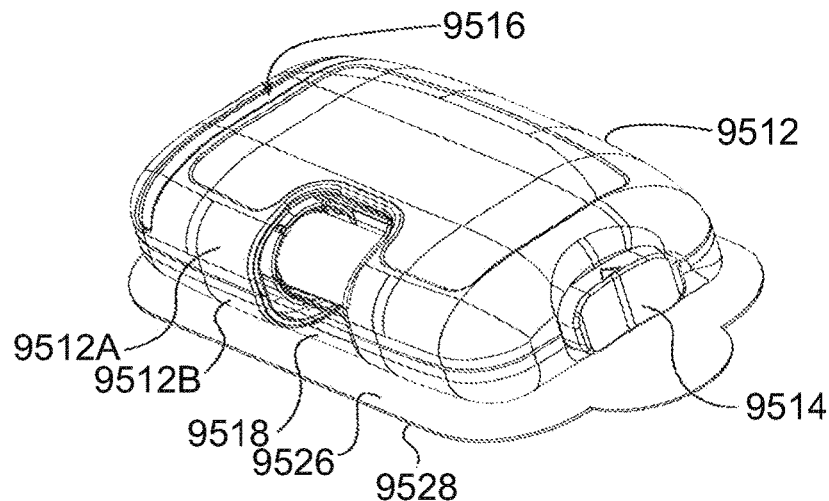
Figure 100B:
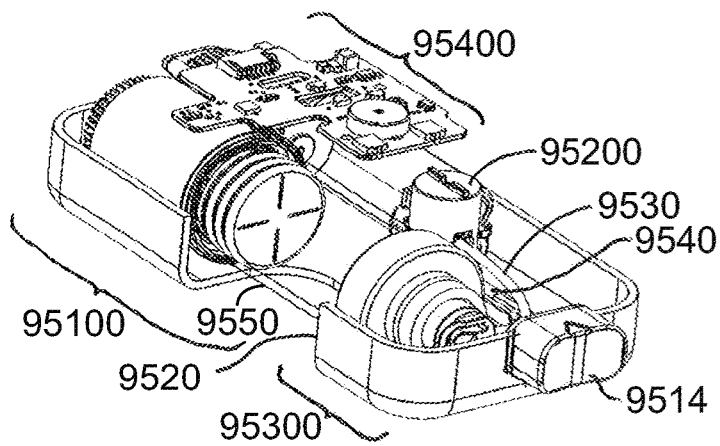
Figure 100C:
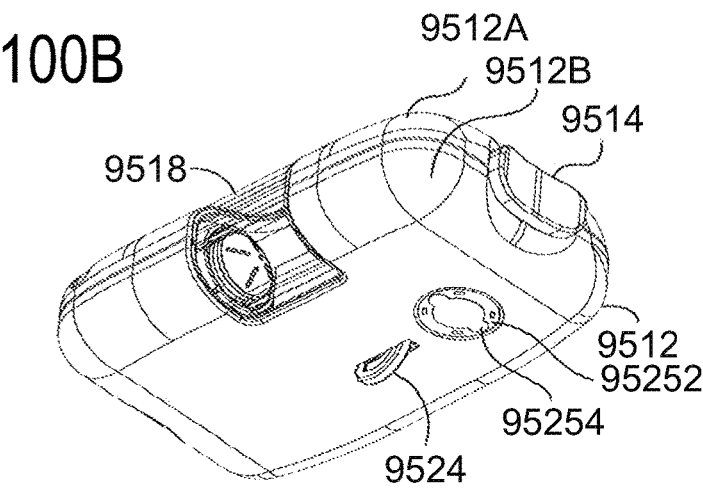
Figure 101:
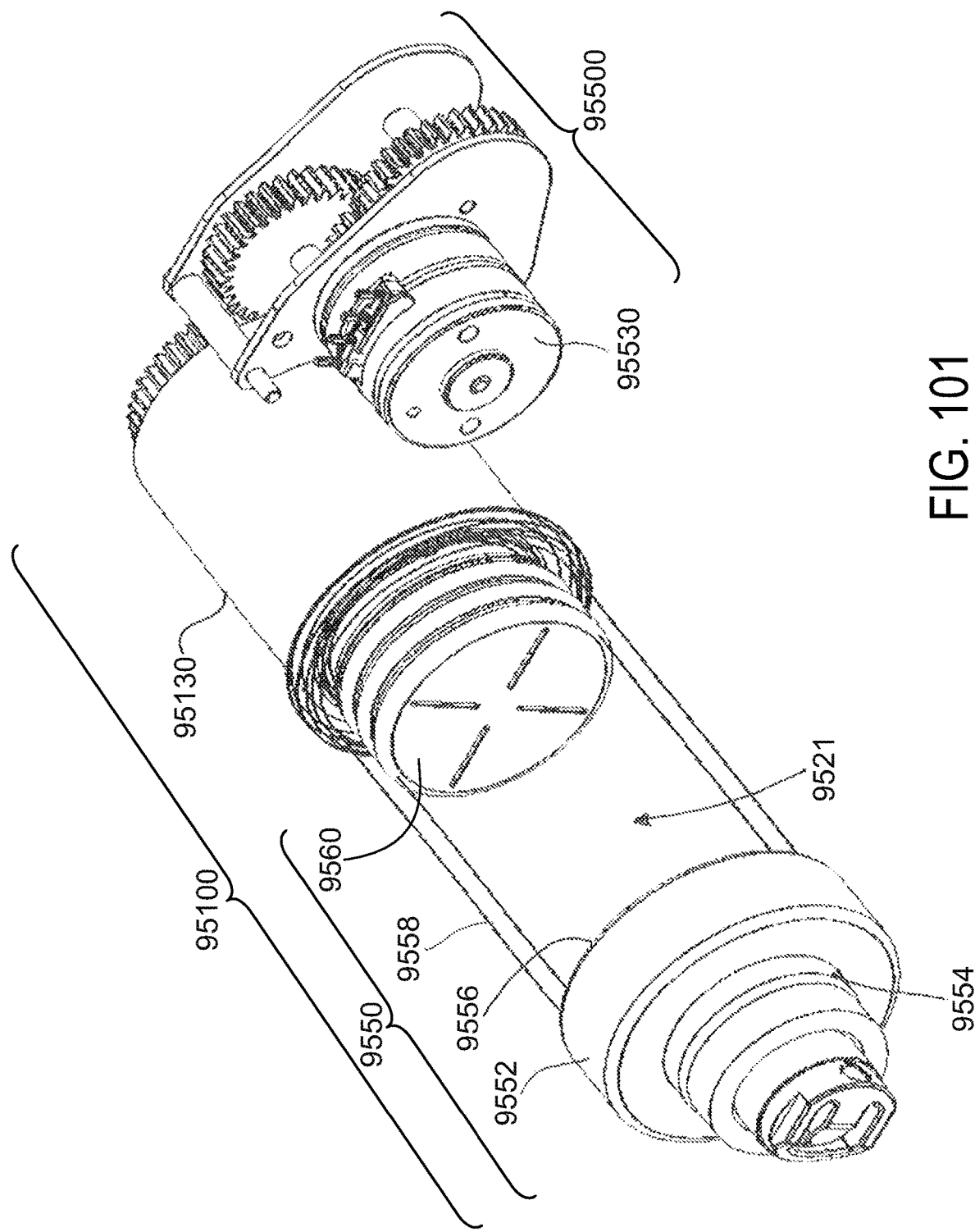
Figure 102:
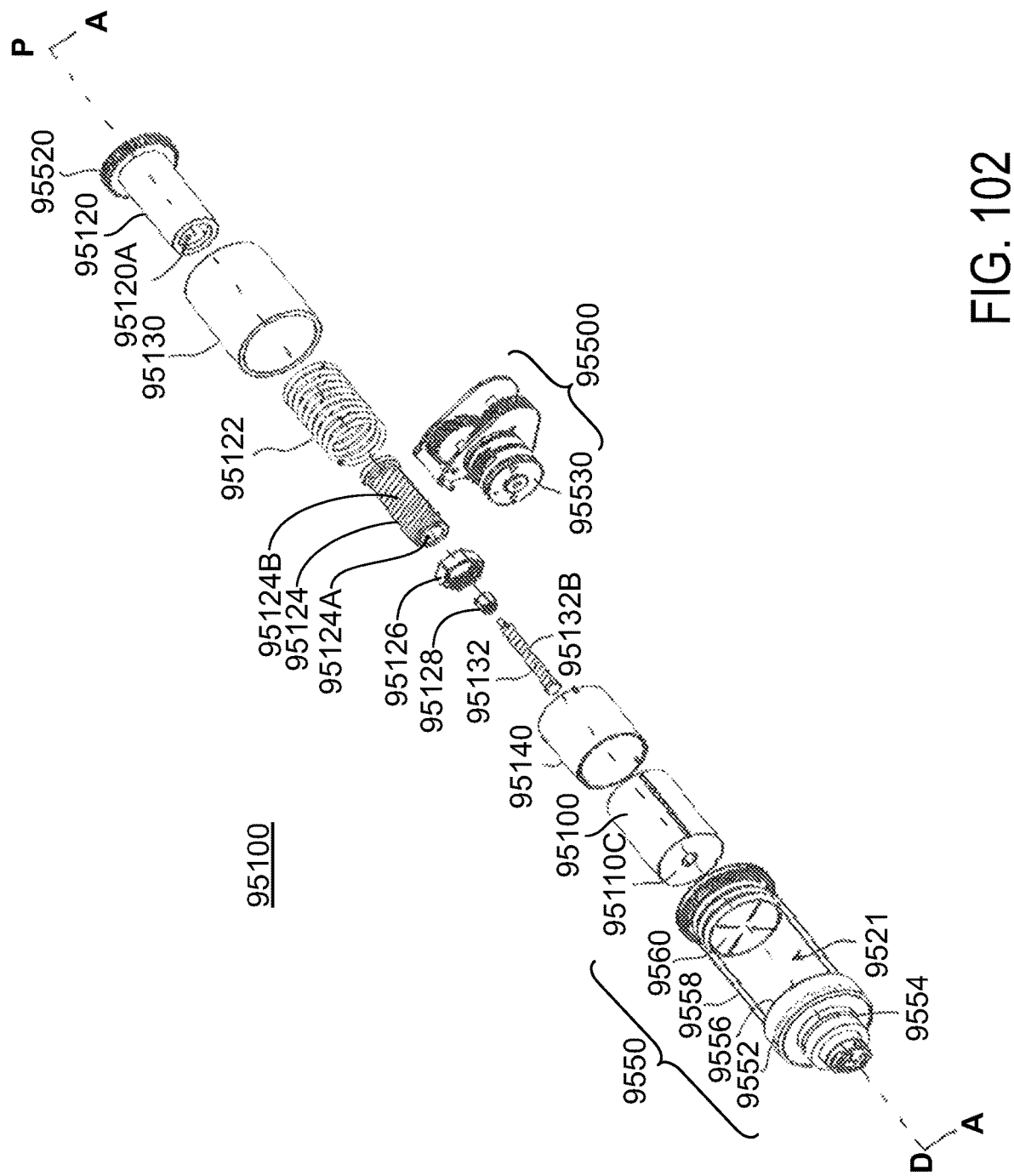
Figure 103A:
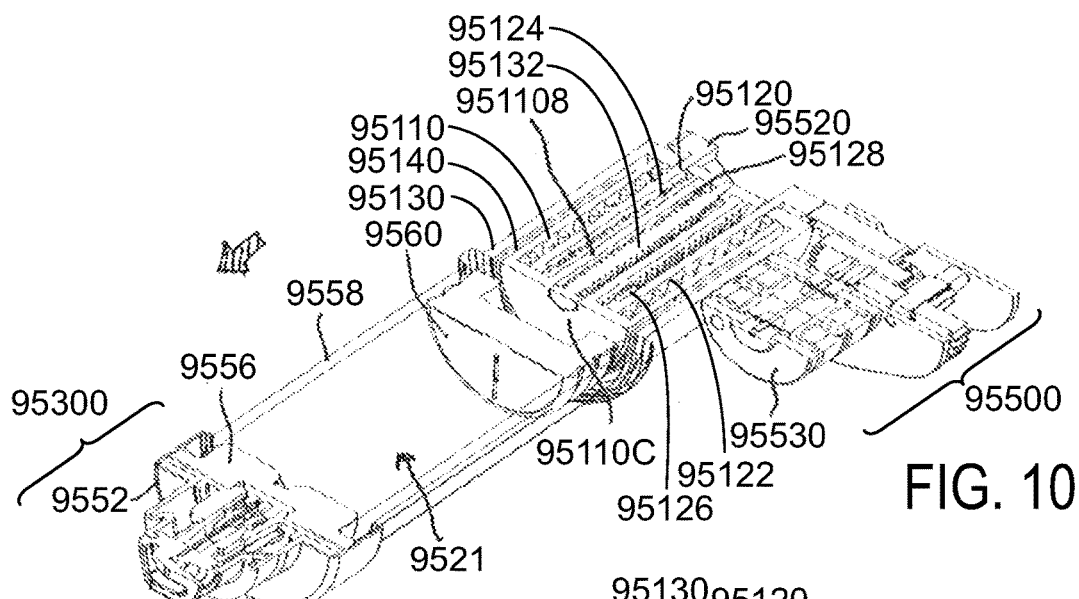
Figure 103B:
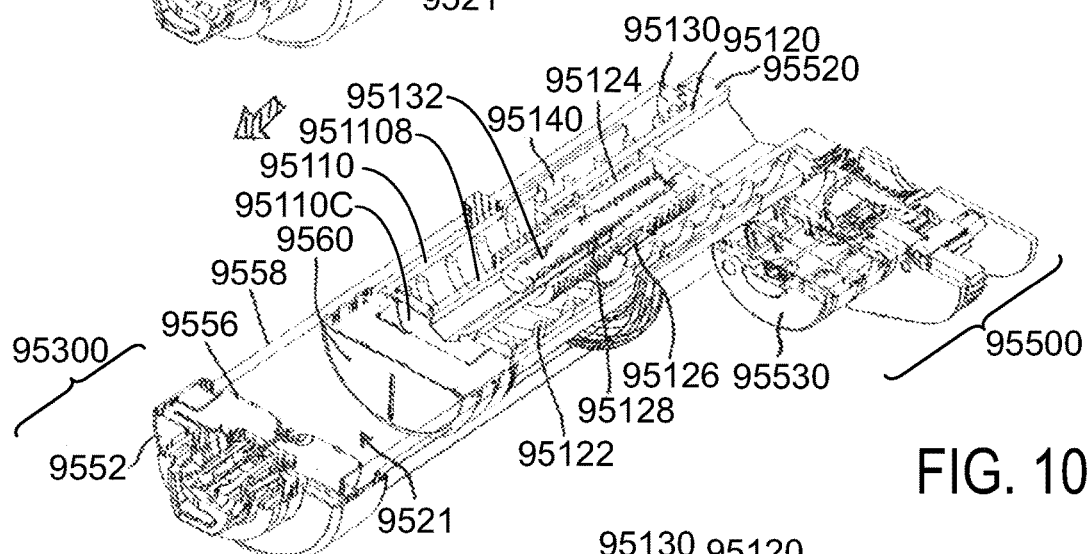
Figure 103C:
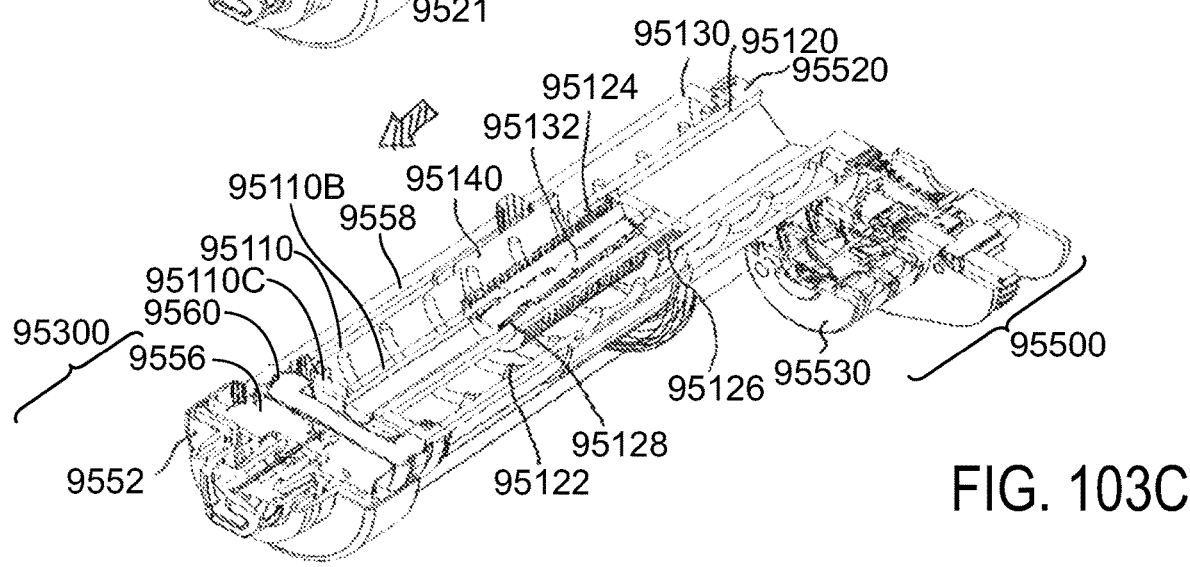
Figure 104A:
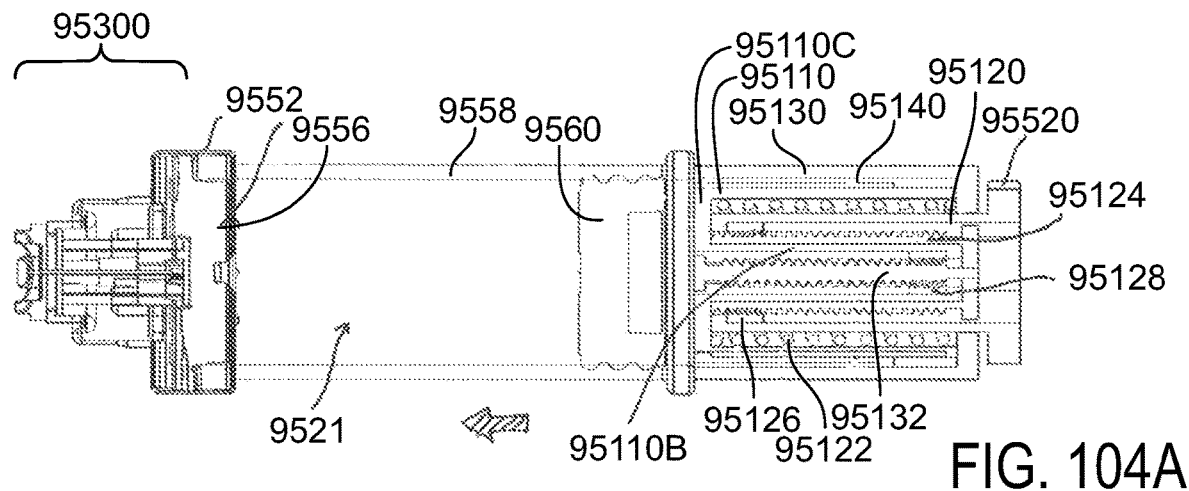
Figure 104B:
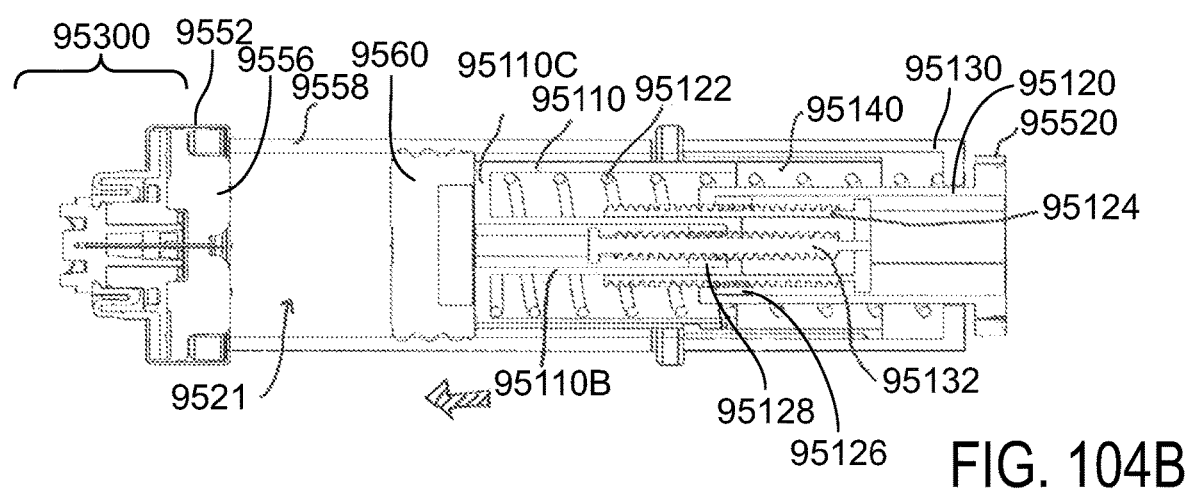
Figure 104C:
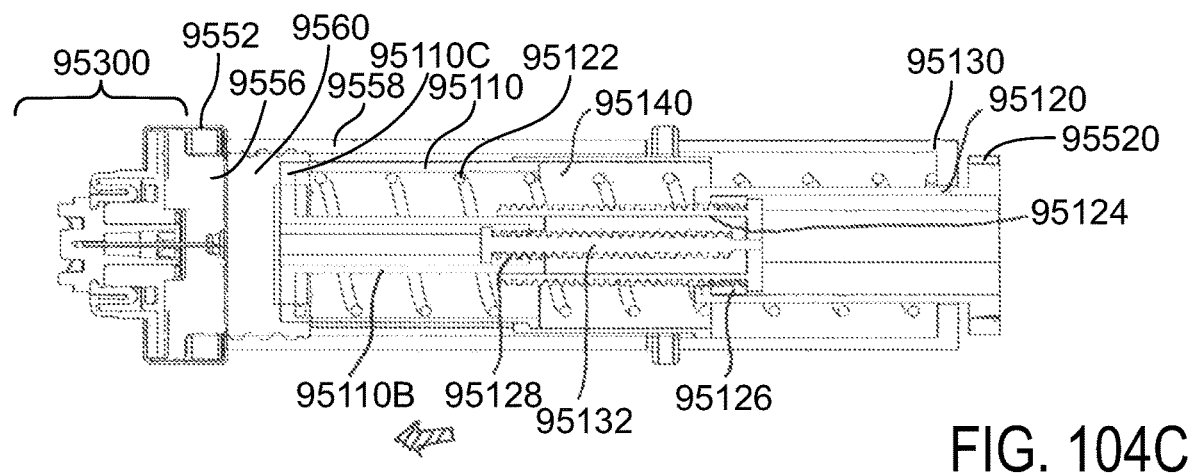
Figure 105:
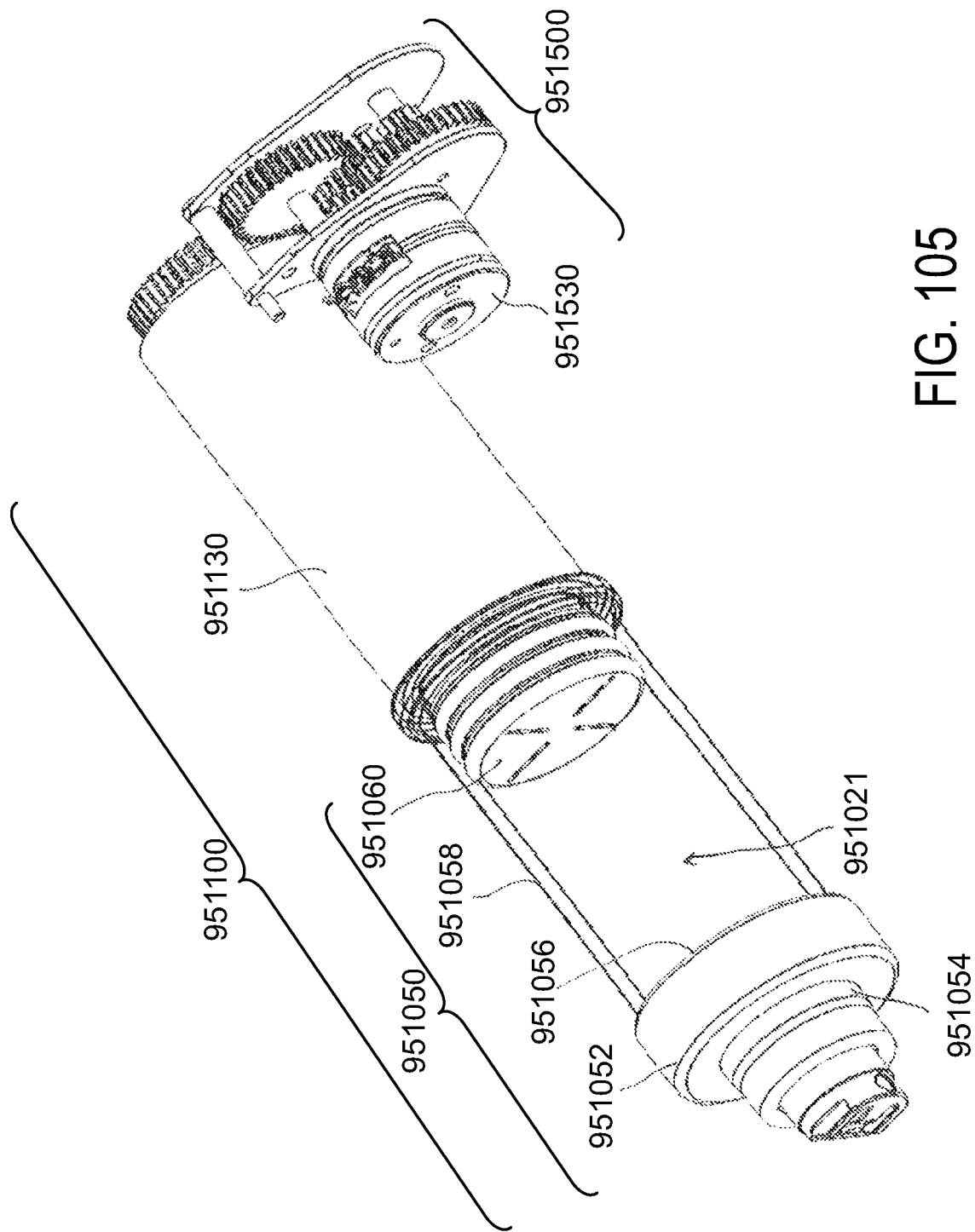
Figure 106:
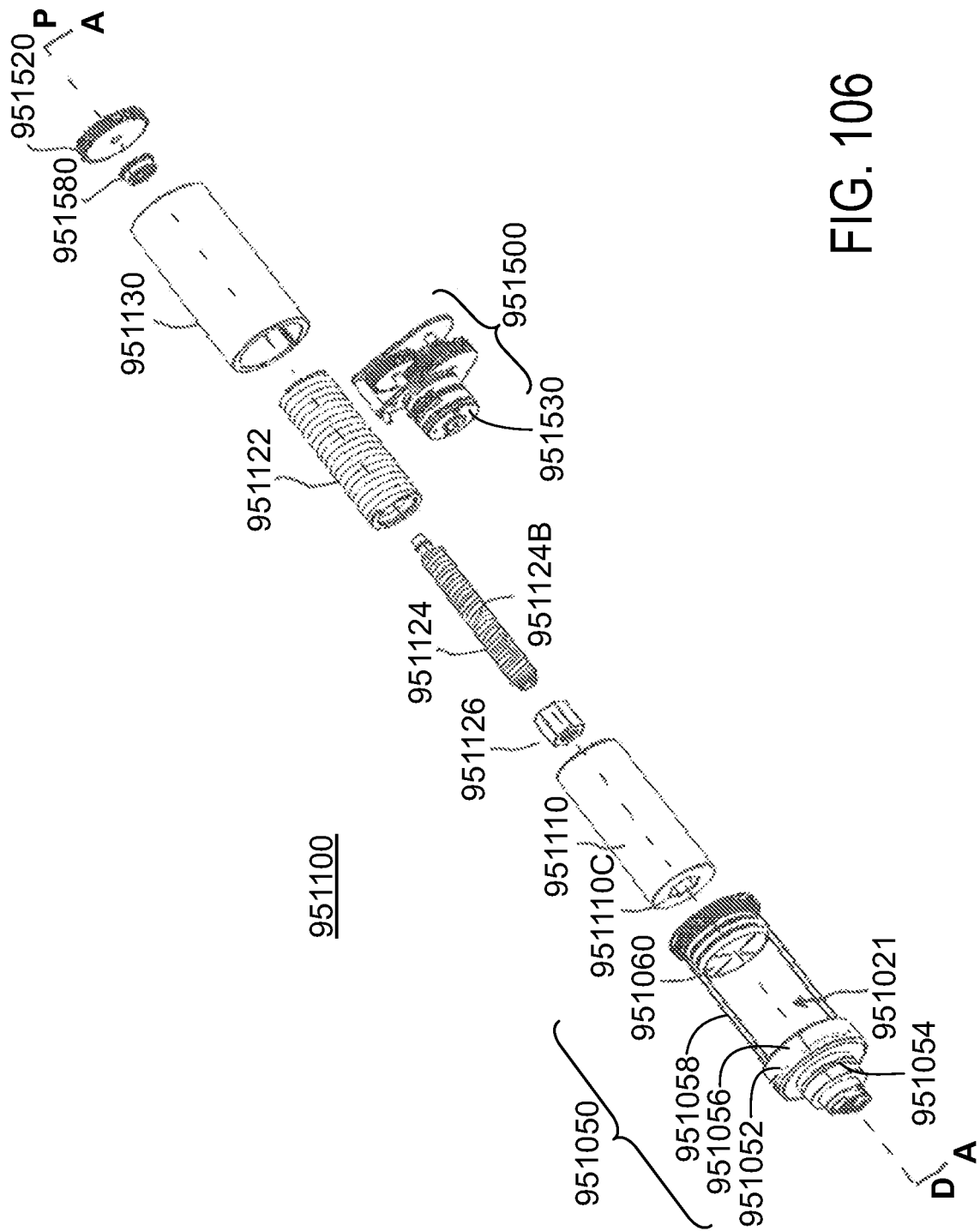
Figure 107A:
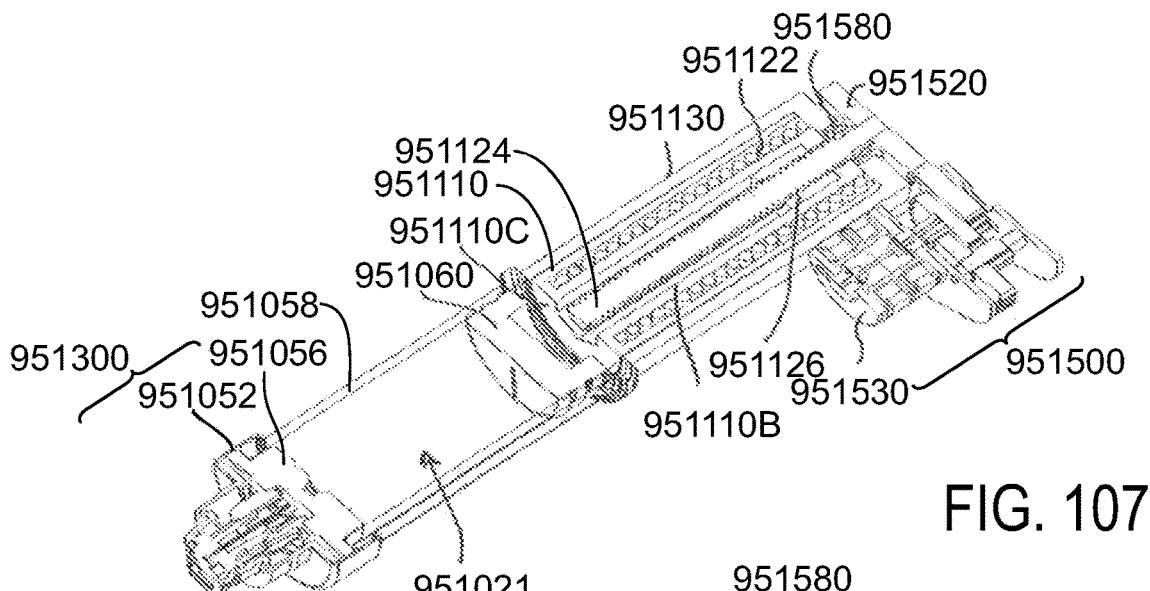
Figure 107B:
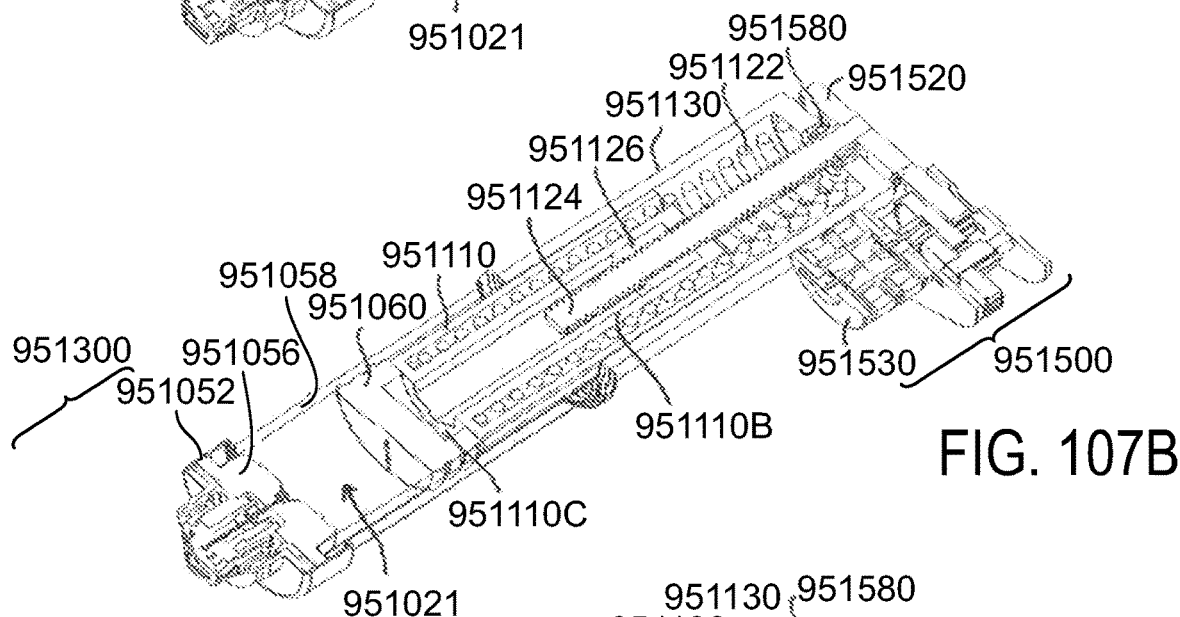
Figure 107C:
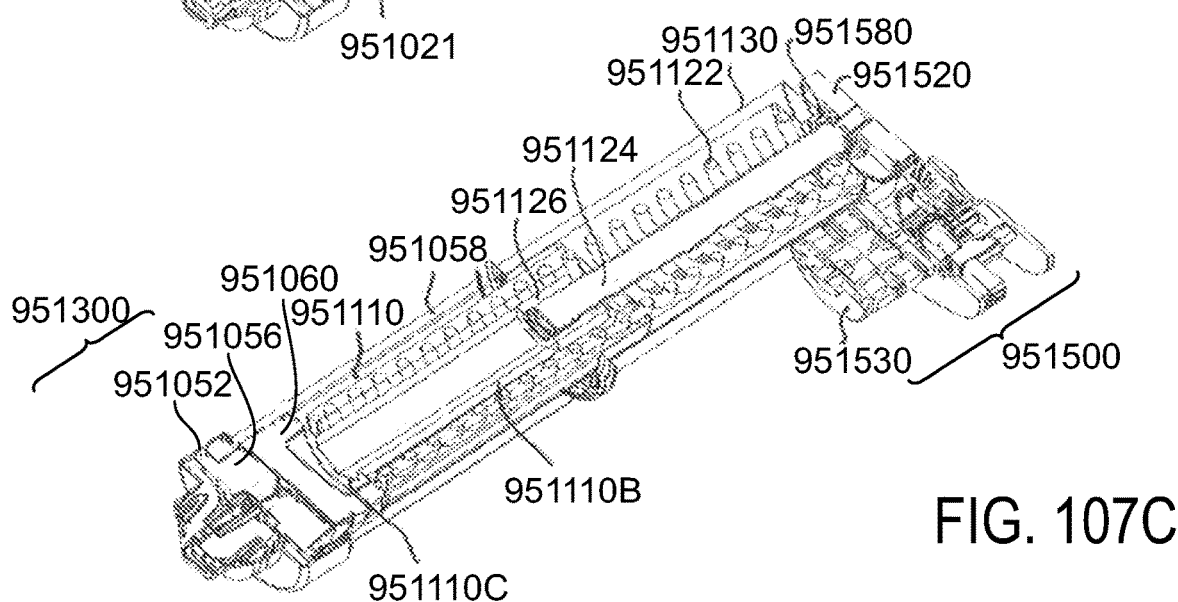
Figure 108A:
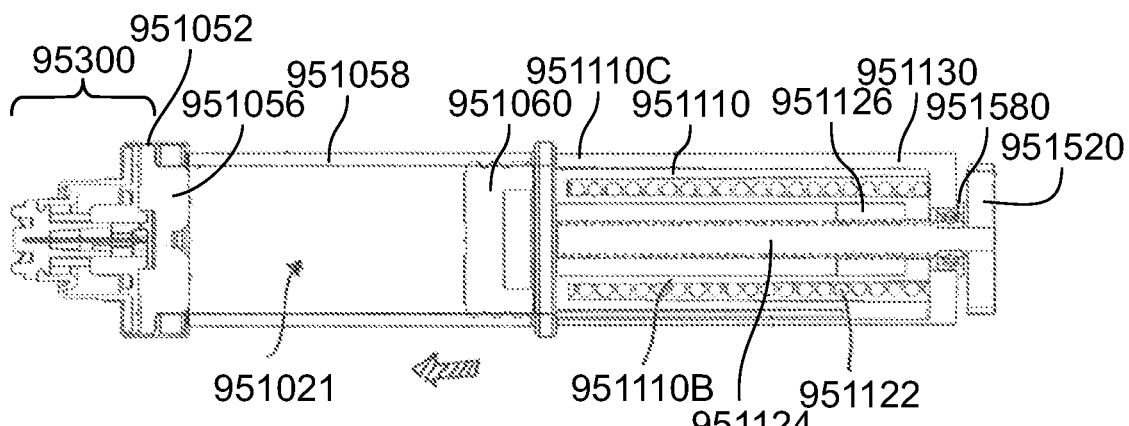
Figure 108B:
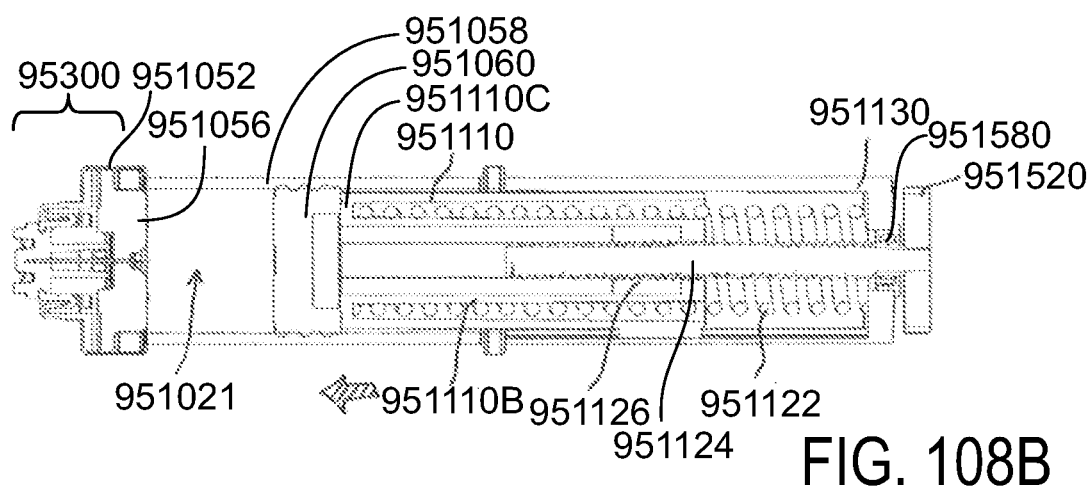
Figure 108C:
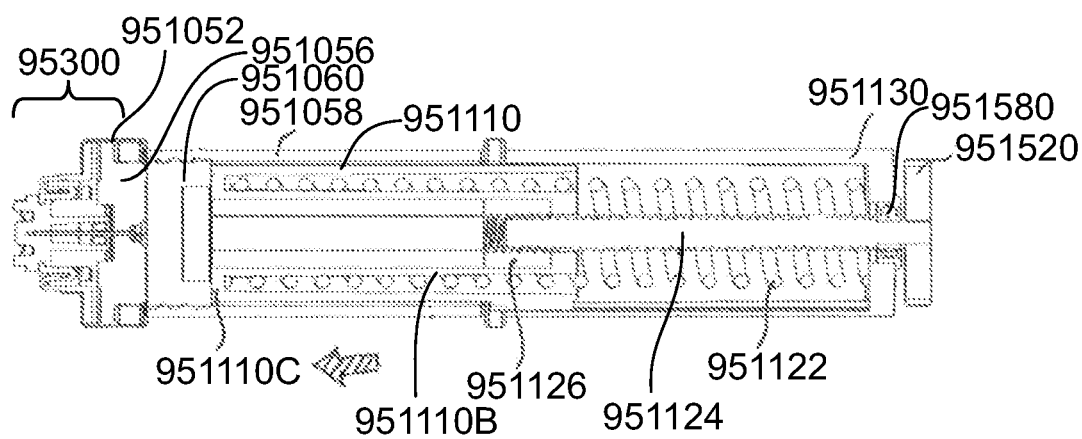
Figure 110A:
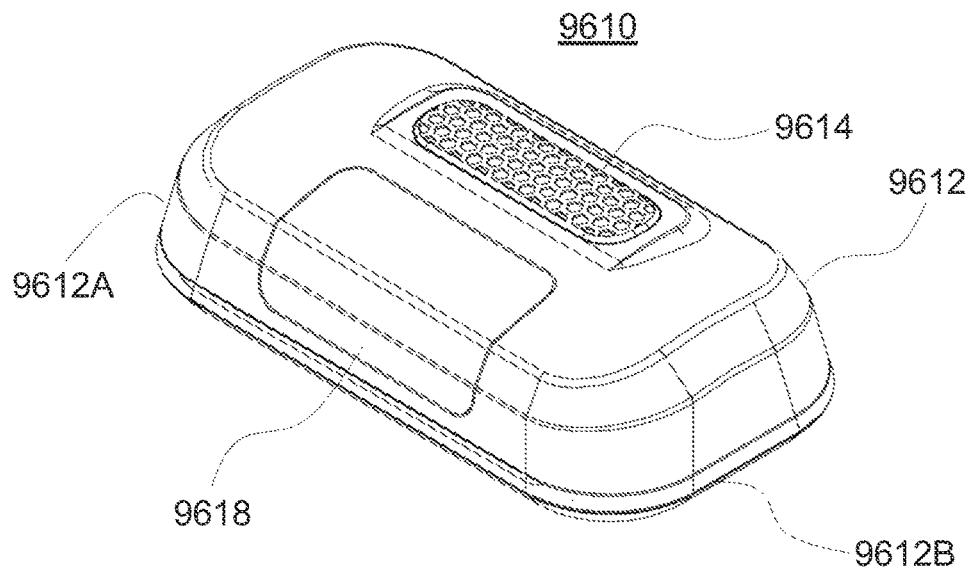
Figure 110B:
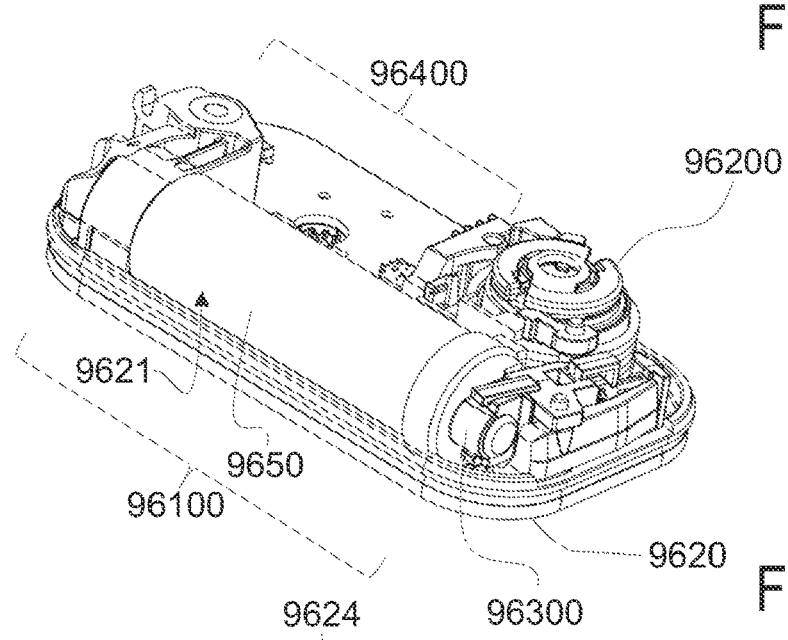
Figure 110C:
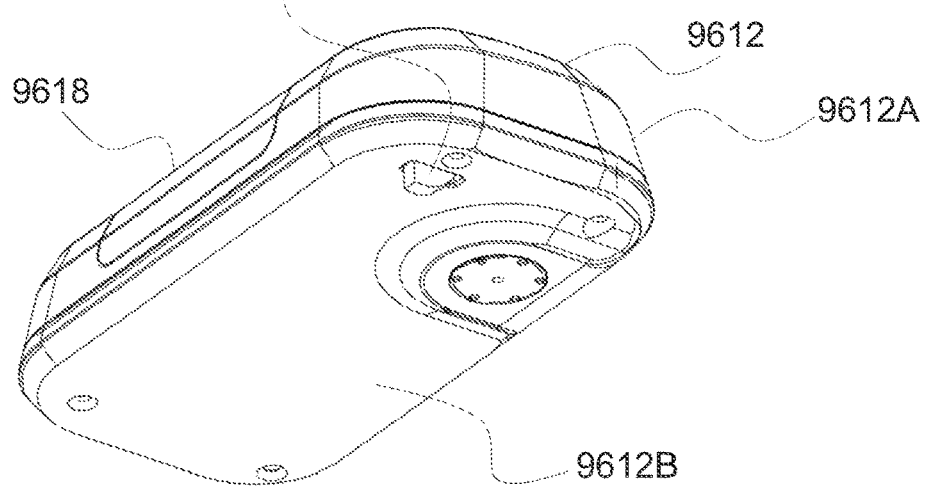
Figure 111A:
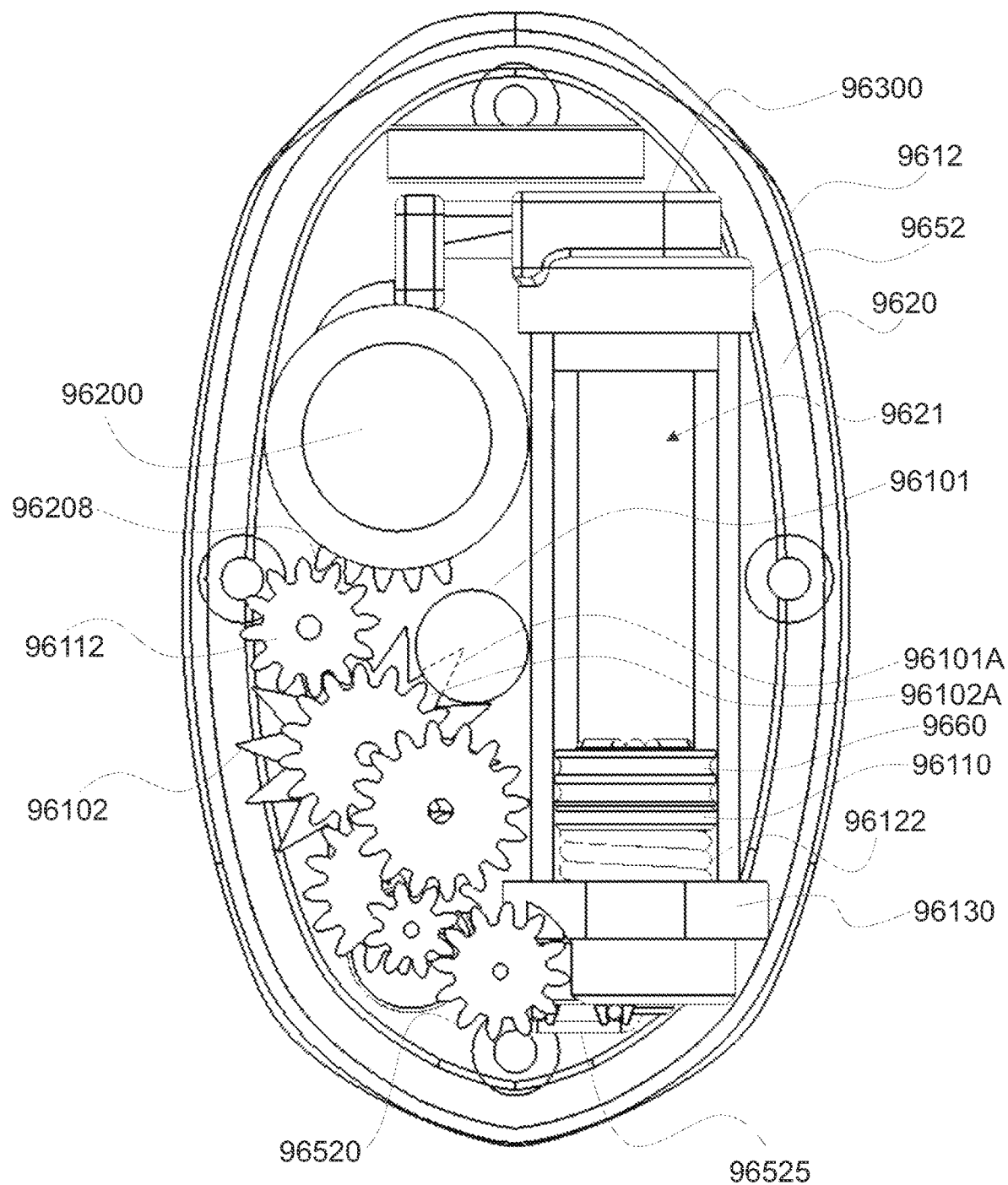
Figure 111B:
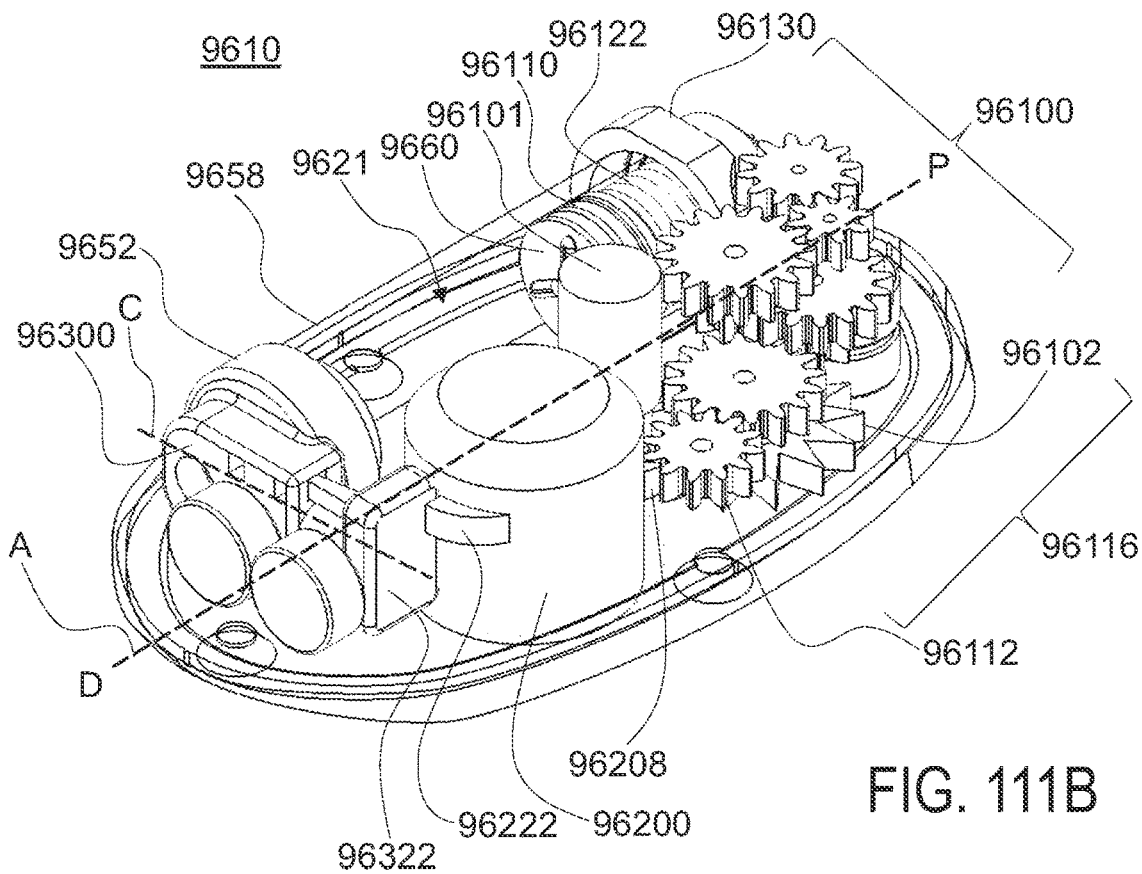
Figure 111C:
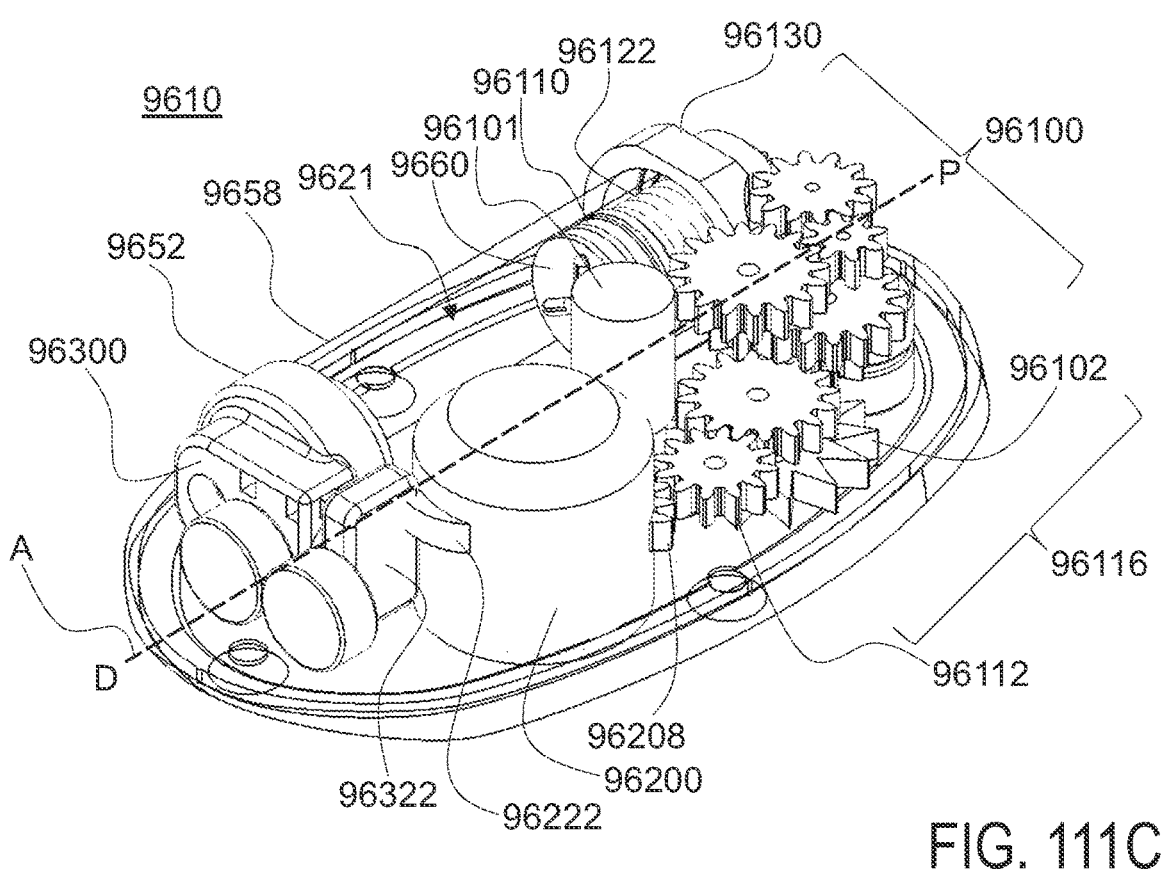
Figure 111D:
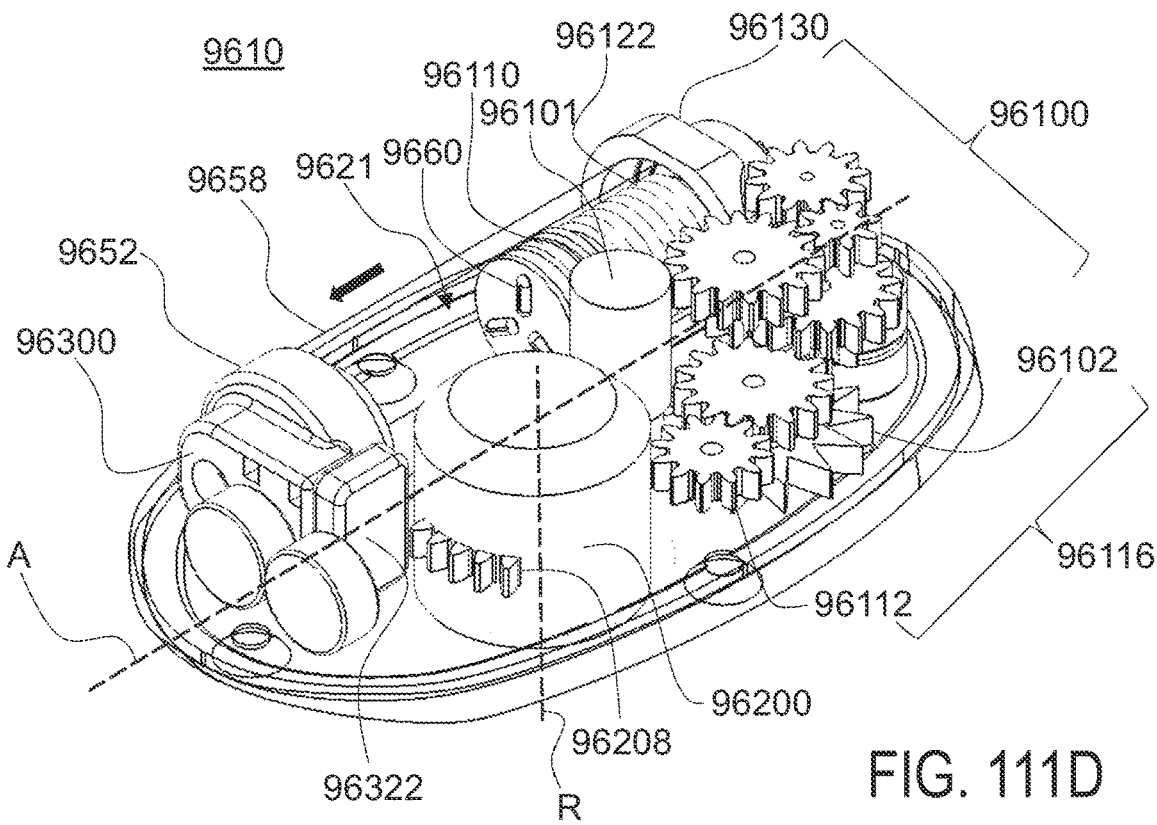
Figure 111E:
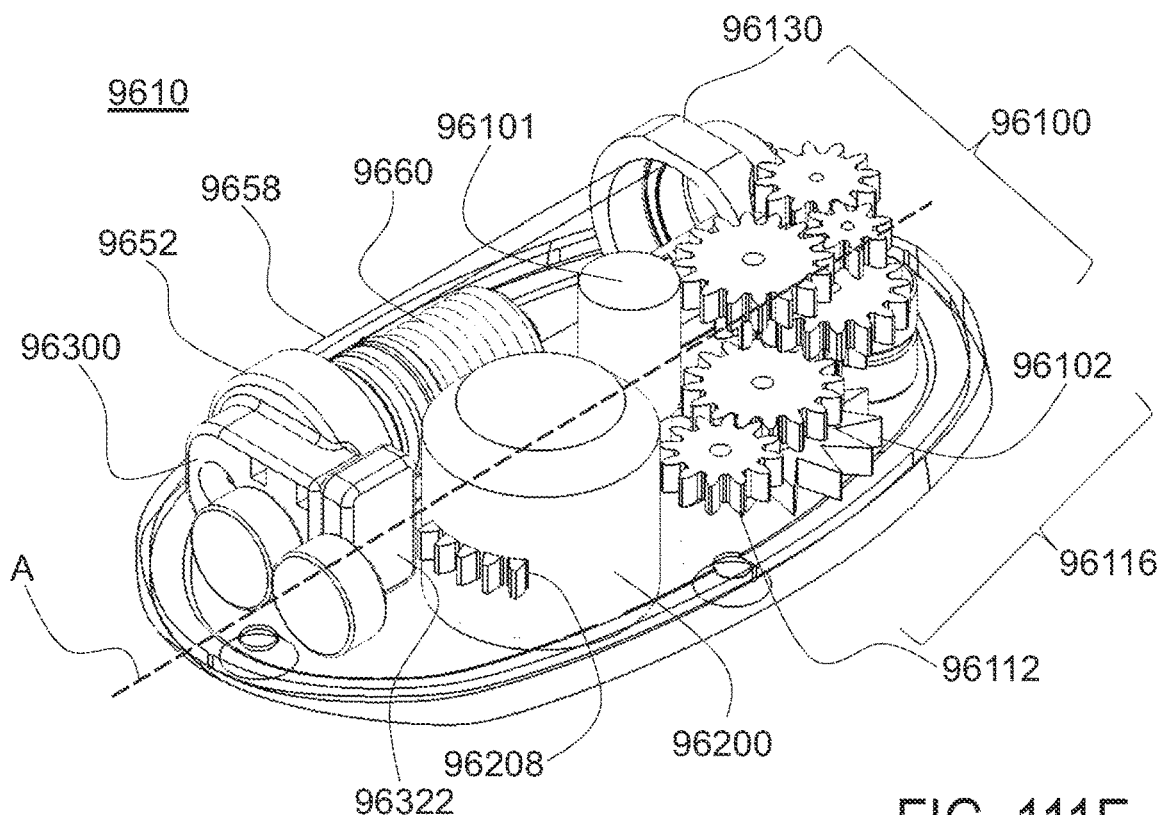
Figure 113:
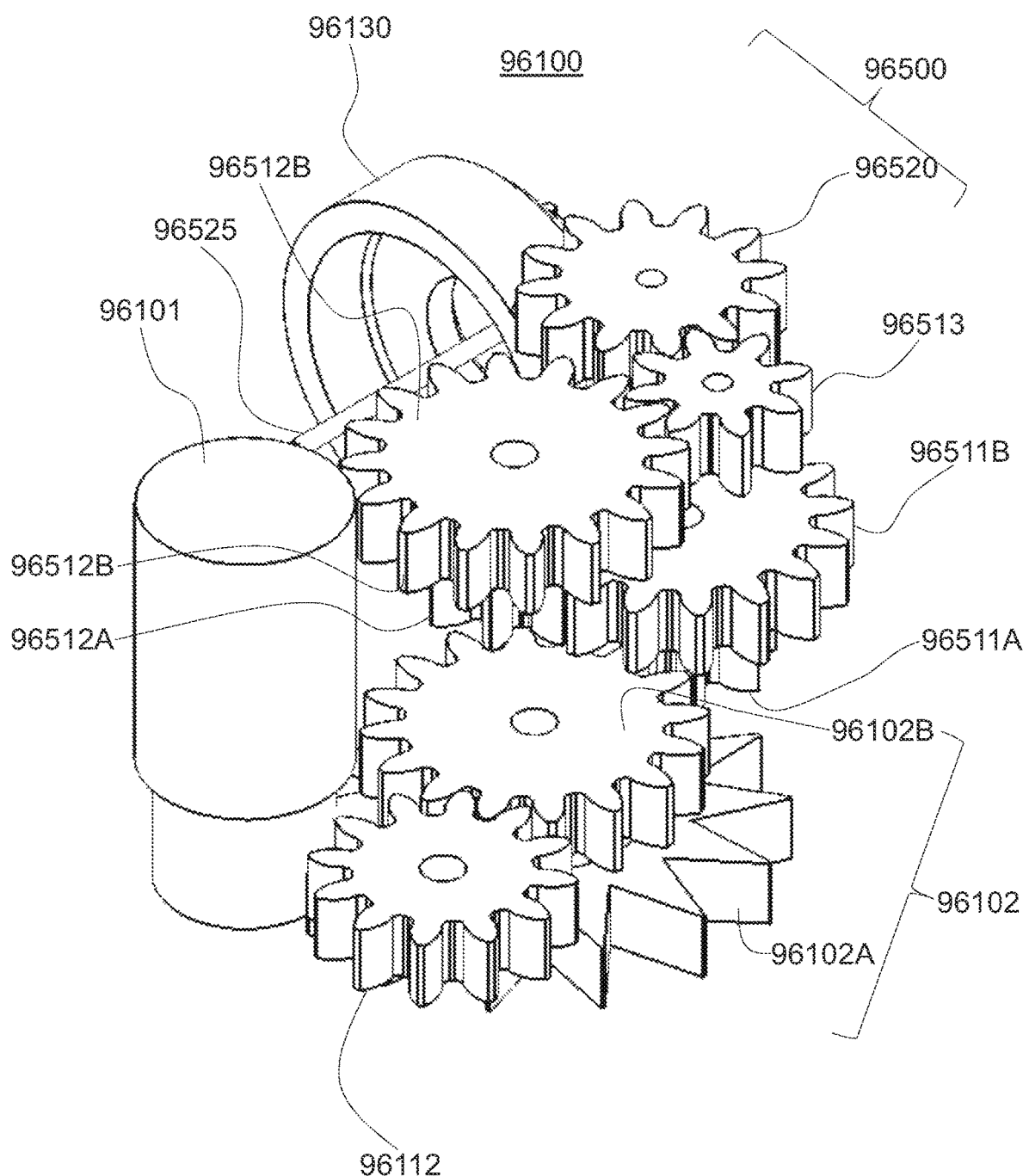
Figure 114A:
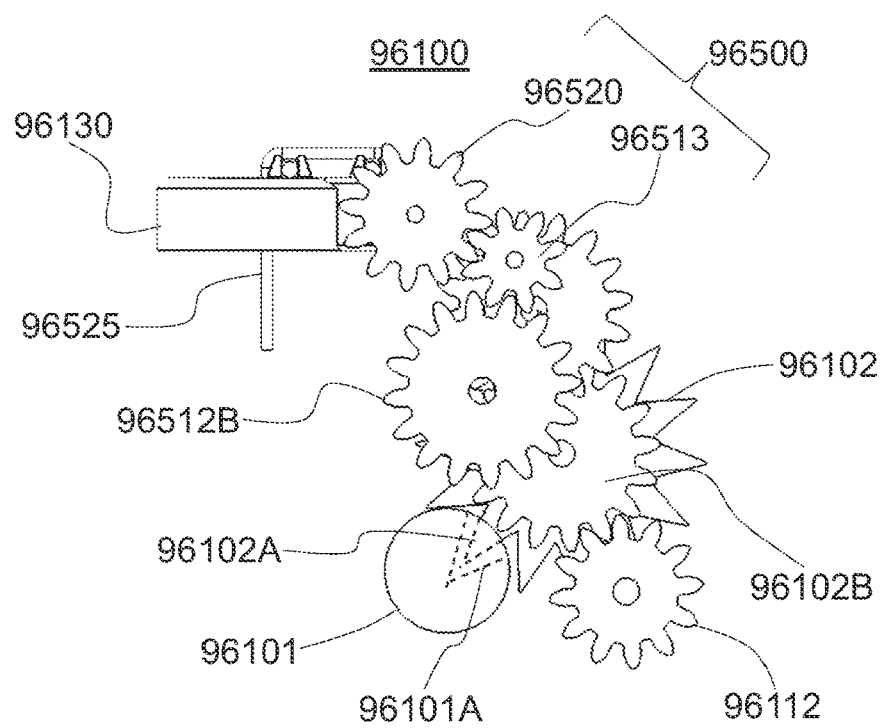
Figure 114B:
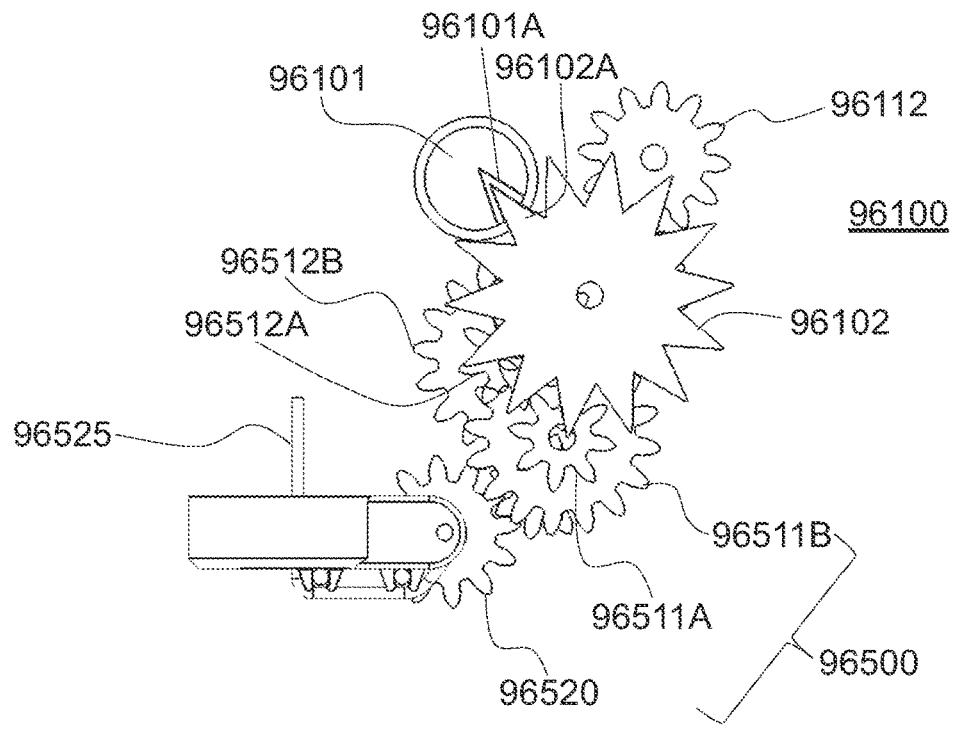
Figure 114C:
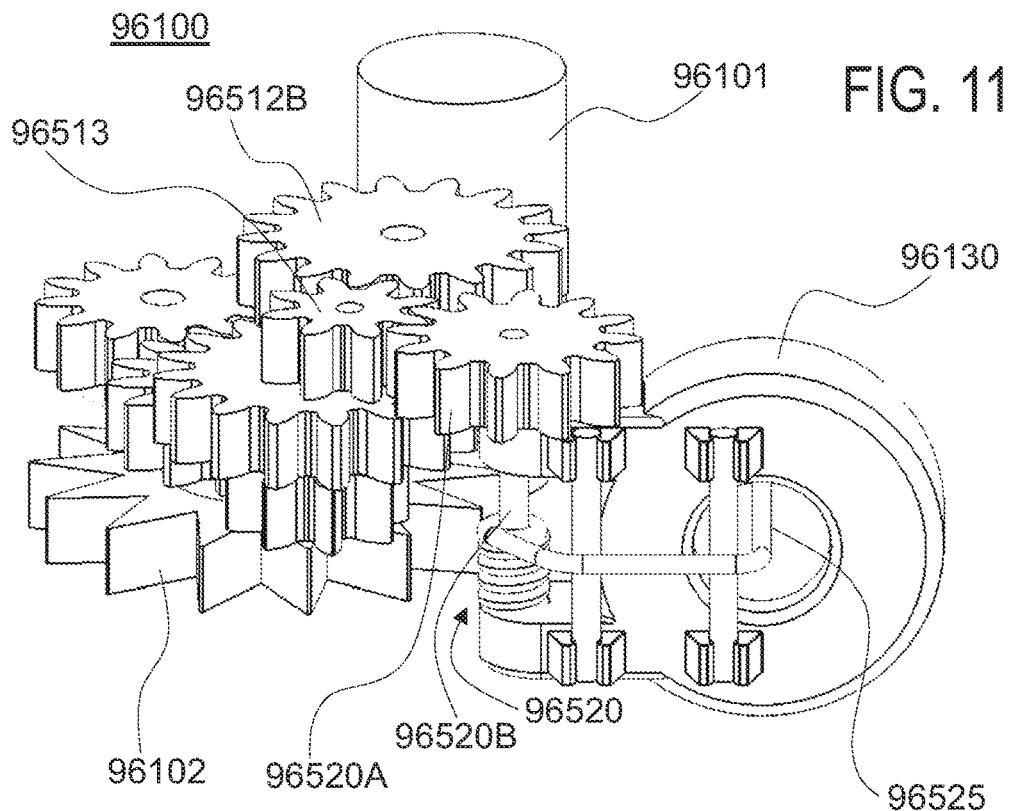
Figure 114D:
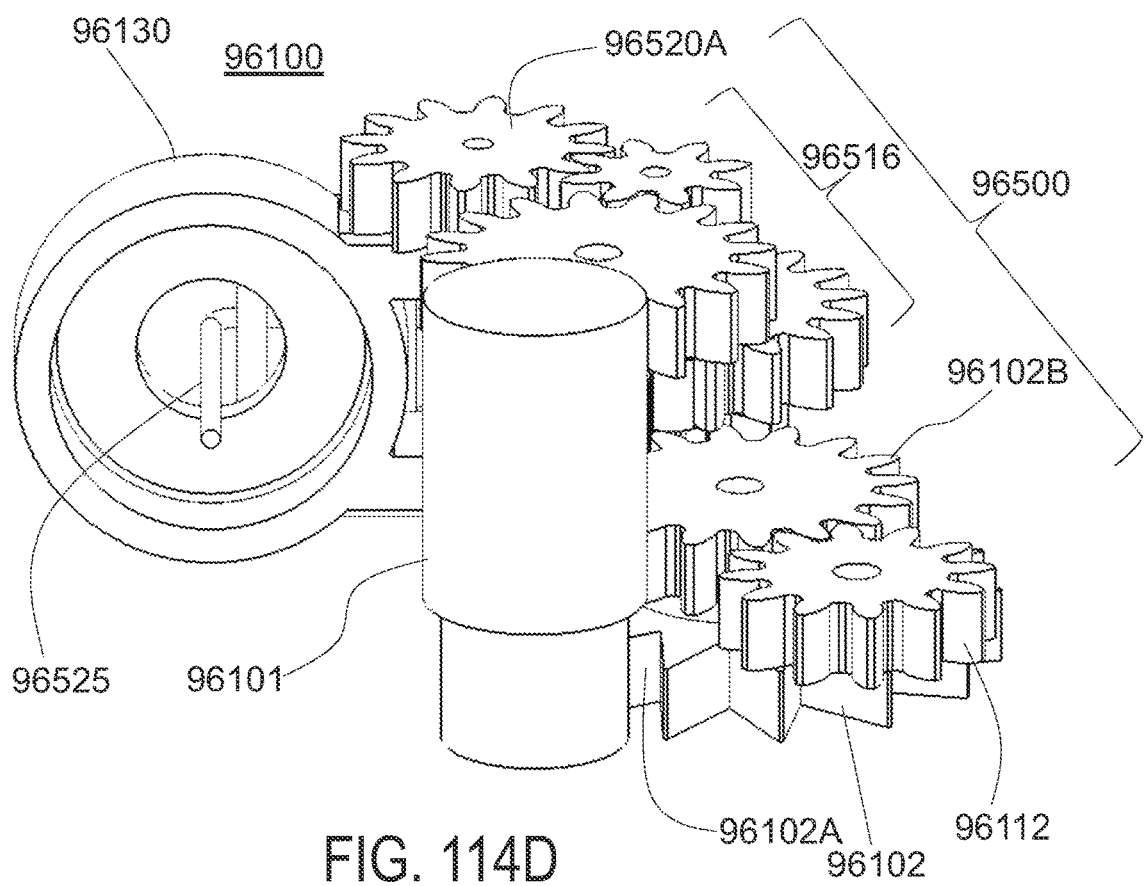
Figure 115A:
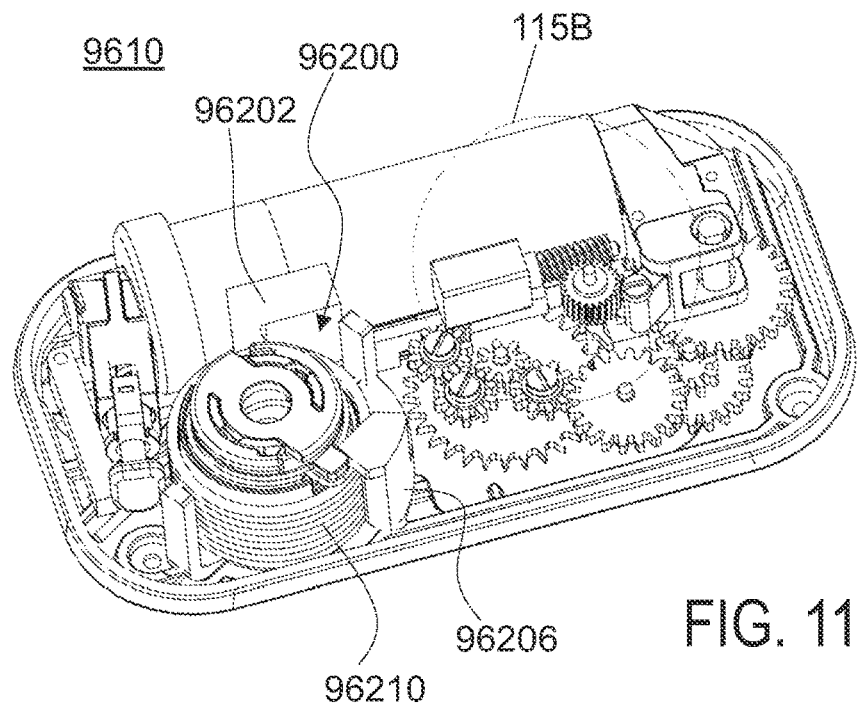
Figure 115B:
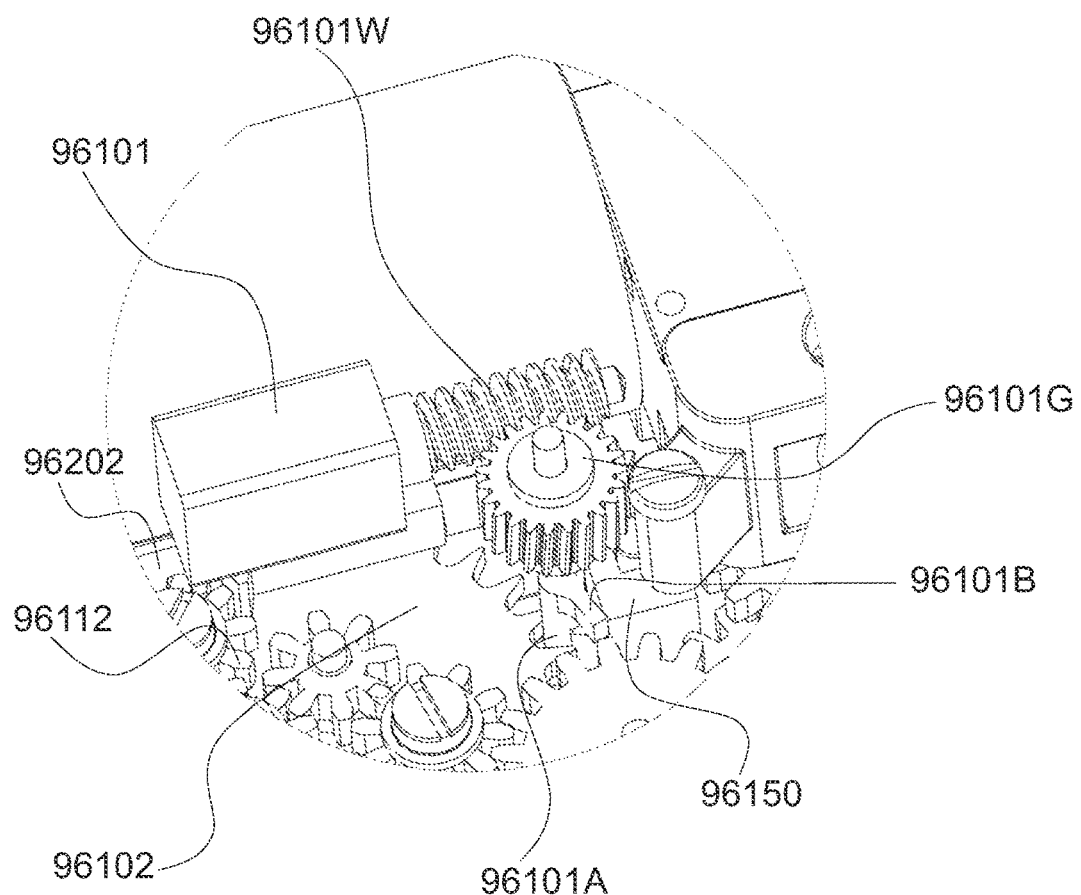

FIG. 76A is an exemplary block diagram illustrating one embodiment of a power and control system of the drug delivery pump;

FIG. 76B is an exemplary block diagram depicting one embodiment of a drive control system of the drug delivery pump;

FIG. 76C is an exemplary block diagram of an embodiment illustrating various control mechanisms of the drug delivery pump;

FIG. 76D is an exemplary block diagram of another embodiment illustrating communication among an exemplary drug delivery pump device, an exemplary mobile device, an exemplary cloud server and one or more exemplary sensors;

FIGS. 77A-77C are flow-charts of embodiments describing methods of drug delivery by the drug delivery device based on one or more mechanisms;

FIG. 78A is an exemplary block diagram illustrating one embodiment of a power and control system of the drug delivery pump;

FIG. 78B is an exemplary block diagram depicting one embodiment of a drive control system of the drug delivery pump;

FIG. 78C is an exemplary block diagram of an embodiment illustrating various control mechanisms of the drug delivery pump;

FIGS. 79A-79B are flow-charts of embodiments describing methods of drug delivery by the drug delivery device based on one or more mechanisms;

FIG. 80A shows an isometric view of a drug delivery pump having a controlled delivery drive mechanism, according to one embodiment of the present invention;

FIG. 80B shows an isometric view of the interior components of the drug delivery pump shown in FIG. 80A (shown without the adhesive patch);

FIG. 80C shows an isometric view of the bottom of the drug delivery pump shown in FIG. 80A (shown without the adhesive patch);

FIG. 81A shows an exploded view, along an axis "A," of a drive mechanism and drug container, of one embodiment of the present invention;

FIG. 81B shows an exploded view, along an axis "B," of one embodiment of the present invention (biasing member, cover sleeve, plunger seal, barrel, and cap are not shown for clarity);

FIG. 82A shows an isometric view of a controlled delivery drive mechanism, according to at least one embodiment of the present invention;

FIG. 82B shows an isometric view of a controlled delivery drive mechanism, according to at least one embodiment of the present invention (the piston is shown exploded to illustrate attachment of tether);

FIGS. 83A-83C shows an enlarged view of an escapement regulating mechanism of a drive mechanism, according to at least one embodiment of the present invention;

FIGS. 83D-83H shows the progression of the escapement regulating mechanism, according to the embodiment shown in FIGS. 83A-83C, during operation;

FIG. 84A shows an isometric view of the drive mechanism and drug container shown in FIG. 81 in an initial inactive state;

FIG. 84B shows an isometric view of the drive mechanism shown in FIG. 81 as the mechanism completes drug delivery;

FIG. 85A shows a cross-sectional view of the drive mechanism shown in FIG. 81 in an initial inactive state;

FIG. 85B shows a cross-sectional view of the drive mechanism shown in FIG. 81 in an actuated state as the mechanism controls the rate or profile of drug delivery;

FIG. 85C shows a cross-sectional view of the drive mechanism shown in FIG. 81 as the mechanism completes drug delivery and, optionally, performs a compliance push to ensure completion of drug delivery;

FIG. 86A shows an isometric view of a drug delivery pump having a controlled delivery drive mechanism, according to one embodiment of the present invention;

FIG. 86B shows an isometric view of the interior components of the drug delivery pump shown in FIG. 86A (shown without the adhesive patch);

FIG. 86C shows an isometric view of the bottom of the drug delivery pump shown in FIG. 86A (shown without the adhesive patch);

FIG. 87 shows an isometric view of a controlled delivery drive mechanism, according to at least one embodiment of the present invention;

FIG. 88 shows an exploded view, along an axis "A," of the drive mechanism shown in FIG. 87 (but excluding the plunger seal, barrel, and cap for clarity);

FIG. 89A shows an isometric view of the drive mechanism shown in FIG. 87 in an initial inactive state;

FIG. 89B shows an isometric view of the drive mechanism shown in FIG. 87 in an actuated state as the mechanism controls the rate or profile of drug delivery;

FIG. 89C shows an isometric view of the drive mechanism shown in FIG. 87 as the mechanism completes drug delivery;

FIG. 90A shows a cross-sectional view of the drive mechanism shown in FIG. 89A in an initial inactive state;

FIG. 90B shows a cross-sectional view of the drive mechanism shown in FIG. 89B in an actuated state as the mechanism controls the rate or profile of drug delivery;

FIG. 90C shows a cross-sectional view of the drive mechanism shown in FIG. 89C as the mechanism completes drug delivery and, optionally, performs a compliance push to ensure completion of drug delivery;

FIG. 91 shows a perspective view of the drive mechanism which incorporates an incremental status indicator, according to a further embodiment of the present invention;

FIG. 92A shows an isometric view of a drug delivery pump having a variable rate controlled delivery drive mechanism, according to one embodiment of the present invention;

FIG. 92B shows an isometric view of the interior components of the drug delivery pump shown in FIG. 92A (shown without the adhesive patch);

FIG. 92C shows an isometric view of the bottom of the drug delivery pump shown in FIG. 92A (shown without the adhesive patch);

FIG. 93 shows an isometric view of a controlled delivery drive mechanism, according to at least one embodiment of the present invention;

FIG. 94A shows a partially exploded view, along an axis "A," of the drive mechanism shown in FIG. 93;

FIG. 94B shows a fully exploded view, along an axis "A" and along a perpendicular axis "B", of certain components of the drive mechanism shown in FIG. 93;

FIGS. 95A-95C shows an enlarged view of an escapement regulating mechanism of a drive mechanism, according to at least one embodiment of the present invention;

FIGS. 95D-95H shows the progression of the escapement regulating mechanism, according the embodiment shown in FIGS. 95A-95C, during operation;

FIG. 96A shows an isometric view of the drive mechanism shown in FIG. 93 in an initial inactive state;

FIG. 96B shows an isometric view of the drive mechanism shown in FIG. 93 in an actuated state as the mechanism controls the rate or profile of drug delivery;

FIG. 96C shows an isometric view of the drive mechanism shown in FIG. 93 as the mechanism completes drug delivery;

FIG. 97A shows a cross-sectional view of the drive mechanism shown in FIG. 96A in an initial inactive state;

FIG. 97B shows a cross-sectional view of the drive mechanism shown in FIG. 96B in an actuated state as the mechanism controls the rate or profile of drug delivery;

FIG. 97C shows a cross-sectional view of the drive mechanism shown in FIG. 96C as the mechanism completes drug delivery and, optionally, performs a compliance push to ensure completion of drug delivery;

FIG. 98 shows an isometric view of a controlled delivery drive mechanism which incorporates a status indicator, according to at least one embodiment of the present invention;

FIG. 99 shows an isometric view of a controlled delivery drive mechanism according to another embodiment of the present invention;

FIG. 100A shows an isometric view of a drug delivery pump having a variable rate controlled delivery drive mechanism, according to one embodiment of the present invention;

FIG. 100B shows an isometric view of the interior components of the drug delivery pump shown in FIG. 100A (shown without the adhesive patch);

FIG. 100C shows an isometric view of the bottom of the drug delivery pump shown in FIG. 100A (shown without the adhesive patch);

FIG. 101 shows an isometric view of a variable rate controlled delivery drive mechanism, according to at least one embodiment of the present invention;

FIG. 102 shows an exploded view, along an axis "A," of the drive mechanism shown in FIG. 101;

FIG. 103A shows an isometric cross-sectional view of the drive mechanism shown in FIG. 101 in an initial inactive state;

FIG. 103B shows an isometric cross-sectional view of the drive mechanism shown in FIG. 101 in an actuated state as the mechanism controls the rate or profile of drug delivery;

FIG. 103C shows an isometric cross-section view of the drive mechanism shown in FIG. 101 as the mechanism completes drug delivery;

FIG. 104A shows a cross-sectional view of the drive mechanism shown in FIG. 103A in an initial inactive state;

FIG. 104B shows a cross-sectional view of the drive mechanism shown in FIG. 103B in an actuated state as the mechanism controls the rate or profile of drug delivery;

FIG. 104C shows a cross-sectional view of the drive mechanism shown in FIG. 103C as the mechanism completes drug delivery and, optionally, performs a compliance push to ensure completion of drug delivery;

FIG. 105 shows an isometric view of a variable rate controlled delivery drive mechanism, according to another embodiment of the present invention;

FIG. 106 shows an exploded view, along an axis "A," of the drive mechanism shown in FIG. 105;

FIG. 107A shows an isometric cross-sectional view of the drive mechanism shown in FIG. 105 in an initial inactive state;

FIG. 107B shows an isometric cross-sectional view of the drive mechanism shown in FIG. 105 in an actuated state as the mechanism controls the rate or profile of drug delivery;

FIG. 107C shows an isometric cross-sectional view of the drive mechanism shown in FIG. 105 as the mechanism completes drug delivery;

FIG. 108A shows a cross-sectional view of the drive mechanism shown in FIG. 107A in an initial inactive state;

FIG. 108B shows a cross-sectional view of the drive mechanism shown in FIG. 107B in an actuated state as the mechanism controls the rate or profile of drug delivery;

FIG. 108C shows a cross-sectional view of the drive mechanism shown in FIG. 107C as the mechanism completes drug delivery and, optionally, performs a compliance push to ensure completion of drug delivery;

FIG. 109A shows an isometric view of a variable rate controlled delivery drive mechanism which incorporates a mechanical status indicator, according to a further embodiment of the present invention;

FIG. 109B shows an isometric view of a variable rate controlled delivery drive mechanism which incorporates an optical status indicator, according to yet another embodiment of the present invention;

FIG. 110A is an isometric view of a drug delivery pump having a drive mechanism, according to one embodiment of the present invention (shown without the adhesive patch);

FIG. 110B is an isometric view of the interior components of the drug delivery pump shown in FIG. 110A (shown without the adhesive patch);

FIG. 110C is an isometric view of the drug delivery pump shown in FIG. 110A (shown without the adhesive patch) from yet another viewpoint;

FIG. 111A is a top view, along an axis "A," of the interior components of an exemplary drug delivery pump;

FIG. 111B is an isometric view of a drive mechanism, according to at least one embodiment of the present invention prior to activation;

FIG. 111C is an isometric view of a drive mechanism, according to at least one embodiment of the present invention during activation;

FIG. 111D is an isometric view of a drive mechanism, according to at least one embodiment of the present invention at a later stage during activation;

FIG. 111E is an isometric view of a drive mechanism, according to at least one embodiment of the present invention near or at completion of drug delivery;

FIGS. 112A-112D are top views which correspond with the stages of operation shown in FIGS. 111A-111E, respectively;

FIG. 113 is an isometric view of the drive mechanism, according to at least one embodiment of the present invention, in isolation from the drug delivery device;

FIGS. 114A-114B are top and bottom views, respectively, of the drive mechanism shown in FIG. 113;

FIGS. 114C-114D are front and back perspective views, respectively, of the drive mechanism shown in FIG. 113;

FIG. 115A is an isometric view of a drug delivery pump in which the insertion mechanism includes a rotational biasing member;

FIG. 115B is an enlarged view of the drive mechanism shown in FIG. 115A

Figure 30:
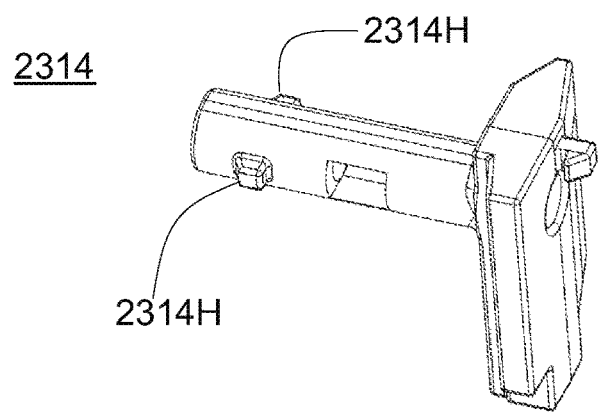
FIG. 30 shows an isometric view of an embodiment of a piercing member retainer according to at least one embodiment of the present invention.
Figure 116A:
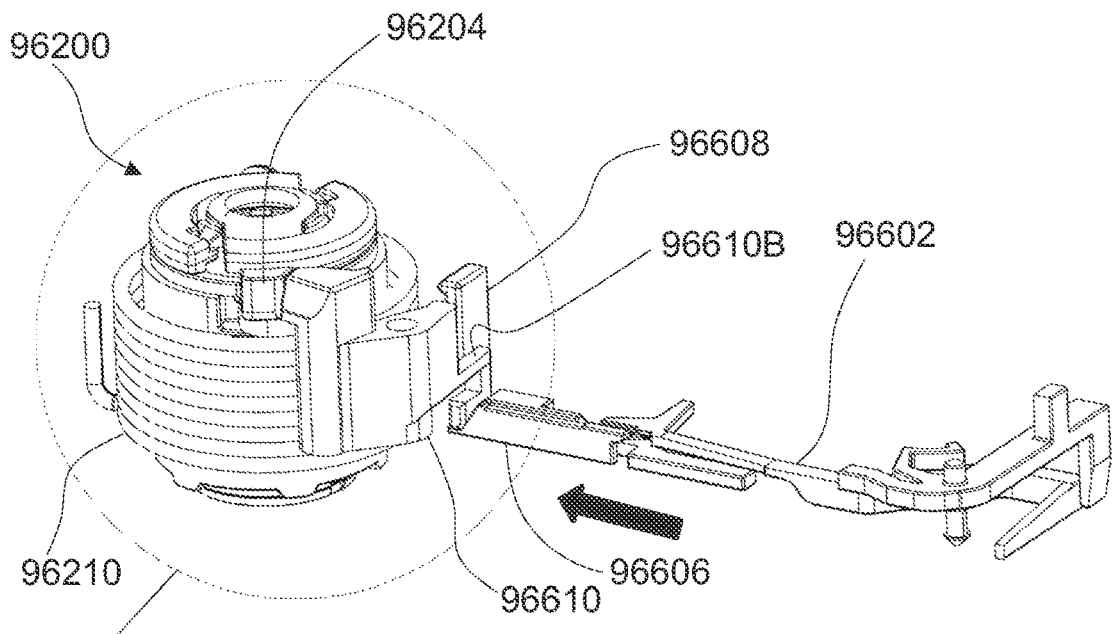
Figure 116B:
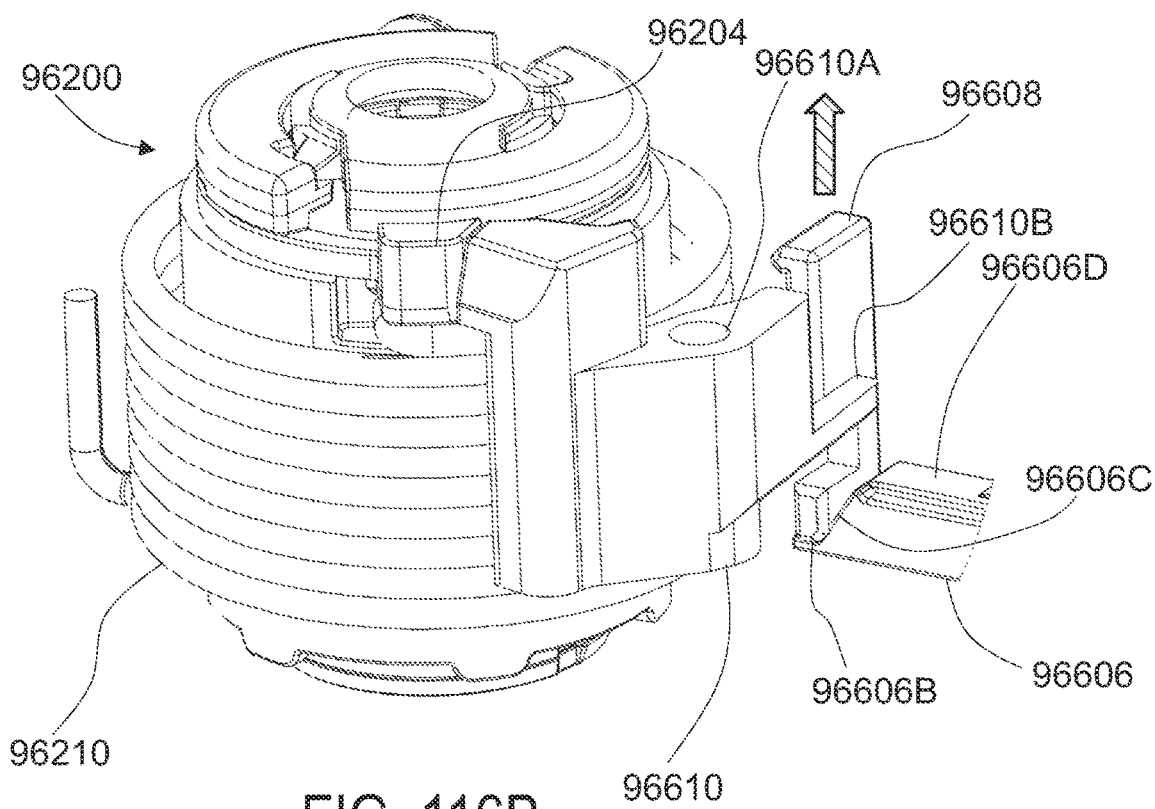
Figure 117A:
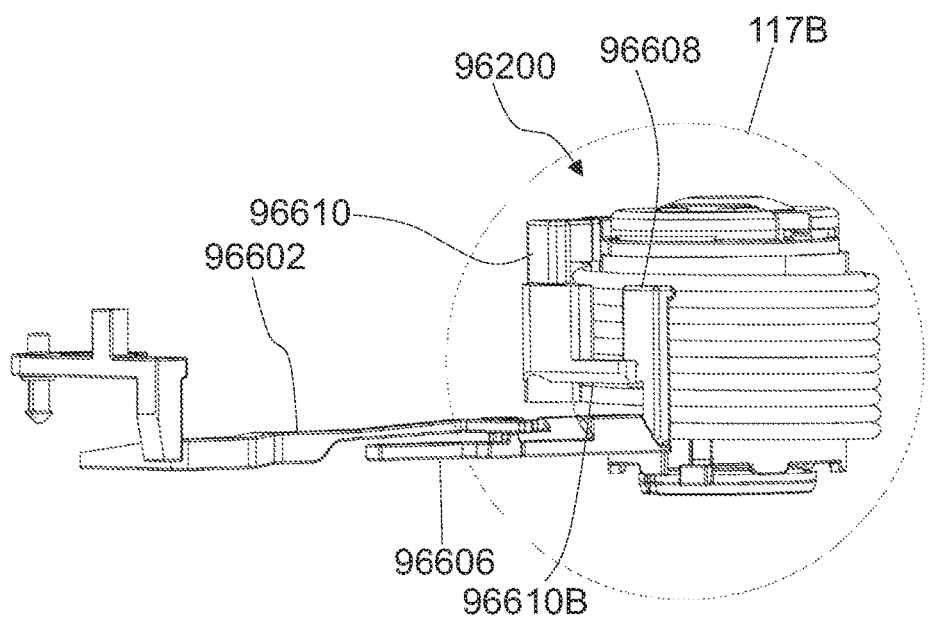
Figure 117B:
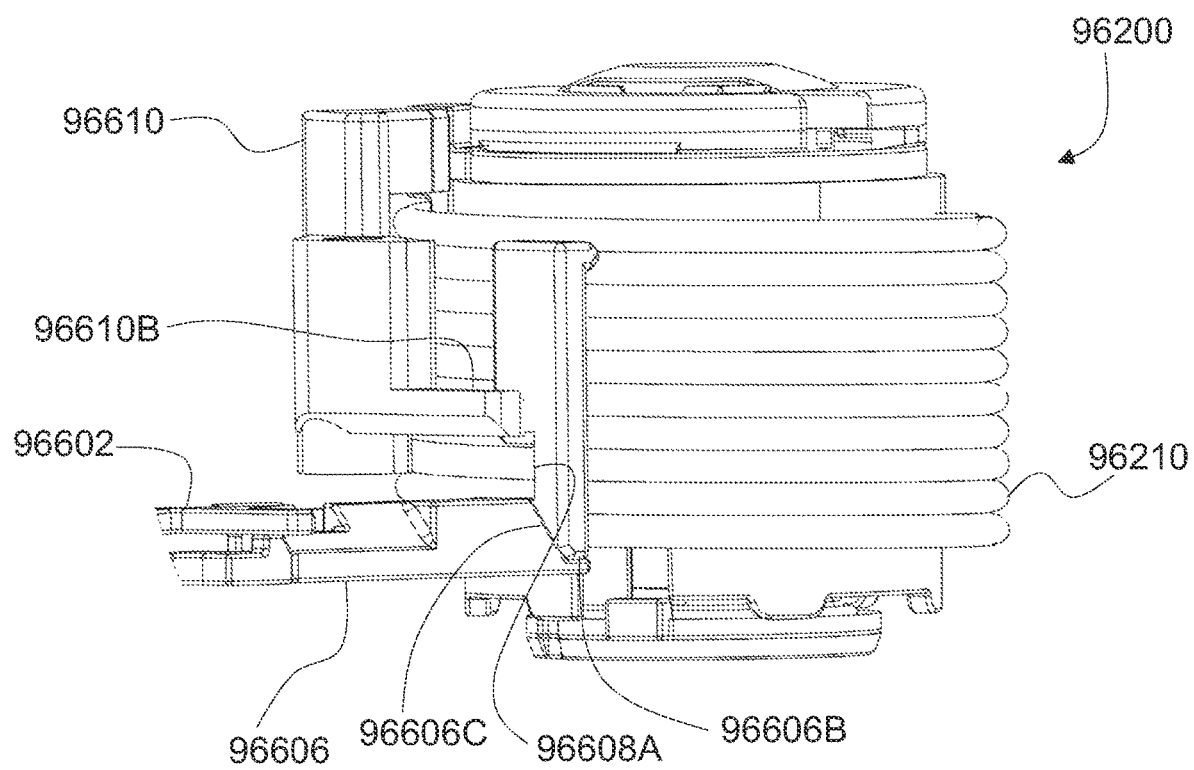
Figure 118A:
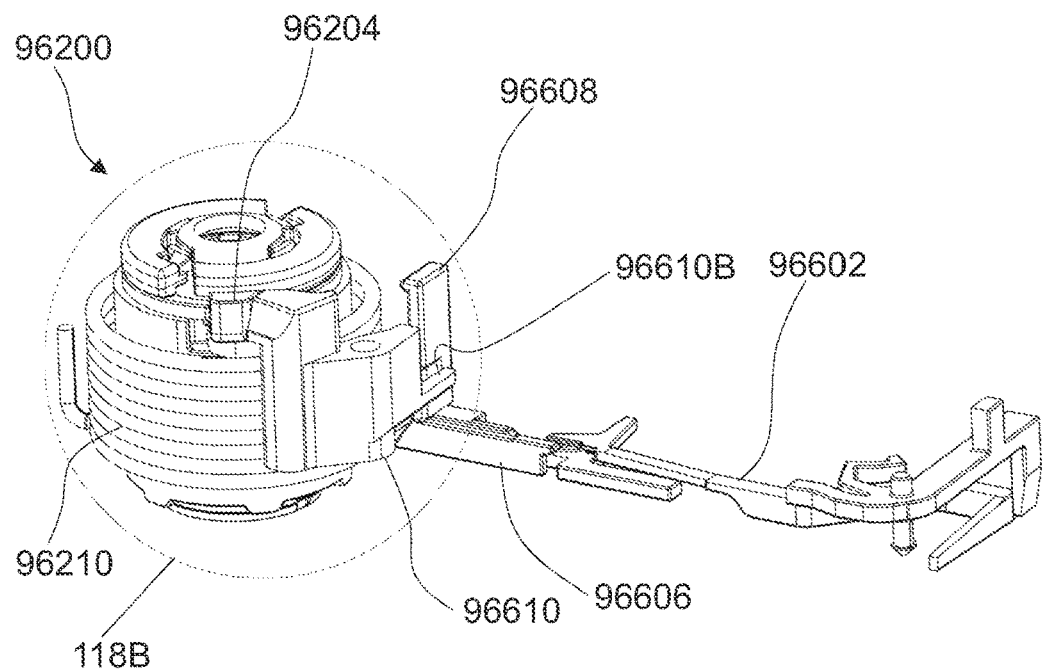
Figure 118B:
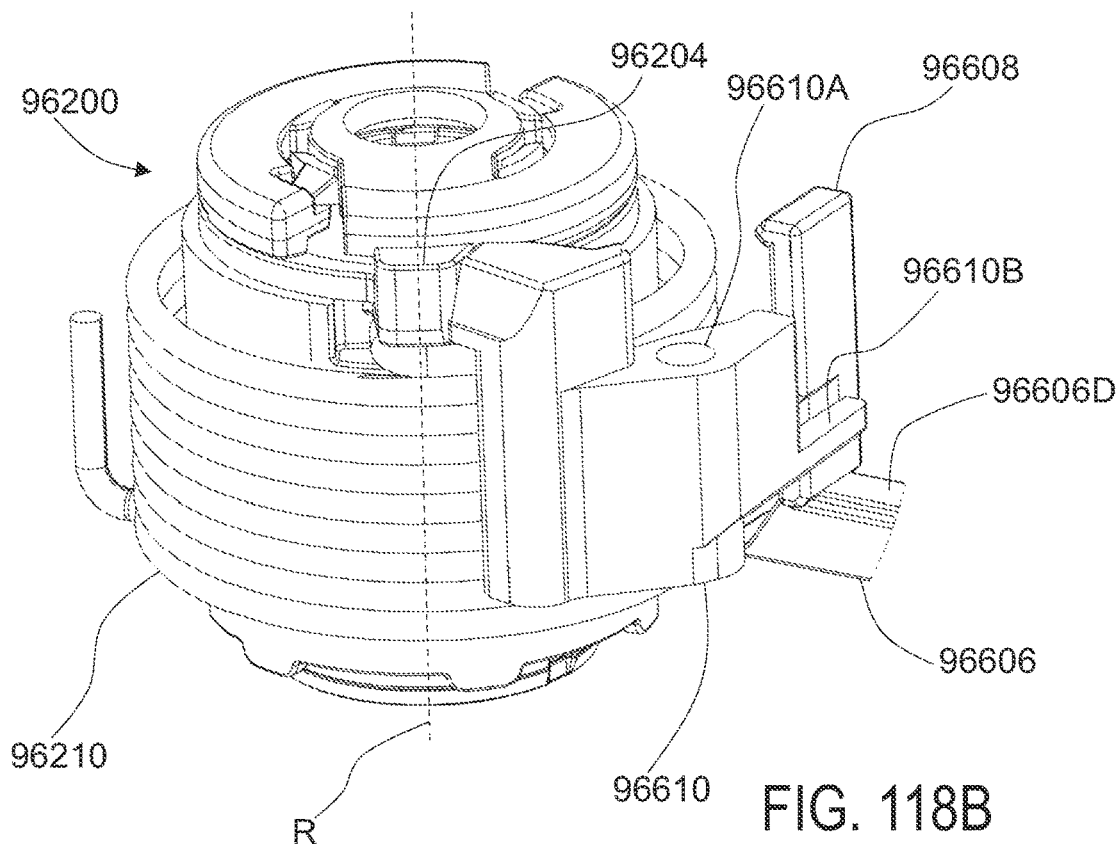
Figure 119A:
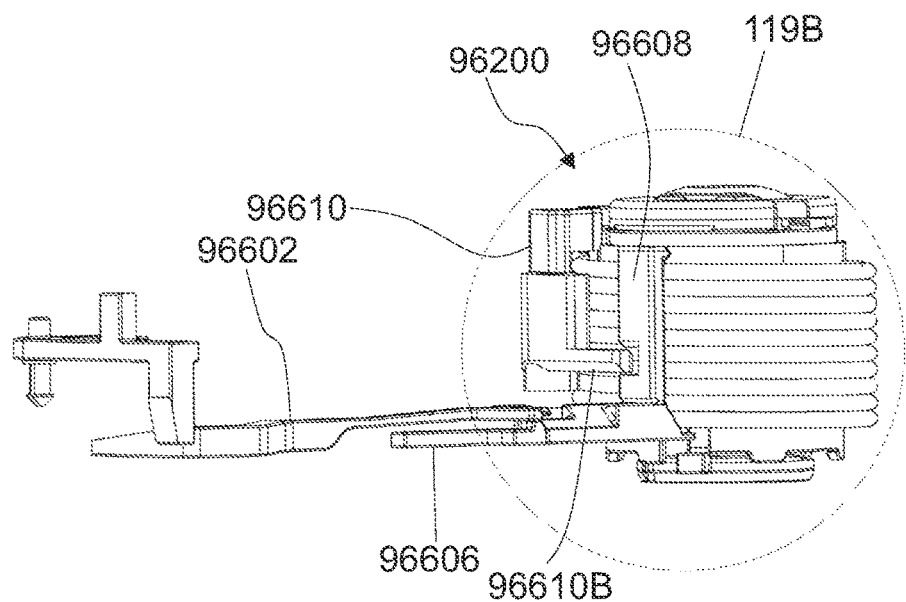
Figure 119B:
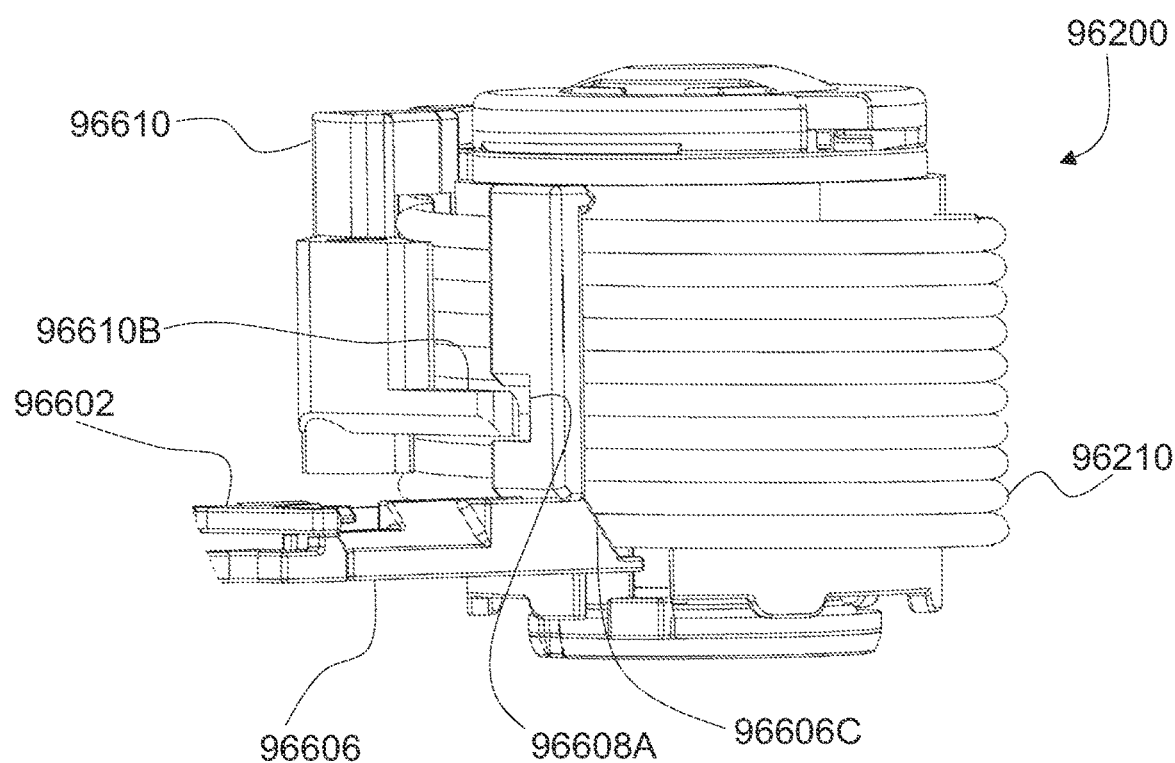
Figure 120A:
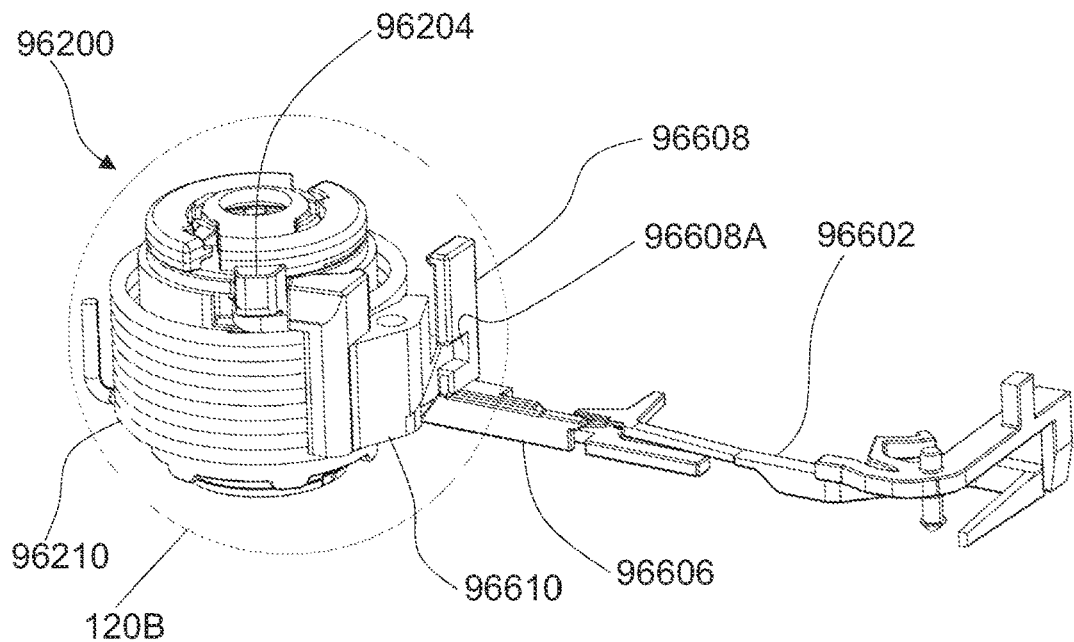
Figure 120B:
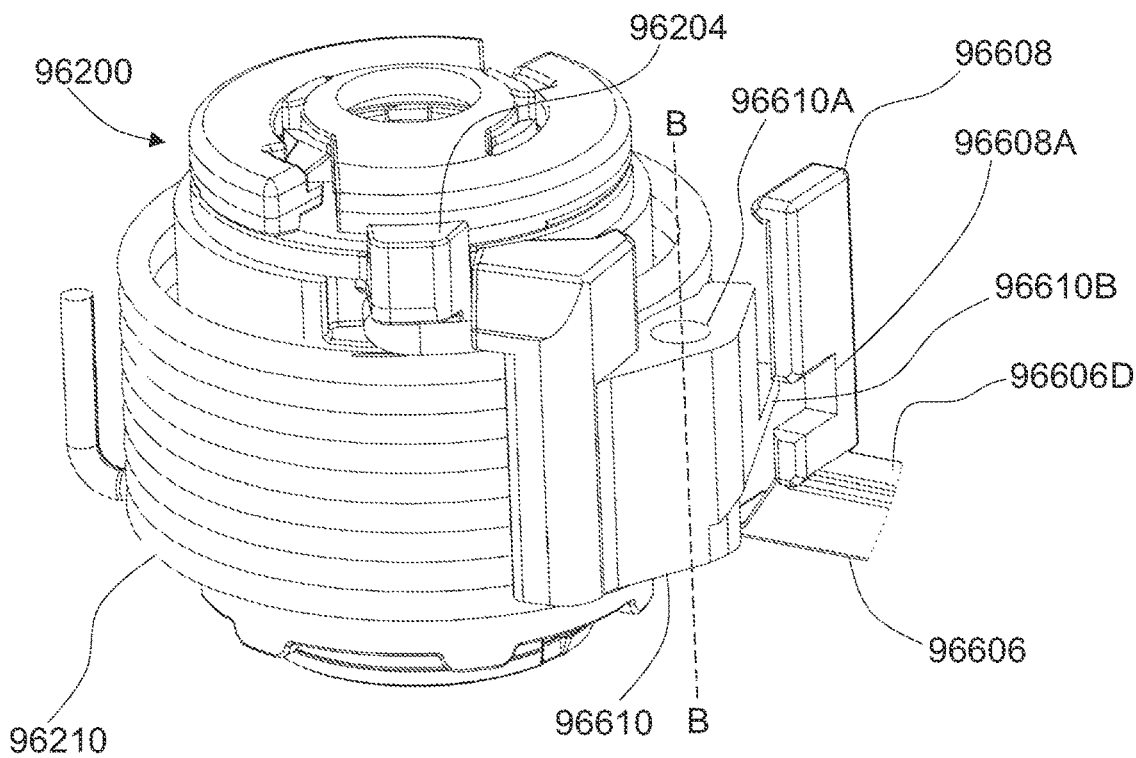
Figure 121A:
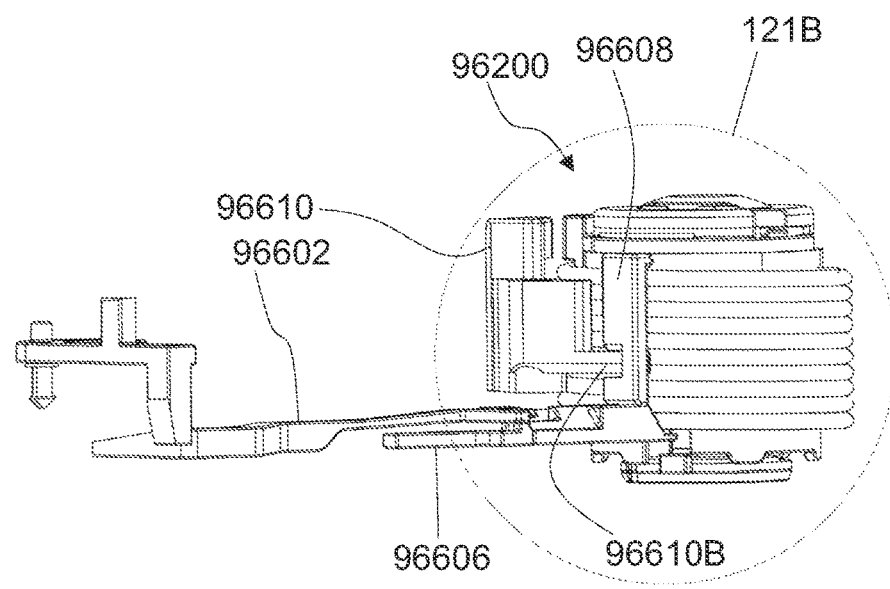
Figure 121B:
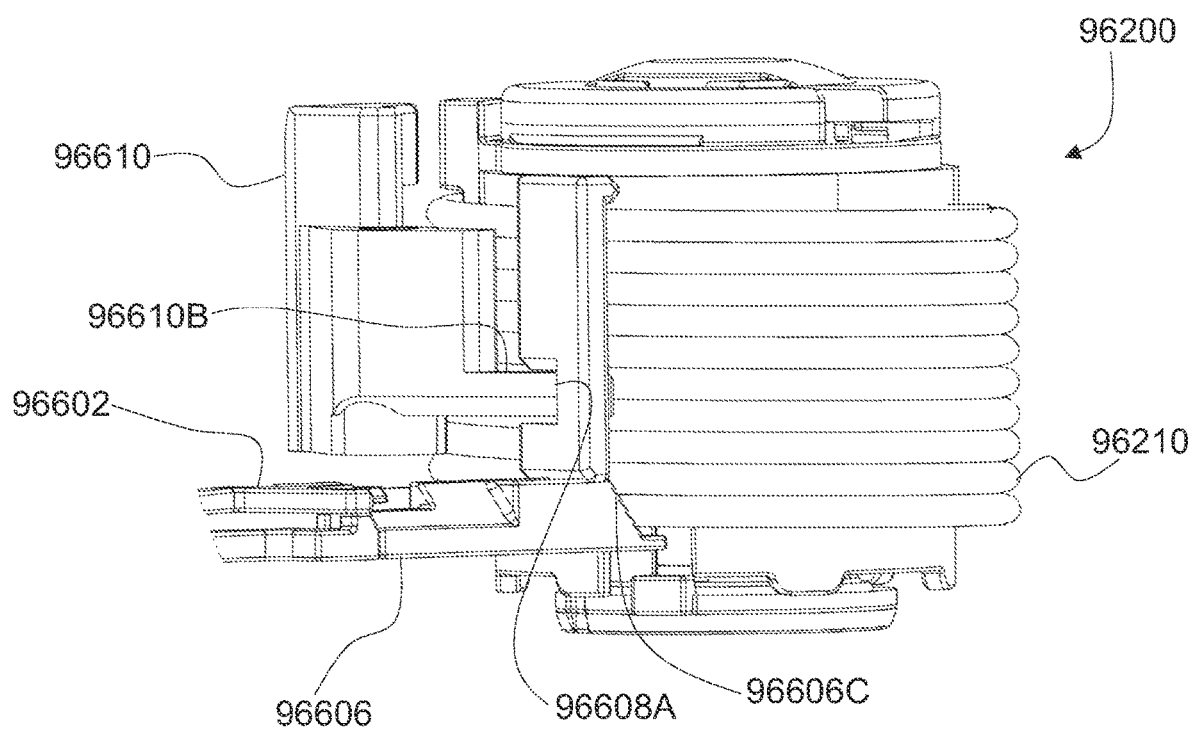
Figure 122A:
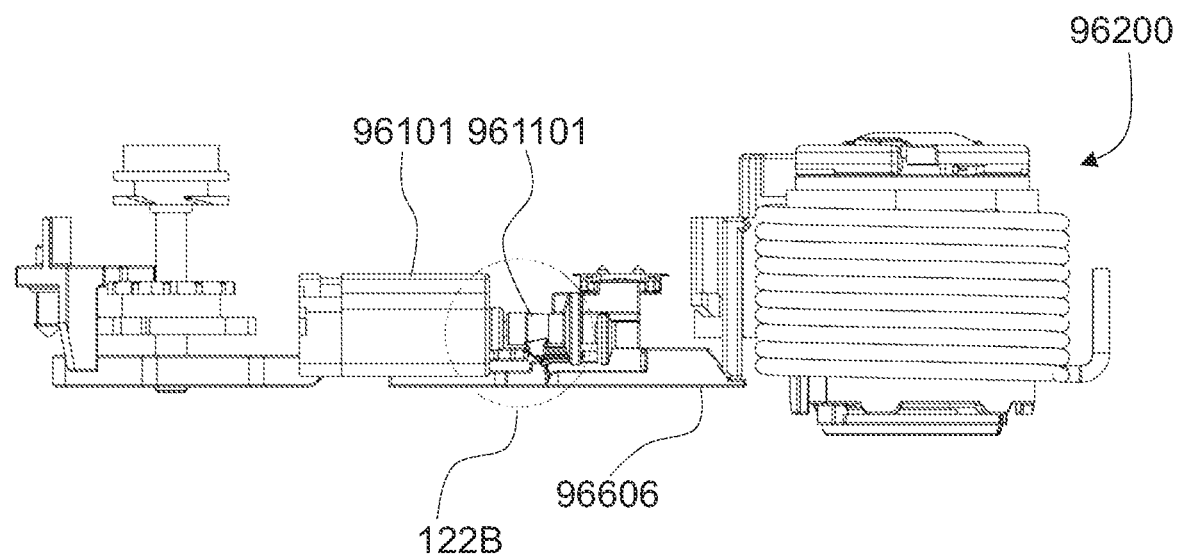
Figure 122B:
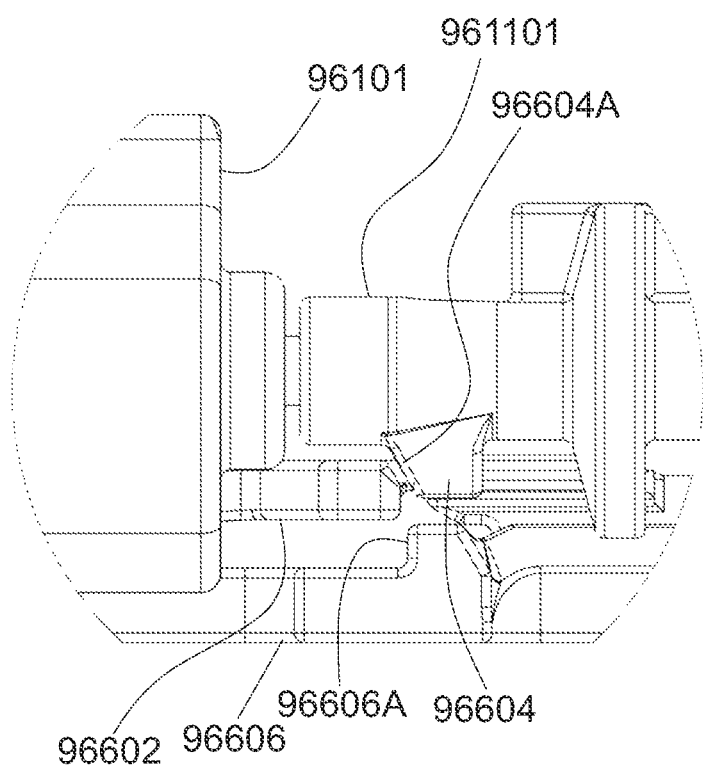
Figure 126A:
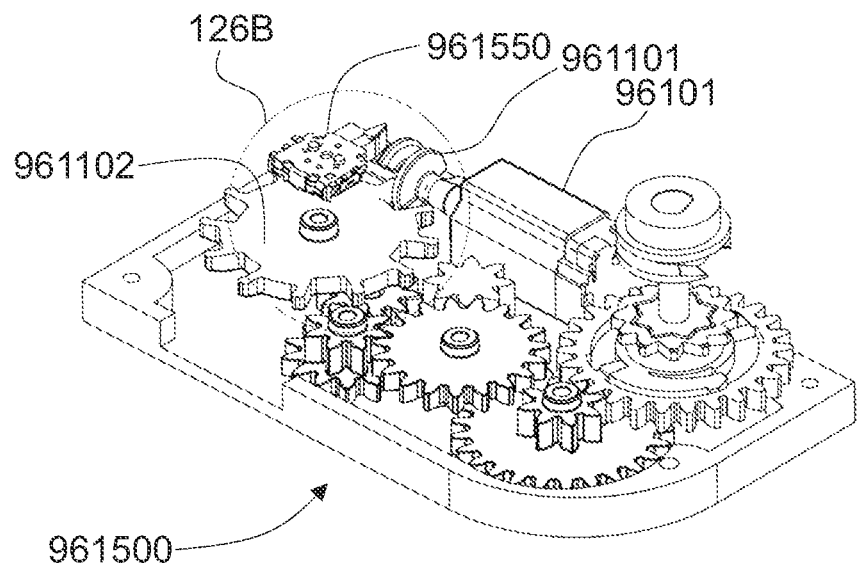
Figure 126B:
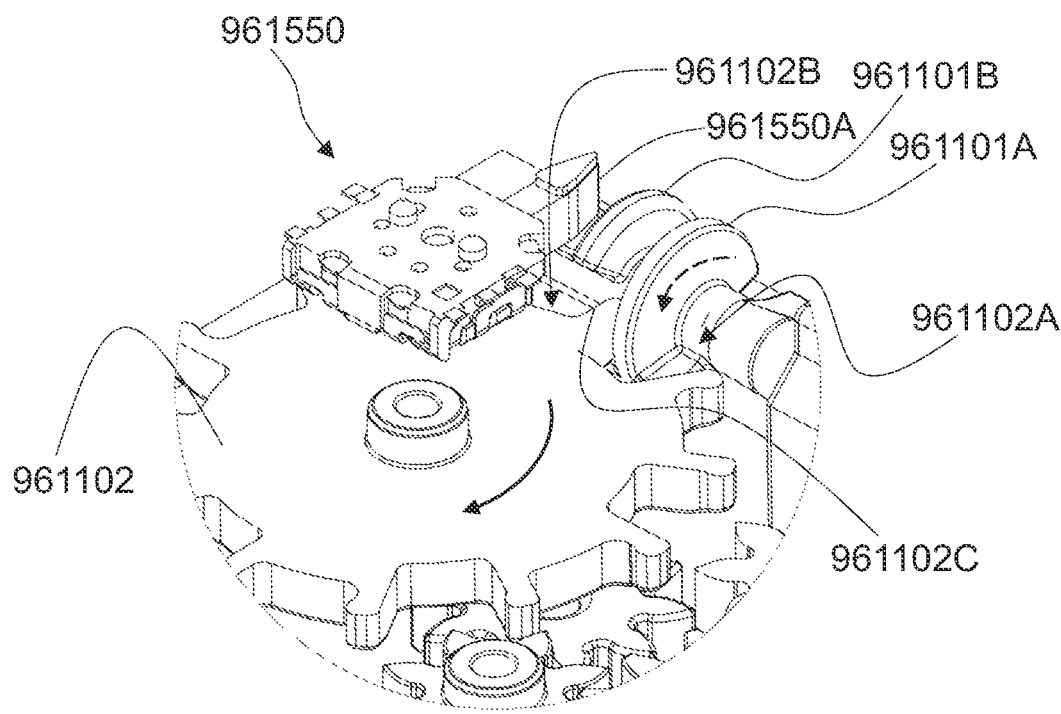
Figure 127A:
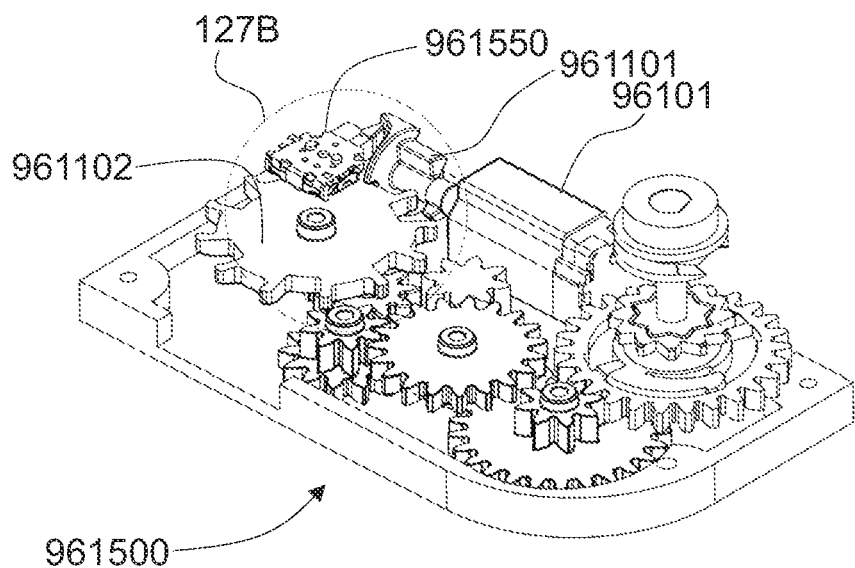
Figure 127B:
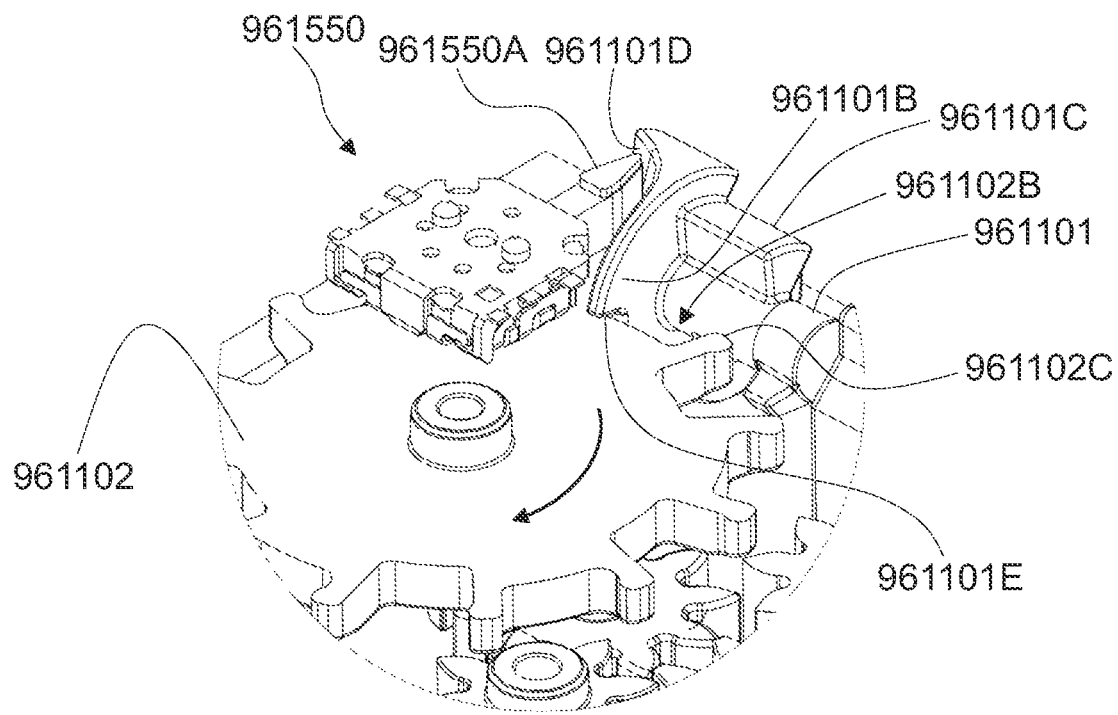
Figure 128A:
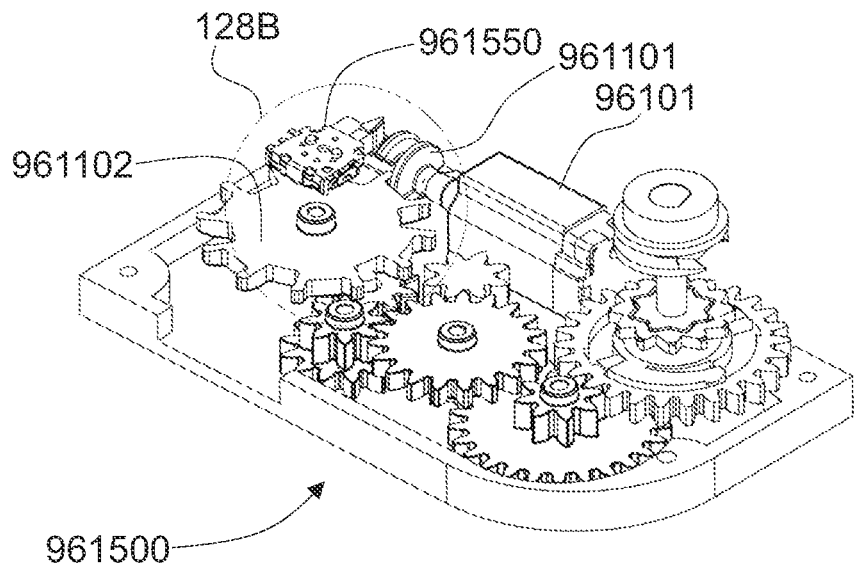
Figure 128B:
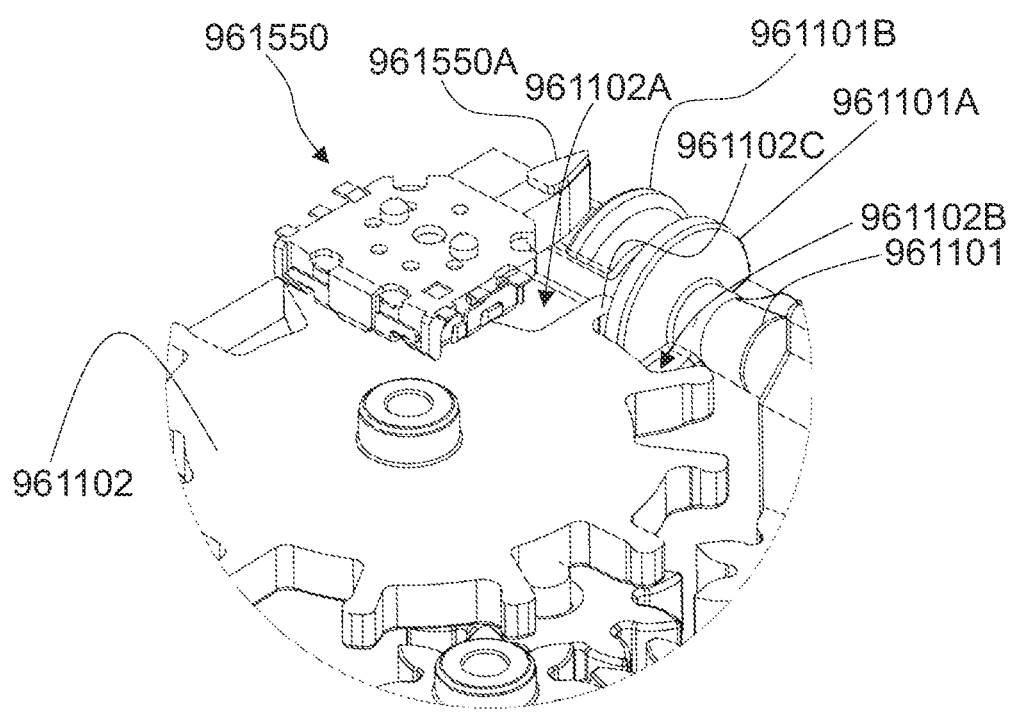
Figure 129A:
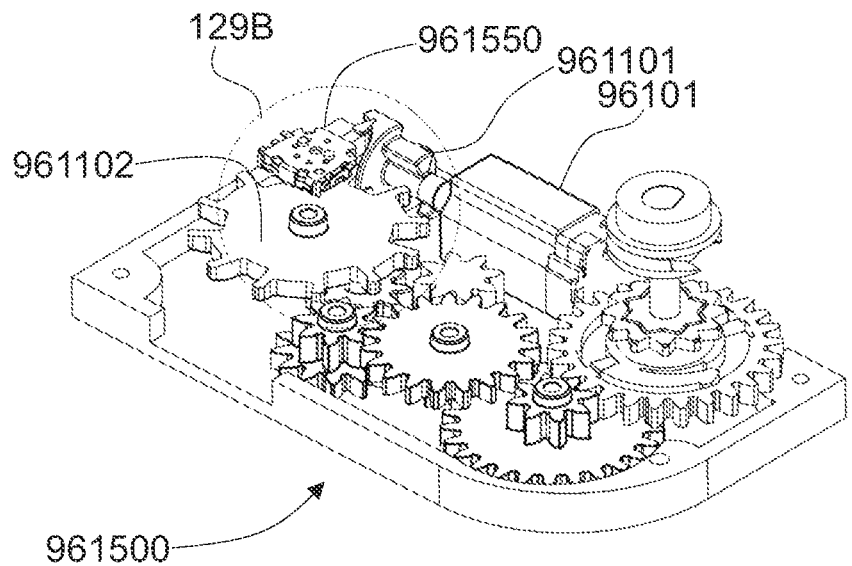
Figure 129B:
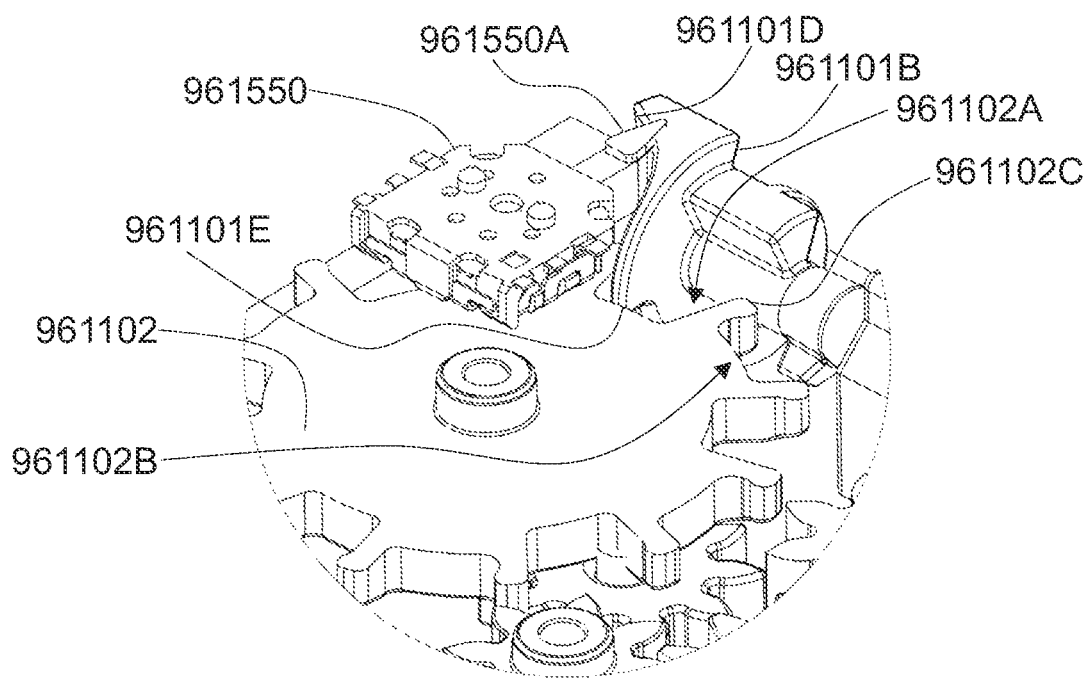
Figure 130A:
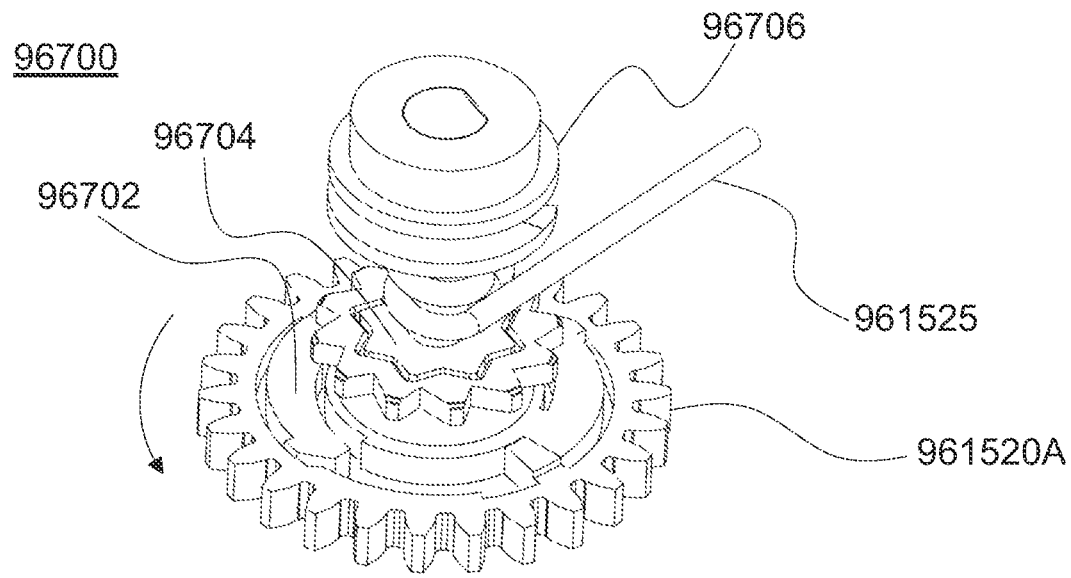
Figure 130B:
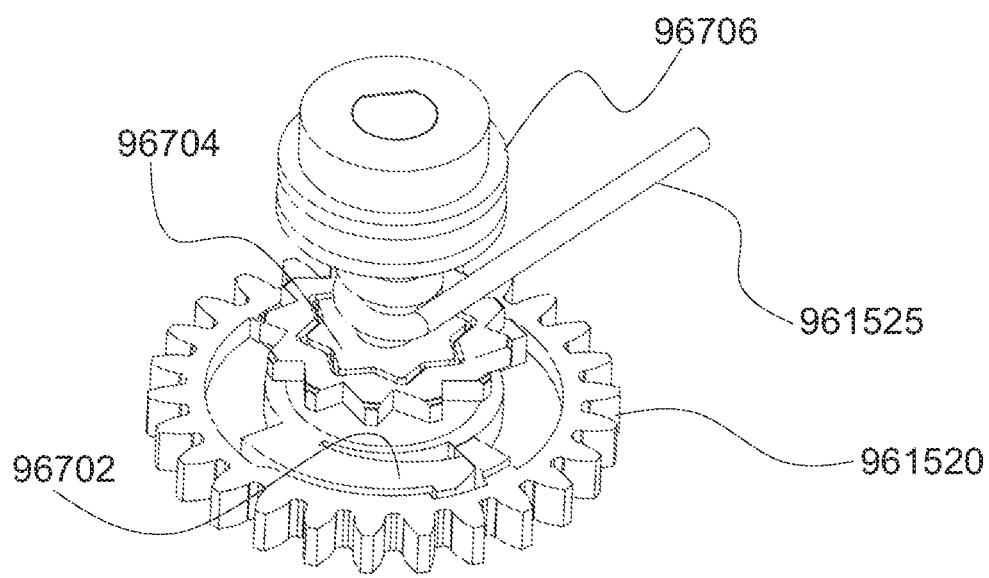
Figure 134A:
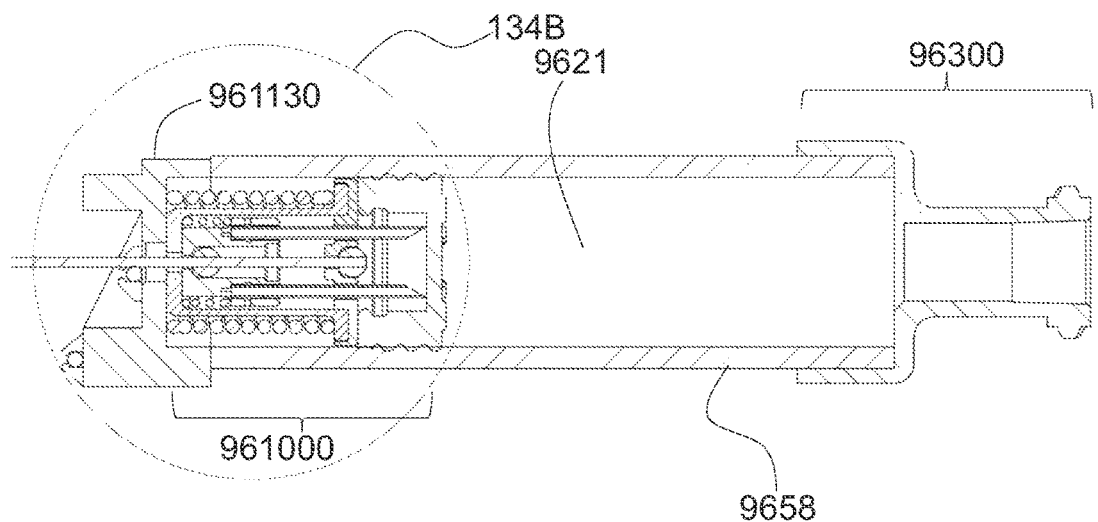
Figure 134B:
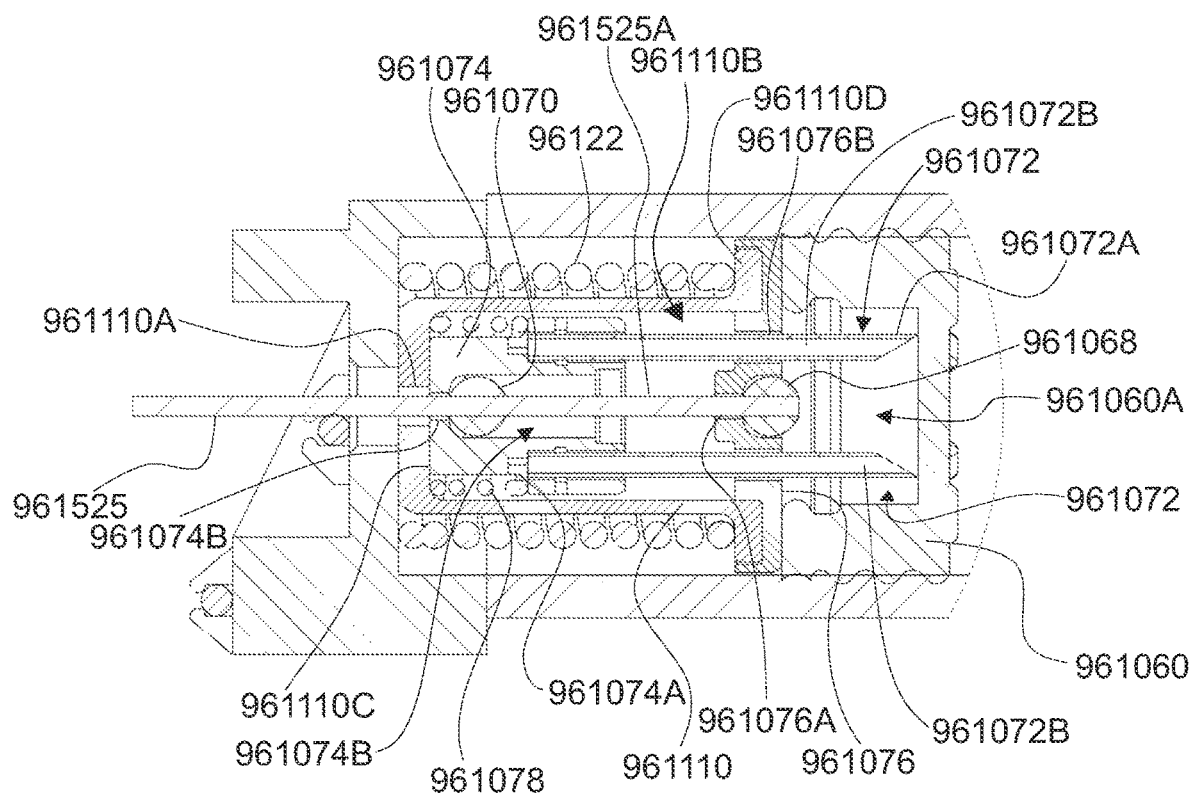
Figure 135A:
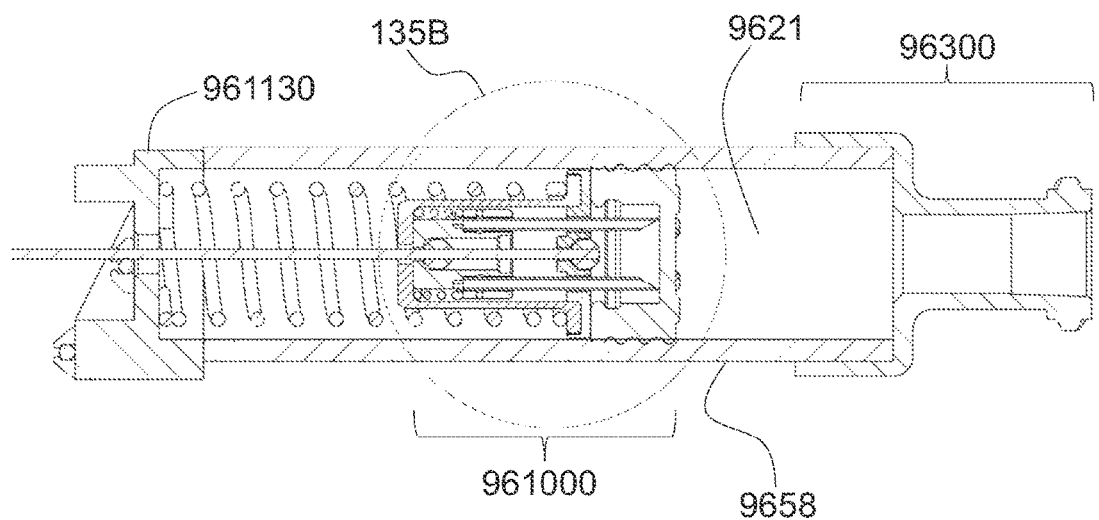
Figure 135B:
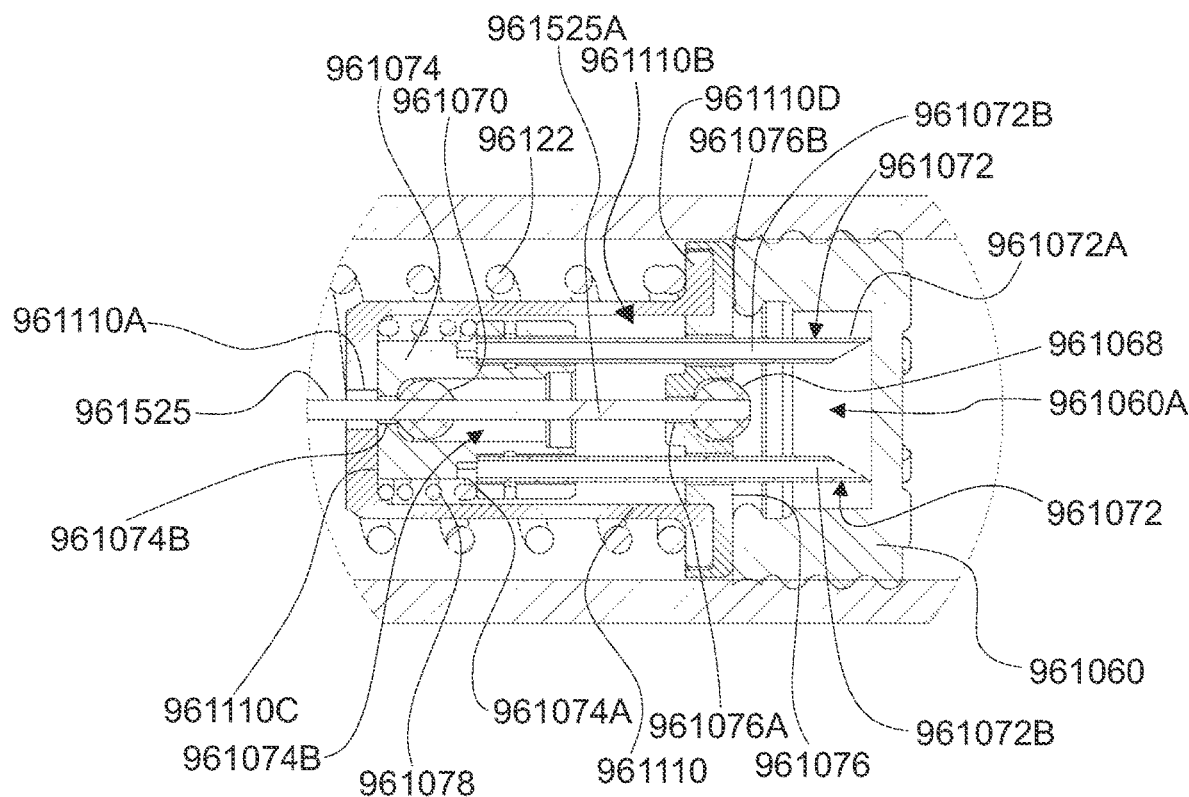
Figure 136A:
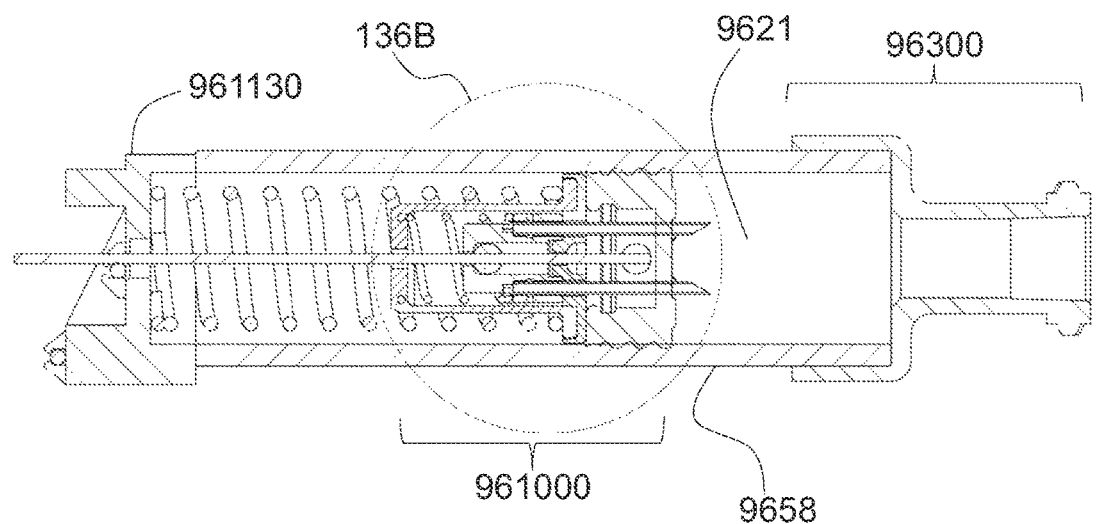
Figure 136B:
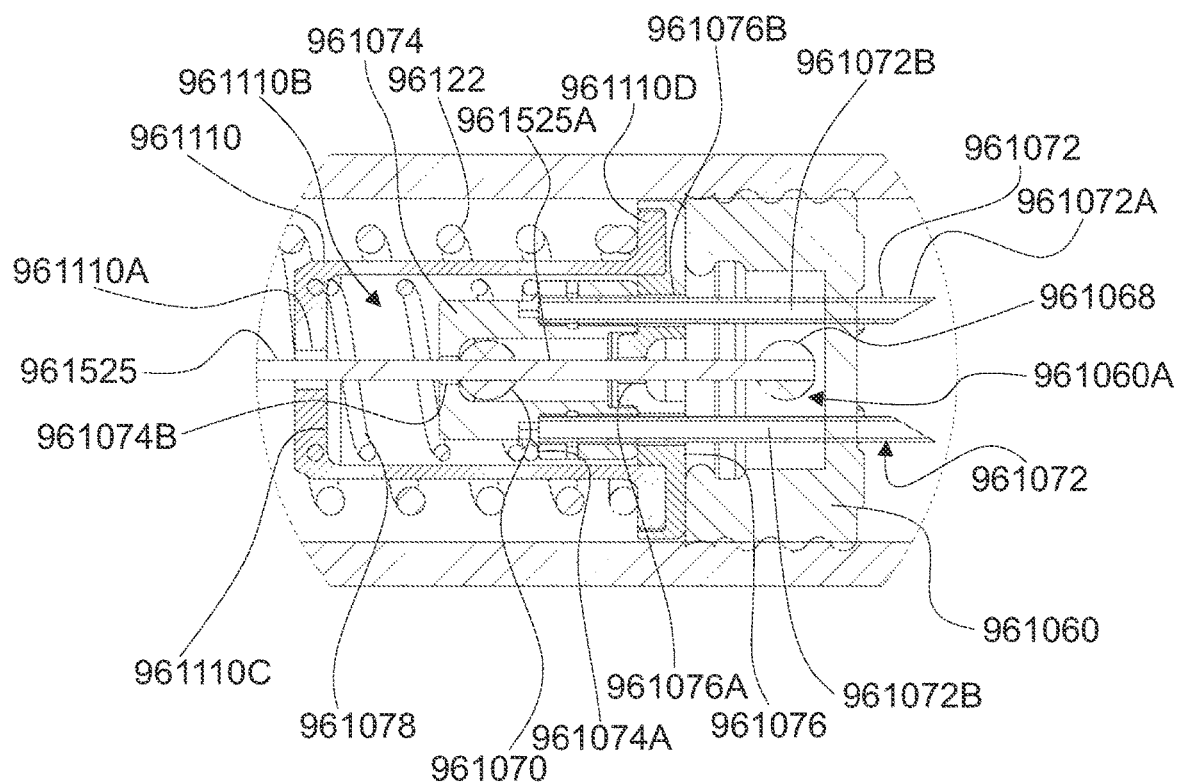
Figure 137A:
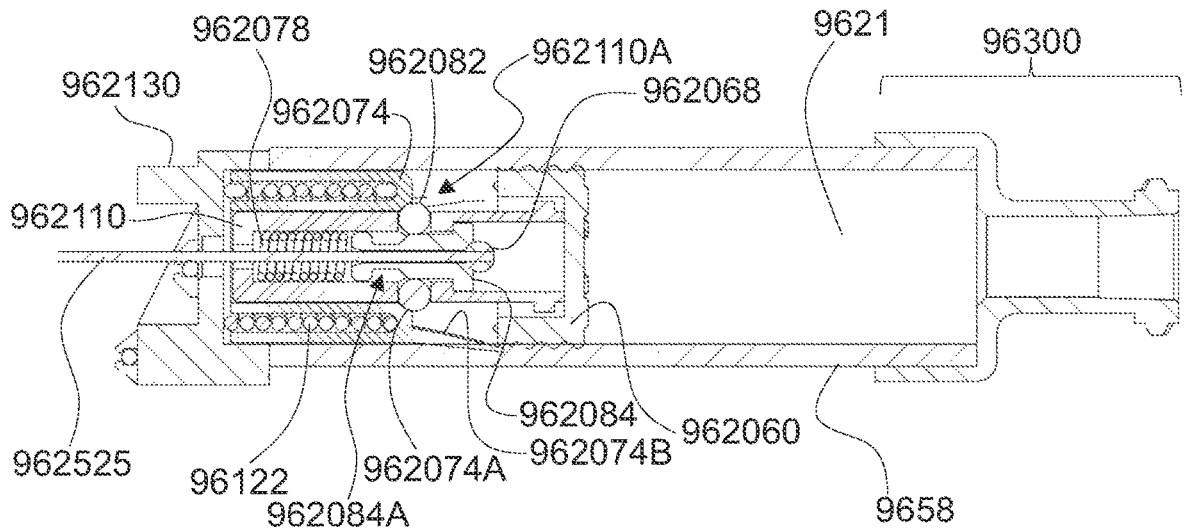
Figure 137B:
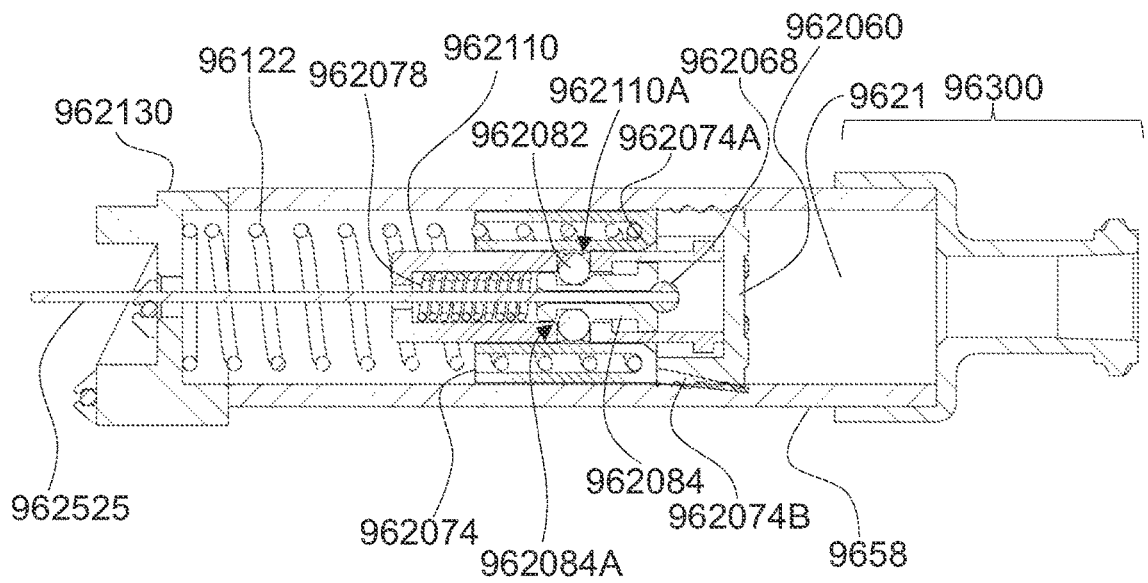
Figure 138:
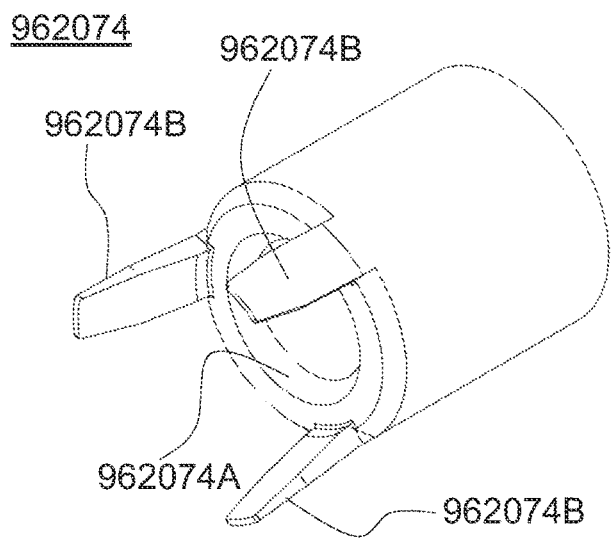
Figure 139:
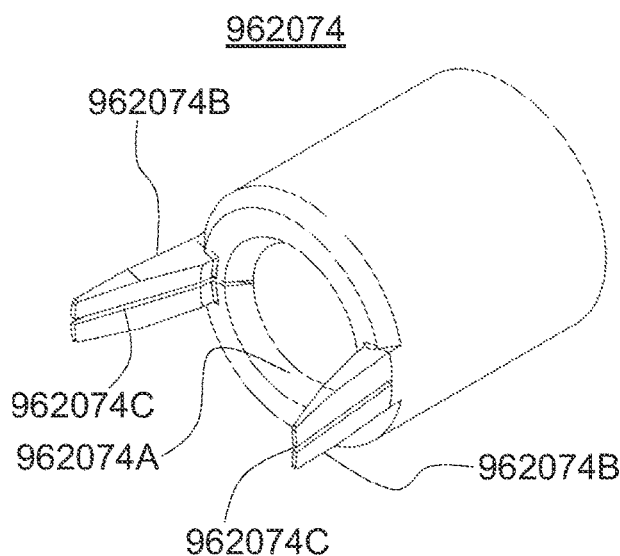
Figure 140:
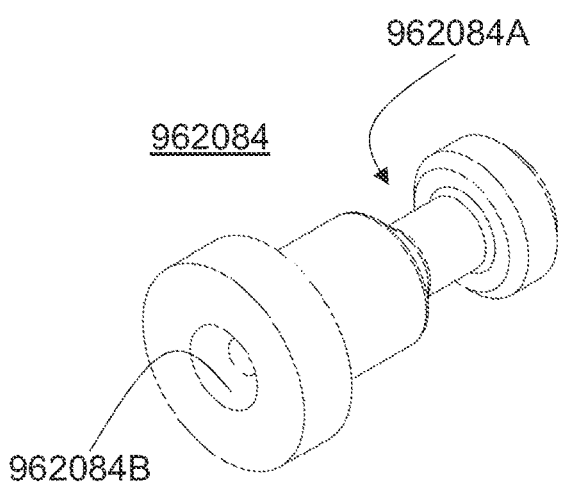
Figure 141A:
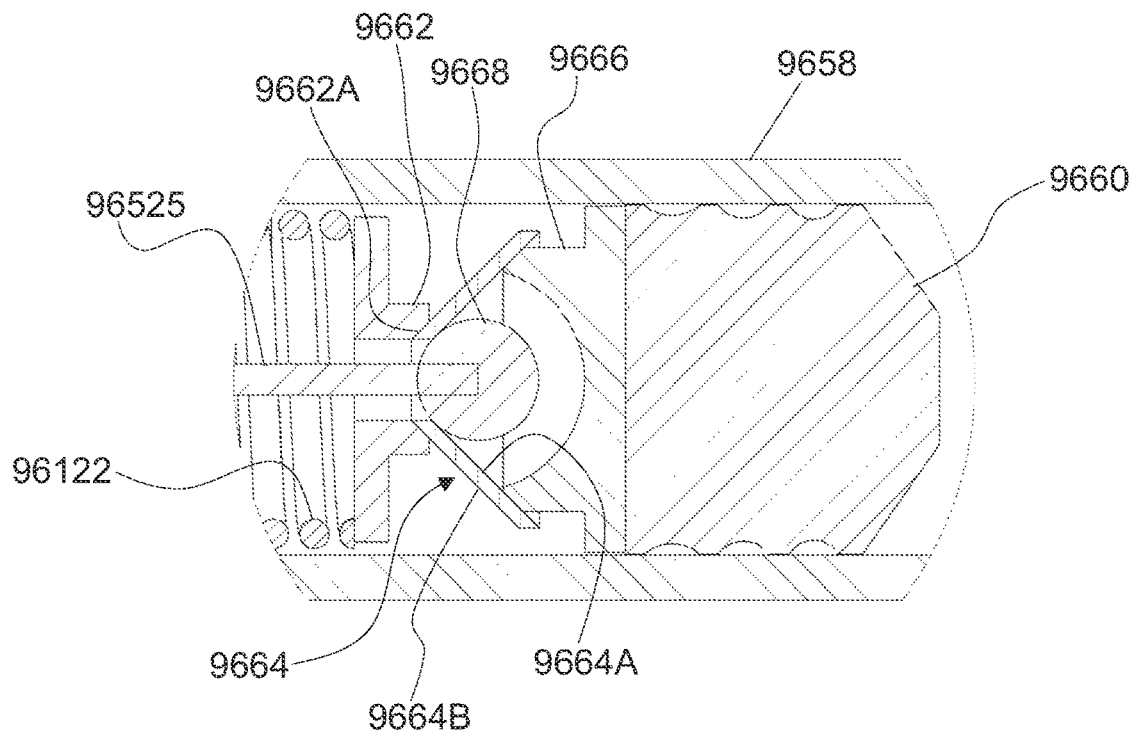
Figure 141B:
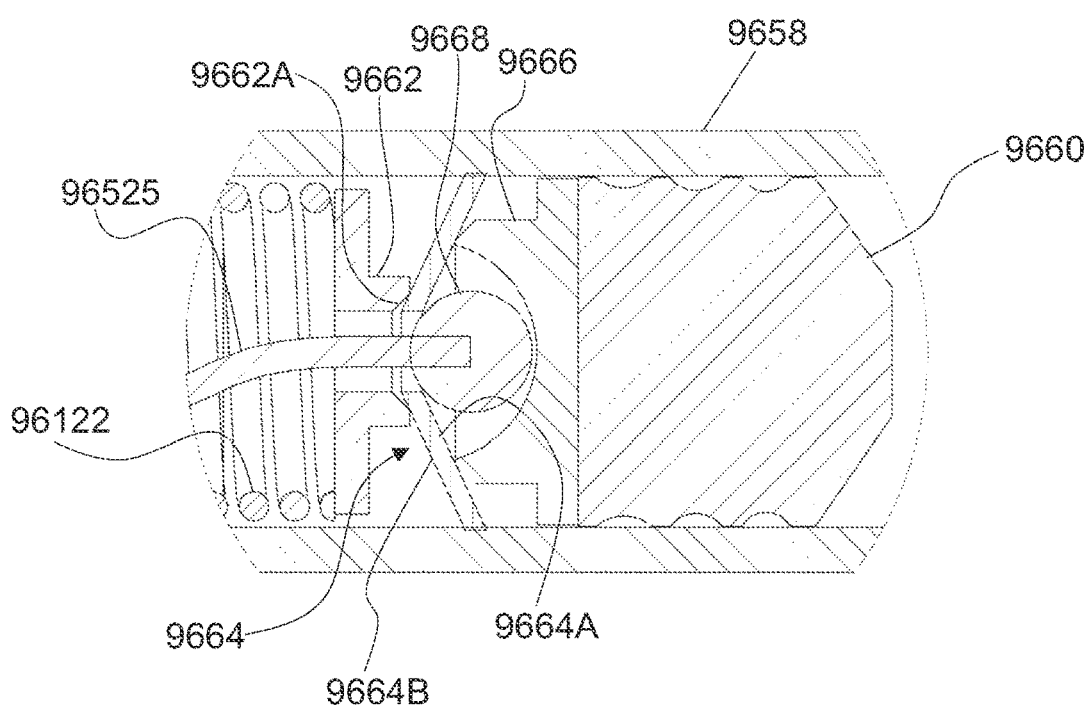
Figure 142A:
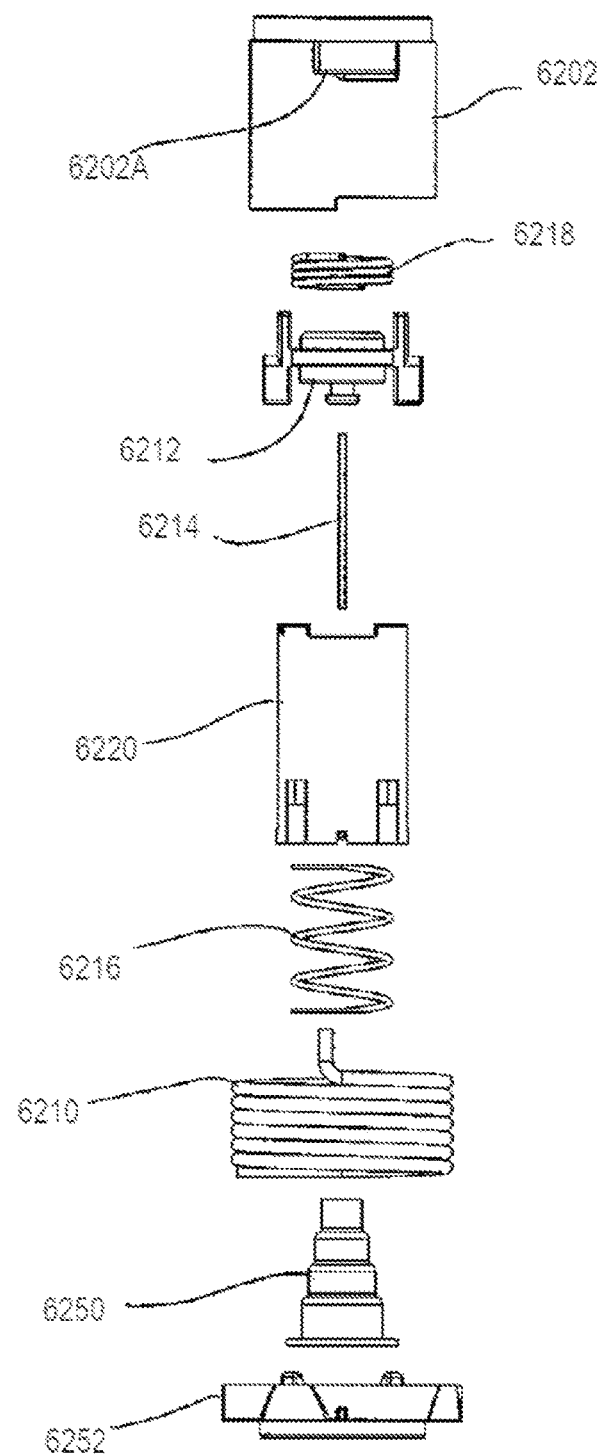
Figure 142B:
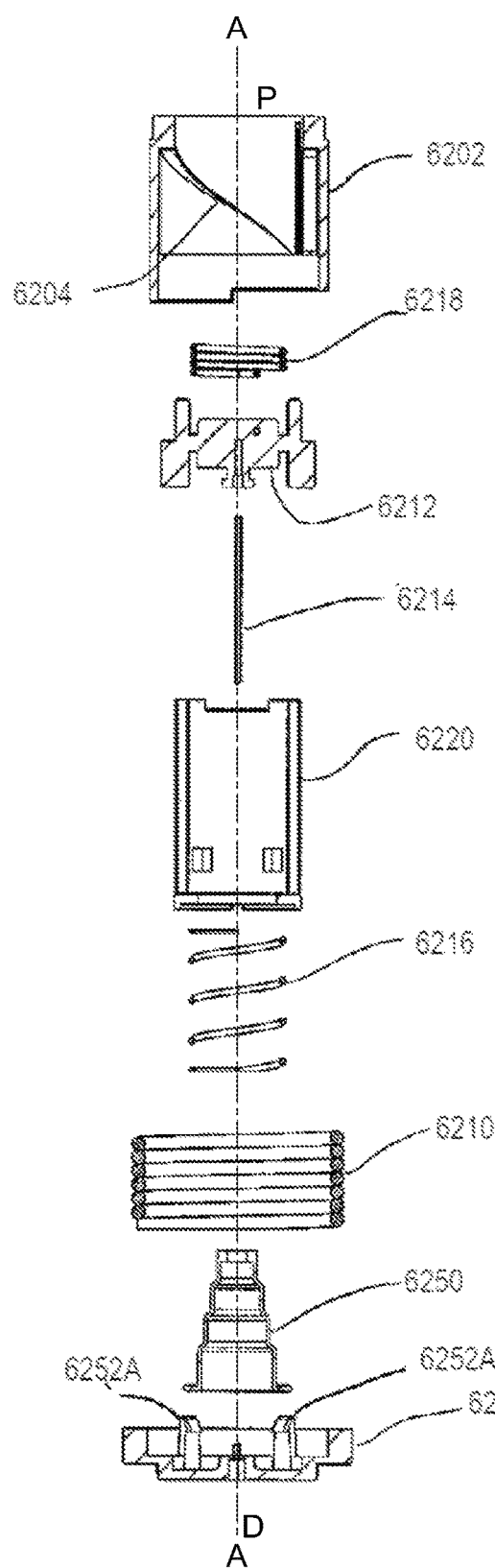
Figure 143A:
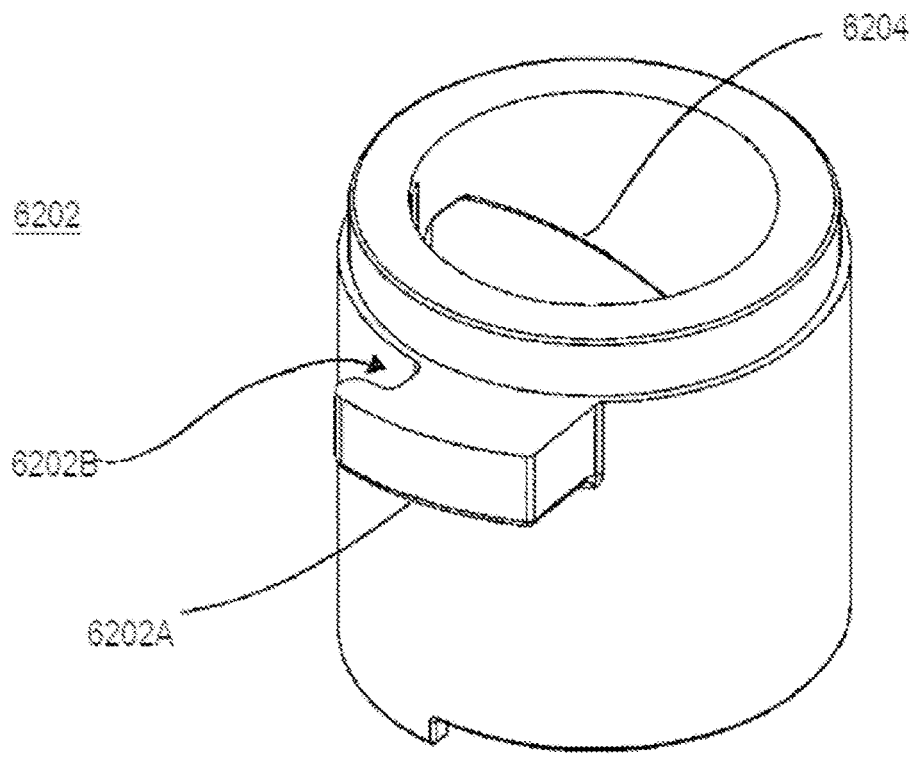
Figure 143B:
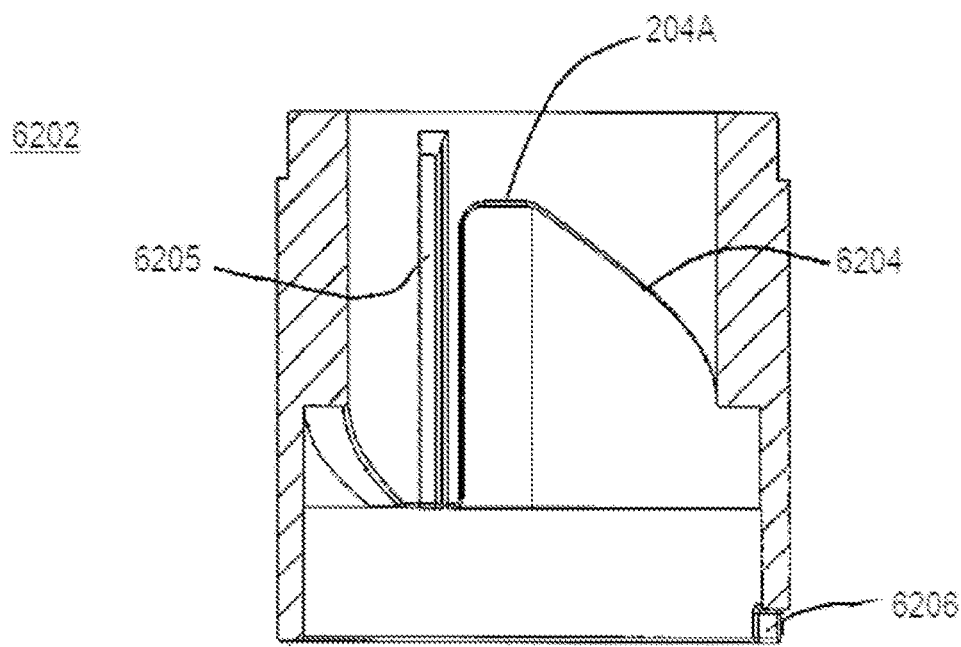
Figure 144:
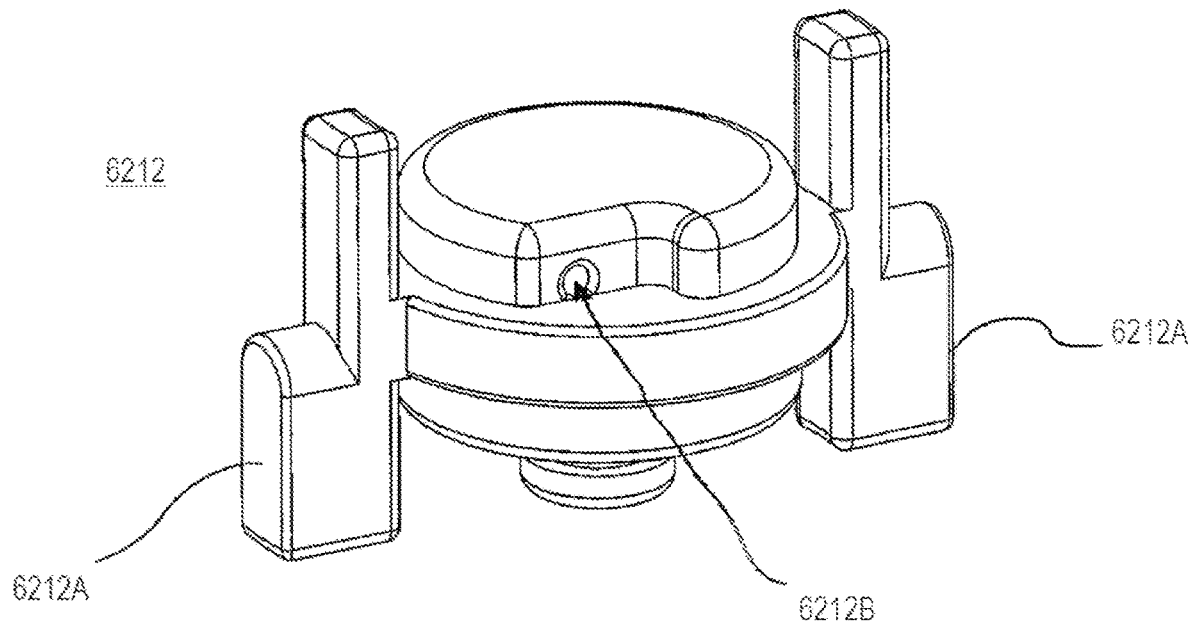
Figure 145:
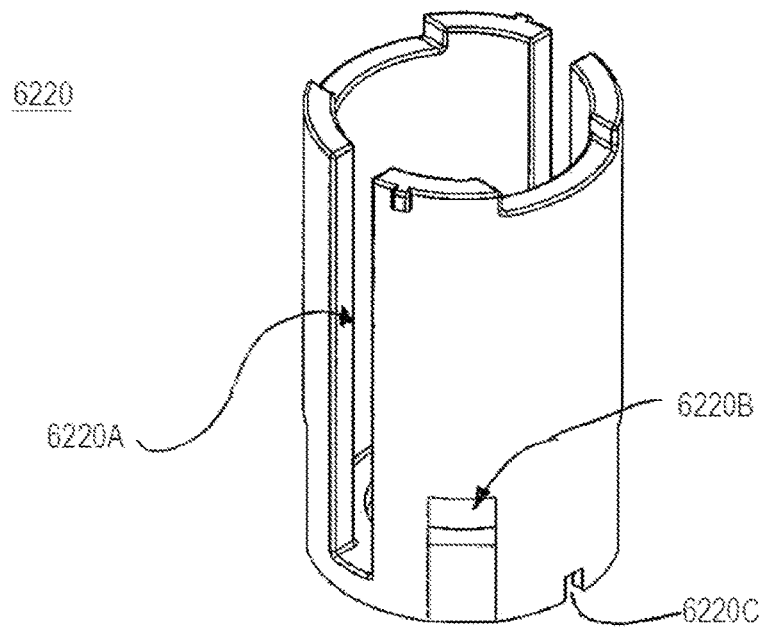
Figure 146:
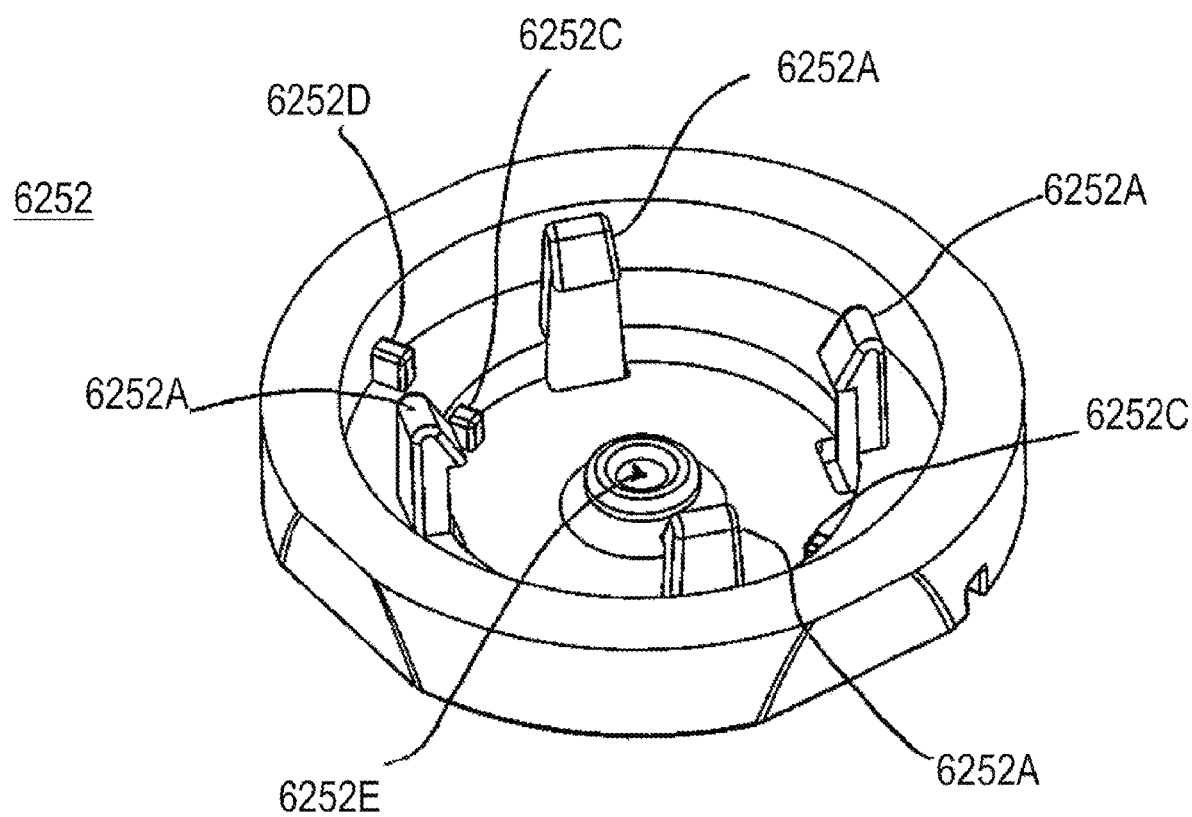
Figure 147A:
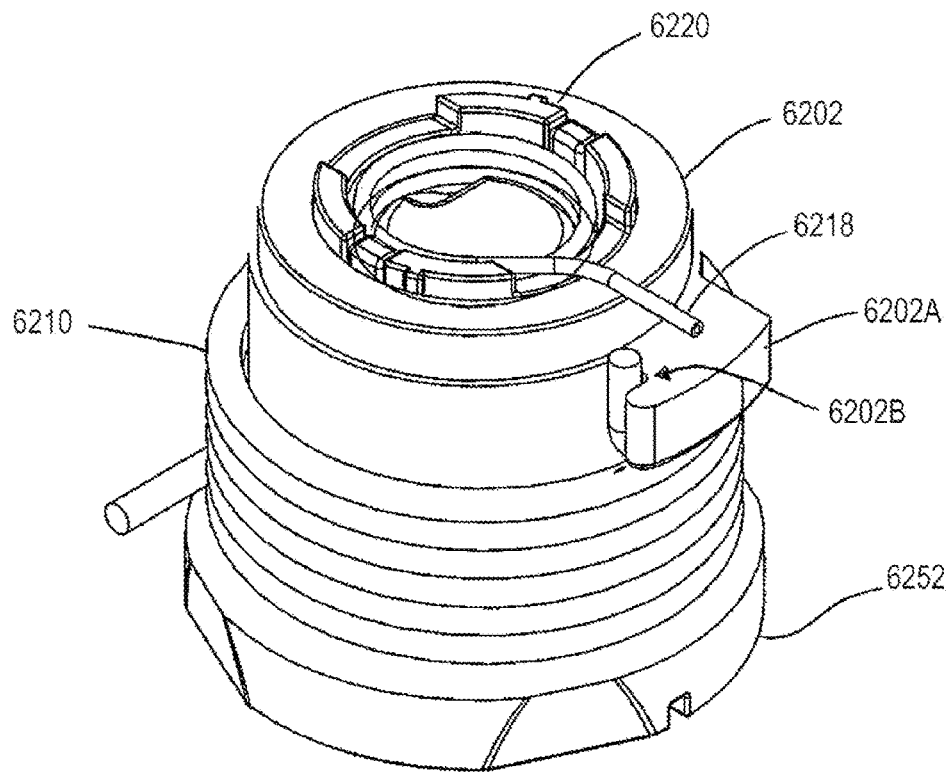
Figure 147B:
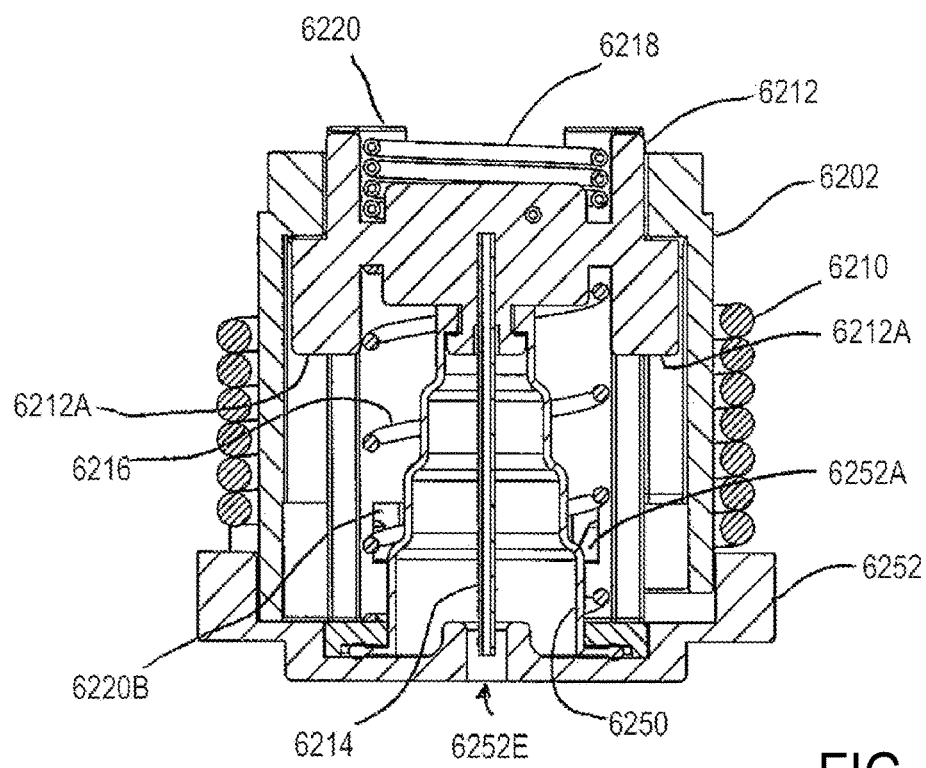
Figure 148A:
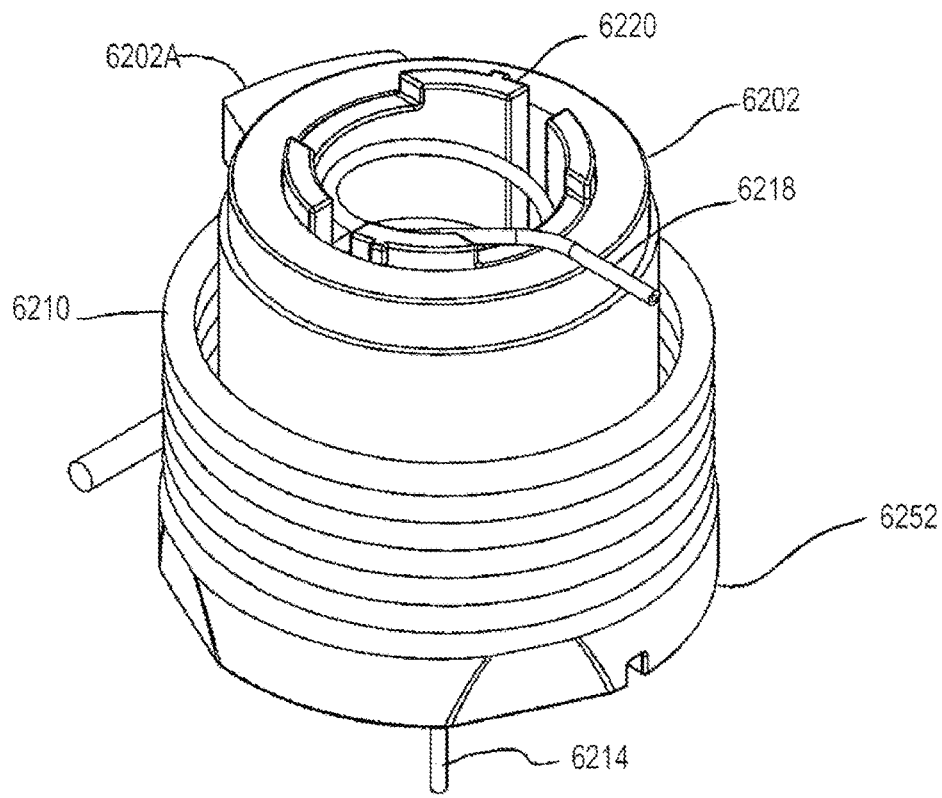
Figure 148B:
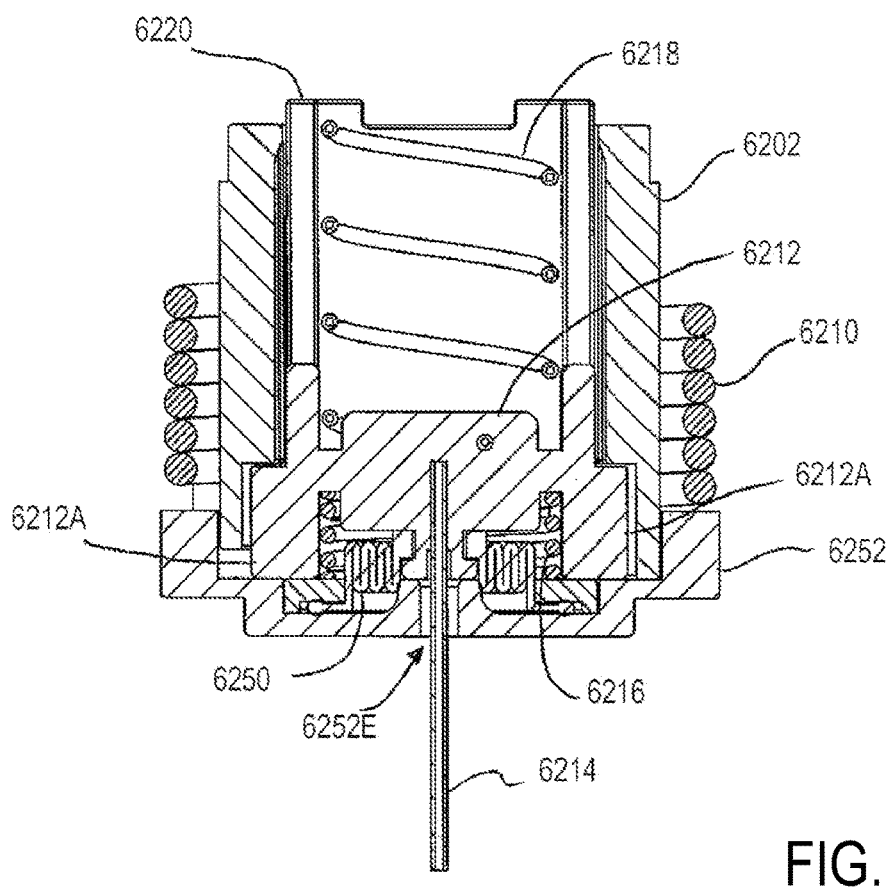
Figure 149A:
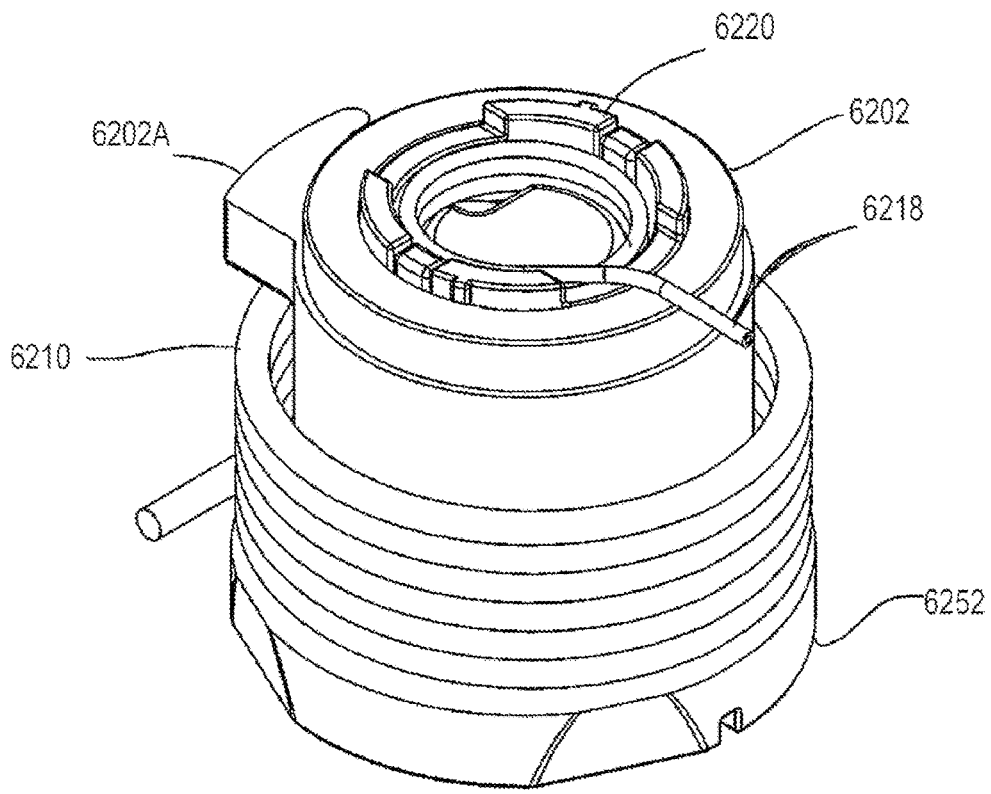
Figure 149B:
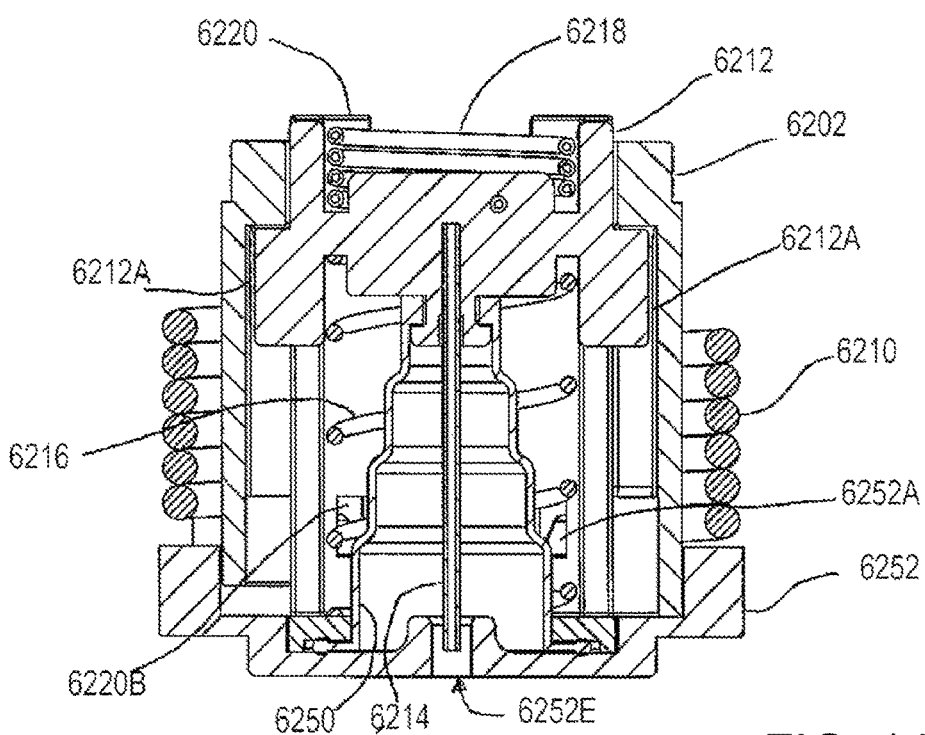
Figure 150:
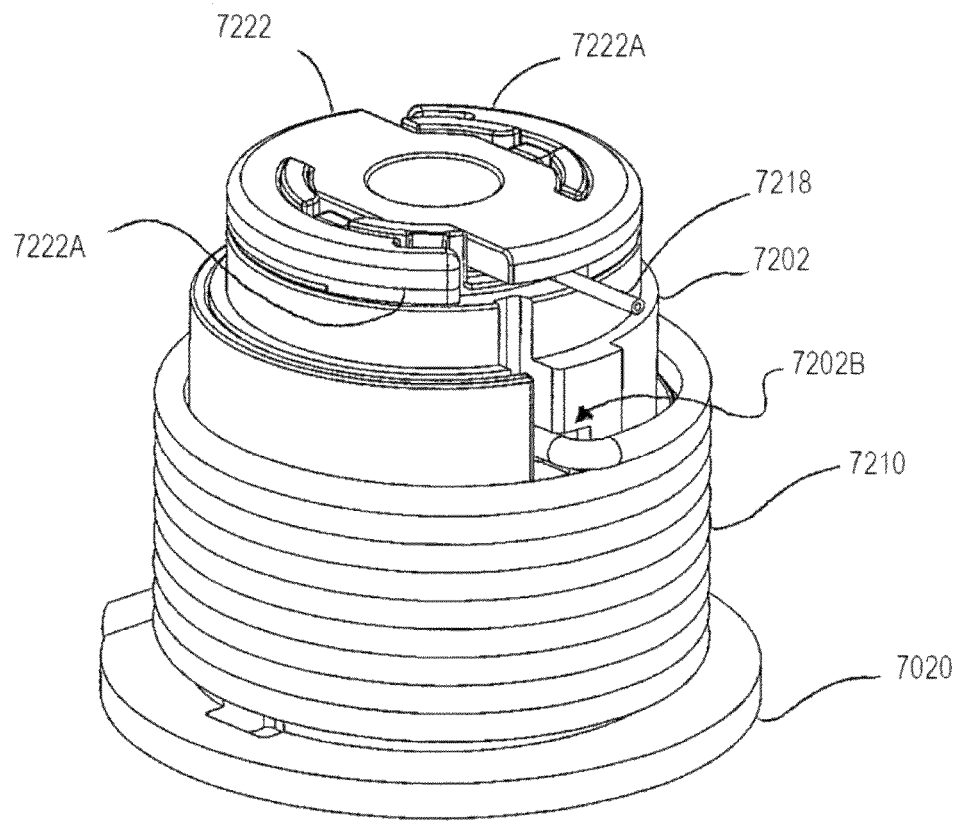
Figure 151:
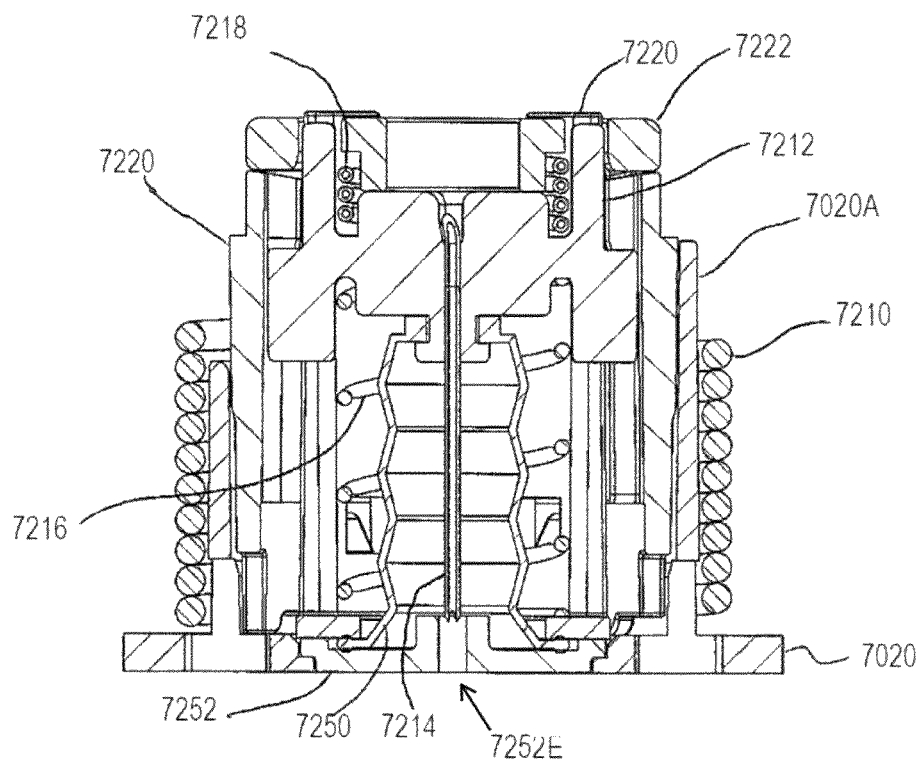
Figure 152:
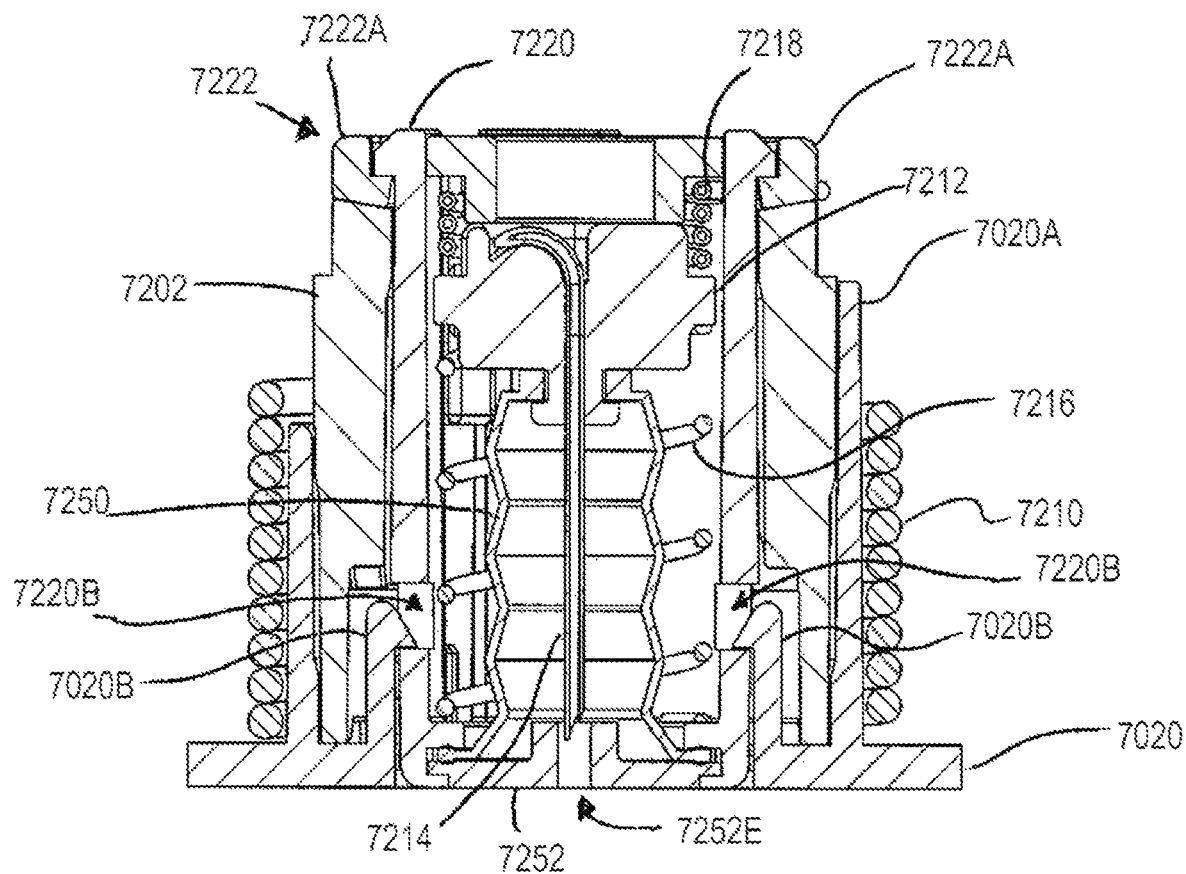
Figure 153A:
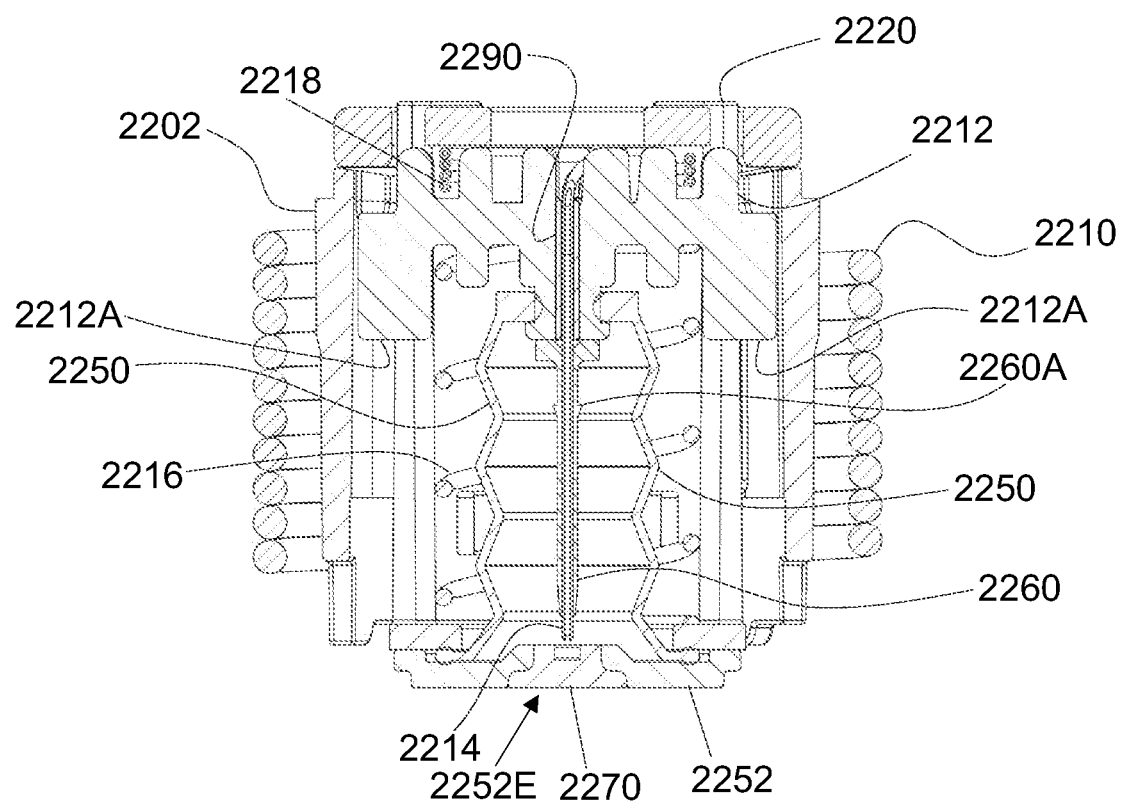
Figure 153B:
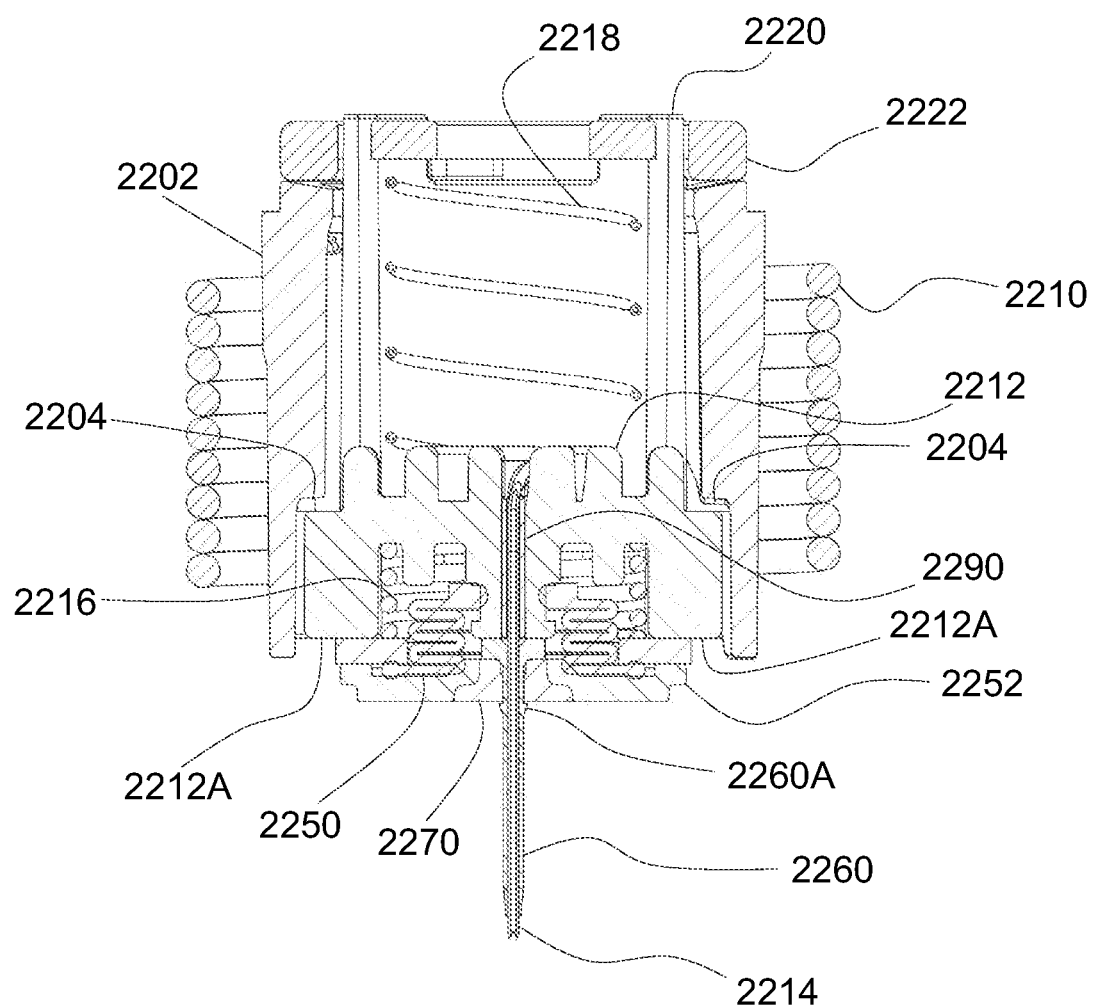
Figure 153C:
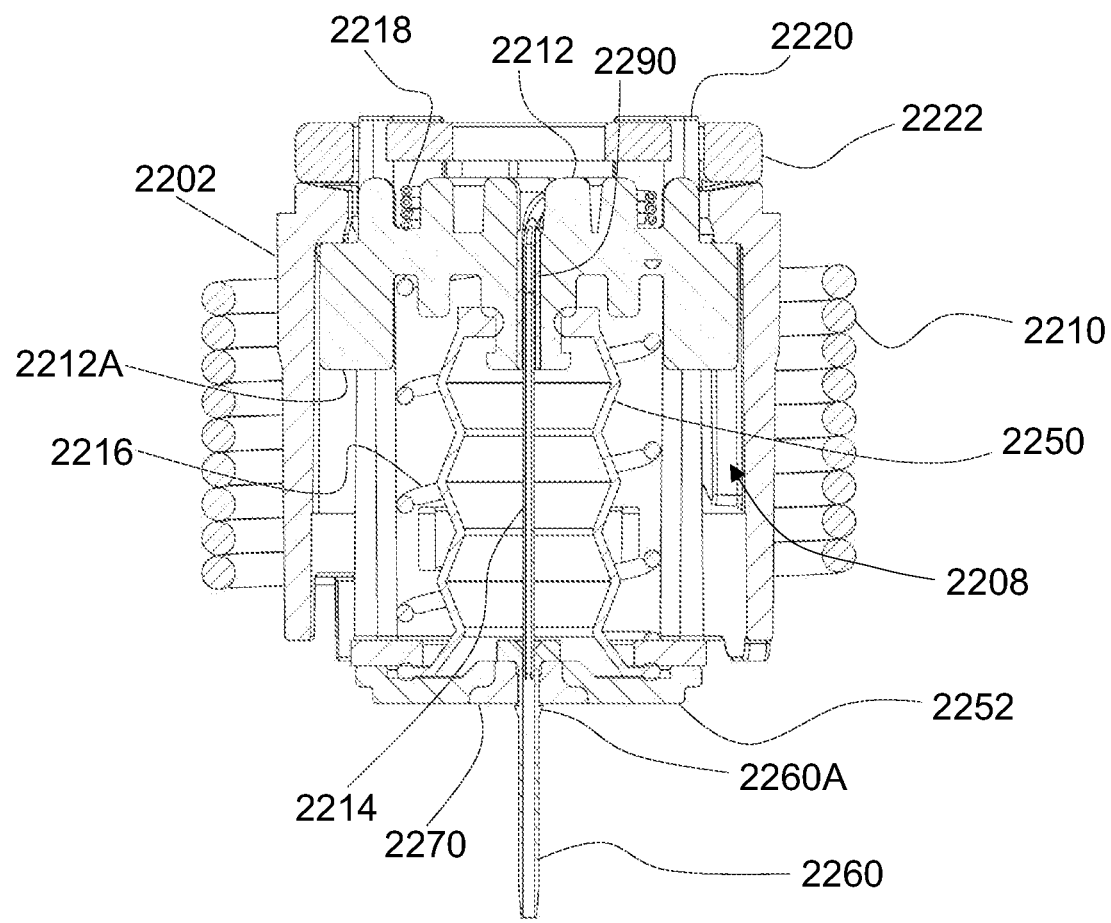
Figure 154A:
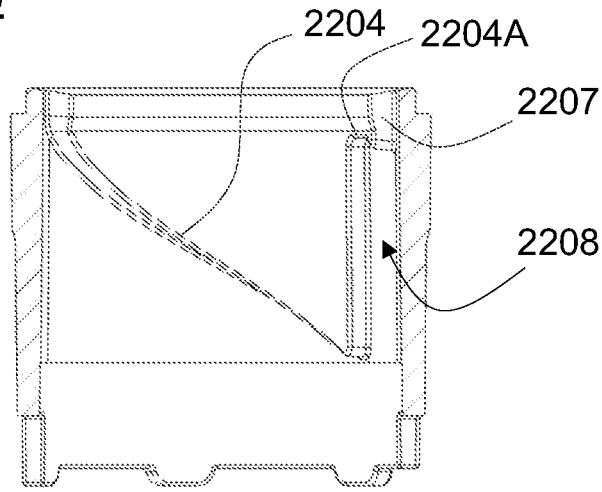
Figure 154B:
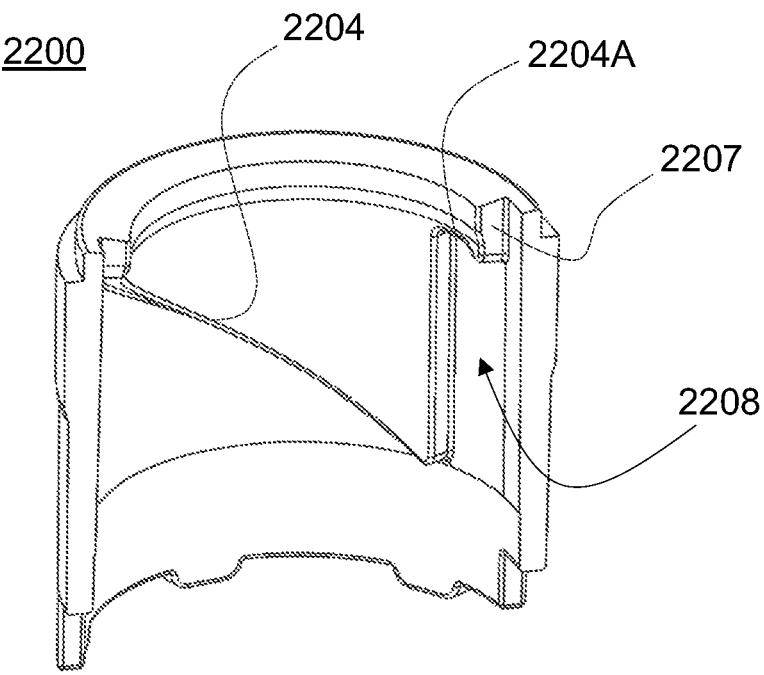
Figure 155A:
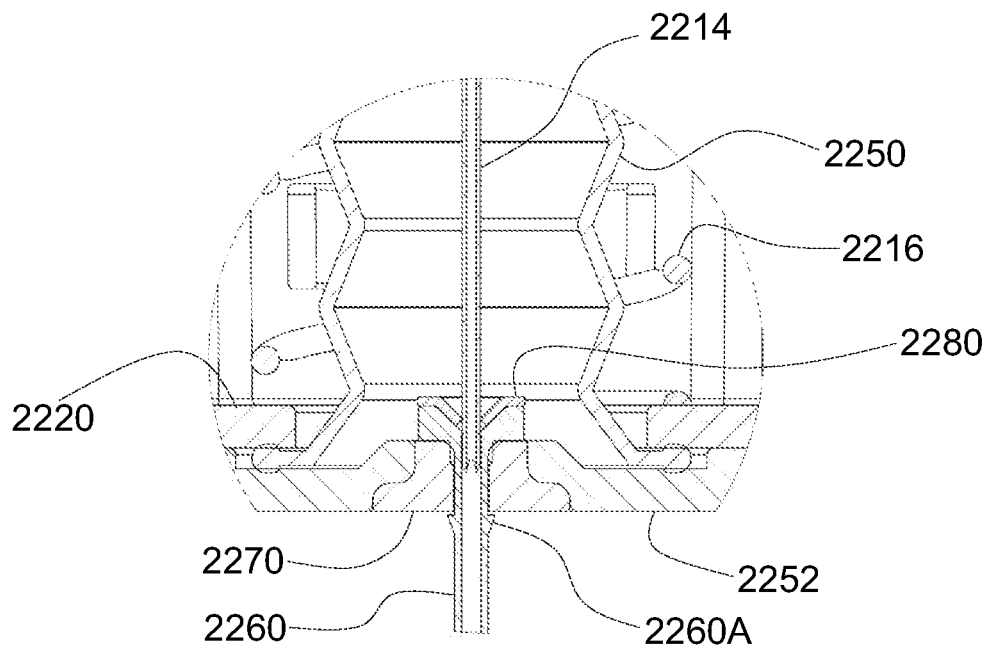
Figure 155B:
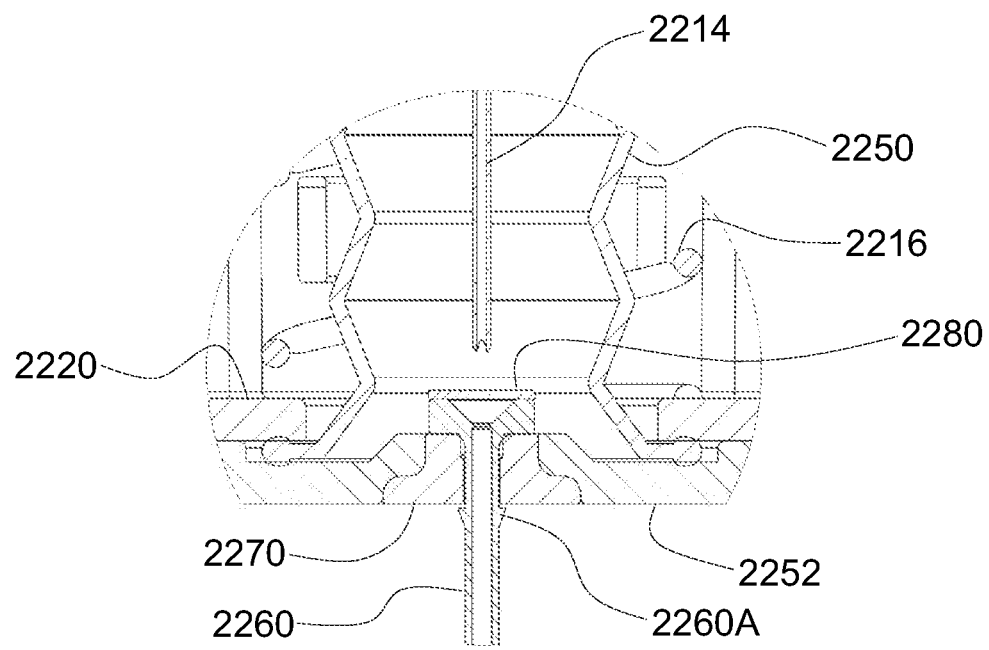
Figure 156A:
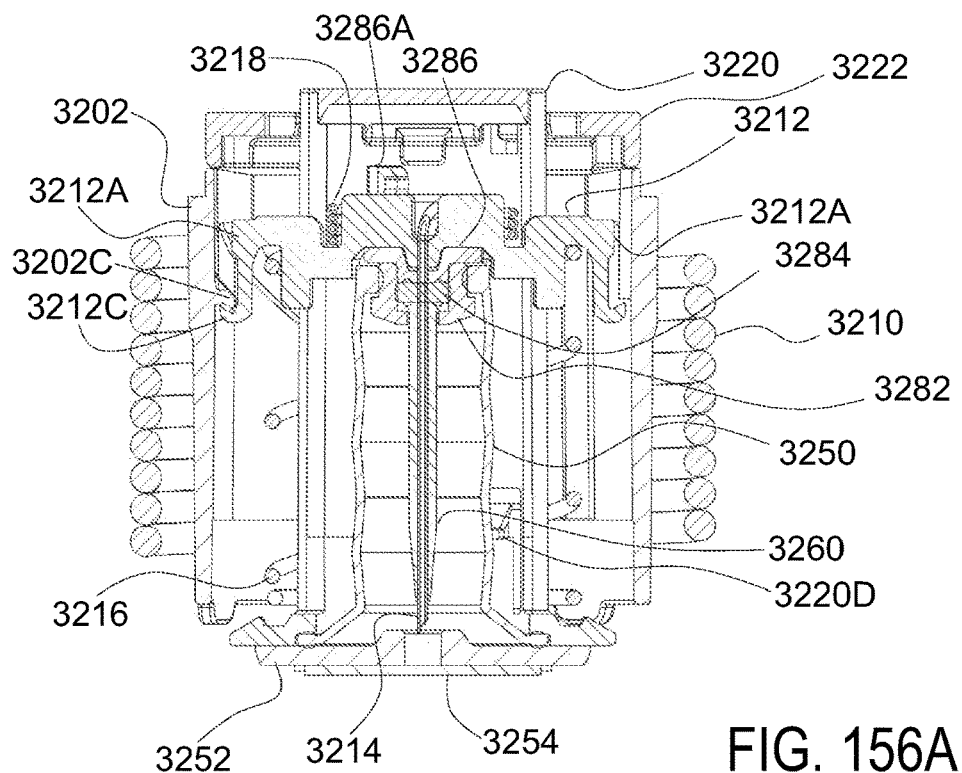
Figure 156B:
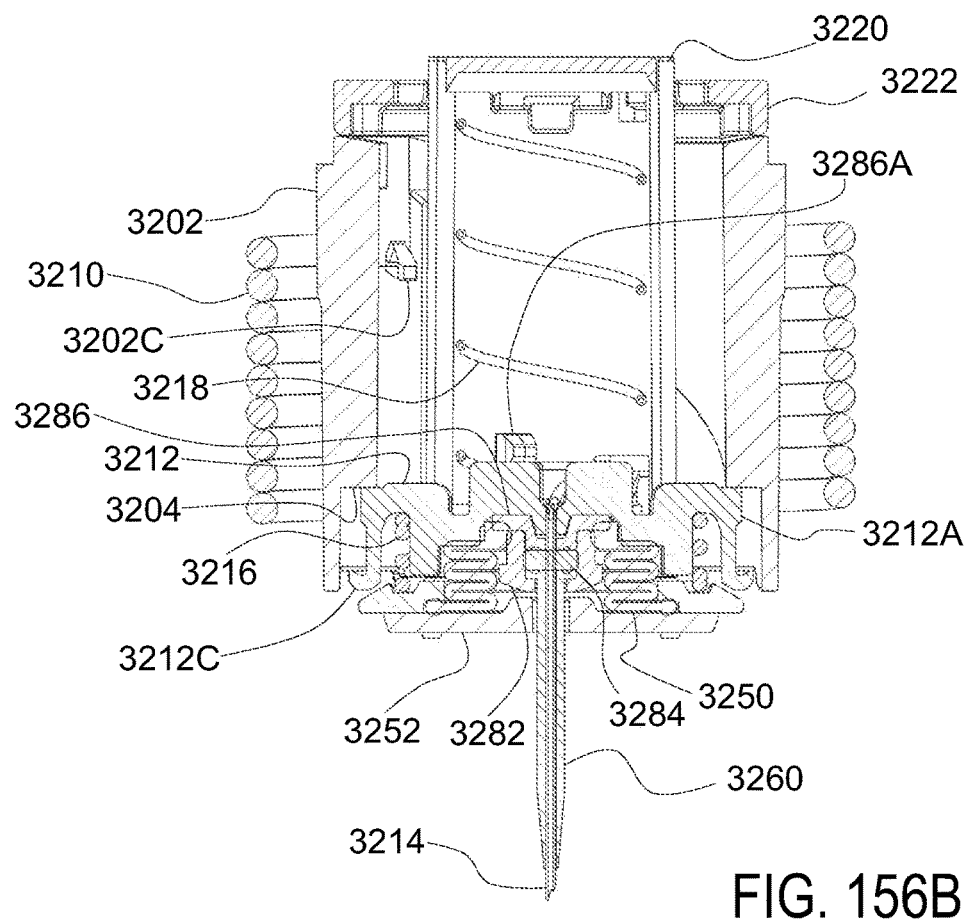
Figure 156C:
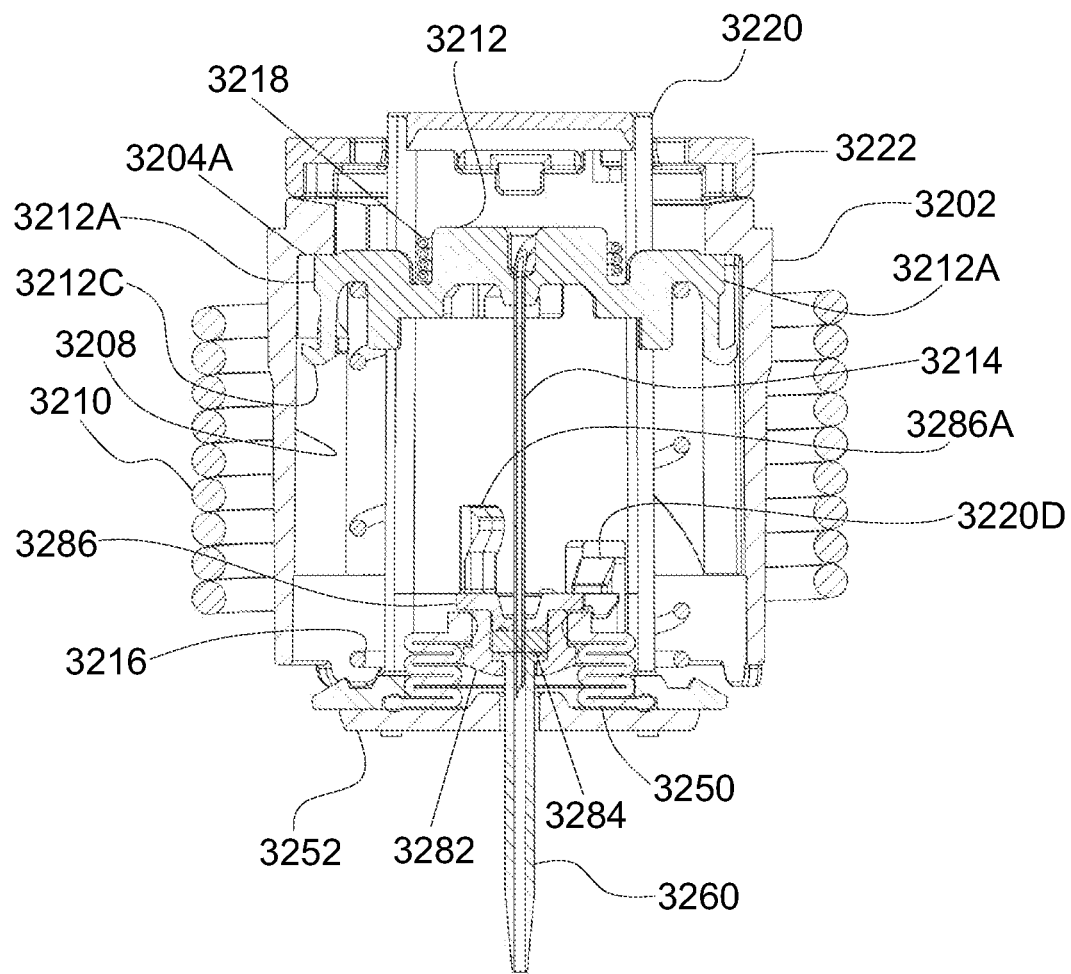
Figure 156D:
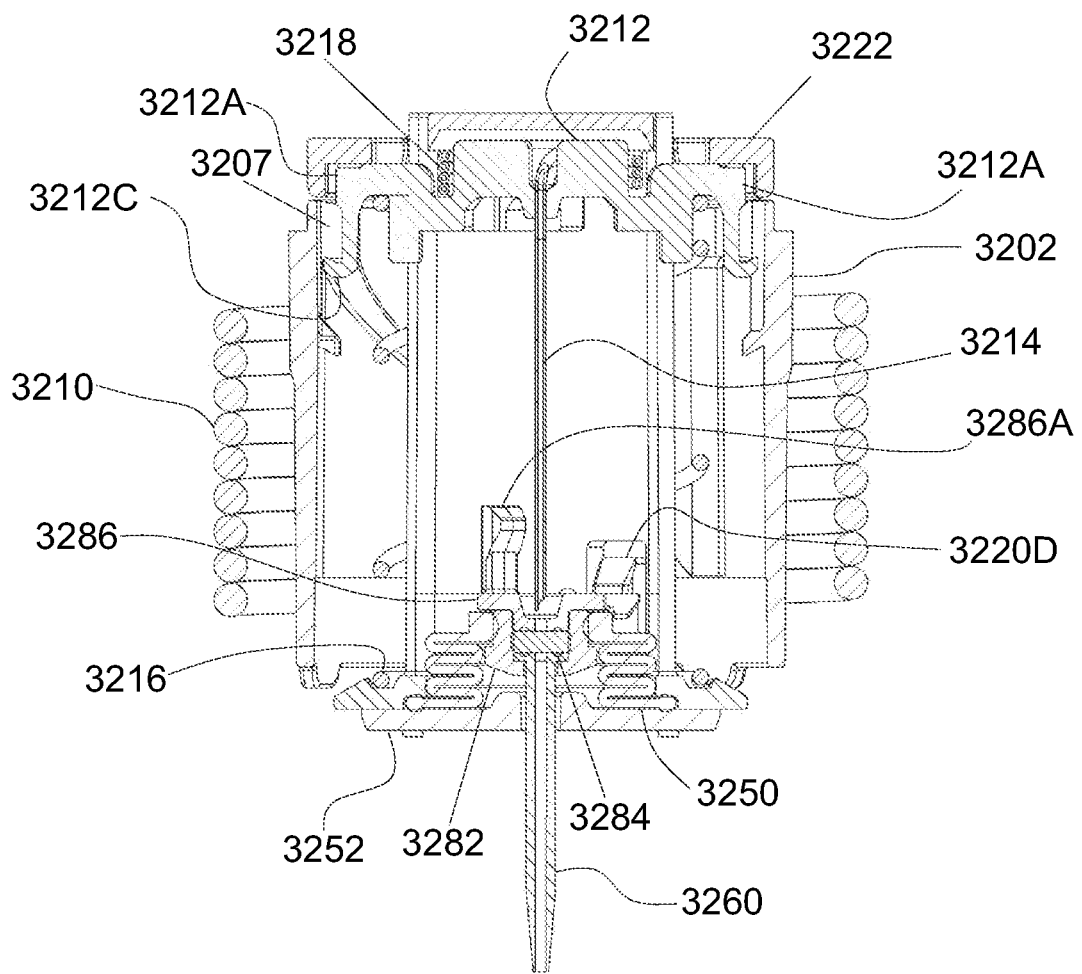
Figure 157A:
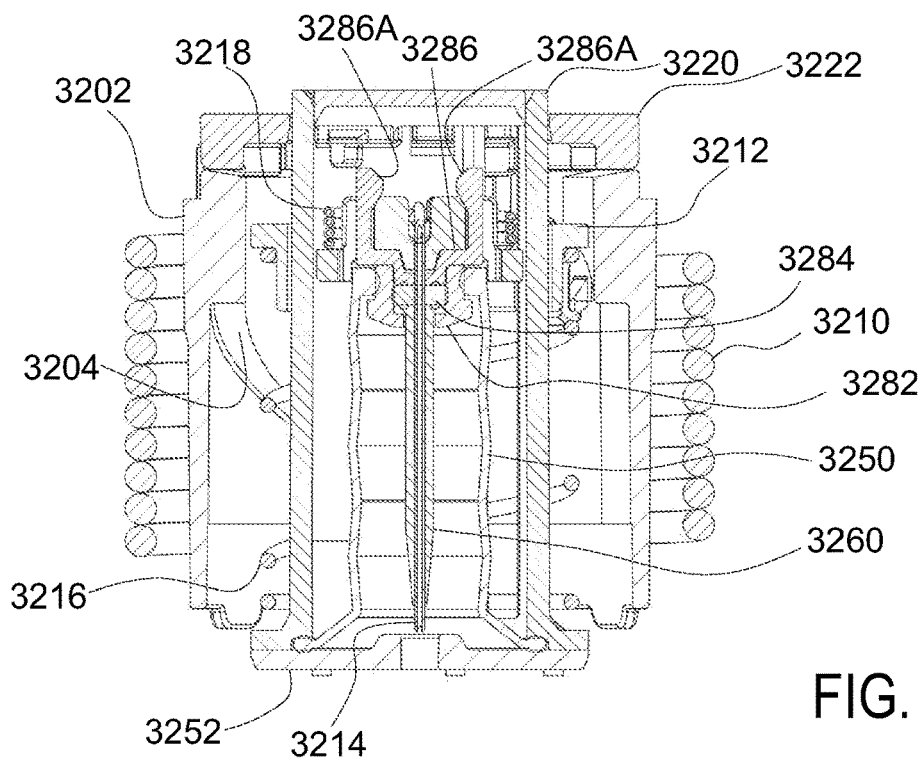
Figure 157B:
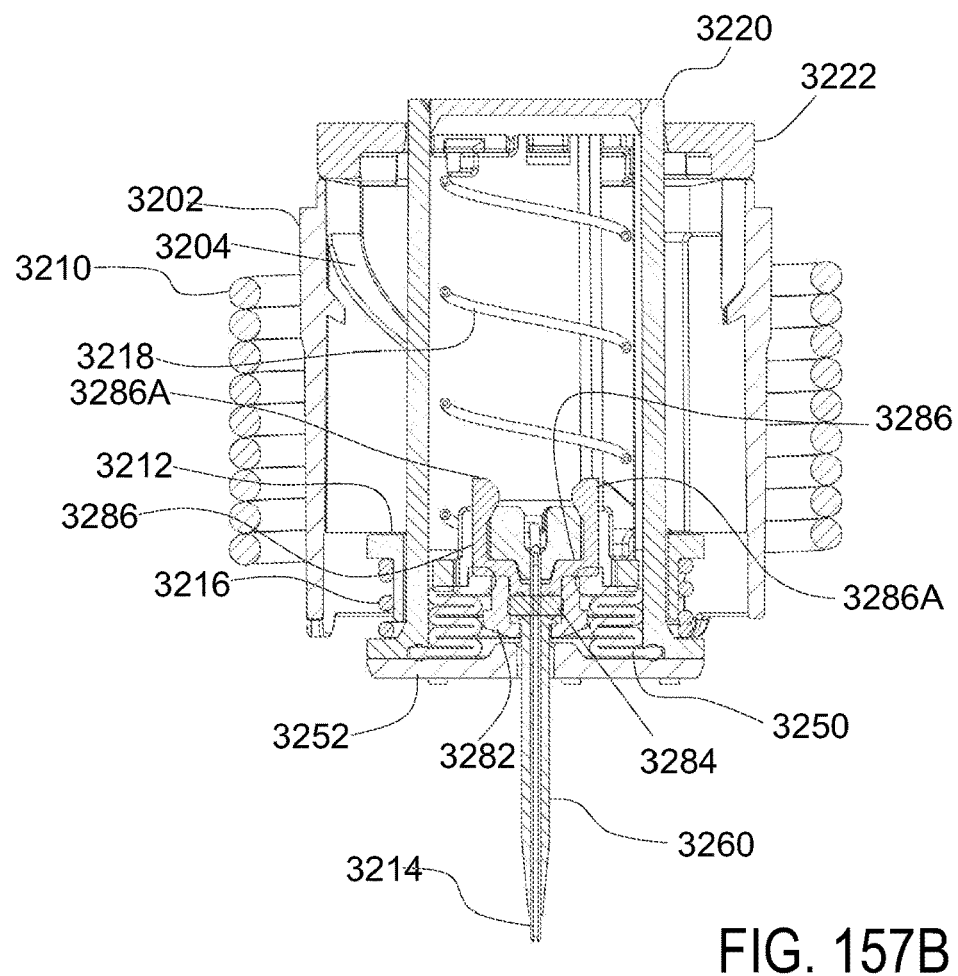
Figure 157C:
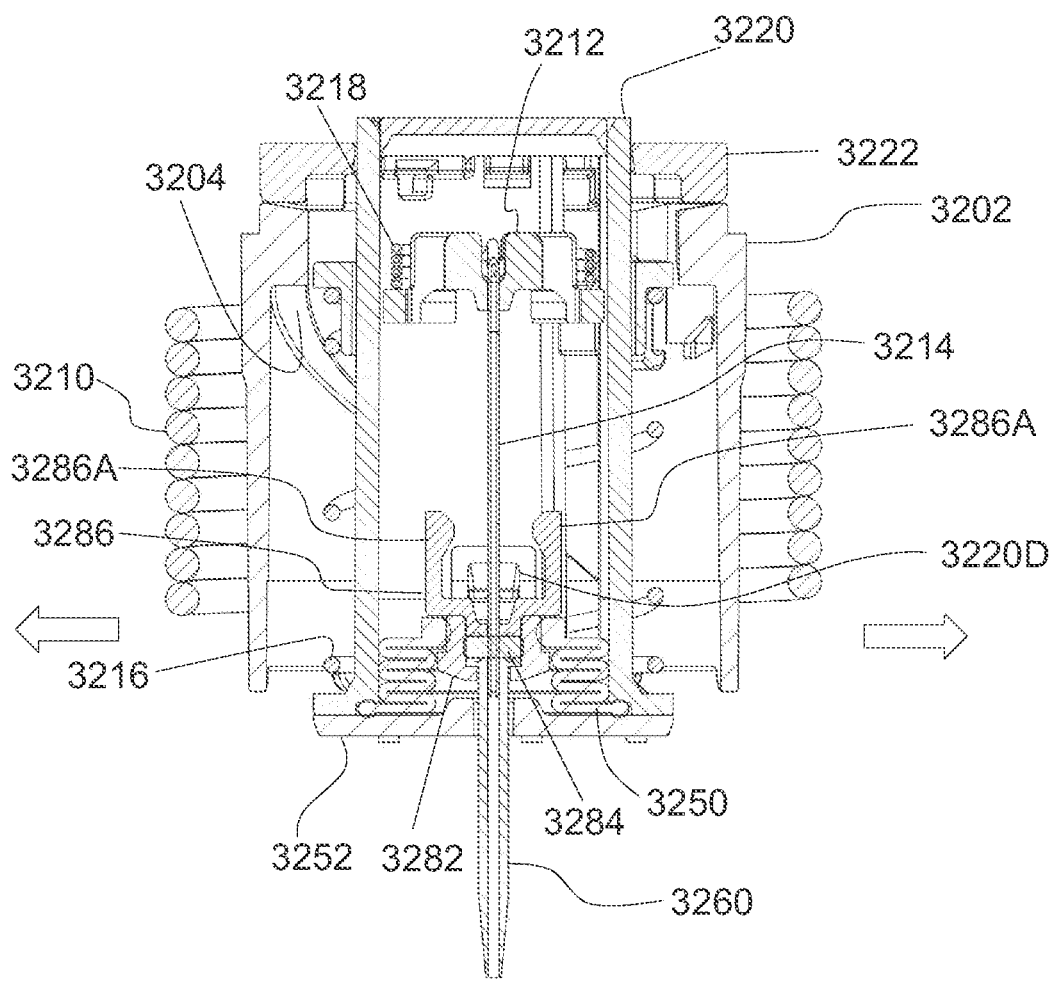
Figure 158A:
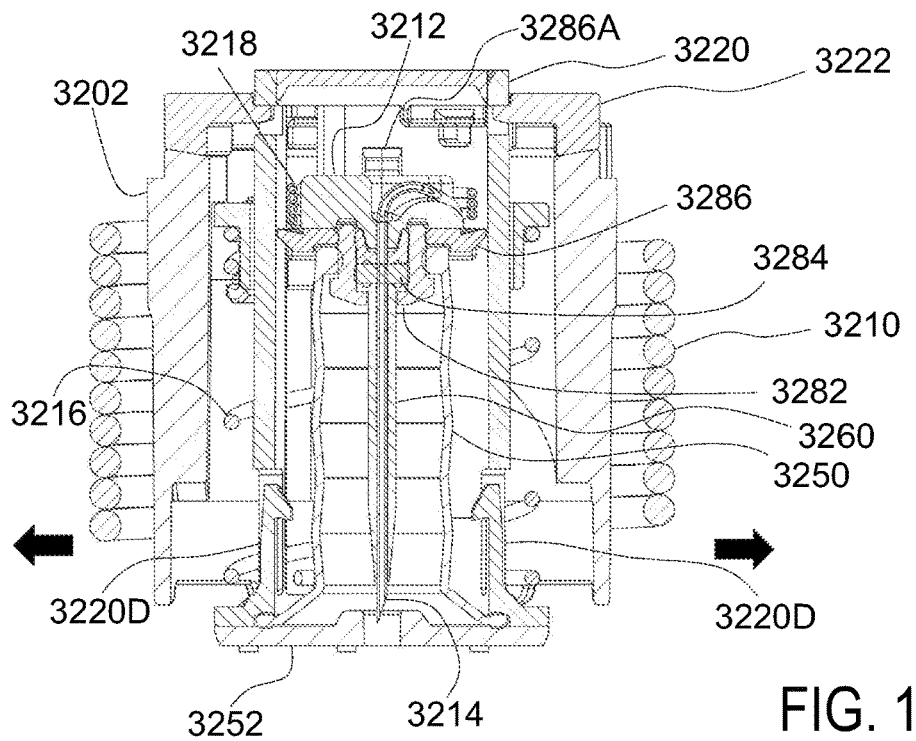
Figure 158B:
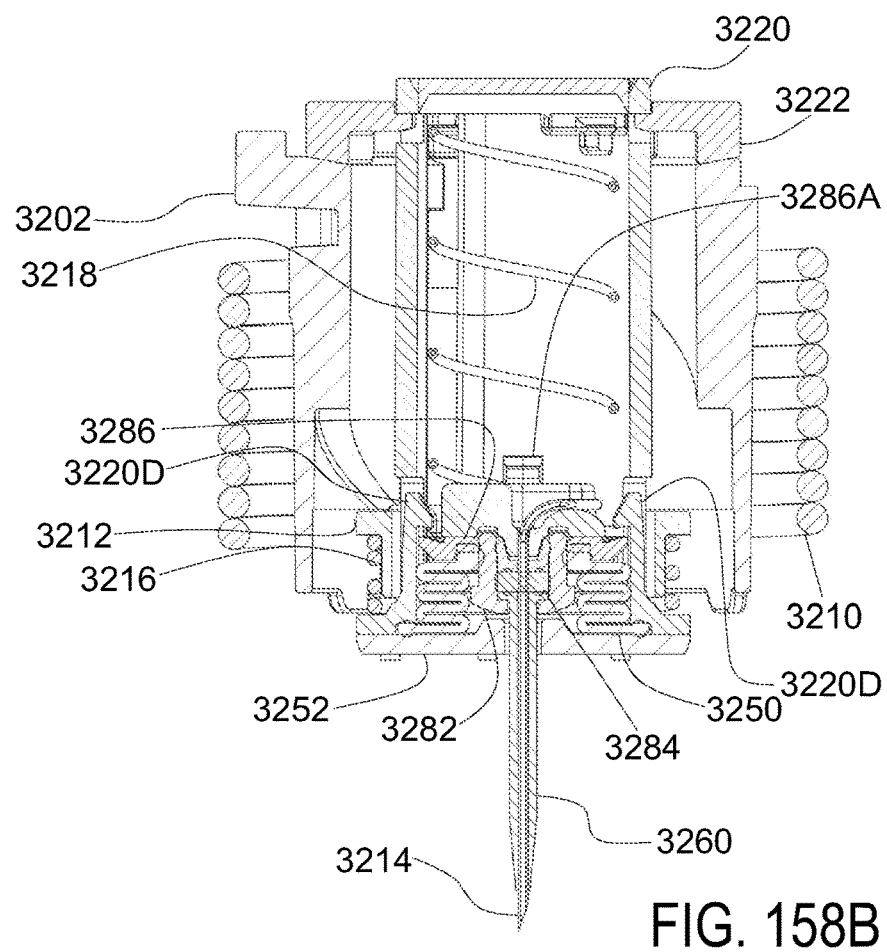
Figure 158C:
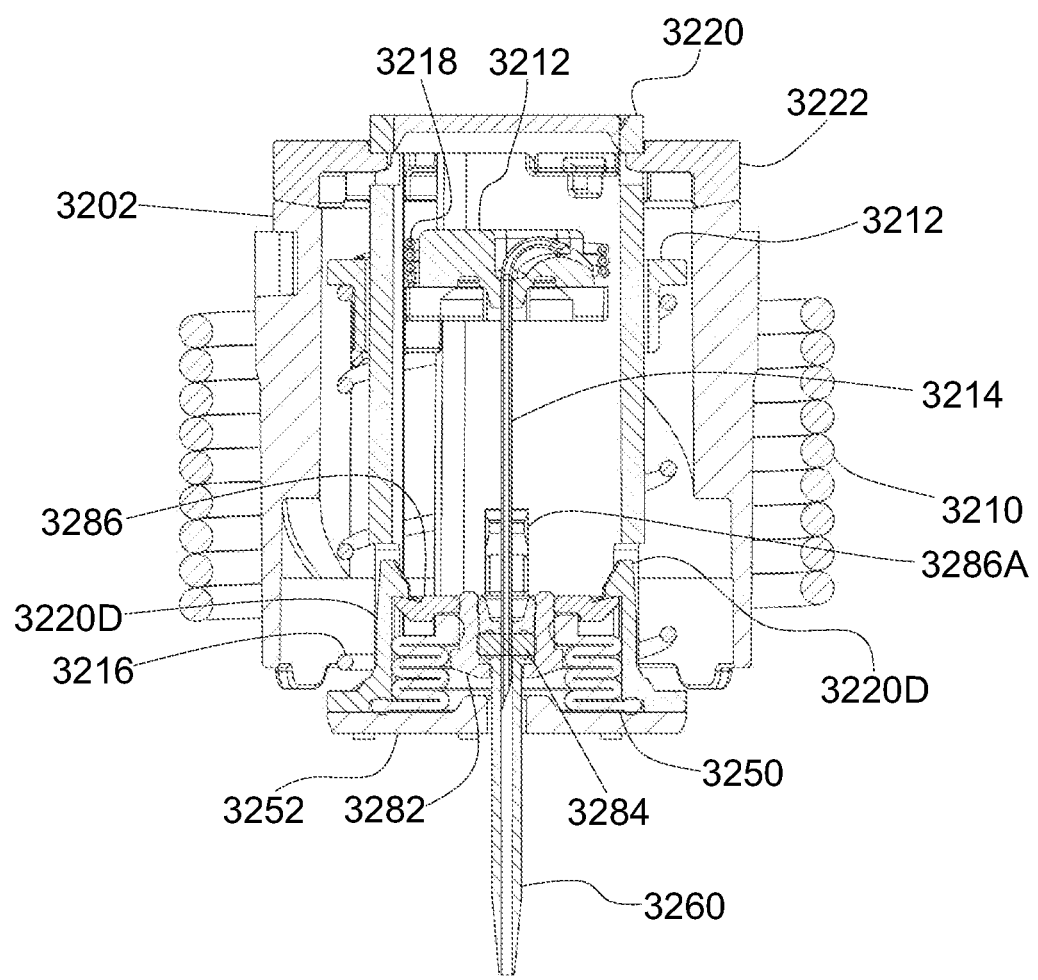
Figure 159:
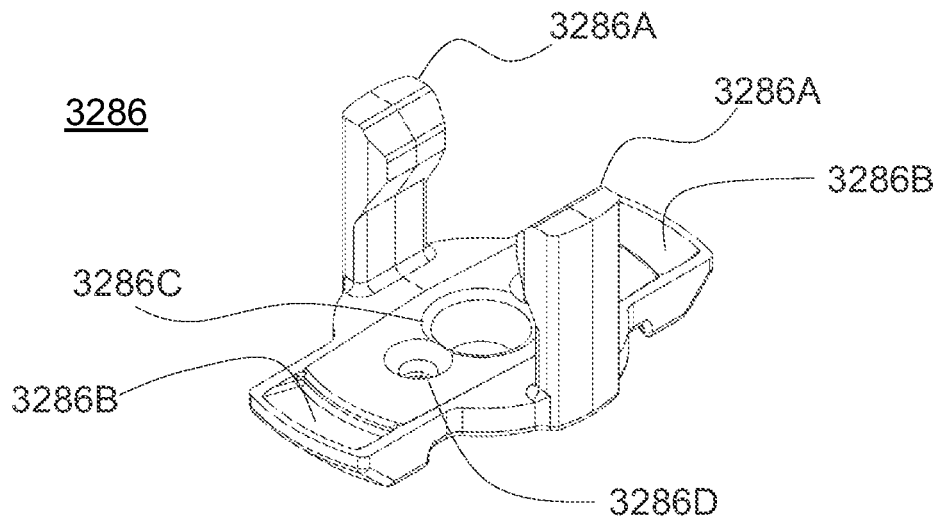
Figure 160:
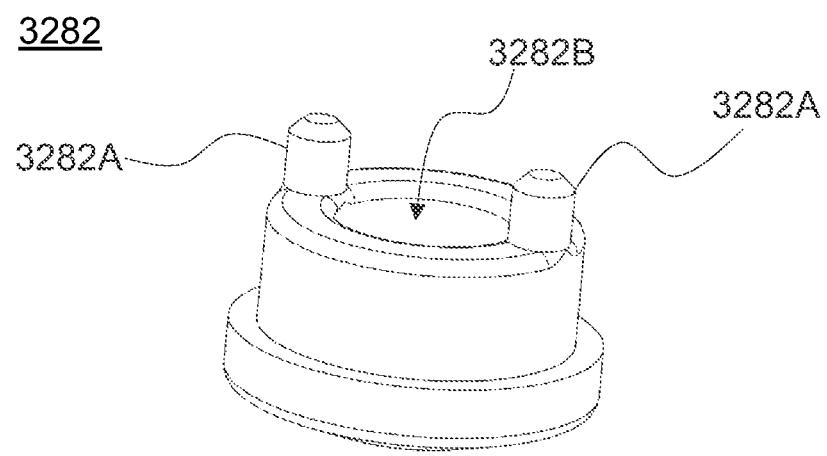
Figure 161:
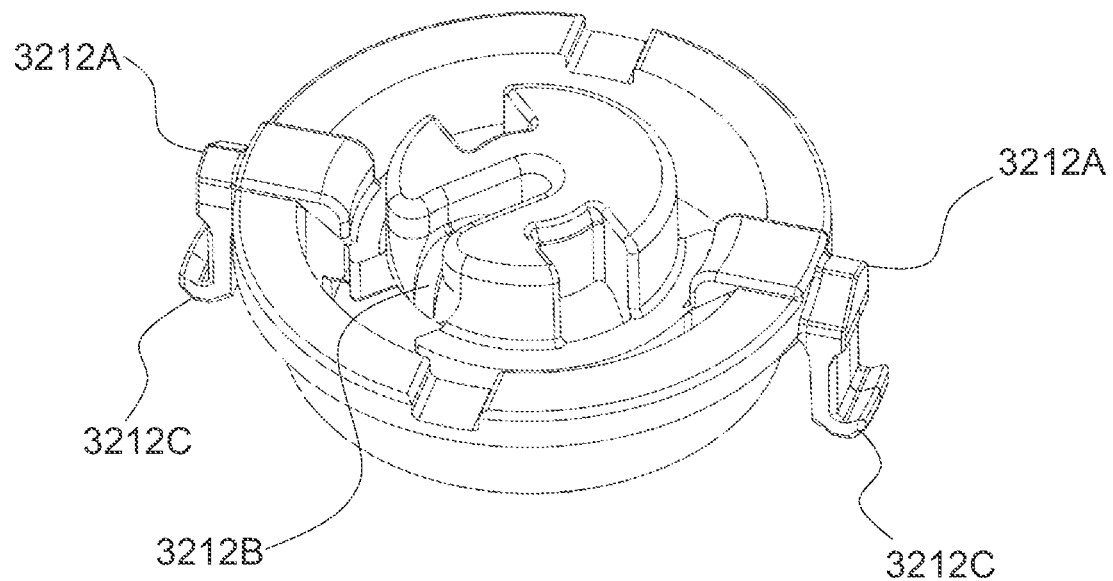
Figure 162:
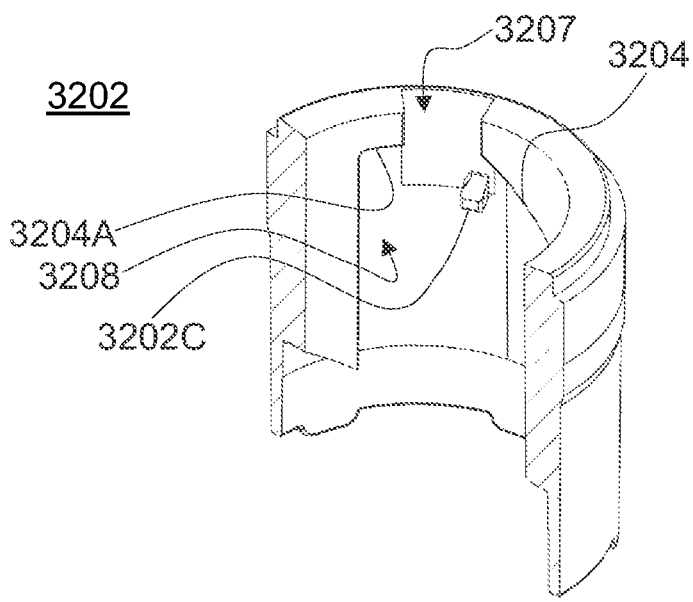
Figure 163A:
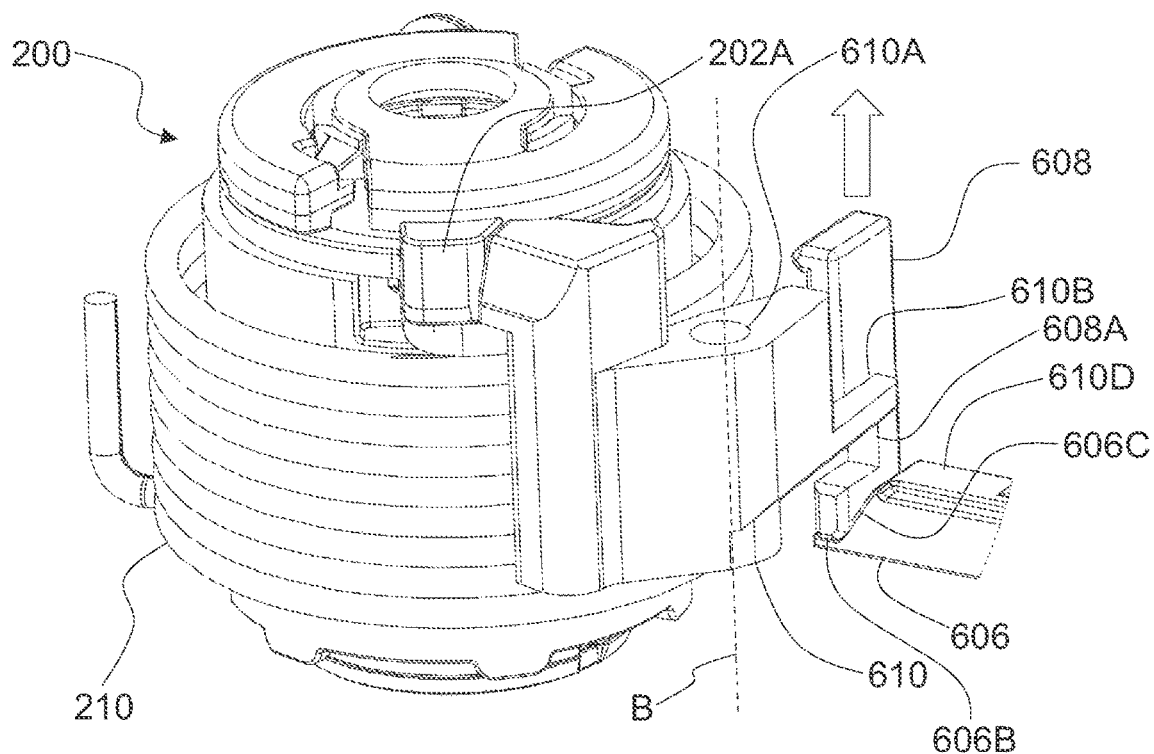
Figure 163B:
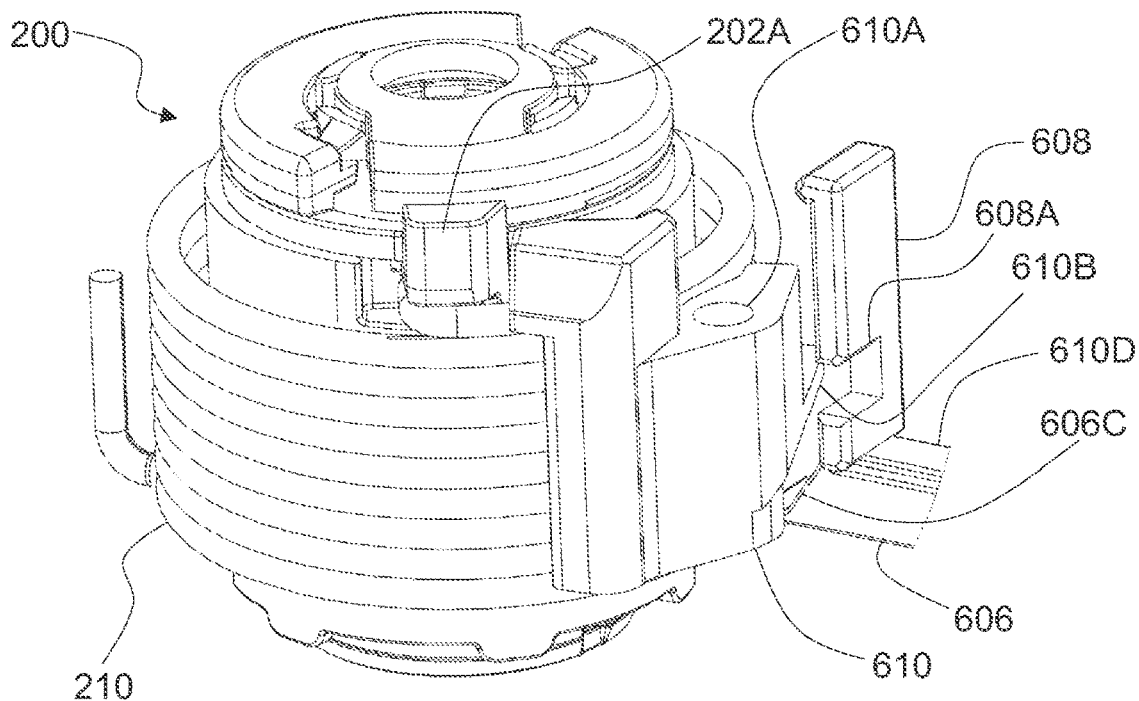
Figure 164A:
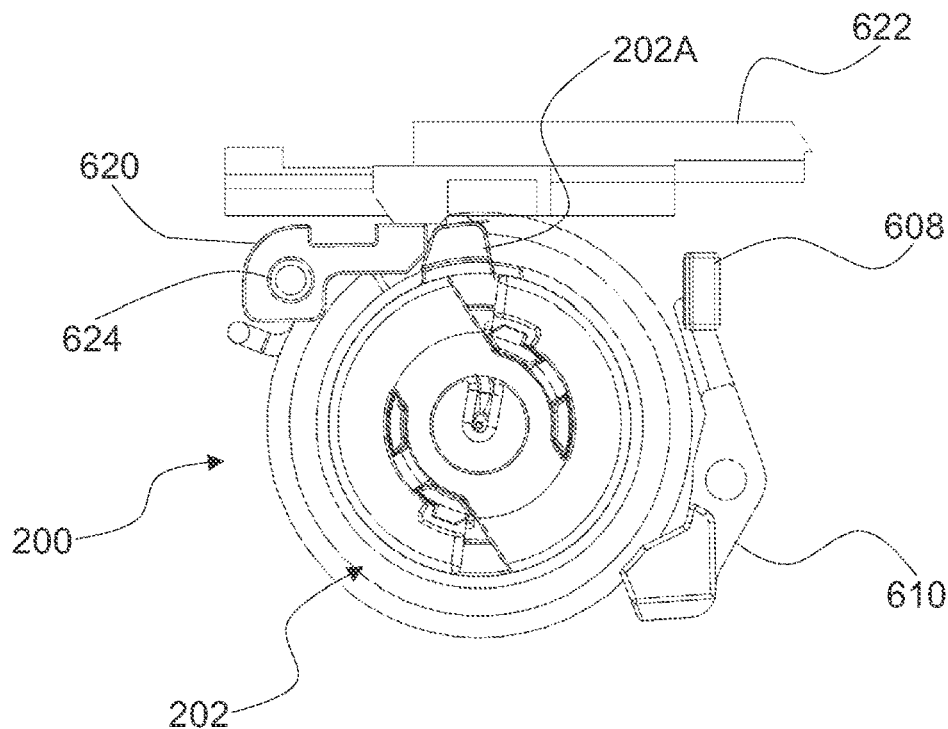
Figure 164B:
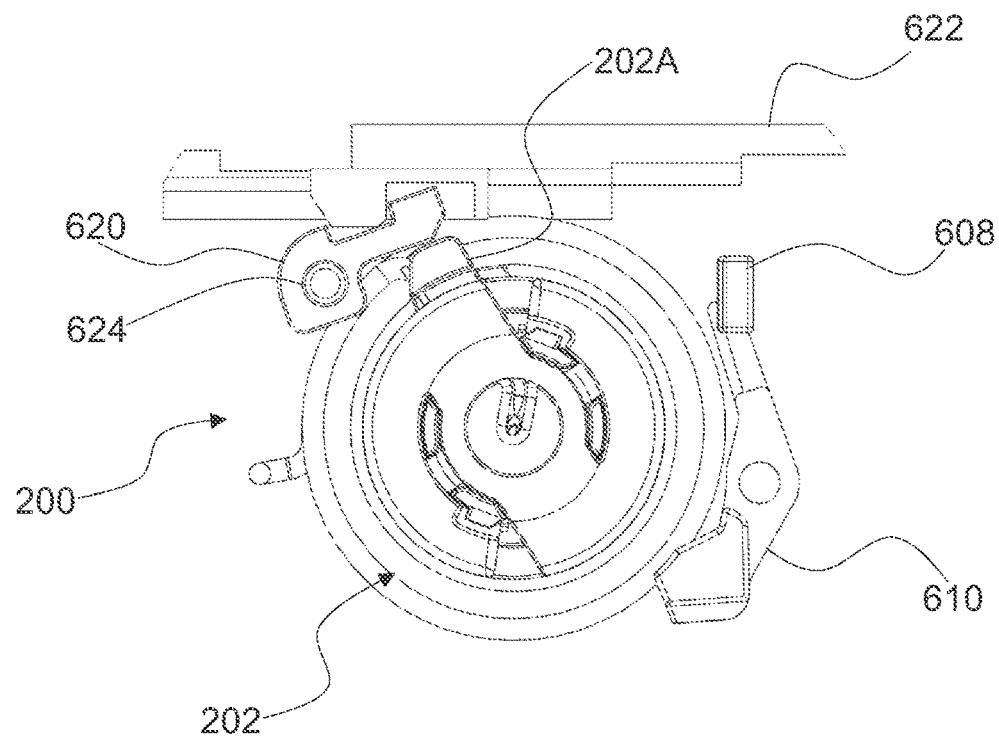
Figure 166A:
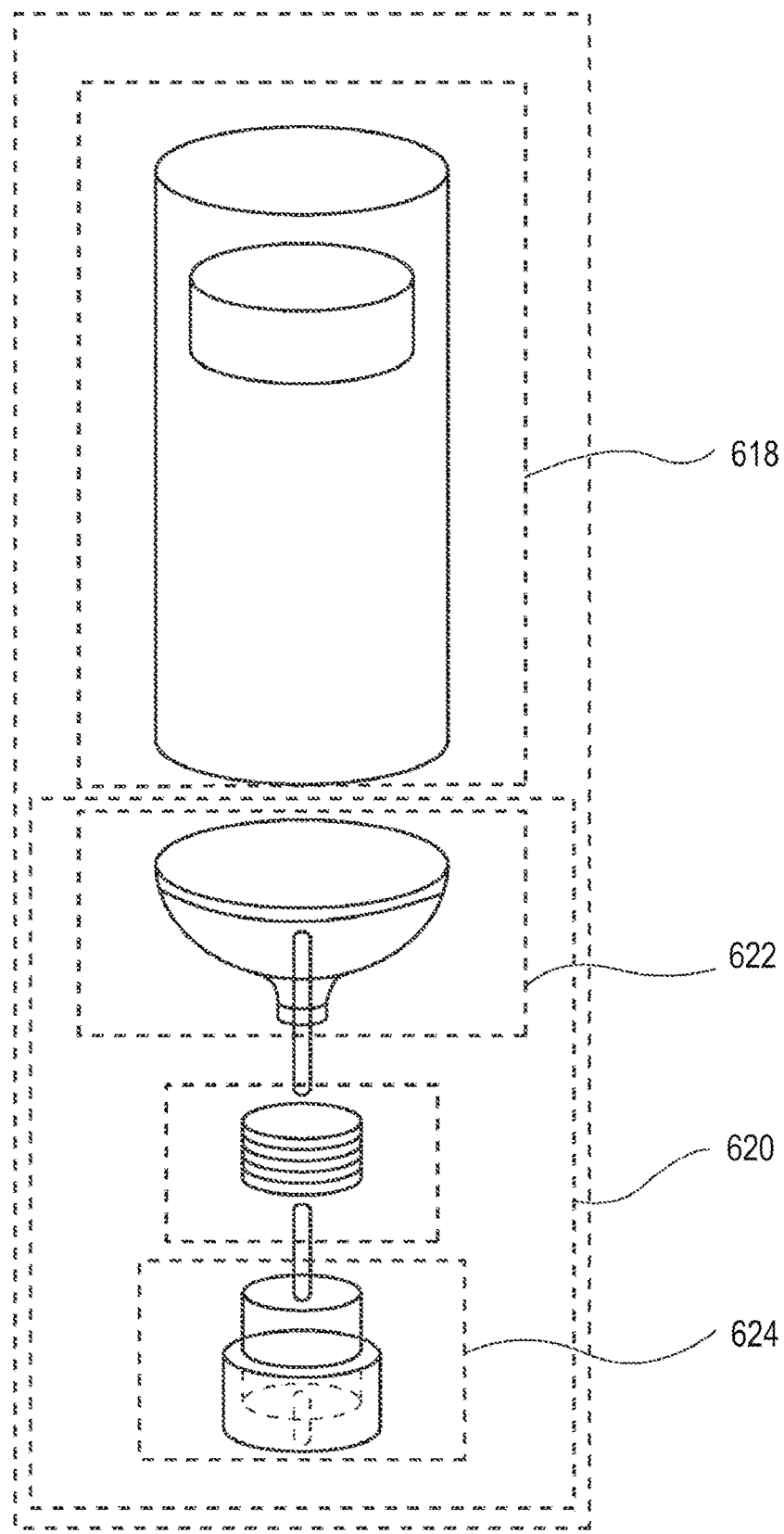
Figures 167, 168:
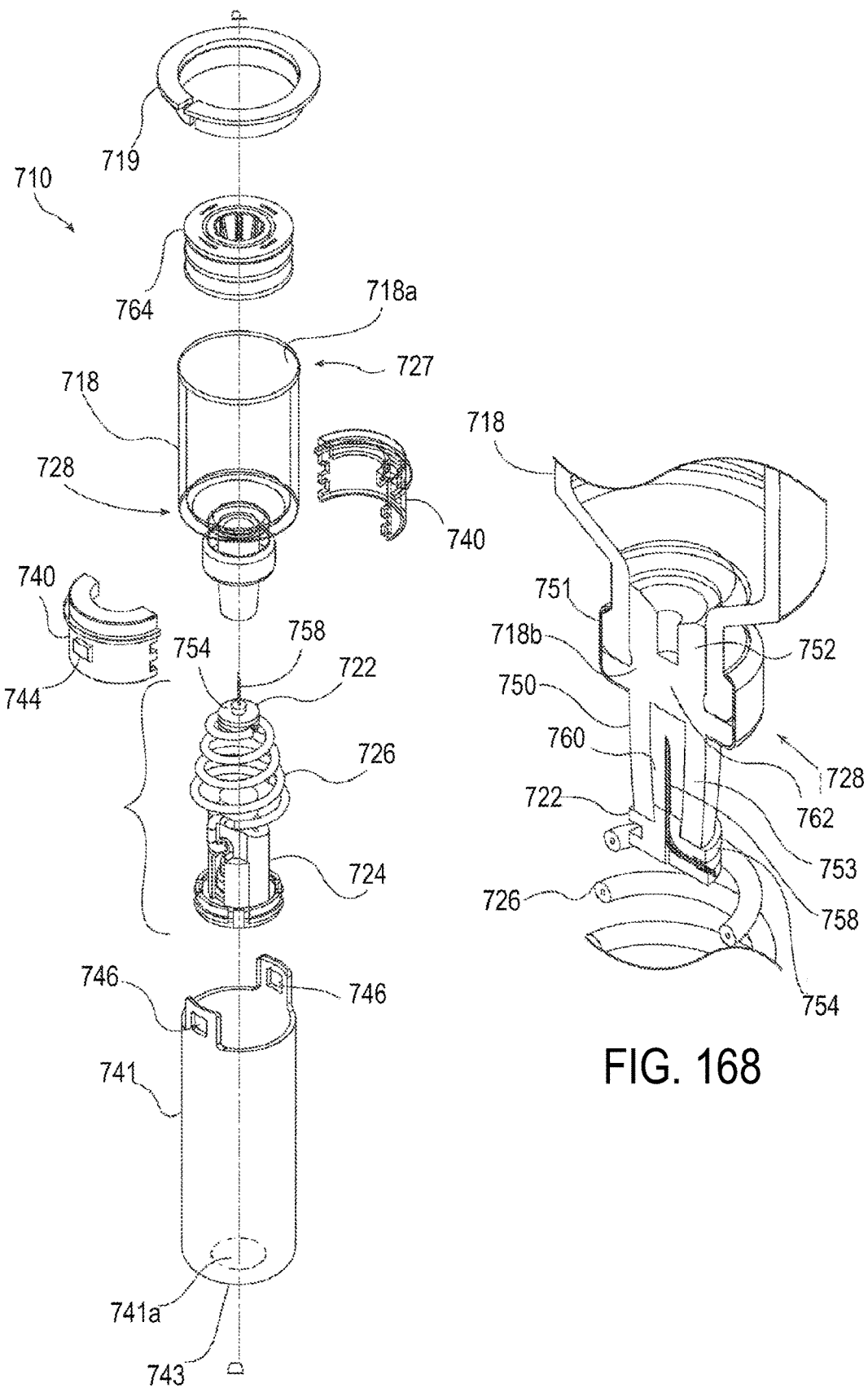
Figure 169:
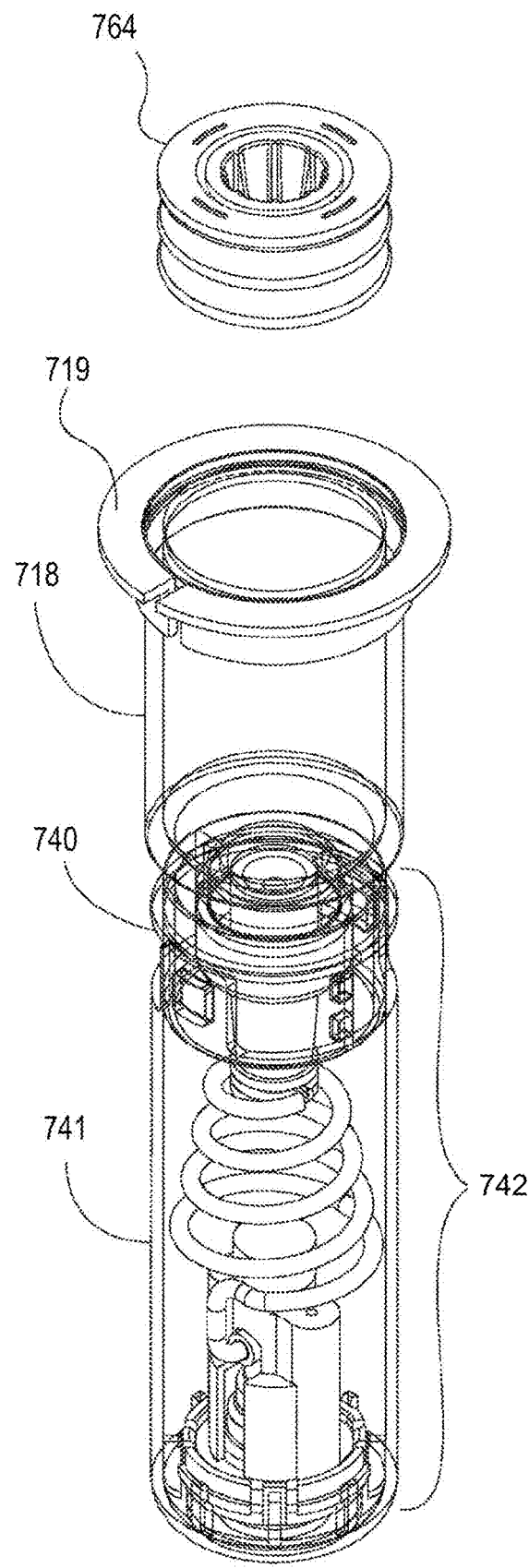
Figure 170:
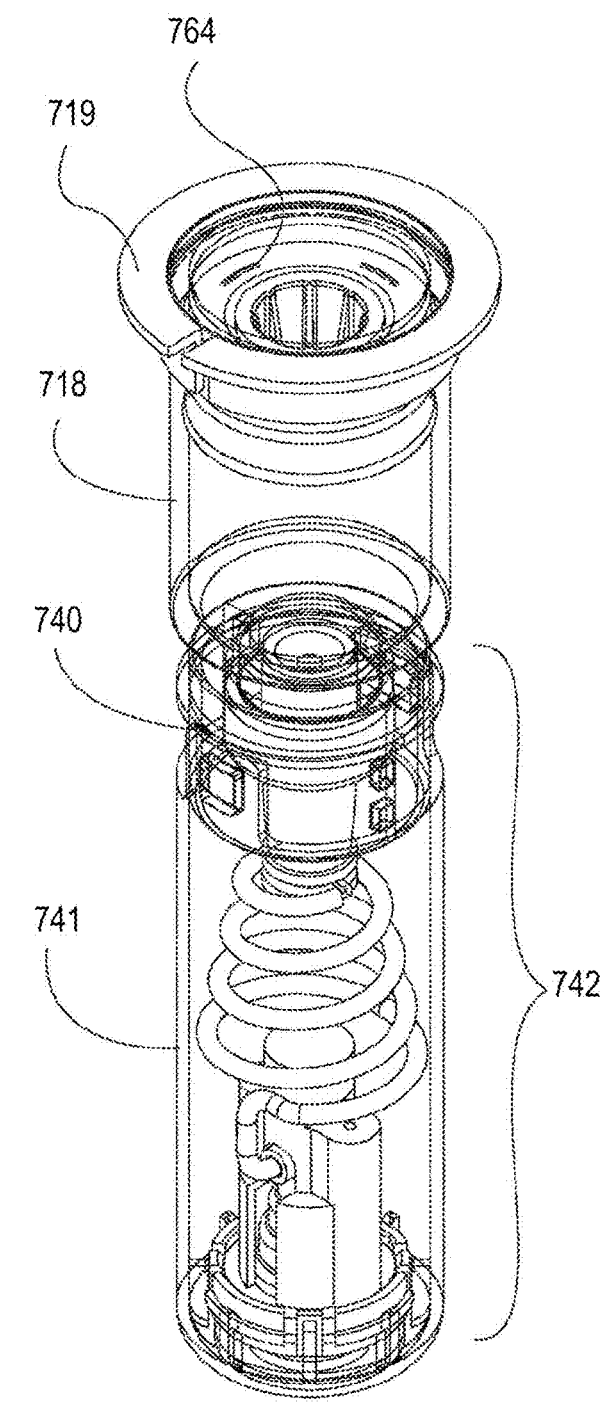
Figure 172:
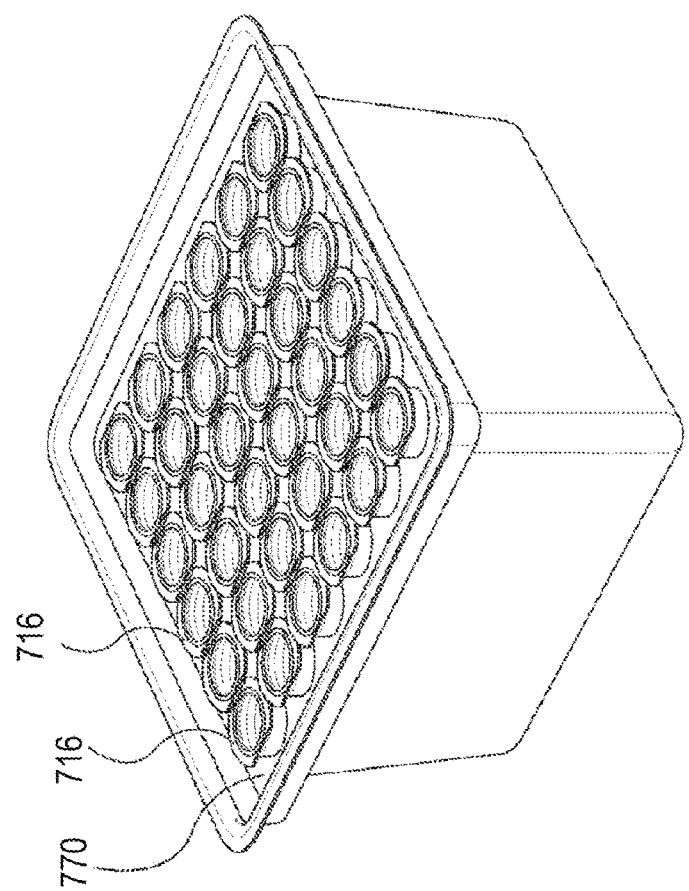
Figure 171:
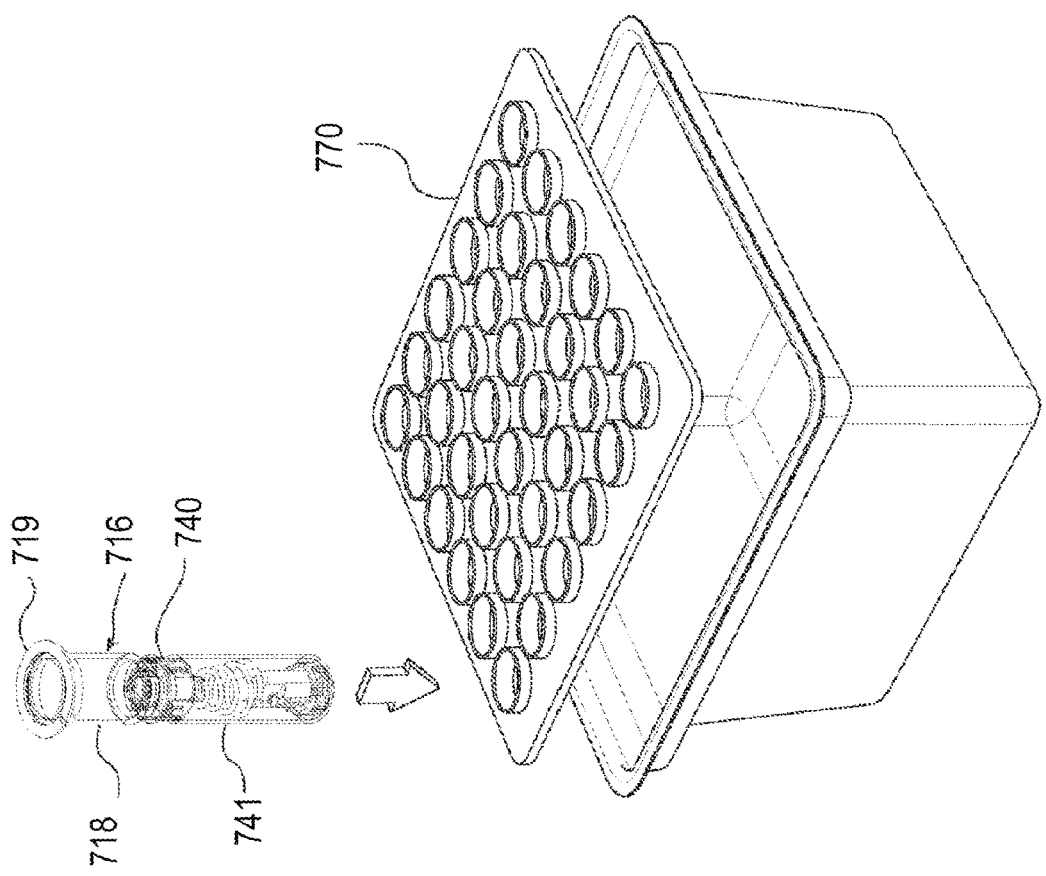
Figure 173:
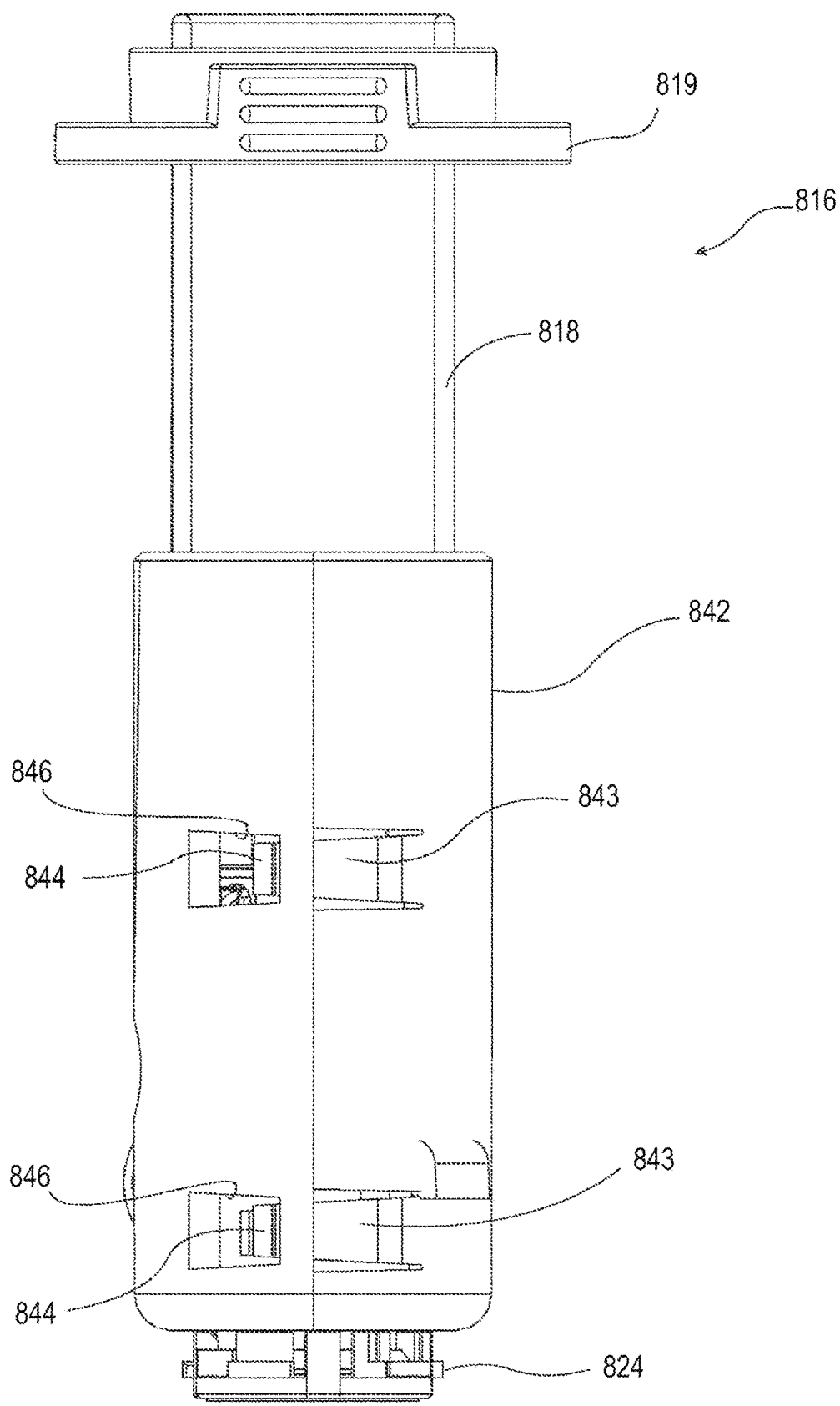
Figure 174:
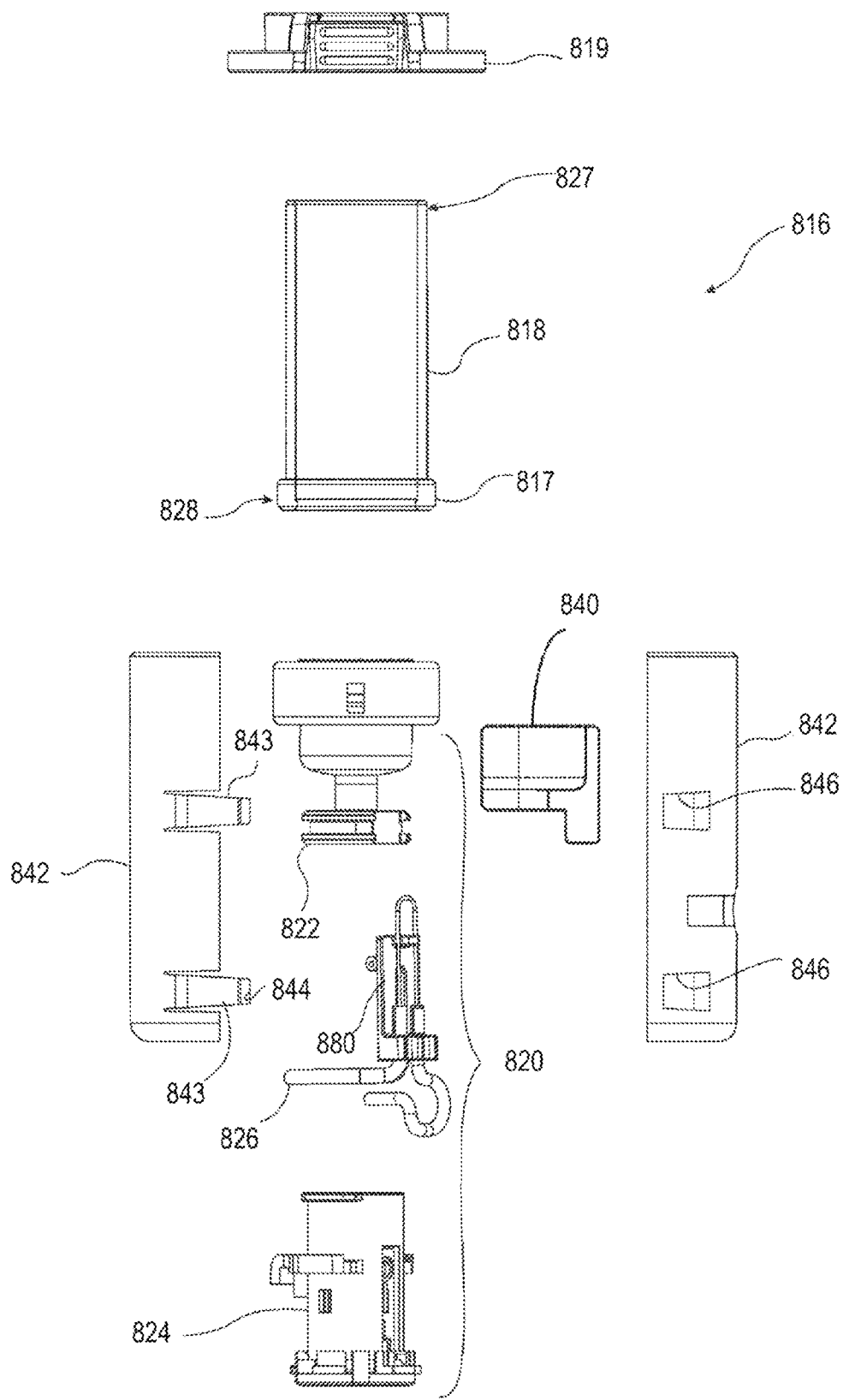
Figure 175:
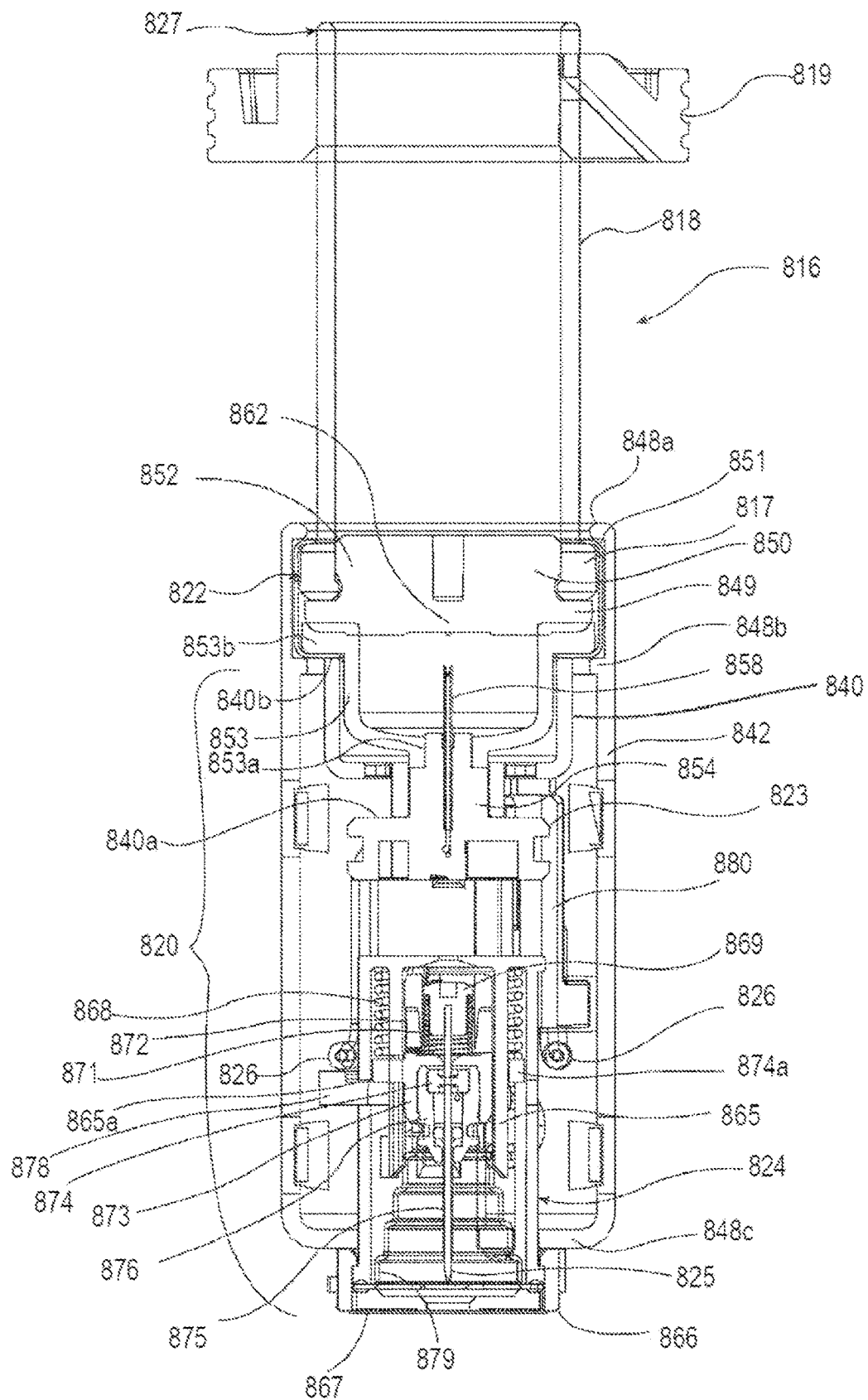
Figure 176:
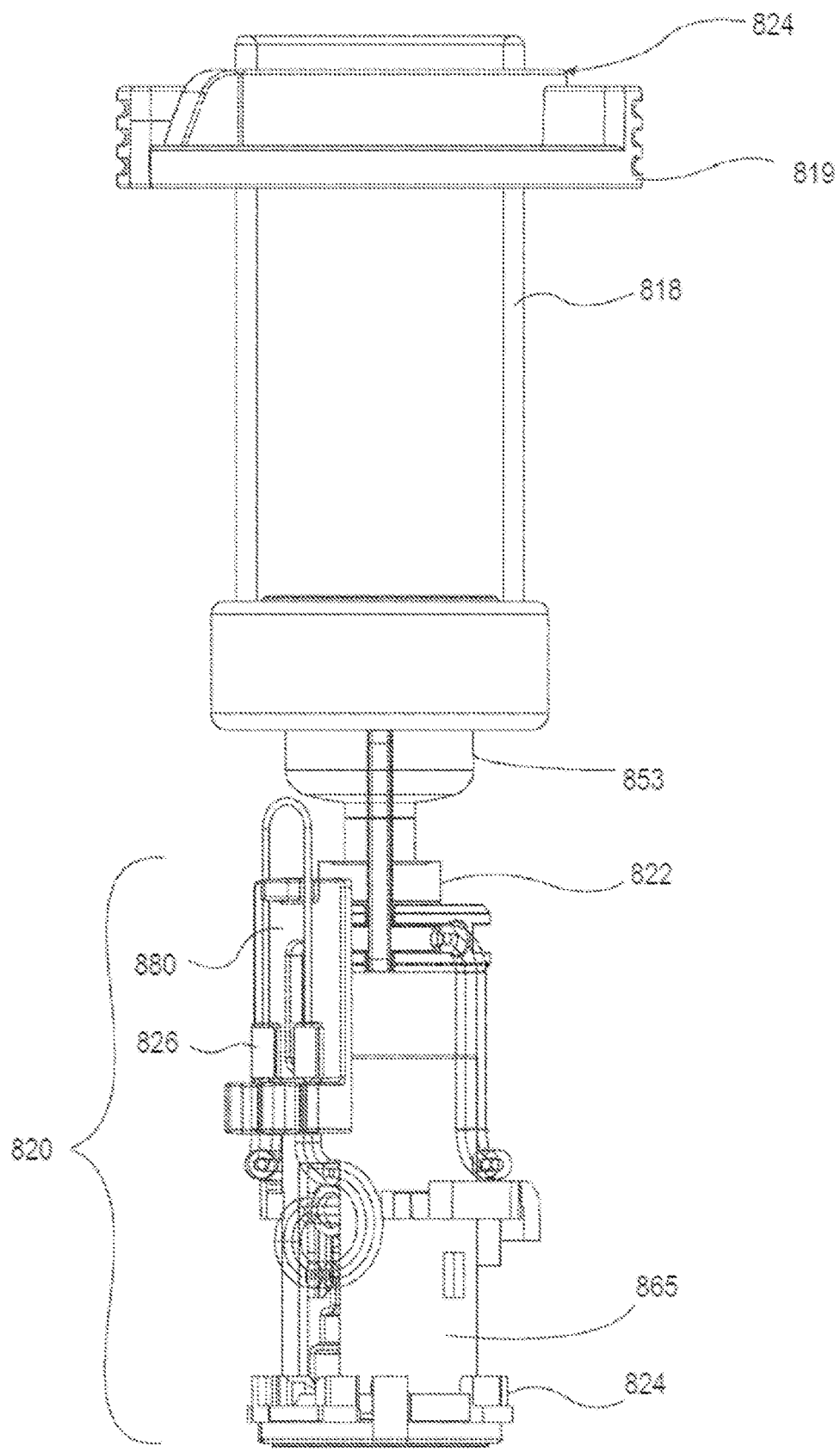
Figure 177:
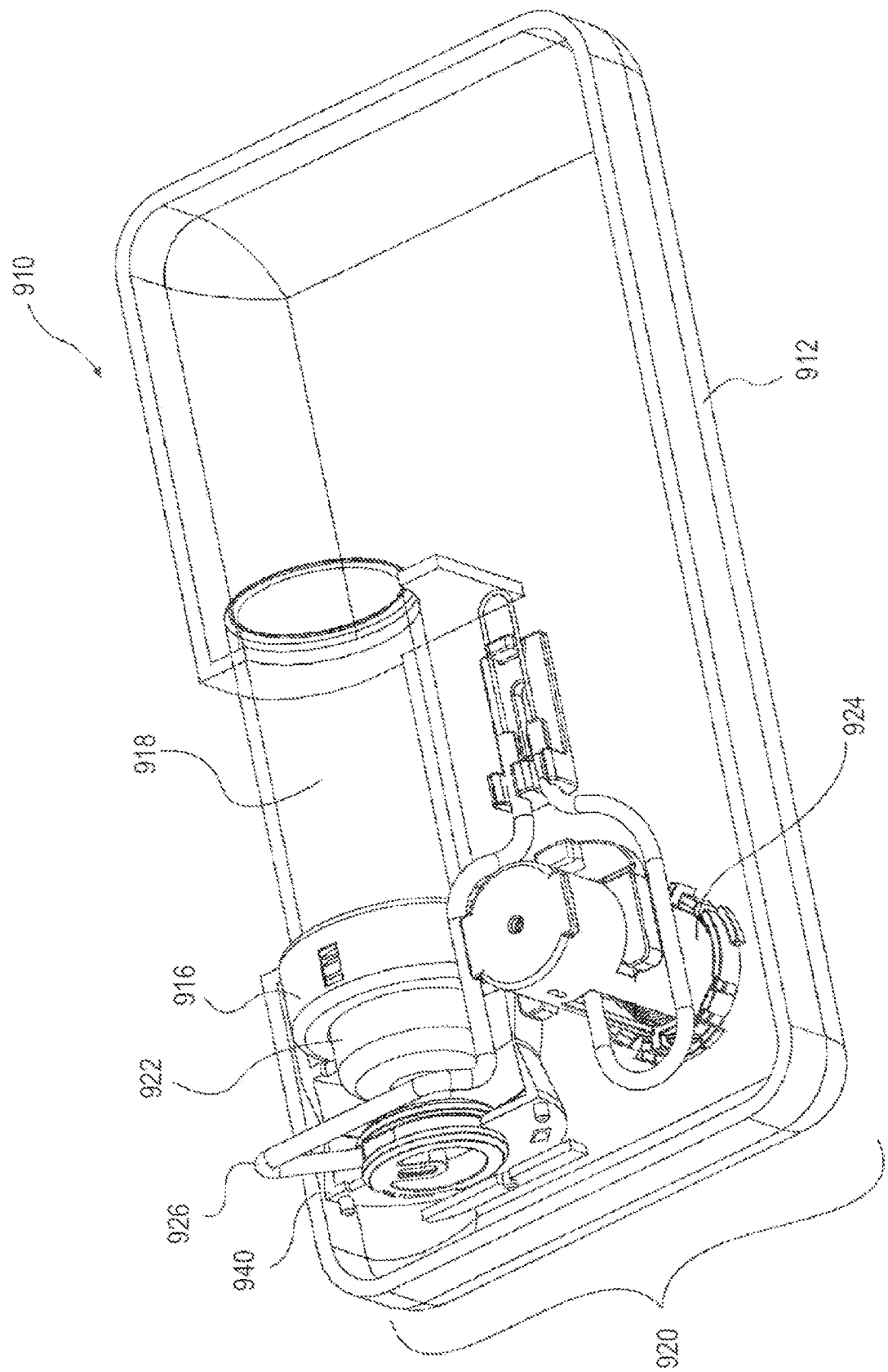
Figure 178:
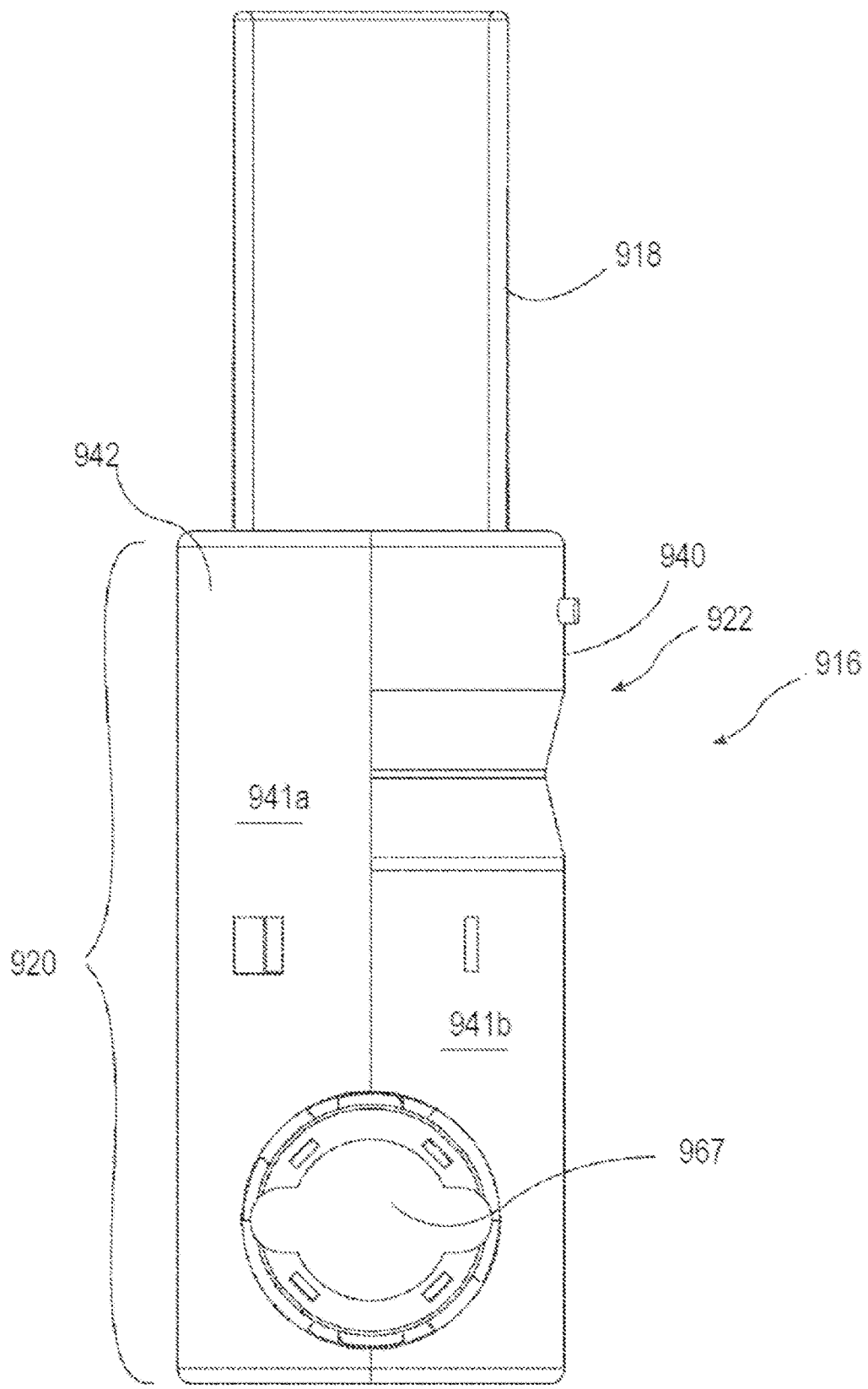
Figure 179:
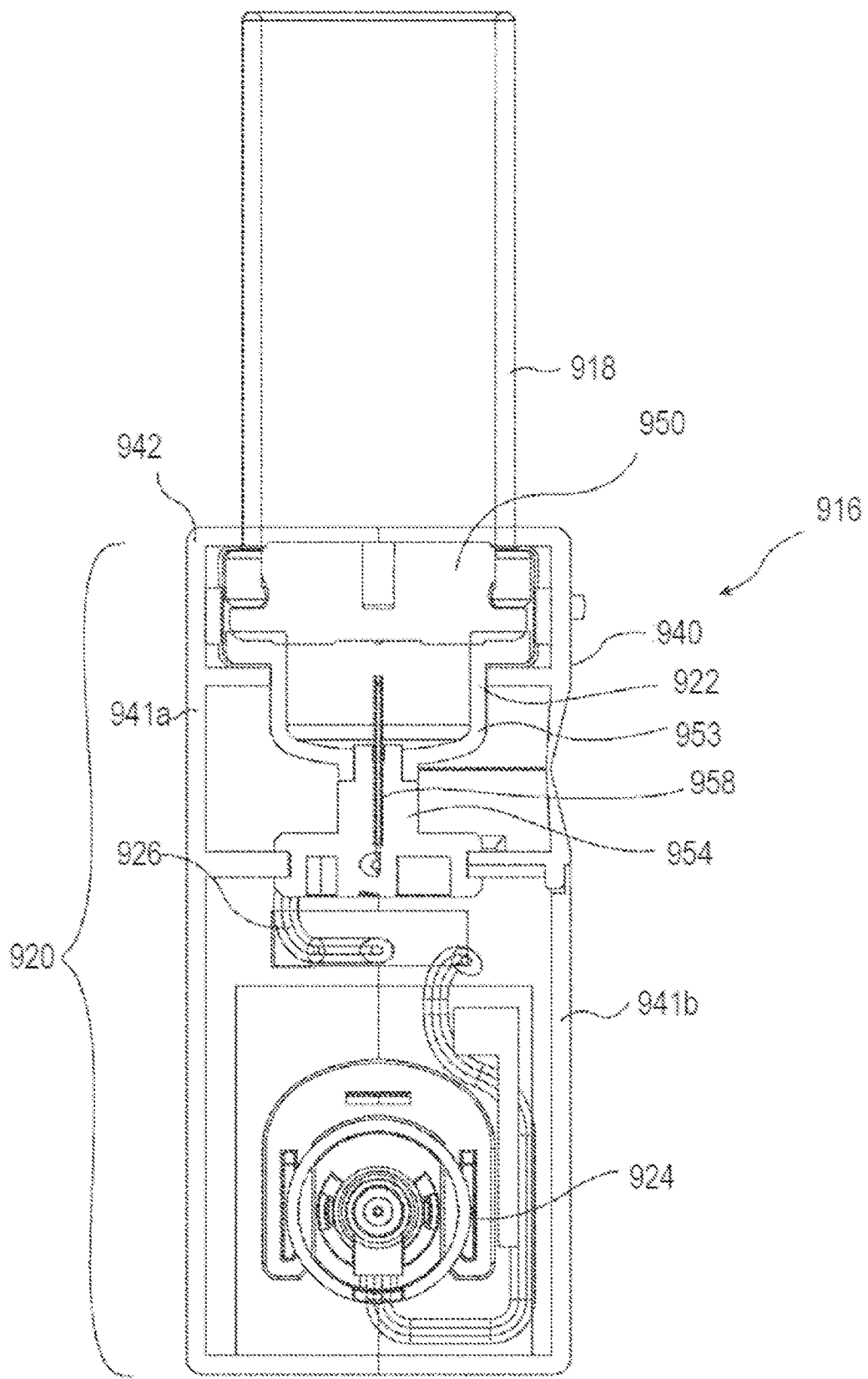
Figure 180:
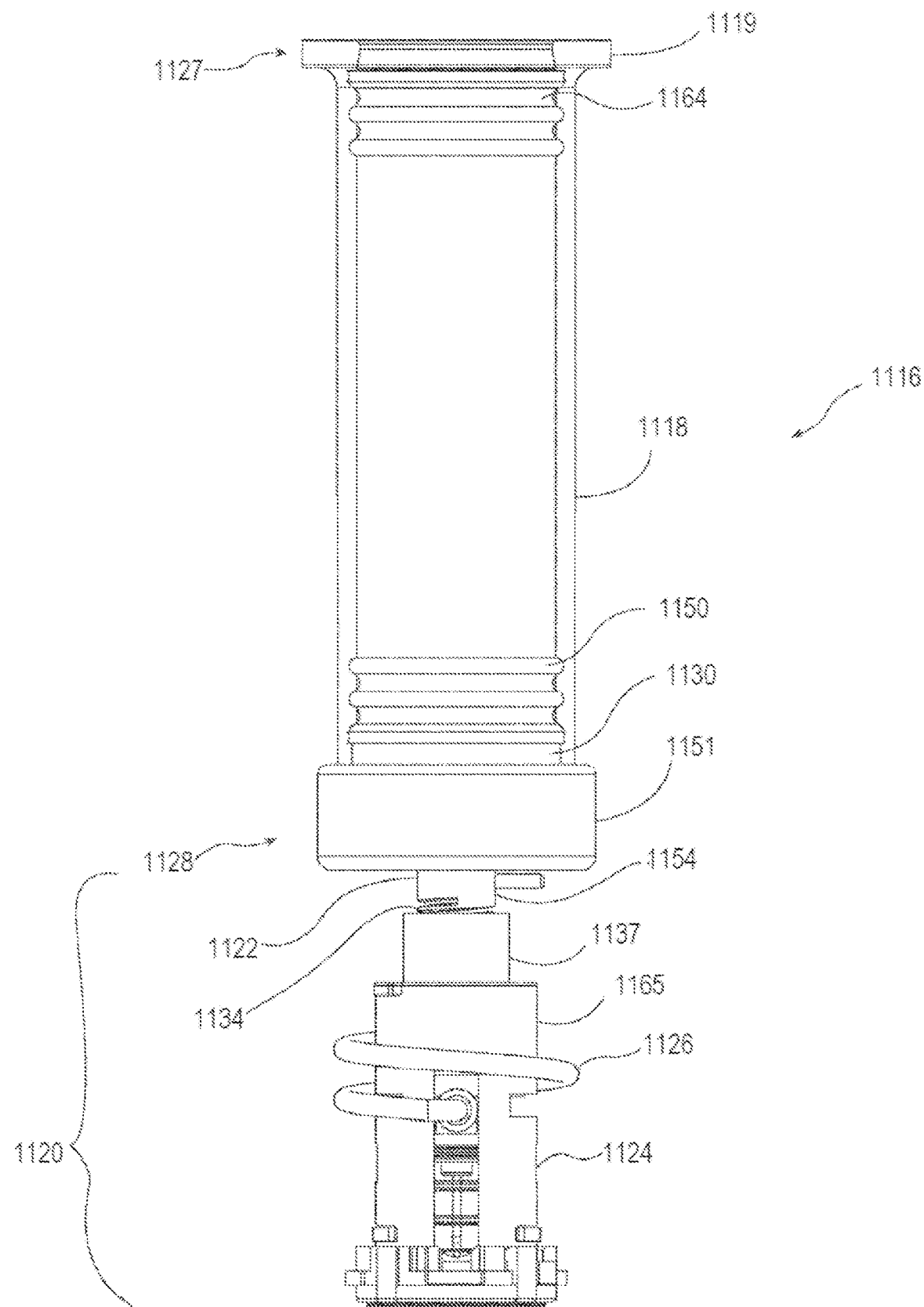
Figure 181:
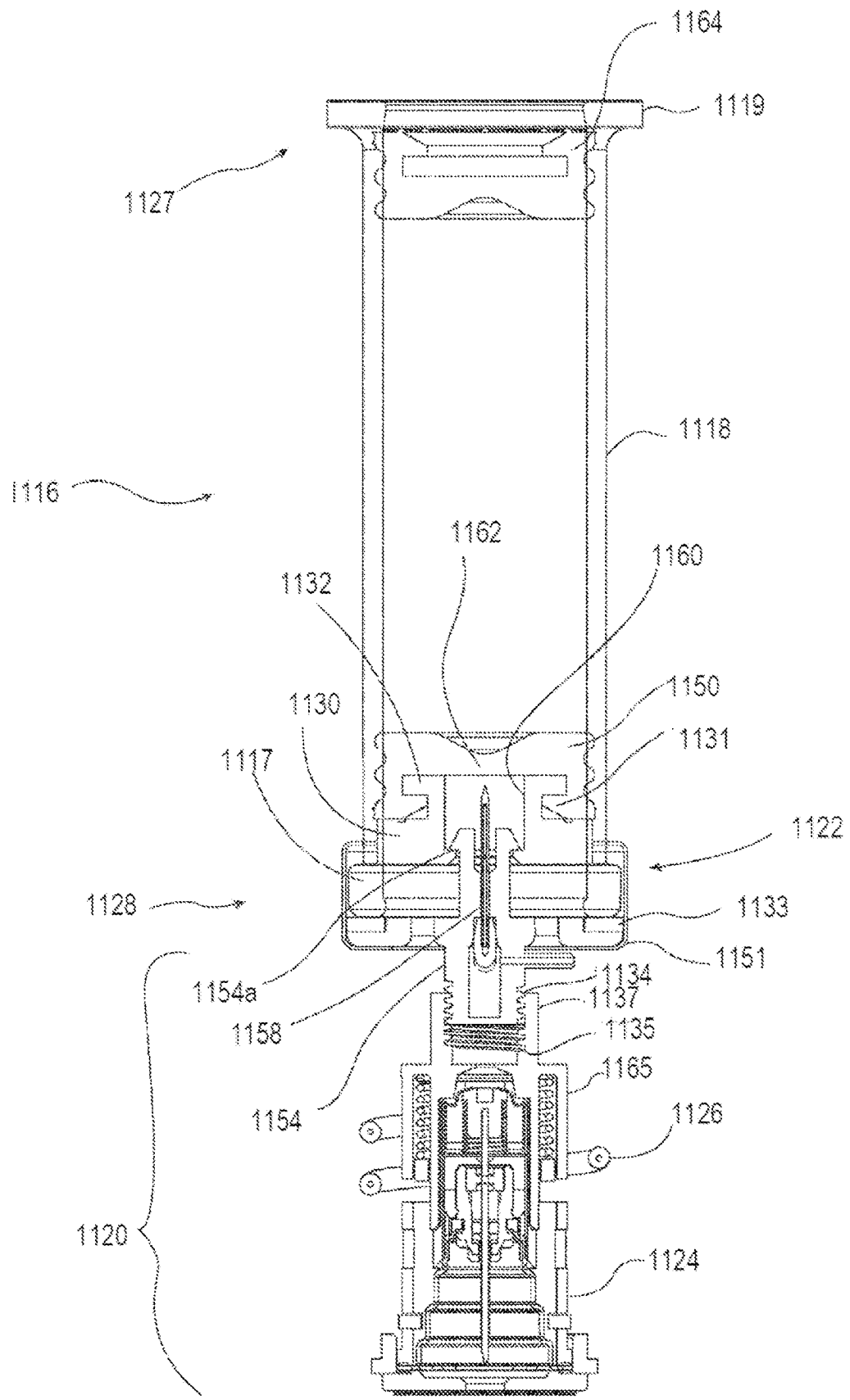
Figure 182:
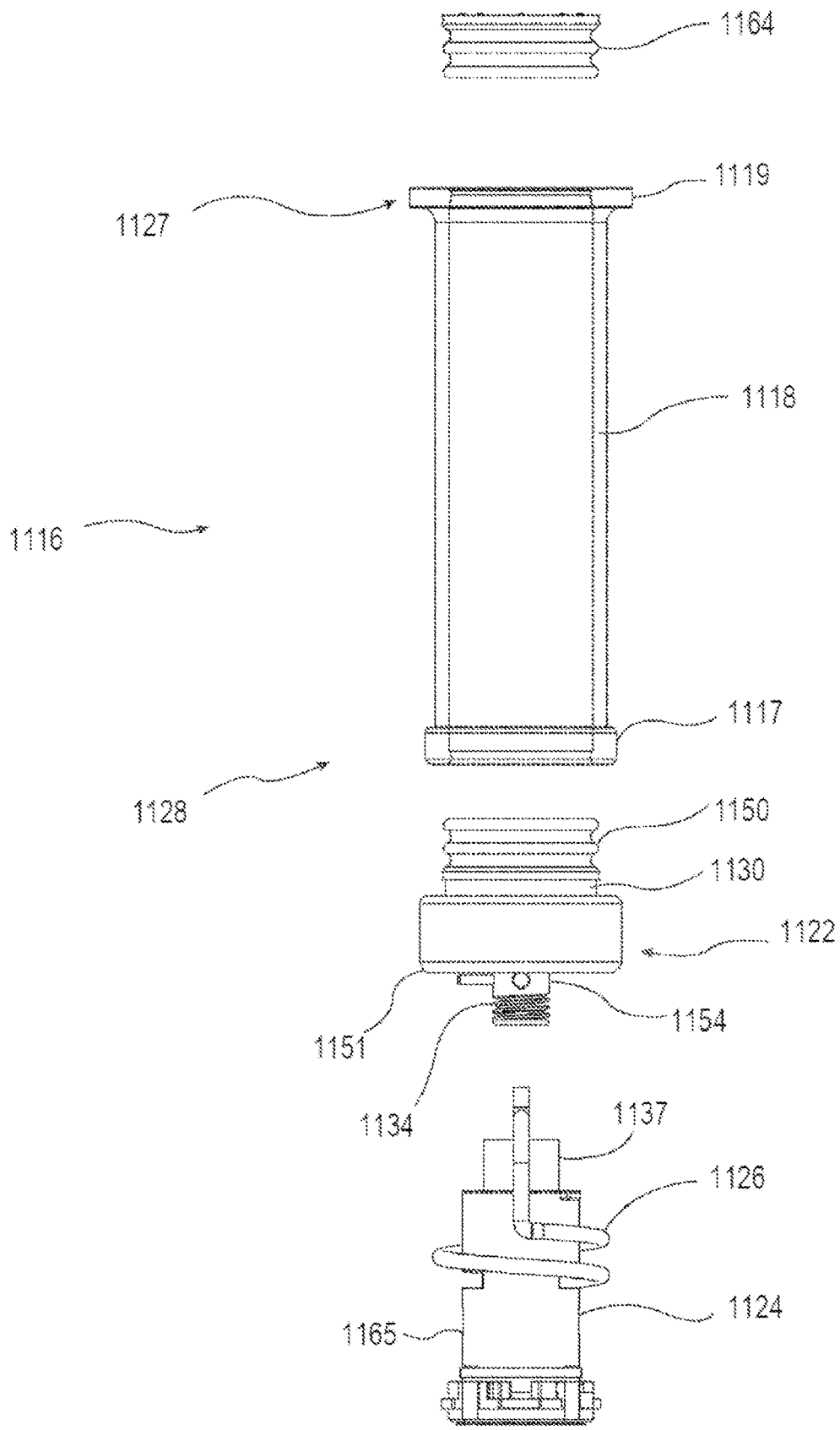
Figure 183:
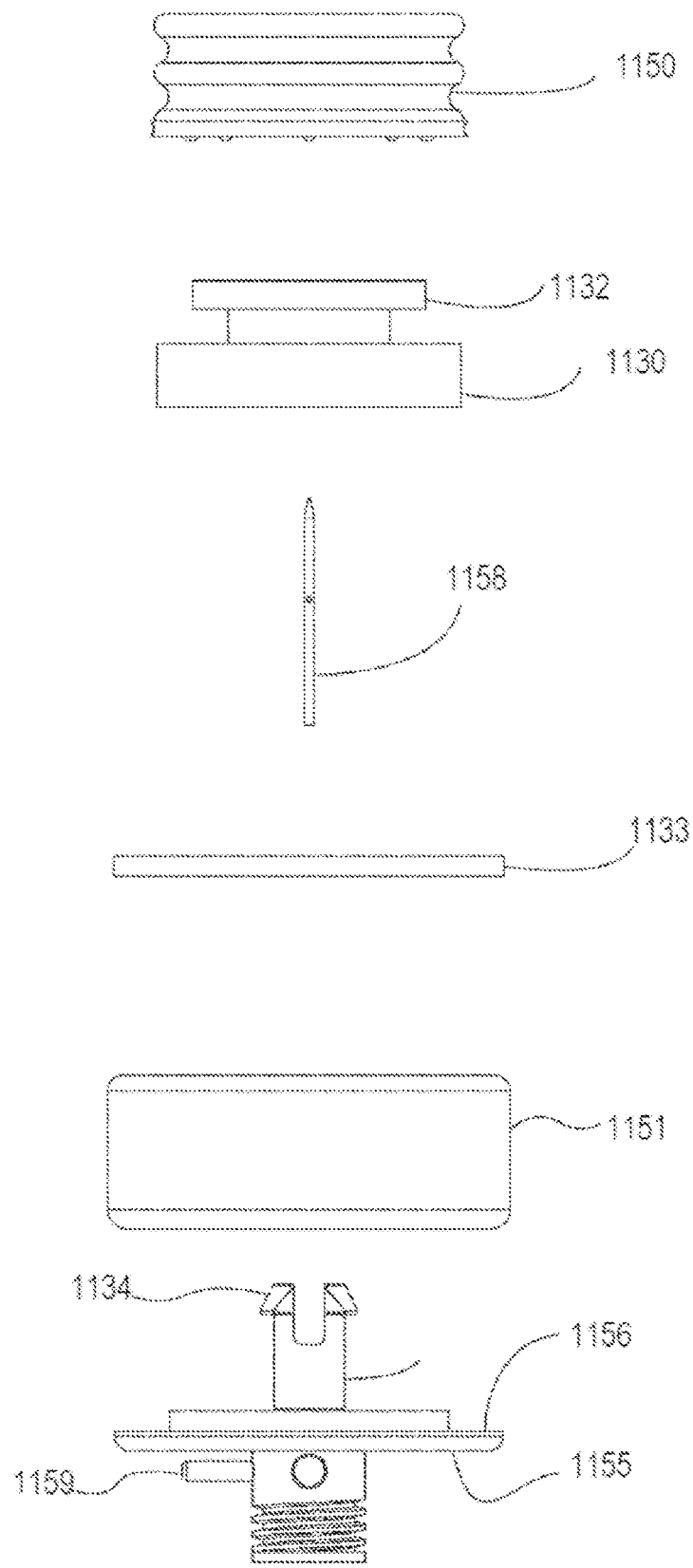
Figure 184:
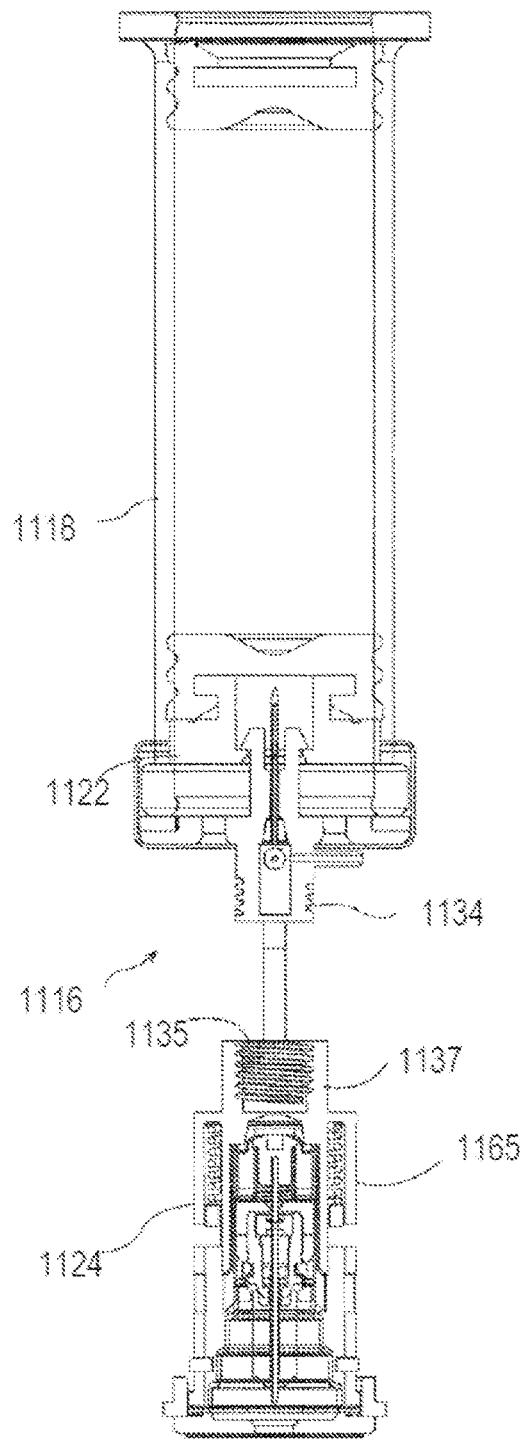
Figure 185:
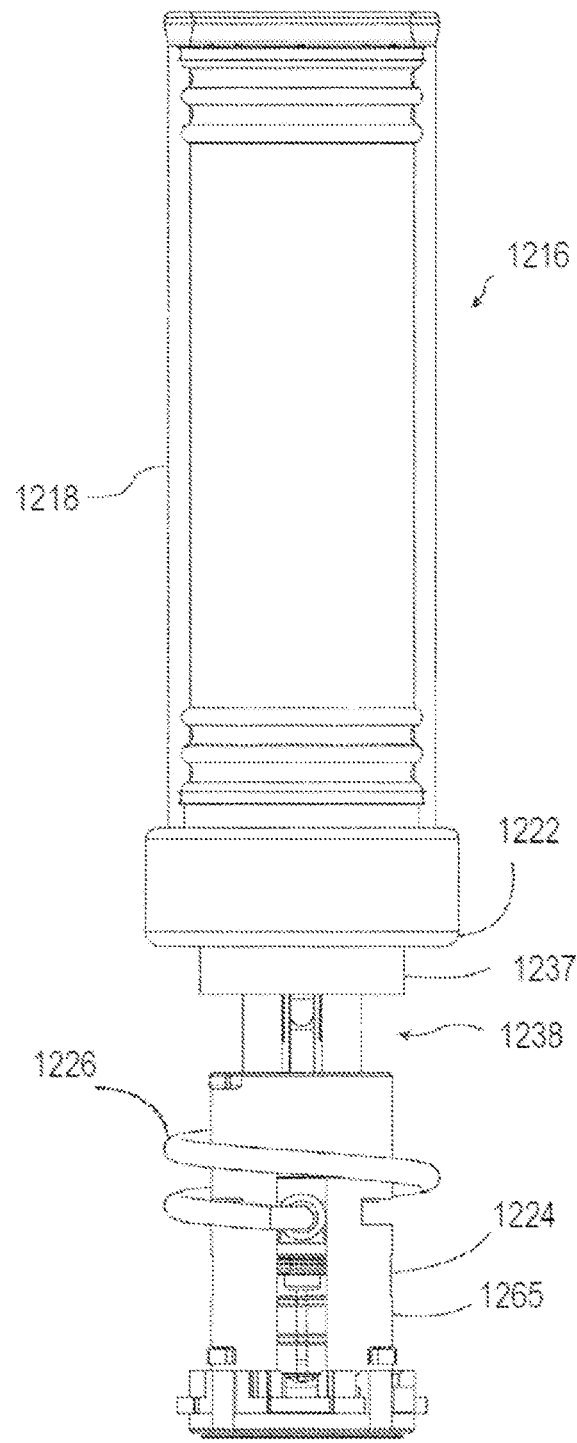
Figure 186:
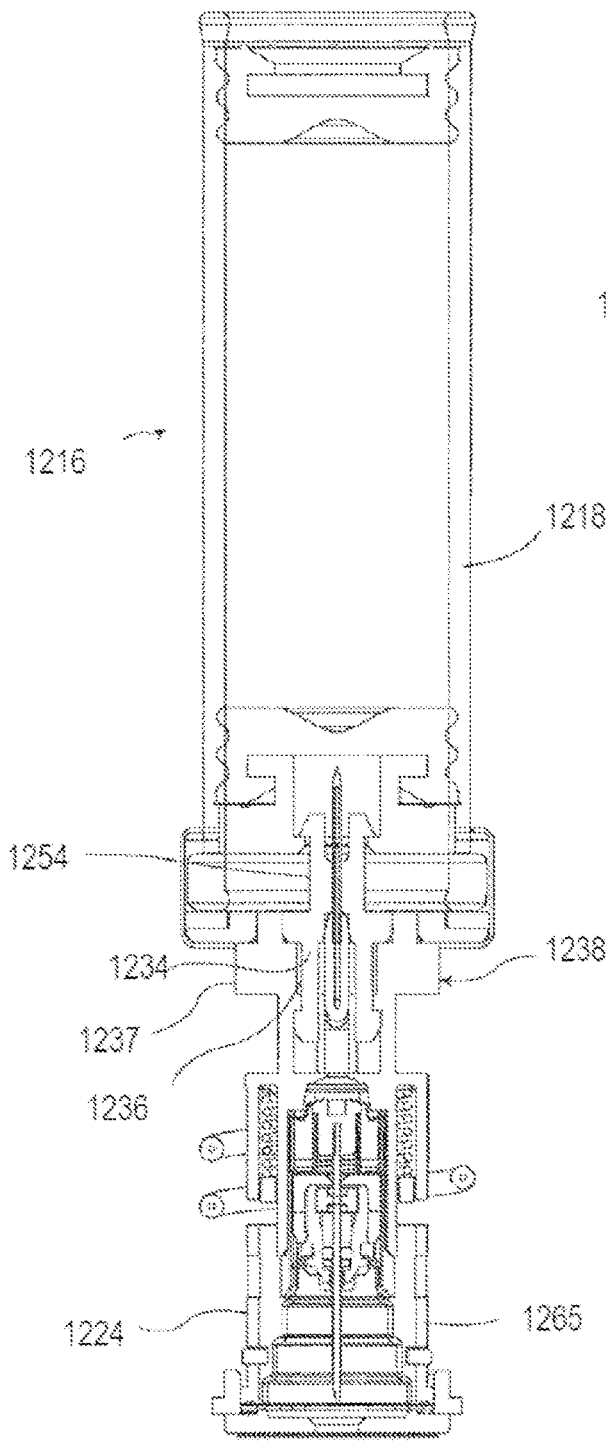
Figure 187:
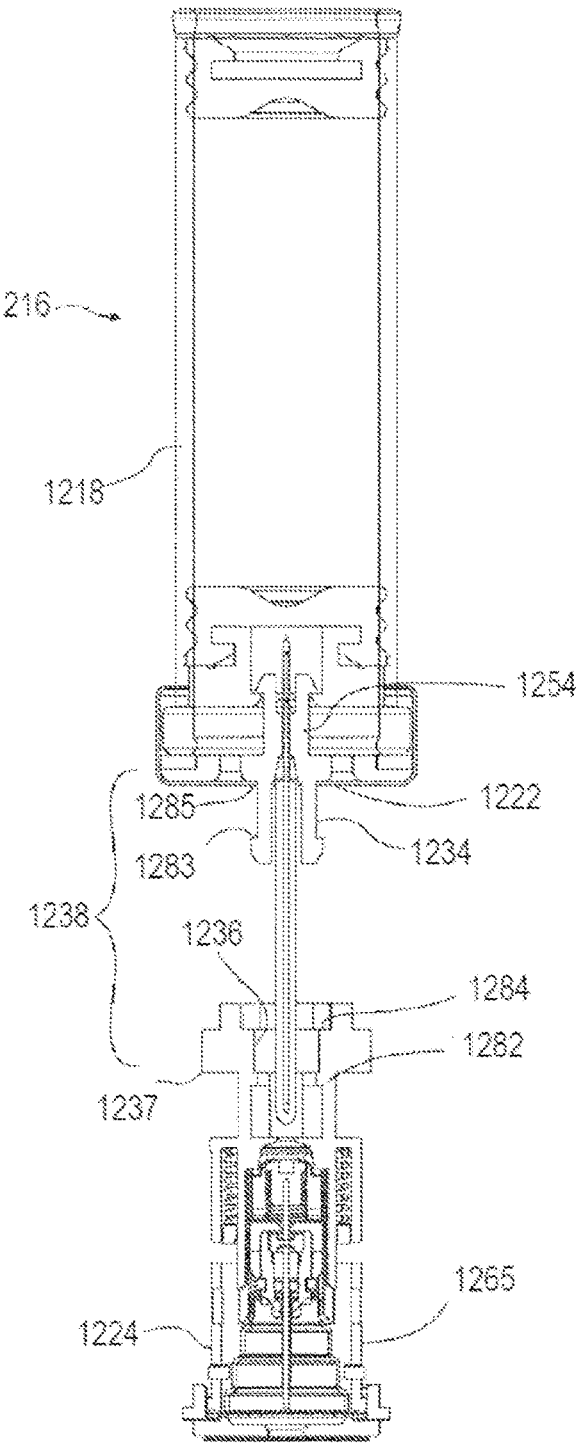
Figure 188:
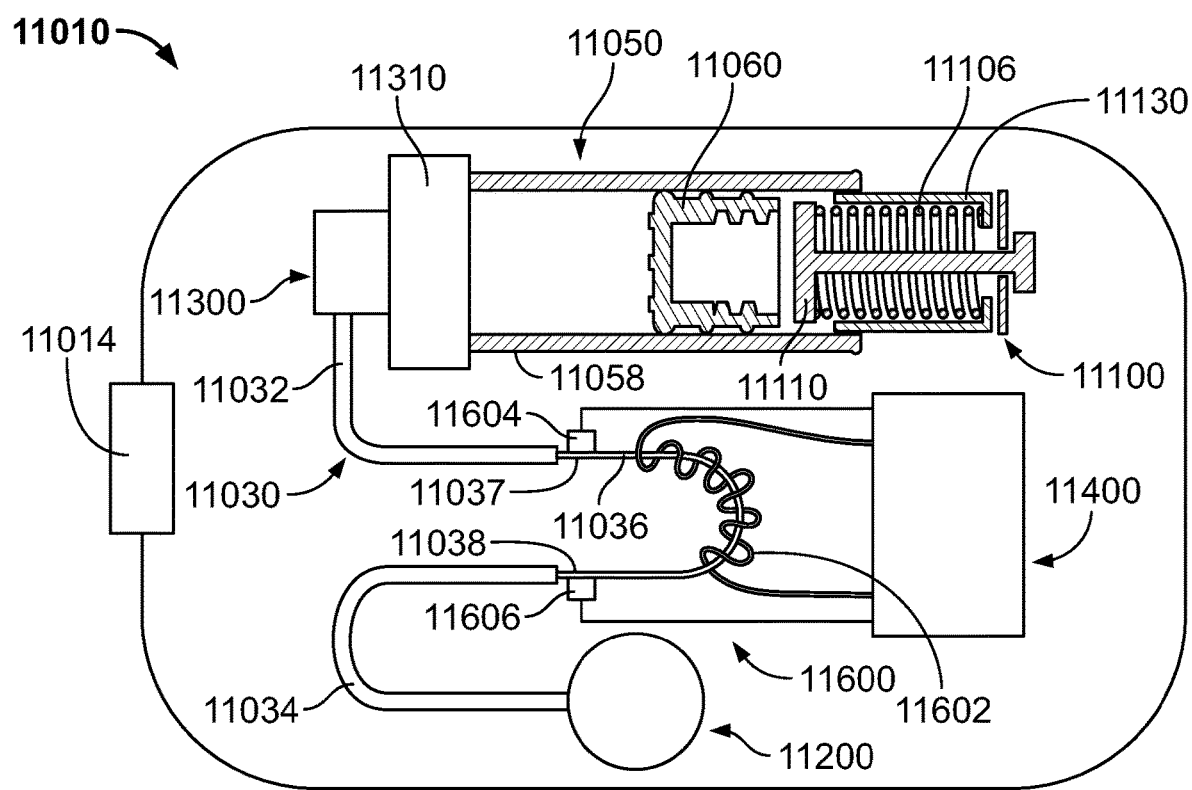
Figure 189A:
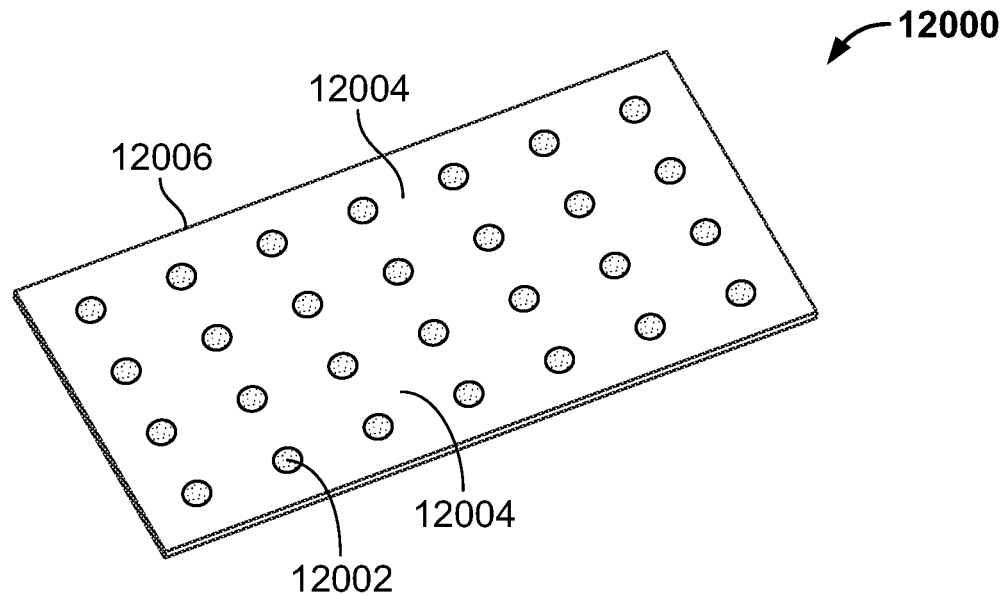
Figure 189B:
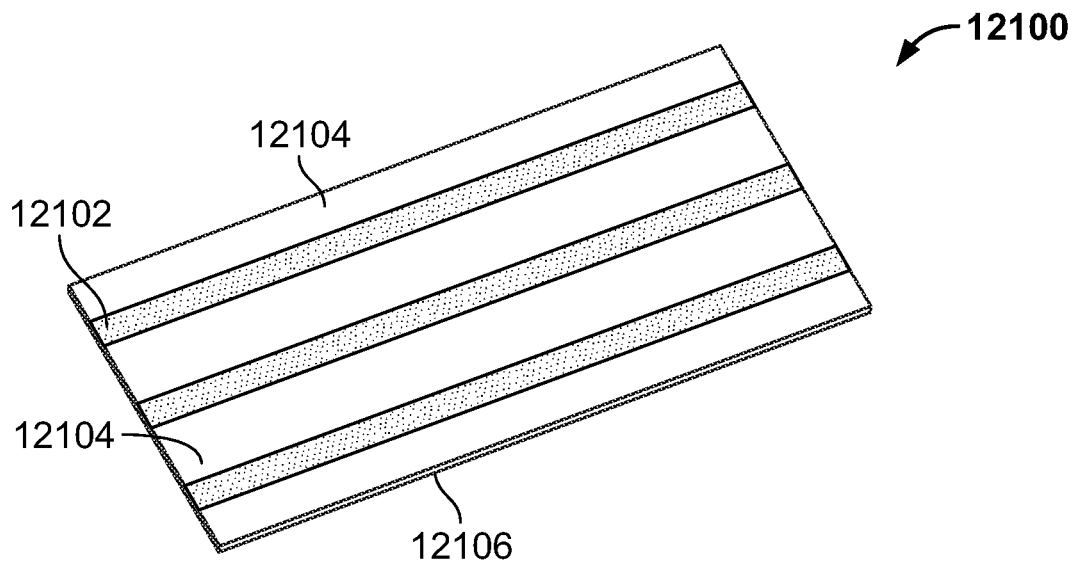
Figure 190:
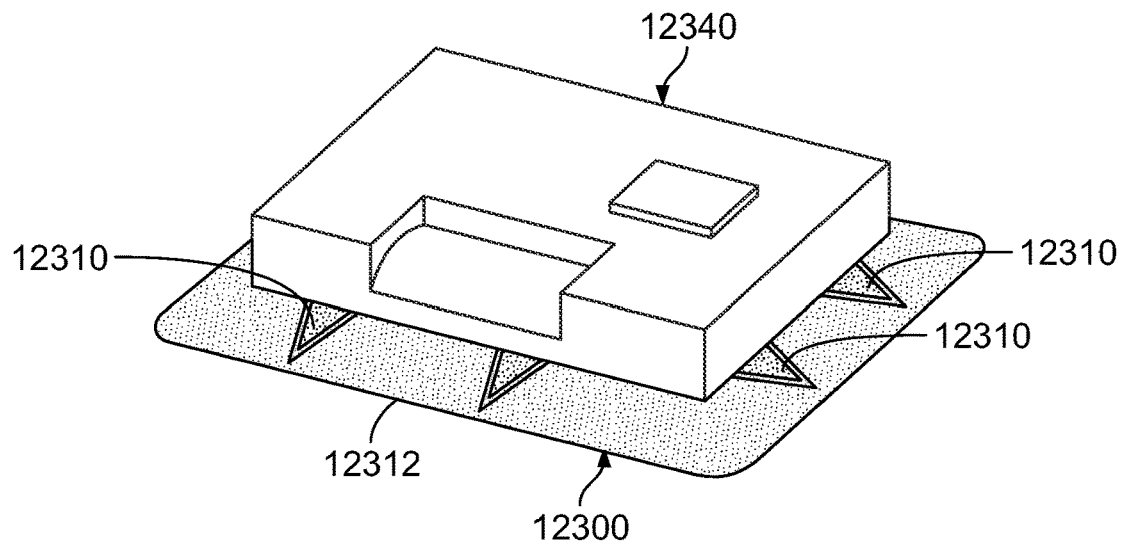
Figure 191A:
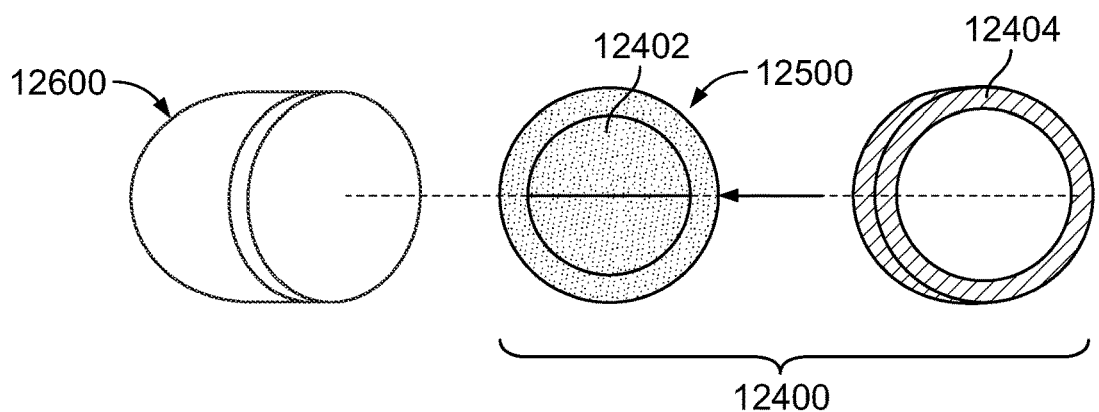
Figure 191B:
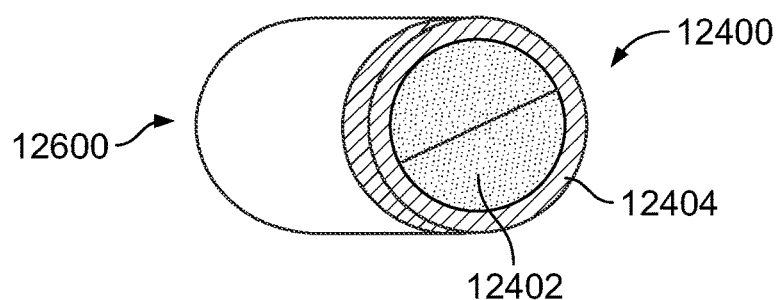
Figure 192:
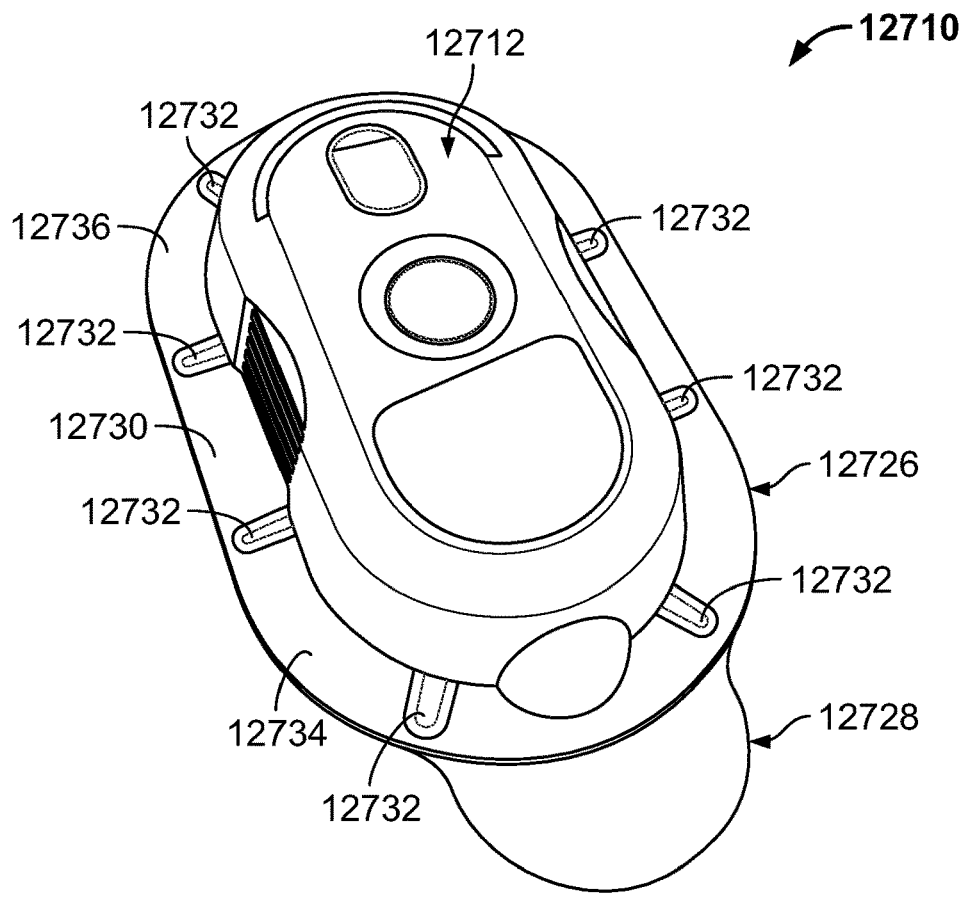
Figure 193:
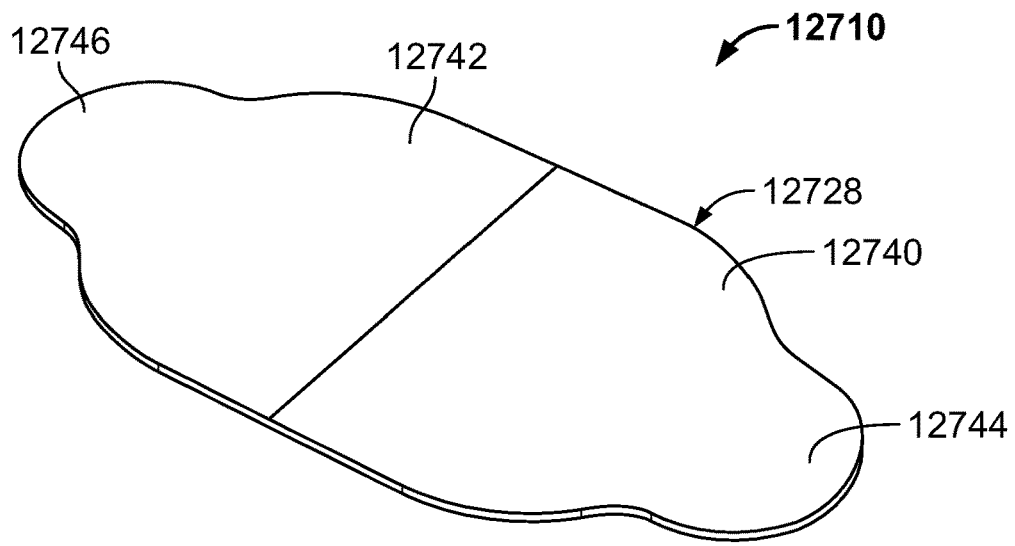
Figure 194A:
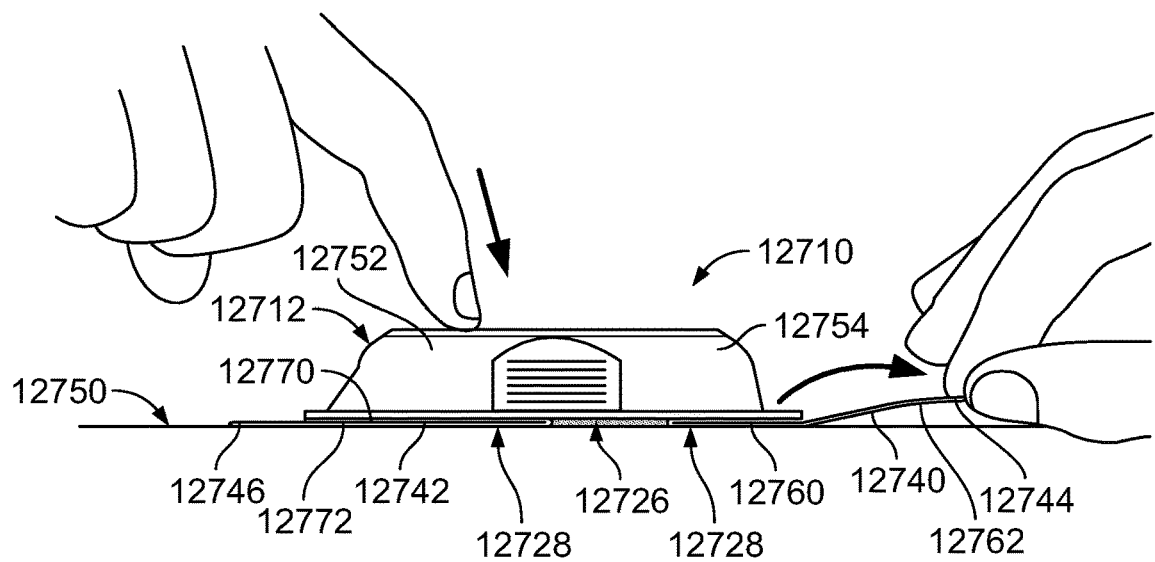
Figure 194B:
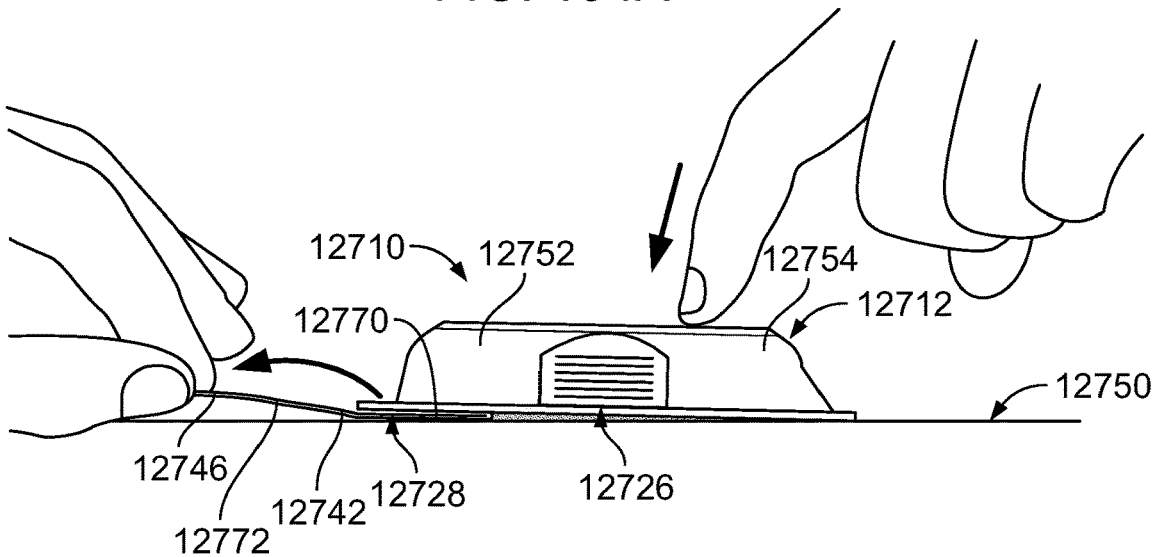
Figure 194C:
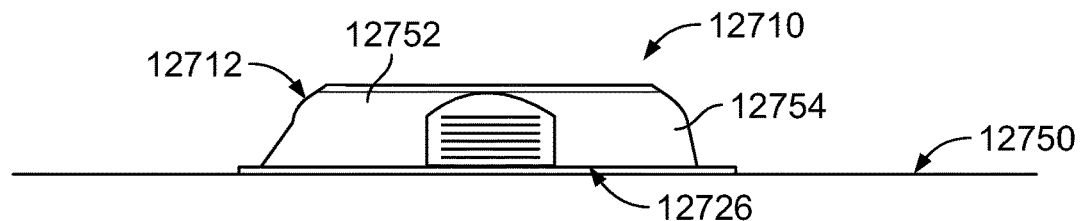
Figure 195:
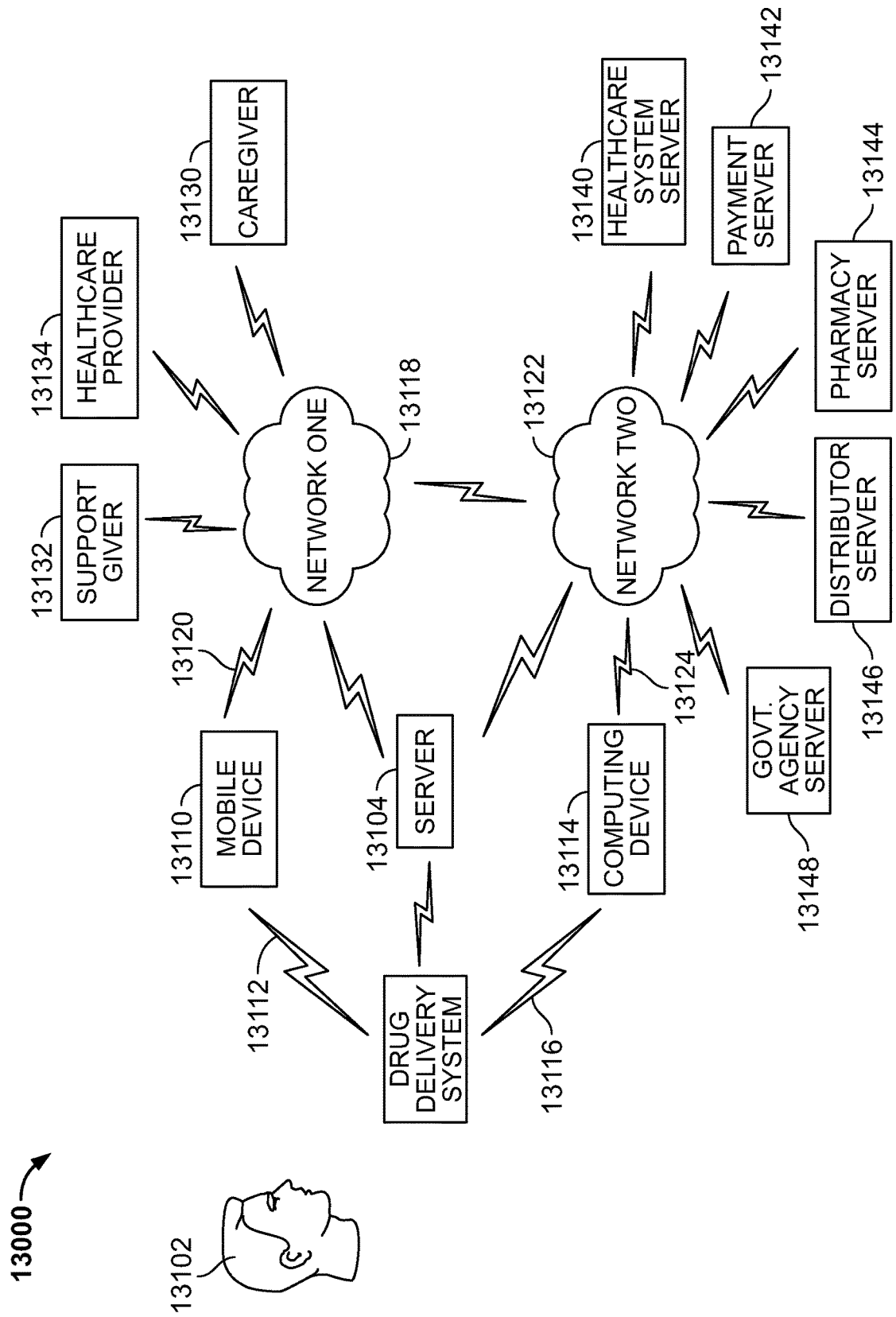
Figure 196A:
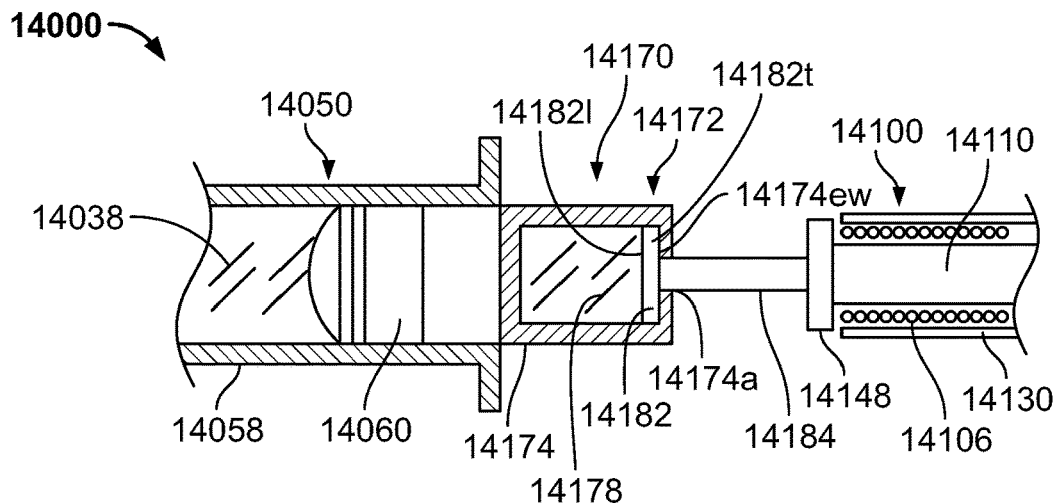
Figure 196B:
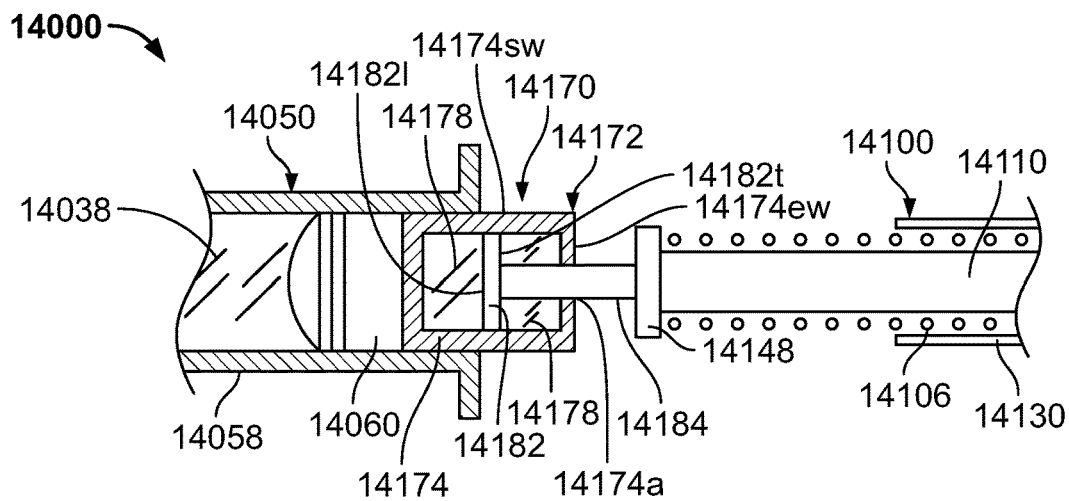
Figure 196C:
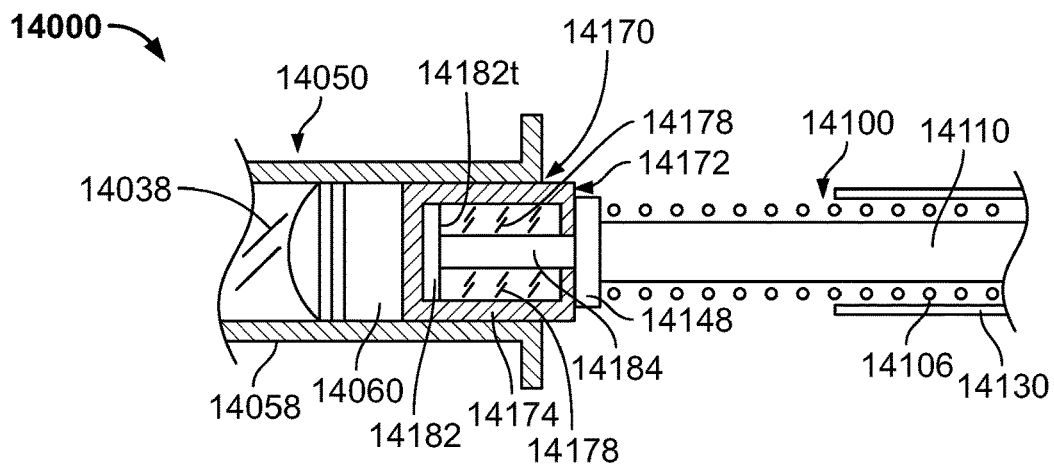
Figure 198A:
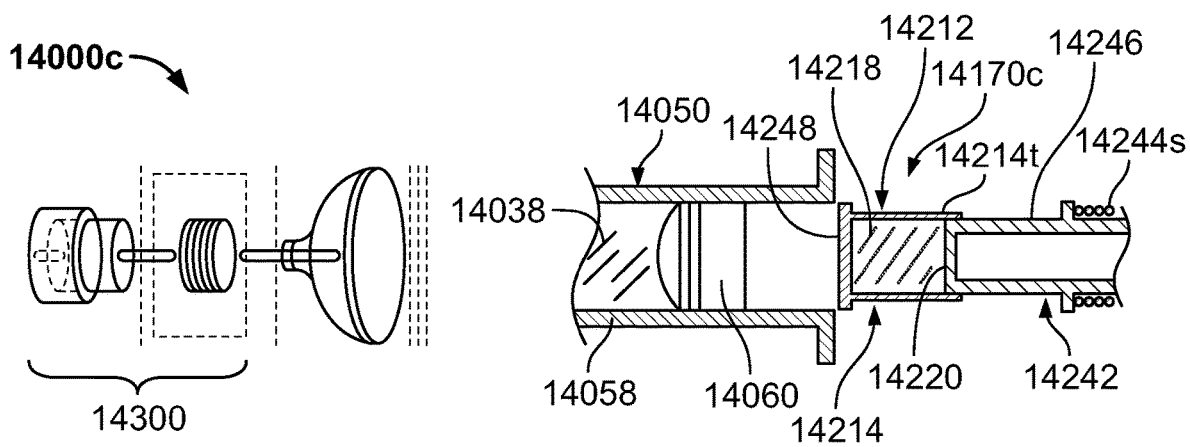
Figure 198B:
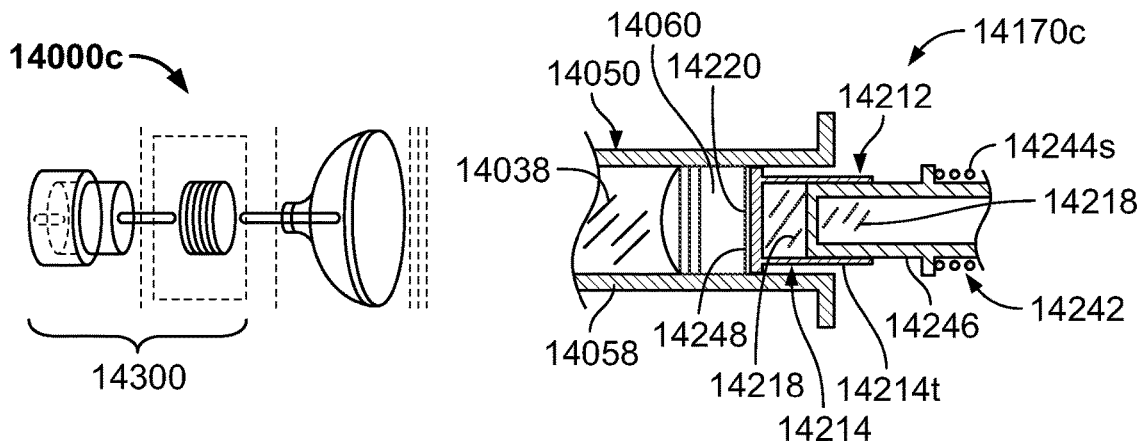
Figure 198C:
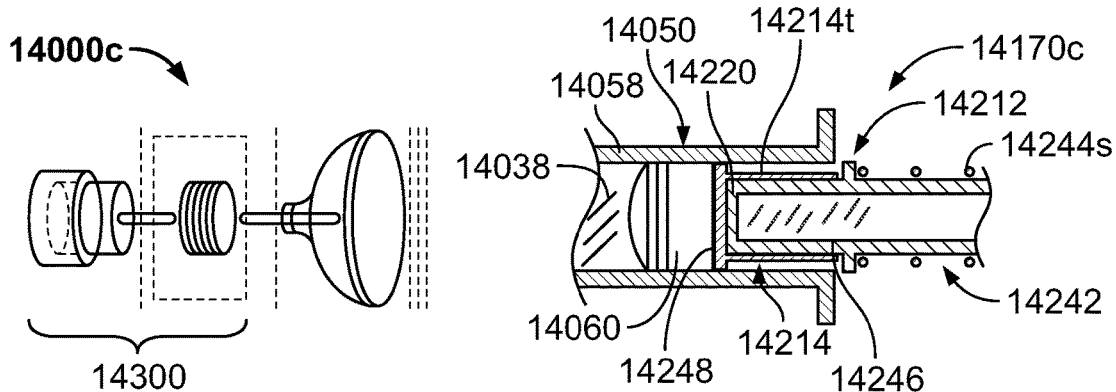
Figure 199:
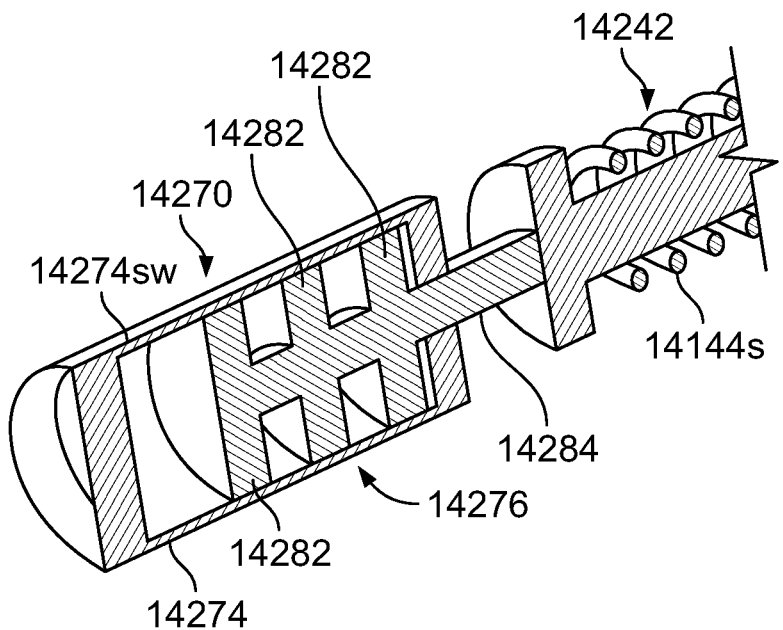
Figure 200:
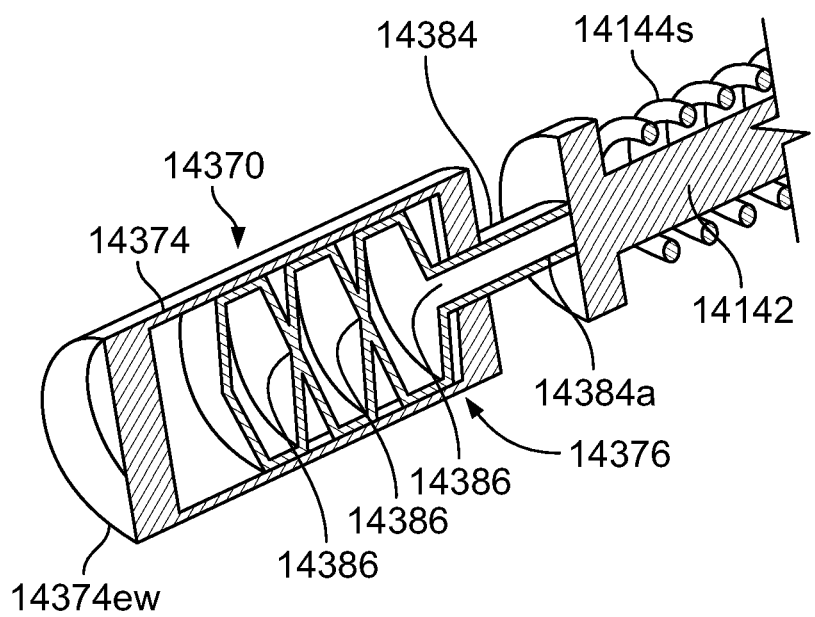
Figure 201A:
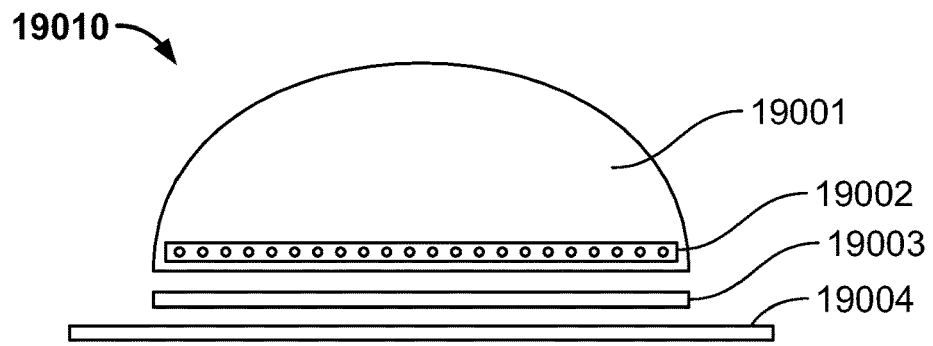
Figure 201B:
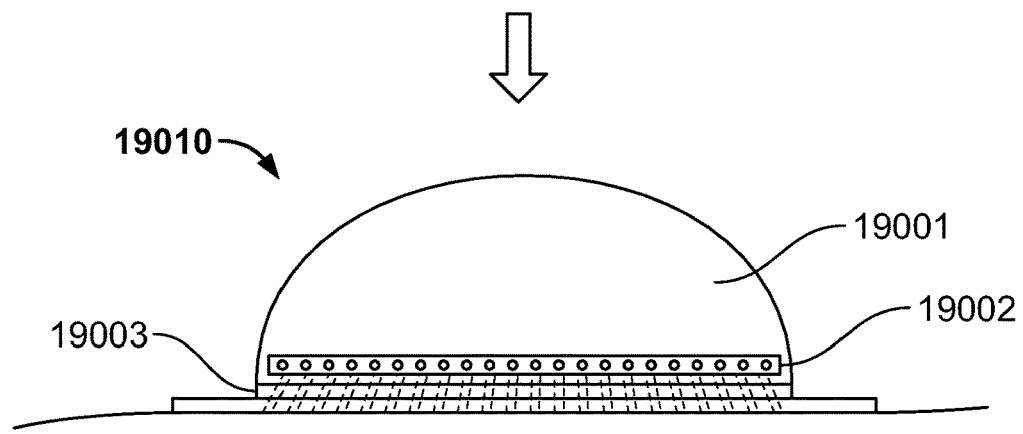
Figure 201C:
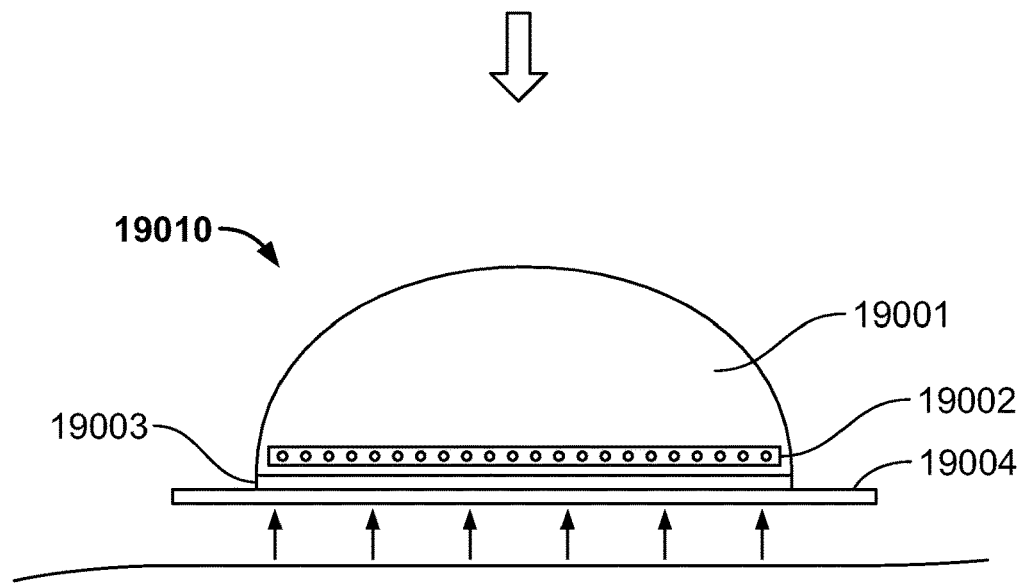
Figure 202A:
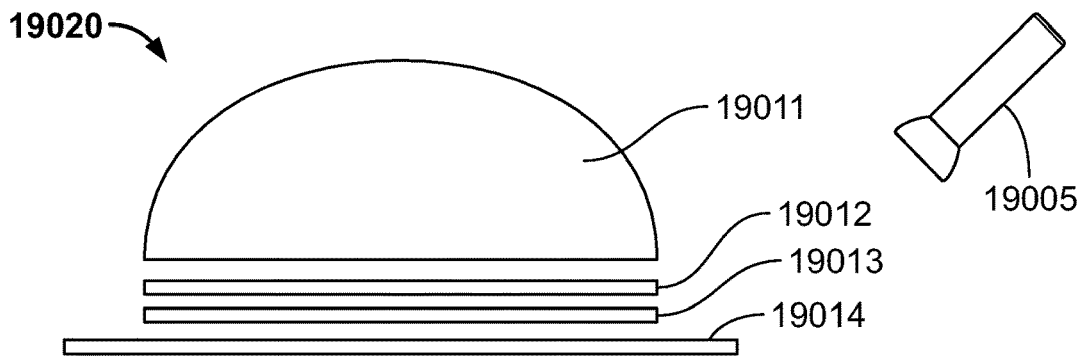
Figure 202B:
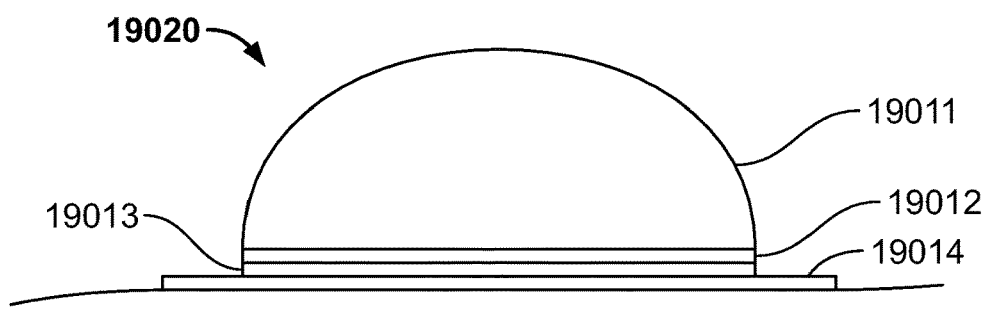
Figure 202C:
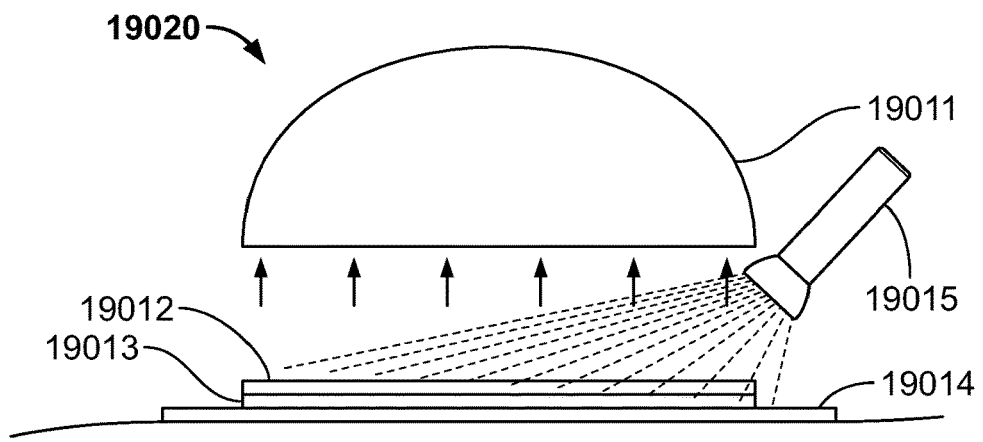
Figure 202D:
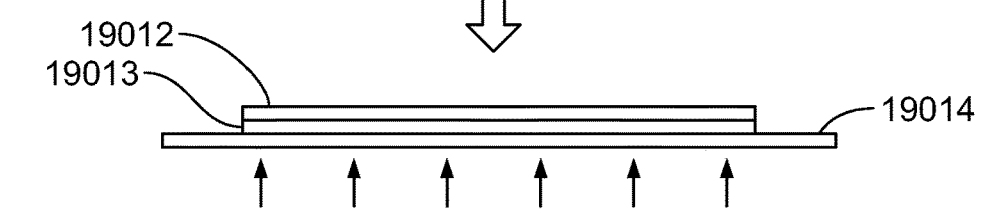
Figure 203A:
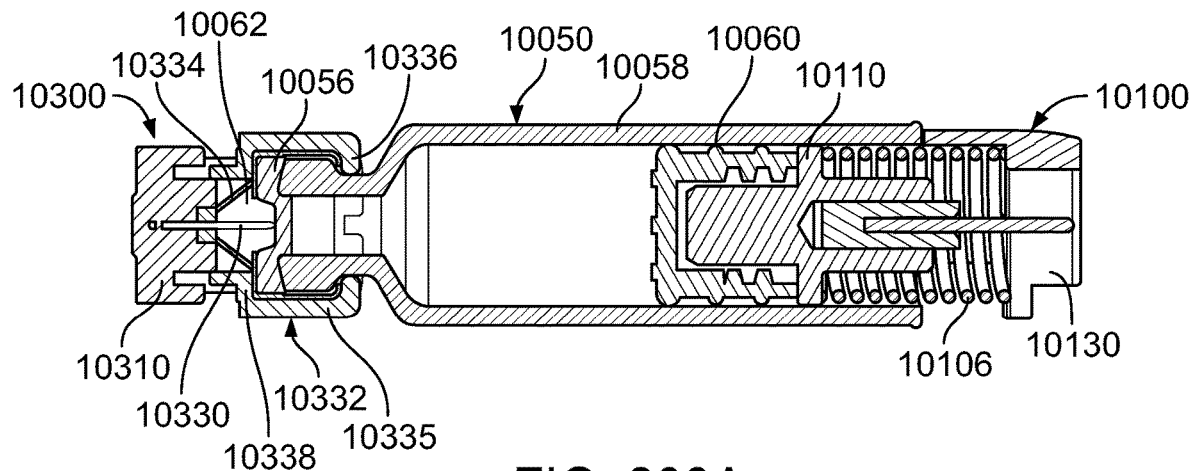
Figure 203B:
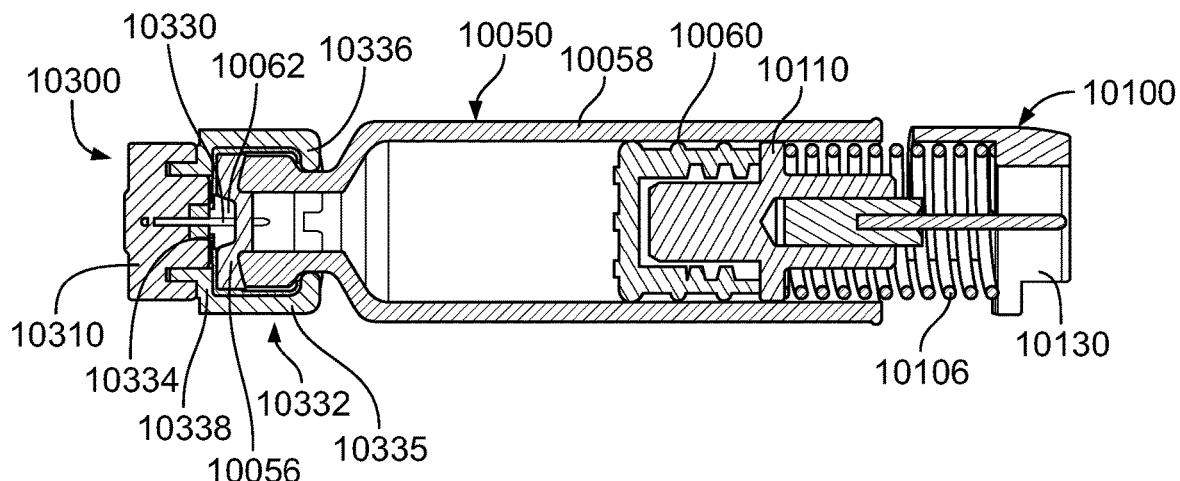
Figure 203C:
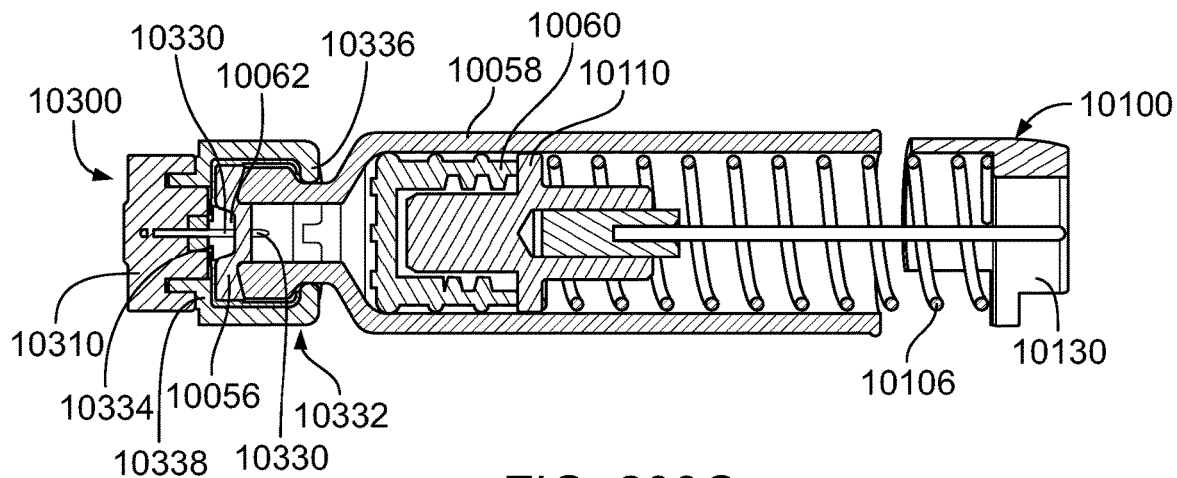

FIG. 116A is an isometric view of an insertion mechanism in an initial configuration;

FIG. 116B is an enlarged, fragmentary isometric view of the insertion mechanism of FIG. 116A;

FIG. 117A is a side elevation view of the insertion mechanism of FIG. 116A in an initial configuration;

FIG. 117B is an enlarged, fragmentary, side elevation view of the insertion mechanism of FIG. 117A;

FIG. 118A is an isometric view of the insertion mechanism of FIG. 116A in an intermediate configuration;

FIG. 118B is an enlarged, fragmentary isometric view of the insertion mechanism of FIG. 118A;

FIG. 119A is a side elevation view of the insertion mechanism of FIG. 118A in an intermediate configuration;

FIG. 119B is an enlarged, fragmentary, side elevation view of the insertion mechanism of FIG. 119A;

FIG. 120A is an isometric view of the insertion mechanism of FIG. 116A in an released configuration;

FIG. 120B is an enlarged, fragmentary isometric view of the insertion mechanism of FIG. 120A;

FIG. 121A is a side elevation view of the insertion mechanism of FIG. 120A in an released configuration;

FIG. 121B is an enlarged, fragmentary, side elevation view of the insertion mechanism of FIG. 121A;

FIG. 122A is a side elevation view of an enabling mechanism according to at least one embodiment of the present invention;

FIG. 122B is an enlarged, fragmentary side elevation view of the enabling mechanism of FIG. 122A;

FIG. 123 is an isometric view of a regulating mechanism according to at least one embodiment of the present invention;

FIGS. 124A-124B are isometric views of a key according to at least one embodiment of the present invention;

FIG. 124C is an isometric views of a key according to another embodiment of the present invention;

FIG. 125 is a plan view of a main gear according to at least one embodiment of the present invention;

FIG. 126A is an isometric view of a drive mechanism according to one embodiment of the invention in a first configuration;

FIG. 126B is an enlarged, fragmentary, isometric view of the drive mechanism of FIG. 126A in the first configuration;

FIG. 127A is an isometric view of the drive mechanism of FIG. 126A in a second configuration;

FIG. 127B is an enlarged, fragmentary, isometric view of the drive mechanism of FIG. 127A in the second configuration;

FIG. 128A is an isometric view of the drive mechanism of FIG. 126A in a third configuration;

FIG. 128B is an enlarged, fragmentary, isometric view of the drive mechanism of FIG. 128A in the third configuration;

FIG. 129A is an isometric view of the drive mechanism of FIG. 126A in a fourth configuration;

FIG. 129B is an enlarged, fragmentary, isometric view of the drive mechanism of FIG. 129A in the fourth configuration;

FIG. 130A is an isometric view of one embodiment of a winch drum and winch gear in a first configuration;

FIG. 130B is an isometric view of the winch drum and winch gear of FIG. 130A in a second configuration;

FIG. 131 is an isometric view of a winch gear of the embodiment of FIGS. 130A-131B;

FIG. 132 is an isometric view of a coupler of a winch drum of the embodiment of FIGS. 131A-131B;

FIG. 133 is an isometric view of a capstan of a winch drum of the embodiment of FIGS. 130A-130B;

FIG. 134A is a cross-sectional view of a safety mechanism according to one embodiment of the invention in an initial configuration;

FIG. 134B is an enlarged, fragmentary, cross-sectional view of the safety mechanism of FIG. 134A in an initial configuration;

FIG. 135A is a cross-sectional view of a safety mechanism of FIG. 134A in an actuated configuration;

FIG. 135B is an enlarged, fragmentary, cross-sectional view of the safety mechanism of FIG. 135A in the actuated configuration;

FIG. 136A is a cross-sectional view of a safety mechanism of FIG. 134A in a retracted configuration;

FIG. 136B is an enlarged, fragmentary, cross-sectional view of the safety mechanism of FIG. 136A in the retracted configuration;

FIGS. 137A-137B are cross-sectional views of a safety mechanism according to another embodiment of the present invention;

FIG. 138 is an isometric view according to one embodiment of a spring retainer for the safety mechanism of FIGS. 137A-137B;

FIG. 139 is an isometric view according to another embodiment of a spring retainer for the safety mechanism of FIGS. 137A-137B;

FIG. 140 is an isometric view of a sleeve for the safety mechanism of FIGS. 137A-137B;

FIG. 141A is a fragmentary cross-sectional view of a drug container and safety mechanism in an initial, unrestrained configuration; and FIG. 141B is a fragmentary cross-sectional view of the drug container and safety mechanism of FIG. 141A in an activated configuration;

FIG. 142A shows an exploded view, exploded along an axis "A," of an insertion mechanism according to at least one embodiment of the present disclosure;

FIG. 142B shows a cross-sectional exploded view, exploded along an axis "A," of an insertion mechanism according to at least one embodiment of the present disclosure;

FIG. 143A shows an isometric view of an insertion mechanism housing according to at least one embodiment of the present disclosure;

FIG. 143B shows a cross-section view of the insertion mechanism housing shown in FIG. 143A;

FIG. 144 shows an isometric view of a hub according to at least one embodiment of the present disclosure;

FIG. 145 shows an isometric view of a sleeve according to at least one embodiment of the present disclosure;

FIG. 146 shows an embodiment of a base of an insertion mechanism according to at least one embodiment of the present disclosure;

FIG. 147A shows an isometric view of an insertion mechanism according to at least one embodiment of the present disclosure in an initial configuration;

FIG. 147B shows a cross-sectional view of an insertion mechanism according to at least one embodiment of the present disclosure in an initial configuration;

FIG. 148A shows an isometric view of an insertion mechanism according to at least one embodiment of the present disclosure in a needle inserted configuration;

FIG. 148B shows a cross-sectional view of an insertion mechanism according to at least one embodiment of the present disclosure in a needle inserted configuration;

FIG. 149A shows an isometric view of an insertion mechanism according to at least one embodiment of the present disclosure in a needle retracted configuration;

FIG. 149B shows a cross-sectional view of an insertion mechanism according to at least one embodiment of the present disclosure in a needle retracted configuration;

FIG. 150 shows an isometric view of an insertion mechanism according to at least one embodiment of the present disclosure;

FIG. 151 shows a cross-sectional side view of the embodiment of FIG. 150;

FIG. 152 shows a cross-sectional front view of the embodiment of FIG. 150;

FIG. 153A shows a cross-sectional view of an insertion mechanism according to at least one embodiment of the present invention in an initial configuration;

FIG. 153B shows a cross-sectional view of the insertion mechanism of FIG. 153A in an inserted configuration;

FIG. 153C shows a cross-sectional view of the insertion mechanism of FIG. 153A in a delivery configuration;

FIG. 154A shows a cross-sectional side elevational view of an insertion mechanism housing according to at least one embodiment of the present invention;

FIG. 154B shows a cross-sectional isometric view of the insertion mechanism housing of FIG. 154A;

FIG. 155A is an enlarged, fragmentary cross-sectional view of the insertion mechanism of FIGS. 153A-153C, while in a delivery configuration;

FIG. 155B is an enlarged, fragmentary cross-sectional view of the insertion mechanism of FIGS. 153A-153C, while in a retracted position FIG. 156A shows a cross-sectional view of an insertion mechanism according to at least one embodiment of the present invention in an initial configuration;

FIG. 156B shows a cross-sectional view of the insertion mechanism of FIG. 156A in an inserted configuration;

FIG. 156C shows a cross-sectional view of the insertion mechanism of FIG. 156A having the needle hub in a partially-retracted configuration;

FIG. 156D shows a cross-sectional view of the insertion mechanism of FIG. 156A having the needle hub in a fully-retracted configuration;

FIG. 157A shows a cross-sectional view of the insertion mechanism of FIG. 156A in an initial configuration taken at 45° rotation to the view of FIG. 156A;

FIG. 157B shows a cross-sectional view of the insertion mechanism of FIG. 157A in an inserted configuration;

FIG. 157C shows a cross-sectional view of the insertion mechanism of FIG. 157A having the needle hub in a retracted configuration;

FIG. 158A shows a cross-sectional view of the insertion mechanism of FIGS. 156A and 157A in an initial configuration taken at 270° rotation to the view of FIG. 157A;

FIG. 158B shows a cross-sectional view of the insertion mechanism of FIG. 158A in an inserted configuration;

FIG. 158C shows a cross-sectional view of the insertion mechanism of FIG. 158A having the needle hub in a retracted configuration;

FIG. 159 is an isometric view of a clip illustrated in FIGS. 156A-158C;

FIG. 160 is an isometric view of a cannula retainer illustrated in FIGS. 156A-158C;

FIG. 161 is an isometric view of a needle hub illustrated in FIGS. 156A-158C;

FIG. 162 is cross-sectional isometric view of a housing illustrated in FIGS. 156A-158C;

FIG. 163A is an isometric view of a NIM activation mechanism according to at least one embodiment of the present invention in an initial configuration;

FIG. 163B is an isometric view of the NIM activation mechanism of FIG. 163A in an activated configuration;

FIG. 164A is a top view of a NIM retraction mechanism according to at least one embodiment of the present invention in a delivery configuration;

FIG. 164B is a top view of the NIM retraction mechanism of FIG. 164A in a retracted configuration;

FIG. 165 is an isometric view of a drug delivery device incorporating an embodiment of a fill-finish cartridge according to aspects of the disclosure;

FIG. 166A is a schematic representation of an exemplary fill-finish cartridge of the present disclosure;

FIG. 166B is a chart of exemplary combinations of components of a fill-finish cartridge according to aspects of the disclosure;

FIG. 167 is an exploded isometric view of a fill-finish cartridge, according to an embodiment of the disclosure;

FIG. 168 is an enlarged fragmentary isometric cross-sectional view of the fluid pathway connector of the fill-finish cartridge shown in FIG. 167, cross-hatching being eliminated for the purposes of clarity;

FIG. 169 is an isometric view of the fill-finish cartridge of FIG. 167 before insertion of a plunger seal, elements of FIG. 169 being shown in partial transparency;

FIG. 170 is an isometric view of the fill-finish cartridge of FIG. 167 after insertion of a plunger seal, elements of FIG. 30 being shown in partial transparency;

FIG. 171 is an exploded isometric view of a tray which may be utilized to retain a plurality of fill-finish cartridges for use in a fill-finish process, elements of FIG. 170 being shown in partial transparency;

FIG. 172 is an isometric view of the a tray of FIG. 171 in an assembled form and holding a plurality of fill-finish cartridges for use in a fill-finish process;

FIG. 173 is a side elevational view of another embodiment of a fill-finish cartridge, wherein the cartridge includes a fully disposable carrier;

FIG. 174 is an exploded view of the fill-finish cartridge of FIG. 173;

FIG. 175 is a cross-sectional view of the fill-finish cartridge of FIGS. 173 and 174, cross-hatching being eliminated for the purposes of clarity;

FIG. 176 is a side elevational view of the fill-finish cartridge of FIGS. 173-175 with the carrier removed;

FIG. 177 is an isometric view of a drug delivery device incorporating another embodiment of a fill-finish cartridge according to the disclosure, a portion of a housing of the drug delivery device being removed;

FIG. 178 is a side elevational view of the fill-finish cartridge of FIG. 177 prior to placement in the housing, and including partially disposable carrier;

FIG. 179 is a cross-sectional view of the fill-finish cartridge of FIG. 177, cross-hatching being eliminated for the purposes of clarity;

FIG. 180 is a side elevational view of another embodiment of a fill-finish cartridge in an assembled configuration;

FIG. 181 is a cross-sectional view of the fill-finish cartridge of FIG. 180, cross-hatching being eliminated for the purposes of clarity;

FIG. 182 is a partially exploded view of the fill-finish cartridge of FIGS. 180 and 181, showing a fluid conduit in the final configuration;

FIG. 183 is an exploded view of the fluid pathway connector of the fill-finish cartridge of FIGS. 180-182;

FIG. 184 is a cross-sectional view of the fill-finish cartridge of FIG. 180 similar to the view of FIG. 181, but prior to the coupling of the fluid pathway connector to the needle insertion mechanism, cross-hatching being eliminated for the purposes of clarity;

FIG. 185 is a side elevational view of another embodiment of a fill-finish cartridge in an assembled configuration;

FIG. 186 is a cross-sectional view of the fill-finish cartridge of FIG. 181, cross-hatching being eliminated for the purposes of clarity;

FIG. 187 is a cross-sectional view of the fill-finish cartridge of FIG. 181 similar to the view of FIG. 182, but prior to the coupling of the fluid pathway connector to the needle insertion mechanism, cross-hatching being eliminated for the purposes of clarity;

FIG. 188 is a schematic illustration of a drug delivery device including a temperature control system, according to one embodiment of the present disclosure;

FIG. 189A illustrates an embodiment of an adhesive patch for a drug delivery device constructed in accordance with principles of the present disclosure;

FIG. 189B illustrates an embodiment of an adhesive patch for a drug delivery device constructed in accordance with principles of the present disclosure;

FIG. 190 depicts an embodiment of a non-adhesive patch liner in combination with a drug delivery device constructed in accordance with principles of the present disclosure;

FIG. 191A illustrates an exploded assembly view of an embodiment of an adhesive patch for a drug delivery device constructed in accordance with principles of the present disclosure;

FIG. 191B depicts the adhesive patch of FIG. 191A in an assembled form;

FIG. 192 illustrates an isometric view of a drug delivery device including an adhesive patch with stiffening members, according to one embodiment of the present disclosure;

FIG. 193 illustrates a bottom view an embodiment of a non-adhesive patch liner;

FIG. 194A-194C illustrate a process of attaching the drug delivery device of FIG. 192 to a patient's skin;

FIG. 195 is a schematic diagram of a drug delivery device in communication with a data processing network according to one embodiment of the present disclosure;

FIGS. 196A-196C are schematic diagrams illustrating the operation of an energy management system according to one embodiment of the present disclosure;

FIGS. 197A-197C are schematic diagrams illustrating the operation of an energy management system according to another embodiment of the present disclosure;

FIGS. 198A-198C are schematic diagrams illustrating the operation of an energy management system according to another embodiment of the present disclosure;

FIG. 199 is an isometric view of an energy management system according to another embodiment of the present disclosure;

FIG. 200 is an isometric view of an energy management system according to another embodiment of the present disclosure;

FIG. 201A shows an exploded view of a medical device with an integrated stimulant source according to at least one embodiment of the present invention;

FIG. 201B shows the medical device of the embodiment of FIG. 201A applied to a patient's skin and the stimulant source activated;

FIG. 201C shows the medical device of the embodiment of FIG. 201A after removal from the patient's skin;

FIG. 202A shows an exploded view of a medical device with an external stimulant source according to at least one embodiment of the present invention;

FIG. 202B shows the medical device of the embodiment of FIG. 202A applied to a patient's skin;

FIG. 202C shows the medical device of the embodiment of FIG. 202A after removal of the body of the medical device and the stimulant source activated;

FIG. 202D illustrates removal of the adhesive from the patient's skin;

FIG. 203A is a cross-sectional view of an embodiment of a fluid pathway connector and drug container prior to drug delivery;

FIG. 203B is a cross-sectional view of the embodiment of a fluid pathway connector and drug container of FIG. 203A during drug delivery; and FIG. 203C is a cross-sectional view of the embodiment of a fluid pathway connector and drug container of FIG. 203A following completion of drug delivery.

DETAILED DESCRIPTION

The present disclosure provides drug delivery devices having advantageous insertion mechanisms, drive mechanisms, sterile fluid pathway assemblies, status indicators, safety features, and other advantageous components. Such drug delivery devices are safe and easy to use, and are aesthetically and ergonomically appealing for self-administering patients. The drug delivery devices described herein incorporate features which make activation, operation, and lock-out of the drug delivery device simple for even untrained patients. The drug delivery devices of the present disclosure provide these desirable features without various problems associated with known prior art devices. Furthermore, the sterile fluid pathway assemblies of the present disclosure may filled with pharmaceutical treatments using standard filling equipment and systems. This advantage is enabled by the fill-finish cartridges of the present disclosure which function to maintain the sterility of the fluid pathway assemblies and allow them to nest, mount, or otherwise be removably inserted into trays for standard fill-finish processes, as discussed is more detail below.

As discussed in more detail below, the drug delivery devices of the present disclosure may contain a drug, which may also be also be referred to as a medication or a medicament. The drug may be, but is not limited to, various biologicals (e.g., peptides, peptibodies, or antibodies), biosimilars, large-molecule drugs (e.g., a drug with a molecular weight of greater than or equal to approximately 900 Daltons), small-molecule drugs (e.g., a drug with a molecular weight of less than or equal to approximately 900 Daltons), high viscosity drugs, low viscosity drugs, drugs exhibiting non-Newtonian fluid characteristics such as shear thinning, and/or drugs exhibiting Newtonian fluid characteristics. The drug may be in a fluid or liquid form, although the disclosure is not limited to a particular state (e.g., no differentiation is intended between a solution, a gel, or a lyophilized product for example).

One perceived disadvantage of certain known drug delivery devices is their inability to deliver highly viscous drugs such as certain biologics in a timely manner and/or with little patient discomfort. High viscosity drugs typically require more time for injection than low viscosity drugs. Patients may find it difficult and/or undesirable to hold an autoinjector or a syringe against their skin for the amount of time necessary to inject a high viscosity drug. While the injection time can be decreased by increasing the force of the drive mechanism, a more powerful drive mechanism increases the risk of breakage of the drug container and other internal components of the device. Also, a more powerful drive mechanism increases the possibility that the patient will experience an impulse or mechanical shockwave that may disturb or surprise the patient. As a result, the patient may attempt to pull the drug delivery device away from skin, which can compromise complete dosing.

Long injection times are more likely to be tolerated by patients if the drug is administered via a wearable drug delivery device. Unlike a syringe or an autoinjector, a wearable drug delivery device does not have to be held in place by the patient during drug delivery. Therefore, the patient can resume physical activities after the wearable drug delivery device has been placed on the skin and initiated or otherwise not burdened by holding the drug delivery device in place.

Certain aspects of wearable drug delivery devices, however, have discouraged their adoption in the field of high viscosity drugs. In order to achieve a compact design with a low profile that does not significantly protrude from the patient's body, wearable drug delivery devices oftentimes include a drug container that is offset and orthogonal to an insertion mechanism. This arrangement usually requires a tubular conduit with one of more turns to fluidly couple the drug container and the insertion mechanism. Therefore, as compared to syringes and autoinjectors, the internal fluid flowpath of wearable drug delivery devices tend to be relatively long and tortuous.

For drugs that behave as Newtonian fluids (i.e., fluids for which shear rate is directly proportional to flow rate), a longer flow path can result in a slower flow rate. Thus, wearable drug delivery devices, due to their long internal flowpaths, have the potential to exacerbate the injection problems associated with high viscosity drugs. The force of the drive mechanism can be increased to compensate for the reduction in flow rate, but a more powerful drive mechanism increases the risk of drug container breakage and therefore is typically considered undesirable. For at least these reasons, wearable drug delivery devices were viewed by some as not being particularly well suited for the delivery of high viscosity drugs.

The inventors of the present disclosure found that various high viscosity drugs (e.g., PCSK9 specific antibodies, G-CSFs, sclerostin antibodies, and CGRP antibodies) exhibit non-Newtonian fluid characteristics when injected via a wearable drug delivery device. One such characteristic is shear thinning, which is the ability of a non-Newtonian fluids to exhibit decreased viscosity when subjected to shear strain. Shear thinning reduces the viscosity of a fluid as it is pushed through a conduit. Accordingly, the force needed to push the fluid through a conduit is less than it would be if the fluid was Newtonian. In the context of wearable drug delivery devices, shear shinning mitigates the clogging effect of the device's long internal flowpath. Therefore, an unexpected benefit of wearable drug delivery devices found by the inventors of the present disclosure is that they are well suited for delivering high viscosity drugs having non-Newtonian characteristics such as shear thinning. The inventors of the present disclosure found that shear thinning oftentimes occurs in drugs such as biologics which have relatively large protein molecules with a molecular weight greater than or equal to approximately (e.g., ±10%) 900 daltons. Any of the wearable drug delivery devices described herein may have a drug container filled with a high viscosity drug having shear thinning capabilities, and therefore realize the unexpected benefits of shear thinning on the operation and use of the device.

Certain non-limiting embodiments of the drug delivery device and its respective components will now be described with reference to the accompanying figures.

As used herein to describe the drive mechanisms, the insertion mechanisms, fluid pathway connectors, drug delivery devices, or any of the relative positions of the components of the present disclosure, the terms "axial" or "axially" refer generally to a longitudinal axis "A" around which a component is preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. As used herein, "fluid" refers primarily to liquids, but can also include suspensions of solids dispersed in liquids, and gasses dissolved in or otherwise present together within liquids inside the fluid-containing portions of drug delivery devices. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present disclosure, the biasing member is a spring, preferably a compression spring. Also, as used herein, the term "drug delivery device" is intended to include any number of devices which are capable of dispensing a fluid to a patient upon activation. Such drug delivery devices include, for example, wearable drug delivery devices, on-body injectors, off-body injectors, autoinjectors, infusion pumps, bolus injectors, and the like. Furthermore, as used herein, the term "wearable drug delivery device" is intended to include any number of devices which are capable dispensing a fluid to a patient upon activation and capable of being attached to the patient's skin or clothing. Such wearable drug delivery devices include, for example, on-body injectors and off-body injectors.

I. Drug Delivery Device

Figure 1A:
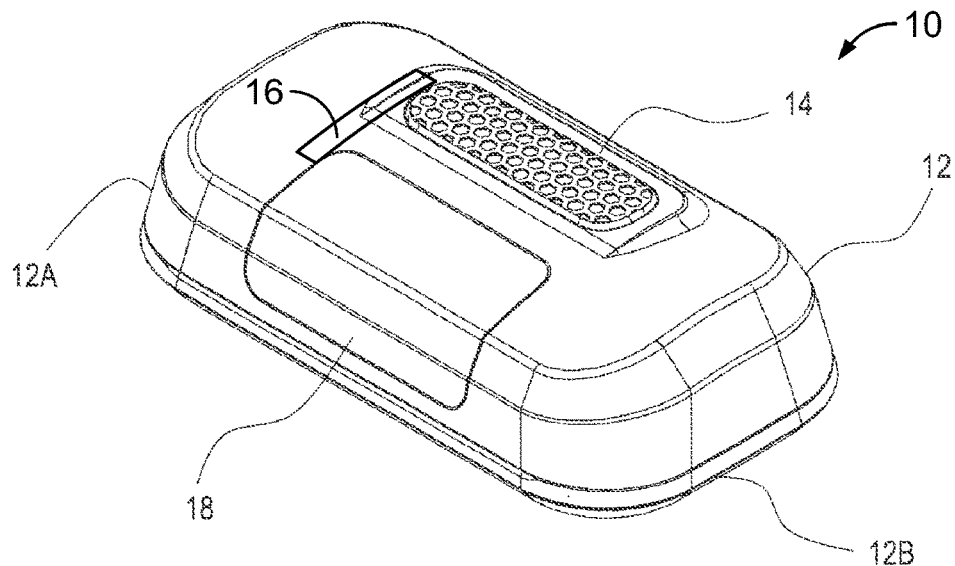
FIG. 1A shows an isometric view of a drug delivery pump having safety integrated insertion mechanisms, according to one embodiment of the present invention.
Figure 1B:
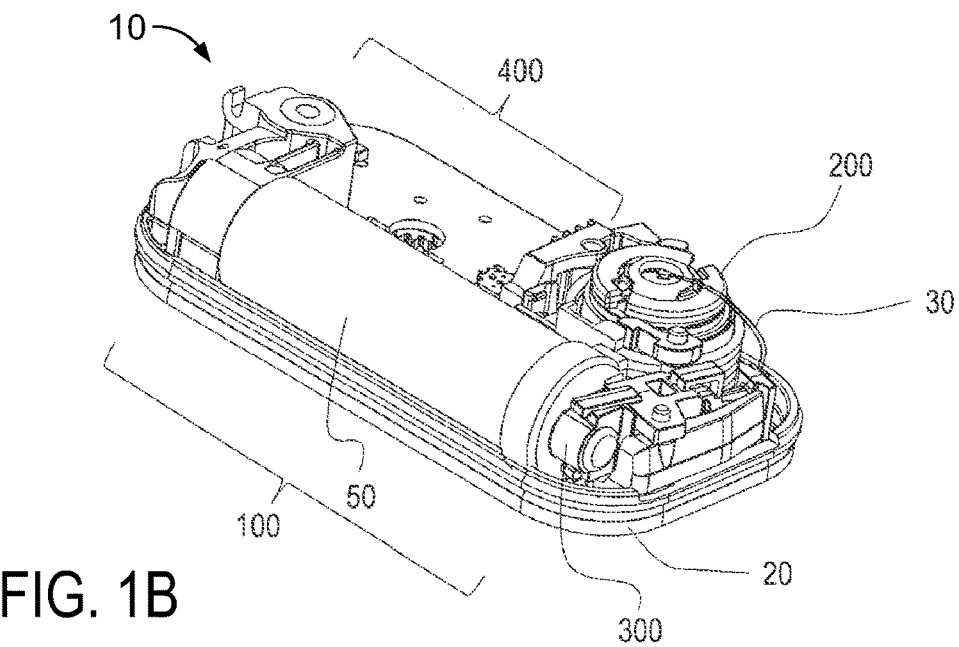
FIG. 1B shows an isometric view of the interior components of the drug delivery pump shown in FIG. 1A.
Figure 1C:
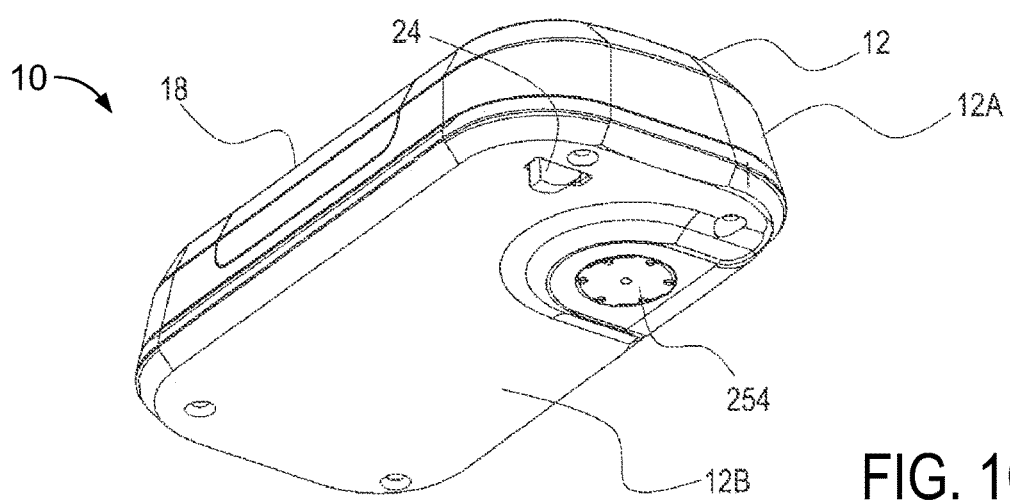
FIG. 1C shows an isometric view of the bottom of the drug delivery pump shown in FIG. 1A.

FIGS. 1A-1C show an exemplary drug delivery device 10 according to at least one embodiment of the present disclosure. The drug delivery device 10 may be utilized to administer delivery of a drug treatment into a body of a patient. As shown in FIGS. 1A-1C, the drug delivery device 10 includes a housing 12. The housing 12 may include one or more housing subcomponents which are fixedly engageable to facilitate easier manufacturing, assembly, and operation of the drug delivery device 10. For example, drug delivery device 10 includes the housing 12 which includes an upper housing 12A and a lower housing 12B. The drug delivery device 10 may further include an activation mechanism 14, a status indicator 16, and a window 18. Window 18 may be any translucent or transmissive surface through which the operation of the drug delivery device 10 may be viewed. In at least one embodiment, the window 18 may be configured to connect and hold together the upper housing 12A and the lower housing 12B. As shown in FIG. 1B, drug delivery device 10 further includes assembly platform 20, sterile fluid conduit 30, drive mechanism 100 having drug container 50, insertion mechanism 200, fluid pathway connector 300 configured to establish a sterile fluid flow path between the drug container 50 and the needle or cannula of the insertion mechanism 200, and power and control system 400. One or more of the components of the drug delivery device 10 may be modular in that they may be, for example, pre-assembled as separate components and configured into position onto the assembly platform 20 of the drug delivery device 10 during manufacturing. In some embodiments, the assembly platform 20 may be a portion of the housing 12, such as a portion of the lower housing 12, or alternatively, may be a separate component.

The housing 12 may contain some or all of the device components. In some embodiments, the housing 12 may provide a means of removably attaching the drug delivery device 10 to the skin or clothing of the patient, thereby rending the drug delivery device 10 a wearable drug delivery device. In some embodiments, a layer of adhesive may be applied to an exterior surface of the housing 12, such as the surface through which a cannula protrudes during operation, for releasably attaching the drug delivery device 10 to a patient's skin.

The housing 12 also provides protection to the interior components of the drug delivery device 10 against environmental influences. In some embodiments, the housing may be configured to at least partially prevent contaminants and other harmful matter from entering the drug delivery device 10. For example, the housing 12 may be configured to restrict the passage of fluids into the drug delivery device 10. As such, this may allow the drug delivery device 10 to be worn in the shower, while swimming, and/or other water-related activities. The housing 12 is ergonomically and aesthetically designed in size, shape, and related features to facilitate easy packaging, storage, handling, and use by patients who may be untrained and/or physically impaired. Furthermore, the external surface of the housing 12 may be utilized to provide product labeling, safety instructions, and the like. Additionally, as described above, housing 12 may include certain components, such as status indicator 16 and window 18, which may provide operation feedback to the patient.

The container 50, or any other container described herein, may be configured to contain variety of different drug dose volumes, including drug dose volumes in a range of approximately (e.g., ±10%) 0.5-20 mL, or 1-10 mL, or 2-10 mL, or 2-8 mL, or 2-6 mL, or 2-4 mL, or 0.5-2 mL, or 0.5-1 mL, or 3.5 mL, or less than or equal to approximately (e.g., ±10%) 3.0 mL, or less than or equal to approximately (e.g., ±10%) 2.5 mL, or less than or equal to approximately (e.g., ±10%) 2.0 mL, or less than or equal to approximately (e.g., ±10%) 1.5 mL, or less than or equal to approximately (e.g., ±10%) 1.0 mL. The container 50 may be completely or partially filled with the drug. The drug may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

In at least one embodiment, the drug delivery device 10 provides an activation mechanism that is displaced by the patient to trigger a start command to a power and control system 400. In a preferred embodiment, the activation mechanism is a start button 14 that is located through the housing 12, such as through an aperture between the upper housing 12A and the lower housing 12B, and which contacts a control arm 40 of the power and control system 400. In at least one embodiment, the start button 14 may be a push button, and in other embodiments, may be an on/off switch, a toggle, or any similar activation feature known in the art. The housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the patient when the drug delivery device 10 is placed on the body of the patient. Housing 12 is described in further detail hereinafter with reference to other components and embodiments of the present disclosure.

The drug delivery device 10 may be configured such that, upon activation by a patient by depression of the activation mechanism, the drug delivery device 10 is initiated to: insert a fluid pathway into the patient; enable, connect, or open necessary connections between a drug container, a fluid pathway, and a sterile fluid conduit; and force drug fluid stored in the drug container through the fluid pathway and fluid conduit for delivery into a patient. One or more optional safety mechanisms may be utilized, for example, to prevent premature activation of the drug delivery device 10. For example, an optional on-body sensor 24 (shown in FIG. 1C) may be provided in one embodiment as a safety feature to ensure that the power and control system 400, or the activation mechanism, cannot be engaged unless the drug delivery device 10 is in contact with the body of the patient. In one such embodiment, the on-body sensor 24 is located on the bottom of lower housing 12B where it may come in contact with the patient's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug delivery device 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a conductive-, capacitive- or impedance-based sensor which must detect tissue before permitting activation of the power and control system 400. In at least one embodiment, such an electrically based on-body sensor may incorporate a resistor with an impedance of approximately (e.g., ±10%) 1 MΩ. These concepts are not mutually exclusive and one or more combinations may be utilized within the breadth of the present disclosure to prevent, for example, premature activation of the drug delivery device 10. In a preferred embodiment, the drug delivery device 10 utilizes one or more mechanical on-body sensors. Additional integrated safety mechanisms are described herein with reference to other components of the drug delivery device 10.

The fluid pathway connector 300 includes a sterile fluid conduit 30, a piercing member, a connection hub, and a sterile sleeve. The fluid pathway connector 300 may further include one or more flow restrictors. Upon proper activation of the drug delivery device 10, the fluid pathway connector 300 is enabled to connect the sterile fluid conduit 30 to the drug container 50. Such connection may be facilitated by a piercing member, such as a needle, penetrating a pierceable seal of the drug container 50. The sterility of this connection may be maintained by performing the connection within a flexible sterile sleeve. Upon substantially simultaneous activation of the insertion mechanism, the fluid pathway between drug container and insertion mechanism is complete to permit drug delivery into the target tissue.

In at least one embodiment of the present disclosure, the piercing member of the fluid pathway connector is caused to penetrate the pierceable seal of the drug container of the drive mechanism by direct action of the user, such as by depression of the activation mechanism by the user. For example, the activation mechanism itself may bear on the fluid pathway connector such that displacement of the activation mechanism from its original position also causes displacement of the fluid pathway connector. In a preferred embodiment, this connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connector. The piercing member may reside within the sterile sleeve until a connection between the fluid pathway connector and the drug container is desired. The sterile sleeve may be sterilized to ensure the sterility of the piercing member and the fluid pathway prior to activation.

Alternatively, or additionally, the sterility of the flow path may be preserved by one or more membranes or foils defining one or more sterile chambers of the fluid pathway connector. The membranes or foils may be pierced at the time of use of the drug pump by the piercing member or, alternatively, by an introducer member. In such an embodiment, the piercing member may be at least partially disposed within a lumen of the introducer member to prevent the piercing member from coming in contact with foreign substances.

The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 300 and the sterile fluid conduit 30 are provided hereinafter in later sections in reference to multiple embodiments.

Figure 2A:
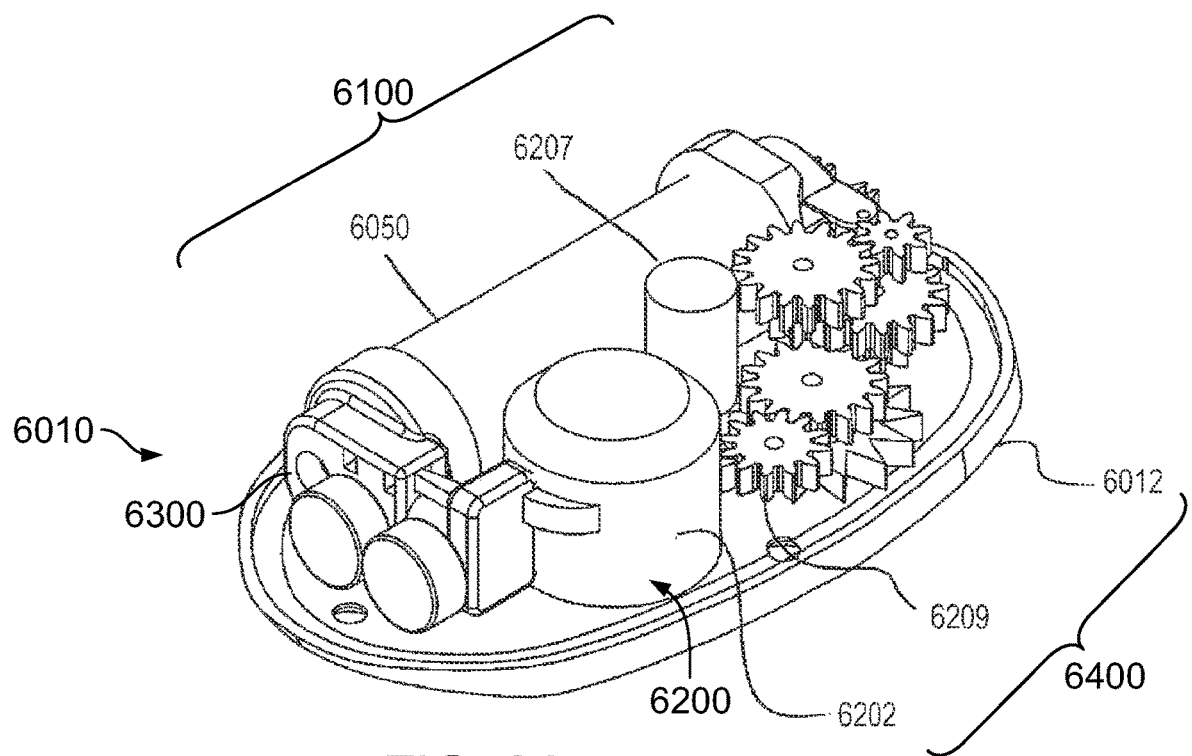
FIG. 2A shows an isometric view of the interior components of a second embodiment of a drug delivery device.
Figure 2B:
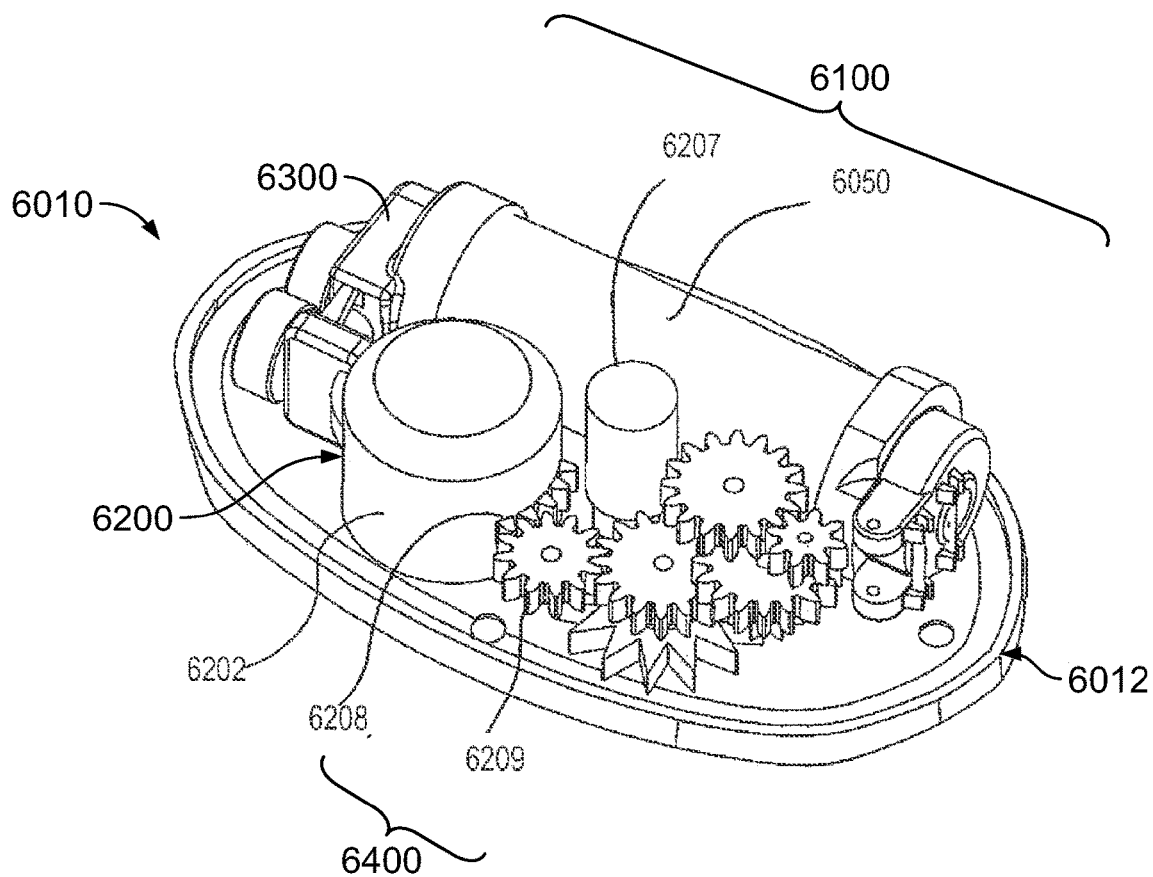
FIG. 2B shows a second view of the interior components of the drug delivery device shown in FIG. 2A.

Another embodiment of a drug delivery device 6010 is shown in FIGS. 2A-2B. The drug delivery device 6010 includes many of the same elements as the drug delivery device 10. Elements of the drug delivery device 6010 which are similar to, or the same as, the drug delivery device 10 are designated by the same reference numeral, incremented by 6010. A description of many of these elements is abbreviated or even eliminated in the interest of brevity. The drug delivery device 6010 may include a container 6050 filled with a volume of a fluid(s) for delivery to a patient. The fluid(s) may include one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody. In drug delivery device 6010, one or more of an insertion mechanism 6200, fluid pathway connector 6300, and a drive mechanism 6100 are controlled by motion of a motor 6207, solenoid or other electrical actuator, as well as the rotation of one or more gears 6209. Additionally, or alternatively, an escapement mechanism may be used to control the rate of rotation of the one or more gears 6209. One of the gears 6209 may be engaged with teeth 6208 of an insertion mechanism housing 6202. As such, the rotation of the one or more gears 209 of the gear train may control the rotation of the insertion mechanism housing 6202 and, thereby, the insertion of the needle or trocar into the skin of the patient. The operation of various embodiments of the insertion mechanism 6200 are described in more detail below.

II. Power and Control System

The power and control system 400 includes a power source, which provides the energy for various electrical components within the drug delivery device 10, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the patient and interfaces with the drive mechanism 100. In one embodiment, the power and control system 400 interfaces either directly or indirectly with the on-body sensor 24 to identify when the device is in contact with patient and/or the activation mechanism 14 to identify when the drug delivery device 10 has been activated. The power and control system 400 may also interface with the status indicator 16 of the housing 12, which may be a transmissive or translucent material which permits light transfer, to provide visual feedback to the patient. The power and control system 400 interfaces with the drive mechanism 100 through one or more interconnects to relay status indication, such as activation, drug delivery, and end-of-dose, to the patient. Such status indication may be presented to the patient via auditory tones, such as through the audible alarms, and/or via visual indicators, such as through the LEDs. In a preferred embodiment, the control interfaces between the power and control system and the other components of the drug delivery device 10 are not engaged or connected until activation by the patient. This is a desirable safety feature that prevents accidental operation of the drug delivery device 10 and may additionally maintain the energy contained in the power source during storage, transportation, and the like.

The power and control system 400 may be configured to provide a number of different status indicators to the patient. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the patient, the power and control system 400 will power the drive mechanism 100 to begin delivery of the drug treatment through the fluid pathway connector 300 and sterile fluid conduit 30 to the needle or cannula of the insertion mechanism 200. In a preferred embodiment of the present disclosure, the insertion mechanism 200 and the fluid pathway connector 300 may be caused to activate directly by patient operation of the activation mechanism 14. During the drug delivery process, the power and control system 400 is configured to provide a dispensing status signal via the status indicator 16. After the drug has been administered into the body of the patient and after the end of any additional dwell time, to ensure that substantially the entire dose has been delivered to the patient, the power and control system 400 may provide an okay-to-remove status signal via the status indicator 16. This may be independently verified by the patient by viewing the drive mechanism 100 and drug dose delivery through the window 18 of the housing 12. Additionally, the power and control system 400 may be configured to provide one or more alert signals via the status indicator 16, such as for example alerts indicative of fault or operation failure situations.

Additionally, the power and control system 400 may be configured to identify removal of the drug delivery device from its packaging. The power and control system 400 may be mechanically, electronically, or electro-mechanically connected to the packaging such that removal of the drug delivery device from the packaging may activate or power-on the power and control system for use, or simply enable the power and control system to be powered-on by the patient. In such an embodiment, without removal of the drug delivery device from the packaging the drug delivery device cannot be activated. This provides an additional safety mechanism of the drug delivery device 10 and for the patient. In at least one embodiment, the drug delivery device 10 or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system 400 has been activated, a multi-function drive mechanism (e.g., drive mechanism 100) is initiated to actuate the insertion mechanism 200 and the fluid pathway connector 300, while also permitting the drug fluid to be forced from the drug container 50. During the drug delivery process, the power and control system 400 is configured to provide a dispensing status signal via a status indicator (e.g., status indicator 16). After the drug has been administered into the body of the patient and after the end of any additional dwell time, to ensure that substantially the entire dose has been delivered to the patient, the power and control system 400 may provide an okay-to-remove status signal via the status indicator. This may be independently verified by the patient by viewing the drive mechanism and drug dose delivery through the window 18 formed in the housing 12. Additionally, the power and control system 400 may be configured to provide one or more alert signals via the status indicator, such as for example alerts indicative of fault or operation failure situations.

The power and control system 400 may additionally be configured to accept various inputs from the patient to dynamically control the drive mechanisms 100 to meet a desired drug delivery rate or profile. For example, the power and control system 400 may receive inputs, such as from partial or full activation, depression, and/or release of the activation mechanism, to set, initiate, stop, or otherwise adjust the control of the drive mechanism 100 via the power and control system 400 to meet the desired drug delivery rate or profile. Similarly, the power and control system 400 may be configured to receive such inputs to adjust the drug dose volume; to prime the drive mechanism, fluid pathway connector, and fluid conduit; and/or to start, stop, or pause operation of the drive mechanism 100. Such inputs may be received by the patient directly acting on the drug delivery device 10, such as by use of the activation mechanism 14 or a different control interface, or the power and control system 400 may be configured to receive such inputs from a remote control device. Additionally or alternatively, such inputs may be pre-programmed.

Other power and control system configurations may be utilized with the drug delivery device of the present disclosure. For example, certain activation delays may be utilized during drug delivery. As mentioned above, one such delay optionally included within the system configuration is a dwell time which ensures that substantially the entire drug dose has been delivered before signaling completion to the patient. Similarly, activation of the drug delivery device 10 may require a delayed depression (i.e., pushing) of the activation mechanism 14 of the drug delivery device 10. Additionally, the system may include a feature which permits the patient to respond to the end-of-dose signals and to deactivate or power-down the drug delivery device 10. Such a feature may similarly require a delayed depression of the activation mechanism, to prevent accidental deactivation of the device. Such features provide desirable safety integration and ease-of-use parameters to the drug delivery device 10. An additional safety feature may be integrated into the activation mechanism to prevent partial depression and, therefore, partial activation of the drug delivery device. For example, the activation mechanism and/or power and control system may be configured such that the device is either completely off or completely on, to prevent partial activation. Such features are described in further detail hereinafter with regard to other aspects of the drug delivery device 10.

The foregoing description of the power and control system 400 applies to the power and control system 6400 of the drug delivery device 6010, where appropriate.

III. Fluid Pathway Connector

At least some of the drug delivery devices described in this application, including at least those described in connection with FIGS. 1A-2B, may be configured to incorporate the embodiments of the fluid pathway connector described below in connection with FIGS. 3A-32B. The embodiments of the fluid pathway connector described below in connection with FIGS. 3A-32B may be used to replace, in its entirety or partially, the above-described fluid pathway connector 300 or 6300, or any other fluid pathway connector described herein, where appropriate.

The present disclosure provides container connections which maintain the sterility and/or aseptic condition of the fluid pathway, and drug delivery pumps which incorporate such sterile fluid pathway connector assemblies to drug containers. Such devices are safe and easy to use, and are aesthetically and ergonomically appealing for self-administering patients. The fluid pathway connector may be initiated directly by the user, or may be activated by another mechanism of the device (as described herein) after some initial user step. The devices described herein incorporate features which make activation, operation, and lock-out of the device simple for even untrained users. The novel devices of the present disclosure provide these desirable features without problems associated with known prior art devices. Certain non-limiting embodiments of the novel drug delivery pumps, fluid pathway connector assemblies, and their respective components are described further herein with reference to the accompanying figures.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present disclosure enable the manufacture, assembly, and use of pre-filled drug delivery devices which maintain the sterility and/or aseptic condition of the fluid pathway assembly through the various manufacturing steps.

Additionally, because the drug delivery devices according to the present disclosure do not need to be terminally sterilized, the components of the devices may be constructed of other, often less expensive, materials which would not normally withstand the sterilization environment. For example, less expensive plastics may be utilized for certain device components because they do not need to be sterilized after assembly. Furthermore, the embodiments of the present disclosure permit device architecture and/or component integration in ways which are not suitable for devices that require terminal sterilization. For example, when sterilization of the entire device is necessary, the device architecture often requires adequate spacing of components to permit the sterilization gas or material to effectively reach the target surfaces. Removing the need for terminal sterilization permits reduction or elimination of those spaces and allows for device architectures that offer smaller overall dimensions, human factors benefits, and/or industrial design options that are not available for devices that require terminal sterilization.

In other words, the embodiments of the present disclosure may allow the manufacturer to sterilize only the components which will be in contact with the drug fluid and/or which are necessary to maintain sterile and/or aseptic fluid pathways. These embodiments may also allow the pharmaceutical filler to maintain the sterility and/or aseptic condition of these components during the filling and finishing steps associated with the assembly of the drug delivery devices. Similarly, drug delivery devices which incorporate the fluid pathway connector assemblies of the present disclosure may have smaller or more efficient geometries as the device does not have to be configured for sterilization after assembly.

Additionally, the embodiments of the present disclosure allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present disclosure enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner. After mounting of the fluid pathway connector assembly the combined assembly can then be mated into a drug delivery device without requiring the remainder of the device components to be sterilized. Accordingly, embodiments of the present disclosure may provide novel components which enable the fluid pathway assemblies to be sterilized, assembled, filled, and incorporated into drug delivery devices in a cost-efficient and streamlined process.

In the processes of filling drug containers and other drug delivery devices, it is sometimes necessary to connect two or more sterile components or subassemblies. For example, wearable injectors or drug delivery devices may include a drug container which may be filled with a fluid drug using standard pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes or particulates to the drug and/or fluid pathway. The connection of two or more aseptic components or subassemblies is typically performed in an aseptic environment, such as a clean room, thereby ensuring that no harmful microbes or particulates are introduced to the assembly. This, however, may lead to increased cost to manufacture the drug delivery devices.

The present disclosure provides fluid pathway connector assemblies with integrated safety features and drug delivery pumps which incorporate such fluid pathway connector assemblies. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery device, fluid pathway connector assemblies, and their respective components are described further herein with reference to the accompanying figures. The devices described herein may be configured for delivery of controlled substances and may further include features that prevent so-called "run-away" delivery of medicament. When delivering controlled substances, this may be an important safety feature to protect the patient. For example, some medicaments can be dangerous, and potentially even deadly, when administered in too large a quantity and/or at too rapid of a rate. By providing such automatic safety stop mechanisms, the safety of the patient may be ensured.

The present disclosure provides devices and methods for establishing aseptic connections between two or more components or subassemblies. The devices may be used in medical devices such as drug delivery pumps. In some embodiments, a connection is made between a drug container and a fluid pathway connector assembly. The fluid pathway connector assembly may include a connection hub, a piercing member, and a piercing member retainer. The mechanism may further include a first film or seal covering an aperture, thereby maintaining the aseptic condition of a cavity adjacent the aperture. The drug container may hold a fluid drug and include a pierceable seal. A second film may cover an aperture of one or more components of the drug container and the seal, and thereby maintain the aseptic condition of the pierceable seal. The piercing member may be caused to pierce the first and second film and the pierceable seal to open a fluid pathway for delivery of the fluid drug to a patient.

In a first embodiment, the present disclosure provides a fluid pathway connector. The fluid pathway connector assembly includes: a connection hub, a piercing member, a piercing member retainer, and a drug container having a cap, a pierceable seal, and a barrel, wherein the piercing member is at least partially disposed in a sterile cavity defined by the connection hub. The drug container may contain a drug fluid for delivery through the fluid pathway connector assembly to the target. The pierceable seal includes a seal barrier that may be penetrated by the piercing member. The fluid pathway connector assembly may further include a first film which is fixedly attached over an aperture over an aperture of the connection hub and prevents foreign substances such as microbes from entering the sterile cavity formed by the connection hub. The drug container may further include a second film fixedly connected over a cavity formed by the pierceable seal and the second film to prevent foreign substances such as microbes from entering the cavity. The first and second films may be pierced by the piercing member. The fluid pathway connector may be initiated directly by the user, or may be activated by another mechanism of the device (as described herein) after some initial user step.

In another embodiment, the present disclosure provides a drug delivery pump with integrated sterility maintenance features having a housing and an assembly platform, upon which an activation mechanism, a fluid pathway connector assembly, a power and control system, and a drive mechanism having a drug container may be mounted, said fluid pathway connector assembly including a connection hub, a piercing member, a piercing member retainer, and a drug container having a cap, a pierceable seal, and a barrel, wherein the piercing member is at least partially disposed in a sterile cavity defined by the connection hub. The drug container may contain a drug fluid for delivery through the fluid pathway connector assembly to the target. The pierceable seal includes a seal barrier that may be penetrated by the piercing member. The fluid pathway connector assembly may further include a first film which is fixedly attached over an aperture over an aperture of the connection hub and prevents foreign substances such as microbes from entering the sterile cavity formed by the connection hub. The fluid pathway connector assembly may further include a second film fixedly connected over a cavity formed by the pierceable seal and prevents foreign substances such as microbes from entering the cavity. The first and second films may be pierced by the piercing member.

The devices described herein may further include features which prevent the delivery of an excess volume of medicament or delivery at too rapid of a rate, e.g., to prevent a run-away condition of uncontrolled or undesired delivery of the medicament. By providing such automatic safety mechanisms, the safety of the patient may be ensured. Some medicaments, such as insulin or other treatments for diabetes, can be dangerous, and potentially even deadly, if they are not delivered according to prescribed parameters. The safety features described below may ensure that delivery of the medicament is terminated if delivery deviates from the specified parameters.

In a further embodiment of the present disclosure, the fluid pathway connector assembly may include one or more biasing members. In one such embodiment, a biasing member may be included to bias the fluid pathway connector assembly to connect, i.e., to open the fluid pathway between the drug container and the fluid conduit which enables drug flow to the needle insertion mechanism and into the target. In such a configuration, the fluid pathway connector assembly is biased to facilitate the connection upon, for example, movement of a pin or blocking aspect. In at least one embodiment, the biasing member(s) may be internal to the fluid pathway connector assembly and/or external to the fluid pathway connector assembly to facilitate the connection once triggered. Additionally or alternatively, one or more biasing members may be included to disconnect the fluid pathway connector assembly. This may provide a desirable safety feature, to disconnect the fluid pathway upon signaling of an error condition either automatically by the drug delivery pump or upon action by the user. Once the fluid pathway connector assembly is disconnected, flow of drug fluid is restricted or blocked between the drug container and the fluid conduit to limit or prevent fluid flow to the needle insertion mechanism and into the target.

According to an aspect of the disclosure, there is provided a fluid pathway connector assembly for use with a drug container in a drug delivery pump. The drug container includes a barrel, a cap and a pierceable seal. The fluid pathway connector assembly includes an unactuated configuration, an actuated configuration, and a delivery configuration. The fluid pathway connector assembly includes a connection hub including an aperture, a first film, an introducer member, a piercing member, and a piercing member retainer. The first film is sealed along the aperture. The connection hub includes a sterile cavity sealed by the first film. The introducer member is at least partially disposed within the sterile cavity in the unactuated configuration. The piercing member is configured to telescope from the introducer member. The piercing member includes a piercing tip at least partially disposed within the introducer member in the unactuated configuration. The piercing member retainer is connected to the piercing member. The introducer member is configured to move relative to the connection hub from the unactuated configuration to the actuated configuration in which the introducer member pierces the first film. The piercing member is configured to telescope from the introducer member to move from the unactuated configuration to the delivery configuration in which the piercing tip is not disposed within the introducer member. The piercing member is adapted to pierce the pierceable seal in the delivery configuration, the piercing member providing a fluid pathway through the piercing member connection hub in the delivery configuration. In at least one embodiment, there is provided a combination of the fluid pathway connector assembly and the drug container. In at least one embodiment, there is provided a drug delivery pump including a housing, an activation mechanism, the fluid pathway connector assembly, and a drug container.

In at least one embodiment, the fluid pathway connector assembly is configured to move the piercing member from the delivery configuration to a retracted configuration wherein the piercing member is disengaged from the pierceable seal in response to a termination mechanism.

Described below are embodiments of fluid pathway connector assemblies to allow connections to be made between two or more components or subassemblies of the drug delivery devices disclosed herein in a septic environment while maintaining the aspect condition of the fluid flow path. As will be seen, the fluid pathway connector assemblies may be arranged in any orientation. For example, as illustrated in FIGS. 3A-11, the piercing member may be axially aligned with the drug container. In other embodiments, as shown in FIGS. 23-30, the fluid pathway connector assembly may be arranged such that the piercing member of the fluid pathway connector assembly is oriented at an angle with respect to the drug container. In an alternative embodiment, the piercing member may be arranged in an arcuate manner. An exemplary embodiment of such an arrangement is shown in FIGS. 12A-22. The orientation of the fluid pathway connector assembly may be chosen based on the desired overall size and shape of drug delivery device 10 and the available space within the drug delivery device 10.

Figure 3A:
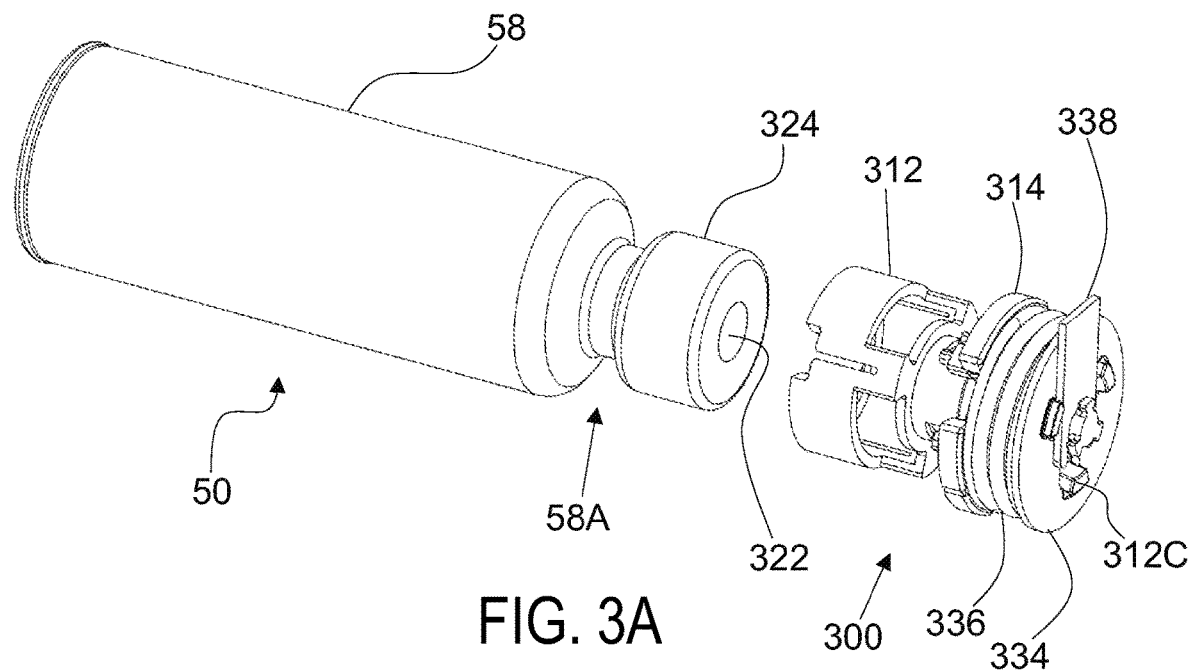
FIG. 3A is an isometric view of an embodiment of a fluid pathway connection assembly and drug container in an unmounted configuration.

FIGS. 3A-11 show one embodiment of such a fluid pathway connector. As seen in FIGS. 3A-3B, the fluid pathway connector 300 may be connected to the drug container 50. FIG. 3A shows these components prior to connection and FIG. 3B shows the components after connection. As will be described herein, fluid pathway connector 300 may be mounted to drug container 50 without compromising the aseptic condition of the fluid flow path. Fluid pathway connector 300 includes introducer member 320, piercing member 316, introducer member retainer 330, piercing member retainer 314, connection hub 312, plate 334, biasing member 336, sterile boot 340, and first film 318. FIGS. 4A-4B show exploded views of the fluid pathway connector 300. As used herein, "piercing member" may refer to any container access needle having at least one pointed end and a hollow interior configured to establish fluid communication with the drug container 50.

According to one aspect of the disclosure (see FIGS. 5A and 5B), the connection hub 312 includes a cavity 312A. Sterile boot 340 may further define the cavity 312A as aseptic. In one embodiment, sterile boot 340 is fixedly connected at a first end to connection hub 312 and at a second end to introducer member retainer 330. Sterile boot 340 may be constructed from a flexible material, such as an elastomer, thereby allowing the sterile boot to deform to maintain engagement with both connection hub 312 and introducer member retainer 330 during operation. A first film 318 is disposed covering an aperture 312B of connection hub 312 to prevent microbes and other contaminants from entering cavity 312A through aperture 312B. In this way, the area contained or bounded by the sterile boot 340, the connection hub 312, and the first film 318 defines cavity 312A and maintains the aseptic condition of the cavity 312A.

Figure 3B:
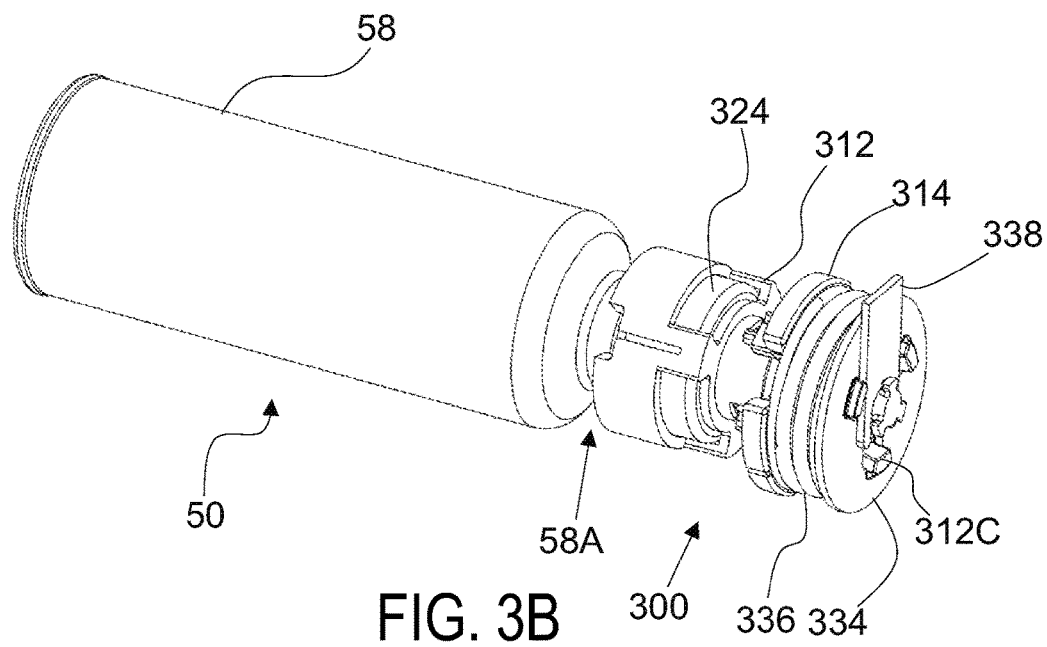
FIG. 3B is an isometric view of the embodiment shown in FIG. 3A in a mounted, but unactuated, configuration.
Figure 5A:
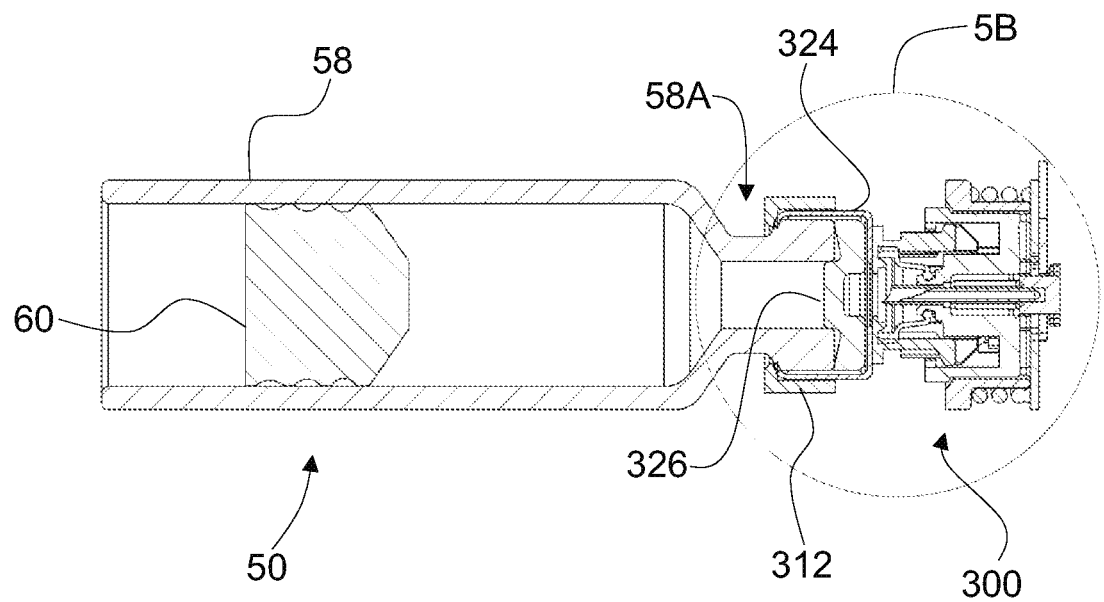
FIG. 5A is a cross-sectional side view of an embodiment of a fluid pathway connection assembly and a drug container in a mounted, but unactuated, configuration.
Figure 5B:
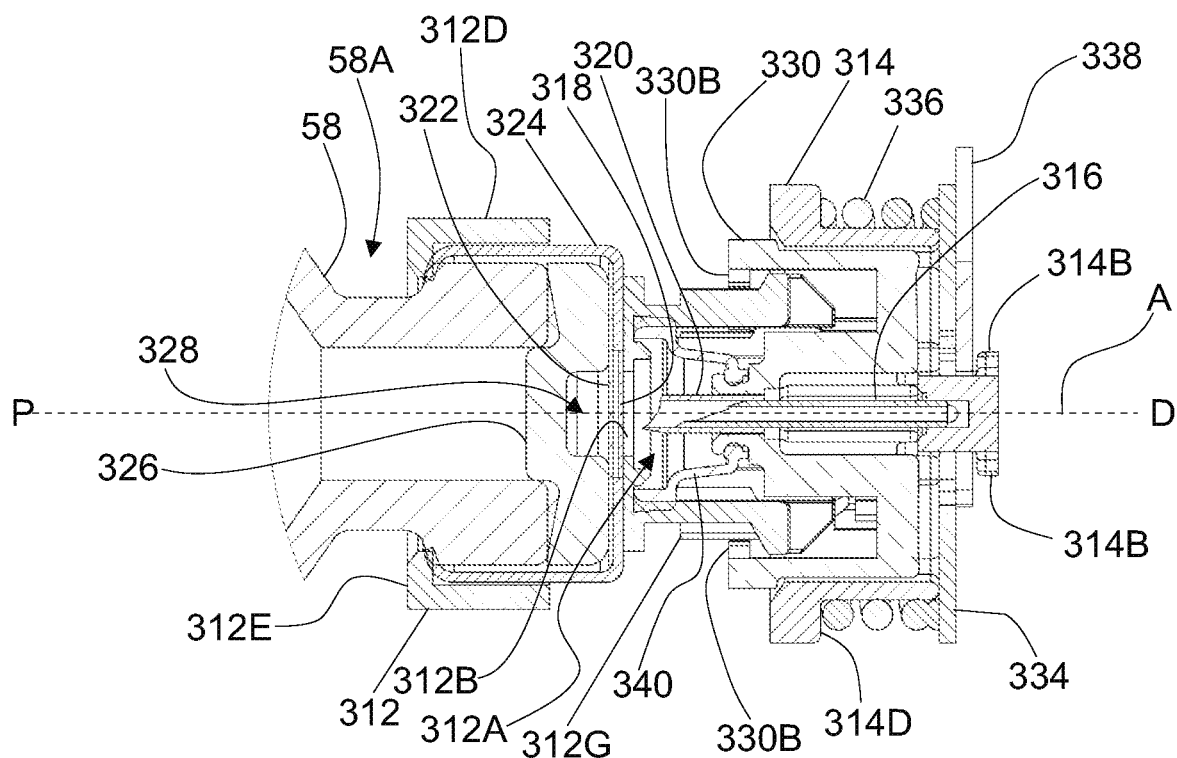
FIG. 5B is an enlarged fragmentary cross-sectional side view of the embodiment shown in FIG. 5A.

In an unmounted configuration, such as illustrated in FIG. 3B, and in an initial, unactuated configuration, as shown in FIGS. 5A-5B, at least a portion of introducer member 320 is disposed within aseptic cavity 312A. At least a piercing tip of the piercing member 316 is partially retained within lumen 320A of introducer member 320, the piercing member 316 being disposed to telescope within the introducer member 320. The piercing member 316 is also at least partially disposed in piercing member retainer 314. In this way, introducer member 320 and piercing member 316 are likewise maintained in an aseptic condition within cavity 312A.

Piercing member 316 is engaged with piercing member retainer 314 such that translation of piercing member retainer 314 is transferred to piercing member 316 such that they maintain a substantially fixed spatial relationship throughout operation. Piercing member 316 may be engaged with piercing member retainer 314 using any method known to one skilled in the art, such as bonding, press-fit, staking, etc. The piercing member 316 may be, for example, a hollow needle.

Introducer member 320 is at least partially retained by introducer member retainer 330 and is engaged with the introducer member retainer 330 such that translation of introducer member retainer 330 is transferred to introducer member 320 such that they maintain a substantially fixed spatial relationship throughout operation. Introducer member 320 may be engaged with introducer member retainer 330 using any method known to one skilled in the art, such as bonding, press-fit, staking, or any other appropriate method.

Piercing member retainer 314 and introducer member retainer 330 are engaged with connection hub 312 and may be configured for translation with respect to the connection hub in a direction parallel to the long axis of piercing member 316 (axis "A" shown in FIG. 5B). Connection hub 312, piercing member retainer 314, and introducer member retainer 330 may include one or more features to maintain orientation and position with respect to one another as will be described in more detail below.

The fluid pathway connector 300 may further be provided with an insertion driver disposed to advance one or both of the piercing member 316 and the introducer member 320 toward the drug container 50. In this embodiment, at least one biasing member 336 is provided to advance one or both of the piercing member 316 and the introducer member 320 toward the drug container 50. Biasing member 336 is initially in a compressed or energized condition and is restrained from decompressing or de-energizing. A first end of biasing member 336 is in contact with plate 334, which is axially stationary, and a second end of biasing member 336 is in contact with piercing member retainer 314. In one embodiment, biasing member 336 is in contact with shoulder 314D of piercing member retainer 314. Motion of plate 334 is restrained by engagement with snaps 312C of connection hub 312 (see FIG. 9) which are inserted through passages 334A of plate 334 (see FIG. 9) during assembly. In an initial configuration, shaft 314A of piercing member retainer 314 (see FIG. 10) passes through central bore 334B of plate 334 and is engaged by interlock 338 (see FIGS. 3A, 3B, 5A, 5B). Interlock 338 is located on the distal side of plate 334 and engages one or more lobes 314B on shaft 314A to prevent translation of piercing member retainer 314 with respect to plate 334. In this way, decompression or de-energizing of biasing member 336 is restrained. As will be described further herein, transformation of interlock 338, to a configuration in which it does not restrain translation of piercing member retainer 314, allows decompression of biasing member 336 and connection of the fluid pathway to drug container 50.

The drug container 50 may include a crimp cap 324 that maintains a connection between a pierceable seal 326 and a barrel 58. The pierceable seal maintains the fluid drug within the barrel and prevents microbes and other substances from entering the drug chamber. A recess 328 (best seen in FIG. 5B) is formed by the geometry of the pierceable seal 326. A second film 322 is affixed to the drug container such that it encloses recess 328, thereby maintaining recess 328 in an aseptic condition.

The first and second films may be constructed of any material capable of providing the barrier properties required to maintain the aseptic condition of the associated surfaces. In a preferred embodiment, the films are constructed from a foil material. Alternatively, the films may be any type of sterilizable membrane, film, or foil. Additionally, the film may be removable and/or pierceable as well as breathable and/or permeable.

A surface treatment may be applied to the exterior surfaces of both first film 318 and second film 322 prior to joining the fluid pathway connector and the drug container. The surface treatment may contain antimicrobial, antibacterial, or antiviral compounds to limit or reduce the number of such substances on the surface of the seals.

Connection hub 312 may include a barrel-engaging aspect 312D. Barrel-engaging aspect 312D may include one or more flex arms 312E configured to engage crimp cap 324 and/or neck 58A of barrel 58. During connection, flex arms 312E may engage crimp cap 324 or another portion of the drug container, thereby limiting axial translation of the fluid pathway connector with respect to the drug container. In this position, first film 318 and second film 322 are in contact with, or in close proximity to, one another. In one embodiment, first film 318 and second film 322 include an adhesive such that the films are bonded to one another during assembly.

FIGS. 5A-5B show a cross-sectional side view of the connection hub 312 and drug container 50 in a mounted, unactuated configuration, that is, after they have been joined. In this configuration, introducer member 320 is at least partially disposed within cavity 312A and engagement of interlock 338 with piercing member retainer 314 retains biasing member 336 in a compressed or energized state. First film 318 and second film 322 are intact, thereby maintaining the aseptic condition of cavity 312A and pierceable seal 326, respectively.

Figure 6A:
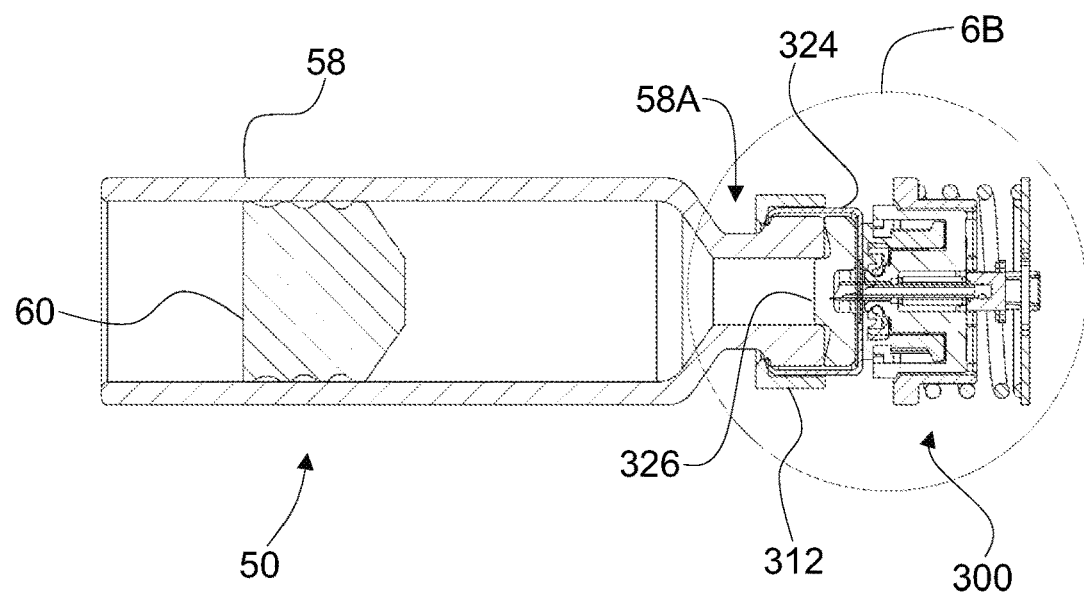
FIG. 6A is a cross-sectional side view of the embodiment of the fluid pathway connection assembly and drug container of FIG. 4A in an actuated configuration.
Figure 6B:
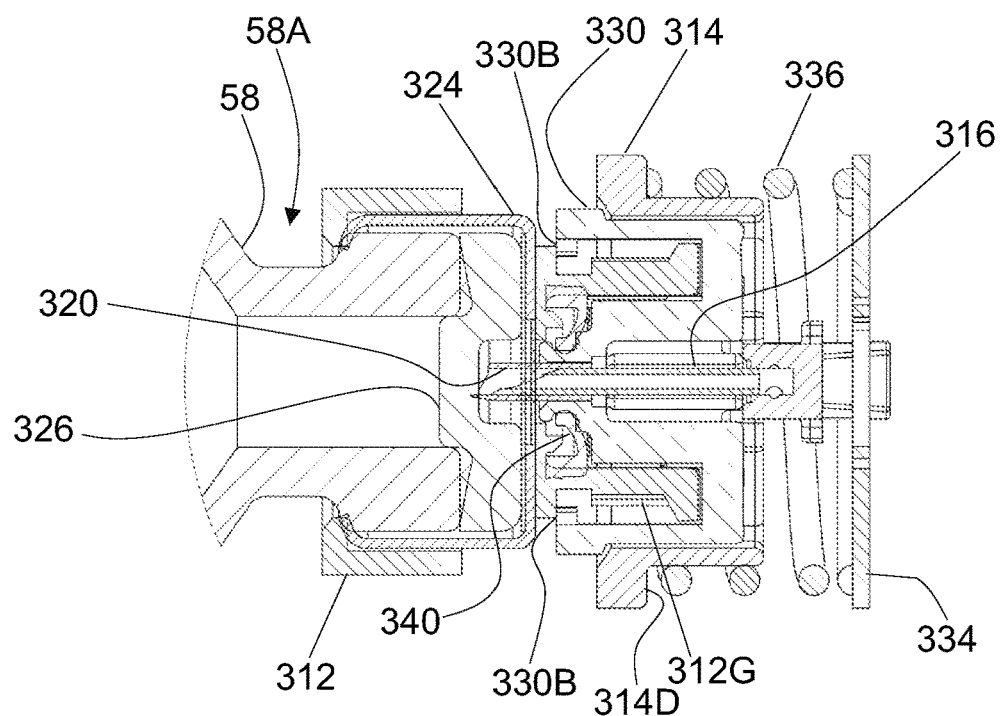
FIG. 6B is an enlarged fragmentary cross-sectional side view of the embodiment shown in FIG. 6A.

An actuated configuration is illustrated in FIGS. 6A-6B. In one embodiment, activation may displace or transform interlock 338 such that it no longer restricts translation of piercing member retainer 314. Upon activation, the piercing member retainer 314 and introducer member retainer 330 may be translated axially with respect to the connection hub and drug container 50. The translation may be caused by decompression or de-energizing of biasing member 336. In one embodiment, biasing member 336 is a compression spring. Because piercing member retainer 314 is in contact with introducer member retainer 330, as piercing member retainer 314 translates, introducer member retainer 330 translates together with piercing member retainer 314. For example, proximal face 314C of piercing member retainer 314 (see FIG. 10) may contact projections 330A of introducer member retainer 330 (see FIG. 11). Proximal face 314C may include a chamfered or radiused portion which contacts projections 330A. The contacting faces of piercing member retainer 314 and introducer member retainer 330 may be configured such that piercing member retainer 314 applies a radially inwardly directed force to projections 330A and, thereby, extensions 330D, in addition to an axial force. However, initially, fingers 330C of extensions 330D are prevented from inward displacement by contact with ribs 312G of connection hub 312 (see FIGS. 4A, 4B, 6B). Hence, introducer member retainer 330 translates along with piercing member retainer 314. Translation of the piercing member retainer 314 causes piercing member 316 to translate and translation of the introducer member retainer 330 causes translation of the introducer member 320. This translation causes the introducer member 320 to pierce first film 318 and second film 322, as shown in FIGS. 6A-6B. It will be appreciated that, because the piercing member 316 is disposed within introducer member 320, it does not contact the first 318 and second 322 films; hence, any contaminants present on the surface of the films do not come in contact with the piercing member 316.

After the introducer member 320 pierces first film 318 and second film 322, translation of introducer member retainer 330 is restricted such that its translation is terminated with the tip of the introducer member disposed in recess 328 (i.e., the introducer member does not pass through pierceable seal 326). Translation of introducer member retainer 330 may, for example, be restricted by contact of a portion of the proximal face 330B with flange 312F of connection hub 312. It is not necessary that the entire proximal face 330B of introducer member retainer 330 contact flange 312F. For example, fingers 330C may contact flange 312F. In this position, fingers 330C are no longer in contact with ribs 312G of connection hub 312. Because of this, extensions 330D are able to flex radially inward. As a result, continued decompression of biasing member 336 and translation of piercing member retainer 314 causes the extensions 330D to move inward and piercing member retainer 314 is able to pass over introducer member retainer 330.

Figure 7A:
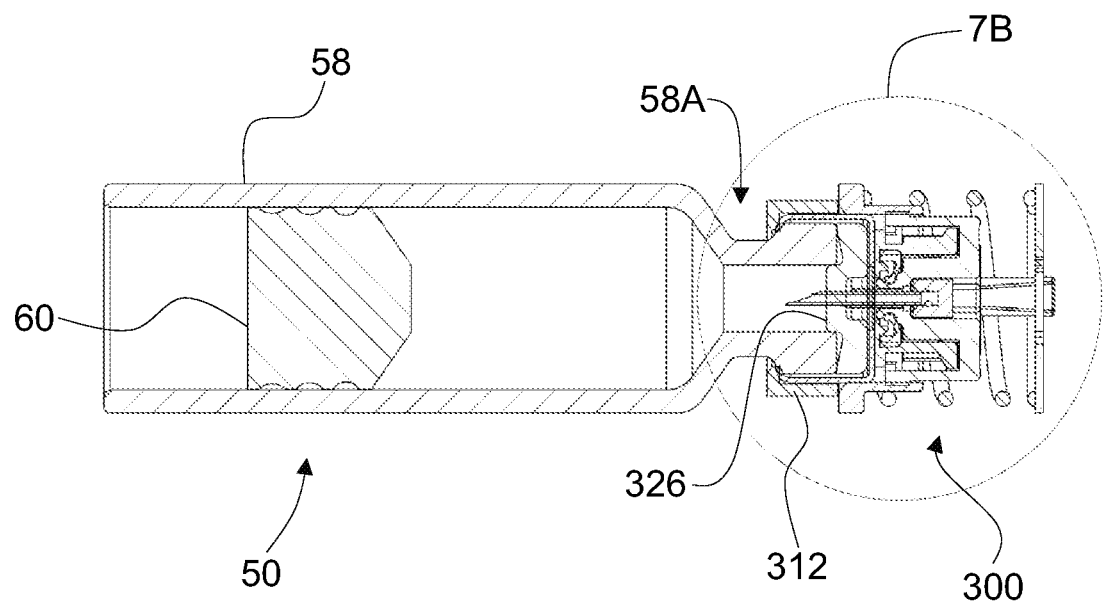
FIG. 7A is a cross-sectional side view of the embodiment of the fluid pathway connection assembly and drug container of FIGS. 4A and 6A in a delivery configuration.
Figure 7B:
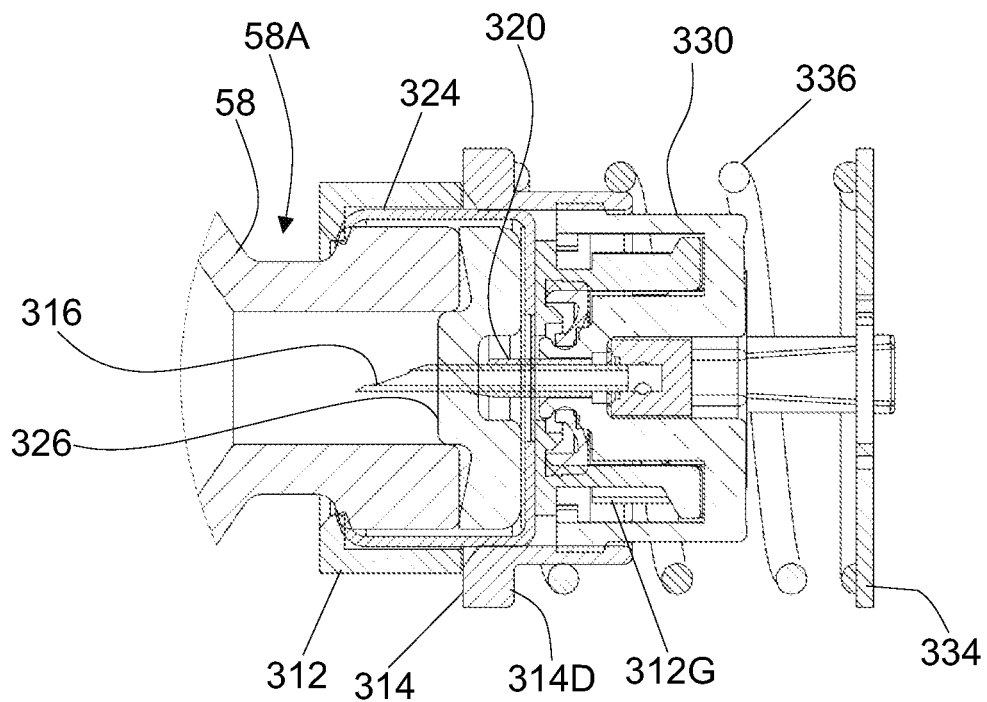
FIG. 7B is an enlarged fragmentary cross-sectional side view of the embodiment shown in FIG. 7A.
Figure 8:
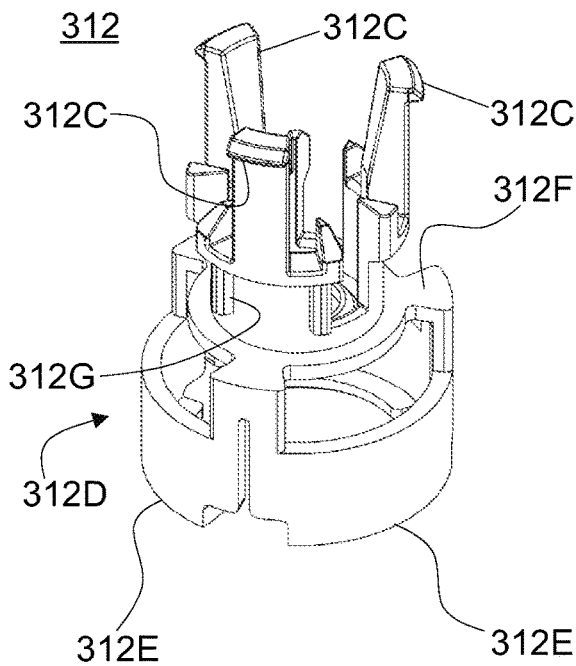
FIG. 8 shows an isometric view of a connection hub according to at least one embodiment of the present invention.
Figure 9:
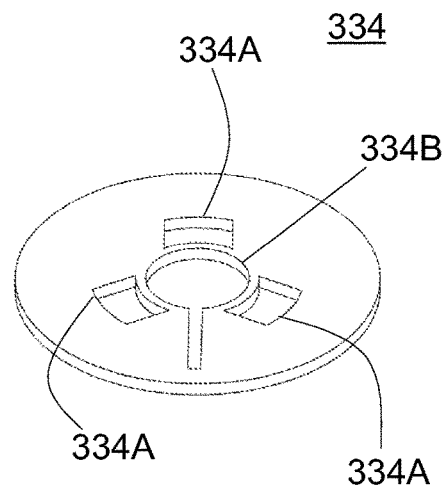
FIG. 9 shows an isometric view of a plate according to at least one embodiment of the present invention.
Figure 10:
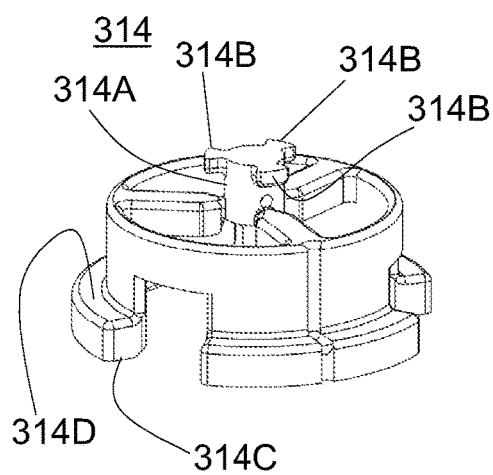
FIG. 10 shows an isometric view of an embodiment of a piercing member retainer according to at least one embodiment of the present invention.
Figure 11:
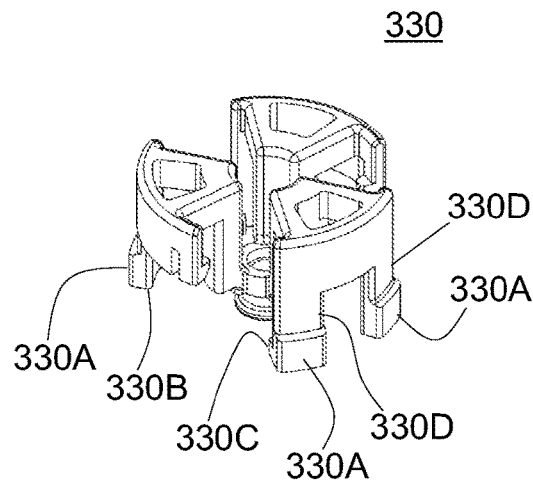
FIG. 11 shows an isometric view of an embodiment of an introducer member retainer according to at least one embodiment of the present invention.
Figure 12A:
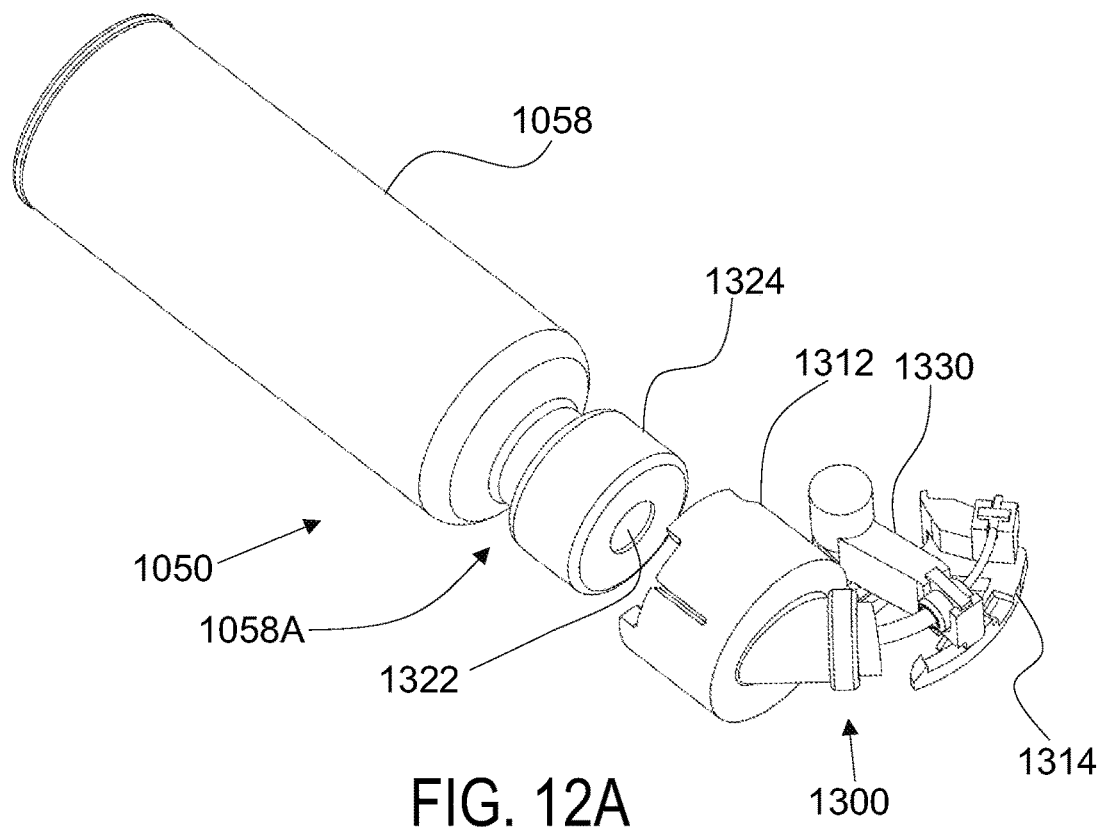
FIG. 12A is an isometric view of a second embodiment of a fluid pathway connection assembly and drug container in an unmounted configuration.
Figure 12B:
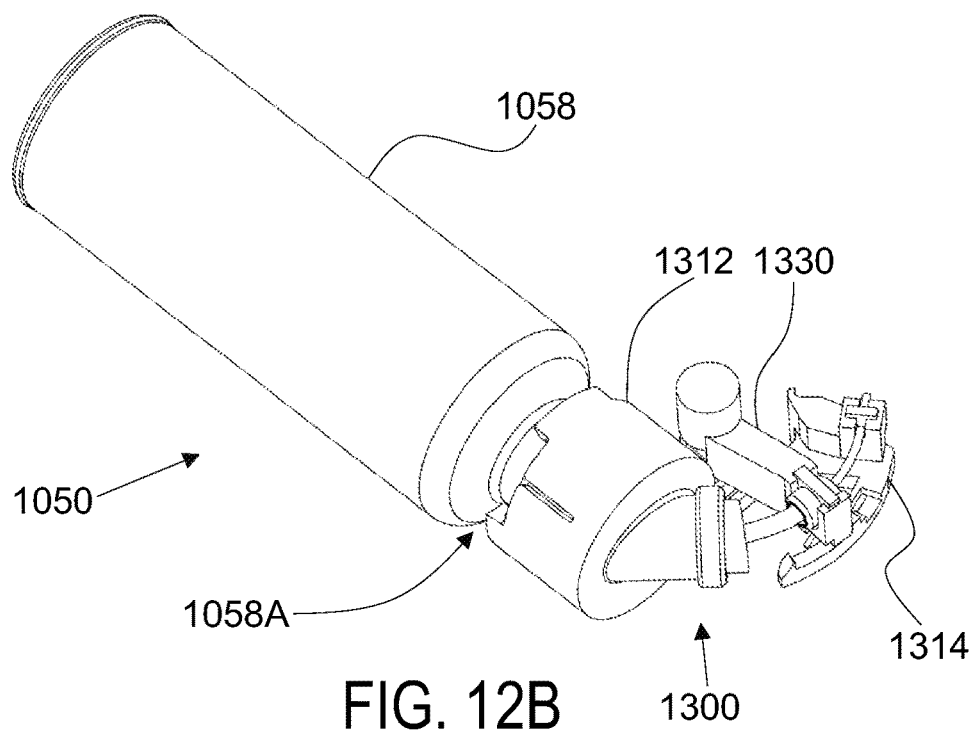
FIG. 12B is an isometric view of the embodiment shown in FIG. 12A in a mounted, but unactuated, configuration.

Turning now to FIGS. 7A-7B, there is illustrated a delivery configuration of the fluid pathway connector 300. Continued decompression of biasing member 336 may cause the piercing member retainer 314 to be further displaced, leading to the piercing of pierceable seal 326 by piercing member 316. Hence, with further translation of introducer member retainer 330 prevented by contact with connection hub 312, continued decompression of biasing member 336 causes piercing member retainer 314 to translate in a proximal direction relative to introducer member retainer 330. After piercing of the pierceable seal, a fluid path is established from the drug container and through the piercing member 316. Those of skill in the art will appreciate that the piercing member 316 may also be in fluid communication with a conduit 30 (as in FIG. 31), the conduit being configured to carry the fluid contents to a delivery mechanism, such as an insertion mechanism, for delivery to a patient.

In an alternative embodiment, piercing of the first and second films occurs at the time of assembly. In such an embodiment, piercing of the pierceable seal at or near the time-of-use may be initiated by interaction with an activation mechanism.

In at least one embodiment, the first and second films are pierced by the introducer member at a first time, for example time of assembly, and the piercing member pierces the pierceable seal at a later time, for example upon activation. In such an embodiment, the end of the piercing member may remain disposed within recess 328 until time-of-use. The pierceable seal may be configured such that, in response to hydraulic and/or pneumatic pressure within the drug chamber, pierceable seal 326 deforms or is displaced and is caused to come into contact with the piercing member. This deformation of the pierceable seal 326 leads to the piercing of the seal by the piercing member 316. In such an embodiment, introducer member 320 may be retracted after piercing the first and second films.

Although the embodiment shown in FIGS. 3A-11 is configured such that piercing member 316 is substantially axially aligned with drug container 50, one skilled in the art would recognize that this orientation can be configured in any orientation. For example, the axis of piercing member 316 may be oriented orthogonal to the central axis of the drug container 50. Alternatively, the axes may be oriented at any angle between parallel and orthogonal. Selection of this angle or orientation may be chosen based on the space requirements of drug delivery device 10.

In another embodiment, shown in FIGS. 12A-22, the introducer member and piercing member are arranged in an arcuate manner. The arcuate configuration of the fluid pathway connector may allow the footprint of the fluid pathway connector to be reduced, allowing for a smaller overall size of drug delivery device 10. Fluid pathway connector 1300 includes introducer member 1320, piercing member 1316, introducer member retainer 1330, piercing member retainer 1314, connection hub 1312, shaft 1342, and first film 1318. As described above, connection hub 1312 may be configured to engage drug container 1050, for example, by engaging crimp cap 1324 and/or neck 1058A of drug container 1050.

Introducer member 1320 may be either directly or indirectly coupled to introducer member retainer 1330. For example, in the embodiment shown, introducer member 1320 is fixedly connected to first sleeve 1344. In turn, first sleeve 1344 is engaged with second sleeve 1346. Finally, second sleeve 1346 is engaged with introducer member retainer 1330, for example by the keyed engagement shown. First sleeve 1344 and second sleeve 1346 may further retain septum 1348, through which piercing member 1316 may pass.

Similarly, piercing member 1316 may be directly or indirectly coupled to piercing member retainer 1314. In the embodiment shown, piercing member 1316 is engaged with keeper 1350. Keeper 1350 is engaged with piercing member retainer 1314 by, for example, the keyed arrangement shown.

Figure 13A:
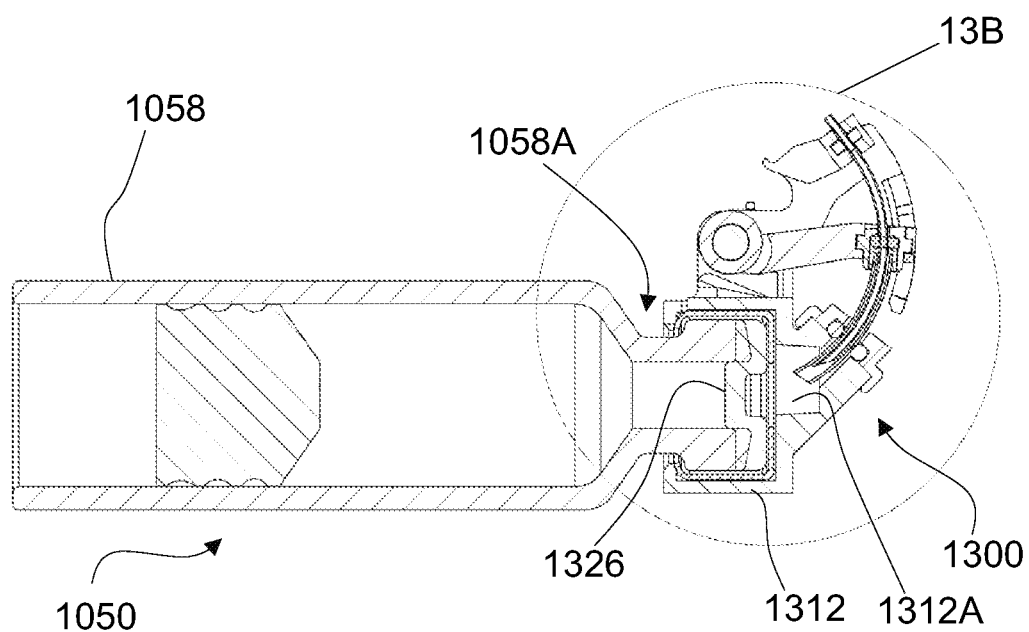
FIG. 13A is a cross-sectional side view of the embodiment of the fluid pathway connection assembly and drug container of FIGS. 11A-11B in a mounted, but unactuated, configuration.
Figure 13B:
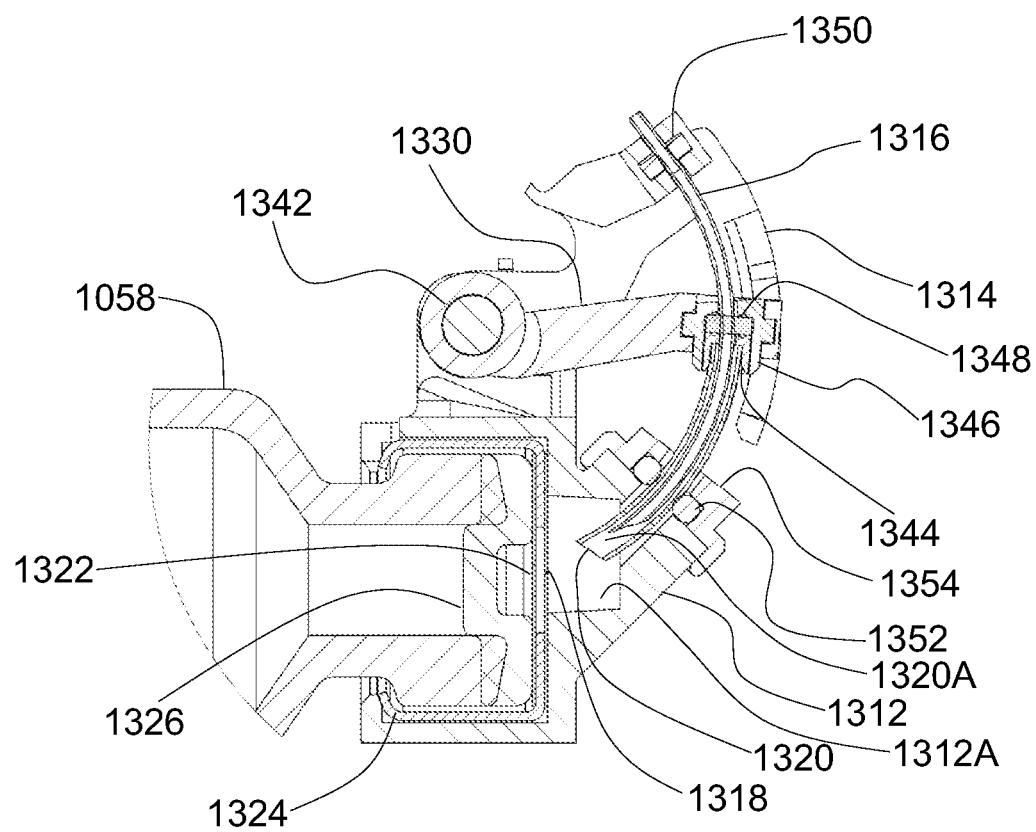
FIG. 13B is an enlarged fragmentary cross-sectional side view of the embodiment shown in FIG. 13A.
Figure 14A:
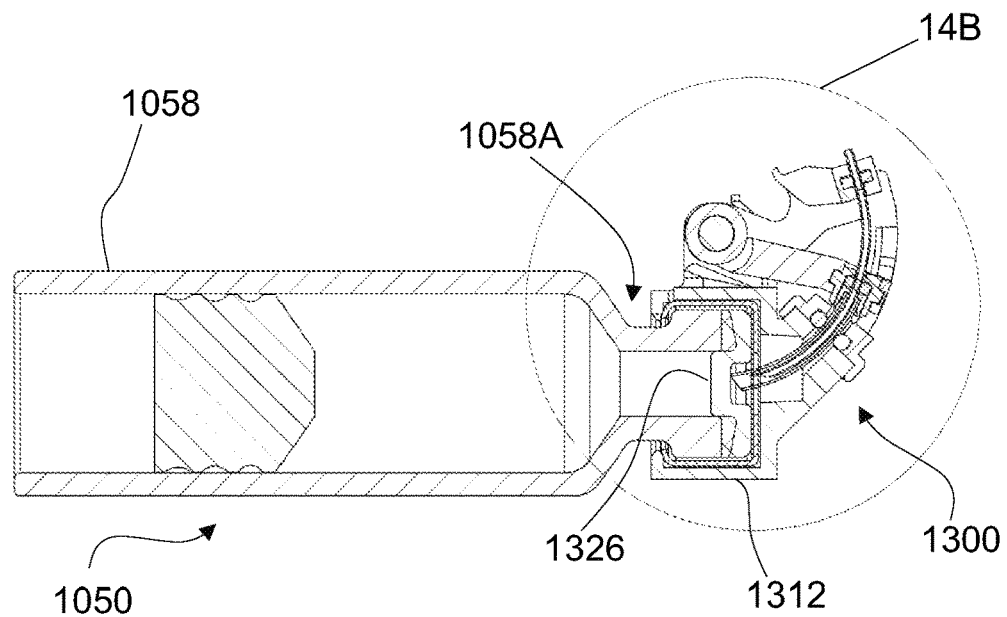
FIG. 14A is a cross-sectional side view of the embodiment of the fluid pathway connection assembly and drug container of FIG. 12A in an actuated configuration.
Figure 14B:
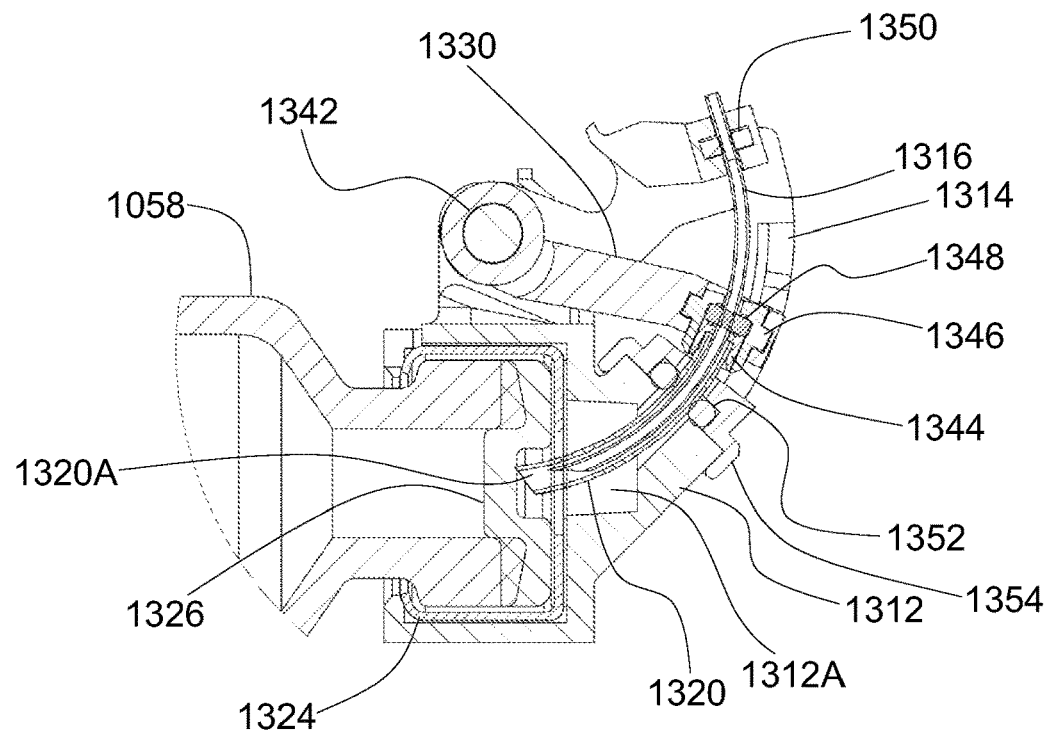
FIG. 14B is an enlarged fragmentary cross-sectional side view of the embodiment shown in FIG. 14A.

In an initial, unactuated configuration, shown in FIGS. 13A-13B, introducer member 1320 is initially at least partially disposed in cavity 1312A. Piercing member 1316 is at least partially disposed within the lumen 1320A of introducer member 1320. Cavity 1312A is maintained in an aseptic condition by first film 1318. The aseptic condition of cavity 1312A may be further maintained by cap 1354 and ring seal 1352. Ring seal 1352 is held in sealing engagement with connection hub 1312 and/or introducer member 1320 by cap 1354. Although ring seal 1352 is shown here with a circular cross-section, the ring seal may take on any shape known to one skilled in the art. Alternatively, for example, the aseptic condition may be maintained by a septum.

Upon activation, introducer member retainer 1330 and piercing member retainer 1314 are caused to rotate about shaft 1342. It will be appreciated that shaft 1342 may be integrally formed with connection hub 1312, as shown in FIG. 20, may be a feature of housing 12, or may be a pin or other component engaged with connection hub 1312 or housing 12. While the latter two of these embodiments are not specifically illustrated, they will be readily understood by those of skill in the art. An insertion driver may be provided to advance one or both of the piercing member 1316 and the introducer member 1320 toward the drug container 1050. For example, the rotation about the axis of the shaft may be caused by de-energizing of a biasing member, such as a torsion spring. Alternatively, the rotation may be caused by a driving member of drug delivery device 10. For example, needle insertion mechanism 200 may include a driving member that, upon activation, contacts an aspect of piercing member retainer 1314 and causes rotation of piercing member retainer 1314 and introducer member retainer 1330. In another embodiment, the biasing member of the needle insertion mechanism bears against the piercing member retainer 1314 and causes rotation thereof.

Figure 16A:
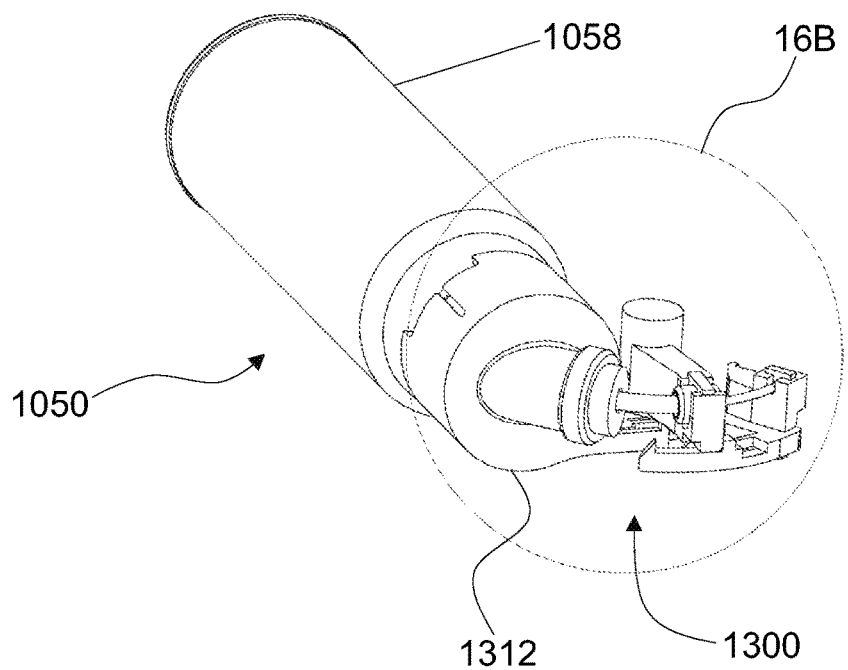
FIG. 16A is a further isometric view of the fluid pathway connection assembly and container of FIGS. 12A-12B in a mounted, but unactuated, configuration.
Figure 16B:
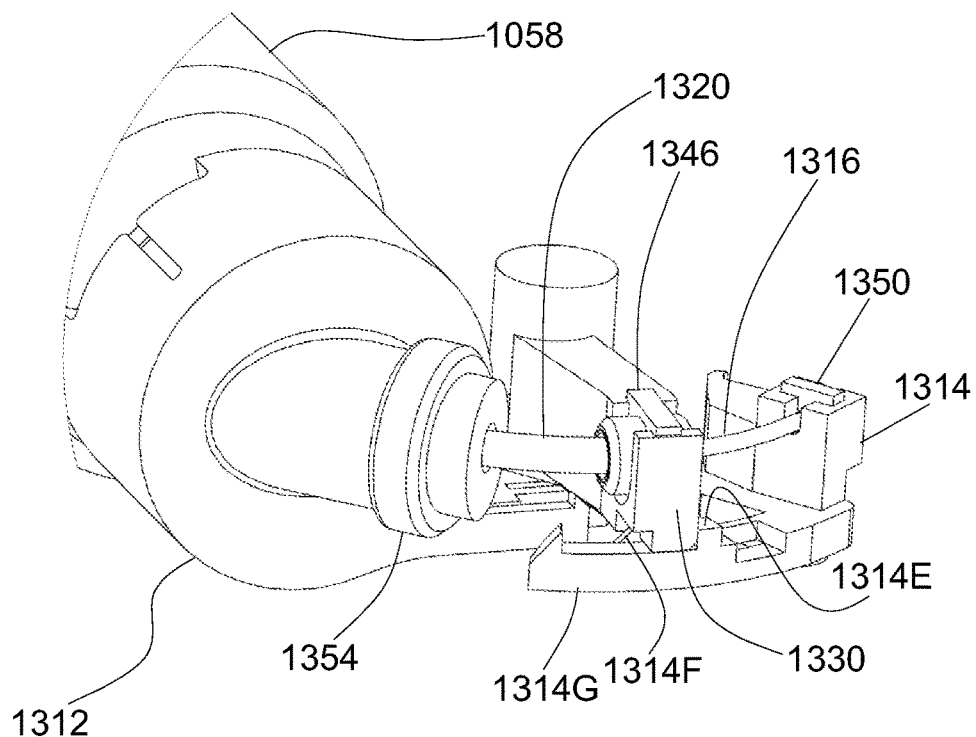
FIG. 16B is an enlarged fragmentary isometric view of the fluid pathway connection assembly of FIG. 16A.
Figure 17A:
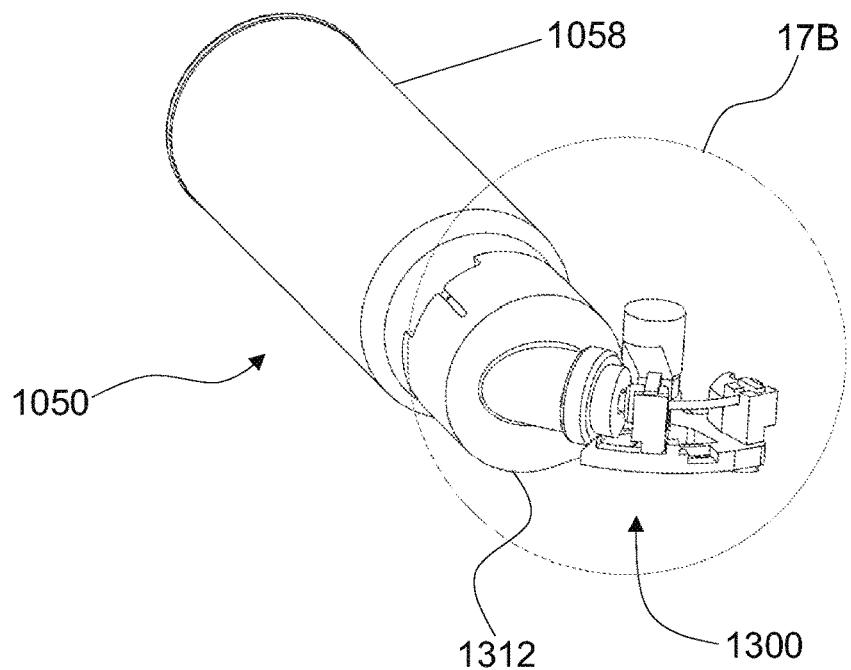
FIG. 17A is a further isometric view of the fluid pathway connection assembly and container of FIGS. 12A-12B in an actuated configuration.
Figure 17B:
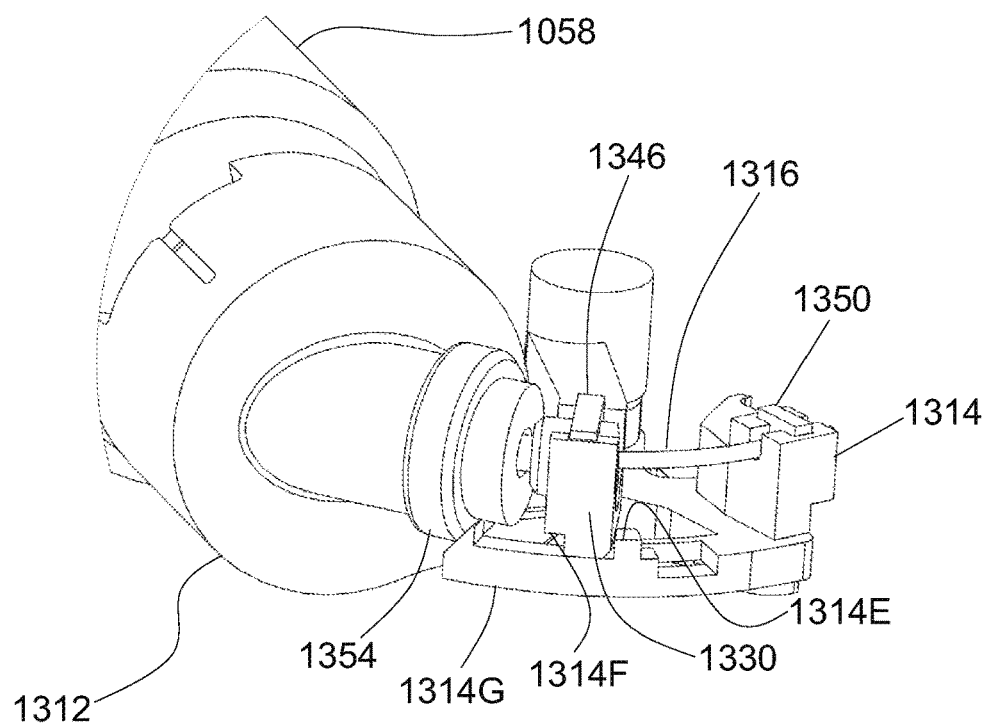
FIG. 17B is an enlarged fragmentary isometric view of the fluid pathway connection assembly of FIG. 17A.
Figure 18A:
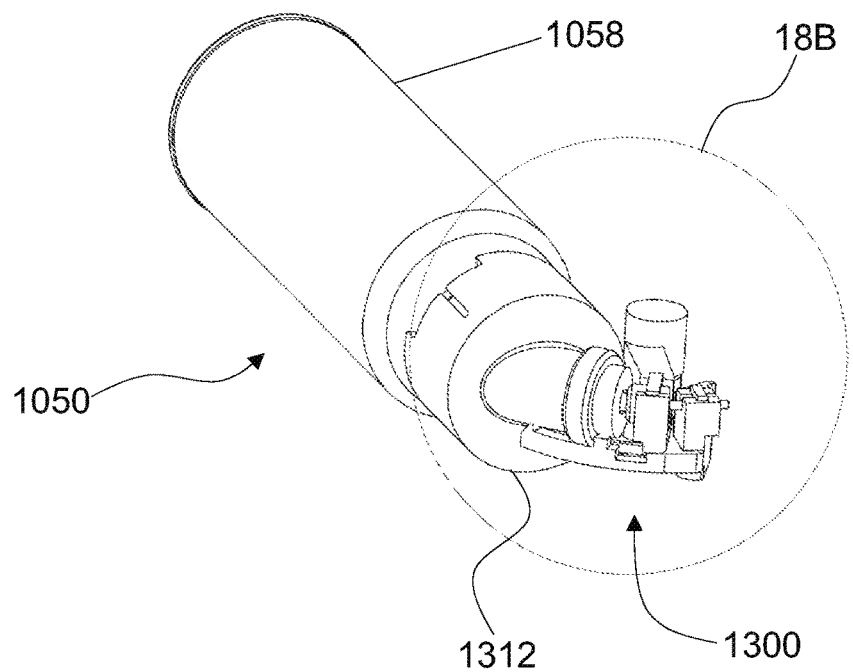
FIG. 18A is a further isometric view of the fluid pathway connection assembly and container of FIGS. 12A-12B in a delivery configuration.
Figure 18B:
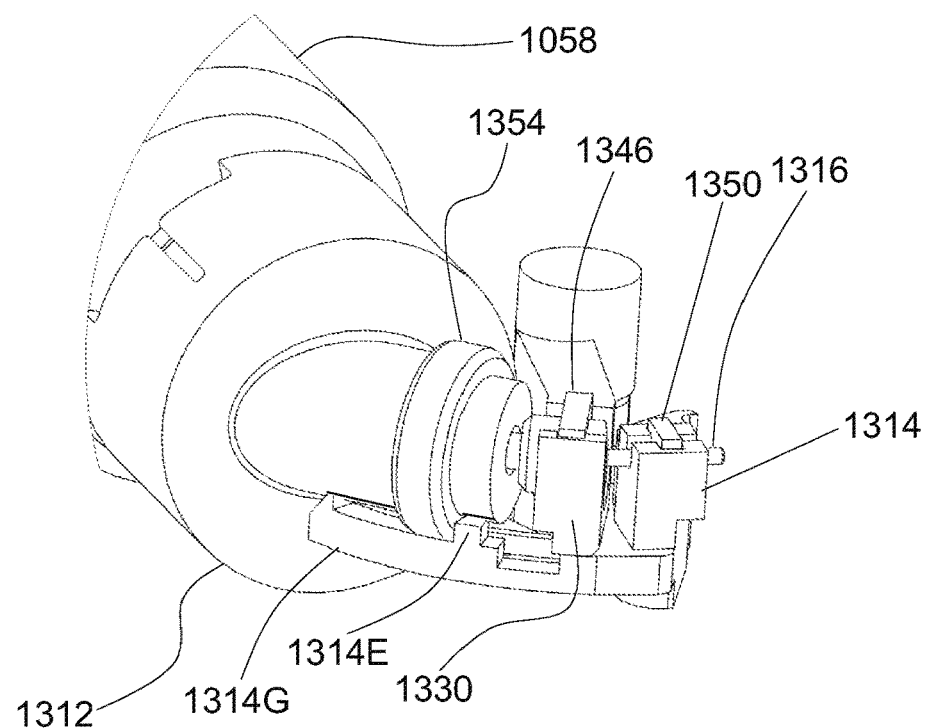
FIG. 18B is an enlarged fragmentary isometric view of the fluid pathway connection assembly of FIG. 18A.

Piercing member retainer 1314 and introducer member retainer 1330 may initially rotate as a unit. Referring to FIGS. 16B and 22, introducer member retainer 1330 may initially be disposed between projection 1314E and tooth 1314F, both features of piercing member retainer 1314. The retainers move in conjunction to the actuated configuration shown in FIGS. 14A-14B. In this position, the introducer member 1320 has pierced the first film 1318 and second film 1322, but has not pierced pierceable seal 1326. At or near to this position, flex arm 1314G of piercing member retainer 1314 contacts connection hub 1312 and/or cap 1354. Hence, continued rotation of piercing member retainer 1314 causes flex arm 1314G to be displaced downward. As a result, contact of projection 1314E with introducer member retainer 1330 no longer causes rotation of introducer member retainer 1330. Thus, further rotation of piercing member retainer 1314 does not cause additional rotation of introducer member retainer 1330.

Figure 15A:
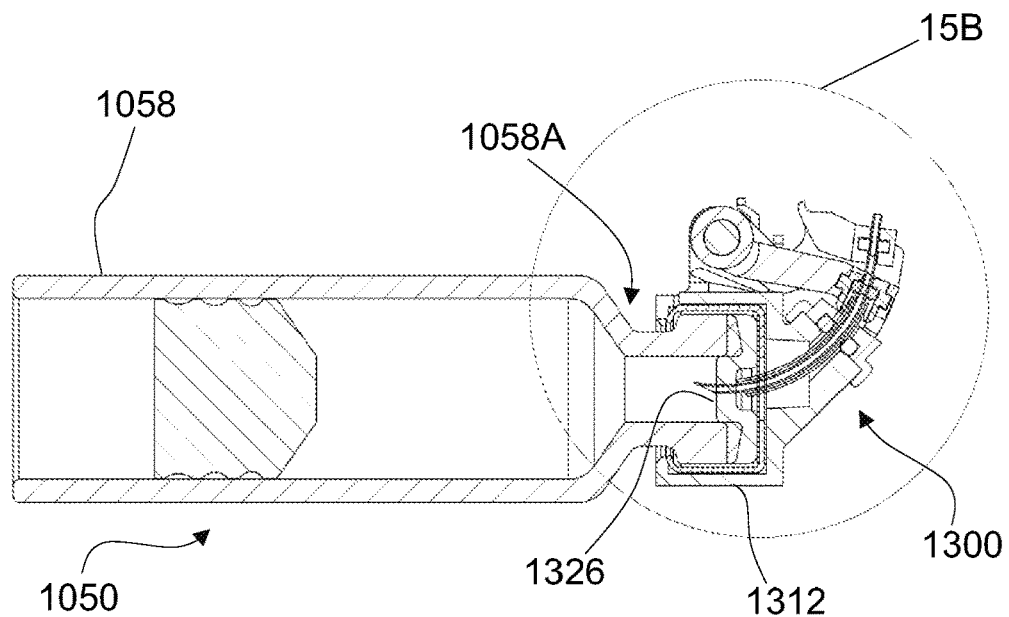
FIG. 15A is a cross-sectional side view of the embodiment of the fluid pathway connection assembly and a drug container of FIGS. 12A and 13A in a delivery configuration.
Figure 15B:
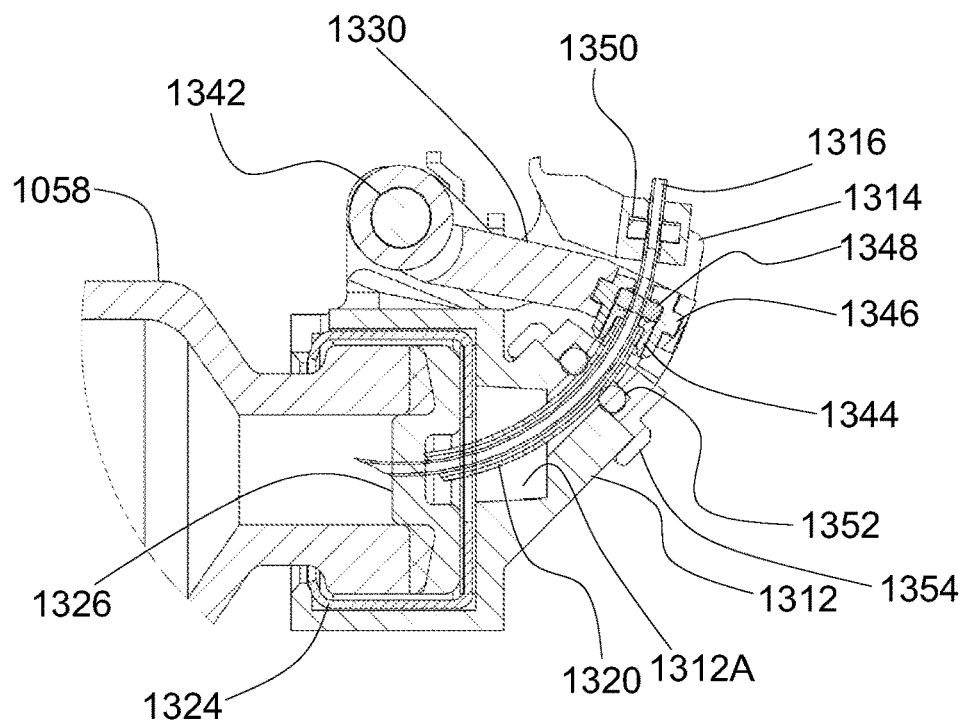
FIG. 15B is an enlarged fragmentary cross-sectional side view of the embodiment shown in FIG. 15A.
Figure 19A:
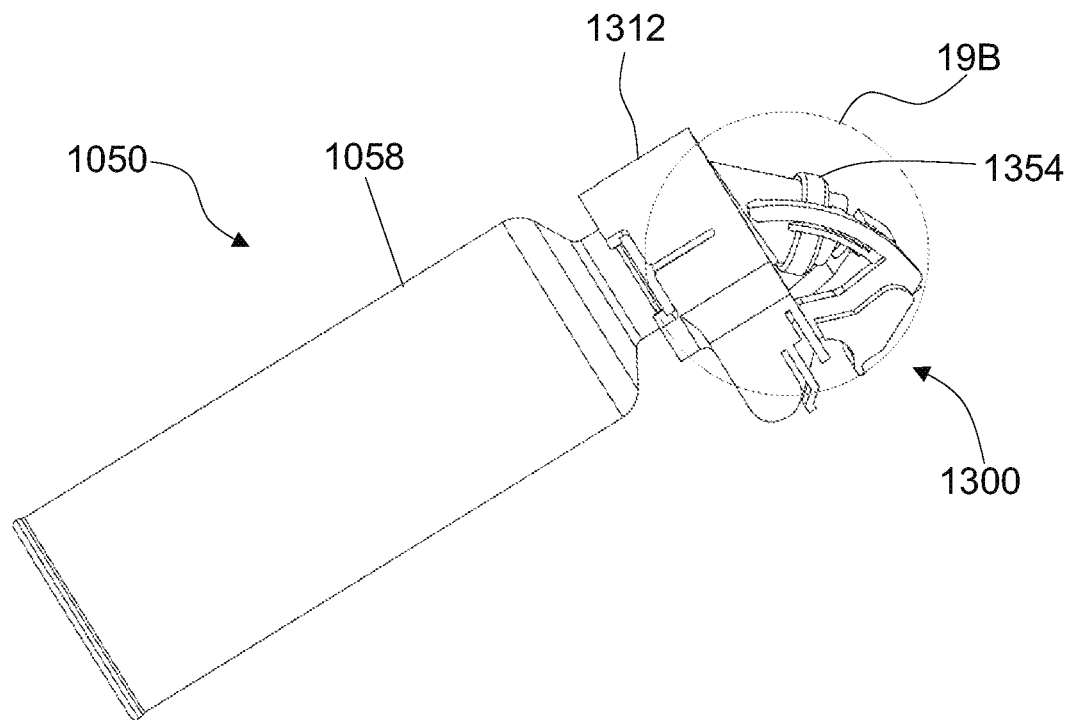
FIG. 19A is a bottom side view of the fluid pathway connection assembly and container of FIG. 18A.
Figure 19B:
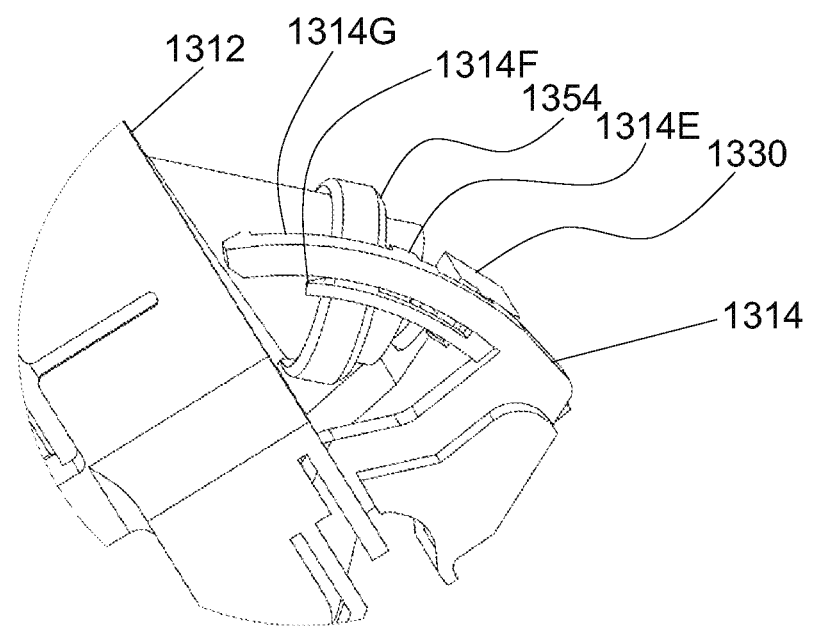
FIG. 19B is an enlarged fragmentary isometric view of the fluid pathway connection assembly and drug container of FIG. 19A.

As shown in the delivery configuration illustrated in FIGS. 15A-15B, continued rotation of piercing member retainer 1314 causes piercing member 1316 to pierce pierceable seal 1326, thus opening a flow path from the drug container 1050, through piercing member 1316. Piercing member 1316 may be in fluid communication with insertion mechanism 200, for example by a fluid conduit, to allow for delivery of the fluid drug to the patient. As shown in FIGS. 19A-19B, in this configuration, tooth 1314F may engage cap 1354 and/or connection hub 1312 to prevent retraction of piercing member 1316.

Figure 23:
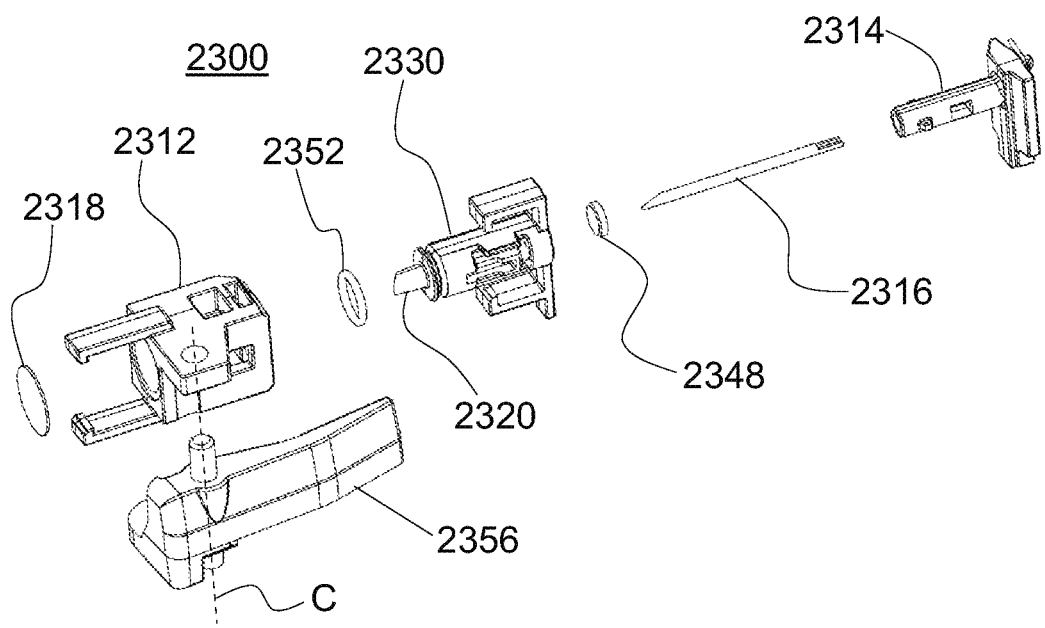
FIG. 23 shows an isometrically exploded view of a fluid pathway connection assembly according to at least one embodiment of the present invention.

FIG. 23 shows an exploded view of another embodiment of a fluid pathway connector 2300. The fluid pathway connector 2300 includes connection hub 2312, introducer member 2320, introducer member retainer 2330, piercing member 2316, piercing member retainer 2314, and, optionally, blocking aspect 2356. Additionally, first film 2318 may be provided such that it maintains the aseptic condition of at least a portion of the fluid pathway connector. The fluid pathway connector may also include ring seal 2352 and septum 2348 configured to maintain the aseptic condition of at least a portion of the fluid pathway connector as described above. Blocking aspect 2356 may be configured with an interlock 2338 engaging connection hub 2312 at coupling aspect 2312H. Additionally, or alternatively, blocking aspect 2356 may be configured to engage an aspect of housing 12. Blocking aspect 2356 may be configured for rotation about these engagement points.

Figure 24A:
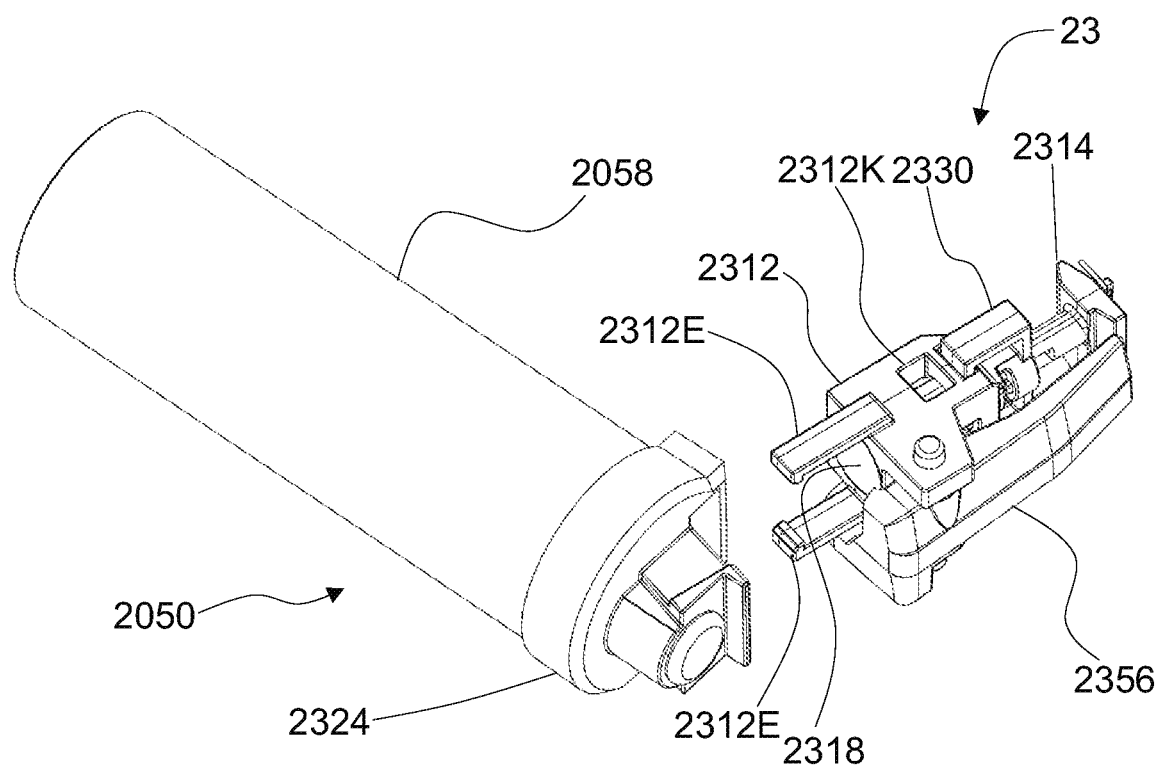
FIG. 24A shows an isometric view of the fluid pathway connection assembly and drug container of FIG. 23 in an unmounted configuration.

FIG. 24A shows the drug container 50 and fluid pathway connector 2300 in an unactuated configuration, prior to assembly. As will be understood from the above discussion, this assembly step may take place in an uncontrolled or less controlled environment than that required for prior art designs. In order to mount the fluid pathway connector 2300 to the crimp cap 2324 coupling the pierceable seal 2326 to the barrel 2058, a barrel-engaging aspect may include one or more flex arms 2312E of the connection hub 2312, which engage the pierceable seal 2326 or crimp cap 2324. FIG. 23B-23D show isometric views of the stages of operation of the fluid pathway connector 2300 once mounted to the drug container 2050.

Figure 24B:
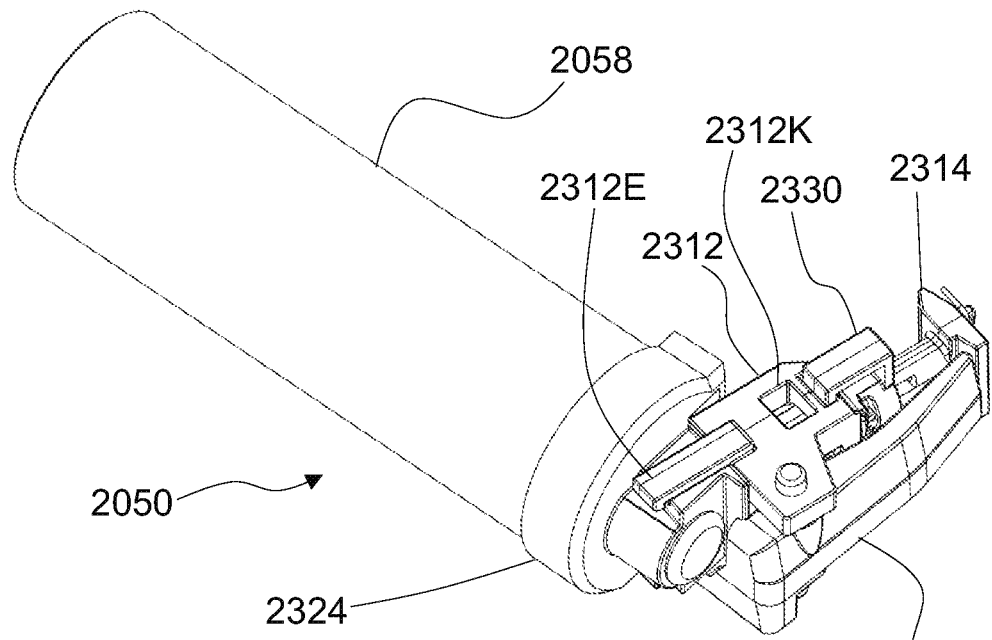
FIG. 24B is an isometric view of the fluid pathway connection assembly and drug container of FIG. 24A in a mounted, but unactuated, configuration.

Initially, in the unactuated configuration illustrated in FIG. 24B, blocking aspect 2356 is initially engaged with piercing member retainer 2314 such that blocking aspect 2356 prevents translation of piercing member retainer 2314 toward drug container 2050. Additionally, or alternatively, one or more arms 2330E of introducer member retainer 2330 (see FIG. 29) are initially disposed in one or more primary windows 2312J of connection hub 2312 (see FIG. 28). This engagement may further prevent inadvertent activation of the fluid pathway connector. For example, in at least one embodiment, arms 2330E are configured to provide sufficient flexural stiffness to resist disengagement from primary windows 2312J and prevent inadvertent activation. Application of sufficient force for activation will cause arms 2330E to disengage from primary windows 2312J, allowing translation of introducer member retainer 2330.

Figure 31:
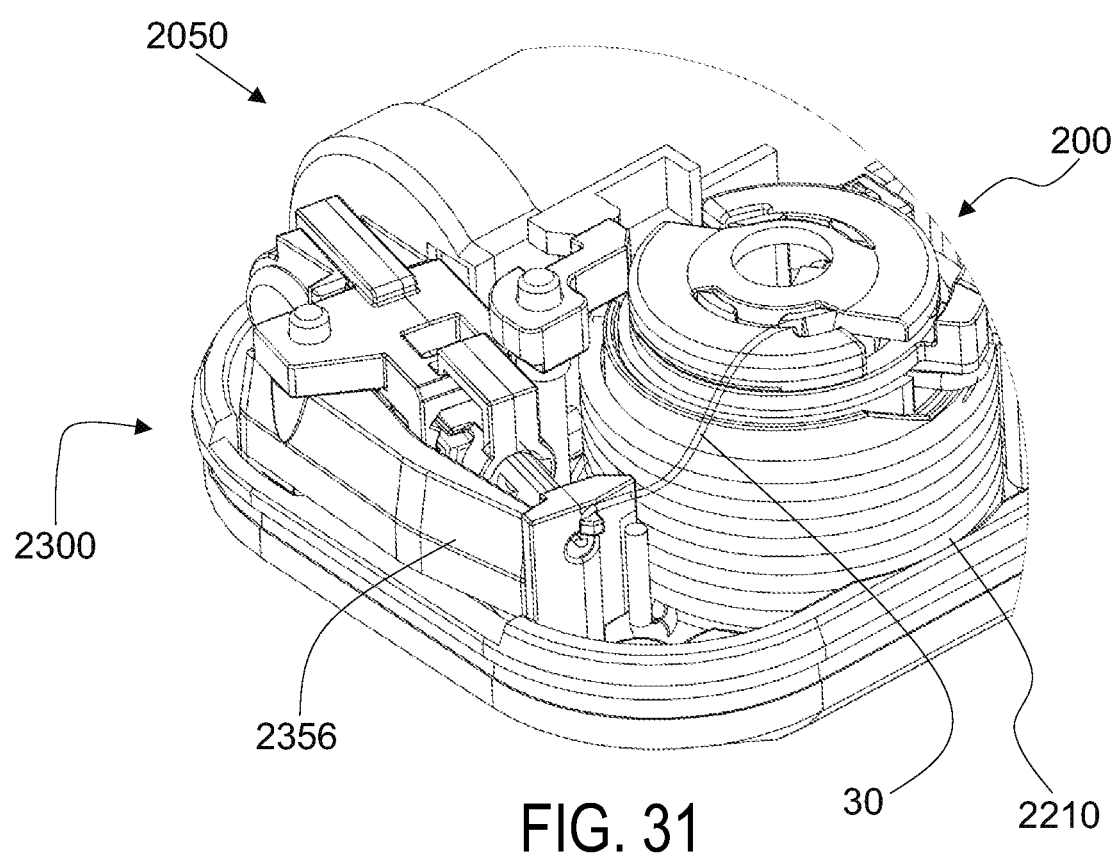
FIG. 31 shows a fragmentary isometric view of the interior components of a drug delivery pump incorporating the fluid pathway connection assembly of FIGS. 23-27B.

Upon activation, blocking aspect 2356 is displaced, for example by rotating about axis C. After displacement of blocking aspect 2356, piercing member retainer 2314 is able to translate toward drug container 2050 in response to application of a driving force from an insertion driver, such as the rotational biasing member 2210 shown in FIG. 31. FIG. 31 is a detail view showing one method of actuating the fluid pathway connector 2300. As shown, rotational biasing member 2210 is initially held in a compressed or energized state. A first end of rotational biasing member 2210 is engaged with an aspect of fluid pathway connector 2300, here piercing member retainer 2314. Further, a blocking aspect 2356, such as a rotatable latch, prevents de-energizing of rotational biasing member 2210 and, hence, activation of fluid pathway connector 2300. To activate the fluid pathway connector 2300, the blocking aspect 2356 may be displaced such that it no longer restricts de-energizing of rotational biasing member 2210. As such, upon displacement of the locking aspect 2356, rotational biasing member 2210 at least partially de-energizes and causes the fluid pathway connector 2300 to open a fluid path to the drug container 2050, fluidly coupling the drug container 2050 to the needle insertion mechanism 200 via the fluid pathway connector 2300 and a sterile fluid conduit 30 coupled to the piercing member 2316 and the needle insertion mechanism 200. Displacement of the blocking aspect 2356 may occur in response to depression, by the user, of activation mechanism 14 or, alternatively, may be controlled by interaction with a separate mechanism.

Figure 24C:
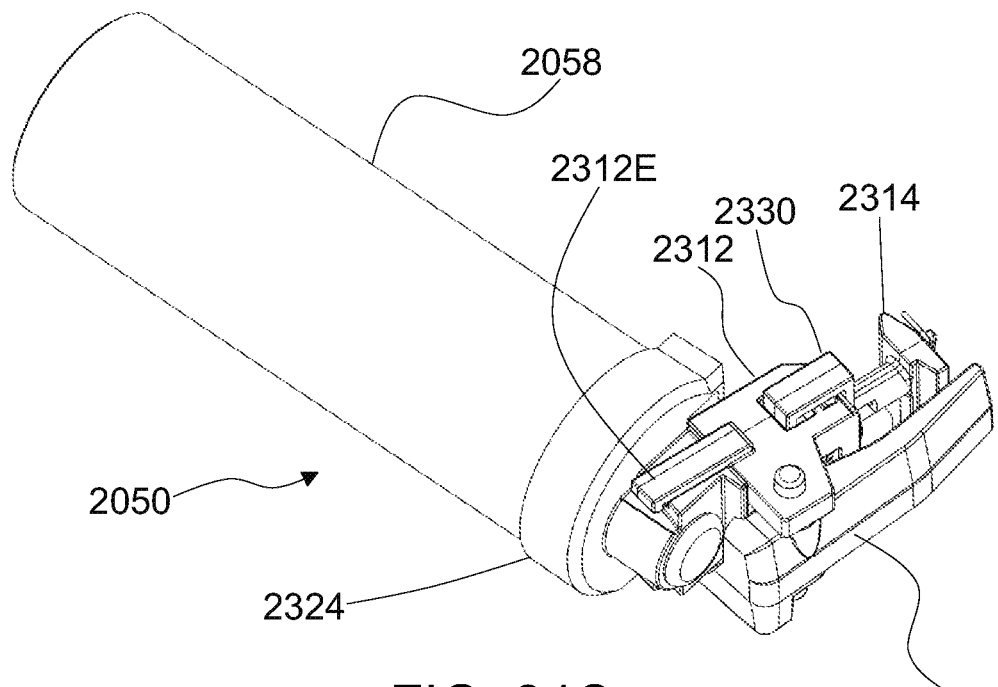
FIG. 24C is an isometric view of the fluid pathway connection assembly and drug container of FIG. 24B in an actuated configuration.
Figure 24D:
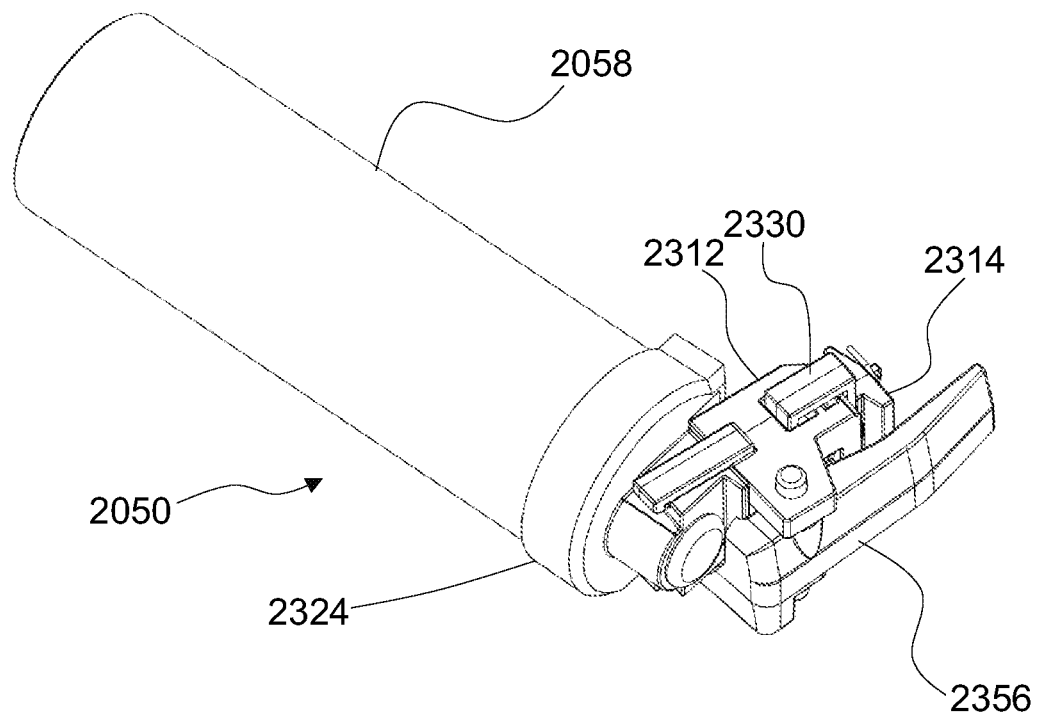
FIG. 24D is an isometric view of the fluid pathway connection assembly and drug container of FIGS. 24B-24C in a delivery configuration.

Returning now to FIGS. 24B-27B, initially, as is described further hereinafter, piercing member retainer 2314 and introducer member retainer 2330 move together toward drug container 2050. FIG. 24C shows the fluid pathway connector in the actuated configuration, that is, after introducer member 2320 pierces first film 2318 and second film 2322. After piercing of first film 2318 and second film 2322, introducer member 2320 is restricted from further movement. In one embodiment, arms 2330E of introducer member retainer 2330 are positioned within one or more secondary windows 2312K, in this configuration. This engagement may lock the introducer member retainer in place, preventing inadvertent translation toward or away from the drug container. Continued translation of piercing member retainer 2314 causes piercing member 2316 to pierce pierceable seal 2326 to open a fluid flow path from drug container 2050. This delivery configuration is shown in FIG. 24D.

Figure 25A:
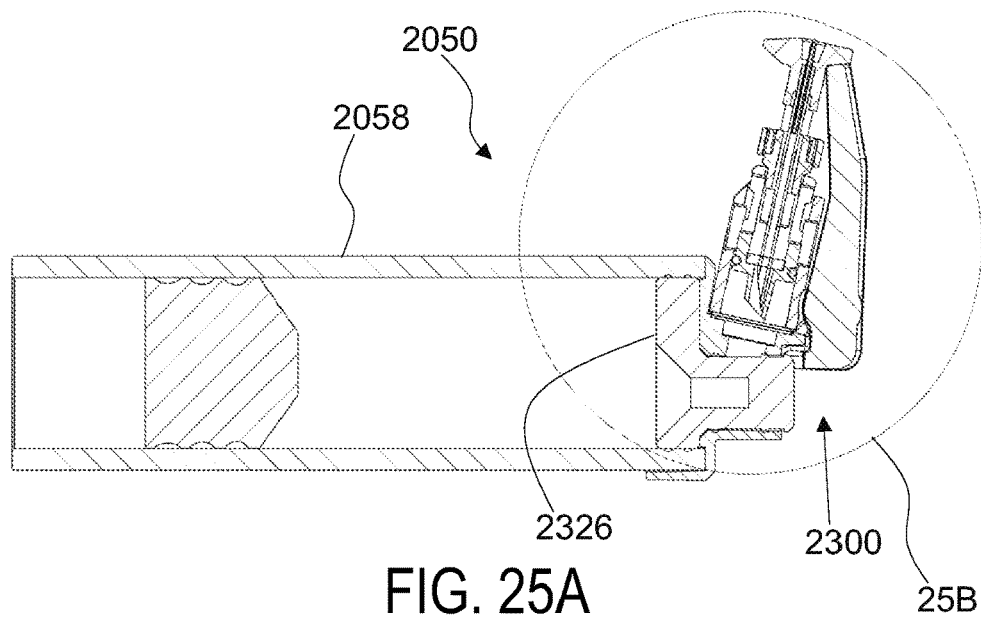
FIG. 25A is a cross-sectional side view of the fluid pathway connection assembly and drug container of FIG. 24B in the mounted, but unactuated, configuration.
Figure 25B:
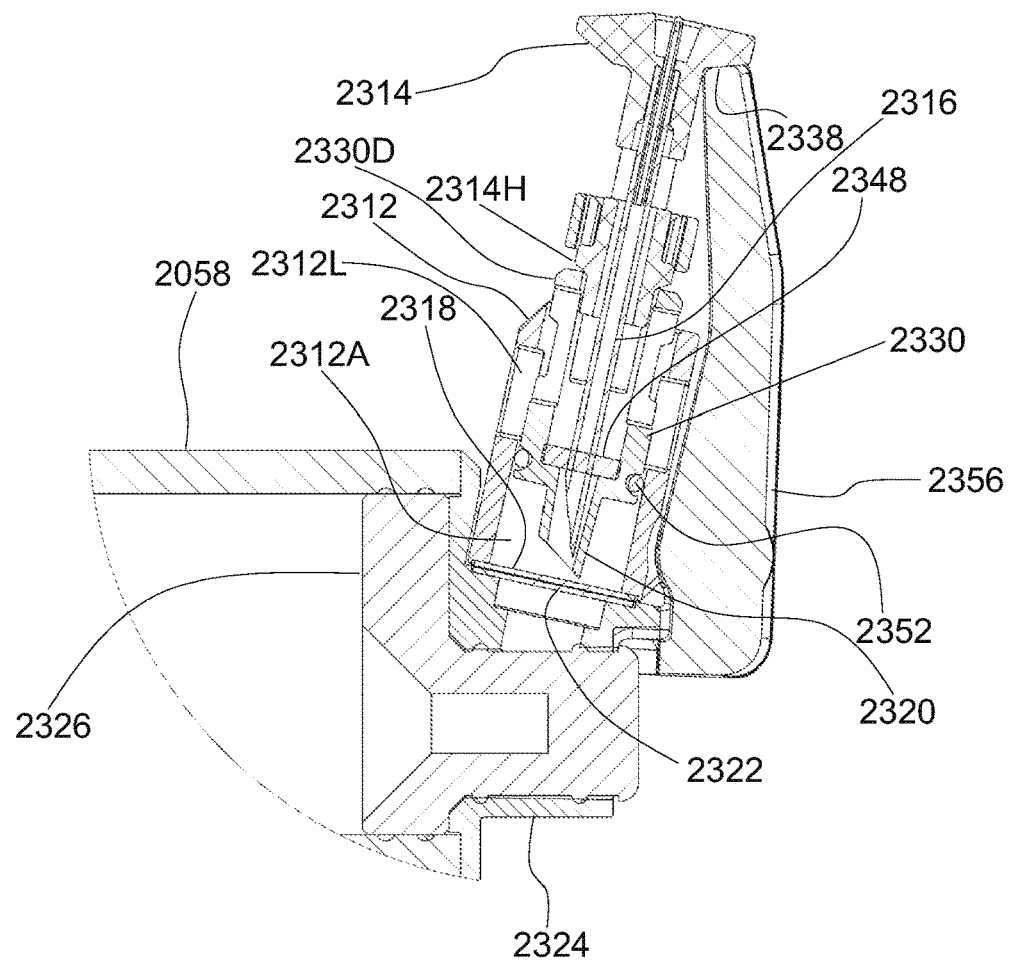
FIG. 25B is an enlarged fragmentary cross-sectional side view of the embodiment shown in FIG. 25A.

FIGS. 25A and 25B show cross-sectional views of the fluid pathway connector in the initial, unactuated configuration. As can be seen in these figures, blocking aspect 2356 is engaged with piercing member retainer 2314 to prevent translation of piercing member retainer 2314 toward the drug container. Piercing member 2316 is disposed at least partially within introducer member 2320. As shown, in this or any embodiment, introducer member 2320 may be an integral portion of introducer member retainer 2330. Introducer member 2320 and piercing member 2316 are both at least partially disposed in sterile cavity 2312A, which is defined by connection hub 2312, first film 2318, ring seal 2352, and septum 2348. Shoulder 2314H of piercing member retainer 2314 is in contact with extensions 2330D of introducer member retainer 2330. Extensions 2330D are configured to be relatively flexible aspects of introducer member retainer 2330. However, in the initial configuration, extensions 2330D are prevented from flexing by contact with connection hub 2312. Hence, initially, translation of piercing member retainer 2314, toward drug container 2050, causes commensurate translation of piercing member retainer 2314.

Figure 26A:
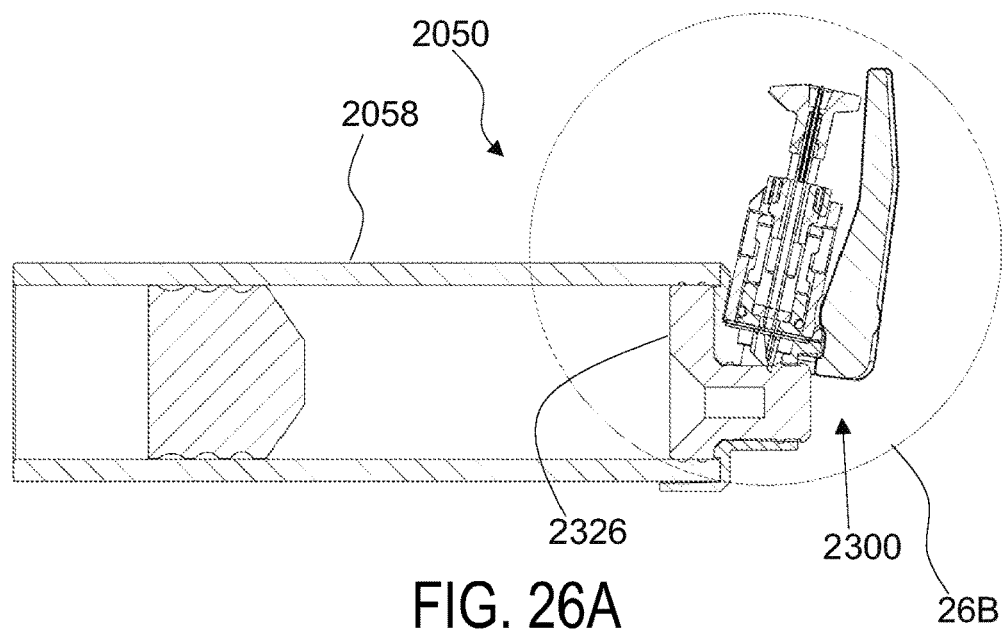
FIG. 26A is a cross-sectional side view of the embodiment of the fluid pathway connection assembly and drug container of FIG. 24B in an actuated configuration.
Figure 26B:
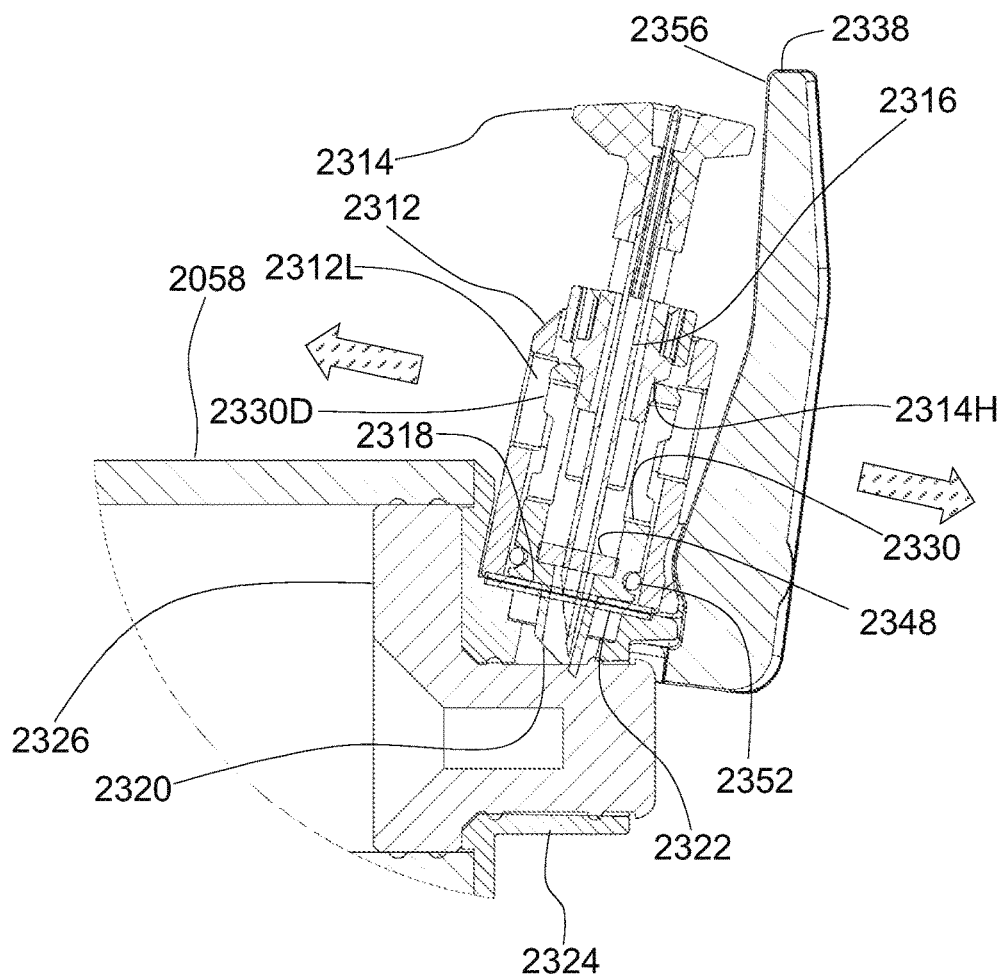
FIG. 26B is an enlarged fragmentary cross-sectional side view of the embodiment shown in FIG. 26A.
Figure 27A:
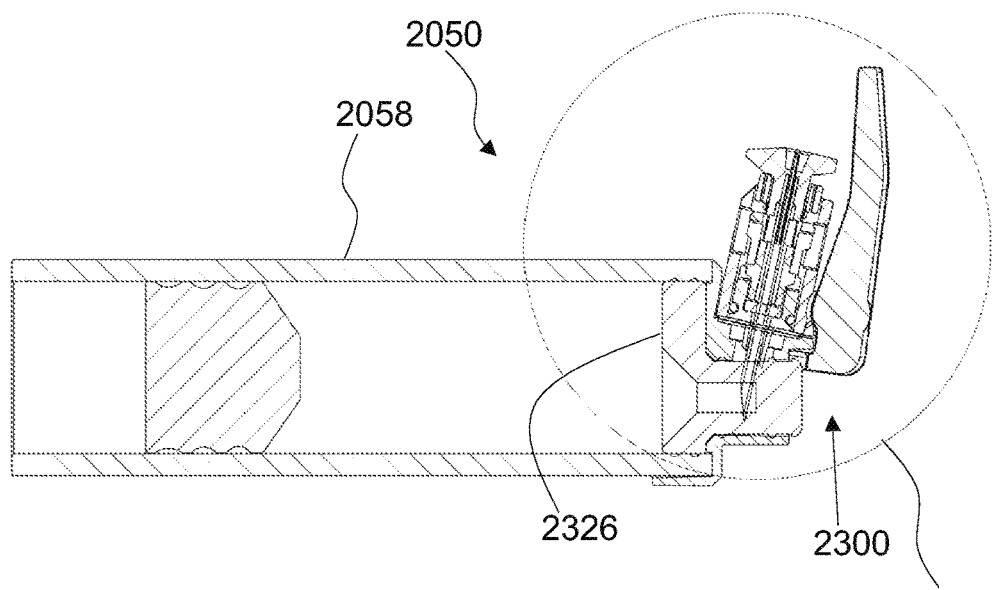
FIG. 27A is a cross-sectional side view of the embodiment of the fluid pathway connection assembly and drug container of FIGS. 25A and 26A in a delivery configuration.
Figure 27B:
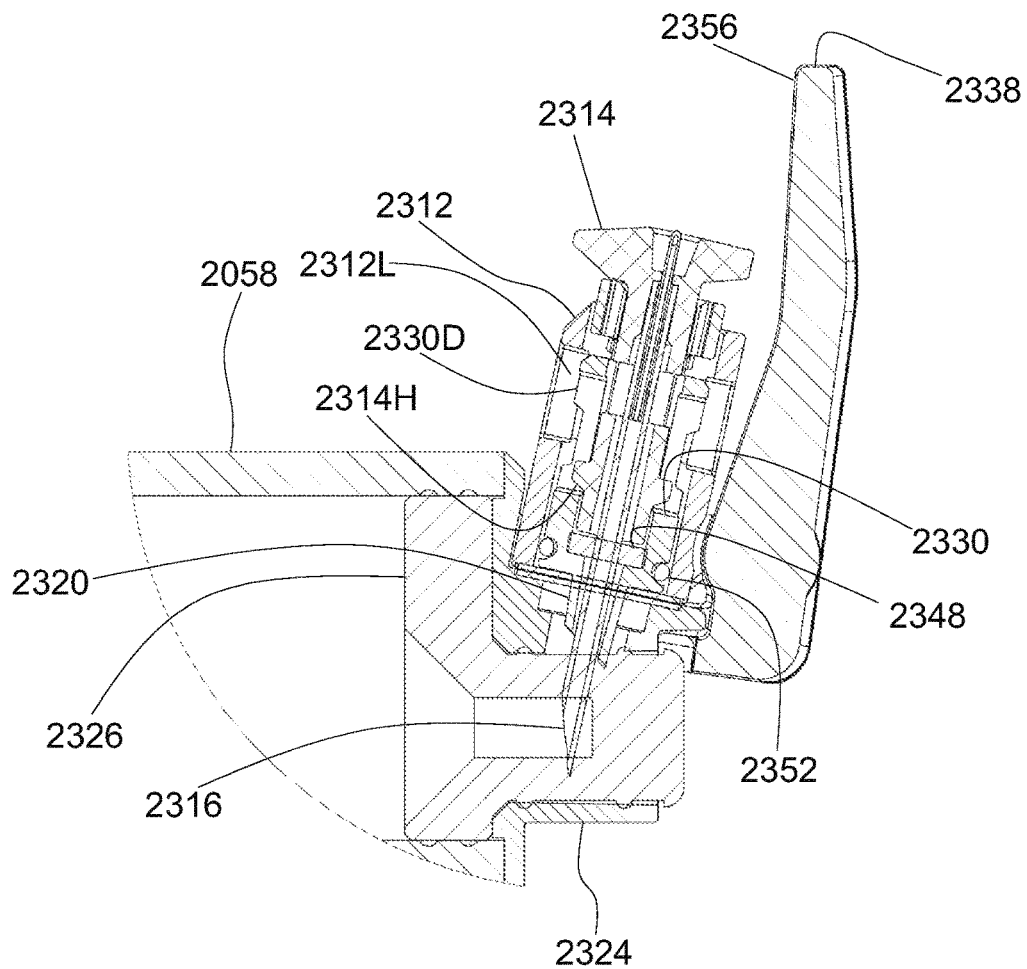
FIG. 27B is an enlarged fragmentary cross-sectional side view of the embodiment shown in FIG. 27A.
Figure 28:
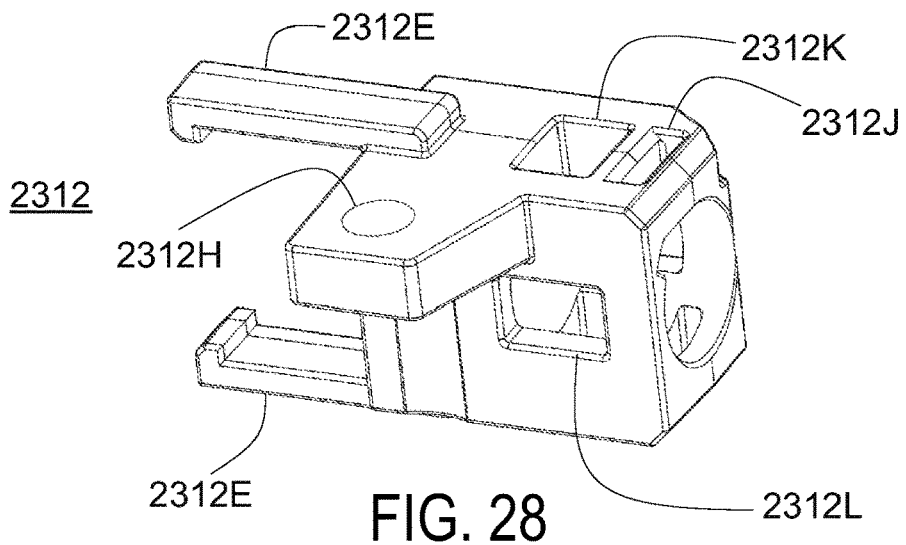
FIG. 28 shows an isometric view of a connection hub according to at least one embodiment of the present invention.
Figure 29:
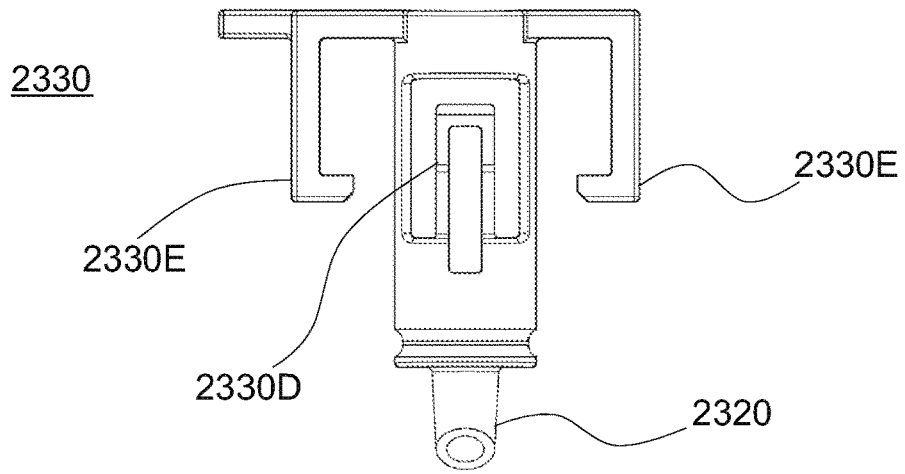
FIG. 29 shows a side elevational view of an embodiment of an introducer member retainer according to at least one embodiment of the present invention.

FIGS. 26A-26B show the fluid pathway connector 2300 in an intermediate, actuated configuration. In this configuration, blocking aspect 2356 has been displaced such that it does not restrict translation of piercing member retainer 2314. Introducer member 2320 has pierced first film 2318 and second film 2322 and piercing member 2316 is positioned adjacent to pierceable seal 2326. Also, in this configuration, extensions 2330D are positioned adjacent to recesses 2312L of connection hub 2312. Hence, extensions 2330D are no longer restricted from flexing outward (i.e., in the direction of the hatched arrows in FIG. 26B). Because extensions 2330D are able to flex outward, into recesses 2312L, additional translation of piercing member retainer 2314 causes shoulders 2314H to disengage from extensions 2330D. This allows piercing member retainer 2314 to translate toward drug container 2050 without causing translation of introducer member retainer 2330. As shown in the delivery configuration of FIGS. 27A-26B, this allows piercing member 2316 to pierce pierceable seal 2326 and open the fluid flow path from the drug container 2050.

In some embodiments, an additional film or seal may be present at the tip of introducer member 320, 1320, 2320 sealing the lumen of the introducer member and, thereby, further isolating the lumen of the introducer member and, hence, the piercing member in order to maintain the aseptic condition of the piercing member. This film may remain intact as the introducer member pierces first film 318, 1318, 2318 and second film 322, 1322, 2322. This may further prevent any microbes or other contaminants that are present on the surfaces of the seals from coming in contact with the piercing member.

In at least one other embodiment, the first and second films are removed from the fluid pathway connector and drug container just prior to mounting of the fluid pathway connector 300 to the drug container 50. Prior to removal of the films, their placement maintains the sterility of the pierceable seal of the drug container and cavity 312A. Connection hub 312 and drug container 50 may be configured such that connection of the connection hub to the barrel provides a sealing engagement to maintain the aseptic condition of the pierceable seal and piercing member. In such an embodiment, connection hub 312 and/or drug container 50 may include an elastomeric aspect which is configured to provide sealing engagement.

In another embodiment, after mounting of connection hub 312 to drug container 50, the cavity 312A and pierceable seal 326 may be sterilized using UV sterilization. The connection hub 312 may be in sealing engagement with the drug container such that after sterilization microbes and other foreign elements are unable to contact the aseptic surfaces. In such embodiments, at least a portion of the connection hub may be constructed from a substantially translucent material, such as glass.

In each of the embodiments described herein, the connection hub, piercing member retainer, and/or the introducer member retainer may include one or more features to prevent the inadvertent activation of the fluid pathway connector during assembly, storage, transportation, and handling. These features may prevent activation unless a force above a threshold value is applied. These features may, for example, include flexible aspects or frangible aspects which are displaced or severed upon application of a force above the threshold.

In addition to the advantages described above, the insertion mechanisms described herein may also be capable of terminating flow of medicament to the target tissue by disconnecting the fluid path. This may be an important safety feature to protect the patient. For example, some medicaments, such as insulin, can be dangerous, and potentially even deadly, when administered in too large a quantity and/or at too rapid of a rate. By providing such automatic safety stop mechanisms, so-called "run-away" delivery of medicament may be prevented, thereby ensuring the safety of the patient. While the methods and associated structures for terminating flow may be discussed with regard to one or more specific insertion mechanisms disclosed herein, it will be appreciated that the method and associated structures may be utilized or adapted for any of the fluid pathway connector assemblies disclosed herein or within the spirit and scope of this disclosure.

An interruption in delivery of medicament through the fluid pathway connector may be triggered, for example, by an error in delivery of the medicament or by an input from the user. For example, the user may realize that they have already taken their drug dose and wish to pause or terminate drug delivery from the device. Upon such user input to the device, the delivery of the drug can be stopped and/or the fluid passageway through the piercing member may be terminated by retraction of the piercing member to a retracted position, as described below.

Additionally or alternatively, the device may pause or terminate drug delivery if it receives an error alert during operation. For example, if the drive mechanism is not functioning correctly, the fluid pathway connector may be triggered to retract the piercing member from the pierceable seal to terminate drug delivery through the fluid pathway connector to prevent over-delivery of a medication. This capability of the fluid pathway connector provides a valuable safety feature for drug delivery to a target.

In some embodiments, retraction is activated upon removal of the drug delivery device from the target tissue. In other embodiments, retraction is activated if it is determined that an error has occurred in the delivery of the substances to the target tissue. For example, an occlusion of the drug delivery pathway which prevents the flow of medicament may be detected by a sensing function of the drug delivery pump. Upon the sensing of the occlusion an electrical or mechanical input may be used to initiate retraction of the needle.

Additionally or alternatively, one or more biasing members may be included to disconnect the fluid pathway connector. This may provide a desirable safety feature, to disconnect the fluid pathway upon signaling of an error condition either automatically by the drug delivery pump or upon action by the user. For example, a locking aspect may initially restrain a secondary biasing member from expanding from its original energized state. Upon activation of the locking aspect, the secondary biasing member is caused to de-energize from its original position and, thereby, act upon and axially translate the piercing member retainer to disconnect the piercing member from the pierceable seal. Once the fluid pathway connector is disconnected, flow of drug fluid is restricted or blocked between the drug container and the fluid conduit to limit or prevent fluid flow to the needle insertion mechanism and into the target. As described herein, the disconnection may be triggered by a number of operations, automatically by the system and/or upon direct or indirect user initiation, as an added safety precaution to prevent over-delivery of the drug fluid to the target.

Figure 32A:
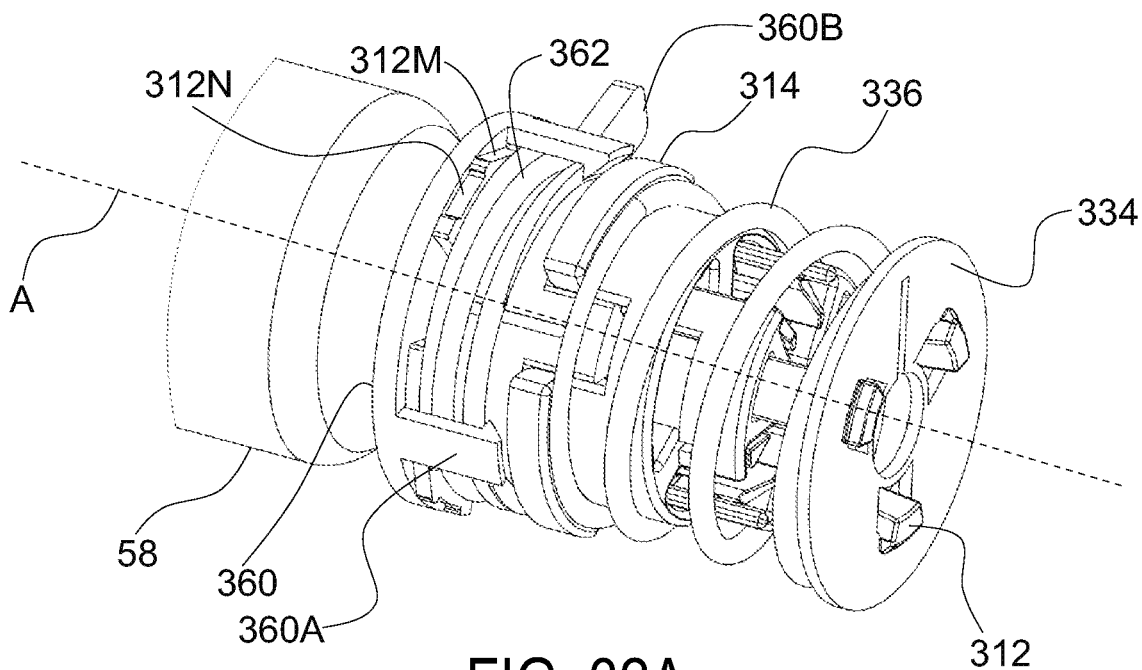
FIG. 32A is a fragmentary isometric view of a fluid pathway connection assembly and a drug container of at least one embodiment of the present invention during fluid connection.
Figure 32B:
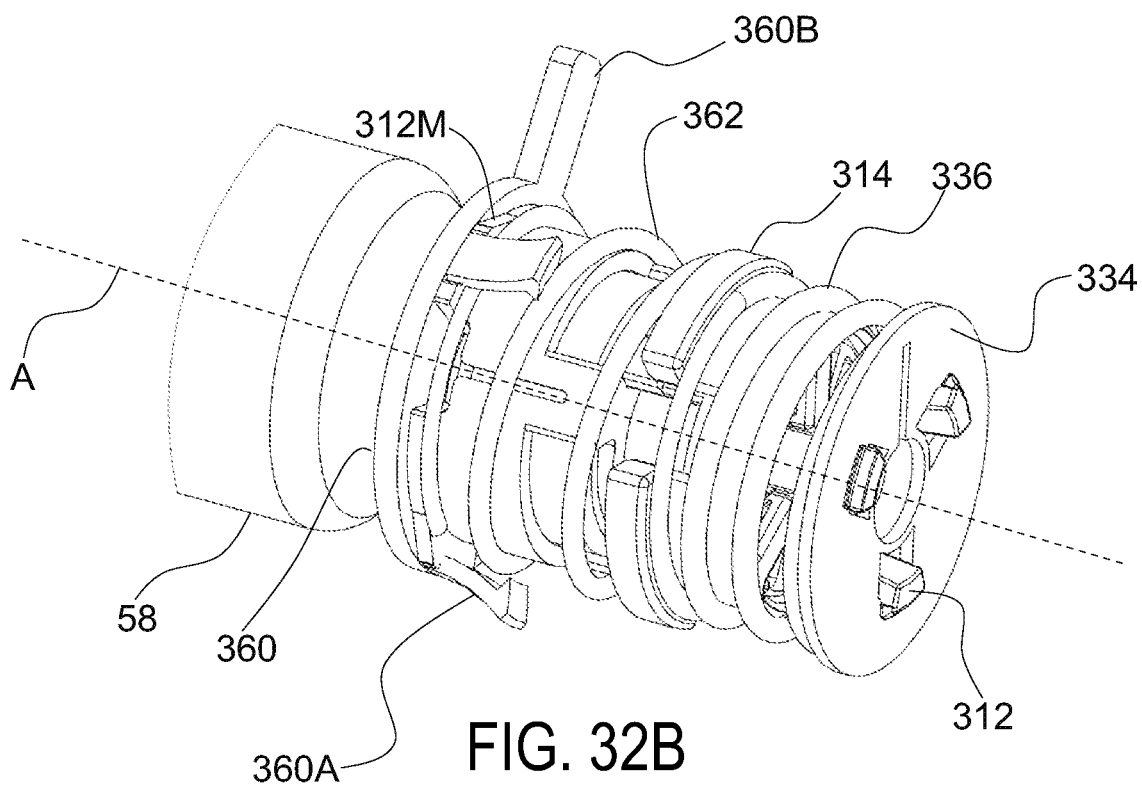
FIG. 32B is a fragmentary isometric view of the fluid pathway connection assembly and drug container of FIG. 32A upon disconnection.

One such embodiment is shown in FIGS. 32A and 32B. As shown in FIG. 32A, secondary biasing member 362 is initially restrained between connection hub 312 and one or more release arms 360A of locking aspect 360. Locking aspect 360 is disposed against the proximal face of connection hub 312 with one or more release arms extending in the distal direction. In the event of a fault in the operation of the drug delivery device, or upon activation by the user, locking aspect 360 is caused to rotate about axis A from the position shown in FIG. 32A to the position shown in FIG. 32B. The rotation may be caused by contact of a throw arm with activation arm 360B, for example. As locking aspect 360 is rotated, each of the one or more release arms 360A contact a ramped surface 312M of connection hub 312. The contact with ramped surface 312M causes displacement of the one or more release arms 360A in an outwardly radial direction or, alternatively, fracture of the one or more release arms 360A. As a result, secondary biasing member 362 is able to decompress or deenergize. Secondary biasing member 362 comes into contact with piercing member retainer 314 and causes piercing member retainer 314 to translate in the distal direction. This translation causes the piercing member to be withdrawn from the pierceable seal. Hence, no additional medicament will be delivered through the piercing member, thereby terminating delivery to the patient. As shown in FIG. 32B, after rotation, each of the one or more release arms 360A may flex radially outward to permit the secondary biasing member 362 to deenergize, and then return radially inward to be disposed in a notch 312N of the connection hub. Locking aspect 360 may thereby be prevented from any further rotation.

Any of the illustrated embodiments may be equipped with such a safety feature. Alternatively, a component of the drug delivery device may directly engage a portion of the fluid pathway connector to withdraw the piercing member from the pierceable seal. For example, a slide or throw arm may contact piercing member retainer 2314, displacement of the slide or throw arm causing displacement of piercing member retainer 2314 to withdraw the piercing member from the pierceable seal.

Withdrawal of the piercing member from the pierceable seal may be activated in the event of, for example, failure or loss of tension in the tether, failure of the drive mechanism, removal of the drug delivery device from the target tissue, or activation by the user. The safety mechanism may be purely mechanical or, alternatively, may include the power and control system. For example, an electrical signal from the power and control system may initiate withdrawal of the piercing member from the pierceable seal.

It will be appreciated from the above description that the fluid pathway connector assemblies and drug delivery devices disclosed herein provide an efficient and easily-operated system for automated drug delivery from a drug container. The novel devices of the present disclosure provide container connections maintain the aseptic condition of the fluid pathway, and drug delivery pumps which incorporate such fluid pathway connector assemblies to drug containers. Such devices are safe and easy to use, and are aesthetically and ergonomically appealing for self-administering patients. The devices described herein incorporate features which make activation, operation, and lock-out of the device simple for even untrained users. Because the fluid path is disconnected until drug delivery is desired by the user, the aseptic condition of the fluid pathway connector, the drug container, the drug fluid, and the device as a whole is maintained. These aspects provide highly desirable storage, transportation, and safety advantages to the user. Furthermore, the novel configurations of the fluid pathway connector assemblies and drug delivery devices of the present disclosure maintain the aseptic condition of the fluid path throughout operation of the device. Because the path that the drug fluid travels within the device is entirely maintained in an aseptic condition, only these components need be sterilized during the manufacturing process. Such components include the drug container of the drive mechanism, the fluid pathway connector, the sterile fluid conduit, and the insertion mechanism. In at least one embodiment, the power and control system, the assembly platform, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. A further benefit is that the components described herein are designed to be modular such that, for example, housing and other components of the pump drug may readily be configured to accept and operate connection hub 312, 1312, 2312, or a number of other variations of the components described herein.

Assembly and/or manufacturing of fluid pathway connector 300, 1300, 2300, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The fluid pathway connector and drug container may be assembled in a number of methodologies. In one method of assembly, the drug container 50 may be assembled and filled with a fluid for delivery to the target. The drug container 50 includes a cap 324, a pierceable seal 326, a barrel 58, and a plunger seal 60. The plunger seal 60 may be inserted into barrel 58. The barrel 58 may be filled with a drug fluid through the open distal end prior to insertion of the pierceable seal at the open distal end of the barrel 58. The pierceable seal 326 may then be fixedly engaged between the cap 324 and the barrel 58, at a distal end of the barrel 58. In this way, the drug container can be filled and sealed using standard fill-finish processes and equipment. For example, drug container 50 may be filled and sealed using processes and equipment commonly employed in the filling and sealing of standard vials. Additionally, cap 324 may be a crimp cap similar to those commonly used in such processes. Before or after applying cap 324, second seal or film 322 may be applied to the distal face of drug container 50.

Piercing member 316 may be fixedly engaged with piercing member retainer 314. Shaft 314A of piercing member retainer 314 may be inserted through central bore 334B of plate 334 and interlock 338 may engage piercing member retainer 314 such that biasing member 336 is prevented from decompressing. Introducer member 320 may be fixedly connected to introducer member retainer 330. Additionally, sterile boot 340 may be connected to introducer member retainer 330. Introducer member retainer 330 may be positioned within piercing member retainer 314 such that piercing member 316 is at least partially disposed within lumen 320A of introducer member 320. Connection hub 312 may then be connected to plate 334 by inserting snaps 312C through passages 334A. In this position, a portion of introducer member 320 is disposed within cavity 312A and sterile boot 340 is engaged with connection hub 312. Second film 322 may be placed over aperture 312B of connection hub 312 to define cavity 312A. Additionally, during assembly, the fluid conduit may be fluidly connected to piercing member 316. The insertion mechanism 200 may be assembled and attached to the other end of the fluid conduit. The fluid pathway connector may then be assembled to drug container 50. The connection of the fluid pathway connector to the drug container may or may not occur in a clean room or sterile environment. Because first film 318 and second film 322 maintain the aseptic condition of pierceable seal 326 and cavity 312A, respectively, the flow path is not exposed to contaminants.

The steps of assembly may, optionally, also include the step of disposing a locking aspect against the proximal face of the connection hub. The steps of assembly may also include disposing a secondary biasing member concentrically around a portion of the connection hub such that the secondary biasing member is retained in a compressed or energized state by the locking aspect.

In the embodiment shown in FIGS. 12A-22, assembly may include the steps outlined above and may also include additional or different steps. The additional or different steps may include connection of cap 1354 to connection hub 1312 such that ring seal 1352 is positioned between connection hub 1312 and cap 1354. The additional or different steps may also include placing piercing member retainer 1314 and introducer member retainer 1330 on shaft 1342 such that they are able to rotate about shaft 1342. Additionally, the steps may include fixedly engaging introducer member 1320 to first sleeve 1344 and engaging first sleeve 1344 to second sleeve 1346 such that septum 1348 is positioned between the sleeves. The steps may also include fixedly engaging piercing member 1316 to keeper 1350.

The embodiment shown in FIGS. 23-30 may also be assembled using any of the steps outlined above and may also include additional or different steps. The additional or different steps may include, for example, coupling a blocking aspect with the connection hub at a coupling aspect of the connection hub.

The drive mechanism 100 may be attached to the proximal end of the drug container 50. Certain components of this sub-assembly may be mounted to the assembly platform 20 or directly to the interior of the housing 12, while other components are mounted to the guide 390 for activation by the user.

Manufacturing of a drug delivery device includes the step of attaching both the fluid pathway connector and drug container, either separately or as a combined component, to an assembly platform or housing of the drug delivery device. The method of manufacturing further includes attachment of the drive mechanism, drug container, and insertion mechanism to the assembly platform or housing. The additional components of the drug delivery device, as described above, including the power and control system, the activation mechanism, and the control arm may be attached, pre-formed, or pre-assembled to the assembly platform or housing. An adhesive patch and patch liner may be attached to the housing surface of the drug delivery device that contacts the target during operation of the device.

A method of operating the drug delivery device includes the steps of: activating, by a user, the activation mechanism; displacing a control arm to actuate an insertion mechanism; actuating a fluid pathway connector; and actuating a power and control system to activate a drive control mechanism to drive fluid drug flow through the drug delivery device, wherein actuating the fluid pathway connector causes a piercing member to penetrate a pierceable seal thereby opening a fluid path from a drug container to the fluid pathway connector. The method may further include the step of: engaging an optional on-body sensor prior to activating the activation mechanism. Furthermore, the method of operation may include translating a plunger seal within the drive control mechanism and drug container to force fluid drug flow through the drug container, the fluid pathway connector, a sterile fluid conduit, and the insertion mechanism for delivery of the fluid drug to the target.

IV. Additional Embodiments of Fluid Pathway Connector

Figure 33A:
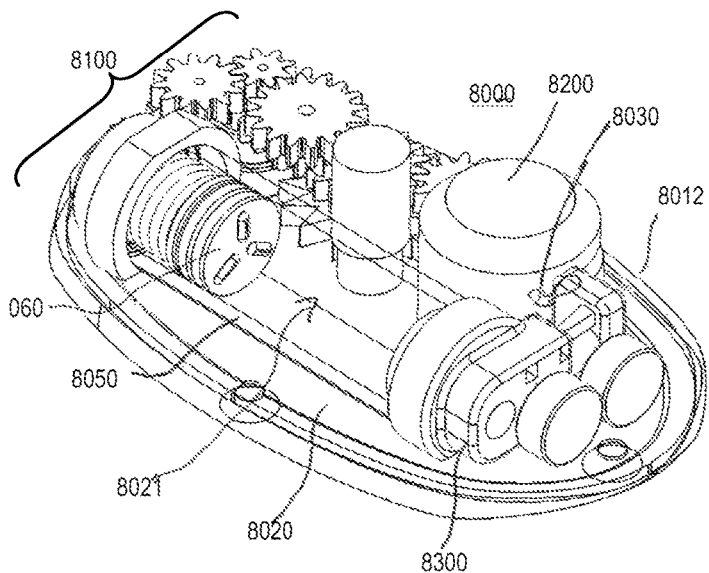
FIG. 33A shows an isometric view of the interior components of a drug delivery device having a multi-function drive mechanism, according to one embodiment of the present disclosure (shown without the adhesive patch)

At least some of the drug delivery devices described in this application, including at least those described in connection with FIGS. 1A-2B, may be configured to incorporate the embodiments of the fluid pathway connector described below in connection with FIGS. 33A-33C. The embodiments of the fluid pathway connector described below in connection with FIGS. 33A-33C may be used to replace, in its entirety or partially, the above-described fluid pathway connector 300 or 6300, or any other fluid pathway connector described herein, where appropriate.

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 8000, the fluid pathway connector 8300 is enabled to connect the sterile fluid conduit 8030 to the drug container of the drive mechanism 8100. Such connection may be facilitated by a piercing member, such as a needle, penetrating a pierceable seal of the drug container of the drive mechanism 8100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the patient. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the patient, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the patient for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the multi-function drive mechanism. Additionally or alternatively, the sterile fluid pathway connector is initiated by movement directly of the multi-function drive mechanism. For example, the multi-function drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 33A-33C, the multi-function drive mechanism performs all of these steps substantially concurrently. The multi-function drive mechanism rotates a gear that acts upon several other components. The gear acts on a gear assembly to control the rate of drug delivery, while also contacting a needle insertion mechanism to introduce a fluid pathway into the patient. As the needle insertion mechanism is initiated, the sterile fluid connection is made to permit drug fluid flow from the drug container, through the fluid conduit, into the needle insertion mechanism, for delivery into the patient as the gear and gear assembly of the multi-function drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 8300 and the sterile fluid conduit 8030 are provided hereinafter in later sections in reference to other embodiments.

V. Other Embodiments of Fluid Pathway Connector

At least some of the drug delivery devices described in this application, including at least those described in connection with FIGS. 1A-2B and 33A-33C, may be configured to incorporate the embodiments of the fluid pathway connector described below in connection with FIGS. 34A-42. The embodiments of the fluid pathway connector described below in connection with FIGS. 34A-42 may be used to replace, in its entirety or partially, the above-described fluid pathway connector 300, 6300, or 8300, or any other fluid pathway connector described herein, where appropriate.

Figure 34A:
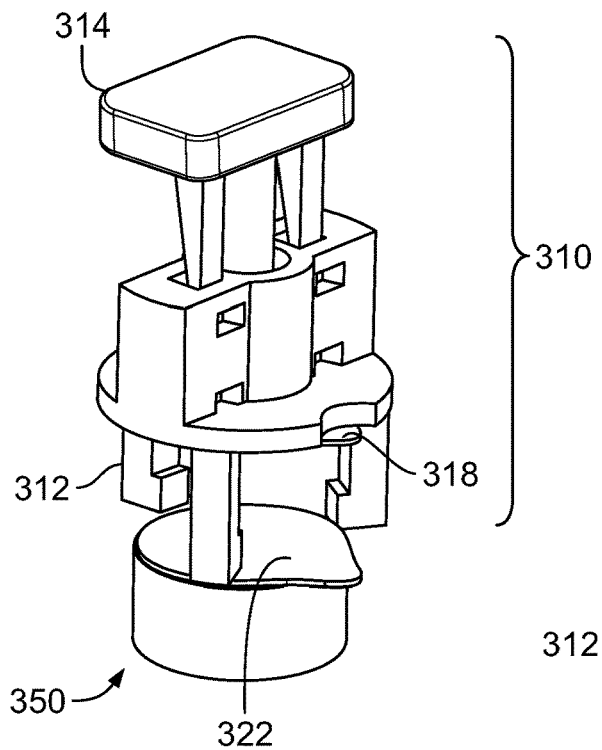
FIG. 34A is an isometric view of an embodiment of a fluid path connection assembly and drug container in an unmounted configuration.
Figure 34B:
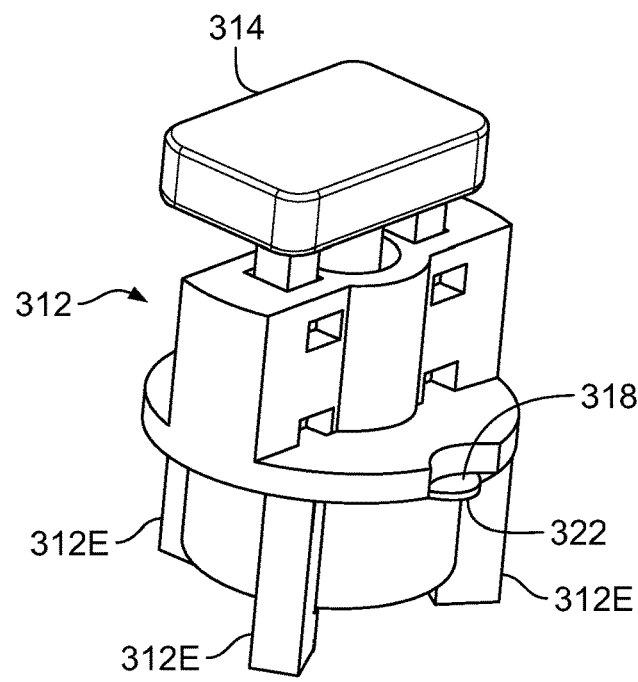
FIG. 34B is an isometric view of the embodiment shown in FIG. 34A in a mounted configuration.
Figure 34C:
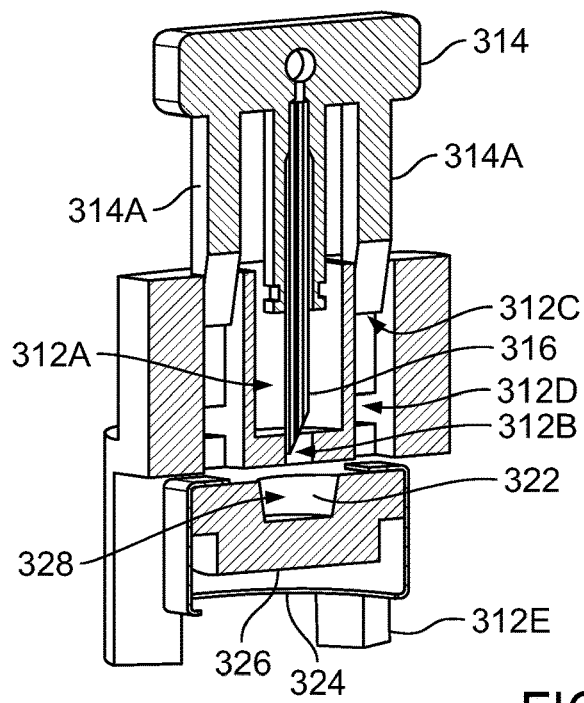
FIG. 34C is a cross-sectional isometric view of the embodiment shown in FIG. 34A in a mounted configuration.

In the processes of filling drug containers and other drug delivery devices, it is sometimes necessary to connect two or more sterile components or subassemblies. For example, wearable injectors or drug pumps may include a drug container which may be filled with a fluid drug using standard pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes to the drug and/or fluid pathway. The connection of two or more aseptic components or subassemblies is typically performed in an aseptic environment, such as a clean room, thereby ensuring that no harmful microbes are introduced to the assembly. This, however, may lead to increased cost to manufacture the drug delivery devices Embodiments of the present disclosure allow aseptic connections to be made between two or components or subassemblies in a septic environment. As seen in FIGS. 34A-34C, the connection hub 310 of a fluid pathway connector (e.g., fluid pathway connectors 300, 6300, and/or 8300) may be connected to a drug container 350. FIG. 34A shows these components prior to connection. A first film 318 is in place on connection hub 312. First film 318 covers aperture 312B of connection hub 312 and prevents microbes from entering cavity 312A through aperture 312B, thereby maintaining cavity 312B and piercing member 316 in an aseptic condition. Piercing member 316 is partially disposed in cavity 312A and at least partially disposed in retainer 314. The piercing member may be a hollow needle. Retainer 314 is engaged with connection hub 312 and may be configured for translation with respect to the connection hub in a direction parallel to the long axis of piercing member 316. The retainer may include one or more locking arms 314A which may engage one or more first recesses 312C in connection hub 312. The locking arms may include protrusions at their lower end, which in the locked position are at least partially disposed in the upper recesses. The engagement of the flex arms maintains the spatial relationship of the retainer and the connection hub.

The drug container 350 may include a crimp cap 324 that maintains a connection between a pierceable seal 326 and a barrel (not shown). The pierceable seal maintains the fluid drug within the barrel and prevents microbes and other substances from entering the drug chamber. A recess 328 is formed by the geometry of the pierceable seal. A second film 322 is affixed to the drug container such that it encloses recess 328, thereby maintaining recess 328 in an aseptic condition. The first and second films may be constructed of any material capable of providing the barrier properties required to maintain the aseptic condition of the associated surfaces. In a preferred embodiment, the films are constructed from a foil material. Alternatively, the films may be any type of sterilizable membrane, film, or foil. Additionally, the film may be removable and/or pierceable as well as breathable and/or permeable.

An adhesive may be applied to the exterior surfaces of both first film 318 and second film 322 prior to joining the fluid pathway connector and the drug container 350. The adhesive may contain antimicrobial, antibacterial, and antiviral compounds to limit or reduce the number of such substances on the surface of the seals. During connection, flex arms 312E may engage crimp cap 324 or another portion of the drug container 350, thereby limiting axial translation of the fluid pathway connector with respect to the drug container 350. In this position, first film 318 and second film 322 are in contact with, or in close proximity to, one another. If an adhesive is present on the faces of one or more of the films the films may be bonded together.

After the fluid pathway connector and drug container 350 are joined, the retainer 314 may be translated axially with respect to the connection hub. Translation of the retainer causes locking arms 314A to flex and become disengaged from first recess 312C. Translation of the retainer causes needle 316 to also translate. This translation causes the needle to pierce first film 318 and second film 322. After translation of the retainer, the piercing member is at least partially disposed in recess 328 of pierceable seal 326. The retainer may be further translated, leading to the piercing of pierceable seal 326 by piercing member 316. After piercing of the pierceable seal a fluid path is established from the drug container and through the needle. The needle may also be in fluid communication with a conduit, the conduit being configured to carry the fluid contents to a delivery mechanism such as an insertion mechanism for delivery to a patient. Piercing of the first and second films may occur at the time of assembly. Alternatively, the piercing of the films may occur at or near the time-of-use of the drug delivery device. Piercing of the pierceable seal at or near the time-of-use may be initiated, by the patient, by interaction with an activation mechanism.

In some embodiments, the end of the piercing member may remain disposed within cavity 328 until time-of-use. The pierceable seal may be configured such that, in response to hydraulic and/or pneumatic pressure within the drug chamber, it deforms and is caused to come into contact with the piercing member. This deformation of the pierceable seal leads to the piercing of the seal by the piercing member.

Figure 35C:
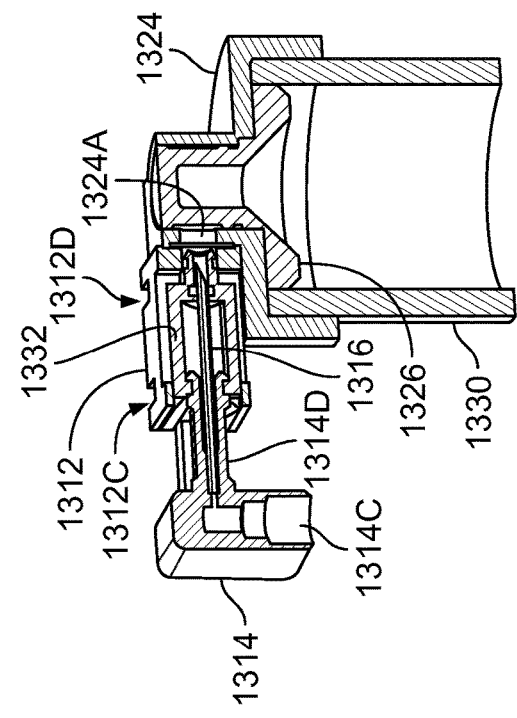
FIG. 35C is a cross-sectional isometric view of the embodiment shown in FIG. 35A in a mounted configuration.
Figure 35D:
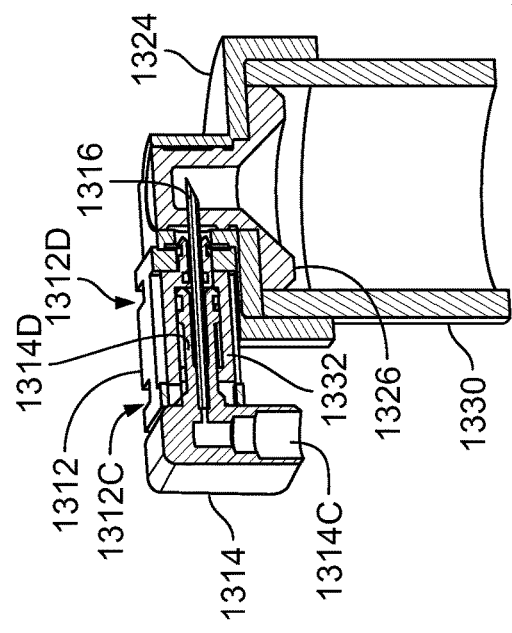
FIG. 35D is a cross-sectional isometric view of the embodiment shown in FIG. 35A after connection of the fluid path.
Figure 35A:
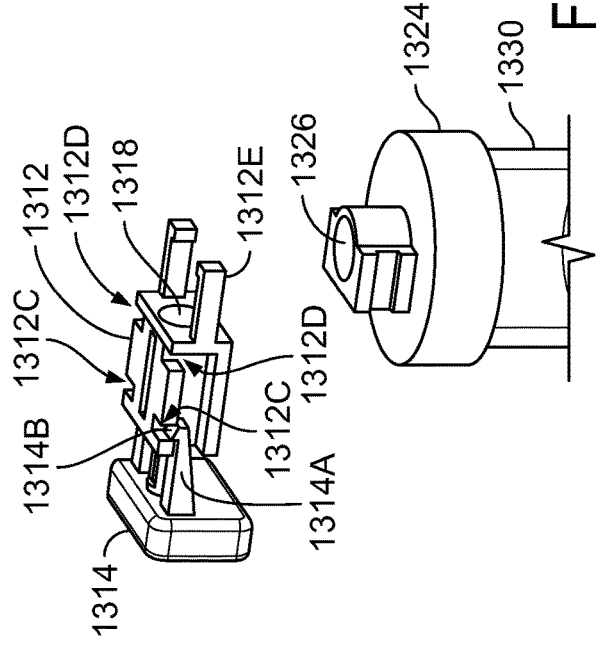
FIG. 35A is an isometric view of an embodiment of a fluid path connection assembly and a drug container in an unmounted configuration.
Figure 35B:
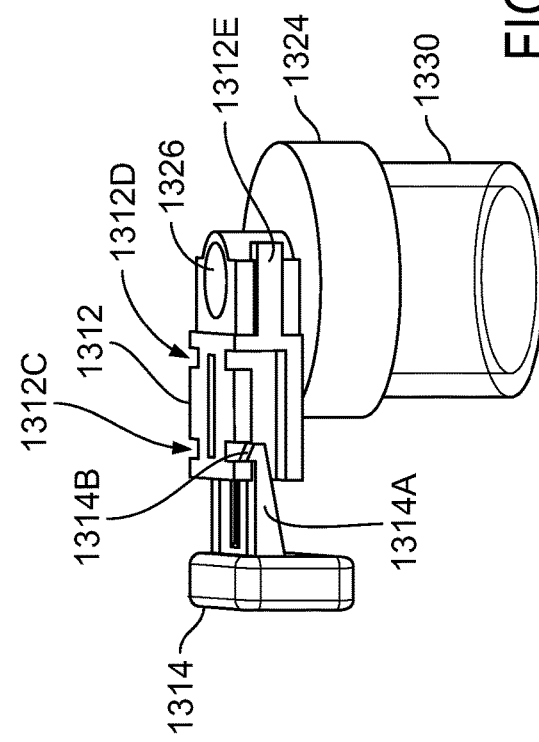
FIG. 35B is an isometric view of the embodiment shown in FIG. 35A in a mounted configuration.

FIGS. 35A-35D show an embodiment in which a connection hub 1312 of a fluid pathway connector is connected to a drug container such that the long axis of the piercing member 1316 is orthogonal to the long axis of the drug barrel 1330 of the drug container. As seen in FIG. 35B, flex arms 1312E engage a portion of cap 1324 to securely attach the fluid pathway connector to the drug container. The fluid pathway connector may further include insert 1332 disposed within connection hub 1312. Extension 1314D of retainer 1314 may be sealingly engaged with insert 1332 and be configured for axial translation with respect to the insert. Protrusions 1314B of retainer 1314 are initially disposed in first recesses 1312C of connection hub 1312. In this position, the piercing end of piercing member 1316 is disposed within insert 1332. FIG. 35C shows a cross-sectional view of the drug container and fluid pathway connector after assembly and before connection of the fluid path. As seen in the cross-section, cap 1324 may contain side port 1324A which allows the piercing member to access the pierceable seal. Also shown in FIG. 35C is conduit port 1314C which may be configured to allow a conduit to be connected to the retainer. This conduit may provide a fluid path that connects the drug container to a delivery mechanism for delivery of the fluid drug to the patient. FIG. 35D is a cross-section showing the assembly in an open fluid path configuration. As shown, retainer 1314 has been displaced toward the center axis of the drug container. Protrusions 1314B of flex arms 1314 have disengaged from first recesses 1312C and have engaged second recesses 1312D. Piercing member 1316 has pierced first film 1318, second film 1322, and pierceable seal 1326. The piercing of each of these may occur at time of use upon patient initiation. Alternatively, the first and second film may be pierced at time of assembly. This creates a fluid path from the drug container, through the piercing member, conduit, and insertion mechanism for delivery to the patient. The connection of the fluid pathway connector such that the long axis of the piercing member is orthogonal to the long axis of the drug container may allow for more compact packaging in a drug delivery device.

Figure 36A:

FIG. 36A is a cross-sectional side view of an embodiment of a fluid path connection assembly and a drug container in an mounted configuration.
Figure 36B:

FIG. 36B is a cross-sectional side view of the embodiment shown in FIG. 36A after the first and second films have been pierced.
Figure 36C:
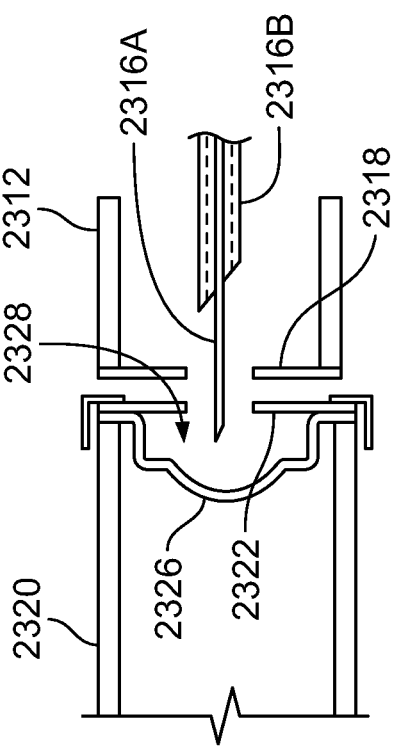
FIG. 36C is a cross-sectional side view of the embodiment shown in FIG. 36A after retraction of the outer piercing member.
Figure 36D:
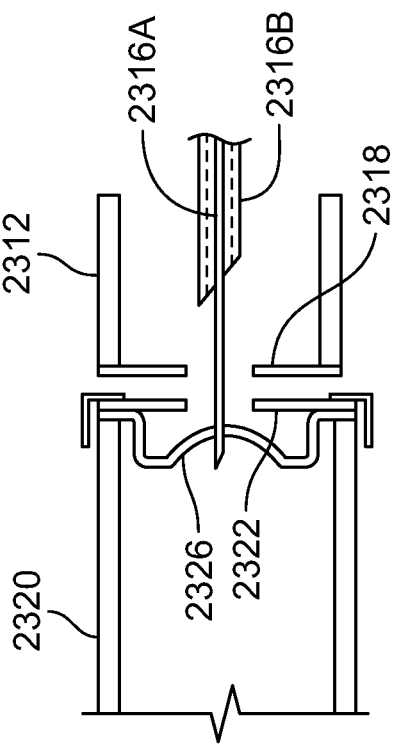
FIG. 36D is a cross-sectional side view of the embodiment shown in FIG. 36A after connection of the fluid path.
Figure 37A:
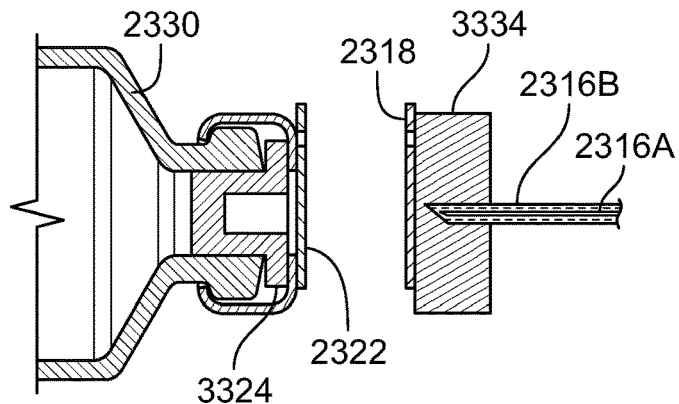
FIG. 37A is a cross-sectional side view of an embodiment of a fluid path connection mechanism and a drug container in an unmounted configuration.
Figure 37B:
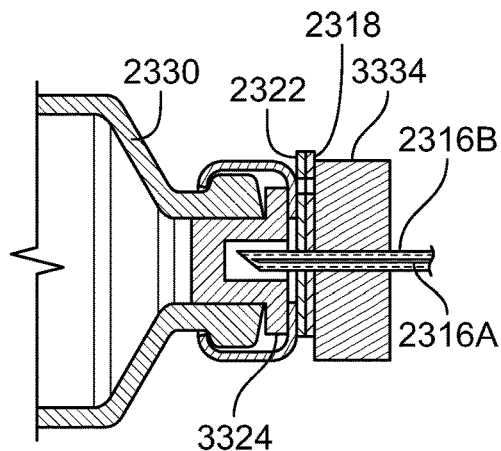
FIG. 37B is a cross-sectional side view of the embodiment shown in FIG. 37A after piercing of the first and second films by the outer piercing member.
Figure 37C:
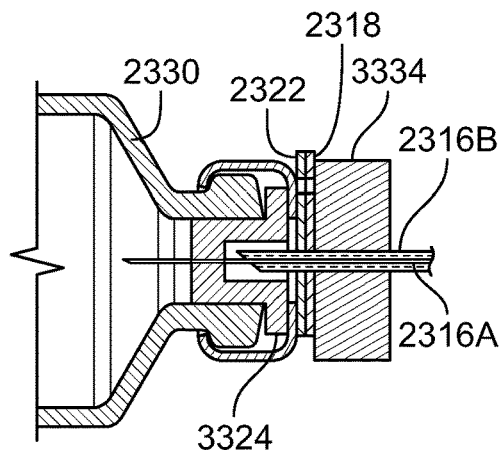
FIG. 37C is a cross-sectional side view of the embodiment shown in FIG. 37A after connection of the fluid path.

In other embodiments, shown in FIGS. 36A-36D, the piercing member includes an inner piercing member 2316A and an outer piercing member 2316B. The inner piercing member 2316A is disposed within the hollow outer piercing member 2316B. After connection of the connection hub 2312 to the drug container 2330, the outer piercing member 2316B pierces the first film 2318 covering terminal end of the connection hub 2312 and the second film 2318 covering the terminal end of the drug container 2330, while maintaining the inner piercing member 2316A within its hollow inner cavity. The piercing may be caused by joint motion of the piercing members 2316A and 2316B toward the drug container or, alternatively, may be caused by the drug container displacing the connection hub, thereby exposing the outer piercing member 2316B. Because the inner piercing member 2316A does not contact the first and second films 2318 and 2322, any contaminants present on the surface of the films 2318 and 2322 are not in contact with the inner piercing member 2316A. After piercing the films 2318 and 2322 the outer piercing member is retracted, thereby exposing the inner piercing member 2316A. In this position, shown in FIG. 36C, the end of the inner piercing member 2316A is disposed in the cavity 2328 created by the pierceable seal 2326. In response to increased hydraulic and/or pneumatic pressure within the drug container the pierceable seal 2326 may deform, as shown in FIG. 36D. The deformation of the pierceable seal 2326 causes the inner piercing member 2316A to pierce the pierceable seal 2326, thereby creating a fluid path from the drug container 2330 through the inner piercing member 2316A for delivery to the patient.

As shown in the alternative embodiment of FIGS. 37-38, the fluid pathway connector may include an elastomeric component 3334. At least a portion of the outer piercing member 2316B may be embedded in the elastomeric component 3334. The outer piercing member 2316B may be embedded in the elastomeric component 334 while in an aseptic environment. The aseptic condition of the embedded portion of the outer piercing member 2316B is maintained when the fluid path connection mechanism is transferred to a septic environment due to the sealing engagement of the outer piercing member 2316B with the elastomeric component 3334. Hence, after mounting the fluid pathway connector to the drug container, the fluid pathway connector may be transformed to the open configuration by initially piercing of the first and second films 2318 and 2322 with the outer piercing member 2316B, and then piercing the pierceable seal 3324 with the inner piercing member 2316A by moving the inner piercing member 2316A relative to the outer piercing member 2316B while keeping the outer piercing member 2316B stationary. In this way, the inner piercing member 2316A is not contaminated by touching the non-sterile exterior surfaces of the first and second foils 2318 and 2322. In alternative embodiments, the outer piercing member 2316B may be the sole piercing member and/or may pierce the pierceable seal 3324 in addition to the first and second films 2318 and 2322. As seen in the further alternative embodiment of FIGS. 38A-D, the first film 2318 and/or the second film 2322 may further include an adhesive containing antimicrobial agents as described above. Initially, the antimicrobial adhesive of the first film 2318 may be covered by a removable liner 2319 and the antimicrobial adhesive of the second film 2322 may be covered by a removable liner 2323. Prior to assembling the first film 2318 in engagement with the second film 2322, the removable liners 2319 and 2323 may be removed. This presence of the antimicrobial adhesive on the exterior surfaces of the first and second films 2318 and 2322 inhibits or prevents contamination of those surfaces if this step of the assembly is performed in a non-sterile environment.

In some embodiments, as shown in FIGS. 39A-B, an additional film or seal 4336 may be present on the outer piercing member 4316B which further isolates the inner cavity of the outer piercing member 4316B and hence the inner piercing member 4316A. This seal 4336 may remain intact as the outer piercing member pierces first film 4318 and second film 4322. This may prevent any microbes that are present on the surfaces of the seals from coming in contact with the inner piercing member. After piercing the first and second films 4318 and 4322 the translation of the outer piercing member 4318B may be restricted prior to the outer piercing member piercing the piercable seal 4326. The inner piercing member 4316A continues to translate toward the drug container 2330 and pierces the first and second films 4318 and 4322 and the pierceable seal 4326, thereby opening the fluid path. Furthermore, in the embodiment shown in FIGS. 39A-B, an antimicrobial adhesive 4325 may initially cover the exterior surface(s) of the first film 4318 and/or the second film 4322.

Figure 40A:
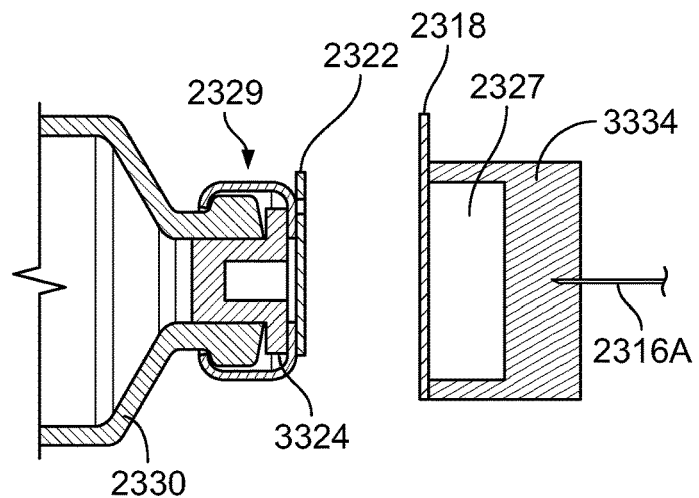
FIG. 40A is a cross-sectional side view of an embodiment of a fluid path connection mechanism and a drug container in an unmounted configuration.
Figure 40B:
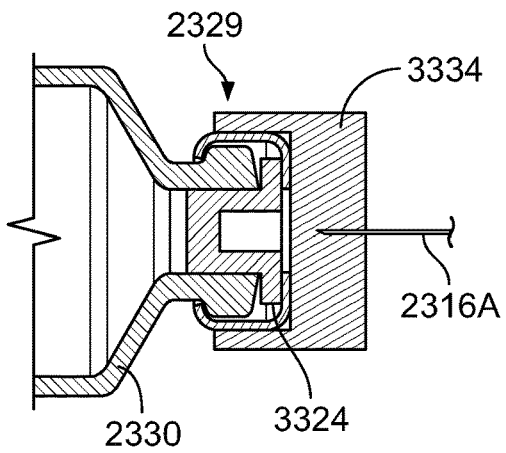
FIG. 40B is a cross-sectional side view of the embodiment shown in FIG. 40A in a mounted configuration.
Figure 40C:
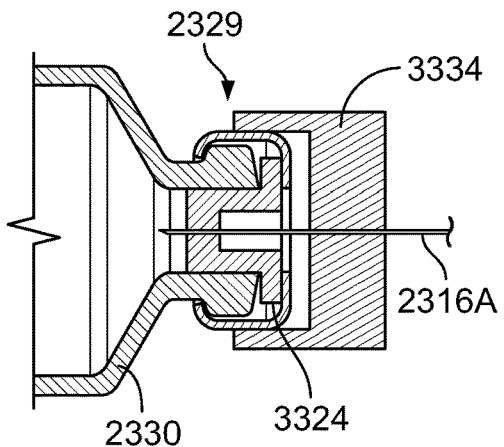
FIG. 40C is a cross-sectional side view of the embodiment shown in FIG. 40A after connection of the fluid path.
Figure 41A:
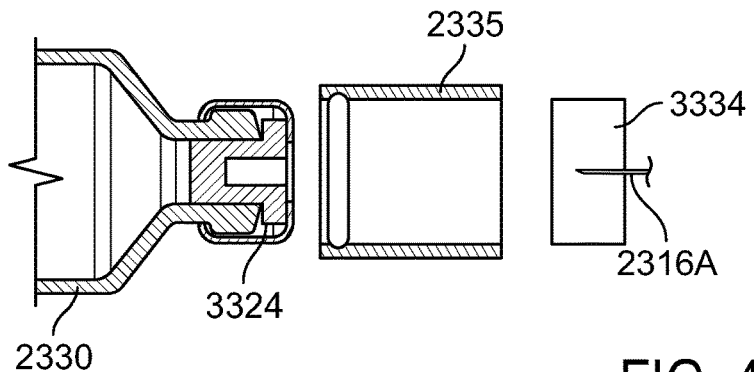
FIG. 41A is a cross-sectional side view of an embodiment of a fluid path connection mechanism and a drug container in an unmounted configuration.
Figure 41B:
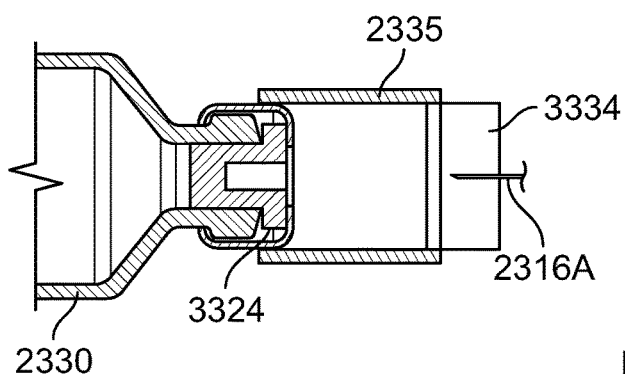
FIG. 41B is a cross-sectional side view of the embodiment shown in FIG. 41A in a mounted configuration.
Figure 41C:
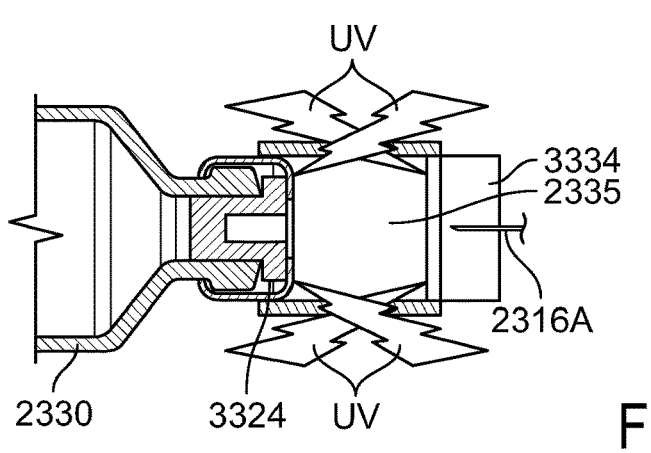
FIG. 41C is a cross-sectional side view of the embodiment shown in FIG. 41A during UV sterilization.
Figure 41D:
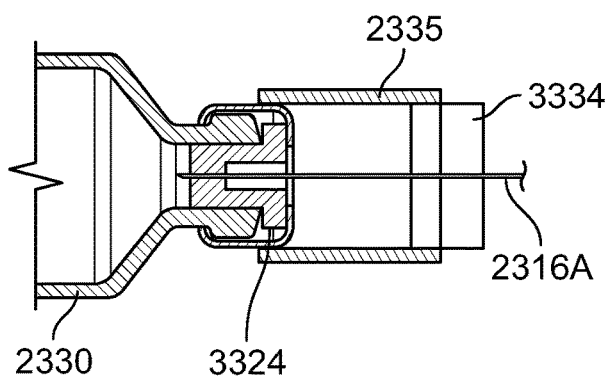
FIG. 41D is a cross-sectional side view of the embodiment shown in FIG. 41A after connection of the fluid path.

In other embodiments, shown in FIGS. 40A-C, the first and second films are removed from the fluid pathway connector and drug container just prior to mounting of the fluid pathway connector. Prior to removal of the films, their placement maintains the sterility of the pierceable seal of the drug container and the face of the elastomeric component of the fluid pathway connector. Except for the removal of the first and second films prior to connection of the fluid pathway connector and the drug container and the omission of the outer piercing member 2316B, the embodiment shown in FIGS. 40A-C includes same or similar elements as the embodiment shown in FIGS. 37A-C. Thus, same reference numerals are used to indicate same or similar elements in both sets of figures. It is noted that the outer piercing member 2316B of the embodiment shown in FIGS. 37A-C can be implemented in an alternative version of the embodiment shown n FIGS. 40A-C. Also, it is noted that the elastomeric component 3334 of the FIGS. 40A-C embodiment, unlike the elastomeric component 3334 of the FIGS. 37A-C embodiment, includes a recess or cavity 2327 configured to receive and form a tight fit (e.g., an airtight interference or press fit) with a distal end 2329 of the drug container 2330. This tight fit may prevent the ingress of contaminants and thereby maintain sterility of the interface between the drug container and the fluid pathway connector. In some embodiments, the distal end 2329 of the drug container 2330 may be inserted into the recess 2327 and the elastomeric component 3334 under non-sterile or aseptic conditions so that contaminants are not trapped between distal end 2329 of the drug container 2330 and the elastomeric component 3334 as the result of assembly.

As shown in the alternative embodiment of FIGS. 41A-D, the fluid pathway connector may also be mounted to the drug container 2330 using a glass tube 2335. After mounting, the glass tube 2335 and the surfaces of the elastomeric piercing member retainer or component 3334 and pierceable seal 3324 may be sterilized using UV sterilization (see FIG. 41C). The glass tube may be in sealing engagement (e.g., an airtight seal) with both the drug container 2330 and the elastomeric component 3334 of the fluid pathway connector such that after sterilization microbes and other foreign elements are unable to enter the glass tube, thereby maintaining the aseptic condition of the interior of the glass tube 2335. Except for the omission of the first and second foils 2318 and 2322 and the inclusion of the glass tube 2335, the embodiment shown in FIGS. 41A-D may include the same or similar elements as the embodiment shown in FIGS. 40A-C. Therefore, same reference numerals are used to indicate same or similar elements in both sets of figures.

The embodiment shown in FIG. 42 shows a connection which is made orthogonal to the long axis of the drug container. In this embodiment, a first film 5318 is initially in place over and maintaining the sterility of a cavity 5312A of the connection hub 5312. During connection, the first film 5318 is pierced by an insert 5340 of the drug container. The pierced portion is retained within the concave portion 5342 of the insert after piercing. By retaining this pierced portion within the concave portion the non-aseptic surface of the first film is isolated and any substances present thereon are prevented from contaminating the drug fluid or fluid path. A second film 5322 is initially in place over an aperture 5340A in the insert 5340, maintaining the aseptic condition of the aperture. The second film 5322 may be a rigid or elastomeric component which is in tight conformity to the insert such that it prevents microbes and other contaminants from entering the aperture. Upon mounting of the connection hub to the drug container the second film may be displaced from its initial position, thereby allowing a fluid path to be established from the drug container through the fluid pathway connector. After mounting of the connection hub to the drug container the aperture 5340A in the insert 5340 is aligned with an aperture 5312B in the connection hub 5312. A pierceable seal may be in place over one or more of the apertures which may be pierced by a piercing member to establish a fluid path. One or more snap arms may retain the insert in position in relation to the drug barrel. The snap arms may connect to the drug barrel itself or another component of the drug container.

VI. Additional Embodiments of Fluid Pathway Connector

At least some of the drug delivery devices described in this application, including at least those described in connection with FIGS. 1A-2B and 33A-33C, may be configured to incorporate the embodiments of the fluid pathway connector described below in connection with FIGS. 43-52D. The embodiments of the fluid pathway connector described below in connection with FIGS. 43-52D may be used to replace, in its entirety or partially, the above-described fluid pathway connectors 300, 6300, or 8300, or any other fluid pathway connector described herein, where appropriate.

Figure 43:
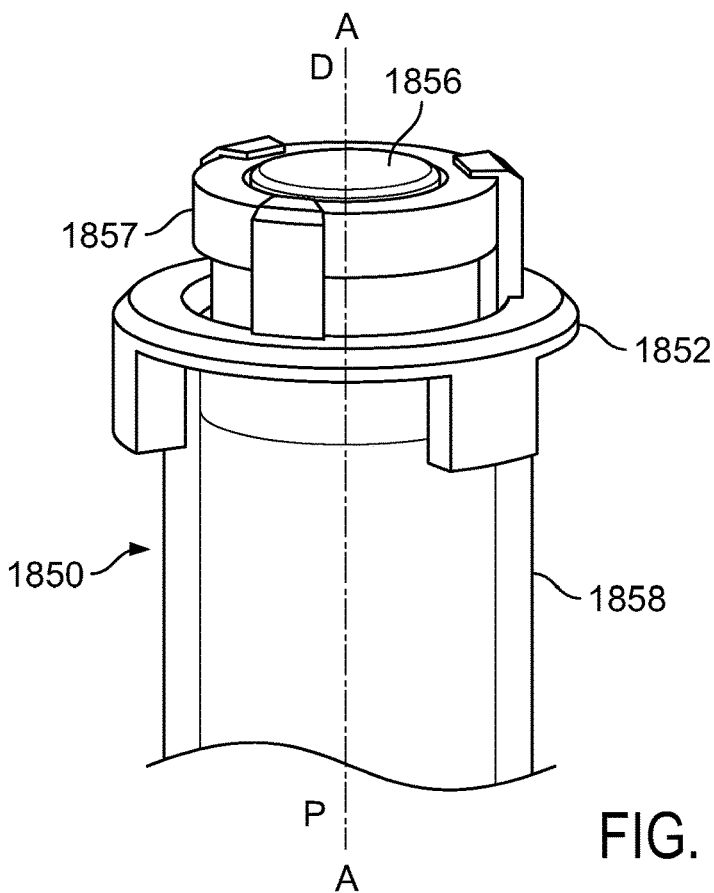
FIG. 43 shows an isometric view of a drug container according to at least one embodiment of the present disclosure.
Figure 44:
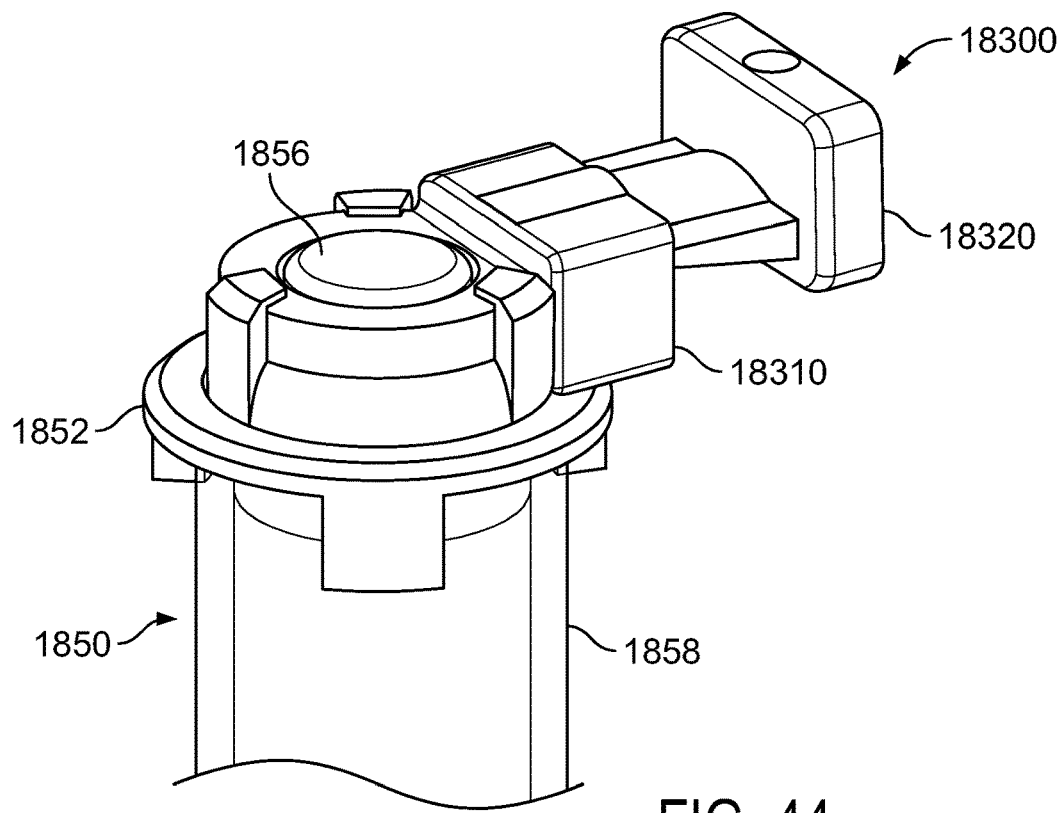
FIG. 44 shows an isometric view of a drug container and a fluid pathway connection according to at least one embodiment of the present disclosure.

As shown in the embodiment of FIGS. 43-45, the drug container 1850 may consist of barrel 1858, cap 1852, and pierceable seal 1856. Base 1856A of pierceable seal 1856 may be in sealing engagement with the inside of barrel 1858. Cap 1852 may be fixedly engaged to the outside of barrel 1858 and may retain pierceable seal 1856 in position and restrict movement of pierceable seal 1856 with respect to barrel 1858. Cap 1852 may include one or more locking arms 1852A which extend from ring 1852B of cap 1852 substantially parallel to axis A-A and in a distal direction. The locking arms 1852A may include a radially extending protrusion 1852C at or near their distal ends. The drug container may further include toroidal seal 1857. In an initial configuration, shown in FIG. 43, the toroidal seal is retained between protrusions 1852B and proximal circumferential rib 1856B of pierceable seal 1856. Pierceable seal 1856 may further include distal circumferential rib 1856C which further retains toroidal seal 1857. By placing the toroidal seal in this position when the drug container is in an aseptic environment the portion of pierceable seal 1856 in contact with the inner face of toroidal seal 1857 (i.e., the area between the proximal circumferential rib and the distal circumferential rib) is maintained in an aseptic condition even if the drug container is moved to a septic environment.

Figure 45A:
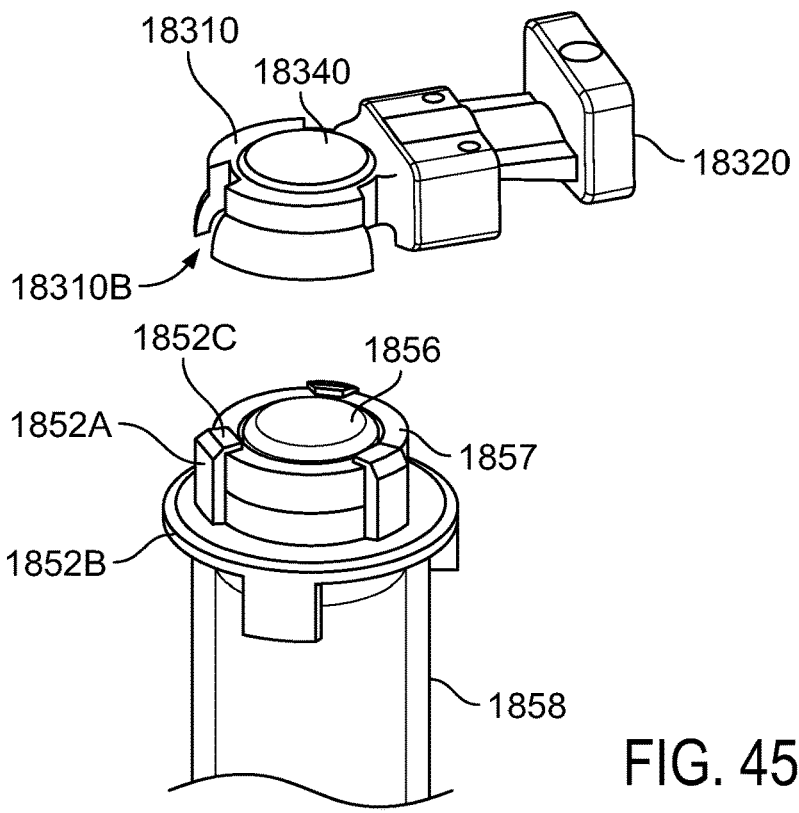
FIG. 45A shows an isometric view of the drug container and fluid pathway connection of FIG. 44 in an unmounted configuration.

The fluid pathway connector 18300 includes connection hub 18310, retainer 18320, piercing member 18330, and plug seal 18330. As shown in FIG. 45A, plug seal 18330 is initially disposed within bore 18310A of connection hub 18310. When the fluid pathway connector is assembled, the plug seal maintains the aseptic condition of at least a portion of the fluid pathway connector by maintaining a sealing engagement with bore 18310A. The retainer is disposed for sliding translation with respect to connection hub 18310 in a direction parallel to axis B-B (shown in FIG. 45D). Initially, translation of retainer 18320 may be restricted. The restriction may be by engagement of flex arms 18320B with recesses in connection hub 18310. Piercing member 18330 may be fixedly engaged with retainer 18320 such that translation of retainer 18320 is transferred to the piercing member. The piercing member may be bonded, press-fit, or engaged to the retainer using other appropriate means. The piercing member may initially be at least partially disposed within cavity 18310D and/or aperture 18310C of connection hub 18310. Both cavities 18310D and 18310C are maintained in an aseptic condition by plug seal 18340. Retainer 18320 may further include conduit connection 18320A to which the sterile fluid conduit 30 (see FIG. 1B) may be attached. This provides a sterile fluid path from the sterile fluid pathway connector to the insertion mechanism. Piercing member 18330 may be a hollow needle such that fluids may pass through the hollow interior of the piercing member and into the sterile fluid conduit.

Figure 45B:
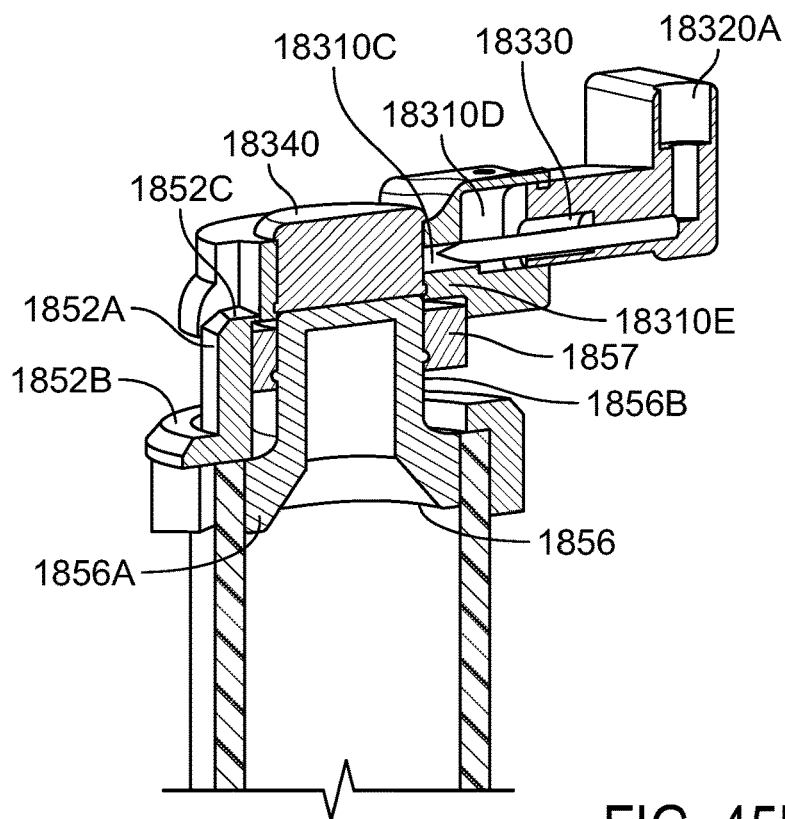
FIG. 45B shows a cross-sectional isometric view of the drug container and fluid pathway connection of FIG. 44 in an initial mounting configuration.
Figure 45C:
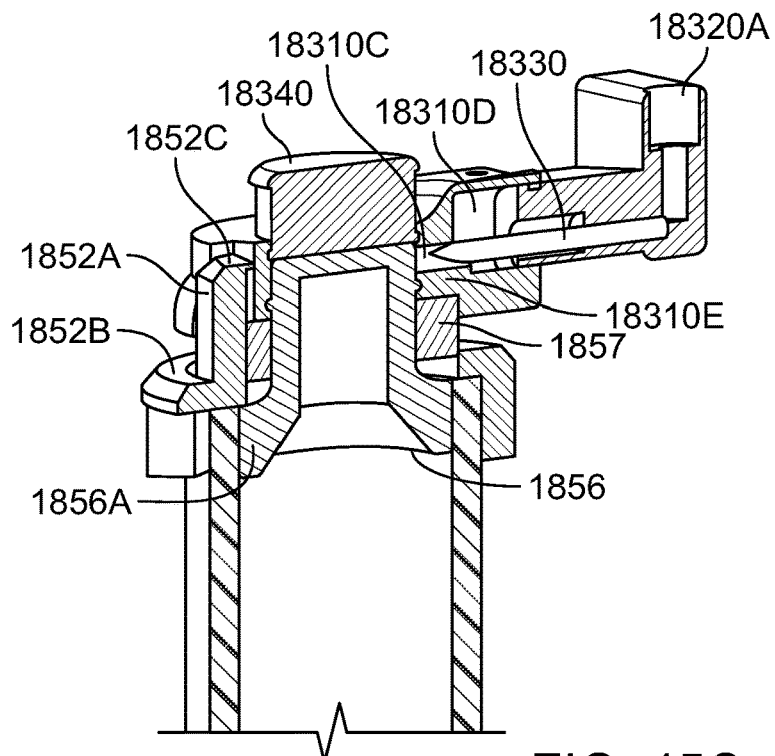
FIG. 45C shows a cross-sectional isometric view of the drug container and fluid pathway connection of FIG. 44 in an intermediate mounting configuration.

FIGS. 45A-D show the steps of connecting the fluid pathway connector to the drug container. This connection may be performed in a non-aseptic environment. In FIG. 45A, the plug seal of the fluid pathway connector is substantially aligned with axis A-A (i.e., the plug seal 18340 is aligned with the distal end of the pierceable seal 56). FIG. 45B shows a cross-section view of the fluid pathway connector 18300 in contact with the drug container. Recesses 18310B of connection hub 18310 are aligned with locking arms 1852A, this alignment guides the installation of the fluid pathway connector and prevents rotation of the fluid pathway connector with respect to the drug container. As shown in FIG. 45C, as the connection hub is translated in the proximal direction along axis A-A the plug seal 18340 is prevented from translating with the connection hub due to contact with pierceable seal 1856. This causes the plug seal to be displaced from its position within bore 18310A. Additionally, contact of shoulder 18310E of connection hub 18310 with toroidal seal 1857 causes the toroidal seal to translate in the proximal direction along axis A-A. As the connection hub is translated along axis A-A only bore 18310A comes in contact with the portion of the pierceable seal which was previously covered by toroidal seal 1857. Further, as the connection hub comes into contact with the toroidal seal these components sealingly engage such that microbes and other foreign substances may not come in contact with the sterile portions of the pierceable seal and fluid pathway connector. In this way the aseptic condition of the pierceable seal 1856, aperture 18310C, cavity 18310D, and piercing member 18330 are maintained during installation of the fluid pathway connector.

Figure 45D:
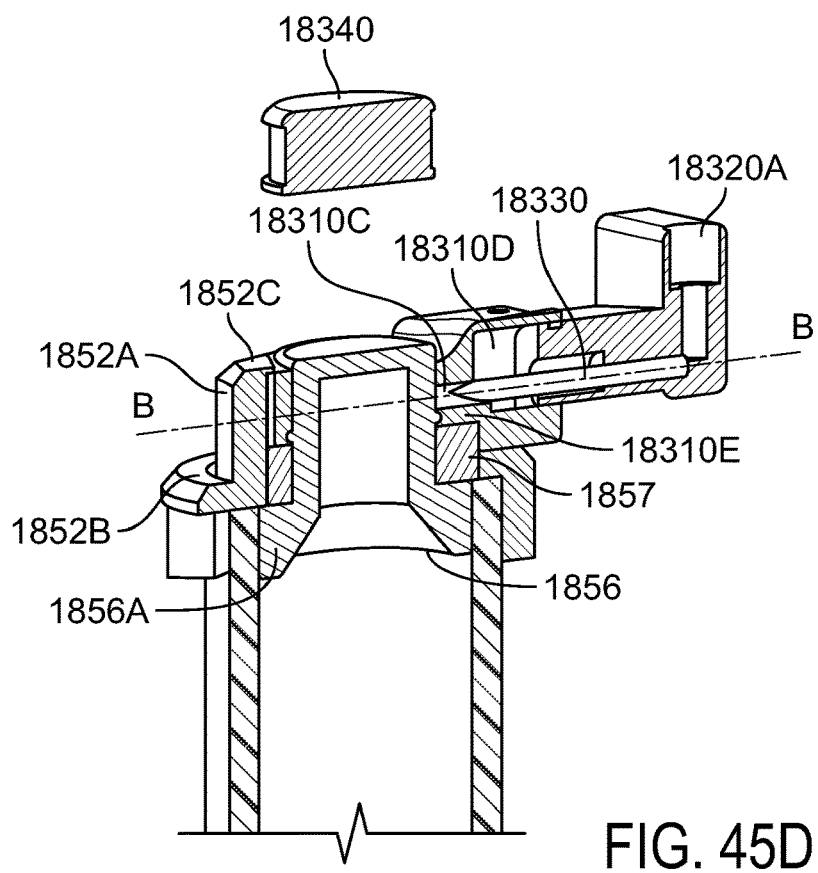
FIG. 45D shows a cross-sectional isometric view of the drug container and fluid pathway connection of FIG. 44 in a mounted configuration.

As seen in FIG. 45D, further proximal translation of the connection hub brings the connection hub into contact with a portion of drug container 1850, thus preventing further distal translation of the connection hub. In the embodiment shown, the connection hub contacts a portion of cap 1852. When the connection hub reaches this position, the plug seal may be removed from the assembly and discarded. Snap arms 1852A may engage one or more aspects of the connection hub and thereby prevent the connection hub from being removed from the drug container.

After installation, the piercing member is aligned with the sterile portion of the pierceable seal which was originally engaged with the toroidal seal. The components may be assembled into the drug delivery device 10 (see FIGS. 1A-1C) and remain in this configuration until activation of the drug pump by the user. Upon activation, the retainer 18320 is translated in a direction parallel to axis B-B with respect to the connection hub, causing translation of piercing member 18330. Due to this translation, the piercing member comes in contact with and, subsequently, pierces the pierceable seal 1856. This opens a fluid pathway from the drug container and through the piercing member. The fluid pathway may further include sterile fluid conduit 30 (see FIG. 1B) which is engaged with conduit connection 18320A of retainer 18320. In this way a sterile fluid path is provided from the drug container to the insertion mechanism for delivery to the patient.

Figure 46A:
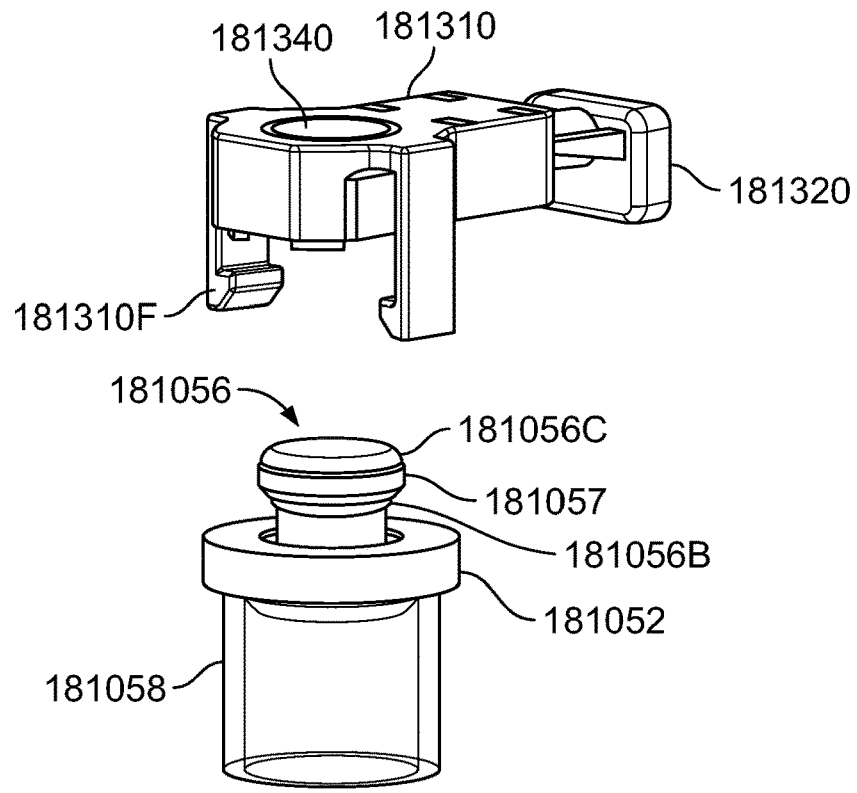
FIG. 46A shows an isometric view of an embodiment of a drug container and fluid pathway connection in an unmounted configuration.
Figure 46B:
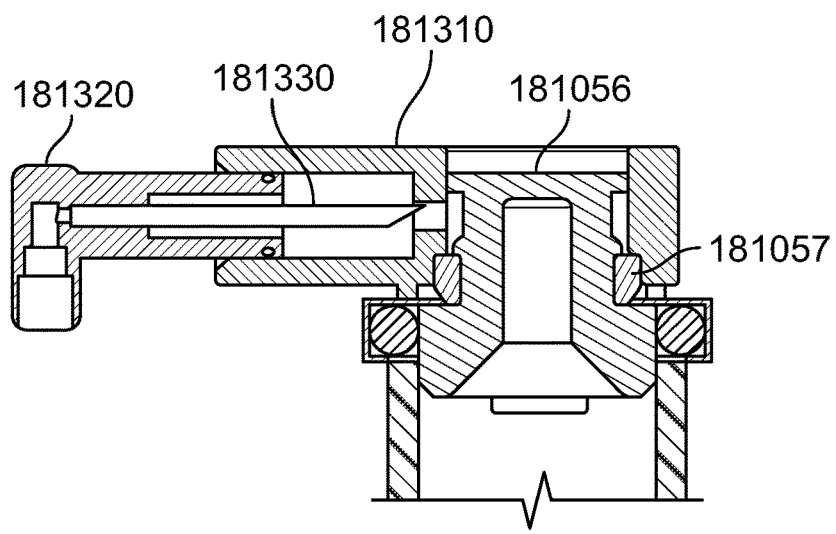
FIG. 46B shows a cross-sectional isometric view of the drug container and fluid pathway connection of FIG. 46A in a mounted configuration.

FIGS. 46A-46B show another embodiment of the present disclosure in which connection hub 181310 includes snap arms 181310F which may engage cap 181052 of drug container 181050. Toroidal seal 181057 is initially retained between proximal circumferential rib 181056B and distal circumferential rib 181056C of pierceable seal 181056 and is caused to translate in the proximal direction by contact with the connection hub. After mounting of the fluid pathway connector to the drug container, opening of the fluid pathway is substantially similar as that described above.

Figure 47:
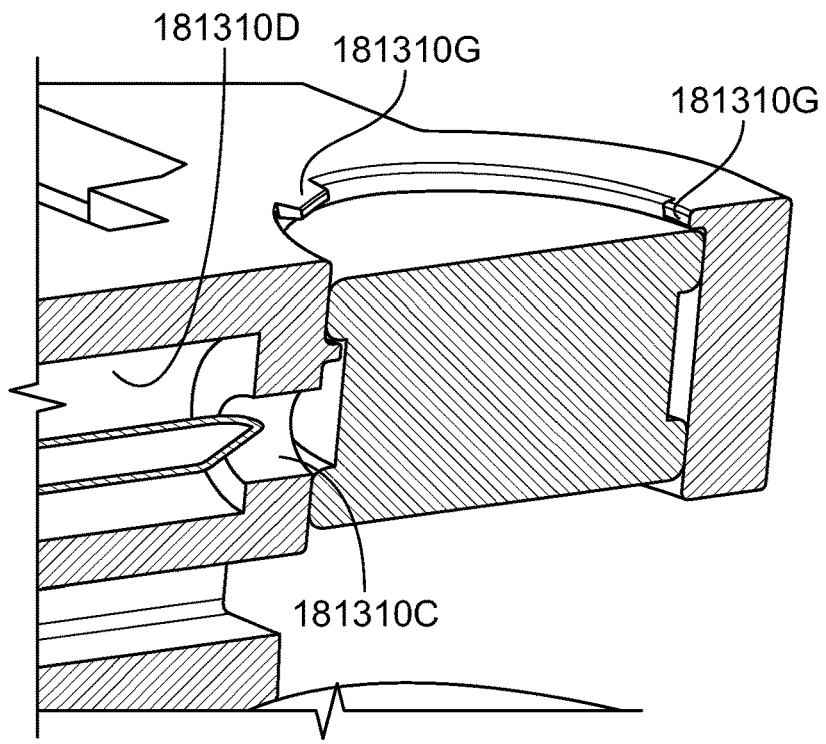
FIG. 47 shows a detail cross-sectional view of a fluid pathway connection according to at least one embodiment of the present disclosure.

FIG. 47 shows a detail view of the plug seal disposed within the bore of the connection hub. This shows a possible method of retaining the plug seal in position using tabs 181310G. These tabs control the location of the plug seal in the inner bore.

Figure 48:
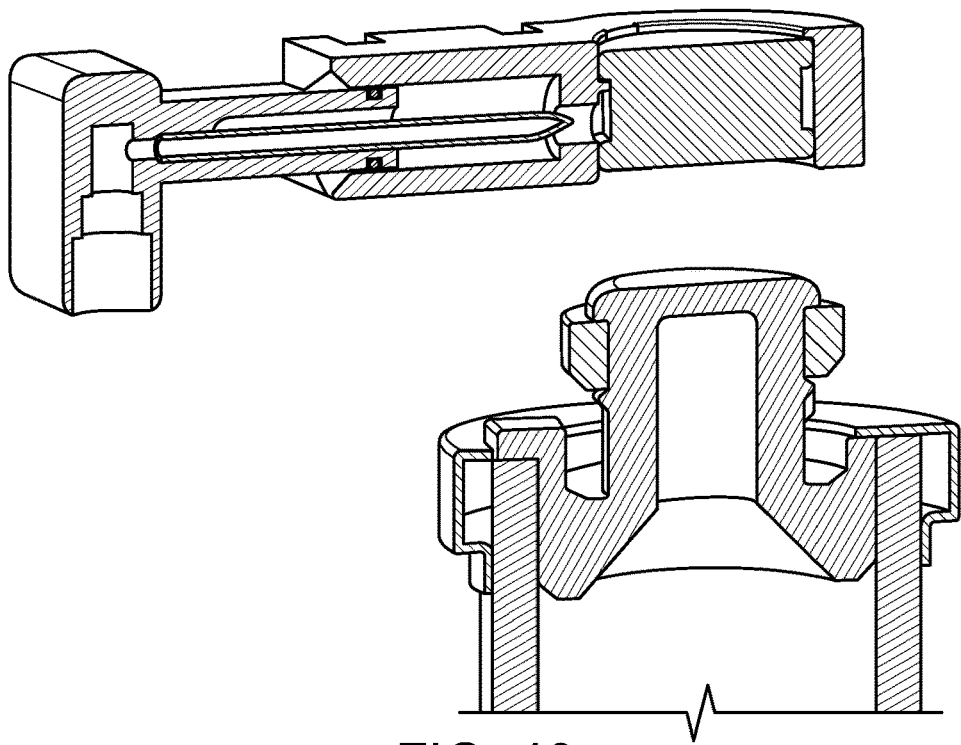
FIG. 48 shows a cross-sectional isometric view of an embodiment of a drug container and fluid pathway connection in an unmounted configuration.
Figure 49:
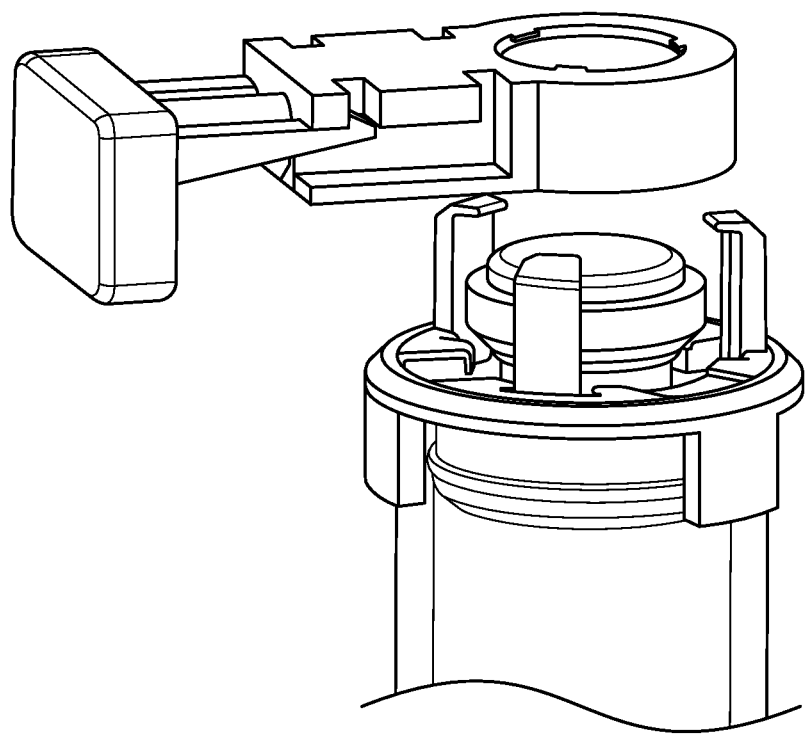
FIG. 49 shows an isometric view of an embodiment of a drug container and fluid pathway connection in an unmounted configuration.
Figure 50:
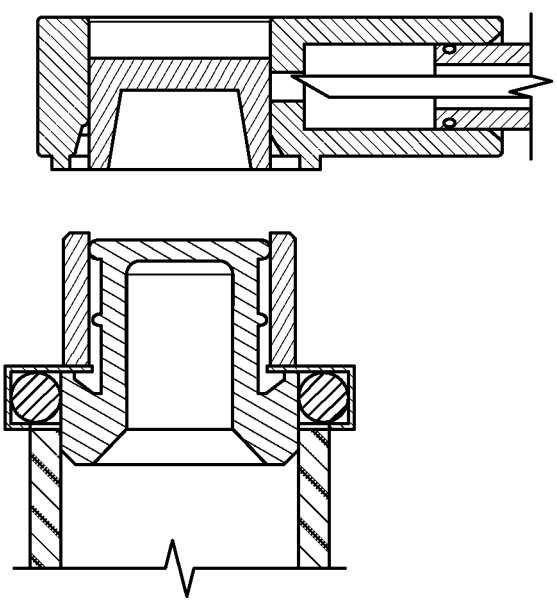
FIG. 50 shows a cross-sectional view of an embodiment of a drug container and fluid pathway connection in an unmounted configuration.

FIGS. 48-50 show additional embodiments of the disclosure illustrating alternative configurations of the cap and pierceable seal.

Figure 51:
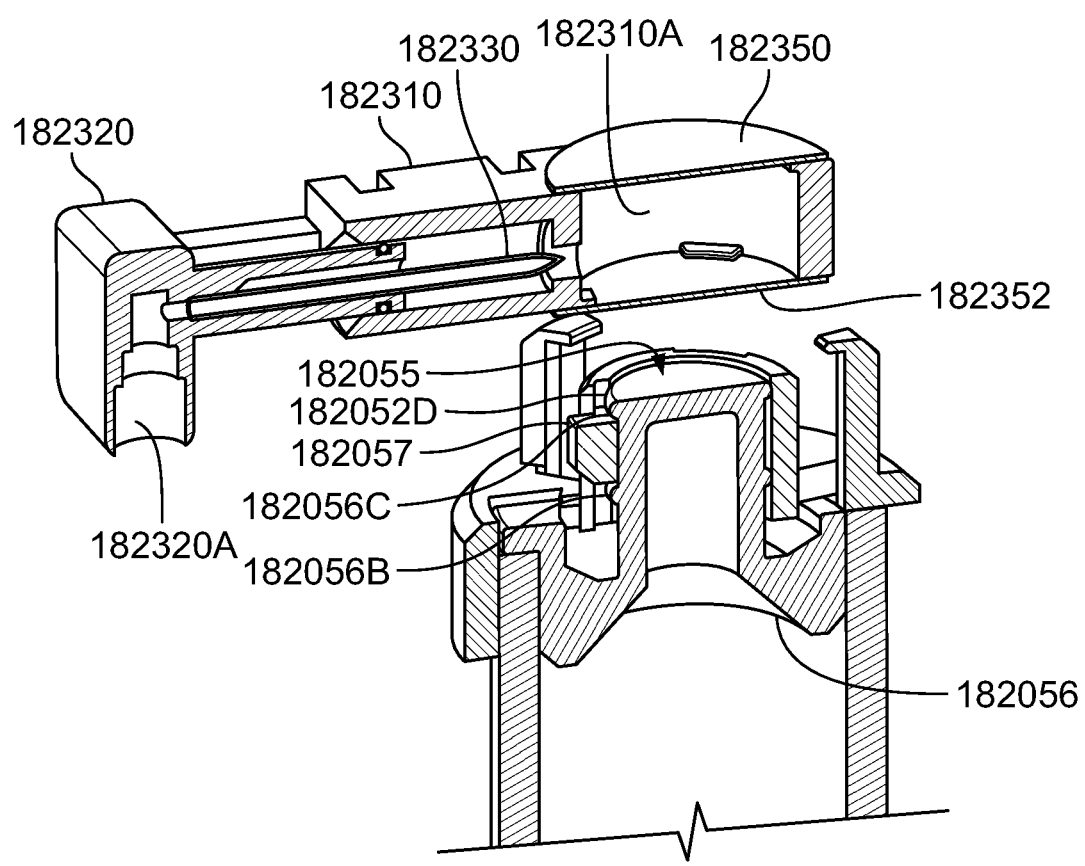
FIG. 51 shows a cross-sectional isometric view of an embodiment of a drug container and fluid pathway connection in an unmounted configuration.

In the embodiment shown in FIG. 51, bore 182310A is enclosed on its distal face by distal film 182350 and on its proximal face by proximal film 182352. The proximal and distal films may be constructed from any material with barrier properties sufficient to prevent the passage of foreign matter. For example, the films may be constructed from a foil material. The films may be bonded or otherwise securely affixed to the connection hub. In this way, bore 182310A is maintained in an aseptic condition.

As the fluid pathway connector is brought into contact with the drug container, a portion of the drug container pierces, tears, or otherwise removes a portion of proximal film 182352 from the connection hub. For example, as shown in FIG. 51, a portion of the cap 182052 contacts the proximal film during installation and disengages a portion thereof from the connection hub. The disengaged portion of proximal seal 182352 may be retained within void 182055 formed by cap 182052 and pierceable seal 182056, thereby preventing the septic portion of proximal film 182352 from contacting the aseptic portion of pierceable seal 182056.

Also shown in FIG. 51, seal 182057 may be configured to maintain the aseptic condition of only a portion of the circumference of pierceable seal 182056. This portion may be configured to be aligned with aperture 182310C and piercing member 182330 after installation of fluid pathway connector 182300. During installation, seal 182057 is displaced by the connection hub as described in reference to other embodiments. Seal 182057 may be retained in position with respect to the pierceable seal by engagement of the seal with slot 182052D of cap 182052, proximal circumferential rib 182056B, and distal circumferential rib 182056C. During displacement, the seal may translate within slot 182052D in the proximal direction.

Figure 52B:
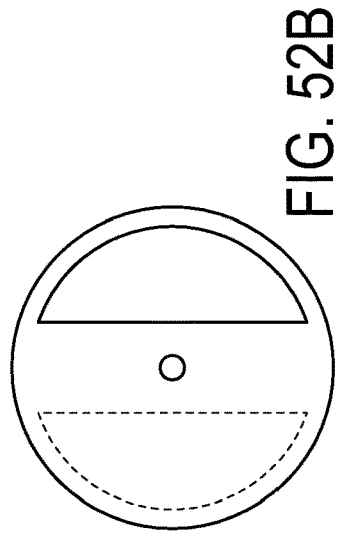
FIG. 52B shows an end view of a drug container.
Figure 52C:
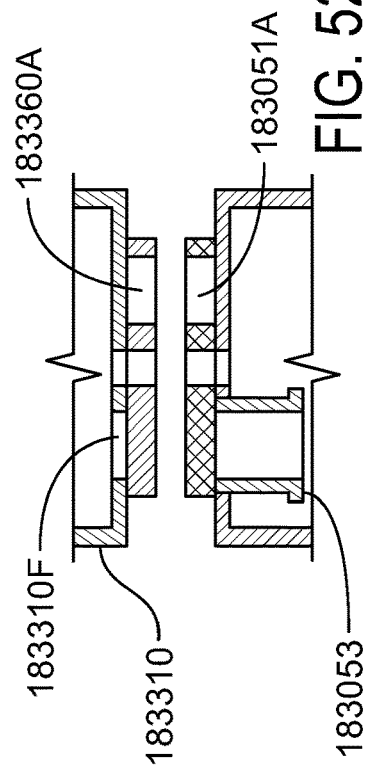
FIG. 52C shows a cross-sectional view of a drug container and fluid pathway connection in an unmounted configuration.
Figure 52D:
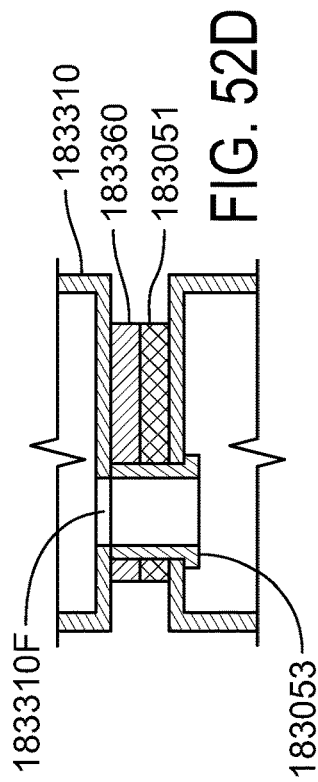
FIG. 52D shows a cross-sectional view of a drug container and fluid pathway connection in a connected configuration.
Figure 52A:
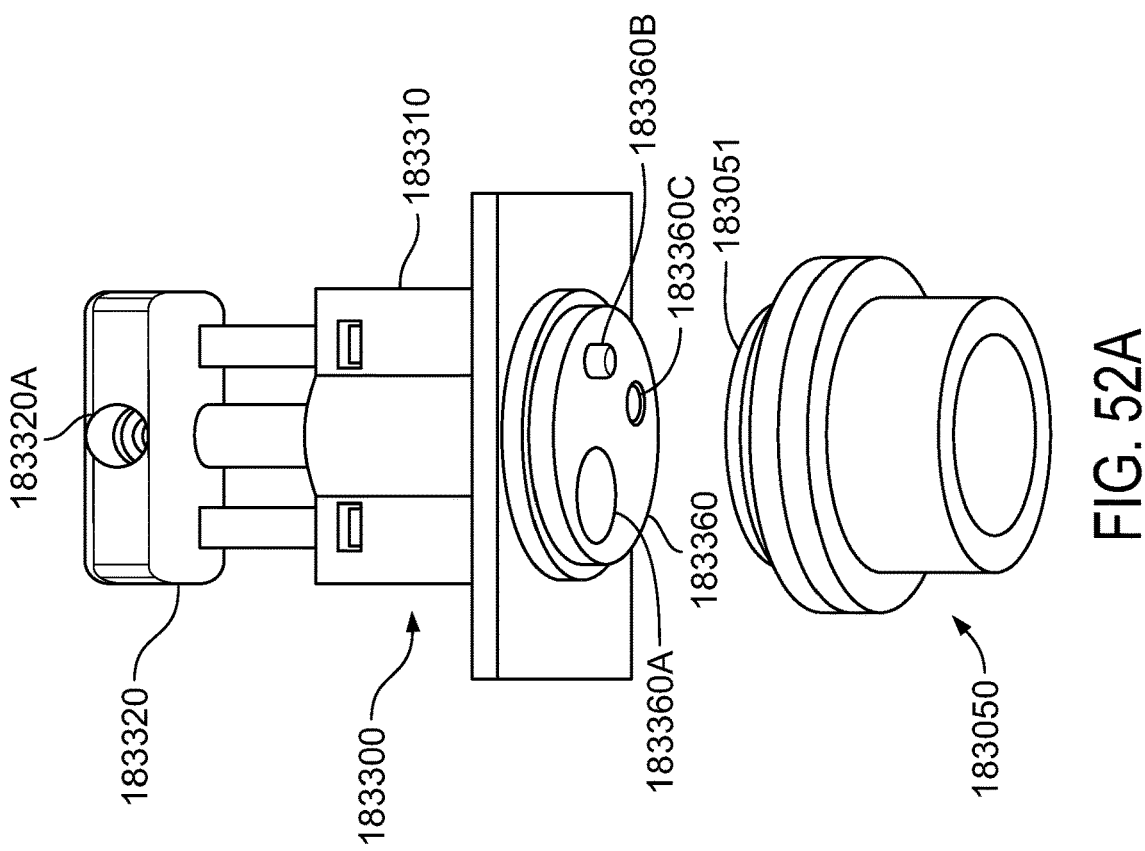
FIG. 52A shows an isometric view of an embodiment of a drug container and fluid pathway connection in an unmounted configuration.

FIGS. 52A-52D show another embodiment of a fluid pathway connector in which the fluid pathway connector includes first rotating disk 183360 and drug container 183050 includes second rotating disk 183051. First rotating disk 183360 may be configured for rotation with respect to connection hub 183310 about a central axis and further include first opening 183360A. As shown in FIG. 52A, the first rotating disk may also include post 183360B and receptacle 183360C. Second rotating disk 183051 may include complementary features to allow for alignment of the first opening 183360A with the second opening 183051A. Second rotating disk 183051 may be configured for rotation with respect to the drug container and have second opening 183051A. One or both of the openings may initially be covered by a film such that the film prevents foreign materials from entering the openings.

As seen in FIG. 52C, during installation the first and second rotating disks are brought into contact such that the first and second openings are aligned. The rotating disks may be joined through the use of an adhesive or, alternatively, may be held in contact by features such as the snap arms described previously in relation to other embodiments. Once connected, the disks may be rotated such that they align with chimney 183053 and third opening 183310F in connection hub 183310. Chimney 183053 may be biased for axial movement in the distal direction, such as by a spring or other biasing member capable of storing energy. As shown in FIG. 52D, upon alignment with the first and second opening, the chimney translates in the distal direction, passing through both the first and second opening. The chimney may have a pass-through which allows contents to flow from the drug container. In this way, a sterile fluid path is created between the drug container and the fluid pathway connector. The fluid pathway connector may further include a piercing member which is configured to, upon activation by a user, pass through the chimney and pierce a pierceable seal of the drug container. After the pierceable seal is pierced, drug fluid may pass through the piercing member and be delivered to the patient. The piercing member may be engaged with retainer 183320. The retainer may also be configured for connection of sterile fluid conduit 30 (see FIG. 1B) at conduit connection 183320A. The translation of the piercing member may be caused by translation of the retainer.

In at least one embodiment, the present disclosure provides a user-initiated fluid pathway connector. The fluid pathway connector includes: a connection hub, a piercing member, a piercing member retainer, and a drug container having a cap, a pierceable seal, and a barrel, wherein the piercing member is at least partially disposed in a sterile chamber defined by the connection hub. The fluid pathway connector is configured such that it may be connected to the drug container while maintaining the aseptic condition of a fluid pathway. The drug container may contain a drug fluid for delivery. The fluid pathway connector may further be in fluid communication with a conduit that provides a fluid pathway for delivery of the fluid drug to the patient. Upon initiation by the user, the fluid drug is delivered through the fluid pathway to the body of the user. The pierceable seal includes a seal barrier that may be penetrated, upon user initiation, by the piercing member.

In another embodiment, the present disclosure provides a drug delivery pump with integrated sterility maintenance features having a housing and an assembly platform, upon which an activation mechanism, a fluid pathway connector, a power and control system, and a drive mechanism having a drug container may be mounted, said fluid pathway connector including a connection hub, a piercing member, a piercing member retainer, and a drug container having a cap, a pierceable seal, and a barrel, wherein the piercing member is at least partially disposed in a sterile chamber defined by the connection hub. The fluid pathway connector is configured such that it may be connected to the drug container while maintaining the aseptic condition of a fluid pathway. The drug container may contain a drug fluid for delivery. The fluid pathway connector may further be in fluid communication with a conduit that provides a fluid pathway for delivery of the fluid drug to the patient. Upon initiation by the user, the fluid drug is delivered through the fluid pathway connector to the body of the user. The pierceable seal includes a seal barrier that may be penetrated, upon user initiation, by the piercing member.

VII. Additional Embodiments of Fluid Pathway Connector

At least some of the drug delivery devices described in this application, including at least those described in connection with FIGS. 1A-2B and 33A-33C, may be configured to incorporate the embodiments of the fluid pathway connector described below in connection with FIGS. 53A-68. The embodiments of the fluid pathway connector described below in connection with FIGS. 53A-68 may be used to replace, in its entirety or partially, the above-described fluid pathway connector 300, 6300, or 8300, or any other fluid pathway connector described herein, where appropriate.

In general, the present embodiments provide for container connections that maintain the sterility of a fluid pathway and are integrated into a fluid container; drug delivery devices that incorporate such sterile fluid pathway connectors to fluid containers; methods of operating such devices; and methods of assembling such devices. The fluid pathway connectors of the present embodiments provide integrated safety features that ensure the sterility of the fluid pathway before, during, and after fluid delivery. In one aspect, the fluid pathway remains disconnected from the fluid container until the device has been initiated by the operator. In another aspect, the fluid pathway maintains the sterility of a piercing member prior to connection with the fluid container within a sterile cavity prior to activation by the operator. Upon activation by the operator, at least a portion of a pierceable seal is translated, such as by pneumatic and/or hydraulic pressure or force within the fluid, towards a substantially fixed piercing member such that the pierceable seal is pierced and the fluid pathway is connected or opened to enable fluid flow through the fluid pathway for fluid delivery from the device.

A drug delivery device, such as an infusion pump or a bolus injector, may be needed to deliver a particular amount of fluid within a period of time. For example, when delivering a drug fluid subcutaneously it is important to control the flow of fluid that is delivered into the patient and to maintain the sterility of the fluid container and fluid pathway prior to activation or operation of the fluid delivery device. It may be desired that the fluid pathway connector remains disconnected, for container integrity, sterility, and other purposes, until the user has activated the device and initiated fluid flow from a container. Some drug delivery devices may utilize one or more active fluid pathway control mechanisms to prevent premature fluid pathway connector or drug delivery. Other drug delivery devices are configured such that fluid pathway connector is made upon manufacture, and fluid delivery is blocked until desired by the user. Such designs do not provide the beneficial advantages associated with maintaining container integrity and sterility of the internal components of the drug delivery device. The present embodiments provide an integrated fluid pathway connector mechanism for sterile drug delivery devices. These novel embodiments provide both a connection mechanism to open or connect a sterile fluid pathway between a fluid container and a fluid conduit, without adding unnecessary steps for the user. This is enabled by activation of the drive mechanism and translation of the plunger seal, resulting in pneumatic and/or hydraulic pressure within the fluid that forces translation of at least a portion of a pierceable seal, causing it to impact upon a substantially stationary piercing member, thus opening a sterile fluid pathway between the fluid container and the fluid conduit.

Accordingly, the embodiments of the present disclosure provide a sterile fluid pathway connector that is integrated into a fluid container and opened, connected, activated, or otherwise enabled by the operation of the device and drive mechanism. The activation of the drive mechanism and the force transferred from the drive mechanism to the plunger seal is, itself, used to open a sterile fluid pathway between the fluid container and the fluid conduit. Accordingly, container integrity and sterility of the fluid container may be maintained prior to and during operation of the device. This novel configuration also automates the sterile fluid pathway connector step, greatly reducing the complexity of the device and operational steps needed to be performed by the device or the user. The novel embodiments of the present disclosure also permit flexibility in device component configurations, and reduce the layout or overall footprint of the device because no separate sterile fluid pathway connector mechanism is needed on the cap-side of the fluid container. The present embodiment may also be implemented fully or utilized in standard production of sterile fluids, including drug fill-finish processes, including applications that require the pulling of a vacuum. Additionally, the present embodiments may also integrate a number of different status indication mechanisms into the device, including utilizing the piercing member or the plunger seal as parts of an indication mechanism that relates status of fluid transfer from the sterile fluid container to the connector. For example, when the fluid container is a drug container, such components and devices provide an end-of-dose indication coupled to the actual travel and drug delivery status of the plunger seal.

At least one embodiment provides for a sterile fluid pathway connector that includes a piercing member, a connector hub, and a pierceable seal. More specifically, at least one embodiment provides for sterile fluid connector comprising a first portion configured to connect a sterile fluid pathway and a second portion comprising a housing configured to mount a sterile fluid container; a connector hub; a pierceable seal disposed at least partially between the connector hub and the sterile fluid container and forming a sterile fluid chamber between the connector hub and the pierceable seal; and a piercing member disposed within the connector hub capable of providing a sterile fluid communication between the sterile fluid chamber and the sterile fluid pathway; wherein at least a portion of the pierceable seal is configured to transform from a non-activated state in which the pierceable seal is intact, to an activated state in which the pierceable seal is disrupted by the piercing member to create a sterile fluid communication between the sterile fluid container and the sterile fluid pathway. The housing may be further configured to recess a portion of the connector within the sterile fluid container. The connector hub may further comprise at least one port or vent. The sterile fluid pathway may also include at least one sensor configured to indicate the status of fluid transfer from the sterile fluid container to the connector. Additionally, the sterile fluid pathway connector may include one or more flow restrictors. In at least one embodiment, the connector hub may at least partially function as a fluid conduit or flow restrictor. In at least one embodiment, the fluid pathway connector further includes a filter. A number of known filters may be utilized within the embodiments of the present disclosure, which would readily be appreciated by an ordinarily skilled artisan. For example, the filter may comprise a permeable membrane, semi-permeable membrane or porous membrane, which encloses the sterile cavity from the outside environment.

The piercing member is initially retained in a substantially fixed position within a sterile cavity between the connector hub and the pierceable seal. Upon activation by the operator (e.g., a patient), at least a portion of the pierceable seal is caused to move to a second position in which the pierceable seal is penetrated by the piercing member. Force, such as pneumatic and/or hydraulic force, applied on the pierceable seal on the side opposing the sterile cavity, causes translation of at least a portion of the pierceable seal towards the piercing member. The translation of the pierceable seal causes it to impact upon the substantially stationary or fixed piercing member to open a fluid pathway through the pierceable seal. Accordingly, at least a portion of the pierceable seal is configured to move from the first position to the second position by force applied by a fluid on the pierceable seal. Penetration by the piercing member of the pierceable seal upon movement of a portion of the pierceable seal from the first position to the second position opens a fluid pathway through the pierceable seal and the piercing member to a fluid conduit.

In at least one embodiment, the pierceable seal comprises a seal barrier that can be penetrated by the piercing member. The piercing member may initially be in contact with, or adjacent to, the seal barrier.

The fluid pathway connector may further include a piercing member guide, wherein the piercing member guide is capable of engaging with or translating upon the connector hub. The piercing member guide may function to ensure that the pierceable seal, or at least a portion thereof such as a seal barrier, properly contacts the piercing member and translates thereupon to become pierced and open the fluid pathway through the pierceable seal and piercing member to a fluid conduit.

The piercing member may be configured to pass into the connector hub and connect to a fluid conduit. In another embodiment, the connector hub may connect the piercing member to the fluid conduit, and the fluid conduit may be at least partially a part of the connector hub. In at least one embodiment, the fluid conduit passes into the connector hub at a port in the connector hub.

In at least one embodiment, the sterile fluid connector includes at least one sensor configured to indicate the status of fluid transfer from the sterile fluid container to the connector. For example, the sterile fluid pathway connector may further include one or more interconnects and, optionally, one or more corresponding contacts, to transmit a signal to the user. For example, the interconnect(s) may be within or at least partially proximal to a plunger seal translatable within a fluid container such that the piercing member is capable of penetrating the plunger seal and acting as a contact(s) for the interconnect(s) to transmit a signal to the user. Additionally or alternatively, the interconnect(s) or the contact(s) is within or at least partially proximal to a plunger seal translatable within a drug container and the other is within or at least partially distal to the pierceable seal to transmit a signal to the user when the plunger seal and the pierceable seal are substantially in contact. Additionally or alternatively, the interconnect(s) and contact(s) are within the sterile cavity between the connector hub and pierceable seal such that release of pneumatic and/or hydraulic pressure at the end of fluid transfer releases interconnection to transmit or cease transmission of a signal to the user. A number of known interconnects and contacts may be utilized within the embodiments of the present disclosure, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Another embodiment provides for an integrated fluid pathway connector and drug container having a piercing member, a connector hub, and a pierceable seal integrated at least partially within a drug container having a barrel and a plunger seal. The pierceable seal is translatable upon a substantially stationary piercing member, and the pierceable seal is configured to move from a first position, where the piercing member is positioned within a sterile cavity between the connector hub and the pierceable seal, to a second position, where the pierceable seal has been penetrated by the piercing member. The fluid container contains a fluid chamber between the pierceable seal and the plunger seal to initially retain a fluid, and the pierceable seal is configured to move from the first position to the second position by a force applied by the fluid on the pierceable seal. In at least one embodiment, the pierceable seal has a seal barrier that can be penetrated by the piercing member, and the piercing member is initially in contact with, or adjacent to, the seal barrier.

The integrated fluid pathway connector may further include a piercing member guide piece attached to the connector hub or piercing member, wherein the piercing member guide slidably engages the connector hub or piercing member to permit translation of the pierceable seal, or a portion thereof, in the direction of fluid exit from the connector. Translation of the pierceable seal in the direction of the fluid container may be prevented by retention of a portion of the pierceable seal by, for example, a housing, such as a crimped cap, mounted to the fluid container barrel that retains the connector hub, piercing member, and pierceable seal in position during operation. Such a configuration may be used to permit the fluid chamber of the fluid container to be evacuated, such as by vacuum, prior to filling with a fluid without compromising the function of the sterile fluid pathway connector.

In at least one embodiment, the connector hub has a header with a conduit port, a chamber, and a vacuum port with a channel that leads into the chamber such that the sterile cavity may be evacuated through the channel. The conduit port may have a membrane or seal that permits fluid flow out of the chamber, and may be capable of being plugged. Similarly, the vacuum port may be capable of being plugged, such as by a polymeric plug. Such configurations allow, for example, the sterile cavity to be evacuated to maintain both sterility and pressure equilibrium between the sterile cavity and the opposing side of the pierceable seal, or otherwise assist in maintaining the relative positions of the components prior to or during operation of the device by the user.

In at least one embodiment, the pierceable seal, or at least a portion thereof, is translatable upon the piercing member and the pierceable seal is further configured to move from the second position, where the pierceable seal has been penetrated by the piercing member, to a third position wherein at least one sensor indicates the status of fluid transfer from the sterile fluid container to the connector. For example, in a third position, one or more interconnects and one or more corresponding contacts are permitted to transmit a signal to the user. In one such embodiment, the interconnect(s) or the contact(s) is upon an aspect of a drive mechanism and the other is within or at least partially proximal to the plunger seal to transmit a signal to the user when the plunger seal and the pierceable seal are substantially in contact. Alternatively, the interconnect(s) or the contact(s) is within or at least partially distal to the pierceable seal and the other is proximal to the connector hub to transmit a signal to the user when the plunger seal and the pierceable seal are substantially in contact. Additionally or alternatively, the interconnect(s) and contact(s) are within the sterile cavity between the connector hub and pierceable seal such that release of pneumatic and/or hydraulic pressure at end of dose releases interconnection to transmit or cease transmission of a signal to the user. A number of known interconnects and contacts may be used with the present embodiments, which would readily be appreciated by a skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Yet another embodiment provides a drug delivery device with integrated sterility maintenance features comprising a housing within which an activation mechanism, an insertion mechanism, and a fluid container having a plunger seal may be mounted. The fluid container is connected at one end to a drive mechanism and at another end to a fluid pathway connector. The fluid pathway connector includes a piercing member, a connector hub, and a pierceable seal, wherein the piercing member is retained within a sterile cavity between the connector hub and the pierceable seal, and wherein the pierceable seal is configured to move from a first position to a second position in which the pierceable seal has been penetrated by the piercing member. The fluid container contains a fluid chamber between the pierceable seal and the plunger seal to initially retain a fluid, and wherein the pierceable fluid seal is configured to move from the first position to the second position by a force applied by the fluid on the pierceable seal. In at least one embodiment, the pierceable seal has a seal barrier that can be penetrated by the piercing member, and the piercing member is initially in contact with, or adjacent to, the seal barrier.

The drug delivery device may further include a piercing member guide engaged with the connector hub or piercing member, wherein the piercing member guide slidably engages the connector hub or piercing member to permit translation of the pierceable seal, or a portion thereof, in the distal direction (i.e., towards the fluid conduit from where fluid exits the connector). Translation of the pierceable seal in the proximal direction may be prevented by retention of the pierceable seal, or a portion thereof, by, for example, a housing such as a crimped cap mounted to the barrel, which housing retains the connector hub, piercing member, and pierceable seal in position during operation. Such a configuration may be used to permit the drug chamber of the drug container to be evacuated, such as by vacuum, prior to filling with a fluid without compromising the function of the sterile fluid pathway connector. In at least one embodiment, the connector hub has a header with a conduit port, a chamber, and a vacuum port with a channel that leads into the chamber such that the sterile cavity may be evacuated through the channel. The conduit port may have a filter, membrane or seal to permit or restrict fluid flow out of the chamber. Similarly, the vacuum port may be capable of being plugged, such as by a polymeric plug. Such configurations may allow, for example, the sterile cavity to be evacuated to maintain sterility, the maintenance of pressure equilibrium between the sterile cavity and the opposing side of the pierceable seal, or assist in maintaining the relative positions of the components prior to or during operation of the device by a user.

In at least one embodiment, the pierceable seal is translatable upon the piercing member or an aspect of the connector hub and is further configured to move from the second position, where the pierceable seal has been penetrated by the piercing member, to a third position where one or more interconnects and one or more corresponding contacts are permitted to transmit a signal to the user. The interconnect(s) and the corresponding contact(s) are configured such that, for example: (a) the interconnect(s) or the contact(s) is positioned upon an aspect of the drive mechanism and the other is positioned within or at least partially proximal to the plunger seal, to transmit a signal to the user when the plunger seal and the pierceable seal are substantially in contact; (b) the interconnect(s) or the contact(s) is positioned within or at least partially distal to the pierceable seal and the other is positioned proximal to the connector hub, to transmit a signal to the user when the plunger seal and the pierceable seal are substantially in contact; (c) the interconnect(s) and the contact(s) are situated within the sterile cavity between the connector hub and the pierceable seal, such after the seal is pierced, continued pressure within the drug chamber causes interconnection which transmits a signal to the user, which signal is terminated once pressure inside the drug chamber drops and interconnection is lost, i.e., at end of dose. A number of known interconnects and contacts may be utilized within the embodiments of the present disclosure, which would readily be appreciated by an ordinarily skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes.

Additionally, the fluid pathway connectors may include one or more flow restrictors. In at least one embodiment, the connector hub may at least partially function as a fluid conduit or flow restrictor. In at least one embodiment, the fluid pathway connector further includes a filter. A number of known filters can be utilized within the embodiments of the present disclosure, which would readily be appreciated by an ordinarily skilled artisan. For example the filter may be a permeable membrane, semi-permeable membrane, or porous membrane, which encloses the sterile cavity from the outside environment.

The novel devices of the present embodiments provide container fluid pathway connectors that maintain the sterility of the fluid pathway and that are integrated into the fluid container, and drug delivery devices that incorporate such integrated sterile fluid pathway connectors to fluid containers. Because the fluid path is disconnected until fluid delivery is desired by the operator, the sterility of the fluid pathway connector, the fluid container, the fluid, and the interior of the device as a whole is maintained. Furthermore, the novel configurations of the fluid pathway connectors and drug delivery devices of the present disclosure maintain the sterility of the fluid path through operation of the device. Because the path that the fluid travels within the device is entirely maintained in a sterile condition, only these components need be sterilized during the manufacturing process. Such components include the fluid container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present embodiments do not require terminal sterilization upon completion of assembly. A further benefit of the present embodiments is that the components described herein are designed to be modular such that, for example, the fluid pathway connector and other components of the device may be integrated into a housing and readily interface to function as a drug delivery device.

A further embodiment provides a method of assembly of an integrated sterile fluid pathway connector and fluid container. The sterile fluid pathway connector may first be assembled and then attached, mounted, connected, or otherwise integrated into fluid container such that at least a portion of the pierceable seal is contained within the drug container. The fluid container can then be filled with a fluid for delivery to the user and plugged with a plunger seal at an end opposite the pierceable seal. The barrel can be filled with a fluid through the open proximal end prior to insertion of the plunger seal from the proximal end of the barrel. A drive mechanism can then be attached to the proximal end of the fluid container such that a component of the drive mechanism is capable of contacting the plunger seal. An insertion mechanism can be assembled and attached to the other end of the fluid conduit. This entire sub-assembly, including drive mechanism, drug container, fluid pathway connector, fluid conduit, and insertion mechanism can be sterilized, as described above, before assembly into a drug delivery device. Certain components of this sub-assembly may be mounted to an assembly platform within the housing or directly to the interior of the housing, and other components may be mounted to a guide, channel, or other component or aspect for activation by the user. A method of manufacturing a drug delivery device includes the step of attaching both the fluid pathway connector and fluid container, either separately or as a combined component, to an assembly platform or housing of the drug delivery device. The method of manufacturing further includes attachment of the drive mechanism, fluid container, and insertion mechanism to the assembly platform or housing. The additional components of the drug delivery device, as described herein, including the power and control system, the activation mechanism, and the control arm may be attached, preformed, or pre-assembled to the assembly platform or housing. In the instance in which the fluid is a drug, and the drug delivery device is an ambulatory infusion device, an adhesive patch and patch liner may be attached to the housing surface of the drug delivery device that contacts the user during operation of the device.

A method of operating the drug delivery device includes one or more of the following steps: activating, by a user, the activation mechanism; displacing a control arm to actuate an insertion mechanism; activating a drive control mechanism to push the plunger seal, connect the sterile fluid pathway connector, and drive fluid flow through the drug delivery device; wherein the pushing of the plunger seal translates the fluid and thus causes a pierceable seal to deform in the direction of the fluid conduit and be pierced by a piercing member, to thereby open a fluid path from the fluid container to the fluid conduit. The drive control mechanism may be activated by actuating a power and control system. The method may further include the step of: engaging an optional on-body sensor prior to activating the activation mechanism. Furthermore, the method of operation may include translating a plunger seal within the drive control mechanism and fluid container to force fluid flow through the fluid container, the fluid pathway connector, the fluid conduit, and the insertion mechanism for delivery of the fluid to the desired target, e.g., to the body of a patient.

The novel devices of the present embodiments provide container connections which maintain the sterility of the fluid pathway and which are integrated into the fluid container, and drug delivery devices which incorporate such integrated sterile fluid pathway connectors to fluid containers. For example, such devices are safe and easy to use, and are aesthetically and ergonomically appealing for self-administering patients.

In at least one embodiment, the presently disclosed sterile fluid pathway connector includes a piercing member, a connector hub, and a pierceable seal; wherein at least a portion of the pierceable seal is configured to move from a first position in which the piercing member is retained within a sterile cavity between the pierceable seal and the connector hub, to a second position in which the pierceable seal has been penetrated by the piercing member. A filter may be utilized to enclose the sterile cavity from the outside environment. Such fluid pathway connectors may be integrated into a fluid container having a barrel and a plunger seal. The components of the fluid pathway connector may further be capable of transmitting a signal to the user upon completion of fluid delivery, for example, upon contact between the plunger seal and the pierceable seal. A fluid delivery pump includes such integrated fluid pathway connectors and fluid containers.

The novel embodiments presented herein provide integrated sterile fluid pathway connectors and fluid containers, and drug delivery devices that utilize such connections, configured to maintain the sterility of the fluid pathway before, during, and after operation of the device, and that enable active safety controls for the device. Integration of the fluid pathway connector into a portion of the fluid container helps ensure container integrity and sterility of the fluid pathway. Additionally, by integrating the sterile fluid pathway connector into a portion of the fluid container, the connection for fluid transfer can be controlled by the user (i.e., is user-activated) and enabled by the function of the drive mechanism. Accordingly, user-activation steps and the internal operation of the drug delivery device can be greatly simplified by the novel integrated sterile fluid pathway connectors of the present embodiments.

The novel embodiments provide container connections that maintain the sterility of the fluid pathway and are integrated into the fluid container, and drug delivery devices that incorporate such integrated sterile fluid pathway connectors to fluid containers. The present embodiments also further integrate the sterile pathway connector into the fluid container, to reduce the necessary components or to provide easier and more efficient operation of the connection and drug delivery devices. The connector, the sterile fluid pathway assembly, and the infusion pump disclosed here are not limited to medical applications, but may include any application, including industrial uses, where sterile or uncontaminated fluid delivery may be desired. When the fluid is a drug, the present embodiments provide for devices that are safe and easy to use, and are aesthetically and ergonomically appealing for self-administering patients. The embodiment described herein incorporate features which make activation, operation, and lock-out of the device simple for even untrained users. One or more of the components of the present embodiments may be modular in that they can be, for example, pre-assembled as separate components and configured into position within the housing of the drug delivery device during manufacturing.

Figure 53A:
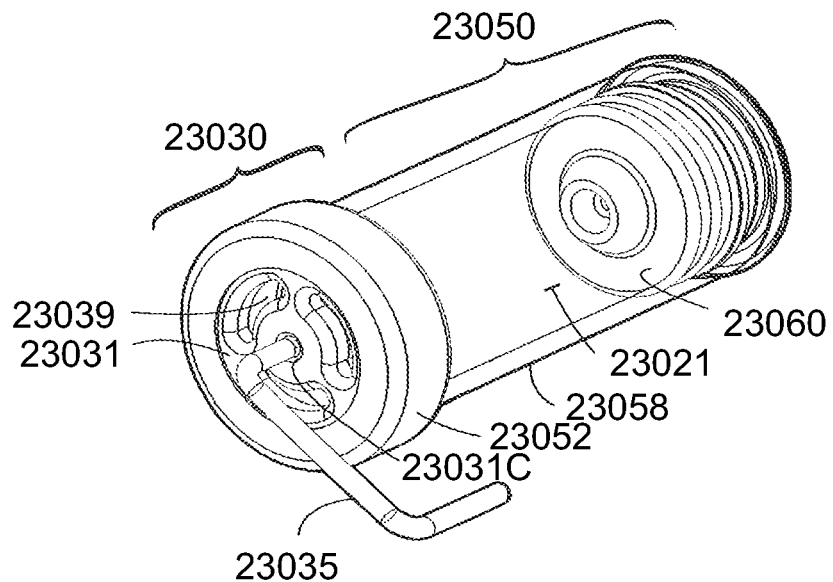
FIG. 53A is an isometric view of an integrated sterile fluid pathway connection and drug container, according to an embodiment.
Figure 53B:
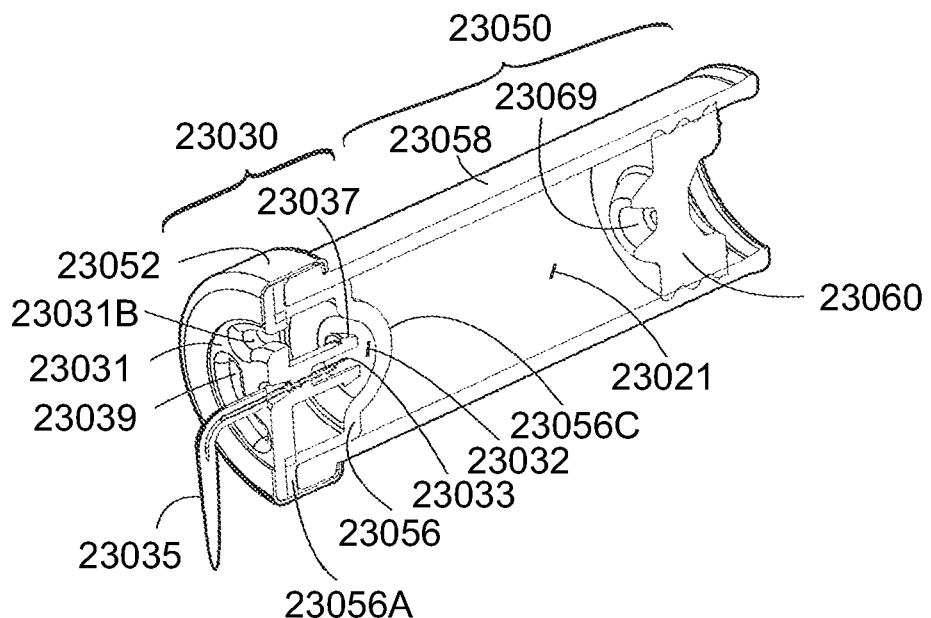
FIG. 53B is a sectional isometric view of the integrated sterile fluid pathway connection and drug container shown in FIG. 53A.

FIG. 53A and FIG. 53B show an initial configuration of an embodiment of a sterile fluid pathway connector 23030 integrated with fluid container 23050 having fluid chamber 23021 and plunger seal 23060. In some embodiments, the fluid pathway connector 23030 and the fluid container 23050 may be substituted, partially or entirely, for the fluid pathway connector 30 and the fluid container 50 illustrated in FIG. 1B of the present application. Fluid pathway connector 23030 may be mounted, connected or otherwise attached, permanently or removably, to fluid container 23050 at an end opposite plunger seal 23060. As shown in the embodiment of FIG. 53A and FIG. 53B, fluid container 23050 has mutable fluid chamber 23021 within barrel 23058, defined by the position of pierceable seal 23056 and plunger seal 23060. The seals described herein can be made of a number of materials, but are typically made of one or more elastomers or rubbers. Fluid chamber 23021 may contain a fluid for delivery through the integrated sterile fluid pathway connector 23030. In the embodiment of FIG. 53A and FIG. 53B, the fluid pathway connector 23030 includes sterile fluid conduit 23035, piercing member 23033, connector hub 23031, and pierceable seal 23056. Fluid pathway connector 23030 includes piercing member guide 37 engaged with connector hub 23031, upon which pierceable seal 23056 may interface with piercing member 23033 of connector hub 23031 during operation. A permeable, semi-permeable, or porous membrane, such as filter 23039, may be used to allow venting of air from within the fluid pathway connector 23030 during operation of the device, such as through port or vent 23031B in connector hub 23031. Filter 23039 may be attached, mounted, bonded, over-molded, co-molded, pre-formed, or otherwise connected to enclose sterile cavity 23032 between the exterior of connector hub 23031 and pierceable seal 23056. The term "enclose" or "enclosure" is used herein to define at least a semi-permeable or porous confined area that is capable of being sterilized, evacuated by vacuum, and vented, but is not penetrable by microorganisms, contaminants, or other undesirable environmental factors. For example, filter 23039 can be over-molded at least partially within connector hub 23031 to separate the sterile cavity 23032 from the outside environment. In some embodiments, the filter is a membrane, e.g., a semi-permeable membrane, which allows the venting of air during the actuation of pierceable seal 23056, fluid pathway connector 23030, and the pump device. Filter 23039 may be sterilized by methods well-known to one having skill in the art, thus the filter can maintain a sterile barrier to prevent exposure of the piercing member 23033 to microorganisms, contaminants, or other undesirable environmental factors.

As shown in FIG. 53B, piercing member 23033 is retained within the integrated sterile fluid pathway connector 23030, at or near seal barrier 23056C of pierceable seal 23056. Piercing member 23033 may be an aspect of fluid conduit 23035 or may be a separate component from fluid conduit 23035, as would readily be appreciated by one having skill in the art. Additionally, fluid pathway connector 23030 may optionally include one or more gaskets, O-rings, or other sealing members, compressed to seal between barrel 23058, particularly at lip 23058A, connector hub 23031, and housing 23052. In at least one embodiment, sealing aspect 23056A of the pierceable seal 23056 may be configured as a seal between barrel lip 23058A, connector hub 23031, and housing 23052. Housing 23052 may be a separate component, such as a crimp cap, or may be an aspect of connector hub 23031 capable of mounting to barrel 23058. The housing or cap could also have screw threads configured to complement screw threads in a fluid container, or use other impermanent means for connecting the fluid container to the sterile fluid pathway connector. As shown in FIG. 53A and FIG. 53B, the sterile fluid pathway connector 23030 may be attached to (i.e., integrated with) fluid container 23050; which in turn can be mounted, by a number of known methods, either fixedly or removably to an assembly platform or housing of a fluid pump, such as the drug delivery device 10 as shown in FIGS. 1A-1C. The assembly platform may be a separate component from the housing, or may be a unified component of the housing such as a pre-formed mounting aspect on the interior surfaces of the housing. In such configurations, the sterility of the fluid pathway is maintained, the pathway for fluid flow is not connected until desired by the user, and user-initiated activation causes the connection of the fluid chamber and the fluid pathway connector. The fluid pathway connector may, optionally, further include one or more separate flow restrictors or one or more of piercing member 23033 and fluid conduit 23035 may additionally function as flow restrictors.

The integrated fluid connection of the present embodiments is further illustrated with reference to a drive mechanism, as shown in FIG. 54A and FIG. 54B. The embodiment comprises fluid conduit 23035, engaged with piercing member 23033 at engagement 23038, connector hub 23031 that includes vent 23031B, filter 23039 which is housed against connector hub 23031, and pierceable seal 23056, which sealing portion 23056A abuts connector hub 23031 and the end of barrel 23058, all of which are housed in cap 23052. Barrel 23058 comprises mutable fluid chamber 23021, and houses plunger seal 23060 which is slidably disposed therein and in contact with a drive mechanism (e.g., the drive mechanism 100 illustrated in FIG. 1B), which includes biasing member 23099. FIG. 54A is an exploded side view of components of an integrated sterile fluid pathway connector and fluid container according to at least one embodiment. FIG. 54B shows a sectional exploded view of the same embodiment. Sterile fluid pathway connector 23030 may be integrated at least partially within fluid container 23050 at an end opposite of plunger seal 23060. An exemplary drive mechanism 23090 is shown in these figures to clarify the orientation of these components. The components of the novel sterile fluid pathway connector 23030 may be pre-assembled (see, e.g., FIG. 56A) and subsequently attached, mounted, connected or otherwise mated, permanently or removably, with a fluid container such as fluid container 23050.

A number of drive mechanisms may be utilized to force fluid from a fluid container for delivery. In one such embodiment, the drive mechanism 23090 may be substantially similar to that described in WO 2013/023033467 (PCT/US2012/023052303241). The components of the drive mechanism upon activation, may be used to drive axial translation in the distal direction (i.e., toward housing 23052 of FIG. 53) of the plunger seal of the fluid container. Optionally, the drive mechanism may include one or more compliance features that enable additional axial translation of the plunger seal to ensure, for example, that substantially the entire drug dose has been delivered to the user and that the feedback contact mechanisms have connected or interconnected. Furthermore, the drive mechanism may include one or more safety mechanisms, such as premature activation prevention mechanisms, to enhance the safety and usability of the mechanism and the device.

In a particular embodiment, drive mechanism 23090 employs one or more compression springs 23099 as biasing member(s), as shown in FIG. 54B. Upon activation of the fluid pump by the user, the power and control system is actuated to directly or indirectly release the compression spring(s) from an energized state. Upon release, the compression spring(s) may bear against and act upon the plunger seal 23060 to force the fluid out of the mutable fluid chamber 23021 of drug container 23050 as further described with reference to FIG. 55A-55C.

Figure 55A:
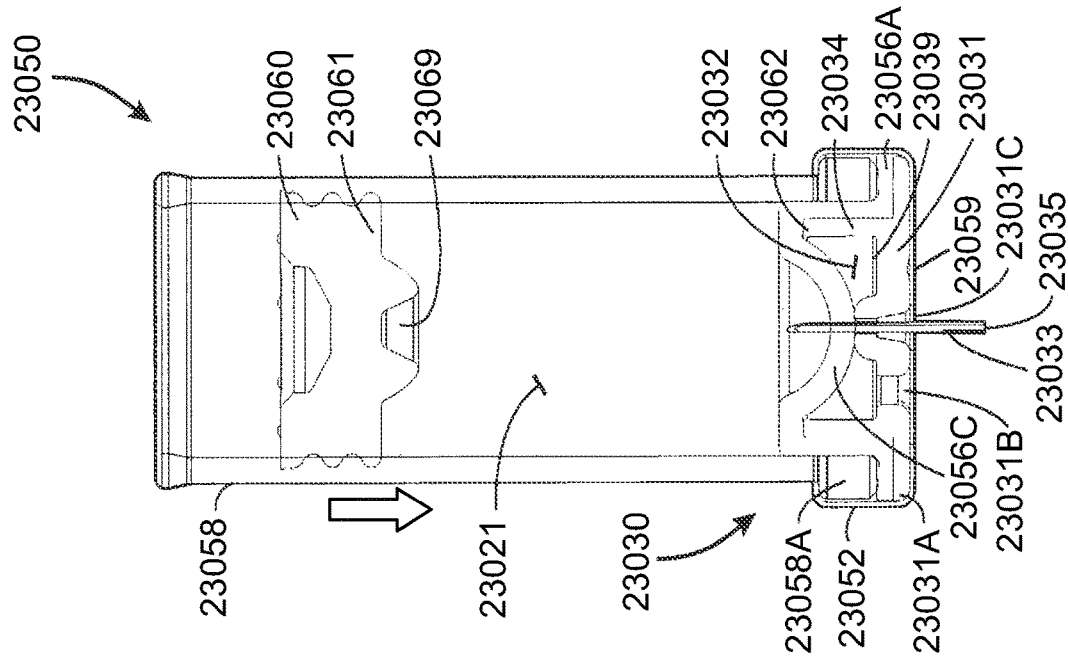
FIG. 55A is a sectional view of an integrated sterile fluid pathway connection and drug container, as shown in FIG. 53A, prior to user activation.
Figure 55B:
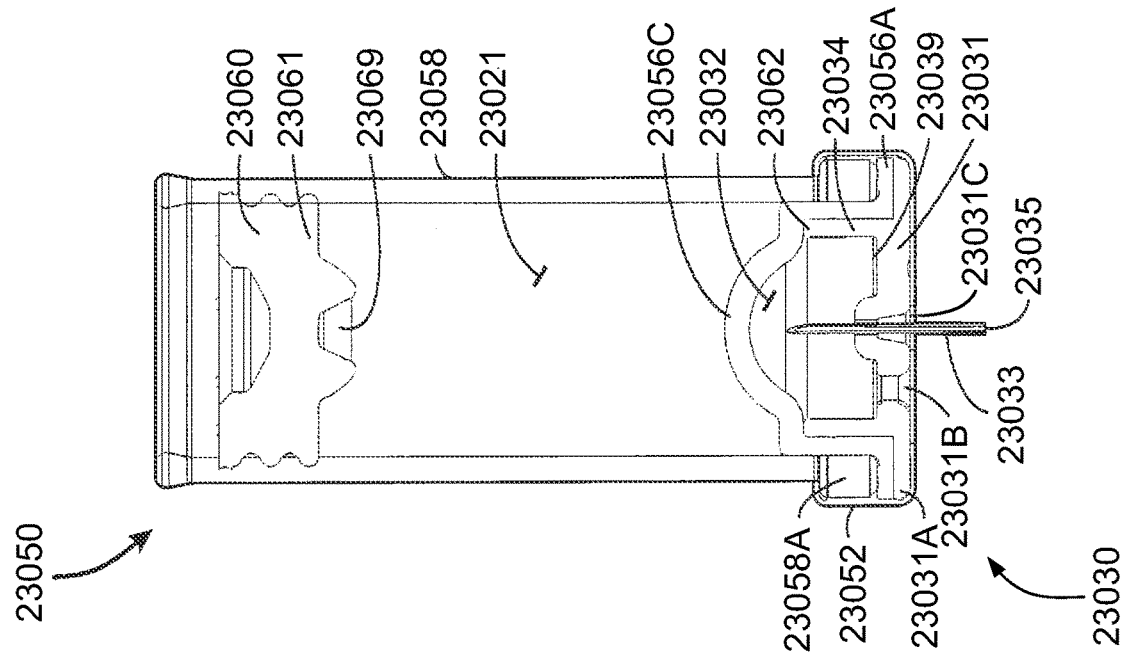
FIG. 55B is a sectional view of the embodiment with the fluid pathway connected.
Figure 55C:
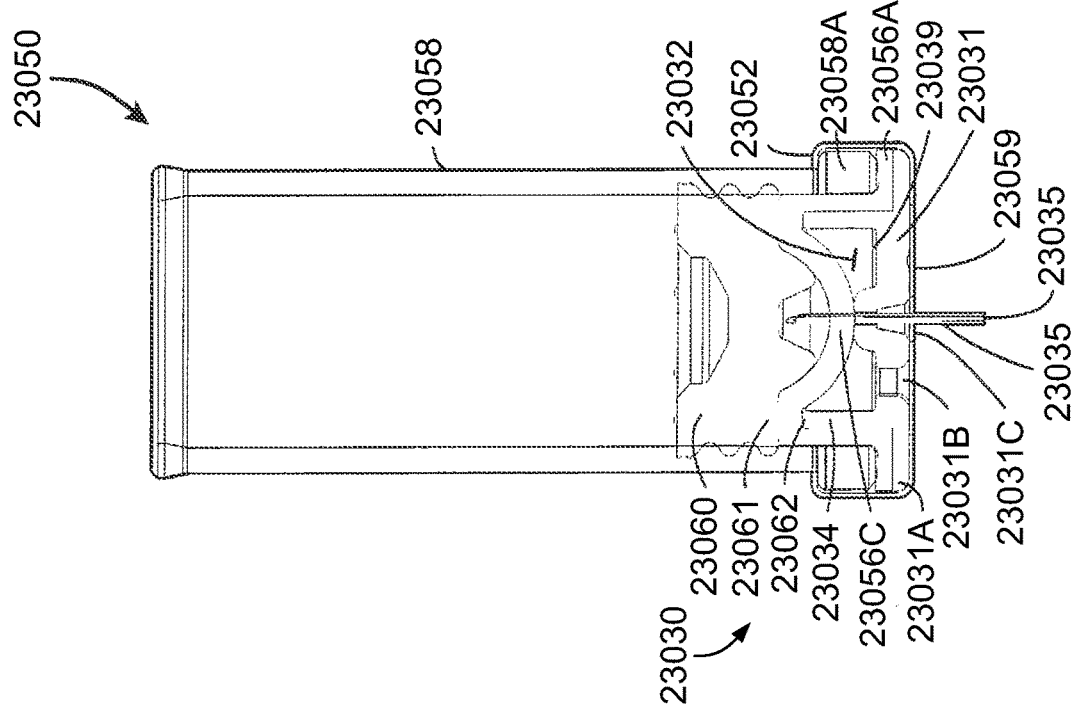
FIG. 55C is a sectional view of the embodiment at the end of drug delivery.

FIG. 55A to FIG. 55C illustrate the features of an embodiment before use, upon piercing of the pierceable seal, and upon completion of fluid delivery. More specifically, in the configuration shown in FIG. 55A, piercing member 23033 is maintained within sterile cavity 23032 with a first end (a proximal end) adjacent to, or contacting, pierceable seal 23056 of fluid pathway connector 23030. The sterility of cavity 23032 and piercing member 23033 is maintained, for example, by filter 23039 disposed between sterile cavity 23032 and the outside environment. In at least one embodiment, as shown in FIG. 55, filter 23039 is connected to, engaged with, or part of connector hub 23031, and encloses sterile cavity 23032 from the outside environment. Sterile cavity 23032 can be vented via vent or port 23031B within hub connection 23031. Accordingly, fluid pathway connector 23030, in at least one embodiment, is mounted to and integrated with fluid container 23050, for example by housing (cap) 23052 engaged with lip 23058A of barrel 23058. The piercing member may be a number of cannulas or conduits, such as rigid needles, and may be comprised of a number of materials, such as steel. In at least one embodiment, piercing member 23033 is a rigid steel needle. Pierceable seal 23056 may have sealing aspect 23056A that permits pierceable seal 23056 to be mounted directly to or otherwise be held in position between barrel 23058, connector hub 23031, and cap 23052. Connector hub 23031 includes an internal seal mount 23034 that further stabilizes the position of more stationary aspects of pierceable membrane 23056. At least a portion of pierceable seal 23056, such as seal barrier 23056C, is translatable upon connector hub 23031, as described herein, to rupture against piercing member 23033 and enable the fluid pathway connector to sterile fluid conduit 23035. Advantageously, such an arrangement permits pierceable seal 23056 to translate towards cap 23052 but not towards the plunger seal 23060. This is a desirable feature that permits the mutable fluid chamber 23021 of the fluid container 23050 to be evacuated, such as by vacuum, prior to filling with a fluid without compromising the function of sterile fluid pathway connector 23030.

In an initial position the proximal end of piercing member 23033 may reside adjacent to, or in contact with, seal barrier 23056C of pierceable seal 23056 to, for example, minimize the distance of translation of the seal barrier 23056C to become pierced and open fluid container 23050 to fluid pathway connector 23030. In a particular embodiment, proximal end of the piercing member 23033 may reside at least partially within seal barrier 23056C of pierceable seal 23056, yet not fully passing there-through, until activation of the device by a user.

As shown in FIG. 55B, once the pump device is activated and the drive mechanism pushes plunger seal 23060, plunger seal 23060 asserts a force on fluid chamber 23021, and pneumatic and/or hydraulic pressure builds by compression of the fluid in chamber 23021. As pneumatic and/or hydraulic pressure builds within fluid chamber 23021, the force is relayed to pierceable seal 23056, causing barrier seal 23056C to transform. This transformation may include a shift, inversion, translation, flexion, deformation, pop, snap, or any other functionally equivalent change, such that a portion of pierceable seal 23056, such as seal barrier 23056C, impinges against the substantially fixed position of piercing member 23033 and causes piercing member 23033 to pierce pierceable seal 23056 at seal barrier 23056C, as shown in FIG. 55B, thereby opening or otherwise connecting the fluid pathway between mutable fluid chamber 23021, piercing member 23033, and fluid conduit 23035.

Accordingly, integrated sterile fluid pathway connector 23030 is connected (i.e., the fluid pathway is opened) by the pneumatic and/or hydraulic force of the fluid within the fluid chamber 23021 created by activation of the drive mechanism. Once integrated sterile fluid pathway connector 23030 is connected or opened, fluid is permitted to flow from the fluid container 23050, through integrated sterile fluid pathway connector 23030 and sterile fluid conduit 23035. In aspects in which the fluid pump is an ambulatory drug infusion pump, fluid drug then flows through the insertion mechanism and into the body of the user for drug delivery. In at least one embodiment, a number of flow restrictors may be optionally utilized to modify the flow of fluid within the fluid pathway connector. In at least one embodiment, the fluid flows through only a manifold and a cannula or needle of the insertion mechanism, thereby maintaining the sterility of the fluid pathway before and during fluid delivery.

Additionally or alternatively, plunger seal 23060 or the pierceable seal 23056 may have some compressibility permitting a compliance push of fluid from drug container 23050. Additionally, the drive mechanism, plunger seal 23060, connector hub 23031, pierceable seal 23056, or a combination thereof, may include one or more sensors or status indication mechanisms, such as interconnects and contacts, to measure and communicate the status of drug delivery drive before, during, and after operation of the device to deliver fluid.

FIG. 55C shows the components of fluid container 23050 and sterile fluid pathway connector 23030 after substantially all of the fluid has been pushed out of the fluid container 23050. In particular, plunger seal 23060 is in the most-distal position in barrel 23058. In the embodiment of FIG. 55C, the connector hub-side (e.g., distal end) of plunger seal 23060 is configured with an optional protrusion and cavity aspect 23069, which structure minimizes residual volume left in fluid chamber 23021, now collapsed. Alternatively, plunger seal may be a flat-faced plunger seal (e.g., plunger seal 23160 in FIG. 57A and FIG. 58), or may have any number of other configurations as would be readily appreciated by one having skill in the art. In the embodiment shown in FIG. 55, plunger seal 23060 further comprises interconnect/contact 23061; and connector hub 23031 further comprises interconnect/contact 62. At end-of-delivery, interconnect/contact 61 of plunger seal 23060 and interconnect/contact 62 of connector hub 23031 interconnect and transduce a signal that may be perceived by a user. As described herein, numerous sensors and signal transducing means can be incorporated or adapted for use in the present embodiments.

Because of the novel design of the fluid pathway connector of the present embodiments and their integration at least partially within fluid containers, sterility of the fluid pathway is maintained throughout transport, storage, and operation of the device; user-activation of the device is simplified; and the fluid pathway is only connected when desired by the user. The sterility of the fluid pathway connector is initially maintained by performing the connection within a sterile cavity 23032 between connector hub 23031, pierceable seal 23056, and piercing member guide 23037. In at least one embodiment, the sterility of cavity 23032 is maintained by filter 23039 that abuts, is engaged with or part of, connector hub 23031. Filter 23039 may be, for example, a semipermeable membrane that allows the venting of air through vent 23031B of connector hub 23031 during the actuation and translation of pierceable seal 23056. Filter 23039 may be sterilized by typical sterilization methods, which would readily be appreciated by one having skill in the art, and may be used to maintain a sterile barrier that prevents exposing piercing member 23033 to microorganisms, contaminants, or other undesirable environmental factors. For example, upon substantially simultaneous activation of the insertion mechanism, the fluid pathway between mutable fluid chamber 23021 and insertion mechanism is complete to permit drug delivery into the body of the user. Because fluid pathway connector 23030 is not in fluid connection or communication with fluid chamber 23021 until activation of the fluid pump and drive mechanism, fluid flow from the fluid container 23050 is prevented until desired by the user. This provides an important safety feature to the user and also maintains the container integrity of the fluid container and sterility of the fluid pathway.

The drive mechanism that translates the plunger seal 23060 may contain one or more drive biasing members (e.g., as shown in FIG. 54B). The components of the drive mechanism function to force a fluid from the mutable fluid chamber 23021 through pierceable seal 23056 and through the piercing member 23033 or sterile fluid conduit 23035, for delivery through fluid pathway connector 23030. Further regarding the drive mechanism, a number of drive mechanisms may be utilized to force fluid from a drug container for delivery into the body of a user. In one such embodiment, the drive mechanism 23090 may be substantially similar to that described in WO 2013/023033467 (PCT/US2012/023052303241), which is hereby incorporated by reference in its entirety. The components of the drive mechanism, upon activation, drive axial translation in the distal direction of the plunger seal of the drug container. Optionally, drive mechanism may include one or more compliance features which enable additional axial translation of the plunger seal to, for example, ensure that substantially the entire fluid dose has been delivered to the user and make sure that the feedback contact mechanisms have connected. Furthermore, the drive mechanism may include one or more safety mechanisms, such as premature activation prevention mechanisms, to enhance the safety and usability of the mechanism and the device.

Figure 56A:
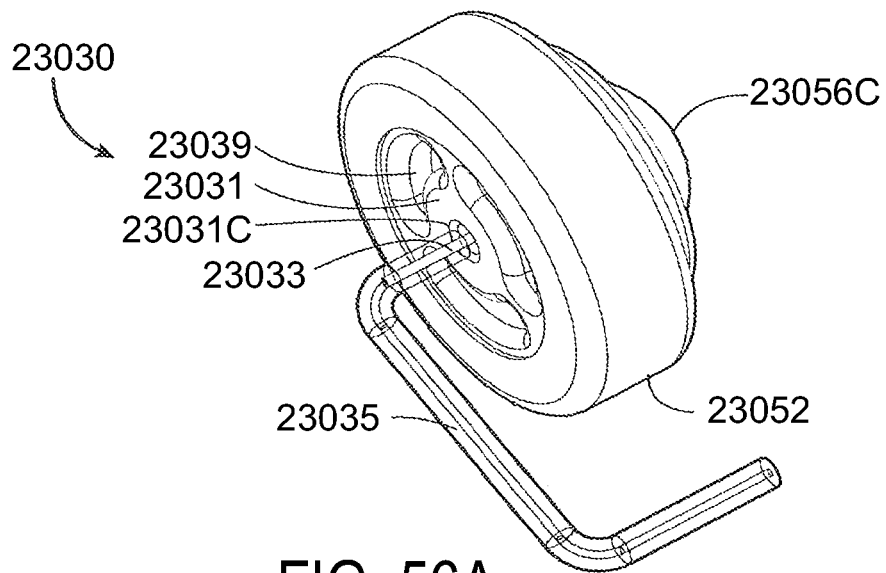
FIG. 56A is an isometric perspective view, of the integrated sterile fluid pathway connection according to an embodiment of the present invention.
Figure 56B:
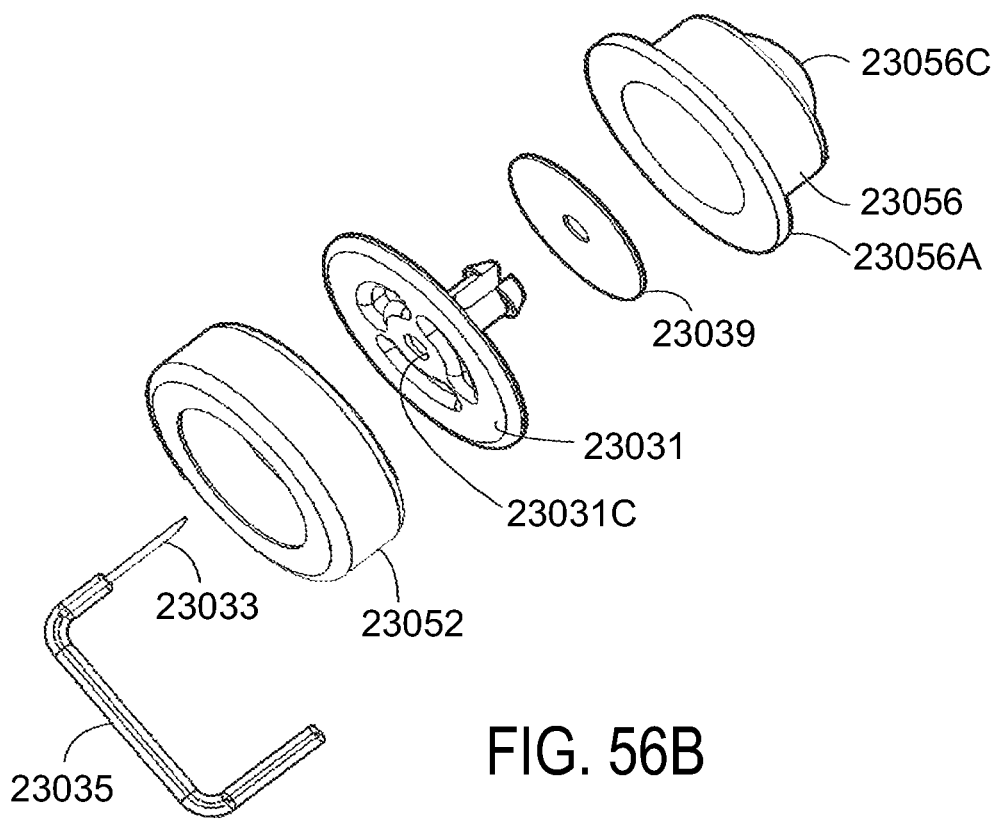
FIG. 56B is an exploded, perspective view of the components of the integrated sterile fluid pathway connection shown in FIG. 56A.

At least one embodiment provides for a modular fluid pathway connector. FIG. 56A and FIG. 56B detail an embodiment of a modular fluid pathway connector that comprises connector hub 23031, which abuts filter 23039 and pierceable seal 23056 at sealing member 23056A. Connector hub 23031, filter 23039 and pierceable seal 23056 are housed within cap 23052, as shown in FIG. 56A. Connector hub 23031 further comprises header 23031C, which forms a junction for fluid conduit 23035 and piercing member 23033. As shown in FIG. 56A and FIG. 56B, fluid conduit 23035 may be connected directly to piercing member 23033. Alternatively, as shown in FIG. 57A fluid conduit 223035 may be connected via conduit port 223038. Nevertheless, a modular fluid pathway connector can be adapted for use with a number of alternative barrel and drive configurations, and used within a variety of ambulatory infusion devices. The components of the novel sterile fluid pathway connector 23030 may be pre-assembled, to appear as exemplified in FIG. 56A, and subsequently attached, mounted, connected, or otherwise mated with a fluid container such as fluid container 23050. Alternatively, the components of sterile fluid pathway connector 23030 may be assembled directly into drug container 23050. As would be readily appreciated by one skilled in the art, a number of glues or adhesives, or other connection methods such as snap-fit, interference fit, screw fit, fusion joining, welding, ultrasonic welding, laser welding, and mechanical fastening, and the like, can be used to engage one or more of the components described herein in permanent or impermanent connection as desired for a particular use. For example, glue can be used between distal end of barrel 23058, sealing member 23056A, or connector hub 23031A. Additionally or alternatively, the components of the sterile fluid pathway connector 23030 may be mounted to barrel 23058 and held in place crimping cap 23052 to distal aspect of barrel 23058, such as to a flanged aspect or lip of barrel 23058A.

In at least one embodiment, as shown in FIG. 57A to FIG. 57C, piercing member guide 230237 may be utilized to guide pierceable seal 23056 and to slidably engage the connector hub 230231. Additionally or alternatively, piercing member guide 230237 may be utilized to ensure that piercing member 230233 remains substantially centered on the axis so as to pierce pierceable seal 23056 at the desired portion of seal barrier 23056C. The embodiment of FIG. 57A shows fluid container comprising barrel 23058 and forming mutable fluid chamber 23021 between plunger seal 230260 and pierceable seal 56. As shown in FIG. 57A, plunger seal 230260 is a flat plunger seal, but a variety of plunger seal shapes can be adapted for use with the fluid connection and infusion pumps of the present embodiments. The embodiment of FIG. 57A further comprises filter 23039, which abuts connector hub 230231 and is used to maintain sterility of sterile chamber 23032 between connector hub 230231 and pierceable seal 23056. Connector hub 230231 also includes seal mount 230234 that abuts pierceable seal 23056; and flange 230231A that abuts seal member 23056A of seal 23056, and that, in turn, abuts the distal lip 23058A of barrel 23058. The meeting surfaces of connector hub 230231A, sealing member 23056A and barrel lip 23058A are positioned in place and secured within the rims of cap 23052. Connector hub 230231 also houses piercing member 230233, which connects to fluid conduit 230235. Connector hub 230231 also has vacuum port 230231B, a filtered channel that leads into sterile chamber 23032. Connector hub 230231 is also configured with conduit port 230231D, which provides exit from sterile fluid connector 230230 to the rest of the infusion device (e.g., injection means), such as via sterile fluid conduit 23035 (not shown). Conduit port 230231D and vacuum port 230231B may contain a membrane or seals, such as one-way seals, which permit fluid flow out of chamber 23032 through the respective ports but do not permit fluid flow into the chamber 23032 through these ports. Additionally, or alternatively, conduit port 230231D and vacuum port 230231B may be plugged at certain points of assembly or operation. For example, vacuum port 230231B may be used to evacuate sterile cavity 23032 during manufacturing, assembly, or at any point prior to operation of the device; and then vacuum port 230231B can be plugged after the evacuation has been completed.

Further regarding piercing member guide 230237, this component may be slidably attached to connector hub 230231. A number of means known in the art may be used to facilitate this slidable attachment such as, for example, engagement between a connector prong 230237D and leg 230237A of piercing member guide 230237 with complementary cavity 230236 in connector hub 230231. These components are more clearly visible in FIG. 57A and FIG. 144B. FIG. 57B shows the orientation of piercing member 230233 within piercing member guide 230237, which emerges from piercing member guide 230237 at header 230237C; and FIG. 57C shows the orientation of piercing member 23033 and piercing member guide 230237 within connector hub 230231. Such an arrangement permits the pierceable seal 23056 and piercing member guide 230237 to translate towards housing 23052 together, at least for a portion of the translation of seal barrier 23056C. Additionally, pierceable seal 23056 may be removably attached to piercing member guide 230237 by a number of means known in the art such as, for example, removable snap-fit engagement or it may be configured to enable contact between the components to guide the translation of the seal barrier 23056C upon the piercing member 230233. When a piercing member guide is used, such as piercing member guide 230237 in FIG. 57A, the piercing member guide may translate with pierceable seal 23056, for at least a portion of the translation, to ensure that the seal barrier 23056C contacts and is pierced by the piercing member 230233. Once the fluid pathway is opened or connected, translation of plunger seal 230160 in the distal direction by the drive mechanism causes fluid within drug chamber 23021 to be forced through the sterile fluid connector. In some embodiments, a needle insertion mechanism, as described herein, may be connected at the other end of the fluid conduit 23035 to insert a needle into the body of the user to facilitate fluid transfer to the user.

The embodiment shown in FIG. 57A also comprises plunger seal 260, which may be used as a part of the status indication mechanism along with piercing member guide 237. More specifically, in this embodiment plunger seal 260 includes interconnect/contact 261 and the corresponding interconnect/contact 262 is located on piercing member guide 237. When plunger seal 260 and piercing member guide 237 reach proximity at end-of-delivery (e.g., as in FIG. 57C), interconnect/contact 261 and interconnect/contact 261 interconnect and transduce a perceptible signal to the user.

The novel embodiments presented herein provide integrated sterile fluid pathway connectors and fluid containers, and fluid pumps that utilize such connections, that are configured to maintain the sterility of the fluid pathway before, during, and after operation of the device, and that enable active safety controls for the device. Integration of the fluid pathway connector into a portion of the fluid container helps ensure container integrity and sterility of the fluid pathway. Additionally, by integrating the sterile fluid pathway connector into a portion of the fluid container, the connection for fluid transfer can be controlled by the user (i.e., user-activated) and enabled by the function of the drive mechanism. Accordingly, user-activation steps and the internal operation of the fluid pump can be greatly simplified by the novel integrated sterile fluid pathway connectors of the present embodiments.

Figure 58:
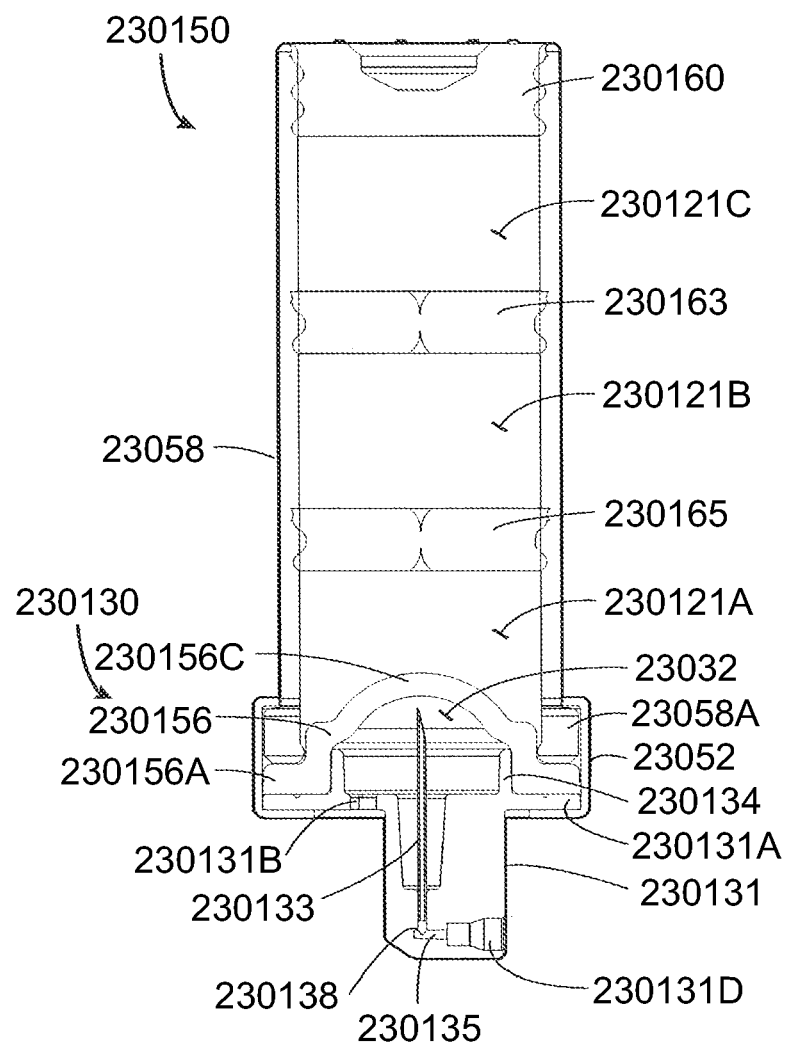
FIG. 58 is a cross-sectional view of an integrated sterile fluid pathway connection and drug container according to an embodiment prior to user activation, in which the drug container comprises more than one drug chamber, each drug chamber separated from the next by a pierceable membrane.

In another embodiment, the fluid container comprises at least two mutable internal compartments, wherein each compartment-compartment interface comprises a distinct pierceable seal capable of being disrupted by the piercing member of the sterile fluid pathway connector to create a sterile fluid communication between the sterile fluid pathway and that compartment of the sterile fluid container. As shown in FIG. 58, container 23050 may utilize one or more seals in addition to plunger seal 230160 and pierceable seal 230156. This may be applicable, for example, when multiple fluid substances are desired to be delivered by the container and the infusion pump device. FIG. 58 shows one such embodiment that utilizes two additional seals, 230163 and 230165, to create compartments or chambers 230121A, 230121B and 230121C, within which one or more fluid substances may be stored for delivery. The embodiment of FIG. 58, pierceable seal 230156 includes seal barrier 230156C and base 230156A, which base 230156A abuts barrel lip 23058A on its distal side and connector hub 230131A on its proximal side, which abutments are held within housing 23052. Connector hub 230151 further includes vacuum port 230131B, with a channel that leads into sterile chamber 23032. Connector hub 230131 is also configured with conduit port 230131D, which provides exit from sterile fluid connector 230130 to the rest of the infusion device (e.g., an injection mechanism). Conduit port 230131D and vacuum port 230131B may each contain a membrane, filter or seals, such as one-way seals, which permit fluid flow out of chamber 23032 through the respective ports but do not permit fluid flow into the chamber 23032 through said ports. Additionally, or alternatively, conduit port 230131D and vacuum port 230131B may be plugged at certain points of assembly or operation. For example, vacuum port 230131B may be used to evacuate sterile cavity 32 during manufacturing, assembly, or at any point prior to operation of the device; and then vacuum port 230131B can be plugged after the evacuation has been completed.

Upon activation of the fluid pump, pressure at interface 230168 of plunger seal 230160 causes distal translation of plunger seal 230160 towards housing 23052. The pneumatic and/or hydraulic pressure within the fluid substance(s) held in drug chambers 230121A, 230121B and 230121C relays the force to, and causes distal translation of, chamber seal 230163, chamber seal 230165, and pierceable seal 230156, causing seal barrier 230156C to translate towards housing 23052 and become pierced by piercing member 230133. This causes the sterile fluid pathway connector to be made or opened, as described herein. Upon further translation of plunger seal 160, the fluid substance held in mutable drug chamber 230121A is dispensed through conduit 230135. Upon further translation of the fluids and seals, seal 230165 may be then be pierced by piercing member 230133, thereby permitting the fluid substance in mutable fluid chamber 230121B to be dispensed from the fluid pathway connector.

If further compartments or chambers are desired, more seals and chambers (such as seal 230163 and mutable chamber 230121C) may be configured, and subsequently engaged in the same manner until plunger seal 230160 has been fully translated towards housing 23052. This configuration may offer advantages over single-compartment fluid containers. For example, a diluent may be stored in mutable fluid chamber 230121A and a therapeutic drug may be stored in mutable fluid chamber 230121B, such that the sterile fluid pathway is first purged by the diluent prior to delivery of the drug therapy to the patient. When drug combinations are desired for delivery, multiple therapeutic agents may be stored and delivered using the configuration provided by this embodiment. Any number of seals and drug chambers may be utilized in such a configuration provided that the piercing member 230133, the drive mechanism, and other components of the embodiments are configured appropriately for such delivery.

The novel integrated sterile fluid pathway connectors of the present disclosure may additionally incorporate status indication into the fluid delivery mechanisms. Such status indication features may be incorporated into the drive mechanism 23090, as described in WO 2013033467. Additionally or alternatively, status indication features may be incorporated into the components of the sterile fluid pathway connectors. In one embodiment, one or more interconnects are contained within, or proximal of, the plunger seal. At the end of fluid delivery, the piercing member may be utilized to contact the, or as a contact for, interconnect to open, close, or otherwise create a signal to the power and control system to provide feedback to the user. In another embodiment, one of either interconnects/contacts are contained within, or proximal of the plunger seal, while the other is contained within or distal of the pierceable seal, such as in or on a seal mount or guide piece. At the end of fluid delivery, interconnects and corresponding contacts are close enough to permit a signal to be sent to the power and control system to provide feedback to the user.

In another embodiment, the surface of the connector hub sequestered in sterile chamber 23032 may incorporate, or itself be utilized as, a contact or interconnect for the status indication mechanism. For example, an end-of-delivery signal can be provided using a leaf/flex arm or spring style switch mechanism contained within sterile compartment 23032, engaged with the surface of the connector hub and connected through the hub to the appropriate electronics. In this arrangement, in the unpressurized state (before device activation), the switch rests in the open position, and there is no contact/interconnect or signal transduced. When the device is activated, i.e., when the drive engages the plunger seal within the drug container, pneumatic and/or hydraulic pressure causes the pierceable seal to translate into the piecing member, thus disrupting the pierceable seal and allowing fluid to flow through the sterile fluid connector. Pneumatic and/or hydraulic pressure further causes the septum of the pierceable seal to press against the switch mechanism until it interconnects with its complementary contacts, which closes the circuit and allows a signal to transduce to the user, indicating that drug delivery has started. At end-of-delivery, the pneumatic and/or hydraulic pressure within the sterile chamber is released and the switch re-opens, breaking the circuit and providing an end-of-delivery signal to the user.

Figure 59A:
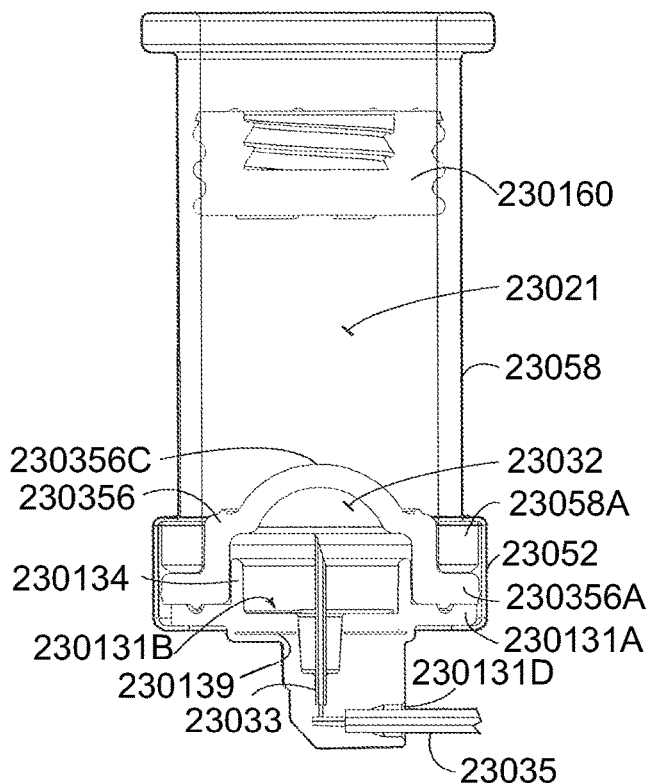
FIG. 59A to FIG. 59E are sectional views of an embodiment of a sterile fluid connector in which the pierceable seal is configured to maintain different positions within the connector in response to pneumatic and/or hydraulic pressure.
Figure 59B:
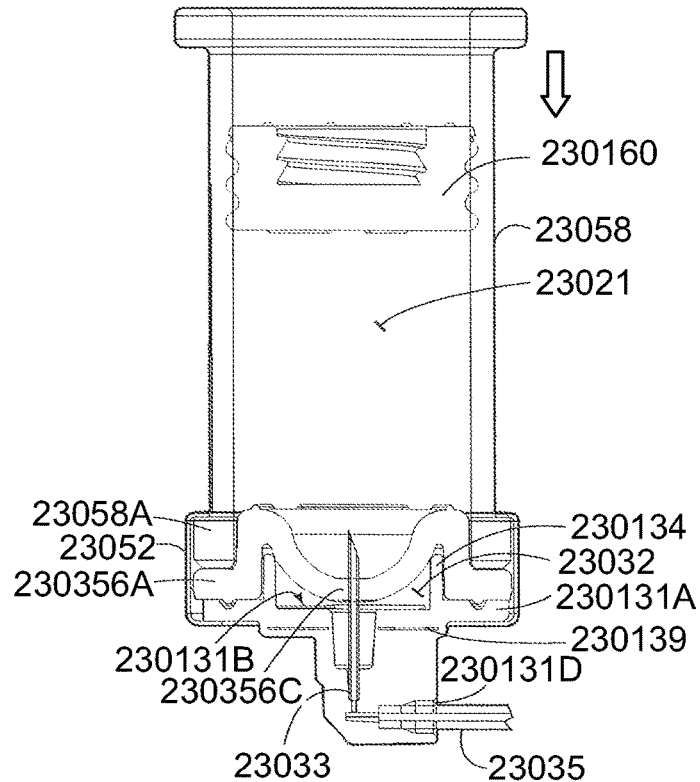
Figure 59C:
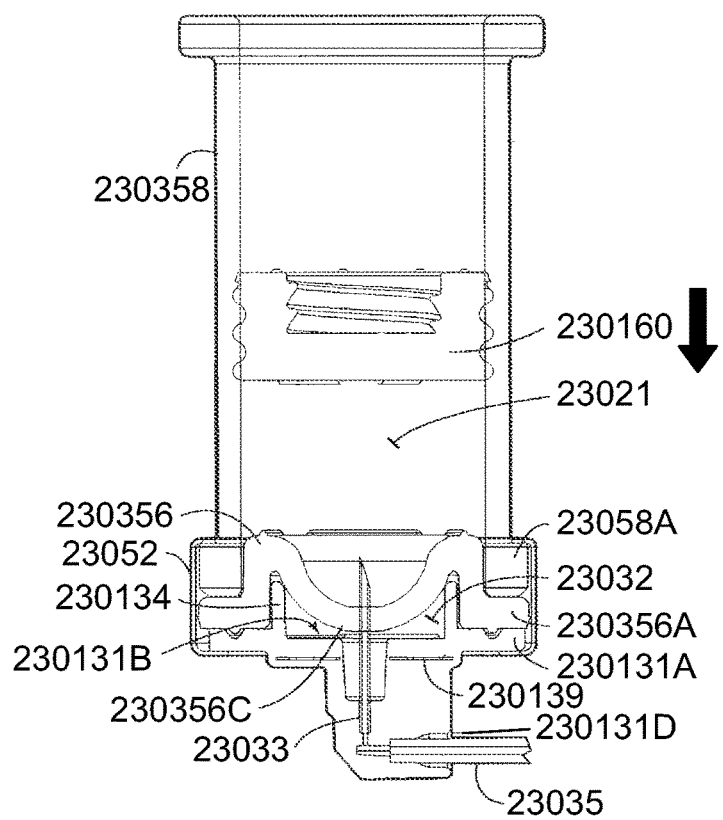
Figure 59D:
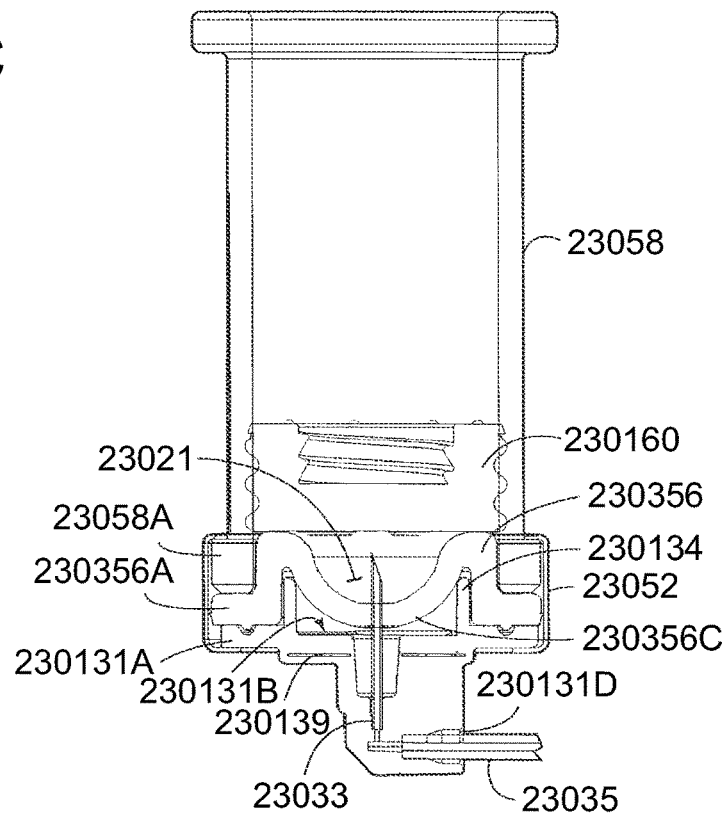
Figure 59E:
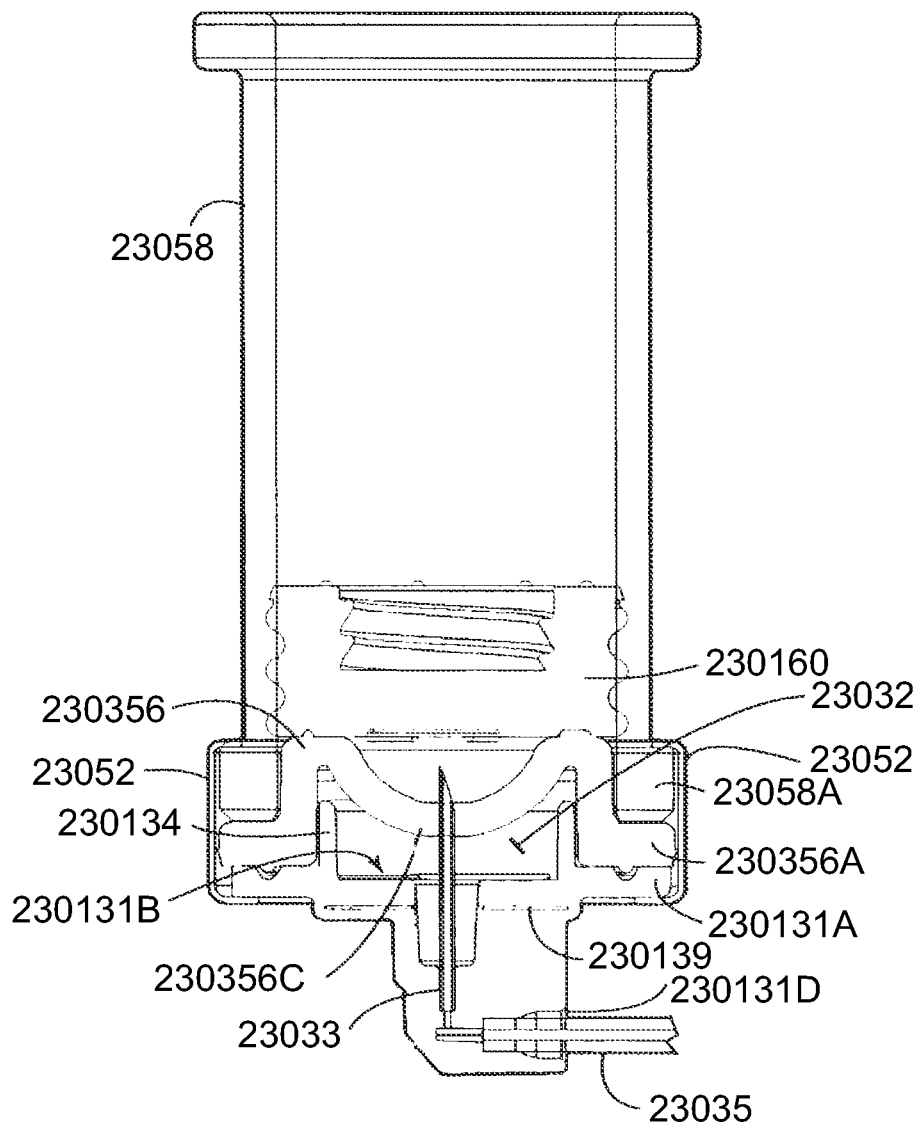

Such a configuration, in which the surface of the connector hub sequestered in the sterile chamber of the sterile fluid pathway connector may incorporate, or itself be utilized as, a contact or interconnect for the status indication mechanism, may be facilitated by a configuration of the pierceable seal. For example, as shown in FIG. 59A to FIG. 59E, fluid chamber 23058 comprises plunger seal 230160, configured to engage a drive mechanism that forces plunger seal 230160 towards sterile fluid connector 230130. In the initial position (i.e., before the drive is engaged), pierceable seal 230356 maintains sterile chamber 23032 within the space defined by pierceable seal 230356 and connector hub 230131, particularly as partially maintained by seal mount 230134, as shown in FIG. 59A. Connector hub 230131 further includes piercing member 23033, and vacuum port or vent 131B in which sterility of chamber 23032 is maintained by filter 23039. Connector hub base 230131A, sealing member 230356A of pierceable member 230356, and barrel lip 23058A are all secured in housing 23052, which housing can be a cap such as a crimp cap. Connector hub 230131 also includes exit port 230131D, which provides an exit passage for fluid conduit 23035 from the sterile fluid pathway connector. Once a pump drive is activated and plunger seal 230160 is forced toward piercing member 23033, pneumatic and/or hydraulic pressure within mutable fluid chamber 23021 forces seal barrier 230356C of pierceable seal 230356 into piercing member 23033, which pierces seal barrier 230356C and opens the sterile fluid pathway. Continued pneumatic and/or hydraulic pressure within mutable chamber 23021 forces at least a portion of pierceable seal 230356 to contact at least a portion of connector hub 230131 within sterile chamber 23032, as shown in FIG. 59B. This continued pneumatic and/or hydraulic pressure, as long as the drive is activated and fluid remains in mutable chamber 23021, maintains the contact between seal 230356 and connector hub 230131, as shown in FIGS. 59C and 59D. When fluid has been pumped out of mutable fluid chamber 23021, such that this chamber essentially no longer exists, pneumatic and/or hydraulic pressure against seal 230356 is released, and seal 230356 returns to a non-pressurized state within chamber 23032, in which there is no longer contact between seal 230356 and hub 230131, as shown in FIG. 59E.

Figure 60A:
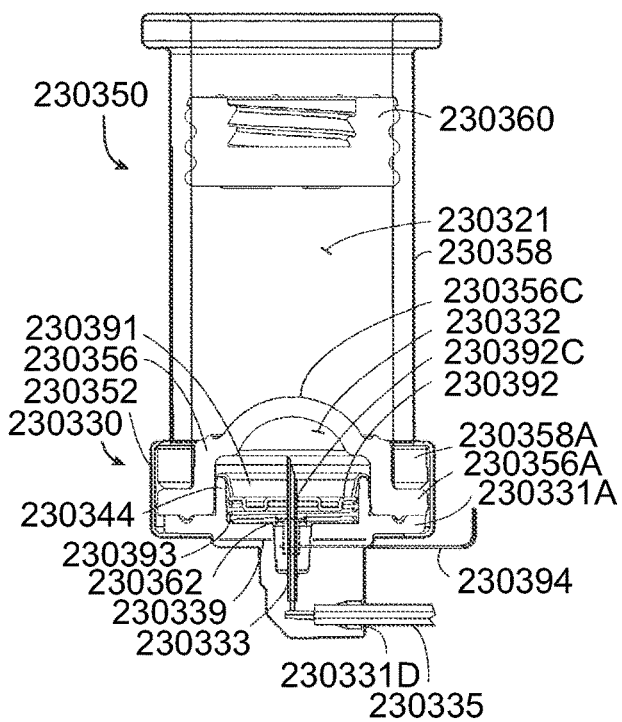
FIG. 60A to FIG. 60H are sectional and isometric sectional views of an embodiment of a sterile fluid connector in which the pierceable seal, in response to pneumatic and/or hydraulic pressure, engages or disengages a sensor mechanism that is capable of transmitting a signal indicating the status of fluid transfer from the sterile fluid container to the connector.
Figure 60B:
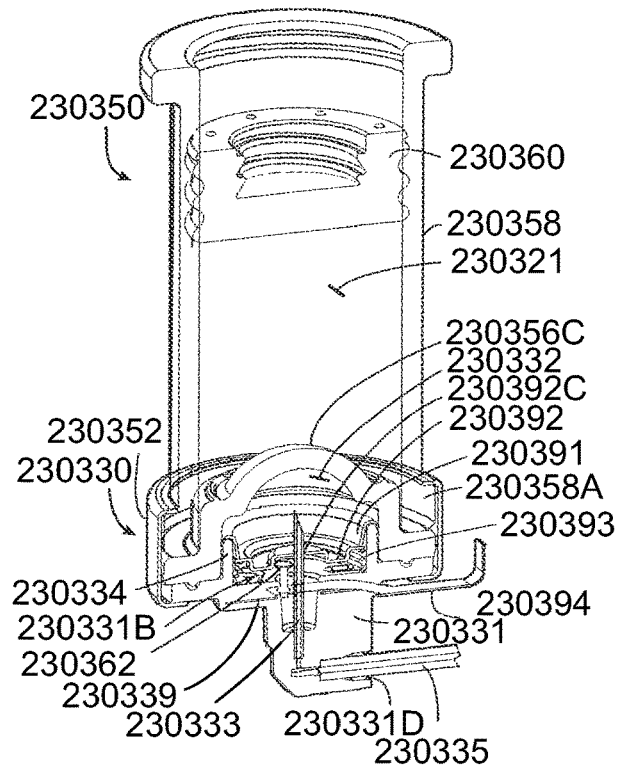

This aspect of the embodiments is advantageous for a number of devices and configurations useful to provide the sterile fluid pathway connector with at least one sensor configured to indicate the status of fluid transfer from the sterile fluid container to the connector. An example of such a sensor is a "switch" mechanism contained within the sterile chamber in the sterile fluid connector. For example, in the embodiment shown in FIG. 60A to FIG. 60H, fluid container 230350 includes barrel 230358, which houses fluid chamber 230321 and plunger seal 230360, configured to engage a drive mechanism that forces plunger seal 230360 and fluid in mutable fluid chamber 230321 toward sterile fluid connector 230330. Pierceable seal 230356 maintains sterile chamber 230332 within the space defined by pierceable seal 230356 and connector hub 230331, as shown in FIG. 60A and FIG. 60B, in which the fluid pathway is "closed." Connector 230330 further includes connector hub 230331, which further vacuum port 230331B, in which sterility of chamber 230332 is maintained by filter 230339; exit port 230331D, which provides an exit passage for fluid conduit 230335 from sterile fluid pathway connector 230330; and engages piercing member 333. Connector hub base 230331A, pierceable seal 230356 sealing member 230356A, and barrel lip 230358A are secured in housing 230352. Connector hub 230331 further houses, in sterile chamber 230332, stamped ring 230391 fitted on seal mount 230334 of connector hub 230331; contact 230392; spring 230393; and interconnects 230362 which are in communication with flexible power strip 230394 (flex). As shown in FIG. 60A and FIG. 60B, in the initial state before activation of the drive, spring 230393 rests in a non-compressed state, and contact 230392 is held between spring 230393 and stamped ring 230391 in a position in which there is no contact between interconnects 230362 and contact 230392. Contact 230392 is further stabilized within sterile chamber 230332 by the position of piercing member 230333 that passes through contact 230392 through passage 230392C.

Figure 60C:
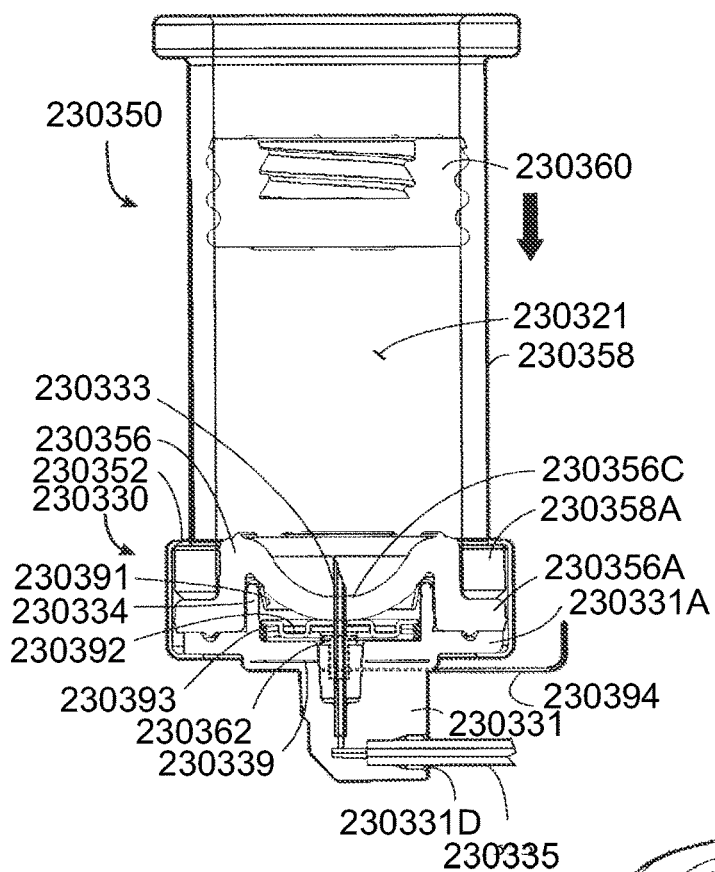
Figure 60D:
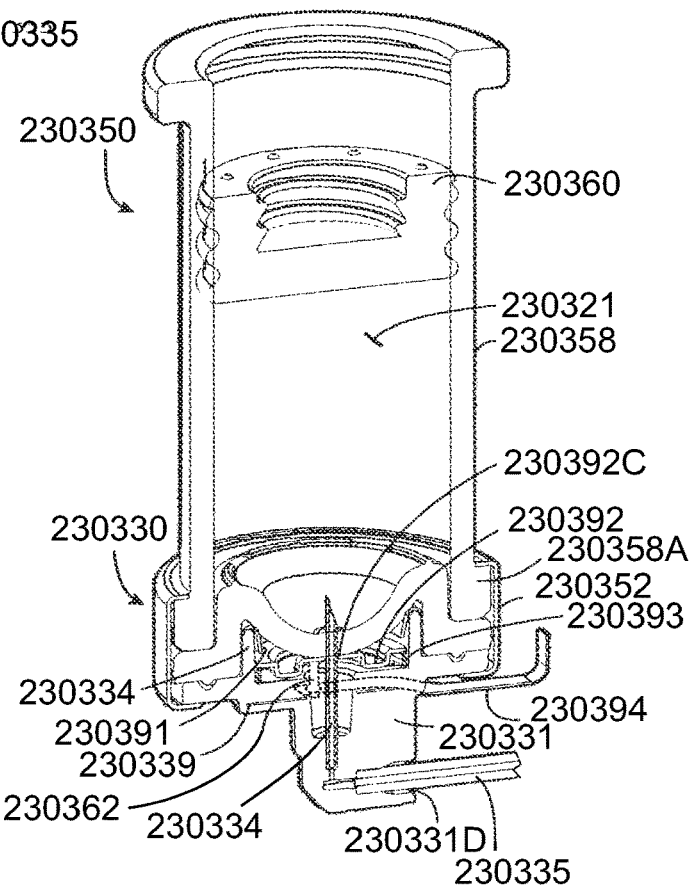
Figure 60E:
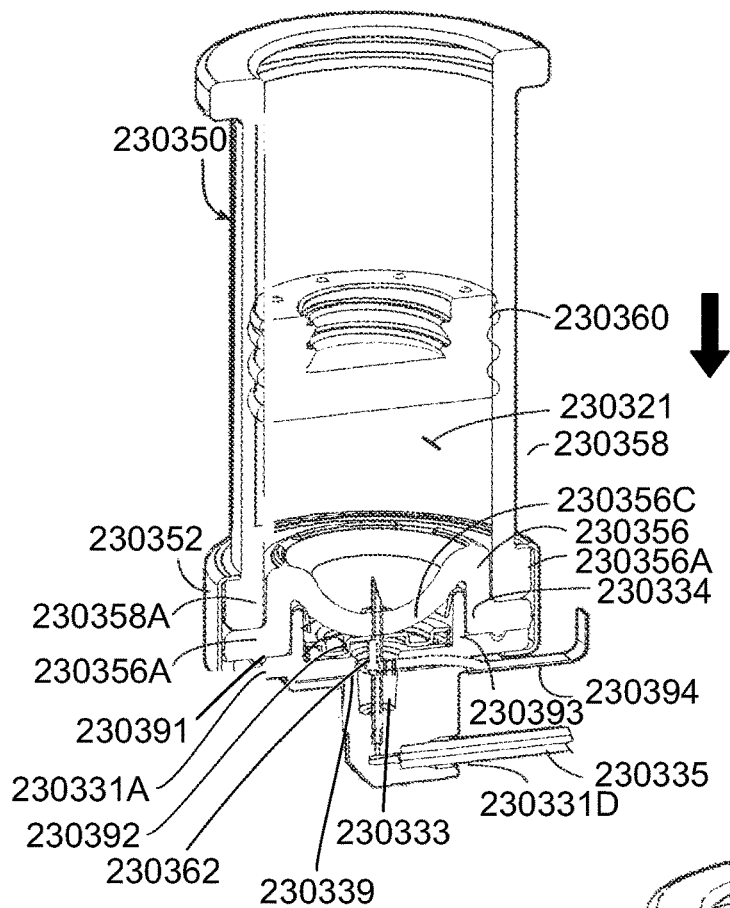
Figure 60F:
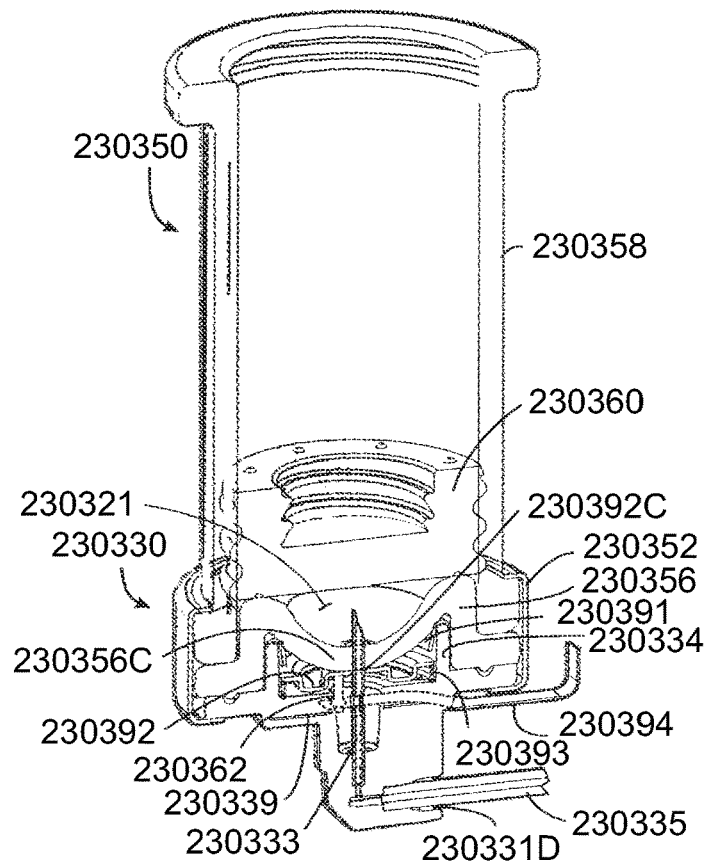
Figure 60G:
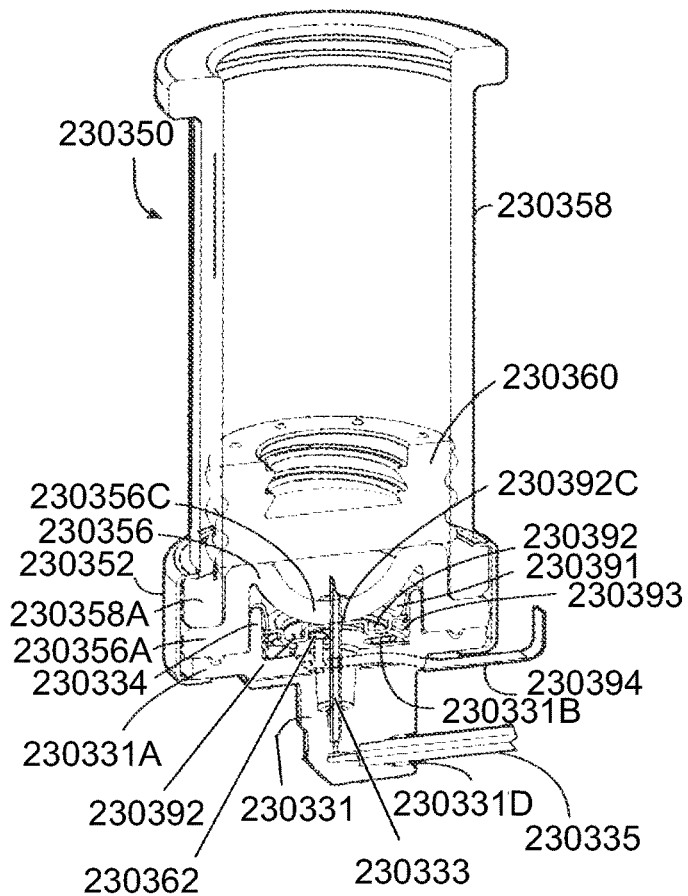
Figure 60H:
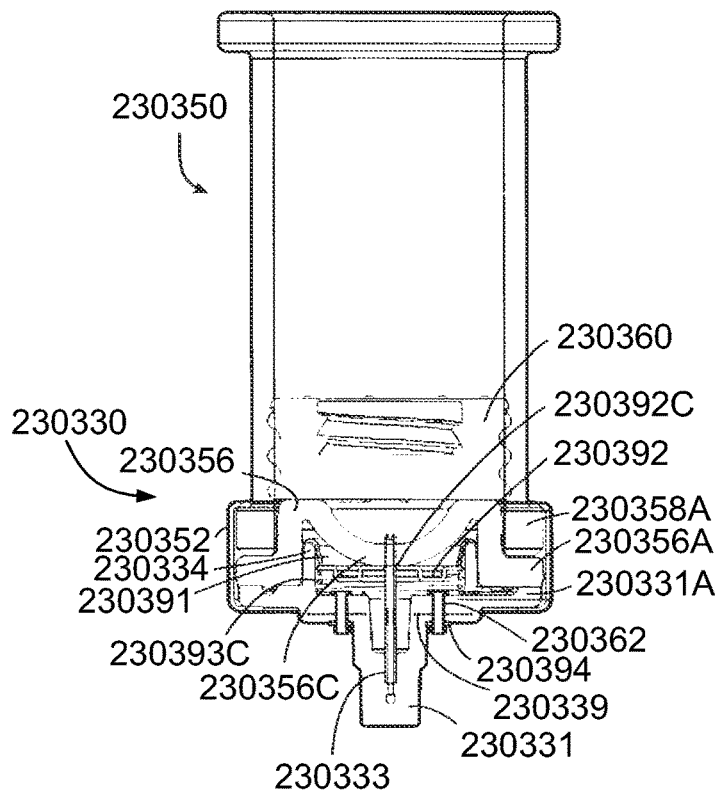

As shown in FIG. 60C and FIG. 60D, once the drive mechanism is activated and plunger seal 230360 is forced toward piercing member 230333, as indicated by the arrow, pneumatic and/or hydraulic pressure within mutable fluid chamber 230321 forces seal barrier 230356C of pierceable seal 230356 into piercing member 230333, thereby piercing seal barrier 230356C and opening the sterile fluid pathway such that fluid can pass to sterile fluid conduit 230335. This pneumatic and/or hydraulic pressure within mutable chamber 230321 also forces at least a portion of barrier seal 230356C against at least a portion of contact 230392, such that spring 230393 is compressed until contact 230392 meets with interconnects 230362 within sterile chamber 230332, forming an interconnection. A signal can then be transduced via contact 230392, interconnect 230362, and flex 230394. Continued pneumatic and/or hydraulic pressure (see arrow), as long as the drive is activated and fluid remains in mutable chamber 230321, compresses spring 230393 and maintains the contact between seal 230356, contact 230392 and interconnect 230362, such that interconnection continues, as shown in FIG. 60E to FIG. 60F. When fluid has been pumped out of mutable fluid chamber 230321, such that this chamber essentially no longer exists and flow through the sterile fluid connector 230330 has ceased, as shown in FIG. 60G and FIG. 60H (the latter is a different sectional view of the sterile fluid pathway connector showing the position of interconnects 230362 within connector hub 230331), pneumatic and/or hydraulic pressure against seal 230356 is released, and spring 230393 returns to the non-compressed state, pushing contact 230362 back toward stamped ring 230391 and breaking interconnection between contact 230392 and interconnect 230362. Once this interconnection is broken, signal can no longer be transduced via flex 230394.

Figure 61A:
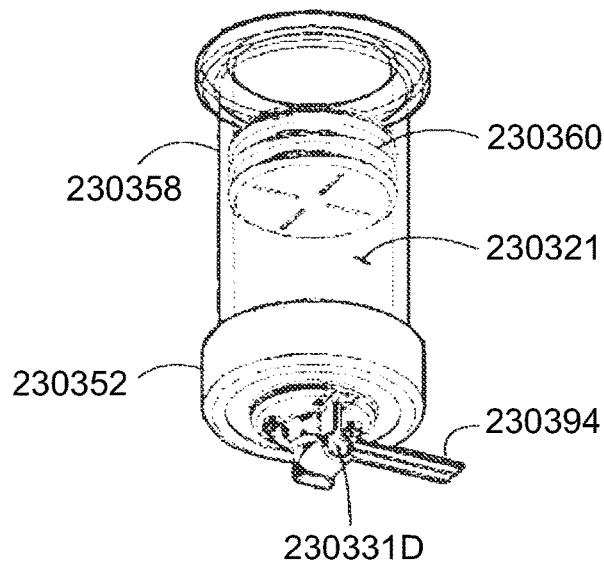
FIG. 61A to FIG. 61G are perspective and sectional views of another embodiment of a sterile fluid connector capable of transmitting a signal indicating the status of fluid transfer from the sterile fluid container to the connector.
Figures 61B, 61C:
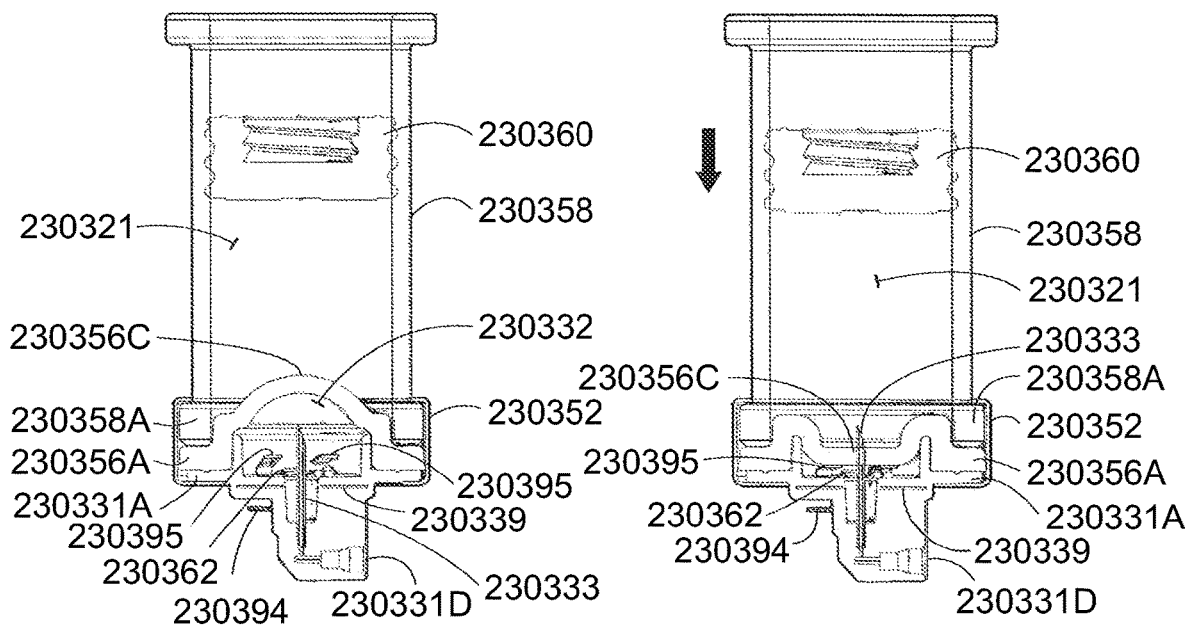
Figure 61D:
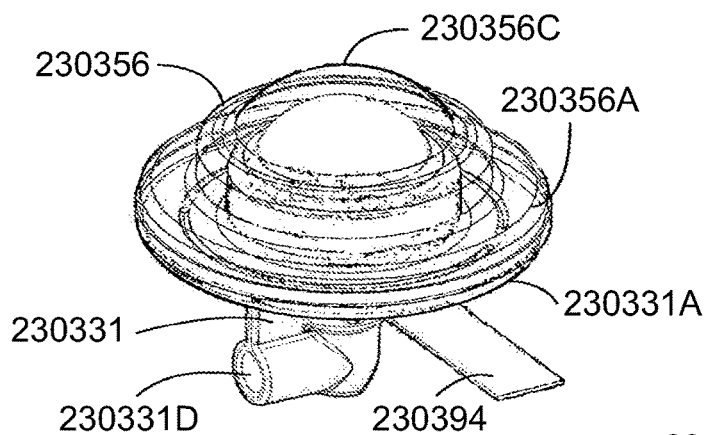
Figure 61E:
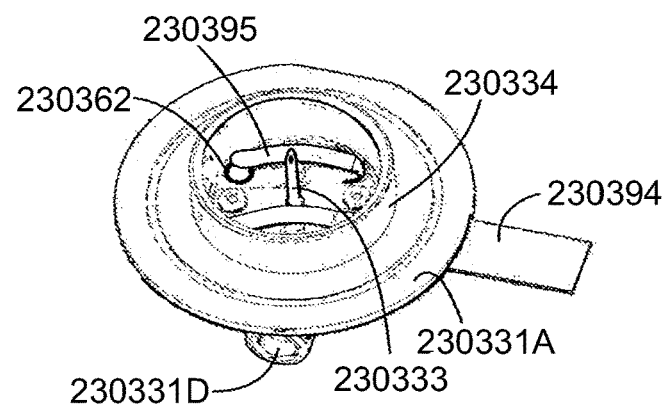
Figure 61F:
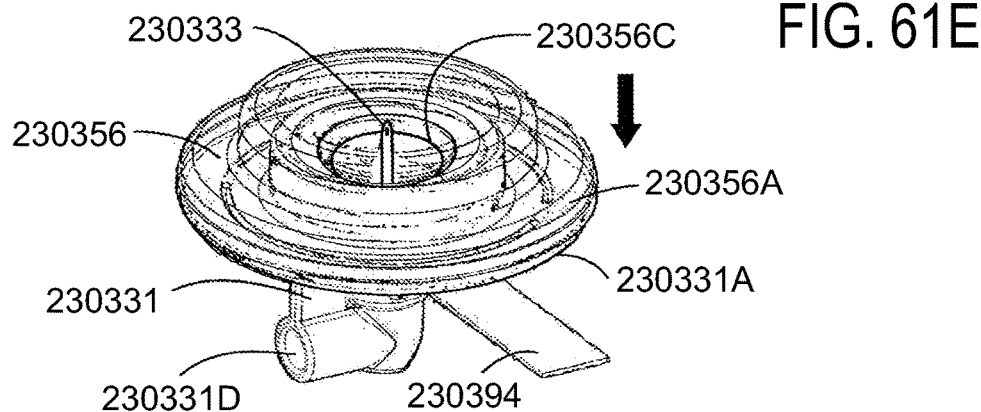
Figure 61G:
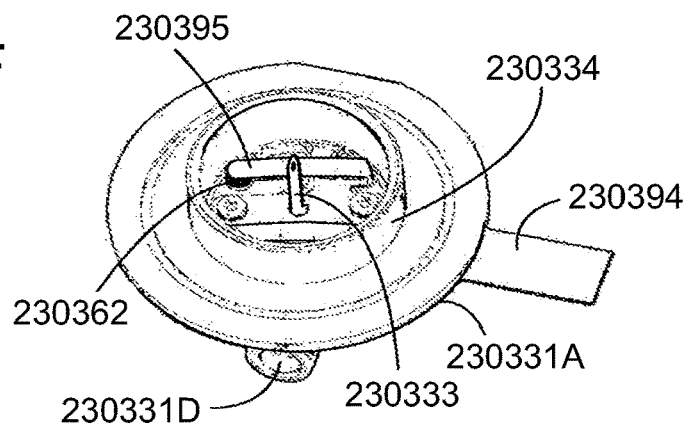

Other switch mechanisms can be designed that use the position of the membrane in pressured and unpressurized states to facilitate transduction of a signal to indicate the status of fluid transfer from the sterile fluid container to the connector. For example, as shown in FIG. 61A to FIG. 61G, connector hub 230331 can house components of a switch comprising a leaf/flex arm contacts 395. FIG. 61B, FIG. 61D and FIG. 61E show the sterile fluid pathway connector in the pre-use position, in which pierceable seal 230356 is unpierced and intact. In this position, contacts 230395 are not touching (or in close enough proximity with) interconnects 230362, and no signal can be transduced. FIG. 61C, FIG. 61F and FIG. 61G show the sterile fluid pathway connector in the activated, pressurized position, in which pneumatic and/or hydraulic pressure from the fluid chamber has deformed barrier seal 230356C against piercing member 230333, piercing pierceable seal 230356 and opening the fluid pathway. In this position, barrier seal 230356C has further been forced against contacts 230395, such that contacts 230395 meet (or become in close enough proximity) with interconnects 230362, such that interconnection forms a signal that can be transduced via flex 230394. FIGS. 148D and 10F are perspectives (in which the barrel and housing are not shown), that illustrate the positions of pierceable seal 230356, connector hub 230331, and piercing member 230333 in pre-use and pressurized positions, respectively. FIGS. 61E and 61G are perspectives in which the barrel, housing and pierceable seal are not shown, to illustrate the positions of contacts 230395 and interconnects 230362 in pre-use (no interconnection) and pressurized (interconnected) positions, respectively.

FIG. 62A to FIG. 62D further illustrate an embodiment in which leaf/arm contacts 230395 do not form interconnection with interconnects 362 until and unless, as shown in FIG. 62B and FIG. 62D, pneumatic and/or hydraulic pressure force seal barrier 230356C onto connects 230395, which force then transferred to place contacts 230395 in contact with interconnects 230362, which then allows signal flow via flex 230394. Additionally, as shown in the embodiment of FIG. 62A to FIG. 62D, connector hub 230331 further includes internal post 230334A, a structure that limits position of contacts 230395 and membrane 230356 to avoid an over-center position that might interfere with fluid passage through the sterile fluid pathway connector.

Figure 63A:
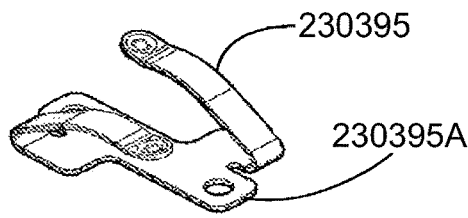
Figure 63B:
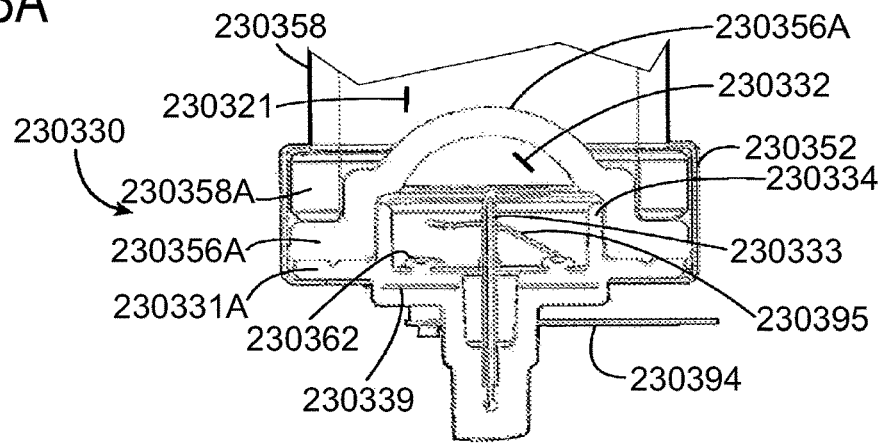
Figure 63C:
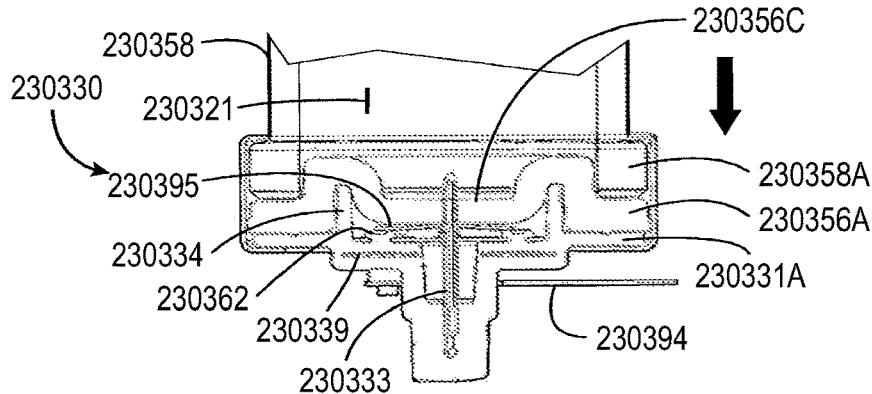
Figure 63D:
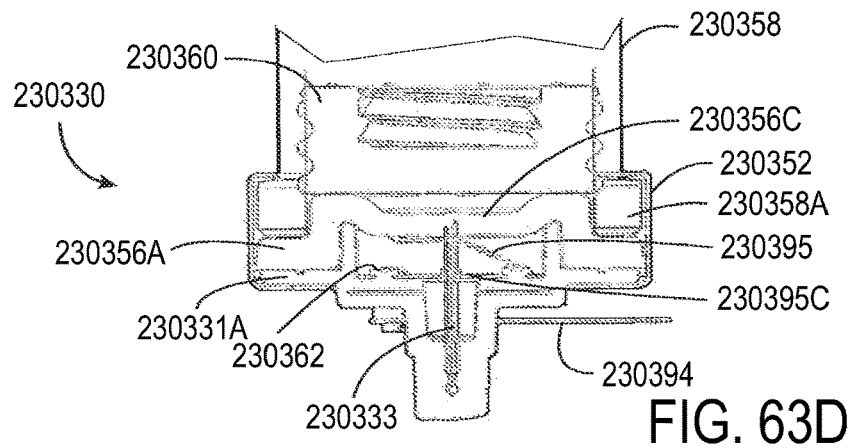
Figure 64A:
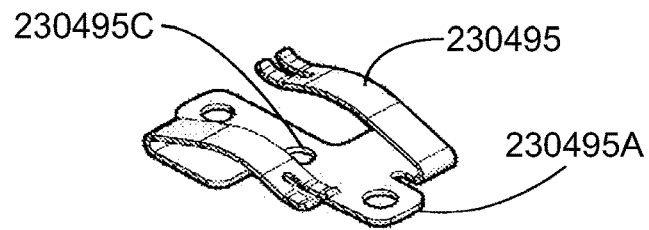
Figure 64B:
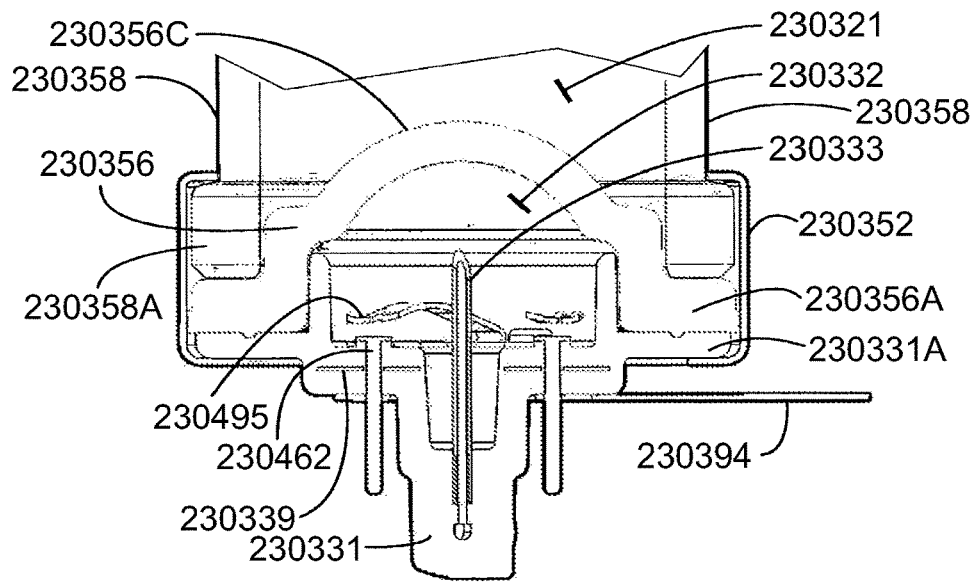
Figure 64C:
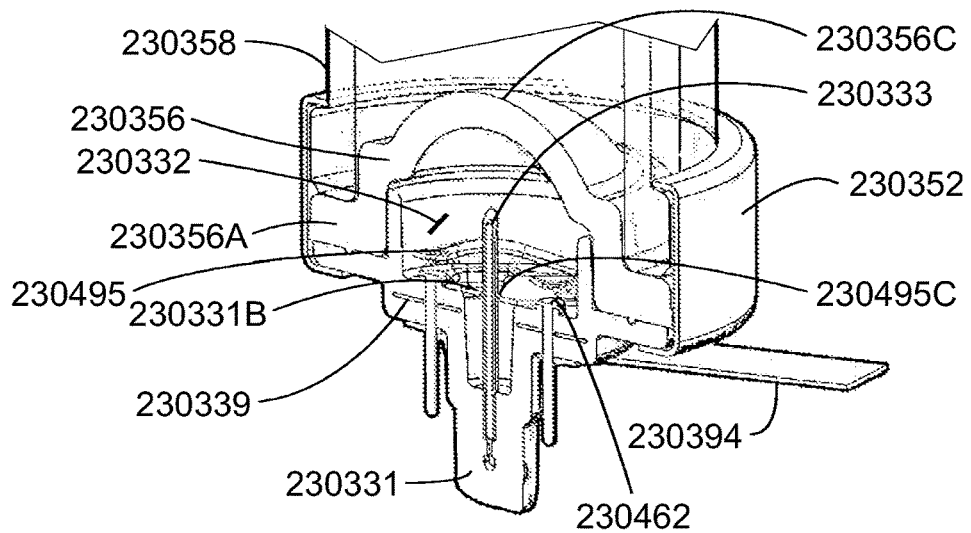

FIG. 63A to FIG. 63D further illustrate an embodiment of a sterile fluid connector capable of transmitting a signal indicating the status of fluid transfer from the sterile fluid container to the connector. FIG. 63B illustrates the position of components of a sterile fluid connector 230330 in an unpressurized state, while FIG. 63C illustrates the pressurized state and FIG. 63D illustrates an end-of-delivery state. Interconnect(s) 230362 and contact(s) 230395 are situated within sterile chamber 230332 between connector hub 230331 and pierceable seal 230356, such that after pierceable seal 230356 is pierced, continued pressure within drug chamber 230321 causes interconnection between one or more interconnect(s) 230362 and one or more contact(s) 230395, which transmits a signal to the user, and which signal is terminated once pressure inside the drug chamber 321 drops and interconnection is lost, i.e., at end-of-delivery. A number of known interconnects and contacts may be used with the present embodiments, which would readily be appreciated by a skilled artisan. For example, a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal to the user may be utilized for such purposes. FIG. 64A to FIG. 64C illustrate another embodiment of a sterile fluid connector capable of transmitting a signal indicating the status of fluid transfer from the sterile fluid container to the connector.

Figure 65A:
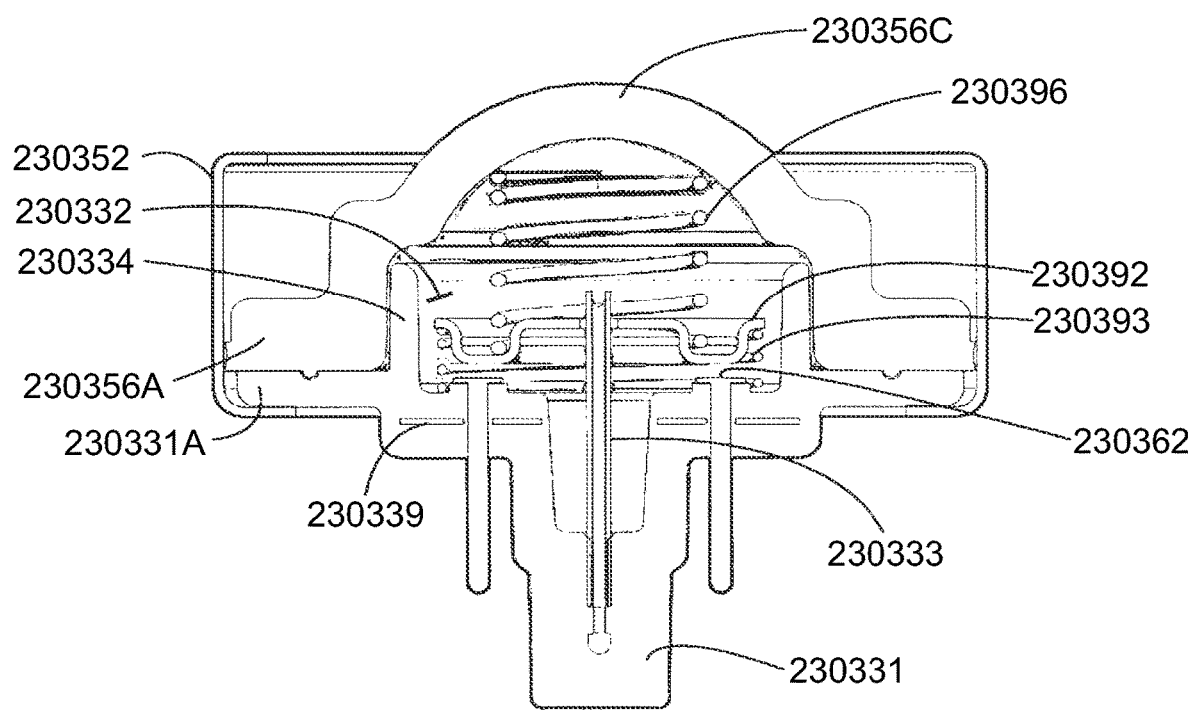
Figure 65B:
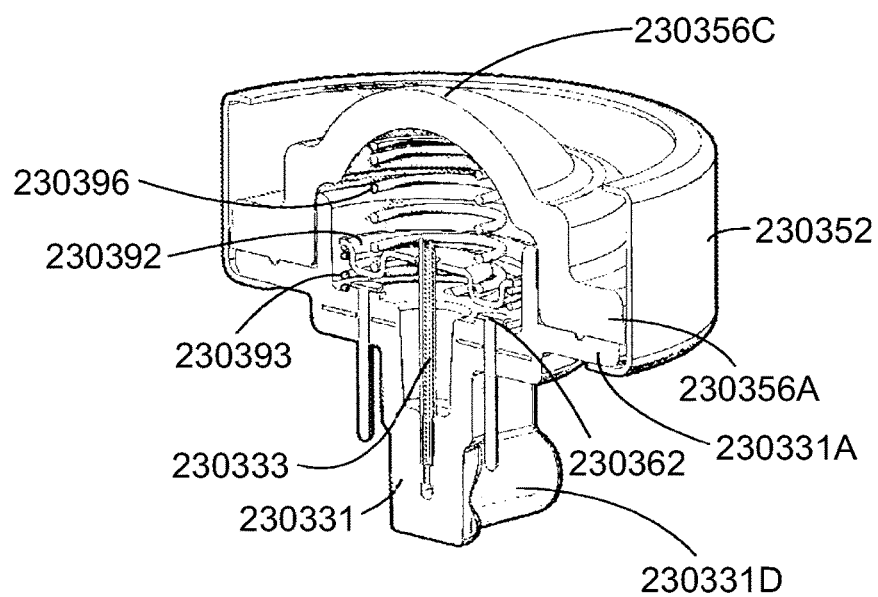

Yet another switch mechanism is shown in FIG. 65A and FIG. 65B, which show sectional and sectional isometric views of a sterile fluid pathway connector (barrel not shown). In this embodiment, sterile chamber 230332, defined in part by the position of pierceable seal 230356 seal mount 230334 and hub connection 230331. Connector hub also holds piercing member 230333 and interconnects 230362 within the sterile chamber 230332. The switch mechanism includes interconnects 230362, first compression spring 230393, contact 230392, and second compression spring 230396. In this embodiment, shown in the un-activated, depressurized state, both compression springs 230393 and 396 compress in order for contact 230392 to form an interconnection with interconnects 230362. Before and upon release of pneumatic and/or hydraulic pressure against seal barrier 230356, compression springs 230393 and 230396 decompress and interconnection is broken.

Figure 66A:
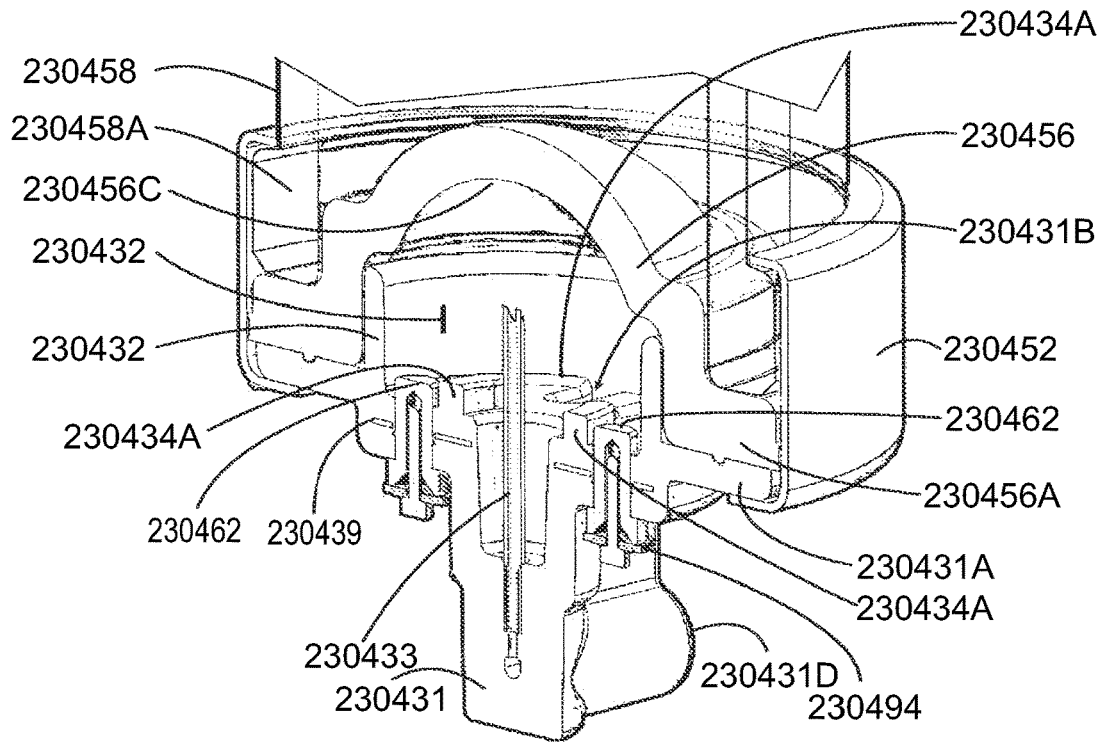
Figure 66B:
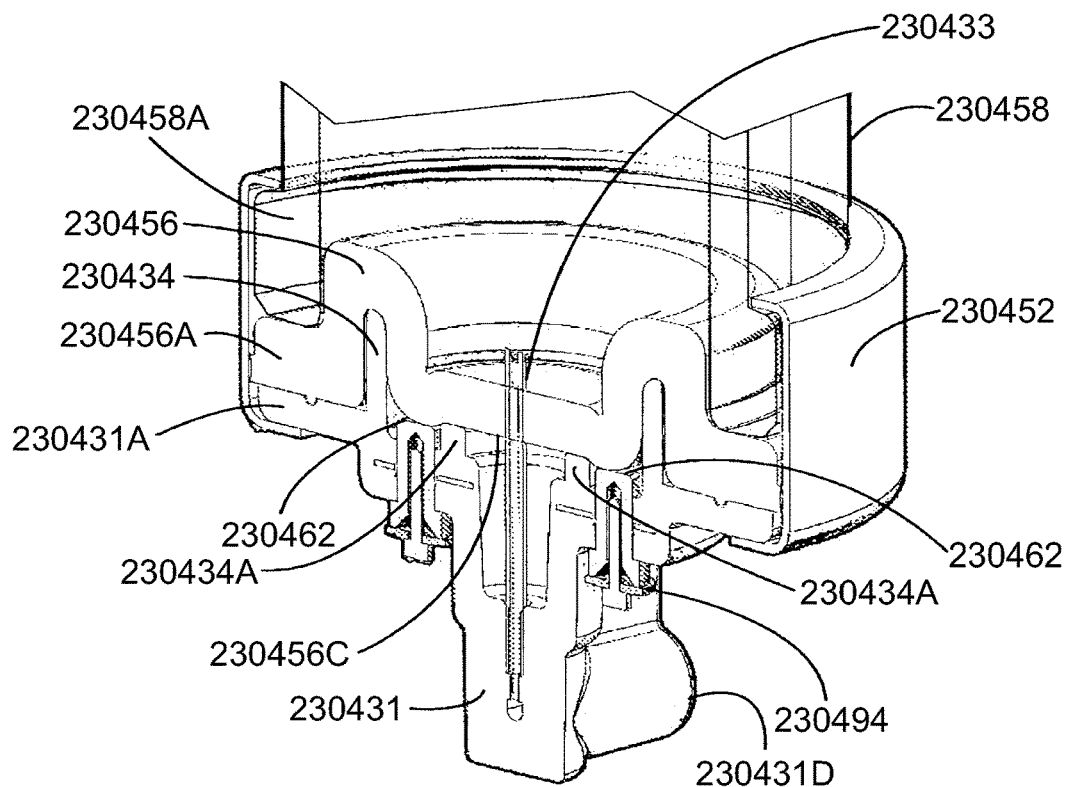

Another embodiment of a switch mechanism is shown in FIG. 66A and FIG. 66B. In this embodiment, pierceable seal 230456 comprises a conductive material or coating. Connector hub 230431 includes rib 434A, a structure that ensures that continuity between conductive pierceable seal 230456 and contacts 230462 is broken when system pressure drops at the end of fluid delivery. More specifically, as shown in FIG. 66B, in the pressurized system in which pneumatic and/or hydraulic pressure has caused conductive pierceable membrane 230456 to have been ruptured by piercing member 230433, conductive pierceable membrane 230456 must deform further proximal to rib 230434 in order to meet interconnects 230462. Once pneumatic and/or hydraulic pressure ceases, i.e., at the end of fluid delivery, conductive pierceable membrane 230456 is naturally released from interconnection by proximal to rib 230434

Figure 67:
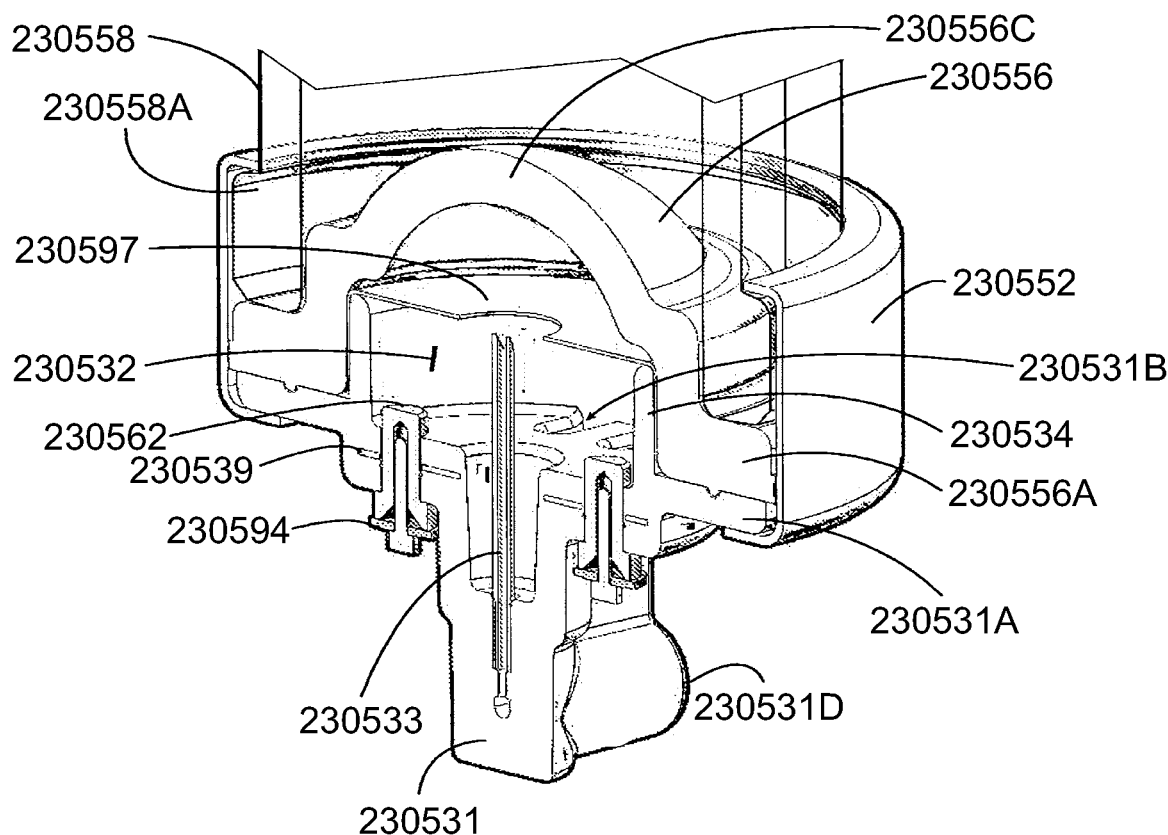

Yet another embodiment of a switch mechanism is shown in FIG. 67. In this embodiment, connector hub 230531 comprises conductive elastomer 230597 held in sterile chamber 230532 between connector hub 230531 and pierceable membrane 230556. In this embodiment, at least a portion of conductive elastomer 230597 is affixed to or otherwise engaged with seal mount 230534, and is configured with a centrally located aperture to allow barrier seal 230556C to be forced into contact with piercing member 230533 upon activation of the pump and creation of pneumatic and/or hydraulic pressure against pierceable membrane 230556. Conductive elastomer 230597 is "springy" in nature and can deform (i.e., stretch) in response to distal force from pierceable seal 230556, thereby deformed into meeting interconnects 230362 under pressure from pierceable seal 230356. The elastomeric nature of conductive elastomer 230597 allows it to return to the pre-deformed state, in which there is no interconnection, in an unpressurized environment. Therefore, once pneumatic and/or hydraulic pressure ceases, i.e., at end-of-delivery, conductive elastomer film 230597 is passively released from contact with interconnections 230562, and signal is interrupted.

Figure 68:
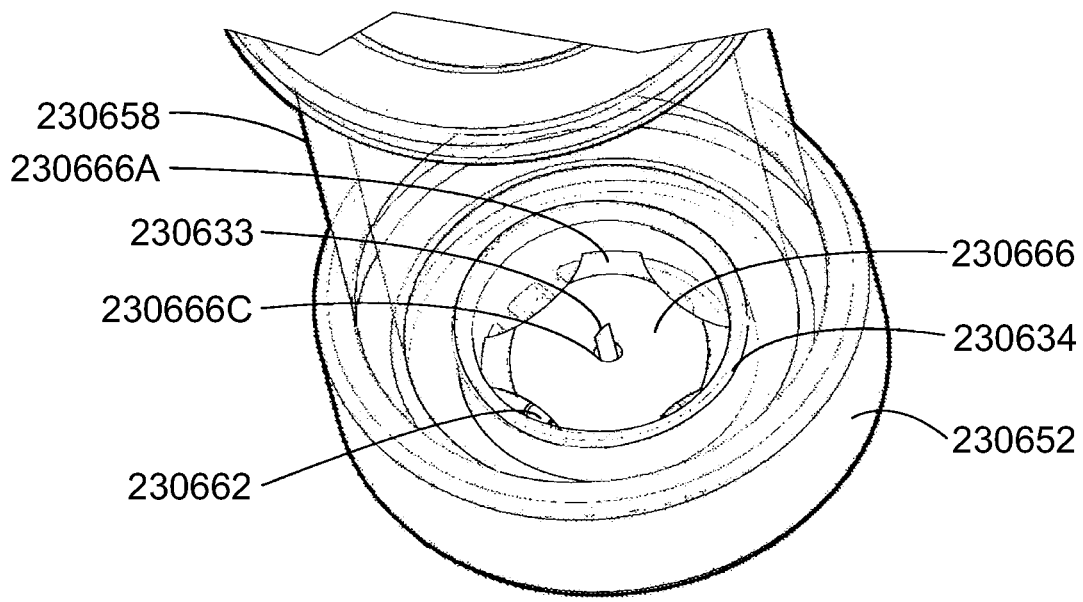

In another embodiment, shown in FIG. 68, the sterile fluid pathway connector includes a sensor mechanism comprising dome switch 230666, which dome is made or of includes conductive material such that dome switch 230666 can act as a contact to create a signal when dome switch 230666 meets with, or moves sufficiently close to, interconnects 230662 to complete the circuit. Dome switch 230666 is configured with at least one outer portion 230666A that resists deformation and engages with or bears against the inner wall of connector hub seal mount 230634. Alternatively, the outer deformation-resistant portion of the dome switch can be a radial ring, or any structure that will stabilize the position of the dome within the sterile fluid pathway connector. The conductive portion of the dome switch may comprise shape-memory alloy that "remembers" its dome shape, but can be deformed into a more flattened shape under pressure, then return to the dome shape once pressure is relieved. In the embodiment of FIG. 68, dome switch 230666 further comprises aperture 230666C through which piercing member 230633 can pass as dome switch 230666 is pressed in the direction of interconnects 230662. More specifically, when the pump device is actuated and pneumatic and/or hydraulic pressure builds against the pierceable membrane (not shown), the pierceable membrane is forced onto piercing member 230633 and ruptured to open the fluid pathway. Dome switch 230666 is similarly deformed by the pneumatic and/or hydraulic pressure or by the distal pressure of the deformed portion of the pierceable seal bearing against it, and dome switch 666 flattens towards interconnects 230662 to allow a signal to be transduced. Once the pneumatic and/or hydraulic pressure stops, i.e., at end-of-delivery, the dome switch returns to its pre-deformed dome shape and interconnection ceases. As shown in FIG. 68, dome switch 230666 is configured for placement under the pierceable seal (not shown), within the sterile cavity of the fluid pathway connector. The dome switch could, however, be configured to "ride" on top of the pierceable seal, and upon pressurization would be pushed in close enough proximity with interconnects 230662 to generate a signal. Alternatively, the dome switch could be made of evenly deformable/resistant shape-memory material with the conductive portion of the dome switch configured in the outer portions or rim of the dome, and be placed "upside down" (as a bowl shape) in the sterile chamber of the fluid pathway connector. In this configuration, the pneumatic and/or hydraulic pressure against the pierced pierceable membrane would sufficiently flatten the dome until the outer conductive part of the dome made sufficient contact with interconnects positioned in the connector hub to allow a signal. Upon cessation of pressure, i.e., at end-of-delivery, the dome would pop back to its remembered dome shape, and thereby remove the connective contacts from interconnection.

As should be clear from the preceding discussions, a number of known interconnects and contacts, or similar components, are known in the art and may be utilized within the novel embodiments disclosed herein. As would readily be appreciated by one having skill in the art, a vast range of magnets, sensors, coils, and the like may be utilized to connect, transmit, or relay a signal for user feedback. Generally, any RLC circuit systems having a resistor, an inductor, and a capacitor, connected in series or in parallel, may be utilized for this purpose. For example, Hall effect sensors; giant magneto resistance (GMR) or magnetic field sensors; optical sensors; capacitive or capacitance change sensors; ultrasonic sensors; or linear travel, LVDT, linear resistive, or radiometric linear resistive sensors may be utilized as interconnects and corresponding contacts used to permit a signal to be sent to the power and control system to provide feedback to the user. The location of the contacts and interconnects may be interchanged or in a number of other configurations which permit completion of an electrical circuit or otherwise permit a transmission between the components. By use of one or more status switch interconnects and one or more corresponding electrical contacts, the status of the drive mechanism before, during, and after operation can be relayed to the power and control system to provide feedback to the user. Such feedback may be tactile, visual or auditory, and may be redundant such that more than one signals or types of feedback are provided to the user during use of the device.

Additionally, the embodiments of the present disclosure provide end-of-delivery compliance to ensure that substantially the entire fluid volume has been delivered and that the status indication features have been properly contacted to provide accurate feedback to the user. Through these mechanisms, confirmation of fluid delivery can accurately be provided to the user or administrator. Accordingly, the novel devices of the present disclosure alleviate one or more of the problems associated with prior art devices. Optionally, the drive mechanism may include one or more compliance features that enable additional axial translation of the plunger seal to, for example, ensure that substantially the entire fluid volume has been delivered and make sure that the feedback contact mechanisms have connected. For example, in one embodiment of the present disclosure, the drive mechanism may be configured to drive further axial translation of at least a portion of the plunger seal for a compliance push of the plunger seal, or of fluid, from the fluid container. Additionally or alternatively, the plunger seal, itself, may have some compressibility permitting a compliance push. For example, when a pop-out plunger seal is employed, i.e., a plunger seal that is deformable from an initial state, the plunger seal may be caused to deform or "pop-out" to provide a compliance push. Similarly, the plunger seal may be porous, compressible, deformable, or the like to itself be capable of providing a compliance push.

As described above, the location of the contacts and interconnects may be interchanged or in a number of other configurations that permit completion of an electrical circuit or otherwise permit a transmission between the components. In one embodiment, the plunger seal may incorporate, or itself be utilized as, a contact or interconnect for the status indication mechanism (e.g., 23061 in FIG. 55C). In one embodiment, the seal mount may incorporate, or itself be utilized as, a contact or interconnect for the status indication mechanism (e.g., 23062 in FIG. 55C). In one embodiment, a guide piece may incorporate, or itself be utilized as, a contact or interconnect for the status indication mechanism (e.g., 230232 in FIG. 57A). In another embodiment, the proximal surface of the connector hub sequestered in sterile chamber 32 may incorporate, or itself be utilized as, a contact or interconnect for the status indication mechanism (e.g., FIG. 60 to FIG. 68).

Other components of the sterile fluid pathway connector may similarly be utilized for multiple functions. Alternatively, other optional components may be utilized within the novel embodiments of the present disclosure. For example, one or more optional flow restrictors may be utilized within the configurations of the fluid pathway connector described herein. In at least one embodiment, a flow restrictor may be utilized at the connection between the piercing member and the fluid conduit. The fluid pump is capable of delivering a range of fluid with different viscosities and volumes. The fluid pump is capable of delivering a fluid at a controlled flow rate (speed) or of a specified volume. In one embodiment, the fluid delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the fluid container to dispense the fluid therein, or combinations thereof. In at least one embodiment of the present disclosure, the connector hub itself may be utilized as part of the fluid path and may, optionally, function as a flow restrictor.

It will be appreciated from the above description that the fluid pathway connectors and fluid pumps disclosed herein provide an efficient and easily-operated system for automated fluid delivery from a fluid container. The novel devices of the present disclosure provide container connections which maintain the sterility of the fluid pathway and which are integrated into the fluid container, and fluid delivery pumps that incorporate such integrated sterile fluid pathway connectors to fluid containers. Such devices are safe and easy to use, and are aesthetically and ergonomically appealing for self-administering patients. The devices described herein incorporate features which make activation, operation, and lock-out of the device simple for even untrained users. Because the fluid path is disconnected until fluid delivery is desired by the operator, the sterility of the fluid pathway connector, the fluid container, the fluid, and the device as a whole is maintained. These aspects of the present embodiments provide highly desirable storage, transportation, and safety advantages to the operator. Furthermore, the novel configurations of the fluid pathway connectors and drug pumps of the present disclosure maintain the sterility of the fluid path through operation of the device. Because the path that the fluid travels within the device is entirely maintained in a sterile condition, only these components need be sterilized during the manufacturing process. Such components include the fluid container of the drive mechanism, the fluid pathway connector, the sterile fluid conduit, and, when the fluid is a drug, the insertion mechanism. In at least one embodiment of the present disclosure, the power and control system, the assembly platform, the control arm, the activation mechanism, the housing, and other components of the fluid pump do not need to be sterilized. This greatly improves the manufacturability of the device and reduces associated assembly costs. Accordingly, the devices of the present disclosure do not require terminal sterilization upon completion of assembly. A further benefit of the present embodiments is that the components described herein are designed to be modular such that, for example, the fluid pathway connector and other components of the device may be integrated into a housing and readily interface to function as a fluid pump.

Assembly or manufacturing of fluid pathway connector 23030 or any of the individual components may utilize a number of known materials and methodologies in the art. For example, a number of known cleaning fluids such as isopropyl alcohol and hexane may be used to clean the components or the devices. A number of known adhesives may similarly be employed in the manufacturing process. Additionally, known siliconization or lubrication fluids and processes may be employed during the manufacture of the novel components and devices. Furthermore, known sterilization processes may be employed at one or more of the manufacturing or assembly stages to ensure the sterility of the final product.

The fluid pathway connector may be assembled in a number of methodologies. In one method of assembly, the sterile fluid pathway connector may be assembled, e.g., as shown in FIG. 56A and FIG. 56B, and then attached, mounted, connected, or otherwise integrated into fluid container 23050 such that at least a portion of the pierceable seal 23056 is contained within the fluid container 23050. The fluid container 23050 may then be filled with a fluid and plugged with a plunger seal 23060 at an end opposite the pierceable seal 23056. The barrel 23058 may be filled with a fluid through the open proximal end prior to insertion of the plunger seal 23060 from the proximal end of the barrel 23058. The drive mechanism 23090 may then be attached to the proximal end of the fluid container 23050 such that a component of the drive mechanism 23090 is capable of contacting the plunger seal 23060. The insertion mechanism 23070 may be assembled and attached to the other end of the fluid conduit 23035. This entire sub-assembly, including drive mechanism 23090, fluid container 23050, fluid pathway connector 23030, fluid conduit 23035, and insertion mechanism 23070, may be sterilized by known techniques before assembly into the drug delivery device. Certain components of this sub-assembly may be mounted to an assembly platform within the housing 12A, 12B or directly to the interior of the housing 12A, 12B, while other components may be mounted to a guide, channel, or other component or aspect for activation by the user.

Manufacturing of a fluid pump includes the step of attaching both the fluid pathway connector and fluid container, either separately or as a combined component, to an assembly platform or housing of the drug pump. The method of manufacturing further includes attachment of the drive mechanism, fluid container, and insertion mechanism to the assembly platform or housing. The additional components of the fluid pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the fluid pump includes one or more of the following steps: activating, by a user, the activation mechanism; displacing a control arm to actuate an insertion mechanism; activating a drive control mechanism to push the plunger seal, connect the sterile fluid pathway connector, and drive fluid flow through the fluid pump, wherein translating the fluid pathway connector causes a pierceable seal to be pierced by a piercing member thereby opening a fluid path from the fluid container to the fluid pathway connector. The drive control mechanism may be activated by actuating a power and control system. The method may further include the step of: engaging an optional on-body sensor prior to activating the activation mechanism. Furthermore, the method of operation may include translating a plunger seal within the drive control mechanism and fluid container to force fluid drug flow through the fluid container, the fluid pathway connector, a sterile fluid conduit, and, optionally the insertion mechanism for delivery of the fluid to the body of a user.

VIII. Multi-Function Drive Mechanism

At least some of the drug delivery devices described in this application, including at least those described in connection with FIGS. 1A-2B and 33A-33C, may be configured to incorporate the embodiments of the drive mechanism described below in connection with FIGS. 69A-77C. The embodiments of the drive mechanism described below in connection with FIGS. 69A-77C may be used to replace, in its entirety or partially, the above-described drive mechanisms 100, 6100, or 8100, or any other drive mechanism described herein, where appropriate.

The present disclosure provides multi-function drive mechanisms for the controlled delivery of drug substances, controlled drug delivery pumps with such drive mechanisms, the methods of operating such devices, and the methods of assembling such devices. Notably, the multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the user. Through these mechanisms, confirmation of drug dose delivery can accurately be provided to the user or administrator. Accordingly, the devices of the present disclosure alleviate one or more of the problems associated with prior art devices, such as those referred to above.

In a first embodiment, the present disclosure provides a multi-function drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the body of the user. A piston, and one or more biasing members, wherein the one or more biasing members are initially retained in an energized state and is configured to bear upon an interface surface of the piston, may also be incorporated in the multi-function drive mechanism. The piston is configured to translate substantially axially within a drug container having a plunger seal and a barrel. A tether is connected at one end to the piston and at another end to a winch drum/gear of a regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of a regulating mechanism of the multi-function drive mechanism to meter the free expansion of the biasing member from its initial energized state and the free axial translation of the piston upon which the biasing member bears upon.

In at least one embodiment of the present disclosure, the regulating mechanism is gear assembly driven by an actuator of the multi-function drive mechanism. The regulating mechanism retards or restrains the distribution of tether, only allowing it to advance at a regulated or desired rate. This restricts movement of piston within barrel, which is pushed by one or more biasing members, hence controlling the movement of plunger seal and delivery of the drug contained in chamber. As the plunger seal advances in the drug container, the drug substance is dispensed through the sterile pathway connection, conduit, insertion mechanism, and into the body of the user for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a winch gear coupled to a winch drum/gear upon which the tether may be releasably wound. Accordingly, rotation of the gear assembly initiated by the actuator may be coupled to winch drum/gear (i.e., through the gear assembly), thereby controlling the distribution of tether, the rate of expansion of the biasing members and the axial translation of the piston, and the rate of movement of plunger seal within barrel to force a fluid from drug chamber. The rotational movement of the winch drum/gear, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, initial motion by the actuator of the multi-function drive mechanism causes rotation of main/star gear. In one manner, main/star gear conveys motion to the regulating mechanism through gear assembly. In another manner, main/star gear conveys motion to the needle insertion mechanism through gear. As gear is rotated by main/star gear, gear engages the needle insertion mechanism to initiate the fluid pathway connector into the user, as described in detail above. In one particular embodiment, needle insertion mechanism is a rotational needle insertion mechanism. Accordingly, gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the user, as described in detail herein.

In at least one embodiment, rotation of the needle insertion mechanism in this manner may also cause a connection of a sterile fluid pathway to a drug container to permit fluid flow from the drug container to the needle insertion mechanism for delivery to the user. Ramp aspect of needle insertion mechanism is caused to bear upon a movable connection hub of the sterile fluid pathway connector. As the needle insertion mechanism is rotated by the multi-function drive mechanism, ramp aspect of needle insertion mechanism bears upon and translates movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum/gear of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum/gear upon which the tether may be releasably wound, rotation of the winch drum/gear releases the tether from the winch drum/gear to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum/gear is coupled to a regulating mechanism which controls rotation of the winch drum/gear and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum/gear and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum/gear on the free axial translation of the piston upon which the biasing member bears upon to meet a desired drug delivery rate or profile, to change the dose volume for delivery to the user, and/or to otherwise start, stop, or pause operation of the drive mechanism.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

The embodiments of the present disclosure provide drive mechanisms which are capable of metering, providing resistance, or otherwise preventing free axial translation of the plunger seal utilized to force a drug substance out of a drug container and, thereby, controlling the rate of delivery of drug substances. The control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present disclosure may include one or more additional components which may be considered standard components in the industry of medical devices. For example, the embodiments may include one or more batteries utilized to power the motor, drive mechanisms, and drug delivery devices of the present disclosure. The components, and the embodiments containing such components, are within the contemplation of the present disclosure and are to be understood as falling within the breadth and scope of the present disclosure.

The present disclosure provides systems and methods that are related to delivery of drug substances at a predetermined time and at an adjusted delivery rate. Particularly, the present disclosure relates to drug delivery device delivery devices that include control systems and sub-systems that are configured to control and drive multi-function drive mechanisms. Additionally, the control systems and sub-systems may be configured to deliver drug substances at appropriate delivery rates after a certain wait time period has elapsed.

In one example, a user may be provided with a pre-filled drug delivery pump device to inject the drug substance via the parenteral method. In such an example, activation of the pump device may establish short range communication with a mobile device (e.g., a smart phone). In one embodiment, the drug delivery device delivery device may be activated by press of an activation button or a power button. The mobile device may include one or more mobile applications that may be configured to process, receive and transmit data related to the drug delivery process. The mobile application may communicate with external sensors (e.g., a heart rate sensor and a glucose rate sensor) and receive information (e.g., heart rate of the user, glucose/insulin information, etc.) related to the health and/or state of the patient during a monitoring period. The mobile application may further calculate an adjusted delivery rate for the drug based on the data received from the sensors.

Moreover, the drug delivery device may request user-activation for the needle insertion, after the device has been activated. The drug delivery device may provide visual or audio cues for the needle activation or, alternatively, cause the mobile device to provide the request notification for needle activation. When the needle insertion has been actuated by the user, the drug delivery device may then initiate a timer to track a wait time period, prior to the delivery of the drug. Alternatively, the timer may be initiated upon activation of the device. The drug delivery device may optionally monitor the temperature to determine whether the drug has reached an optimal temperature for delivery. Additionally, the power and control system may be configured to determine whether the predetermined wait time period has elapsed, and based on the determination may notify the user about the initiation of the drug delivery process. Optionally, the user may have the option of initiating drug delivery after the predetermined wait time has elapsed.

It is noted that, based on the type of the drug and the dose, the drug delivery device may regulate the delivery rate of the drug. The regulation and/or adjustment of the delivery rate may also be based on information received from sensors (e.g., temperature sensor, heart rate sensor, glucose monitor sensor).

The drug delivery device may further determine whether the drug delivery has ended, and based on the determination, may transmit the end of drug delivery information to the mobile device.

The mobile device may further provide the received end of delivery information to a remote server (e.g., a cloud computer server). The end of delivery information may include, but not limited to, end of delivery indication, delivery rate, delivery start and end times, total delivery time, drug temperature, and data gathered by the sensors. The information may also include information related to the drug and/or pump device such as drug volume, manufacturing date, filling date, serial/lot number, etc.

Moreover, the drug delivery device may switch between an active power mode and a non-active power mode. During the active power mode, the power and control system may interact with one or more motors of a drive control system to actuate one or more drive mechanisms, and as such, both the power and control system and the motors may receive power from an energy source (e.g., batteries). On the other hand, in some instances, the power and control system may not need to interact with the drive control system to execute one or more operations of the drug delivery pump device. For example, the drug delivery device may establish and communicate with the mobile device, or monitor temperature of the drug without interacting with the drive control system of the drug delivery device. In such instances, the power and control system may only be powered, and the drive control system may not receive power from the batteries. Additionally, one or more components or functions of the pump device may be powered intermittently in one or more modes.

The switching between the active power mode and the non-active power mode may substantially save power resources of the drug delivery device. For example, upon switching to the non-active power mode, the drug delivery device does not need to provide power to the motors, which may, otherwise, significantly drain the batteries.

Particularly, during the active power mode, the power and control system of the drug delivery pump device controls the multi-function drive mechanisms to initiate several subsystems or functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user.

The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may include integrated status indication features, such as sensors, which may provide feedback to the power and control system, and in turn, to the user before, during, and after drug delivery. For example, the user may be prompted by one or more sensors to identify that the devices are operational and ready for drug delivery. Upon activation of one or more devices, the sensors may provide one or more drug delivery status indications to the user such as an end-of-dose indication at completion of drug delivery.

As used herein to describe the drive mechanisms, drug delivery pumps, or any of the relative positions of the components of the present disclosure, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present disclosure, the biasing member is a spring, preferably a compression spring.

The devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The devices of the present disclosure provide these desirable features without any of the problems associated with known prior art devices. Certain non-limiting embodiments of the drug delivery pumps, drive mechanisms, and their respective components are described further herein with reference to the accompanying figures.

Figure 69D:
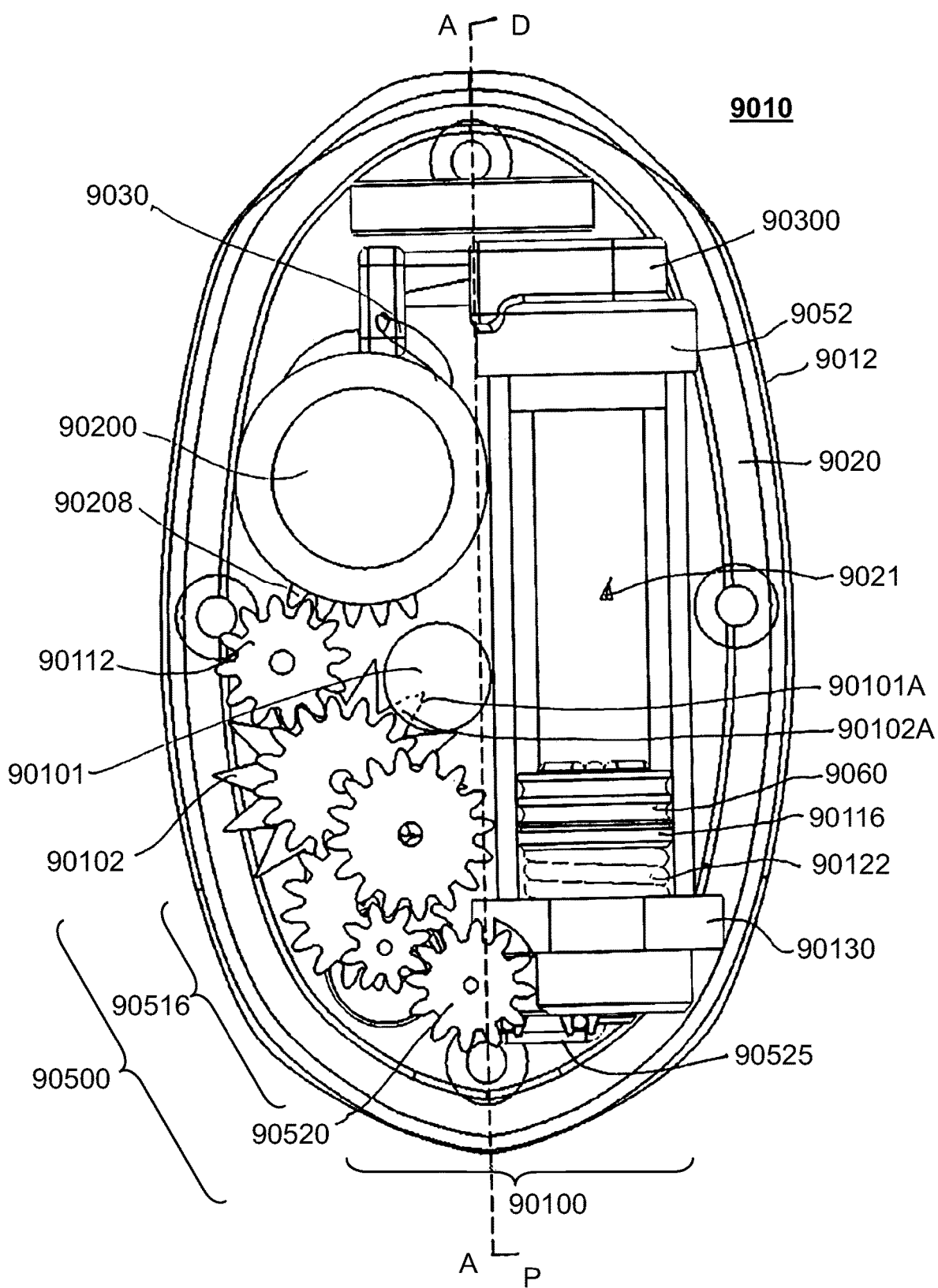

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 69A-

69C show an exemplary drug delivery device according to at least one embodiment of the present disclosure with the top housing removed so that the internal components are visible. The drug delivery device may be utilized to administer delivery of a drug treatment into a body of a user. As shown in FIGS. 69A-69C, the drug delivery device 9010 includes a pump housing 9012. Pump housing 9012 may include one or more housing subcomponents which are fixedly engageable to facilitate easier manufacturing, assembly, and operation of the drug pump. For example, drug delivery device 9010 includes a pump housing 9012 which may include an upper housing and a lower housing (not shown for ease of viewing internal components). The pump housing 9012 may include one or more tamper evidence features to identify if the drug delivery device has been opened or tampered with. For example, the pump housing 9012 may include one or more tamper evidence labels or stickers, such as labels that bridge across the upper housing and the lower housing. Additionally or alternatively, the housing 9012 may include one or more snap arms or prongs connecting between the upper housing and the lower housing. A broken or altered tamper evidence feature would signal to the user, the physician, the supplier, the manufacturer, or the like, that the drug delivery device has potentially been tampered, e.g., by accessing the internal aspects of the device, so that the device is evaluated and possibly discarded without use by or risk to the user. The drug delivery device may further include an activation mechanism, a status indicator, and a window. Window may be any translucent or transmissive surface through which the operation of the drug delivery device may be viewed. As shown in FIG. 69B, drug delivery device 9010 further includes assembly platform 9020, sterile fluid conduit 9030, drive mechanism 90100 having drug container 9050, insertion mechanism 90200, fluid pathway connector 90300, and a power and control system (not shown). One or more of the components of such drug delivery devices may be modular in that they may be, for example, pre-assembled as separate components and configured into position onto the assembly platform 9020 of the drug delivery device 9010 during manufacturing.

The pump housing 9012 contains all of the device components and provides a means of removably attaching the device 9010 to the skin of the user. The pump housing 9012 also provides protection to the interior components of the device 9010 against environmental influences. The pump housing 9012 is ergonomically and aesthetically designed in size, shape, and related features to facilitate easy packaging, storage, handling, and use by users who may be untrained and/or physically impaired. Furthermore, the external surface of the pump housing 9012 may be utilized to provide product labeling, safety instructions, and the like. Additionally, as described above, housing 9012 may include certain components, such as one or more status indicators (e.g., LED lights, audio tones via speakerphones) and windows, which may provide operation feedback to the user.

In one example, the power and control system may be configured to provide a number of different status indications to the user. For example, the power and control system may be configured such that after the on-body sensor (e.g., skin sensor) is triggered, the power and control system provides a ready-to-start status signal via the status indicator (e.g., audio tones and/or blinking lights) if device start-up checks provide no errors. After providing the ready-to-start status signal and, in an embodiment with the optional on-body sensor, if the on-body sensor remains in contact with the body of the user, the power and control system will power the drive mechanism 90100 to begin delivery of the drug treatment through the fluid pathway connector 90300 and sterile fluid conduit 9030.

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the user. In such an embodiment, without removal of the drug delivery device from the packaging the drug delivery device cannot be activated. This provides an additional safety mechanism of the drug delivery device and for the user. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between.

Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, and after a predetermined wait time period, the multi-function drive mechanism is initiated to actuate the drug fluid to be forced from the drug container.

During the drug delivery process, the power and control system may be further configured to provide a dispensing status signal via the status indicator. After the drug has been administered into the body of the user and after the end of any additional dwell time, to ensure that substantially the entire dose has been delivered to the user, the power and control system may provide an okay-to-remove status signal via the status indicator. This may be independently verified by the user by viewing the drive mechanism and drug dose delivery through the window of the pump housing 9012. Additionally, the power and control system may be configured to provide one or more alert signals via the status indicator, such as for example alerts indicative of fault or operation failure situations.

The power and control system may additionally be configured to accept various inputs (e.g., via an activation button) from the user to dynamically control the drive mechanisms 90100 to meet a desired drug delivery rate or profile. For example, the power and control system may receive inputs, such as from partial or full activation, depression, and/or release of the activation mechanism, to set, initiate, stop, or otherwise adjust the control of the drive mechanism 90100 via the power and control system to meet the desired drug delivery rate or profile. Similarly, the power and control system may be configured to receive such inputs to initiate communication with the mobile device, adjust the drug dose volume, to prime the drive mechanism, fluid pathway connector, and fluid conduit; and/or to start, stop, or pause operation of the drive mechanism 90100. Such inputs may be received by the user directly acting on the drug delivery device 9010, such as by use of the activation mechanism 9014 or a different control interface, or the power and control system may be configured to receive such inputs from a remote device (e.g., a mobile device). Additionally or alternatively, such inputs may be pre-programmed.

Other power and control system configurations may be utilized with the drug delivery devices of the present disclosure. For example, certain activation delays may be utilized prior to, or during drug delivery. For example, a wait-time period may be a pre-determined time that may be set in the power and control system, and which may delay the delivery of the drug by the pre-determined amount of time. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug delivery device 9010 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the drug delivery devices.

In one embodiment, the drug delivery pump device 9010 may include one or more control systems such as, but not limited to, power and control system 90800 and drive control system 90820. As disclosed above, the drug delivery pump 9010 may further include various mechanisms or sub-systems such as, but not limited to, drive mechanism or sub-system 90100, needle insertion mechanism (NIM) or sub-system 90200, sterile fluid pathway connector (SFPC) or sub-system 90300, and regulating mechanism or sub-system 90500. In some examples, the control systems may include printed circuit board (PCB), motherboards and/or daughter boards.

In some embodiments, the sub-systems may be included in the control systems. For example, the drive control system 90820 may include the drive sub-system 90100, NIM sub-system 90200, and/or the regulating sub-system 90500. In such examples, the power and control system 90800 may control the sub-systems by sending command signals to the drive control system 90820.

In other examples, the drive control system 90820 may not include the sub-systems. As such, in those examples, the power and control system 90800 may control the sub-systems via the drive control system 90820. For example, the power and control system 90800 may send command signals to the drive control system 90820. The drive control system 90820, for example, may then selectively control one or more of the sub-systems based on the received command signals from the power and control system 90810.

Yet in another embodiment, the power and control system 90800 may directly control the sub-systems. In that embodiment, the sub-systems may include respective control units or controller and storage units (not shown) that may be configured to directly communicate with the power and control system 90800.

Alternatively, in some implementations, the power and control system 90800 may include the drive control system 90820 and the sub-systems, and one or more other control systems and sub-systems.

As shown in FIG. 76A, in one exemplary embodiment, the power and control system 90800 may be included in the drug delivery pump 9010. The power and control system 90800 may include one or more control units that are connected to one or more sensors, timers and storage units of the drug delivery pump 9010.

In some implementations, the power and control system 90800 may be configured to control a delay time period related to drug delivery. In such implementations, the power and control system 90800 may monitor and control time parameters for initiating and delivering the drug after the activation of the drug delivery pump 9010. For example, upon the activation of the device 9010, the power and control system 90800 may monitor a wait period time (e.g., a predetermined delay time) prior to the initiation of the drug delivery. In one example, during the wait period, the power and control system 90800 may optionally prime the device.

In one example, the power and control system 90800 may provide request notification to activate the NIM mechanism after the device has been activated. The request notification may be provided directly by the drug delivery device delivery device 9010, or via the mobile device 9011. Upon notifying the user to initiate the NIM mechanism 90200, the power and control system may further determine whether an activation/initiation signal (e.g., from the user) is received via the activation button.

When the power and control system 90800 determines that the activation signal is received (e.g., within an NIM activation predetermined time), the power and control system may cause the NIM sub-system to activate. Alternatively, the NIM may be directly activated by the user. The power and control system 90800 may further notify the user that the delivery of the drug has been initiated. It is noted that, the power and control system 800 may activate the NIM mechanism upon receiving the activation signal related for the NIM activation and, upon further receiving signal from on-body sensor that indicates that the drug delivery device 9010 is sensing the skin of the user. Optionally, when the power and control system determines that the activation signal is not received, and/or the on-body sensor is not sensing a skin portion of the user, the power and control system 90800 may notify the user (e.g., via an audible tone), and optionally terminate drug delivery process.

Moreover, in some implementations, when the power and control system 90800 determines that the wait period time has elapsed, the power and control system may notify the user about the initiation of the delivery of the drug. The power and control system may further notify the user that the delivery of the drug has been initiated.

Optionally, the power and control system 90800 may further notify the user of a time period of the drug delivery (e.g., the total time that will be taken for delivering the drug). The power and control system 90800 may communicate the notification to an external device via the communication unit 90830.

Upon the initiation of the drug delivery, the power and control system may further control timing and/or rate parameters for the drug delivery. For example, the power and control system may control the regulating sub-system or mechanism to deliver the drug in a given period of time.

Moreover, the power and control system may process various data captured by the internal and external sensors to determine the timing and/or rate parameters for the drug delivery. Based on the determination, the power and control system may deliver the drug to the user within the appropriate time period.

The power and control system may or may not include all the elements of the power and control system 90800, and/or may include additional elements. Additionally, in some examples, the drug delivery device 9010 may include one or more control systems, including, but not limited to, the power and control system, and may include additional elements for the operations of the drug delivery device.

In some implementations, control system 90800 may include a main control unit or control unit 90810. The main control unit 90810 may include one or more controllers, microcontrollers, microprocessors, or application specific integrated circuits (ASICs). Main control unit 90810 may be implemented as hardware or a combination of hardware and software that may be programmed with instructions. The main control unit 90810 may be configured to execute such instructions to effect various operations of the drug delivery device 9010. Moreover, the power and control system or the main control unit 90810 may communicate, for example, by receiving and/or sending signal or data to and from the communication unit 90830, timer unit 90812, storage unit 90813, on-body sensor 90840, temperature sensor 90880, and I/O unit 90850. The main control unit 90810 may process and interpret the data collected or monitored by the various elements in the one or more control systems in order to determine and execute various functions and operations of the drug delivery device 9010.

It is noted that, the drug delivery device 9010 may operate in two power modes, namely, an active power mode and a non-active power mode. During the active power mode, the power and control system 90800 and the motor 90101 may receive power from the power source (e.g., batteries), and the power and control system 90800 may command the drive control system 90820 to drive various operations, such as the NIM mechanism 90200, and/or regulating mechanism 90500. Whereas, during the non-active power mode, the power and control system 90800 may be powered, and the motor 90101 may not be powered. During the non-active power mode, the power and control system 90800 may execute various operations of the drug delivery device 9010 that may not require operations related to the motor 90101. For example, the power and control system 90800 may establish communication link with the mobile device 9011, and further communicate intermittently or continuously with the mobile device 9011 during the non-active power mode. Additionally, during the non-drive mode, the power and control system 90800 may provide notifications, and alert to the user, and may further communicate with the various sensors (e.g., the temperature sensor and on-body sensor), and/or determine timings of various operations. Optionally, the drug delivery device 9010 may be primed during the non-active power mode.

Moreover, the drug delivery device 9010 may switch between the active power mode and the non-active power mode.

The different power modes may be initiated, based on: (a) type of activation (e.g., device activation, activation of the drug delivery, control of the drug delivery, initiation of the timer, etc.), (b) predetermined time set (e.g., after, or, during the wait time period), and/or (c) operations (e.g., communication with the mobile device and/or sensors, control of the various operations by the power and control system 90800) of the drug delivery device 9010. Alternatively, the activation and/or switching between the modes may be performed manually by the user of the drug delivery device 9010.

It will be appreciated that, by appropriately powering up the motor 90101 and the power and control system 90800, the overall power requirement of the drug delivery device 9010 may be reduced. For example, powering the motor 90101 while the motor 90101 is idle may prematurely drain the power source or battery of the drug delivery device 9010. As such, by managing the power cycle, for example, by providing power to the motor 90101 only when activities related to the motor 90101 are initiated, the life of the battery to operate the drug delivery device 9010 may be suitably increased or the demand for power to operate the drug delivery device 9010 over the life of the drug delivery period may be significantly reduced.

Timer unit 90812 may be a digital clock that may be programmed, for example, to set up time periods for various operations of the drug delivery device 9010. For example, the timer unit 90812 may be configured to indicate, to the main control unit 90810, a wait time or a delay period time for a drug (i.e., a time period before the drug can be forced to be delivered).

Additionally, timer unit 90812 may indicate a time-out period for receiving an activation signal (i.e., a time period within which a user may provide an activation signal to initiate drug delivery or NIM 90200). In some embodiments, timer unit 90812 may directly communicate with the control units of various sensors. In some implementations, the timer unit 90812 may be included in the main control unit 90810.

Control system 90800 may include storage unit 90813. Storage unit 90813 may include one more storage units, such as a random access memory (RAM) or other dynamic storage device, and/or a read only memory (ROM), and/or an electrically erasable programmable read only memory (EEPROM) for storing temporary parameters, information and instructions for the main control unit 90810. In some implementations, the storage unit may be implemented as a non-transitory computer readable medium which stores instructions that may be processed and executed by the control unit to control operations of the control system of the drug delivery device. Additionally, storage unit 90813 may store error codes or error notification for various operations associated with the sensors and control unit of the drug delivery device 9010. The error codes may be pre-programmed into the storage unit 90813.

Storage unit 90813, may additionally, store various predetermined delay or wait time periods related to the drug delivery.

In some examples, power and control system 90800 may include communication unit 90830. Communication unit 90830 may include one or more 90802.11 Wi-Fi transceivers, a cellular transceiver, IEEE 90802.14 ZigBee transceiver, a Bluetooth transceiver, and/or a Bluetooth Low Energy (BLE) transceiver, and for other wireless communication protocols, such as near-field communication (NFC), infrared or ultrasonic. The drug delivery device 9010 may include appropriate antenna (not shown), for communication with an external computer device, and may receive/transmit data via the communication unit 90830.

As shown in FIG. 76D, the drug delivery device 9010 may communicate with an external computing device (via the communication unit 90830). The external computing device may be mobile computing device 9011 such as a smart phone which may include various mobile applications and may be configured with the appropriate communication protocols.

In one example, the mobile device 9011 may include a pump device mobile application (app) 9010a that communicates with the drug delivery device 9010. In such an example, the mobile app 9010a may be provided (from the manufacturer of the drug or drug delivery device 9010) to the user upon purchasing the drug or the drug delivery device 9010. For example, the container or the box of the drug delivery device 9010 may include a unique download identifier that the user may use to download the drug delivery device mobile app 10a. For example, the user may use the download identifier to download the app 9010a from Apple Store or Google Play store.

Upon downloading the drug delivery device app 9010a to the mobile device 9010a, the user may communicate with the drug delivery device 9010 using the drug delivery device application 9010a (e.g., upon establishing a wireless communication link with the drug delivery device 9010). The mobile app 9010a may be configured to cause the mobile device 9011 to process various information received from the drug delivery device 9010, external entities, such as sensors 9011a and 9011b, and/or optionally data received from a cloud server. Based on the processing of such data, the mobile app 9010a may cause the mobile device 9011 to transfer appropriate data to the external cloud server 9011c. Mobile app 10a may further cause the mobile device 9011 to display appropriate notification to the user based on the processing of such data.

In one example, the user may optionally select the activation button 9010b to establish a short range wireless connection with the drug delivery device 9010. In one example, the activation button 9010b may initiate a Bluetooth discovery and pairing process for the mobile device 9011.

Moreover, when the drug delivery device 9010 is activated and in communication with the mobile device 9011, mobile app 9010a may receive a notification from the drug delivery device 9010 (via the communication unit 90830) that indicates activation of the drug delivery device 9010. In some examples, activation button 9010b may additionally be configured to initiate, modify and/or terminate various mechanisms of the drug delivery process.

In some examples, drug delivery device app 9010a may gather and provide various time period information of the drug delivery process to the user. Particularly, in one example, selection of the timer button 9010c may provide information related to various timing periods related to the drug delivery process. The timer button 9010c may be triggered, in one example, upon the selection of the activation button 10b. In one example, the selection of the timer button 9010c may evoke a clock or stop watch application of the mobile device 9011.

In one example, upon the activation of the drug delivery device 9010 and the initiation of the timer unit 90812, the user may gather information related to the predetermined wait time period prior to the initiation of the drug delivery.

Optionally, drug delivery device app 9010a may provide alarm notification. For example, the timer button 9010c may be configured to provide alarm notification prior to the initiation of the drug delivery process. In one example, the user may optionally indicate how often to receive alarm notification prior to the drug delivery process. Timer button 9010c may be further configured to indicate the delivery time period when the drug is being delivered to the user.

Moreover, drug delivery device app 9010a may be configured to receive information, for example, from the drug delivery device 9010. For example, a user may select the Tx/Rx notification and data button 9010d to receive notification related to the drug delivery process (e.g., from the drug delivery pump device 9010), and transmit information related to the drug delivery process (e.g., to the cloud server 9011c).

In one example, upon the selection of the Tx/Rx button 9010d, the user may view notification related to the drug delivery process, such as the activation of the drug delivery device 9010, and/or end of dose notification.

Additionally, the user may view data via the Tx/Rx button 9010d related to the drug delivery process, such as the rate at which the drug was delivered, the total time period of the delivery process. In one example, the user may further transfer the data and/or notification to a cloud server 9011c of relevant entities (e.g., physician, health insurance company, etc.) In such a scenario, the drug delivery device application 9010a may evoke the communication interface (e.g., a cellular communication interface) of the mobile device 9011 to communicate such information that is received from drug delivery device 9010 to the external cloud server 9011c.

In one example, the mobile app 9010a may collect information from other sensors that are local or external to the mobile device. For example, the mobile app 9010a may collect information from a wireless heart rate sensor 9011a, a wireless glucose rate monitor 9011b and cause the mobile device 9011 to process such information. Based on the processed information, the mobile app 9010a may determine delivery rate for the drug, and provide instruction to the user about the delivery rate information and activation inputs for the drug delivery device 9010.

It is contemplated that, the drug delivery device 9010 may wirelessly communicate with the heart rate sensor 9011a and/or the glucose rate monitor 9011b and process the received information to determine the drug delivery rate for the drug.

Referring back to FIG. 76A the power and control system 90800 may include on-body sensors 90840, such as mechanical, electro-mechanical skin sensors, and/or electrical skin sensors, for example, capacitive skin sensor. In one example, the on-body sensor 90840 may be configured to detect whether the pump device 9010 is in contact with the skin of the patient. Based on the determination, the on-body sensor may provide appropriate indication (e.g., signals) to the control unit 90810. The control unit 90810 may then control various functions of the drug delivery device 9010. For example, the control unit 90810 may notify the user to initiate a delivery of the drug only when the pump device 9010 is in contact with the skin of the user. This may be a safety feature of the drug delivery device 9010, as the drive control system 90820 may not be activated until the power and control system receives a signal from the on-body sensor 90840.

In one example, on-body sensor 90840 may be a mechanical switch, and the depression of the mechanical on-body sensor 90840 may trigger the activation of the power and control system 90810, and/or the drive control system 90820. In another embodiment, the on-body sensor may be a capacitive- or impedance-based skin sensor, and the power and control system and/or the drive control system 90820 may be functional upon receiving signal from the on-body sensor. These concepts are not mutually exclusive and one or more combinations may be utilized within the breadth of the present disclosure to prevent, for example, premature activation of the drug delivery device 9010. In a preferred embodiment, the drug delivery device 9010 utilizes one or more mechanical on-body sensors. Additional integrated safety mechanisms are described herein with reference to other components of the drug delivery devices.

Power and control system 90800 may optionally include one or more temperature sensors 90880. The temperature sensor 90880 may be suitably positioned near the drug or the drug container 9050, and configured to detect the temperature of the drug. The temperature sensor may be thermocouples or thermistors (i.e., resistors whose resistances vary significantly with temperature), and electrically coupled to the control unit 90810. The control unit 90810 may process the detected temperature information that is received from the temperature sensor 90880 to control various operations of the drug delivery device 9010. In one example, based on the detected temperature of the drug, the control unit 90810 may notify the user to initiate the delivery of the drug prior to, or after a predetermined time has elapsed. In such a scenario, the control unit 90810 may be configured to override the pre-defined wait period time related to the drug delivery.

The power and control system 90800 may include a power source, such as batteries (not shown), that provides power to various electrical components of the drug delivery device 9010.

Moreover, the input/output electro-mechanical unit 90850 may include an activation button, one or more feedback mechanisms, for example, audible alarms such as piezo alarms and/or light indicators such as light emitting diodes (LEDs).

In one embodiment, the control unit 90810 of the power and control system 90800 interfaces with the mechanical on-body sensor 9024 or the electrical and/or electro mechanical on-body sensor 90840 to identify when the device is in contact with the user and/or the activation mechanism to identify when the device has been activated.

The power and control system 90800 interfaces and controls the drive control system 90820 through one or more interconnects to relay status indication, such as activation, drug delivery, and end-of-dose, and receives status feedback from the drive control system. The status indication or the status feedback may be presented to the user via the I/O unit 90850, such auditory tones or alarms, and/or via visual indicators, such as through the LEDs.

In one embodiment, the control interfaces between the power and control system 90800 and the other components of the drive control system 90820 are not engaged or connected until activation by the user (e.g., via the activation button). This is a desirable safety feature that prevents accidental operation of the drug delivery device, and may additionally maintain and save the battery power during storage, transportation, and the like.

In one implementation, upon activation of the drug delivery device 9010 (e.g., via the activation button of the I/O unit 90850), the multi-function drive mechanism 90100 of the drive control system 90820 is activated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In at least one embodiment, such delivery of drug fluid into a user is performed by the drive control system multi-function drive mechanism in a controlled manner (e.g., via the flow rate control sub-system 90825).

FIG. 76B illustrates an exemplary drive control system 90820 that may be configured to drive and control various mechanical and electro-mechanical components of the drug delivery device 9010. One or more components of the power and control system 90800 (e.g., the control unit 90810) may interface with the drive control system 90820, and instruct the actuator/motor 90101 to drive various elements of the drug delivery device 9010.

In some embodiments, control unit 90810 is electrically coupled and configured to communicate with motor 90101, and any other elements of the drive control system 90820.

In some examples, the drive control system 90820 may optionally include various sensors such as, but not limited to, pressure sensor 90870 (not shown) that may be configured to provide information of the pressure in the container 9050, tether sensor 90875 (not shown) that may be configured to provide a status information of the tether 90525 and a valve senor 90877 (not shown) that may be configured to provide a status information of the valve (not shown) that may be provided on the container. The sensors 90870, 90875 and 90877 may be electrical and/or electro-mechanical components and may communicate with the control unit 90810 by providing status signals corresponding to the respective sensors. The control unit 90810 may process such signals to execute and/or delay execution of the control of various sub-systems via the motor 90101.

In one example, the drive control system 90820 may optionally include timer unit 90860. Timer unit 90860 may be a digital clock that is coupled to the control unit 90810. In one example, the timer unit 90860 may be included in the control unit 90810. In some examples, the timer unit 90860 may be the same as timer unit 90812.

The drive control system may include an actuator or motor 90101. The actuator 90101 may be a number of power/motion sources including, for example, a solenoid, a stepper motor, or a rotational drive motor. In one embodiment, the actuator 90101 is a rotational stepper motor with a notch that corresponds with the gear teeth of the main/star gear 90102. Commonly, such a rotational stepper motor may be referred to as a 'Pac-Man' motor.

In some embodiments (see FIGS. 69A-73D), the actuator 90101 is in vertical alignment and in direct engagement with the main/star gear 90102. As would be readily appreciated by one having ordinary skill in the mechanical arts, the actuator 90101 could be modified to be in horizontal alignment. Additionally or alternatively, the actuator 90101 may be modified to be in indirect engagement with the main/star gear 90102, as discussed below with reference to FIG. 75.

With reference to FIG. 76C, the drive control system 90820 may control the multiple drive mechanisms of the drug delivery device 9010. In one example, the drive control system may control the drive mechanism or sub-system 90100 to control the NIM or sub-system 90200, establish the SFPC 90300 and further control the regulating mechanism 90200 of the drug delivery device 9010.

In one example, the initiation time of the needle insertion mechanism 90200, time to establish the fluid pathway connector 90300, and a drug delivery rate of the drug may be determined by the power and control system 90800 based on the various inputs received by the power and control system from external sensors (e.g., the glucose rate, heart rate, etc.) The power and control system 90800 may then transmit the appropriate command signals and information (e.g., the delivery rate information) to the drive control system 90820.

Furthermore, the storage unit 90865 of the drive control system 90820, and/or the storage unit 90813 may store, in a lookup table and/or database, pre-programmed configurations and setting information such as ratio of gear assembly information (e.g., ratio of gear assembly 90516), rate of rotation of gear information (e.g., rate of rotation of the main star gear 90102), and diameter information of gears and drums. As such, upon receiving the delivery rate information, the control unit 90810 may consult the storage unit 90865 or storage unit 90813 to identify and select the appropriate configuration of the gear assembly and the motor from the lookup table or the database. Based on the selection, the control unit 90810 may drive the motor 90101 to control the drive mechanism 90100, NIM mechanism 90200 and the regulating mechanism 90500 to deliver the drug at the desired rate.

Moreover, the drive control system 90820 may interact with the power and control system 90810 and receive command signals after a predetermined time to control the various drive mechanisms of the drug delivery device 9010.

For example, the drive control system 90820 may receive the command signal and timing information to control or initiate the driving mechanism after a predetermined time. In this example, the control unit 90810 may consult the timer unit 90860 or timer unit 90812 to determine the initiation time of the activation of the drive mechanism. Upon determination, control unit 90810 may command the actuator/motor 90101 after the predetermined time to initiate a drug delivery process by controlling the drive mechanisms as discussed below.

After the initiation of the drug delivery, the control unit 90810 may further consult the timer unit 90860 or timer unit 90812 to complete the drug delivery in a predetermined time. The power and control system 90800 may determine the timing periods, and may send command signals to the drive control system 90820 prior to, during, and after the drug delivery process to control the drug delivery process.

It is noted that, the drive mechanism 90100, insertion mechanism 90200, fluid pathway connector 90300 and the regulating mechanism 90500 may be controlled by the drive control system 90820, concurrently, sequentially and/or non-sequentially, based on a timing period set by the power and control system 90810.

In some examples, the drive control system 90820 may drive or control the insertion mechanism or sub-system 90200 via the drive mechanism 90100. The controlling of the insertion mechanism 90200 may be performed based on the predetermined wait time period or delay time period, either directly by the power and control system 90810, or by the drive control system 90820.

In one example, the drive control system 90820 may additionally control the insertion mechanism 90200 to concurrently provide a fluid pathway connector for drug delivery to a user.

Alternatively, the drive control system 90820 may separately (and prior to or after the insertion mechanism 90200) establish the sterile fluid pathway connector 90300 by connecting a sterile fluid pathway to a drug container to permit fluid flow from the drug container to the needle insertion mechanism for delivery to the user. Details of the control of the insertion mechanism 90200 are discussed below.

VIII.A. Insertion Mechanism

A number of insertion mechanisms may be utilized within the drug delivery devices to activate the needle insertion into the body of the patient. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. The fluid may be introduced into the body through any number of means, including but not limited to: an automatically inserted needle, cannula, micro-needle array, or infusion set tubing.

In one example, the control unit 90810 of the power and control system 90800 may receive activation inputs to initiate the drug delivery device 9010. After a predetermined time or after the determination that the on-body sensor 90840 is sensing a skin portion of the user, the power and control system 90800 may instruct the drive control system 90820 to initiate the NIM 90200. After the wait time period, the control unit 90810 may actuate one or more biasing members to initiate the needle insertion mechanism or sub-system 90200. For example, a biasing member such as a spring may be actuated by the motor 90101 to provide sufficient force to cause the needle and cannula to pierce the skin of the patient. The same spring, an additional spring, or another similar mechanism may be utilized to retract the needle from the patient.

In one embodiment, the power and control system 90800 and/or the drive control system 90820 may actuate the insertion mechanism 90200 as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as developed by the assignee of the present disclosure.

In at least one embodiment, the insertion mechanism 90200 includes an insertion mechanism housing having one or more lockout windows, and a base for connection to the assembly platform and/or pump housing (as shown in FIG. 69B and FIG. 69C). The connection of the base to the assembly platform 9020 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9010. The insertion mechanism may further include one or more insertion biasing members, a needle, a retraction biasing member, a cannula, and a manifold. The manifold may connect to sterile fluid conduit 9030 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9027 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. In one example, the power and control system 90800 may send command signals to the drive control system 90820 to initiate the needle insertion mechanism 90200 after the wait time period. Upon receiving the command signal, the actuator 90101 may cause displacement of the lockout pin(s), such as pulling, pushing, sliding, and/or rotation. This may cause the insertion biasing member to decompress from its initial compressed, energized state. Particularly, the decompression of the insertion biasing member drives the needle and, optionally, the cannula into the body of the user. At the end of the insertion stage or at the end of drug delivery (as triggered by the multi-function drive mechanism 90100 and/or the regulating mechanism 90500), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the user. Accordingly, the insertion mechanism may be used to insert a needle and cannula into the user and, subsequently, retract the needle while retaining the cannula in position for drug delivery to the body of the user.

As further discussed below, in some examples, the power and control system 90800 and/or the drive control system 90820 may control the needle insertion mechanism 90200 via the multi-function drive mechanism 90100. Additionally, the power and control system 90800 and/or the drive control system 90820 may control the rate of drug delivery via the drive mechanism 90100 and regulating mechanism 90500 such as by metering, providing resistance, or otherwise preventing free axial translation of the plunger seal utilized to force a drug substance out of a drug container (thereby delivering drug substances at variable rates and/or delivery profiles).

Referring back to FIGS. 70A-70D and 71A-71D, the multi-function drive mechanisms 90100 may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user.

In at least one embodiment, as shown in FIGS. 70A-70D and 71A-71D, the control unit 90810 may initiate motion of the actuator 90101 of the drive control system 90820, which may cause rotation of the main/star gear 90102 of the multi-function drive mechanism 90100. Main/star gear 90102 is shown as a compound gear with aspects 90102A and 90102B (see FIG. 72). In one example, main/star gear 90102 conveys motion to the regulating mechanism 90500 through gear assembly 90516.

In another example, main/star gear 90102 conveys motion to the needle insertion mechanism 90200 through gear 90112. As gear 90112 is rotated by main/star gear 90102, gear 90112 engages the needle insertion mechanism 90200 to initiate the fluid pathway connector into the user, as described in detail above. In one particular embodiment, needle insertion mechanism 90200 is a rotational needle insertion mechanism. Accordingly, gear 90112 is configured to engage a corresponding gear surface 90208 of the needle insertion mechanism 90200 (see FIGS. 70A and 71B). Rotation of gear 90112 causes rotation of needle insertion mechanism 90200 through the gear interaction between gear 90112 of the drive mechanism 90100 and corresponding gear surface 90208 of the needle insertion mechanism 90200. Once suitable rotation of the needle insertion mechanism 90200 occurs, for example rotation along axis 'R' shown in FIG. 70B-70C, the needle insertion mechanism may be initiated to create the fluid pathway connector into the user.

In an alternative embodiment, as shown in FIG. 75A, the insertion mechanism 90200 includes a rotationally biased member 90210 which is initially held in an energized state. In one example, the rotationally biased member is a torsional spring. The drive control system 90820 may actuate one or more components of the multi-function drive mechanism 90100, insertion mechanism 90200 and/or the regulating mechanism 90500 to prevent and/or control the rotation of the rotational biasing member 90210.

The gear 90112 may be configured to engage a corresponding gear surface of a control arm 90202 (visible in FIG. 75B) that contacts or blocks the needle insertion mechanism 90200. Rotation of gear 90112 causes movement of the control arm 90202, which may initiate or permit rotation of needle insertion mechanism 90200.

Moreover, the rotational biasing member may be prevented from de-energizing by contact of a component of the insertion mechanism with a rotation prevention feature, such as a blocking aspect of the control arm, of the drug delivery device. In one example, the rotational biasing member 90210 may be prevented from de-energizing by interaction of gear surface 90208 with gear 90112.

It is contemplated that, in one example, at least the prevention of the rotation of the rotational biasing member 90210 may be implemented prior to the on-body sensing. As such, when the on-body sensor 90840 senses skin portion of the user, and/or the power and control system 90800 receives input for initiation of the drug delivery (e.g., via the activation button) and/or input for needle insertion, the power and control system 90800 may command the drive control system 90820 to permit the rotationally biased member 90210 to, at least partially, de-energize. This may cause one or more components of the insertion mechanism 90200, drive control mechanism 90100 and/or regulating mechanism 90500 to rotate and, in turn, cause, or allow, the insertion of the needle into the patient. Furthermore, a cannula may be inserted into the patient as described above.

As detailed below, during the delivery of the drug, based on the interactions among the drive control system 90820, the drive mechanism 100 and the regulating mechanism 90500, the insertion mechanism may be further controlled. For example, when the control arm or another component of the drive control system 90820 recognizes a slack in the tether, the rotationally biased member may be allowed to further de-energize, causing additional rotation of one or more components of the insertion mechanism 90200.

This rotation may cause, or allow, the drive control system 90820 to retract the needle from the patient. The needle may be fully retracted in a single step or there may be multiple steps of retraction.

In at least one embodiment, the needle insertion mechanism 90200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism 90500 and/or one or more of the sensors (e.g., the tether sensor, pressure sensor, etc.) During these stages of operation, delivery of fluid substances from the drug chamber 9021 may be initiated, on-going, and/or completed by the expansion of the biasing member 90122 from its initial energized state acting upon the piston 90110A, 90110B and plunger seal 9060.

Additionally or alternatively, the drive control system 90820 may indirectly engage the needle insertion mechanism 90200 in order to establish the sterile fluid connection sub-system 90300, as described below.

VIII.B. Fluid Pathway Connector

The power and control system 90800 and/or drive control system 90820 may additionally establish the fluid pathway connector or sub-system 90300 by connecting the sterile fluid conduit to the drug container, to enable the fluid pathway connector.

The establishment of the fluid pathway connector 90300 may be performed prior to, during, or after the wait time period. Additionally, the pathway connection 90300 may be established prior to, or during the actuation of the insertion mechanism 90200. In some embodiments, the power and control system 90800 may cause the establishment of the fluid pathway connector 90300 via the multi-function drive mechanism 90100, and/or one of the other sub-systems such as the needle insertion mechanism or sub-system 90200. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon activation of the device 9010, the fluid pathway connector 90300 is established to connect the sterile fluid conduit 9030 to the drug container of the drive mechanism 90100. Such connection may be facilitated by a piercing member, such as a needle, penetrating a pierceable seal of the drug container of the drive mechanism 90100. The sterility of this connection may be maintained by performing the connection within a flexible sterile sleeve. Upon substantially simultaneous activation of the insertion mechanism 90200, the fluid pathway between drug container and insertion mechanism is complete to permit drug delivery into the body of the user. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes.

According to such an embodiment, a drug container 9050 may have a drug chamber 9021 within a barrel between a pierceable seal (not shown) and a plunger seal 9060. A drug fluid is contained in the drug chamber 9021. Upon activation of the device by the user, a drive mechanism (e.g., multi-function drive mechanism 90100) asserts a force on a plunger seal 9060 contained in the drug container. As the plunger seal 9060 asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap 9052, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism 90100. Once the integrated sterile fluid pathway connector is connected or opened, drug fluid is permitted to flow from the drug container 9050, through the integrated sterile fluid pathway connector 90300, sterile fluid conduit 9030, and insertion mechanism 90200, and into the body of the user for drug delivery. In at least one embodiment, the fluid flows through only a manifold and a cannula and/or needle of the insertion mechanism, thereby maintaining the sterility of the fluid pathway before and during drug delivery.

In one embodiment, the power and control system 90800 may command the drive control system 90820 to establish or activate the sterile fluid pathway subsystem or connection 90300. For example, the connection 90300 may be established via the needle insertion mechanism 90200 which may be activated or controlled by the multi-function drive mechanism 90100.

Additionally or alternatively, the sterile fluid pathway connector 90300 may be directly initiated directly by the multi-function drive mechanism 90100. For example, the control unit 90810 may command the motor 90101 to actuate a rotational gear, such as the star gear 90102 described in detail herein, that may operate concurrently or sequentially to: (a) control the rate of drug delivery, (b) to actuate the needle insertion mechanism 90200, and/or (c) initiate the sterile fluid pathway connector 90300, based on various predetermined times (e.g., the wait time period, the drug delivery period) as provided by the power and control system 90800.

In one embodiment, shown in FIGS. 69A-69C, the multi-function drive mechanism 90100 performs all of these steps substantially concurrently. In that embodiment, the drive control system 90820 causes the multi-function drive mechanism 90100 to rotate a gear (e.g., star gear 90102) that acts upon several other components (e.g., other gear assemblies). For example, the gear acts on a gear assembly to control the rate of drug delivery, while also contacting a needle insertion mechanism 90200 to introduce a fluid pathway connector 90200 into the user. As the needle insertion mechanism 90200 is initiated, the sterile fluid connection is made to permit drug fluid flow from the drug container 9050, through the fluid conduit 9030, into the needle insertion mechanism 90200, for delivery into the patient as the gear and gear assembly of the multi-function drive mechanism control the rate of drug delivery.

It will be appreciated that, the drug delivery device 9010 is configured to deliver a range of drugs with different viscosities and volumes via the established sterile fluid pathway subsystem or connection 90300. In addition, the drug delivery device 9010 delivers a drug at a controlled flow rate (speed) and/or of a specified volume. In one embodiment, the drug delivery process is controlled by one or more flow restrictors (not shown) within the fluid pathway connector and/or the sterile fluid conduit. In other embodiments, other flow rates may be provided by varying the geometry of the fluid flow path or delivery conduit As shown in FIGS. 70A-70D and 71A-71D, rotation of the needle insertion mechanism 90200 in this manner may also cause a connection of a sterile fluid pathway to a drug container to permit fluid flow from the drug container to the needle insertion mechanism for delivery to the user. In such an example, the control unit 90810 may command and control: (a) drive mechanism 90100, (b) the needle insertion mechanism 200, and (c) the sterile fluid pathway connector 90300. For example, ramp aspect 90222 of needle insertion mechanism 90200 is caused to bear upon a movable connection hub 90322 of the sterile fluid pathway connector 90300. As the needle insertion mechanism 90200 is rotated by the multi-function drive mechanism 90100 (based on the control unit 90810 command), ramp aspect 90222 of needle insertion mechanism 90200 bears upon and translates movable connection hub 90322 of the sterile fluid pathway connector 90300 to facilitate a fluid connection therein. Such translation may occur, for example, in the direction of the hollow arrow along axis 'C' shown in FIGS. 70B and 71B.

Moreover, the drug delivery device 9010 may control the flow rate of the drug. In one example, the flow rate may be controlled by the drive control system 90820 (e.g., the motor of the drive control system) by varying the speed at which one or more components of the drive mechanism 90100 advances into the drug container 9050 to dispense the drug. It is noted that, a combination of the different flow rate control methods may be implemented to control the flow of the drug via the sterile fluid pathway connector 90300.

The power and control system 90800 (e.g., the control unit 90810) may send command signal to the drive control system 90820 to control the flow rate control sub-system or regulating mechanism 90500 via the multifunction drive mechanism 90100 as discussed below. The rate of drug delivery as controlled by the drive control system 90820 may be determined by: selection of the gear ratio of gear assembly 90516; selection of the main/star gear 90102; selection of the diameter of winding drum/gear 90520 and further driving such elements by commanding the actuator 90101 to control the rate of rotation of the main/star gear 90102; or any other method known to one skilled in the art. By using electromechanical actuator 90101 to control and adjust the rate of rotation of the main/star gear 90102, it may be possible to configure the drug delivery device 9010 to provide a variable dose rate (i.e., the rate of drug delivery is varied during a treatment).

Additionally, the drive control system 90820 may control the regulating mechanism or sub-system 90500 which may include controlling the rate of drug delivery by metering, providing resistance, or otherwise preventing free axial translation of the plunger seal utilized to force a drug substance out of a drug container.

With references to the embodiments shown in FIGS. 70A-70D and 71A-71D, the power and control system 90820 may control the drive mechanism 90100 via the motor 90101. The drive mechanism 90100 may include a gear assembly 90110 including a main gear 90102, a drive housing 130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism 90100 may further contain one or more drive biasing members, one or more release mechanisms, and one or more guides, as are described further herein. The components of the drive mechanism 90100 function to force a fluid from the drug container out through the pierceable seal, or preferably through the piercing member of the fluid pathway connector 90300, for delivery through the fluid pathway connector, sterile fluid conduit, and insertion mechanism into the body of the user.

In one particular embodiment, the drive mechanism 90100 employs one or more compression springs as the drive biasing member(s) 90122. In such embodiment, upon the activation of the drug delivery device by the user (e.g., via the activation button) the power and control system 90800 may be configured to directly or indirectly (and electromechanically) release the drive biasing members 90122 from an energized state. Upon release, the drive biasing members 90122 may bear against and act upon the plunger seal 9060 to force the fluid drug out of the drug container. The compression spring may bear against and act upon a piston which, in turn, acts upon the plunger seal 9060 to force the fluid drug out of the drug container. In one example, one or more drive biasing members 90122 may be compressed between the drive housing 90130 and piston 90110, wherein the drive biasing members 90122 may bear upon an interface surface 90110C of the piston.

Optionally, a cover sleeve (not shown) may be utilized between the drive biasing members 90122 and the interface surface 90110C of the piston 90110 for example, to promote even distribution of force from the drive biasing member 90122 to the piston 90110, prevent buckling of the drive biasing members 90122, and/or hide biasing members 90122 from user view. Interface surface 90110C of piston 90110 is caused to rest substantially adjacent to, or in contact with, a proximal end of seal 9060. Although the embodiments shown in FIGS. 70A-70D and 71A-71D show a singular biasing member it is also contemplated that one or more biasing members disposed to act in parallel may be used.

As discussed below, in some embodiments, the drive control system 90820 and/or the power and control system 90800 may control the delivery rate of the drug via the drive mechanism 90100, insertion mechanism 90200 and the regulating mechanism 90500.

Figure 71D:
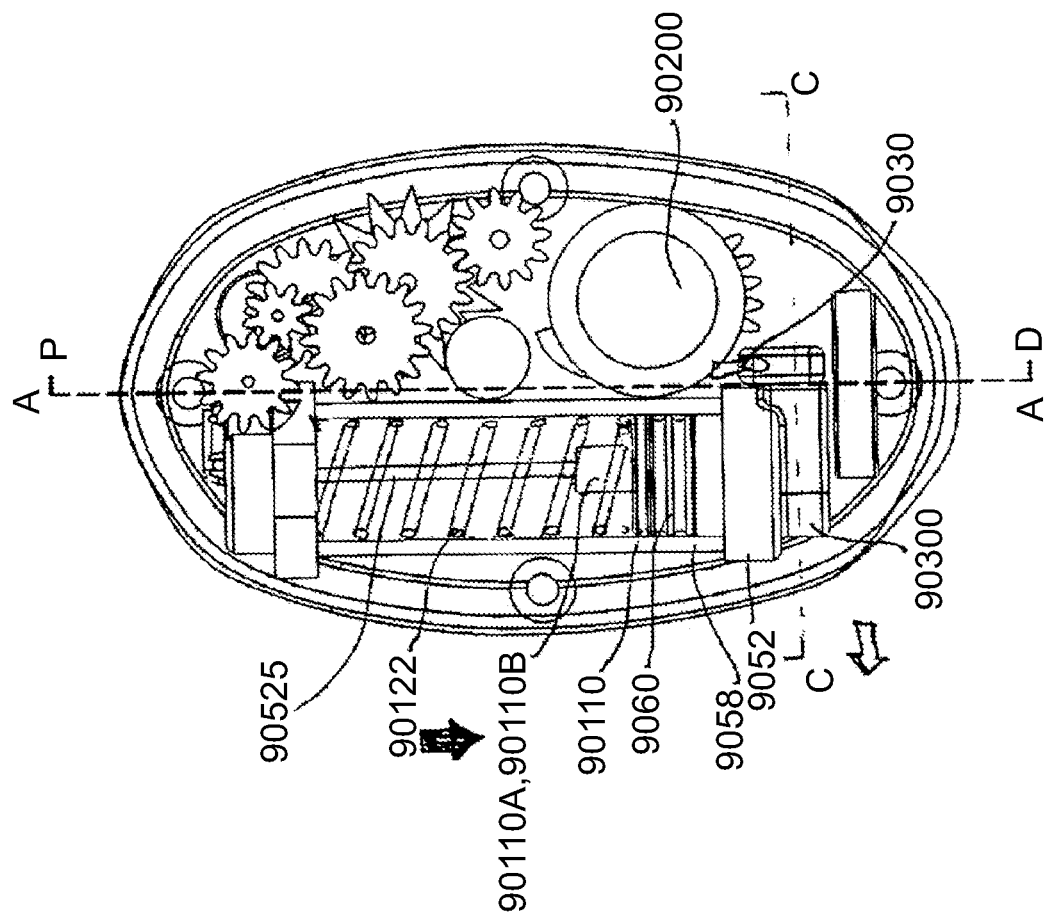

As best shown in FIG. 70D and FIG. 71D, the piston 90110 may be comprised of two components 90110A and 90110B and have an interface surface 90110C to contact the plunger seal 9060.

Moreover, a tether, ribbon, string, or other retention strap (referred to herein as the "tether" 90525) may be connected at one end to the piston 90110A, 90110B. For example, the tether 90525 may be connected to the piston 90110A, 90110B by retention between the two components of the piston 90110A, 90110B when assembled. The tether 90525 is connected at another end to a winch drum/gear 90520 of regulating control mechanism 90500. Through the use of the winch drum/gear 90520 connected to one end of the tether 90525, and the tether 90525 connected at another end to the piston 90110A, 90110B, the regulating mechanism 90500 functions to control, meter, provide resistance, or otherwise prevent free axial translation of the piston 90110A, 90110B and plunger seal 9060 utilized to force a drug substance out of a drug container 9050.

Accordingly, the power and control system 90800 may control the regulating sub-system or mechanism 90500 which may be a portion of the gear assembly 90116 aspect of the multi-function drive mechanism, and which together may function to control the rate or profile of drug delivery to the user.

With reference to FIG. 76C, the power and control system, via the drive control system 90820, may control the regulating mechanism 500 (e.g., via the drive control mechanism 90100). For example, the control unit 90810 may drive the actuator or Pac-Man motor 90101 to drive various gear assembly (e.g., gear assembly 90516) of the regulating mechanism 90500, by selecting appropriate configurations for the motor 90101 and gear assembly. Moreover, the driving of the regulating mechanism may be time-controlled, as discussed herein.

As shown in FIGS. 70A-70D and 71A-71D, and in isolation in FIGS. 72 and 73A-73B, in the embodiments of the present disclosure, the regulating mechanism 90500 is gear assembly driven by an actuator 90101. Moreover, upon receiving command signals from the control unit 90810, the motor 90101 may control the regulating mechanism 90500 to retard or restrain the distribution of tether 90525, thus allowing the tether 90525 to advance at a regulated or desired rate. This restricts movement of piston 90110 within barrel 9058, which is pushed by one or more biasing members 90122, hence controlling the movement of plunger seal 9060 and delivery of the drug contained in chamber 9021. As the plunger seal 9060 advances in the drug container 9050, the drug substance is dispensed through the sterile pathway connection 90300, conduit 9030, insertion mechanism 90200, and into the body of the user for drug delivery. In one example, the regulated motion of the tether 90525 may be monitored by an optional tether sensor 90875 which may provide status feedback to the control unit 90810 of the power and control system 90800. The control unit 90810 may process the feedback status information of the regulated motion of the tether 90525 to further control the regulating mechanism 90500.

As discussed above, in at least one embodiment, the motor 90101 may be a Pac-Man motor that has a gear interface within which one or more teeth of the main gear may partially reside during operation of the drug delivery pump device 9010. The operation of the Pac-Man motor may be controlled by the control unit 90810. (see FIGS. 73A-73B).

In one example, when the gear interface 90101A of the Pac-Man motor 90101 is in alignment with a tooth 90102A of the main gear 90102, rotational motion of the Pac-Man motor 90101 causes gear interface rotation of the main gear 90102. When the Pac-Man motor 90101 is between gear teeth of the main gear, it may act as a resistance for, for example, back-spinning or unwinding of the gear assembly 90116. In one particular embodiment, the Pac-Man motor 90101 utilizes an alternating direction type motor to rotate the Pac-Man motor 90101 backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the motor, coupled with the use of the gear interface cut within the Pac-Man motor, may provide suitable safety features to prevent a runaway condition that could potentially lead to over-delivery of drug to the user. Further detail about the gear assembly 90116, regulating mechanism 90500, and multi-function drive mechanism 90100 are provided herein. In a particular embodiment shown in FIGS. 73A-73B, the regulating mechanism 90500 further includes one or more gears 90511, 90512, 90513, 90514, of a gear assembly 90516. One or more of the gears 90511, 90512, 90513, 90514 may be, for example, compound gears having a small diameter gear attached at a shared center point to a large diameter gear. Gear 90513 may be rotationally coupled to winch drum/gear 90520, for example by a keyed shaft, thereby coupling rotation of gear assembly 90516 to winch drum/gear 90520. Compound gear 90512 engages the small diameter gear 90513 such that rotational movement of the compound gear aspect 90512B is conveyed by engagement of the gears (such as by engagement of corresponding gear teeth) to gear 90513. Compound gear aspect 90512A, the rotation of which is coupled to gear aspect 90512B, is caused to rotate by action of compound gear aspect 102B of the main/star gear 90102. Compound gear aspect 90102B, the rotation of which is coupled to main/star gear 90102, is caused to rotate by interaction between main/star gear 90102A and interface 90101A of the actuator 90101. Thus, rotation of main/star gear 90102 is conveyed to winch drum/gear 90520. Accordingly, rotation of the gear assembly 90516 initiated by the actuator 90101 (of the drive control system 90820) may be coupled to winch drum/gear 90520 (i.e., through the gear assembly 90516), thereby controlling the distribution of tether 90525, and the rate of movement of plunger seal 9060 within barrel 9058 to force a fluid from drug chamber 9021. The rotational movement of the winch drum/gear 90520, and thus the axial translation of the piston 90110 and plunger seal 9060, are metered, restrained, or otherwise prevented from free axial translation by other components of the regulating element 90500, as described herein. As described above, the actuator 90101 may be a number of known power/motion sources including, for example, a motor (e.g., a DC motor, AC motor, or stepper motor) or a solenoid (e.g., linear solenoid, rotary solenoid).

As discussed above, the embodiments shown in FIGS. 75A-75B show an actuator 90101 that is driven by the control unit 90810, and is in horizontal alignment and indirect engagement with the main/star gear 90102. Such an embodiment may utilize a rack and pinion engagement, a drive screw, or a worm gear 90101W, as shown in FIGS. 75A-75B, to change the direction of motion from horizontal to vertical (i.e., perpendicular interaction). Actuator 90101 (based on command signals received from the control unit 90810) rotates worm gear 90101W, which engages gear 90101G and conveys the motion to the Pac-Man gear 90101A. The Pac-Man gear 90101A engages main/star gear 90102 to enable operation of the drive mechanism and the drug delivery device, as described herein.

The control unit 90810 controls main star gear 90102 via the motor 90101. The main star gear 90102 may then drive other gear assembly. For example, main/star gear 90102 may drive operation of gear 90112 to enable operation of the needle insertion mechanism 90200, as described herein.

In one embodiment, the control unit 90810 provides command signals such that the actuator 90101 rotate the worm gear 90101W, gear 90101G, and Pac-Man gear 90101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 90101, coupled with the use of the gear interface of the worm gear 90101W, gear 90101G, and Pac-Man gear 90101A with the main/star gear 90102, provide suitable safety features to prevent a runaway condition that could potentially lead to over-delivery of drug to the user.

Additionally, the motor 90101 may include a stop member 90101B that stops the rotation of the Pac-Man gear 90101A against a stop block 90150. Stop block 90150 further prevents over-rotation of the Pac-Man gear 90101A and, accordingly, the main/star gear 90102 to prevent a runaway condition that could potentially lead to over-delivery of drug to the user. For the device to function in this configuration, the Pac-Man gear 90101A must be rotated backwards the other direction before rotating forwards again to progress the main/star gear 90102 because the stop member 90101B prevents over rotation in one direction by interaction with the stop block 90150.

Additionally, the geometry of worm gear 90101W may be configured such that it is self-locking and/or cannot be back-driven by gear 90101G. This may be done by configuration of parameters such as: pitch, lead angle, pressure angle, and number of threads. In so doing, runaway conditions of the drive mechanism will be prevented by the worm gears resistance to rotations that are not caused by actuator 90101. Alternatively or additionally, the control unit 90810 may be configured to determine whether there is any feedback from the worm gear 90101W that is caused by the rotations of other gears (e.g., gear 90101G) and not by the motor 90101. If the control unit 90810 determines or receives such feedback, the control unit 90810 may terminate further operations.

It is noted that, the power and control system 90800 does not control the regulating mechanisms 90500 of the present disclosure to drive the delivery of fluid substances from the drug chamber 9021. The delivery of fluid substances from the drug chamber 9021 is caused by the expansion of the biasing member 90122 from its initial energized state acting upon the piston 90110A, 90110B and plunger seal 9060 (which may be actuated by the control unit 90810 via the motor 101). The regulating mechanisms 90500 instead function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. According to a preferred embodiment, the controlled delivery drive mechanisms and drug delivery devices of the present disclosure include a regulating mechanism indirectly or directly connected to a tether metering the axial translation of the piston 90110A, 90110B and plunger seal 9060, which are being driven to axially translate by the biasing member 90122.

In one example, the power and control system 90800 of the drug delivery device 9010 may be configured to receive one or more regulating parameters for controlling the regulating mechanism 90500. Alternatively, or additionally the power and control system 90800 may receive sensor inputs (e.g., heart rate sensor, glucose monitor sensor information) and may then translate the sensor inputs into regulating parameters. The control unit 90810 may then control the regulating mechanism 90500 after a predetermined time (e.g., after the wait time period). Based on the inputs, the control unit 90810 may meter the release of the tether 90525 by the winch drum/gear 90520 and thereby permit axial translation of the piston 90110 by the biasing member 90122 to translate a plunger seal 9060 within a barrel 9058.

Based on the regulating parameters, the control unit 90810 and motor 90101 may additionally control the restraint provided by the tether 90525 and winch drum/gear 90520 on the free axial translation of the piston 90110 upon which the biasing member 90122 bears upon via the motor 90101. The control unit 90810 may control such operations to provide a desired drug delivery rate or profile, to change the dose volume for delivery to the user, and/or to otherwise start, stop, or pause operation of the drive mechanism. In one example, the control unit 90810 may control the drug delivery rate in order to complete a drug delivery dose within a desired or a predetermined time.

During the drug delivery process, and after a predetermined wait time period, the power and control system may provide delivery instructions to the drive control system 90820. Based on the instructions, the drive control system 90820 may control the components of the drive mechanism 90100, to axially translate the plunger seal 9060 of the drug container 9050 in the distal direction. Optionally, the drive mechanism 90100 and/or the regulating mechanism 90500 may include one or more compliance features which enable additional axial translation of the plunger seal 9060 to, for example, ensure that substantially the entire drug dose has been delivered to the user. For example, the plunger seal 9060, itself, may have some compressibility permitting a compliance push of drug fluid from the drug container.

For example, the controlled delivery drive mechanisms and/or drug delivery devices of the present disclosure may additionally enable a compliance push to ensure that substantially all of the drug substance has been pushed out of the drug chamber 9021. The plunger seal 9060, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch may be utilized to contact, connect, or otherwise enable a transmission to the control unit 90810 of the power and control system 90800 to signal end-of-dose to the user. This configuration may further enable true end-of-dose indication to the user.

As discussed with reference to FIG. 76B, the drive control system 90820 may include various sensors (e.g., the tether sensor 90875, valve sensor 90877, pressure sensor 90870) that may be coupled to the control unit 90810 and/or to the motor 90101. The sensors may be configured to provide signal or status information for various elements of the systems and sub-systems of the drug delivery device 9010. In one example, the control unit 90810 may process the feedback signals or the status information received from the sensors to control the sub-systems, such as the regulating sub-system or mechanism 90500.

Additionally, the power and control system 90800 may provide notification to the user based on the feedback provided by the sensors to the control unit. The notification may be tactile, visual, and/or auditory, as described above, and may be redundant such that more than one signal or type of notification is provided to the user during use of the device. For example, the user may be provided an initial notification to indicate that the drug delivery device 9010 is operational and ready for drug delivery and may further may provide an end-of-dose notification, based on the feedback signal provided, for example, by one or more sensors. In one example, pressure sensor 90870 and/or a valve sensor 90877, positioned at appropriate location in the drug delivery device 9010, may sense the end-of-dose when the piston reaches the end of its axial translation. Accordingly, the control unit 90810 may then provide an end-of-dose notification based on the sensor signals received from the sensors.

Additionally or alternatively, tether 90525 may have one or more sensor triggers such as electrical contacts, optical markings, and/or electromechanical pins or recesses that are configured to provide status feedback to the tether sensors 90875, and in turn, to the control unit 90820. In at least one embodiment, an end-of-dose status notification may be provided to the user once the tether sensor 90875 detects that the final status trigger positioned on the tether 90525 has reached a final position upon the end of axial travel of the piston 90110A, 90110B and plunger 9060 within the barrel 9058 of the drug container 9050. The tether sensor 90875 may be, for example, an electrical switch reader to contact the corresponding electrical contacts, an optical reader to recognize the corresponding optical markings, or a mechanical or electromechanical reader configured to contact corresponding pins, holes, or similar aspects on the tether 90525.

In one example, the status triggers (not shown) may be positioned along the tether 90525 to be read or detected at positions which correspond with the beginning and end of drug delivery, as well as at desired increments during drug delivery.

In some examples, the drive control system 90820 initiates the drug delivery (upon actuation of the drive mechanism 90100) by release of the biasing member 90122 and the resulting force applied to the piston 90110A, 90110B and plunger seal 9060. The power and control system 90800 further instructs the drive control system 90820 to control the rate or profile of drug delivery to the user by controlling the regulating mechanism 90500, gear assembly 90516, winch drum/gear 90520, releasing the tether 90525 and permitting expansion of the biasing member 90122 and axial translation of the piston 90110A, 90110B and plunger seal 9060. As this occurs, the status triggers of the tether 90525 are contacted or recognized by the tether sensor and the status of the drive mechanism before, during, and after operation can then be relayed to the control unit 90810 of the power and control system 90800 to provide feedback to the user. Depending on the number of status triggers located on the tether 90525, the frequency of the incremental status indication may be varied as desired. As described above, a range of tether sensors may be utilized depending on the status triggers utilized.

In some embodiments, the tether sensor may include one or more sensors of similar type, and/or a combination of different types of sensors. In one example, a tension force may be applied to the tether 90525 (e.g., according to one or more command signals from the control unit 90810). When the drug delivery device 9010 reaches the end-of-dose, the tether 90525 goes slack which may be detected by a tether sensor 90875 such as an electrical or electromechanical switch. The tether sensor 90875 may signal a slack in the tether 90525 to the control unit 90810 of the power and control system 90800.

Additionally, gear 90511A and/or gear 90511B of gear assembly 90516 may be configured as an encoder along with a sensor. For example, the sensor/encoder combination may be configured to provide feedback of gear assembly rotation. In one example, the encoder/sensor may be calibrated to an initial position of the piston (e.g., the position of piston 90110 when there is no slack in the tether 90525). Moreover, this positional information may be recorded or stored in the control unit 90810. As such, the control unit 90810 or the power and control system 800 may receive positional feedback, end-of-dose signal, and error indication, such as an occlusion, for example, due to a slack in the tether 90525 prior to reaching the expected number of motor rotations as counted by the sensor/encoder. Alternatively or additionally, the drive control system 90820 may control the rate of flow of drug via the tether 90525 in combination with the regulating mechanism 90500.

It will be appreciated that, additional and/or alternative means may be implemented for terminating or restraining the flow of the medicament in the case of slack in, or failure of, the tether 90525 (e.g., during a breakage of the tether).

FIGS. 74A-74B shows one such embodiment for a safety-stop during a failure of the tether 90525. Disposed within barrel 9058 are brake 9064, sleeve 9062, and plug 9068, and optionally retainer 9066. Biasing member 90122 bears against sleeve 9062. Initially, the tether 90525 is engaged with plug 9068, thereby allowing tether 90525 to restrain the motion of sleeve 9062. This restraint controls the rate of expansion or de-energizing of biasing member 90122. When tether 90525 is under tension, plug 9068 bears against distal face 9064A of brake 9064, causing proximal face 9064B of brake 9064 to bear against sleeve 9062. Due to this contact, and the profile of the distal end 9062A of sleeve 9062, brake 9064 is maintained in a substantially conical configuration as shown in FIG. 74A. In this configuration, expansion or de-energizing of biasing member 90122 is restrained. Also, in this conical configuration, the outer diameter of brake 9064 is less than the inner diameter of barrel 9058, thus translation of the brake is not restrained by contact with the inner wall of the drug container. Also, a portion of brake 64 is in contact with retainer 9066. Because brake 9064 is maintained in this configuration by plug 9068 and sleeve 9062, translation of sleeve 9062, caused by decompression of biasing member 90122, is transferred to retainer 9066. Likewise, contact of retainer 9066 with plunger seal 9060 causes translation of plunger seal 9060.

As shown in FIG. 74B, in the event of slack in, or failure of, tether 90525, plug 9068 is no longer held in position by tether 90525 and, therefore, no longer restrains motion of sleeve 9062. As biasing member 90122 decompresses or de-energizes, brake 9064 transforms to a relatively less conical or flatter configuration. This may be caused by a natural bias of brake 9064 to transform to this configuration or, alternatively, may be caused by contact of brake 9064 with both retainer 9066 and sleeve 9062. As the brake is transformed, it comes into contact with the inner wall of barrel 9058. The brake thus acts as a wedge to restrict translation of sleeve 9062. This may prevent further translation or may act to restrict the rate of translation. Optionally, restoring tension in the tether may cause the plug to contact the brake and to transform the brake back to its conical configuration and thus restore normal operation of the drug delivery device.

FIGS. 74A-74B shows the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 9062 (i.e., applying a braking force). In another embodiment, the brake 9064 could employ a star-shaped or other configuration when in a substantially flattened position so as to make contact with the inner diameter of the barrel 9058 to prevent or restrict further axial translation of sleeve 9062. Without further translation of sleeve 9062, biasing member 90122 cannot expand or de-energize further which, in turn, prevents or restricts further drug delivery to the user. This provides a necessary and useful safety measure for drug delivery, to prevent over-delivery or accelerated delivery of drug to the user.

Moreover, as discussed above, the control of the tether 90525 may be provided by the control unit 90810. Additionally, any feedback related to slack or failure of the tether 90525 may be provided to the drive control system 90820 and/or to the power and control system 90800.

As described above, the regulating mechanisms 90500 provide resistance to the free motion of the piston 90110A, 90110B and plunger seal 9060 as they are pushed by the expansion of the biasing member 90122 from its initial energized state. The regulating mechanism 90500 may not drive the delivery but may only control the delivery motion.

It is noted that, the tether may limit or restrain the motion of the piston 90110 and plunger seal 9060, but may not apply the force for the delivery (see FIGS. 70A-70D and 71A-71D). The motion of the piston 90110A, 90110B and plunger seal 9060 as they are pushed by the expansion of the biasing member 90122 from its initial energized state are shown in the direction of the solid arrow along axis 'A' from proximal or first position 'P' to the distal or second position 'D', as shown in the transition of FIGS. 70A-70D and 71A-71D.

Control of the tether 90525 is further described with reference to FIG. 72 and FIGS. 73A-73B.

FIG. 72 shows a perspective view of the multi-function drive mechanism, according to at least a first embodiment, during its initial locked stage. Initially, the tether 90525 may retain the biasing member 90122 in an initial energized position within piston 90110A, 90110B. When the power and control system 90800 receives inputs for activation, it commands the drive control system to initiate the multi-function drive mechanism 90100. In one example, the drive mechanism 90100 may cause the biasing member to impart a force to piston 90110 and therefore to tether 90525. This force on tether 90525 imparts a torque on winding drum 90520 which causes the gear assembly 90516 and regulating mechanism 90500 to begin motion.

Figure 71C:
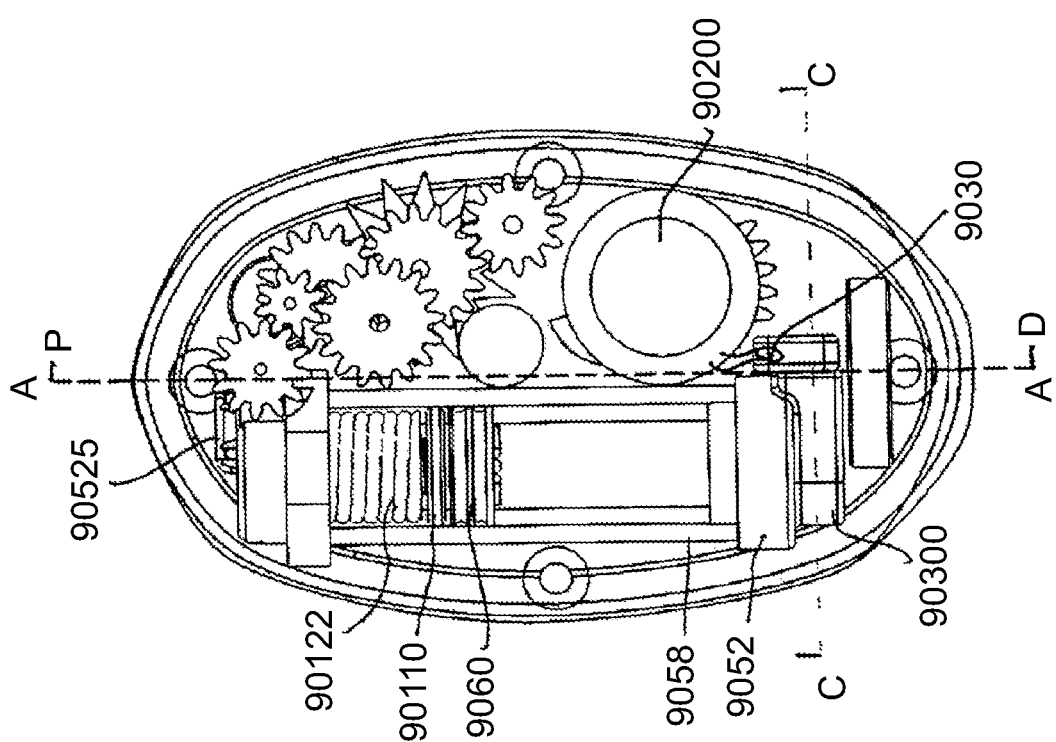

Moreover, as shown in FIG. 71C, the piston 90110 and biasing member 90122 are both initially in a compressed, energized state behind the plunger seal 9060. The biasing member 90122 may be maintained in this state until activation of the device between internal features of drive housing 90130 and interface surface 90110C of piston 90110A, 90110B. As the drug delivery device 9010 is activated and the drive mechanism 90100 is triggered to operate, biasing member 90122 is permitted to expand (i.e., decompress) axially in the distal direction (i.e., in the direction of the solid arrow shown in FIGS. 70A-70D and FIGS. 71A-71D). Such expansion causes the biasing member 90122 to act upon and distally translate interface surface 90110C and piston 90110, thereby distally translating plunger seal 9060 to push drug fluid out of the drug chamber 9021 of barrel 9058.

As discussed above, an end-of-dose status indication may also be provided to the user once one or more sensors contacts or detects the end of axial travel of the piston 90110A, 90110B and plunger seal 9060 within the barrel 9058 of the drug container 9050 (e.g., based on a status trigger positioned on the tether 90525). The status triggers may be positioned along the tether 90525 at various increments, such as increments which correspond to certain volume measurement, to provide incremental status indication to the user. In at least one embodiment, the sensor is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status triggers which contact or are otherwise recognized by the corresponding electrical sensors. The status triggers may be positioned along the tether 90525 to be read or recognized at positions which correspond with the beginning and end of drug delivery, as well as at desired increments during drug delivery. As shown, tether 90525 passes substantially axially through the drive mechanism housing 90130, the biasing member 90122, and connects to the piston 90110 A, 90110B to restrict the axial translation of the piston 90110A, 90110B and the plunger seal 9060 that resides adjacent thereto. The sensors may communicate the detected information (e.g., the end of dose information, incremental motion, restricted motion, etc.) to the drive control system 90820 and/or to the power and control system 90800 to notify or provide feedback of the controlled motion of the various components.

As mentioned above various sensors may be coupled directly to the power and control system 800 or via the drive control system 90820, and may be configured to provide the incremental status indication. A user may then be notified of such indication based on, for example, the detection of the rotational movement of one or more gears of gear assembly 90516. For example, as the gear assembly 90516 rotates, a sensor may read or detect one or more corresponding status triggers on one of the gears in the gear assembly to provide incremental status indication before, during, and after operation of the variable rate controlled delivery drive mechanism. A number of sensors may be utilized within the embodiments of the present disclosure.

In one example, the drive mechanism 90100 may utilize an electro-mechanical sensor which may be physically in contact with the gear teeth of one of the gears of the gear assembly. As the sensor is contacted by the status or sensor trigger(s), which in this exemplary embodiment may be the gear teeth of one of the gears (or holes, pins, ridges, markings, electrical contacts, or the like, upon the gear), the sensor measures or detects the rotational position of the gear and transmits a signal to the power and control system 90800 for status indication or notification to the user.

Additionally or alternatively, the drive mechanism 90100 may utilize an electro-optical sensor. The optical sensor may include a light beam that may be configured detect a motion and transmit a status signal to the power and control system.

For example, the optical sensor may be configured to detect motion of the gear teeth of one of the gears in the gear assembly (or holes, pins, ridges, markings, electrical contacts, or the like, upon the gear). In another embodiment, the sensor may be an electrical switch configured to recognize electrical contacts on the gear. In any of these embodiments, the sensor may be utilized to then transmit a signal to the power and control system to provide notification feedback to the user about the controlled motion and/or the delivery of the drug.

As would be appreciated by one having ordinary skill in the art, electro-optical sensors and corresponding triggers, electromechanical sensors and corresponding triggers, and/or electrical or mechanical sensor and corresponding triggers may all be implemented by the embodiments of the present disclosure to provide incremental status indication to the user power and control system 90800. While the drive mechanisms of the present disclosure are described with reference to the gear assembly and regulating mechanism, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

Moreover, in at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 90101. The change in the rate of movement of actuator 90101 causes a change in the rotation rate of regulating mechanism 500 which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

Details of an exemplary method associated with drug delivery in a predetermined time are now provided with references to FIG. 9A. One or more steps of the method 90900 may be executed during active power mode or non-active power mode of the power and control system 90800. The method 90900, for example, includes steps related to initiating and delivering drug at an adjusted rate to a user by a drug delivery device 9010 after a predetermined wait time period. The method includes steps of communication between the drug delivery device 9010 and a mobile device 9011. The method may optionally monitor and receive information (e.g., heart rate of the user, glucose/insulin information, etc.) related to the health of the patient during the monitoring period. Particularly, the method requests a user of the drug delivery device 9010 to activate the needle insertion (i.e., initiate NIM 90200), after the device has been activated. When the needle insertion has been actuated, the drug delivery device 9010 may then initiate a timer to track delay time period. Alternatively, a timer may be initiated by the activation of the device.

Furthermore, the method determines whether the predetermined wait time period has elapsed, and based on the determination notifies the user accordingly about the initiation of the drug delivery process. The method regulates the delivery rate of the drug based on information received from sensors (e.g., temperature sensor, heart rate sensor, glucose monitor sensor). Regulation of the delivery rate may be based on optimization of the effectiveness of the drug. Alternatively, or additionally, the delivery rate may be regulated to reduce and/or minimize the user's discomfort. For example, delivery of a relatively cold drug may cause pain to the user. Hence, if the temperature sensor provides a signal to the control unit that the drug and/or drug container is low, the delivery rate may be reduced.

The method may further determine whether the drug delivery has ended, and based on the determination, in one example may further transmit the end of drug delivery information to the mobile device. The mobile device may further provide the received information to a remote server (e.g., a cloud server). Other parameters may be regulated based on the inputs from the sensors. For example, the delay between activation of an end-of-dose sensor and notification, to the user, that drug delivery has completed. The viscosity of the drug may be dependent on the temperature of the drug and a more viscous drug may require additional time to be fully delivered to the user. Hence, the control unit may use the input from the temperature sensor to determine how long to delay notification to the user of completion of delivery. The control unit may, for example, compare the input from the temperature sensor to a look-up table which is either stored locally or is accessed remotely. Alternatively, the control unit may use the input from the temperature sensor as an input in an equation used to calculate the delay.

Referring now to FIG. 77A, the process flows depicted are merely embodiments of the disclosure and are not intended to limit the scope of the disclosure. For example, the steps recited in any of the method or process descriptions may be executed in any order and are not limited to the order presented. Furthermore, it will be appreciated that the following description makes appropriate references not only to the steps depicted in FIG. 77A, but also to the various system components as described with reference to the present disclosure.

Referring now to FIG. 77A, at step 90901, the pump device 9010 is activated. The drug delivery device 9010 may be configured with an activation mechanism that may include receiving a trigger signal from the user to power the power and control system 90800. In one example, a user may activate the drug delivery device 9010 by pressing a start button that may be an on/off switch, and/or a toggle switch. The activation button or the switch may be located through the pump housing 9012, such as through an aperture between upper housing and lower housing, and which contacts either directly or indirectly the power and control system 90800 (e.g., a via electrical contacts). The user may press the activation button or the switch a predetermined number of times (e.g., one single press) to initially activate the drug delivery device 9010. Alternatively, the pump device 9010 may be configured such that it is activated upon removal from a portion of its packaging. The pump device 9010 may include one or more packaging status sensors that are configured to detect the removal of the pump device from a portion of the packaging. The packaging status sensor may take any form capable of detecting a removal of the pump device from a portion of the packaging. For example, the packaging status sensor may be in the form of a pin interconnect on the power and control system 800 that is either connected or disconnected when packaged. Removal from the packaging may cause the pin interconnect to change state from connected to disconnected or vice versa. This change of state may cause initiation of the timer. Alternatively, the packaging status sensor may consist of an optical sensor which is configured to detect a change in lighting conditions caused by a removal of the pump device 9010 from a portion of the packaging.

In one example, upon receiving the activation input, a short-range wireless communication link may be initiated between the drug delivery device 9010 and the mobile device 9011. In one example, the wireless communication link may be established based on a Bluetooth pairing between the mobile device 9011 and the drug delivery device 9010.

In one example, during and/or upon the activation, the drug delivery device 9010 may be in a discovery mode, during which the mobile device 9011 may discover the drug delivery device 9010, and establish the wireless communication with the drug delivery device 9010. Alternatively, the drug delivery device 9010 may initiate and establish the wireless communication with the mobile device 9011 by sending short-burst signals or pings to the mobile device 9011.

Upon receiving the activation signal, the pump device 9010 may provide notification or feedback to the user to indicate that the device 9010 has been activated. For example, notification signals, such as audible tones, and/or visual notification such as LED lights, may be provided by the power and control system 90800.

It is contemplated that, in one example, a user may use the mobile device 9011 to activate the drug delivery device 9010. In such an example, prior to activation, the drug delivery device 9010 may be in communication only mode during which the drug delivery device 9010 may be configured to establish a communication link with the mobile device 9011 (e.g., Bluetooth pairing). Upon establishing the communication link between the two devices, the user may select or press activation/start button 9010*b* to activate the drug delivery device 9010.

In one example, the housing 9012 may include one or more status indicators (e.g., light emitting diodes (LEDs) and/or speakers) and windows that may provide indication of the activation of the drug delivery device 9010. The activation mechanism, the status indicator, the window, and combinations thereof may be provided on the upper housing or the lower housing such as, for example, on a side visible to the user when the drug delivery device 9010 is placed on the body of the user. Housing 9012 is described in further detail hereinafter with reference to other components and embodiments of the present disclosure.

Additionally or alternatively, the drug delivery device 9010 may push the activation notification to the mobile device 9011. In this example, the mobile app 9010*a* may cause the mobile device 9011 to provide the notification via speakers or LED lights (not shown) of the mobile device 9011. Alternatively, the user may select the notification/data button 9010*d* to receive the notification of the activation.

When the drug delivery device 9010 and the mobile device 9011 are linked via the short range wireless communication based on the device activation, the mobile device 9011 may provide notification and guidance related to the operation of the drug delivery device 9010. In one example, the mobile device 9011 may provide instruction to place the drug delivery device 9010 on the body of the user.

It is noted that, during the device activation step, the drug delivery device 9010 may be in the non-active power mode (i.e., the power and control system 90800 may be receiving power from the power source and the drive control system 90820 (i.e., motor 90101) may not be receiving power from the power source).

At step 90903, after the drug delivery device 9010 has been activated, the control unit 90810 may determine the status of the on-body skin sensor 90840. For example, the control unit 90810 may monitor signals from the on-body skin sensor 90840 and/or the electro-mechanical skin sensor to determine whether the drug delivery device 9010 is in contact with the users skin or body. When the control unit 90810 determines that the on-body skin sensor 90840 is in contact with the skin of the user for a predetermined amount of time (e.g., 2 minutes), the control unit 90810 may set a flag to "on".

It will be appreciated that, the status check of the on-body sensor provides safety measure for the drug delivery device 9010. Specifically, because the control unit 90810 monitors the on-body sensor indication signal for substantial amount of time prior to setting the flag to "on", any quick contact (for a few seconds) or touch (e.g., by mistake) between the drug delivery device 9010 and the skin of the user may be disregarded by the control unit 90810. Moreover, any subsequent activation button press by the user for various operations of the drug delivery device 9010 may only be recognized by the control unit, upon determining that the on-body sensor 90840 is on.

At step 90904, the drug delivery device 9010 may provide notification to terminate the drug delivery process if the control unit 90810 determines that the drug delivery device 9010 is not in contact with the body of the user for the predetermined amount of time. Additionally or alternatively, the drug delivery device 9010 may notify the user of the termination of the drug delivery process or to properly position the drug delivery device 9010 via the mobile app 9010*a*.

At step 905, the drug delivery device 9010 provides a request notification to the user to activate the needle insertion. For example, as described above the request notification may be provided via audible tones (continuous or variable tones) and/or via LED lights of the drug delivery device 9010 to press the activation button a predetermined number of times (e.g., two times) to activate the needle insertion.

In another example, the request notification may be provided via the mobile device 9011 after control unit 90810 determines that the "on" status of the on-body skin sensor 90840. In that example, the drug delivery device mobile app 9010*a* may cause the mobile device 9011 to provide the request notification for activation of the needle insertion. In one example, the mobile device may provide the user with a request notification to press the activation button (e.g., two times) to activate the needle insertion. For example, the request and/or notification may be provided via a text message. In another example, the user may receive an indication of the notification of the request message via the notification button 9010*d*. Upon selecting the button 9010*d*, the user may be provided with the request notification message.

At step 90907, the control unit 90810 may determine whether the user has provided the appropriate input for the activation of the needle insertion (e.g., double press of the activation button).

At step 90908, when the control unit 90810 determines that the needle activation has not been activated within a predetermined amount of time, the method may notify the user to terminate the drug delivery process. In such an example, the control unit 90810 may wait for the predetermined amount of time, prior to providing the termination notification.

At step 90907, the control unit may determine that the user has responded to the request notification by executing the needle insertion activation (e.g., by pressing the activation button according to the request message). The method then proceeds to step 90909. Alternatively, the user may directly activate the NIM. (i.e., the pump device may be configured such that the NIM is mechanically activated by input by the user).

It is noted that, the user initiated needle insertion activation is beneficial, as this makes the user aware of the activation of the needle insertion into the body of the user and/or initiation of the drug delivery process.

At step 90909, the power and control system 90800, may prepare or prime the drug delivery device 9010. In one example, the power and control system 90800 may activate the needle insertion mechanism 90200, upon receiving user activation at step 90907.

Additionally, the power and control system may prime or initiate the SFPC sub-system 90300. It is contemplated that, in some embodiments, the SFPC may be initiated when the drug is being delivered (e.g., at step 90921), or concurrently with the needle insertion activation. In one example, during the priming of the device, the piston may be controlled to fill the fluid conduit with fluid drug, thereby displacing any air originally present therein.

It is noted that, during the steps 90901, 90903, 90904, 90907 and 90908 the power and control system may be in non-active power mode (i.e., the drive control system 90820 or motor 90101 may not be receiving any power from the power source). Whereas, during the needle insertion activation and/or SFPC, for example, the drug delivery device 9010 may be in active power mode.

At step 90911, timer unit 90812 may be initiated automatically. For example, the control unit 90810 may initialize the timer unit 90812 which may start the wait time period. Optionally, the wait time period may be monitored by the mobile device 9011. For example, upon the initiation of the timer unit 90812, the control unit 90810 may communicate the timing information (e.g., when the timer was initiated, the amount of time left before the drug delivery, etc.) to the mobile device 9011. The user may receive such timing information via app 9011*a* (e.g., by pressing timer button 9010*c*).

It is noted that, the control unit 90810 may access or consult the timer unit 90812 to monitor a wait time period or a delay period. The wait time period may correspond to a time period that needs to be elapsed prior to the initiation of the drug delivery. In one example, the wait time period may be pre-programmed in the power and control system 90800. In one example, the wait time period may be 27 hours. Alternatively, the wait time period may be any other suitable time period for the drug delivery process.

Moreover, during the wait time period, the drug delivery device 9010 may be in the non-active power mode. In one example, the drug delivery device 9010 may communicate with the mobile device 9011 intermittently during the wait time period. For example, the control unit 90810 via the communication unit 90830 of the drug delivery device 9010 may send a status signal (e.g., a ping signal) to the mobile device 9011 to indicate that the drug delivery device 9010 is operational. Additionally, the drug delivery device 9010 may send information related to timing information (as discussed above) to the mobile device 9011.

At step 90913, the power and control system 90800 may monitor sensor signals from the various internal and/or external sensors. For example, the control unit 90810 may monitor signals from the temperature sensor 90880 to determine the temperature of the drug. In one example, the control unit 90810 may process the detected temperature values to determine that the drug has reached predetermined optimal temperature for drug delivery. The drug delivery device 9010 may send the temperature information of the drug to the mobile device 9011, during the wait time period. The mobile device 9011 may process such received data to provide further notification to the user during the wait time period. Step 90913 may also include the continuous monitoring of the on-body sensor by the control unit. In the event that the on-body sensor indicates to the control system 90800 that the pump device 9010 is not in contact with the patient's skin, the control system may provide a notification to the user.

Optionally, the control unit 90810 may request the mobile device 9011 to monitor signals or data from external sensors such as the glucose rate monitor 9011*b* and the heart rate monitor 9011*a*, and further process the captured data.

In one example, based on the request signal from the drug delivery device 9010, the mobile app 9010*a* may process the data received from the external sensors to determine various operations of the drug delivery process. For example, based on the data received from the external sensors, the mobile app 9010*a* may determine an adjusted drug delivery rate of the drug that may be delivered to the patient.

In one example, a user may work-out during the wait time period, during which, the mobile app 9010*a* may monitor the heart rate of the user by communicating with the heart rate monitor 9011*a*. The mobile app 9010*a* may execute an algorithm to determine and adjust the drug delivery rate based on the change in the heart rate of the user. Additionally, or alternatively, the mobile app 9010*a* may communicate with the glucose rate monitor 9011*b* to determine and adjust the drug delivery rate based on the change in the glucose rate of the user. Accordingly, the mobile app 9011*a* may provide notification and instruction that provides information as to how to deliver the drug at the adjusted rate. In one example, the user may access such information via the notification button 9010*d*. For example, the notification may include the number of times the user needs to press the activation button on the drug delivery device 9010 to deliver the drug at the adjusted rate. During the drug delivery period, the control unit 90810 of drug delivery device 9010, upon receiving such specified activation signal (e.g., the number of the press of activation button), may consult the storage unit 90813 to translate the adjusted delivery rate information into the drive mechanism information (e.g., gear ratio of various gear assemblies, rate of rotation of the motor 90101, etc.) in order to deliver the drug at the adjusted delivery rate. For example, the control unit 90810 may control the regulating mechanism 90500 or the flow-rate control sub-system 90825 via the drive control system 90820.

Optionally, in another example, the mobile device 9011 may wirelessly communicate the adjusted drug delivery rate to the drug delivery device 9010, and the drug delivery device 9010 may automatically deliver the drug at the adjusted rate when the predetermined wait time period expires. In that example, the user may not need to press the activation button to adjust the delivery rate of the drug.

Yet in another example, for a bolus delivery of the drug, the drug delivery device 9010 may not adjust the delivery rate. In that example, the control unit 90810 may monitor the temperature of the drug during the wait time period, and deliver the drug to the user after the wait time period elapses. Optionally, after the wait time period has elapsed, drug delivery may be further delayed if the temperature of the drug and/or drug container is below a predefined value. Additionally, the mobile app 9011*a* may provide notification to the user prior to the delivery of the drug.

At step 90915, the drug delivery device 9010 may determine whether the wait time period has elapsed and/or nearing the end of the wait time period. For example, the control unit 810, upon consulting the timer unit 90812, may perform the determination.

In one example, the control unit 90810 may determine that the wait time period has elapsed and/or nearing the end of the wait time period. The method may then proceed to step 90917.

However, if it is determined that the wait time period has not elapsed and/or not near the wait time period (e.g., if the control unit 90810 performs the check 4 hours prior to the end of the wait time period), the method goes back to step 90913.

In one example, for a bolus delivery process, at step 90917, the drug delivery device 9010 provides notification to the user to indicate that the wait time period has elapsed and/or the end of the wait time period is approaching. The notification may further indicate that the drug delivery will be initiated. For example, as described above, the notification may be provided via audible tones (continuous or variable tones) and/or via LED lights of the drug delivery device 9010. In another example, the notification may be provided via the mobile device 9011. As described above, the mobile device 9010 may receive indication signal from the drug delivery device 9010, or alternatively, may determine that the drug is to be delivered. Accordingly, the mobile device 9011 may then provide the appropriate notification to the user.

In another example, the drug device may be configured such that the user has the option of initiating drug delivery near to the completion of the wait time, or soon thereafter. In such a scenario, the notification may be provided just before the predetermined time has elapsed (e.g., about 5 minutes before the 27 hour wait period). This may provide the user with sufficient time to prepare and initiate the drug delivery process. For example, the user may be in an office meeting when the predetermined wait time period is about to elapse, and may not be aware of the wait time period. As such, if the user receives the alarm or notification alert prior to end of the wait time period, the user may have sufficient time to step out of the office meeting to initiate the drug delivery, or simply initiate the drug delivery while at the meeting.

In another example, the notification may be provided via the pump device 9010 or mobile device 9011 after or near the wait time period expiration. In that example, the drug delivery device mobile app 9010*a* may cause the mobile device 9011 to provide notification, as described above. In one example, the mobile app 9010*a* may further provide the user with a request message to prepare to initiate the drug delivery (based on the monitored external sensor data). For example, the request and/or notification may be provided via a text message. In another example, the user may receive an indication of the notification of the request message via the notification button 9010*d*. Upon selecting the button 9010*d*, the user may be provided with the request and/or the notification message. Alternatively, or in addition, the pump device may provide notification to the user of the expiration of the wait time period through audible tones, visual indications, or other means.

It is contemplated that, the mobile drug delivery device app 9010*a* may track the wait time period. For example, the user may select the timer button 9010*c* to gather information such as how much time is left or how much time has elapsed in the wait time period prior to the drug delivery. In some examples, based on the information, the user may terminate the drug delivery process, or send information to the drug delivery device 9010.

As described above, the notification may further provide instruction related to the delivery of adjusted drug delivery rate to the user. The power and control system 800 may determine if the user has activated the initiation of the drug delivery within a predetermined time. For example, the control unit 90810 may determine whether the activation button has been pressed (e.g., within about 2 minutes), after the notification.

If the drug delivery device 9010 determines that the user has not provided any input to initiate the drug delivery process within the predetermined time at the adjusted rate, the control unit 90810 may terminate the drug delivery process. However, if the user provides the input for activation within the predetermined time upon receiving the notification, the method then proceeds to step 90919.

Optionally, as shown in FIG. 9B, the pump device 9010 may be configured such that, the user has the option to initiate drug delivery within some predetermined time after completion of the wait time period. If the user does not initiate drug delivery within this predetermined time, the pump device may automatically initiate drug delivery at the expiration of the predetermined time.

At step 90919, the power and control system 90800 may provide instructions to the drive control system 90820 to control the various drive mechanisms of the drug delivery device 9010 to deliver the drug after the predetermined wait time period.

For example, the control unit of the power and control system 90800 may translate the delivery rate information to the settings and configurations for the various components of the drive control system to enable the delivery of the drug according to the determined delivery rate. As described above, the translation may include consulting lookup tables and/or databases stored in the storage units. Alternatively, the power and control system 90810 may send the delivery rate information to the drive control system 90820, and another controller (not shown) of the drive control system may perform the translation to enable the delivery of the drug according to the determined delivery rate, as described above.

Optionally, at step 90919, the power and control system 90800 may appropriately change (e.g., increase or decrease) the drug delivery rate, based on the processed data received from the external sensors (e.g., based on the heart rate and/or the glucose rate information of the user, as described at step 90913).

Accordingly, the control unit 90810 may instruct the drive control system 90820 to initiate the drug delivery process (irrespective of the user activation). The drive control system may then deliver the drug by controlling via the drive mechanism 90100.

It is contemplated that, in some examples, the power and control system 90800 may instruct the drive control system to initiate the insertion mechanism 90200 and create the connection between the drug container and the sterile pathway during the drug delivery, after the predetermined wait time period has elapsed. In such a scenario, the user may provide the input for the NIM activation after the predetermined time has elapsed. In another embodiment, the NIM is activated by the power and control system 90800 prior to initiation of drug delivery.

At step 90921, the power and control system 90810 may determine whether the delivery of the drug has ended. For example, motor 90101 may receive signal from the tether sensor 90875, a valve sensor 90877 and/or pressure sensor 90870 that indicates an end-of-dose of the drug. Accordingly, the drive control system 90820 may then communicate the end-of-dose information to the control unit 90810. The method then proceeds to step 90923.

When the drug delivery device 9010 determines that the drug has been delivered, the power and control system 90800 may provide notification via audible tones and/or LED lights as described above. Additionally and/or alternatively, notification of the end-of-dose information may be provided by the drug delivery device 9010 via the drug delivery device mobile app 9010*a*.

In one example, the drug delivery device 9010 may determine that the drug has not been delivered or the end-of-dose did not occur in a predetermined amount of time. In such a case, the drug delivery device 9010 may provide error notification (e.g., via the LED lights and/or via the drug delivery device mobile app 9010*a*), and the method may then go back to step 90919. Alternatively, the power and control system 90800 may terminate drug delivery and/or activate retraction of the NIM if an end-of-dose signal is not received within the expected delivery time.

At step 90923, upon the determination that the end-of-dose of the drug has occurred (i.e., the drug has been delivered in a predetermined time and/or according to a desired rate of delivery), the drug delivery device 9010 may communicate various end-of delivery information to the drug delivery device mobile app 9010*a*. The mobile app 9010*a* may then cause the mobile device 9011 to transmit such information to one or more remote servers or storage 9011*c* of various entities (e.g., healthcare provider, health insurance provider, drug manufacturer, etc.). In one example, data stored in the drug delivery device app 9010*a* related to the end of delivery information may be transmitted to the cloud server 9011*c* via cellular network interface. Moreover, the end of delivery information may include, but is not limited to, validation of the end-of-dose, total time period of the drug delivery, delivery rate information, etc. In one example, a user may select the button 9010*d* of the mobile app 9010*a* to transfer such information. In one example, the mobile app 9010*a* may be configured to selectively transfer the end of delivery information to the various entities. It is contemplated that, the end of delivery information, and/or any other information related to the drug delivery may not be stored permanently upon transfer of such information to the cloud server 9011*c*.

FIGS. 77B and 77C show alternative methods of operation of the pump device 9010 and/or mobile device 9011. In the methods illustrated in FIGS. 77B and 9C, activation of the device initiates the timer to mark the beginning of the predetermined wait time. Additionally, device activation also initiates the first step in the NIM activation process. As shown in the figures, the first step in the NIM activation process may be to determine if the on-body sensor detects the presence of a target. If the target is detected for the required time period, the device may be prepared for NIM activation. The preparation of the device for NIM activation may include configuring one or more of the drive mechanism, regulating mechanism, and actuation mechanism such that the user may activate the NIM. After the device is prepared for NIM activation, the user may be notified to activate the NIM. The notification may be in the form of audible, visual, or tactile feedback from the pump device. Alternatively, or additionally, the notification may be provided by the mobile device.

After notification, the user may activate the NIM to insert the fluid path into the target. For example, the user may activate the NIM by depressing or actuating the actuation mechanism or another mechanism of the pump device.

As shown in FIG. 77B, after the predetermined wait time has elapsed, the user may be notified that the pump device may be activated to begin drug delivery. The user may be able to initiate drug delivery within a predetermined "user initiation time." After the user initiation time has elapsed, the pump device may automatically initiate drug delivery. The user may, optionally, be notified upon initiation of drug delivery. The notification may in the form of visual, audible, or tactile indication by the pump device or, alternatively, by notification by the mobile device.

In the method shown in FIG. 77C, the pump device 9010 is configured such that drug delivery is automatically initiated after the wait time elapses. The user may be notified that drug delivery will be, or has been, initiated. The user may be notified by an audible, visual, or tactile notification from the pump device. Alternatively, the user may be notified by the mobile device.

Assembly and/or manufacturing of controlled delivery drive mechanism 90100, drug delivery pump 9010, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the components and devices. Furthermore, known sterilization processes may be employed at one or more of the manufacturing or assembly stages to ensure the sterility of the final product.

The drive mechanism may be assembled in a number of methodologies. In one method of assembly, the drug container 9050 may first be assembled and filled with a fluid for delivery to the user. The drug container 9050 includes a cap 9052, a pierceable seal 9056, a barrel 9058, and a plunger seal 9060. The pierceable seal 9056 may be fixedly engaged between the cap 9052 and the barrel 9058, at a distal end of the barrel 9058. The barrel 9058 may be filled with a drug fluid through the open proximal end prior to insertion of the plunger seal 9060 from the proximal end of the barrel 9058. An optional connection mount 9054 may be mounted to a distal end of the pierceable seal 9056. The connection mount 9054 may guide the insertion of the piercing member of the fluid pathway connector into the barrel 9058 of the drug container 9050. The drug container 9050 may then be mounted to a distal end of drive housing 90130.

One or more drive biasing members 90122 may be inserted into a distal end of the drive housing 90130. Optionally, a cover sleeve 90140 may be inserted into a distal end of the drive housing 90130 to substantially cover biasing member 90122. A piston may be inserted into the distal end of the drive housing 90130 such that it resides at least partially within an axial pass-through of the biasing member 90122 and the biasing member 90122 is permitted to contact a piston interface surface 90110C of piston 90110A, 90110B at the distal end of the biasing member 90122. An optional cover sleeve 90140 may be utilized to enclose the biasing member 90122 and contact the piston interface surface 90110C of piston 90110A, 90110B. The piston 90110A, 90110B and drive biasing member 90122, and optional cover sleeve 90140, may be compressed into drive housing 90130. Such assembly positions the drive biasing member 90122 in an initial compressed, energized state and preferably places a piston interface surface 90110C in contact with the proximal surface of the plunger seal 9060 within the proximal end of barrel 9058. The piston, piston biasing member, contact sleeve, and optional components, may be compressed and locked into the ready-to-actuate state within the drive housing 90130 prior to attachment or mounting of the drug container 9050. The tether 90525 is pre-connected to the proximal end of the piston 90110A, 90110B and passed through the axial aperture of the biasing member 90122 and drive mechanism 90130, and then wound through the interior of the drug delivery device with the other end of the tether 90525 wrapped around the winch drum/gear 90520 of the regulating mechanism 90500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 90100 or drug delivery device 9010 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9018 to enable the user to view the operation of the drug delivery device 9010 or verify that drug dose has completed. Similarly, the drug delivery device 9010 may contain an adhesive patch 9026 and a patch liner 9028 on the bottom surface of the housing 9012. The adhesive patch 9026 may be utilized to adhere the drug delivery device 9010 to the body of the user for delivery of the drug dose. As would be readily understood by one having ordinary skill in the art, the adhesive patch 9026 may have an adhesive surface for adhesion of the drug delivery device to the body of the user. The adhesive surface of the adhesive patch 9026 may initially be covered by a non-adhesive patch liner 9028, which is removed from the adhesive patch 9026 prior to placement of the drug delivery device 9010 in contact with the body of the user. Removal of the patch liner 9028 may further remove the sealing membrane 254 of the insertion mechanism 90200, opening the insertion mechanism to the body of the user for drug delivery (as shown in FIG. 69C).

Similarly, one or more of the components of controlled delivery drive mechanism 90100 and drug delivery device 9010 may be modified while remaining functionally within the breadth and scope of the present disclosure. For example, as described above, while the housing of drug delivery device 9010 is shown as two separate components upper housing 9012A and lower housing 9012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The controlled delivery drive mechanisms of the present disclosure may be directly or indirectly activated by the user. Furthermore, the configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a user, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

IX. Additional Embodiments of Multi-Function Drive Mechanism

At least some of the drug delivery devices described in this application, including at least those described in connection with FIGS. 1A-2B and 33A-33C, may be configured to incorporate the embodiments of the drive mechanism described below in connection with FIGS. 69A-75B and 78A-79B. The embodiments of the drive mechanism described below in connection with FIGS. 69A-75B and 78A-79B may be used to replace, in its entirety or partially, the above-described drive mechanism 100, 6100, or 8100, or any other drive mechanism described herein, where appropriate.

The present disclosure provides multi-function drive mechanisms for the controlled delivery of drug substances, controlled drug delivery pumps with such drive mechanisms, the methods of operating such devices, and the methods of assembling such devices. Notably, the multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a multi-function drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the body of the user. A piston, and one or more biasing members, wherein the one or more biasing members are initially retained in an energized state and is configured to bear upon an interface surface of the piston, may also be incorporated in the multi-function drive mechanism. The piston is configured to translate substantially axially within a drug container having a plunger seal and a barrel. A tether is connected at one end to the piston and at another end to a winch drum/gear of a regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of a regulating mechanism of the multi-function drive mechanism to meter the free expansion of the biasing member from its initial energized state and the free axial translation of the piston upon which the biasing member bears upon.

In at least one embodiment of the present disclosure, the regulating mechanism is gear assembly driven by an actuator of the multi-function drive mechanism. The regulating mechanism retards or restrains the distribution of tether, only allowing it to advance at a regulated or desired rate. This restricts movement of piston within barrel, which is pushed by one or more biasing members, hence controlling the movement of plunger seal and delivery of the drug contained in chamber. As the plunger seal advances in the drug container, the drug substance is dispensed through the sterile pathway connection, conduit, insertion mechanism, and into the body of the user for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a winch gear coupled to a winch drum/gear upon which the tether may be releasably wound. Accordingly, rotation of the gear assembly initiated by the actuator may be coupled to winch drum/gear (i.e., through the gear assembly), thereby controlling the distribution of tether, the rate of expansion of the biasing members and the axial translation of the piston, and the rate of movement of plunger seal within barrel to force a fluid from drug chamber. The rotational movement of the winch drum/gear, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, initial motion by the actuator of the multi-function drive mechanism causes rotation of main/star gear. In one manner, main/star gear conveys motion to the regulating mechanism through gear assembly. In another manner, main/star gear conveys motion to the needle insertion mechanism through gear. As gear is rotated by main/star gear, gear engages the needle insertion mechanism to initiate the fluid pathway connector into the user, as described in detail above. In one particular embodiment, needle insertion mechanism is a rotational needle insertion mechanism. Accordingly, gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the user, as described in detail herein.

In at least one embodiment, rotation of the needle insertion mechanism in this manner may also cause a connection of a sterile fluid pathway to a drug container to permit fluid flow from the drug container to the needle insertion mechanism for delivery to the user. Ramp aspect of needle insertion mechanism is caused to bear upon a movable connection hub of the sterile fluid pathway connector. As the needle insertion mechanism is rotated by the multi-function drive mechanism, ramp aspect of needle insertion mechanism bears upon and translates movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum/gear of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum/gear upon which the tether may be releasably wound, rotation of the winch drum/gear releases the tether from the winch drum/gear to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum/gear is coupled to a regulating mechanism which controls rotation of the winch drum/gear and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum/gear and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum/gear on the free axial translation of the piston upon which the biasing member bears upon to meet a desired drug delivery rate or profile, to change the dose volume for delivery to the user, and/or to otherwise start, stop, or pause operation of the drive mechanism.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

The novel embodiments of the present disclosure provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present disclosure may include one or more additional components which may be considered standard components in the industry of medical devices. For example, the embodiments may include one or more batteries utilized to power the motor, drive mechanisms, and drug delivery devices of the present disclosure. The components, and the embodiments containing such components, are within the contemplation of the present disclosure and are to be understood as falling within the breadth and scope of the present disclosure.

The present disclosure provides multi-function drive mechanisms for the controlled delivery of drug substances and drug delivery pumps which incorporate such multi-function drive mechanisms. The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

As used herein to describe the drive mechanisms, drug delivery pumps, or any of the relative positions of the components of the present disclosure, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug delivery devices. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present disclosure, the biasing member is a spring, preferably a compression spring.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 69A-69C show an exemplary drug delivery device according to at least one embodiment of the present disclosure with the top housing removed so that the internal components are visible. The drug delivery device may be utilized to administer delivery of a drug treatment into a body of a user. As shown in FIGS. 69A-69C, the drug delivery device 9010 includes a pump housing 9012. Pump housing 9012 may include one or more housing subcomponents which are fixedly engageable to facilitate easier manufacturing, assembly, and operation of the drug delivery device. For example, drug delivery device 9010 includes a pump housing 9012 which may include an upper housing and a lower housing (not shown for ease of viewing internal components). The pump housing 9012 may include one or more tamper evidence features to identify if the drug delivery device has been opened or tampered with. For example, the pump housing 9012 may include one or more tamper evidence labels or stickers, such as labels that bridge across the upper housing and the lower housing. Additionally or alternatively, the housing 9012 may include one or more snap arms or prongs connecting between the upper housing and the lower housing. A broken or altered tamper evidence feature would signal to the user, the physician, the supplier, the manufacturer, or the like, that the drug delivery device has potentially been tampered, e.g., by accessing the internal aspects of the device, so that the device is evaluated and possibly discarded without use by or risk to the user. The drug delivery device may further include an activation mechanism, a status indicator, and a window. Window may be any translucent or transmissive surface through which the operation of the drug delivery device may be viewed. As shown in FIG. 69B, drug delivery device 9010 further includes assembly platform 9020, sterile fluid conduit 30, drive mechanism 90100 having drug container 9050, insertion mechanism 90200, fluid pathway connector 90300, and a power and control system (not shown). One or more of the components of such drug delivery devices may be modular in that they may be, for example, pre-assembled as separate components and configured into position onto the assembly platform 9020 of the drug delivery device 9010 during manufacturing.

The pump housing 9012 contains all of the device components and provides a means of removably attaching the device 9010 to the skin of the user. The pump housing 9012 also provides protection to the interior components of the device 9010 against environmental influences. The pump housing 9012 is ergonomically and aesthetically designed in size, shape, and related features to facilitate easy packaging, storage, handling, and use by users who may be untrained and/or physically impaired. Furthermore, the external surface of the pump housing 9012 may be utilized to provide product labeling, safety instructions, and the like. Additionally, as described above, housing 9012 may include certain components, such as one or more status indicators and windows, which may provide operation feedback to the user.

In at least one embodiment, the drug delivery device 9010 provides an activation mechanism that is displaced by the user to trigger the start command to the power and control system. In a preferred embodiment, the activation mechanism is a start button that is located through the pump housing 9012, such as through an aperture between upper housing and lower housing, and which contacts either directly or indirectly the power and control system. In at least one embodiment, the start button may be a push button, and in other embodiments, may be an on/off switch, a toggle, or any similar activation feature known in the art. The pump housing 9012 also provides one or more status indicators and windows. In other embodiments, one or more of the activation mechanism, the status indicator, the window, and combinations thereof may be provided on the upper housing or the lower housing such as, for example, on a side visible to the user when the drug delivery device 9010 is placed on the body of the user. Housing 9012 is described in further detail hereinafter with reference to other components and embodiments of the present disclosure.

Drug delivery device 9010 is configured such that, upon activation by a user by depression of the activation mechanism, the multi-function drive mechanism is activated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In at least one embodiment, such delivery of drug fluid into a user is performed by the multi-function drive mechanism in a controlled manner. One or more optional safety mechanisms may be utilized, for example, to prevent premature activation of the drug delivery device. For example, an optional on-body sensor (not visible) may be provided in one embodiment as a safety feature to ensure that the power and control system, or the activation mechanism, cannot be engaged unless the drug delivery device 9010 is in contact with the body of the user. In one such embodiment, the on-body sensor is located on the bottom of lower housing where it may come in contact with the users body. Upon displacement of the on-body sensor, depression of the activation mechanism is permitted. Accordingly, in at least one embodiment the on-body sensor is a mechanical safety mechanism, such as for example a mechanical lock out, that prevents triggering of the drug delivery device 9010 by the activation mechanism. In another embodiment, the on-body sensor may be an electromechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present disclosure to prevent, for example, premature activation of the drug delivery device. In a preferred embodiment, the drug delivery device 9010 utilizes one or more mechanical on-body sensors. Additional integrated safety mechanisms are described herein with reference to other components of the novel drug delivery devices.

IX.A. Power and Control System

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 90100. In one embodiment, the power and control system interfaces either directly or indirectly with the on-body sensor 9024 to identify when the device is in contact with the user and/or the activation mechanism to identify when the device has been activated. The power and control system may also interface with the status indicator of the pump housing 9012, which may be a transmissive or translucent material which permits light transfer, to provide visual feedback to the user. The power and control system interfaces with the drive mechanism 90100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the body of the user, the power and control system will power the drive mechanism 90100 to begin delivery of the drug treatment through the fluid pathway connector 90300 and sterile fluid conduit 9030 (not shown).

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the user. In such an embodiment, without removal of the drug delivery device from the packaging the drug delivery device cannot be activated. This provides an additional safety mechanism of the drug delivery device and for the user. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, the multi-function drive mechanism is initiated to actuate the insertion mechanism 90200 and the fluid pathway connector 90300, while also permitting the drug fluid to be forced from the drug container. During the drug delivery process, the power and control system is configured to provide a dispensing status signal via the status indicator. After the drug has been administered into the body of the user and after the end of any additional dwell time, to ensure that substantially the entire dose has been delivered to the user, the power and control system may provide an okay-to-remove status signal via the status indicator. This may be independently verified by the user by viewing the drive mechanism and drug dose delivery through the window of the pump housing 9012.

Additionally, the power and control system may be configured to provide one or more alert signals via the status indicator, such as for example alerts indicative of fault or operation failure situations.

The power and control system may additionally be configured to accept various inputs from the user to dynamically control the drive mechanisms 90100 to meet a desired drug delivery rate or profile. For example, the power and control system may receive inputs, such as from partial or full activation, depression, and/or release of the activation mechanism, to set, initiate, stop, or otherwise adjust the control of the drive mechanism 90100 via the power and control system to meet the desired drug delivery rate or profile. Similarly, the power and control system may be configured to receive such inputs to adjust the drug dose volume; to prime the drive mechanism, fluid pathway connector, and fluid conduit; and/or to start, stop, or pause operation of the drive mechanism 90100. Such inputs may be received by the user directly acting on the drug delivery device 9010, such as by use of the activation mechanism 9014 or a different control interface, or the power and control system may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug delivery device 9010 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

IX.B. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as developed by the assignee of the present disclosure.

In at least one embodiment, the insertion mechanism 90200 includes an insertion mechanism housing having one or more lockout windows, and a base for connection to the assembly platform and/or pump housing (as shown in FIG. 69B and FIG. 69C). The connection of the base to the assembly platform 9020 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9010. The insertion mechanism may further include one or more insertion biasing members, a needle, a retraction biasing member, a cannula, and a manifold. The manifold may connect to sterile fluid conduit 9030 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9027 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the body of the user. At the end of the insertion stage or at the end of drug delivery (as triggered by the multi-function drive mechanism), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the user. Accordingly, the insertion mechanism may be used to insert a needle and cannula into the user and, subsequently, retract the needle while retaining the cannula in position for drug delivery to the body of the user.

In at least one embodiment, as shown in FIG. 75, the insertion mechanism includes a rotationally biased member 90210 which is initially held in an energized state. In a preferred embodiment, the rotationally biased member is a torsional spring. The rotational biasing member may be prevented from de-energizing by interaction of gear surface 90208 with gear 90112 or, alternatively, by contact of a component of the insertion mechanism with a rotation prevention feature of the drug delivery device. Upon activation of the device, or another input, the rotationally biased member 90210 is permitted to, at least partially, de-energize. This causes one or more components of the insertion mechanism to rotate and, in turn, cause, or allow, the insertion of the needle into the patient. Further, a cannula may be inserted into the patient as described above. At a later time, such as when the control arm or another component of the device recognizes a slack in the tether, the rotationally biased member may be allowed to further de-energize, causing additional rotation of one or more components of the insertion mechanism. This rotation may cause, or allow, the needle to be retracted from the patient. The needle may be fully retracted in a single step or there may be multiple steps of retraction.

IX.C. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9010, the fluid pathway connector 90300 is enabled to connect the sterile fluid conduit 9030 to the drug container of the drive mechanism 90100. Such connection may be facilitated by a piercing member, such as a needle, penetrating a pierceable seal of the drug container of the drive mechanism 90100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the multi-function drive mechanism. Additionally or alternatively, the sterile fluid pathway connector is initiated by movement directly of the multi-function drive mechanism. For example, the multi-function drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 69A-69C, the multi-function drive mechanism performs all of these steps substantially concurrently. The multi-function drive mechanism rotates a gear that acts upon several other components. The gear acts on a gear assembly to control the rate of drug delivery, while also contacting a needle insertion mechanism to introduce a fluid pathway into the user. As the needle insertion mechanism is initiated, the sterile fluid connection is made to permit drug fluid flow from the drug container, through the fluid conduit, into the needle insertion mechanism, for delivery into the patient as the gear and gear assembly of the multi-function drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 90300 and the sterile fluid conduit 9030 are provided hereinafter in later sections in reference to other embodiments.

IX.D. Multi-Function Drive Mechanism

The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. With reference to the embodiments shown in FIGS. 70A-70D and 3A-3D, multi-function drive mechanism 100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism 90100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 90100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the multi-function drive mechanism shown in FIGS. 70A-70D and 71A-71D, multi-function drive mechanism 100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. Compressed within the drive housing 90130, between the drug container 9050 and the proximal end of the housing 90130, are one or more drive biasing members 90122 and a piston 90110, wherein the drive biasing members 90122 are configured to bear upon an interface surface 90110C of the piston 90110, as described further herein. Optionally, a cover sleeve (not shown) may be utilized between the drive biasing members 90122 and the interface surface 90110C of the piston 90110 to, for example, promote more even distribution of force from the drive biasing member 90122 to the piston 90110, prevent buckling of the drive biasing members 90122, and/or hide biasing members 90122 from user view. Interface surface 90110C of piston 90110 is caused to rest substantially adjacent to, or in contact with, a proximal end of seal 9060. Although the embodiments shown in FIGS. 70A-70D and 71A-71D show a singular biasing member it is also contemplated that one or more biasing members disposed to act in parallel may be used.

As best shown in FIG. 70D and FIG. 71D, the piston 90110 may be comprised of two components 90110A and 90110B and have an interface surface 90110C to contact the plunger seal. A tether, ribbon, string, or other retention strap (referred to herein as the "tether" 90525) may be connected at one end to the piston 90110A, 90110B. For example, the tether 90525 may be connected to the piston 90110A, 90110B by retention between the two components of the piston 90110A, 90110B when assembled. The tether 90525 is connected at another end to a winch drum/gear 90520 of a delivery control mechanism 90500. Through the use of the winch drum/gear 90520 connected to one end of the tether 90525, and the tether 90525 connected at another end to the piston 90110A, 90110B, the regulating mechanism 90500 functions to control, meter, provide resistance, or otherwise prevent free axial translation of the piston 90110A, 90110B and plunger seal 9060 utilized to force a drug substance out of a drug container 9050. Accordingly, the regulating mechanism 90500 is a portion of the gear assembly 90116 aspect of the multi-function drive mechanism, which together function to control the rate or profile of drug delivery to the user.

As shown in FIGS. 70A-70D and 71A-71D, and in isolation in FIGS. 72 and 73A-73B, in the embodiments of the present disclosure, the regulating mechanism 90500 is gear assembly driven by an actuator 90101 of the multi-function drive mechanism 90100. The regulating mechanism retards or restrains the distribution of tether 90525, only allowing it to advance at a regulated or desired rate. This restricts movement of piston 90110 within barrel 9058, which is pushed by one or more biasing members 90122, hence controlling the movement of plunger seal 9060 and delivery of the drug contained in chamber 9021. As the plunger seal 9060 advances in the drug container 9050, the drug substance is dispensed through the sterile fluid pathway connector 90300, conduit 9030, insertion mechanism 90200, and into the body of the user for drug delivery. The actuator 90101 may be a number of power/motion sources including, for example, a solenoid, a stepper motor, or a rotational drive motor. In a particular embodiment, the actuator 90101 is a rotational stepper motor with a notch that corresponds with the gear teeth of the main/star gear 90102. Commonly, such a rotational stepper motor may be referred to as a 'Pac-Man' motor. In at least one embodiment, the Pac-Man motor has a gear interface within which one or more teeth of the main gear may partially reside during operation of the system. This is more clearly visible in FIGS. 73A-73B. When the gear interface 90101A of the Pac-Man motor 90101 is in alignment with a tooth 90102A of the main gear 90102, rotational motion of the Pac-Man motor 90101 causes gear interface rotation of the main gear 90102. When the Pac-Man motor 90101 is between gear teeth of the main gear, it may act as a resistance for, for example, back-spinning or unwinding of the gear assembly 90116. In one particular embodiment, the Pac-Man motor 90101 utilizes an alternating direction type motor to rotate the Pac-Man motor 90101 backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the motor, coupled with the use of the gear interface cut within the Pac-Man motor, provide suitable safety features to prevent a runaway condition that could potentially lead to over-delivery of drug to the user. Further detail about the gear assembly 90116, regulating mechanism 90500, and multi-function drive mechanism 90100 are provided herein.

In a particular embodiment shown in FIGS. 73A-73B, the regulating element 90500 further includes one or more gears 90511, 90512, 90513, 90514, of a gear assembly 90516. One or more of the gears 90511, 90512, 90513, 90514 may be, for example, compound gears having a small diameter gear attached at a shared center point to a large diameter gear. Gear 90513 may be rotationally coupled to winch drum/gear 90520, for example by a keyed shaft, thereby coupling rotation of gear assembly 90516 to winch drum/gear 90520. Compound gear 90512 engages the small diameter gear 90513 such that rotational movement of the compound gear aspect 90512B is conveyed by engagement of the gears (such as by engagement of corresponding gear teeth) to gear 90513. Compound gear aspect 90512A, the rotation of which is coupled to gear aspect 90512B, is caused to rotate by action of compound gear aspect 90102B of the main/star gear 90102. Compound gear aspect 90102B, the rotation of which is coupled to main/star gear 90102, is caused to rotate by interaction between main/star gear 90102A and interface 90101A of the actuator 90101. Thus, rotation of main/star gear 90102 is conveyed to winch drum/gear 90520. Accordingly, rotation of the gear assembly 90516 initiated by the actuator 90101 may be coupled to winch drum/gear 90520 (i.e., through the gear assembly 90516), thereby controlling the distribution of tether 90525, and the rate of movement of plunger seal 9060 within barrel 9058 to force a fluid from drug chamber 9021. The rotational movement of the winch drum/gear 90520, and thus the axial translation of the piston 90110 and plunger seal 9060, are metered, restrained, or otherwise prevented from free axial translation by other components of the regulating element 90500, as described herein. As described above, the actuator 90101 may be a number of known power/motion sources including, for example a motor (e.g., a DC motor, AC motor, or stepper motor) or a solenoid (e.g., linear solenoid, rotary solenoid).

The embodiment described above and shown in FIGS. 69A-73D show an actuator 90101 that is in vertical alignment and in direct engagement with the main/star gear 90102. As would readily be appreciated by one having ordinary skill in the mechanical arts, the actuator 90101 could be modified to be in horizontal alignment. Additionally or alternatively, the actuator 90101 could be modified to be in indirect engagement with the main/star gear 90102. The embodiments shown in FIGS. 75A-75B show an actuator 90101 that is in horizontal alignment and indirect engagement with the main/star gear 90102. Such an embodiment may utilize a rack and pinion engagement, a drive screw, or a worm gear 90101W, as shown in FIGS. 75A-75B, to change the direction of motion from horizontal to vertical (i.e., perpendicular interaction). Actuator 90101 rotates worm gear 90101W, which engages gear 90101G and conveys the motion to the Pac-Man gear 90101A. The Pac-Man gear 90101A engages main/star gear 90102 to enable operation of the drive mechanism and the drug delivery device, as described herein. Main/star gear 90102 also drives operation of gear 90112 to enable operation of the needle insertion mechanism 90200, as described herein. In one particular embodiment, the actuator 90101 utilizes an alternating direction type motor to rotate the worm gear 90101W, gear 90101G, and Pac-Man gear 90101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 90101, coupled with the use of the gear interface of the worm gear 90101W, gear 90101G, and Pac-Man gear 90101A with the main/star gear 90102, provide suitable safety features to prevent a runaway condition that could potentially lead to over-delivery of drug to the user. Additionally, the actuator 90101 may include a stop member 90101B that stops the rotation of the Pac-Man gear 90101A against a stop block 90150. Stop block 90150 further prevents over-rotation of the Pac-Man gear 90101A and, accordingly, the main/star gear 90102 to prevent a runaway condition that could potentially lead to over-delivery of drug to the user. For the device to function in this configuration, the Pac-Man gear 90101A must be rotated backwards the other direction before rotating forwards again to progress the main/star gear 90102 because the stop member 90101B prevents over rotation in one direction by interaction with the stop block 90150. Additionally, the geometry of worm gear 90101W may be configured such that it is self-locking and/or cannot be back-driven by gear 90101G. This may be done by configuration of parameters such as: pitch, lead angle, pressure angle, and number of threads. In so doing, runaway conditions of the drive mechanism will be prevented by the worm gears resistance to rotations that are not caused by actuator 90101.

Notably, the regulating mechanisms 90500 of the present disclosure do not drive the delivery of fluid substances from the drug chamber 9021. The delivery of fluid substances from the drug chamber 9021 is caused by the expansion of the biasing member 90122 from its initial energized state acting upon the piston 90110A, 90110B and plunger seal 9060. The regulating mechanisms 90500 instead function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. According to a preferred embodiment, the controlled delivery drive mechanisms and drug delivery devices of the present disclosure include a regulating mechanism indirectly or directly connected to a tether metering the axial translation of the piston 90110A, 90110B and plunger seal 9060, which are being driven to axially translate by the biasing member 90122. The rate of drug delivery as controlled by the regulating mechanism may be determined by: selection of the gear ratio of gear assembly 90516; selection of the main/star gear 90102; selection of the diameter of winding drum/gear 90520; using electromechanical actuator 90101 to control the rate of rotation of the main/star gear 90102; or any other method known to one skilled in the art. By using electromechanical actuator 90101 the rate of rotation of the main/star gear 90102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 90525 by the winch drum/gear 90520 and thereby permit axial translation of the piston 90110 by the biasing member 90122 to translate a plunger seal 9060 within a barrel 9058. The one or more inputs may be provided by the actuation of the activation mechanism, a control interface, and/or a remote control mechanism. The power and control system may be configured to receive one or more inputs to adjust the restraint provided by the tether 90525 and winch drum/gear 90520 on the free axial translation of the piston 90110 upon which the biasing member 90122 bears upon to meet a desired drug delivery rate or profile, to change the dose volume for delivery to the user, and/or to otherwise start, stop, or pause operation of the drive mechanism.

The components of the drive mechanism 90100, upon activation, may be used to drive axial translation in the distal direction of the plunger seal 9060 of the drug container 9050. Optionally, the drive mechanism 90100 may include one or more compliance features which enable additional axial translation of the plunger seal 9060 to, for example, ensure that substantially the entire drug dose has been delivered to the user. For example, the plunger seal 9060, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

The tether 90525 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 90525 that would contact the status reader at the end of axial travel of the piston 90110A, 90110B and plunger 9060 within the barrel 9058 of the drug container 9050. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 90525 to be read or recognized at positions which correspond with the beginning and end of drug delivery, as well as at desired increments during drug delivery. As the drug delivery device is activated and drug delivery is begun by release of the biasing member 90122 and the resulting force applied to the piston 90110A, 90110B and plunger seal 6900, the rate or profile of drug delivery to the user is controlled by the regulating mechanism 90500, gear assembly 90516, and winch drum/gear 90520 releasing the tether 90525 and permitting expansion of the biasing member 90122 and axial translation of the piston 90110A, 90110B and plunger seal 9060. As this occurs, the status triggers of the tether 90525 are contacted or recognized by the status reader and the status of the drive mechanism before, during, and after operation can be relayed to the power and control system to provide feedback to the user. Depending on the number of status triggers located on the tether 90525, the frequency of the incremental status indication may be varied as desired. As described above, a range of status readers may be utilized depending on the status triggers utilized by the system.

In a preferred embodiment, the status reader may apply a tensioning force to the tether 90525. When the system reaches end-of-dose, the tether 90525 goes slack and the status reader 90544 is permitted to rotate about a fulcrum. This rotation may operate an electrical or electromechanical switch, for example a switch, signaling slack in the tether 90525 to the power and control system. Additionally, a gear 90511 of gear assembly 90516 may act as an encoder along with a sensor. The sensor/encoder combination is used to provide feedback of gear assembly rotation, which in turn can be calibrated to the position of piston 90110 when there is no slack in the tether 90525. Together, the status reader and sensor/encoder may provide positional feedback, end-of-dose signal, and error indication, such as an occlusion, by observing slack in the tether 90525 prior to reaching the expected number of motor rotations as counted by the sensor/encoder.

Additional means may exist for terminating or restraining the flow of the medicament in the case of slack in, or failure of, the tether. FIGS. 74A-74B show one such embodiment. Disposed within barrel 9058 are brake 9064, sleeve 9062, and plug 9068, and optionally retainer 9066. Biasing member 90122 bears against sleeve 9062. Tether 90525 is engaged with plug 9068, thereby allowing tether 90525 to restrain the motion of sleeve 9062. This restraint controls the rate of expansion or de-energizing of biasing member 90122. When tether 90525 is under tension, plug 9068 bears against distal face 9064A of brake 9064, causing proximal face 9064B of brake 9064 to bear against sleeve 9062. Due to this contact, and the profile of the distal end 9062A of sleeve 9062, brake 9064 is maintained in a substantially conical configuration as shown in FIG. 74A. In this configuration, expansion or de-energizing of biasing member 90122 is restrained. Also, in this conical configuration, the outer diameter of brake 9064 is less than the inner diameter of barrel 9058, thus translation of the brake is not restrained by contact with the inner wall of the drug container. Also, a portion of brake 9064 is in contact with retainer 9066. Because brake 9064 is maintained in this configuration by plug 9068 and sleeve 9062, translation of sleeve 9062, caused by decompression of biasing member 90122, is transferred to retainer 9066. Likewise, contact of retainer 9066 with plunger seal 9060 causes translation of plunger seal 9060.

As shown in FIG. 74B, in the event of slack in, or failure of, tether 90525, plug 9068 is no longer held in position by tether 90525 and, therefore, no longer restrains motion of sleeve 9062. As biasing member 90122 decompresses or de-energizes, brake 9064 transforms to a relatively less conical or flatter configuration. This may be caused by a natural bias of brake 9064 to transform to this configuration or, alternatively, may be caused by contact of brake 9064 with both retainer 9066 and sleeve 9062. As the brake is transformed, it comes into contact with the inner wall of barrel 9058. The brake thus acts as a wedge to restrict translation of sleeve 9062. This may prevent further translation or may act to restrict the rate of translation. Optionally, restoring tension in the tether may cause the plug to contact the brake and to transform the brake back to its conical configuration and thus restore normal operation of the drug delivery device.

FIGS. 74A-74B show the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 9062 (i.e., applying a braking force). In another embodiment, the brake 9064 could employ a star-shaped or other configuration when in a substantially flattened position so as to make contact with the inner diameter of the barrel 9058 to prevent or restrict further axial translation of sleeve 9062. Without further translation of sleeve 9062, biasing member 90122 cannot expand or de-energize further which, in turn, prevents or restricts further drug delivery to the user. This provides a necessary and useful safety measure for drug delivery, to prevent over-delivery or accelerated delivery of drug to the user.

Referring back to FIGS. 70A-70D and 71A-71D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, as shown in FIGS. 70A-70D and 71A-71D, initial motion by the actuator 90101 of the multi-function drive mechanism 90100 causes rotation of main/star gear 90102. Main/star gear 90102 is shown as a compound gear with aspects 90102A and 90102B (see FIG. 72). In one manner, main/star gear 90102 conveys motion to the regulating mechanism 90500 through gear assembly 90516. In another manner, main/star gear 90102 conveys motion to the needle insertion mechanism 90200 through gear 90112. As gear 90112 is rotated by main/star gear 90102, gear 90112 engages the needle insertion mechanism 90200 to initiate the fluid pathway connector into the user, as described in detail above. In one particular embodiment, needle insertion mechanism 90200 is a rotational needle insertion mechanism. Accordingly, gear 90112 is configured to engage a corresponding gear surface 90208 of the needle insertion mechanism 90200. Rotation of gear 90112 causes rotation of needle insertion mechanism 90200 through the gear interaction between gear 90112 of the drive mechanism 90100 and corresponding gear surface 90208 of the needle insertion mechanism 90200. Once suitable rotation of the needle insertion mechanism 90200 occurs, for example rotation along axis 'R' shown in FIG. 70B-70C, the needle insertion mechanism may be initiated to create the fluid pathway connector into the user, as described in detail above. In an alternative embodiment, as shown in FIGS. 75A-75B, gear 90112 may indirectly engage the needle insertion mechanism 90200 to initiate the fluid pathway connector into the user. For example, gear 90112 may be configured to engage a corresponding gear surface of a control arm 90202 (visible in FIG. 75) that contacts or blocks the needle insertion mechanism 90200. Rotation of gear 90112 causes movement of the control arm 90202, which may initiate or permit rotation of needle insertion mechanism 90200. Such a needle insertion mechanism, as shown in FIGS. 75A-75B, includes a rotationally biased member 90210 which is initially held in an energized state. The rotational biasing member may be prevented from de-energizing by contact of a component of the insertion mechanism with a rotation prevention feature, such as a blocking aspect of the control arm, of the drug delivery device. Upon activation of the device, or another input, the rotationally biased member 90210 is permitted to, at least partially, de-energize. This causes one or more components of the insertion mechanism to rotate and, in turn, cause, or allow, the insertion of the needle into the patient. Further, a cannula may be inserted into the patient as described above. At a later time, such as when the control arm or another component of the device recognizes a slack in the tether 90525, the rotationally biased member may be allowed to further de-energize, such as by further interaction with the control arm, causing additional rotation of one or more components of the insertion mechanism. This rotation may cause, or allow, the needle to be retracted from the patient. The needle may be fully retracted in a single step or there may be multiple steps of retraction.

As shown in FIGS. 70A-70D and 71A-71D, rotation of the needle insertion mechanism 90200 in this manner may also cause a connection of a sterile fluid pathway to a drug container to permit fluid flow from the drug container to the needle insertion mechanism for delivery to the user. Ramp aspect 90222 of needle insertion mechanism 90200 is caused to bear upon a movable connection hub 90322 of the sterile fluid pathway connector 90300. As the needle insertion mechanism 90200 is rotated by the multi-function drive mechanism 90100, ramp aspect 90222 of needle insertion mechanism 90200 bears upon and translates movable connection hub 90322 of the sterile fluid pathway connector 90300 to facilitate a fluid connection therein. Such translation may occur, for example, in the direction of the hollow arrow along axis 'C' shown in FIGS. 70B and 71B. In at least one embodiment, the needle insertion mechanism 90200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism 90500 and/or one or more of the status readers as described above. During these stages of operation, delivery of fluid substances from the drug chamber 9021 may be initiated, on-going, and/or completed by the expansion of the biasing member 90122 from its initial energized state acting upon the piston 90110A, 90110B and plunger seal 60. As described above, the regulating mechanisms 90500 function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. This is visible through the progression of the components shown in FIGS. 70A-70D and 71A-71D. The motion of the piston 90110A, 90110B and plunger seal 9060 as they are pushed by the expansion of the biasing member 90122 from its initial energized state are shown in the direction of the solid arrow along axis 'A' from proximal or first position 'P' to the distal or second position 'D', as shown in the transition of FIGS. 70A-70D and 71A-71D.

Further aspects of the novel drive mechanism will be described with reference to FIG. 72 and FIGS. 73A-73B. FIG. 72 shows a perspective view of the multi-function drive mechanism, according to at least a first embodiment, during its initial locked stage. Initially, the tether 90525 may retain the biasing member 90122 in an initial energized position within piston 90110A, 90110B. Directly or indirectly upon activation of the device by the user, the multi-function drive mechanism 90100 may be activated to permit the biasing member to impart a force to piston 90110 and therefore to tether 90525. This force on tether 90525 imparts a torque on winding drum 90520 which causes the gear assembly 90516 and regulating mechanism 90500 to begin motion. As shown in FIG. 73A, the piston 90110 and biasing member 90122 are both initially in a compressed, energized state behind the plunger seal 60. The biasing member 90122 may be maintained in this state until activation of the device between internal features of drive housing 90130 and interface surface 90110C of piston 90110A, 90110B. As the drug delivery device 9010 is activated and the drive mechanism 90100 is triggered to operate, biasing member 90122 is permitted to expand (i.e., decompress) axially in the distal direction (i.e., in the direction of the solid arrow shown in FIGS. 70A-70D and FIGS. 71A-71D). Such expansion causes the biasing member 90122 to act upon and distally translate interface surface 90110C and piston 90110, thereby distally translating plunger seal 9060 to push drug fluid out of the drug chamber 9021 of barrel 9058. In at least one embodiment, an end-of-dose status indication may be provided to the user once the status reader contacts or recognizes a status trigger positioned on the tether 90525 to substantially correspond with the end of axial travel of the piston 90110A, 90110B and plunger seal 9060 within the barrel 9058 of the drug container 9050. The status triggers may be positioned along the tether 90525 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 90525 to be read or recognized at positions which correspond with the beginning and end of drug delivery, as well as at desired increments during drug delivery. As shown, tether 90525 passes substantially axially through the drive mechanism housing 90130, the biasing member 90122, and connects to the piston 90110A, 90110B to restrict the axial translation of the piston 90110A, 90110B and the plunger seal 9060 that resides adjacent thereto.

The novel embodiments of the present disclosure may be utilized to meter, restrain, or otherwise prevent free rotational movement of winding drum 90520 and, thus, axial translation of the components of the controlled delivery drive mechanism 90100. Accordingly, the regulating mechanism 90500 only controls the motion of the drive mechanism, but does not apply the force for the drug delivery. One or more additional biasing members 90122, such as compression springs, may be utilized to drive or assist the driving of the piston 90110. For example, a compression spring may be utilized within the drive housing 90130 for this purpose. The regulating mechanism 90500 only controls, meters, or regulates such action. The controlled delivery drive mechanisms and/or drug delivery devices of the present disclosure may additionally enable a compliance push to ensure that substantially all of the drug substance has been pushed out of the drug chamber 9021. The plunger seal 9060, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear assembly 90516. As the gear assembly 90516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear assembly and regulating mechanism shown in the figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 90101. The change in the rate of movement of actuator 90101 causes a change in the rotation rate of regulating mechanism 90500 which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

Assembly and/or manufacturing of controlled delivery drive mechanism 90100, drug delivery pump 9010, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9050 may first be assembled and filled with a fluid for delivery to the user. The drug container 9050 includes a cap 9052, a pierceable seal 9056, a barrel 9058, and a plunger seal 9060. The pierceable seal 9056 may be fixedly engaged between the cap 9052 and the barrel 9058, at a distal end of the barrel 9058. The barrel 9058 may be filled with a drug fluid through the open proximal end prior to insertion of the plunger seal 9060 from the proximal end of the barrel 9058. An optional connection mount 9054 may be mounted to a distal end of the pierceable seal 9056. The connection mount 9054 may guide the insertion of the piercing member of the fluid pathway connector into the barrel 58 of the drug container 9050. The drug container 9050 may then be mounted to a distal end of drive housing 90130.

One or more drive biasing members 90122 may be inserted into a distal end of the drive housing 90130. Optionally, a cover sleeve 90140 may be inserted into a distal end of the drive housing 90130 to substantially cover biasing member 90122. A piston may be inserted into the distal end of the drive housing 90130 such that it resides at least partially within an axial pass-through of the biasing member 90122 and the biasing member 90122 is permitted to contact a piston interface surface 90110C of piston 90110A, 90110B at the distal end of the biasing member 90122. An optional cover sleeve 90140 may be utilized to enclose the biasing member 90122 and contact the piston interface surface 90110C of piston 90110A, 90110B. The piston 90110A, 90110B and drive biasing member 90122, and optional cover sleeve 90140, may be compressed into drive housing 90130. Such assembly positions the drive biasing member 90122 in an initial compressed, energized state and preferably places a piston interface surface 90110C in contact with the proximal surface of the plunger seal 9060 within the proximal end of barrel 9058. The piston, piston biasing member, contact sleeve, and optional components, may be compressed and locked into the ready-to-actuate state within the drive housing 90130 prior to attachment or mounting of the drug container 9050. The tether 90525 is pre-connected to the proximal end of the piston 90110A, 90110B and passed through the axial aperture of the biasing member 90122 and drive mechanism 90130, and then wound through the interior of the drug delivery device with the other end of the tether 90525 wrapped around the winch drum/gear 90520 of the regulating mechanism 90500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 90100 or drug delivery device 9010 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9018 to enable the user to view the operation of the drug delivery device 9010 or verify that drug dose has completed. Similarly, the drug delivery device 9010 may contain an adhesive patch 9026 and a patch liner 9028 on the bottom surface of the housing 9012. The adhesive patch 9026 may be utilized to adhere the drug delivery device 9010 to the body of the user for delivery of the drug dose. As would be readily understood by one having ordinary skill in the art, the adhesive patch 9026 may have an adhesive surface for adhesion of the drug delivery device to the body of the user. The adhesive surface of the adhesive patch 9026 may initially be covered by a non-adhesive patch liner 9028, which is removed from the adhesive patch 9026 prior to placement of the drug delivery device 9010 in contact with the body of the user. Removal of the patch liner 9028 may further remove the sealing membrane 90254 of the insertion mechanism 90200, opening the insertion mechanism to the body of the user for drug delivery (as shown in FIG. 69C).

Similarly, one or more of the components of controlled delivery drive mechanism 90100 and drug delivery device 9010 may be modified while remaining functionally within the breadth and scope of the present disclosure. For example, as described above, while the housing of drug delivery device 9010 is shown as two separate components upper housing 9012A and lower housing 9012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a user, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

In some embodiments, the power and control system 91810: (a) determines optimal temperature of the drug, appropriate time for delivery, etc. based on signals from an on-body sensor 91840, temperature sensor 91880, and/or other sensors; (b) sends command signals to the drive control system 91820 for initiating drug delivery; (c) provides a "delivery rate" information to the drive control system 91820; and (d) receives 'drug delivery information' and transmits 'end of delivery information' to a remote computing device via a communication unit 91830.

In some embodiments, the drive control system 91820: (a) drives the multi-function drive mechanism, such as the drive mechanism 90100, regulating mechanism 90500, needle insertion mechanism, connecting fluid pathway (see FIG. 78C); and (b) controls the regulating element 90500 or gear assembly.

In some embodiments, the controller may be included in the drive control system 91820. The controller 91822 may drive the actuator/motor 90101 based on the command signals received from the power and control system 91810. The controller 91822 may translate the delivery rate information into: selection of gears, selection of diameters, rate of rotation, selection, etc. The controller 91822 may then drive the various components of the drive control system 91820 to deliver the drug according to the required "delivery rate (see FIG. 78B).

X. Other Embodiments of Multi-Function Drive Mechanism

At least some of the drug delivery devices described in this application, including at least those described in connection with FIGS. 1A-2B and 33A-33C, may be configured to incorporate the embodiments of the drive mechanism described below in connection with FIGS. 69A-73D. The embodiments of the drive mechanism described below in connection with FIGS. 69A-73D may be used to replace, in its entirety or partially, the above-described drive mechanism 100, 6100, or 8100, or any other drive mechanism described herein, where appropriate.

The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a patient; and (iii) connecting a sterile fluid pathway to a drug container to permit fluid flow from the drug container to the needle insertion mechanism for delivery to the patient. With reference to the embodiments shown in FIGS. 70A-70D and 71A-71D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the patient. The seals described herein may be comprised of a number of materials but are, in a preferred embodiment, comprised of one or more elastomers or rubbers. The drive mechanism 90100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the patient.

In one particular embodiment, the drive mechanism 90100 employs one or more compression springs as the biasing member(s). Upon activation of the drug delivery device by the patient, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the patient for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the multi-function drive mechanism shown in FIGS. 70A-70D and 70A-70D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the patient. Compressed within the drive housing 90130, between the drug container 9050 and the proximal end of the housing 90130, are one or more drive biasing members 90122 and a piston 90110, wherein the drive biasing members 90122 are configured to bear upon an interface surface 90110C of the piston 90110, as described further herein. Optionally, a cover sleeve (not shown) may be utilized between the drive biasing members 90122 and the interface surface 90110C of the piston 90110 to, for example, promote more even distribution of force from the drive biasing member 90122 to the piston 90110, prevent buckling of the drive biasing members 90122, and/or hide biasing members 90122 from patient view. Interface surface 90110C of piston 90110 is caused to rest substantially adjacent to, or in contact with, a proximal end of seal 9060. Although the embodiments shown in FIGS. 70A-70D and 71A-71D show a singular biasing member it is also contemplated that one or more biasing members disposed to act in parallel may be used.

As best shown in FIG. 70D and FIG. 71D, the piston 90110 may be comprised of two components 90110A and 90110B and have an interface surface 90110C to contact the plunger seal. A tether, ribbon, string, or other retention strap (referred to herein as the "tether" 90525) may be connected at one end to the piston 90110A, 90110B. For example, the tether 90525 may be connected to the piston 90110A, 90110B by retention between the two components of the piston 8110A, 8110B when assembled. The tether 8525 is connected at another end to a winch drum/gear 90520 of a delivery control mechanism 90500. Through the use of the winch drum/gear 90520 connected to one end of the tether 90525, and the tether 90525 connected at another end to the piston 90110A, 90110B, the regulating mechanism 90500 functions to control, meter, provide resistance, or otherwise prevent free axial translation of the piston 90110A, 90110B and plunger seal 9060 utilized to force a drug substance out of a drug container 9050. Accordingly, the regulating mechanism 90500 is a portion of the gear assembly 90116 aspect of the multi-function drive mechanism, which together function to control the rate or profile of drug delivery to the patient.

As shown in FIGS. 70A-70D and 71A-71D, and in isolation in FIGS. 72 and 73A-73B, in the embodiments of the present disclosure, the regulating mechanism 90500 is gear assembly driven by an actuator 90101 of the multi-function drive mechanism 90100. The regulating mechanism retards or restrains the distribution of tether 90525, only allowing it to advance at a regulated or desired rate. This restricts movement of piston 90110 within barrel 9058, which is pushed by one or more biasing members 90122, hence controlling the movement of plunger seal 9060 and delivery of the drug contained in chamber 9021. As the plunger seal 9060 advances in the drug container 9050, the drug substance is dispensed through the sterile pathway connection 90300, conduit 9030, insertion mechanism 90200, and into the body of the patient for drug delivery. The actuator 90101 may be a number of power/motion sources including, for example, a solenoid, a stepper motor, or a rotational drive motor. In a particular embodiment, the actuator 90101 is a rotational stepper motor with a notch that corresponds with the gear teeth of the main/star gear 90102. Commonly, such a rotational stepper motor may be referred to as a Pac-Man' motor. In at least one embodiment, the Pac-Man motor has a gear interface within which one or more teeth of the main gear may partially reside during operation of the system. This is more clearly visible in FIGS. 73A-73B. When the gear interface 90101A of the Pac-Man motor 90101 is in alignment with a tooth 90102A of the main gear 90102, rotational motion of the Pac-Man motor 90101 causes gear interface rotation of the main gear 90102. When the Pac-Man motor 90101 is between gear teeth of the main gear, it may act as a resistance for, for example, back-spinning or unwinding of the gear assembly 90116. Further detail about the gear assembly 90116, regulating mechanism 90500, and multi-function drive mechanism 90100 are provided herein.

In a particular embodiment shown in FIGS. 73A-73B, the regulating element 90500 further includes one or more gears 90511, 90512, 90513, 90514, of a gear assembly 90516. One or more of the gears 90511, 90512, 90513, 90514 may be, for example, compound gears having a small diameter gear attached at a shared center point to a large diameter gear. Gear 90513 may be rotationally coupled to winch drum/gear 90520, for example by a keyed shaft, thereby coupling rotation of gear assembly 90516 to winch drum/gear 90520. Compound gear 90512 engages the small diameter gear 90513 such that rotational movement of the compound gear aspect 90512B is conveyed by engagement of the gears (such as by engagement of corresponding gear teeth) to gear 90513. Compound gear aspect 90512A, the rotation of which is coupled to gear aspect 90512B, is caused to rotate by action of compound gear aspect 90102B of the main/star gear 90102. Compound gear aspect 90102B, the rotation of which is coupled to main/star gear 90102, is caused to rotate by interaction between main/star gear 90102A and interface 90101A of the actuator 90101. Thus, rotation of main/star gear 90102 is conveyed to winch drum/gear 90520. Accordingly, rotation of the gear assembly 90516 initiated by the actuator 90101 may be coupled to winch drum/gear 90520

(i.e., through the gear assembly 90516), thereby controlling the distribution of tether 90525, and the rate of movement of plunger seal 9060 within barrel 9058 to force a fluid from drug chamber 9021. The rotational movement of the winch drum/gear 90520, and thus the axial translation of the piston 90110 and plunger seal 9060, are metered, restrained, or otherwise prevented from free axial translation by other components of the regulating element 90500, as described herein. As described above, the actuator 90101 may be a number of known power/motion sources including, for example, a motor (e.g., a DC motor, AC motor, or stepper motor) or a solenoid (e.g., linear solenoid, rotary solenoid).

Notably, the regulating mechanisms 90500 of the present disclosure do not drive the delivery of fluid substances from the drug chamber 9021. The delivery of fluid substances from the drug chamber 9021 is caused by the expansion of the biasing member 90122 from its initial energized state acting upon the piston 90110A, 90110B and plunger seal 9060. The regulating mechanisms 90500 instead function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. According to a preferred embodiment, the controlled delivery drive mechanisms and drug delivery devices of the present disclosure include a regulating mechanism indirectly or directly connected to a tether metering the axial translation of the piston 90110A, 90110B and plunger seal 9060, which are being driven to axially translate by the biasing member 90122. The rate of drug delivery as controlled by the regulating mechanism may be determined by: selection of the gear ratio of gear assembly 90516; selection of the main/star gear 90102; selection of the diameter of winding drum/gear 90520; using electromechanical actuator 90101 to control the rate of rotation of the main/star gear 90102; or any other method known to one skilled in the art. By using electromechanical actuator 90101 the rate of rotation of the main/star gear 90102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 90525 by the winch drum/gear 90520 and thereby permit axial translation of the piston 90110 by the biasing member 90122 to translate a plunger seal 9060 within a barrel 9058. The one or more inputs may be provided by the actuation of the activation mechanism, a control interface, and/or a remote control mechanism. The power and control system may be configured to receive one or more inputs to adjust the restraint provided by the tether 90525 and winch drum/gear 90520 on the free axial translation of the piston 90110 upon which the biasing member 90122 bears upon to meet a desired drug delivery rate or profile, to change the dose volume for delivery to the patient, and/or to otherwise start, stop, or pause operation of the drive mechanism.

The components of the drive mechanism 90100, upon activation, may be used to drive axial translation in the distal direction of the plunger seal 9060 of the drug container 9050. Optionally, the drive mechanism 8100 may include one or more compliance features which enable additional axial translation of the plunger seal 9060 to, for example, ensure that substantially the entire drug dose has been delivered to the patient. For example, the plunger seal 9060, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the patient. Such feedback may be tactile, visual, and/or auditory, as described above, and may be redundant such that more than one signal or type of feedback is provided to the patient during use of the device. For example, the patient may be provided an initial feedback to identify that the system is operational and ready for drug delivery. Upon activation, the system may then provide one or more drug delivery status indications to the patient. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the patient.

The tether 90525 may have one or more status triggers, such as electrical contacts, optical markings, or electromechanical pins or recesses, which are capable of contacting or being recognized by a status reader. In at least one embodiment, an end-of-dose status indication may be provided to the patient once the status reader contacts or recognizes the final status trigger positioned on the tether 90525 that would contact the status reader at the end of axial travel of the piston 90110A, 90110B and plunger 9060 within the barrel 8058 of the drug container 9050. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 90525 to be read or recognized at positions which correspond with the beginning and end of drug delivery, as well as at desired increments during drug delivery. As the drug delivery device is activated and drug delivery is begun by release of the biasing member 90122 and the resulting force applied to the piston 90110A, 90110B and plunger seal 9060, the rate or profile of drug delivery to the patient is controlled by the regulating mechanism 90500, gear assembly 90516, and winch drum/gear 90520 releasing the tether 90525 and permitting expansion of the biasing member 90122 and axial translation of the piston 90110A, 90110B and plunger seal 9060. As this occurs, the status triggers of the tether 8525 are contacted or recognized by the status reader and the status of the drive mechanism before, during, and after operation can be relayed to the power and control system to provide feedback to the patient. Depending on the number of status triggers located on the tether 90525, the frequency of the incremental status indication may be varied as desired. As described above, a range of status readers may be utilized depending on the status triggers utilized by the system.

In a preferred embodiment, the status reader may apply a tensioning force to the tether 90525. When the system reaches end-of-dose, the tether 90525 goes slack and the status reader 90544 is permitted to rotate about a fulcrum. This rotation may operate an electrical or electromechanical switch, for example a switch, signaling slack in the tether 90525 to the power and control system. Additionally, a gear 90511 of gear assembly 90516 may act as an encoder along with a sensor. The sensor/encoder combination is used to provide feedback of gear assembly rotation, which in turn can be calibrated to the position of piston 90110 when there is no slack in the tether 90525. Together, the status reader and sensor/encoder may provide positional feedback, end-of-dose signal, and error indication, such as an occlusion, by observing slack in the tether 90525 prior to reaching the expected number of motor rotations as counted by the sensor/encoder.

Referring back to FIGS. 70A-70D and 71A-71D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a patient; and connecting a sterile fluid pathway to a drug container to permit fluid flow from the drug container to the needle insertion mechanism for delivery to the patient. In at least one embodiment, as shown in FIGS. 70A-70D and 71A-71D, initial motion by the actuator 90101 of the multi-function drive mechanism 90100 causes rotation of main/star gear 90102. Main/star gear 90102 is shown as a compound gear with aspects 90102A and 90102B (see FIG. 72). In one manner, main/star gear 90102 conveys motion to the regulating mechanism 90500 through gear assembly 90516. In another manner, main/star gear 90102 conveys motion to the needle insertion mechanism 90200 through gear 90112. As gear 90112 is rotated by main/star gear 90102, gear 90112 engages the needle insertion mechanism 90200 to initiate the fluid pathway connector into the patient, as described in detail above. In one particular embodiment, needle insertion mechanism 90200 is a rotational needle insertion mechanism. Accordingly, gear 90112 is configured to engage a corresponding gear surface 90208 of the needle insertion mechanism 90200. Rotation of gear 90112 causes rotation of needle insertion mechanism 90200 through the gear interaction between gear 90112 of the drive mechanism 90100 and corresponding gear surface 90208 of the needle insertion mechanism 90200. Once suitable rotation of the needle insertion mechanism 90200 occurs, for example rotation along axis 'R' shown in FIG. 70B-70C, the needle insertion mechanism may be initiated to create the fluid pathway connector into the patient, as described in detail above.

As shown in FIGS. 70A-70D and 71A-71D, rotation of the needle insertion mechanism 90200 in this manner may also cause a connection of a sterile fluid pathway to a drug container to permit fluid flow from the drug container to the needle insertion mechanism for delivery to the patient. Ramp aspect 90222 of needle insertion mechanism 90200 is caused to bear upon a movable connection hub 322 of the sterile fluid pathway connector 90300. As the needle insertion mechanism 90200 is rotated by the multi-function drive mechanism 90100, ramp aspect 90222 of needle insertion mechanism 90200 bears upon and translates movable connection hub 322 of the sterile fluid pathway connector 90300 to facilitate a fluid connection therein. Such translation may occur, for example, in the direction of the hollow arrow along axis 'C' shown in FIGS. 70B and 71B. In at least one embodiment, the needle insertion mechanism 90200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a patient-activity or upon movement or function of another component of the drug delivery device. In at least one embodiment, needle/trocar retraction may be configured to occur upon end-of-drug-delivery, as triggered by, for example, the regulating mechanism 90500 and/or one or more of the status readers as described above. During these stages of operation, delivery of fluid substances from the drug chamber 9021 may be initiated, on-going, and/or completed by the expansion of the biasing member 90122 from its initial energized state acting upon the piston 90110A, 90110B and plunger seal 9060. As described above, the regulating mechanisms 90500 function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. This is visible through the progression of the components shown in FIGS. 70A-70D and 71A-71D. The motion of the piston 90110A, 90110B and plunger seal 9060 as they are pushed by the expansion of the biasing member 90122 from its initial energized state are shown in the direction of the solid arrow along axis 'A' from proximal or first position 'P' to the distal or second position 'D', as shown in the transition of FIGS. 70A-70D and 71A-71D.

Further aspects of the novel drive mechanism will be described with reference to FIG. 72 and FIGS. 73A-73B. FIG. 4 shows a perspective view of the multi-function drive mechanism, according to at least a first embodiment, during its initial locked stage. Initially, the tether 90525 may retain the biasing member 90122 in an initial energized position within piston 90110A, 90110B. Directly or indirectly upon activation of the device by the patient, the multi-function drive mechanism 90100 may be activated to permit the biasing member to impart a force to piston 90110 and therefore to tether 90525. This force on tether 90525 imparts a torque on winding drum 90520 which causes the gear assembly 90516 and regulating mechanism 90500 to begin motion. As shown in FIG. 73A, the piston 90110 and biasing member 90122 are both initially in a compressed, energized state behind the plunger seal 9060. The biasing member 90122 may be maintained in this state until activation of the device between internal features of drive housing 90130 and interface surface 90110C of piston 90110A, 90110B. As the drug delivery device 9010 is activated and the drive mechanism 90100 is triggered to operate, biasing member 90122 is permitted to expand (i.e., decompress) axially in the distal direction (i.e., in the direction of the solid arrow shown in FIGS. 70A-70D and FIGS. 71A-71D). Such expansion causes the biasing member 90122 to act upon and distally translate interface surface 90110C and piston 90110, thereby distally translating plunger seal 9060 to push drug fluid out of the drug chamber 9021 of barrel 9058. In at least one embodiment, an end-of-dose status indication may be provided to the patient once the status reader contacts or recognizes a status trigger positioned on the tether 90525 to substantially correspond with the end of axial travel of the piston 90110A, 90110B and plunger seal 9060 within the barrel 9058 of the drug container 9050. The status triggers may be positioned along the tether 90525 at various increments, such as increments which correspond to certain volume measurement, to provide incremental status indication to the patient. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 90525 to be read or recognized at positions which correspond with the beginning and end of drug delivery, as well as at desired increments during drug delivery. As shown, tether 90525 passes substantially axially through the drive mechanism housing 90130, the biasing member 90122, and connects to the piston 90110A, 90110B to restrict the axial translation of the piston 90110A, 90110B and the plunger seal 9060 that resides adjacent thereto.

The novel embodiments of the present disclosure may be utilized to meter, restrain, or otherwise prevent free rotational movement of winding drum 90520 and, thus, axial translation of the components of the controlled delivery drive mechanism 90100. Accordingly, the regulating mechanism 90500 only controls the motion of the drive mechanism, but does not apply the force for the drug delivery. One or more additional biasing members 90122, such as compression springs, may be utilized to drive or assist the driving of the piston 90110. For example, a compression spring may be utilized within the drive housing 90130 for this purpose. The regulating mechanism 90500 only controls, meters, or regulates such action. The controlled delivery drive mechanisms and/or drug delivery devices of the present disclosure may additionally enable a compliance push to ensure that substantially all of the drug substance has been pushed out of the drug chamber 9021. The plunger seal 9060, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the patient. This configuration further enables true end-of-dose indication to the patient.

In at least one embodiment, incremental status indication may be provided to the patient by reading or recognizing the rotational movement of one or more gears of gear assembly 90516. As the gear assembly 90516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the patient. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the patient.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the patient. While the drive mechanisms of the present disclosure are described with reference to the gear assembly and regulating mechanism shown in the Figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

Assembly and/or manufacturing of controlled delivery drive mechanism 90100, drug delivery drug delivery device 9010, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9050 may first be assembled and filled with a fluid for delivery to the patient. The drug container 9050 includes a cap 9052, a pierceable seal 9056, a barrel 9058, and a plunger seal 9060. The pierceable seal 9056 may be fixedly engaged between the cap 9052 and the barrel 9058, at a distal end of the barrel 9058. The barrel 9058 may be filled with a drug fluid through the open proximal end prior to insertion of the plunger seal 9060 from the proximal end of the barrel 9058. An optional connection mount 9054 may be mounted to a distal end of the pierceable seal 9056. The connection mount 9054 may guide the insertion of the piercing member of the fluid pathway connector into the barrel 9058 of the drug container 9050. The drug container 9050 may then be mounted to a distal end of drive housing 90130.

One or more drive biasing members 90122 may be inserted into a distal end of the drive housing 90130. Optionally, a cover sleeve 90140 may be inserted into a distal end of the drive housing 90130 to substantially cover biasing member 90122. A piston may be inserted into the distal end of the drive housing 90130 such that it resides at least partially within an axial pass-through of the biasing member 90122 and the biasing member 90122 is permitted to contact a piston interface surface 90110C of piston 90110A, 90110B at the distal end of the biasing member 90122. An optional cover sleeve 90140 may be utilized to enclose the biasing member 90122 and contact the piston interface surface 90110C of piston 90110A, 90110B. The piston 90110A, 90110B and drive biasing member 90122, and optional cover sleeve 90140, may be compressed into drive housing 90130. Such assembly positions the drive biasing member 90122 in an initial compressed, energized state and preferably places a piston interface surface 90110C in contact with the proximal surface of the plunger seal 9060 within the proximal end of barrel 9058. The piston, piston biasing member, contact sleeve, and optional components, may be compressed and locked into the ready-to-actuate state within the drive housing 90130 prior to attachment or mounting of the drug container 9050. The tether 90525 is pre-connected to the proximal end of the piston 90110A, 90110B and passed through the axial aperture of the biasing member 90122 and drive mechanism 90130, and then wound through the interior of the drug delivery device with the other end of the tether 90525 wrapped around the winch drum/gear 90520 of the regulating mechanism 90500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a patient. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 90100 or drug delivery device 9010 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 18 to enable the patient to view the operation of the drug delivery device 9010 or verify that drug dose has completed. Similarly, the drug delivery device 9010 may contain an adhesive patch 9026 and a patch liner 9028 on the bottom surface of the housing 9012. The adhesive patch 9026 may be utilized to adhere the drug delivery device 9010 to the body of the patient for delivery of the drug dose. As would be readily understood by one having ordinary skill in the art, the adhesive patch 9026 may have an adhesive surface for adhesion of the drug delivery device to the body of the patient. The adhesive surface of the adhesive patch 9026 may initially be covered by a non-adhesive patch liner 9028, which is removed from the adhesive patch 9026 prior to placement of the drug delivery device 9010 in contact with the body of the patient. Removal of the patch liner 9028 may further remove the sealing membrane 254 of the insertion mechanism 90200, opening the insertion mechanism to the body of the patient for drug delivery (as shown in FIG. 69C). In some embodiments, removal of the patch liner 9028 may also wake-up onboard electronics (e.g., the power and control system 2400) by supplying them with electricity from an onboard battery.

Similarly, one or more of the components of controlled delivery drive mechanism 90100 and drug delivery device 9010 may be modified while remaining functionally within the breadth and scope of the present disclosure. For example, as described above, while the housing of drug delivery device 9010 is shown as two separate components upper housing 9012A and lower housing 9012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the patient before, during, and after drug delivery. For example, the patient may be provided an initial feedback to identify that the system is operational and ready for drug delivery. Upon activation, the system may then provide one or more drug delivery status indications to the patient. At completion of drug delivery, the drive mechanism and drug delivery device may provide an end-of-dose indication. The novel controlled delivery drive mechanisms of the present disclosure may be directly or indirectly activated by the patient. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the patient during operation of the device.

A method of operating the drug delivery device includes the steps of: activating, by a patient, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a patient, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

XI. Other Embodiments of Multi-Function Drive Mechanism

At least some of the drug delivery devices described in this application, including at least those described in connection with FIGS. 1A-2B, 33A-33C, and 69A-73D may be configured to incorporate the embodiments of the drive mechanism described below in connection with FIGS. 80A-85C. The embodiments of the drive mechanism described below in connection with FIGS. 80A-85C may be used to replace, in its entirety or partially, the above-described drive mechanism 100, 6100, 8100, or 9010, or any other drive mechanism described herein, where appropriate.

The present disclosure provides drive mechanisms for the controlled delivery of drug substances, drug delivery pumps with controlled delivery drive mechanisms, the methods of operating such devices, and the methods of assembling such devices. Notably, the drive mechanisms of the present disclosure control the rate of drug delivery by metering, providing resistance, or otherwise preventing free axial translation of the plunger seal utilized to force a drug substance out of a drug container. The novel embodiments of the present disclosure thus are capable of delivering drug substances at variable rates. The controlled delivery drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a controlled delivery drive mechanism which includes a drive housing, a piston, and one or more biasing members, wherein the one or more biasing members are initially retained in an energized state and is configured to bear upon an interface surface of the piston. The piston is configured to translate substantially axially within a drug container having a plunger seal and a barrel. A tether is connected at one end to the piston and at another end to a winch drum of a regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum of the regulating mechanism to meter the free expansion of the biasing member from its initial energized state and the free axial translation of the piston upon which the biasing member bears upon.

In at least one embodiment, the regulating mechanism is an escapement regulating mechanism coupled to, or acting with, the winch drum. The escapement regulating mechanism may further include a gear train having one or more gears, wherein the rotation of at least one gear of the gear train is coupled to the rotation of the winch drum. In a particular embodiment, the escapement regulating mechanism further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. An electromechanical actuator such as a motor or solenoid may additionally be used to control the oscillation and/or rotation of the balance wheel. For example, a DC or stepper motor may be used, or a linear or rotary solenoid may be used. The escape wheel is a compound gear having escape teeth around the circumference of a large diameter escape gear and a small diameter gear configured to engage and meter the gear train. The metering of the gear train and/or winch drum by an escapement regulating mechanism controls the rate or profile of drug delivery to a user.

The gear train may include a winch gear coupled to a winch drum upon which the tether may be releasably wound. The winch gear may be configured to engage a first compound gear, such that rotation of the winch gear and the small gear of the first compound gear are linked. The gear assembly may additionally include a second compound gear, wherein the large gear of the first compound gear is engaged with the small gear of the second compound gear. The large gear of the second compound gear may be engaged with a gear of the escape wheel such that rotation of the second compound gear and escape wheel are coupled. In this way rotation of the escape wheel is coupled to rotation of the winch drum and can thereby control the release of the tether from the winch drum to meter the free expansion of the biasing member from its initial energized state and the free axial translation of the piston upon which the biasing member bears upon. The metering of the tether by the regulating mechanism controls the rate or profile of drug delivery to a user. The piston may be one or more parts and connects to a distal end of the tether.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum upon which the tether may be releasably wound, rotation of the winch drum releases the tether from the winch drum to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum is coupled to a regulating mechanism which controls rotation of the winch drum and hence metering of the translation of the piston.

The drug delivery device may utilize the regulating mechanism described above in the first embodiment, which configuration utilizes an escapement regulating mechanism to control the metering of the tether. The escapement regulating mechanism may further include a gear train having one or more gears. In a particular embodiment, the escapement regulating mechanism further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. A motor, such as a DC motor or stepper motor, or a linear or rotary solenoid may additionally be used to control the oscillation and/or rotation of the balance wheel. The escape wheel is a compound gear having escape teeth around the circumference of a large diameter escape gear and a small diameter gear configured to engage and meter the gear train. The metering of the gear train by an escapement regulating mechanism controls the rate or profile of drug delivery to a user. The piston is configured to contact and axially translate the plunger seal within the barrel.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum on the free axial translation of the piston upon which the biasing member bears upon to meet a desired drug delivery rate or profile, to change the dose volume for delivery to the user, and/or to otherwise start, stop, or pause operation of the drive mechanism.

The novel embodiments of the present disclosure provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. As will be described further below, the embodiments of the present disclosure may include one or more additional components which may be considered standard components in the industry of medical devices. For example, the embodiments may include one or more batteries utilized to power the motor, drive mechanisms, and drug delivery devices of the present disclosure. The components, and the embodiments containing such components, are within the contemplation of the present disclosure and are to be understood as falling within the breadth and scope of the present disclosure.

The present disclosure provides drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 80A-80C show an exemplary drug delivery device according to at least one embodiment of the present disclosure. The drug delivery device may be utilized to administer delivery of a drug treatment into a body of a user. As shown in FIGS. 80A-80C, the drug delivery device 9210 includes a pump housing 9212. Pump housing 9212 may include one or more housing subcomponents which are fixedly engageable to facilitate easier manufacturing, assembly, and operation of the drug delivery device. For example, drug delivery device 9210 includes a pump housing 9212 which includes an upper housing 9212A and a lower housing 9212B. The drug delivery device may further include an activation mechanism 9214, a status indicator 9216, and a window 9218. Window 9218 may be any translucent or transmissive surface through which the operation of the drug delivery device may be viewed. As shown in FIG. 80B, drug delivery device 9210 further includes assembly platform 9220, sterile fluid conduit 9230, drive mechanism 92100 having drug container 9250, insertion mechanism 92200, fluid pathway connector 92300, and a power and control system (not shown). One or more of the components of such drug delivery devices may be modular in that they may be, for example, pre-assembled as separate components and configured into position onto the assembly platform 9220 of the drug delivery device 9210 during manufacturing.

The pump housing 9212 contains all of the device components and provides a means of removably attaching the device 9210 to the skin of the user. The pump housing 9212 also provides protection to the interior components of the device 9210 against environmental influences. The pump housing 9212 is ergonomically and aesthetically designed in size, shape, and related features to facilitate easy packaging, storage, handling, and use by users who may be untrained and/or physically impaired. Furthermore, the external surface of the pump housing 9212 may be utilized to provide product labeling, safety instructions, and the like. Additionally, as described above, housing 9212 may include certain components, such as status indicator 9216 and window 9218, which may provide operation feedback to the user.

In at least one embodiment, the drug delivery device 9210 provides an activation mechanism 9214 that is displaced by the user to trigger the start command to the power and control system. In a preferred embodiment, the activation mechanism is a start button 9214 that is located through the pump housing 9212, such as through an aperture between upper housing 9212A and lower housing 9212B, and which contacts a control arm 40 of the power and control system. In at least one embodiment, the start button 14 may be a push button, and in other embodiments, may be an on/off switch, a toggle, or any similar activation feature known in the art. The pump housing 9212 also provides a status indicator 16 and a window 9218. In other embodiments, one or more of the activation mechanism 9214, the status indicator 9216, the window 9218, and combinations thereof may be provided on the upper housing 9212A or the lower housing 9212B such as, for example, on a side visible to the user when the drug delivery device 9210 is placed on the body of the user. Housing 9212 is described in further detail hereinafter with reference to other components and embodiments of the present disclosure.

Drug delivery device 9210 is configured such that, upon activation by a user by depression of the activation mechanism, the drug delivery device is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug delivery device. For example, an optional on-body sensor 9224 (shown in FIG. 80C) may be provided in one embodiment as a safety feature to ensure that the power and control system, or the activation mechanism 9214, cannot be engaged unless the drug delivery device 9210 is in contact with the body of the user. In one such embodiment, the on-body sensor 9224 is located on the bottom of lower housing 9212B where it may come in contact with the users body. Upon displacement of the on-body sensor 9224, depression of the activation mechanism is permitted. Accordingly, in at least one embodiment the on-body sensor 9224 is a mechanical safety mechanism, such as for example a mechanical lock out, that prevents triggering of the drug delivery device 9210 by the activation mechanism 9214. In another embodiment, the on-body sensor may be an electro-mechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present disclosure to prevent, for example, premature activation of the drug delivery device. In a preferred embodiment, the drug delivery device 10 utilizes one or more mechanical on-body sensors. Additional integrated safety mechanisms are described herein with reference to other components of the novel drug delivery devices.

XI.A. Power and Control System

The power and control system includes a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 92100. In one embodiment, the power and control system interfaces with the control arm 9240 to identify when the on-body sensor 9224 and/or the activation mechanism 9214 have been activated. The power and control system may also interface with the status indicator 9216 of the pump housing 9212, which may be a transmissive or translucent material which permits light transfer, to provide visual feedback to the user. The power and control system interfaces with the drive mechanism 92100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator 9216 if device start-up checks provide no errors. After providing the ready-to-start status signal and, in an embodiment with the optional on-body sensor, if the on-body sensor remains in contact with the body of the user, the power and control system will power the drive mechanism 92100 to begin delivery of the drug treatment through the fluid pathway connector 92300 and sterile fluid conduit 9230 (not shown). In a preferred embodiment of the present disclosure, the insertion mechanism 92200 and the fluid pathway connector 92300 may be caused to activate directly by user operation of the activation mechanism 9214. During the drug delivery process, the power and control system is configured to provide a dispensing status signal via the status indicator 9216. After the drug has been administered into the body of the user and after the end of any additional dwell time, to ensure that substantially the entire dose has been delivered to the user, the power and control system may provide an okay-to-remove status signal via the status indicator 9216. This may be independently verified by the user by viewing the drive mechanism and drug dose delivery through the window 9218 of the pump housing 9212. Additionally, the power and control system may be configured to provide one or more alert signals via the status indicator 9216, such as for example alerts indicative of fault or operation failure situations.

The power and control system may additionally be configured to accept various inputs from the user to dynamically control the drive mechanisms 92100 to meet a desired drug delivery rate or profile. For example, the power and control system may receive inputs, such as from partial or full activation, depression, and/or release of the activation mechanism 9214, to set, initiate, stop, or otherwise adjust the control of the drive mechanism 92100 via the power and control system to meet the desired drug delivery rate or profile. Similarly, the power and control system may be configured to receive such inputs to adjust the drug dose volume; to prime the drive mechanism, fluid pathway connector, and fluid conduit; and/or to start, stop, or pause operation of the drive mechanism 92100. Such inputs may be received by the user directly acting on the drug delivery device 9210, such as by use of the activation mechanism 9214 or a different control interface, or the system 92400 may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 9214 of the drug delivery device 9210 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XI.B. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9210, the fluid pathway connector 92300 is enabled to connect the sterile fluid conduit 30 to the drug container of the drive mechanism 92100. Such connection may be facilitated by a piercing member, such as a needle, penetrating a pierceable seal of the drug container of the drive mechanism 92100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present disclosure, the piercing member of the fluid pathway connector is caused to penetrate the pierceable seal of the drug container of the drive mechanism by direct action of the user, such as by depression of the activation mechanism by the user. For example, the activation mechanism itself may bear on the fluid pathway connector such that displacement of the activation mechanism from its original position also causes displacement of the fluid pathway connector. In one such embodiment, the fluid pathway connector may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 92300 and the sterile fluid conduit 30 are provided hereinafter in later sections in reference to other embodiments.

XI.C. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure.

In at least one embodiment, the insertion mechanism 92200 includes an insertion mechanism housing having one or more lockout windows, and a base for connection to the assembly platform and/or pump housing (as shown in FIG. 80B and FIG. 80C). The connection of the base to the assembly platform 9220 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9210. The insertion mechanism may further include one or more insertion biasing members, a needle, a retraction biasing member, a cannula, and a manifold. The manifold may connect to sterile fluid conduit 9230 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9227 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 92254 (shown in FIG. 80C).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 80B, the lockout pin(s) 92208 may be directly displaced by user depression of the activation mechanism 9214. As the user disengages any safety mechanisms, such as an optional on-body sensor 9224 (shown in FIG. 80C), the activation mechanism 9214 may be depressed to initiate the drug delivery device. Depression of the activation mechanism 9214 may directly cause translation or displacement of control arm 40 and directly or indirectly cause displacement of lockout pin(s) 92208 from their initial position within locking windows 92202A of insertion mechanism housing 92202. Displacement of the lockout pin(s) 92208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

XI.D. Drive Mechanism

With reference to the embodiments shown in FIGS. 81 and 82, drive mechanism 92100 includes a drive housing 92130, and a drug container 9250 having a cap 9252, a pierceable seal (not visible), a barrel 9258, and a plunger seal 9260. A drug chamber 9221, located within the barrel 9258 between the pierceable seal and the plunger seal 9260, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism may further include a connection mount 9254 to guide the insertion of the piercing member of the fluid pathway connector into the barrel 9258 of the drug container 9250. The drive mechanism 92100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 92100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the drive mechanism shown in FIG. 81 and FIG. 82, the drive mechanism 92100 includes a drug container 9250 having a cap 9252, a pierceable seal (not visible), a barrel 9258, and a plunger seal 9260, and optionally a connection mount 9254. The drug container 9250 is mounted to a distal end of a drive housing 92130. Compressed within the drive housing 92130, between the drug container 9250 and the proximal end of the housing 92130, are drive biasing members 92122a and 92122b and a piston 92110, wherein the drive biasing members 92122a, 92122b are configured to bear upon an interface surface 92110C of the piston 92110, as described further herein. Optionally, a cover sleeve 92140 may be utilized between the drive biasing members 92122 and the interface surface 92110C of the piston 92110 to, for example, promote more even distribution of force from the drive biasing member 92122 to the piston 92110, prevent buckling of the drive biasing member 92122, and/or hide biasing members 92122 from user view. Interface surface 92110C of piston 92110 is caused to rest substantially adjacent to, or in contact with, a proximal end of seal 9260. Although the embodiments shown in FIGS. 81 and 82 show a plurality of biasing members it is also contemplated that a single biasing member may be used.

As best shown in FIG. 82B, the piston 92110 may be comprised of two components 92110A and 92110B and have an interface surface 92110C to contact the plunger seal. A tether, ribbon, string, or other retention strap (referred to herein as the "tether" 92512) may be connected at one end to the piston 9210A, 92110B. For example, the tether 92512 may be connected to the piston 92110A, 92110B by retention between the two components of the piston 92110A, 92110B when assembled. The tether 92512 is connected at another end to a winch drum 92520 of a delivery control mechanism 92500. Through the use of the winch drum 92520 connected to one end of the tether 92512, and the tether 92512 connected at another end to the piston 92110A, 92110B, the regulating mechanism 92500 functions to control, meter, provide resistance, or otherwise prevent free axial translation of the piston 92110A, 92110B and plunger seal 9260 utilized to force a drug substance out of a drug container 9250. Accordingly, the regulating mechanism 92500 and the drive mechanism 92100 (collectively referred to herein as the "controlled delivery drive mechanism") together function to control the rate or profile of drug delivery to the user.

As shown in FIGS. 81 and 82, in the embodiments of the present disclosure, the regulating mechanism 92500 is an escapement regulating mechanism. The escapement regulating mechanism retards or restrains the distribution of tether 92512, only allowing it to advance at a regulated or desired rate. This restricts movement of piston 92110 within barrel 9258, hence controlling the movement of plunger seal 9260 and delivery of the drug contained in chamber 9221. As the plunger seal 9260 advances in the drug container 9250, the drug substance is dispensed through the sterile pathway connection 92300, conduit 9230, insertion mechanism 92200, and into the body of the user for drug delivery. In turn, tension on tether 92512, caused by the force of biasing member 92122 on piston 92110, imparts a torque on winch drum 92520 which is transferred through gear train 92510 to the escapement regulating mechanism. Optionally, a power spring may be included, coupled to the escapement regulating mechanism. This may be done in order to impart additional torque to the winding drum and/or gear train.

In at least one embodiment of the present disclosure, the drive mechanism 92100 utilizes an escapement regulating element 92500. The regulating element 92500 further includes one or more gears 92512, 92514, 92516 of a gear train 92510. One or more of the gears 92512, 92514, 92516 may be, for example, compound gears having a small diameter gear attached at a shared center point to a large diameter gear. First gear 92512 may be rotationally coupled to winch drum 92520, for example by a keyed shaft, thereby coupling rotation of gear train 92510 to winch drum 92520. First compound gear 92512 engages the small diameter gear 92514B of compound gear 92514 such that rotational movement of the first gear 92512 is conveyed by engagement of the gears (such as by engagement of corresponding gear teeth) to the second compound gear 92514. Large gear 92514A of compound gear 92514 engages the small gear 92516B of second compound gear 92516, conveying rotation thereto. Large gear 92516A of second compound gear 92516 engages small gear 92562B of escape wheel 92562, thereby coupling rotation of escape wheel 92562 to winch drum 92520. Rotation of the gear train 92510 may be coupled to winch drum 92520 thereby controlling the distribution of tether 92512, and the rate of movement of plunger seal 9260 within barrel 9258 to force a fluid from drug chamber 9221. The rotational movement of the winch drum 92520, and thus the axial translation of the piston 92110 and plunger seal 9260, are metered, restrained, or otherwise prevented from free axial translation by other components of the escapement regulating element 92500, as described herein.

The escape wheel 92562 is a compound gear having escape teeth around the circumference of a large diameter escape gear 92562A and a small diameter gear 92562B (not visible) configured to engage the gear train 92510 and meter, restrain, or otherwise prevent free rotational movement thereof. The escapement regulating element 500 further includes a lever 92564. The lever 92564 has pins 92564A,B and prong 92564C. Prong 92564C movably engages a post 92566A and is configured to removably engage an impulse pin 92566B of a balance wheel 92566. The balance wheel 92566 engages and functions as an oscillator around a pivot point 92564D in combination with a hair spring 92568. The gear train 92510, escape wheel 92562, balance wheel 92566, hair spring 92568, and lever 92564 may be mounted on and able to freely rotate or move on a first plate 92504 and/or a second plate 92506. The first plate 92504 and second plate 92506 may utilize one or more spacer columns to maintain the desired spacing between components and one or more pivot pins upon which the components may be mounted and freely rotated. An electromechanical actuator 92570 may be provided in addition to or in lieu of the hair spring 92568. Electromechanical actuator 92570 may be configured to control and/or adjust the rotation and/or oscillation of balance wheel 92566 as will be discussed further hereinafter.

The function of the escape wheel 92562, balance wheel 92566, hair spring 92568, and lever 92564 components of the escapement regulating element 92500 are explained with reference to FIG. 81B and FIGS. 83A-83H. The escape wheel 92562 and lever 92564 may initially be in an activation position, as shown in FIG. 83A. The escape wheel 562 and lever 92564 generally function to perform two steps, termed the locking action and the impulse action. These two actions are illustrated in FIG. 83B and FIG. 83C, respectively, and in which the gear train 510 is applying a clockwise torque on the escape wheel 92562. The clockwise torque may come as a result of biasing members 92122 applying a force to piston 92110 which in turn applies a tension to tether 92512. The tension of tether 92512 imparts a torque on winding drum 92520 which is transmitted through gear train 92510 to escape wheel 92562. Optionally, a power spring may additionally be used to impart torque to gear train 92510. In the locking action, one of two lever pins 92564A,B blocks escape wheel 92562 rotation on the radial face of a tooth on the escape gear 92562A. This locks the gear train 92510 between impulse actions. In the impulse action, a lever pin 92564A,B slides up to this tooth face due to action of the balance wheel 92566 on the lever 92564. The escape wheel becomes unlocked and does mechanical work on the lever pin 92564A, B via a sliding action, which in turn imparts kinetic energy to the balance wheel 92566. The lever 92564 pivots upon a pivot point 92564D until the opposite pin 92564A,B engages with an escape wheel tooth on the escape gear 92562A, and the locked state is re-entered after a half tooth advance of the escape wheel 92562. The transition from locking action to impulse action is triggered by the balance wheel 92566, which functions as an oscillator in combination with the hair spring 92568 and/or electromechanical actuator 92570. It cycles at a natural frequency that serves as the rate control. Alternatively, the rate can be controlled and/or varied by the electromechanical actuator 92570. The balance wheel 92566 contains an impulse pin 92566B which interacts with the lever 92564 at prong 92564C. For the impulse phase depicted in FIG. 83C, a clockwise moment on the lever 92564 exerts a counterclockwise moment on the balance wheel 92566, adding to its kinetic energy. The balance wheel 92566 rotates until its kinetic energy is absorbed by the hair spring 92568 or until it is caused to stop by electromechanical actuator 92570. It stops, reverses, and reengages the impulse pin 92566B with the lever 92564. A complete cycle is shown in the transition between FIGS. 83D-83H. For example, a motor (e.g., a DC motor, AC motor, or stepper motor) or a solenoid (e.g., linear solenoid, rotary solenoid) may be used to rotate the balance wheel. This electromechanical actuator may be used in addition to the hair spring or in place of the hair spring. The electromechanical actuator may be controlled by the power and control system. By providing an electromechanical actuator the rate of drug delivery may be adjusted and/or controlled. In one embodiment, electromechanical actuator 92570 is a rotary solenoid. Upon receipt of an input signal from the power and control system the core of the rotary solenoid may rotate. This rotation may be imparted to balancing wheel 92566 by, for example, a keyed shaft. The rotary solenoid may later, upon either removal of the input signal or the receipt of a second input signal, rotate the balancing wheel back in the opposite direction or, alternatively, a hair spring may be used to return the balancing wheel in the opposite direction. This action could similarly be performed by a linear solenoid using an appropriate linkage to convert the linear motion of the solenoid core to rotational motion of the balancing wheel. A motor may also be configured to perform similarly.

To unlock the escapement regulating mechanism 92500, the balance wheel 92566 must have enough kinetic energy to drag the lever pin 92564A,B up the face of the tooth of the escape gear 92562A of the escape wheel 92562. If the impulse action adds less energy than is lost to friction, the balance wheel 92566 will rotate less and less and finally stall, locking the escapement regulating mechanism 92500. If the escapement stops in this way under load, it will not restart easily. To be self-starting, the hair spring 92568 must align the lever 92564 along the axis connecting the pivot of the escape wheel 92562 and the pivot of the balance wheel 92566, as shown in FIG. 83A. The lever pins 92564A,B will be positioned so that a bevel tooth face can immediately start an impulse action upon application of a drive torque. This alignment can occur only with the escapement regulating mechanism 92500 in an unloaded state. The tension on the tether provided by the force of the biasing member 92122 on the piston 92110 must be isolated from the escapement regulating mechanism 500 until the start of delivery. This may be done by, for example, providing a lock-out feature which, in a first configuration, prevents motion of piston 92110. After transformation to a second configuration, the lock-out feature does not prevent motion of piston 92110 and thereafter the tension on tether 92512 acts to create a torque on winding drum 92520. Alternatively, escapement regulating mechanism 92500 may be initiated by a user imparting a force on an activation mechanism and, directly or indirectly through a power and control system, applying a drive torque to start the initial impulse action. Once the escapement regulating mechanism 92500 is initiated, it can be effectively utilized to meter, restrain, or otherwise prevent free rotational movement of the gear train 92510, winding drum 92520 and piston 92110, and, thus, plunger seal 9260. In a particular embodiment, the escape wheel 92562 is a compound gear having escape teeth around the circumference of a large diameter escape gear 92562A and a small diameter gear 92562B (not visible). The small diameter gear 92562B of the escape wheel 92562 engages the drive train 92510, which engages with winding drum 92520 through rotation shaft 92518. This novel configuration directly permits the escape wheel 92562 to regulate the rotation of the drive train 92510 and winding drum 92520, which then efficiently regulates the tether 92512 and the piston 92110.

Notably, the regulating mechanisms 92500 of the present disclosure do not drive the delivery of fluid substances from the drug chamber 9221. The delivery of fluid substances from the drug chamber 9221 is caused by the expansion of the biasing member 92122 from its initial energized state acting upon the piston 92110A, 92110B and plunger seal 9260. The regulating mechanisms 92500 instead function to provide resistance to the free motion of the piston 92110A, 92 110B and plunger seal 9260 as they are pushed by the expansion of the biasing member 92122 from its initial energized state. The regulating mechanism 92500 does not drive the delivery but only controls the delivery motion. The tether limits or otherwise restrains the motion of the piston 92110 and plunger seal 9260, but does not apply the force for the delivery. According to a preferred embodiment, the controlled delivery drive mechanisms and drug delivery devices of the present disclosure include an escapement regulating mechanism indirectly or directly connected to a tether metering the axial translation of the piston 92110A, 92110B and plunger seal 9260, which are being driven to axially translate by the biasing member 92122. The rate of drug delivery as controlled by the regulating mechanism may be determined by: selection of the gear ratio of gear train 92510; selection of the spring rate of hair spring 92568; selection of the diameter of winding drum 92520; using electromechanical actuator 92570 to control the rate of oscillation and/or rotation of balance wheel 92566; or any other method known to one skilled in the art. By using electromechanical actuator 92570 to control the oscillation and/or rotation of balance wheel 92566 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 92512 by the winch drum 92520 and thereby permit axial translation of the piston 92110 by the biasing member 92122 to translate a plunger seal 9260 within a barrel 9258. The one or more inputs may be provided by the actuation of the activation mechanism 9214, a control interface, and/or a remote control mechanism. The power and control system may be configured to receive one or more inputs to adjust the restraint provided by the tether 59212 and winch drum 92520 on the free axial translation of the piston 92110 upon which the biasing member 92122 bears upon to meet a desired drug delivery rate or profile, to change the dose volume for delivery to the user, and/or to otherwise start, stop, or pause operation of the drive mechanism.

The components of the drive mechanism 92100, upon activation, may be used to drive axial translation in the distal direction of the plunger seal 9260 of the drug container 9250. Optionally, the drive mechanism 92100 may include one or more compliance features which enable additional axial translation of the plunger seal 9260 to, for example, ensure that substantially the entire drug dose has been delivered to the user. For example, the plunger seal 9260, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

The tether 92512 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 92512 that would contact the status reader at the end of axial travel of the piston 92110A, 92110B and plunger 60 within the barrel 9258 of the drug container 9250. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 92512 to be read or recognized at positions which correspond with the beginning and end of drug delivery, as well as at desired increments during drug delivery. As the drug delivery device is activated and drug delivery is begun by release of the biasing member 92122 and the resulting force applied to the piston 92110A, 92110B and plunger seal 9260, the rate or profile of drug delivery to the user is controlled by the escapement regulating mechanism, gear assembly, and winch drum 92520 releasing the tether 92512 and permitting expansion of the biasing member 92122 and axial translation of the piston 92110A, 92110B and plunger seal 9260. As this occurs, the status triggers of the tether 92512 are contacted or recognized by the status reader and the status of the drive mechanism before, during, and after operation can be relayed to the power and control system to provide feedback to the user. Depending on the number of status triggers located on the tether 92512, the frequency of the incremental status indication may be varied as desired. As described above, a range of status readers may be utilized depending on the status triggers utilized by the system.

In a preferred embodiment, the status reader may apply a tensioning force to the tether 92512. When the system reaches end-of-dose, the tether 92512 goes slack and the status reader 92544 is permitted to rotate about a fulcrum. This rotation may operate an electrical or electromechanical switch, for example a switch, signaling slack in the tether 92512 to the power and control system. Additionally, a gear of gear train 92510 may act as an encoder along with a sensor. The sensor/encoder combination is used to provide feedback of gear train rotation, which in turn can be calibrated to the position of piston 92110 when there is no slack in the tether 92512. Together, the status reader and sensor/encoder may provide positional feedback, end-of-dose signal, and error indication, such as an occlusion, by observing slack in the tether 92512 prior to reaching the expected number of motor rotations as counted by the sensor/encoder.

Further aspects of the novel drive mechanism will be described with reference to FIGS. 84A-84B and 85A-85C.

FIG. 84A shows an isometric view of the drive mechanism, according to at least a first embodiment, during its initial locked stage. A fluid, such as a drug fluid, may be contained within barrel 9258, in a drug chamber 9221 between plunger seal 9260 and a pierceable seal (not visible), for delivery to a user. The pierceable seal is adjacent or retained at least partially within cap 9252. Upon activation by the user, a fluid pathway connector may be connected to the drug container through the pierceable seal 9256. As described above, this fluid connection may be facilitated by a piercing member of the fluid pathway connector which pierces the pierceable seal and completes the fluid pathway from the drug container, through the fluid pathway connector, the fluid conduit, the insertion mechanism, and the cannula for delivery of the drug fluid to the body of the user. Initially, one or more locking mechanisms (not shown) may retain the biasing member 92122 in an initial energized position within piston 92110A, 92110B. Directly or indirectly upon activation of the device by the user, the locking mechanism may be removed to permit operation of the drive mechanism. Removal of the locking mechanism may permit the biasing member to impart a force to piston 92110 and therefore to tether 92512. This force on tether 92512 imparts a torque on winding drum 92520 which causes the gear train and escapement regulating mechanism to begin motion. As shown in FIG. 85A, the piston 92110 and biasing member 92122 are both initially in a compressed, energized state behind the plunger seal 9260. The biasing member 92122 may be maintained in this state until activation of the device between internal features of drive housing 92130 and interface surface 92110C of piston 92110A, 92110B. As the locking mechanism is removed or displaced, biasing member 92122 is permitted to expand (i.e., decompress) axially in the distal direction (i.e., in the direction of the hatched arrow). Such expansion causes the biasing member 92122 to act upon and distally translate interface surface 92110C and piston 92110, thereby distally translating plunger seal 9260 to push drug fluid out of the drug chamber 9221 of barrel 9258.

As shown in FIG. 85B, such distal translation of the piston 92110A, 92110B and plunger seal 9260 continues to force fluid flow out from barrel 9258 through the pierceable seal 9256. In at least one embodiment, an end-of-dose status indication may be provided to the user once the status reader contacts or recognizes a status trigger positioned on the tether 92512 to substantially correspond with the end of axial travel of the piston 92110A, 92110B and plunger seal 9260 within the barrel 9258 of the drug container 9250. The status triggers are positioned along the tether 92512 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 92512 to be read or recognized at positions which correspond with the beginning and end of drug delivery, as well as at desired increments during drug delivery. As shown, tether 92512 passes substantially axially through the drive mechanism housing 130, the biasing member 92122, and connects to the piston 92110 A, 92110B to restrict the axial translation of the piston 92110A, 92110B and the plunger seal 9260 that resides adjacent thereto.

The novel embodiments of the present disclosure may be utilized to meter, restrain, or otherwise prevent free rotational movement of winding drum 92520 and, thus, axial translation of the components of the controlled delivery drive mechanism 92100. Accordingly, the escapement regulating mechanism 92500 only controls the motion of the drive mechanism, but does not apply the force for the drug delivery. One or more additional biasing members 92122, such as compression springs, may be utilized to drive or assist the driving of the piston 92110. For example, a compression spring may be utilized within the drive housing 92130 for this purpose. The escapement regulating mechanism 92500 only controls, meters, or regulates such action. A mechanical timing system, such as the escapement regulating mechanism described herein, may be utilized to allow the piston 92110 and plunger seal 9260 to translate axially a controlled distance, or a controlled volume, and may be utilized to meet a desired delivery rate or profile. The timing system can be controlled by quartz timing instead of mechanical timing, as would be appreciated by one having ordinary skill in the art. For quartz timing, a battery provides power to a microchip and circuit. The quartz crystal oscillates at a precise frequency. Alternate electrical timing mechanisms such as, for example, RC timing mechanisms, may also be used, including clock functions commonly found in microprocessors. Depending on the period that the delivery is planned to occur over, the microchip drives a motor based on a number of quartz crystal oscillations or other timing signals. The motor releases motion of a drive train to control the axial translation of a plunger in a similar manner as described herein for the mechanical timing system.

The delivery control mechanisms 92500 of the present disclosure do not drive the delivery of fluid substances from the drug chamber 9221. The delivery of fluid substances from the drug chamber 9221 is caused by the expansion of the biasing member 92122 from its initial energized state acting upon the piston 92110A, 92110B and plunger seal 9260. The delivery control mechanisms 92500 instead function to provide resistance to the free motion of the piston 92110A, 92110B and plunger seal 9260 as they are pushed by the expansion of the biasing member 92122 from its initial energized state. As the delivery control mechanisms 92500 release the tether 92512, the biasing member 92122 is permitted to continue its expansion from its energized state and drive the piston 92110A, 92110B and plunger seal 9260 until the plunger seal 9260 has substantially contacted the pierceable seal 9256. This is visible in the cross-sectional view provided in FIG. 85C. At this point, substantially all of the drug substance has been pushed out of the drug chamber 9221 through the fluid pathway connector 92300 for drug delivery to the user. A status trigger may be configured along the tether 92512 to correspond with this position of the piston 92110A, 92110B, such that, as the piston 92110A, 92110B reaches its end of axial travel, a status trigger is read or recognized by the status reader to provide true end-of-dose indication to the user. As stated above, the status triggers may be positioned along the tether 92512 to be read or recognized at positions which correspond with the beginning and end of drug delivery, as well as at desired increments during drug delivery. The controlled delivery drive mechanisms and/or drug delivery devices of the present disclosure may additionally enable a compliance push to ensure that substantially all of the drug substance has been pushed out of the drug chamber 9221. The plunger seal 9260, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container, as shown in FIG. 85C. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 9256 and the interconnect located proximal to the plunger seal 9260 such that, upon substantially complete axial translation (and optional compliance push) of the plunger seal 9260 within the barrel 9258, the status switch and interconnect coordinate to enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear train 92510. As the gear train 92510 rotates, a status reader may read or recognize one or more corresponding status triggers on one of the gears in the gear train to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear train. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear train (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear train and escapement regulating mechanism shown in the figures, a range of configurations may be acceptable and capable of being employed within the embodiments of the present disclosure, as would readily be appreciated by an ordinarily skilled artisan. Accordingly, the embodiments of the present disclosure are not limited to the specific gear train and escapement regulating mechanism described herein, which is provided as an exemplary embodiment of such mechanisms for employment within the controlled delivery drive mechanisms and drug delivery pumps.

Assembly and/or manufacturing of controlled delivery drive mechanism 100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9250 may first be assembled and filled with a fluid for delivery to the user. The drug container 9250 includes a cap 9252, a pierceable seal 9256, a barrel 9258, and a plunger seal 9260. The pierceable seal 9256 may be fixedly engaged between the cap 9252 and the barrel 9258, at a distal end of the barrel 9258. The barrel 9258 may be filled with a drug fluid through the open proximal end prior to insertion of the plunger seal 9260 from the proximal end of the barrel 9258. An optional connection mount 9254 may be mounted to a distal end of the pierceable seal 9256. The connection mount 9254 may guide the insertion of the piercing member of the fluid pathway connector into the barrel 9258 of the drug container 9250. The drug container 9250 may then be mounted to a distal end of drive housing 92130.

One or more drive biasing members 92122 may be inserted into a distal end of the drive housing 92130. Optionally, a cover sleeve 92140 may be inserted into a distal end of the drive housing 92130 to substantially cover biasing member 92122. A piston may be inserted into the distal end of the drive housing 92130 such that it resides at least partially within an axial pass-through of the biasing member 92122 and the biasing member 92122 is permitted to contact a piston interface surface 92110C of piston 92110A, 92110B at the distal end of the biasing member 92122. An optional cover sleeve 92140 may be utilized to enclose the biasing member 92122 and contact the piston interface surface 92110C of piston 92110A, 92110B. The piston 92110A, 92110B and drive biasing member 92122, and optional cover sleeve 92140, may be compressed into drive housing 92130. Such assembly positions the drive biasing member 92122 in an initial compressed, energized state and preferably places a piston interface surface 110C in contact with the proximal surface of the plunger seal 9260 within the proximal end of barrel 58. The piston, piston biasing member, contact sleeve, and optional components, may be compressed and locked into the ready-to-actuate state within the drive housing 92130 prior to attachment or mounting of the drug container 9250. The tether 92512 is pre-connected to the proximal end of the piston 92110A, 92110B and passed through the axial aperture of the biasing member 92122 and drive mechanism 92130, and then wound through the interior of the drug delivery device with the other end of the tether 92512 wrapped around the winch drum 92520 of the regulating mechanism 92500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 80B.

Certain optional standard components or variations of drive mechanism 92100 or drug delivery device 9210 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9218, as shown in FIG. 80A, to enable the user to view the operation of the drug delivery device 9210 or verify that drug dose has completed. Similarly, the drug delivery device 9210 may contain an adhesive patch 9226 and a patch liner 9228 on the bottom surface of the housing 9212. The adhesive patch 9226 may be utilized to adhere the drug delivery device 9210 to the body of the user for delivery of the drug dose. As would be readily understood by one having ordinary skill in the art, the adhesive patch 9226 may have an adhesive surface for adhesion of the drug delivery device to the body of the user. The adhesive surface of the adhesive patch 9226 may initially be covered by a non-adhesive patch liner 9228, which is removed from the adhesive patch 9226 prior to placement of the drug delivery device 9210 in contact with the body of the user. Removal of the patch liner 9228 may further remove the sealing membrane 92254 of the insertion mechanism 92200, opening the insertion mechanism to the body of the user for drug delivery (as shown in FIG. 80C).

Similarly, one or more of the components of controlled delivery drive mechanism 92100 and drug delivery device 9210 may be modified while remaining functionally within the breadth and scope of the present disclosure. For example, as described above, while the housing of drug delivery device 9210 is shown as two separate components upper housing 9212A and lower housing 9212B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a user, wherein a regulating mechanism acting to restrain the distribution of a tether is utilized to meter the free axial translation of the piston. The method of operation of the insertion mechanism and the drug delivery device may be better appreciated with reference to FIGS. 84A-84B and FIGS. 85A-85C, as described above.

XII. Additional Embodiments of Multi-Function Drive Mechanism

At least some of the drug delivery devices described in this application, including at least those described in connection with FIGS. 1A-2B, 33A-33C, 69A-73D, and 80A-85C may be configured to incorporate the embodiments of the drive mechanism described below in connection with FIGS. 86A-91. The embodiments of the drive mechanism described below in connection with FIGS. 86A-91 may be used to replace, in its entirety or partially, the above-described drive mechanism 100, 6100, 8100, 9010, or 9210, or any other drive mechanism described herein, where appropriate.

The present disclosure provides drive mechanisms for the controlled delivery of drug substances, drug delivery pumps with controlled delivery drive mechanisms, the methods of operating such devices, and the methods of assembling such devices. Notably, the drive mechanisms of the present disclosure control the rate of drug delivery by metering, providing resistance, or otherwise preventing free axial translation of the plunger seal utilized to force a drug substance out of a drug container. The novel embodiments of the present disclosure thus are capable of delivering drug substances at variable rates. The controlled delivery drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a controlled delivery drive mechanism which includes a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum of a delivery control mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum of the delivery control mechanism to meter the free expansion of the biasing member from its initial energized state and the free axial translation of the piston upon which the biasing member bears upon.

In another embodiment, the drive mechanism further includes a gear assembly. The gear assembly may include a winch gear connected to a winch drum upon which the tether may be releasably wound, a worm gear engageably connected to the winch gear, a compound gear engageably connected to the worm gear, and a motor having a pinion engageably connected to the compound gear, wherein the motor is configured to drive the gear assembly to release the tether from the winch drum to meter the free expansion of the biasing member from its initial energized state and the free axial translation of the piston upon which the biasing member bears upon. The metering of the tether by the motor controls the rate or profile of drug delivery to a user. The piston may be one or more parts and connects to a distal end of the tether.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum of a delivery control mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum of the delivery control mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum upon which the tether may be releasably wound, a worm gear engageably connected to the winch gear, a compound gear engageably connected to the worm gear, and a motor having a pinion engageably connected to the compound gear, wherein the motor is configured to drive the gear assembly to release the tether from the winch drum to meter the free expansion of the biasing member from its initial energized state and the free axial translation of the piston upon which the biasing member bears upon. The metering of the tether by the motor controls the rate or profile of drug delivery to a user. The piston may be one or more parts and connects to a distal end of the tether.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restrain provided by the tether and winch drum on the free axial translation of the piston upon which the biasing member bears upon to meet a desired drug delivery rate or profile, to change the dose volume for delivery to the user, and/or to otherwise start, stop, or pause operation of the drive mechanism.

The novel embodiments of the present disclosure provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present disclosure may include one or more additional components which may be considered standard components in the industry of medical devices. For example, the embodiments may include one or more batteries utilized to power the motor, drive mechanisms, and drug delivery devices of the present disclosure. The components, and the embodiments containing such components, are within the contemplation of the present disclosure and are to be understood as falling within the breadth and scope of the present disclosure.

The present disclosure provides drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 86A-86C show an exemplary drug delivery device according to at least one embodiment of the present disclosure. The drug delivery device may be utilized to administer delivery of a drug treatment into a body of a user. As shown in FIGS. 86A-86C, the drug delivery device 9310 includes a pump housing 9312. Pump housing 9312 may include one or more housing subcomponents which are fixedly engageable to facilitate easier manufacturing, assembly, and operation of the drug delivery device. For example, drug delivery device 9310 includes a pump housing 9312 which includes an upper housing 9312A and a lower housing 9312B. The drug delivery device may further include an activation mechanism 9314, a status indicator 9316, and a window 9318. Window 9318 may be any translucent or transmissive surface through which the operation of the drug delivery device may be viewed. As shown in FIG. 86B, drug delivery device further includes assembly platform 9320, sterile fluid conduit 9330, drive mechanism 93100 having drug container 9350, insertion mechanism 93200, fluid pathway connector 93300, and power and control system 93400. One or more of the components of such drug delivery devices may be modular in that they may be, for example, pre-assembled as separate components and configured into position onto the assembly platform 9320 of the drug delivery device 9310 during manufacturing.

The pump housing 9312 contains all of the device components and provides a means of removably attaching the device 9310 to the skin of the user. The pump housing 9312 also provides protection to the interior components of the device 9310 against environmental influences. The pump housing 9312 is ergonomically and aesthetically designed in size, shape, and related features to facilitate easy packaging, storage, handling, and use by users who may be untrained and/or physically impaired. Furthermore, the external surface of the pump housing 9312 may be utilized to provide product labeling, safety instructions, and the like. Additionally, as described above, housing 9312 may include certain components, such as status indicator 9316 and window 9318, which may provide operation feedback to the user.

In at least one embodiment, the drug delivery device 9310 provides an activation mechanism 9314 that is displaced by the user to trigger the start command to the power and control system 93400. In a preferred embodiment, the activation mechanism is a start button 9314 that is located through the pump housing 9312, such as through an aperture between upper housing 9312A and lower housing 9312B, and which contacts a control arm 9340 of the power and control system 93400. In at least one embodiment, the start button 9314 may be a push button, and in other embodiments, may be an on/off switch, a toggle, or any similar activation feature known in the art. The pump housing 9312 also provides a status indicator 9316 and a window 9318. In other embodiments, one or more of the activation mechanism 9314, the status indicator 9316, the window 9318, and combinations thereof may be provided on the upper housing 9312A or the lower housing 9312B such as, for example, on a side visible to the user when the drug delivery device 9310 is placed on the body of the user. Housing 9312 is described in further detail hereinafter with reference to other components and embodiments of the present disclosure.

Drug delivery device is configured such that, upon activation by a user by depression of the activation mechanism, the drug delivery device is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug delivery device. For example, an optional on-body sensor 9324 (shown in FIG. 86C) may be provided in one embodiment as a safety feature to ensure that the power and control system 93400, or the activation mechanism, cannot be engaged unless the drug delivery device 9310 is in contact with the body of the user. In one such embodiment, the on-body sensor 9324 is located on the bottom of lower housing 9312B where it may come in contact with the user's body. Upon displacement of the on-body sensor 9324, depression of the activation mechanism is permitted. Accordingly, in at least one embodiment the on-body sensor 9324 is a mechanical safety mechanism, such as for example a mechanical lock out, that prevents triggering of the drug delivery device 9310 by the activation mechanism 9314. In another embodiment, the on-body sensor may be an electromechanical sensor such as a mechanical lock out that sends a signal to the power and control system 93400 to permit activation. In still other embodiments, the on-body sensor can be electrically based such as, for example, a capacitive- or impedance-based sensor which must detect tissue before permitting activation of the power and control system 93400. These concepts are not mutually exclusive and one or more combinations may be utilized within the breadth of the present disclosure to prevent, for example, premature activation of the drug delivery device. In a preferred embodiment, the drug delivery device 9310 utilizes one or more mechanical on-body sensors. Additional integrated safety mechanisms are described herein with reference to other components of the novel drug delivery devices.

XII.A. Power and Control System

The power and control system 93400 includes a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 93400 controls several device interactions with the user and interfaces with the drive mechanism 93100. In one embodiment, the power and control system 93400 interfaces with the control arm 9340 to identify when the on-body sensor 9324 and/or the activation mechanism 9314 have been activated. The power and control system 93400 may also interface with the status indicator 9316 of the pump housing 9312, which may be a transmissive or translucent material which permits light transfer, to provide visual feedback to the user. The power and control system 93400 interfaces with the drive mechanism 93100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system 93400 may be configured to provide a number of different status indicators to the user. For example, the power and control system 93400 may be configured such that after the on-body sensor and/or trigger mechanism have been pressed, the power and control system 93400 provides a ready-to-start status signal via the status indicator 9316 if device start-up checks provide no errors. After providing the ready-to-start status signal and, in an embodiment with the optional on-body sensor, if the on-body sensor remains in contact with the body of the user, the power and control system 93400 will power the drive mechanism 93100 to begin delivery of the drug treatment through the fluid pathway connector 93300 and sterile fluid conduit 9330. In a preferred embodiment of the present disclosure, the insertion mechanism 93200 and the fluid pathway connector 93300 may be caused to activate directly by user operation of the activation mechanism 9314. During the drug delivery process, the power and control system 93400 is configured to provide a dispensing status signal via the status indicator 9316. After the drug has been administered into the body of the user and after the end of any additional dwell time, to ensure that substantially the entire dose has been delivered to the user, the power and control system 93400 may provide an okay-to-remove status signal via the status indicator 9316. This may be independently verified by the user by viewing the drive mechanism and drug dose delivery through the window 9318 of the pump housing 9312. Additionally, the power and control system 93400 may be configured to provide one or more alert signals via the status indicator 9316, such as for example alerts indicative of fault or operation failure situations.

The power and control system 93400 may additionally be configured to accept various inputs from the user to dynamically control the drive mechanisms 93100 to meet a desired drug delivery rate or profile. For example, the power and control system 93400 may receive inputs, such as from partial or full activation, depression, and/or release of the activation mechanism 9314, to set, initiate, stop, or otherwise adjust the control of the drive mechanism 93100 via the power and control system 93400 to meet the desired drug delivery rate or profile. Similarly, the power and control system 93400 may be configured to receive such inputs to adjust the drug dose volume; to prime the drive mechanism, fluid pathway connector, and fluid conduit; and/or to start, stop, or pause operation of the drive mechanism 93100. Such inputs may be received by the user directly acting on the drug delivery device 9310, such as by use of the activation mechanism 9314 or a different control interface, or the system 93400 may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 9314 of the drug delivery device 9310 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XII.B. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9310, the fluid pathway connector 93300 is enabled to connect the sterile fluid conduit 9330 to the drug container of the drive mechanism 93100. Such connection may be facilitated by a piercing member, such as a needle, penetrating a pierceable seal of the drug container of the drive mechanism 93100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present disclosure, the piercing member of the fluid pathway connector is caused to penetrate the pierceable seal of the drug container of the drive mechanism by direct action of the user, such as by depression of the activation mechanism by the user. For example, the activation mechanism itself may bear on the fluid pathway connector such that displacement of the activation mechanism from its original position also causes displacement of the fluid pathway connector. In one such embodiment, the fluid pathway connector may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/ hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 93300 and the sterile fluid conduit 9330 are provided hereinafter in later sections in reference to other embodiments.

XII.C. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure.

In at least one embodiment, the insertion mechanism 93200 includes an insertion mechanism housing having one or more lockout windows, and a base for connection to the assembly platform and/or pump housing (as shown in FIG. 86B and FIG. 86C). The connection of the base to the assembly platform 9320 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9310. The insertion mechanism may further include one or more insertion biasing members, a needle, a retraction biasing member, a cannula, and a manifold. The manifold may connect to sterile fluid conduit 9330 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9327 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 93254 (shown in FIG. 86C).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 86B, the lockout pin(s) 93208 may be directly displaced by user depression of the activation mechanism 9314. As the user disengages any safety mechanisms, such as an optional on-body sensor 9324 (shown in FIG. 86C), the activation mechanism 9314 may be depressed to initiate the drug delivery device. Depression of the activation mechanism 9314 may directly cause translation or displacement of control arm 9340 and directly or indirectly cause displacement of lockout pin(s) 93208 from their initial position within locking windows 93202A of insertion mechanism housing 93202. Displacement of the lockout pin(s) 93208 permits insertion biasing member to decompress from its initial compressed, energized state. This decompression of the insertion biasing member drives the needle and the cannula into the body of the user. At the end of the insertion stage, the refraction biasing member is permitted to expand in the proximal direction from its initial energized state. This axial expansion in the proximal direction of the refraction biasing member refracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

XII.D. Drive Mechanism

With reference to the embodiments shown in FIGS. 87 and 88, drive mechanism 93100 includes a drive housing 93130, and a drug container 9350 having a cap 9352, a pierceable seal (not visible), a barrel 9358, and a plunger seal 9360. A drug chamber 9321, located within the barrel 9358 between the pierceable seal and the plunger seal 9360, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism may further include a connection mount 9354 to guide the insertion of the piercing member of the fluid pathway connector into the barrel 9358 of the drug container 9350. The drive mechanism 93100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 93100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 87 and FIG. 88, the drive mechanism 93100 includes a drug container 9350 having a cap 9352, a pierceable seal (not visible), a barrel 9358, and a plunger seal 9360, and optionally a connection mount 9354. The drug container 9350 is mounted to a distal end of a drive housing 93130. Compressed within the drive housing 93130, between the drug container 9350 and the proximal end of the housing 93130, are a drive biasing member 93122 and a piston 93110, wherein the drive biasing member 93122 is configured to bear upon an interface surface 93110C of the piston 93110, as described further herein. Optionally, a cover sleeve 93140 may be utilized between the drive biasing member 93122 and the interface surface 93110C of the piston 93110 to, for example, promote more even distribution of force from the drive biasing member 93122 to the piston 93110, prevent buckling of the drive biasing member 93122, and/or hide biasing member from user view. Interface surface 93110C of piston 93110 is caused to rest substantially adjacent to, or in contact with, a proximal end of seal 9360.

As shown in FIG. 88, the piston 93110A, 93110B may be comprised of two components and have an interface surface 93110C to contact the plunger seal. A tether, ribbon, string, or other retention strap (referred to herein as the "tether" 93512) may be connected at one end to the piston 93110A, 93110B. For example, the tether 93512 may be connected to the piston 93110A, 93110B by retention between the two components of the piston 93110A, 93110B when assembled. The tether 93512 is connected at another end to a winch drum 93520 of a delivery control mechanism 93500. Through the use of a motor 93530, a gear assembly, and the winch drum 93520 connected to one end of the tether 93512, and the tether 93512 connected at another end to the piston 93110A, 93110B, the delivery control mechanism 93500 functions to control, meter, provide resistance, or otherwise prevent free axial translation of the piston 93110A, 93110B and plunger seal 9360 utilized to force a drug substance out of a drug container 9350. Accordingly, the delivery control mechanism 93500 and the drive mechanism 93100 (collectively referred to herein as the "controlled delivery drive mechanism") together function to control the rate or profile of drug delivery to the user.

Notably, the delivery control mechanisms 93500 of the present disclosure do not drive the delivery of fluid substances from the drug chamber 9321. The delivery of fluid substances from the drug chamber 9321 is caused by the expansion of the biasing member 93122 from its initial energized state acting upon the piston 93110A, 93110B and plunger seal 9360. The delivery control mechanisms 93500 instead function to provide resistance to the free motion of the piston 93110A, 93110B and plunger seal 9360 as they are pushed by the expansion of the biasing member 93122 from its initial energized state. Because the motor 93530 is utilized only to control, meter, provide resistance, or otherwise prevent free axial translation of the plunger seal, instead of driving the translation of the plunger seal, a smaller and/or more energy efficient motor may be utilized by the novel embodiments of the present disclosure. The delivery control mechanism 93500, and specifically the motor 93530, does not drive the delivery but only controls the delivery motion. The tether limits or otherwise restrains the motion of the piston 93110, 93110B and plunger seal 9360, but does not apply the force for the delivery. According to a preferred embodiment, the controlled delivery drive mechanisms and drug delivery devices of the present disclosure include a motor 93530 indirectly or directly connected to a tether metering the axial translation of the piston 93110A, 93110B and plunger seal 9360, which are being driven to axially translate by the biasing member 93122. The motor 93530 may, accordingly, be selected from a variety of electromechanical sources capable of incremental motion, such as brushed DC motors, EC motors, stepper motors, solenoids, or other technologies that can produce controlled motion. In at least one embodiment, the motor is most preferably a stepper motor.

The components of the drive mechanism 93100, upon activation, may be used to drive axial translation in the distal direction of the plunger seal 9360 of the drug container 9350. Optionally, the drive mechanism 93100 may include one or more compliance features which enable additional axial translation of the plunger seal 9360 to, for example, ensure that substantially the entire drug dose has been delivered to the user. For example, the plunger seal 9360, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

In at least one embodiment, as shown in FIG. 87 and FIG. 88, an end-of-dose status indication may be provided to the user once the status reader 93544 contacts or recognizes the final status trigger 93512A positioned on the tether 93512 that would contact the status reader 93544 at the end of axial travel of the piston 93110A, 93110B and plunger 9360 within the barrel 9358 of the drug container 9350. For clarity, the tether 93512 may have one or more status triggers 93512A, such as electrical contacts, optical markings, or electromechanical pins or recesses, which are capable of contacting or being recognized by a status reader 93544. The status reader 93544 may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers 93512A may be positioned along the tether 93512 to be read or recognized at positions which correspond with the beginning and end of drug delivery, as well as at desired increments during drug delivery. As the drug delivery device is activated and drug delivery is begun by release of the biasing member 93122 and the resulting force applied to the piston 93110A, 93110B and plunger seal 9360, the rate or profile of drug delivery to the user is controlled by the motor 93530, gear assembly, and winch drum 93520 releasing the tether 93512 and permitting expansion of the biasing member 93122 and axial translation of the piston 93110A, 93110B and plunger seal 9360. As this occurs, the status triggers 93512A of the tether 93512 are contacted or recognized by the status reader 93544 and the status of the drive mechanism before, during, and after operation can be relayed to the power and control system to provide feedback to the user. Depending on the number of status triggers 93512A located on the tether 93512, the frequency of the incremental status indication may be varied as desired. As described above, a range of status readers 93544 may be utilized depending on the status triggers 93512A utilized by the system.

In a preferred embodiment, as described herein with reference to FIG. 91, the status reader 93544 may apply a tensioning force to the tether 93512. When the system reaches end-of-dose, the tether 93512 goes slack and the status reader 93544 is permitted to rotate about a fulcrum (shown in FIG. 91 as a cylindrical protrusion from the side of the status reader 93544). This rotation may operate an electrical or electromechanical switch, for example a switch within sensor 93540, signaling slack in the tether 93512 to the power and control system 93400. Additionally, the status gear 93528 may act as an encoder along with sensor 93540. The sensor/encoder combination is used to provide feedback of motor rotation, which in turn can be calibrated to the position of piston 93110 when there is no slack in the tether 93512. Together, the status reader 93544 and sensor/encoder 93540 provide positional feedback, end-of-dose signal, and error indication, such as an occlusion, by observing slack in the tether 93512 prior to reaching the expected number of motor rotations as counted by the sensor/encoder 93540.

Returning now to the embodiment shown in FIG. 87 and FIG. 88, further aspects of the novel drive mechanism will be described with reference to FIGS. 89A-89C and 90A-90C. FIG. 89A shows an isometric view of the drive mechanism, according to at least a first embodiment, during its initial locked stage. A fluid, such as a drug fluid, may be contained within barrel 9358, in a drug chamber 9321 between plunger seal 9360 and pierceable seal (not visible), for delivery to a user. The pierceable seal is adjacent or retained at least partially within cap 9352. Upon activation by the user, a fluid pathway connector may be connected to the drug container through the pierceable seal 9356. As described above, this fluid connection may be facilitated by a piercing member of the fluid pathway connector which pierces the pierceable seal and completes the fluid pathway from the drug container, through the fluid pathway connector, the fluid conduit, the insertion mechanism, and the cannula for delivery of the drug fluid to the body of the user. Initially, one or more locking mechanisms (not shown) may retain the biasing member 93122 in an initial energized position within piston 93110A, 93110B. Directly or indirectly upon activation of the device by the user, the locking mechanism may be removed to permit operation of the drive mechanism. As shown in FIG. 90A, the piston 9310 and biasing member 93122 are both initially in a compressed, energized state behind the plunger seal 9360. The biasing member 93122 may be maintained in this state until activation of the device between internal features of drive housing 130 and interface surface 93110C of piston 93110A, 93110B. As the locking mechanism is removed or displaced, biasing member 93122 is permitted to expand (i.e., decompress) axially in the distal direction (i.e., in the direction of the hatched arrow). Such expansion causes the biasing member 93122 to act upon and distally translate interface surface 93110C and piston 93110, thereby distally translating plunger seal 9360 to push drug fluid out of the drug chamber 9321 of barrel 9358.

As shown in FIG. 89B, such distal translation of the piston 93110A, 93110B and plunger seal 9360 continues to force fluid flow out from barrel 9358 through the pierceable seal 9356. In at least one embodiment, an end-of-dose status indication may be provided to the user once the status reader 93544 contacts or recognizes a status trigger 93512A positioned on the tether 93512 to substantially correspond with the end of axial travel of the piston 93110A, 93110B and plunger seal 9360 within the barrel 9358 of the drug container 9350. As shown in FIG. 89B, the status triggers 93512A are positioned along the tether 93512 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers 93512A may be positioned along the tether 93512 to be read or recognized at positions which correspond with the beginning and end of drug delivery, as well as at desired increments during drug delivery. FIG. 90B shows a cross-sectional view of the view shown in FIG. 89B. As shown, tether 93512 passes substantially axially through the drive mechanism housing 93130, the biasing member 93122, and connects to the piston 93110 A, 93110B to restrict the axial translation of the piston 93110A, 93110B and the plunger seal 9360 that resides adjacent thereto.

As shown in FIG. 89C, the delivery control mechanisms 93500 of the present disclosure do not drive the delivery of fluid substances from the drug chamber 9321. The delivery of fluid substances from the drug chamber 9321 is caused by the expansion of the biasing member 93122 from its initial energized state acting upon the piston 93110A, 93110B and plunger seal 9360. The delivery control mechanisms 93500 instead function to provide resistance to the free motion of the piston 93110A, 93110B and plunger seal 9360 as they are pushed by the expansion of the biasing member 93122 from its initial energized state. As the motor 93530 and the delivery control mechanisms 93500 release the tether 93512, the biasing member 93122 is permitted to continue its expansion from its energized state and drive the piston 93110A, 93110B and plunger seal 9360 until the plunger seal 9360 has substantially contacted the pierceable seal 9356. This is visible in the cross-sectional view provided in FIG. 90C. At this point, substantially all of the drug substance has been pushed out of the drug chamber 9321 through the fluid pathway connector 93300 for drug delivery to the user. A status trigger 93512A may be configured along the tether 93512 to correspond with this position of the piston 93110A, 93110B, such that, as the piston 93110A, 93110B reaches its end of axial travel, a status trigger 93512A is read or recognized by the status reader 93544 to provide true end-of-dose indication to the user. As stated above, the status triggers 93512A may be positioned along the tether 93512 to be read or recognized at positions which correspond with the beginning and end of drug delivery, as well as at desired increments during drug delivery. The controlled delivery drive mechanisms and/or drug delivery devices of the present disclosure may additionally enable a compliance push to ensure that substantially all of the drug substance has been pushed out of the drug chamber 9321. The plunger seal 9360, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container, as shown in FIG. 90C. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 9356 and the interconnect located proximal to the plunger seal 9360 such that, upon substantially complete axial translation (and optional compliance push) of the plunger seal 9360 within the barrel 9358, the status switch and interconnect coordinate to enable a transmission to the power and control system to signal end-of-dose to the user. This configuration further enables true end-of-dose indication to the user.

FIG. 91 shows a perspective view of certain components of a controlled delivery drive mechanism, according to at least one embodiment of the present disclosure. The controlled delivery drive mechanism incorporates an incremental status indicator mechanism having a status reader and one or more corresponding status triggers. In at least one embodiment, the gear assembly of the delivery control mechanism 93500 utilizes a motor 93530 with pinion 93530A. The pinion 93530A contacts a first gear 93526A of a compound gear 93526, and the second gear 93526B of the compound gear 93526 contacts a gear aspect 93524B of a worm gear 93524. The worm aspect 93524A of the worm gear 93524 contacts a drum gear 93522 which is connected to a winch drum 93520. The tether 93512 is at least partially wrapped around the winch drum 93520. As the motor 93530 acts upon the gear assembly, the motion is conveyed by interfacing gear teeth of the pinion 93530A, compound gear 93526, worm gear 93524, and drum gear 93522 to the winch drum 93520 to unwind the tether 93512 therefrom. As detailed above, unwinding the tether 93512 reduces the resistance it provides on the piston 93110A, 93110B and permits the biasing member 93122 to expand from its energized state, thereby driving the plunger seal 9360 for drug delivery. As the tether 93512 is unwound from the winch drum 93520, a status reader 93544 may read or recognize one or more corresponding status triggers 93512A on the tether 93512 to provide incremental status indication before, during, and after operation of the controlled delivery drive mechanism. As described above, a number of status readers may be utilized within the embodiments of the present disclosure. For example, the drive mechanism shown in FIG. 91 may utilize a mechanical status reader 93544 which is physically contacted by ridges, holes, or other aspects incrementally spaced on the tether 93512 to correspond with desired status indications (e.g., volume delivered, volume remaining, changes in delivery rates or profiles, etc.). As the status reader 93544 is contacted by the status trigger(s) 93512A, the status reader 93544 causes the sensor 93540 to measure the position of the status gear 93528 and transmit a signal to the power and control system for status indication to the user. As described above, optical status readers and corresponding triggers, electromechanical status readers and corresponding triggers, and/or mechanical status readers and corresponding triggers may all be utilized by the embodiments of the present disclosure to provide incremental status indication to the user.

Assembly and/or manufacturing of controlled delivery drive mechanism 93100, drug delivery pump 9310, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9350 may first be assembled and filled with a fluid for delivery to the user. The drug container 9350 includes a cap 9352, a pierceable seal 9356, a barrel 9358, and a plunger seal 9360. The pierceable seal 9356 may be fixedly engaged between the cap 9352 and the barrel 9358, at a distal end of the barrel 9358. The barrel 9358 may be filled with a drug fluid through the open proximal end prior to insertion of the plunger seal 9360 from the proximal end of the barrel 9358. An optional connection mount 9354 may be mounted to a distal end of the pierceable seal 9356. The connection mount 9354 may guide the insertion of the piercing member of the fluid pathway connector into the barrel 9358 of the drug container 9350. The drug container 9350 may then be mounted to a distal end of drive housing 93130.

A drive biasing member 93122 may be inserted into a distal end of the drive housing 93130. Optionally, a cover sleeve 93140 may be inserted into a distal end of the drive housing 130 to substantially cover biasing member 93122. A piston may be inserted into the distal end of the drive housing 93130 such that it resides at least partially within an axial pass-through of the biasing member 93122 and the biasing member 93122 is permitted to contact a piston interface surface 93110C of piston 93110A, 93110B at the distal end of the biasing member 93122. An optional cover sleeve 93140 may be utilized to enclose the biasing member 93122 and contact the piston interface surface 93110C of piston 93110A, 93110B. The piston 93110A, 93110B and drive biasing member 93122, and optional cover sleeve 93140, may be compressed into drive housing 93130. Such assembly positions the drive biasing member 93122 in an initial compressed, energized state and preferably places a piston interface surface 93110C in contact with the proximal surface of the plunger seal 9360 within the proximal end of barrel 9358. The piston, piston biasing member, contact sleeve, and optional components, may be compressed and locked into the ready-to-actuate state within the drive housing 93130 prior to attachment or mounting of the drug container 9350. The tether 93512 is pre-connected to the proximal end of the piston 93110A, 93110B and passed through the axial aperture of the biasing member 93122 and drive mechanism 93130, and then wound through the interior of the drug delivery device with the other end of the tether 93512 wrapped around the winch drum 93520 of the delivery control mechanism 93500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 86B.

Certain optional standard components or variations of drive mechanism 93100 or drug delivery device 9310 are contemplated while remaining within the breadth and scope of the present disclosure. For example, the embodiments may include one or more batteries utilized to power the motor, drive mechanisms, and drug delivery devices of the present disclosure. A range of batteries known in the art may be utilized for this purpose. Additionally, upper or lower housings may optionally contain one or more transparent or translucent windows 9318, as shown in FIG. 86A, to enable the user to view the operation of the drug delivery device 9310 or verify that drug dose has completed. Similarly, the drug delivery device 9310 may contain an adhesive patch 9326 and a patch liner 9328 on the bottom surface of the housing 9312. The adhesive patch 9326 may be utilized to adhere the drug delivery device 9310 to the body of the user for delivery of the drug dose. As would be readily understood by one having ordinary skill in the art, the adhesive patch 9326 may have an adhesive surface for adhesion of the drug delivery device to the body of the user. The adhesive surface of the adhesive patch 9326 may initially be covered by a non-adhesive patch liner 9328, which is removed from the adhesive patch 9326 prior to placement of the drug delivery device 9310 in contact with the body of the user. Removal of the patch liner 9328 may further remove the sealing membrane 93254 of the insertion mechanism 93200, opening the insertion mechanism to the body of the user for drug delivery (as shown in FIG. 86C).

Similarly, one or more of the components of controlled delivery drive mechanism 93100 and drug delivery device 9310 may be modified while remaining functionally within the breadth and scope of the present disclosure. For example, as described above, while the housing of drug delivery device 9310 is shown as two separate components upper housing 9312A and lower housing 9312B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a user, wherein a tether is utilized to restrain the free axial translation of the piston. The method of operation of the insertion mechanism and the drug delivery device may be better appreciated with reference to FIGS. 89A-89C and FIGS. 90A-90C, as described above.

XIII. Additional Embodiments of Multi-Function Drive Mechanism

At least some of the drug delivery devices described in this application, including at least those described in connection with FIGS. 1A-2B, 33A-33C, 69A-73D, 80A-85C, and 86A-91 may be configured to incorporate the embodiments of the drive mechanism described below in connection with FIGS. 92-99. The embodiments of the drive mechanism described below in connection with FIGS. 92-99 may be used to replace, in its entirety or partially, the above-described drive mechanism 100, 6100, 8100, 9010, 9210, or 9310, or any other drive mechanism described herein, where appropriate.

The present disclosure provides drive mechanisms for the controlled delivery of drug substances, drug delivery pumps with such drive mechanisms, the methods of operating such devices, and the methods of assembling such devices. Notably, the drive mechanisms of the present disclosure control the rate of drug delivery by metering, providing resistance, or otherwise preventing free axial translation of the plunger seal utilized to force a drug substance out of a drug container. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a controlled delivery drive mechanism which includes a drug container having a barrel and a plunger seal; a drive housing within which at least initially partially resides a piston having an interface surface and a drive rack; and a power spring coupled, directly or indirectly, to a drive pinion which interfaces with drive rack of the piston to convert rotational movement of power spring and the drive pinion to axial translation of the drive rack. The piston is configured to contact and axially translate the plunger seal within barrel. This configuration converts rotational movement of the drive pinion to axial translation of the drive rack. A regulating mechanism meters the drive pinion such that the piston is axially translated at a controlled rate. The drug container may contain a drug fluid within a drug chamber for drug delivery at a controlled rate.

In another embodiment, the present disclosure provides a controlled delivery drive mechanism having a drug container having a barrel and a plunger seal; a drive housing within which at least initially partially resides a linear power spring and a piston having an interface surface and a drive rack, wherein the linear power spring is coupled, directly or indirectly, to the piston to convert axial force of the linear power spring into torsional motion of a drive pinion. The piston is configured to contact and axially translate the plunger seal within barrel. A regulating mechanism meters the drive pinion such that the piston is axially translated by the linear power spring at a controlled rate.

In at least one embodiment, the regulating mechanism is an escapement regulating mechanism coupled to, or acting with, the power spring. The escapement regulating mechanism further includes a gear train having one or more gears, a rotation shaft, and a gear transmission having one or more gears, wherein at least one gear of the gear transmission is capable of engaging the drive pinion such that rotation of the gear causes rotation of the drive pinion. In a particular embodiment, the escapement regulating element further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. The escape wheel is a compound gear having escape teeth around the circumference of a large diameter escape gear and a small diameter gear configured to engage and meter the gear train. The metering of the drive pinion and/or the gear train by an escapement regulating mechanism controls the rate or profile of drug delivery to a user.

In at least one embodiment, the drive mechanism utilizes a status reader configured to read or recognize one or more corresponding status triggers, wherein, during operation of the drive mechanism, interaction between the status reader and the status triggers transmit a signal to a power and control system to provide feedback to a user. The status reader may be an optical status reader and the corresponding status triggers are gear teeth of a drive gear, a mechanical status reader and the corresponding status triggers are gear teeth of the drive gear, a mechanical status reader and the corresponding status triggers are external features of the piston and/or drive rack, or an optical status reader and the corresponding status triggers are external features of the piston and/or drive rack.

In a further embodiment, the present disclosure provides a drug delivery pump having a controlled delivery drive mechanism. The drug delivery device includes a housing and an assembly platform, upon which an activation mechanism, an insertion mechanism, a fluid pathway connector, a power and control system, and the controlled delivery drive mechanism may be mounted. The drug container of the drug delivery device contains a drug fluid within a drug chamber for drug delivery at a controlled rate.

The drug delivery device may utilize the first controlled delivery drive mechanism described above in the first embodiment, which configuration utilizes a power spring and converts rotational movement of the drive pinion to axial translation of the drive rack, or the second controlled delivery drive mechanism described above in the second embodiment, which configuration utilizes a linear power spring to convert axial force into torsional motion of a drive pinion. In either embodiment, the piston is configured to contact and axially translate the plunger seal within barrel. Each embodiment may also utilize a regulating mechanism to meter the drive pinion such that the piston is axially translated by the linear power spring at a controlled rate.

In at least one embodiment, the regulating mechanism is an escapement regulating mechanism coupled to, or acting with, the power spring. The escapement regulating mechanism further includes a gear train having one or more gears, a rotation shaft, and a gear transmission having one or more gears, wherein at least one gear of the gear transmission is capable of engaging the drive pinion such that rotation of the gear causes rotation of the drive pinion. In a particular embodiment, the escapement regulating element further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. The escape wheel is a compound gear having escape teeth around the circumference of a large diameter escape gear and a small diameter gear configured to engage and meter the gear train. The metering of the drive pinion and/or the gear train by an escapement regulating mechanism controls the rate or profile of drug delivery to a user.

In at least one embodiment, the drug delivery device utilizes a status reader configured to read or recognize one or more corresponding status triggers, wherein, during operation of the drive mechanism, interaction between the status reader and the status triggers transmit a signal to a power and control system to provide feedback to a user. The status reader may be an optical status reader and the corresponding status triggers are gear teeth of a drive gear, a mechanical status reader and the corresponding status triggers are gear teeth of the drive gear, a mechanical status reader and the corresponding status triggers are external features of the piston and/or drive rack, or an optical status reader and the corresponding status triggers are external features of the piston and/or drive rack.

The present disclosure provides drive mechanisms for the controlled delivery of drug substances and drug delivery pumps which incorporate such drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the variable rate drive mechanism and drug delivery device may provide an end-of-dose indication.

The novel devices of the present disclosure provide variable rate controlled delivery drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 92A-92C show an exemplary drug delivery device or drug delivery device according to at least one embodiment of the present disclosure. The drug delivery device may be utilized to administer delivery of a drug treatment into a body of a user. As shown in FIGS. 92A-92C, the drug delivery device 9410 includes a pump housing 9412. Pump housing 9412 may include one or more housing subcomponents which are fixedly engageable to facilitate easier manufacturing, assembly, and operation of the drug delivery device. For example, drug delivery device 9410 includes a pump housing 9412 which includes an upper housing 9412A and a lower housing 9412B. The drug delivery device may further include an activation mechanism 9414, a status indicator 9416, and a window 9418. Window 9418 may be any translucent or transmissive surface through which the operation of the drug delivery device may be viewed. As shown in FIG. 92B, drug delivery device further includes assembly platform 9420, sterile fluid conduit 9430, drive mechanism 94100 having drug container 9450, insertion mechanism 94200, fluid pathway connector 94300, and power and control system 94400. One or more of the components of such drug delivery devices may be modular in that they may be, for example, pre-assembled as separate components and configured into position onto the assembly platform 9420 of the drug delivery device 9410 during manufacturing.

The pump housing 9412 contains all of the device components and provides a means of removably attaching the device 9410 to the skin of the user. The pump housing 9412 also provides protection to the interior components of the device 9410 against environmental influences. The pump housing 9412 is ergonomically and aesthetically designed in size, shape, and related features to facilitate easy packaging, storage, handling, and use by users who may be untrained and/or physically impaired. Furthermore, the external surface of the pump housing 9412 may be utilized to provide product labeling, safety instructions, and the like. Additionally, as described above, housing 9412 may include certain components, such as status indicator 9416 and window 9418, which may provide operation feedback to the user.

In at least one embodiment, the drug delivery device 9410 provides an activation mechanism 9414 that is displaced by the user to trigger the start command to the power and control system 94400. In a preferred embodiment, the activation mechanism is a start button 9414 that is located through the pump housing 9412, such as through an aperture between upper housing 9412A and lower housing 9412B, and which contacts a control arm 9440 of the power and control system 94400. In at least one embodiment, the start button 9414 may be a push button, and in other embodiments, may be an on/off switch, a toggle, or any similar activation feature known in the art. The pump housing 9412 also provides a status indicator 9416 and a window 9418. In other embodiments, one or more of the activation mechanism 9414, the status indicator 9416, the window 9418, and combinations thereof may be provided on the upper housing 9412A or the lower housing 9412B such as, for example, on a side visible to the user when the drug delivery device 9410 is placed on the body of the user. Housing 9412 is described in further detail hereinafter with reference to other components and embodiments of the present disclosure.

Drug delivery device is configured such that, upon activation by a user by depression of the activation mechanism, the drug delivery device is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug delivery device. For example, an optional on-body sensor 9424 (shown in FIG. 92C) may be provided in one embodiment as a safety feature to ensure that the power and control system 94400, or the activation mechanism, cannot be engaged unless the drug delivery device 9410 is in contact with the body of the user. In one such embodiment, the on-body sensor 9424 is located on the bottom of lower housing 9412B where it may come in contact with the user's body. Upon displacement of the on-body sensor 9424, depression of the activation mechanism is permitted. Accordingly, in at least one embodiment the on-body sensor 9424 is a mechanical safety mechanism, such as for example a mechanical lock out, that prevents triggering of the drug delivery device 9410 by the activation mechanism 9414. In another embodiment, the on-body sensor may be an electromechanical sensor such as a mechanical lock out that sends a signal to the power and control system 94400 to permit activation. In still other embodiments, the on-body sensor can be electrically based such as, for example, a capacitive- or impedance-based sensor which must detect tissue before permitting activation of the power and control system 94400. These concepts are not mutually exclusive and one or more combinations may be utilized within the breadth of the present disclosure to prevent, for example, premature activation of the drug delivery device. In a preferred embodiment, the drug delivery device 9410 utilizes one or more mechanical on-body sensors. Additional integrated safety mechanisms are described herein with reference to other components of the novel drug delivery devices.

XIII.A. Power and Control System

The power and control system 94400 includes a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 94400 controls several device interactions with the user and interfaces with the drive mechanism 94100. In one embodiment, the power and control system 94400 interfaces with the control arm 9440 to identify when the on-body sensor 9424 and/or the activation mechanism 9414 have been activated. The power and control system 94400 may also interface with the status indicator 9416 of the pump housing 9412, which may be a transmissive or translucent material which permits light transfer, to provide visual feedback to the user. The power and control system 94400 interfaces with the drive mechanism 94100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system 94400 may be configured to provide a number of different status indicators to the user. For example, the power and control system 94400 may be configured such that after the on-body sensor and/or trigger mechanism have been pressed, the power and control system 94400 provides a ready-to-start status signal via the status indicator 9416 if device start-up checks provide no errors. After providing the ready-to-start status signal and, in an embodiment with the optional on-body sensor, if the on-body sensor remains in contact with the body of the user, the power and control system 94400 will power the drive mechanism 94100 to begin delivery of the drug treatment through the fluid pathway connector 94300 and sterile fluid conduit 9430. In a preferred embodiment of the present disclosure, the insertion mechanism 94200 and the fluid pathway connector 94300 may be caused to activate directly by user operation of the activation mechanism 9414. During the drug delivery process, the power and control system 94400 is configured to provide a dispensing status signal via the status indicator 9416. After the drug has been administered into the body of the user and after the end of any additional dwell time, to ensure that substantially the entire dose has been delivered to the user, the power and control system 94400 may provide an okay-to-remove status signal via the status indicator 9416. This may be independently verified by the user by viewing the drive mechanism and drug dose delivery through the window 9418 of the pump housing 9412. Additionally, the power and control system 94400 may be configured to provide one or more alert signals via the status indicator 9416, such as for example alerts indicative of fault or operation failure situations.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 9414 of the drug delivery device 9410 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XIII.B. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9410, the fluid pathway connector 94300 is enabled to connect the sterile fluid conduit 9430 to the drug container of the drive mechanism 94100. Such connection may be facilitated by a piercing member, such as a needle, penetrating a pierceable seal of the drug container of the drive mechanism 94100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present disclosure, the piercing member of the fluid pathway connector is caused to penetrate the pierceable seal of the drug container of the drive mechanism by direct action of the user, such as by depression of the activation mechanism by the user. For example, the activation mechanism itself may bear on the fluid pathway connector such that displacement of the activation mechanism from its original position also causes displacement of the fluid pathway connector. In one such embodiment, the fluid pathway connector may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 94300 and the sterile fluid conduit 9430 are provided hereinafter in later sections in reference to other embodiments.

XIII.C. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure.

In at least one embodiment, the insertion mechanism 94200 includes an insertion mechanism housing having one or more lockout windows, and a base for connection to the assembly platform and/or pump housing (as shown in FIG. 92B and FIG. 92C). The connection of the base to the assembly platform 9420 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9410. The insertion mechanism may further include one or more insertion biasing members, a needle, a retraction biasing member, a cannula, and a manifold. The manifold may connect to sterile fluid conduit 9430 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9427 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 94254 (shown in FIG. 92C).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 92B, the lockout pin(s) 94208 may be directly displaced by user depression of the activation mechanism 9414. As the user disengages any safety mechanisms, such as an optional on-body sensor 9424 (shown in FIG. 92C), the activation mechanism 9414 may be depressed to initiate the drug delivery device. Depression of the activation mechanism 9414 may directly cause translation or displacement of control arm 9440 and directly or indirectly cause displacement of lockout pin(s) 94208 from their initial position within locking windows 94202A of insertion mechanism housing 94202. Displacement of the lockout pin(s) 94208 permits insertion biasing member to decompress from its initial compressed, energized state. This decompression of the insertion biasing member drives the needle and the cannula into the body of the user. At the end of the insertion stage, the refraction biasing member is permitted to expand in the proximal direction from its initial energized state. This axial expansion in the proximal direction of the refraction biasing member refracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

XIII.D. Drive Mechanism

With reference to the embodiments shown in FIGS. 93 and 94, drive mechanism 94100 includes a drive housing 94130, and a drug container 9450 having a cap 9452, a pierceable seal 9456, a barrel 9458, and a plunger seal 9460. A drug chamber 9421, located within the barrel 9458 between the pierceable seal and the plunger seal 9460, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism may further include a connection mount 9454 to guide the insertion of the piercing member of the fluid pathway connector into the barrel 9458 of the drug container 9450. The drive mechanism 94100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 94100 employs one or more springs as the drive biasing member(s). Upon activation of the drug delivery device by the user, the power and control system may be actuated to directly or indirectly release the spring(s) from an energized state. Upon release, the spring(s) may be utilized, directly or indirectly, to drive the plunger seal and force the fluid drug out of the drug container. More specifically, the spring may be utilized, directly or indirectly, to drive a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 93 and FIG. 94, the drive mechanism 94100 includes a drug container 9450 having a cap 9452, a pierceable seal 9456, a barrel 9458, and a plunger seal 9460, and optionally a connection mount 9454. The drug container 9450 is mounted to a distal end of a drive housing 94130. A piston 94110 having an interface surface 94110C and a drive rack 94110A is retained at least partially within the drive housing 94130, between the drug container 9450 and the proximal end of the housing 94130. Optionally, a cover sleeve may be utilized to engage the piston 94110 and cover the drive rack 94110A to hide such components from user view upon expansion from its initial position. The cover sleeve may be configured to engage and slide upon the piston 94110, between the piston 94110 and the distal end of the drive mechanism housing 94130 to hide the drive rack 94110A from user view upon expansion from its initial energized state.

As shown in FIGS. 94A and 94B, the controlled delivery drive mechanism 94100 of the present disclosure may utilize a power spring 94122 coupled, directly or indirectly to the drive pinion 94120 which interfaces with drive rack 94110A of the piston 94110 to convert rotational movement of the drive pinion 94120 to axial translation of the drive rack 94110A, thereby pushing plunger seal 9460 within barrel 9458 to force a fluid from drug chamber 9421. Notably, the power spring 94122 imparts torque to a gear assembly, such as the drive pinion 94120, which pushes a plunger seal 9460 within barrel 9458 which contains the drug substance. Alternatively a linear power spring 941122 can be coupled directly or indirectly to the piston 94110 with drive rack 94110A to convert axial force into torsional motion which is coupled to drive pinion 94120 and into the regulating mechanism 94500, as shown in FIG. 99. In both configurations, the plunger seal 9460 advances into the drug container 9450, the drug substance is dispensed through the sterile pathway connection 94300, conduit 9430, insertion mechanism 94200, and into the body of the user for drug delivery. Certain reaction forces on the plunger seal, such as hydraulic resistance from the flow of the drug substance and friction of the plunger seal against the barrel, can vary significantly. As such, it is desirable to have a regulating mechanism 94500 in the drive mechanism 94100 which keeps a constant rate of delivery as these forces vary. In the embodiments of the present disclosure, the regulating mechanism 94500 is an escapement regulating mechanism. The escapement regulating mechanism retards or restrains the gear assembly, only allowing it to advance at a regulated or desirable rate. In such a configuration, the power spring 94122 is designed to supply sufficient torque to overcome worst case variations in the hydraulic and frictional forces. In theory, any excess force which occurs under more nominal reaction force conditions is absorbed by the escapement regulating mechanism and the delivery rate remains constant.

In at least one embodiment of the present disclosure, the drive mechanism 94100 utilizes an escapement regulating element 94500 and a power spring 94122. The power spring 94122 is configured to provide rotational movement, around an axis "B", to one or more gears 94512, 94514, 94516 of a gear train 94510 (and/or to gear 94522 of gear transmission 94550). Each of the gears 94512, 94514, 94516 may be, for example, compound gears having a small diameter gear attached at a shared center point to a large diameter gear. For example first compound gear 94512 has small diameter gear 94512B (not visible) attached to large diameter gear 94512A. The small diameter gear of each compound gear engages the large diameter gear, for example, of the next compound gear in the gear train 94510 such that rotational movement of the first compound gear 94512 is conveyed by engagement of the gears (such as by engagement of corresponding gear teeth) to the second compound gear 94514, and so on through the gear train 94510. Such rotational movement of the gear train 94510 may be conveyed by a rotation shaft 94518 to a gear transmission 94550 having one or more gears, including drive gear 94520. For example, the gear transmission 94550 may include gear 94522 and gear 94524 in addition to drive gear 94520. The drive gear 94520 is connected to drive pinion 94120 (such as by connection protrusion 94120A) such that rotation of the drive gear 94520 causes rotation of the drive pinion 94120. The drive pinion 94120 is configured to engage the drive rack 94110A of the piston 94110 to convert rotational movement of the drive pinion 94120 to axial translation of the drive rack 94110A, thereby pushing plunger seal 9460 within barrel 9458 to force a fluid from drug chamber 9421. The rotational movement of the drive gear 94520, and thus the axial translation of the drive rack 94110A and plunger seal 9460, are metered, restrained, or otherwise prevented from free axial translation by other components of the escapement regulating element 94500, as described herein.

In at least one embodiment of the present disclosure, the rotation shaft 94518 is keyed to both the first compound gear 94512 and the first gear 94522 of the gear transmission 94550. This configuration permits rotational movement of the first compound gear 94512, which is in direct rotational alignment and/or relationship with the power spring 94122, to be keyed and cause power transfer and rotation of the gear transmission 94550 (such as at gear 94522). In this configuration, at least some of power from the power spring 94122 is directed for use in axially translating the drive rack 94110A of the piston 94110 and the plunger seal 9460; while at least a portion of the power from the power spring 94122 is directed for use by the escape wheel 94562, balance wheel 94566, hair spring 94568, and lever 94564 components of the escapement regulating element 500. Accordingly, while the power spring provides force used for axial translation of the plunger seal 9460, it also powers the escapement regulating element 94500 which functions to meter or restrain the force provided for such axial translation. The compound gear structure of the gear train 94510 permits the splitting of the force provided by the power spring 94122. Some of the power from the power spring 94122 is transferred directly to gear 94522, rotation shaft 94518, and first gear 94522 of the gear transmission 94550; while some of the power is transferred to gear 94514, gear 94516, lever 94564, and escape wheel 94562, for regulation or metering by interaction with the balance wheel 94566 and hair spring 94568, to permit a small diameter gear 94562B of the escape wheel 94562 to regulate or meter the gear train 94510.

The escapement regulating element 94500 further includes an escape wheel 94562 and a lever 94564. The escape wheel 94562 is a compound gear having escape teeth around the circumference of a large diameter escape gear 94562A and a small diameter gear 94562B (not visible) configured to engage the gear train 94510 and meter, restrain, or otherwise prevent free rotational movement thereof. The lever 94564 has pins 94564A,B and prong 94564C. Prong 94564C movably engages a post 94566A and is configured to removably engage an impulse pin 94566B of a balance wheel 94566. The balance wheel 94566 engages and functions as an oscillator around a pivot point 94564D in combination with a hair spring 94568. The power spring 94122 may be retained or braced within a winder 94502 in a manner that permits the power spring 94122 to rotationally move freely within the winder 94502. The gear train 94510, escape wheel 94562, balance wheel 94566, hair spring 94568, and lever 94564 may be mounted on and able to freely rotate or move on a plate 94504. Similarly, gear transmission 94550 may be mounted on and able to freely rotate on a platform 94506. The winder 94502, plate 94504, and platform 94506 may utilize one or more spacer columns to maintain the desired spacing between components and one or more pivot pins upon which the components may be mounted and freely rotated.

The function of the escape wheel 94562, balance wheel 94566, hair spring 94568, and lever 94564 components of the escapement regulating element 94500 are explained with reference to FIG. 94B and FIGS. 95A-95H. The escape wheel 94562 is a compound gear having escape teeth around the circumference of a large diameter escape gear 94562A and a small diameter gear 94562B (not visible) configured to engage the gear train 94510 and meter, restrain, or otherwise prevent free rotational movement thereof. The lever 94564 has pins 94564A,B and prong 94564C. Prong 94564C movably engages a post 94566A and is configured to removably engage an impulse pin 94566B of a balance wheel 94566. The balance wheel 94566 engages and functions as an oscillator around a pivot point 94564D in combination with a hair spring 94568. The escape wheel 94562 and lever 94564 may initially be in an activation position, as shown in FIG. 95A. The escape wheel 94562 and lever 94564 generally function to perform two steps, termed the locking action and the impulse action. These two actions are illustrated in FIG. 95B and FIG. 95C, respectively, and in which the gear train 94510 is applying a clockwise torque on the escape wheel 94562. In the locking action, one of two lever pins 94564A,B blocks escape wheel 94562 rotation on the radial face of a tooth on the escape gear 94562A. This locks the gear train 94510 between impulse actions. In the impulse action, a lever pin 94564A,B slides up to this tooth face due to action of the balance wheel 94566 on the lever 94564. The escape wheel becomes unlocked and does mechanical work on the lever pin 94564A, B via a sliding action, which in turn imparts kinetic energy to the balance wheel 94566. The lever 94564 pivots upon a pivot point 94564D until the opposite pin 94564A,B engages with an escape wheel tooth on the escape gear 94562A, and the locked state is re-entered after a half tooth advance of the escape wheel 94562. The transition from locking action to impulse action is triggered by the balance wheel 94566, which functions as an oscillator in combination with the hair spring 94568. It cycles at a natural frequency that serves as the rate control. The balance wheel 94566 contains an impulse pin 94566B which interacts with the lever 94564 at prong 94564C. For the impulse phase depicted in FIG. 95C, a clockwise moment on the lever 94564 exerts a counterclockwise moment on the balance wheel 94566, adding to its kinetic energy. The balance wheel 94566 rotates until its kinetic energy is absorbed by the hair spring 94568. It stops, reverses, and reengages the impulse pin 94566B with the lever 94564. A complete cycle is shown in the transition between FIGS. 95D-95H.

To unlock the escapement regulating mechanism 94500, the balance wheel 94566 must have enough kinetic energy to drag the lever pin 94564A,B up the face of the tooth of the escape gear 94562A of the escape wheel 94562. If the impulse action adds less energy than is lost to friction, the balance wheel 94566 will rotate less and less and finally stall, locking the escapement regulating mechanism 94500. If the escapement stops in this way under load, it will not restart easily. To be self-starting, the hair spring 94568 must align the lever 94564 along the axis connecting the pivot of the escape wheel 94562 and the pivot of the balance wheel 94566, as shown in FIG. 95A. The lever pins 94564A,B will be positioned so that a bevel tooth face can immediately start an impulse action upon application of a drive torque. This alignment can occur only with the escapement regulating mechanism 94500 in an unloaded state. The power spring 94122 torque must be isolated from the escapement regulating mechanism 94500 until the start of delivery. This action may be initiated by a user imparting a force on an activation mechanism and, directly or indirectly through a power and control system 94400, applying a drive torque to start the initial impulse action. Once the escapement regulating mechanism 94500 is initiated, it can be effectively utilized to meter, restrain, or otherwise prevent free rotational movement of the gear train 94510, gear transmission 94550, drive gear 94520 and drive pinion 94120, and, thus, axial translation of the drive rack 94110A and plunger seal 9460. In a particular embodiment, the escape wheel 94562 is a compound gear having escape teeth around the circumference of a large diameter escape gear 94562A and a small diameter gear 94562B (not visible). The small diameter gear 94562B of the escape wheel 94562 engages the drive train 94510, which engages with gear transmission 94550 through rotation shaft 94518. This novel configuration directly permits the escape wheel 94562 to regulate the rotation of the drive train 94510 imparted by the power spring 94122, which then efficiently regulates the drive transmission 94550, drive gear 94520, drive pinion 94120, and drive rack 94110A of the piston 94110.

The novel embodiments of the present disclosure may be utilized to meter, restrain, or otherwise prevent free rotational movement and, thus, axial translation of the components of the controlled delivery drive mechanism 94100. Accordingly, the escapement regulating mechanism 94500 only controls the motion of the drive mechanism, but does not apply the force for the drug delivery. One or more additional biasing members, such as compression springs, may be utilized to drive or assist the driving of the piston 94110 (as shown in FIG. 99). For example, a compression spring may be utilize within the drive housing 94130 for this purpose, with the power spring 94122 partly driving the piston 110 and plunger seal 9460 and partly driving the escapement regulating element 94500 to perform the metering as described above. Accordingly, the means to control flow is separate from the load on the piston 94110 and the plunger seal 9460. While the power spring 94122 applies the force that is utilized to drive the piston 94110 and plunger seal 9460 for drug delivery, the escapement regulating mechanism 94500 only controls, meters, or regulates such action. A mechanical timing system, such as the escapement regulating mechanism described herein, may be utilized to allow the piston 94110 and plunger seal 9460 to translate axially a controlled distance, or a controlled volume, and may be utilized to meet a desired delivery rate or profile. The timing system can be controlled by quartz timing instead of mechanical timing, as would be appreciated by one having ordinary skill in the art. For quartz timing, a battery provides power to a microchip and circuit. The quartz crystal oscillates at a precise frequency. Alternate electrical timing mechanisms such as, for example, RC timing mechanisms, may also be used, including clock functions commonly found in microprocessors. Depending on the period that the delivery is planned to occur over, the microchip drives a motor based on a number of quartz crystal oscillations or other timing signals. The motor releases motion of a drive train, drive transmission, and/or drive rack, to control the axial translation of a plunger in a similar manner as described herein for the mechanical timing system.

The drive mechanism 94100 having an escapement regulating mechanism 94500 functions to control the rate of drug delivery forced by the axial translation of a piston 94110 and a plunger seal 9460 within a barrel 9458 of a drug container 9450. This is shown in the transition from FIGS. 96A-96C and FIGS. 97A-97C. As described above, the power spring 94122 imparts a force to the drive mechanism which is regulated, metered, or otherwise controlled by the escapement regulating mechanism 94500 to control the rate of axial translation of the piston 94110 and plunger seal 9460 for drug delivery. Upon initiation by the user, the power spring 94122 is permitted to apply a force or torque to the system which is regulated by the escapement regulating mechanism 94500. This causes the drive mechanism shown in FIG. 96A and FIG. 97A to activate and permit metered axial translation of the piston 94110 and plunger seal 9460 in the distal direction within a barrel 9458 (i.e., in the direction of the hatched arrow). This metered activity continues through drug delivery at a controlled rate or drug delivery profile, as shown in FIG. 96B and FIG. 97B, until substantially all of the drug fluid has been dispensed from drug chamber 9421 through the sterile pathway connection 94300, as shown in FIG. 96C and FIG. 97C.

The components of the drive mechanism 94100, upon activation, may be used to drive axial translation in the distal direction of the plunger seal 9460 of the drug container 9450. Optionally, the drive mechanism 94100 may include one or more compliance features which enable additional axial translation of the plunger seal 9460 to, for example, ensure that substantially the entire drug dose has been delivered to the user. For example, the plunger seal 9460, itself, may have some compressibility permitting a compliance push of drug fluid from the drug container. The plunger seal 9460, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Similarly, an optional cover sleeve may be utilized to hide the visibility of the drive rack 94110A and other internal components from the user as the piston 94110 is axially translated within the barrel 58.

The novel variable rate drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 9456 and the interconnect located proximal to the plunger seal 9460 such that, upon substantially complete axial translation (and the optional compliance push) of the plunger seal 9460 within the barrel 9458, the status switch and interconnect coordinate to enable a transmission to the power and control system to signal end-of-dose to the user. This configuration further enables true end-of-dose indication to the user.

In at least one embodiment, as shown in FIG. 98, incremental status indication may be provide to the user by reading or recognizing the rotational movement of drive gear 94520. As the drive gear 94520 rotates, a status reader 94600 may read or recognize one or more corresponding status triggers on the drive gear 94520 to provide incremental status indication before, during, and after operation of the variable rate controlled delivery drive mechanism. A number of status readers may be utilized within the embodiments of the present disclosure. For example, the drive mechanism shown in FIG. 98 may utilize a mechanical status reader 94600 which is physically contacted by gear teeth of the drive gear 9420. As the status reader 94600 is contacted by the status trigger(s), which in this exemplary embodiment may be the gear teeth of the drive gear 94520 (or holes, pins, ridges, markings, electrical contacts, or the like, upon the drive gear 94520), the status reader 94600 measures the rotational position of the drive gear 94520 and transmits a signal to the power and control system for status indication to the user. Additionally or alternatively, the drive mechanism shown in FIG. 98 may utilize an optical status reader 94600. The optical status reader 94600 may be, for example, a light beam that is capable of recognizing a motion and transmitting a signal to the power and control system. For example, the drive mechanism may utilize an optical status reader 94600 that is configured to recognize motion of the gear teeth of the drive gear 94520 (or holes, pins, ridges, markings, electrical contacts, or the like, upon the drive gear 94520). Similarly, the status reader 94600 may be an electrical switch configured to recognize electrical contacts on drive gear 94520. In any of these embodiments, sensor 94602 may be utilized to then relay a signal to the power and control system 94400 to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear transmission, gear train, and escapement regulating mechanism shown in FIG. 98, a range of configurations may be utilized for these components with the appropriate gear reduction based on the load and power spring chosen would be acceptable and capable of being employed within the embodiments of the present disclosure, as would readily be appreciated by an ordinarily skilled artisan. Accordingly, the embodiments of the present disclosure are not limited to the specific gear transmission, gear train, and escapement regulating mechanism described herein, which is provided as an exemplary embodiment of such mechanisms for employment within the controlled delivery drive mechanisms and drug delivery pumps.

Returning now to the embodiments shown in FIGS. 96A-96C and FIGS. 97A-97C, a fluid, such as a drug fluid, may be contained within barrel 9458, in a drug chamber 9421, between plunger seal 9460 and pierceable seal 9456, for delivery to a user. The pierceable seal is adjacent or retained at least partially within cap 9452. Upon activation by the user, a fluid pathway connector may be connected to the drug container through the pierceable seal. As described above, this fluid connection may be facilitated by a piercing member of the fluid pathway connector which pierces the pierceable seal and completes the fluid pathway from the drug container, through the fluid pathway connector, the fluid conduit, the insertion mechanism, and the cannula for delivery of the drug fluid to the body of the user. Distal translation of the piston 94110 and plunger seal 9460, but the drive mechanisms and regulating mechanisms described herein, continues to force fluid flow out from barrel 9458 through pierceable seal 9456. In at least one embodiment, an end-of-dose status indication may be provided to the user once the status reader recognizes a status trigger positioned on the drive gear to substantially correspond with the end of axial travel of the piston 94110 and plunger seal 9460. The novel escapement regulating mechanism 94500 and drive mechanisms 94100 of the present disclosure thus permit, meter, or otherwise restrain the free axial expansion of the biasing member 94122 to control the rate or profile of drug delivery. The novel embodiments of the present disclosure also thus provide incremental status indication to the user.

Assembly and/or manufacturing of variable rate controlled delivery drive mechanism 94100, drug delivery pump 9410, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9450 may first be assembled and filled with a fluid for delivery to the user. The drug container 9450 includes a cap 9452, a pierceable seal 9456, a barrel 9458, and a plunger seal 9460. The pierceable seal 9456 may be fixedly engaged between the cap 9452 and the barrel 9458, at a distal end of the barrel 9458. The barrel 9458 may be filled with a drug fluid through the open proximal end prior to insertion of the plunger seal 9460 from the proximal end of the barrel 9458. An optional connection mount 9454 may be mounted to a distal end of the pierceable seal 9456. The connection mount 9454 may guide the insertion of the piercing member of the fluid pathway connector into the barrel 9458 of the drug container 9450. The drug container 9450 may then be mounted to a distal end of drive housing 94130. The piston 94110 having a drive rack 94110A may be mounted into the drive mechanism housing 94130 and connected to drive pinion 94120 and gear drive gear 94520. The drive pinion 94120 is placed in position adjacent the drive mechanism housing 94130 such that it extends at least partly into the drive housing 94130 to engage the drive rack 94110A for operation.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 92B.

Certain optional standard components or variations of drive mechanism 94100, or drug delivery device 9410, are contemplated while remaining within the breadth and scope of the present disclosure. For example, upper or lower housings may optionally contain one or more transparent or translucent windows 9418, as shown in FIG. 92A, to enable the user to view the operation of the drug delivery device 9410 or verify that drug dose has completed. Similarly, the drug delivery device 9410 may contain an adhesive patch 9426 and a patch liner 9428 on the bottom surface of the housing 9412. The adhesive patch 9426 may be utilized to adhere the drug delivery device 9410 to the body of the user for delivery of the drug dose. As would be readily understood by one having ordinary skill in the art, the adhesive patch 9426 may have an adhesive surface for adhesion of the drug delivery device to the body of the user. The adhesive surface of the adhesive patch 9426 may initially be covered by a non-adhesive patch liner 9428, which is removed from the adhesive patch 9426 prior to placement of the drug delivery device 10 in contact with the body of the user. Removal of the patch liner 9428 may further remove the sealing membrane 94254 of the insertion mechanism 94200, opening the insertion mechanism to the body of the user for drug delivery (as shown in FIG. 92C).

Similarly, one or more of the components of controlled delivery drive mechanism 94100 and drug delivery device 9410 may be modified while remaining functionally within the breadth and scope of the present disclosure. For example, as described above, while the housing of drug delivery device 9410 is shown as two separate components upper housing 9412A and lower housing 9412B, these components may be a single unified component. As discussed above, a glue, adhesive, or other known materials or methods may be utilized to affix one or more components of the variable rate controlled delivery drive mechanism and/or drug delivery device to each other. Alternatively, one or more components of the variable rate controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at desired rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the force applied by a torsional power spring acting upon (directly or indirectly) a piston within a drug container to force fluid drug flow through the drug container, the fluid pathway connector, a sterile fluid conduit, and the insertion mechanism for delivery of the fluid drug to the body of a user, wherein a regulating mechanism acting to restrain the force applied by the power spring is utilized to meter the free axial translation of the piston. The method of operation of the insertion mechanism and the drug delivery device may be better appreciated with reference to FIGS. 96A-96C and FIGS. 97A-97C, as described above.

XIV. Additional Embodiments of Multi-Function Drive Mechanism

At least some of the drug delivery devices described in this application, including at least those described in connection with FIGS. 1A-2B, 33A-33C, 69A-73D, 80A-85C, 86A-91, and 92-99 may be configured to incorporate the embodiments of the drive mechanism described below in connection with FIGS. 100A-109B. The embodiments of the drive mechanism described below in connection with FIGS. 100A-109B may be used to replace, in its entirety or partially, the above-described drive mechanism 100, 6100, 8100, 9010, 9210, 9310, or 9410, or any other drive mechanism described herein, where appropriate.

The present disclosure provides drive mechanisms for the variable rate controlled delivery of drug substances, drug delivery pumps with variable rate drive mechanisms, the methods of operating such devices, and the methods of assembling such devices. Notably, the drive mechanisms of the present disclosure control the rate of drug delivery by metering, providing resistance, or otherwise preventing free axial translation of the plunger seal utilized to force a drug substance out of a drug container. The novel embodiments of the present disclosure thus are capable of delivering drug substances at variable rates. The variable rate drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a variable rate controlled delivery drive mechanism which includes a drive mechanism housing, at least partially within which initially resides a biasing member positioned in an initially energized state within an inner cavity of a piston. The drive mechanism may further includes a gear drive having a gear and a substantially axial internal pass-through; a first screw which at least partially resides within the axial internal pass-through, said first screw also having a substantially axial pass-through and an external first pitch wherein the external first pitch is configured to engage a first nut which also resides within the internal pass-through of the gear drive; a second nut configured to engage a second screw having an external second pitch, said second nut positioned within an axial post of a piston, said axial post and second nut positioned to reside at least partially within the axial pass-through of the first screw. The piston has an interface surface adjacent to a plunger seal and is configured to axially translate the plunger seal, by force asserted upon it from the biasing member, from a first position to a second position within a drug container for drug delivery. The biasing member is member is metered or otherwise restrained from free expansion from its energized state. The first nut may be rotationally constrained (i.e. keyed) to the gear drive, while the second nut is rotationally constrained to the piston.

In another embodiment, the present disclosure provides a variable rate controlled delivery drive mechanism having a drive mechanism housing, at least partially within which initially resides a biasing member positioned in an initially energized state within an inner cavity of a piston. A gear may be connected to the proximal end of a drive screw having an external pitch configured to engage a nut. The nut may be rotationally constrained (i.e., keyed) to the piston. The piston has an interface surface adjacent to a plunger seal and is configured to axially translate the plunger seal, by force asserted upon it from the biasing member, from a first position to a second position within a drug container for drug delivery. The biasing member is metered or otherwise restrained from free expansion from its energized state.

In at least one embodiment, the drive mechanism may further include a gear assembly mechanism having a motor, the gear assembly mechanism configured to engage a gear to meter the free expansion of the biasing member from its energized state. The gear assembly mechanism having a motor may further include a pinion extending from motor; one or more compound gears each having a first gear and a second gear; and a trigger gear; wherein the pinion contacts the one or more compound gears which contacts the trigger gear, and the trigger gear contacts a gear to relay motion to the drive mechanism. The metering of the biasing member by the motor controls the rate or profile of drug delivery to a user.

In a further embodiment, the drive mechanism includes a status reader configured to read or recognize one or more corresponding status triggers, wherein, during operation of the drive mechanism, interaction between the status reader and the status triggers transmits a signal to a power and control system to provide feedback to a user. The status reader may be, for example, an optical status reader and the corresponding status triggers are gear teeth of the trigger gear, a mechanical status reader and the corresponding status triggers are gear teeth of the trigger gear, a mechanical status reader and the corresponding status triggers are external features of the piston and/or sleeve an optional sleeve, or an optical status reader and the corresponding status triggers are external features of the piston and/or an optional sleeve. The function of the gear assembly mechanism having a motor may be pre-programmed or dynamically controlled by a power and control system to meet a desired drug delivery rate or profile.

In yet another embodiment, the present disclosure provides a drug delivery pump with a variable rate controlled delivery mechanism. The drive mechanism may be as described above. In at least one embodiment, the drug delivery device may further include a gear assembly mechanism having a motor, the gear assembly mechanism configured to engage a gear to meter the free expansion of the biasing member from its energized state. The gear assembly mechanism having a motor may further include a pinion extending from motor; one or more compound gears each having a first gear and a second gear; and a trigger gear; wherein the pinion contacts the one or more compound gears which contacts the trigger gear, and the trigger gear contacts a gear to relay motion to the drive mechanism. The metering of the biasing member by the motor controls the rate or profile of drug delivery to a user.

In a further embodiment, the drug delivery device includes a status reader configured to read or recognize one or more corresponding status triggers, wherein, during operation of the drive mechanism, interaction between the status reader and the status triggers transmits a signal to a power and control system to provide feedback to a user. The status reader may be, for example, an optical status reader and the corresponding status triggers are gear teeth of the trigger gear, a mechanical status reader and the corresponding status triggers are gear teeth of the trigger gear, a mechanical status reader and the corresponding status triggers are external features of the piston and/or sleeve an optional sleeve, or an optical status reader and the corresponding status triggers are external features of the piston and/or an optional sleeve. The function of the gear assembly mechanism having a motor may be pre-programmed or dynamically controlled by a power and control system to meet a desired drug delivery rate or profile.

The present disclosure provides variable rate drive mechanisms for the controlled delivery of drug substances and drug delivery pumps which incorporate such variable rate drive mechanisms. The variable rate drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the variable rate drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the variable rate drive mechanism and drug delivery device may provide an end-of-dose indication.

The novel devices of the present disclosure provide variable rate controlled delivery drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 100A-100C show an exemplary drug delivery device or drug delivery device according to at least one embodiment of the present disclosure. The drug delivery device may be utilized to administer delivery of a drug treatment into a body of a user. As shown in FIGS. 100A-100C, the drug delivery device 9510 includes a pump housing 9512. Pump housing 9512 may include one or more housing subcomponents which are fixedly engageable to facilitate easier manufacturing, assembly, and operation of the drug delivery device. For example, drug delivery device 9510 includes a pump housing 9512 which includes an upper housing 9512A and a lower housing 9512B. The drug delivery device may further include an activation mechanism 9514, a status indicator 9516, and a window 9518. Window 9518 may be any translucent or transmissive surface through which the operation of the drug delivery device may be viewed. As shown in FIG. 100B, drug delivery device further includes assembly platform 9520, sterile fluid conduit 9530, drive mechanism 95100 having drug container 9550, insertion mechanism 95200, fluid pathway connector 95300, and power and control system 95400. One or more of the components of such drug delivery devices may be modular in that they may be, for example, pre-assembled as separate components and configured into position onto the assembly platform 9520 of the drug delivery device 9510 during manufacturing.

The pump housing 9512 contains all of the device components and provides a means of removably attaching the device 9510 to the skin of the user. The pump housing 9512 also provides protection to the interior components of the device 9510 against environmental influences. The pump housing 9512 is ergonomically and aesthetically designed in size, shape, and related features to facilitate easy packaging, storage, handling, and use by users who may be untrained and/or physically impaired. Furthermore, the external surface of the pump housing 9512 may be utilized to provide product labeling, safety instructions, and the like. Additionally, as described above, housing 9512 may include certain components, such as status indicator 9516 and window 9518, which may provide operation feedback to the user.

In at least one embodiment, the drug delivery device 9510 provides an activation mechanism 9514 that is displaced by the user to trigger the start command to the power and control system 95400. In a preferred embodiment, the activation mechanism is a start button 9514 that is located through the pump housing 9512, such as through an aperture between upper housing 9512A and lower housing 9512B, and which contacts a control arm 9540 of the power and control system 95400. In at least one embodiment, the start button 9514 may be a push button, and in other embodiments, may be an on/off switch, a toggle, or any similar activation feature known in the art. The pump housing 9512 also provides a status indicator 9516 and a window 9518. In other embodiments, one or more of the activation mechanism 9514, the status indicator 16, the window 9518, and combinations thereof may be provided on the upper housing 9512A or the lower housing 9512B such as, for example, on a side visible to the user when the drug delivery device 9510 is placed on the body of the user. Housing 9512 is described in further detail hereinafter with reference to other components and embodiments of the present disclosure.

Drug delivery device is configured such that, upon activation by a user by depression of the activation mechanism, the drug delivery device is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug delivery device. For example, an optional on-body sensor 9524 (shown in FIG. 100C) may be provided in one embodiment as a safety feature to ensure that the power and control system 95400, or the activation mechanism, cannot be engaged unless the drug delivery device 9510 is in contact with the body of the user. In one such embodiment, the on-body sensor 9524 is located on the bottom of lower housing 9512B where it may come in contact with the user's body. Upon displacement of the on-body sensor 9524, depression of the activation mechanism is permitted. Accordingly, in at least one embodiment the on-body sensor 9524 is a mechanical safety mechanism, such as for example a mechanical lock out, that prevents triggering of the drug delivery device 9510 by the activation mechanism 9514. In another embodiment, the on-body sensor may be an electromechanical sensor such as a mechanical lock out that sends a signal to the power and control system 95400 to permit activation. In still other embodiments, the on-body sensor can be electrically based such as, for example, a capacitive- or impedance-based sensor which must detect tissue before permitting activation of the power and control system 95400. These concepts are not mutually exclusive and one or more combinations may be utilized within the breadth of the present disclosure to prevent, for example, premature activation of the drug delivery device. In a preferred embodiment, the drug delivery device 9510 utilizes one or more mechanical on-body sensors. Additional integrated safety mechanisms are described herein with reference to other components of the novel drug delivery devices.

XIV.A. Power and Control System

The power and control system 95400 includes a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 95400 controls several device interactions with the user and interfaces with the drive mechanism 95100. In one embodiment, the power and control system 95400 interfaces with the control arm 9540 to identify when the on-body sensor 9524 and/or the activation mechanism 9514 have been activated. The power and control system 95400 may also interface with the status indicator 9516 of the pump housing 9512, which may be a transmissive or translucent material which permits light transfer, to provide visual feedback to the user. The power and control system 95400 interfaces with the drive mechanism 95100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system 95400 may be configured to provide a number of different status indicators to the user. For example, the power and control system 95400 may be configured such that after the on-body sensor and/or trigger mechanism have been pressed, the power and control system 95400 provides a ready-to-start status signal via the status indicator 9516 if device start-up checks provide no errors. After providing the ready-to-start status signal and, in an embodiment with the optional on-body sensor, if the on-body sensor remains in contact with the body of the user, the power and control system 95400 will power the drive mechanism 95100 to begin delivery of the drug treatment through the fluid pathway connector 95300 and sterile fluid conduit 9530. In a preferred embodiment of the present disclosure, the insertion mechanism 95200 and the fluid pathway connector 95300 may be caused to activate directly by user operation of the activation mechanism 9514. During the drug delivery process, the power and control system 95400 is configured to provide a dispensing status signal via the status indicator 9516. After the drug has been administered into the body of the user and after the end of any additional dwell time, to ensure that substantially the entire dose has been delivered to the user, the power and control system 95400 may provide an okay-to-remove status signal via the status indicator 9516. This may be independently verified by the user by viewing the drive mechanism and drug dose delivery through the window 18 of the pump housing 9512. Additionally, the power and control system 95400 may be configured to provide one or more alert signals via the status indicator 9516, such as for example alerts indicative of fault or operation failure situations.

The power and control system 95400 may additionally be configured to accept various inputs from the user to dynamically control the drive mechanisms 95100 to meet a desired drug delivery rate or profile. For example, the power and control system 95400 may receive inputs, such as from partial or full activation, depression, and/or release of the activation mechanism 9514, to set, initiate, stop, or otherwise adjust the control of the drive mechanism 95100 via the power and control system 95400 to meet the desired drug delivery rate or profile. Similarly, the power and control system 95400 may be configured to receive such inputs to adjust the drug dose volume; to prime the drive mechanism, fluid pathway connector, and fluid conduit; and/or to start, stop, or pause operation of the drive mechanism 95100. Such inputs may be received by the user directly acting on the drug delivery device 9510, such as by use of the activation mechanism 9514 or a different control interface, or the system 95400 may be configured to receive such inputs from a remote device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 9514 of the drug delivery device 9510 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XIV.B. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9510, the fluid pathway connector 95300 is enabled to connect the sterile fluid conduit 9530 to the drug container of the drive mechanism 95100. Such connection may be facilitated by a piercing member, such as a needle, penetrating a pierceable seal of the drug container of the drive mechanism 95100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present disclosure, the piercing member of the fluid pathway connector is caused to penetrate the pierceable seal of the drug container of the drive mechanism by direct action of the user, such as by depression of the activation mechanism by the user. For example, the activation mechanism itself may bear on the fluid pathway connector such that displacement of the activation mechanism from its original position also causes displacement of the fluid pathway connector. In one such embodiment, the fluid pathway connector may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 95300 and the sterile fluid conduit 9530 are provided hereinafter in later sections in reference to other embodiments.

XIV.C. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure.

In at least one embodiment, the insertion mechanism 95200 includes an insertion mechanism housing having one or more lockout windows, and a base for connection to the assembly platform and/or pump housing (as shown in FIG. 100B and FIG. 100C). The connection of the base to the assembly platform 9520 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9510. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9527 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 95254 (shown in FIG. 100C).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 100B, the lockout pin(s) 95208 may be directly displaced by user depression of the activation mechanism 9514. As the user disengages any safety mechanisms, such as an optional on-body sensor 9524 (shown in FIG. 100C), the activation mechanism 9514 may be depressed to initiate the drug delivery device. Depression of the activation mechanism 9514 may directly cause translation or displacement of control arm 9540 and directly or indirectly cause displacement of lockout pin(s) 95208 from their initial position within locking windows 95202A of insertion mechanism housing 95202. Displacement of the lockout pin(s) 95208 permits insertion biasing member to decompress from its initial compressed, energized state. This decompression of the insertion biasing member drives the needle and the cannula into the body of the user. At the end of the insertion stage, the refraction biasing member is permitted to expand in the proximal direction from its initial energized state. This axial expansion in the proximal direction of the refraction biasing member refracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

XIV.D. Drive Mechanism

With reference to the embodiments shown in FIGS. 101 and 102, drive mechanism 95100 includes a drive housing 95130, and a drug container 9550 having a cap 9552, a pierceable seal 9556, a barrel 9558, and a plunger seal 9560. A drug chamber 9521, located within the barrel 9558 between the pierceable seal and the plunger seal 9560, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism may further include a connection mount 9554 to guide the insertion of the piercing member of the fluid pathway connector into the barrel 9558 of the drug container 9550. The drive mechanism 95100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 95100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 101 and FIG. 102, the drive mechanism 95100 includes a drug container 9550 having a cap 9552, a pierceable seal 9556, a barrel 9558, and a plunger seal 9560, and optionally a connection mount 9554. The drug container 9550 is mounted to a distal end of a drive housing 130. Compressed within the drive housing 95130, between the drug container 9550 and the proximal end of the housing 95130, are a drive biasing member 95122 and a piston 95110, wherein the drive biasing member 95122 is configured to bear upon an interface surface 95110C of the piston

95110, as described further herein. Optionally, a cover sleeve 95140 may be utilized to engage the piston 95110 and cover the drive biasing member 95122 to hide the biasing member 95122 from user view upon expansion from its initial energized state. The cover sleeve 95140 may be configured to engage and slide upon the piston 95110, between the piston 95110 and the distal end of the drive mechanism housing 95130 to hide the biasing member 95122 from user view upon expansion from its initial energized state.

As shown in FIG. 102, the variable rate controlled delivery drive mechanism 95100 of the present disclosure may utilize a telescoping drive assembly which incorporates a gear drive 95120 having a gear 95520 and a substantially axial internal pass-through 95120A, within which at least partially resides a first screw 95124 having a substantially axial pass-through 95124A and an external first pitch 95124B. The external first pitch 95124B is configured to engage and rotationally translate upon or within a first nut 95126 which also resides within the internal pass-through 95120A of the gear drive 95120 (such as at the distal end of the internal pass-through 95120A). Similarly, a second nut 95128 resides within the axial pass-through 95124A of the first screw 95124 and is configured to engage and rotationally translate a second screw 95132 having an external second pitch 95132B. More accurately, the second nut 95128 resides within an axial post 95110B of the piston 95110, which itself resides at least partially within the axial pass-through 124A of the first screw 95124. The second nut 95128 is configured to engage and rotationally translate upon or around the second screw 95132 having the external second pitch 95132B. These aspects are more clearly visible with reference to FIGS. 103A-103C and FIGS. 104A-104C. Because of this configuration of components, and because the axial rotation of the gear drive 95120 indirectly causes axial translation of the piston 95110, the variable rate controlled delivery drive mechanism shown in FIGS. 101, 102, 103A-103C and 104A-104C is referred to as a "telescoping" drive mechanism. The gear drive 95120, notably, does not drive the delivery but only controls the delivery motion. The gear drive 95120 controls the motion of the piston 95110 and plunger seal 9560, but does not apply the force necessary for drug delivery. Instead, the gear drive 95120 merely meters or permits translation of the piston 95110 and plunger seal 9560 which are being driven to axially translate by the biasing member 95122. Because the axial translation of the piston 95110 and plunger seal 9560 are driven by biasing member 95122, and the gear drive 95120 is merely metering or permitting axial translation, the force or power needed to meter the axial translation by the gear drive 95120 is much smaller than that which would be required if the gear drive did drive the delivery. Accordingly, a smaller motor may be utilized by the embodiments of the present disclosure. The motor 95530 may, accordingly, be selected from a variety of electromechanical sources capable of incremental motion, such as brushed DC motors, EC motors, stepper motors, solenoids, or other technologies that can produce controlled motion. In at least one embodiment, the motor 95530 is most preferably a stepper motor.

Alternatively, a non-telescoping drive mechanism, as shown in FIGS. 105, 106, 107A-107C and 108A-108C may be utilized within the embodiments of the present disclosure. Referring now to the embodiment of the drive mechanism shown in FIG. 105 and FIG. 106, the drive mechanism 951100 includes a drug container 951050 having a cap 951052, a pierceable seal 951056, a barrel 951058, and a plunger seal 951060, and optionally a connection mount 951054. The drug container 951050 is mounted to a distal end of a drive housing 951130. Compressed within the drive housing 951130, between the drug container 951050 and the proximal end of the housing 951130, are a drive biasing member 951122 and a piston 951110, wherein the drive biasing member 951122 is configured to bear upon an interface surface 951110C of the piston 951110, as described further herein. As shown in FIG. 106, the variable rate controlled delivery drive mechanism 951100 of the present disclosure may utilize a non-telescoping drive assembly which incorporates a gear 951520 connected to the proximal end of a drive screw 951124 having an external pitch 951124B. The external pitch 951124B is configured to engage and rotationally translate upon or within a nut 951126. As the gear 951520 and drive screw 951124 are axially rotated, the threaded engagement between the drive screw 951124 and the nut 951126 permits axial translation of the piston 951110 by the biasing member 951122. These aspects are more clearly visible with reference to FIGS. 107A-107C and FIGS. 108A-108C. Because the axial rotation of the drive screw 951124 directly causes axial translation of the piston 951110, such embodiments of the present disclosure are referred to herein as "non-telescoping". As stated above with regard to the first embodiment, the drive screw 951124, notably, does not drive the delivery but only controls the delivery motion. The drive screw 951124 controls the motion of the piston 951110 and plunger seal 951060, but does not apply the force necessary for drug delivery. Instead, the drive screw 951124 merely meters or permits translation of the piston 951110 and plunger seal 951060 which are being driven to axially translate by the biasing member 951122. Because the axial translation of the piston 951110 and plunger seal 951060 are driven by biasing member 951122, and the drive screw 951124 is merely metering or permitting axial translation, the force or power needed to meter the axial translation by the drive screw 951124 is much smaller than that which would be required if the drive screw did drive the delivery. Accordingly, a smaller motor may be utilized by the embodiments of the present disclosure. The motor 951530 may, accordingly, be selected from a variety of electromechanical sources capable of incremental motion, such as brushed DC motors, EC motors, stepper motors, solenoids, or other technologies that can produce controlled motion. In at least one embodiment, the motor 951530 is most preferably a stepper motor.

FIGS. 103A-103C and FIGS. 104A-104C show the progression of the variable rate controlled delivery drive mechanism, according to the embodiment shown in FIGS. 101-102 having a telescoping drive mechanism configuration, as it progresses through activation, controlled delivery of a drug substance, and completion of drug delivery. As shown, a gear transmission assembly 95500 having a motor 95530 may be utilized to meter or otherwise prevent free axial translation of the biasing member 95122 used to push a plunger seal 9560 for the delivery of a drug substance out of drug chamber 9521. The gear transmission assembly 95500 is further detailed below with reference to FIGS. 109A-109B. Upon actuation of the variable rate controlled delivery drive mechanism 95100 by the user, such as by activation of the power and control system, the motor 95530 is caused to rotate the components of the gear transmission assembly 95500 to correspondingly rotate gear 95520. Substantially simultaneously or in advance of such activation of the motor 95530, the biasing member 95122 is unlocked or otherwise permitted to release from its initial energized state. The biasing member 95122 is positioned within the drive mechanism housing 95130 and held in an initial energized state between the drive mechanism housing 95130 and the interior of the interface surface 95110C of piston 95110. Upon such unlocking or release the biasing member 95122 will act upon and push the piston 95110 (and the plunger seal 9560 located substantially adjacent the piston 95110 on the other side of the interface surface 95110C) to drive the plunger seal 60 for drug delivery, if the biasing member 95122 is unrestrained or not otherwise metered. The novel variable rate controlled delivery drive mechanisms of the present disclosure are configured to provide such restraint or metering on the expansion of the biasing member 95122. Depending on a desired drug delivery rate or profile, as may be pre-programmed or dynamically controlled by the power and control system, the motor 95530 of the gear assembly mechanism 95500 may function to incrementally permit axial expansion of the biasing member 95122 and, thus, axial translation of the piston 95110 and plunger seal 9560.

As the components of the gear assembly mechanism 95500 are rotated by function of the motor 530 and corresponding gear interactions, gear 95520 is caused to rotate. A gear drive 95120 is connected to, or formed as part of, gear 95520 such that axial rotation of the gear 9520 causes axial rotation of the gear drive 95120. Gear drive 95520 has an internal pass-through 95120 that is substantially axial, within which at least partially resides a first screw 95124 having a substantially axial pass-through 95124A and an external first pitch 95124B. The external first pitch 95124B is configured to engage and rotationally translate upon or within a first nut 95126 which also resides within the internal pass-through 95120A of the gear drive 95120 (such as at the distal end of the internal pass-through 95120A). The first nut 95126 is rotationally keyed (i.e., constrained) or otherwise held in position (but permitted to axially translate) within the internal pass-through 95120A of gear drive 95120. As stated above, upon activation of the drive mechanism by the user, biasing member 95122 will apply a force to piston 95110 which is metered or restrained by the drive mechanism. As the gear drive 95120 is caused to axially rotate, the keyed engagement of the first nut 95126 with the gear drive 95120 and the movable engagement between corresponding gear teeth of the first screw 95124 (at the external first pitch 95124B) with the first nut 95126 permits axial translation of the first screw 95124. Similarly, a second nut 95128 resides within the axial pass-through 95124A of the first screw 95124 and is configured to engage and rotationally translate a second screw 95132 having an external second pitch 95132B. More accurately, the second nut 95128 resides within an axial post 95110B of the piston 95110, which itself resides at least partially within the axial pass-through 95124A of the first screw 95124. The second nut 95128 is configured to engage and rotationally translate upon or around the second screw 95132 having the external second pitch 95132B.

Accordingly, axial rotation (and translation) of the first screw 95124 permits axial rotation and axial translation of the second screw 95132. Accordingly, axial rotation of the gear 95520 and gear drive 95120 causes axial rotation and axial translation of the first screw 95124. This is shown in the transition from FIG. 103A to FIG. 103B to FIG. 103C, and in the transition from FIG. 104A to FIG. 104B to FIG. 104C. Because the biasing member 95122 is applying a force to piston 95110, the metering by the components of the drive mechanism permits the biasing member 95122 to axially translate the piston 95110 and plunger seal 9560 at variable rates or profiles for controlled drug delivery.

The variable rate controlled delivery drive mechanisms of the present disclosure can, of course, be configured such that both the first screw and second screw are caused to axially translate simultaneously, such as by manipulating the pitch ratio of the external first pitch 95124B to the external second pitch 95132B and their respective interactions with first nut 95126 and second nut 95128. As stated above, the gear drive 95120 notably does not drive the delivery but only controls the delivery motion. The gear drive 95120 controls the motion of the piston 19510 and plunger seal 9560, but does not apply the force necessary for drug delivery. Instead, the gear drive 95120 merely meters or permits translation of the piston 95110 and plunger seal 9560 which are being driven to axially translate by the biasing member 95122. Because the axial translation of the piston 95110 and plunger seal 9560 are driven by biasing member 95122, and the gear drive 95120 is merely metering or permitting axial translation, the force or power needed to meter the axial translation by the gear drive 95120 is much smaller than that which would be required if the gear drive did drive the delivery. Optionally, a cover sleeve 140 may be utilized to hide the visibility of the biasing member 95122 and other internal components from the user as the piston 95110 is axially translated by the biasing member 95122. The cover sleeve 95140 may also assist in maintaining a rotationally fixed relationship between the non-rotating (relative to gear drive 95120) components of the drive mechanism, including for example the drive mechanism housing 95130 and the piston 95110. This rotational constraint permits the screws and corresponding nuts to axially rotate, while the piston is permitted to axially translate. The embodiments shown in these figures utilize a telescoping drive mechanism configuration to obtain greater available axial translation while maintaining a smaller arrangement or dimensional footprint when in the compressed position.

FIGS. 107A-107C and FIGS. 108A-108C show the progression of the variable rate controlled delivery drive mechanism, according to the embodiment shown in FIGS. 105-106 having a non-telescoping drive mechanism configuration, as it progresses through activation, controlled delivery of a drug substance, and completion of drug delivery. As shown, a gear transmission assembly 951500 having a motor 951530 may be utilized to meter or otherwise prevent free axial translation of the biasing member 951122 used to push a plunger seal 951060 for the delivery of a drug substance out of drug chamber 951021. The gear transmission assembly 951500 is further detailed below with reference to FIGS. 109A-109B. Upon actuation of the variable rate controlled delivery drive mechanism 951100 by the user, such as by activation of the power and control system, the motor 95530 is caused to rotate the components of the gear transmission assembly 951500 to correspondingly rotate gear 951520. Substantially simultaneously or in advance of such activation of the motor 951530, the biasing member 951122 is unlocked or otherwise permitted to release from its initial energized state. The biasing member 951122 is positioned within the drive mechanism housing 951130 and held in an initial energized state between the drive mechanism housing 951130 and the interior of the interface surface 951110C of piston 951110. Upon such unlocking or release the biasing member 951122 will act upon and push the piston 951110 (and the plunger seal 951060 located substantially adjacent the piston 951110 on the other side of the interface surface 951110C) to drive the plunger seal 951060 for drug delivery, if the biasing member 951122 is unrestrained or not otherwise metered. The novel variable rate controlled delivery drive mechanisms of the present disclosure are configured to provide such restraint or metering on the expansion of the biasing member 951122. Depending on a desired drug delivery rate or profile, as may be pre-programmed or dynamically controlled by the power and control system, the motor 951530 of the gear assembly mechanism 951500 may function to incrementally permit axial expansion of the biasing member 951122 and, thus, axial translation of the piston 951110 and plunger seal 951060.

As the components of the gear assembly mechanism 951500 are rotated by function of the motor 951530 and corresponding gear interactions, gear 951520 is caused to rotate. A drive screw 951124 having an external pitch 951124B is connected to, or formed as part of, gear 951520. The external pitch 951124B is configured to engage and rotationally translate upon or within a nut 951126. As the gear 951520 and drive screw 951124 are axially rotated, the threaded engagement and corresponding interaction between the external pitch 951124B of the drive screw 951124 and the nut 951126 permits axial translation of the piston 951110 by the biasing member 951122. As stated above with reference to the telescoping embodiments of the present disclosure, the piston 951110 of the non-telescoping embodiments is rotationally keyed (i.e., constrained) to the drive housing 951130, relative to the drive screw 951124. Nut 951126 is likewise keyed to piston 951110, which configuration allows for axial translation of the piston 951110. Because the axial rotation of the drive screw 951124 directly permits axial translation of the piston 951110, such embodiments of the present disclosure are referred to herein as "non-telescoping". As stated above with regard to the first embodiment, the drive screw 951124, notably, does not drive the delivery but only controls the delivery motion. The drive screw 951124 controls the motion of the piston 951110 and plunger seal 951060, but does not apply the force necessary for drug delivery. Instead, the drive screw 951124 merely meters or permits translation of the piston 951110 and plunger seal 1060 which are being driven to axially translate by the biasing member 951122. Optionally, a washer or bearing 951580 may be utilized to facilitate axial rotation of gear 951520 within the drive mechanism housing 951130. Additionally, the drive mechanisms described herein may include one or more compliance features which enable additional axial translation of the plunger seal 9560, 951060 to, for example, ensure that substantially the entire drug dose has been delivered to the user. For example, the plunger seal 9560, 951060, itself, may have some compressibility permitting a compliance push of drug fluid from the drug container.

The novel variable rate drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 9556 and the interconnect located proximal to the plunger seal 9560 such that, upon substantially complete axial translation (and the optional compliance push) of the plunger seal 9560 within the barrel 9558, the status switch and interconnect coordinate to enable a transmission to the power and control system to signal end-of-dose to the user. This configuration further enables true end-of-dose indication to the user.

FIGS. 109A and 109B shows an isometric view of certain components of a variable rate controlled delivery drive mechanism, according to at least one embodiment of the present disclosure. While such components are shown with reference to the embodiment detailed in FIGS. 101, 102, 103A-103C, and 104A-104C, the same or similar components may be utilized with the other embodiments of the present disclosure. In at least one embodiment, the gear assembly mechanism 95500 of the variable rate drive mechanisms 95100 of the present disclosure utilizes a motor 95530 with pinion 95530A. The pinion 95530A contacts a first gear 95526B of a first compound gear 95526. A second gear 95526A of the first compound gear 95526 contacts a first gear 95528B of a second compound gear 95528, and a second gear 95528A (not visible) of the second compound gear 95528 contacts a trigger gear 95524. Trigger gear 95524 contacts gear 95520 to relay motion to the remainder of drive mechanism 95100. As the motor 95530 acts upon the gear assembly mechanism 95500, the motion is conveyed by interfacing gear teeth of the pinion 95530A, first compound gear 95526, second compound gear 95528, trigger gear 95524, and gear 95520. As detailed above, such motion is utilized to permit, meter or otherwise restrain the axial translation of the piston 95110 by the biasing member 95122, thereby driving the plunger seal for drug delivery. As the trigger gear 95524 rotates, a status reader 95600 may read or recognize one or more corresponding status triggers on the trigger gear 95524 to provide incremental status indication before, during, and after operation of the variable rate controlled delivery drive mechanism. While the drive mechanisms of the present disclosure are described with reference to the gear assembly mechanism shown in FIGS. 109A and 95109B, a range of gear assembly configurations with the appropriate gear reduction based on the load and motor chosen would be acceptable and capable of being employed within the embodiments of the present disclosure, as would readily be appreciated by an ordinarily skilled artisan. Accordingly, the embodiments of the present disclosure are not limited to the specific gear assembly mechanism described herein, which is provided as an exemplary embodiment of such mechanisms for employment within controlled delivery drive mechanisms and drug delivery pumps.

As described above, a number of status readers may be utilized within the embodiments of the present disclosure. For example, the drive mechanism shown in FIG. 109A may utilize a mechanical status reader 95600 which is physically contacted by gear teeth of the trigger gear 95524. As the status reader 95600 is contacted by the status trigger(s), which in this exemplary embodiment are the gear teeth of the trigger gear 95524, the status reader 95600 measures the rotational position of the trigger gear 95524 and transmits a signal to the power and control system for status indication to the user. Additionally or alternatively, as shown in FIG.

95109B, the drive mechanism may utilize an optical status reader 951600. The optical status reader 951600 may be, for example, a light beam that is capable of recognizing a motion and transmitting a signal to the power and control system. For example, the drive mechanism shown in FIG. 109B may utilize an optical status reader 951600 that is configured to recognize motion of the gear teeth of the trigger gear 95524. As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user.

Returning now to the embodiments shown in FIGS. 101-102 and FIGS. 105-106, a fluid, such as a drug fluid, may be contained within barrel 9558, 951058, in a drug chamber 9521, 951021 between plunger seal 9560, 951060 and pierceable seal 9556, 951056, for delivery to a user. The pierceable seal is adjacent or retained at least partially within cap 9552, 951052. Upon activation by the user, a fluid pathway connector may be connected to the drug container through the pierceable seal. As described above, this fluid connection may be facilitated by a piercing member of the fluid pathway connector which pierces the pierceable seal and completes the fluid pathway from the drug container, through the fluid pathway connector, the fluid conduit, the insertion mechanism, and the cannula for delivery of the drug fluid to the body of the user. Initially, one or more locking mechanisms (not shown) may retain the biasing member 95122, 951122 in an initial energized position within piston 95110, 951110. Directly or indirectly upon activation of the device by the user, the locking mechanism may be removed to permit operation of the drive mechanism. The piston 95110, 951110 and biasing member 95122, 951122 are both initially in a compressed, energized state behind (i.e., proximal to) the plunger seal 9560, 951060. The biasing member 95122, 951122 may be maintained in this state until activation of the device between internal features of drive housing 95130, 951130 and interface surface 95110C, 951110C of piston 95110, 951110. As the locking mechanism is removed or displaced, biasing member 95122, 951122 is permitted to expand (i.e., decompress) axially in the distal direction (i.e., in the direction of the hatched arrow). Such expansion causes the biasing member 95122, 1122 to act upon and distally translate interface surface 95110C, 951110C and piston 95110, 951110, thereby distally translating plunger seal 9560, 951060 to push drug fluid out of the drug chamber 9521, 951021 of barrel 9558, 951058. Distal translation of the piston 95110, 951110 and plunger seal 60, 1060 continues to force fluid flow out from barrel 9558, 951058 through pierceable seal 56, 1056. In at least one embodiment, an end-of-dose status indication may be provided to the user once the status reader recognizes a status trigger positioned on the trigger gear to substantially correspond with the end of axial travel of the piston 95110, 951110 and plunger 9560, 951060. The gear assembly mechanism 95500, 951500 and novel drive mechanisms 95100, 951100 of the present disclosure thus permit, meter, or otherwise restrain the free axial expansion of the biasing member 95122, 951122 to control the rate or profile of drug delivery. The novel embodiments of the present disclosure also thus provide incremental status indication to the user.

Assembly and/or manufacturing of variable rate controlled delivery drive mechanism 95100, 951100, drug delivery pump 9510, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9550 may first be assembled and filled with a fluid for delivery to the user. The drug container 9550 includes a cap 9552, a pierceable seal 9556, a barrel 9558, and a plunger seal 9560. The pierceable seal 9556 may be fixedly engaged between the cap 9552 and the barrel 9558, at a distal end of the barrel 9558. The barrel 9558 may be filled with a drug fluid through the open proximal end prior to insertion of the plunger seal 9560 from the proximal end of the barrel 9558. An optional connection mount 9554 may be mounted to a distal end of the pierceable seal 9556. The connection mount 9554 may guide the insertion of the piercing member of the fluid pathway connector into the barrel 9558 of the drug container 9550. The drug container 50 may then be mounted to a distal end of drive housing 95130.

A drive biasing member 95122 may be inserted into a distal end of the drive housing 95130. Optionally, a cover sleeve 95140 may be inserted into a distal end of the drive housing 130 to substantially cover biasing member 95122. A piston may be inserted into the distal end of the drive housing 95130 such that it resides at least partially within an axial pass-through of the biasing member 95122 and the biasing member 95122 is permitted to contact a piston interface surface 95110C of piston 110 at the distal end of the biasing member 95122. The piston 110 and drive biasing member 95122, and optional cover sleeve 95140, may be compressed into drive housing 95130. Such assembly positions the drive biasing member 95122 in an initial compressed, energized state and preferably places a piston interface surface 95110C in contact with the proximal surface of the plunger seal 9560 within the proximal end of barrel 9558. The piston, piston biasing member, contact sleeve, and optional components, may be compressed and locked into the ready-to-actuate state within the drive housing 95130 prior to attachment or mounting of the drug container 9550. The drive screw 951124, or combination of first screw 95124 and second screw 95132, and their corresponding engagement components may be pre-assembled, connected to the piston 95110, mounted into the drive mechanism housing 95130 and connected to gear drive 95120 and gear 95520 (or alternatively connected to gear 951520) which is placed in position through the proximal end of the drive mechanism housing 95130 such that it extends proximally therefrom to engage the gear assembly mechanism 95500, 951500 for operation.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 100B.

Certain optional standard components or variations of drive mechanism 95100, drive mechanism 951100, or drug delivery device 9510 are contemplated while remaining within the breadth and scope of the present disclosure. For example, the embodiments may include one or more batteries utilized to power the motor, drive mechanisms, and drug delivery devices of the present disclosure. A range of batteries known in the art may be utilized for this purpose. Additionally, upper or lower housings may optionally contain one or more transparent or translucent windows 9518, as shown in FIG. 100A, to enable the user to view the operation of the drug delivery device 9510 or verify that drug dose has completed. Similarly, the drug delivery device 9510 may contain an adhesive patch 9526 and a patch liner 9528 on the bottom surface of the housing 9512. The adhesive patch 9526 may be utilized to adhere the drug delivery device 9510 to the body of the user for delivery of the drug dose. As would be readily understood by one having ordinary skill in the art, the adhesive patch 9526 may have an adhesive surface for adhesion of the drug delivery device to the body of the user. The adhesive surface of the adhesive patch 9526 may initially be covered by a non-adhesive patch liner 9528, which is removed from the adhesive patch 9526 prior to placement of the drug delivery device 9510 in contact with the body of the user. Removal of the patch liner 9528 may further remove the sealing membrane 95254 of the insertion mechanism 95200, opening the insertion mechanism to the body of the user for drug delivery (as shown in FIG. 100C).

Similarly, one or more of the components of variable rate controlled delivery drive mechanism 95100, drive mechanism 951100, and drug delivery device 9510 may be modified while remaining functionally within the breadth and scope of the present disclosure. For example, as described above, while the housing of drug delivery device 9510 is shown as two separate components upper housing 9512A and lower housing 9512B, these components may be a single unified component. As discussed above, a glue, adhesive, or other known materials or methods may be utilized to affix one or more components of the variable rate controlled delivery drive mechanism and/or drug delivery device to each other. Alternatively, one or more components of the variable rate controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the variable rate drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such variable rate drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel variable rate drive mechanisms of the present disclosure may be directly or indirectly activated by the user. Furthermore, the novel configurations of the variable rate controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the variable rate controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a variable rate controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the variable rate controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a user, wherein a drive gear or screw acting on the piston is utilized to restrain the free axial translation of the piston. The method of operation of the insertion mechanism and the drug delivery device may be better appreciated with reference to FIGS. 103A-103C, FIGS. 104A-104C, FIGS. 107A-107C, and FIGS. 108A-108C, as described above.

XV. Additional Embodiments of Multi-Function Drive Mechanism

At least some of the drug delivery devices described in this application, including at least those described in connection with FIGS. 1A-2B, 33A-33C, 80A-85C, 86A-91, 92-99, and 100A-109B may be configured to incorporate the embodiments of the drive mechanism described below in connection with FIGS. 69A-75B. The embodiments of the drive mechanism described below in connection with FIGS. 69A-75B may be used to replace, in its entirety or partially, the above-described drive mechanism 100, 6100, 8100, 9210, 9310, 9410, or 9510, or any other drive mechanism described herein, where appropriate.

The present disclosure provides multi-function drive mechanisms for the controlled delivery of drug substances, controlled drug delivery pumps with such drive mechanisms, the methods of operating such devices, and the methods of assembling such devices. Notably, the multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a multi-function drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the body of the user. A piston, and one or more biasing members, wherein the one or more biasing members are initially retained in an energized state and is configured to bear upon an interface surface of the piston, may also be incorporated in the multi-function drive mechanism. The piston is configured to translate substantially axially within a drug container having a plunger seal and a barrel. A tether is connected at one end to the piston and at another end to a winch drum/gear of a regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of a regulating mechanism of the multi-function drive mechanism to meter the free expansion of the biasing member from its initial energized state and the free axial translation of the piston upon which the biasing member bears upon.

In at least one embodiment of the present disclosure, the regulating mechanism is gear assembly driven by an actuator of the multi-function drive mechanism. The regulating mechanism retards or restrains the distribution of tether, only allowing it to advance at a regulated or desired rate. This restricts movement of piston within barrel, which is pushed by one or more biasing members, hence controlling the movement of plunger seal and delivery of the drug contained in chamber. As the plunger seal advances in the drug container, the drug substance is dispensed through the sterile pathway connection, conduit, insertion mechanism, and into the body of the user for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a winch gear coupled to a winch drum/gear upon which the tether may be releasably wound. Accordingly, rotation of the gear assembly initiated by the actuator may be coupled to winch drum/gear (i.e., through the gear assembly), thereby controlling the distribution of tether, the rate of expansion of the biasing members and the axial translation of the piston, and the rate of movement of plunger seal within barrel to force a fluid from drug chamber. The rotational movement of the winch drum/gear, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, initial motion by the actuator of the multi-function drive mechanism causes rotation of main/star gear. In one manner, main/star gear conveys motion to the regulating mechanism through gear assembly. In another manner, main/star gear conveys motion to the needle insertion mechanism through gear. As gear is rotated by main/star gear, gear engages the needle insertion mechanism to initiate the fluid pathway connector into the user, as described in detail above. In one particular embodiment, needle insertion mechanism is a rotational needle insertion mechanism. Accordingly, gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the user, as described in detail herein.

In at least one embodiment, rotation of the needle insertion mechanism in this manner may also cause a connection of a sterile fluid pathway to a drug container to permit fluid flow from the drug container to the needle insertion mechanism for delivery to the user. Ramp aspect of needle insertion mechanism is caused to bear upon a movable connection hub of the sterile fluid pathway connector. As the needle insertion mechanism is rotated by the multi-function drive mechanism, ramp aspect of needle insertion mechanism bears upon and translates movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum/gear of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum/gear upon which the tether may be releasably wound, rotation of the winch drum/gear releases the tether from the winch drum/gear to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum/gear is coupled to a regulating mechanism which controls rotation of the winch drum/gear and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum/gear and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum/gear on the free axial translation of the piston upon which the biasing member bears upon to meet a desired drug delivery rate or profile, to change the dose volume for delivery to the user, and/or to otherwise start, stop, or pause operation of the drive mechanism.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

The novel embodiments of the present disclosure provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present disclosure may include one or more additional components which may be considered standard components in the industry of medical devices. For example, the embodiments may include one or more batteries utilized to power the motor, drive mechanisms, and drug delivery devices of the present disclosure. The components, and the embodiments containing such components, are within the contemplation of the present disclosure and are to be understood as falling within the breadth and scope of the present disclosure.

The present disclosure provides multi-function drive mechanisms for the controlled delivery of drug substances and drug delivery pumps which incorporate such multi-function drive mechanisms. The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 69A-69C show an exemplary drug delivery device according to at least one embodiment of the present disclosure with the top housing removed so that the internal components are visible. The drug delivery device may be utilized to administer delivery of a drug treatment into a body of a user. As shown in FIGS. 69A-69C, the drug delivery device 9010 includes a pump housing 9012. Pump housing 9012 may include one or more housing subcomponents which are fixedly engageable to facilitate easier manufacturing, assembly, and operation of the drug delivery device. For example, drug delivery device 9010 includes a pump housing 9012 which may include an upper housing and a lower housing (not shown for ease of viewing internal components). The pump housing 9012 may include one or more tamper evidence features to identify if the drug delivery device has been opened or tampered with. For example, the pump housing 9012 may include one or more tamper evidence labels or stickers, such as labels that bridge across the upper housing and the lower housing. Additionally or alternatively, the housing 9012 may include one or more snap arms or prongs connecting between the upper housing and the lower housing. A broken or altered tamper evidence feature would signal to the user, the physician, the supplier, the manufacturer, or the like, that the drug delivery device has potentially been tampered, e.g., by accessing the internal aspects of the device, so that the device is evaluated and possibly discarded without use by or risk to the user. The drug delivery device may further include an activation mechanism, a status indicator, and a window. Window may be any translucent or transmissive surface through which the operation of the drug delivery device may be viewed. As shown in FIG. 69B, drug delivery device 9010 further includes assembly platform 9020, sterile fluid conduit 9030, drive mechanism 90100 having drug container 9050, insertion mechanism 90200, fluid pathway connector 90300, and a power and control system (not shown). One or more of the components of such drug delivery devices may be modular in that they may be, for example, pre-assembled as separate components and configured into position onto the assembly platform 9020 of the drug delivery device 9010 during manufacturing.

The pump housing 9012 contains all of the device components and provides a means of removably attaching the device 9010 to the skin of the user. The pump housing 9012 also provides protection to the interior components of the device 9010 against environmental influences. The pump housing 9012 is ergonomically and aesthetically designed in size, shape, and related features to facilitate easy packaging, storage, handling, and use by users who may be untrained and/or physically impaired. Furthermore, the external surface of the pump housing 9012 may be utilized to provide product labeling, safety instructions, and the like. Additionally, as described above, housing 9012 may include certain components, such as one or more status indicators and windows, which may provide operation feedback to the user.

In at least one embodiment, the drug delivery device 9010 provides an activation mechanism that is displaced by the user to trigger the start command to the power and control system. In a preferred embodiment, the activation mechanism is a start button that is located through the pump housing 9012, such as through an aperture between upper housing and lower housing, and which contacts either directly or indirectly the power and control system. In at least one embodiment, the start button may be a push button, and in other embodiments, may be an on/off switch, a toggle, or any similar activation feature known in the art. The pump housing 9012 also provides one or more status indicators and windows. In other embodiments, one or more of the activation mechanism, the status indicator, the window, and combinations thereof may be provided on the upper housing or the lower housing such as, for example, on a side visible to the user when the drug delivery device 9010 is placed on the body of the user. Housing 9012 is described in further detail hereinafter with reference to other components and embodiments of the present disclosure.

Drug delivery device 9010 is configured such that, upon activation by a user by depression of the activation mechanism, the multi-function drive mechanism is activated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In at least one embodiment, such delivery of drug fluid into a user is performed by the multi-function drive mechanism in a controlled manner. One or more optional safety mechanisms may be utilized, for example, to prevent premature activation of the drug delivery device. For example, an optional on-body sensor (not visible) may be provided in one embodiment as a safety feature to ensure that the power and control system, or the activation mechanism, cannot be engaged unless the drug delivery device 9010 is in contact with the body of the user. In one such embodiment, the on-body sensor is located on the bottom of lower housing where it may come in contact with the users body. Upon displacement of the on-body sensor, depression of the activation mechanism is permitted. Accordingly, in at least one embodiment the on-body sensor is a mechanical safety mechanism, such as for example a mechanical lock out, that prevents triggering of the drug delivery device 9010 by the activation mechanism. In another embodiment, the on-body sensor may be an electromechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present disclosure to prevent, for example, premature activation of the drug delivery device. In a preferred embodiment, the drug delivery device 9010 utilizes one or more mechanical on-body sensors. Additional integrated safety mechanisms are described herein with reference to other components of the novel drug delivery devices.

XV.A. Power and Control System

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 90100. In one embodiment, the power and control system interfaces either directly or indirectly with the on-body sensor 9024 to identify when the device is in contact with the user and/or the activation mechanism to identify when the device has been activated. The power and control system may also interface with the status indicator of the pump housing 9012, which may be a transmissive or translucent material which permits light transfer, to provide visual feedback to the user. The power and control system interfaces with the drive mechanism 90100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the body of the user, the power and control system will power the drive mechanism 90100 to begin delivery of the drug treatment through the fluid pathway connector 90300 and sterile fluid conduit 9030 (not shown).

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the user. In such an embodiment, without removal of the drug delivery device from the packaging the drug delivery device cannot be activated. This provides an additional safety mechanism of the drug delivery device and for the user. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, the multi-function drive mechanism is initiated to actuate the insertion mechanism 90200 and the fluid pathway connector 90300, while also permitting the drug fluid to be forced from the drug container. During the drug delivery process, the power and control system is configured to provide a dispensing status signal via the status indicator. After the drug has been administered into the body of the user and after the end of any additional dwell time, to ensure that substantially the entire dose has been delivered to the user, the power and control system may provide an okay-to-remove status signal via the status indicator. This may be independently verified by the user by viewing the drive mechanism and drug dose delivery through the window of the pump housing 9012. Additionally, the power and control system may be configured to provide one or more alert signals via the status indicator, such as for example alerts indicative of fault or operation failure situations.

The power and control system may additionally be configured to accept various inputs from the user to dynamically control the drive mechanisms 90100 to meet a desired drug delivery rate or profile. For example, the power and control system may receive inputs, such as from partial or full activation, depression, and/or release of the activation mechanism, to set, initiate, stop, or otherwise adjust the control of the drive mechanism 90100 via the power and control system to meet the desired drug delivery rate or profile. Similarly, the power and control system may be configured to receive such inputs to adjust the drug dose volume; to prime the drive mechanism, fluid pathway connector, and fluid conduit; and/or to start, stop, or pause operation of the drive mechanism 90100. Such inputs may be received by the user directly acting on the drug delivery device 9010, such as by use of the activation mechanism 9014 or a different control interface, or the power and control system may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug delivery device 9010 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XV. B. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as developed by the assignee of the present disclosure.

In at least one embodiment, the insertion mechanism 90200 includes an insertion mechanism housing having one or more lockout windows, and a base for connection to the assembly platform and/or pump housing (as shown in FIG. 69B and FIG. 69C). The connection of the base to the assembly platform 9020 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9010. The insertion mechanism may further include one or more insertion biasing members, a needle, a retraction biasing member, a cannula, and a manifold. The manifold may connect to sterile fluid conduit 9030 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9027 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the body of the user. At the end of the insertion stage or at the end of drug delivery (as triggered by the multi-function drive mechanism), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the user. Accordingly, the insertion mechanism may be used to insert a needle and cannula into the user and, subsequently, retract the needle while retaining the cannula in position for drug delivery to the body of the user.

In at least one embodiment, as shown in FIG. 75A, the insertion mechanism includes a rotationally biased member 90210 which is initially held in an energized state. In a preferred embodiment, the rotationally biased member is a torsional spring. The rotational biasing member may be prevented from de-energizing by interaction of gear surface

90208 with gear 90112 or, alternatively, by contact of a component of the insertion mechanism with a rotation prevention feature of the drug delivery device. Upon activation of the device, or another input, the rotationally biased member 90210 is permitted to, at least partially, de-energize. This causes one or more components of the insertion mechanism to rotate and, in turn, cause, or allow, the insertion of the needle into the patient. Further, a cannula may be inserted into the patient as described above. At a later time, such as when the control arm or another component of the device recognizes a slack in the tether, the rotationally biased member may be allowed to further de-energize, causing additional rotation of one or more components of the insertion mechanism. This rotation may cause, or allow, the needle to be retracted from the patient. The needle may be fully retracted in a single step or there may be multiple steps of retraction.

XV.C. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9010, the fluid pathway connector 90300 is enabled to connect the sterile fluid conduit 9030 to the drug container of the drive mechanism 90100. Such connection may be facilitated by a piercing member, such as a needle, penetrating a pierceable seal of the drug container of the drive mechanism 90100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the multi-function drive mechanism. Additionally or alternatively, the sterile fluid pathway connector is initiated by movement directly of the multi-function drive mechanism. For example, the multi-function drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 69A-69C, the multi-function drive mechanism performs all of these steps substantially concurrently. The multi-function drive mechanism rotates a gear that acts upon several other components. The gear acts on a gear assembly to control the rate of drug delivery, while also contacting a needle insertion mechanism to introduce a fluid pathway into the user. As the needle insertion mechanism is initiated, the sterile fluid connection is made to permit drug fluid flow from the drug container, through the fluid conduit, into the needle insertion mechanism, for delivery into the patient as the gear and gear assembly of the multi-function drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 90300 and the sterile fluid conduit 9030 are provided hereinafter in later sections in reference to other embodiments.

XV.D. Multi-Function Drive Mechanism

The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. With reference to the embodiments shown in FIGS. 70A-70D and 71A-

71D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism 90100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 90100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the multi-function drive mechanism shown in FIGS. 70A-70D and 71A-71D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. Compressed within the drive housing 90130, between the drug container 9050 and the proximal end of the housing 90130, are one or more drive biasing members 90122 and a piston 90110, wherein the drive biasing members 90122 are configured to bear upon an interface surface 90110C of the piston 90110, as described further herein. Optionally, a cover sleeve (not shown) may be utilized between the drive biasing members 90122 and the interface surface 90110C of the piston 90110 to, for example, promote more even distribution of force from the drive biasing member 90122 to the piston 90110, prevent buckling of the drive biasing members 90122, and/or hide biasing members 90122 from user view. Interface surface 90110C of piston 90110 is caused to rest substantially adjacent to, or in contact with, a proximal end of seal 9060. Although the embodiments shown in FIGS. 70A-70D and 71A-71D show a singular biasing member it is also contemplated that one or more biasing members disposed to act in parallel may be used.

As best shown in FIG. 70D and FIG. 71D, the piston 90110 may be comprised of two components 90110A and 90110B and have an interface surface 90110C to contact the plunger seal. A tether, ribbon, string, or other retention strap (referred to herein as the "tether" 90525) may be connected at one end to the piston 90110A, 90110B. For example, the tether 90525 may be connected to the piston 90110A, 90110B by retention between the two components of the piston 90110A, 90110B when assembled. The tether 90525 is connected at another end to a winch drum/gear 90520 of a delivery control mechanism 90500. Through the use of the winch drum/gear 90520 connected to one end of the tether 90525, and the tether 90525 connected at another end to the piston 90110A, 90110B, the regulating mechanism 90500 functions to control, meter, provide resistance, or otherwise prevent free axial translation of the piston 90110A, 90110B and plunger seal 9060 utilized to force a drug substance out of a drug container 9050. Accordingly, the regulating mechanism 90500 is a portion of the gear assembly 90116 aspect of the multi-function drive mechanism, which together function to control the rate or profile of drug delivery to the user.

As shown in FIGS. 70A-70D and 71A-71D, and in isolation in FIGS. 72 and 73A-73B, in the embodiments of the present disclosure, the regulating mechanism 90500 is gear assembly driven by an actuator 90101 of the multi-function drive mechanism 90100. The regulating mechanism retards or restrains the distribution of tether 90525, only allowing it to advance at a regulated or desired rate. This restricts movement of piston 90110 within barrel 9058, which is pushed by one or more biasing members 90122, hence controlling the movement of plunger seal 9060 and delivery of the drug contained in chamber 9021. As the plunger seal 9060 advances in the drug container 9050, the drug substance is dispensed through the sterile pathway connection 90300, conduit 9030, insertion mechanism 90200, and into the body of the user for drug delivery. The actuator 90101 may be a number of power/motion sources including, for example, a solenoid, a stepper motor, or a rotational drive motor. In a particular embodiment, the actuator 90101 is a rotational stepper motor with a notch that corresponds with the gear teeth of the main/star gear 90102. Commonly, such a rotational stepper motor may be referred to as a 'Pac-Man' motor. In at least one embodiment, the Pac-Man motor has a gear interface within which one or more teeth of the main gear may partially reside during operation of the system. This is more clearly visible in FIGS. 73A-73B. When the gear interface 90101A of the Pac-Man motor 90101 is in alignment with a tooth 90102A of the main gear 90102, rotational motion of the Pac-Man motor 90101 causes gear interface rotation of the main gear 90102. When the Pac-Man motor 90101 is between gear teeth of the main gear, it may act as a resistance for, for example, back-spinning or unwinding of the gear assembly 90116. In one particular embodiment, the Pac-Man motor 90101 utilizes an alternating direction type motor to rotate the Pac-Man motor 90101 backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the motor, coupled with the use of the gear interface cut within the Pac-Man motor, provide suitable safety features to prevent a runaway condition that could potentially lead to over-delivery of drug to the user. Further detail about the gear assembly 90116, regulating mechanism 90500, and multi-function drive mechanism 90100 are provided herein.

In a particular embodiment shown in FIGS. 73A-73B, the regulating element 90500 further includes one or more gears 90511, 90512, 90513, 90514, of a gear assembly 90516. One or more of the gears 90511, 90512, 90513, 90514 may be, for example, compound gears having a small diameter gear attached at a shared center point to a large diameter gear. Gear 90513 may be rotationally coupled to winch drum/gear 90520, for example by a keyed shaft, thereby coupling rotation of gear assembly 90516 to winch drum/gear 90520. Compound gear 90512 engages the small diameter gear 90513 such that rotational movement of the compound gear aspect 90512B is conveyed by engagement of the gears (such as by engagement of corresponding gear teeth) to gear 90513. Compound gear aspect 90512A, the rotation of which is coupled to gear aspect 90512B, is caused to rotate by action of compound gear aspect 90102B of the main/star gear 90102. Compound gear aspect 90102B, the rotation of which is coupled to main/star gear 90102, is caused to rotate by interaction between main/star gear 90102A and interface 90101A of the actuator 90101. Thus, rotation of main/star gear 90102 is conveyed to winch drum/gear 90520. Accordingly, rotation of the gear assembly 90516 initiated by the actuator 90101 may be coupled to winch drum/gear 90520 (i.e., through the gear assembly 90516), thereby controlling the distribution of tether 90525, and the rate of movement of plunger seal 9060 within barrel 9058 to force a fluid from drug chamber 9021. The rotational movement of the winch drum/gear 90520, and thus the axial translation of the piston 90110 and plunger seal 9060, are metered, restrained, or otherwise prevented from free axial translation by other components of the regulating element 90500, as described herein. As described above, the actuator 90101 may be a number of known power/motion sources including, for example, a motor (e.g., a DC motor, AC motor, or stepper motor) or a solenoid (e.g., linear solenoid, rotary solenoid).

The embodiment described above and shown in FIGS. 69A-73D show an actuator 90101 that is in vertical alignment and in direct engagement with the main/star gear 90102. As would readily be appreciated by one having ordinary skill in the mechanical arts, the actuator 90101 could be modified to be in horizontal alignment. Additionally or alternatively, the actuator 90101 could be modified to be in indirect engagement with the main/star gear 90102. The embodiments shown in FIGS. 75A-75B show an actuator 90101 that is in horizontal alignment and indirect engagement with the main/star gear 90102. Such an embodiment may utilize a rack and pinion engagement, a drive screw, or a worm gear 90101W, as shown in FIGS. 75A-75B, to change the direction of motion from horizontal to vertical (i.e., perpendicular interaction). Actuator 90101 rotates worm gear 90101W, which engages gear 90101G and conveys the motion to the Pac-Man gear 90101A. The Pac-Man gear 90101A engages main/star gear 90102 to enable operation of the drive mechanism and the drug delivery device, as described herein. Main/star gear 90102 also drives operation of gear 90112 to enable operation of the needle insertion mechanism 90200, as described herein. In one particular embodiment, the actuator 90101 utilizes an alternating direction type motor to rotate the worm gear 90101W, gear 90101G, and Pac-Man gear 90101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 90101, coupled with the use of the gear interface of the worm gear 90101W, gear 90101G, and Pac-Man gear 90101A with the main/star gear 90102, provide suitable safety features to prevent a runaway condition that could potentially lead to over-delivery of drug to the user. Additionally, the actuator 90101 may include a stop member 90101B that stops the rotation of the Pac-Man gear 90101A against a stop block 90150. Stop block 90150 further prevents over-rotation of the Pac-Man gear 90101A and, accordingly, the main/star gear 90102 to prevent a runaway condition that could potentially lead to over-delivery of drug to the user. For the device to function in this configuration, the Pac-Man gear 90101A must be rotated backwards the other direction before rotating forwards again to progress the main/star gear 90102 because the stop member 90101B prevents over rotation in one direction by interaction with the stop block 90150. Additionally, the geometry of worm gear 90101W may be configured such that it is self-locking and/or cannot be back-driven by gear 90101G. This may be done by configuration of parameters such as: pitch, lead angle, pressure angle, and number of threads. In so doing, runaway conditions of the drive mechanism will be prevented by the worm gears resistance to rotations that are not caused by actuator 90101.

Notably, the regulating mechanisms 90500 of the present disclosure do not drive the delivery of fluid substances from the drug chamber 9021. The delivery of fluid substances from the drug chamber 9021 is caused by the expansion of the biasing member 90122 from its initial energized state acting upon the piston 90110A, 90110B and plunger seal 9060. The regulating mechanisms 90500 instead function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. According to a preferred embodiment, the controlled delivery drive mechanisms and drug delivery devices of the present disclosure include a regulating mechanism indirectly or directly connected to a tether metering the axial translation of the piston 90110A, 90110B and plunger seal 9060, which are being driven to axially translate by the biasing member 90122. The rate of drug delivery as controlled by the regulating mechanism may be determined by: selection of the gear ratio of gear assembly 90516; selection of the main/star gear 90102; selection of the diameter of winding drum/gear 90520; using electromechanical actuator 90101 to control the rate of rotation of the main/star gear 90102; or any other method known to one skilled in the art. By using electromechanical actuator 90101 the rate of rotation of the main/star gear 90102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 90525 by the winch drum/gear 90520 and thereby permit axial translation of the piston 90110 by the biasing member 90122 to translate a plunger seal 9060 within a barrel 9058. The one or more inputs may be provided by the actuation of the activation mechanism, a control interface, and/or a remote control mechanism. The power and control system may be configured to receive one or more inputs to adjust the restraint provided by the tether 90525 and winch drum/gear 90520 on the free axial translation of the piston 90110 upon which the biasing member 90122 bears upon to meet a desired drug delivery rate or profile, to change the dose volume for delivery to the user, and/or to otherwise start, stop, or pause operation of the drive mechanism.

The components of the drive mechanism 90100, upon activation, may be used to drive axial translation in the distal direction of the plunger seal 9060 of the drug container 9050. Optionally, the drive mechanism 90100 may include one or more compliance features which enable additional axial translation of the plunger seal 9060 to, for example, ensure that substantially the entire drug dose has been delivered to the user. For example, the plunger seal 9060, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

The tether 90525 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 90525 that would contact the status reader at the end of axial travel of the piston 90110A, 90110B and plunger 9060 within the barrel 9058 of the drug container 9050. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 90525 to be read or recognized at positions which correspond with the beginning and end of drug delivery, as well as at desired increments during drug delivery. As the drug delivery device is activated and drug delivery is begun by release of the biasing member 90122 and the resulting force applied to the piston 90110A, 90110B and plunger seal 9060, the rate or profile of drug delivery to the user is controlled by the regulating mechanism 90500, gear assembly 90516, and winch drum/gear 90520 releasing the tether 90525 and permitting expansion of the biasing member 90122 and axial translation of the piston 90110A, 90110B and plunger seal 9060. As this occurs, the status triggers of the tether 90525 are contacted or recognized by the status reader and the status of the drive mechanism before, during, and after operation can be relayed to the power and control system to provide feedback to the user. Depending on the number of status triggers located on the tether 90525, the frequency of the incremental status indication may be varied as desired. As described above, a range of status readers may be utilized depending on the status triggers utilized by the system.

In a preferred embodiment, the status reader may apply a tensioning force to the tether 90525. When the system reaches end-of-dose, the tether 90525 goes slack and the status reader 90544 is permitted to rotate about a fulcrum. This rotation may operate an electrical or electromechanical switch, for example a switch, signaling slack in the tether 90525 to the power and control system. Additionally, a gear 90511 of gear assembly 90516 may act as an encoder along with a sensor. The sensor/encoder combination is used to provide feedback of gear assembly rotation, which in turn can be calibrated to the position of piston 90110 when there is no slack in the tether 90525. Together, the status reader and sensor/encoder may provide positional feedback, end-of-dose signal, and error indication, such as an occlusion, by observing slack in the tether 90525 prior to reaching the expected number of motor rotations as counted by the sensor/encoder.

Additional means may exist for terminating or restraining the flow of the medicament in the case of slack in, or failure of, the tether. FIGS. 74A-74B show one such embodiment. Disposed within barrel 9058 are brake 9064, sleeve 9062, and plug 9068, and optionally retainer 9066. Biasing member 90122 bears against sleeve 9062. Tether 90525 is engaged with plug 9068, thereby allowing tether 90525 to restrain the motion of sleeve 9062. This restraint controls the rate of expansion or de-energizing of biasing member 90122. When tether 90525 is under tension, plug 9068 bears against distal face 9064A of brake 9064, causing proximal face 9064B of brake 9064 to bear against sleeve 9062. Due to this contact, and the profile of the distal end 9062A of sleeve 9062, brake 9064 is maintained in a substantially conical configuration as shown in FIG. 74A. In this configuration, expansion or de-energizing of biasing member 90122 is restrained. Also, in this conical configuration, the outer diameter of brake 9064 is less than the inner diameter of barrel 9058, thus translation of the brake is not restrained by contact with the inner wall of the drug container. Also, a portion of brake 9064 is in contact with retainer 9066. Because brake 9064 is maintained in this configuration by plug 9068 and sleeve 9062, translation of sleeve 9062, caused by decompression of biasing member 90122, is transferred to retainer 9066. Likewise, contact of retainer 9066 with plunger seal 9060 causes translation of plunger seal 9060.

As shown in FIG. 74B, in the event of slack in, or failure of, tether 90525, plug 9068 is no longer held in position by tether 90525 and, therefore, no longer restrains motion of sleeve 9062. As biasing member 90122 decompresses or de-energizes, brake 9064 transforms to a relatively less conical or flatter configuration. This may be caused by a natural bias of brake 9064 to transform to this configuration or, alternatively, may be caused by contact of brake 9064 with both retainer 9066 and sleeve 9062. As the brake is transformed, it comes into contact with the inner wall of barrel 9058. The brake thus acts as a wedge to restrict translation of sleeve 9062. This may prevent further translation or may act to restrict the rate of translation. Optionally, restoring tension in the tether may cause the plug to contact the brake and to transform the brake back to its conical configuration and thus restore normal operation of the drug delivery device.

FIGS. 74A-74B show the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 9062 (i.e., applying a braking force). In another embodiment, the brake 9064 could employ a star-shaped or other configuration when in a substantially flattened position so as to make contact with the inner diameter of the barrel 9058 to prevent or restrict further axial translation of sleeve 9062. Without further translation of sleeve 9062, biasing member 90122 cannot expand or de-energize further which, in turn, prevents or restricts further drug delivery to the user. This provides a necessary and useful safety measure for drug delivery, to prevent over-delivery or accelerated delivery of drug to the user.

Referring back to FIGS. 70A-70D and 71A-71D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, as shown in FIGS. 70A-70D and 71A-71D, initial motion by the actuator 90101 of the multi-function drive mechanism 90100 causes rotation of main/star gear 90102. Main/star gear 90102 is shown as a compound gear with aspects 90102A and 90102B (see FIG. 72). In one manner, main/star gear 90102 conveys motion to the regulating mechanism 90500 through gear assembly 90516. In another manner, main/star gear 90102 conveys motion to the needle insertion mechanism 90200 through gear 90112. As gear 90112 is rotated by main/star gear 90102, gear 90112 engages the needle insertion mechanism 90200 to initiate the fluid pathway connector into the user, as described in detail above. In one particular embodiment, needle insertion mechanism 90200 is a rotational needle insertion mechanism. Accordingly, gear 90112 is configured to engage a corresponding gear surface 90208 of the needle insertion mechanism 90200. Rotation of gear 90112 causes rotation of needle insertion mechanism 90200 through the gear interaction between gear 90112 of the drive mechanism 90100 and corresponding gear surface 90208 of the needle insertion mechanism 90200. Once suitable rotation of the needle insertion mechanism 90200 occurs, for example rotation along axis 'R' shown in FIG. 2B-2C, the needle insertion mechanism may be initiated to create the fluid pathway connector into the user, as described in detail above. In an alternative embodiment, as shown in FIGS. 75A-75B, gear 90112 may indirectly engage the needle insertion mechanism 90200 to initiate the fluid pathway connector into the user. For example, gear 90112 may be configured to engage a corresponding gear surface of a control arm 90202 (visible in FIG. 75B) that contacts or blocks the needle insertion mechanism 90200. Rotation of gear 90112 causes movement of the control arm 90202, which may initiate or permit rotation of needle insertion mechanism 90200. Such a needle insertion mechanism, as shown in FIGS. 75A-75B, includes a rotationally biased member 90210 which is initially held in an energized state. The rotational biasing member may be prevented from de-energizing by contact of a component of the insertion mechanism with a rotation prevention feature, such as a blocking aspect of the control arm, of the drug delivery device. Upon activation of the device, or another input, the rotationally biased member 90210 is permitted to, at least partially, de-energize. This causes one or more components of the insertion mechanism to rotate and, in turn, cause, or allow, the insertion of the needle into the patient. Further, a cannula may be inserted into the patient as described above. At a later time, such as when the control arm or another component of the device recognizes a slack in the tether 90525, the rotationally biased member may be allowed to further de-energize, such as by further interaction with the control arm, causing additional rotation of one or more components of the insertion mechanism. This rotation may cause, or allow, the needle to be retracted from the patient. The needle may be fully retracted in a single step or there may be multiple steps of retraction.

As shown in FIGS. 70A-70D and 71A-71D, rotation of the needle insertion mechanism 90200 in this manner may also cause a connection of a sterile fluid pathway to a drug container to permit fluid flow from the drug container to the needle insertion mechanism for delivery to the user. Ramp aspect 90222 of needle insertion mechanism 90200 is caused to bear upon a movable connection hub 90322 of the sterile fluid pathway connector 90300. As the needle insertion mechanism 90200 is rotated by the multi-function drive mechanism 90100, ramp aspect 90222 of needle insertion mechanism 90200 bears upon and translates movable connection hub 90322 of the sterile fluid pathway connector 90300 to facilitate a fluid connection therein. Such translation may occur, for example, in the direction of the hollow arrow along axis 'C' shown in FIGS. 70B and 71B. In at least one embodiment, the needle insertion mechanism 90200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism 90500 and/or one or more of the status readers as described above. During these stages of operation, delivery of fluid substances from the drug chamber 9021 may be initiated, on-going, and/or completed by the expansion of the biasing member 90122 from its initial energized state acting upon the piston 90110A, 90110B and plunger seal 9060. As described above, the regulating mechanisms 90500 function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. This is visible through the progression of the components shown in FIGS. 70A-70D and 71A-71D. The motion of the piston 90110A, 90110B and plunger seal 9060 as they are pushed by the expansion of the biasing member 90122 from its initial energized state are shown in the direction of the solid arrow along axis 'A' from proximal or first position 'P' to the distal or second position 'D', as shown in the transition of FIGS. 70A-70D and 71A-71D.

Further aspects of the novel drive mechanism will be described with reference to FIG. 72 and FIGS. 73A-73B. FIG. 72 shows a perspective view of the multi-function drive mechanism, according to at least a first embodiment, during its initial locked stage. Initially, the tether 90525 may retain the biasing member 90122 in an initial energized position within piston 90110A, 90110B. Directly or indirectly upon activation of the device by the user, the multi-function drive mechanism 90100 may be activated to permit the biasing member to impart a force to piston 90110 and therefore to tether 90525. This force on tether 90525 imparts a torque on winding drum 90520 which causes the gear assembly 90516 and regulating mechanism 90500 to begin motion. As shown in FIG. 73A, the piston 90110 and biasing member 90122 are both initially in a compressed, energized state behind the plunger seal 9060. The biasing member 90122 may be maintained in this state until activation of the device between internal features of drive housing 90130 and interface surface 90110C of piston 90110A, 90110B. As the drug delivery device 9010 is activated and the drive mechanism 90100 is triggered to operate, biasing member 90122 is permitted to expand (i.e., decompress) axially in the distal direction (i.e., in the direction of the solid arrow shown in FIGS. 70A-70D and FIGS. 71A-71D). Such expansion causes the biasing member 90122 to act upon and distally translate interface surface 90110C and piston 90110, thereby distally translating plunger seal 9060 to push drug fluid out of the drug chamber 9021 of barrel 9058. In at least one embodiment, an end-of-dose status indication may be provided to the user once the status reader contacts or recognizes a status trigger positioned on the tether 90525 to substantially correspond with the end of axial travel of the piston 90110A, 90110B and plunger seal 9060 within the barrel 9058 of the drug container 9050. The status triggers may be positioned along the tether 90525 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 90525 to be read or recognized at positions which correspond with the beginning and end of drug delivery, as well as at desired increments during drug delivery. As shown, tether 90525 passes substantially axially through the drive mechanism housing 90130, the biasing member 90122, and connects to the piston 90110 A, 90110B to restrict the axial translation of the piston 90110A, 90110B and the plunger seal 9060 that resides adjacent thereto.

The novel embodiments of the present disclosure may be utilized to meter, restrain, or otherwise prevent free rotational movement of winding drum 90520 and, thus, axial translation of the components of the controlled delivery drive mechanism 90100. Accordingly, the regulating mechanism 90500 only controls the motion of the drive mechanism, but does not apply the force for the drug delivery. One or more additional biasing members 90122, such as compression springs, may be utilized to drive or assist the driving of the piston 90110. For example, a compression spring may be utilized within the drive housing 90130 for this purpose. The regulating mechanism 90500 only controls, meters, or regulates such action. The controlled delivery drive mechanisms and/or drug delivery devices of the present disclosure may additionally enable a compliance push to ensure that substantially all of the drug substance has been pushed out of the drug chamber 9021. The plunger seal 9060, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear assembly 90516. As the gear assembly 90516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear assembly and regulating mechanism shown in the figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 90101. The change in the rate of movement of actuator 90101 causes a change in the rotation rate of regulating mechanism 90500 which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

Assembly and/or manufacturing of controlled delivery drive mechanism 90100, drug delivery device 9010, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9050 may first be assembled and filled with a fluid for delivery to the user. The drug container 9050 includes a cap 9052, a pierceable seal 9056, a barrel 9058, and a plunger seal 9060. The pierceable seal 9056 may be fixedly engaged between the cap 9052 and the barrel 9058, at a distal end of the barrel 9058. The barrel 9058 may be filled with a drug fluid through the open proximal end prior to insertion of the plunger seal 9060 from the proximal end of the barrel 9058. An optional connection mount 9054 may be mounted to a distal end of the pierceable seal 9056. The connection mount 9054 may guide the insertion of the piercing member of the fluid pathway connector into the barrel 9058 of the drug container 9050. The drug container 9050 may then be mounted to a distal end of drive housing 90130.

One or more drive biasing members 90122 may be inserted into a distal end of the drive housing 90130. Optionally, a cover sleeve 90140 may be inserted into a distal end of the drive housing 90130 to substantially cover biasing member 90122. A piston may be inserted into the distal end of the drive housing 90130 such that it resides at least partially within an axial pass-through of the biasing member 90122 and the biasing member 90122 is permitted to contact a piston interface surface 90110C of piston 90110A, 90110B at the distal end of the biasing member 90122. An optional cover sleeve 90140 may be utilized to enclose the biasing member 90122 and contact the piston interface surface 90110C of piston 90110A, 90110B. The piston 90110A, 90110B and drive biasing member 90122, and optional cover sleeve 90140, may be compressed into drive housing 90130. Such assembly positions the drive biasing member 90122 in an initial compressed, energized state and preferably places a piston interface surface 90110C in contact with the proximal surface of the plunger seal 9060 within the proximal end of barrel 9058. The piston, piston biasing member, contact sleeve, and optional components, may be compressed and locked into the ready-to-actuate state within the drive housing 90130 prior to attachment or mounting of the drug container 9050. The tether 90525 is pre-connected to the proximal end of the piston 90110A, 90110B and passed through the axial aperture of the biasing member 90122 and drive mechanism 90130, and then wound through the interior of the drug delivery device with the other end of the tether 90525 wrapped around the winch drum/gear 90520 of the regulating mechanism 90500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 90100 or drug delivery device 9010 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9018 to enable the user to view the operation of the drug delivery device 9010 or verify that drug dose has completed. Similarly, the drug delivery device 9010 may contain an adhesive patch 9026 and a patch liner 9028 on the bottom surface of the housing 9012. The adhesive patch 9026 may be utilized to adhere the drug delivery device 9010 to the body of the user for delivery of the drug dose. As would be readily understood by one having ordinary skill in the art, the adhesive patch 9026 may have an adhesive surface for adhesion of the drug delivery device to the body of the user. The adhesive surface of the adhesive patch 9026 may initially be covered by a non-adhesive patch liner 9028, which is removed from the adhesive patch 9026 prior to placement of the drug delivery device 9010 in contact with the body of the user. Removal of the patch liner 9028 may further remove the sealing membrane 90254 of the insertion mechanism 90200, opening the insertion mechanism to the body of the user for drug delivery (as shown in FIG. 69C).

Similarly, one or more of the components of controlled delivery drive mechanism 90100 and drug delivery device 9010 may be modified while remaining functionally within the breadth and scope of the present disclosure. For example, as described above, while the housing of drug delivery device 9010 is shown as two separate components upper housing 9012A and lower housing 9012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connection, a sterile fluid conduit, and the insertion mechanism for delivery of the fluid drug to the body of a user, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

XVI. Additional Embodiments of Multi-Function Drive Mechanism

At least some of the drug delivery devices described in this application, including at least those described in connection with FIGS. 1A-2B, 33A-33C, 80A-85C, 86A-91, 92-99, and 100A-109B may be configured to incorporate the embodiments of the drive mechanism described below in connection with FIGS. 69A-75B. The embodiments of the drive mechanism described below in connection with FIGS. 69A-75B may be used to replace, in its entirety or partially, the above-described drive mechanism 100, 6100, 8100, 9210, 9310, 9410, or 9510, or any other drive mechanism described herein, where appropriate.

The present disclosure provides multi-function drive mechanisms for the controlled delivery of drug substances, controlled drug delivery pumps with such drive mechanisms, the methods of operating such devices, and the methods of assembling such devices. Notably, the multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a multi-function drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the body of the user. A piston, and one or more biasing members, wherein the one or more biasing members are initially retained in an energized state and is configured to bear upon an interface surface of the piston, may also be incorporated in the multi-function drive mechanism. The piston is configured to translate substantially axially within a drug container having a plunger seal and a barrel. A tether is connected at one end to the piston and at another end to a winch drum/gear of a regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of a regulating mechanism of the multi-function drive mechanism to meter the free expansion of the biasing member from its initial energized state and the free axial translation of the piston upon which the biasing member bears upon.

In at least one embodiment of the present disclosure, the regulating mechanism is gear assembly driven by an actuator of the multi-function drive mechanism. The regulating mechanism retards or restrains the distribution of tether, only allowing it to advance at a regulated or desired rate. This restricts movement of piston within barrel, which is pushed by one or more biasing members, hence controlling the movement of plunger seal and delivery of the drug contained in chamber. As the plunger seal advances in the drug container, the drug substance is dispensed through the sterile pathway connection, conduit, insertion mechanism, and into the body of the user for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a winch gear coupled to a winch drum/gear upon which the tether may be releasably wound. Accordingly, rotation of the gear assembly initiated by the actuator may be coupled to winch drum/gear (i.e., through the gear assembly), thereby controlling the distribution of tether, the rate of expansion of the biasing members and the axial translation of the piston, and the rate of movement of plunger seal within barrel to force a fluid from drug chamber. The rotational movement of the winch drum/gear, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, initial motion by the actuator of the multi-function drive mechanism causes rotation of main/star gear. In one manner, main/star gear conveys motion to the regulating mechanism through gear assembly. In another manner, main/star gear conveys motion to the needle insertion mechanism through gear. As gear is rotated by main/star gear, gear engages the needle insertion mechanism to initiate the fluid pathway connector into the user, as described in detail above. In one particular embodiment, needle insertion mechanism is a rotational needle insertion mechanism. Accordingly, gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the user, as described in detail herein.

In at least one embodiment, rotation of the needle insertion mechanism in this manner may also cause a connection of a sterile fluid pathway to a drug container to permit fluid flow from the drug container to the needle insertion mechanism for delivery to the user. Ramp aspect of needle insertion mechanism is caused to bear upon a movable connection hub of the sterile fluid pathway connector. As the needle insertion mechanism is rotated by the multi-function drive mechanism, ramp aspect of needle insertion mechanism bears upon and translates movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum/gear of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum/gear upon which the tether may be releasably wound, rotation of the winch drum/gear releases the tether from the winch drum/gear to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum/gear is coupled to a regulating mechanism which controls rotation of the winch drum/gear and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum/gear and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum/gear on the free axial translation of the piston upon which the biasing member bears upon to meet a desired drug delivery rate or profile, to change the dose volume for delivery to the user, and/or to otherwise start, stop, or pause operation of the drive mechanism.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

The present disclosure provides multi-function drive mechanisms for the controlled delivery of drug substances and drug delivery pumps which incorporate such multi-function drive mechanisms. The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 69A-169 show an exemplary drug delivery device according to at least one embodiment of the present disclosure with the top housing removed so that the internal components are visible. The drug delivery device may be utilized to administer delivery of a drug treatment into a body of a user. As shown in FIGS. 69A-69C, the drug delivery device 9010 includes a pump housing 9012. Pump housing 9012 may include one or more housing subcomponents which are fixedly engageable to facilitate easier manufacturing, assembly, and operation of the drug delivery device. For example, drug delivery device 9010 includes a pump housing 9012 which may include an upper housing and a lower housing (not shown for ease of viewing internal components). The pump housing 9012 may include one or more tamper evidence features to identify if the drug delivery device has been opened or tampered with. For example, the pump housing 9012 may include one or more tamper evidence labels or stickers, such as labels that bridge across the upper housing and the lower housing. Additionally or alternatively, the housing 9012 may include one or more snap arms or prongs connecting between the upper housing and the lower housing. A broken or altered tamper evidence feature would signal to the user, the physician, the supplier, the manufacturer, or the like, that the drug delivery device has potentially been tampered, e.g., by accessing the internal aspects of the device, so that the device is evaluated and possibly discarded without use by or risk to the user. The drug delivery device may further include an activation mechanism, a status indicator, and a window. Window may be any translucent or transmissive surface through which the operation of the drug delivery device may be viewed. As shown in FIG. 69B, drug delivery device 9010 further includes assembly platform 9020, sterile fluid conduit 30, drive mechanism 90100 having drug container 9050, insertion mechanism 90200, fluid pathway connector 90300, and a power and control system (not shown). One or more of the components of such drug delivery devices may be modular in that they may be, for example, pre-assembled as separate components and configured into position onto the assembly platform 9020 of the drug delivery device 9010 during manufacturing.

The pump housing 9012 contains all of the device components and provides a means of removably attaching the device 9010 to the skin of the user. The pump housing 9012 also provides protection to the interior components of the device 9010 against environmental influences. The pump housing 9012 is ergonomically and aesthetically designed in size, shape, and related features to facilitate easy packaging, storage, handling, and use by users who may be untrained and/or physically impaired. Furthermore, the external surface of the pump housing 9012 may be utilized to provide product labeling, safety instructions, and the like. Additionally, as described above, housing 9012 may include certain components, such as one or more status indicators and windows, which may provide operation feedback to the user.

In at least one embodiment, the drug delivery device 9010 provides an activation mechanism that is displaced by the user to trigger the start command to the power and control system. In a preferred embodiment, the activation mechanism is a start button that is located through the pump housing 9012, such as through an aperture between upper housing and lower housing, and which contacts either directly or indirectly the power and control system. In at least one embodiment, the start button may be a push button, and in other embodiments, may be an on/off switch, a toggle, or any similar activation feature known in the art. The pump housing 9012 also provides one or more status indicators and windows. In other embodiments, one or more of the activation mechanism, the status indicator, the window, and combinations thereof may be provided on the upper housing or the lower housing such as, for example, on a side visible to the user when the drug delivery device 9010 is placed on the body of the user. Housing 9012 is described in further detail hereinafter with reference to other components and embodiments of the present disclosure.

Drug delivery device 9010 is configured such that, upon activation by a user by depression of the activation mechanism, the multi-function drive mechanism is activated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In at least one embodiment, such delivery of drug fluid into a user is performed by the multi-function drive mechanism in a controlled manner. One or more optional safety mechanisms may be utilized, for example, to prevent premature activation of the drug delivery device. For example, an optional on-body sensor (not visible) may be provided in one embodiment as a safety feature to ensure that the power and control system, or the activation mechanism, cannot be engaged unless the drug delivery device 9010 is in contact with the body of the user. In one such embodiment, the on-body sensor is located on the bottom of lower housing where it may come in contact with the users body. Upon displacement of the on-body sensor, depression of the activation mechanism is permitted. Accordingly, in at least one embodiment the on-body sensor is a mechanical safety mechanism, such as for example a mechanical lock out, that prevents triggering of the drug delivery device 9010 by the activation mechanism. In another embodiment, the on-body sensor may be an electro-mechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present disclosure to prevent, for example, premature activation of the drug delivery device. In a preferred embodiment, the drug delivery device 9010 utilizes one or more mechanical on-body sensors. Additional integrated safety mechanisms are described herein with reference to other components of the novel drug delivery devices.

XVI.A. Power and Control System

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 90100. In one embodiment, the power and control system interfaces either directly or indirectly with the on-body sensor 9024 to identify when the device is in contact with the user and/or the activation mechanism to identify when the device has been activated. The power and control system may also interface with the status indicator of the pump housing 9012, which may be a transmissive or translucent material which permits light transfer, to provide visual feedback to the user. The power and control system interfaces with the drive mechanism 90100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the body of the user, the power and control system will power the drive mechanism 90100 to begin delivery of the drug treatment through the fluid pathway connector 90300 and sterile fluid conduit 9030 (not shown).

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the user. In such an embodiment, without removal of the drug delivery device from the packaging the drug delivery device cannot be activated. This provides an additional safety mechanism of the drug delivery device and for the user. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, the multi-function drive mechanism is initiated to actuate the insertion mechanism 90200 and the fluid pathway connector 90300, while also permitting the drug fluid to be forced from the drug container. During the drug delivery process, the power and control system is configured to provide a dispensing status signal via the status indicator. After the drug has been administered into the body of the user and after the end of any additional dwell time, to ensure that substantially the entire dose has been delivered to the user, the power and control system may provide an okay-to-remove status signal via the status indicator. This may be independently verified by the user by viewing the drive mechanism and drug dose delivery through the window of the pump housing 9012. Additionally, the power and control system may be configured to provide one or more alert signals via the status indicator, such as for example alerts indicative of fault or operation failure situations.

The power and control system may additionally be configured to accept various inputs from the user to dynamically control the drive mechanisms 90100 to meet a desired drug delivery rate or profile. For example, the power and control system may receive inputs, such as from partial or full activation, depression, and/or release of the activation mechanism, to set, initiate, stop, or otherwise adjust the control of the drive mechanism 90100 via the power and control system to meet the desired drug delivery rate or profile. Similarly, the power and control system may be configured to receive such inputs to adjust the drug dose volume; to prime the drive mechanism, fluid pathway connector, and fluid conduit; and/or to start, stop, or pause operation of the drive mechanism 90100. Such inputs may be received by the user directly acting on the drug delivery device 9010, such as by use of the activation mechanism 9014 or a different control interface, or the power and control system may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug delivery device 9010 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XVI.B. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as developed by the assignee of the present disclosure.

In at least one embodiment, the insertion mechanism 90200 includes an insertion mechanism housing having one or more lockout windows, and a base for connection to the assembly platform and/or pump housing (as shown in FIG. 69B and FIG. 69C). The connection of the base to the assembly platform 9020 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9010. The insertion mechanism may further include one or more insertion biasing members, a needle, a retraction biasing member, a cannula, and a manifold. The manifold may connect to sterile fluid conduit 9030 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9027 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the body of the user. At the end of the insertion stage or at the end of drug delivery (as triggered by the multi-function drive mechanism), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the user. Accordingly, the insertion mechanism may be used to insert a needle and cannula into the user and, subsequently, retract the needle while retaining the cannula in position for drug delivery to the body of the user.

In at least one embodiment, as shown in FIG. 75, the insertion mechanism includes a rotationally biased member 90210 which is initially held in an energized state. In a preferred embodiment, the rotationally biased member is a torsional spring. The rotational biasing member may be prevented from de-energizing by interaction of gear surface 90208 with gear 90112 or, alternatively, by contact of a component of the insertion mechanism with a rotation prevention feature of the drug delivery device. Upon activation of the device, or another input, the rotationally biased member 90210 is permitted to, at least partially, de-energize. This causes one or more components of the insertion mechanism to rotate and, in turn, cause, or allow, the insertion of the needle into the patient. Further, a cannula may be inserted into the patient as described above. At a later time, such as when the control arm or another component of the device recognizes a slack in the tether, the rotationally biased member may be allowed to further de-energize, causing additional rotation of one or more components of the insertion mechanism. This rotation may cause, or allow, the needle to be retracted from the patient. The needle may be fully retracted in a single step or there may be multiple steps of retraction.

XVI.C. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9010, the fluid pathway connector 90300 is enabled to connect the sterile fluid conduit 9030 to the drug container of the drive mechanism 90100. Such connection may be facilitated by a piercing member, such as a needle, penetrating a pierceable seal of the drug container of the drive mechanism 90100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the multi-function drive mechanism. Additionally or alternatively, the sterile fluid pathway connector is initiated by movement directly of the multi-function drive mechanism. For example, the multi-function drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 69A-69C, the multi-function drive mechanism performs all of these steps substantially concurrently. The multi-function drive mechanism rotates a gear that acts upon several other components. The gear acts on a gear assembly to control the rate of drug delivery, while also contacting a needle insertion mechanism to introduce a fluid pathway into the user. As the needle insertion mechanism is initiated, the sterile fluid connection is made to permit drug fluid flow from the drug container, through the fluid conduit, into the needle insertion mechanism, for delivery into the patient as the gear and gear assembly of the multi-function drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 300 and the sterile fluid conduit 30 are provided hereinafter in later sections in reference to other embodiments.

XVI.D. Multi-Function Drive Mechanism

The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. With reference to the embodiments shown in FIGS. 70A-70D and 3A-3D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism 90100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 90100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the multi-function drive mechanism shown in FIGS. 70A-70D and 71A-71D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. Compressed within the drive housing 90130, between the drug container 9050 and the proximal end of the housing 90130, are one or more drive biasing members 90122 and a piston 90110, wherein the drive biasing members 90122 are configured to bear upon an interface surface 90110C of the piston 90110, as described further herein. Optionally, a cover sleeve (not shown) may be utilized between the drive biasing members 90122 and the interface surface 90110C of the piston 90110 to, for example, promote more even distribution of force from the drive biasing member 90122 to the piston 90110, prevent buckling of the drive biasing members 90122, and/or hide biasing members 90122 from user view. Interface surface 90110C of piston 90110 is caused to rest substantially adjacent to, or in contact with, a proximal end of seal 9060. Although the embodiments shown in FIGS. 70A-70D and 71A-71D show a singular biasing member it is also contemplated that one or more biasing members disposed to act in parallel may be used.

As best shown in FIG. 70D and FIG. 71D, the piston 90110 may be comprised of two components 90110A and 90110B and have an interface surface 90110C to contact the plunger seal. A tether, ribbon, string, or other retention strap (referred to herein as the "tether" 90525) may be connected at one end to the piston 90110A, 90110B. For example, the tether 90525 may be connected to the piston 90110A, 90110B by retention between the two components of the piston 90110A, 90110B when assembled. The tether 90525 is connected at another end to a winch drum/gear 90520 of a delivery control mechanism 90500. Through the use of the winch drum/gear 90520 connected to one end of the tether 90525, and the tether 90525 connected at another end to the piston 90110A, 90110B, the regulating mechanism 90500 functions to control, meter, provide resistance, or otherwise prevent free axial translation of the piston 90110A, 90110B and plunger seal 9060 utilized to force a drug substance out of a drug container 9050. Accordingly, the regulating mechanism 90500 is a portion of the gear assembly 90116 aspect of the multi-function drive mechanism, which together function to control the rate or profile of drug delivery to the user.

As shown in FIGS. 70A-70D and 71A-71D, and in isolation in FIGS. 72 and 73A-73B, in the embodiments of the present disclosure, the regulating mechanism 90500 is gear assembly driven by an actuator 90101 of the multi-function drive mechanism 90100. The regulating mechanism retards or restrains the distribution of tether 90525, only allowing it to advance at a regulated or desired rate. This restricts movement of piston 90110 within barrel 9058, which is pushed by one or more biasing members 90122, hence controlling the movement of plunger seal 9060 and delivery of the drug contained in chamber 9021. As the plunger seal 9060 advances in the drug container 9050, the drug substance is dispensed through the sterile pathway connection 90300, conduit 9030, insertion mechanism 90200, and into the body of the user for drug delivery. The actuator 90101 may be a number of power/motion sources including, for example, a solenoid, a stepper motor, or a rotational drive motor. In a particular embodiment, the actuator 90101 is a rotational stepper motor with a notch that corresponds with the gear teeth of the main/star gear 90102. Commonly, such a rotational stepper motor may be referred to as a 'Pac-Man' motor. In at least one embodiment, the Pac-Man motor has a gear interface within which one or more teeth of the main gear may partially reside during operation of the system. This is more clearly visible in FIGS. 73A-73B. When the gear interface 90101A of the Pac-Man motor 90101 is in alignment with a tooth 90102A of the main gear 90102, rotational motion of the Pac-Man motor 90101 causes gear interface rotation of the main gear 90102. When the Pac-Man motor 90101 is between gear teeth of the main gear, it may act as a resistance for, for example, back-spinning or unwinding of the gear assembly 90116. In one particular embodiment, the Pac-Man motor 90101 utilizes an alternating direction type motor to rotate the Pac-Man motor 90101 backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the motor, coupled with the use of the gear interface cut within the Pac-Man motor, provide suitable safety features to prevent a runaway condition that could potentially lead to over-delivery of drug to the user. Further detail about the gear assembly 90116, regulating mechanism 90500, and multi-function drive mechanism 90100 are provided herein.

In a particular embodiment shown in FIGS. 73A-73B, the regulating element 90500 further includes one or more gears 90511, 90512, 90513, 90514, of a gear assembly 90516. One or more of the gears 90511, 90512, 90513, 90514 may be, for example, compound gears having a small diameter gear attached at a shared center point to a large diameter gear. Gear 90513 may be rotationally coupled to winch drum/gear 90520, for example by a keyed shaft, thereby coupling rotation of gear assembly 90516 to winch drum/gear 90520. Compound gear 90512 engages the small diameter gear 90513 such that rotational movement of the compound gear aspect 90512B is conveyed by engagement of the gears (such as by engagement of corresponding gear teeth) to gear 90513. Compound gear aspect 90512A, the rotation of which is coupled to gear aspect 90512B, is caused to rotate by action of compound gear aspect 90102B of the main/star gear 90102. Compound gear aspect 90102B, the rotation of which is coupled to main/star gear 90102, is caused to rotate by interaction between main/star gear 90102A and interface 90101A of the actuator 90101. Thus, rotation of main/star gear 90102 is conveyed to winch drum/gear 90520. Accordingly, rotation of the gear assembly 90516 initiated by the actuator 90101 may be coupled to winch drum/gear 90520 (i.e., through the gear assembly 90516), thereby controlling the distribution of tether 90525, and the rate of movement of plunger seal 9060 within barrel 9058 to force a fluid from drug chamber 9021. The rotational movement of the winch drum/gear 90520, and thus the axial translation of the piston 90110 and plunger seal 9060, are metered, restrained, or otherwise prevented from free axial translation by other components of the regulating element 90500, as described herein. As described above, the actuator 90101 may be a number of known power/motion sources including, for example, a motor (e.g., a DC motor, AC motor, or stepper motor) or a solenoid (e.g., linear solenoid, rotary solenoid).

The embodiment described above and shown in FIGS. 69A-73D show an actuator 90101 that is in vertical alignment and in direct engagement with the main/star gear 90102. As would readily be appreciated by one having ordinary skill in the mechanical arts, the actuator 90101 could be modified to be in horizontal alignment. Additionally or alternatively, the actuator 90101 could be modified to be in indirect engagement with the main/star gear 90102.

The embodiments shown in FIGS. 75A-75B show an actuator 90101 that is in horizontal alignment and indirect engagement with the main/star gear 90102. Such an embodiment may utilize a rack and pinion engagement, a drive screw, or a worm gear 101W, as shown in FIGS. 5A-75B, to change the direction of motion from horizontal to vertical (i.e., perpendicular interaction). Actuator 90101 rotates worm gear 90101W, which engages gear 90101G and conveys the motion to the Pac-Man gear 90101A. The Pac-Man gear 90101A engages main/star gear 90102 to enable operation of the drive mechanism and the drug delivery device, as described herein. Main/star gear 90102 also drives operation of gear 90112 to enable operation of the needle insertion mechanism 90200, as described herein. In one particular embodiment, the actuator 90101 utilizes an alternating direction type motor to rotate the worm gear 90101W, gear 90101G, and Pac-Man gear 90101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 90101, coupled with the use of the gear interface of the worm gear 90101W, gear 90101G, and Pac-Man gear 90101A with the main/star gear 90102, provide suitable safety features to prevent a runaway condition that could potentially lead to over-delivery of drug to the user. Additionally, the actuator 90101 may include a stop member 90101B that stops the rotation of the Pac-Man gear 90101A against a stop block 90150. Stop block 90150 further prevents over-rotation of the Pac-Man gear 90101A and, accordingly, the main/star gear 90102 to prevent a runaway condition that could potentially lead to over-delivery of drug to the user. For the device to function in this configuration, the Pac-Man gear 90101A must be rotated backwards the other direction before rotating forwards again to progress the main/star gear 90102 because the stop member 90101B prevents over rotation in one direction by interaction with the stop block 90150. Additionally, the geometry of worm gear 90101W may be configured such that it is self-locking and/or cannot be back-driven by gear 90101G. This may be done by configuration of parameters such as: pitch, lead angle, pressure angle, and number of threads. In so doing, runaway conditions of the drive mechanism will be prevented by the worm gears resistance to rotations that are not caused by actuator 90101.

Notably, the regulating mechanisms 90500 of the present disclosure do not drive the delivery of fluid substances from the drug chamber 9021. The delivery of fluid substances from the drug chamber 9021 is caused by the expansion of the biasing member 90122 from its initial energized state acting upon the piston 90110A, 90110B and plunger seal 9060. The regulating mechanisms 90500 instead function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. According to a preferred embodiment, the controlled delivery drive mechanisms and drug delivery devices of the present disclosure include a regulating mechanism indirectly or directly connected to a tether metering the axial translation of the piston 90110A, 90110B and plunger seal 9060, which are being driven to axially translate by the biasing member 90122. The rate of drug delivery as controlled by the regulating mechanism may be determined by: selection of the gear ratio of gear assembly 90516; selection of the main/star gear 90102; selection of the diameter of winding drum/gear 90520; using electromechanical actuator 90101 to control the rate of rotation of the main/star gear 90102; or any other method known to one skilled in the art. By using electromechanical actuator 90101 the rate of rotation of the main/star gear 90102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 90525 by the winch drum/gear 90520 and thereby permit axial translation of the piston 90110 by the biasing member 90122 to translate a plunger seal 9060 within a barrel 9058. The one or more inputs may be provided by the actuation of the activation mechanism, a control interface, and/or a remote control mechanism. The power and control system may be configured to receive one or more inputs to adjust the restraint provided by the tether 90525 and winch drum/gear 90520 on the free axial translation of the piston 90110 upon which the biasing member 90122 bears upon to meet a desired drug delivery rate or profile, to change the dose volume for delivery to the user, and/or to otherwise start, stop, or pause operation of the drive mechanism.

The components of the drive mechanism 90100, upon activation, may be used to drive axial translation in the distal direction of the plunger seal 60 of the drug container 9050. Optionally, the drive mechanism 90100 may include one or more compliance features which enable additional axial translation of the plunger seal 9060 to, for example, ensure that substantially the entire drug dose has been delivered to the user. For example, the plunger seal 9060, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

The tether 90525 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 90525 that would contact the status reader at the end of axial travel of the piston 90110A, 90110B and plunger 9060 within the barrel 9058 of the drug container 9050. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 90525 to be read or recognized at positions which correspond with the beginning and end of drug delivery, as well as at desired increments during drug delivery. As the drug delivery device is activated and drug delivery is begun by release of the biasing member 90122 and the resulting force applied to the piston 90110A, 90110B and plunger seal 9060, the rate or profile of drug delivery to the user is controlled by the regulating mechanism 90500, gear assembly 90516, and winch drum/gear 90520 releasing the tether 90525 and permitting expansion of the biasing member 90122 and axial translation of the piston 90110A, 90110B and plunger seal 9060. As this occurs, the status triggers of the tether 90525 are contacted or recognized by the status reader and the status of the drive mechanism before, during, and after operation can be relayed to the power and control system to provide feedback to the user. Depending on the number of status triggers located on the tether 90525, the frequency of the incremental status indication may be varied as desired. As described above, a range of status readers may be utilized depending on the status triggers utilized by the system.

In a preferred embodiment, the status reader may apply a tensioning force to the tether 90525. When the system reaches end-of-dose, the tether 90525 goes slack and the status reader 90544 is permitted to rotate about a fulcrum. This rotation may operate an electrical or electromechanical switch, for example a switch, signaling slack in the tether 90525 to the power and control system. Additionally, a gear 90511 of gear assembly 90516 may act as an encoder along with a sensor. The sensor/encoder combination is used to provide feedback of gear assembly rotation, which in turn can be calibrated to the position of piston 90110 when there is no slack in the tether 90525. Together, the status reader and sensor/encoder may provide positional feedback, end-of-dose signal, and error indication, such as an occlusion, by observing slack in the tether 90525 prior to reaching the expected number of motor rotations as counted by the sensor/encoder.

Additional means may exist for terminating or restraining the flow of the medicament in the case of slack in, or failure of, the tether. FIGS. 6A-6B show one such embodiment. Disposed within barrel 9058 are brake 9064, sleeve 9062, and plug 9068, and optionally retainer 66. Biasing member 90122 bears against sleeve 9062. Tether 90525 is engaged with plug 9068, thereby allowing tether 90525 to restrain the motion of sleeve 9062. This restraint controls the rate of expansion or de-energizing of biasing member 90122. When tether 90525 is under tension, plug 9068 bears against distal face 9064A of brake 9064, causing proximal face 9064B of brake 9064 to bear against sleeve 9062. Due to this contact, and the profile of the distal end 9062A of sleeve 9062, brake 9064 is maintained in a substantially conical configuration as shown in FIG. 6A. In this configuration, expansion or de-energizing of biasing member 90122 is restrained. Also, in this conical configuration, the outer diameter of brake 64 is less than the inner diameter of barrel 9058, thus translation of the brake is not restrained by contact with the inner wall of the drug container. Also, a portion of brake 9064 is in contact with retainer 9066. Because brake 9064 is maintained in this configuration by plug 9068 and sleeve 9062, translation of sleeve 9062, caused by decompression of biasing member 90122, is transferred to retainer 9066.

Likewise, contact of retainer 9066 with plunger seal 9060 causes translation of plunger seal 9060.

As shown in FIG. 74B, in the event of slack in, or failure of, tether 90525, plug 9068 is no longer held in position by tether 90525 and, therefore, no longer restrains motion of sleeve 9062. As biasing member 90122 decompresses or de-energizes, brake 9064 transforms to a relatively less conical or flatter configuration. This may be caused by a natural bias of brake 9064 to transform to this configuration or, alternatively, may be caused by contact of brake 9064 with both retainer 9066 and sleeve 9062. As the brake is transformed, it comes into contact with the inner wall of barrel 9058. The brake thus acts as a wedge to restrict translation of sleeve 9062. This may prevent further translation or may act to restrict the rate of translation. Optionally, restoring tension in the tether may cause the plug to contact the brake and to transform the brake back to its conical configuration and thus restore normal operation of the drug delivery device.

FIGS. 74A-74B show the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 9062 (i.e., applying a braking force). In another embodiment, the brake 9064 could employ a star-shaped or other configuration when in a substantially flattened position so as to make contact with the inner diameter of the barrel 9058 to prevent or restrict further axial translation of sleeve 9062. Without further translation of sleeve 9062, biasing member 90122 cannot expand or de-energize further which, in turn, prevents or restricts further drug delivery to the user. This provides a necessary and useful safety measure for drug delivery, to prevent over-delivery or accelerated delivery of drug to the user.

Referring back to FIGS. 70A-70D and 71A-71D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, as shown in FIGS. 70A-70D and 71A-71D, initial motion by the actuator 90101 of the multi-function drive mechanism 90100 causes rotation of main/star gear 90102. Main/star gear 90102 is shown as a compound gear with aspects 90102A and 90102B (see FIG. 72). In one manner, main/star gear 90102 conveys motion to the regulating mechanism 90500 through gear assembly 90516. In another manner, main/star gear 90102 conveys motion to the needle insertion mechanism 90200 through gear 90112. As gear 90112 is rotated by main/star gear 90102, gear 90112 engages the needle insertion mechanism 90200 to initiate the fluid pathway connector into the user, as described in detail above. In one particular embodiment, needle insertion mechanism 90200 is a rotational needle insertion mechanism. Accordingly, gear 90112 is configured to engage a corresponding gear surface 90208 of the needle insertion mechanism 90200. Rotation of gear 90112 causes rotation of needle insertion mechanism 90200 through the gear interaction between gear 90112 of the drive mechanism 90100 and corresponding gear surface 90208 of the needle insertion mechanism 90200. Once suitable rotation of the needle insertion mechanism 90200 occurs, for example rotation along axis 'R' shown in FIG. 70B-70C, the needle insertion mechanism may be initiated to create the fluid pathway connector into the user, as described in detail above. In an alternative embodiment, as shown in FIGS. 75A-75B, gear 90112 may indirectly engage the needle insertion mechanism 90200 to initiate the fluid pathway connector into the user. For example, gear 90112 may be configured to engage a corresponding gear surface of a control arm 90202 (visible in FIG. 75) that contacts or blocks the needle insertion mechanism 90200. Rotation of gear 90112 causes movement of the control arm 90202, which may initiate or permit rotation of needle insertion mechanism 90200. Such a needle insertion mechanism, as shown in FIGS. 75A-75B, includes a rotationally biased member 90210 which is initially held in an energized state. The rotational biasing member may be prevented from de-energizing by contact of a component of the insertion mechanism with a rotation prevention feature, such as a blocking aspect of the control arm, of the drug delivery device. Upon activation of the device, or another input, the rotationally biased member 90210 is permitted to, at least partially, de-energize. This causes one or more components of the insertion mechanism to rotate and, in turn, cause, or allow, the insertion of the needle into the patient. Further, a cannula may be inserted into the patient as described above. At a later time, such as when the control arm or another component of the device recognizes a slack in the tether 90525, the rotationally biased member may be allowed to further de-energize, such as by further interaction with the control arm, causing additional rotation of one or more components of the insertion mechanism. This rotation may cause, or allow, the needle to be retracted from the patient. The needle may be fully retracted in a single step or there may be multiple steps of retraction.

As shown in FIGS. 70A-70D and 71A-71D, rotation of the needle insertion mechanism 90200 in this manner may also cause a connection of a sterile fluid pathway to a drug container to permit fluid flow from the drug container to the needle insertion mechanism for delivery to the user. Ramp aspect 90222 of needle insertion mechanism 90200 is caused to bear upon a movable connection hub 90322 of the sterile fluid pathway connector 90300. As the needle insertion mechanism 90200 is rotated by the multi-function drive mechanism 90100, ramp aspect 90222 of needle insertion mechanism 90200 bears upon and translates movable connection hub 90322 of the sterile fluid pathway connector 90300 to facilitate a fluid connection therein. Such translation may occur, for example, in the direction of the hollow arrow along axis 'C' shown in FIGS. 70B and 71B. In at least one embodiment, the needle insertion mechanism 90200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism 90500 and/or one or more of the status readers as described above. During these stages of operation, delivery of fluid substances from the drug chamber 9021 may be initiated, on-going, and/or completed by the expansion of the biasing member 90122 from its initial energized state acting upon the piston 90110A, 90110B and plunger seal 9060. As described above, the regulating mechanisms 90500 function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. This is visible through the progression of the components shown in FIGS. 70A-70D and 71A-71D. The motion of the piston 90110A, 90110B and plunger seal 9060 as they are pushed by the expansion of the biasing member 90122 from its initial energized state are shown in the direction of the solid arrow along axis 'A' from proximal or first position 'P' to the distal or second position 'D', as shown in the transition of FIGS. 70A-70D and 71A-71D.

Further aspects of the novel drive mechanism will be described with reference to FIG. 72 and FIGS. 73A-73B. FIG. 72 shows a perspective view of the multi-function drive mechanism, according to at least a first embodiment, during its initial locked stage. Initially, the tether 90525 may retain the biasing member 90122 in an initial energized position within piston 90110A, 90110B. Directly or indirectly upon activation of the device by the user, the multi-function drive mechanism 90100 may be activated to permit the biasing member to impart a force to piston 90110 and therefore to tether 90525. This force on tether 90525 imparts a torque on winding drum 90520 which causes the gear assembly 90516 and regulating mechanism 90500 to begin motion. As shown in FIG. 73A, the piston 90110 and biasing member 90122 are both initially in a compressed, energized state behind the plunger seal 9060. The biasing member 90122 may be maintained in this state until activation of the device between internal features of drive housing 90130 and interface surface 90110C of piston 90110A, 90110B. As the drug delivery device 9010 is activated and the drive mechanism 90100 is triggered to operate, biasing member 90122 is permitted to expand (i.e., decompress) axially in the distal direction (i.e., in the direction of the solid arrow shown in FIGS. 70A-70D and FIGS. 71A-71D). Such expansion causes the biasing member 90122 to act upon and distally translate interface surface 90110C and piston 90110, thereby distally translating plunger seal 9060 to push drug fluid out of the drug chamber 9021 of barrel 9058. In at least one embodiment, an end-of-dose status indication may be provided to the user once the status reader contacts or recognizes a status trigger positioned on the tether 90525 to substantially correspond with the end of axial travel of the piston 90110A, 90110B and plunger seal 9060 within the barrel 9058 of the drug container 9050. The status triggers may be positioned along the tether 90525 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 90525 to be read or recognized at positions which correspond with the beginning and end of drug delivery, as well as at desired increments during drug delivery. As shown, tether 90525 passes substantially axially through the drive mechanism housing 90130, the biasing member 90122, and connects to the piston 90110 A, 90110B to restrict the axial translation of the piston 90110A, 90110B and the plunger seal 9060 that resides adjacent thereto.

The novel embodiments of the present disclosure may be utilized to meter, restrain, or otherwise prevent free rotational movement of winding drum 90520 and, thus, axial translation of the components of the controlled delivery drive mechanism 90100. Accordingly, the regulating mechanism 90500 only controls the motion of the drive mechanism, but does not apply the force for the drug delivery. One or more additional biasing members 90122, such as compression springs, may be utilized to drive or assist the driving of the piston 90110. For example, a compression spring may be utilized within the drive housing 90130 for this purpose. The regulating mechanism 500 only controls, meters, or regulates such action. The controlled delivery drive mechanisms and/or drug delivery devices of the present disclosure may additionally enable a compliance push to ensure that substantially all of the drug substance has been pushed out of the drug chamber 9021. The plunger seal 9060, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear assembly 90516. As the gear assembly 90516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear assembly and regulating mechanism shown in the figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 90101. The change in the rate of movement of actuator 90101 causes a change in the rotation rate of regulating mechanism 90500 which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

Assembly and/or manufacturing of controlled delivery drive mechanism 90100, drug delivery pump 9010, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9050 may first be assembled and filled with a fluid for delivery to the user. The drug container 9050 includes a cap 9052, a pierceable seal 9056, a barrel 9058, and a plunger seal 9060. The pierceable seal 56 may be fixedly engaged between the cap 9052 and the barrel 9058, at a distal end of the barrel 9058. The barrel 9058 may be filled with a drug fluid through the open proximal end prior to insertion of the plunger seal 9060 from the proximal end of the barrel 9058. An optional connection mount 9054 may be mounted to a distal end of the pierceable seal 9056. The connection mount 9054 may guide the insertion of the piercing member of the fluid pathway connector into the barrel 9058 of the drug container 9050. The drug container 9050 may then be mounted to a distal end of drive housing 90130.

One or more drive biasing members 90122 may be inserted into a distal end of the drive housing 90130. Optionally, a cover sleeve 90140 may be inserted into a distal end of the drive housing 90130 to substantially cover biasing member 90122. A piston may be inserted into the distal end of the drive housing 90130 such that it resides at least partially within an axial pass-through of the biasing member 90122 and the biasing member 90122 is permitted to contact a piston interface surface 90110C of piston 90110A, 90110B at the distal end of the biasing member 90122. An optional cover sleeve 90140 may be utilized to enclose the biasing member 90122 and contact the piston interface surface 90110C of piston 90110A, 90110B. The piston 90110A, 90110B and drive biasing member 90122, and optional cover sleeve 90140, may be compressed into drive housing 90130. Such assembly positions the drive biasing member 90122 in an initial compressed, energized state and preferably places a piston interface surface 90110C in contact with the proximal surface of the plunger seal 9060 within the proximal end of barrel 9058. The piston, piston biasing member, contact sleeve, and optional components, may be compressed and locked into the ready-to-actuate state within the drive housing 90130 prior to attachment or mounting of the drug container 9050. The tether 90525 is pre-connected to the proximal end of the piston 90110A, 90110B and passed through the axial aperture of the biasing member 90122 and drive mechanism 90130, and then wound through the interior of the drug delivery device with the other end of the tether 90525 wrapped around the winch drum/gear 90520 of the regulating mechanism 90500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 90100 or drug delivery device 9010 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9018 to enable the user to view the operation of the drug delivery device 9010 or verify that drug dose has completed. Similarly, the drug delivery device 9010 may contain an adhesive patch 9026 and a patch liner 9028 on the bottom surface of the housing 9012. The adhesive patch 9026 may be utilized to adhere the drug delivery device 9010 to the body of the user for delivery of the drug dose. As would be readily understood by one having ordinary skill in the art, the adhesive patch 9026 may have an adhesive surface for adhesion of the drug delivery device to the body of the user. The adhesive surface of the adhesive patch 9026 may initially be covered by a non-adhesive patch liner 9028, which is removed from the adhesive patch 9026 prior to placement of the drug delivery device 9010 in contact with the body of the user. Removal of the patch liner 9028 may further remove the sealing membrane 90254 of the insertion mechanism 90200, opening the insertion mechanism to the body of the user for drug delivery (as shown in FIG. 69C).

Similarly, one or more of the components of controlled delivery drive mechanism 90100 and drug delivery device 10 may be modified while remaining functionally within the breadth and scope of the present disclosure. For example, as described above, while the housing of drug delivery device 9010 is shown as two separate components upper housing 9012A and lower housing 9012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the body of a user, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

XVII. Additional Embodiments of Multi-Function Drive Mechanism

At least some of the drug delivery devices described in this application, including at least those described in connection with FIGS. 1A-2B, 33A-33C, 80A-85C, 86A-91, 92-99, and 100A-109B may be configured to incorporate the embodiments of the drive mechanism described below in connection with FIGS. 69A-73D. The embodiments of the drive mechanism described below in connection with FIGS. 69A-73D may be used to replace, in its entirety or partially, the above-described drive mechanism 100, 6100, 8100, 9210, 9310, 9410, or 9510, or any other drive mechanism described herein, where appropriate.

The present disclosure provides multi-function drive mechanisms for the controlled delivery of drug substances, controlled drug delivery pumps with such drive mechanisms, the methods of operating such devices, and the methods of assembling such devices. Notably, the multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a multi-function drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the body of the user. A piston, and one or more biasing members, wherein the one or more biasing members are initially retained in an energized state and is configured to bear upon an interface surface of the piston, may also be incorporated in the multi-function drive mechanism. The piston is configured to translate substantially axially within a drug container having a plunger seal and a barrel. A tether is connected at one end to the piston and at another end to a winch drum/gear of a regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of a regulating mechanism of the multi-function drive mechanism to meter the free expansion of the biasing member from its initial energized state and the free axial translation of the piston upon which the biasing member bears upon.

In at least one embodiment of the present disclosure, the regulating mechanism is gear assembly driven by an actuator of the multi-function drive mechanism. The regulating mechanism retards or restrains the distribution of tether, only allowing it to advance at a regulated or desired rate. This restricts movement of piston within barrel, which is pushed by one or more biasing members, hence controlling the movement of plunger seal and delivery of the drug contained in chamber. As the plunger seal advances in the drug container, the drug substance is dispensed through the sterile pathway connection, conduit, insertion mechanism, and into the body of the user for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a winch gear coupled to a winch drum/gear upon which the tether may be releasably wound. Accordingly, rotation of the gear assembly initiated by the actuator may be coupled to winch drum/gear (i.e., through the gear assembly), thereby controlling the distribution of tether, the rate of expansion of the biasing members and the axial translation of the piston, and the rate of movement of plunger seal within barrel to force a fluid from drug chamber. The rotational movement of the winch drum/gear, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, initial motion by the actuator of the multi-function drive mechanism causes rotation of main/star gear. In one manner, main/star gear conveys motion to the regulating mechanism through gear assembly. In another manner, main/star gear conveys motion to the needle insertion mechanism through gear. As gear is rotated by main/star gear, gear engages the needle insertion mechanism to initiate the fluid pathway connector into the user, as described in detail above. In one particular embodiment, needle insertion mechanism is a rotational needle insertion mechanism. Accordingly, gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the user, as described in detail herein.

In at least one embodiment, rotation of the needle insertion mechanism in this manner may also cause a connection of a sterile fluid pathway to a drug container to permit fluid flow from the drug container to the needle insertion mechanism for delivery to the user. Ramp aspect of needle insertion mechanism is caused to bear upon a movable connection hub of the sterile fluid pathway connector. As the needle insertion mechanism is rotated by the multi-function drive mechanism, ramp aspect of needle insertion mechanism bears upon and translates movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch drum/gear of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a user. Optionally, a cover sleeve may be utilized between the biasing member and the interface surface of the piston to hide the interior components of the barrel (namely, the piston and the biasing member) from view during operation of the drive mechanism. The tether is configured to be released from a winch drum/gear of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch drum/gear upon which the tether may be releasably wound, rotation of the winch drum/gear releases the tether from the winch drum/gear to meter the free expansion of the biasing member from its initial energized state and the free axial translation of the piston upon which the biasing member bears upon. The metering of the tether controls the rate or profile of drug delivery to a user. The piston may be one or more parts and connects to a distal end of the tether. The winch drum/gear is coupled to a regulating mechanism which controls rotation of the winch drum/gear and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch drum/gear and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch drum/gear on the free axial translation of the piston upon which the biasing member bears upon to meet a desired drug delivery rate or profile, to change the dose volume for delivery to the user, and/or to otherwise start, stop, or pause operation of the drive mechanism.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

The present disclosure provides multi-function drive mechanisms for the controlled delivery of drug substances and drug delivery pumps which incorporate such multi-function drive mechanisms. The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

The novel devices of the present disclosure provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 69A-69C show an exemplary drug delivery device according to at least one embodiment of the present disclosure with the top housing removed so that the internal components are visible. The drug delivery device may be utilized to administer delivery of a drug treatment into a body of a user. As shown in FIGS. 69A-69C, the drug delivery device 9010 includes a pump housing 9012. Pump housing 9012 may include one or more housing subcomponents which are fixedly engageable to facilitate easier manufacturing, assembly, and operation of the drug delivery device. For example, drug delivery device 9010 includes a pump housing 9012 which may include an upper housing and a lower housing (not shown for ease of viewing internal components). The drug delivery device may further include an activation mechanism, a status indicator, and a window. Window may be any translucent or transmissive surface through which the operation of the drug delivery device may be viewed. As shown in FIG. 69B, drug delivery device 9010 further includes assembly platform 9020, sterile fluid conduit 9030, drive mechanism 90100 having drug container 9050, insertion mechanism 90200, fluid pathway connector 90300, and a power and control system (not shown). One or more of the components of such drug delivery devices may be modular in that they may be, for example, pre-assembled as separate components and configured into position onto the assembly platform 9020 of the drug delivery device 9010 during manufacturing.

The pump housing 9012 contains all of the device components and provides a means of removably attaching the device 9010 to the skin of the user. The pump housing 9012 also provides protection to the interior components of the device 9010 against environmental influences. The pump housing 9012 is ergonomically and aesthetically designed in size, shape, and related features to facilitate easy packaging, storage, handling, and use by users who may be untrained and/or physically impaired. Furthermore, the external surface of the pump housing 9012 may be utilized to provide product labeling, safety instructions, and the like. Additionally, as described above, housing 9012 may include certain components, such as one or more status indicators and windows, which may provide operation feedback to the user.

In at least one embodiment, the drug delivery device 9010 provides an activation mechanism that is displaced by the user to trigger the start command to the power and control system. In a preferred embodiment, the activation mechanism is a start button that is located through the pump housing 9012, such as through an aperture between upper housing and lower housing, and which contacts either directly or indirectly the power and control system. In at least one embodiment, the start button may be a push button, and in other embodiments, may be an on/off switch, a toggle, or any similar activation feature known in the art. The pump housing 9012 also provides one or more status indicators and windows. In other embodiments, one or more of the activation mechanism, the status indicator, the window, and combinations thereof may be provided on the upper housing or the lower housing such as, for example, on a side visible to the user when the drug delivery device 9010 is placed on the body of the user. Housing 9012 is described in further detail hereinafter with reference to other components and embodiments of the present disclosure.

Drug delivery device 9010 is configured such that, upon activation by a user by depression of the activation mechanism, the multi-function drive mechanism is activated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In at least one embodiment, such delivery of drug fluid into a user is performed by the multi-function drive mechanism in a controlled manner.

One or more optional safety mechanisms may be utilized, for example, to prevent premature activation of the drug delivery device. For example, an optional on-body sensor (not visible) may be provided in one embodiment as a safety feature to ensure that the power and control system, or the activation mechanism, cannot be engaged unless the drug delivery device 9010 is in contact with the body of the user. In one such embodiment, the on-body sensor is located on the bottom of lower housing where it may come in contact with the users body. Upon displacement of the on-body sensor, depression of the activation mechanism is permitted. Accordingly, in at least one embodiment the on-body sensor is a mechanical safety mechanism, such as for example a mechanical lock out, that prevents triggering of the drug delivery device 9010 by the activation mechanism. In another embodiment, the on-body sensor may be an electromechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present disclosure to prevent, for example, premature activation of the drug delivery device. In a preferred embodiment, the drug delivery device 9010 utilizes one or more mechanical on-body sensors. Additional integrated safety mechanisms are described herein with reference to other components of the novel drug delivery devices.

XVII.A. Power and Control System

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 90100. In one embodiment, the power and control system interfaces either directly or indirectly with the on-body sensor 9024 to identify when the device is in contact with the user and/or the activation mechanism to identify when the device has been activated. The power and control system may also interface with the status indicator of the pump housing 9012, which may be a transmissive or translucent material which permits light transfer, to provide visual feedback to the user. The power and control system interfaces with the drive mechanism 90100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the body of the user, the power and control system will power the drive mechanism 90100 to begin delivery of the drug treatment through the fluid pathway connector 90300 and sterile fluid conduit 9030 (not shown).

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the user. In such an embodiment, without removal of the drug delivery device from the packaging the drug delivery device cannot be activated. This provides an additional safety mechanism of the drug delivery device and for the user. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, the multi-function drive mechanism is initiated to actuate the insertion mechanism 90200 and the fluid pathway connector 90300, while also permitting the drug fluid to be forced from the drug container. During the drug delivery process, the power and control system is configured to provide a dispensing status signal via the status indicator. After the drug has been administered into the body of the user and after the end of any additional dwell time, to ensure that substantially the entire dose has been delivered to the user, the power and control system may provide an okay-to-remove status signal via the status indicator. This may be independently verified by the user by viewing the drive mechanism and drug dose delivery through the window of the pump housing 9012. Additionally, the power and control system may be configured to provide one or more alert signals via the status indicator, such as for example alerts indicative of fault or operation failure situations.

The power and control system may additionally be configured to accept various inputs from the user to dynamically control the drive mechanisms 90100 to meet a desired drug delivery rate or profile. For example, the power and control system may receive inputs, such as from partial or full activation, depression, and/or release of the activation mechanism, to set, initiate, stop, or otherwise adjust the control of the drive mechanism 90100 via the power and control system to meet the desired drug delivery rate or profile. Similarly, the power and control system may be configured to receive such inputs to adjust the drug dose volume; to prime the drive mechanism, fluid pathway connector, and fluid conduit; and/or to start, stop, or pause operation of the drive mechanism 90100. Such inputs may be received by the user directly acting on the drug delivery device 9010, such as by use of the activation mechanism 9014 or a different control interface, or the power and control system may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug delivery device 9010 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

XVII.B. Insertion Mechanism

A number of insertion mechanisms may be utilized within the drug delivery devices of the present disclosure. The pump-type delivery devices of the present disclosure may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as developed by the assignee of the present disclosure.

In at least one embodiment, the insertion mechanism 90200 includes an insertion mechanism housing having one or more lockout windows, and a base for connection to the assembly platform and/or pump housing (as shown in FIG. 69B and FIG. 69C). The connection of the base to the assembly platform 9020 may be, for example, such that the bottom of the base is permitted to pass-through a hole in the assembly platform to permit direct contact of the base to the body of the user. In such configurations, the bottom of the base may include a sealing membrane that is removable prior to use of the drug delivery device 9010. The insertion mechanism may further include one or more insertion biasing members, a needle, a retraction biasing member, a cannula, and a manifold. The manifold may connect to sterile fluid conduit 9030 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 9027 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the body of the user. At the end of the insertion stage or at the end of drug delivery (as triggered by the multi-function drive mechanism), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the user. Accordingly, the insertion mechanism may be used to insert a needle and cannula into the user and, subsequently, retract the needle while retaining the cannula in position for drug delivery to the body of the user.

XVII.C. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9010, the fluid pathway connector 90300 is enabled to connect the sterile fluid conduit 9030 to the drug container of the drive mechanism 90100. Such connection may be facilitated by a piercing member, such as a needle, penetrating a pierceable seal of the drug container of the drive mechanism 90100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user. In one such embodiment, the fluid pathway connector may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the multi-function drive mechanism. Additionally or alternatively, the sterile fluid pathway connector is initiated by movement directly of the multi-function drive mechanism. For example, the multi-function drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 69A-69C, the multi-function drive mechanism performs all of these steps substantially concurrently. The multi-function drive mechanism rotates a gear that acts upon several other components. The gear acts on a gear assembly to control the rate of drug delivery, while also contacting a needle insertion mechanism to introduce a fluid pathway into the user. As the needle insertion mechanism is initiated, the sterile fluid connection is made to permit drug fluid flow from the drug container, through the fluid conduit, into the needle insertion mechanism, for delivery into the patient as the gear and gear assembly of the multi-function drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 90300 and the sterile fluid conduit 30 are provided hereinafter in later sections in reference to other embodiments.

XVII.D. Multi-Function Drive Mechanism

The multi-function drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. With reference to the embodiments shown in FIGS. 70A-70D and 3A-3D, multi-function drive mechanism 90100 includes an actuator 90101, a gear assembly 90110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. The seals described herein may be comprised of a number of materials but are, in a preferred embodiment, comprised of one or more elastomers or rubbers. The drive mechanism 90100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the body of the user.

In one particular embodiment, the drive mechanism 90100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail herein.

Referring now to the embodiment of the multi-function drive mechanism shown in FIGS. 70A-70D and 71A-71D, multi-function drive mechanism 90100 includes an actuator 90101, a gear assembly 110 including a main gear 90102, a drive housing 90130, and a drug container 9050 having a cap 9052, a pierceable seal (not visible), a barrel 9058, and a plunger seal 9060. The main gear 90102 may be, for example, a star gear disposed to contact multiple secondary gears or gear surfaces. A drug chamber 9021, located within the barrel 9058 between the pierceable seal and the plunger seal 9060, may contain a drug fluid for delivery through the insertion mechanism and drug delivery device into the body of the user. Compressed within the drive housing 90130, between the drug container 9050 and the proximal end of the housing 90130, are one or more drive biasing members 90122 and a piston 90110, wherein the drive biasing members 90122 are configured to bear upon an interface surface 90110C of the piston 90110, as described further herein. Optionally, a cover sleeve (not shown) may be utilized between the drive biasing members 90122 and the interface surface 90110C of the piston 90110 to, for example, promote more even distribution of force from the drive biasing member 90122 to the piston 90110, prevent buckling of the drive biasing members 90122, and/or hide biasing members 90122 from user view. Interface surface 90110C of piston 90110 is caused to rest substantially adjacent to, or in contact with, a proximal end of seal 9060. Although the embodiments shown in FIGS. 70A-70D and 71A-71D show a singular biasing member it is also contemplated that one or more biasing members disposed to act in parallel may be used.

As best shown in FIG. 70D and FIG. 71D, the piston 90110 may be comprised of two components 90110A and 90110B and have an interface surface 90110C to contact the plunger seal. A tether, ribbon, string, or other retention strap (referred to herein as the "tether" 90525) may be connected at one end to the piston 90110A, 90110B. For example, the tether 90525 may be connected to the piston 90110A, 90110B by retention between the two components of the piston 90110A, 90110B when assembled. The tether 90525 is connected at another end to a winch drum/gear 90520 of a delivery control mechanism 90500. Through the use of the winch drum/gear 90520 connected to one end of the tether 90525, and the tether 90525 connected at another end to the piston 90110A, 90110B, the regulating mechanism 90500 functions to control, meter, provide resistance, or otherwise prevent free axial translation of the piston 90110A, 90110B and plunger seal 9060 utilized to force a drug substance out of a drug container 9050. Accordingly, the regulating mechanism 90500 is a portion of the gear assembly 90116 aspect of the multi-function drive mechanism, which together function to control the rate or profile of drug delivery to the user.

As shown in FIGS. 70A-70D and 71A-71D, and in isolation in FIGS. 72 and 73A-73B, in the embodiments of the present disclosure, the regulating mechanism 90500 is gear assembly driven by an actuator 90101 of the multi-function drive mechanism 90100. The regulating mechanism retards or restrains the distribution of tether 90525, only allowing it to advance at a regulated or desired rate. This restricts movement of piston 90110 within barrel 9058, which is pushed by one or more biasing members 90122, hence controlling the movement of plunger seal 9060 and delivery of the drug contained in chamber 9021. As the plunger seal 9060 advances in the drug container 9050, the drug substance is dispensed through the sterile pathway connection 90300, conduit 9030, insertion mechanism 90200, and into the body of the user for drug delivery. The actuator 90101 may be a number of power/motion sources including, for example, a solenoid, a stepper motor, or a rotational drive motor. In a particular embodiment, the actuator 90101 is a rotational stepper motor with a notch that corresponds with the gear teeth of the main/star gear 90102. Commonly, such a rotational stepper motor may be referred to as a 'Pac-Man' motor. In at least one embodiment, the Pac-Man motor has a gear interface within which one or more teeth of the main gear may partially reside during operation of the system. This is more clearly visible in FIGS. 73A-73B. When the gear interface 90101A of the Pac-Man motor 90101 is in alignment with a tooth 90102A of the main gear 90102, rotational motion of the Pac-Man motor 90101 causes gear interface rotation of the main gear 90102. When the Pac-Man motor 90101 is between gear teeth of the main gear, it may act as a resistance for, for example, back-spinning or unwinding of the gear assembly 90116. Further detail about the gear assembly 90116, regulating mechanism 90500, and multi-function drive mechanism 90100 are provided herein.

In a particular embodiment shown in FIGS. 73A-73B, the regulating element 90500 further includes one or more gears 90511, 90512, 90513, 90514, of a gear assembly 90516. One or more of the gears 90511, 90512, 90513, 90514 may be, for example, compound gears having a small diameter gear attached at a shared center point to a large diameter gear. Gear 90513 may be rotationally coupled to winch drum/gear 90520, for example by a keyed shaft, thereby coupling rotation of gear assembly 90516 to winch drum/gear 90520. Compound gear 90512 engages the small diameter gear 90513 such that rotational movement of the compound gear aspect 90512B is conveyed by engagement of the gears (such as by engagement of corresponding gear teeth) to gear

90513. Compound gear aspect 90512A, the rotation of which is coupled to gear aspect 90512B, is caused to rotate by action of compound gear aspect 90102B of the main/star gear 90102. Compound gear aspect 90102B, the rotation of which is coupled to main/star gear 90102, is caused to rotate by interaction between main/star gear 90102A and interface 90101A of the actuator 90101. Thus, rotation of main/star gear 90102 is conveyed to winch drum/gear 90520. Accordingly, rotation of the gear assembly 90516 initiated by the actuator 90101 may be coupled to winch drum/gear 90520 (i.e., through the gear assembly 90516), thereby controlling the distribution of tether 90525, and the rate of movement of plunger seal 9060 within barrel 9058 to force a fluid from drug chamber 9021. The rotational movement of the winch drum/gear 90520, and thus the axial translation of the piston 90110 and plunger seal 9060, are metered, restrained, or otherwise prevented from free axial translation by other components of the regulating element 90500, as described herein. As described above, the actuator 90101 may be a number of known power/motion sources including, for example, a motor (e.g., a DC motor, AC motor, or stepper motor) or a solenoid (e.g., linear solenoid, rotary solenoid).

Notably, the regulating mechanisms 90500 of the present disclosure do not drive the delivery of fluid substances from the drug chamber 9021. The delivery of fluid substances from the drug chamber 9021 is caused by the expansion of the biasing member 90122 from its initial energized state acting upon the piston 90110A, 90110B and plunger seal 9060. The regulating mechanisms 90500 instead function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. According to a preferred embodiment, the controlled delivery drive mechanisms and drug delivery devices of the present disclosure include a regulating mechanism indirectly or directly connected to a tether metering the axial translation of the piston 90110A, 90110B and plunger seal 9060, which are being driven to axially translate by the biasing member 90122. The rate of drug delivery as controlled by the regulating mechanism may be determined by: selection of the gear ratio of gear assembly 90516; selection of the main/star gear 90102; selection of the diameter of winding drum/gear 90520; using electromechanical actuator 90101 to control the rate of rotation of the main/star gear 90102; or any other method known to one skilled in the art. By using electromechanical actuator 90101 the rate of rotation of the main/star gear 90102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 90525 by the winch drum/gear 90520 and thereby permit axial translation of the piston 90110 by the biasing member 90122 to translate a plunger seal 9060 within a barrel 9058. The one or more inputs may be provided by the actuation of the activation mechanism, a control interface, and/or a remote control mechanism. The power and control system may be configured to receive one or more inputs to adjust the restraint provided by the tether 90525 and winch drum/gear 90520 on the free axial translation of the piston 90110 upon which the biasing member 90122 bears upon to meet a desired drug delivery rate or profile, to change the dose volume for delivery to the user, and/or to otherwise start, stop, or pause operation of the drive mechanism.

The components of the drive mechanism 90100, upon activation, may be used to drive axial translation in the distal direction of the plunger seal 9060 of the drug container 9050. Optionally, the drive mechanism 90100 may include one or more compliance features which enable additional axial translation of the plunger seal 9060 to, for example, ensure that substantially the entire drug dose has been delivered to the user. For example, the plunger seal 9060, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

The tether 90525 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 90525 that would contact the status reader at the end of axial travel of the piston 90110A, 90110B and plunger 9060 within the barrel 9058 of the drug container 9050. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 90525 to be read or recognized at positions which correspond with the beginning and end of drug delivery, as well as at desired increments during drug delivery. As the drug delivery device is activated and drug delivery is begun by release of the biasing member 90122 and the resulting force applied to the piston 90110A, 90110B and plunger seal 9060, the rate or profile of drug delivery to the user is controlled by the regulating mechanism 90500, gear assembly 90516, and winch drum/gear 90520 releasing the tether 90525 and permitting expansion of the biasing member 90122 and axial translation of the piston 90110A, 90110B and plunger seal 9060. As this occurs, the status triggers of the tether 90525 are contacted or recognized by the status reader and the status of the drive mechanism before, during, and after operation can be relayed to the power and control system to provide feedback to the user. Depending on the number of status triggers located on the tether 90525, the frequency of the incremental status indication may be varied as desired.

As described above, a range of status readers may be utilized depending on the status triggers utilized by the system.

In a preferred embodiment, the status reader may apply a tensioning force to the tether 90525. When the system reaches end-of-dose, the tether 90525 goes slack and the status reader 90544 is permitted to rotate about a fulcrum. This rotation may operate an electrical or electromechanical switch, for example a switch, signaling slack in the tether 90525 to the power and control system. Additionally, a gear 90511 of gear assembly 90516 may act as an encoder along with a sensor. The sensor/encoder combination is used to provide feedback of gear assembly rotation, which in turn can be calibrated to the position of piston 90110 when there is no slack in the tether 90525. Together, the status reader and sensor/encoder may provide positional feedback, end-of-dose signal, and error indication, such as an occlusion, by observing slack in the tether 90525 prior to reaching the expected number of motor rotations as counted by the sensor/encoder.

Referring back to FIGS. 70A-70D and 71A-71D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the multi-function drive mechanisms of the present disclosure may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user. In at least one embodiment, as shown in FIGS. 70A-70D and 71A-71D, initial motion by the actuator 90101 of the multi-function drive mechanism 90100 causes rotation of main/star gear 90102. Main/star gear 90102 is shown as a compound gear with aspects 90102A and 90102B (see FIG. 72). In one manner, main/star gear 90102 conveys motion to the regulating mechanism 90500 through gear assembly 90516. In another manner, main/star gear 90102 conveys motion to the needle insertion mechanism 90200 through gear 90112. As gear 90112 is rotated by main/star gear 90102, gear 90112 engages the needle insertion mechanism 90200 to initiate the fluid pathway connector into the user, as described in detail above. In one particular embodiment, needle insertion mechanism 90200 is a rotational needle insertion mechanism. Accordingly, gear 90112 is configured to engage a corresponding gear surface 90208 of the needle insertion mechanism 90200. Rotation of gear 90112 causes rotation of needle insertion mechanism 90200 through the gear interaction between gear 90112 of the drive mechanism 90100 and corresponding gear surface 90208 of the needle insertion mechanism 90200. Once suitable rotation of the needle insertion mechanism 90200 occurs, for example rotation along axis 'R' shown in FIG. 70B-70C, the needle insertion mechanism may be initiated to create the fluid pathway connector into the user, as described in detail above.

As shown in FIGS. 70A-70D and 71A-71D, rotation of the needle insertion mechanism 90200 in this manner may also cause a connection of a sterile fluid pathway to a drug container to permit fluid flow from the drug container to the needle insertion mechanism for delivery to the user. Ramp aspect 90222 of needle insertion mechanism 90200 is caused to bear upon a movable connection hub 90322 of the sterile fluid pathway connector 90300. As the needle insertion mechanism 90200 is rotated by the multi-function drive mechanism 90100, ramp aspect 90222 of needle insertion mechanism 90200 bears upon and translates movable connection hub 90322 of the sterile fluid pathway connector 90300 to facilitate a fluid connection therein. Such translation may occur, for example, in the direction of the hollow arrow along axis 'C' shown in FIGS. 70B and 71B. In at least one embodiment, the needle insertion mechanism 90200 may be configured such that a particular degree of rotation upon rotational axis 'R' (shown in FIGS. 70B-70C) enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism 90500 and/or one or more of the status readers as described above. During these stages of operation, delivery of fluid substances from the drug chamber 9021 may be initiated, on-going, and/or completed by the expansion of the biasing member 90122 from its initial energized state acting upon the piston 90110A, 90110B and plunger seal 9060. As described above, the regulating mechanisms 90500 function to provide resistance to the free motion of the piston 90110A, 90110B and plunger seal 9060 as they are pushed by the expansion of the biasing member 90122 from its initial energized state. The regulating mechanism 90500 does not drive the delivery but only controls the delivery motion. The tether limits or otherwise restrains the motion of the piston 90110 and plunger seal 9060, but does not apply the force for the delivery. This is visible through the progression of the components shown in FIGS. 70A-70D and 71A-71D. The motion of the piston 90110A, 90110B and plunger seal 9060 as they are pushed by the expansion of the biasing member 90122 from its initial energized state are shown in the direction of the solid arrow along axis 'A' from proximal or first position 'R' to the distal or second position 'D', as shown in the transition of FIGS. 70A-70D and 71A-71D.

Further aspects of the novel drive mechanism will be described with reference to FIG. 72 and FIGS. 73A-73B. FIG. 72 shows a perspective view of the multi-function drive mechanism, according to at least a first embodiment, during its initial locked stage. Initially, the tether 90525 may retain the biasing member 90122 in an initial energized position within piston 90110A, 90110B. Directly or indirectly upon activation of the device by the user, the multi-function drive mechanism 90100 may be activated to permit the biasing member to impart a force to piston 90110 and therefore to tether 90525. This force on tether 90525 imparts a torque on winding drum 90520 which causes the gear assembly 90516 and regulating mechanism 90500 to begin motion. As shown in FIG. 73A, the piston 90110 and biasing member 90122 are both initially in a compressed, energized state behind the plunger seal 9060. The biasing member 90122 may be maintained in this state until activation of the device between internal features of drive housing 90130 and interface surface 90110C of piston 90110A, 90110B. As the drug delivery device 10 is activated and the drive mechanism 90100 is triggered to operate, biasing member 90122 is permitted to expand (i.e., decompress) axially in the distal direction (i.e., in the direction of the solid arrow shown in FIGS. 70A-70D and FIGS. 71A-71D). Such expansion causes the biasing member 90122 to act upon and distally translate interface surface 90110C and piston 90110, thereby distally translating plunger seal 9060 to push drug fluid out of the drug chamber 9021 of barrel 9058. In at least one embodiment, an end-of-dose status indication may be provided to the user once the status reader contacts or recognizes a status trigger positioned on the tether 90525 to substantially correspond with the end of axial travel of the piston 90110A, 90110B and plunger seal 9060 within the barrel 9058 of the drug container 9050. The status triggers may be positioned along the tether 90525 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 90525 to be read or recognized at positions which correspond with the beginning and end of drug delivery, as well as at desired increments during drug delivery. As shown, tether 90525 passes substantially axially through the drive mechanism housing 90130, the biasing member 90122, and connects to the piston 90110 A, 90110B to restrict the axial translation of the piston 90110A, 90110B and the plunger seal 9060 that resides adjacent thereto.

The novel embodiments of the present disclosure may be utilized to meter, restrain, or otherwise prevent free rotational movement of winding drum 90520 and, thus, axial translation of the components of the controlled delivery drive mechanism 90100. Accordingly, the regulating mechanism 90500 only controls the motion of the drive mechanism, but does not apply the force for the drug delivery. One or more additional biasing members 90122, such as compression springs, may be utilized to drive or assist the driving of the piston 90110. For example, a compression spring may be utilized within the drive housing 90130 for this purpose. The regulating mechanism 90500 only controls, meters, or regulates such action. The controlled delivery drive mechanisms and/or drug delivery devices of the present disclosure may additionally enable a compliance push to ensure that substantially all of the drug substance has been pushed out of the drug chamber 9021. The plunger seal 9060, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear assembly 90516. As the gear assembly 90516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear assembly and regulating mechanism shown in the figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 90101. The change in the rate of movement of actuator 90101 causes a change in the rotation rate of regulating mechanism 90500 which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present disclosure are capable of producing a change to the rate of medicament delivery from the drug container thereby providing a dynamic control capability to the multi-function drive mechanism and/or the drug delivery device.

Assembly and/or manufacturing of controlled delivery drive mechanism 90100, drug delivery pump 9010, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9050 may first be assembled and filled with a fluid for delivery to the user. The drug container 9050 includes a cap 9052, a pierceable seal 9056, a barrel 9058, and a plunger seal 9060. The pierceable seal 9056 may be fixedly engaged between the cap 9052 and the barrel 9058, at a distal end of the barrel 9058. The barrel 9058 may be filled with a drug fluid through the open proximal end prior to insertion of the plunger seal 9060 from the proximal end of the barrel 9058. An optional connection mount 9054 may be mounted to a distal end of the pierceable seal 9056. The connection mount 9054 may guide the insertion of the piercing member of the fluid pathway connector into the barrel 9058 of the drug container 9050. The drug container 9050 may then be mounted to a distal end of drive housing 90130.

One or more drive biasing members 90122 may be inserted into a distal end of the drive housing 90130. Optionally, a cover sleeve 90140 may be inserted into a distal end of the drive housing 90130 to substantially cover biasing member 90122. A piston may be inserted into the distal end of the drive housing 90130 such that it resides at least partially within an axial pass-through of the biasing member 90122 and the biasing member 90122 is permitted to contact a piston interface surface 90110C of piston 90110A, 90110B at the distal end of the biasing member 90122. An optional cover sleeve 90140 may be utilized to enclose the biasing member 122 and contact the piston interface surface 90110C of piston 90110A, 90110B. The piston 90110A, 90110B and drive biasing member 90122, and optional cover sleeve 90140, may be compressed into drive housing 90130. Such assembly positions the drive biasing member 90122 in an initial compressed, energized state and preferably places a piston interface surface 90110C in contact with the proximal surface of the plunger seal 9060 within the proximal end of barrel 9058. The piston, piston biasing member, contact sleeve, and optional components, may be compressed and locked into the ready-to-actuate state within the drive housing 90130 prior to attachment or mounting of the drug container 9050. The tether 90525 is pre-connected to the proximal end of the piston 90110A, 90110B and passed through the axial aperture of the biasing member 90122 and drive mechanism 90130, and then wound through the interior of the drug delivery device with the other end of the tether 90525 wrapped around the winch drum/gear 90520 of the regulating mechanism 90500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug delivery device, as shown in FIG. 69B.

Certain optional standard components or variations of drive mechanism 90100 or drug delivery device 9010 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9018 to enable the user to view the operation of the drug delivery device 9010 or verify that drug dose has completed. Similarly, the drug delivery device 9010 may contain an adhesive patch 9026 and a patch liner 9028 on the bottom surface of the housing 9012. The adhesive patch 9026 may be utilized to adhere the drug delivery device 9010 to the body of the user for delivery of the drug dose. As would be readily understood by one having ordinary skill in the art, the adhesive patch 9026 may have an adhesive surface for adhesion of the drug delivery device to the body of the user. The adhesive surface of the adhesive patch 9026 may initially be covered by a non-adhesive patch liner 9028, which is removed from the adhesive patch 9026 prior to placement of the drug delivery device 9010 in contact with the body of the user. Removal of the patch liner 9028 may further remove the sealing membrane 90254 of the insertion mechanism 90200, opening the insertion mechanism to the body of the user for drug delivery (as shown in FIG. 69C).

Similarly, one or more of the components of controlled delivery drive mechanism 90100 and drug delivery device 9010 may be modified while remaining functionally within the breadth and scope of the present disclosure. For example, as described above, while the housing of drug delivery device 9010 is shown as two separate components upper housing 9012A and lower housing 9012B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connection, a sterile fluid conduit, and the insertion mechanism for delivery of the fluid drug to the body of a user, wherein a regulating mechanism acting to restrain the distribution of a tether is utilized to meter the free axial translation of the piston. The method of operation of the drive mechanism and the drug delivery device may be better appreciated with reference to FIGS. 70A-70D and FIGS. 71A-71D, as described above.

XVIII. Additional Embodiments of Multi-Function Drive Mechanism

At least some of the drug delivery devices described in this application, including at least those described in connection with FIGS. 1A-2B, 33A-33C, 69A-75B, 80A-85C, 86A-91, 92A-99, and 100A-109B may be configured to incorporate the embodiments of the drive mechanism described below in connection with FIGS. 110A-141B. The embodiments of the drive mechanism described below in connection with FIGS. 110A-141B may be used to replace, in its entirety or partially, the above-described drive mechanism 100, 6100, 8100, 90100, 92100, 93100, 94100, or 95100, or any other drive mechanism described herein, where appropriate.

The present disclosure provides drive mechanisms for the controlled delivery of drug substances, controlled drug delivery pumps with such drive mechanisms, the methods of operating such devices, and the methods of assembling such devices. Notably, the drive mechanisms of the present disclosure enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a target; and (iii) connecting a sterile fluid pathway to a drug container to permit fluid flow from the drug container to the needle insertion mechanism for delivery to the target. The novel embodiments of the present disclosure thus are capable of delivering drug substances at variable rates. The drive mechanisms of the present disclosure may be pre-configurable or dynamically configurable, such as by control by the power and control system, to meet desired delivery rates or profiles, as explained in detail below. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. Because the end-of-dose indication is related to the physical end of axial translation and/or travel of one or more components of the drive mechanism, the drive mechanism and drug delivery device provide a true end-of-dose indication to the user. Through these mechanisms, confirmation of drug dose delivery can accurately be provided to the user or administrator. Accordingly, the novel devices of the present disclosure alleviate one or more of the problems associated with prior art devices, such as those referred to above.

In a first embodiment, the present disclosure provides a drive mechanism which includes an actuator, a gear assembly including a main gear, a drive housing, and a drug container having a cap, a pierceable seal (not visible), a barrel, and a plunger seal. The main gear may be, for example, a star gear disposed to contact multiple secondary gears or gear surfaces. A drug chamber, located within the barrel between the pierceable seal and the plunger seal, may contain a drug fluid for delivery through the insertion mechanism and drug delivery device into the target. A piston, and one or more biasing members, wherein the one or more biasing members are initially retained in an energized state and is configured to bear upon an interface surface of the piston, may also be incorporated in the drive mechanism. The piston is configured to translate substantially axially within a drug container having a plunger seal and a barrel. A tether is connected at one end to the piston and at another end to a winch assembly of a regulating mechanism, wherein the tether restrains the free expansion of the biasing member from its initial energized state and the free axial translation of the piston upon which the biasing member bears upon. The drug container may contain a drug fluid within a drug chamber for delivery to a target. Optionally, a cover sleeve may be utilized between the biasing member and the interface surface of the piston to hide the interior components of the barrel (namely, the piston and the biasing member) from view during operation of the drive mechanism. The tether is configured to be released from a winch assembly of a regulating mechanism of the drive mechanism to meter the free expansion of the biasing member from its initial energized state and the free axial translation of the piston upon which the biasing member bears upon.

Alternatively, the present disclosure provides a drive mechanism for utilization with a drug container in a drug delivery device, the drug container including a barrel and a plunger seal, including a tether, an electrical actuator, and a gear interface. Rotation of the gear interface is controlled by the electrical actuator. A gear assembly is in rotational engagement with the gear interface and includes a main gear and a regulating mechanism, wherein release of the tether is metered by operation of the gear assembly through the regulating mechanism. A drive housing is provided. A piston is connected to the tether and configured for disposition in the barrel adjacent the plunger seal. The piston is configured to translate substantially axially within the drug container and a biasing member is configured for disposition at least partially within the barrel, the biasing member being retained in an energized state between the piston and drive housing. The release of the tether controls the free expansion of the biasing member from its energized state and the free axial translation of the piston upon which the biasing member bears upon.

The present disclosure provides in other aspects a drug delivery pump, including a drive mechanism of any of the disclosed embodiments and a drug container including a barrel and a plunger seal, a needle insertion mechanism and a fluid pathway connector. The disclosure also may provide a safety mechanism configured to terminate or slow delivery of the drug fluid through the fluid pathway connector upon a loss of tension in the tether.

In yet another embodiment, the present disclosure provides a primable drive mechanism for utilization with a drug container in a drug delivery device, the drug container including a barrel and a plunger seal, including a tether, a drive housing, and a winch drum. A piston is connected to the tether and configured for disposition in the barrel adjacent the plunger seal, the piston configured to translate substantially axially within the drug container and a biasing member is configured for disposition at least partially within the barrel, the biasing member being retained in an energized state between the piston and drive housing. The tether is disposed and wound upon the winch drum and is configured to be released from the winch drum by rotation of the winch drum to meter the free expansion of the biasing member from its energized state and the free axial translation of the piston upon which the biasing member bears upon.

In at least one embodiment of the present disclosure, the regulating mechanism is a gear assembly driven by an actuator of the drive mechanism. The regulating mechanism retards or restrains the distribution of the tether, only allowing it to advance at a regulated or desired rate. This restricts movement of the piston within the barrel, which is pushed by one or more biasing members, hence controlling the movement of the plunger seal and delivery of the drug contained in the chamber. As the plunger seal advances in the drug container, the drug substance is dispensed through the sterile pathway connection, conduit, insertion mechanism, and into the target for drug delivery. The actuator may be a number of power/motion sources including, for example, a motor (e.g., a DC motor, AC motor, or stepper motor) or a solenoid (e.g., linear solenoid, rotary solenoid). In a particular embodiment, the actuator is a rotational stepper motor with a notch that corresponds with the gear teeth of the main/star gear.

The regulating mechanism may further include one or more gears of a gear assembly. One or more of the gears may be, for example, compound gears having a small diameter gear attached at a shared center point to a large diameter gear. The gear assembly may include a gear coupled to a winch assembly upon which the tether may be releasably wound. Accordingly, rotation of the gear assembly initiated by the actuator may be coupled to winch assembly (i.e., through the gear assembly), thereby controlling the distribution of the tether, the rate of expansion of the biasing members and the axial translation of the piston, and the rate of movement of the plunger seal within the barrel to force a fluid from the drug chamber. The rotational movement of the winch assembly, and thus the axial translation of the piston and plunger seal, are metered, restrained, or otherwise prevented from free axial translation by other components of the regulating element, as described herein. Notably, the regulating mechanisms of the present disclosure do not drive the delivery of fluid substances from the drug chamber. The delivery of fluid substances from the drug chamber is caused by the expansion of the biasing member from its initial energized state acting upon the piston and plunger seal. The regulating mechanisms instead function to provide resistance to the free motion of the piston and plunger seal as they are pushed by the expansion of the biasing member from its initial energized state. The regulating mechanism does not drive the delivery but only controls the delivery motion. The tether limits or otherwise restrains the motion of the piston and plunger seal, but does not apply the force for the delivery.

In addition to controlling the rate of drug delivery by metering, providing resistance, or otherwise preventing free axial translation of the plunger seal utilized to force a drug substance out of a drug container (thereby delivering drug substances at variable rates and/or delivery profiles); the drive mechanisms of the present disclosure may concurrently or sequentially perform the steps of: triggering a needle insertion mechanism (NIM) to provide a fluid pathway for drug delivery to a target; and connecting a sterile fluid pathway to a drug container to permit fluid flow from the drug container to the needle insertion mechanism for delivery to the target. In at least one embodiment, initial motion by the actuator of the drive mechanism causes rotation of the main/star gear. In one manner, the main/star gear conveys motion to the regulating mechanism through the gear assembly. In another manner, the main/star gear conveys motion to the needle insertion mechanism through a gear. As the gear is rotated by the main/star gear, the gear engages the needle insertion mechanism to initiate the fluid pathway connector into the target, as described in detail above. In one particular embodiment, the needle insertion mechanism is a rotational needle insertion mechanism. Accordingly, the gear is configured to engage a corresponding gear surface of the needle insertion mechanism. Rotation of gear causes rotation of needle insertion mechanism through the gear interaction between gear of the drive mechanism and corresponding gear surface of the needle insertion mechanism. Once suitable rotation of the needle insertion mechanism occurs, the needle insertion mechanism may be initiated to create the fluid pathway connector into the target, as described in detail herein.

In another embodiment, the drive mechanism may configure a NIM activation mechanism for activation by a user. For example, the NIM activation mechanism may be in an initial configuration in which depression of an actuation of an activation mechanism does not activate the NIM. The drive mechanism may subsequently transform the NIM activation mechanism to a configuration in which actuation of the activation mechanism does activate needle insertion. For example, actuation of the activation mechanism may cause translation of a slide. The drive mechanism may cause a selector member to be positioned such that contact between the slide and the selector member causes at least a portion of the slide to be displaced. This displacement brings the slide into contact with a throw arm which is caused to translate with the slide. This translation of the throw arm causes activation of needle insertion. For example, the throw arm may cause displacement of a NIM interlock which, in an initial configuration, prevents rotation of a NIM retainer. The NIM retainer initially prevents activation of needle insertion. After translation of the NIM interlock, an aperture of the NIM interlock is aligned with a portion of the NIM retainer, allowing rotation of the NIM retainer. This rotation allows activation of needle insertion.

In at least one embodiment, rotation of the needle insertion mechanism in this manner may also cause a connection of a sterile fluid pathway to a drug container to permit fluid flow from the drug container to the needle insertion mechanism for delivery to the target. Ramp aspect of needle insertion mechanism is caused to bear upon a movable connection hub of the sterile fluid pathway connector. As the needle insertion mechanism is rotated by the drive mechanism, a ramp aspect of the needle insertion mechanism bears upon and translates a movable connection hub of the sterile fluid pathway connector to facilitate a fluid connection therein. In at least one embodiment, the needle insertion mechanism may be configured such that a particular degree of rotation enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism and/or one or more of the status readers as described herein.

In yet another embodiment, the drive mechanism may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In a further embodiment, the present disclosure provides a drug delivery pump with controlled drug delivery. The drug delivery pump having a housing and an assembly platform, upon which an activation mechanism, an insertion mechanism, a fluid pathway connector, a power and control system, and a controlled delivery drive mechanism may be mounted, said drive mechanism having a drive housing, a piston, and a biasing member, wherein the biasing member is initially retained in an energized state and is configured to bear upon an interface surface of the piston. The piston is configured to translate substantially axially within a drug container having a plunger seal and a barrel. A tether is connected at one end to the piston and at another end to a winch assembly of a delivery regulating mechanism, wherein the tether restrains the free expansion of the biasing member from its initial energized state and the free axial translation of the piston upon which the biasing member bears upon. The drug container may contain a drug fluid within a drug chamber for delivery to a target. Optionally, a cover sleeve may be utilized between the biasing member and the interface surface of the piston to hide the interior components of the barrel (namely, the piston and the biasing member) from view during operation of the drive mechanism. The tether is configured to be released from a winch assembly of the delivery regulating mechanism to meter the free expansion of the biasing member from its initial energized state and the free axial translation of the piston upon which the biasing member bears upon.

In another embodiment, the drug delivery device further includes a gear assembly. The gear assembly may include a winch gear connected to a winch assembly upon which the tether may be releasably wound, rotation of the winch assembly releases the tether from the winch assembly to meter the free expansion of the biasing member from its initial energized state and the free axial translation of the piston upon which the biasing member bears upon. The metering of the tether controls the rate or profile of drug delivery to a target. The piston may be one or more parts and connects to a distal end of the tether. The winch assembly is coupled to a regulating mechanism which controls rotation of the winch assembly and hence metering of the translation of the piston.

In yet another embodiment, the drug delivery device may include a status reader configured to read or recognize one or more corresponding status triggers. The status triggers may be incrementally spaced on the tether, wherein, during operation of the drive mechanism, interaction between the status reader and the status triggers transmit a signal to a power and control system to provide feedback to a user. The status reader may be an optical status reader and the corresponding status triggers are optical status triggers, an electromechanical status reader and the corresponding status triggers are electromechanical status triggers, or a mechanical status reader and the corresponding status triggers are mechanical status triggers.

In another embodiment, the power and control system of the drug delivery device is configured to receive one or more inputs to meter the release of the tether by the winch assembly and thereby permit axial translation of the piston by the biasing member to translate a plunger seal within a barrel. The one or more inputs may be provided by the actuation of the activation mechanism, a control interface, and/or a remote control mechanism. The power and control system may be configured to receive one or more inputs to adjust the restraint provided by the tether and winch assembly on the free axial translation of the piston upon which the biasing member bears upon to meet a desired drug delivery rate or profile, to change the dose volume for delivery to the target, and/or to otherwise start, stop, or pause operation of the drive mechanism.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered, often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the target. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the target. Accordingly, one or more embodiments of the present disclosure are capable of producing a change to the rate of medicament delivery from the drug container thereby providing a dynamic control capability to the drive mechanism and/or the drug delivery device.

The devices described herein may further include features which prevent the delivery of an excess volume of medicament or delivery at too rapid of a rate, e.g., to prevent a run-away condition of uncontrolled or undesired delivery of the medicament. By providing such automatic safety mechanisms, the safety of the target may be ensured. Some medicaments, such as insulin or other treatments for diabetes, can be dangerous, and potentially even deadly, if they are not delivered according to prescribed parameters. Such safety mechanisms can include a brake mechanism, a plunger seal piercing mechanism, and a plunger seal displacing mechanism, such as those described in detail herein. The safety features described below may ensure that delivery of the medicament is terminated if delivery deviates from the specified parameters.

The present disclosure provides drive mechanisms for the delivery of drug substances and drug delivery pumps which incorporate such drive mechanisms. The drive mechanisms of the present disclosure may enable or initiate one or more functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a target; and (iii) connecting a sterile fluid pathway to a drug container to permit fluid flow from the drug container to the needle insertion mechanism for delivery to the target. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication.

The devices described herein may be configured for delivery of controlled substances and may further include features that prevent so-called "run-away" delivery of medicament. When delivering controlled substances, this may be an important safety feature to protect the target. For example, some medicaments, such as insulin, can be dangerous, and potentially even deadly, when administered in too large a quantity and/or at too rapid of a rate. By providing such automatic safety stop mechanisms, the safety of the target may be ensured.

The novel devices of the present disclosure provide drive mechanisms with integrated status indication and drug delivery pumps which incorporate such drive mechanisms. Such devices are safe and easy to use, and are aesthetically and ergonomically appealing. The devices described herein incorporate features which make activation, operation, and lock-out of the device simple for even untrained users. The novel devices of the present disclosure provide these desirable features without any of the problems associated with known prior art devices. Certain non-limiting embodiments of the novel drug delivery pumps, drive mechanisms, and their respective components are described further herein with reference to the accompanying figures.

As used herein, the terms "pump" and "delivery device" are intended to include any number of drug delivery systems which are capable of dispensing a fluid to a user upon activation. Such drug delivery systems include, but are not limited to, for example, injection systems, infusion pumps, bolus injectors, on-body injectors, and the like. FIGS. 110A-111A show an exemplary drug delivery device according to at least one embodiment of the present disclosure. FIGS. 110B and 111A show the drug delivery device with the top housing removed so that the internal components are visible. The drug delivery device may be utilized to administer delivery of a drug treatment into a target. As shown in FIGS. 110A-110C, the drug delivery device 9610 includes a pump housing 9612. Pump housing 9612 may include one or more housing subcomponents which are fixedly engageable to facilitate easier manufacturing, assembly, and operation of the drug delivery device. For example, drug delivery device 9610 includes a pump housing 9612 which may include an upper housing 9612A and a lower housing 9612B. The pump housing 9612 may include one or more tamper evidence features to identify if the drug delivery device has been opened or tampered with. For example, the pump housing 9612 may include one or more tamper evidence labels or stickers, such as labels that bridge across the upper housing and the lower housing. Additionally or alternatively, the housing 9612 may include one or more snap arms or prongs connecting between the upper housing and the lower housing. A broken or altered tamper evidence feature would signal to the user, the physician, the supplier, the manufacturer, or the like, that the drug delivery device has potentially been tampered with, e.g., by accessing the internal aspects of the device, so that the device is evaluated and possibly discarded without use by or risk to the user. The drug delivery device may further include an activation mechanism 9614, a status indicator (not shown), and a window 9618. The window 9618 may be any translucent or transmissive surface through which the operation of the drug delivery device may be viewed. As shown in FIGS. 110B and 111A, drug delivery device 9610 further includes assembly platform 9620, drive mechanism 96100 having drug container 9650, insertion mechanism 96200, fluid pathway connector 96300, and a power and control system 96400. One or more of the components of such drug delivery devices may be modular in that they may be, for example, pre-assembled as separate components and configured into position onto the assembly platform 9620 of the drug delivery device 9610 during manufacturing.

The pump housing 9612 contains all of the device components and provides a means of removably attaching the device 9610 to the target. The pump housing 9612 also provides protection to the interior components of the device 9610 against environmental influences. The pump housing 9612 is ergonomically and aesthetically designed in size, shape, and related features to facilitate easy packaging, storage, handling, and use by users who may be untrained and/or physically impaired. Furthermore, the external surface of the pump housing 9612 may be utilized to provide product labeling, safety instructions, and the like. Additionally, as described above, housing 9612 may include certain components, such as one or more status indicators and windows, which may provide operation feedback to the user.

In at least one embodiment, the drug delivery device 9610 provides an activation mechanism 14 that is displaced by the user to trigger the start command to the power and control system. In a preferred embodiment, the activation mechanism 9614 is a start button that is located through the pump housing 9612, such as through an aperture between upper housing 9612A and lower housing 9612B, and which contacts either directly or indirectly the power and control system 96400. In at least one embodiment, the start button may be a push button, and in other embodiments, may be an on/off switch, a toggle, or any similar activation feature known in the art. The pump housing 9612 also provides one or more status indicators and windows. In other embodiments, one or more of the activation mechanism 9614, the status indicator, the window 9618, and combinations thereof may be provided on the upper housing 9612A or the lower housing 9612B such as, for example, on a side visible to the user when the drug delivery device 9610 is placed on the target. Housing 9612 is described in further detail hereinafter with reference to other components and embodiments of the present disclosure.

Drug delivery device 9610 is configured such that, upon activation by a user by depression of the activation mechanism, the drive mechanism is activated to perform one or more of the following functions: insert a fluid pathway into the target; enable, connect, or open necessary connections between a drug container, a fluid pathway, and a sterile fluid conduit; and force drug fluid stored in the drug container through the fluid pathway and fluid conduit for delivery into a target. In at least one embodiment, such delivery of drug fluid into a target is performed by the drive mechanism in a controlled manner. One or more optional safety mechanisms may be utilized, for example, to prevent premature activation of the drug delivery device. For example, an optional on-body sensor 9624 may be provided in one embodiment as a safety feature to ensure that the power and control system, or the activation mechanism, cannot be engaged unless the drug delivery device 9610 is in contact with the target. In one such embodiment, the on-body sensor is located on the bottom of lower housing 9612B where it may come in contact with the target. Upon displacement or activation of the on-body sensor 9624, depression of the activation mechanism is permitted. Accordingly, in at least one embodiment the on-body sensor is a mechanical safety mechanism, such as for example a mechanical lock out, that prevents triggering of the drug delivery device 9610 by the activation mechanism. In another embodiment, the on-body sensor may be an electro-mechanical sensor such as a mechanical lock out that sends a signal to the power and control system to permit activation. In still other embodiments, the on-body sensor can be electrically based such as, for example, a conductive, capacitive- or impedance-based sensor which must detect tissue before permitting activation of the power and control system. In at least one embodiment, housing 9612 is configured to at least partially prevent harmful matter from entering the drug delivery device. For example, the housing may be configured to restrict the passage of fluids into the drug delivery device. This may allow the device to be worn in the shower, while swimming, or during other activities. Use of an electrically based on-body sensor may eliminate potential points of entry into the drug delivery device for such fluids. These concepts are not mutually exclusive and one or more combinations may be utilized within the breadth of the present disclosure to prevent, for example, premature activation of the drug delivery device. In a preferred embodiment, the drug delivery device 9610 utilizes one or more electrically based on-body sensors. Additional integrated safety mechanisms are described herein with reference to other components of the novel drug delivery devices.

XVIII.A. Power and Control System

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 96100. In one embodiment, the power and control system interfaces either directly or indirectly with an on-body sensor 9624 to identify when the device is in contact with the target and/or the activation mechanism 9614 to identify when the device has been activated. The power and control system may also interface with the status indicator of the pump housing 9612, which may be a transmissive or translucent material which permits light transfer, to provide visual feedback to the user. The power and control system interfaces with the drive mechanism 96100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator if device start-up checks provide no errors. After providing the ready-to-start status signal and, in an embodiment with the optional on-body sensor, if the on-body sensor remains in contact with the target, the power and control system will power the drive mechanism 96100 to begin delivery of the drug treatment through the fluid pathway connector 96300 and sterile fluid conduit (not shown).

Additionally, the power and control system may be configured to identify removal of the drug delivery device from its packaging. The power and control system may be mechanically, electronically, or electro-mechanically connected to the packaging such that removal of the drug delivery device from the packaging may activate or power-on the power and control system for use, or simply enable the power and control system to be powered-on by the user. In such an embodiment, without removal of the drug delivery device from the packaging the drug delivery device cannot be activated. This provides an additional safety mechanism of the drug delivery device and for the user. In at least one embodiment, the drug delivery device or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between. Additionally or alternatively, the drug delivery device or the power and control system may be mechanically connected to the packaging, such as by a pin and slot relationship which activates the system when the pin is removed (i.e., once the drug delivery device is removed from the packaging).

In a preferred embodiment of the present disclosure, once the power and control system has been activated, the drive mechanism is initiated to perform one or more of the steps of actuating the insertion mechanism 96200 and the fluid pathway connector 96300, while also permitting the drug fluid to be forced from the drug container. During the drug delivery process, the power and control system is configured to provide a dispensing status signal via the status indicator. After the drug has been administered into the target and after the end of any additional dwell time, to ensure that substantially the entire dose has been delivered to the target, the power and control system may provide an okay-to-remove status signal via the status indicator. This may be independently verified by the user by viewing the drive mechanism and drug dose delivery through the window 9618 of the pump housing 9612. Additionally, the power and control system may be configured to provide one or more alert signals via the status indicator, such as for example alerts indicative of fault or operation failure situations.

The power and control system may additionally be configured to accept various inputs from the user to dynamically control the drive mechanisms 96100 to meet a desired drug delivery rate or profile. For example, the power and control system may receive inputs, such as from partial or full activation, depression, and/or release of the activation mechanism, to set, initiate, stop, or otherwise adjust the control of the drive mechanism 96100 via the power and control system to meet the desired drug delivery rate or profile. Similarly, the power and control system may be configured to do one or more of the following: receive such inputs to adjust the drug dose volume; to prime the drive mechanism, fluid pathway connector, and fluid conduit; and/or to start, stop, or pause operation of the drive mechanism 96100. Such inputs may be received by the user directly acting on the drug delivery device 9610, such as by use of the activation mechanism 9614 or a different control interface, or the power and control system may be configured to receive such inputs from a remote control device. Additionally or alternatively, such inputs may be pre-programmed.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug delivery device 9610 prior to drug delivery device activation. Additionally, the system may include a feature which permits the user to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

Additionally, the power and control system may be configured to maintain regulation of the system's power source while providing momentary power to an actuator. During operation of the drug delivery device, as will be described further herein, momentary power is needed to move an actuator clockwise and counterclockwise between mechanical limits. This motion controls the motion of the drive system and, hence, the rate of delivery of the medicament. Directly supplying power to the actuator may lead to a large voltage drop which could interrupt the power source to other components of the drug delivery device. To avoid this, the power and control system may be configured to decouple the power source from the actuator when power is supplied to the actuator. To this end, the power and control system may include a switching device, such as a field-effect transistor; a charge-slowing device, such as a resistor; and a storage device, such as a capacitor. The three devices are serially connected between the power source and ground. The output is obtained from the capacitor and is connected to the actuator via a control device, such as an H-bridge. During operation the system operates in the following manner: First, the switching device is set to a fully closed configuration, connecting the power source, to the storage device and allowing the storage device to be charged by the power source in a length of time defined by, for example, the RC time constant. Second, the switch is opened, thereby disconnecting the power source from the storage device with the storage device remaining fully charged. Third, the charged storage device is applied to the control device. Fourth, the control device applies the stored power to the actuator and controls the actuator direction (clockwise or counterclockwise). In this way, the power source is not connected to the actuator when the actuator is powered, ensuring that the power source does not experience a voltage drop. This process repeats as needed to provide continued actuator clockwise and counterclockwise inputs to the pump drive mechanism without collapsing the system power source.

XVIII.B. Insertion Mechanism

A number of insertion mechanisms may be utilized within the drug delivery devices of the present disclosure. The pump-type delivery devices of the present disclosure may be connected in fluid flow communication to a target, for example, through any suitable hollow tubing. A hollow needle or a solid bore needle may be used to pierce the target and place a hollow cannula at the appropriate delivery position, with the needle being at least partially removed or retracted prior to drug delivery to the target. As stated above, the fluid can be introduced into the body through any number of means, including but not limited to: an automatically inserted needle, cannula, micro-needle array, or infusion set tubing. A number of mechanisms may also be employed to activate the needle insertion into the target. For example, a biasing member such as a spring may be employed to provide sufficient force to cause the needle and cannula to pierce the target. The same spring, an additional spring, or another similar mechanism may be utilized to retract the needle from the target. In one embodiment, the insertion mechanism may generally be as described in International Patent Application No. PCT/US2012/53174, which is included by reference herein in its entirety for all purposes. Such a configuration may be utilized for insertion of the drug delivery pathway into, or below, the target in a manner that minimizes pain. Other known methods for insertion of a fluid pathway may be utilized and are contemplated within the bounds of the present disclosure, including a rigid needle insertion mechanism and/or a rotational needle insertion mechanism as developed by the assignee of the present disclosure.

In at least one embodiment, the insertion mechanism 96200 includes an insertion mechanism housing that may have a base for connection to the assembly platform and/or pump housing (as shown in FIG. 110B and FIG. 110C). The connection of the base to the assembly platform 9620 may be, for example, such that the bottom of the base is permitted to pass-through a hole in the assembly platform to permit direct contact of the base to the target. In such configurations, the bottom of the base may include a sealing membrane that is removable prior to use of the drug delivery device 9610. The insertion mechanism may further include one or more insertion biasing members, a needle, a retraction biasing member, a cannula, and a manifold. The manifold may connect to a sterile fluid conduit to permit fluid flow through the manifold, cannula, and into the target during drug delivery.

As used herein, "needle" is intended to refer to a variety of needles including but not limited to conventional hollow needles, such as a rigid hollow steel needles, and solid core needles more commonly referred to as a "trocars." In some embodiments, the needle is a 9627 gauge solid core trocar and in other embodiments, the needle may be any size needle suitable to insert the cannula for the type of drug and drug administration (e.g., subcutaneous, intramuscular, intradermal, etc.) intended. In one or more embodiments, the insertion mechanism may generally be as described in International Patent Application No. PCT/US2012/53174 published as WO 2013/033421 A2, International Patent Application No. PCT/US2012/053241 published as WO 2013/033467 A2 or International Patent Application No. PCT/US2015/052815, which are included by reference herein in their entirety for all purposes.

The base includes a base opening through which the needle and cannula may pass-through during operation of the insertion mechanism. Sterility of the cannula and needle are maintained by their initial positioning within the sterile portions of the insertion mechanism. The base opening of base may be closed from non-sterile environments as well, such as by for example a sealing membrane.

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the target. At the end of the insertion stage or at the end of drug delivery (as triggered by the drive mechanism), the retraction biasing member is permitted to expand in the proximal direction from its initial energized state. This axial expansion in the proximal direction of the retraction biasing member retracts the needle. If an inserter needle/trocar and cannula configuration is utilized, retraction of the needle may occur while maintaining the cannula in fluid communication with the target. Accordingly, the insertion mechanism may be used to insert a needle and cannula into the target and, subsequently, retract the needle while retaining the cannula in position for drug delivery to the target.

In one or more embodiments, the insertion mechanism may generally be as described in International Patent Application No. PCT/US2016/017534 filed Feb. 10, 2016, which is included by reference herein in its entirety for all purposes. In at least one embodiment, as shown in FIG. 115A, the insertion mechanism includes a rotationally biased member 96210 which is initially held in an energized state. In a preferred embodiment, the rotationally biased member is a torsional spring. The rotational biasing member may be prevented from de-energizing by interaction of gear surface 96208 with gear 96112 as shown in FIG. 111A or, alternatively, by contact of a component of the insertion mechanism with a rotation prevention feature of the drug delivery device, as described further herein. Upon activation of the device, or another input, the rotationally biased member 96210 is permitted to, at least partially, de-energize. This causes one or more components of the insertion mechanism to rotate and, in turn, cause, or allow, the insertion of the needle into the target. Further, a cannula may be inserted into the target as described above. At a later time, such as when the control arm or another component of the device recognizes a slack in the tether, the rotationally biased member may be allowed to further de-energize, causing additional rotation of one or more components of the insertion mechanism. This rotation may cause, or allow, the needle to be retracted from the target. The needle may be fully retracted in a single step or there may be multiple steps of retraction.

In one embodiment, translation of the activation mechanism may be a part of, or operate, a NIM activation mechanism. The NIM activation mechanism may include an enabling mechanism as shown in FIGS. 122A-122B. In this embodiment, translation of the activation mechanism 9614 may be directly or indirectly coupled to a slide 96602. In a first configuration, the enabling mechanism is configured such that translation of the activation mechanism and slide does not cause activation of the needle insertion mechanism 96200 or sterile fluid pathway connector 96300.

FIGS. 122A-122B illustrate the enabling mechanism configured such that translation of the activation mechanism 9614 (See FIG. 110A) and slide 96602 causes activation of the needle insertion mechanism 96200. Transformation of the enabling mechanism from the first configuration to the second configuration may be initiated by, for example, triggering of an on-body sensor, or by the elapsing of a predetermined amount of time after power-on of the device. The transformation of the enabling mechanism from the first to the second configuration may be performed by rotation of the actuator 96101 which may cause a selector member 96604 to become aligned with an aspect of the slide 96602. The selector member 96604 may include a ramped surface 96604A which is configured to contact a portion of the slide 96602 upon translation of the activation mechanism 14 and slide 96602. The selector member 96604 may be mounted to or be an integral portion of the gear interface such as key 961101. Contact of the slide 96602 with the selector member 96604 may cause the slide 96602 to be displaced such that a portion of the slide is aligned with a portion of a throw arm or control arm 96606, such as protrusion 96606A. In this configuration, translation of the activation mechanism 14 causes translation of the throw arm 96606. Translation of the throw arm 96606 causes activation of the needle insertion mechanism 96200 to insert the fluid path into the target. During manufacturing, transportation, and storage, the enabling mechanism is in the first configuration in which depression of the activation mechanism 9614 does not activate the needle insertion mechanism 96200. In this way, the needle insertion mechanism is prevented from activating prematurely. Contact of the slide 96602 with the selector member 96604 may cause substantially rigid body displacement of the slide or, alternatively, the contact may cause a deformation of the slide. For example, the slide may include a deformable (i.e., less rigid) portion which may be displaced by the contact.

One example of a NIM activation mechanism is shown in FIGS. 116A-121B. For clarity, a number of components of the drug delivery device are hidden in these figures. The NIM activation mechanism includes: a slide 96602, a throw arm 96606, a NIM interlock 96608, and a NIM retainer 96610. Initially, as shown in FIGS. 116A-117B, the NIM retainer 96610 is positioned such that the NIM retainer 96610 is in contact with a protrusion 96204 of the NIM 96200 such that the protrusion 96204 is prevented from rotating about axis R (see FIG. 118B), thereby preventing activation of the NIM 96200. In the embodiment shown, the NIM retainer 96610 is configured for rotational movement about axis B (see FIG. 120B). The NIM retainer 96610 may, for example, be mounted to the housing 9612 or to the top plate 961530 at the bore 96610A. For example, a pin or shaft may be disposed in bore 96610A around which the NIM retainer 96610 may rotate. The pin or shaft may an integral portion of the housing 9612 or top plate 961530 or, alternatively, may be a separate component. The NIM retainer 96610 is prevented from rotating by contact between an arm 96610B of the NIM retainer 96610 with the NIM interlock 96608. The NIM interlock 96608 is disposed for translational motion (in the direction of the hatched arrow of FIG. 116B) and is initially held in position by a flex arm 961530A which may be a portion of the top plate 961530. The NIM interlock 96608 is initially in a first position or lock configuration in which it is in contact with or adjacent to a lower surface 96606B of the throw arm 96606.

With the selector member 96604 in the second configuration (shown in FIGS. 122A-122B) depression of the activation mechanism 9614 causes translation of the throw arm 96606 as described above (in the direction of the solid arrow in FIG. 116A). The ramped surface 96606C of the throw arm 96606 contacts the NIM interlock 96608 and causes the NIM interlock 96608 to translate in a direction substantially orthogonal to the direction of translation of the throw arm 96606. FIGS. 118A-119B show the position of the throw arm 96606 and NIM interlock 96608 after translation of the throw arm. As shown, in this configuration (e.g., an unlock configuration), the NIM interlock 96608 is positioned adjacent to or in contact with an upper surface 96608D of the throw arm 96606. The window 96608A of the NIM interlock 96608 is aligned with the arm 96610B of the NIM retainer 96610. Hence, as shown in FIGS. 120A-121B, the NIM retainer 96610 is able to rotate about axis B. The contact surfaces of protrusion 96204 and retainer 96610 may be configured such that the protrusion 96204 applies a rotational force to NIM retainer 96610, thereby causing rotation of NIM retainer 96610 about axis B. Alternatively, or additionally, the NIM retainer 96610 may be biased to rotate by a biasing member. The biasing member may be, for example, a torsion spring. Rotation of the NIM retainer 96610 causes the NIM retainer 96610 to disengage the protrusion 96204 of the NIM 96200. Hence, the NIM 96200 is able to activate to insert a fluid path into a target.

In other embodiments, the NIM interlock 96608 may directly engage a portion of the NIM 96200, such as the protrusion 96204, to initially prevent activation of the NIM 96200. Translation of the NIM interlock 96608 in the direction orthogonal to the translation of the throw arm 96606 may cause the NIM interlock 96608 to disengage the NIM 96200 and allow the NIM 96200 to activate. Also, while the slide 96602 and the throw arm 96606 are shown here as separate components, it is contemplated that these can be combined into a single, unified component. In such an embodiment, the selector member may initially be configured to prevent translation of the slide and/or throw arm.

In another embodiment, the throw arm 96606 is engaged with a portion of the NIM whereby translation of the throw arm 96606 allows activation of the NIM 96200.

In addition to the advantages described above, the insertion mechanisms described herein may also be capable of terminating flow of medicament to the target tissue by disconnecting the fluid path. This may be an important safety feature to protect the target. For example, some medicaments, such as insulin, can be dangerous, and potentially even deadly, when administered in too large a quantity and/or at too rapid of a rate. By providing such automatic safety stop mechanisms, so-called "run-away" delivery of medicament may be prevented, thereby ensuring the safety of the target. While the methods and associated structures for terminating flow may be discussed with regard to one or more specific insertion mechanisms disclosed herein, it will be appreciated that the method and associated structures may be utilized or adapted for any of the insertion mechanisms disclosed herein or within the spirit and scope of this disclosure.

An interruption in delivery of medicament to the target tissue may be triggered, for example, by an error in delivery of the medicament or by an input from the user. For example, the user may realize that they have already taken their drug dose and wish to pause or terminate drug delivery from the device. Upon such user input to the device, the delivery of the drug can be stopped and/or the fluid passageway through the needle or cannula may be terminated by retraction of the needle to its fully retracted position.

Additionally or alternatively, the device may pause or terminate drug delivery if it receives an error alert during operation. For example, if the drive mechanism is not functioning correctly, the needle insertion mechanism may be triggered to retract fully and terminate drug delivery to the target tissue to prevent over-delivery of a medication to the target tissue. This capability of the needle insertion mechanism provides a valuable safety feature for drug delivery to a target.

In some embodiments, retraction is activated upon removal of the drug delivery device from the target tissue. In other embodiments, retraction is activated if it is determined that an error has occurred in the delivery of the substances to the target tissue. For example, an occlusion of the drug delivery pathway which prevents the flow of medicament may be detected by a sensing function of the drug delivery pump. Upon the sensing of the occlusion an electrical or mechanical input may be used to initiate retraction of the needle.

XVIII.C. Fluid Pathway Connector

A number of fluid pathway connectors may be utilized within the embodiments of the present disclosure. Generally, a suitable fluid pathway connector includes a sterile fluid conduit, a piercing member, and a sterile sleeve attached to a drug container or a sliding pierceable seal integrated within a drug container. The fluid pathway connector may further include one or more flow restrictors. Upon proper activation of the device 9610, the fluid pathway connector 96300 is enabled to connect the sterile fluid conduit 9630 to the drug container of the drive mechanism 96100. Such connection may be facilitated by a piercing member, such as a needle, penetrating a pierceable seal of the drug container of the drive mechanism 96100. The sterility of this connection may be maintained by performing the connection within a flexible sterile sleeve. Upon substantially simultaneous activation of the insertion mechanism, the fluid pathway between drug container and insertion mechanism is complete to permit drug delivery into the target. In one such embodiment, the fluid pathway connector may be substantially similar to that described in International Patent Application No. PCT/US2012/054861, published as WO 2015027174 A4 or International Patent Application No. PCT/US2016/020486 filed Mar. 2, 2016, which are included by reference herein in its entirety for all purposes. In such an embodiment, a compressible sterile sleeve may be fixedly attached between the cap of the drug container and the connection hub of the fluid pathway connector. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connector may be integrated into a drug container as described in International Patent Applications No. PCT/US2013/030478 or No. PCT/US2014/052329, for example, which are included by reference herein in their entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap, causing it to be pierced by the piercing member retained within the integrated sterile fluid pathway connector. Accordingly, the integrated sterile fluid pathway connector is connected (i.e., the fluid pathway is opened) by the combination pneumatic/hydraulic force of the air/gas and drug fluid within the drug chamber created by activation of a drive mechanism. Once the integrated sterile fluid pathway connector is connected or opened, drug fluid is permitted to flow from the drug container, through the integrated sterile fluid pathway connector, sterile fluid conduit, and insertion mechanism, and into the target for drug delivery. In at least one embodiment, the fluid flows through only a manifold and a cannula and/or needle of the insertion mechanism, thereby maintaining the sterility of the fluid pathway before and during drug delivery.

In a preferred embodiment, the sterile fluid pathway connector is initiated by movement of the needle insertion mechanism, which itself is initiated by the drive mechanism. Additionally or alternatively, the sterile fluid pathway connector is initiated by movement directly of the drive mechanism. For example, the drive mechanism may include a rotational gear, such as the star gear described in detail herein, that acts concurrently or sequentially to control the rate of drug delivery, to actuate the needle insertion mechanism, and/or initiate the sterile fluid pathway connector. In one particular embodiment, shown in FIGS. 110A-110C, the drive mechanism performs all of these steps substantially concurrently. The drive mechanism rotates a gear that acts upon several other components. The gear acts on a gear assembly to control the rate of drug delivery, while also contacting a needle insertion mechanism to introduce a fluid pathway into the target. As the needle insertion mechanism is initiated, the sterile fluid connection is made to permit drug fluid flow from the drug container, through the fluid conduit, into the needle insertion mechanism, for delivery into the target as the gear and gear assembly of the drive mechanism control the rate of drug delivery.

Regardless of the fluid pathway connector utilized by the drug delivery device, the drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connector and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connector 300 and the sterile fluid conduit 30 are provided hereinafter in later sections in reference to other embodiments.

XVIII.D. Drive Mechanism

The drive mechanisms of the present disclosure may enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a target; and (iii) connecting a sterile fluid pathway to a drug container to permit fluid flow from the drug container to the needle insertion mechanism for delivery to the target. With reference to the embodiments shown in FIGS. 111A-111E and 112A-112D, drive mechanism 96100 includes an actuator 96101, a gear assembly 96116 including a main gear 96102, a drive housing 96130, and a drug container 9650 having a cap 9652, a pierceable seal (not visible), a barrel 9658, and a plunger seal 9660. The main gear 96102 may be, for example, a star gear disposed to contact multiple secondary gears or gear surfaces. A drug chamber 9621, located within the barrel 9658 between the pierceable seal and the plunger seal 9660, may contain a drug fluid for delivery through the insertion mechanism and drug delivery device into the target. The seals described herein may be comprised of a number of materials but are, in a preferred embodiment, comprised of one or more elastomers or rubbers. The drive mechanism 96100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connector, for delivery through the fluid pathway connector, sterile fluid conduit, and insertion mechanism into the target.

In one particular embodiment, the drive mechanism 96100 employs one or more compression springs as the biasing member(s). Upon activation of the drug delivery device by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. Optionally, as will be described further hereinafter, the piston may include one or more safety mechanisms which may be configured to restrict the translation of the piston to restrict flow of medicament to the target. Such safety mechanisms can include a brake mechanism, a plunger seal piercing mechanism, and a plunger seal displacing mechanism, such as those described in detail herein. The fluid pathway connector may be connected through the pierceable seal prior to, concurrently with, or after activation of the drive mechanism to permit fluid flow from the drug container, through the fluid pathway connector, sterile fluid conduit, and insertion mechanism, and into the target for drug delivery. In at least one embodiment, the fluid flows through only a manifold or needle and a cannula of the insertion mechanism, thereby maintaining the sterility of the fluid pathway before and during drug delivery. Such components and their functions are described in further detail herein.

Referring now to the embodiment of the drive mechanism shown in FIGS. 111A-111E and 112A-112D, drive mechanism 96100 includes an actuator 96101, a gear assembly 96116 including a main gear 96102, a drive housing 96130, and a drug container 9650 having a cap 9652, a pierceable seal (not visible), a barrel 9658, and a plunger seal 9660. The main gear 96102 may be, for example, a star gear disposed to contact multiple secondary gears or gear surfaces. A drug chamber 9621, located within the barrel 9658 between the pierceable seal and the plunger seal 9660, may contain a drug fluid for delivery through the insertion mechanism and drug delivery device into the target. Compressed within the drive housing 96130, between the drug container 9650 and the proximal end of the housing 96130, are one or more drive biasing members 96122 and a piston 96110, wherein the drive biasing members 96122 are configured to bear upon an interface surface 96110C of the piston 96110, as described further herein. Optionally, a cover sleeve (not shown) may be utilized between the drive biasing members 96122 and the interface surface 96110C of the piston 96110 to, for example, promote more even distribution of force from the drive biasing member 96122 to the piston 96110, prevent buckling of the drive biasing members 96122, and/or hide the biasing members 96122 from user view. Interface surface 96110C of piston 96110 is caused to rest substantially adjacent to, or in contact with, a proximal end of seal 9660. Although the embodiments shown in FIGS. 111A-111E and 112A-112D show a singular biasing member it is also contemplated that one or more biasing members disposed to act in parallel or in series may be used.

Figure 112A:
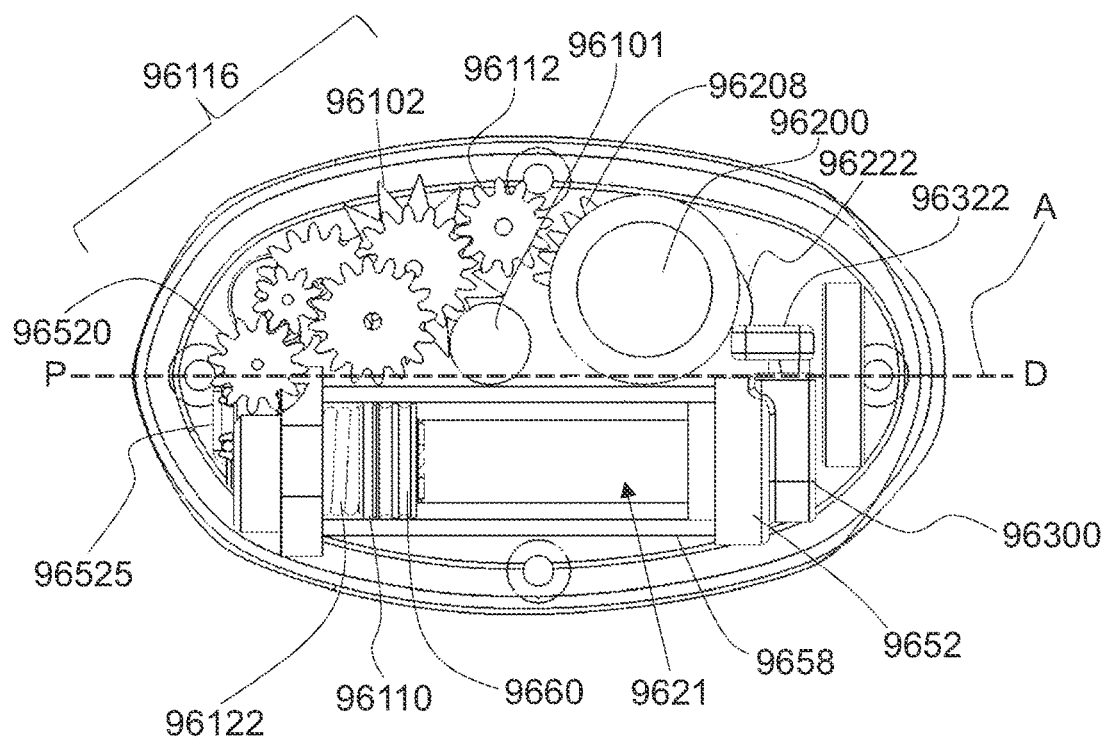
Figure 112B:
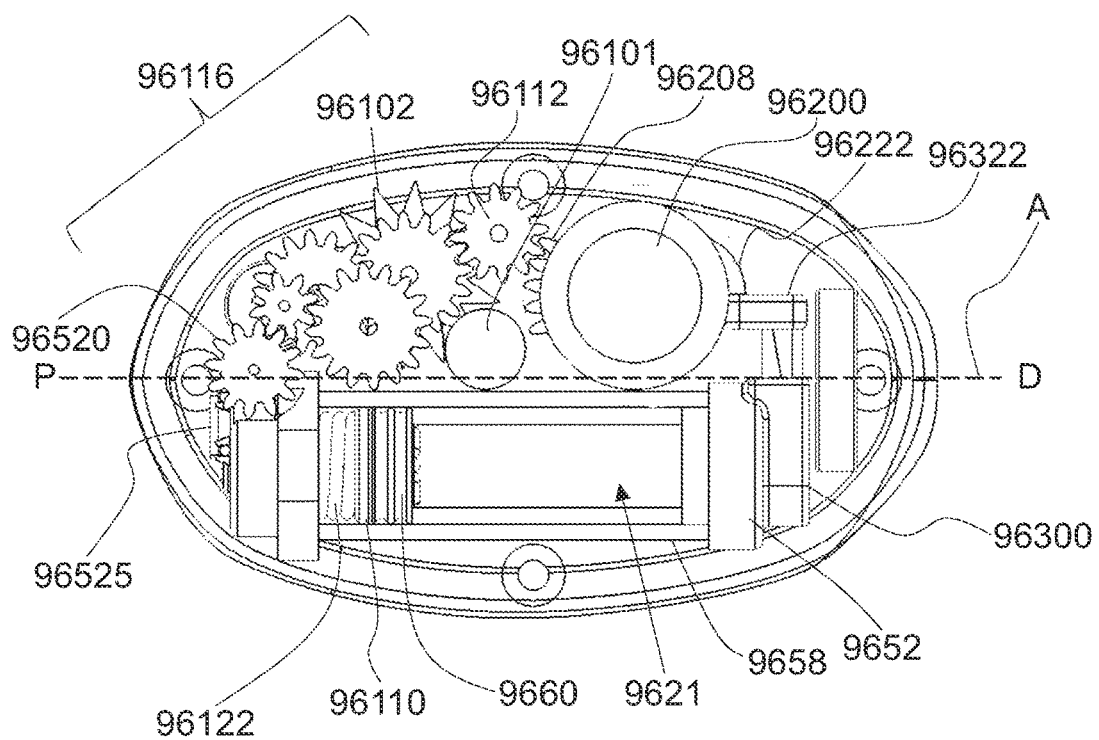
Figure 112C:
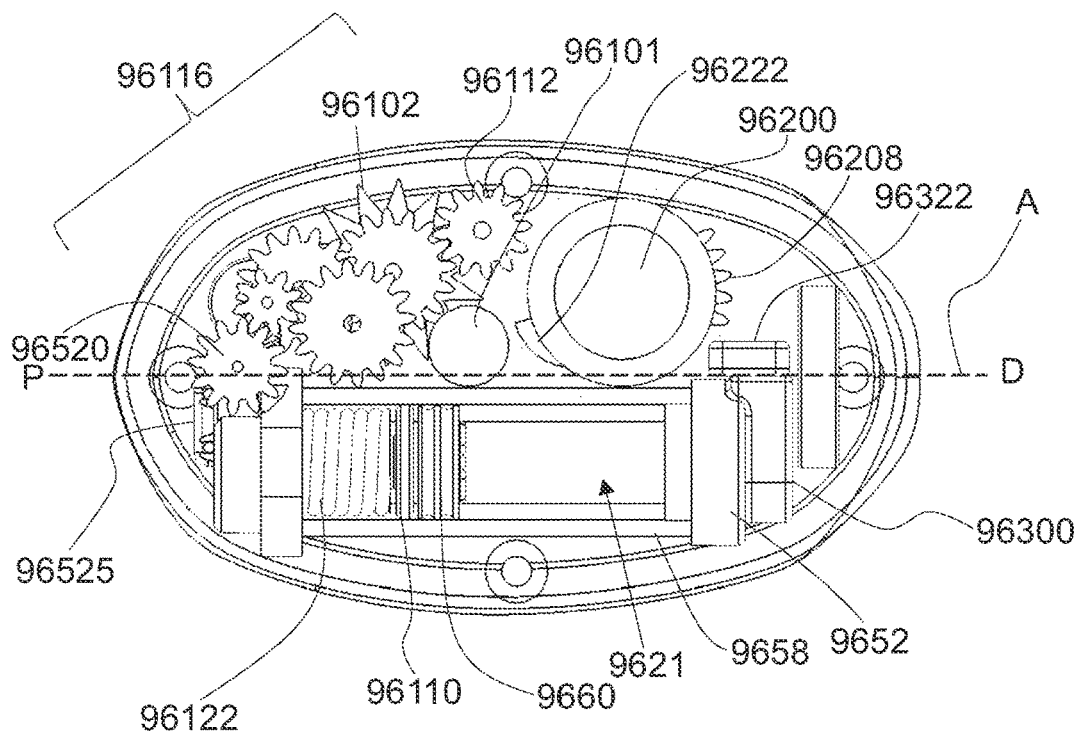
Figure 112D:
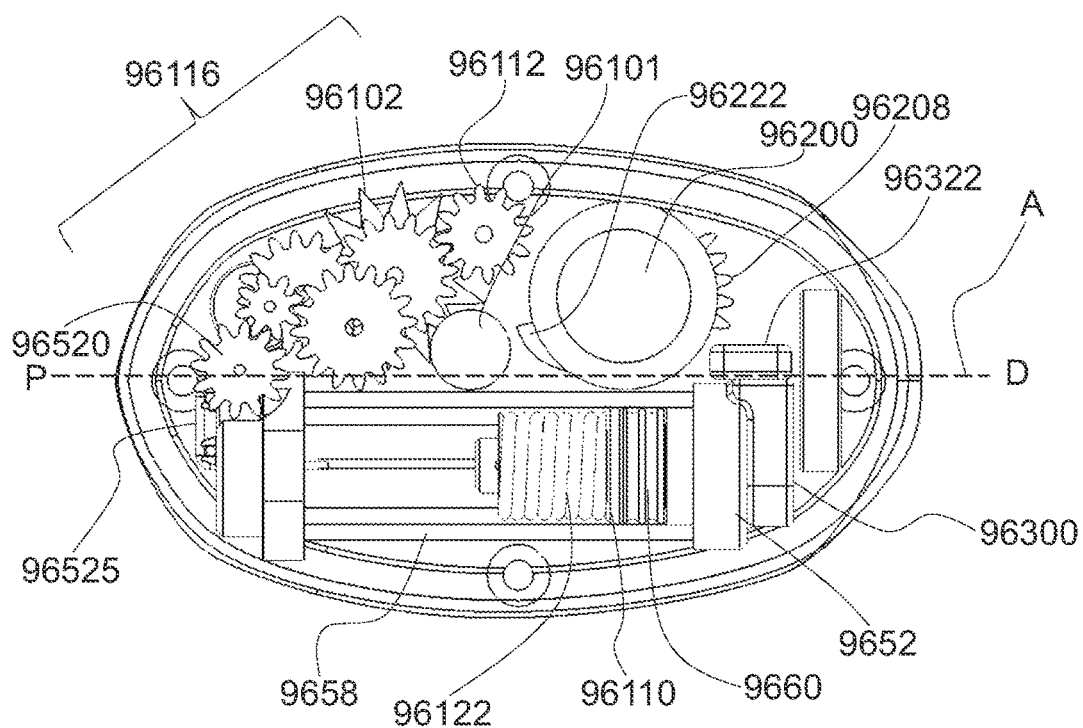

As best shown in FIG. 111E and FIG. 112D, the piston 96110 may be comprised of one or more components and have an interface surface to contact the plunger seal. A tether, ribbon, string, or other retention strap (referred to herein as the "tether" 96525; See FIG. 112D) may be connected at one end to the piston 96110. For example, the tether 96525 may be connected to the piston 96110 by retention between the two components of the piston 96110 when assembled. FIG. 112D shows the biasing member partially hidden to allow the connection of the tether to the piston to be viewed. The tether 96525 is connected at another end to a winch assembly 96520 of a delivery control or regulating mechanism 96500. Winch assembly 96520 includes winch gear 96520A and winch drum 96520B rotation of which is coupled, for example by a keyed relationship. Through the use of the winch assembly 96520 connected to one end of the tether 96525, and the tether 96525 connected at another end to the piston 96110, the regulating mechanism 96500 functions to control, meter, provide resistance, or otherwise prevent free axial translation of the piston 96110 and plunger seal 9660 utilized to force a drug substance out of a drug container 9650. Accordingly, the regulating mechanism 96500 is a portion of the gear assembly 96116 aspect of the drive mechanism, which together function to control the rate or profile of drug delivery to the target.

As shown in FIGS. 111A-111E and 112A-112D, and in isolation in FIGS. 113 and 114A-114B, in embodiments of the present disclosure, the regulating mechanism 96500 includes a gear assembly controlled by an actuator 96101 of the drive mechanism 96100. The regulating mechanism retards or restrains the distribution of tether 96525, only allowing it to advance at a regulated or desired rate or according to selected intervals. This restricts movement of piston 96110 within barrel 9658, which is pushed by one or more biasing members 96122, hence, controlling the movement of plunger seal 9660 and delivery of the drug contained in chamber 9621. As the plunger seal 9660 advances in the drug container 9650, the drug substance is dispensed through the sterile pathway connection 96300, conduit 9630, insertion mechanism 96200, and into the target for drug delivery. The actuator 96101 may be a number of power/motion sources including, for example, a solenoid, a stepper motor, or a rotational drive motor. In a particular embodiment, the actuator 96101 is a rotational stepper motor engaged with a gear interface such as a shaft with a notch that corresponds with the gear teeth of the main/star gear 96102. In at least one embodiment, the notch of the gear interface forms a recess within which one or more teeth of the main gear may partially reside during operation of the system. This is more clearly visible in FIGS. 114A-114B. When the gear interface 96101A is in alignment with a tooth 96102A of the main gear 96102, rotational motion of the motor 96101 allows rotation of the main gear 96102. When the notch is between gear teeth of the main gear, it may act as a resistance for, for example, rotation, back-spinning or unwinding of the gear assembly 96116. In one particular embodiment, the motor 96101 utilizes an alternating direction type motor to rotate the motor 96101 backwards and forwards. This configuration aids in the prevention of a runaway condition, where the motor and the gears are freely permitted to rotate, by using the multi-direction of the motor to prevent continuous spin in one direction (as would be needed for a runaway condition). Further, because main gear 96102 is only able to advance when a tooth 96102A is aligned with the notch of the gear interface 96101A, main gear 96102 is only able to incrementally rotate. The bi-directional movement of the motor, coupled with the use of the gear interface coupled to the motor, provide suitable safety features to prevent a runaway condition that could potentially lead to over-delivery of drug to the target. Further detail about the gear assembly 96116, regulating mechanism 96500, and drive mechanism 96100 are provided herein. In a particular embodiment shown in FIGS. 114A-114B, the regulating element 96500 further includes one or more gears 96511, 96512, 96513, 96514, of a gear assembly 96516. One or more of the gears 96511, 96512, 96513, 96514 may be, for example, compound gears having a small diameter gear attached at a shared center axis to a large diameter gear. Gear 96513 may be rotationally coupled to winch gear 96520A, thereby coupling rotation of gear assembly 96516 to winch assembly 96520. Compound gear 96512 engages the small diameter gear 96513 such that rotational movement of the compound gear aspect 96512B is conveyed by engagement of the gears (such as by engagement of corresponding gear teeth) to gear 96513. Gear aspect 96512A is engaged with gear aspect 96512B, thereby coupling rotation of compound gear 96512 with compound gear 96511. Compound gear aspect 96511A, the rotation of which is coupled to gear aspect 96511B, is caused to rotate by action of compound gear aspect 96102B of the main/star gear 96102A. Compound gear aspect 96102B, the rotation of which is coupled to main/star gear 96102A, is caused to rotate by interaction between main/star gear 96102A and interface 96101A of the actuator 96101. Thus, rotation of main/star gear 96102A is conveyed to winch assembly 96520. Accordingly, rotation of the gear assembly 96516 initiated by the actuator 96101 may be coupled to winch assembly 96520 (i.e., through the gear assembly 96516), thereby controlling the distribution of tether 96525, and the rate of movement of plunger seal 9660 within barrel 9658 to force a fluid from drug chamber 9621. The rotational movement of the winch assembly 96520, and thus the axial translation of the piston 96110 and plunger seal 9660, are metered, restrained, or otherwise prevented from free axial translation by other components of the regulating element 96500, as described herein. As described above, the actuator 96101 may be a number of known power/motion sources including, for example, a motor (e.g., a DC motor, AC motor, or stepper motor) or a solenoid (e.g., linear solenoid, rotary solenoid). One of skill in the art will recognize that regulating mechanism 96500 may include any number of gears to achieve the desired gear ratio. The regulating mechanism may provide any desirable gear ratio between main gear 96102A and winch gear 96520A. The gear ratio may, for example, be selected based on the desired drug delivery profile. Additionally, the resolution of the gear assembly may be configured based on the number of teeth of main gear 96102. The more teeth that main gear 96102 has, the finer the resolution of the gear assembly. Conversely, if the main gear 96102 has fewer teeth the gear assembly will have a coarser resolution (i.e., more drug fluid will be delivered per each rotation of the actuator).

The embodiment described above and shown in FIGS. 110A-114D show an actuator 96101 that is in vertical alignment and in direct engagement with gear interface 96101A and, thereby, the main/star gear 96102. As would readily be appreciated by one having ordinary skill in the mechanical arts, the actuator 96101 could be modified to be in horizontal alignment. Additionally or alternatively, the actuator 96101 could be modified to be in indirect engagement with the gear interface 96101A and main/star gear 96102. The embodiments shown in FIGS. 115A-115B show an actuator 96101 that is in horizontal alignment and indirect engagement with the gear interface 96101A and main/star gear 96102. Such an embodiment may utilize a rack and pinion engagement, a drive screw, or a worm gear 96101W, as shown in FIGS. 115A-96115B, to change the direction of motion from horizontal to vertical (i.e., perpendicular interaction). Actuator 96101 rotates worm gear 96101W, which engages gear 96101G and conveys the motion to the gear interface 96101A, in this embodiment a shaft with a notch. The gear interface 96101A engages main/star gear 96102 to enable operation of the drive mechanism and the drug delivery device, as described herein. Main/star gear 96102 may also drive operation of gear 96112 to enable operation of the needle insertion mechanism 96200, as described herein. In one particular embodiment, the actuator 96101 utilizes an alternating direction type motor to rotate the worm gear 96101W, gear 96101G, and gear interface 96101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 96101, coupled with the use of the worm gear 96101W, gear 96101G, and gear interface 96101A with the main/star gear 96102, provide suitable safety features to prevent a runaway condition that could potentially lead to over-delivery of drug to the target. Additionally, the gear interface 96101A may include a stop member 96101B that stops the rotation of the gear interface 96101A against a stop block 150. Stop block 96150 further prevents over-rotation of the gear interface 96101A and, accordingly, the main/star gear 96102 to prevent a runaway condition that could potentially lead to over-delivery of drug to the target. For the device to function in this configuration, the gear interface 96101A must be rotated backwards in the other direction before rotating forwards again to progress the main/star gear 96102 because the stop member 96101B prevents over rotation in one direction by interaction with the stop block 96150. Additionally, the geometry of worm gear 96101W may be configured such that it is self-locking and/or cannot be back-driven by gear 96101G. This may be done by configuration of parameters such as: pitch, lead angle, pressure angle, and number of threads. In so doing, runaway conditions of the drive mechanism will be prevented by the worm gears resistance to rotations that are not caused by actuator 96101.

In another embodiment, the actuator 96101 is rotationally coupled to a gear interface such as a key 961101, such as that shown in FIGS. 124A-124B. The actuator may be an alternating direction type motor as described above. The key 961101 may be a shaft with one or more flanges 961101A, 961101B, which interface with main gear 961102. The first flange 961101A and second flange 961101B are offset along the length of the shaft. Alternating clockwise and anti-clockwise rotation of the key 961101 allows stepwise rotation of the main gear 961102. In the embodiment shown, the key 961101 has two flanges but it is contemplated that the key 961101 may include any number of flanges. As shown, the key 961101 may further include a rotation limiter 961101C and a status reader interface 961101D. The second flange 961101B may further include a step 961101E. These features are configured to interact with the main gear 961102 during operation to control rotation of the gear assembly 961516 and, optionally, interact with a status reader 961550 to monitor the rotation of the regulating mechanism 961500. The rotation limiter 961101C and status step 961101E are configured such that contact of these features with the main gear 961102 restricts continued rotation of the key.

As shown in FIG. 125, the main gear 961102 includes variable pass-throughs that allow passage of the flanges 961101A, 961101B of the key 961101 and, thereby, rotation of the key 961101. As shown, the main gear 961102 may include cyclically alternating large 961102A and small 961102B pass-throughs, each separated by a tooth 961102C. The size of the pass-throughs may be configured to control rotation of the key 961101 to allow operation of the regulating mechanism 961500 to be monitored, as will be described further hereinafter.

The steps of operation of the key 961101 and main gear 961102 are described further with reference to FIGS. 126A-129B. Although sequential terms such as first, second, third, and fourth are used to describe the stages of operation, these terms are used for explanatory purposes only. The key and gear train may begin in any of the described configurations. FIGS. 126A-126B show the key 961101 and main gear 961102 in a first configuration. A tooth of the main gear 961102 is contacting the first flange 961101A of the key 961101 and rotation of the main gear 961102 is thereby restricted. A portion of the first flange 961101A of the key 961101 is disposed in a large pass-through 961102A of the main gear 961102. The tension applied to the tether by the drive biasing member applies a torque to the main gear (through the regulating mechanism 961500) that is in the direction of the solid arrow shown in FIG. 126B. The contact between the tooth 961102C of the main gear 961102 and the first flange 961101A of the key resists rotation in this direction.

To allow the main gear 961102 to advance, the key 961101 may be rotated such that the first aperture 961101F of the first flange 961101A is aligned with the tooth 961102C of the main gear 961102. In the embodiment shown, the rotation is in the direction of the dashed arrow of FIG. 126B. The amount of rotation of the key 961101 will be limited by contact of the step 961101E of the second flange 961101B with the main gear 961102. In this position, the key 961101 is not preventing rotation of the main gear 961102 as no teeth of the main gear are in contact with the key. If the regulating mechanism 961500 is operating properly, the tension on the tether will cause the main gear 961102 to rotate (in the direction of the solid arrow of FIG. 126B) until a tooth 961102C of the main gear 961102 comes into contact with the second flange 961101B of the key 961101. Hence, the main gear 961102 advances a controlled amount, allowing the rotation of the key 961101 to control unspooling of the tether and translation of the piston. As shown in FIGS. 127A-127B, in this position, the contact between the step 961101E of the second flange 961101B and the main gear 961102 restricts rotation of key 961101 and, thereby, prevents the status reader interface 961101D from coming into contact with the status reader 961550.

From this position, the main gear 961102 may be allowed to advance another step by rotation of the key 961101 in the opposite direction to that rotated previously. For example, if the key was rotated in an anti-clockwise direction to transform from the first position to the second position, the key would now be rotated in a clockwise direction to transform from the second position to the third position. After rotation of the second flange 961101B past the main gear 961102 such that the second aperture 961101G is aligned with the main gear 961102, the tooth 961102C of the main gear 961102 that was in contact with the second flange 961101B is able to advance until it comes in contact with the first flange 961101A. This, third position, is shown in FIGS. 128A-28B. In this position, the first flange 961101A is disposed in a small pass-through 961102B of the main gear 961102 and the second flange 961101B is aligned with, but not disposed in, a large pass-through 961102A of the main gear 961102.

Rotation of the key 961101 will again allow advancement of the main gear 961102. In transforming from the third position to the fourth position, however, the step 961101E of the second flange 961101B will not make contact with the main gear 961102 as the large pass-through 961102A of the main gear 961102 is configured to allow passage of the step 961101E (i.e., the large pass-through is large enough to allow the step to pass through it). Hence, as shown in FIGS. 129A-129B, in the fourth position, the status reader interface 961101D of the key 961101 contacts the status reader 961550. This contact causes a signal to be sent to the power and control system. The status reader may be, for example, a detector switch which creates or modifies an electrical signal upon contact with, or displacement of, the status reader arm 961550A. The status reader 961550 may be mounted to the housing 9612 or top plate 961530 and be in electrical communication with the power and control system.

In this way, the operation of the regulating mechanism may be monitored. In the embodiment described above, when the main gear 961102 is operating properly, the key 961101 will contact the status reader 961550 at a predefined rotation interval during operation, for example once every four rotations of the key 961101. However, if the main gear 961102 is not rotating properly, the key 961101 will contact the status reader 961550 at some other interval or not contact the status reader at all. For example, if the main gear 961102 stops rotating in a position, wherein the second flange 961101B is aligned with a large pass-through 961102A of the main gear 961102, the key 961101 will contact the status reader 961550 every other rotation of the key 961101 (i.e., each time the key is rotated in the direction of the dashed arrow in FIG. 126B). Alternatively, if the main gear 961102 stops rotating in a position wherein the second flange 961101B is aligned with a small pass-through 961102B of the main gear 961102, the key 961101 will be prevented from contacting the status reader 961550. Hence, the power and control system can compare the frequency of contact between the key and the status reader with an expected frequency and determine whether the regulating mechanism is operating properly.

This may provide safety advantages to the target. For example, if the key 961101 rotates four times and the power and control system does not receive a signal from the status reader 961550, the power and control system may terminate delivery of medicament to the target. Similarly, if the power and control system receives a signal from the status reader 961550 after only two rotations, this would also signal a fault in the regulating mechanism and initiate termination of delivery. The power and control system may terminate delivery by activating one or more actions such as retraction of the needle or cannula from the target.

While the embodiment described above is configured such that the key 961101 contacts the status reader 961550 once every four rotations, these components may be configured for any frequency of activation by, for example, varying the distribution of large 961102A and small 961102B pass-throughs in the main gear 961102.

Further, the key 961101 may be configured to provide additional advantages in preventing runaway drug delivery scenarios. In the embodiment shown in FIGS. 124A-124B, the key 961101 is configured such that the main gear 961102 is only able to rotate one rotational increment at a time. At all times, because first aperture 961101F and second aperture 961101G are not aligned (i.e., they are offset around the circumference of the shaft), at least one of the first flange 961101A and the second flange 961101B is positioned to prevent rotation of the main gear 961102 by being in the path of travel of the teeth 961102C of the main gear 961102. Further, in the embodiment shown, the flanges 961101A, 961101B of the key 961101 are oriented substantially perpendicular to the path of travel of the teeth 961102C of the main gear. Hence, the force applied to the key by the main gear does not impart a torque on the key and therefore the key 961101 cannot be backdriven by the main gear 961102. Hence, rotation of the main gear 961102 will be restricted by the key 961101 even when the actuator 96101 is not powered to prevent rotation of the key 961101.

The drive mechanism may also be configured to allow unrestrained unspooling of the tether. FIG. 124C shows an embodiment of a key 962101 which would allow such a configuration of the drive mechanism. As shown, aperture 962101F of first flange 962101A is circumferentially aligned with aperture 962101G of second flange 962101B. Hence, upon rotation of key 961101, tooth 961102C of main gear 961102 is aligned with both apertures. This allows main gear 961102 to rotate freely, without being restrained by key 962101. As a result, biasing member 96122 is able to expand without being restrained by the tether. This results in substantially all of the contents of the drug container being delivered at one time, at a rate controlled by the stiffness of the biasing member and the pneumatic/hydraulic resistance of the system. The versatility of being able to configure the drug delivery device to deliver a metered drug profile over an extended period as described above or, alternatively, to deliver the drug in a single, relatively short dose provides a number of advantages. Specifically, it allows the device to use like components across a platform of drug delivery devices, thereby providing economies of scale in terms of component and assembly prices.

Notably, the regulating mechanisms 96500, 961500 and actuators 96101 of the present disclosure do not drive the delivery of fluid substances from the drug chamber 9621. The delivery of fluid substances from the drug chamber 9621 is caused by the expansion of the biasing member 96122 from its initial energized state acting upon the piston 96110 and plunger seal 9660. The regulating mechanisms 96500, 961500 instead function to provide resistance to the free motion of the piston 96110 and plunger seal 9660 as they are pushed by the expansion of the biasing member 96122 from its initial energized state. The regulating mechanism 96500, 961500 does not drive the delivery but only controls the delivery motion. The tether limits or otherwise restrains the motion of the piston 96110 and plunger seal 9660, but does not apply the force for the delivery. According to a preferred embodiment, the controlled delivery drive mechanisms and drug delivery devices of the present disclosure include a regulating mechanism indirectly or directly connected to a tether metering the axial translation of the piston 96110 and plunger seal 9660, which are being driven to axially translate by the biasing member 96122. The rate of drug delivery as controlled by the regulating mechanism may be determined by: selection of the gear ratio of gear assembly 96516; selection of the main/star gear 96102; selection of the diameter of winch drum 96520B; using electromechanical actuator 96101 to control the rate of rotation of the main/star gear 96102, 961102; or any other method known to one skilled in the art. By using electromechanical actuator 96101 to control the rate of rotation of the main/star gear 96102, 961102 it may be possible to configure a drug delivery device to provide a variable dose rate (i.e., the rate of drug delivery is varied during a treatment).

In another embodiment, the power and control system of the drug delivery device is configured to receive one or more inputs to meter the release of the tether 96525 by the winch assembly 96520 and thereby permit axial translation of the piston 96110 by the biasing member 96122 to translate a plunger seal 9660 within a barrel 9658. The one or more inputs may be provided by the actuation of the activation mechanism, a control interface, and/or a remote control mechanism. The power and control system may be configured to receive one or more inputs to adjust the restraint provided by the tether 96525 and winch assembly 96520 on the free axial translation of the piston 96110 upon which the biasing member 96122 bears upon to meet a desired drug delivery rate or profile, to change the dose volume for delivery to the target, and/or to otherwise start, stop, or pause operation of the drive mechanism. For example, if the power and control system has determined that the pump is not operating properly, the power and control system may terminate rotation of actuator 96101.

The components of the drive mechanism 96100, upon activation, may be used to drive axial translation in the distal direction of the plunger seal 9660 of the drug container 9650. Optionally, the drive mechanism 96100 may include one or more compliance features which enable additional axial translation of the plunger seal 9660, for example, to ensure that substantially the entire drug dose has been delivered to the target. For example, the plunger seal 9660, itself, may have some compressibility permitting a compliance push of drug fluid from the drug container.

The novel controlled delivery drive mechanisms of the present disclosure may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. As the end-of-dose indication is tied to the piston reaching the end of its axial translation, the drive mechanism and drug delivery device provide a true end-of-dose indication to the user.

The tether 96525 may have one or more status triggers, such as electrical contacts, optical markings, or electromechanical pins or recesses, which are capable of contacting or being recognized by a status reader. In at least one embodiment, an end-of-dose status indication may be provided to the user once the status reader contacts or recognizes the final status trigger positioned on the tether 96525 that would contact the status reader at the end of axial travel of the piston 96110 and plunger 9660 within the barrel 9658 of the drug container 9650. The status reader may be, for example, an electrical switch reader to contact the corresponding electrical contacts, an optical reader to recognize the corresponding optical markings, or a mechanical or electromechanical reader configured to contact corresponding pins, holes, or similar aspects on the tether. The status triggers may be positioned along the tether 96525 to be read or recognized at positions which correspond with the beginning and end of drug delivery, as well as at desired increments during drug delivery. As the drug delivery device is activated and drug delivery is begun by release of the biasing member 96122 and the resulting force applied to the piston 96110 and plunger seal 9660, the rate or profile of drug delivery to the target is controlled by the regulating mechanism 96500, gear assembly 96516, and winch assembly 96520 releasing the tether 96525 and permitting expansion of the biasing member 96122 and axial translation of the piston 96110 and plunger seal 9660. As this occurs, the status triggers of the tether 96525 are contacted or recognized by the status reader and the status of the drive mechanism before, during, and after operation can be relayed to the power and control system to provide feedback to the user. Depending on the number of status triggers located on the tether 96525, the frequency of the incremental status indication may be varied as desired. As described above, a range of status readers may be utilized depending on the status triggers utilized by the system.

In a preferred embodiment, the status reader may apply a tensioning force to the tether 96525. When the system reaches end-of-dose, the tether 96525 goes slack and the status reader 544 is permitted to rotate about a fulcrum. This rotation may operate an electrical or electromechanical switch, for example a switch, signaling slack in the tether 96525 to the power and control system. Additionally, a gear of gear assembly may act as an encoder along with a sensor. The sensor/encoder combination is used to provide feedback of gear assembly rotation, which in turn can be calibrated to the position of piston 96110 when there is no slack in the tether 96525. For example, rotation of main gear 96102, 961102 may be configured to be monitored by an optical sensor. A reflective surface coating may be applied to at least a portion of the face of main gear 96102, 961102 to improve the accuracy of the optical sensor. Together, the status reader and sensor/encoder may provide positional feedback, end-of-dose signal, and error indication, such as an occlusion, by observing slack in the tether 96525 or another component of the drive mechanism prior to reaching the expected number of motor rotations as counted by the sensor/encoder.

Referring back to FIGS. 111A-111E and 112A-112D, in addition to controlling the rate of drug delivery by metering, providing resistance, or otherwise preventing free axial translation of the plunger seal utilized to force a drug substance out of a drug container (thereby delivering drug substances at variable rates and/or delivery profiles); the drive mechanisms of the present disclosure may concurrently or sequentially perform the steps of: triggering a needle insertion mechanism to provide a fluid pathway for drug delivery to a target; and connecting a sterile fluid pathway to a drug container to permit fluid flow from the drug container to the needle insertion mechanism for delivery to the target. In at least one embodiment, as shown in FIGS. 111A-111E and 96112A-96112D, initial motion by the actuator 96101 of the drive mechanism 96100 causes rotation of main/star gear 96102. Main/star gear 96102 is shown as a compound gear with aspects 96102A and 96102B (see FIG. 113). In one manner, main/star gear 96102 conveys motion to the regulating mechanism 96500 through gear assembly 96516. In another manner, main/star gear 96102 conveys motion to the needle insertion mechanism 96200 through gear 96112. As gear 96112 is rotated by main/star gear 96102, gear 96112 engages the needle insertion mechanism 96200 to initiate the fluid pathway connector into the target, as described in detail above. In one particular embodiment, needle insertion mechanism 96200 is a rotational needle insertion mechanism. Accordingly, gear 96112 is configured to engage a corresponding gear surface 96208 of the needle insertion mechanism 96200. Rotation of gear 96112 causes rotation of needle insertion mechanism 96200 through the gear interaction between gear 96112 of the drive mechanism 96100 and corresponding gear surface 96208 of the needle insertion mechanism 96200. Once suitable rotation of the needle insertion mechanism 96200 occurs, for example rotation along axis 'R' shown in FIG. 111D, the needle insertion mechanism may be initiated to create the fluid pathway connector into the target, as described in detail above.

In an alternative embodiment, as shown in FIGS. 115A-115B, gear 96112 may indirectly engage the needle insertion mechanism 96200 to initiate the fluid pathway connector into the target. For example, gear 96112 may be configured to engage a corresponding gear surface of a control arm 96202 (visible in FIGS. 115A and 6B) that contacts or blocks the needle insertion mechanism 96200. Rotation of gear 96112 causes movement of the control arm 96202, which may initiate or permit rotation of needle insertion mechanism 96200. Such a needle insertion mechanism, as shown in FIGS. 115A-115B, includes a rotationally biased member 96210 which is initially held in an energized state. The rotational biasing member may be prevented from de-energizing by contact of a component of the insertion mechanism with a rotation prevention feature, such as a blocking aspect 96206, of the drug delivery device. Rotation or translation of blocking aspect 96206 is initially prevented by contact with control arm 96202. Translation of control arm 96202, caused by rotation of gear 96112, positions control arm 96202 such that it no longer prevents rotation of blocking aspect 96206. Upon activation of the device, or another input, the rotationally biased member 96210 is permitted to, at least partially, de-energize. This causes one or more components of the insertion mechanism to rotate and, in turn, cause, or allow, the insertion of the needle into the target. Further, a cannula may be inserted into the target as described above. At a later time, such as when the control arm or another component of the device recognizes a slack in the tether 96525, the rotationally biased member may be allowed to further de-energize, such as by further interaction with the control arm, causing additional rotation of one or more components of the insertion mechanism. This rotation may cause, or allow, the needle to be retracted from the target. The needle may be fully retracted in a single step or there may be multiple steps of retraction.

As shown in FIGS. 111A-111E and 112A-112D, rotation of the needle insertion mechanism 96200 in this manner may also cause a connection of a sterile fluid pathway to a drug container to permit fluid flow from the drug container to the needle insertion mechanism for delivery to the target. Ramp aspect 96222 of needle insertion mechanism 96200 is caused to bear upon a movable connection hub 96322 of the sterile fluid pathway connector 96300. As the needle insertion mechanism 96200 is rotated by the drive mechanism 96100, ramp aspect 96222 of needle insertion mechanism 96200 bears upon and translates movable connection hub 96322 of the sterile fluid pathway connector 96300 to facilitate a fluid connection therein. Such translation may occur, for example, in the direction of the hollow arrow along axis 'C' shown in FIG. 111B. In at least one embodiment, the needle insertion mechanism 96200 may be configured such that a particular degree of rotation upon rotational axis 'R' (shown in FIG. 111D) enables the needle/trocar to retract as detailed above. Additionally or alternatively, such needle/trocar retraction may be configured to occur upon a user-activity or upon movement or function of another component of the drug delivery device. In at least one embodiment, needle/trocar retraction may be configured to occur upon end-of-drug-delivery, as triggered by, for example, the regulating mechanism 96500 and/or one or more of the status readers as described above. During these stages of operation, delivery of fluid substances from the drug chamber 9621 may be initiated, on-going, and/or completed by the expansion of the biasing member 96122 from its initial energized state acting upon the piston 96110 and plunger seal 9660. As described above, the regulating mechanism 96500 functions to provide resistance to the free motion of the piston 96110 and plunger seal 9660 as they are pushed by the expansion of the biasing member 96122 from its initial energized state. The regulating mechanism 96500 does not drive the delivery but only controls the delivery motion. The tether limits or otherwise restrains the motion of the piston 96110 and plunger seal 9660, but does not apply the force for the delivery. This is visible through the progression of the components shown in FIGS. 111A-111E and 112A-112D. The motion of the piston 96110 and plunger seal 9660 as they are pushed by the expansion of the biasing member 96122 from its initial energized state are shown in the direction of the solid arrow (FIG. 2D) along axis 'A' from proximal or first position 'P' to the distal or second position 'D', as shown in the transition of FIGS. 111A-111E and 112A-112D.

Further aspects of the novel drive mechanism will be described with reference to FIG. 113 and FIGS. 114A-114B. FIG. 113 shows a perspective view of the drive mechanism, according to at least a first embodiment, during its initial locked stage. Initially, the tether 96525 may retain the biasing member 96122 in an initial energized position within piston 96110. Directly or indirectly upon activation of the device by the user, the drive mechanism 96100 may be activated to permit the biasing member to impart a force to piston 96110 and therefore to tether 96525. This force on tether 96525 imparts a torque on winch drum 96520B which causes the gear assembly 96516 and regulating mechanism 96500 to begin motion. As shown in FIG. 114A, the piston 96110 and biasing member 96122 are both initially in a compressed, energized state behind the plunger seal 9660. The biasing member 96122 may be maintained in this state until activation of the device between internal features of drive housing 96130 and interface surface 96110C of piston 96110. As the drug delivery device 9610 is activated and the drive mechanism 96100 is triggered to operate, biasing member 96122 is permitted to expand (i.e., decompress) axially in the distal direction (i.e., in the direction of the solid arrow shown in FIG. 96111D). Such expansion causes the biasing member 96122 to act upon and distally translate interface surface 96110C and piston 96110, thereby distally translating plunger seal 9660 to push drug fluid out of the drug chamber 9621 of barrel 9658. In at least one embodiment, an end-of-dose status indication may be provided to the user once the status reader contacts or recognizes a status trigger positioned on the tether 96525 to substantially correspond with the end of axial travel of the piston 96110 and plunger seal 9660 within the barrel 9658 of the drug container 9650. The status triggers may be positioned along the tether 96525 at various increments, such as increments which correspond to certain volume measurement, to provide incremental status indication to the user. In at least one embodiment, the status reader is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status indicators which contact or are otherwise recognized by the corresponding electrical status reader. The status triggers may be positioned along the tether 96525 to be read or recognized at positions which correspond with the beginning and end of drug delivery, as well as at desired increments during drug delivery. As shown, tether 96525 passes substantially axially through the drive mechanism housing 96130, the biasing member 96122, and connects to the piston 96110 to restrict the axial translation of the piston and the plunger seal 9660 that resides adjacent thereto.

The novel embodiments of the present disclosure may be utilized to meter, restrain, or otherwise prevent free rotational movement of winch drum 96520B and, thus, axial translation of the components of the controlled delivery drive mechanism 96100. Accordingly, the regulating mechanism 96500 only controls the motion of the drive mechanism, but does not apply the force for the drug delivery. One or more additional biasing members 96122, such as compression springs, may be utilized to drive or assist the driving of the piston 96110. For example, a compression spring may be utilized within the drive housing 96130 for this purpose. The regulating mechanism 96500 only controls, meters, or regulates such action. The controlled delivery drive mechanisms and/or drug delivery devices of the present disclosure may additionally enable a compliance push to ensure that substantially all of the drug substance has been pushed out of the drug chamber 9621. The plunger seal 9660, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch and interconnect assembly may be utilized to contact, connect, or otherwise enable a transmission to the power and control system to signal end-of-dose to the user. This configuration further enables true end-of-dose indication to the user.

In at least one embodiment, incremental status indication may be provided to the user by reading or recognizing the rotational movement of one or more gears of gear assembly

96516. As the gear assembly 96516 rotates, a status reader may read or recognize one or more corresponding status triggers on one of the gears in the gear assembly to provide incremental status indication before, during, and after operation of the variable rate controlled delivery drive mechanism. A number of status readers may be utilized within the embodiments of the present disclosure. For example, the drive mechanism may utilize a mechanical status reader which is physically contacted by gear teeth of one of the gears of the gear assembly. As the status reader is contacted by the status trigger(s), which in this exemplary embodiment may be the gear teeth of one of the gears (or holes, pins, ridges, markings, electrical contacts, or the like, upon the gear), the status reader measures the rotational position of the gear and transmits a signal to the power and control system for status indication to the user. Additionally or alternatively, the drive mechanism may utilize an optical status reader. The optical status reader may be, for example, a light beam that is capable of recognizing a motion and transmitting a signal to the power and control system. For example, the drive mechanism may utilize an optical status reader that is configured to recognize motion of the gear teeth of one of the gears in the gear assembly (or holes, pins, ridges, markings, electrical contacts, or the like, upon the gear). Similarly, the status reader may be an electrical switch configured to recognize electrical contacts on the gear. In any of these embodiments, the sensor may be utilized to then relay a signal to the power and control system to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present disclosure to provide incremental status indication to the user. While the drive mechanisms of the present disclosure are described with reference to the gear assembly and regulating mechanism shown in the figures, a range of configurations may be acceptable and capable of being employed within the embodiments of the present disclosure, as would readily be appreciated by an ordinarily skilled artisan. Accordingly, the embodiments of the present disclosure are not limited to the specific gear assembly and regulating mechanism described herein, which is provided as an exemplary embodiment of such mechanisms for employment within the controlled delivery drive mechanisms and drug delivery pumps.

In at least one embodiment of the present disclosure, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present disclosure, the delivery profile may be adjusted automatically based on one or more inputs. For example, the delivery profile may be adjusted based on activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 96101. The change in the rate of movement of actuator 96101 causes a change in the rotation rate of regulating mechanism 96500, 961500 which, in turn, controls the rate of drug delivery to the target. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the target. Accordingly, one or more embodiments of the present disclosure are capable of producing a change to the rate of medicament delivery from the drug container thereby providing a dynamic control capability to the drive mechanism and/or the drug delivery device.

In order to quickly prime the drug delivery device, while conserving energy, the drug delivery device may include a priming mechanism such as that shown in FIGS. 130A-113. Priming mechanism 96700 may allow unwinding of the tether and displacement of the piston without rotation of actuator 96101. This displacement of piston 96110 may provide at least two benefits. First, any gap that is present between piston 96110 and plunger seal 9660 after assembly will be quickly closed, bringing the two into contact such that they are ready to begin delivery of the medicament. Second, after piston 96110 is brought into contact with plunger seal 9660, continued translation of piston 96110 will cause commensurate displacement of plunger seal 9660. This may allow the primable drug delivery device containing the priming mechanism to be primed. Upon activation of the fluid pathway connector and the opening of the fluid path from the drug container, translation of plunger seal 9660 may cause air or gas that is initially present in fluid pathway connector 96300, fluid conduit 9630, and needle insertion mechanism 96200 to be expelled. This air or gas may be replaced by the medicament contained in the drug container to allow for delivery of the medicament to the target tissue to begin.

In the embodiment shown in FIGS. 130A-133, the priming mechanism includes winch gear 961520 and winch drum 961522. The winch drum 961522 includes coupler 96702, capstan 96704, and winder 96706. Winch gear 961520 is rotationally coupled to the gear interface through the gear assembly. Tether 961525 is wound around capstan 96704 and is engaged with winder 79606. As a result, tension applied to the tether, by the piston, results in a torque being applied to capstan 96704. Capstan 96704 is keyed to coupler 96702 such that rotation of capstan 96704 is transferred to coupler 96702. In the embodiment illustrated, external key aspect 96704A of capstan 96704 is engaged with internal key aspect 96702A of coupler 96702 to transfer rotation from one component to another. In one embodiment, the key aspects are in the form of complementary teeth. Hence, application of a force to tether 961525 causes a rotational force to be applied to coupler 96702 in the direction of the arrow in FIG. 130A.

Winch gear 961520 includes a gear interface such as the spur gear interface 961520A shown in FIG. 131 which is engaged, through gear assembly 96116 with actuator 96101. Winch gear 961520 further includes hollow 961520E within which coupler 96702 is at least partially disposed. Hollow 961520E is configured with features for controlling the rotation of coupler 96702, such as ramp 961520D and stop 961520C. Coupler 96702, shown in FIG. 132, includes one or more extensions 96702B which are configured to be relatively flexible. As shown in FIG. 130A, coupler 96702 is initially positioned such that angled face 96702C of extension 96702B is adjacent to, or in contact with ramp 961520D of winch gear 961520. Contact between angled face 96702C and ramp 961520D prevents inadvertent rotation of coupler 96702 with respect to winch gear 961520.

One or more components of drug delivery device 9610 form a release mechanism which is initially engaged with release aspect 96702D of coupler 96702. This engagement initially prevents rotation of coupler 96702. The release mechanism may be caused to release rotation of coupler 96702 by an action of the user, such as depression of activation mechanism 9614. Alternatively, the rotation mechanism may be caused to allow rotation of coupler 96702 by an action of power and control system 96400. Upon disengagement of the release mechanism, and in response to a torque applied by tether 96525, coupler 96702 rotates to the position shown in FIG. 130B. In this position, extension 96702B is in contact with stop 961520C. This contact prevents further relative rotation of coupler 96702 with respect to winch gear 961520 in the direction of the arrow in FIG. 130A. Additionally, extension 96702B may engage step 961520F of winch gear 961520 to thereby lock coupler 96702 in position with respect to winch gear 961520. With coupler 96702 and winch gear 961520 in the configuration shown in FIG. 130B, any further rotation of coupler 96702 must be accompanied by commensurate rotation of winch gear 961520. Because winch gear 961520 is engaged with actuator 96101 through gear assembly 96116, rotation of coupler 96702 is also controlled by actuator 96101. In this way, the rate of translation of piston 96110 and the rate of delivery of medicament can be controlled by actuator 96101. Also, the initial translation of piston 96110 and rotation of coupler 96702, from the position shown in FIG. 130A to that shown in FIG. 130B, allows assembly tolerances to be taken up and the primable drug delivery device to be primed without rotation of the actuator. This allows the primable drug delivery device to conserve energy during this initial stage of operation.

In at least one embodiment, the drug delivery device and or drive mechanism include one or more safety mechanisms for automatically slowing or terminating the flow of medicament to the target in the event of a fault in delivery. This may be a beneficial feature in the delivery of controlled substances. Some substances, such as insulin, can be harmful or even deadly if delivered in too large a quantity or at too rapid of a delivery rate. The safety mechanisms described herein may be used to ensure that a so-called "run-away" delivery does not occur. For example, means may exist for terminating or restraining the flow of the medicament in the case of slack in, or failure of, the tether during operation.

In one embodiment, the safety mechanism is a brake mechanism as shown in FIGS. 141A-141B. Disposed within barrel 9658 are brake 9664, sleeve 9662, and plug 9668, and optionally retainer 9666. Biasing member 96122 bears against sleeve 9662. Tether 96525 is engaged with plug 9668, thereby allowing tether 96525 to restrain the motion of sleeve 9662. This restraint controls the rate of expansion or de-energizing of biasing member 96122. When tether 96525 is under tension, plug 9668 bears against distal face 9664A of brake 9664, causing proximal face 9664B of brake 9664 to bear against sleeve 9662. Due to this contact, and the profile of the distal end 9662A of sleeve 9662, brake 9664 is maintained in a substantially conical configuration as shown in FIG. 141A. In this configuration, expansion or de-energizing of biasing member 96122 is restrained by the tether. Also, in this conical configuration, the outer diameter of brake 9664 is less than the inner diameter of barrel 9658, thus translation of the brake is not restrained by contact with the inner wall of the drug container. This permits the brake to be in a position that is not sufficient for braking contact with the inner wall of the barrel. Braking contact is contact sufficient to restrain or prevent further de-energizing of the biasing member and does not necessarily require complete contact of the brake with the inner wall of the barrel. Similarly, the brake may be retained in an initial state not in braking contact with the inner wall of the barrel, but does not necessarily require no contact with the inner wall of the barrel. In at least one embodiment, some contact between the brake and the inner wall of the barrel may be desired prior to activation of the brake mechanism, for example to center the brake within the barrel, as long as the brake does not substantially restrain or prevent further de-energizing of the biasing member prior to activation of the brake mechanism. Also, a portion of brake 9664 is in contact with retainer 9666. Because brake 9664 is maintained in this configuration by plug 9668 and sleeve 9662, translation of sleeve 9662, caused by decompression of biasing member 96122, is transferred to retainer 9666. Likewise, contact of retainer 9666 with plunger seal 9660 causes translation of plunger seal 9660.

As shown in FIG. 141B, in the event of slack in, or failure of, tether 96525, plug 9668 is no longer held in position by tether 59625 and, therefore, no longer restrains motion of sleeve 9662. As biasing member 96122 decompresses or de-energizes, brake 9664 transforms to a relatively less conical or flatter configuration. This may be caused by a natural bias of brake 9664 to transform to this configuration or, alternatively, may be caused by contact of brake 9664 with both retainer 9666 and sleeve 9662. As the brake is transformed, it comes into contact with the inner wall of barrel 9658. The brake thus acts as a wedge to restrict translation of sleeve 9662. This may prevent further translation or may act to restrict the rate of translation. Optionally, restoring tension in the tether may cause the plug to contact the brake and to transform the brake back to its conical configuration and thus restore normal operation of the drug delivery device.

FIGS. 141A-141B show the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface with the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 9662 (i.e., applying a braking force). In another embodiment, the brake 9664 could employ a star-shaped or other configuration when in a substantially flattened position so as to make contact with the inner diameter of the barrel 9658 to prevent or restrict further axial translation of sleeve 9662. Without further translation of sleeve 9662, biasing member 96122 cannot expand or de-energize further which, in turn, prevents or restricts further drug delivery to the target. This provides a necessary and useful safety measure for drug delivery, to prevent over-delivery or accelerated delivery of drug to the target.

In another embodiment, shown in FIGS. 134A-136B, the safety mechanism may be a plunger seal piercing mechanism 961000 and be positioned at least partially within the barrel 9658 or the drive housing 961130. The plunger seal piercing mechanism 961000 may include one or more safety piercing members 961072, a hub 961074, a piston 961110, and a safety biasing member 961078. The piston may additionally have an aperture 961110A through which the tether 961525 may pass and an internal chamber 961110B wherein one or more components of the plunger seal piercing mechanism 961000 may be disposed. The piston may additionally be engaged with a safety base 961076. The base 961076 may include a central aperture 961076A through which the tether 961525 may pass and one or more peripheral apertures 961076B in which the one or more piercing members 961072 may be disposed. The one or more safety piercing members 961072 may be, for example, a hollow needle, such as a stainless steel needle. Alternatively, the piercing members 961072 may be solid trocars. They may also be constructed of any other material such as a thermoplastic or thermosetting polymer. The one or more piercing members 961072 may have a beveled end to increase the efficacy of piercing the plunger seal 961060 and have a lumen 961072B through which material may pass. The one or more piercing members 961072 may be connected to the hub 961074 by any means known to one skilled in the art such as staking, press-fit, and adhesive. Alternatively, the piercing members may be integrally formed portions of the hub. A proximal plug 961070 and a distal plug 961068 may be fixedly engaged with the tether 961525 such that the plugs are fixed in position along the length of the tether 961525. The plugs 961068, 961070 may be, for example, ball cable fittings. Alternatively, they may be an integral feature of the tether 961525. The plunger seal 961060 may include a cavity 961060A within which the distal end 961072A of the one or more piercing members 961072 are initially disposed.

In an initial configuration, as shown in FIGS. 134A-134B, the safety biasing member 961078 is held in a compressed or energized state between a portion of hub 961074 such as shoulder 961074A and an internal face 961110C of the piston 961110 by tension in the tether 961525. In the embodiment shown, tension of the tether 961525 restricts motion of the hub 961074 by way of the proximal plug 961070 disposed in a cavity 961074B of the hub 961074. The stiffness of the safety biasing member 961078 is such that during normal operation the tension in the tether 961525 is sufficient to prevent decompression of the safety biasing member 961078. Hence, during normal operation, the hub 961074 and the one or more piercing members 961072 do not translate with respect to the piston 961110. In the absence of a failure or fault of the drive mechanism tension will be sustained in the tether 961525 and the safety biasing member 961078 will be prevented from decompressing throughout the drug delivery process. The distal plug 961068 may be positioned distal to at least a portion of the safety mechanism base 961076. Hence, the tension of the tether 961525 is transmitted to the plunger seal piercing mechanism 961000 by both the distal 961068 and proximal 961070 plugs. The piston 961110 may include a flange 961110D disposed between the plunger seal 961060 and the drive biasing member 96122. Alternatively, the drive biasing member 96122 may act on the safety mechanism base 961076. Motion of the drive biasing member 96122 is transmitted through the flange 961110D of the piston 961110 and/or the safety mechanism base 961076 to the plunger seal 961060. This also allows decompression of the drive biasing member 96122 and translation of the plunger seal 961060 to be restricted by the tether 961525. FIGS. 135A-135B show the drive biasing member 96122 in a partially decompressed state in which the plunger seal 961060 has translated distally within the barrel 9658.

In the event of failure of the drive mechanism or regulating mechanism, and a resulting reduction in tension in the tether, the safety biasing member 961078 is able to decompress or de-energize. As shown in FIGS. 136A-136B, this decompression of the safety biasing member 961078 causes the hub 961074 and the one or more piercing members 961072 to translate in the distal direction with respect to the piston 961110. As a result, the distal end 961072A of the one or more piercing members 961072 pierces the plunger seal 961060. Upon piercing of the plunger seal 961060, a fluid pathway is created from the drug chamber 9621, through or around the one or more piercing members 961072, and into the piston 961110, proximal portion of the barrel 9658, or another aspect of the drug delivery device 9610. Because the fluid pathway through or around the one or more piercing members 961072 has a lower pressure (i.e., is a fluid path of lower resistance) than the fluid pathway through the sterile fluid pathway connector 96300, continued translation of the plunger seal 961060 toward the distal end of the barrel 9658 will result in the fluid drug traveling through or around the one or more piercing members 961072. Thus, the volume of drug delivered through the sterile fluid pathway connector 96300 and delivered to the target will be reduced or terminated. In this way, the safety mechanism 961000 may reduce or eliminate the risk of a runaway fluid delivery scenario, thereby increasing the safety of the device.

As noted above, the tether 961525 may directly or indirectly restrict translation of the piston 961110 at one or more locations. For example, in the embodiment shown in FIGS. 134A-136B, the tether 961525 may restrict translation of the piston 961110 at the distal plug 961068 and proximal plug 961070 wherein the distal 961068 and proximal 961070 plugs are separated by an intermediate portion 961525A of the tether 961525. This may provide additional, redundant safety mechanisms. For example, if a failure occurs at the distal plug 961068 or in the intermediate portion 961525A of the tether 961525, the rate of decompression of the drive biasing member 96122 will continue to be restricted due to engagement of the tether 961525 with the piston 961110 at the proximal plug 961070. Failure of the drive mechanism or tether 961525 proximal to the proximal plug 961070 will result in decompression of the safety biasing member 961078, piercing of the plunger seal 961060 by the one or more piercing members 961072, and a restriction or reduction in flow of drug fluid to the target as described above. The intermediate portion 961525A may be an integral portion of the tether 961525 or may be a separate component that is directly or indirectly coupled to the tether 961525.

During normal operation, the components of the plunger seal piercing mechanism 961000 do not come in contact with the drug. Additionally, in the event of activation of the plunger seal piercing mechanism 961000, the fluid that passes through or around the one or more piercing members 961072 will not be delivered to the target. Therefore, components of the plunger seal piercing mechanism 961000 do not require sterilization although they may be configured for sterilization if desired.

A method of manufacture of a plunger seal piercing mechanism includes one or more of the steps of: passing a tether 961525 through an aperture 961110A of a piston 961110; affixing one or more piercing members 961072 to a hub 961074; positioning a safety biasing member 961078 against an internal proximal face 961110C of the piston 961110; passing the tether 961525 through an aperture 961074B of the hub 196074; securing a proximal plug 961070 to the tether 961525; passing the tether 961525 through a central aperture 961076A of the safety base 961076; securing a distal plug 961068 to the tether 961525.

In another embodiment, shown in FIGS. 137A-137B, the safety mechanism is a plunger seal displacing mechanism 962000. The displacing mechanism includes piston 962110, spring retainer 962074, sleeve 962084, safety biasing member 962078, plug 962068, and one or more transfer elements 962082. The plug 962068 may be fixedly engaged with the tether 962525. Further, plug 962068 may be positioned distal with respect to at least a portion of the sleeve 962084 such that the plug 962068 restricts distal displacement of the sleeve 962084. For example, plug 962068 may be disposed in recess 962084B of sleeve 962084 (shown in FIG. 140).

The safety biasing member 962078 is positioned between the piston 962110 and the sleeve 962084 and is initially prevented from decompressing and/or de-energizing due to the restriction of displacement of the sleeve 962084. In an initial position, the transfer elements 962082 are disposed within apertures 962110A of the piston and are retained in that position by contact with the sleeve 962084. The transfer elements 962082 are also in contact with a portion of the spring retainer 962074—such as the contact surface 962074A—and, thereby, prevent translation of the spring retainer 962074 relative to the piston 962110. Hence, the force imparted on the spring retainer 962074 by the drive biasing member 122 is transferred through the transfer elements 962082 to the piston 962110 and from the piston 962110 to the plunger seal 962060. The contact surface 2074A of the spring retainer 962074 may be angled such that it applies a force to the transfer elements 2082 that is at least partially in an inward, radial direction.

Upon failure or fault of the drive mechanism or the tether, the safety biasing member 962078 will no longer be restricted from decompressing by tension in the tether. The decompression of the safety biasing member 962078 causes the sleeve 962084 to translate in the distal direction with respect to the piston 962110. As the sleeve 962084 translates, the receiving slot 962084A of the sleeve 962084 becomes aligned with the transfer elements 962082. When so aligned, the force applied to the transfer elements 962082 by the spring retainer 962074 causes the transfer elements 962082 to drop into the receiving slot 962084A. In this position, the transfer elements 962082 no longer prevent axial, distal translation of the spring retainer 962074 with respect to the piston 962110. Because of this, and in response to continued decompression of the drive biasing member 96122, the spring retainer 962074 translates distally with respect to the piston 962110, allowing the prongs 962074B of the spring retainer 962074 to contact the plunger seal 2060.

The spring retainer 962074 may include any number of prongs 962074B and preferably includes two or three prongs. The prongs 962074B may be equally spaced around the circumference of the spring retainer 962074 or, alternatively, may be unequally spaced. As shown in FIGS. 138-139, the prongs 962074B may include a ramped surface. Contact of the ramped surface with the plunger seal 962060 may cause inwardly radial displacement of the plunger seal 962060. This displacement of the plunger seal 962060 may cause at least a partial loss of contact with the barrel 9658, allowing the contents of the barrel to flow past the seal 962060 and into the proximal portion of the barrel 9658. Continued distal translation of the plunger seal 962060 will result in the contents of the barrel flowing past the seal due to this being a flow path of lesser resistance than the flow path through the sterile fluid pathway connector 96300. The prongs 962074B of the spring retainer 962074 may include bypass features 962074C such as slots or scallops that facilitate the flow of fluid past the plunger seal 962060.

In another embodiment, the spring retainer 962074 is configured to cause the plunger seal 962060 to skew within the barrel upon contact (i.e., cause the central axis of the plunger seal to not be parallel to the central axis of the barrel). This allows the contents of the barrel 9658 to flow past the plunger seal 962060 and restricts or eliminates further delivery to the target. To cause the skewing of the plunger seal 962060, the spring retainer 962074 may be configured such that it applies pressure to the plunger seal 962060 unevenly such as, for example, by only having a single prong 962074B.

Other forms of safety mechanisms may be used to ensure that the contents of the drug container are not delivered at too high a rate. For example, the fluid pathway connector may include a pressure relief or "blowoff" valve which opens in response to increased pressure within the fluid pathway. This increased pressure may be caused by the plunger seal distally translating at too rapid of a rate. With the valve in the open position, the delivery of the drug fluid to the target may be terminated or reduced.

Assembly and/or manufacturing of controlled delivery drive mechanism 96100, drug delivery pump 9610, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 9650 may first be assembled and filled with a fluid for delivery to the target. The drug container 9650 includes a cap 9652, a pierceable seal 9656, a barrel 9658, and a plunger seal 9660. The pierceable seal 9656 may be fixedly engaged between the cap 9652 and the barrel 9658, at a distal end of the barrel 9658. The barrel 9658 may be filled with a drug fluid through the open proximal end prior to insertion of the plunger seal 9660 from the proximal end of the barrel 9658. An optional connection mount 9654 may be mounted to a distal end of the pierceable seal 9656. The connection mount 9654 may guide the insertion of the piercing member of the fluid pathway connector into the barrel 9658 of the drug container 9650. The drug container 9650 may then be mounted to a distal end of drive housing 96130.

One or more drive biasing members 96122 may be inserted into a distal end of the drive housing 96130. Optionally, a cover sleeve may be inserted into a distal end of the drive housing 96130 to substantially cover biasing member 96122. A piston may be inserted into the distal end of the drive housing 96130 such that it resides at least partially within an axial pass-through of the biasing member 96122 and the biasing member 96122 is permitted to contact a piston interface surface 96110C of piston 96110 at the distal end of the biasing member 96122. An optional cover sleeve may be utilized to enclose the biasing member 96122 and contact the piston interface surface 96110C of piston 96110. The piston 96110 and drive biasing member 96122, and the optional cover sleeve, may be compressed into drive housing 96130. Such assembly positions the drive biasing member 96122 in an initial compressed, energized state and preferably places a piston interface surface 96110C in contact with the proximal surface of the plunger seal 9660 within the proximal end of barrel 9658. The piston, piston biasing member, contact sleeve, and optional components, may be compressed and locked into the ready-to-actuate state within the drive housing 96130 prior to attachment or mounting of the drug container 9650. The tether 96525 is pre-connected to the piston 96110 and passed through the axial aperture of the biasing member 96122 and drive mechanism housing 96130, and then wound through the interior of the drug delivery device with the other end of the tether 96525 wrapped around the winch drum 96520B of the regulating mechanism 96500.

A fluid pathway connector, and specifically a sterile sleeve of the fluid pathway connector, may be connected to the cap and/or pierceable seal of the drug container. A fluid conduit may be connected to the other end of the fluid pathway connector which itself is connected to the insertion mechanism such that the fluid pathway, when opened, connected, or otherwise enabled travels directly from the drug container, fluid pathway connector, fluid conduit, insertion mechanism, and through the cannula for drug delivery into the target. The components which constitute the pathway for fluid flow are now assembled. These components may be sterilized, by a number of known methods, and then mounted either fixedly or removably to an assembly platform 9620 or housing 9612 of the drug delivery device, as shown in FIG. 110B.

Certain optional standard components or variations of drive mechanism 96100 or drug delivery device 9610 are contemplated while remaining within the breadth and scope of the present disclosure. For example, the embodiments may include one or more batteries utilized to power a motor or solenoid, drive mechanisms, and drug delivery devices of the present disclosure. A range of batteries known in the art may be utilized for this purpose. Additionally, upper or lower housings may optionally contain one or more transparent or translucent windows 9618 to enable the user to view the operation of the drug delivery device 9610 or verify that drug dose has completed. Similarly, the drug delivery device 9610 may contain an adhesive patch and a patch liner on the bottom surface of the housing 9612. The adhesive patch may be utilized to adhere the drug delivery device 9610 to the target for delivery of the drug dose. As would be readily understood by one having ordinary skill in the art, the adhesive patch may have an adhesive surface for adhesion of the drug delivery device to the target. The adhesive surface of the adhesive patch may initially be covered by a non-adhesive patch liner, which is removed from the adhesive patch prior to placement of the drug delivery device 9610 in contact with the target. Removal of the patch liner may further remove the sealing membrane 96254 of the insertion mechanism 96200, opening the insertion mechanism to the target for drug delivery.

Similarly, one or more of the components of controlled delivery drive mechanism 96100 and drug delivery device 9610 may be modified while remaining functionally within the breadth and scope of the present disclosure. For example, as described above, while the housing of drug delivery device 9610 is shown as two separate components upper housing 9612A and lower housing 9612B, these components may be a single unified component. As discussed above, a glue, adhesive, or other known materials or methods may be utilized to affix one or more components of the controlled delivery drive mechanism and/or drug delivery device to each other. Alternatively, one or more components of the controlled delivery drive mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the controlled delivery drive mechanisms and drug delivery devices disclosed herein provide an efficient and easily-operated system for automated drug delivery from a drug container. The novel embodiments described herein provide drive mechanisms for the controlled delivery of drug substances and drug delivery pumps which incorporate such controlled delivery drive mechanisms. The drive mechanisms of the present disclosure control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present disclosure may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug delivery device may provide an end-of-dose indication. The novel controlled delivery drive mechanisms of the present disclosure may be directly or indirectly activated by the user. Furthermore, the novel configurations of the controlled delivery drive mechanism and drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. Furthermore, the embodiments of the present disclosure permit device architecture and/or component integration in ways which are not suitable for devices that require terminal sterilization. For example, when sterilization of the entire device is necessary, the device architecture often requires adequate spacing of components to permit the sterilization gas or material to effectively reach the target surfaces. Removing the need for terminal sterilization permits reduction or elimination of those spaces and allows for device architectures that offer smaller overall dimensions, human factors benefits, and/or industrial design options that are not available for devices that require terminal sterilization.

Manufacturing of a drug delivery device includes the step of attaching both the controlled delivery drive mechanism and drug container, either separately or as a combined component, to an assembly platform or housing of the drug delivery device. The method of manufacturing further includes attachment of the fluid pathway connector, drug container, and insertion mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the user during operation of the device. The method of assembly of the drug delivery device may further include positioning a safety mechanism such as a plunger seal piercing mechanism at least partially within the barrel and adjacent to or in contact with the plunger seal.

A method of operating the drug delivery device includes the steps of: activating, by a user, the activation mechanism; displacing a control arm to actuate an insertion mechanism; and actuating a power and control system to activate a controlled delivery drive mechanism to drive fluid drug flow through the drug delivery device according to a controlled rate or drug delivery profile. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the controlled delivery drive mechanism by the expansion of the biasing member acting upon a piston within a drug container to force fluid drug flow through the drug container, the fluid pathway connector, a sterile fluid conduit, and the insertion mechanism for delivery of the fluid drug to the target, wherein a regulating mechanism acting to restrain the distribution of a tether is utilized to meter the free axial translation of the piston. The method of operation of the drive mechanism and the drug delivery device may be better appreciated with reference to FIGS. 111A-111E and FIGS. 112A-112D, as described above.

XIX. Insertion Mechanism

At least some of the drug delivery devices described in this application, including at least those described in connection with FIGS. 1A-2B, 33A-33C, 69A-75B, 80A-85C, 86A-91, 92A-99, 100A-109B, and 110A-141B may be configured to incorporate the embodiments of the insertion mechanism described below in connection with FIGS. 142A-152. The embodiments of the insertion mechanism described below in connection with FIGS. 142A-152 may be used to replace, in its entirety or partially, the above-described insertion mechanism 200, 90200, 92200, 93200, 94200, 95200, or 96200, or any other insertion mechanism described herein, where appropriate.

In one embodiment, the insertion mechanism 6200 includes an insertion mechanism housing 6202 having one or more extension arms 6202A, a base 6252, and a sterile boot 6250, as shown in the exploded view of FIGS. 142A and 142B. Base 6252 may be connected to assembly platform 6020 to integrate the insertion mechanism into the drug delivery device 6010 (as shown in FIG. 2B) or the or the drug delivery device 6010. The connection of the base 6252 to the assembly platform 6020 may be, for example, such that the bottom of the base is permitted to pass-through a hole in the assembly platform to permit direct contact of the base to the body of the patient. In such configurations, the bottom of the base 6252 may include a sealing membrane 6254 that, at least in one embodiment, is removable prior to use of the drug delivery device 6010 or the drug delivery device 6010. Alternatively, the sealing membrane 6254 may remain attached to the bottom of the base 6252 such that the needle 6214 pierces the sealing membrane 6254 during operation of the drug delivery device 6010 or the drug delivery device 6010. As shown in FIGS. 142A and 142B, the insertion mechanism 6200 may further include a rotational biasing member 6210, a needle hub 6212, a needle 6214, a retraction biasing member 6216, a sleeve 6220, and a conduit 6218. The conduit 6218 may connect to sterile fluid conduit 30 or to sterile access connection 300 to permit fluid flow through the conduit 6218, needle 6214, and into the body of the patient during drug delivery, as will be described in further detail herein.

As used herein, "needle" is intended to refer to a variety of needles including but not limited to conventional hollow needles, such as a rigid hollow steel needles. Upon assembly, the proximal end of needle 6214 is maintained in fixed contact with hub 6212, while the remainder of needle 6214 is preferably located within sterile boot 6250. The needle 6214 may further pass-through base opening 6252E.

Sterile boot 6250 is a collapsible or compressible sterile membrane that is in fixed engagement at a proximal end with the hub 6212 and at a distal end with the sleeve 6220 and/or base 6252. The term "sterile boot" is used to describe a boot within which certain internal components may reside, at one or more stages of operation, in a sterile condition. The boot need not be sterile through the entire operation of the mechanism or drug delivery device and, in fact, may not be initially sterile until assembly and sterilization of certain components has occurred. Additionally, the term "boot" is not intended to mean any specific shape or configuration, but is instead utilized to describe a component that can provide an interior space within which other components may reside at one or more stages of operation. In at least one embodiment, the sterile boot 6250 is maintained in fixed engagement at a distal end between base 6252 and sleeve 6220. In other embodiments sterile boot 6250 is maintained in fixed engagement at a distal end between base 6252 and insertion mechanism housing 6202. Base 6252 includes a base opening 6252E through which the needle may pass during operation of the insertion mechanism, as will be described further below. Sterility of the needle is maintained by its initial positioning within the sterile portions of the insertion mechanism. Specifically, as described above, needle 6214 is maintained in the sterile environment of the sterile boot 6250. The base opening 6252E of base 6252 may be closed from non-sterile environments as well, such as by for example a sealing membrane 6254.

FIGS. 143A-143B and 60-62 show the components of the insertion mechanism, according to at least a first embodiment, in greater detail. As shown in FIGS. 59A-59B, insertion mechanism housing 6202 may be a substantially cylindrical component having an inner chamber within which conduit 6218, hub 6212, needle 6214, sleeve 6220, retraction biasing member 6216, and sterile boot 6250 are substantially disposed in an initial configuration. Guide surfaces 6204 (as best seen in FIG. 143B) are located on the inner surface of housing 6202 and are configured to interact with extension arms 6212A of hub 6212. As will be described in further detail hereinafter rotation of housing 6202 is transferred to axial movement of hub 6212 by interaction of guide surfaces 6204 with extension arms 6212A of hub 6212.

In order to provide rotational movement to the housing 6202, the housing 6202 may further include one or more engagement surfaces 6202B disposed for interaction with the rotational biasing member 6210. In the illustrated embodiment, the housing 6202 is provided with one or more protrusions 202A configured to engage a proximal end of rotational biasing member 6210. Protrusion 6202A may form an engagement surface 202B in the form of a recess in which the proximal end of rotational biasing member 6210 may be disposed. In this way, unwinding and/or de-energizing of rotational biasing member 6210 causes rotation of housing 6202 about axis A.

Although the illustrated embodiments show the rotational biasing member engaging protrusion 6202A, rotation of housing 6202 and rotational biasing member 6210 may be coupled in any way. For example, the rotational biasing member 6210 may engage a slot, aperture, or bore in housing 6202. As in the illustrated embodiment, rotational biasing member 6210 may be located on the outside of housing 6202 in a substantially concentric relationship. The distal end of the rotational biasing member may be engaged with base 6252 or another axially-stationary feature of drug delivery device 6010 such that movement of the distal end of rotational biasing member 6210 is restricted.

Additionally, protrusion 6202A, or another feature of housing 6202, may further contact a portion of the sterile access connection during rotation of housing 6202. This contact, in conjunction with rotation of housing 6202, may be used to initiate the piercing of the pierceable seal and thereby allow the contents of the drug container to flow through the conduit Hub 6212, as seen in FIG. 144, includes extension arms 6212A as described above. It further includes aperture 6212B configured to receive a portion of conduit 6218. Aperture 6212B allows conduit 6218 to be in fluid communication with needle 6214 for delivery of the fluid drug to the patient. Needle 6214 is securely engaged with hub 6212 by bonding, press-fit or other means known to one skilled in the art.

The central body portion 6212C of the hub 6212 is disposed to axially translate within sleeve 6220, which is shown in greater detail in FIG. 145. In order to control the axial movement of the hub 6212 relative to the sleeve 6220, the hub 6212 and sleeve 6220 are provided with protrusions 6212D and recesses configured to engage one another. In the illustrated embodiment, the protrusions 6212D of the hub 6212 are configured as part of the extension arms 6212A, and the sleeve 6220 includes slots 6220A within which extension arms 6212A of hub 6212 are at least partially disposed during operation of the insertion mechanism. This interaction restricts the ability of hub 6212 to rotate relative to the sleeve 6220.

Sleeve 6220, as shown in FIG. 145, includes slots 6220A within which extension arms 6212A of hub 6212 are at least partially disposed during operation of the insertion mechanism. These slots restrict the ability of hub 6212 to rotate. Sleeve 6220 further includes one or more apertures 6220B which are configured to interface with flex arms 6252A of base 6252. During assembly, flex arms 6252A engage apertures 6220B, thereby restricting movement of sleeve 6220 with respect to base 6252. Base 6252, as shown in FIG. 147, may further include one or more lower alignment members 6252C configured to engage one or more alignment notches 6220C of sleeve 6220. This engagement aligns sleeve 6220 to base 6252 and limits rotation of sleeve 6220 with respect to base 6252. Base 6252 may also include one or more upper alignment members 6252D configured to engage face 6206 of housing 6202 during installation, thereby positioning housing 6202 with respect to base 6252.

The operation of the insertion mechanism is described herein with reference to the above components, in view of FIGS. 147-149. FIG. 147A shows an isometric view and FIG. 147B shows a cross-sectional view of the insertion mechanism, according to at least one embodiment of the present disclosure, in a locked and ready to use stage. The proximal end of rotational biasing member 6210 is disposed in recess 6202B of housing 6202 and rotational biasing member 6210 is in an energized state. In this initial position, hub 6212 is in a retracted, proximal position such that needle 6214 does not extend past opening 6252E of base 6252. Sterile boot 6250 is in an extended configuration with one end engaged with hub 6212 and the other engaged with shell 6220 and base 6252. Retraction biasing member 6216 is in a relatively decompressed and/or de-energized state. Extension arms 6212A of hub 6212 are located within or substantially adjacent to proximal portion 6204A of guide surfaces 6204. Coiled fluid conduit 6218 may be located proximally to hub 6212. Fluid conduit 6218 may be connected at one end to hub 6212, allowing fluid drug contents to pass from the drug container 6050 to needle 6214 for delivery to the patient.

In this embodiment, retraction biasing member 6216 is disposed between the hub 6212 and one or more axially-stationary elements of the insertion mechanism in a relatively decompressed and/or de-energized state. Here, the axially-stationary element is a portion of the sleeve 6220. It will be appreciated, however, that the axially-stationary elements may include alternate components, such as, for example, the base 6252, or a combination of two or more such axially-stationary elements.

It will further be appreciated that the retraction biasing member may be alternately disposed, and may include any appropriate type of retraction biasing member. For example, in an alternate embodiment, the retraction biasing member may include a tension spring, as opposed to a compression spring. In such an embodiment, the retraction biasing member may be disposed proximally to the hub 6212 and coupled to the hub and an axially-stationary member in a de-energized state such that axial translation of the hub 6212 in a distal direction energizes the tension spring.

As will be understood by those of skill in the art, insertion mechanism 6200 may be held in this initial configuration by interaction with other components of drug delivery device 6010. For example, drug delivery device 6010 may include a NIM activation mechanism. The NIM activation mechanism may be initiated or activated by depression of activation member 14. Alternatively, the NIM activation mechanism may include a separate member configured for activation by the user. By way of example, activation member 14 may be engaged with a slide which, in an initial configuration, prevents rotation of housing 6202 by interaction with protrusion 6202A. Depression of trigger member 14 may displace the slide, disengaging the slide, or another component, from the protrusion 6202A of housing 6202, thereby allowing rotation of housing 6202.

One example of a NIM activation mechanism is shown in FIGS. 163A-163B. The NIM activation mechanism includes: a throw arm 606, a NIM interlock 608, and a NIM retainer 610. Initially, as shown in FIG. 163A, the NIM retainer 610 is positioned such that the NIM retainer 610 is in contact with a protrusion 202A of the housing 202 such that the housing 202 is prevented from rotating about axis A, thereby preventing activation of the NIM 200. In the embodiment shown, the NIM retainer 610 is configured for rotational movement about axis B. The NIM retainer 610 may, for example, be mounted to the housing 12 at bore 610A. For example, a pin or shaft may be disposed in bore 610A around which the NIM retainer 610 may rotate. The pin or shaft may an integral portion of the housing 12 or, alternatively, may be a separate component. The NIM retainer 610 is initially prevented from rotating by contact between an arm 610B of the NIM retainer 610 with the NIM interlock 608. The NIM interlock 608 is initially in a first position in which it is in contact with or adjacent to a lower surface 606B of the throw arm 606.

Depression of the activation mechanism 14 causes translation of the throw arm 606. The ramped surface 606C of the throw arm 606 contacts the NIM interlock 608 and causes the NIM interlock 608 to translate in a direction substantially orthogonal to the direction of translation of the throw arm 606 (i.e., in the direction of the shaded arrow in FIG. 163A). FIG. 24B shows the position of the throw arm 606 and NIM interlock 608 after translation of the throw arm. As shown, in this configuration, the NIM interlock is positioned adjacent to or in contact with an upper surface 606D of the throw arm 606. The window 608A of the NIM retainer 608 is aligned with the arm 610B of the NIM retainer 610. Hence, as shown in FIG. 163B, the NIM retainer 610 is able to rotate about axis B.

In at least one embodiment, the NIM retainer 610 is biased to rotate by a biasing member. The biasing member may be, for example, a torsion spring. Rotation of the NIM retainer 610 causes the NIM retainer 610 to disengage the protrusion 202A of the housing 202. Hence, the NIM 200 is able to activate to insert a fluid path into a patient. Alternatively, force applied to NIM retainer 610 by protrusion 202A causes rotation of NIM retainer 610.

In other embodiments, the NIM interlock 608 may directly engage a portion of the NIM 200, such as the protrusion 202A, to initially prevent activation of the NIM 200. Translation of the NIM interlock 608 in the direction orthogonal to the translation of the throw arm 606 may cause the NIM interlock 608 to disengage the NIM 200 and allow the NIM 200 to activate.

In another embodiment, the throw arm 606 is directly engaged with a portion of the NIM whereby translation of the throw arm 606 allows activation of the NIM 200.

In an alternative embodiment, shown in FIGS. 2A-2B, a portion of housing 6202 may have gear teeth 6208 configured to interact with a gear 6209 which prevents rotation of the housing. In this configuration, the gear may be connected to a motor 6207 which controls the rotation of the gear and therefore the housing. The housing may be able to be disengaged from the gear, thereby allowing free rotation of the housing in response to de-energizing of the rotational biasing member. Gear 6209 may be connected to motor 6207 through a gear train, the gear train controlling the relationship between rotation of motor 6207 and gear 6209. Additionally, or alternatively, an escapement mechanism may be used to control rotation of the gear train.

FIG. 148A shows an isometric view and FIG. 148B shows a cross-sectional view of an insertion mechanism in a needle inserted stage. As shown in FIG. 147A unwinding and/or de-energizing of rotational biasing member 6210 causes housing 6202 to rotate about axis A. As housing 6202 rotates contact of guide surfaces 6204 with extension arms 6212A of hub 6212 causes hub 6212 to translate in the distal direction. Hub 6212 is prevented from rotating by interaction between extension arms 6212A and slots 6220A of sleeve 6220. Sleeve 6220 is connected to base 6252 by engagement of flex arms 6252B with apertures 6220B. As shown, sterile boot 6250 is permitted to collapse as housing 6202 rotates and hub 6212 translates in the distal direction and inserts the needle 6214 into the body of the patient. At this stage, shown in FIG. 147B, needle 6214 is introduced into the body of the patient for drug delivery. Due to the distal translation of hub 6212, retraction biasing member 6216 is compressed or energized. Rotation of housing 6202 is preferably limited or stopped at a position in which guide surfaces 6204 retain hub 6212 in a distal position. Rotation of housing 6202 may be stopped at this position by interaction between protrusion 6202A and a stop component of the drug delivery device 6010 or the drug delivery device 6010. Alternatively, a stop component may interact with another portion of housing 6202. Upon insertion of the needle 6214, the fluid pathway from the conduit to the body of the patient through the needle 6214 is opened. As the fluid pathway connector is made to the drug container and the drive mechanism is activated, the fluid drug treatment is forced from the drug container through the fluid pathway connector and the sterile fluid conduit into the needle 6214 for delivery into the body of the patient.

As shown in FIGS. 149A and 149B, upon completion of drug delivery, the needle 6214 is retracted back (i.e., axially translated in the proximal direction) into the insertion mechanism housing 6202. Continued rotation of housing 6202 aligns the proximal portion 6204A of guide surfaces 6204 with extension arms 6212A of hub 6212 such that proximal translation of hub 6212 is no longer restricted. In this position, retraction biasing member 6216 is able to decompress or de-energize. Expansion of the retraction biasing member 6216 translates hub 6212, and needle 6214 to which it is connected, axially in the proximal direction. Accordingly, activation of the insertion mechanism inserts the needle 6214 into the body of the patient, and sequentially retracts the needle 6214 after completion of drug delivery or upon some other retraction initiation mechanism.

FIGS. 150-152 show another embodiment of an insertion mechanism 7200. As shown in FIG. 150, one end of the rotational biasing member 7210 is disposed in a recess 7202B formed in the housing 7202 of the insertion mechanism. By engaging the housing in this way the requirement for a protrusion extending outwardly from the housing is eliminated, thereby allowing the overall size of the insertion mechanism to be reduced. Further, as shown in FIG. 151 the sterile boot 7250 may be configured in an "accordion" configuration, which may allow the diameter of the sterile boot to be less than the sterile boot shown in previous embodiments. It may also be seen in FIG. 151 that platform 7020 may have upwardly extending boss 7020A that aids in locating and retaining the needle insertion mechanism. The rotational biasing member 7210 may be positioned around the outside of boss 7020A. The needle insertion mechanism may also include cap 7222. The cap may engage the shell 7220 and act to retain the components of the needle insertion mechanism in place. Specifically, the cap may retain the conduit in position within housing 7202. The cap may include one or more circumferential flex arms 7222A which, during installation, may flex outward in response to contact with protrusions of the shell 7220. The flex arms may then return to their natural position and thereby be retained in place with respect to the shell as seen best in the cross-section view of FIG. 152. Also seen in FIG. 152, one or more flex arms 7020B of platform 7020 may engage apertures 7220B of the housing 7220. This engagement retains and positions the insertion mechanism with respect to platform 7020. The platform 7020 of the drug delivery device may further include locking arms 7020B which are configured to engage apertures 7220B of the shell. This engagement retains the insertion mechanism in position with respect to the drug delivery device. The stages of operation of this embodiment may be substantially similar to those described above (i.e., de-energizing of the rotational biasing member leads to insertion of the needle and de-energizing of the retraction biasing member leads to retraction of the needle).

An additional embodiment of a needle insertion mechanism is shown in FIGS. 153A-155B. In this embodiment, utilizing a rigid needle 2214 to assist in placement, a flexible cannula 2260 is inserted into the target tissue for delivery of medicament. The rigid needle 2214 may be a hollow needle or a solid trocar. In the embodiment shown in FIGS. 153A-153C, a hollow needle is used to insert the cannula 2260. For ease of understanding, structures in this embodiment are identified by the reference numbers utilized for similar structures in the embodiment of FIGS. 1A-1C prefaced by the number "2", or as in the embodiment of FIGS. 2A-2C and 142A-152, changing the reference number from "6XXX" to "2XXX". That is structures are identified by "2XXX" wherein the "XXX" refers to similar structures in the embodiment of FIGS. 1A-1C, or the similar structures in the embodiment of FIGS. 2A-2C and 142A-152 identified by "6XXX". Accordingly, in the absence of a specific discussion below with regard to a reference number shown in FIGS. 153A-155B, those of skill in the art will understand that structures identified by reference numbers "2XXX" refer to the same or similar structures as discussed with regard to the embodiments of FIGS. 1A-1C, 2A-2C, and 142A-152. For the purpose of clarity, a platform is not shown in FIGS. 153A-155B, one of skill the art will understand that a platform similar to that illustrated in previous embodiments may be used in this and subsequent embodiments.

FIG. 153A shows the insertion mechanism in an initial configuration prior to activation. In the initial configuration, flexible cannula 2260 is disposed such that the rigid needle 2214 passes through the lumen of the flexible cannula. Additionally, the proximal end of flexible cannula 2260 is in contact with, or is in proximity to, needle hub 2212. As shown, the cannula 2260 is initially disposed within sterile boot 2250 and septum 2270 is disposed in aperture 2252E in base 2252. In this way, needle 2214 and cannula 2260 are thereby maintained in an aseptic condition. The cannula may be engaged with the needle by press-fit, bonding, or any other joining method. The needle may be further retained and/or located in the hub 2212 by retainer 2290. Upon activation of the insertion mechanism, rotation of housing 2202, caused by de-energizing of rotational biasing member 2210, causes needle hub 2212 to translate in the distal direction. This translation may be guided by contact of followers/arms 2212A of hub 2212 with guide surfaces 2204 on the interior of housing 2202 as described above and as shown in FIGS. 154A-154B. Translation of needle hub 2212 causes needle 2214 and cannula 2260 to also translate in the distal direction, pierce septum 2270, and be inserted into the target tissue. FIG. 153B shows the insertion mechanism at the completion of the insertion step.

As the housing 2202 continues to rotate, for example, under the force of the rotational biasing member 2210, the secondary rotation of the housing 2202 relatively positions the housing 2202 and the hub 2212 to permit the retraction biasing member 2216 to at least partially de-energize. In other words, this further rotation of housing 2202 aligns extension arms 2212A of hub 2212 with axial slot 2208 of housing 2202. In this position, retraction biasing member 2216 is able to de-energize or decompress, causing hub 2212 and needle 2214 to translate in the proximal direction. FIG. 153C shows the insertion mechanism at the completion of this step. Cannula 2260 is maintained in the inserted position and in the target tissue and needle 2214 is at least partially disposed within the cannula. This creates a fluid path through conduit 2218, needle 2214, and cannula 2260 for delivery of the medicament to the target tissue. Because only the flexible cannula 2260 is disposed within the target tissue, the cannula 2260 may flex in response to movement. This may provide advantages in patient comfort. Barb 2260A of cannula 2260 may be configured to engage septum 2270 and thereby resist retraction of the cannula 2260 into the insertion mechanism. Optionally, the needle 2214 may be partially disposed in the target tissue when in this position.

In addition to the advantages described above, the insertion mechanisms described herein may also be capable of terminating flow of medicament to the target tissue by disconnecting the fluid path. This may be an important safety feature to protect the patient. For example, some medicaments, such as insulin, can be dangerous, and potentially even deadly, when administered in too large a quantity and/or at too rapid of a rate. By providing such automatic safety stop mechanisms, so-called "run-away" delivery of medicament may be prevented, thereby ensuring the safety of the patient. While the methods and associated structures for terminating flow may be discussed with regard to one or more specific insertion mechanisms disclosed herein, it will be appreciated that the method and associated structures may be utilized or adapted for any of the insertion mechanisms disclosed herein or within the spirit and scope of this disclosure.

An interruption in delivery of medicament to the target tissue may be triggered, for example, by an error in delivery of the medicament or by an input from the user. For example, the user may realize that they have already taken their drug dose and wish to pause or terminate drug delivery from the device. Upon such user input to the device, the delivery of the drug can be stopped and/or the fluid passageway through the needle or cannula may be terminated by retraction of the needle to its fully retracted position, as described below.

Additionally or alternatively, the device may pause or terminate drug delivery if it receives an error alert during operation. For example, if the drive mechanism is not functioning correctly, the needle insertion mechanism may be triggered to retract fully and terminate drug delivery to the target tissue to prevent over-delivery of a medication to the target tissue. This capability of the needle insertion mechanism provides a valuable safety feature for drug delivery to a user.

In some embodiments, retraction is activated upon removal of the drug delivery device from the patient's body. In other embodiments, retraction is activated if it is determined that an error has occurred in the delivery of the substances to the patient. For example, an occlusion of the drug delivery pathway which prevents the flow of medicament may be detected by a sensing function of the drug delivery device. Upon the sensing of the occlusion an electrical or mechanical input may be used to initiate retraction of the needle.

Activating retraction of the needle may be accomplished through many mechanisms. For example, a button may be provided on the outside of housing 6012 which, when depressed by the patient, activates retraction of the needle from the patient's body. For example, in one embodiment, depressing the button may allow housing 6202 to rotate, hence allowing retraction biasing member 6216 to expand and retract needle 6214. Actuation of the button may be spring assisted such that the travel and/or force required to depress the button is reduced. Alternatively, or additionally, upon drive mechanism 6100 reaching end-of-dose an electrical or mechanical actuator may cause activation of retraction. For example, upon end-of-dose, an electrical connection may be made such that a current is applied to a nitinol component. Upon application of the current the nitinol component's temperature rises. Because of nitinol's shape memory characteristics this component may be configured, upon an increase in temperature, to transform from a first configuration to a second configuration. In this second configuration, the nitinol component may allow or cause the actuation of the retraction of the needle by, for example, allowing rotation of housing 6202.

Alternatively, or additionally, a sensor such as on-body sensor 24 may, when drug delivery device 6010 is removed from the patient's body, cause or allow activation of the retraction of the needle. For example, when drug delivery device 6010 is installed on the patient the position of on-body sensor 24 may prevent rotation of housing 6202 to the retraction position. Upon removal from the patient a change in configuration of on-body sensor 24 may allow rotation. In another embodiment, a light sensor may be placed on drug delivery device 6010 near to base opening 6252. When drug delivery device 6010 is in place on the patient's body light would be substantially blocked from entering the light sensor. Upon removal of drug delivery device 6010 from the patient's body light may be sensed by the light sensor and the light sensor may trigger an electromechanical actuator to allow or cause activation of retraction. In other embodiments, a pin-type press-fit interconnect is used to initiate retraction of the needle. The pin may be biased to at least partially protrude from housing 6012 and be displaced upon placement of drug delivery device 6010 on the patient. When displaced, the pin may engage a female hole on a PCB which may be a part of power and control system 6400. Upon removal of drug delivery device 6010 from the patient, the biased pin disengages the female PCB hole, thereby causing a signal to activate the retraction of the needle.

Retraction of the needle and/or cannula may further be initiated upon a failure and/or fault of drive mechanism 100. For example, the drive mechanism may include a tether which serves to meter or control the rate of delivery of the contents of drug container 50. The tension applied to, or sustained by, the tether may be monitored by one or more sensors. A reduction in the tension of the tether may be an indication that the tether is not properly metering or controlling the delivery of the medicament. The sensor may be a mechanical component or linkage which is in contact with a portion of the tether, the contact at least partially controlling the position and/or configuration of the sensor. In a response to a reduction in tension in the tether, the sensor transforms from a first position to a second position. This transformation may, directly or indirectly, cause retraction of the needle and/or cannula. The retraction may be caused by a purely mechanical action or, alternatively, may involve an electrical signal received and/or generated by power and control system 400.

In other embodiments, the sensor may be a strain gauge, load cell, force sensor or other sensor which is configured to measure and/or monitor the strain, load, or tension present in the tether. In these embodiments, the sensor is at least partially affixed to the tether and generates an electrical signal based on the tension of the tether. The electrical signal may vary in magnitude in proportion to the magnitude of tension in the tether. Alternatively, the signal may be either interrupted or initiated when the tension in the tether falls below or exceeds a specified magnitude. The signal may be monitored by the power and control system which, based on the presence, absence, or magnitude of the signal, may cause or allow the retraction of the needle and/or cannula.

In still other embodiments, a mechanical failure of the tether may directly cause an electrical signal to be initiated or interrupted. For example, the tether may be constructed, at least partially, from a conductive material. The tether may be in electrical communication with the power and control system. The mechanical failure of the tether may interrupt a current path through the tether and cause a change in the flow of current in one or more circuits. This change may initiate or allow the retraction of the needle and/or cannula.

Additionally, or alternatively, the position and/or velocity of one or more features of the drive system may be monitored by a sensor such as: an optical sensor, such as an encoder; a potentiometer; or a transducer. If the position and/or velocity of the monitored feature exceeds or falls below a specified threshold, the power and control system may initiate and/or allow retraction of the needle and/or cannula.

In one example, in the embodiment shown in FIGS. 153A-153C, flow of medicament to the target tissue can be terminated by retracting needle 2214 from cannula 2260. FIG. 16A shows a detail view of the needle 2214 in a delivery position. In this position, the needle 2214 is at least partially disposed within the cannula 2260, thereby creating a fluid path through the conduit, needle, and cannula and into the target tissue. FIG. 155B shows a detail view of a configuration in which the needle 2214 has been retracted such that it is no longer disposed within the cannula 2260. That is, as the housing 2200 is continued to rotate, for example, under the force of the rotation biasing member 2210, this tertiary rotation of the housing 2200 aligns the followers 2212A with retraction apertures 2207 in the housing 2200, allowing the retraction biasing member 2216 to further de-energize and move the needle 2214 to a fully retracted position. Because the needle 2214 is no longer disposed within the cannula 2260, a fluid path does not exist for delivery of medicament to the target tissue. Any additional fluid that passes through the conduit 2218 will be discharged through the needle 2214 to the interior of the drug pump, for example within sterile boot 2250. A barrier 2280 may be included to further prevent any medicament from entering cannula 2260 after retraction of the needle from the cannula. The barrier 2280 may be, for example, a septum which is pierced by the needle during assembly of the needle and cannula. Alternatively, the barrier 2280 may be a membrane or a clip which is displaced by the needle during assembly but which, upon retraction of the needle from the cannula, substantially covers the lumen of the cannula. A pressure differential within the cannula may also prevent the flow of medicament there-through after retraction of the needle, with or without the utilization of a barrier 2280.

As shown in FIGS. 164A-164B, the secondary or tertiary rotation of the housing may be controlled by a NIM retraction mechanism. In one example of a NIM retraction mechanism, with the needle and needle hub in the delivery position, protrusion 202A may be in contact with stop member 620, as shown in FIG. 164A. In this position, stop member 620 is prevented from rotating about spindle 624 by contact with slide member 622. Thus, further rotation of housing 202 is prevented. For example, in embodiments having a flexible cannula, such as that shown in FIGS. 153A-153C and described above, or as shown in FIGS. 156A-161 and described below, this position may correspond with the positions illustrated in FIG. 153C and FIG. 157C, respectively. In response to a triggering mechanism, slide member 622 may be displaced such that stop member 620 is able to rotate, about spindle 624, to the position shown in FIG. 164B. Hence, stop member 620 no longer restricts rotation of housing 202, allowing the needle to be fully retracted to a position in which medicament is no longer delivered to the target tissue, such as that shown in FIG. 155B and FIG. 156D. The triggering mechanism that causes displacement of slide member 622 may, for example, be caused by user input, a fault of the operation of the drug pump or any other event described above. In addition, displacement of slide member 622 may be purely mechanical or, alternatively, may be occur at least partially in response to a signal from power and control system 400.

Another embodiment is shown in FIGS. 156A-161. As in the embodiment of FIGS. 153A-153C described above, the present embodiment is configured to insert a flexible cannula into the target. For ease of understanding, structures in this embodiment are identified by the reference numbers utilized for similar structures in the embodiment of FIGS. 1A-1C prefaced by the number "3", or as in the embodiment of FIGS. 153A-155B, changing the reference number from "2XXX" to "3XXX". That is structures are identified by "3XXX" wherein the "XXX" refers to similar structures in the embodiment of FIGS. 1A-1C, or the similar structures in the embodiment of FIGS. 153A-155B identified by "2XXX". Accordingly, in the absence of a specific discussion below with regard to a reference number shown in FIGS. 156A-161, those of skill in the art will understand that structures identified by reference numbers "3XXX" refer to the same or similar structures as discussed with regard to the previous embodiments.

The stages of operation are shown in three different cross-sections in FIGS. 156-158, while individual components clip 3286, cannula retainer 3282, needle hub 3212, and housing 3202 are illustrated in FIGS. 159-162, respectively. The first cross-section, shown in FIGS. 156A-156D, shows the interaction of followers 3212A of needle hub 3212 with guide surfaces 3204 of the housing 3202 at various stages of operation. Initially, as shown in FIG. 156A, hook arm 3212C is engaged with notch 3202C of housing 3202. This allows proper positioning and alignment of needle hub 3212 with respect to housing 3202.

Rotation of the housing, caused by de-energizing of rotational biasing member 3210, disengages hook arm 3212C from notch 3202C. Further rotation of housing 3202, and contact between followers 3212A and guide surfaces 3204, causes needle hub 3212 to translate in the distal direction until needle 3214 and cannula 3260 are fully inserted in the target as shown in FIG. 156B.

After insertion of the needle 3214 and cannula 3260, continued, that is, secondary rotation of housing 3202 aligns axial slot 3208 of housing 3202 with followers 3212A. Hence, retraction biasing member 3216 is able to de-energize, which causes proximal translation of needle hub 3212 to the at least partially retracted position as shown in FIG. 156C. In this position, needle 3214 is at least partially disposed in cannula 3260 and through septum 3284 and followers 3212A are in contact with proximal portion 3204A of guide surfaces 3204. Therefore, contents may be delivered through needle 3214, cannula 3260, and to the target tissue.

In order to terminate delivery of medicament to the target tissue, continued rotation of housing 3202 may cause needle 3214 to be further retracted to the position shown in FIG. 156D. That is, as the housing 3200 is continued to rotate, for example, under the force of the rotation biasing member 3210, this tertiary rotation of the housing 3200 causes followers 3212A to disengage proximal portion 3204A and be aligned with retraction aperture 3207, thereby allowing additional proximal translation of needle hub 3212 in response to de-energizing of retraction biasing member 3216. In this position, needle 3214 is withdrawn from septum 3284. Hence, contents that flow through needle 3214 are not able to enter cannula 3260. Retraction of the needle may be caused by any of the safety mechanisms described, such as, for example, the safety mechanism illustrated in FIGS. 164A and 164B.

The second cross-section, shown in FIGS. 157A-157C, shows the interaction of connection arms 3286A of clip 3286 with needle hub 3212. The clip 3286 and the needle hub 3212 are shown in more detail in FIGS. 159 and 161, respectively. Initially, as seen in FIG. 1157A, connection arms 3286A are engaged with needle hub 3212, thereby coupling axial translation of clip 3286 and needle hub 3212. As seen in FIG. 1157B, connection arms 3286A remain engaged with needle hub 3212 as needle 3214 and cannula 3260 are inserted into the target. As will be described below, and as best seen in FIGS. 158A-158C, as clip 3286 translates in the distal direction it engages flex arms 3220D of sleeve 3220. Due to this engagement, clip 3286 is prevented from translating in the proximal direction. Hence, upon alignment of followers 3212A with proximal portion 3204A of guide surfaces 3204, connection arms 3286A disengage from needle hub 3212 by flexing outward (i.e., in the direction of the hatched arrows in FIG. 157C). As a result, upon alignment of followers 3212A with proximal portion 3204A of guide surfaces 3204, needle hub 3212 and needle 3214 translate in the proximal direction and needle 3214 is at least partially withdrawn from the target. Cannula 3260 remains disposed within the target.

The third cross-section is shown in FIGS. 158A-158C. The interaction between flex arms 3220D of sleeve 3220 and clip 3286 may be seen in these figures. As clip 3286 is translated distally during needle and cannula insertion, clip 3286 comes in contact with flex arms 3220D and causes them to be displaced outward (i.e., in the direction of the solid arrows shown in FIG. 158A). As shown in FIG. 158B, continued distal translation of clip 3286 allows flex-arms 3220D to at least partially return to their initial positions. As shown in FIG. 158C, as biasing member 3216 begins to expand, translation of clip 3286 is restricted by contact with flex arms 3220D. This restriction causes cannula 3260 to remain disposed within the target. As shown in FIG. 149, clip 3286 may include ramped surfaces 3286B configured to engage flex-arms 3320D. The ramped surfaces may create an undercut which ensures that contact of ramped surfaces 3286B with flex arms 3320D does not cause outward flexion of flex-arms 3320D.

As shown in FIG. 160, cannula retainer 3282 includes bore 3282B and pins 3282A. As assembled, a shoulder of cannula 3260 and septum 3284 are disposed within bore 3282B. They are retained in this position by the position of clip 3286. Pins 3282A are configured to engage holes 3286D of clip 3286. This engagement may be configured to be a press-fit engagement to maintain the relative positions of cannula retainer 3282 and clip 3286. The central hole 3286C of the clip 3286 is adapted to receive needle 3214.

Certain optional standard components or variations of insertion mechanism 6200 or the drug delivery devices 6010 are contemplated while remaining within the breadth and scope of the present disclosure. For example, upper or lower housings may optionally contain one or more transparent or translucent windows 18, as shown in FIGS. 1A-1C, to enable the patient to view the operation of the drug delivery device 6010 or verify that drug dose has completed. Additionally, the drug delivery device 6010 may contain an adhesive patch and a patch liner on the bottom surface of the housing 6012. The adhesive patch may be utilized to adhere the drug delivery device 6010 to the body of the patient for delivery of the drug dose. As would be readily understood by one having ordinary skill in the art, the adhesive patch may have an adhesive surface for adhesion of the drug delivery device to the body of the patient. The adhesive surface of the adhesive patch may initially be covered by a non-adhesive patch liner, which is removed from the adhesive patch prior to placement of the drug delivery device 6010 in contact with the body of the patient. Adhesive 26 may optionally include a protective shroud that prevents actuation of the optional on-body sensor 24 and covers base opening 6252E. Removal of the patch liner may remove the protective shroud or the protective shroud may be removed separately. Removal of the patch liner may further remove the sealing membrane 6254 of the insertion mechanism 6200, opening the insertion mechanism to the body of the patient for drug delivery.

Similarly, one or more of the components of insertion mechanism 6200 and the drug delivery devices 6010 and 6010 may be modified while remaining functionally within the breadth and scope of the present disclosure. For example, as described above, while the housing of drug delivery device 6010 is shown as two separate components upper housing 12A and lower housing 12B, these components may be a single unified component. As discussed above, a glue, adhesive, or other known materials or methods may be utilized to affix one or more components of the insertion mechanism and/or drug delivery device to each other. Alternatively, one or more components of the insertion mechanism and/or drug delivery device may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present disclosure.

It will be appreciated from the above description that the insertion mechanisms and drug delivery devices disclosed herein provide an efficient and easily-operated system for automated drug delivery from a drug container. The novel embodiments described herein provide integrated safety features; enable direct patient activation of the insertion mechanism; and are configured to maintain the sterility of the fluid pathway. As described above, the integrated safety features include optional on-body sensors, redundant lockouts, automated needle insertion and retraction upon patient activation, and numerous patient feedback options, including visual and auditory feedback options. The novel insertion mechanisms of the present disclosure may be directly activated by the patient. For example, in at least one embodiment the rotation prevention feature, whether it is a stop component configured to engage protrusion 6202A or a gear engaged with teeth of housing 6202, which maintain the insertion mechanism in its locked, retracted state is directly displaced from its locked position by patient depression of the activation mechanism. Alternatively, one or more additional components may be included, such as a spring mechanism, which displaces the rotation prevention feature upon direct displacement of the activation mechanism by the patient without any intervening steps. In at least one configuration, rotation of a motor causes or allows rotation of a gear, thereby allowing rotation of the housing of the insertion mechanism.

Furthermore, the novel configurations of the insertion mechanism and drug delivery devices of the present disclosure maintain the sterility of the fluid pathway during storage, transportation, and through operation of the device.

Because the path that the drug fluid travels within the device is entirely maintained in a sterile condition, only these components need be sterilized during the manufacturing process. Such components include the drug container of the drive mechanism, the fluid pathway connector, the sterile fluid conduit, and the insertion mechanism. In at least one embodiment of the present disclosure, the power and control system, the assembly platform, the control arm, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly. A further benefit of the present disclosure is that the components described herein are designed to be modular such that, for example, the housing and other components of the drug delivery device may readily be configured to accept and operate insertion mechanism 6200 or a number of other variations of the insertion mechanism described herein.

Assembly and/or manufacturing of insertion mechanism 6200, drug delivery device 6010, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

In a further embodiment, the present disclosure provides a method of assembling the insertion mechanism including the steps of: connecting a hub to a proximal end of a needle; connecting a conduit to the hub; connecting a sterile boot to the hub; inserting a retraction biasing member into a sleeve of the needle insertion mechanism; inserting the hub, needle, conduit, and sterile boot into the sleeve (in this position, the retraction biasing member is constrained between the hub at one end and the shell at the other end); placing a housing around the sleeve; inserting a retraction biasing member into the sleeve; and connecting a base to the sleeve by engagement of flex arms with apertures in the housing. A rotational biasing member may be placed around the housing such that a portion of the rotational biasing member is engaged with a portion of the housing, thereby coupling de-energizing of the biasing member with rotation of the housing.

The distal end of the sterile boot may be positioned and held in fixed engagement with the distal end of the insertion mechanism housing by engagement of the housing with a base. In this position, the sterile boot is in an expanded configuration around the needle and creates an annular volume which may be sterile. A fluid conduit may be connected to the hub such that the fluid pathway, when open, travels directly from the fluid conduit, through the hub, and through the needle. A fluid pathway connector may be attached to the opposite end of the fluid conduit. The fluid pathway connector, and specifically a sterile sleeve of the fluid pathway connector, may be connected to a cap and pierceable seal of the drug container. The plunger seal and drive mechanism may be connected to the drug container at an end opposing the fluid pathway connector. A sealing membrane may be attached to the bottom of the base to close off the insertion mechanism from the environment. The components which constitute the pathway for fluid flow are now assembled. These components may be sterilized, by a number of known methods, and then mounted either fixedly or removably to an assembly platform or housing of the drug delivery device.

Manufacturing of a drug delivery device includes the step of attaching the base of the insertion mechanism to an assembly platform or housing of the drug delivery device. In at least one embodiment, the attachment is such that the base of the insertion mechanism is permitted to pass-through the assembly platform and/or housing to come in direct contact with the body of the patient. The method of manufacturing further includes attachment of the fluid pathway connector, drug container, and drive mechanism to the assembly platform or housing. The additional components of the drug delivery device, as described above, including the power and control system, the activation mechanism, and the control arm may be attached, preformed, or pre-assembled to the assembly platform or housing. An adhesive patch and patch liner may be attached to the housing surface of the drug delivery device that contacts the patient during operation of the device.

A method of operating the drug delivery device may include the steps of: activating, by a patient, the activation mechanism; displacing a control arm to actuate an insertion mechanism; and actuating a power and control system to activate a drive control mechanism to drive fluid drug flow through the drug delivery device. The method may further include the step of: engaging an optional on-body sensor prior to activating the activation mechanism. The method similarly may include the step of: establishing a connection between a fluid pathway connector to a drug container. Furthermore, the method of operation may include translating a plunger seal within the drive control mechanism and drug container to force fluid drug flow through the drug container, the fluid pathway connector, a sterile fluid conduit, and the insertion mechanism for delivery of the fluid drug to the body of a patient.

XX. Additional Embodiments of Insertion Mechanism

At least some of the drug delivery devices described in this application, including at least those described in connection with FIGS. 1A-2B, 33A-33C, 69A-75B, 80A-85C, 86A-91, 92A-99, 100A-109B, and 110A-141B may be configured to incorporate the embodiments of the insertion mechanism described below in connection with FIGS. 33A-33C. The embodiments of the insertion mechanism described below in connection with FIGS. 33A-33C may be used to replace, in its entirety or partially, the above-described insertion mechanism 200, 6200, 7200, 90200, 92200, 93200, 94200, 95200, or 96200, or any other insertion mechanism described herein, where appropriate.

A number of insertion mechanisms may be utilized within the drug delivery devices of the present disclosure. The pump-type delivery devices of the present disclosure may be connected in fluid flow communication to a patient or patient, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient.

For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present disclosure, including a rigid needle insertion mechanism and/or a rotational needle insertion mechanism as described by the present disclosure.

Figure 33B:
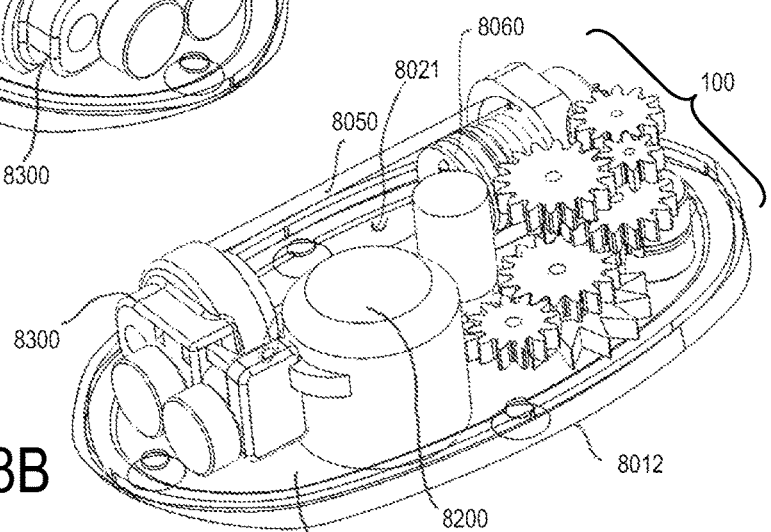
FIG. 33B shows an isometric view of the interior components of the drug delivery device shown in FIG. 33A (shown without the adhesive patch) from another viewpoint.
Figure 33C:
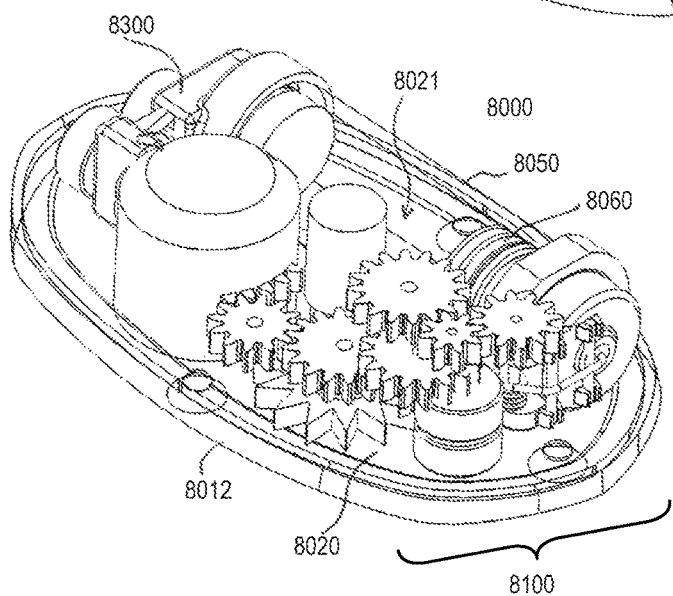
FIG. 33C shows an isometric view of the interior components of the drug delivery device shown in FIG. 33A (shown without the adhesive patch) from yet another viewpoint.

In at least one embodiment, the insertion mechanism 8200 includes an insertion mechanism housing having one or more lockout windows, and a base for connection to the assembly platform and/or pump housing (as shown in FIG. 33B and FIG. 33C). The connection of the base to the assembly platform 8020 may be, for example, such that the bottom of the base is permitted to pass-through a hole in the assembly platform to permit direct contact of the base to the body of the patient. In such configurations, the bottom of the base may include a sealing membrane that is removable prior to use of the drug delivery device 8000. The insertion mechanism may further include one or more insertion biasing members, a needle, a retraction biasing member, a cannula, and a manifold. The manifold may connect to sterile fluid conduit 8030 to permit fluid flow through the manifold, cannula, and into the body of the patient during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present disclosure, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. Displacement of the lockout pin(s), by one or more methods such as pulling, pushing, sliding, and/or rotation, permits insertion biasing member to decompress from its initial compressed, energized state. This decompression of the insertion biasing member drives the needle and, optionally, the cannula into the body of the patient. At the end of the insertion stage or at the end of drug delivery (as triggered by the multi-function drive mechanism), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the patient. Accordingly, the insertion mechanism may be used to insert a needle and cannula into the patient and, subsequently, retract the needle while retaining the cannula in position for drug delivery to the body of the patient.

XXI. Fill Finish Cartridge

The sterile fluid pathway assemblies described above may be filled with pharmaceutical treatments, such as the drugs described below, using standard filling equipment and systems. This advantage is enabled by the fill-finish cartridges described below which function to maintain the sterility of the fluid pathway assemblies and allow them to nest, mount, or otherwise be removably inserted into trays for standard fill-finish processes, as discussed further below. The drive mechanisms, fluid pathway connectors, insertion mechanisms, and other components and sub-components of the drug delivery devices described below in connection with FIGS. 165-87 may be implemented in any of the drug delivery devices described above in connection with FIGS. 1A-164B or any other drug delivery devices disclosed herein, where appropriate. Furthermore, any of the methods of manufacture and methods of use described below may be applied to the drug delivery devices described above in connection with FIGS. 1A-164B or any other drug delivery devices disclosed herein, where appropriate.

Turning to FIG. 165, there is illustrated a schematic representation of an example of a drug delivery device 10 incorporating aspects of the disclosure. The device 10 includes a housing 612 having an activation mechanism 614. For ease of understanding, the housing 612 is shown schematically. In accordance with the disclosure, the device further includes a fill-finish cartridge 616. The fill-finish cartridge 616 includes a drug container 618, a fluid pathway assembly 620 including a fluid pathway connector 622 and a needle insertion mechanism 624. The fluid pathway assembly 620 may include further structure that facilitates disposition of various components, including, for example, a fluid conduit 26. The fluid pathway connector 622 is disposed substantially adjacent a distal end 628 of the drug container 618, and the needle insertion mechanism 624 is disposed substantially adjacent a distal end 630 of the fluid pathway connector 622. In the illustrated embodiment, the drug container 618 is generally horizontally positioned and perpendicular from a vertically positioned needle insertion mechanism 624. It will be appreciated, however, that the components may be positioned in any appropriate manner.

Administration of a drug contained in the drug container 618 may be initiated by the activation mechanism 614. The activation mechanism 614 may include, for example, activation mechanisms that are manually actuated by a patient, or that are automatically actuated by, for example, a power and control module 632 that may include, by way of further example, a microprocessor or other automatic administration arrangement with appropriate connections. In this embodiment, the activation mechanism 614 is a button 634 that may be disposed, for example, along an outer surface of the housing 612, and may be selectively depressed by the patient. It will be appreciated that the drug delivery device 10 as well as the activation mechanism 614 may be of any appropriate design.

The power and control module 632, if included, may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control module 632 controls several device interactions with the patient and may interface with one or more other components of the drug delivery device 10. In one embodiment, the power and control module 632 may identify when an on-body sensor and/or the activation mechanism 614 have been activated. The power and control module 632 may also interface with a status indicator, which may be a transparent or translucent material which permits light transfer, to provide visual feedback to the patient. The power and control module 632 may interface with a drive mechanism and/or the integrated sterile fluid pathway connector and drug container 618 through one or more interconnects to relay status indication, such as activation, drug delivery, and/or end-of-dose, to the patient. Such status indication may be presented to the patient via tactile feedback, such as vibration; auditory tones, such as through the audible alarms; and/or via visual indicators, such as through the LEDs. In a preferred embodiment, the control interfaces between the power and control system and the other components of the drug delivery device are not engaged or connected until activation by the patient. This is a desirable safety feature that prevents accidental operation of the drug delivery device and may also maintain the energy stored in the power source during storage, transport, and the like.

The power and control module 632 may be configured to provide a number of different status indicators to the patient. For example, the power and control module 632 may be configured such that after the on-body sensor and/or trigger mechanism have been pressed, the power and control module 632 provides a ready-to-start status signal via the status indicator if device start-up checks provide no errors. After providing the ready-to-start status signal and, in an embodiment with the optional on-body sensor, if the on-body sensor remains in contact with the body of the patient, the power and control module 632 will power the drive mechanism to begin delivery of the drug treatment through the integrated sterile fluid pathway connector 622 and sterile fluid conduit 26. In a preferred embodiment of the present disclosure, the insertion mechanism 624 and the drive mechanism may be caused to activate directly by patient operation of the activation mechanism 614. The integrated sterile fluid pathway connector is connected (i.e., the fluid pathway is opened) by the pneumatic force of the drug fluid within the drug container 618 created by activation of the drive mechanism, as is detailed further herein. During the drug delivery process, the power and control module 632 is configured to provide a dispensing status signal via the status indicator. After the drug has been administered into the body of the patient and after the end of any additional dwell time, to ensure that substantially the entire dose has been delivered to the patient, the power and control module 632 may provide an okay-to-remove status signal via the status indicator. This may be independently verified by the patient by viewing the drive mechanism and delivery of the drug dose within the drug container through a window of the housing 612. Additionally, the power and control module 632 may be configured to provide one or more alert signals via the status indicator, such as for example alerts indicative of fault or operation failure situations.

Other power and control system configurations may be utilized with the novel drug delivery devices of the present disclosure. For example, certain activation delays may be utilized during drug delivery. As mentioned above, one such delay optionally included within the system configuration is a dwell time which ensures that substantially the entire drug dose has been delivered before signaling completion to the patient. Similarly, activation of the device may require a prolonged depression (i.e., pushing) of the activation mechanism 614 of the drug delivery device 10 prior to drug delivery device activation. Additionally, the system may include a feature which permits the patient to respond to the end-of-dose signals and to deactivate or power-down the drug delivery device. Such a feature may similarly require a delayed depression of the activation mechanism, to prevent accidental deactivation of the device. Such features provide desirable safety integration and ease-of-use parameters to the drug delivery devices. An additional safety feature may be integrated into the activation mechanism to prevent partial depression and, therefore, partial activation of the drug delivery devices. For example, the activation mechanism and/or power and control system may be configured such that the device is either completely off or completely on, to prevent partial activation. Such features are described in further detail hereinafter with regard to other aspects of the novel drug delivery devices.

When included, the power and control module 632 may include a processor (not shown) and a memory component (not shown). The processor may be microprocessors or other processors as known in the art. In some embodiments the processor may be made up of multiple processors. The processor may execute instructions for generating administration signal and controlling administration of a drug contained in the drug container 618. Such instructions may be read into or incorporated into a computer readable medium, such as the memory component or provided external to processor. In alternative embodiments, hard-wired circuitry may be used in place of or in combination with software instructions to implement drug administration. Thus, embodiments are not limited to any specific combination of hardware circuitry and software.

The term "computer-readable medium" as used herein refers to any medium or combination of media that participates in providing instructions to processor for execution. Such a medium may take many forms. The memory component may include any form of computer-readable media as described above. The memory component may include multiple memory components.

The power and control module 632 may be enclosed in a single housing. In alternative embodiments, the power and control module 632 may include a plurality of components operably connected and enclosed in a plurality of housings.

The power and control module 632 may be configured to generate an administration signal as a function of patient actuation, preprogrammed actuation or remote actuation. The power and control module 632 may be communicatively coupled to fill-finish cartridge 616, and/or the drug container 618, the fluid pathway connector 622, and/or the needle insertion mechanism 624 individually.

In accordance with an aspect of embodiments of the disclosure, in the illustrated embodiment, actuation of the activation mechanism 614, here, depression of the button 634, results in engagement of the fluid pathway connector 622, as will be discussed in greater detail below. This same action by the patient may trigger the needle insertion mechanism 624 to inject a needle or cannula into the patient, as will likewise be explained in greater detail below. Thus, actuation of activation mechanism 614 results in the completion of a drug pathway from the drug container 618 through the fluid pathway connector 622, the fluid conduit 26, and the needle insertion mechanism 624 to the patient (not shown). Actuation of the activation mechanism 614 may also result in a drive mechanism acting upon structure associated with the drug container 618 to force fluid through the sterile pathway. In an embodiment of the present disclosure, the needle insertion mechanism 624 may be triggered to retract the needle from the patient, giving a clear end of dose delivery indication upon completion of drug delivery. The housing 612 may additionally include, for example, a window through which the drug container 618 may be viewed to confirm drug delivery.

According to an aspect of embodiments of the disclosure, the fill-finish cartridge 616 is constructed and filled prior to assembly into the housing 612 of the drug delivery device 10. In this regard, the fill-finish cartridge 616 is sufficiently robust to withstand procedures for sterilizing the fill-finish cartridge 616, in some embodiments prior to fill, and in some embodiments after fill. After the sterile construction and filling of the fill-finish cartridges 616, the device may be positioned as needed within a drug delivery device 10. In any event, the sterility of the fluid pathway assembly 620 and the drug container 618 are maintained through aspects of the assembly, filling, and manufacturing processes. Final assembly of the drug delivery device 10 can thus be performed outside of a sterile environment. Because only the components of the sterile fluid pathway assembly 620 need to be, and have been, sterilized, the remainder of the drug delivery device 10 does not need sterilization (i.e., terminal sterilization). This provides a number of advantages. Novel embodiments of the present disclosure may also alleviate the need to fill the drug delivery device at time-of-use, although some embodiments of the present disclosure may be utilized in devices configured for time-of-use filling as well.

According to another aspect of embodiments of the disclosure, various embodiments of individual components of the fill-finish cartridge 616 may be assembled in various configurations to provide various embodiments of the fill-finish cartridge 616. The following disclosures disclose exemplary structures of individual elements that may be incorporated into the fill-finish cartridge 616: U.S. application Ser. No. 13/600,114 filed Aug. 30, 2012; U.S. application Ser. No. 13/599,727 filed Aug. 30, 2012; U.S. application Ser. No. 13/612,203 filed Sep. 12, 2012; and Ser. No. 13/796,156 filed Mar. 12, 2013. FIG. 166B is a chart of examples of variables for possible structures of connections between individual components that may yield various configurations of embodiments of fill-finish cartridges 616, while FIG. 166A shows an example of a fill-finish cartridge 616 identifying aspects referenced in FIG. 166A. For ease of understanding, the same reference numbers are utilized as in FIG. 165. The individual components, as well as the interactions and connections between the individual components may have various designs. For example, the needle insertion mechanism 624 may be of any suitable design. Similarly, the container 618 and the fluid pathway connector 622 may each be of any appropriate design.

Likewise, the interactions between the components may be of any appropriate design. For example, the engagement of the fluid pathway connector 622 with the drug container 618 may include a threaded or snap connection, an interference fit, or an external support or other arrangement, so long as a tight seal is obtained. Similarly, the engagement of the fluid pathway connector 622 with the needle insertion mechanism 624 may include a threaded or snap connection, an interference fit, a tongue and groove arrangement, an external support, or some other arrangement including, but not limited to, utilizing a fluid conduit between the fluid pathway connector 622 and the needle insertion mechanism 624 for the connection. Moreover, in some embodiments, the engagement of the fluid pathway connector 622 with the needle insertion mechanism 624 may be disassembled following the fill-finish process in order to permit the needle insertion mechanism 624 to be oriented other than axially with the remainder of the fill-finish cartridge 616, so long as the sterile fluid connection is maintained.

In various embodiments, the fill-finish cartridge 616 may be maintained with the components in axial alignment during the fill-finish process, as well as in use with a drug delivery device 10. That is, for example, the needle insertion mechanism 624 may be disposed axially with the remainder of the fill-finish cartridge 616 during both the fill-finish process, such as is shown in FIG. 166B, and in use in a drug delivery. In other embodiments, the fill-finish cartridge 616 may be maintained with the components in axial alignment during the fill-finish process, such as is illustrated in FIG. 166B, while the components may be maintained in other than axial alignment in use with a drug delivery device 10. For example, as illustrated in FIG. 165, the needle insertion mechanism 624 is disposed spaced from the fluid pathway connector 622 and the drug container 618, and at a 90.degree. orientation. In other embodiments, the fill-finish cartridge may be maintained with the components in other than axial alignment during the fill-finish process, yet be axially aligned in use with a drug delivery device 10. In other embodiments, the fill-finish cartridge 616 may be maintained with the components in other than axial alignment during both the fill-finish process and in use with a drug delivery device 10.

Further, while not included in all embodiments, in order to provide added structural integrity to the fill-finish cartridge 616, a carrier may be provided, as will be explained in more detail below. Such a carrier may be integrated with the structure of the fill-finish cartridge 616 such that it is maintained about or along at least a portion of the fill-finish cartridge 616 in the drug delivery device 10, or such a carrier may be fully or partially disposable. A carrier may perform a number of functions, such as, the maintenance of the relative positions of various of the fill-finish cartridge components during assembly, a fill-finish process, or other operations performed on the fill-finish cartridge or a drug delivery device incorporating the same; a carrier or a portion of a carrier may be utilized in the interaction of the fill-finish cartridge with a drug delivery device 10, such as, in attachment of the fill-finish cartridge 616 into a drug delivery device 10 or in connection with operation of a drug delivery device 10. More detailed explanations of various examples of such structures in varied configurations follow; it is not the intention to limit the structures to those particular configurations. Rather, the individual arrangements explained are provided as examples of various possible configurations and structures within the purview of this disclosure.

FIG. 167 shows an exploded view of one embodiment of the fill-finish cartridge 716 of the present disclosure. For ease of understanding, the number utilized in FIG. 165 are utilized in further examples of embodiments of the disclosure with numerical prefixes; in this embodiment, 1XX will be utilized. The fill-finish cartridge 716 of this embodiment includes a fluid pathway assembly 720 connected to a drug container 718.

The fluid pathway assembly 720 includes a needle insertion mechanism 724 coupled to a fluid pathway connector 722 by a fluid conduit 726. A proximal end of the needle insertion mechanism 724 is connected to a distal end of a fluid conduit 726, which is connected at its proximal end to the fluid pathway connector 722.

The needle insertion mechanism 724 may be of any appropriate design so long as it may be sterilized prior to the placement of the fill-finish cartridge 716 in a drug delivery device. Examples of such needle insertion mechanisms 724 for implants and liquid drugs are disclosed in U.S. application Ser. No. 13/599,727 filed Aug. 30, 2012. It will be noted that the needle insertion mechanism 724 of FIG. 167 includes an axial structure, such that the administration needle (not visible in FIG. 167) extends axially from a distal end of the fill-finish cartridge 716 for administration. It will be appreciated, however, that a needle insertion mechanism 724 that is disposed at an angle to an axis of the fluid pathway connector 722 and/or drug container 718 could alternately be utilized.

The components of the fluid pathway assembly 720, including the needle insertion mechanism 724, the fluid pathway connector 722, and the fluid conduit 726 are formed of materials that may be sterilized by conventional sterilization techniques and machinery. The fluid conduit 726 may be formed of any appropriate material, for example, a length of flexible tubing, such as plastic tubing. It will be appreciated, however, that fluid pathway connector 722 and the needle insertion mechanism 724 may be directly attached in some embodiments (not illustrated in FIGS. 167 and 168).

The components of the fluid pathway assembly 720 may be sterilized in advance of such connections, or may be connected prior to sterilization as a unified component. If sterilized in advance of such connections, the fluid pathway assembly 720 may include an additional seal at the fluid pathway connector 722, such as a permeable seal that may be pierced during assembly or actuation (not illustrated).

The drug container 718 of this and each of the embodiments may be of any appropriate material and of any appropriate shape and size, and may include a seal to maintain the integrity and sterility of a drug contained therein. For example, the drug container 718 may be formed of glass, plastic, or other appropriate material. The drug container 718 of this and each of the embodiments may include structure that facilitates handling, mounting within a drug delivery device, sterilization, and/or interface with other components of the fill-finish cartridge 716. For example, a flange 719 may be provided at any appropriate location along the drug container 716. Such a flange 719 may be integrally formed with the drug container 718 or may be a separate element that is secured to the drug container. In the illustrated embodiment, the flange 719 is a separate component that is coupled to a proximal end of the drug container 718.

It will be appreciated that any appropriate drive mechanism may be provided for moving the medication from the drug container 718 to the fluid pathway assembly 720 in embodiments of the disclosure. For example, U.S. application Ser. No. 13/600,114 filed Aug. 30, 2013, discloses an embodiment of a drive mechanism associated with a drug container.

In order to facilitate both filling the drug container 718 and administering medication from the drug delivery container, the drug container 718 may include openings 718a, 718b at the proximal and distal ends 6127, 728, respectively. In order to seal the drug container 718, a permeable seal 150 may be provided at a distal end 728 of the drug container 718. In this way, once filled, a drug contained within the drug container 718 may be maintained in a sterile environment until such time as the seal 150 is pierced by the fluid pathway connector 722 to complete the fluid pathway. The permeable seal 150 may be of any appropriate design and material.

The distal end 728 of the drug container 718 may be assembled with the fluid pathway assembly 720 for sterilization prior to or after fill, as will be explained in greater detail below. FIG. 168 shows an enlarged cross-sectional view of the fluid pathway connector 722 and the permeable seal 150 of FIG. 168, after these components are assembled and ready for sterilization. While the permeable seal 150 may be a single thin membrane 762 or the like across the opening 718b at the distal end 728 of the drug container 718, the permeable seal 150 may include further structure that facilitates connection with the drug container 718 and/or the fluid pathway connector 722. As shown, in at least one embodiment of the present disclosure, the permeable seal 150 is in the form of a container tip which caps the drug container 718, as well as provides support for the fluid pathway connector 722. In this embodiment, the permeable seal 150 may include a portion 152 that rests inside the drug container 718, providing a mating surface to mount the permeable seal 150 to the drug container 718. To assist in maintaining the connection of the seal 150 with the drug container 718 a cap 151 may be provided about portions of the permeable seal 150 and the drug container 718, such as around a lip on the drug container 718. Such a cap 151 may be of any appropriate material, such as a foil. While the drug container 718 necks in at the interface with the permeable seal 150, it will be appreciated that alternate designs may likewise be provided.

The permeable seal 150 may also have an extension 153 which facilitates mounting with the fluid pathway connector 722. In the embodiment shown in FIG. 168, the fluid pathway connector 722 includes a hub 154 through which a cannula 158 may extend. It will be appreciated by those of skill in the art that, as used herein the term "cannula" 158 includes a needle or a cannula that may be operative to provide the required fluid connection. The fluid conduit 726 is fluidly connected to the cannula 158 as it extends from a surface of the hub 154. The hub 154 of the fluid pathway connector 722 may be employed, as shown here, to mount, attach, or otherwise connect with the extension 153 of the permeable seal 150, the proximal end of the cannula 158 being disposed within a bore 760 of the extension 153. Prior to the completion of a fluid pathway between the drug container 718 and the fluid conduit 726, the cannula 158 is held in position as illustrated in FIG. 168.

The permeable seal 150 has a portion that acts as a membrane 762 that may be pierced by the cannula 158. In the embodiment of FIGS. 167 and 168, the membrane 762 is disposed generally perpendicular to the cannula 158 to close off the drug container 718 from the fluid pathway connector 722, thereby blocking the fluid pathway from the drug container 718 to the fluid conduit 726. Upon activation by the patient, a portion of the permeable seal 150 blocking the drug container 718, here, membrane 762, is caused to be pierced by the cannula 158 of the fluid pathway connector 722, thereby completing the fluid pathway and permitting drug fluid to pass from the container 718 to the cannula 158 and the fluid conduit 726, and on to the needle insertion mechanism 724. In order to facilitate piercing, the extension 153 of the permeable seal 150 may bow outward in response to sufficient axial pressure, for example, to allow the cannula 158 to pierce the membrane 762 to complete the fluid pathway.

Accordingly to another aspect of embodiments of the disclosure, the drug container 718, fluid pathway connector 722, and the needle insertion mechanism 724 of the fill-finish cartridge 716 exhibit sufficient structural integrity to be utilized in a fill-finish process and to be assembled into a housing of a drug delivery device. It will be appreciated that any appropriate fluid pathway connector 722 may be incorporated into embodiments of the disclosure. For example, a mounted fluid pathway connector, such as is disclosed, for example, in U.S. application Ser. No. 13/612,203 filed Sep. 12, 2012, may be utilized. Likewise, an integrated fluid pathway connector, such as is disclosed, for example, in U.S. application Ser. No. 13/796,156 filed Mar. 12, 2013, and may be utilized.

Similarly, it will be appreciated that any appropriate connection may be provided between the fluid pathway connector 722 and the needle insertion mechanism 724. While examples of some connections are disclosed in detail herein, it is not the applicant's intention to limit the disclosure. Such a connection may include, for example, a snap connection (see FIGS. 210-187), a threaded connection (see FIGS. 180-184), an interference connection, a tongue and groove connection, an external support (see FIG. 167), or other appropriate connection.

Returning to FIG. 167, In order to provide further structural integrity to such an interface between the fluid pathway connector 722 and the permeable seal 150, and/or between the fluid pathway connector 722 and the needle insertion mechanism 724, a carrier 742 may be provided. The carrier 742 of this embodiment includes a connection collar 740 and a barrel 6141. For manufacturing purposes, the connection collar 740 may itself include multiple components, as illustrated in FIG. 167, that may be coupled together about the fluid pathway connector 722, the permeable seal 150, and a portion of the drug container 718 by any appropriate mechanism. It will be appreciated, however, that a unitary connection collar 740 could alternately be provided. It will further be appreciated that the connection collar 740 may not be required or desirable in all embodiments, and that such a connection collar 740 may be provided as an integrated part of the design, or may be fully or partially disposable during the assembly or sterilization processes.

Further structural integrity may be provided by the barrel 6141, which may support the fluid pathway assembly 720 during the sterilization and assembly processes. While any appropriate coupling may be provided, the connection collar 740 may facilitate coupling of the barrel 6141 about the fluid pathway assembly 720. In the illustrated embodiment, the connection collar 740 includes a pair of protrusions 744 (only one being visible in FIG. 167) that mate with a pair of recesses 746 in the barrel 6141. As with the connection collar 740, it will further be appreciated that the barrel 6141 may not be required or desirable in all embodiments, and that such a barrel 6141 may be provided as an integrated part of the design, or may be fully or partially disposable during the assembly or sterilization processes. In order to permit the needle insertion mechanism 724 to operate to administer medication, the barrel 6141 may include an opening 6 741a through which an administration needle may extend during use.

For operational efficiency, the needle insertion mechanism 724 may be coupled to the fluid pathway connector 722, and the fluid pathway connector 722 may be connected to the permeable seal 150 with the needle insertion mechanism 724 maintained in the non-piercing configuration through the sterilization, filling, and assembly processes. In this way, the fill-finish cartridge 716 may appear as shown in FIG. 169, with the fluid pathway assembly 720 residing entirely hidden from the external environment by the carrier 742. Once the drug container 718 is filled with a pharmaceutical treatment, a seal 764 may be provided in the proximal end 6127 of the drug container 718 to provide a closed fill-finish cartridge 716 that may be inserted into an appropriate drug delivery device. In the embodiment illustrated in FIGS. 169-170, an elastomeric plunger seal 764 is inserted into the proximal end 6127 of the drug container 718. It will be appreciated, however, that other appropriate sealing arrangement may be provided. In FIGS. 169 and 170, the arrangement of the fluid pathway connector 722, the container 718, and the insertion mechanism 724 relative to each other may be considered to be a first configuration. The first configuration may facilitate the manufacturing process, for example, by enabling the use of standard filling equipment and systems. While the first configuration shown in FIGS. 169 and 170 involves the axial alignment of the container 718 and the insertion mechanism 724, in other embodiments, the first configuration may involve a non-axial alignment of the container 718 and the insertion mechanism 724, or any other relative positioning of the container 718 and the insertion mechanism 724. Subsequently, when assembled in the drug delivery device 610, as illustrated in FIG. 165, the fluid pathway connector 722, the container 718, and the insertion mechanism 724 may be arranged relative to each other such they have a second configuration. The second configuration may involve the non-alignment of the container 718 and the insertion mechanism 724 as illustrate in FIG. 165, or, in alternative embodiments, the axial alignment of the container 718 and the insertion mechanism 724, or any other relative positioning of the container 718 and the insertion mechanism 724. In some embodiments, the first configuration is different from the second configuration.

According to another aspect of the disclosure, the fluid pathway assemblies may be maintained in a sterile condition and the drug containers of each assembly may be filled with a pharmaceutical compound aseptically using processes similar to those known in the art. After a pharmaceutical treatment is filled into the drug container and the container is sealed, for example with the plunger seal 764 of the embodiment of FIGS. 167-170, the fill-finish cartridge 716 may be removed from the sterile filling environment without comprising the sterility or container integrity of the drug container 718, fluid pathway assembly 720, or their individual components.

Alternatively, the fill-finish process may be such that the plunger seal 764 is inserted to the proximal end of the drug container 718 prior to filling the container 718 with a pharmaceutical treatment. In such an embodiment, the pharmaceutical treatment may be filled from the distal end 728 of the drug container 718 prior to insertion and connection of the fluid pathway connector 722 and the fluid pathway assembly 720. Accordingly, the fill-finish cartridges of the present disclosure enable the fluid pathway assemblies of the present disclosure to be filled with pharmaceutical treatments in standard fill-finish processes, greatly reducing the complexities associated with manufacturing and operation of the components and the drug delivery devices in which they are incorporated.

According to another aspect of the disclosure, embodiments of the fill-finish cartridges of the present disclosure may enable the fluid pathways assemblies to be filled in standard fill-finish processes. In this regard, the fill-finish cartridges may utilize existing or standardized fill-finish equipment. A plurality of fill-finish cartridges 716, such as is illustrated in FIGS. 167-170, for example, may be removably mounted, mated, inserted, or otherwise placed into a standard fill-finish tray 770, such as illustrated in FIGS. 171-172, for filling with pharmaceutical treatments. As explained above, the flange 719 of the drug container 718 may assist in placement and handling of the fill-finish cartridges 716. The fill-finish tray 770 illustrated in FIGS. 171-172 is configured to hold thirty-six drug containers, here, fill-finish cartridges 716, but trays of any configuration or capable of holding any number of containers may be utilized.

According to another aspect of the disclosure, fill-finish cartridges may be configured to be fixed cartridges or adjustable cartridges. For example, the cartridges may have a flexible or adjustable portion that enables them to bend, rotate, expand, or contract to fit a number of different fluid pathway assemblies or to mate with fill-finish processing trays of different dimensions.

According to yet another aspect of the disclosure, components of some embodiments of the fill-finish cartridges may be incorporated into the drug delivery devices, while in other embodiments, components of the fill-finish cartridges may be utilized for the fill-finish process and then discarded upon mounting the fluid pathway assembly and drug container into a drug delivery device. For example, in an embodiment such as is illustrated in FIGS. 167-170 is utilized as shown in FIG. 165, by removing the barrel, the connection collar may be utilized to mount and/or brace the drug container into position within the drug delivery device, while the needle insertion mechanism is mounted remotely from and 90.degree. to the drug container.

In the embodiment of FIGS. 173-175, there is illustrated a fill-finish cartridge 816 that includes a carrier 842 that may be disposed of after the fill-finish process, that is prior to insertion into a drug delivery device. The fill-finish cartridge 816 of this embodiment includes a fluid pathway assembly 820 connected to a drug container 818. The fluid pathway assembly 820 includes a needle insertion mechanism 824 coupled to a fluid pathway connector 822 by a fluid conduit 826. A proximal end of the needle insertion mechanism 824 is connected to a distal end of a fluid conduit 826, which is connected at its proximal end to the fluid pathway connector 822. In order to provide further support to the fill-finish cartridge 816, the illustrated carrier 842 is disposed about portions of the drug container 818 and the fluid pathway assembly 820, that is, the fluid pathway connector 822, the fluid conduit 826, and a portion of the needle insertion mechanism 824.

The carrier 842 is generally an elongated tubular structure that may be fabricated in multiple components to facilitate assembly and disassembly, if desired. In the illustrated embodiment, one portion of the carrier 842 includes circumferentially extending arms 843 having protrusions 844, while a mating portion of the carrier 842 includes recesses or openings 846 through which the protrusions 844 may extend when assembled about the fill-finish cartridge 816.

In order to assist in maintaining the components of the fill-finish cartridge 816 in their relative positions, the carrier 842 may further include one or more radially projecting flanges 848a, 848b, 848c. As will be apparent from the explanation below, flanges 848a and 848b may be disposed to further secure aspects of the fluid pathway connector 822 and the drug container 818 in their relative positions. Further, as will likewise be apparent from the explanation below, flanges 848b and 848c may be disposed to maintain the fill-finish cartridge 816 in an un-actuated position during filling, and, optionally, placement within a drug delivery device. In order to permit actuation of the device, the carrier 842 may be removed from the fill-finish cartridge 816 and discarded. The carrier 842 may further include a removable brace 840. The removable brace 840 may have a generally U-shaped structure and surfaces that confront the surfaces of the fill-finish cartridge 816 to prevent premature completion of the fluid pathway from the drug container 818 to the fluid pathway connector 822. The removable brace 840 may remain with the fill-finish cartridge 816 as it is assembled into a housing of a drug delivery device; in some embodiments, structure within the housing of the drug delivery device may confront one or more surfaces of the removable brace 840 to cause the removable brace 840 to disengage from the fill-finish cartridge 816 as it is assembled into the housing.

The drug container 818 is an elongated, generally annular structure, although the drug container 818 may be of an alternate design. For example, a flange 819 may be provided at any appropriate location along the drug container 818. Such a flange 819 may be integrally formed with the drug container 818 or may be a separate element that is secured to the drug container 818. In the illustrated embodiment, the flange 819 is a separate component that is coupled to a proximal end 827 of the drug container 818. In an embodiment, the flange 819 may interface with a wall of a housing of a drug delivery device incorporating the fill-finish cartridge 816. Further, in this embodiment, a flange 817 is provided at the distal end 828 of the drug container 818. As illustrated in FIG. 175, the flange 817 may engage with flange 848a of the carrier 842 to facilitate the maintenance of the relative positions of the components of the fill-finish cartridge 816 during the fill-finish process and handling.

In order to seal the drug container 818, a permeable seal 850 may be provided at the distal end 828 of the drug container 818. In this way, a drug contained within the drug container 818 may be maintained in a sterile environment until such time as the seal 850 is pierced by the fluid pathway connector 822 to complete the fluid pathway. The drug container 818 may be assembled with the permeable seal 850 and the fluid pathway assembly 820 for sterilization prior to or after fill. The permeable seal 850 may be of any appropriate design and material. The permeable seal 850 includes a thin membrane 862 or the like that may be pierced in order to complete the fluid pathway from the drug container 818 through the fluid pathway connector 822 and fluid conduit 826 to the needle insertion assembly 824.

The permeable seal 850 may include structure that facilitates connection with the drug container 818 and/or the fluid pathway connector 822. For example, the permeable seal 850 may include a portion 852 that rests inside the drug container 818, providing a mating surface to mount the permeable seal 850 to the drug container 818.

The fluid pathway connector 822 maybe of any appropriate design. Such piercing arrangements are disclosed, for example, in U.S. application Ser. No. 13/612,203, and in U.S. application Ser. No. 13/796,156.

Referring to FIG. 175, the illustrated fluid pathway connector 822 includes a cannula 858 that is disposed to pierce the membrane 862 of the permeable seal 850 during actuation, the cannula 858 being spaced from the permeable seal 850 in the un-actuated position (see FIG. 175), and progressing respectively axially in a proximal direction to confront and pierce the membrane 862 as a result of actuation. In the embodiment shown in FIG. 175, the fluid pathway connector 822 includes a hub 854 through which the cannula 858 extends. A pathway from the cannula 858 secured within the hub 854 extends from the lumen of the cannula 858 to a lumen of the fluid conduit 826. Accordingly, when the cannula 858 pierces the membrane 862 of the permeable seal 850, the fluid pathway is provided between the drug container 818, the fluid conduit 826 and the needle 825 of the needle insertion mechanism 824.

In order to maintain the hub 854 and, therefore, the cannula 858 in a desired position relative to the permeable seal 850 closing the drug container 818, the fluid pathway connector 822 further includes a boot 853 formed of collapsible material, such as an elastomeric material. A distal end of the boot 853 includes a generally axially extending bore 853a that is disposed about a portion of the hub 854, while a proximal end of the boot 853 includes a generally radially extending flange 853b. The permeable seal 850 may also include a flange 849 that may be sandwiched between the flange 853b of the boot 853 of the fluid pathway connector 822 and the flange 817 at the distal end 828 of the drug container 818. As with the embodiment illustrated in FIGS. 167-170, a retaining structure, such as a cap 851 may be provided about the periphery of the flanges 817, 849, 853b.

The fluid pathway connector 822 of the fill-finish cartridge 816 may be caused to pierce the membrane 862 of the permeable seal 850 to complete the fluid pathway, for example, by manual depression of the proximal end 827 of the drug container 818 or by an alternate arrangement. During actuation, the boot 853 bows outward to allow relative axial movement between the hub 854 and the permeable seal 850 such that the cannula 858 pierces the membrane 862 of the permeable seal 850 to fluidly connect the drug container 818 to the delivery needle 825 of the needle insertion mechanism 824 via the fluid conduit 826.

In order to inhibit inadvertent activation of the fluid pathway connector 822 once the carrier 842 is removed, the removable brace 840 may be provided about a portion of the circumference of the sterile boot 853 and/or between surfaces that inhibit axial movement of the hub 854 relative to the drug container 818. The removable brace 840 may be a relatively rigid structure that confronts opposing surfaces 840a, 840b, for example, on a surface of the hub 854, and the flange 853b of the sterile boot 853 or, as here the cap 851 along the flange 853b; as a result, the removable brace 840 inhibits axial movement of hub 854 relative to the seal 850. The removable brace 840 illustrated also closely follows at least a portion of the periphery of the sterile boot 853; as a result, the removable brace 840 likewise prevents the sterile boot 853 from bowing outward as the cannula 858 moves axially to pierce the seal 850. In this embodiment, the removable brace 840 may be slid out of position on the sterile boot 853 by the patient prior to assembling the fill-finish cartridge 816 into the drug delivery device or by the action of placement into the drug delivery device, for example, as the removable brace 840 engages confronting surfaces of the housing of the delivery device (not illustrated).

The needle insertion mechanism 824 may be of any appropriate design. The needle insertion mechanism 824 illustrated in connection with the embodiment of FIGS. 173-176 likewise includes a needle retraction mechanism, and is shown and explained in greater detail in U.S. application Ser. No. 13/599,727, which is incorporated by reference.

The insertion mechanism 824 includes an insertion mechanism housing 865 having one or more lockout windows 865a, a base 866, and a sterile boot 879. The base 866 includes an opening to passage of the needle 825 and may include a sealing membrane 867 that, at least in one embodiment, is removable prior to use of the fill-finish cartridge 816. Alternatively, the sealing membrane 867 may remain attached to the bottom of the base 866 such that the needle 825 pierces the sealing membrane 867 during operation of the fill-finish cartridge 816 within the drug delivery device incorporating the same.

The insertion mechanism 824 may further include an insertion biasing member 868, a hub 869, a needle 825, a refraction biasing member 871, a clip 872, a manifold guide 873, a septum 874, a cannula 875, and a manifold 876. As illustrated in FIG. 175, both the insertion and retraction biasing members 868, 871 are held in energized states. The manifold 876 may connect to sterile fluid conduit 826 to permit fluid flow through the manifold 876, cannula 875, and into the body of the patient during drug delivery, as will be described in further detail herein.

As used herein, "needle" is intended to refer to a variety of needles including but not limited to conventional hollow needles, such as a rigid hollow steel needles, and solid core needles often referred to as "trocars". In an embodiment, the needle 825 may be a 27 gauge solid core trocar and in other embodiments, the needle may be any size needle suitable to insert the cannula for the type of drug and drug administration (e.g., subcutaneous, intramuscular, intradermal, etc.) intended.

Upon assembly, the proximal end of needle 825 is maintained in fixed contact with hub 869. The needle 825 may be positioned to move through a cannula 875, if provided, in order to further control movement of the needle 825. The hub 869, and therefore the needle 825, is maintained in selective contact with the manifold guide 873 by the clip 872. While biasing members 868 and 871 bear on the manifold guide 873, the manifold guide 873 is maintained in position by at least one lockout pin 878, which extends through window 865a of the housing 865.

Actuation of the needle insertion 824 device results from removal of the lockout pin 878. The lockout pin 878 may be removed from the window 865a either directly or indirectly as a result of actuation of the fill-finish cartridge 816. Upon removal of the lockout pin 878, the manifold guide 873 carrying the hub 869 and needle 825 is permitted to move axially under the biasing force of the injection biasing member 868. That is, the needle 825 moves into the injection position. As the hub 869 and needle 825 move to the injection position, the sterile boot 879 collapses.

In at least some embodiments, such as the embodiment shown in FIG. 175, the needle insertion mechanism 824 further includes a refraction mechanism that retracts the needle 825 following injection. Such a retraction mechanism may be of any appropriate design. As the manifold guide 873 moves axially in the distal direction, the clip 872 releases the hub 869. Upon release, the biasing force of the retraction biasing member 871 causes hub 869 and the associated needle 825 to retract.

As with the embodiment of FIGS. 167-170, the needle insertion mechanism 824 of FIGS. 173-176 includes an axially aligned structure, such that the administration needle 825 extends axially from a distal end of the fill-finish cartridge 816 during administration. It will be appreciated that the components may be secured together by any appropriate structure and method. The relative positions of the fluid pathway connector 822 and the needle insertion mechanism 824 may be maintained by, for example, a bracket 880, as may be seen in FIGS. 174-176. The illustrated bracket 880 extends between the hub 854 of the fluid pathway connector 822 and the insertion mechanism housing 865, as may best be seen in FIG. 175. The bracket 880 may perform additional functions such as, for example, management of the fluid conduit 826.

It will be appreciated that in some embodiments wherein the bracket 880 is removed from its connection with either of the fluid pathway connector 822 or the needle insertion mechanism 824, or wherein the fill-finish cartridge does not include the bracket 880, the fluid conduit 826 may provide a flexible fluid connection between the fluid pathway connector 822 and the needle insertion mechanism 824, allowing the needle insertion mechanism 824 and the fluid pathway connector 822 to be placed other than in axial alignment. Such embodiments are illustrated, for example, in FIG. 165 or FIGS. 177-180.

Referring to FIG. 177, there is illustrated another embodiment of a drug delivery device 910 according to teachings of the disclosure. A portion of the housing 912 of the drug delivery device 910 is broken away in order to illustrate the relative positions of the components contained therein. The fill-finish cartridge 916 includes a drug container 918 to which a fluid pathway assembly 920 is coupled. The fluid pathway assembly 920 includes a fluid pathway connector 922, fluidly coupled to a needle insertion mechanism 924 by a fluid conduit 926. It will be appreciated that, in this embodiment, while they remain fluidly coupled, the needle insertion mechanism 924 is decoupled from the fluid pathway connector 922 of the fill-finish cartridge 916 when assembled into the housing 912. As shown in FIGS. 178 and 179, during the fill-finish process, the components are aligned to allow the fill-finish cartridge 916 to be readily placed in a tray, such as are illustrated in FIGS. 171 and 172. It is noted, however, that the components are not in axial alignment in the fill-finish cartridge 916 during the fill-finish process inasmuch as the axis of the needle insertion mechanism 924 extends perpendicular to the axis of the drug container 918 and fluid path connection 922. As may be best seen in FIG. 178, the needle insertion mechanism 924 may include a sealing membrane 967 that, at least in one embodiment, is removable prior to use of the fill-finish cartridge 916 within the drug delivery device to allow passage of a needle from the needle insertion mechanism 924. Alternatively, the sealing membrane 967 may remain attached to the bottom of the needle insertion mechanism 924 such that the needle pierces the sealing membrane 967 during operation of the fill-finish cartridge 916 within the drug delivery device 910 incorporating the same.

Referring to FIG. 178, there is illustrated the fill-finish cartridge 916 along with a carrier 942 that partially surrounds the assembled fill-finish cartridge 916 during the fill-finish process. As may be seen in FIG. 178, the carrier 942 substantially surrounds a distal portion of the drug container 918, the fluid pathway connector 922, and the needle insertion mechanism 924. The carrier 942 of this embodiment includes three separate sections, although a greater or lesser number may be provided. In this embodiment, a portion of the carrier 942 is disposable prior to placement of the fill-finish cartridge 916 into the housing 912 of the drug delivery device 910, while a portion remains on the fill-finish cartridge 916 when disposed in the housing 912, and may be utilized in operation of the device 910.

As may be seen in FIGS. 178 and 179, the carrier 942 includes a first barrel section 941a and a second barrel section 941b. The first and second barrel sections 941a, 941b may be selectively coupled together by any appropriate mechanism. In the illustrated embodiment, a coupling arrangement similar to that illustrated in FIGS. 173-75 is utilized such that the first and second sections 941a, 941b may be decoupled and removed prior to placement into the housing 912 of the drug delivery device 910. The carrier 942 further includes a collar 940 that, when assembled to the fill-finish cartridge 916, completes the barrel.

The fluid pathway connector 922 and the needle insertion mechanism 924 may be of any appropriate design. The illustrated fluid pathway connector 922, for example, is as explained with regard to FIGS. 173-176, and the needle insertion mechanism 924 may likewise be as described with regard to FIGS. 173-176. Referring to FIG. 179, in short, a permeable seal 950 is disposed between the drug container 918 and a sterile boot 953 of the fluid pathway connector 922. A cannula 958 extending from a hub 954 is axially disposed within the sterile boot 953. Continued relative axial, proximal movement of the cannula 958 toward the permeable seal 950 results in a piercing of the permeable seal 950, and completion of the fluid pathway to the needle insertion mechanism 924.

In assembly of the filled fill-finish cartridge 916 into the drug delivery device housing 912, the collar 940 remains coupled to the fluid pathway connector 922, as illustrated in FIG. 177. In some embodiments of the disclosure, the carrier, or a portion of the same such as the collar 940 here, may be utilized in the operation or actuation of the fill-finish cartridge 916. In this embodiment, an activation mechanism 914, such as a button, may be provided along an outer surface of the drug delivery device housing 912 in order to permit the patient to selectively provide medication. In this embodiment, the activation mechanism 914 asserts an axial, proximally directed force on the collar 940. The collar 940 further asserts an axial, proximally directed force on the hub 954, causing the cannula 958 to pierce the permeable seal 950 of the fluid pathway connector 922 to complete the fluid pathway from the drug container 918 to the needle insertion mechanism 924. The needle insertion mechanism 924 may be actuated by any appropriate operation. For example, the movement of a portion of the collar 940 may cause the dislodgement of the lockout pin, causing actuation of the needle insertion mechanism 924, as explained in greater detail with regard to the embodiment illustrated in FIGS. 173-176.

Turning now to the embodiment of FIGS. 180-186, the fill-finish cartridge 1116 includes a drug container 1118 having proximal and distal ends 1127, 1128. The proximal end 1127 may include a flange 1119 and is adapted to receive a plug or plunger seal 1164, while the distal end 1128 may include a flange 1117 and is adapted to receive a permeable seal 1150 in conjunction with a fluid pathway assembly 1120. The fluid pathway assembly 1120 includes a fluid pathway connector 1122 and a needle insertion mechanism 824 fluidly coupled by a fluid conduit 1126.

In this embodiment, the fluid pathway connector 1122 is integrated with the permeable seal of the drug container 1118. The fluid pathway connector 1122 may best be seen in the cross-sectional view of FIG. 181 and the exploded view of FIG. 183. The fluid pathway connector 1122 includes a hub assembly 1156 having a hub 1154 and a cap 1155. A cannula 1158 is secured to the hub 1154 to provide a fluid path therethrough. The fluid conduit 1126 may be coupled to the cannula 1158 by any appropriate structure. In this embodiment, the fluid conduit 1126 is coupled to a nipple 1159 that is fluidly open to the cannula 1158.

In order to maintain the hub assembly 1156 along with the associated cannula 1158 in position relative to the permeable seal 1150, a seal mount 1130 is provided. While the seal mount 1130 may be coupled to the permeable seal 1150 by any appropriate structure, in the illustrated embodiment, the permeable seal 1150 and the seal mount 1130 include mating structure in the form of respective interlocking flanges 1131, 1132.

While the hub assembly 1156 may be assembled with the seal mount 1130 and permeable seal 1150 for coupling to the drug container 1118, the permeable seal 1150 and seal mount 1130 are slidably disposed relative to the hub assembly 1156. In order to allow this sliding, yet coupled relationship, the hub 1154 includes one or more resilient posts 1154*a* that present surfaces that interlock with a complimentarily disposed bore 1160 in the seal mount 1130. As shown in FIG. 181, the when assembled together, the cannula 1158 is disposed subjacent the membrane 1162 of the permeable seal 1150. In this way, the permeable seal 1150, the seal mount 1130 and the coupled hub assembly 1156 form an integrated fluid pathway connector 1122 that may be assembled into the distal end 1128 of the container 1118.

In order to further facilitate assembly of the fluid pathway connector 1122 to the container 1118, a cap 1151 may be provided. One or more gaskets 1133 may be provided between adjacent surfaces of the fluid pathway connector 1122 and, for example, the flange 1117 of the drug container 1118. One such gasket 1133 is illustrated in FIG. 181, although additional gaskets may be provided.

The needle insertion mechanism 1124 may be of any appropriate design, such as, for example, the needle insertion mechanism 1124 illustrated in FIG. 175. The cannula 1158 of the fluid pathway connector 1122 is fluidly connected to the needle 425 of the needle insertion mechanism 1124 by way of the fluid conduit 1126.

In this embodiment the fluid pathway connector 1122 and the needle insertion mechanism 1124 are coupled, for example by mechanical coupling, by way of complimentary threads 1134, 1135. In the illustrated embodiment, fluid pathway connector 1122, here, the hub 1154, includes external threads 1134, while the needle insertion mechanism 1124, here, a bore 436 of an extension 1137 of the insertion mechanism housing 1165, includes complimentary internal threads 1135. It will be appreciated that alternate arrangements are envisioned. For example, the threading arrangement could be reversed, the fluid pathway connector 1122 including internal threads and the needle insertion mechanism 1124 including external threads. Alternately, a threaded collar, or the like, could be provided to couple the components together.

Moreover, although the fluid pathway connector 1122 and the needle insertion mechanism 1124 are coupled in axial alignment in the fill-finish cartridge 1116 for the fill process, the components could be alternately disposed. For example, the axis of the needle insertion mechanism 1124 could be disposed at a right angle to the axis of the fluid pathway connector 1122 and the drug container 1118.

According to another aspect of the disclosure, the fill-finish cartridge 1116 provides controlled management of the fluid conduit 1126. In this embodiment, the threaded coupling of the needle insertion mechanism 1124 and the fluid pathway connector 1122 may provide controlled placement of the fluid conduit 1126. The uncoupled needle insertion mechanism 1124 and fluid pathway connector 1122 are illustrated in FIG. 184. As the needle insertion mechanism 1124 and the fluid pathway connector 1122 are threaded together to the positions illustrated in FIGS. 180 and 181, the fluid conduit 1126 winds about the housing 1165 of the needle insertion mechanism 1124. While the needle insertion mechanism 1124 and the fluid pathway connector 1122 are illustrated in a disassembled configuration with the fluid pathway connector 1122 being assembled to the container 1118 in FIG. 184, it will be appreciated that the components may be assembled in any order. For example, the needle insertion mechanism 1124 and the fluid pathway connector 1122 may be assembled together prior to coupling the fluid pathway connector 1122 to the container 1118 to form the fill-finish cartridge 1116.

Turning to the embodiment illustrated in FIGS. 185-187, the fill-finish cartridge 1216 illustrated is similar in operation to the fill-finish cartridge 1116 of FIGS. 180-184. The fill-finish cartridge 1216 of FIGS. 185-187 differs, however, in that the fluid pathway connector 1222 is coupled to the needle insertion mechanism 1224 by way of a snap connection 1238, the needle insertion mechanism 1224 and the fluid pathway connector 1222 including complementary structure that allow the components to snap together. For example, the housing 1265 of the needle insertion mechanism 1224 may include an extension 1237 having a recess or bore 1236, or female portion, adapted to receive a corresponding male portion 1234 of the fluid pathway connector 1222. In order to ensure axial alignment of the extension 1237 and male portion 1234, each may present one or more confronting shoulders. For example, the recess 1236 of the may include shoulders 1282, 1284 against which one or more outwardly extending shoulders 1283, 1285 of the fluid pathway connector 1222 seat. To facilitate connection, the hub 1254 of the fluid pathway connector 1222 may include one or more resilient fingers 586 extending from the hub 1254. During assembly, the fingers 586 may flex such that the shoulders 1283 may move generally radially inward as the fingers 586 are moved through the recess or bore 1236, and snap outward into engagement with shoulders 1282 when the fluid pathway connector 1222 and the needle insertion mechanism 1224 are in their final assembled axial positions. It will be appreciated, however, that the snap connection 1238 may have alternate structure as, for example if the fluid pathway connector 1222 included a shouldered recess and the needle insertion mechanism 1224 included mating outwardly extending shoulders.

As with the embodiment of FIGS. 180-184, the embodiment of FIGS. 185-187 allows for controlled management of fluid conduit 1226 fluidly connecting the fluid pathway connector 1222 and the needle insertion mechanism 1224. For example, the conduit may be wound around the periphery of the housing 1265 of needle insertion mechanism 1224, as illustrated in FIG. 187, before, after, or during the engagement of the snap connection 1238.

While a threaded connection has been described with regard to FIGS. 180-184, and a snap connection with regard to FIGS. 185-187, it will be appreciated that alternate mechanical connections may be utilized to provide sufficient structural integrity to the cartridge to facilitate filling the container in a conventional fill-finish process. For example, a tongue and groove type connection may be utilized. Alternately, or additionally, an external support, such as the bracket 880 of FIGS. 173-176 may be utilized, or the relative positions may be maintained by way of a carrier, such as the carrier 742 of FIGS. 167-170. Other mechanical coupling arrangements are likewise within the purview of the disclosure.

It will thus be appreciated that the inventive arrangement described herein provide varied designs of components that may be assembled in various configurations to provide various designs of fill-finish cartridges that may be sterilized and filled in conventional fill finish processes.

As a further benefit, because the embodiments of the present disclosure enable the manufacture of pre-filled infusion or injection pumps, these pumps may be configured to be single-use or reusable pumps. For example, the fluid pathway assemblies and/or fill-finish cartridge of the present disclosure may be configured to be cartridges which can be replaced within reusable pump devices.

Some embodiments of the present disclosure enable the drug container to be filled in a standard fill-finish process, without the need to expose the drug treatment to the sterilization environment or conditions. Some drug treatments, however, are capable of withstanding the sterilization conditions without degrading, losing efficacy, or the like. Accordingly, in at least one embodiment of the present disclosure, sterilization of the fluid pathway assembly and/or the fill-finish cartridge may occur after the components have been assembled and the drug container has been filled with a pharmaceutical treatment. This method of manufacturing, filling, and using the novel embodiments of the present disclosure still may provide the benefit of being adaptable to a standard fill-finish process. Additionally, this method enables drug delivery device manufacturers and fillers the benefit of only needing to sterilize the components of the fluid pathway (i.e., components which may come in contact with the drug fluid). The fill-finish cartridges, fluid pathway assemblies, and individual components of the present disclosure may be sterilized prior to their integration in a drug delivery device. As such, the other components of the drug delivery device which generally never contact the drug fluid do not need to be sterilized because of the advantages offered by the present disclosure. Accordingly, the embodiments of the present disclosure enable more complex geometries and more standard materials, for example, to be employed for the manufacture of advanced drug delivery devices.

The novel configurations of the fluid pathway assemblies and the fill-finish cartridges of the present disclosure may provide substantial benefits in the marketplace. Embodiments of the present disclosure can readily be manufactured in a sterile environment, integrated into standard drug filling (e.g., fill-finish) process lines for aseptic filling of pharmaceutical treatments, and utilized for cost-effective assembly into drug delivery devices. Each of these advantages has substantial benefits over existing methodologies.

For example, because the fluid pathway assemblies themselves can be sterilized and maintained in a sterile condition during the filling and device assembly processes, the resulting drug delivery device does not need to be sterilized after assembly (i.e., terminally sterilized). This avoids a number of known challenges faced by existing methodologies for the manufacture of drug delivery devices.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present disclosure enable the manufacture, assembly, and use of pre-filled drug delivery devices which maintain the sterility of the fluid pathway assembly through the various manufacturing steps.

Additionally, because the drug delivery devices which incorporate the novel embodiments of the present disclosure do not need to be terminally sterilized, the components of the devices may comprise of other, often less expensive, materials which would not normally withstand the sterilization environment. For example, less expensive plastics may be utilized for certain device components because they do not need to be sterilized after assembly.

In other words, the embodiments of the present disclosure may allow the manufacturer to sterilize only the components which will be in contact with the drug fluid and/or which are necessary to maintain sterile fluid pathways. These embodiments may also allow the pharmaceutical filler to maintain the sterility of these components during the filling and finishing steps associated with the assembly of the drug delivery devices. Similarly, drug delivery devices which incorporate the fluid pathway assemblies of the present disclosure may have smaller or more efficient geometries as the device does not have to be configured for sterilization after assembly.

Additionally, the embodiments of the present disclosure allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present disclosure enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner that preserves the sterility of the fluid pathway assembly. After mounting of the fluid pathway connector mechanism, the combined assembly can then be mated into a drug delivery device without requiring the remainder of the device components to be sterilized. Accordingly, embodiments of the present disclosure may provide novel components which enable the fluid pathway assemblies to be sterilized, assembled, filling, and incorporated into drug delivery devices in a cost-efficient and streamlined process.

Additionally, the fluid pathway assemblies of the present disclosure utilize materials that are substantially non-reactive with therapeutic fluids or drugs, and are suitable for use in pharmaceutical grade applications. The novel fluid pathway assemblies and fill-finish cartridges are configured to minimize or eliminate the possibility of contact or interaction between degradable materials, such as certain plastics, with the therapeutic fluids or drugs. The fluid pathway assemblies, with adaptable needle injection and retraction mechanisms, also may provide fluid conduits from the drug container to the patient, through the needle or cannula, which are substantially absent of degradable materials. Such configurations, when integrated into the fill-finish cartridges or drug delivery devices, may provide increased stability and shelf-life parameters to the drug and drug delivery devices. These characteristics are thought to be highly desirable for generally all pharmaceutical treatments, but perhaps especially of value in drug delivery devices for use with biologics and other complex therapies.

One or more embodiments of the present disclosure may further include certain standard components. For example, the fill-finish cartridge configurations and drug delivery devices of the present disclosure may include one or more membranes. In at least one embodiment, one or more permeable membranes are employed to seal the drug container and/or to ensure a sterile environment and container integrity within the drug chamber. Similarly, the drug container may include a flange. The flange may be pre-formed along any portion of the container, or may be a separate component that is connected to or affixed to the container. In at least one embodiment, the flange is a removable connected component that is connected at the proximal end of the drug container. The flange may be configured to allow the fill-finish cartridge and drug container to rest within a fill-finish tray, for filling with a pharmaceutical compound within a standard fill-finish process. The position, shape, number, and materials for such components may vary, as would be readily appreciated by a skilled artisan, to meet any number of desired characteristics.

Similarly, while the components of the fill-finish cartridge and the fluid pathway assembly are described herein as separate components, it is within the contemplation of the present disclosure that certain groups of these components may be combined to form a single component capable of performing the functions of the individual components. In at least one embodiment the needle insertion and needle retraction mechanisms may be one unified component that may provide a dual function. Additionally, as would be appreciated by one having ordinary skill in the art, the components of the devices may be manufactured as individual components or as single components. For example, the flange may be a component that is pre-formed, during the manufacturing process, as a part of the drug container itself. Accordingly, in at least one embodiment, the flange may be a glass flange extension of the container. Furthermore, while the components of the fill-finish cartridge and fluid pathway assembly are described herein as separate components, they may be unified components having multiple functions. The configuration of the components and their assembly may vary based on the assembly process, the device parameters, and other desired characteristics.

Embodiments of the present disclosure may provide fluid pathway assemblies, fill-finish cartridges, methods of manufacturing such cartridges, and their methods of use. The fill-finish cartridges and fluid pathway assemblies may be utilized in a number of different configurations and may themselves comprise of one or more components. Such modifications are contemplated by and encompassed in the embodiments of the present disclosure. Other components may similarly be single components, unified components, or multi-purpose components, as described in the embodiments discussed above. Thus, it is intended that the present disclosure covers the modifications and variations of this disclosure, provided they come within the scope of the appended claims and their equivalents.

XXII. Temperature Control System

At least some of the drug delivery devices described in this application, including at least those described in connection with FIGS. 1A-187 may be configured to incorporate the embodiments of the temperature control system described below in connection with FIG. 188, where appropriate.

For some drugs, temperature is an important consideration both during and prior to patient delivery. Biologic drugs, for example, oftentimes require refrigeration or frozen storage prior to patient delivery. While cold temperatures may help extend the shelf life of the drug, they can result in an increased viscosity of the drug. A more viscous drug may take longer to inject and/or require additional injection force. Furthermore, injecting a cold drug can be uncomfortable, and potentially even painful, for some patients. Therefore, a drug which has been stored in a cold state usually is allowed to warm to near room temperature prior to patient delivery. This warming up period can take upwards of 30 minutes, which can be inconvenient to the patient and consequently have an adverse impact on patient compliance rates.

The drug delivery devices of the present disclosure can be configured to include a temperature control system for monitoring and/or controlling the temperature of the drug within the device. One embodiment of a drug delivery device, denoted by reference numeral 11010, incorporating a temperature control system 11600 according to principles of the present disclosure is illustrated by FIG. 188. While the temperature control system 11600 is described in conjunction with particular elements and features of the drug delivery device 11010, the temperature control system 11600 can be implemented, where appropriate, in any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020. Various elements of the drug delivery device 11010 are similar in structure and/or function to those previously described in connection with the drug delivery device 10. These elements are assigned reference numbers similar to those previously provided with the addition of the two-digit prefix "11," and, for the sake of brevity, are not described in detail below. For example, the drug delivery device 11010 includes a needle insertion mechanism 11200 which bears at least some similarities in structure and/or function to the needle insertion mechanism 200 of the drug delivery device 10. It should be noted, however, that the temperature control system 11600 is not limited to being used in conjunction with elements of the drug delivery device 10, and can be implemented in any one of the drug delivery devices disclosed herein, where appropriate.

Turning to FIG. 188, the drug delivery device 11600 may include a start button 11014, a drug container 11050, a drive mechanism 11100, a needle insertion mechanism 11200, a fluid pathway connector 11300, a power and control system 11400, and a temperature control system 11600. The drug container 11050 may include a barrel 11058 and a plunger seal 11060 moveable through the barrel 11058 to discharge a drug from the barrel 11058, and a pierceable seal (not illustrated) controlling access to an interior of the barrel 11058. The drive mechanism 11100 may include a drive housing 11130, a piston 11110 moveable relative to the drive housing 11130 and configured to impart movement to the plunger seal 11060, and a piston biasing member 11106 disposed between the drive housing 11130 and the piston 11110. The fluid pathway connector 11300 may define a sterile fluid flowpath between the drug container 11050 and the insertion mechanism 11200. The fluid pathway connector 11300 may include a connection hub 11310, a tubular conduit 11030 providing fluid communication between the connection hub 11310 and the insertion mechanism 11200, and a piercing member (not illustrated) configured to pierce the pierceable seal to establish fluid communication between the between the barrel 11058 and the tubular conduit 11030 during drug delivery.

The tubular conduit 11030 may include a first flexible tube 11032, a second flexible tube 11034, and a rigid tube 11036 connected and providing fluid communication between the first and second flexible tubes 11032 and 11034. The first flexible tube 11032 may fluidly connect the connection hub 11310 with a proximal end 11037 of the rigid tube 11036, and the second flexible tube 11032 may fluidly connect the needle insertion mechanism 11200 with a distal end 11038 of the rigid tube 11036. The first and second flexible tubes 11032 and 11034 each may be made of a material that is more flexible than the material used to construct the rigid tube 11036. In at least one embodiment, the first and second flexible tubes 11032, 11034 are made of a polymeric material, and the rigid tube 11036 is made of metal. As described below, the material used to construct the rigid tube 11036 may possess a relatively high thermal conductivity such that heat can be transferred from a heating element to a drug flowing through the rigid tube 11036 during delivery.

An inner diameter of the rigid tube 11036 may be less than an inner diameter of the first flexible tube 11032 and/or the second flexible tube 11034. Accordingly, the rigid tube 11036 may serve as a flow restrictor that reduces and/or regulates the flow rate of the drug during delivery. The rigid tube 11036 may be replaced with other rigid tubes having different inner diameters depending on the target flow rate. Furthermore, the inclusion of a flow restrictor may provide broadened design space when coupled with other contributing elements such as a drive spring. In an alternative embodiment, the rigid tube 11036 may have an inner diameter that is equal to that of the first flexible tube 11032 and/or the second flexible tube 11034.

Still referring to FIG. 188, the temperature control system 11600 may include a heating element 11602, a first temperature sensor 11604, and a second temperature sensor 11606. In the illustrated embodiment, the heating element 11602 includes an electrically-conductive coil that is wrapped around and contacts an exterior of the rigid tube 10036. The heating element 11602 may be electrically connected to the power and control system 11400, such that the heating element 11602 is supplied with electricity from the power and control system 11400 in a controlled manner. The impedance of the material used to construct the heating element 11602 may cause the heating element 11602 to convert at least some of the electricity it is supplied with into heat. Due to the contact or close proximity of the heating element 11602 to the rigid tube 11036, the heat generated by the heating element 11602 may warm the rigid tube 11036, and due to the thermal conductivity of the rigid tube 11036, warm a drug flowing through the rigid tube 11036.

The inclusion of the heating element 11602 may eliminate the need for a pre-delivery warming period in the case where the drug delivery device 11010 has been removed from cold storage. Furthermore, heat transfer from the heating element 11602 to the drug may be relatively efficient, because the volume of drug per unit length of the rigid tube 11036 is relatively small. Therefore, it may be possible to warm the drug to a target temperature without reducing the flow rate or increasing the length of the flow path. Accordingly, it may be possible to heat the drug during delivery without altering the duration of delivery. Moreover, the heating element 11602 can be installed with little or no modifications to a pre-existing fluid pathway connector, thereby reducing manufacturing and/or design costs.

In some embodiments, the heating element 11602 may be dynamically controlled based on real-time drug temperature measurements to ensure that the drug is delivered to the patient at a desired temperature. As shown in FIG. 77, the first temperature sensor 11604 may be connected to the proximal end 11037 of the rigid tube 11036 so that the first temperature sensor 11604 can measure the temperature of the drug flowing into the rigid tube 11036. The second temperature sensor 11606 may be connected to the distal end 11038 of the rigid tube 11036 so that the second temperature sensor 11606 can measure the temperature of the drug flowing out of the rigid tube 11036. In some embodiments, the first and second temperature sensors 11604 and 11606 may not directly measure the temperature of the drug. Rather, the first and second temperatures sensors 11604 and 11060 may measure the temperature of, respectively, the inlet and outlet portions of the rigid tube 11036 (or other portions of the drug delivery device proximate to the drug). These temperatures measurements could be used to extrapolate the temperature of the drug based on heat transfer characteristics of the material used to construct the rigid tube 11036 (or the other portions of the drug delivery device proximate to the drug).

The first and second temperature sensors 11604 and 11606 may be output their temperature measurements to the power and control system 11400, which may analyze the temperature measurements to determine an amount of electricity that must be supplied to the heating element 11602 to achieve a target drug temperature. Additionally, the temperature measurements of the first and second temperature sensors 11604 and 11606 may be analyzed by the power and control system 11400 according to thermal dilution techniques in order to determine the flow rate of the drug. Furthermore, in an embodiment where the drug delivery device incorporates a motor-controlled regulating mechanism to control the expansion of the piston biasing member (e.g., akin to the drug delivery device 6010 or 8000), the power and control system 11400 may control the motor (e.g., the motor 6207 or any other motor described herein) based on the output of the first and second temperature sensors 11604 and 11606 to reduce the flow rate if the drug has not been sufficiently warmed by the heating element 11602, so that the patient does not experience a painful injection due to cold temperatures. Furthermore, input from the first and second temperature sensors 11604 and 11606 may be used to determine if the drug has been overheated by the heating element 11602 and therefore no longer suitable for injection, in which case the drive mechanism 11100 may be locked out. Additional temperature sensors may be included to monitor the temperature of the drug in the container during, for example, storage to determine if the drug has been stored at an appropriate temperature. If not, the power and control system 11400 may lockout the device and/or alert the patient that the drug is no longer viable.

The temperature control system 11600 may additionally include temperature indicators (e.g., lights, sounds, graphical displays, etc.) or other output devices for informing the user of the drug temperature and/or whether the drug temperature is suitable for injection.

While the embodiment of the tubular conduit illustrated in FIG. 188 incorporates two flexible tubes and a rigid tube connected therebetween, alternative embodiments may forgo the rigid tube so that the tubular conduit is formed by a single, unitary flexible tube. In such an embodiment, the heating element 11602 may be wrapped around the single, unitary flexible tube.

In one alternative embodiment, the power and control system 11400 may serve as the heating element 11602, or as a supplemental heating element. The power and control system 11400 may include a circuit board and/or other electronics that heat up while performing their data processing functions. By positioning the circuit board and/or other electronics immediately adjacent to the tubular conduit 11030 (e.g., immediately above the tubular conduit 11030), the heat generated by the circuit board and/or other electronics can be used to warm the drug as it flows through the tubular conduit 11030. Also, in some embodiments, it may be desirable that the heat generated by the power and control system 11400 is not permitted to warm the drug. In such embodiments, the power and control system 11400 may include a heat sink that is remote from the drug container, the fluid pathway connector, and/or the insertion mechanism, so that the heat sink can draw heat away from regions of the drug delivery device including the drug.

While the heating element 11602 described above generates heat primarily through electrical resistance, other embodiments of the heating element may generate heat through other means, including, but not limited to, induction, the Peltier effect, and/or a chemical reaction.

Furthermore, other embodiments of the temperature control system 11600 may include a cooling system (not illustrated) for lowering the temperature of the drug while it is disposed in the container 11050 and/or flows through the tubular conduit 11030. Such a cooling system may employ a fan which draws in cool air from outside the drug delivery device and/or expels warm air from inside the drug delivery device. Alternatively, or additionally, the cooling system may employ the following to reduce the temperature of the drug: a thermoelectric cooling element the exploits the Peltier effect and/or a chemical reaction.

XXIII. Skin Attachment

At least some of the drug delivery devices described in this application, including at least those described in connection with FIGS. 1A-188 may be configured to incorporate the embodiments of the skin attachment members described below in connection with FIG. 189A-194C, where appropriate.

The drug delivery devices of the present disclosure may be configured for temporary attachment to a patient's body tissue (e.g., the patient's skin) while the drug is delivered. The drug delivery device may be attached to the tissue of the patient's abdomen, thigh, arm or some other portion of the patient's body. As described above, an adhesive patch (e.g., the adhesive patch 26) may be disposed on or over a base of the housing to adhere the drug delivery device to the patient's body tissue. The adhesive surface of the adhesive patch may initially be covered by a non-adhesive patch liner (e.g., the non-adhesive patch liner 28), which is removed from the adhesive patch 26 prior to placement of the drug delivery device in contact with the patient's body tissue.

Disengaging the adhesive from the patient's body tissue may cause to patient discomfort, particularly if the adhesive engages a large surface area of the patient's body tissue. Therefore, to reduce the amount of body tissue in contact with adhesive, only a limited portion of drug delivery device's base may be covered with adhesive. FIGS. 189A and 189B illustrate, respectively, adhesive patches 12000 and 12100 which reduce the amount body tissue in contact with adhesive, yet still provide adequate adhesion to secure the drug delivery device to the patient's body tissue during drug delivery. The adhesive patches 12000 and 12100 each may be applied to the base of any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020.

FIG. 189A shows that the adhesive patch 12000 includes a pattern of adhesive dots 12002 with non-adhesive regions 12004 located therebetween. The illustrated pattern is symmetric and includes equally-spaced rows and columns of circular adhesive dots 12202. Alternative embodiments may have a non-symmetric pattern and/or non-circular adhesive dots. The adhesive patch 12000 includes a base 12006 having a first side (not illustrated) for attachment to the drug delivery device and an opposite second side 12006 including the pattern of adhesive dots 12002. In alternative embodiments, the base 12006 may be omitted, and the pattern of adhesive dots 12002 may be applied directly to an exterior surface of the drug delivery device.

Instead of adhesive dots, the adhesive patch 12100 shown in FIG. 189B includes a plurality of adhesive strips 12102, with non-adhesive regions 12104 located therebetween. The adhesive strips 12102 are equally-spaced and extend lengthwise across the adhesive patch 12100. Alternative embodiments may have non-linear (e.g., curved) adhesive strips and/or the adhesive strips may extend widthwise across the adhesive patch 12100. The adhesive patch 12100 includes a base 12106 having a first side (not illustrated) for attachment to the drug delivery device and an opposite second side 12106 including the adhesive strips 12102. In alternative embodiments, the base 12106 may be omitted, and the pattern of adhesive strips 12102 may be applied directly to an exterior surface of the drug delivery device. A non-adhesive patch liner (e.g., the non-adhesive patch liner 28) may be used to cover the adhesive sides of each of the adhesive patches 12100 and 12200 prior to use.

FIG. 190 illustrates an embodiment of a non-adhesive patch liner, denoted by reference numeral 12300, including stiffening members 12310 for imparting rigidity to the non-adhesive patch liner 12300 as well as an adhesive patch (e.g., the adhesive patch 28, 12100, or 12200) covered by the non-adhesive patch liner 12300. A body 12312 of the non-adhesive patch liner 12300 may be co-extensive with the adhesive patch to prevent unintended adhesion prior to use of the drug delivery device. The stiffening members 12310 may each be made of a more rigid material (e.g., metal or hardened plastic) than the body 12312 of the non-adhesive patch liner 12300. Additionally, as shown in FIG. 190, each of the stiffening members 12310 may have a tapered shape, with a width that narrows as the stiffening member 12310 approaches the outer peripheral edge of the body 12312. The rigidity imparted by the stiffening members 12300 to the outer peripheral edge of the adhesive patch, which may extend beyond the outer edge of the body of the drug delivery 12340 device as shown in FIG. 190, renders the outer peripheral edge of the adhesive patch less likely to experience curling. Accordingly, the stiffening members 12310 may help the adhesive patch retain its planar shape so that the patient can press the adhesive patch flushly against the patient's body tissue upon removal of the non-adhesive patch liner 12300.

While the embodiment of the non-adhesive patch liner illustrated in FIG. 190 includes stiffening members located at discrete points around the periphery of the non-adhesive patch liner, other embodiments of the non-adhesive patch liner may include a stiffening member that extends continuously around the periphery of the non-adhesive patch liner. FIG. 191A illustrates an exploded assembly view of a non-adhesive patch liner 12400, an adhesive patch 12500, and a base 12600 of a drug delivery device. The adhesive patch 12500 may be similar to one of the adhesive patches disclosed herein, including, but not limited to, any one of the adhesive patches 28, 12100, or 12200. The non-adhesive patch liner 12400 may include a central body portion 12402 and a ring-shaped stiffening portion 12404 positioned around the periphery of the central body portion 12402 (as seen in the assembled view shown in FIG. 191B). The central body portion 12402 may cover a central portion of the adhesive patch 12500, leaving an outer peripheral edge of the adhesive patch 12500 exposed. The ring-shaped stiffening portion 12404 may be used to cover this exposed outer peripheral edge of the adhesive patch 12500, thereby preventing it from curling. In some embodiments, the ring-shaped stiffening portion 12404 may cover and contact each of: an outer peripheral edge of the central body portion 12402, an outer peripheral edge of the adhesive patch 12500, and a portion of the base 12600 of the drug delivery device surrounding the adhesive patch 12500. In such an embodiment, the underside of the ring-shaped stiffening portion 12404 may be include an adhesive for adhering the ring-shaped stiffening portion 12404 directly to the base 12600 of the drug delivery device and the central body portion 12402. As such, removing the central body portion 12402 (e.g., by pulling a tab extending from the central body 12402) may disengage the ring-shaped stiffening portion 12404 from the base 12600 of the drug delivery device as well as the adhesive patch 12500.

While the stiffening members described above may be attached to or integrally formed with the non-adhesive patch liner, alternative embodiments of the stiffening members may be attached to or integrally formed with the adhesive patch. FIG. 192 illustrates a drug delivery device 12710 (which may correspond to any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020) including a housing 12712, an adhesive patch 12726 attached to the underside of the housing 12712, and a non-adhesive patch liner 12728 removably attached to the underside of the adhesive patch 12726.

The adhesive patch 12726 may include a base 12730 and a plurality of stiffening members 12732. The base 12730 may have an upper surface 12734 rigidly attached to the underside of the housing 12712 and a lower surface (hidden in FIG. 192) covered with a skin adhesive. The base 12730 may have a larger footprint than the housing 12712 such that an outer peripheral portion 12736 of the base 12730 forms a skirt that extends beyond the outer edge of the housing 12712.

Still referring to FIG. 192, the stiffening members 12732 may be formed in the outer peripheral portion 12736 of the base 12730. In the illustrated embodiment, the stiffening members 12732 and the base 12730 are integrally formed such that the stiffening members 12732 and the base 12730 form a single, unitary structure made of a single material. Alternatively, the stiffening members 12732 may be distinct structures from the base 12730. As illustrated in FIG. 192, the stiffening members 12732 may be designed as a plurality of equally spaced ribs located at discrete locations around the periphery of the base 12730. Furthermore, the stiffening members 12732 may protrude upwardly from the upper surface 12734 of the outer peripheral portion 12736 of the base 12730. Nevertheless, the height of the stiffening members 12732 may be such that the tops of the stiffening members 12732 are located below the bottom surface of the housing 12712.

The stiffening members 12732 may impart rigidity to the adhesive patch 12726 so that the adhesive patch 12726 can retain its generally planar shape. Accordingly, the periphery of the adhesive patch 12726 is less likely to fold over on itself, or experience, curling when the drug delivery device 12710 is being applied to the patient's skin or when the non-adhesive patch liner 12728 is being removed.

Referring to FIG. 193, in at least one embodiment, the non-adhesive patch liner 12728 may be comprised of separate first and second sections 12740 and 12742 covering respective portions of the underside of the adhesive patch 12726. The first section 12740 may have a first tab 12744 which protrudes outwardly from a side of the adhesive patch 12726, and the second section 12742 may have a second tab 12746 which protrudes outwardly from an opposite side of the adhesive patch 12726. The first and second sections 12740 and 12742 may be removed separately by pulling, respectively, on the first and second tabs 12744 and 12746, as described below with reference to FIGS. 192A-8192C.

In at least one embodiment, the process of attaching the drug delivery device 12710 to the patient's skin 12750 may involve the following steps. Initially, the non-adhesive patch liner 12728 may be disposed against the patient's skin 12750. Next, while the user or patient pushes down on a first end 12752 of the housing 12712 (opposite to the first tab 12744), the first tab 12744 may be pulled outwardly to remove the first section 12740 of the non-adhesive patch liner 12728 from the adhesive patch 12726, as illustrated in FIG. 192A. Subsequently, while the user or patient pushes down on a second end 12754 of the housing 12712 (opposite to the second tab 12746), the second tab 12746 may be pulled outwardly to remove the second section 12742 of the non-adhesive patch liner 12728 from the adhesive patch 12726, as seen in FIG. 192B. This will result in the adhesive patch 12726 being flush with the patient's skin 12750, as shown in FIG. 192C.

In some embodiments, such as the one illustrated in FIGS. 192A-192C, the first tab 12744 may be formed by a portion of the first section 12740 of the non-adhesive patch liner 12728 that is folded back on itself. More particularly, the first section 12740 may have a first end 12760 in contact with the adhesive patch 12726 and a second end 12762 folded over the first end 12760 and configured to initially contact the patient's skin 12750. The second end 12762 may include the first tab 12744. By pulling the first tab 12744 outwardly, the first end 12760 of the first section 12740 may unroll such that it is peeled away from the adhesive patch 12726. This configuration of the first section 12740 of the non-adhesive patch liner 12728 may facilitate the removal of the first section 12740 from the adhesive patch 12726 despite the drug delivery device 12710 being push against the patient's skin 12750, as shown in FIG. 192A.

Similarly, the second tab 12746 may be formed a portion of the second section 12742 of the non-adhesive patch liner 12728 that is folded back on itself. More particularly, the second section 12742 may have a first end 12770 in contact with the adhesive patch 12726 and a second end 12772 folded over the first end 12770 and configured to initially contact the patient's skin 12750. The second end 12772 may include the second tab 12746. By pulling the second tab 12746 outwardly, the second end 12770 of the second section 12746 may unroll such that it is peeled away from the adhesive patch 12726. Like the first section 12740, this configuration of the second section 12742 of the non-adhesive patch liner 12728 may facilitate the removal of the second section 12742 from the adhesive patch 12728 despite the drug delivery device 12710 being push against the patient's skin 12750, as shown in FIG. 192B.

Attachment of the drug delivery devices disclosed herein to the patient's body tissue is not limited to adhesive means. Instead of an adhesive patch, or as a supplement to an adhesive patch, the drug delivery device may incorporate a pneumatic system for temporarily attaching the drug delivery device to the patient's body tissue. Such a pneumatic system may include at least one pressure communication channel or aperture which extends through a base of the drug delivery device and distributes a negative fluid pressure across the base that draws body tissue against the base. Embodiments of such adhesive and/or pneumatic systems for temporarily attaching a drug delivery device to body tissue are described in U.S. Provisional Patent Application No. 62/117,420 entitled "DRUG DELIVERY DEVICE WITH VACUUM ASSISTED SECUREMENT AND/OR FEEDBACK", which is hereby incorporated by reference in its entirety for all purposes. Any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020, may be configured to incorporate one or more of the embodiments of the adhesive and/or pneumatic systems for temporarily attaching a drug delivery device to body tissue as described in U.S. Provisional Patent Application No. 62/117,420.

In yet still further embodiments, the drug delivery devices disclosed herein may be temporarily attached to a patient's soft body tissue by way of a mechanism (e.g., a strap) that clamps or squeezes the drug delivery device between the patient's soft body tissue and bones or other more rigid anatomical structures behind the soft body tissue.

XIV. Connectivity Aspects

At least some of the drug delivery devices described in this application, including at least those described in connection with FIGS. 1A-194C may be configured to incorporate and/or communicate with the embodiments of the data processing system described below in connection with FIG. 195, where appropriate.

The drug delivery devices of the present disclosure may be configured to include various data processing functionalities and/or operate within various data processing networks. Embodiments of such data processing functionalities and networks related to drug delivery devices are disclosed in International Patent Application Publication No. WO/2015/187793, International Patent Application Publication No. WO/2015/187797, International Patent Application Publication No. WO/2015/187799, International Patent Application Publication No. WO/2015/187802, and International Patent Application Publication No. WO/2015/187805, each of which is hereby incorporated by reference in its entirety for all purposes. Any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020, may be configured to incorporate one or more of the data processing functionalities and/or operate within one or more of the data processing networks disclosed in International Patent Application Publication No. WO/2015/187793, International Patent Application Publication No. WO/2015/187797, International Patent Application Publication No. WO/2015/187799, International Patent Application Publication No. WO/2015/187802, and International Patent Application Publication No. WO/2015/187805.

The presently-disclosed drug delivery devices, or data processing systems in communication with the presently-disclosed drug delivery devices, may be configured to determine of one or more states of the drug delivery device, which states may be determined through the use of one or more sensors in combination with one or more controllers. The sensors may rely on mechanical, electrical or chemical sensing mechanisms, and the controllers may be mechanical, electrical, and/or electro-mechanical. By way of example and not by way of limitation, the states may relate to the operation of the drug delivery device, and/or to the condition of the drug delivery device. The drug delivery device, or data processing system in communication with the drug delivery device, may use the state determination to control the operation of the drug delivery device, and/or may communicate the state determination to other devices, such as third-party servers that may collect, process, and/or further disseminate the state determinations received from the drug delivery device. In at least one embodiment, the drug delivery device may communicate the state determination to one or more local computing devices, such as a mobile computing device (e.g., smartphone, smartwatch, tablet, laptop, etc.).

In at least one embodiment, a drug delivery device according to the present disclosure may communicate data related to the device or the patient to a social support network. For example, the drug delivery device may monitor a patient's use of the device with sensors or other means, and link the patient to a support group who can encourage the patient to comply with a treatment regimen (e.g., a therapeutic regimen). In this way, the drug delivery device may leverage the capabilities of social networking services (e.g., Facebook, Twitter, etc.) to identify a support group whose advice the patient is likely to follow, thereby increasing the likelihood of the patient's compliance with his or her treatment regimen.

FIG. 195 illustrates an embodiment of a data processing network 13000 in communication with a drug delivery device 13100 corresponding to any one of the other drug delivery device disclosed herein (including, but not limited to, any one of the drug delivery devices 10, 910, 6010, 8000, 9010, 9210, 9310, 9410, 9510, 9610, 11600, 12340, 12710, 11010, 13100, 19010, or 19020). The drug delivery device 13100 is associated with a patient 13102 who may use the drug delivery device 13100 to inject a drug as part of a treatment regime. The drug delivery device 13100 may communicate with a server 13104 via one or more intermediate computing devices and/or one or more networks. In turn, the server 13104 may communicate with the drug delivery device 13100, the patient 13102, and one or more computing devices (with their associated parties) via one or more intermediate computing devices and/or one or more networks. As is also illustrated in FIG. 195, the server 13104 may communicate directly and/or wirelessly with the wearable drug delivery device 13100, using a 4G antenna for example.

Still referring to FIG. 195, the drug delivery device 13100 is illustrated as communicating with a mobile computing device 13110 (e.g., a smartphone) via a first communication link 13112, and with a computing device (e.g., a personal computer or dedicated hub) 13114 via a second communication link 13116. Both links 13112 and 13116 may operate according to a near field communication protocol, such as Bluetooth, for example. The mobile computing device 13110 may communicate with a cellular network 13118 via a communication link 13120, while the computing device 13114 may communicate with a hard-wired network (e.g., local area network or wide area network) 13122 via a communication link 13124. These networks 13118 and 122 may also communicate with the server 13104.

The networks 13118 and 13122 may facilitate communication between the server 13104 and one or more parties associated with the patient 13102, such as his or her caregiver 13130, support giver 13132, and healthcare provider 13134, via their mobile computing devices (e.g., smartphones). The server 13104 may also be in communication with one or more computing devices (e.g., servers) associated with one or more additional parties associated with the patient 13102. For example, a healthcare system server 13140, a payment server 13142, a pharmacy server 13144, a distributor server 13146, and a governmental agency server 13148 are illustrated in communication with the server 13104 via the network 13122. It will also be recognized that the networks 13118 and 13122 may be in communication with each other.

In at least one embodiment, the mobile computing device 13110 may include a processor (e.g., microprocessor) and a memory (e.g., a random access memory (RAM), a non-volatile memory such as a hard disk, a flash memory, a removable memory, a non-removable memory, etc.) for storing computer-executable instructions to be executed by the processor. In some embodiments, the computer-executable instructions may be included in a software application (e.g., a mobile software application, also commonly referred to as a "mobile app") stored in the memory of the mobile computing device 13110. The software application may be installed on the mobile computing device 13110 as one or more downloaded files, such as an executable package installation file downloaded from a suitable application store via a connection to the Internet. Examples of package download files may include downloads via the iTunes store, the Google Play Store, the Windows Phone Store, downloading a package installation file from another computing device, etc. The software application may be developed for a mobile operating system such as Android™ or iOS®, developed by Google and Apple, respectively. In some embodiments, the application may be initiated by a user selecting an icon shown on a home screen of a display (e.g., a touchscreen) of the mobile computing device 13110. Various displays, including those having informational prompts and/or instructional prompts similar to those shown in the figures of International Patent Application Publication No. WO/2015/187797, may be generated in the software application and displayed to a user and/or patient via the display of the mobile computing device 13110.

XXV. Energy Management

At least some of the drug delivery devices described in this application, including at least those described in connection with FIGS. 1A-195 may be configured to incorporate the embodiments of the energy management mechanisms described below in connection with FIG. 196A-200, where appropriate.

As described above, the drug delivery devices of the present disclosure may incorporate a drive mechanism including one or more springs to provide energy for moving a plunger seal to expel a drug from a container. The use of springs can offer benefits of simplicity and low cost, but can have certain limitations.

There is a linear relationship between force and displacement in spring actuators. To provide sufficient energy for drug delivery at the end of the stroke of the plunger seal, an excessive amount of energy may be input to the system as drug delivery commences.

Further, as higher viscosity drugs are delivered via drug delivery devices, requisite spring forces can increase. Springs with higher spring constants transmit more force to the drug product and container. Because kinetic energy is proportional to velocity squared, even incremental increases in the spring constant can result in large changes in the net kinetic energy applied to the drug and container.

The patient may feel this excessive energy as a "slap" or similar physical "bump", as the spring-driven piston impacts the plunger seal of the container storing the drug. It is known that such mechanical bumps can also be distracting or disturbing to users of the injectors and can therefore prevent proper dose completion. It is therefore desirable to eliminate such disturbances.

Accordingly, a need exists for a drug delivery device with an energy management system which can maintain the intended spring force load of the drive mechanism while reducing the transmitted force and resultant energy to the drug product, thereby reducing the potential for structural damage to the container or other components of the drug delivery device. Such a drug delivery device may be potentially more comfortable and safer to use, and applicable to a greater range of drugs.

The drug delivery devices of the present disclosure may be configured to include an energy management system that maintains the intended spring force load of the drive mechanism while reducing the transmitted force and resultant energy to the drug product. Embodiments of such energy management systems are disclosed in International Patent Application No. PCT/US15/29485 entitled "AUTOINJECTOR WITH SHOCK REDUCING ELEMENTS" and International Patent Application Publication No. WO/2016/003813, International Patent Application Publication No. WO/2015/187799, each of which is hereby incorporated by reference in its entirety for all purposes. Any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020, may be configured to incorporate one or more of aspects, features, and/or functionalities of the energy management systems disclosed in International Patent Application No. PCT/US15/29485 and International Patent Application Publication No. WO/2015/187799.

FIGS. 196A-196C, 197A-197C, and 198A-198C illustrate, respectively, assemblies 14000a, 14000b, 14000c, each of which includes a drug container 14050 (which may correspond to, but is not limited to, any one of the container 50, 350, 618, 718, 818, 918, 1050, 6050, 8050, or 9050), a drive mechanism 14100 (which may correspond to, but is not limited to, any one of the drive mechanism 100, 130, 1100, 2100, 6100, 8100, 8130 11100, 14100, 23090, or 90100), a fluid pathway connector 14300 (which may correspond to, but is not limited to, any one of the fluid pathway connector 300, 622, 722, 822, 922, 1122, 1222, 1300, 2300, 8300, 18300, 23030, 90300 182300, 230330, or 230130), and a drive damper mechanism 14170a, 14170b, or 14170c that functions as an energy management system. The assemblies 14000a, 14000b, and 14000c each may be implemented in any one of the drug delivery devices disclosed herein, including, but not limited to, any one of the drug delivery devices 10, 910, 6010, 8000, 9010, 9210, 9310, 9410, 9510, 9610, 11600, 12340, 12710, 11010, 13100, 19010, or 19020.

The drug container 14050 may include a barrel 14058 and a plunger seal 14060 moveable through the barrel 14058 to discharge a drug 14038 from the barrel 14058, and a pierceable seal (not illustrated) controlling access to an interior of the barrel 14058. The drive mechanism 14100 may include a drive housing 14130, a piston 14110 moveable relative to the drive housing 14130 and configured to impart movement to the plunger seal 14060, and a piston biasing member 14106 disposed between the drive housing 14130 and the piston 14110. The piston 14110 may include a head member 14148 disposed at its distal end.

The drive damper mechanism 14170 reduces the velocity of the piston 14110 while retaining the intended force of the drive mechanism 14100, before the piston 14110 begins to move the plunger seal 14060 distally through the barrel 14058. By reducing the velocity of the piston 14110, the damper mechanism 14170 essentially operates as a shock reducing element, as it reduces the kinetic energy applied to the drug 14038 and the drug container 14050. The damper mechanism 14170 can be adapted to reduce the velocity of the piston 14110 to ensure that pressure delivered to the system does not induce syringe breakage, pressure delivered to the system prevents appreciable "slap" or discomfort to the patient, and/or pressure delivered to the drug 14038 prevents shear forces from damaging the drug 14038.

In some embodiments, the drive damper mechanism can be adapted to reduce the velocity of the piston by less than 1%. In other embodiments, the drive damper mechanism can be adapted to reduce the velocity of the piston by about 1-5%. In further embodiments, the drive damper mechanism can be adapted to reduce the velocity of the piston by about 5-10%. In further embodiments, the drive damper mechanism can be adapted to reduce the velocity of the piston by about 10-15%. In further embodiments, the drive damper mechanism can be adapted to reduce the velocity of the piston by about 15-20%. In further embodiments, the drive damper mechanism can be adapted to reduce the velocity of the piston by about 20-30%. In still further embodiments, the drive damper mechanism can be adapted to reduce the velocity of the piston by about 30-50%. In yet further embodiments, the drive damper mechanism can be adapted to reduce the velocity of the piston by about 51%-100%. The reduction in velocity provided by the drive damper mechanism can be selected to prevent a physical disturbance and/or discomfort to the patient by preventing appreciable "slap", and/or reduce breakage of the drug storage device, and/or reduce drug product damage caused by shear load, and/or allow the injection device to be used for injecting drugs with higher viscosities.

As shown in FIGS. 196A-196C, the damper mechanism 14170 can be disposed inline between the plunger seal 14060 of the drug container 14050 and the plunger head 14148 of the piston 14110 to minimize the size of the assembly 14000a and to more effectively damp the motion of piston 14110 at the plunger head/stopper interface. In other embodiments, as shown in FIGS. 197A-8197C, the drive damper mechanism can be disposed inline between the proximal end of the piston 14110 of the drive mechanism and the main housing of the drug delivery device. In further embodiments, the drive damper mechanism can be integrated into the piston.

In accordance with various embodiments of the assembly 14000a, the damper mechanism 14170 may comprise a dashpot. The dashpot uses viscous friction to resist the motion of the piston 14110, thereby reducing the velocity of the piston 14110. FIGS. 196A-196C depict an exemplary embodiment of a linear dashpot 14172 that can be used in the assembly 14000a. As shown, the linear dashpot 14172 includes a drive damping mechanism housing 14174, a working fluid 14178 contained inside the housing 14174, and a piston assembly 14176 movably disposed within the housing 14174. The housing 14174 can comprise a cylindrical sidewall 14174sw that is closed at each of its first and second ends by an end wall 14174ew. In some embodiments, the housing 14174 can be made of a rigid material, such as a plastic or a metal. The working fluid 14178 contained within the housing 14174 can comprise, without limitation, oil (e.g., mineral oil), silicone material, water or air.

As shown in FIGS. 196A-8196C, the piston assembly 14176 may comprise a piston 14180 and a rod 14184 for pushing the piston 14180 through the housing 14174. In other embodiments, such as shown in FIGS. 196A-196C, the piston rod can be configured and adapted to pull the piston through the dashpot housing 14174. As shown in FIGS. 196A-196C, the piston 14180 can comprise a single disc-like structure or member 14182 (piston disc member 14182) having leading and trailing surfaces 14182l and 14182t, respectively. The piston rod 14184 extends through an aperture 14174a in one of the end walls 14174ew of the housing 14174 and can have one end attached to or unitary with the leading surface 14182l or trailing surface 14182t of the piston disc member 14182, depending upon whether it pushes (see FIGS. 196A-196C) or pulls (FIGS. 197A-197C) the piston disc member 14182 in the damping stroke. The free end of the piston rod 14184, which is typically disposed external to the housing 14174, can be attached to the plunger head 14148, as shown in FIGS. 196A-196C. A seal, such as an O-ring (not visible), may be provided in or adjacent to the aperture 14174a to prevent the working fluid 14178 from leaking out of the housing 14174 between the piston rod 14184 and the aperture 14174a in the end wall 14174ew of the housing 14174. In some embodiments, the piston assembly 14176 can be made of a rigid material, such as a plastic or a metal. In other embodiments, the piston assembly 14176 can be made of a resilient material, such as a natural or synthetic polymer. In still further embodiments, the piston assembly 14176 can be made of a porous, rigid material.

FIGS. 196A-196C depict one exemplary mode of operation of the dashpot 14172. As shown in FIG. 196A, upon the actuation of the drive triggering mechanism, the energy source (e.g., piston biasing member 14106) of the drive mechanism 14100 advances the piston 14110 toward plunger seal 14060 disposed in the barrel 14058 of the drug container 14050. Once the linear dashpot 14172 contacts the plunger seal 14060, as shown in FIG. 196B, the load from the piston biasing member 14106 begins to be transmitted to the linear dashpot 14172, thereby causing the working fluid 178 located in front of the dashpot piston disc member 14182 to be pushed or displaced through one or more constrictions to a location behind the piston disc member 14182 as the piston disc member 14182 moves from one end of the housing 14174 to the other. The flow of the working fluid 14178 through the one or more constrictions generates a viscous friction, which resists the movement of the piston disc member 14182, thereby damping plunger motion. In some embodiments in which the piston disc member 14182 is made of a rigid material, the constriction(s) can comprise a small gap (not shown) between the peripheral edge of the piston disc member 14182 and the sidewall 174sw of the dashpot housing 14174. In other embodiments, the constriction(s) further or alternatively comprise one or more grooves 14186 provided in the peripheral edge of the piston disc member and/or one or more openings extending through the piston disc member 14182 through which the working fluid 178 flows as it is displaced from in front of the piston disc member 14182, to behind the piston disc member 14182. In other embodiments in which the piston disc member 14182 is made of a resilient material, the peripheral edge of the piston disc member 14182 can bend backwards enough to generate a narrow gap or constriction between the peripheral edge of the piston disc member 14182 and the sidewall 174sw of the dashpot housing 14174 (not shown) so that the working fluid 178 can flow therethrough. In other embodiments in which the piston disc member 14182 is made of a porous material, the working fluid 178 will flow through the pores (constrictions) of the piston disc member 14182. In each of these embodiments, the one or more constrictions of the linear dashpot 14172 provide a velocity-dependent resistance to the force of the energy source 144 (e.g., piston biasing member 14106) acting on the piston 14110. This resistance, when coupled to the piston 14110, reduces the velocity of the piston 14110 while maintaining the force of the energy source 144 (e.g., piston biasing member 14106) before the piston 14110 starts to move the plunger seal 14060. The size, number and type of constrictions, the type of working fluid 178 used in the linear dashpot 14172, the configuration of the housing 14174 and piston assembly 14176, and any combination thereof, can be adjusted and/or selected to allow the damping characteristics of the damper mechanism 14170 to be tuned to properly damp the shock characteristics of the drive mechanism 14100.

As shown in FIG. 196C, the piston disc member 14182 engages the leading one of the end walls of the dashpot housing 14174, and the force of the piston biasing member 14106 moves the plunger seal 14060, linear dashpot 14172 and piston 14110 distally through the barrel 14058 of the drug container 14050 at a reduced velocity, to expel the drug 14038 from the barrel 14058.

FIGS. 197A-197C depict one exemplary mode of operation of a dashpot 14192 disposed inline between the proximal end 14146pe of the piston rod 14146 of the injection drive mechanism and the main housing of the drug delivery device. In this embodiment, the dashpot housing 14194 can be retained in a tubular support member 14122 of the main housing by a detent 14123 integrally formed with the tubular support member 14122. Such an arrangement can be provided on a cantilever spring 14125 defined in the tubular support member 14122. The end of the piston rod 14204 disposed within the dashpot housing 14194 can be attached to the leading surface 14202l of the piston disc member 14202 and the free end of the piston rod 14204 can be attached to the proximal end 14146pe of the piston rod 14146 such that as the piston rod 14146 is driven distally by the energy source (e.g., piston biasing member 14106). The piston rod 14204 pulls the piston disc member 14202 through the dashpot housing 14194.

As shown in FIGS. 197A-197C, upon the actuation of the drive triggering mechanism, the energy source (e.g., piston biasing member 14106) of the injection drive mechanism begins to advance the piston 14110 toward the plunger seal 14060 disposed in the barrel 14058 of the drug container 14050. The load applied by the piston biasing member 14106 to the piston 14110 can be transmitted to the dashpot 14192. The working fluid 194 located in front of the piston disc member 14202 is pushed or displaced through the one or more constrictions to a location behind the piston disc member 14202, as the piston disc member 14202 is pulled from one end of the dashpot housing 14194 to the other. The resistance generated by the working fluid 14198 flowing through the one or more constrictions maintains the force of the piston biasing member 14106 while reducing the velocity of the piston 14110 before the head member of the piston 14110 impacts the plunger seal 14060. The head member of the piston 14110 impacts the plunger seal 14060 at the reduced velocity, and the force of the energy source (e.g., piston biasing member 14106) begins to move the plunger seal 14060 and piston 14110 distally through the barrel 14058 of the drug container 14050, to expel the drug 14038 from the barrel 14058. At about the same time, the piston disc member 14202 of the dashpot 14192 reaches the end of its stroke and engages the leading end wall 194ew of the dashpot housing 14194. The energy source (e.g., piston biasing member 14106) can be selected to apply enough energy to the piston 14110 to overcome the detent and cantilever arrangement 123/125 so that it releases the dashpot 14192 from the tubular support member 14122 to allow for movement of the piston 14110 as the energy source (e.g., piston biasing member 14106) drives the piston 14110, plunger seal 14060, and drug 14038 through the barrel 14058 of the drug container 14050. The release of the dashpot 14192 from the tubular support member 14122 reduces the duration of engagement, which allows the overall length of the injection device to be reduced.

FIGS. 198A-198C depict an exemplary mode of operation of dashpot 14212 that is integrated into piston 14242. As shown in FIGS. 198A-198C, the integrated dashpot 14212 includes a housing 14214 formed by a tubular wall 14214t and plunger head 14248, which closes the open distal end of the tubular wall 14214t. The dashpot 14212 further includes a piston formed by a distal end wall 14220 of hollow plunger rod 14246, which is initially disposed in the open proximal end of the tubular wall 14214t of the dashpot housing 14214. The working fluid 14218 of the dashpot 14212 is initially provided in the dashpot housing 14214, in front of the distal end wall 14220 of the plunger rod 14246. As shown in FIG. 198A, upon actuation of the drive triggering mechanism (not shown), the energy source (e.g., spring 14244s) of the injection drive mechanism applies a force to the plunger rod 14246 and advances the piston 14242 toward plunger seal 14060 disposed in the barrel 14058 of the drug container 14050. Once the plunger head 14248 makes contact with the plunger seal 14060, as shown in FIG. 198B, the load from the spring 14244s is transmitted to the dashpot 14212 integrally formed in the piston 14242. The working fluid 14218 located in front of the end wall 220 of the plunger rod 14246 is pushed or displaced through one or more constrictions (as previously described) provided in the end wall 220 and into the space defined by the hollow plunger rod 14246, behind the end wall 220 as it moves distally into the dashpot housing 14214. The resistance or damping provided by dashpot 14212 reduces the velocity of the plunger rod 14246 before the plunger rod 14246 engages the plunger head 14248 to move the plunger seal 14060, and performs the damping while maintaining the force of the spring 14244s.

As shown in FIG. 198C, the end wall 220 of the plunger rod 14246 engages the plunger head 14248, which marks the end of the damping stroke of the dashpot. The spring 14244s then propels or forces the plunger rod 14246 and plunger head 14248 as a single component (i.e., the plunger) against the plunger seal 14060 to drive the plunger seal 14060 distally through the barrel 14058 of the drug container 14050, to expel the drug 14038 from the barrel 14058.

FIG. 199 shows another exemplary embodiment of the dashpot. The dashpot 14270 is substantially similar to the dashpots previously described except that the piston of the piston assembly 14276 comprises two or more disc members 14282 spaced apart from one another along the piston rod 14284. The two or more piston disc members 14282 and the previously described constrictions, which may be associated with each piston disc member 14282, provide a series of resistances to piston movement, where each of the resistances can be the same and/or different. The series resistance of the dashpot 14270 allows the velocity of the plunger to be reduced in stages or increments while maintaining the force of the energy source (e.g. spring 14144*s*). In some embodiments, the multi-disc piston assembly 14276 can be made of a rigid material, such as a plastic or a metal. In such embodiments, the constriction(s), which control or define the resistance provided by each piston disc member 14282, can comprise a small gap (not shown) between the peripheral edge of one or more of the piston disc members 14282 and the sidewall 14274*sw* of the dashpot housing 14274. In other such embodiments, the constriction(s) can comprise one or more grooves provided in the peripheral edge of one or more of the piston disc members 14182 or one or more openings 14188 extending through the one or more piston disc members 14182, forming one or more of the piston disc members as porous discs, and any combination thereof. In other embodiments, the multi-disc piston assembly 14276 can be made of a resilient material, such as a natural or synthetic elastomer, such that the marginal peripheral edge of each piston disc member 14282 can bend backwards enough to generate a narrow gap or constriction between the peripheral edge of the piston disc members 14282 and the sidewall 14274*sw* of the dashpot housing 14274 so that the working fluid can flow therethrough. If air is used as the working fluid, the resilient piston disc members 282 of the piston assembly 276 may be used to create a squeeze-film damping effect. Any of the dashpots described above with respect to FIGS. 196A-85C, 86A-86C, and 87A-87C, can utilize the piston assembly 14276 of FIG. 199.

FIG. 200 shows an exemplary embodiment of the dashpot of the present disclosure. The dashpot 14370 comprises a housing 14374 and a piston assembly 14376 comprising a hollow piston rod 14384 and a piston configured as a bellows-like structure (bellows piston structure) attached to an end of the piston rod 14384 disposed within the housing 14374. The hollow piston rod 14384 may have an aperture 14384*a* for exhausting working fluid (not shown) flowing through the hollow piston rod 14384 outside of the dashpot housing 14374. The bellows piston structure can comprise one or more collapsible lobes that contain the working fluid, which fluid can be air or any other suitable working fluid. An opening 14386 (constriction) can be provided in the portions of the lobe walls connecting each adjacent pair lobes of the bellows piston structure to one another and to the hollow piston rod 14384. The openings 14386 allow the working fluid contained in the lobes to flow from one lobe to another, thereby functioning as constrictions. The dashpot 14370 provides damping when the bellows piston structure is pushed or pulled into the end wall 14374*ew* of the dashpot housing 14374 and collapsed by the force acting on the plunger 14142 supplied by the energy source (e.g., spring 14144*s*) of the drive plunger mechanism. The damping action is provided as the working fluid contained inside the lobes flows through the openings 14386, the hollow piston rod 14384 and the rod aperture 14384*a* as the lobes of the bellows piston structure are collapsed. Any of the dashpots embodiments described above with respect to FIGS. 196A-196C, 197A-197C, and 198A-198C, can utilize the piston assembly 14376 of FIG. 200.

XXVI. Additional Embodiments Relating to Skin Attachment

At least some of the drug delivery devices described in this application, including at least those described in connection with FIGS. 1A-200, may be configured to incorporate the embodiments of the adhesive described below in connection with FIGS. 201A-202D.

The present embodiments disclose adhesives which have bond strengths which are sensitive to the presence of a stimulant. The adhesive may be used to adhere the drug delivery device to the skin of a patient. The introduction of a stimulus may cause the bond strength of the adhesive to decrease such that the device may be more easily removed from the patient's skin as well as possibly reducing the pain or discomfort to the patient due to the removal. The stimulus may be chosen from any of the group of stimuli that is capable of decreasing the strength of the bond including: light, such as a UV light, heat, and electricity. The stimulant source may be integrated into the medical device or, alternatively, may be independent from the medical device. Methods of use and assembly are also described.

As seen in FIGS. 201A-201C, the drug delivery device 19010 may include a body 19001, stimulant source 19002, first adhesive patch 19003, and second adhesive patch 19004. Body 19001 may encompass or enclose stimulant source 19002 or, alternatively, stimulant source 19002 may be located on the outside of body 19001. The stimulant source 19002 has an inactive state and an active state. In the inactive state the stimulant source does not produce and/or emit a stimulus. In the active state, the stimulant source does produce and emit a stimulus. The bond strength of first adhesive 19003 may be such that it does not decrease in response to activation of stimulant source 19002. The first adhesive may retain the second adhesive in connection with the medical device. The bond strength of second adhesive 19004 may initially have a first bond strength in the absence of a stimulant and a second bond strength in the presence of a stimulant. The device 190010 may, optionally, include a removable adhesive cover which protects and isolates the adhesive during shipment and prior to application of the medical device to the patient.

Prior to initiation of delivery of the medicament, the patient or a medical practitioner may remove the adhesive cover, if equipped. The medical device may then be secured to the patient using the adhesive. The first bond strength of the second adhesive may be such that it securely attaches the device to the patient's skin, preventing unintentional removal. After delivery of the medicament or, at any other desired time, stimulant source 19002 may be activated. The activation may occur automatically at completion of medicament delivery or may occur in response to an input by the patient. For example, the device may include a stimulant activation mechanism such as a button, switch, or any other mechanism known to one skilled in the art. Activation of the stimulant source causes the bond strength of at least a portion of second adhesive patch 19004 to decrease to the second bond strength. In at least one embodiment, the bond strength of the outer perimeter of the second adhesive may be decreased to the second bond strength, thereby allowing the user to easily engage the edge of the adhesive and thereby remove or peel off the remainder of the adhesive from the patient's skin. In these embodiments, a stimulant source may be arranged around the outer profile of the device, the position of the stimulant source and the intensity of the stimulant controlling the portion of the second adhesive which is affected. In other embodiments, the bond strength of substantially all of the second adhesive is decreased, thereby allowing easy removal of the device from the patient's skin. The bond strength of the second adhesive does not need to be decreased uniformly in response to activation of the stimulant source. In other words, the bond strength of some portion of the second adhesive may be decreased to a greater extent than other portions. The cohesive properties of the adhesive may be completely eliminated or, alternatively, may retain some bonding strength. For example, the bond strength of the adhesive, in the presence of the activated stimulant may be sufficient to maintain its adhesion to the patient's skin until a removal operation is performed by the patient.

The stimulant may be a UV light source and be an integral aspect of the device as seen in FIGS. 201A-201C. The UV light source may be located on the bottom portion of the device such that it is in proximity to the adhesive patch. The UV light source may be in electronic communication with one or more other aspects of the device such that activation of the UV light source may be performed and/or controlled by a PCB or other type of electronic controller. Activation, by the electronic controller, may occur in response to completion of the delivery of a medicament to the patient. The activation may also be triggered by an input by the user, such as by depression of a button.

In other embodiments, shown in FIGS. 202A-202D, the stimulant source 190015 is an external stimulant source (i.e., not physically connected to the medical device). In these embodiments, the stimulant source may be supplied, with the drug delivery device 19020, to the user or may be supplied separately. The external stimulant source may be used multiple times and for multiple devices. To facilitate application of the stimulant to the adhesive, one or more aspects of the body of the device may be at least partially translucent, thereby allowing a stimulant such as a UV light to pass through. In at least one embodiment, the medical device may have a removable portion 19011. The removal of this portion of the medical device may expose a translucent portion 19012. Translucent portion 19012 may be a thin portion of the device thereby allowing the stimulant source to come into close proximity with the adhesive. A first adhesive 19013 may be bonded to translucent portion 19012. The bond strength of the first adhesive may not be affected by the presence of the stimulant. A second adhesive 19014 may be applied, the bond strength of which is altered by the presence of a stimulant as described previously. The external stimulus may be in the form of a handheld UV light source such that the user may direct the light source toward the adhesive.

In another aspect of the invention, the secondary adhesive may be re-useable. Removal of the stimulant may allow the adhesive to return to its first bond strength. After returning to the first bond strength the device may be re-applied to the patient's skin. This may be useful in applications of re-usable medical devices.

In applications in which the bond strength of the adhesive is affected by light, the adhesive may be configured such that it responds only to light of certain wavelengths. This may allow filters to be applied that prevent an inadvertent decrease in bond strength.

The bond strength of the adhesive may be immediately decreased in the presence of the stimulant. Alternatively, it may be necessary that the adhesive be exposed to the stimulus for a prolonged period of time in order to decrease the bond strength. The time may be as short as a few seconds to as long as a few minutes.

In other embodiments, a method of use is provided. The method of use may include the steps of: applying a medical device to a patient's skin using an adhesive; initiating operation of the medical device; activating a stimulant source to decrease the bond strength of at least a portion of the adhesive; and removal of the medical device from the patient. The stimulant source may be integral to the medical device or may be independent from the device. The method may optionally also include the step of removing an adhesive patch cover. The method may also include removal of one or more portions of the medical device from one or more other portions of the medical device.

In still other embodiments, a method of assembly is provided. The method of assembly may include the steps of: applying a first adhesive to a portion of the medical device; applying a second adhesive at least partially to the second adhesive. The method of assembly may further include assembling a stimulant source into the medical device.

XXVII. Additional Embodiments of Fluid Pathway Connector

At least some of the drug delivery devices described in this application, including at least those described in connection with FIGS. 1-202D, may be configured to incorporate the embodiments of the fluid pathway connector described below in connection with FIGS. 203A-203C. The embodiments of the fluid pathway connector described below in connection with FIGS. 203A-203C may be used to replace, in its entirety or partially, the above-described fluid pathway connector 300, 622, 722, 822, 1222, 1300, 2300, 6300, 8300, 14300, 18300, 90300, 94300, 95300, or, 96300, or any other fluid pathway connector described herein, where appropriate.

In the processes of filling drug containers and other drug delivery devices, it is sometimes necessary to connect two or more sterile components or subassemblies. For example, wearable injectors or drug pumps may include a drug container which may be filled with a fluid drug using standard pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes to the drug and/or fluid pathway. The connection of two or more aseptic components or subassemblies is typically performed in an aseptic environment, such as a clean room, thereby ensuring that no harmful microbes are introduced to the assembly. This, however, may lead to increased cost to manufacture the drug delivery devices.

While many of the above-described embodiments of the fluid pathway connector incorporate a piercing member which moves to access the drug container upon activation of the drug delivery device, alternative embodiments of the fluid pathway connector, such as the embodiment illustrated in FIGS. 203A-203C, may include a piercing member that remains stationary throughout drug delivery. In such alternative embodiments, the drug container may move toward the stationary piercing member upon activation of the drug delivery device. The movement of the drug container may result in the stationary piercing member accessing the drug container through the pierceable seal located at the distal end of the drug container.

FIGS. 203A-203C illustrate a subassembly of a drug delivery device (e.g., the drug delivery device 10, 910, 6010,

8000, 9010, 9210, 9310, 9410, 9510, 9610, 11600, 12340, 12710, 11010, 13100, 19010, or 19020 or any other drug delivery device described herein) including a drug container 10050 (which may be substituted for any one of the drug containers 300, 622, 722, 822, 922, 1122, 1222, 1300, 2300, 8300, 18300, 23030, 90300 182300, 230330, or 230130, or any other fluid pathway connector described herein), a drive mechanism 10100 (which may be substituted for any one of the drive mechanisms 100, 130, 1100, 2100, 6100, 8100, 8130 11100, 14100, 23090, or 90100, or any other fluid pathway connector described herein) and a fluid pathway connector 10300. The drug container 10050 may include a barrel 10058, a plunger seal 10060 moveable through the barrel 10058, and a pierceable seal 10056 covering an open distal end of the barrel 10058 and controlling access to the interior of the barrel 10058.

The drive mechanism 10100 may include a drive housing 10130, a piston 10110 moveable relative to the drive housing 10130 and configured to impart movement to the plunger seal 10060, and a piston biasing member 10106 disposed between the drive housing 10130 and the piston 10110. Prior to delivery, the piston biasing member 10106 may be retained in a piston biasing member energized state, as depicted in FIG. 203A. When the piston biasing member 10106 is released and consequently de-energizes (as seen in FIGS. 203B and 203C), the piston biasing member 10106 may move the piston 10110 and/or the plunger seal 10060 toward the fluid pathway connector 10300.

The fluid pathway connector 10300 may define a sterile fluid flowpath between the drug container 10050 and an insertion mechanism (e.g., the needle insertion mechanism 200, 624, 724, 824, 924, 1124, 1224, 6200, 7200, 8200, 11200, 23070, 90200, 92200, 93200, 94200, 95200, or 96200, or any other insertion mechanism described herein). The fluid pathway connector 10300 may include a connection hub 10310, a tubular conduit (not illustrated) providing fluid communication between the connection hub 10310 and the insertion mechanism, a piercing member 10330 (e.g., a container access needle) configured to pierce the pierceable seal 10056 to establish fluid communication between the between the barrel 10058 and the tubular conduit during drug delivery, a barrel connector 10332, and a flexible sealing member 10334. In some embodiments, the tubular conduit may be a single, unitary tube made of a flexible material and may extend directly between the connection hub 10310 and the insertion mechanism. In other embodiments, depending on the need to regulate or modify the fluid pressure, fluid flow rate, or other characteristic of the drug, the tubular conduit may include one or more flow restrictors made of a relatively rigid material and connected at opposite ends via flexible tubes to the connection hub 10310 and the insertion mechanism, respectively.

Still referring to FIGS. 203A-203C, the flexible sealing member 10334 may define a sterile chamber 10062 with a collapsible volume between the distal end of the barrel 10058 and the connection hub 10310. In at least one embodiment, the flexible sealing member 10334 may have a generally conical shape and function as a flexible bellows. A proximal end of the flexible sealing member 10334 may be clamped between the barrel connector 10332 and a distal end surface of the barrel 10058. At its distal end, the flexible sealing member 10334 may be connected to the connection hub 10310.

The barrel connector 10332 may have a tubular body portion 10335 configured to fit snugly around a circumferential surface of the barrel 10058, and first and second radially inwardly depending annular protrusions 10336, 10338 at opposite ends of the tubular body portion 10335. The first annular protrusion 10336 may grip a neck of the barrel 10058, and the second annular protrusion 10338 may clamp the proximal end of the flexible sealing member 10334 against the distal end surface of the barrel 10332.

The connection hub 10310 may be fixed relative to a housing (e.g., the housing 12) of the drug delivery device such that the connection hub 10310 is prevented from moving relative to the housing of the drug delivery device. A distal end of the piercing member 10330 may be rigidly connected to the connection hub 10310 so that the piercing member 10330 is also fixed relative to the housing of the drug delivery device. The barrel 10058 may be slidably connected to the housing of the drug delivery device such that the barrel 10058 can move (e.g., translate in a linear direction) relative to the housing of the drug delivery device. As the barrel 10058 moves toward the connection hub 10310, the flexible sealing member 10334 may elastically or in-elastically deform such that the volume of the sterile chamber 10062 decreases, as illustrated in FIGS. 203B and 203C.

In a pre-delivery state (FIG. 203A), a proximal end of the piercing member 10330 may be disposed within the sterile chamber 10062 defined by the flexible sealing member 10334. Upon release of the piston biasing member 10106, the piston biasing member 10106 may begin to de-energize and thereby cause the piston 10110 and the plunger seal 10060 to move toward the piercing member 10330. Friction between the plunger seal 10060 and the inner wall of the barrel 10058 may cause the barrel 10058, which is slidably connected to the housing, to initially move in a distal direction together with the plunger seal 10060. The movement of the barrel 10058 causes the pierceable seal 10056 to be pierced by the piercing member 10330. As a result, the piercing member 10330 may access the interior of the barrel 10058 and establish fluid communication between the barrel 10058 and the connection hub 10310.

FIG. 203B shows that the barrel 10058 continues to move in the distal direction until it contacts a stopping member, which in the present embodiment corresponds to the connection hub 10310. The reaction force exerted on the barrel 10058 by the stopping member overcomes the frictional force between the plunger seal 10060 and the inner wall of the barrel 10058, thereby allowing the plunger seal 10060 to move relative to the barrel 10058 and discharge the drug from the barrel 10058 via the piercing member 10330. FIG. 203C shows that movement of the plunger seal 10060 is halted, thereby ending drug delivery, when the plunger seal 10060 impacts a portion of the inner wall of the barrel 10058 at the neck of the barrel 10058.

The combination of the fluid pathway connector 10300 having a stationary piercing member 10330 and the drug container 10050 having a moveable barrel 10058 removes the need for a separate mechanism to establish fluid communication with the interior of the barrel 10058 upon activation of the drug delivery device. Instead, the force of the piston biasing member 10106 is utilized to move the pierceable seal 10056 into the stationary piercing member 10330 to establish fluid communication with the interior of the barrel 10058. Accordingly, the design and manufacture of the drug delivery device may be simplified, and the overall size of the drug delivery device may be reduced.

XXVIII. Drug Information

The above description describes various systems and methods for use with various drug delivery devices. It should be clear that the systems, drug delivery devices or methods can further comprise use of a medicament listed below with the caveat that the following list should neither be considered to be all inclusive nor limiting. The medicament will be contained in any one of the reservoirs or containers described herein, including, but not limited to, any one of the containers 50, 350, 618, 718, 818, 918, 1050, 1118, 1850, 2050, 2330, 6050, 8050, 9050, 9250, 9350, 9450, 9550, 9650, 11050, 14050, 23050, 230350, or 951050. In some instances, the reservoir is a primary container that is either filled or pre-filled for treatment with the medicament. The primary container can be a cartridge or a pre-filled syringe. Additionally, in some instances, the reservoir may be a primary container that is pre-loaded.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858) as well as erythropoietin molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/ 0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4;

Myostatin binding proteins, peptibodies, and related proteins, and the like, including myostatin specific peptibodies, particularly those described in U.S. Publication No. 2004/0181033 and PCT Publication No. WO 2004/058988, in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS: 439-446; the mL21 family of SEQ ID NOS:447-452; the mL24 family of SEQ ID NOS:453-454; and those of SEQ ID NOS:615-631;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694 particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1;

Interleukin 1-receptor 1 ("IL1-R1") specific antibodies, peptibodies, and related proteins, and the like, including but not limited to those described in U.S. Publication No. 2004/097712, in parts pertinent to IL1-R1 specific binding proteins, monoclonal antibodies in particular, especially, without limitation, those designated therein: 15CA, 26F5, 27F2, 24E12, and 10H7;

Ang2 specific antibodies, peptibodies, and related proteins, and the like, including but not limited to those described in PCT Publication No. WO 03/057134 and U.S. Publication No. 2003/0229023, particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein;

NGF specific antibodies, peptibodies, and related proteins, and the like including, in particular, but not limited to those described in U.S. Publication No. 2005/0074821 and U.S. Pat. No. 6,919,426 particularly as to NGF-specific antibodies and related proteins in this regard, including in particular, but not limited to, the NGF-specific antibodies therein designated 4D4, 4G6, 6H9, 7H2, 14D10 and 14D11;

CD22 specific antibodies, peptibodies, and related proteins, and the like, such as those described in U.S. Pat. No. 5,789,554, as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein);

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing publication and in Thakur et al. (1999), Mol. Immunol. 36:1107-1115. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, as to TALL-1 binding proteins, particularly the molecules of Tables 4 and 5B;

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in U.S. Publication No. 2009/0234106, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, particularly in parts pertinent to proteins that bind TGF-beta;

Amyloid-beta protein specific antibodies, peptibodies, related proteins, and the like, including but not limited to those described in PCT Publication No. WO 2006/081171, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2015/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

XXIX. Additional Aspects

The drug delivery devices, assemblies, mechanisms, components, features, functionalities, methods of manufacture, and methods of use described above may incorporate various aspects of the drug delivery devices, assemblies, mechanisms, components, features, functionalities, methods of manufacture, and methods of use described in the following documents, each of which is incorporated in its entirety for all purposes: U.S. Pat. No. 8,939,935; U.S. Patent Application Publication No. 2013/0060233; U.S. Patent Application Publication No. 2013/0066274; U.S. Patent Application Publication No. 2013/0237916; U.S. Patent Application Publication No. 2014/0200510; U.S. Patent Application Publication No. 2014/0288511A1; U.S. Patent Application Publication No. 2015/0290390; U.S. Patent Application Publication No. 2015/0374919A1; U.S. Patent Application Publication No. 2015/0209505; U.S. Patent Application Publication No. 2015/0297827; U.S. Patent Application Publication No. 2015/0359965; U.S. Patent Application Publication No. 2015/0190588; U.S. Patent Application Publication No. 2015/0217045; U.S. Patent Application Publication No. 2015/0057613; U.S. Patent Application Publication No. 2014/0296787; U.S. Provisional Patent Application No. 62/094,395 entitled "DRUG DELIVERY DEVICE WITH PROXIMITY SENSOR"; U.S. Provisional Patent Application No. 62/114,200 entitled "ROTATIONALLY BIASED INSERTION MECHANISM FOR A DRUG DELIVERY PUMP"; U.S. Provisional Patent Application No. 62/117,420 entitled "DRUG DELIVERY DEVICE WITH VACUUM ASSISTED SECUREMENT AND/OR FEEDBACK"; U.S. Provisional Patent Application No. 62/127,021 entitled "DEVICE AND METHOD FOR MAKING ASEPTIC CONNECTIONS"; U.S. Provisional Patent Application No. 62/130,318 entitled "MULTI-FUNCTION DRIVE MECHANISMS FOR CONTROLLED DRUG DELIVERY PUMPS"; U.S. Provisional Patent Application No. 62/266,788 entitled "DRUG DELIVERY STORAGE DEVICE AND SYSTEM"; U.S. Provisional Patent Application No. 62/293,556 filed on Feb. 10, 2016 entitled "DRUG DELIVERY DEVICE"; U.S. Provisional Patent Application No. 62/133,690 entitled "ROTATIONALLY BIASED INSERTION MECHANISM FOR A DRUG DELIVERY PUMP"; U.S. Provisional Patent Application No. 62/201,456 entitled "MULTI-FUNCTION DRIVE MECHANISMS FOR CONTROLLED DRUG DELIVERY PUMPS"; U.S. Provisional Patent Application No. 62/147,435 entitled "MULTI-FUNCTION DRIVE MECHANISMS FOR CONTROLLED DRUG DELIVERY PUMPS"; U.S. Provisional Patent Application No. 62/134,226 entitled "MULTI-FUNCTION DRIVE MECHANISMS FOR CONTROLLED DRUG DELIVERY PUMPS"; U.S. Provisional Patent Application No. 62/147,403 entitled "ROTATIONALLY BIASED INSERTION MECHANISM FOR A DRUG DELIVERY PUMP"; U.S. Provisional Patent Application No. 62/220,754 entitled "CONTROLLED DELIVERY DRIVE MECHANISMS FOR DRUG DELIVERY PUMPS"; U.S. Provisional Patent Application No. 62/290,064 entitled "ASEPTIC CONNECTIONS FOR DRUG DELIVERY DEVICES"; U.S. Provisional Patent Application No. 62/201,468 entitled "DRUG DELIVERY PUMPS HAVING MULTIPLE CHAMBERS"; U.S. Provisional Patent Application No. 62/262,666 entitled "SYSTEMS FOR THE CONTROL OF DRUG DELIVERY PUMPS BASED ON INPUT DATA"; U.S. Provisional Patent Application No. 62/241,906 entitled "FILL-FINISH CARRIERS FOR DRUG CONTAINERS"; U.S. Provisional Patent Application No. 62/262,683 entitled "SYSTEMS AND METHODS FOR CONTROLLED DRUG DELIVERY PUMPS"; U.S. Provisional Patent Application No. 62/204,866 entitled "AUTOMATIC DRUG INJECTORS AND ASSOCIATED DEVICES INCORPORATING DATA RECORDING, TRANSMISSION, AND RECEIVING"; U.S. Provisional Patent Application No. 62/239,116 entitled "AUTOMATIC INJECTORS FOR INJECTABLE CARTRIDGES INCORPORATING SIMPLIFIED LOADING OF CARTRIDGES"; U.S. Provisional Patent Application No. 62/206,503 entitled "ARCUATE DRIVE MECHANISMS FOR AUTOMATIC INJECTORS"; U.S. Provisional Patent Application No. 62/278,028 entitled "MEDICAL DEVICE INCORPORATING ADHESIVE WITH STIMULANT SENSITIVE BONDING STRENGTH"; International Patent Application Publication No. WO/2015/061386; International Patent Application Publication No. WO/2015/061389; International Patent Application Publication No. WO/2015/187793; International Patent Application Publication No. WO/2015/187797; International Patent Application Publication No. WO/2015/187799; International Patent Application Publication No. WO/2015/187802; International Patent Application Publication No. WO/2015/187805; International Patent Application Publication No. WO/2016/003813; International Patent Application No. PCT/US2016/017534 entitled "ROTATIONALLY BIASED INSERTION MECHANISM FOR A DRUG DELIVERY PUMP"; International Patent Application No. PCT/US2016/017534 entitled "ROTATIONALLY BIASED INSERTION MECHANISM FOR A DRUG DELIVERY PUMP"; International Patent Application No. PCT/US2015/052311 entitled "CONCENTRIC BARREL DRUG CONTAINERS AND DRUG DELIVERY PUMPS THAT ALLOW MIXING AND DELIVERY"; International Patent Application No. PCT/US2015/052367 entitled "SEQUENTIAL CHAMBER DRUG DELIVERY PUMPS FOR DRUG MIXING AND DELIVERY"; International Patent Application No. PCT/US2015/047487 entitled "SKIN SENSORS FOR DRUG DELIVERY DEVICES"; International Patent Application No. PCT/US2015/052815 entitled "RIGID NEEDLE INSERTION MECHANISM FOR A DRUG DELIVERY PUMP"; International Patent Application No. PCT/US2015/047503 entitled "SENSOR SYSTEMS FOR DRUG DELIVERY DEVICES"; International Patent Application No. PCT/US2016/021585 entitled "DRIVE MECHANISMS FOR DRUG DELIVERY PUMPS"; International Patent Application No. PCT/US2016/020486 entitled "DEVICE AND METHOD FOR MAKING ASEPTIC CONNECTIONS"; International Patent Application No. PCT/US15/29485 entitled "AUTOINJECTOR WITH SHOCK REDUCING ELEMENTS". Furthermore, the drug delivery devices, assemblies, mechanisms, components, features, functionalities, methods of manufacture, and methods of use described in any of the above-listed-incorporated-by-reference disclosures may include a container filled partially or entirely with one or more of the drugs described above, including, for example, a PCSK9 specific antibody, a G-CSF, a sclerostin antibody, or a CGRP antibody.

Throughout the specification, the aim has been to describe the preferred embodiments of the disclosure without limiting the disclosure to any one embodiment or specific collection of features. Various changes and modifications may be made to the embodiments described and illustrated without departing from the present disclosure. The disclosure of each patent and scientific document, computer program and algorithm referred to in this specification is incorporated by reference in its entirety.

What is claimed is:

1. A wearable drug delivery device comprising:
   a housing;
   a container disposed at least partially within the housing;
   a plunger movably disposed within the container; and
   a drive mechanism disposed at least partially within the housing and comprising:
      a spring configured to move the plunger within the container when released, wherein at least a portion of the plunger is disposed within at least a portion of the spring,
      a gear operably coupled to the plunger,
      a lever operably coupled to the gear, and
      an electrical actuator configured to oscillate the lever to cause the gear to rotate in increments,
      wherein, to oscillate the lever, the electrical actuator is configured to selectively drive the lever in a first direction and a second direction.

2. The wearable drug delivery device of claim 1, wherein the gear includes a plurality of teeth and the lever is configured to selectively engage the teeth when oscillating.

3. The wearable drug delivery device of claim 1, comprising:
   a needle; and
   an insertion mechanism configured to move the needle between a retracted position and an inserted position.

4. The wearable drug delivery device of claim 3, wherein the insertion mechanism comprises a rotational biasing member.

5. The wearable drug delivery of claim 4, the insertion mechanism comprising a hub operably coupled to the needle and an insertion mechanism housing, wherein the rotational biasing member configured to rotate the insertion mechanism housing.

6. The wearable drug delivery of claim 5, wherein the insertion mechanism housing is operably coupled to the hub such that initial rotation of the insertion mechanism housing causes the needle to move axially from the retracted position to the insertion position.

7. The wearable drug delivery of claim 6, wherein the insertion mechanism housing comprises a cylindrical portion and at least a portion of the needle is positioned within the cylindrical portion when the needle is in the retracted position.

8. The wearable drug delivery of claim 6, wherein the insertion mechanism housing comprises a first guide surface and the hub comprises an outwardly extending follower configured to slidably engage the first guide surface during rotation of the insertion mechanism housing.

9. The wearable drug delivery of claim 8, wherein at least a portion of the first guide surface extends in an axial direction and a circumferential direction.

10. The wearable drug delivery of claim 5, wherein the insertion mechanism housing is rotatable about a rotational axis and the rotational axis is parallel to a longitudinal axis of the needle.

11. The wearable drug delivery of claim 5, comprising a first abutment member having a first position wherein the first abutment member engages the insertion mechanism housing to prevent the rotational biasing member from rotating the insertion mechanism housing and second position wherein the first abutment member is disengaged from the insertion mechanism housing to allow the rotational biasing member to rotate the insertion mechanism housing.

12. The wearable drug delivery of claim 11, wherein the insertion mechanism housing includes a cylindrical portion and a second abutment member extending outwardly from the cylindrical portion, the second abutment member engaging the first abutment member when the first abutment member is in the first position.

13. The wearable drug delivery of claim 3, wherein the insertion mechanism is at least partially disposed within the housing.

14. The wearable drug delivery of claim 1, comprising an adhesive applied to an exterior surface of the housing for attaching the housing to skin of a patient.

15. The wearable drug delivery device of claim 1, comprising a drug disposed in the container, the drug comprising at least one of: a Proprotein Convertase Subtilisin/Kexin Type 9 (PCSK9) specific antibody, a granulocyte colony-stimulating factor (G-CSF), a sclerostin antibody, or a calcitonin gene-related peptide (CGRP) antibody.

16. The wearable drug delivery device of claim 1, wherein the spring comprises a coiled spring.

17. The wearable drug delivery device of claim 16, wherein the coiled spring is configured to bear upon a surface of the plunger.

18. A wearable drug delivery device comprising:
a housing;
a container disposed at least partially within the housing;
a plunger movably disposed within the container;
a drive mechanism disposed at least partially within the housing and comprising:
a biasing member configured to move the plunger within the container when released,
a gear operably coupled to the plunger,
a lever operably coupled to the gear, and
an electrical actuator configured to oscillate the lever to cause the gear to rotate in increments;
a needle; and
an insertion mechanism configured to move the needle between a retracted position and an inserted position, wherein the insertion mechanism comprises a rotational biasing member and a hub operably coupled to the needle and an insertion mechanism housing, wherein the rotational biasing member configured to rotate the insertion mechanism housing.

19. A wearable drug delivery device comprising:
a housing;
a container disposed at least partially within the housing;
a plunger movably disposed within the container; and
a drive mechanism disposed at least partially within the housing and comprising:
a spring configured to move the plunger within the container when released, wherein at least a portion of the plunger is disposed within at least a portion of the spring,
a gear operably coupled to the plunger,
a lever operably coupled to the gear, and
an electrical actuator configured to oscillate the lever to cause the gear to rotate in increments,
wherein the electrical actuator is configured to output linear motion.

20. The wearable drug delivery device of claim 19, wherein the electrical actuator comprises a linear solenoid.

21. A wearable drug delivery device comprising:
a housing;
a container disposed at least partially within the housing;
a plunger movably disposed within the container;
a drive mechanism disposed at least partially within the housing and comprising:
a spring configured to move the plunger within the container when released, wherein at least a portion of the plunger is disposed within at least a portion of the spring,
a gear operably coupled to the plunger,
a lever operably coupled to the gear, and
an electrical actuator configured to oscillate the lever to cause the gear to rotate in increments; and
an insertion mechanism disposed at least partially within the housing, wherein the insertion mechanism comprises:
a delivery member moveable between a first position wherein an insertion portion of the delivery member is disposed within the housing and a second position wherein the insertion portion of the delivery member is disposed exterior to the housing for insertion into a patient,
a rotatable member,
a rotational biasing member configured to rotate the rotatable member, and
a hub operably coupled with the rotatable member and the delivery member.

* * * * *

UNITED STATES PATENT AND TRADEMARK OFFICE
CERTIFICATE OF CORRECTION

| | | |
|---|---|---|
| PATENT NO. | : 12,201,809 B2 | Page 1 of 1 |
| APPLICATION NO. | : 17/386659 | |
| DATED | : January 21, 2025 | |
| INVENTOR(S) | : Scott R. Gibson et al. | |

It is certified that error appears in the above-identified patent and that said Letters Patent is hereby corrected as shown below:

In the Claims

At Column 440, Line 41, "delivery of claim 4, the" should be -- delivery device of claim 4, wherein the --.

At Column 440, Line 46, "delivery" should be -- delivery device --.

At Column 440, Line 51, "delivery" should be -- delivery device --.

At Column 440, Line 56, "delivery" should be -- delivery device --.

At Column 440, Line 61, "delivery" should be -- delivery device --.

At Column 440, Line 64, "delivery" should be -- delivery device --.

At Column 441, Line 1, "delivery" should be -- delivery device --.

At Column 441, Line 9, "delivery" should be -- delivery device --.

At Column 441, Line 15, "delivery" should be -- delivery device --.

At Column 441, Line 18, "delivery" should be -- delivery device --.

Signed and Sealed this
Twenty-first Day of October, 2025

John A. Squires
*Director of the United States Patent and Trademark Office*